US010668167B2

(12) United States Patent
McPherson et al.

(10) Patent No.: US 10,668,167 B2
(45) Date of Patent: Jun. 2, 2020

(54) GLUCOCORTICOID RECEPTOR AGONIST AND IMMUNOCONJUGATES THEREOF

(71) Applicant: AbbVie Inc., North Chicago, IL (US)

(72) Inventors: Michael J. McPherson, Ashby, MA (US); Adrian D. Hobson, Shrewsbury, MA (US); Martin E. Hayes, Pepperell, MA (US); Christopher C. Marvin, Grayslake, IL (US); Diana Schmidt, Antioch, IL (US); Wendy Waegell, Brookfield, MA (US); Christian Goess, Sturbridge, MA (US); Jason Z. Oh, Worcester, MA (US); Axel Hernandez, Jr., Charlton, MA (US); John T. Randolph, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/408,602

(22) Filed: May 10, 2019

(65) Prior Publication Data

US 2019/0262465 A1 Aug. 29, 2019

Related U.S. Application Data

(62) Division of application No. 15/611,037, filed on Jun. 1, 2017.

(60) Provisional application No. 62/344,948, filed on Jun. 2, 2016, provisional application No. 62/371,134, filed on Aug. 4, 2016.

(51) Int. Cl.
| | | |
|---|---|---|
| *A61K 47/68* | (2017.01) | |
| *C07K 16/24* | (2006.01) | |
| *A61P 37/06* | (2006.01) | |
| *C07J 71/00* | (2006.01) | |
| *A61K 39/00* | (2006.01) | |
| *C07K 16/18* | (2006.01) | |

(52) U.S. Cl.
CPC ...... *A61K 47/6845* (2017.08); *A61K 47/6803* (2017.08); *A61K 47/6849* (2017.08); *A61K 47/6889* (2017.08); *A61P 37/06* (2018.01); *C07J 71/0031* (2013.01); *C07K 16/241* (2013.01); *A61K 2039/505* (2013.01); *C07K 16/18* (2013.01); *C07K 2317/21* (2013.01); *C07K 2317/24* (2013.01); *C07K 2317/31* (2013.01); *C07K 2317/55* (2013.01); *C07K 2317/569* (2013.01); *C07K 2317/73* (2013.01); *C07K 2317/92* (2013.01); *C07K 2318/20* (2013.01); *C07K 2319/30* (2013.01)

(58) Field of Classification Search
CPC ................ A61K 47/6889; A61K 47/68; A61K 47/6835; A61K 47/6849
See application file for complete search history.

(56) References Cited

U.S. PATENT DOCUMENTS

| | | |
|---|---|---|
| 3,126,375 A | 3/1964 | Ringold et al. |
| 3,886,145 A | 5/1975 | Diamanti |
| 4,588,585 A | 5/1986 | Mark et al. |
| 5,010,176 A | 4/1991 | Barton |
| 5,225,539 A | 7/1993 | Winter |
| 5,545,807 A | 8/1996 | Surani et al. |
| 5,728,826 A | 3/1998 | Gutterer |
| 5,733,901 A | 3/1998 | Gutterer |
| 5,792,758 A | 8/1998 | Tjoeng et al. |
| 5,824,669 A | 10/1998 | Garvey et al. |
| 6,090,382 A | 7/2000 | Salfeld et al. |
| 6,579,863 B1 | 6/2003 | Garvey et al. |
| 6,787,533 B1 | 9/2004 | Gutterer |
| 7,012,135 B2 | 3/2006 | Athwal et al. |
| 7,160,920 B2 | 1/2007 | Garvey et al. |
| 7,227,003 B2 | 6/2007 | Le et al. |
| 7,468,433 B2 | 12/2008 | Schmidt |
| 7,524,502 B2 | 4/2009 | Hellendoorn et al. |
| 7,709,226 B2 | 5/2010 | Foote |
| 7,744,885 B2 | 6/2010 | Le et al. |
| 8,158,780 B2 | 4/2012 | Phull et al. |
| 8,232,304 B2 | 7/2012 | Goldstein et al. |
| 8,371,292 B2 | 2/2013 | Bethke et al. |
| 8,501,906 B2 | 8/2013 | McTavish |
| 8,524,697 B2 | 9/2013 | Anthes et al. |
| 8,597,648 B2 | 12/2013 | Guo et al. |
| 8,747,854 B2 | 6/2014 | Okun et al. |
| 8,765,696 B2 | 7/2014 | Ishii |
| 8,822,439 B2 | 9/2014 | Glossop et al. |
| 8,877,194 B2 | 11/2014 | Hsieh et al. |
| 9,101,670 B2 | 8/2015 | Bossard et al. |
| 9,109,005 B2 | 8/2015 | Puder et al. |
| 9,422,327 B2 | 8/2016 | Schmidt |

(Continued)

FOREIGN PATENT DOCUMENTS

| | | |
|---|---|---|
| CA | 2754589 A1 | 9/2010 |
| DE | 10055820 C1 | 7/2002 |

(Continued)

OTHER PUBLICATIONS

Knight. Organic Process Research and Development, 2012, 16, 697-703 (Year: 2012).*

Aggarwal, B.B., "Historical Perspectives on Tumor Necrosis Factor and Its Superfamily: 25 Years Later, a Golden Journey," Blood 119(3):651-665, American Society of Hematology,United States (2012).

Alley, S.C., et al., "Contribution of Linker Stability to the Activities of Anticancer Immunoconjugates," Bioconjugate Chemistry 19(3):759-765, American Chemical Society, United States (2008).

(Continued)

*Primary Examiner* — Noble E Jarrell

(74) *Attorney, Agent, or Firm* — Womble Bond Dickinson (US) LLP; Cristin H. Cowles; Danielle L. Herritt

(57) ABSTRACT

Provided herein are glucocorticoid receptor agonist immunoconjugates, glucocorticoid receptor agonists, and methods of using the same, e.g., to treat autoimmune or inflammatory diseases.

4 Claims, 24 Drawing Sheets

Specification includes a Sequence Listing.

(56) References Cited

U.S. PATENT DOCUMENTS

| | | |
|---|---|---|
| 9,428,540 B2 | 8/2016 | Myhren et al. |
| 2002/0022720 A1 | 2/2002 | Le et al. |
| 2003/0130189 A1 | 7/2003 | Senter et al. |
| 2003/0175837 A1 | 9/2003 | Le et al. |
| 2003/0199679 A1 | 10/2003 | Adair et al. |
| 2003/0235585 A1 | 12/2003 | Fischkoff et al. |
| 2004/0156869 A1 | 8/2004 | Bakthavatchalam et al. |
| 2005/0107408 A1 | 5/2005 | Goldstein |
| 2005/0143381 A1 | 6/2005 | Yu et al. |
| 2006/0073141 A1 | 4/2006 | Ignatovich et al. |
| 2006/0088523 A1 | 4/2006 | Andya et al. |
| 2006/0093601 A1 | 5/2006 | Fong et al. |
| 2007/0160617 A1 | 7/2007 | Ma et al. |
| 2008/0050310 A1 | 2/2008 | Ebens et al. |
| 2008/0312425 A1 | 12/2008 | Bonnerjea et al. |
| 2009/0227548 A1 | 9/2009 | Glossop et al. |
| 2009/0318396 A1 | 12/2009 | Baker et al. |
| 2010/0028346 A1 | 2/2010 | Lutz et al. |
| 2010/0034773 A1 | 2/2010 | Tran et al. |
| 2010/0056488 A1 | 3/2010 | Teicher et al. |
| 2010/0099654 A1 | 4/2010 | Finn et al. |
| 2010/0120733 A1 | 5/2010 | Gant et al. |
| 2010/0209508 A1 | 8/2010 | Baker et al. |
| 2010/0233079 A1 | 9/2010 | Jakob et al. |
| 2010/0266496 A1 | 10/2010 | Hansen et al. |
| 2010/0331539 A1 | 12/2010 | La Loggia et al. |
| 2011/0172278 A1 | 7/2011 | He et al. |
| 2011/0250130 A1 | 10/2011 | Benatuil et al. |
| 2011/0262368 A1 | 10/2011 | Anthes et al. |
| 2011/0287009 A1 | 11/2011 | Scheer et al. |
| 2011/0294766 A1 | 12/2011 | Burkamp et al. |
| 2011/0300150 A1 | 12/2011 | Eliasof |
| 2011/0318349 A1 | 12/2011 | Ghayur et al. |
| 2012/0059158 A1 | 3/2012 | Ishii |
| 2013/0017200 A1 | 1/2013 | Scheer et al. |
| 2013/0115269 A1 | 5/2013 | Smith et al. |
| 2013/0164256 A1 | 6/2013 | Hsieh et al. |
| 2014/0161804 A1 | 6/2014 | Cuff et al. |
| 2014/0179650 A1 | 6/2014 | Aven et al. |
| 2014/0200332 A1 | 7/2014 | Kaymakcalan et al. |
| 2015/0158943 A1 | 6/2015 | Robblee et al. |
| 2015/0250896 A1 | 9/2015 | Zhao |
| 2017/0196975 A1 | 7/2017 | Bossard et al. |

FOREIGN PATENT DOCUMENTS

| | | |
|---|---|---|
| EP | 0315456 A2 | 5/1989 |
| EP | 2641900 A1 | 9/2013 |
| GB | 933867 A | 8/1963 |
| JP | 2749778 B2 | 5/1998 |
| JP | 2016190798 A | 11/2016 |
| JP | 2017066075 A | 4/2017 |
| WO | WO-9425478 A1 | 11/1994 |
| WO | WO-9734871 A1 | 9/1997 |
| WO | WO-9809982 A1 | 3/1998 |
| WO | WO-0049993 A2 | 8/2000 |
| WO | WO-01/94585 A1 | 12/2001 |
| WO | WO-03031464 A2 | 4/2003 |
| WO | WO-2004/017904 A2 | 3/2004 |
| WO | WO-2004056847 A2 | 7/2004 |
| WO | WO-2004066957 A2 | 8/2004 |
| WO | WO-2005028495 A1 | 3/2005 |
| WO | WO-2005044759 A2 | 5/2005 |
| WO | WO-2005063777 A1 | 7/2005 |
| WO | WO-2005065435 A2 | 7/2005 |
| WO | WO-2005074924 A1 | 8/2005 |
| WO | WO-2006019447 A1 | 2/2006 |
| WO | WO-2006027377 A1 | 3/2006 |
| WO | WO-2006097458 A1 | 9/2006 |
| WO | WO-2006108556 A2 | 10/2006 |
| WO | WO-2006110593 A2 | 10/2006 |
| WO | WO-2006135479 A2 | 12/2006 |
| WO | WO-2007054974 A2 | 5/2007 |
| WO | WO-2007/117685 A2 | 10/2007 |
| WO | WO-2008015696 A2 | 2/2008 |
| WO | WO-2008052350 A1 | 5/2008 |
| WO | WO-2009003199 A1 | 12/2008 |
| WO | WO-09069032 A2 | 6/2009 |
| WO | WO-2010075249 A2 | 7/2010 |
| WO | WO-2010080538 A1 | 7/2010 |
| WO | WO-2010126953 A1 | 11/2010 |
| WO | WO-2010132743 A1 | 11/2010 |
| WO | WO-2010136940 A1 | 12/2010 |
| WO | WO-2011039510 A2 | 4/2011 |
| WO | WO-2011072124 A1 | 6/2011 |
| WO | WO-2011081937 A1 | 7/2011 |
| WO | WO-2012040228 A2 | 3/2012 |
| WO | WO-2012040229 A1 | 3/2012 |
| WO | WO-2012082947 A1 | 6/2012 |
| WO | WO-2012089247 A1 | 7/2012 |
| WO | WO-2012/131053 A1 | 10/2012 |
| WO | WO-2013087912 A1 | 6/2013 |
| WO | WO-201314995 A1 | 10/2013 |
| WO | WO-2013170761 A1 | 11/2013 |
| WO | WO-2014058389 A1 | 4/2014 |
| WO | WO-2014152247 A1 | 9/2014 |
| WO | WO-2015012904 A2 | 1/2015 |
| WO | WO-2015047510 A1 | 4/2015 |
| WO | WO-2015073884 A2 | 5/2015 |
| WO | WO-2015127685 A1 | 9/2015 |
| WO | WO-2015153401 A1 | 10/2015 |
| WO | WO-2016003869 A1 | 1/2016 |
| WO | WO-2016042163 A2 | 3/2016 |
| WO | WO-2016120891 A1 | 8/2016 |
| WO | WO-2018089373 A2 | 5/2018 |

OTHER PUBLICATIONS

Alperovich, A. and Younes, A., "Targeting CD30 Using Brentuximab Vedotin in the Treatment of Hodgkin Lymphoma," Cancer Journal 22(1):23-26, Lippincott Williams & Wilkins, United States (2016).

Belvisi, M.G., et al., "Preclinical Profile of Ciclesonide, a Novel Corticosteroid for the Treatment of Asthma," Journal of Pharmacology and Experimental Therapeutics 314(2):568-574, Williams and Wilkins, United States (Aug. 2005).

Berger, W.E., "Ciclesonide: A Novel Inhaled Corticosteroid for the Treatment of Persistent Asthma—A Pharmacologic and Clinical Profile," Therapy 2(2):167-178 (2005).

Bidard, F.C. and Tredan, O., "Trends in Cancer-targeted Antibody-drug Conjugates," Targeted Oncology 9(1):1-8, Springer-Verlag France, France (2014).

Bodor, N. and Buchwald, P., Corticosteroid Design for the Treatment of Asthma: Structural Insights and the Therapeutic Pharmaceutical Design 12(25):3241-3260, Bentham Science Publishers, Netherlands (2006).

Boero, S., et al., "Modulation of Human Lung Fibroblast Functions by Ciclesonide: Evidence for Its Conversion Into the Active Metabolite Desisobutyryl-ciclesonide," Immunology Letters 112(1):39-46, Elsevier/North-Holland Biomedical Press, Netherlands (2007).

Bradley, J.R., "TNF-mediated Inflammatory Disease," The Journal of Pathology 214(2):149-160, John Wiley and Sons, England (2008).

Brandish, P.E., et al., "Development of Anti-CD74 Antibody-Drug Conjugates to Target Glucocorticois to Immune Cells," Bioconjugate Chemistry (2018).

Brandt, "Steroid Chemistry and Steroid Hormone Action," Endocrine, pp. 1-18.

Breedveld, F.C., et al., "The Premier Study: A Multicenter, Randomized, Double-blind Clinical Trial of Combination Therapy With Adalimumab Plus Methotrexate Versus Methotrexate Alone or Adalimumab Alone in Patients With Early, Aggressive Rheumatoid Arthritis Who Had Not Had Previous Methotrexate Treatment," Arthritis and Rheumatism 54(1):26-37, Wiley-Blackwell, United States (2006).

Buchwald, P., "Glucocorticoid Receptor Binding: A Biphasic Dependence on Molecular Size as Revealed by the Bilinear LinBiExp Model," Steroids 73(2):193-208, Elsevier, United States (2008).

Carter, P., et al., "Humanization of an Anti-p185HER2 Antibody for Human Cancer Therapy," Proceedings of the National Academy of Sciences USA 89(10):4285-4289, National Academy of Sciences, United States (May 1992).

(56) References Cited

OTHER PUBLICATIONS

Chiang, M.J., et al., "An Fc Domain Protein-small Molecule Conjugate as an Enhanced Immunomodulator," Journal of the American Chemical Society 136(9):3370-3373, American Chemical Society, United States (2014).
Dahl, R.., "Ciclesonide for the Treatment of Asthma," Therapeutics and Clinical Risk Management 2(1):25-37, Dove Medical Press, New Zealand (2006).
Derendorf, H., "Pharmacokinetic and Pharmacodynamic Properties of Inhaled Ciclesonide," Journal of Clinical Pharmacology 47(6):782-789, Wiley, England (2007).
Domain, E., "Modifications of the Self-lmmolative Spacer PABOH in Antibody Drug Conjugates," 42 pages (2014).
Drug Bank, Certolizumab Pegol, Accession No. DB08904, Biotech, Accessed at Hyperlink "http://www.drugbank.ca/drugs/DB08904." \h http://www.drugbank.ca/drugs/DB08904.
Edman K., et al., "Ligand Binding Mechanism in Steroid Receptors: From Conserved Plasticity to Differential Evolutionary Constraints, " Structure, Dec. 2015, vol. 23 (12), pp. 2280-2290, Cambridge, Mass : Cell Press.
Elias, D.J., et al., "Phase I Clinical Comparative Study of Monoclonal Antibody KS1/4 and KS1/4-methotrexate Immunconjugate in Patients with Non-small Cell Lung Carcinoma," Cancer Research 50(13):4154-4159, American Association for Cancer Research, United States (1990).
Elkady, E.F. and Fouad, M.A., "Forced Degradation Study to Develop and Validate Stability-indicating RP-LC Method for the Determination of Ciclesonide in Bulk Drug and Metered Dose Inhalers," Talanta 87:222-229, Elsevier, Netherlands (2011).
Endo, N., et al., "Nature of Linkage and Mode of Action of Methotrexate Conjugated With Antitumor Antibodies: Implications for Future Preparation of Conjugates," Cancer Research 48(12):3330-3335, American Association for Cancer Research, United States (1988).
Eran Sella, "The Chemistry Behind Antibody-Drug Conjugation," Baran Lab Group Meeting, pp. 1-14.
Everts, M., et al., "Selective Intracellular Delivery of Dexamethasone into Activated Endothelial Cells Using an E-Selectin-Directed Immunoconjugate," The Journal of Immunology 168(2):883889, American Association of Immunologists, United States (2002).
Fried, J., et al., "Stereochemistry of Unsymmetrically Substituted 16a,17a-methylenedioxyprogesterones," Hormonal Steroids 2:15-21 (1964).
Fukase, H., "Single Dose Study of Ciclesonide in Healthy Male Volunteers: Phase I Study," Japanese Pharmacology & Therapeutics 34(11):1191-1199 (2006).
Gonzalez, D., et al., "Ciclesonide in the Management of Asthma," Clinical Medicine: Therapeutics 1:1437-1449 (2009).
Graversen, J.H. and Moestrup, S.K., "Drug Trafficking into Macrophages via the Endocytotic Receptor CD163," Membranes 5(2):228-252, MDPI Publishing, Switzerland (2015).
Graversen, J.H., et al., "Targeting the Hemoglobin Scavenger Receptor CD163 in Macrophages Highly Increases the Anti-inflammatory Potency of Dexamethasone," Molecular Therapy 20(8):1550-1558, Cell Press, United States (2012).
Hamblett, K.J., et al., "Effects of Drug Loading on the Antitumor Activity of a Monoclonal Antibody Drug Conjugate," Clinical Cancer Research 10(20):7063-7070, American Association for Cancer Research, United States (2004).
Jain, N., et al., "Current ADC Linker Chemistry," Pharmaceutical Research 32(11):3526-3540, Kluwer Academic/Plenum Publishers, United States (2015).
Kern, J.C., et al., "Discovery of Pyrophosphate Diesters as Tunable, Soluble, and Bioorthogonal Linkers for Site-Specific Antibody-Drug Conjugates," Journal of the American Chemical Society 138(4)1 430-1445, American Chemical Society, United States (2016).
Kroszczynski, W., et al., "Effective High-pressure Cleavage of Sterically Hindered Steroid Esters," Helvetica Chimica Acta 87(6):1488-1492 (2004).

Kvirkvelia, N., et al., "Human Anti-a3(IV)NC1 Antibody Drug Conjugates Target Glomeruli to Resolve Nephritis," American Journal of Physiology Renal Physiology 309(8):F680-F684, American Physiological Society, United States (2015).
Levin, A.D., et al., "Mechanism of Action of Anti-TNF Therapy in Inflammatory Bowel Disease," Journal of Crohn's and Colitis 10(8):989-997, Oxford University Press, England (2016).
Lin, J., et al., "TNFalpha Blockade in Human Diseases: An Overview of Efficacy and Safety," Clinical Immunology 126(1):13-30, Academic Press, United States (2008).
Lyon, R.P., et al., "Self-hydrolyzing Maleimides Improve the Stability and Pharmacological Properties of Antibody-drug Conjugates," Nature Biotechnology 32(10):1059-1065, Nature America Publishing, United States (2014).
Mack, F., et al., "The Next Generation of Antibody Drug Conjugates," Seminars in Oncology 41(5):637-652, W.B. Saunders, United States (2014).
Majumdar, S., et al., "MTX-cIBR Conjugate for Targeting Methotrexate to Leukocytes: Conjugate Stability and in vivo Efficacy in Suppressing Rheumatoid Arthritis," Journal of Pharmaceutical Sciences 101(9):3275-3291, Elsevier, United States (2012).
Mark et al., Proceedings of the National Academy of Sciences, USA 81:5662-5666 (1984).
Mars, U., et al., "Tissue Accumulation Kinetics of Ciclesonide-Active Metabolite and Budesonide in Mice," Basic and Clinical Pharmacology and Toxicology112(6):401-411,Blackwell, England (Jun. 2013).
Mascher, H.J., et al., "Sensitive Simultaneous Determination of Ciclesonide, Ciclesonide-m1-metabolite and Fluticasone Propionate in Human Serum by HPLC-MS/MS with APPI," Journal of Chromatography. B, Analytical Technologies in the Biomedical and Life Sciences 869(12):84-92, Elsevier, Netherlands (2008).
McRae, B.L., et al., "Fc Receptor-mediated Effector Function Contributes to the Therapeutic Response of Anti-TNF Monoclonal Antibodies in a Mouse Model of Inflammatory Bowel Disease," Journal of Crohn's & Colitis 10(1):69-76, Oxford University Press, England (2016).
Millan, D.S., et al., "Design and Synthesis of Long Acting Inhaled Corticosteroids for the Treatment of Asthma," Bioorganic & Medicinal Chemistry Letters 21(19):5826-5830, Elsevier Science Ltd, England (2011).
Mok, C.C., et al., "Immunogenicity of Anti-TNF Biologic Agents in the Treatment of Rheumatoid Arthritis," Expert Opinion on Biological Therapy 16(2):201-211, Taylor & Francis, England (2016).
Moller, L.N., et al., "Anti-CD163-dexamethasone Protects Against Apoptosis After Ischemia/reperfusion Injuries in the Rat Liver," Annals of Medicine and Surgery 4(4):331-337, Elsevier, England (2015).
Moore, A.R., et al., "Collagen II Antibody-induced Arthritis in Tg1278TNFko Mice: Optimization of a Novel Model to Assess Treatments Targeting Human TNFa in Rheumatoid Arthritis," Journal of Translational Medicine 12(1):285, BioMed Central, England (2014).
Nave, R., et al., "Pharmacokinetics of [14C]ciclesonide After Oral and Intravenous Administration to Healthy Subjects," Clinical Pharmacokinetics 43(7):479-486, ADIS Press, Switzerland (2004).
Nave, R., et al., "Safety, Tolerability, and Exposure of Ciclesonide Nasal Spray in Healthy and Asymptomatic Subjects With Seasonal Allergic Rhinitis," Journal of Clinical Pharmacology 46(4):461-467, Wiley, England (2006).
Neffen, H. And Wingertzahn, M.A., "Ciclesonide, A Hypotonic Intranasal Corticosteroid,"Allergy and Asthma Proceedings 31(1):S29-S37, OceanSide Publications, United States (2010).
Nolting, B., "Linker Technologies for Antibody-Drug Conjugates," Methods in Molecular Biology 1045:71-100, Humana Press, United States (2013).
Panowski, S., et al., "Site-specific Antibody Drug Conjugates for Cancer Therapy," mAbs 6(1):34-45, Taylor & Francis, United States (2014).
Perez, C., et al., "A Nonsecretable Cell Surface Mutant of Tumor Necrosis Factor (TNF) Kills by Cell-to-cell Contact," CELL 63(2):251-258, Cell Press, United States (1990).

(56) References Cited

OTHER PUBLICATIONS

Pietersz, G.A., et al., "Specific in Vitro Anti-tumour Activity of Methotrexate-monoclonal Antibody Conjugates Prepared Using Human Serum Albumin as an Intermediary," Immunology and Cell Biology 66(Pt 1):43-49, Nature Publishing Group, England (1988).

Ritchie, M., et al., "Implications of Receptor-mediated Endocytosis and Intracellular Trafficking Dynamics in the Development of Antibody Drug Conjugates," mAbs 5(1):13-21, Taylor & Francis, United States (2013).

Rosen, J. and Miner, J.N., "The Search for Safer Glucocorticoid Receptor Ligands," Endocrine Reviews 26(3):452-464, Oxford University Press, United States (2005).

Schacke, H., et al., "Mechanisms Involved in the Side Effects of Glucocorticoids," Pharmacology & Therapeutics 96(1):23-43, Pergamon Press, England (2002).

Shen, B.Q., et al., "Conjugation Site Modulates the in Vivo Stability and Therapeutic Activity of Antibody-Drug Conjugates," Nature Biotechnology 30(2):184-189, Nature America Publishing, United States (2012).

Shin, J.M., et al., "Hyaluronic Acid-methotrexate Conjugate for Targeted Therapy of Rheumatoid Arthritis," Revised Electronic Supplementary Information for Chemical Communications, 13 pages (2014).

Stoeck, M., et al., "In Vitro and In Vivo Anti-Inflammatory Activity of the New Glucocorticoid Ciclesonide," Journal of Pharmacology and Experimental Therapeutics 309(1):249-258, Williams & Wilkins, United States(Apr. 2004).

Storz, U., "Antibody-drug Conjugates: Intellectual Property Considerations," mAbs 7(6):989-1009, Taylor and Francis, United States (2015).

Tumey, L.N., et al., "Mild Method for Succinimide Hydrolysis on ADSs: Impact on ADC Potency, Stability, Exposure, and Efficacy," Bioconjugate Chemistry 25(10):1871-1880, American Chemical Society, United States (2014).

Wei, C., et al., "Where Did the Linker-Payload Go? A Quantitative Investigation on the Destination of the Released Linker-Payload from an Antibody-Drug Conjugate with a Maleimide Linker in Plasma," Analytical Chemistry 88(9):4979-4986, American Chemical Society, United States (2016).

Yao, H., et al., "Methods to Design and Synthesize Antibody-Drug Conjugates (ADCs)," International Journal of Molecular Sciences 17(2):16 pages, MDPI, Switzerland (2016).

Verma, et al., "The cryptophycins as potent payloads for antibody drug conjugates," Bioorganic & Medicinal Chemistry Letters 25(4): 864-868 (2015).

Gébleux, et al., "Antibody-drug conjugates: Current status and future perspectives," Pharmacology & Therapeutics 167:48-59 (2016).

Rivkin, "Certolizumab Pegol for the Management of Crohn's Disease in Adults," Clinical Therapeutics 31 (6):1158-1176 (2009).

Sau, et al., "Cationic lipid-conjugated dexamethasone as a selective antitumor agent," European Journal of Medicinal Chemistry 83:433-447 (2014).

* cited by examiner

US 10,668,167 B2

GLUCOCORTICOID RECEPTOR AGONIST AND IMMUNOCONJUGATES THEREOF

RELATED APPLICATIONS

This application is a divisional application of application Ser. No. 15/611,037 filed on Jun. 1, 2017 which claims priority to U.S. Provisional Application No. 62/344,948, filed Jun. 2, 2016, and U.S. Provisional Application No. 62/371,134, filed Aug. 4, 2016, all of which are herein incorporated by reference in their entirety.

REFERENCE TO A SEQUENCE LISTING SUBMITTED ELECTRONICALLY VIA EFS-WEB

The instant application contains a Sequence Listing which has been submitted electronically in ASCII format via EFS-Web and is hereby incorporated by reference in its entirety. Said ASCII copy, created on May 10, 2019, is named ABV12265USD1 SL .txt and is 95,247 bytes in size.

FIELD OF THE INVENTION

The field of the invention generally relates to glucocorticoid receptor agonist immunoconjugates, and methods of making and using the same, e.g., to treat autoimmune or inflammatory diseases.

BACKGROUND OF THE INVENTION

Tumor Necrosis Factor alpha (TNFa) plays a central role in the pathophysiology of several human disorders, and anti-TNFa agents (e.g., adalimumab, etanercept, and infliximab) have clinically validated therapeutic utility in the treatment of autoimmune and inflammatory disorders, such as rheumatoid arthritis, psoriasis and inflammatory bowel disease. Despite their success in the clinic, anti-TNFa biologics are still limited in the maximal efficacy they can achieve in patients, necessitating the identification and development of more potent and effective therapeutics. Patients treated with anti-TNFa biologics may also develop an immunogenic response to the therapeutic thus limiting its effectiveness. Therefore anti-TNFa therapies with lower immunogenicity and high efficacy would be useful for further controlling disease.

Synthetic glucocorticoid receptor agonists (e.g., dexamethasone, prednisolone, and budesonide) are a potent class of small molecules used in the treatment of inflammatory disorders, but their utility in the chronic treatment of disease is limited due to severe side effects. Several approaches to retain the anti-inflammatory efficacy of synthetic glucocorticoids while sparing the unwanted toxicities have been described (Rosen, J and Miner, J N Endocrine Reviews 26: 452-64 (2005)). However these methodologies have met with little success. There is a need in the field of autoimmune and inflammatory disease therapeutics to develop therapeutics with enhanced efficacy and longer duration of action compared to anti-TNF antibodies and with minimal unwanted effects.

BRIEF SUMMARY OF THE INVENTION

In one aspect, the present disclosure provides a glucocorticoid receptor agonist immunoconjugate represented by Formulae I-a and I-b, below, and the pharmaceutically acceptable salts, solvates, or prodrugs thereof. In another aspect, the present disclosure provides a glucocorticoid receptor agonist immunoconjugate represented by Formulae I-a and I-b, below. Glucocorticoid receptor agonist immunoconjugates having Formulae I-a and I-b are useful for treating autoimmune diseases such as, but not limited to, rheumatoid arthritis, juvenile idiopathic arthritis, psoriatic arthritis, ankylosing spondylitis, adult Crohn's disease, pediatric Crohn's disease, ulcerative colitis, plaque psoriasis, hidradenitis suppurativa, uveitis, Behcets disease, a spondyloarthropathy, or psoriasis. In one aspect, glucocorticoid receptor agonist immunoconjugates having Formulae I-a and I-b are useful for treating rheumatoid arthritis. In one aspect, glucocorticoid receptor agonist immunoconjugates having Formulae I-a and I-b are useful for treating juvenile idiopathic arthritis. In one aspect, glucocorticoid receptor agonist immunoconjugates having Formulae I-a and I-b are useful for treating psoriatic arthritis. In one aspect, glucocorticoid receptor agonist immunoconjugates having Formulae I-a and I-b are useful for treating ankylosing spondylitis. In one aspect, glucocorticoid receptor agonist immunoconjugates having Formulae I-a and I-b are useful for treating adult Crohn's disease. In one aspect, glucocorticoid receptor agonist immunoconjugates having Formulae I-a and I-b are useful for treating pediatric Crohn's disease. In one aspect, glucocorticoid receptor agonist immunoconjugates having Formulae I-a and I-b are useful for treating ulcerative colitis. In one aspect, glucocorticoid receptor agonist immunoconjugates having Formulae I-a and I-b are useful for treating plaque psoriasis. In one aspect, glucocorticoid receptor agonist immunoconjugates having Formulae I-a and I-b are useful for treating hidradenitis suppurativa. In one aspect, glucocorticoid receptor agonist immunoconjugates having Formulae I-a and I-b are useful for treating uveitis. In one aspect, glucocorticoid receptor agonist immunoconjugates having Formulae I-a and I-b are useful for treating Behcets disease. In one aspect, glucocorticoid receptor agonist immunoconjugates having Formulae I-a and I-b are useful for treating a spondyloarthropathy. In one aspect, glucocorticoid receptor agonist immunoconjugates having Formulae I-a and I-b are useful for treating psoriasis.

In another aspect, the present disclosure provides a glucocorticoid receptor agonist represented by Formulae VII, VII-A, VII-B, VIII, VIII-a, VIII-b, IX, IX-a, and IX-b, or by Formulae VII', VII-A', VII-B', VIII', VIII-a', VIII-b', IX', IX-a', IX-b', VII", VII-A", VII-B", VIII", VIII-a", VIII-b", IX", IX-a", and IX-b", below, (wherein $R^{7b}$ is hydrogen) and the pharmaceutically acceptable salts, solvates, or prodrugs thereof. In another aspect, the present disclosure provides a glucocorticoid receptor agonist represented by Formulae VII, VII-A, VII-B, VIII, VIII-a, VIII-b, IX, IX-a, and IX-b, or by Formulae VII', VII-A', VII-B', VIII', VIII-a', VIII-b', IX', IX-a', IX-b', VII", VII-A", VII-B", VIII", VIII-a", VIII-b", IX", IX-a", and IX-b", below, (wherein $R^{7b}$ is hydrogen). Compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII", VII-A", VII-B", VIII", VIII-a", VIII-b", IX", IX-a", and IX-b", are useful for treating autoimmune diseases such as, but not limited to, rheumatoid arthritis, juvenile idiopathic arthritis, psoriatic arthritis, ankylosing spondylitis, adult Crohn's disease, pediatric Crohn's disease, ulcerative colitis, plaque psoriasis, hidradenitis suppurativa, uveitis, Behcets disease, a spondyloarthropathy, or psoriasis. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII", VII-A", VII-B", VIII", VIII-a", VIII-b", IX", IX-a", and IX-b", are useful for treating rheumatoid arthritis. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating juvenile idiopathic arthritis. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating psoriatic arthritis. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating ankylosing spondylitis. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating adult Crohn's disease. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating pediatric Crohn's disease. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating ulcerative colitis. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating plaque psoriasis. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating hidradenitis suppurativa. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating uveitis. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating Behcets disease. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating a spondyloarthropathy. In one aspect, compounds having Formulae VII, VII-A, VII-B, VIII, VIII-a, VIII-b, IX, IX-a, and IX-b, or Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', are useful for treating psoriasis.

In another aspect, the present disclosure provides compounds represented by Formulae VII, VII-A, VII-B, VIII, VIII-a, VIII-b, IX, IX-a, and IX-b, or by Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', as synthetic intermediates that can be used to prepare glucocorticoid receptor agonist immunoconjugates having Formulae I-a and I-b.

In another aspect, the present disclosure provides a pharmaceutical composition comprising a glucocorticoid receptor agonist immunoconjugate represented by Formulae I-a and I-b, or a glucocorticoid receptor agonist represented by Formulae VII, VII-A, VII-B, VIII, VIII-a, VIII-b, IX, IX-a, and IX-b, or by Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', and an excipient and/or a pharmaceutically acceptable carrier.

In another aspect, the present disclosure provides a glucocorticoid receptor agonist immunoconjugate represented by Formulae I-a and I-b, or a glucocorticoid receptor agonist represented by Formulae VII, VII-A, VII-B, VIII, VIII-a, VIII-b, IX, IX-a, and IX-b or by Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', for use in treatment of autoimmune diseases.

In another aspect, the present disclosure provides a use of a glucocorticoid receptor agonist immunoconjugates represented by Formulae I-a and I-b, or a glucocorticoid receptor agonist represented by Formulae VII, VII-A, VII-B, VIII, VIII-a, VIII-b, IX, IX-a, and IX-b, or by Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', and IX-b'', for the manufacture of a medicament for treating autoimmune diseases.

In another aspect, the present disclosure provides methods of preparing glucocorticoid receptor agonist immunoconjugates represented by Formulae I-a and I-b.

BRIEF DESCRIPTION OF THE DRAWINGS/FIGURES

Figure 5:
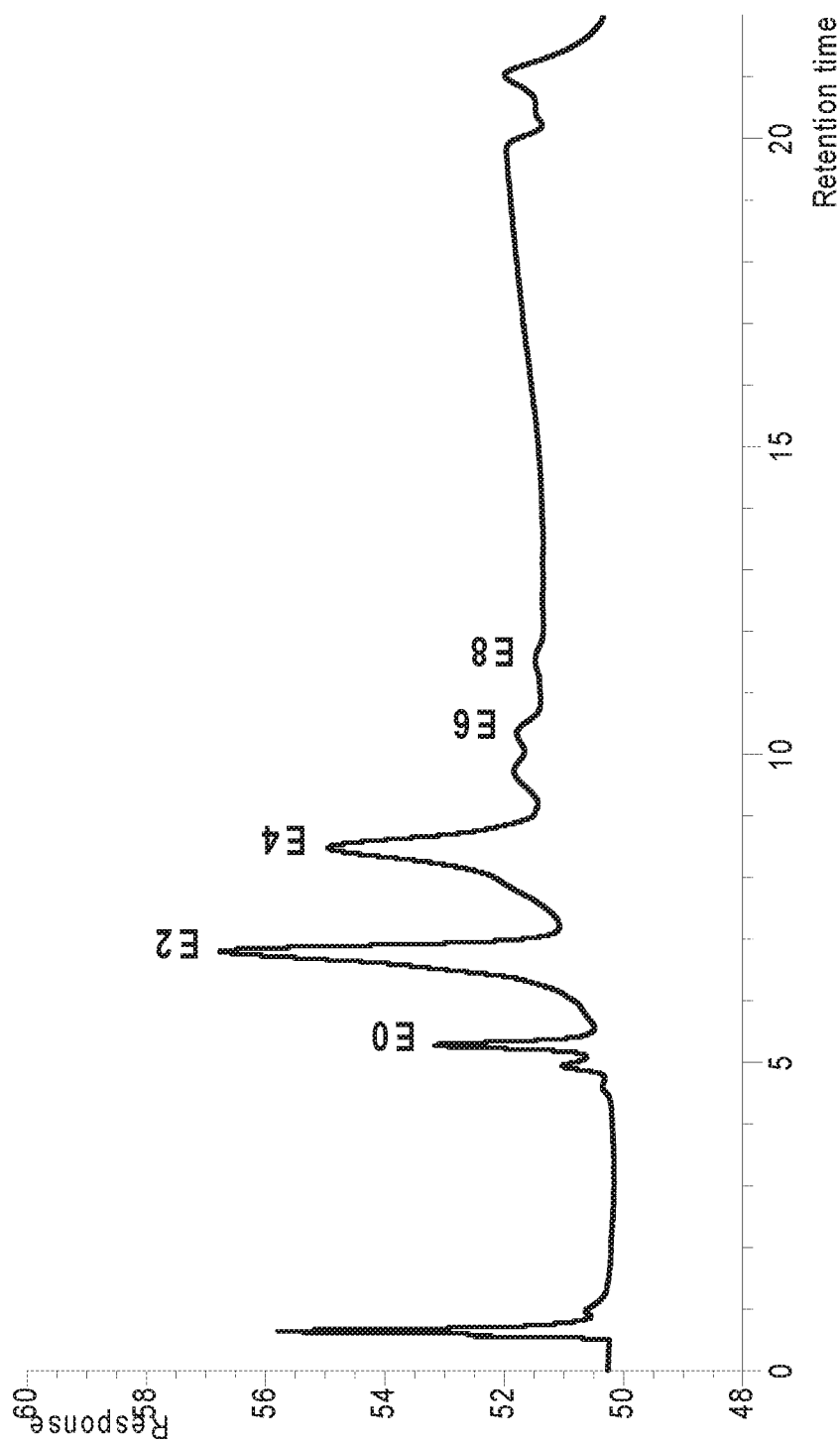

FIG. 5 is a HIC chromatogram showing a heterogenous mixture containing antibodies having zero SM-L-Q- molecules attached ("E0" peak), two SM-L-Q- molecules attached ("E2" peak), four SM-L-Q- molecules attached ("E4" peak), SM-L-Q- moieties attached ("E6" peak), and eight SM-L-Q-molecules attached ("E8" peak), depending upon the number of interchain disulfide bonds that have been reduced. (SM is a radical of a glucocorticosteroid; L is a linker, and Q is a heterobifunctional group or heterotrifunctional group; or Q is absent.) (See Example 74.)

Figure 6:
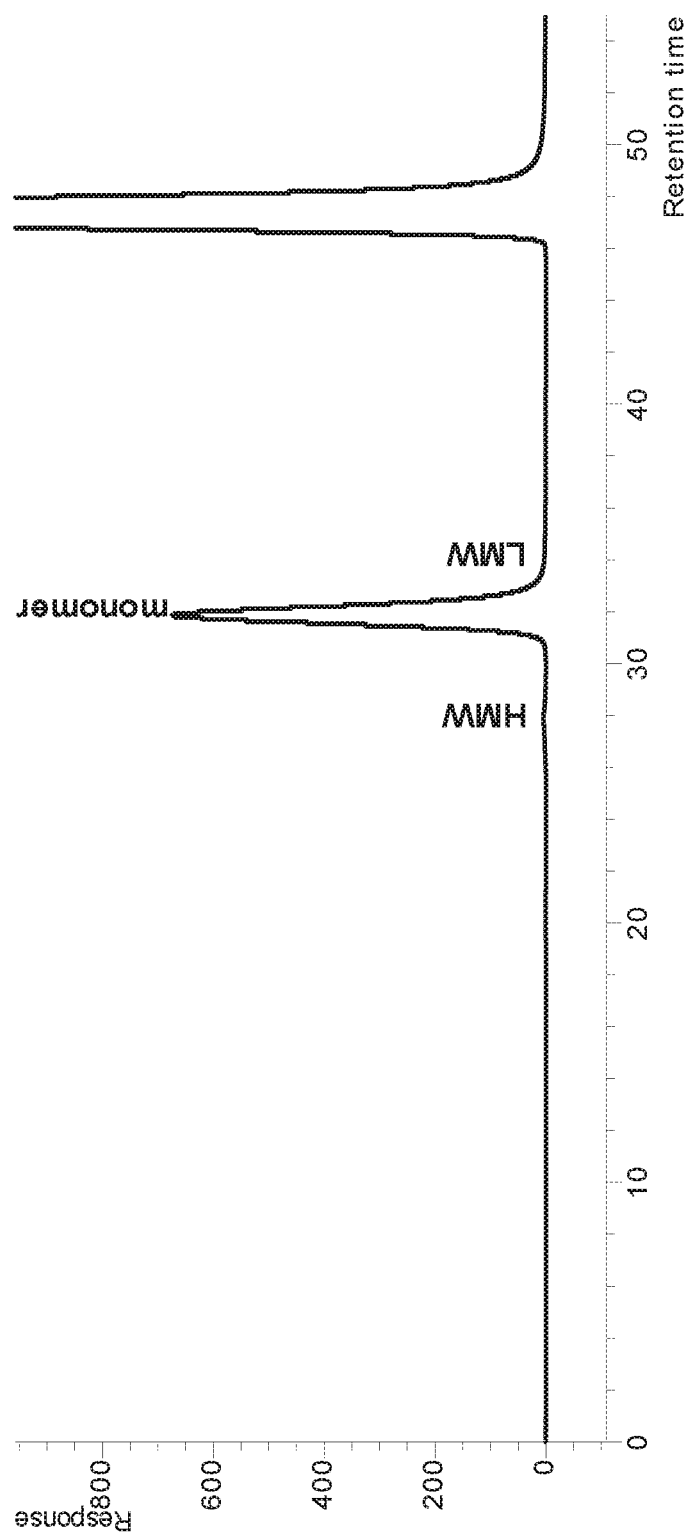

FIG. 6 is a SEC chromatogram of adalimumab conjugated with a glucocorticosteroid. (See Example 74.)

Figure 7:
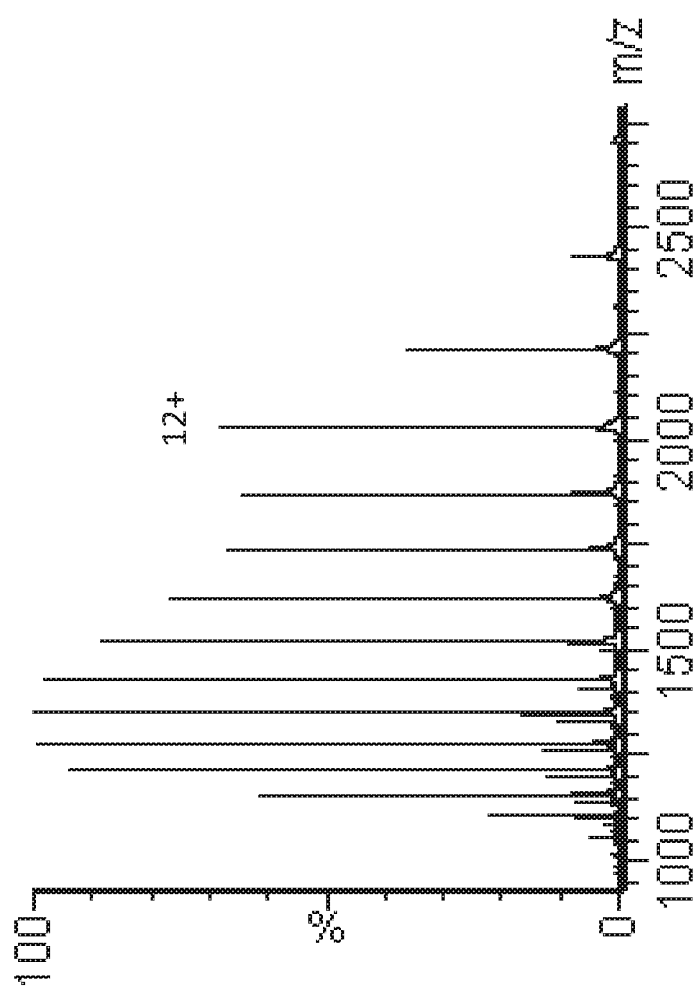

FIG. 7 is a line graph showing raw MS data of adalimumab conjugated with a glucocorticosteroid. (See Example 74.)

Figure 8:
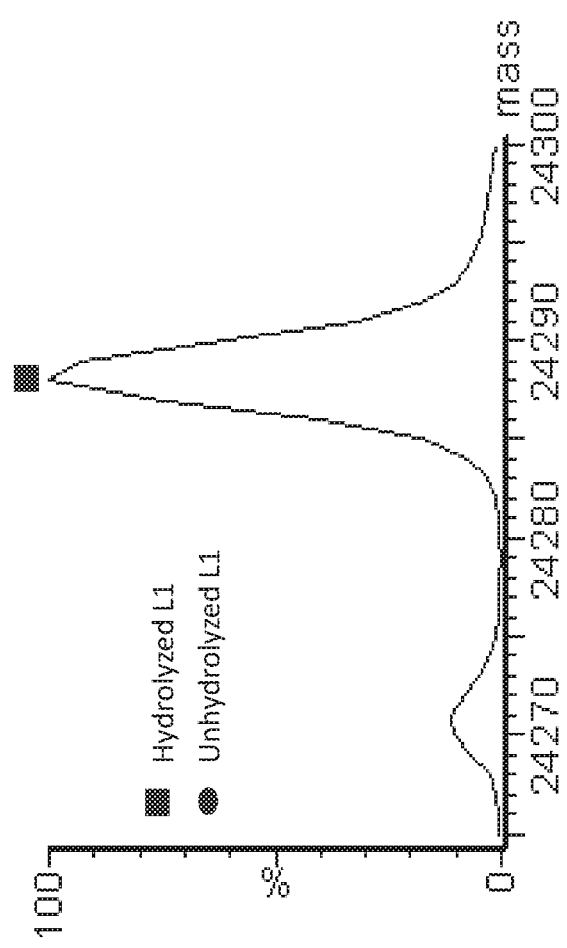

FIG. 8 is a line graph showing deconvoluted MS data of adalimumab conjugated with a glucocorticosteroid. Black square and circle represent the ADC with succinimide hydrolyzed and unhydrolyzed, respectively. The relative abundance of hydrolyzed and unhydrolyzed ADC is used to determine hydrolysis conversion. (See Example 74.)

Figure 9:
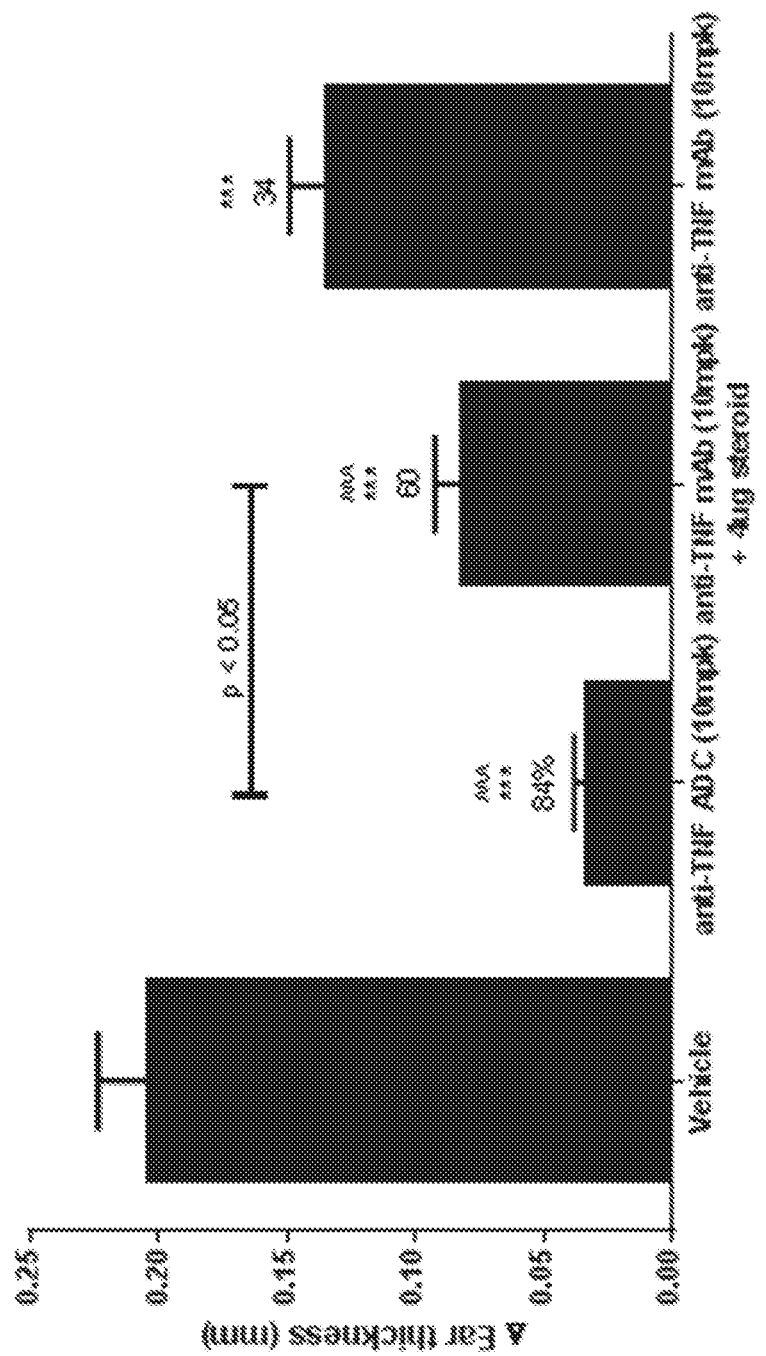

FIG. 9 shows that an anti-TNF steroid ADC is significantly more effective in reducing ear inflammation in mice than the concurrent combination of the anti-TNF antibody and the steroid or than the anti-TNF antibody alone. (See Example 84.)

Figure 10:
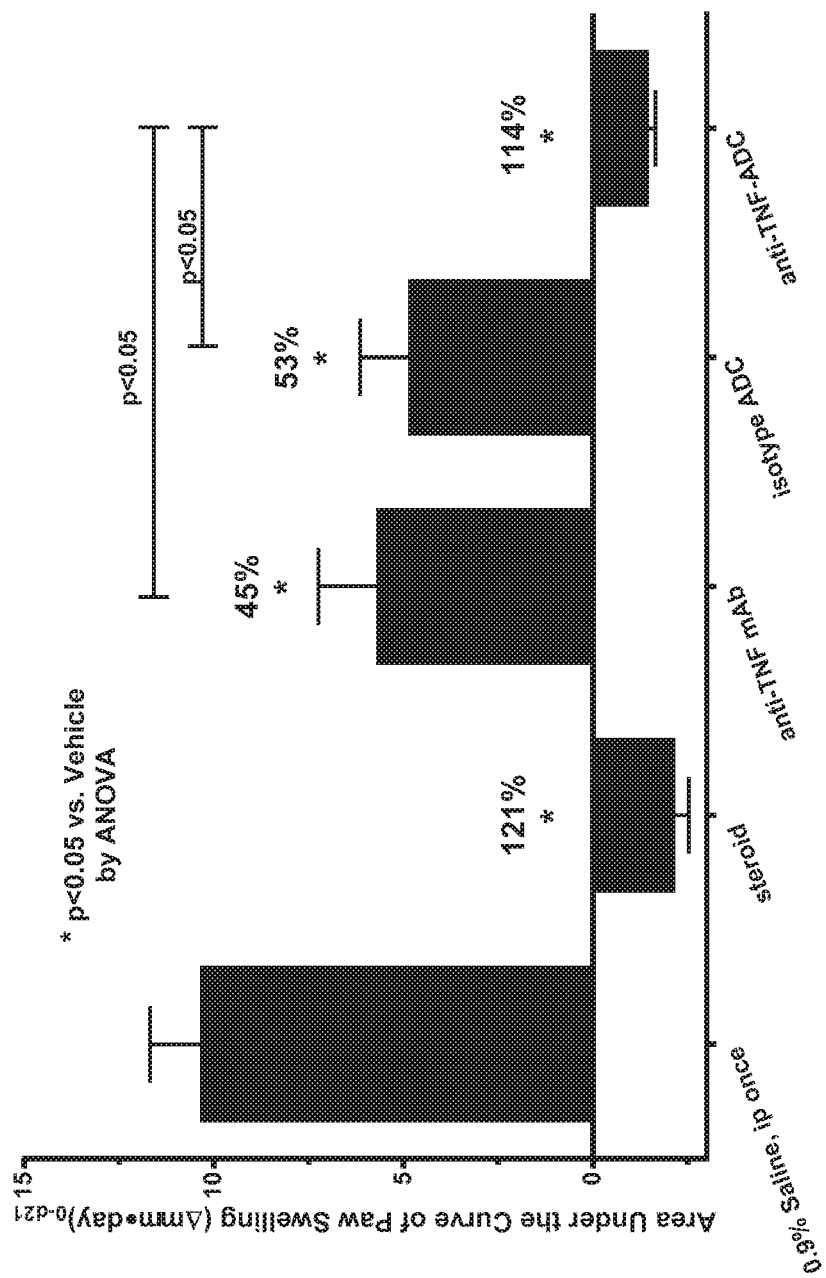

FIG. 10 shows that a single dose of an anti-TNF steroid ADC is as effective in reducing paw swelling as 21 days of daily dosing of a steroid. (See Example 85.)

Figure 11:
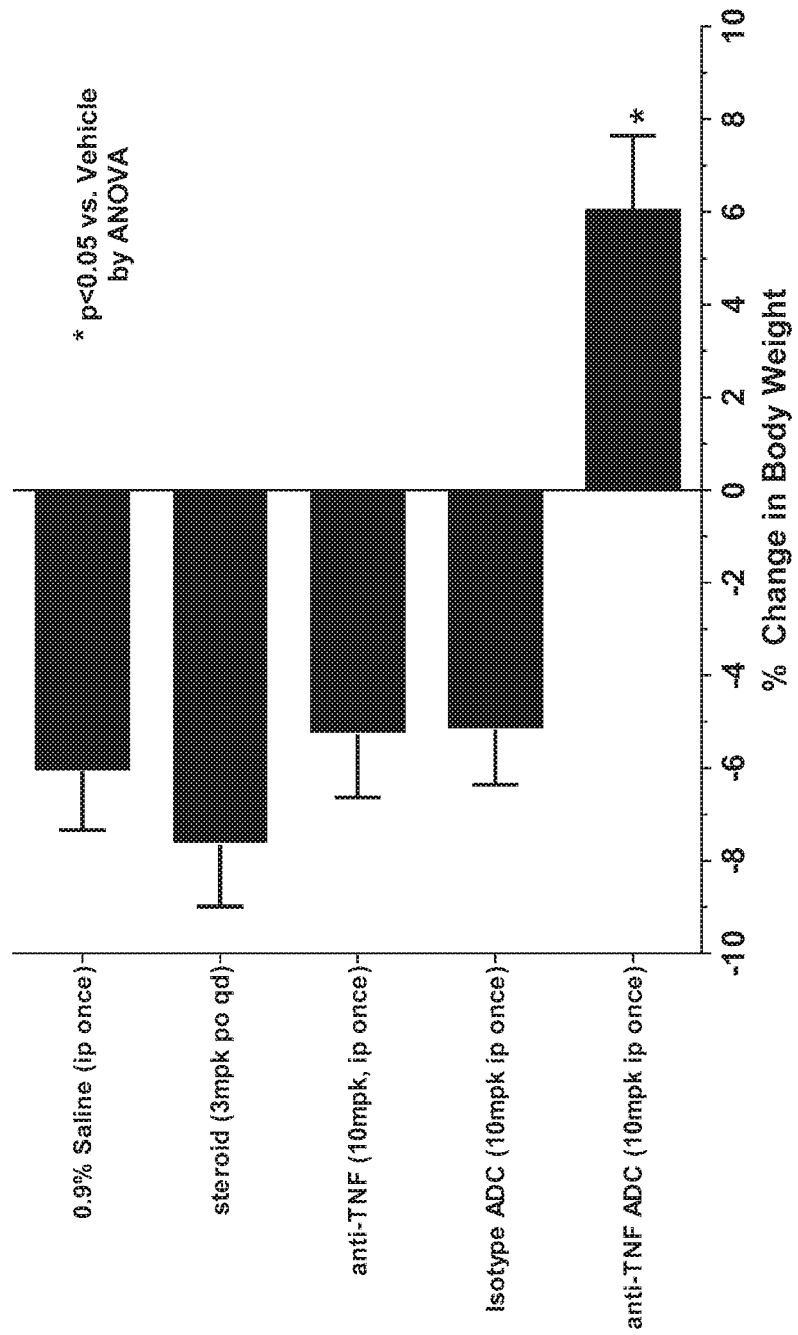

FIG. 11 shows the change in weights of animals treated with steroid, an anti-TNF antibody, an anti-TNF ADC, or an isotype ADC. (See Example 85.)

Figure 12:
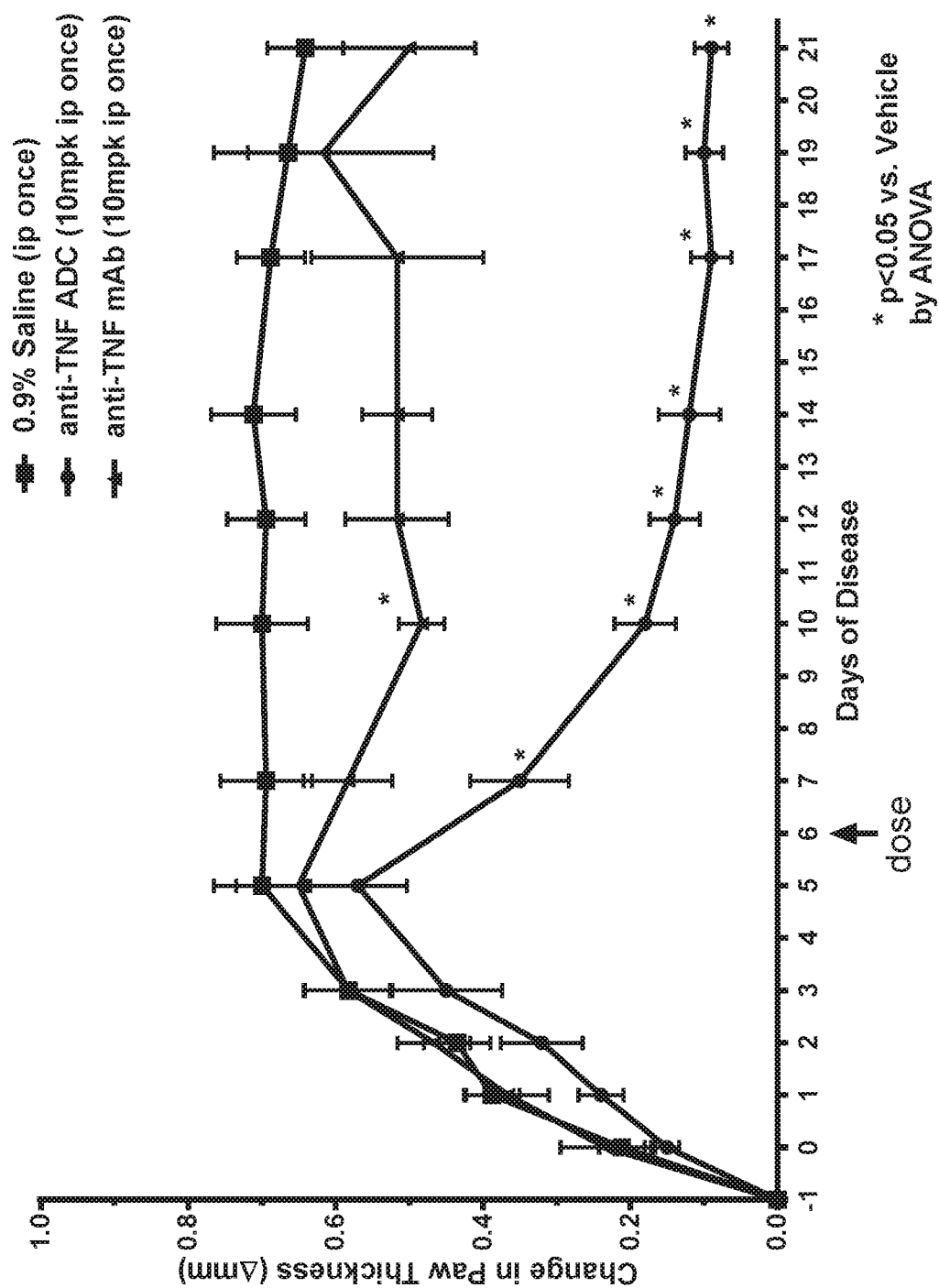

FIG. 12 shows that a single dose of an anti-TNF steroid ADC can reduce established paw swelling, whereas a single dose of an anti-TNF antibody had a minimal effect. (See Example 88.)

Figure 13:
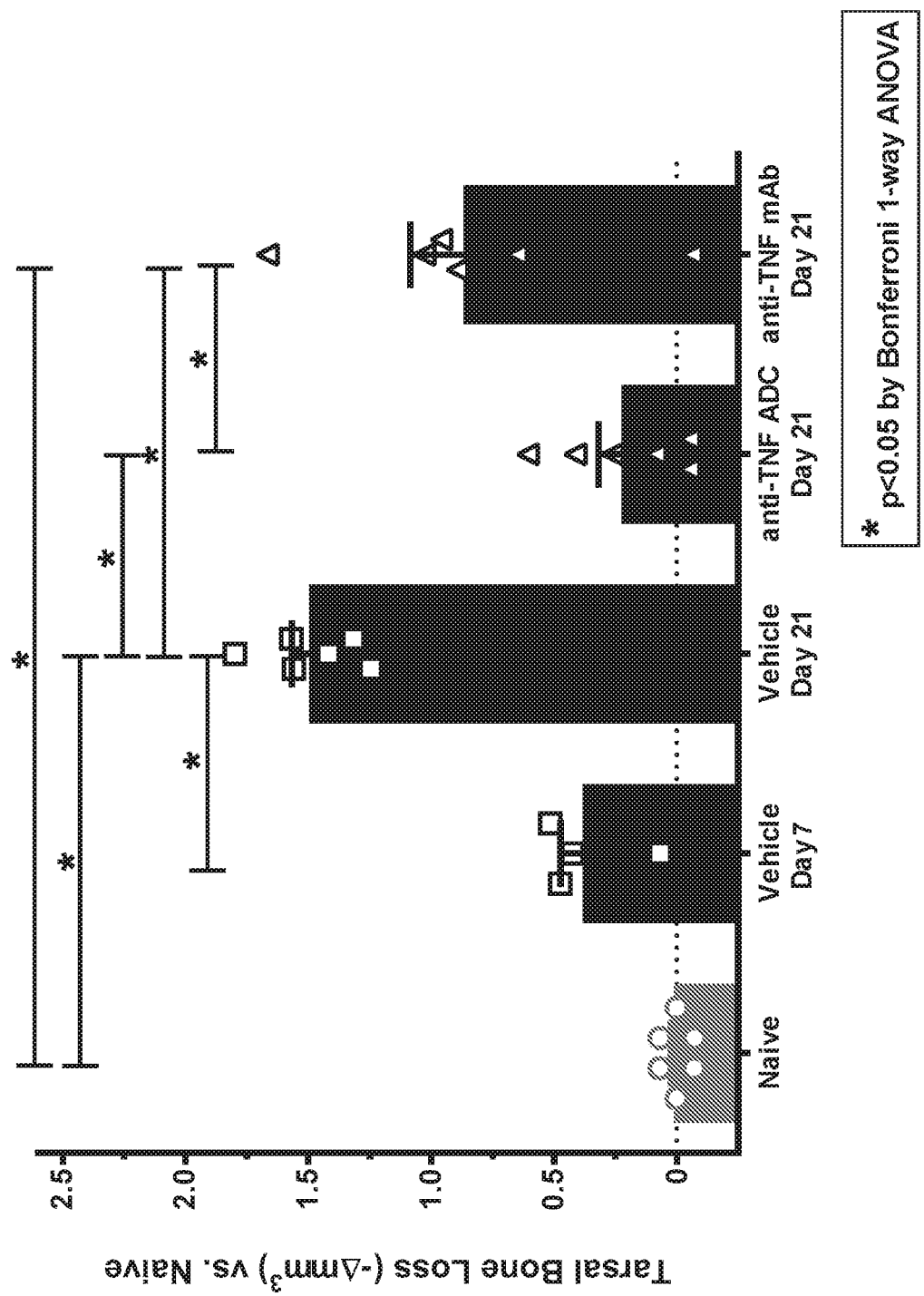

FIG. 13 shows the effect of treatment with an anti-TNF steroid ADC on tarsal bone loss as measured by Micro-Computed Tomography (μCT). (The individual data points (e.g., circles, squares, or triangles) represent individual animals.) (See Example 88.)

Figure 14:
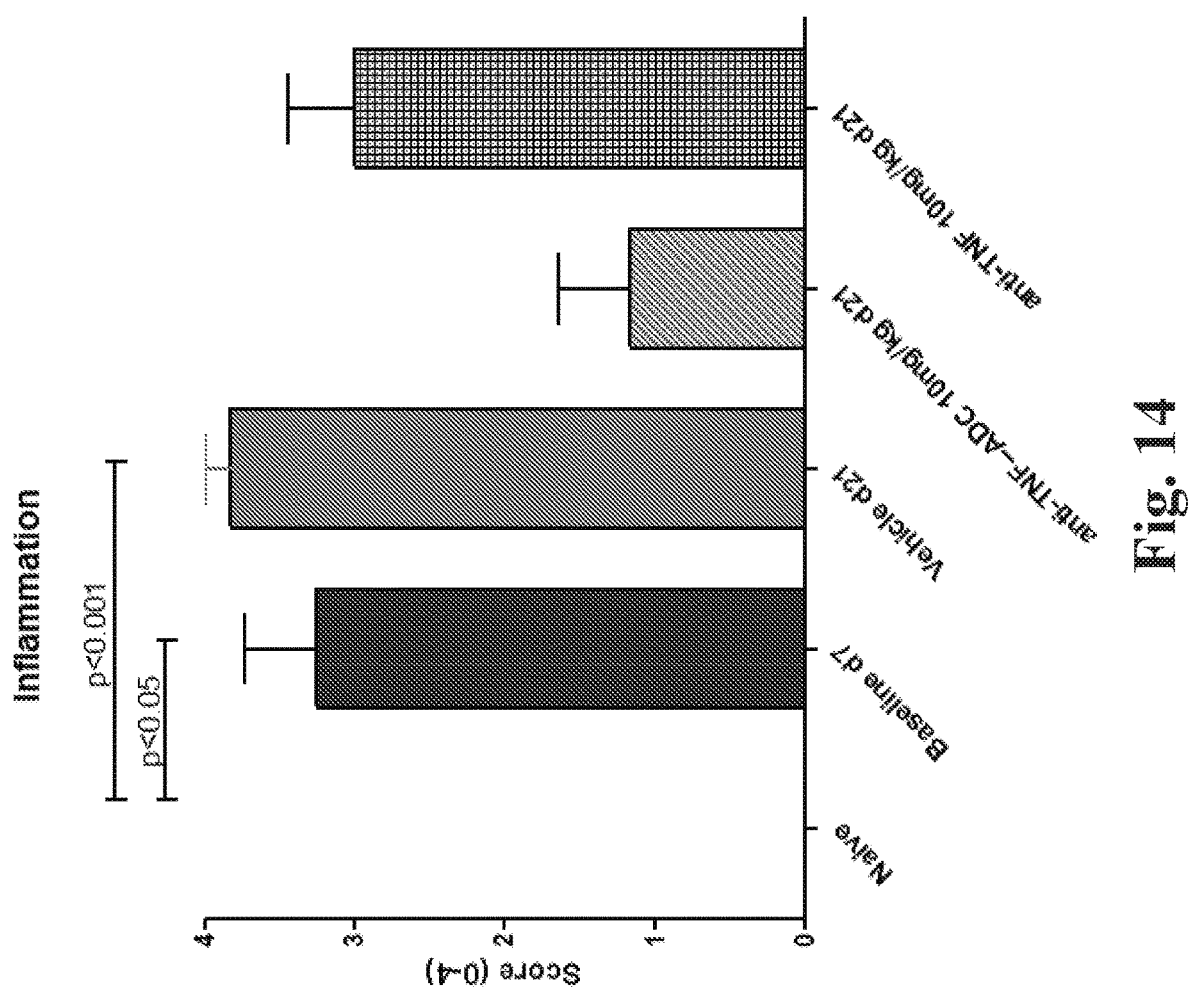

FIG. 14 shows the effect of treatment with an anti-TNF steroid ADC on inflammation. (The individual data points (e.g., circles, squares, or triangles) represent individual animals.) (See Example 88.)

Figure 15:
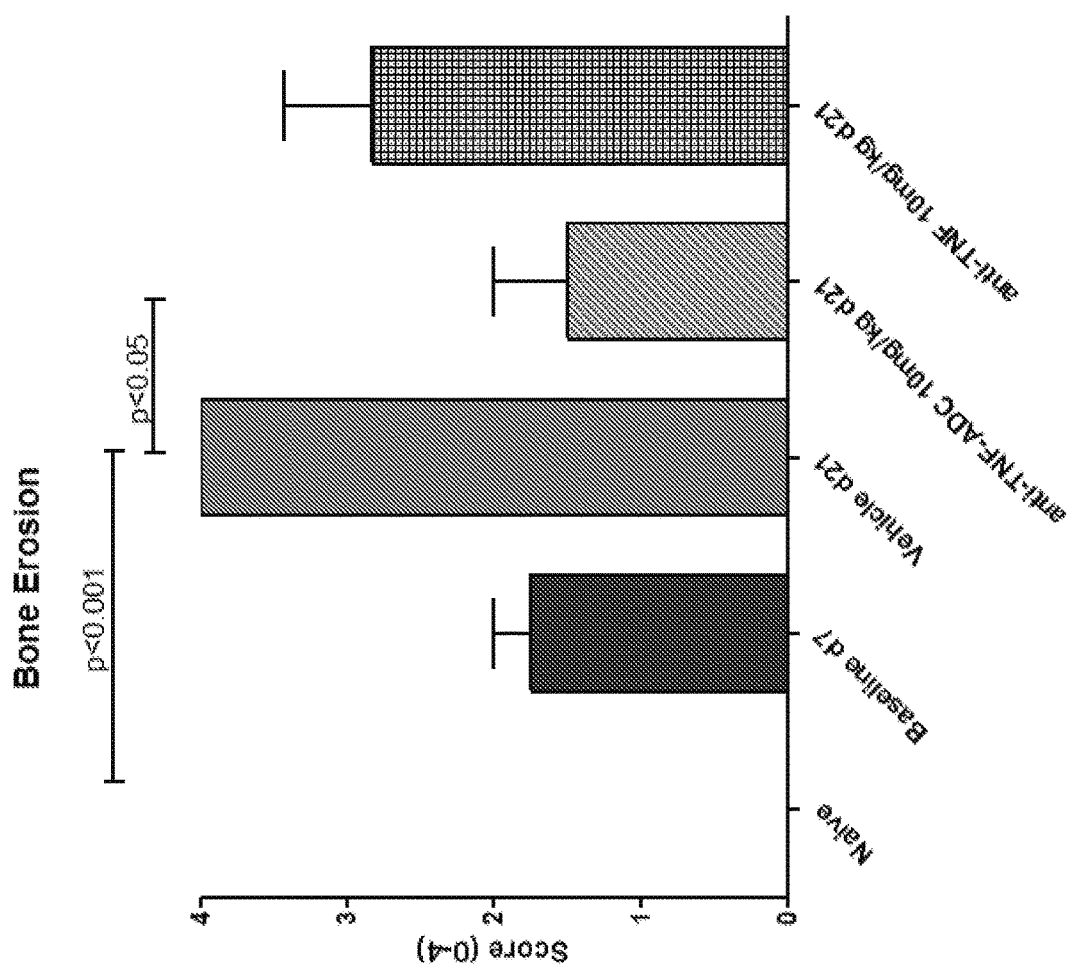

FIG. 15 shows the effect of treatment with an anti-TNF steroid ADC on pannus formation. (The individual data points (e.g., circles, squares, or triangles) represent individual animals.) (See Example 88.)

Figure 16:
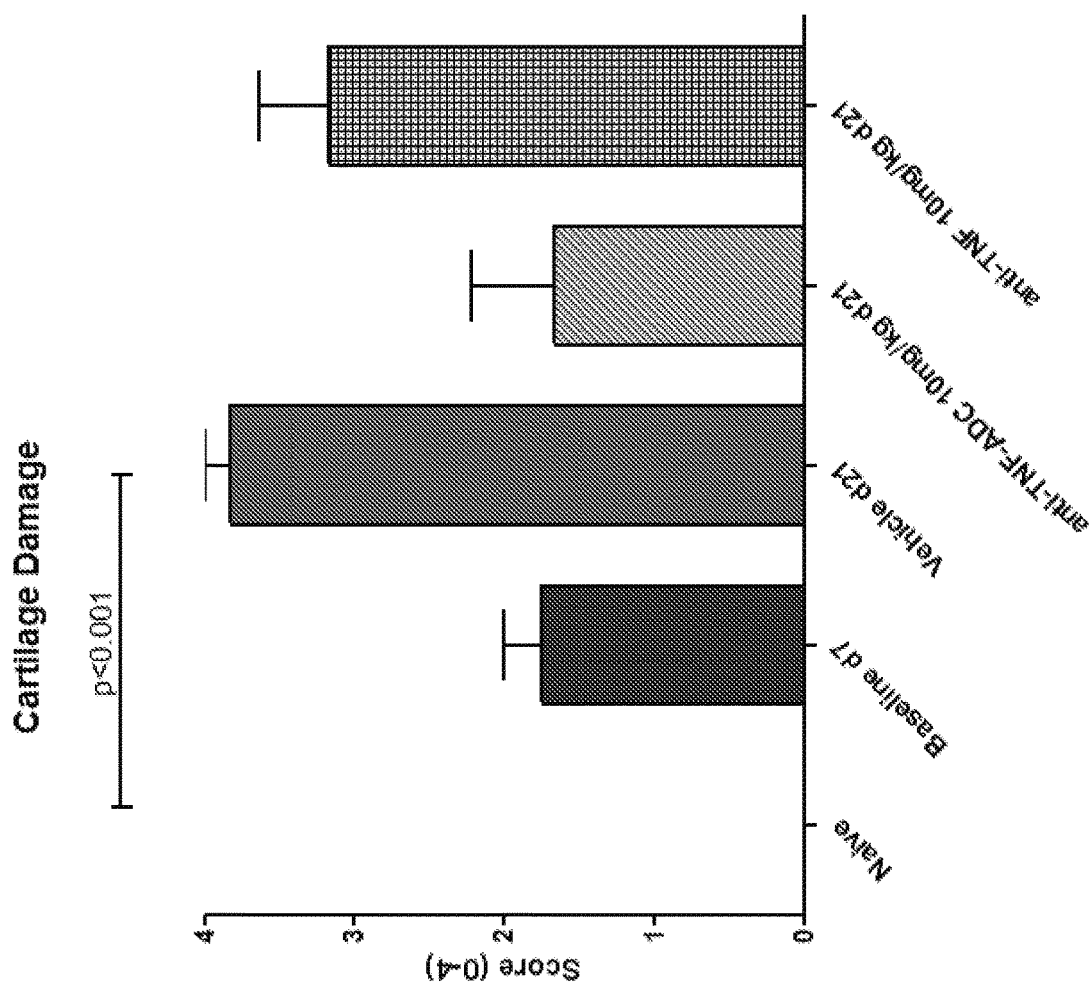

FIG. 16 shows the effect of treatment with an anti-TNF steroid ADC on bone erosion. (The individual data points (e.g., circles, squares, or triangles) represent individual animals.) (See Example 88.)

Figure 17:
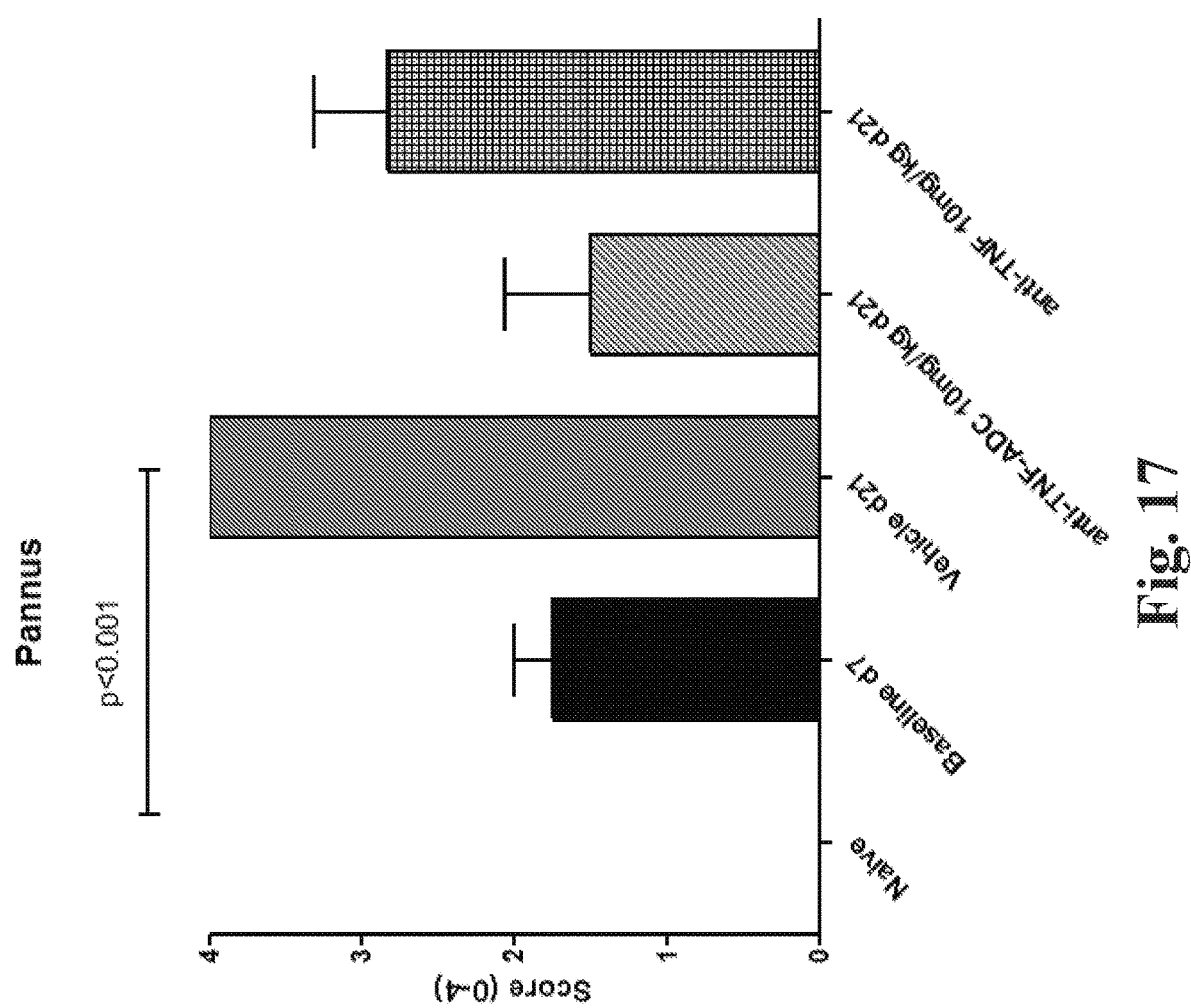

FIG. 17 shows the effect of treatment with an anti-TNF steroid ADC on cartilage damage. (The individual data points (e.g., circles, squares, or triangles) represent individual animals.) (See Example 88.)

Figure 18:
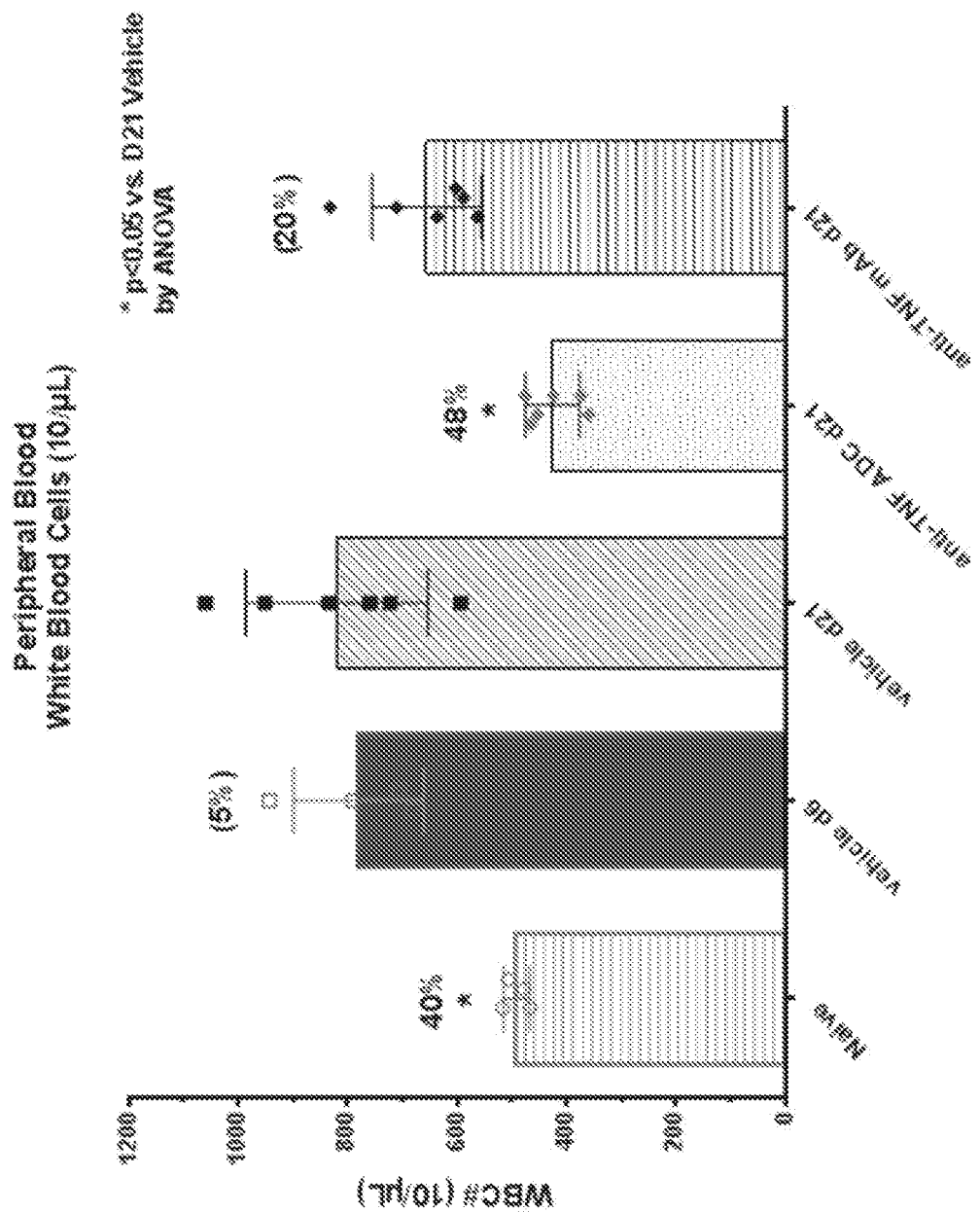

FIG. 18 shows effect of treatment with an anti-TNF steroid ADC on white blood cells in peripheral blood. (The individual data points (e.g., circles, squares, or diamonds) represent individual animals.) (See Example 88.)

Figure 19:
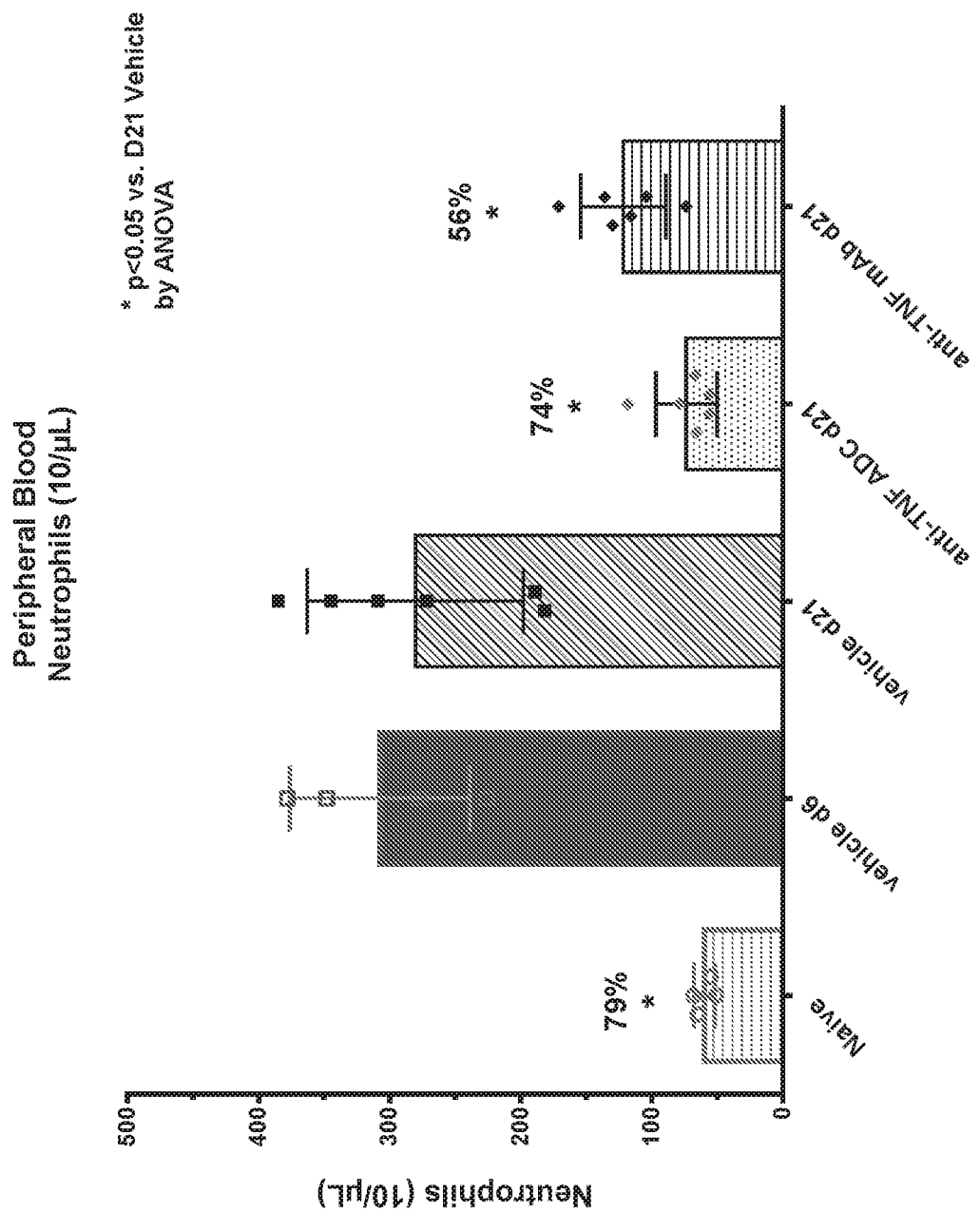

FIG. 19 shows effect of treatment with an anti-TNF steroid ADC on neutrophils in peripheral blood. (The individual data points (e.g., circles, squares, or diamonds) represent individual animals.) (See Example 88.)

Figure 20:
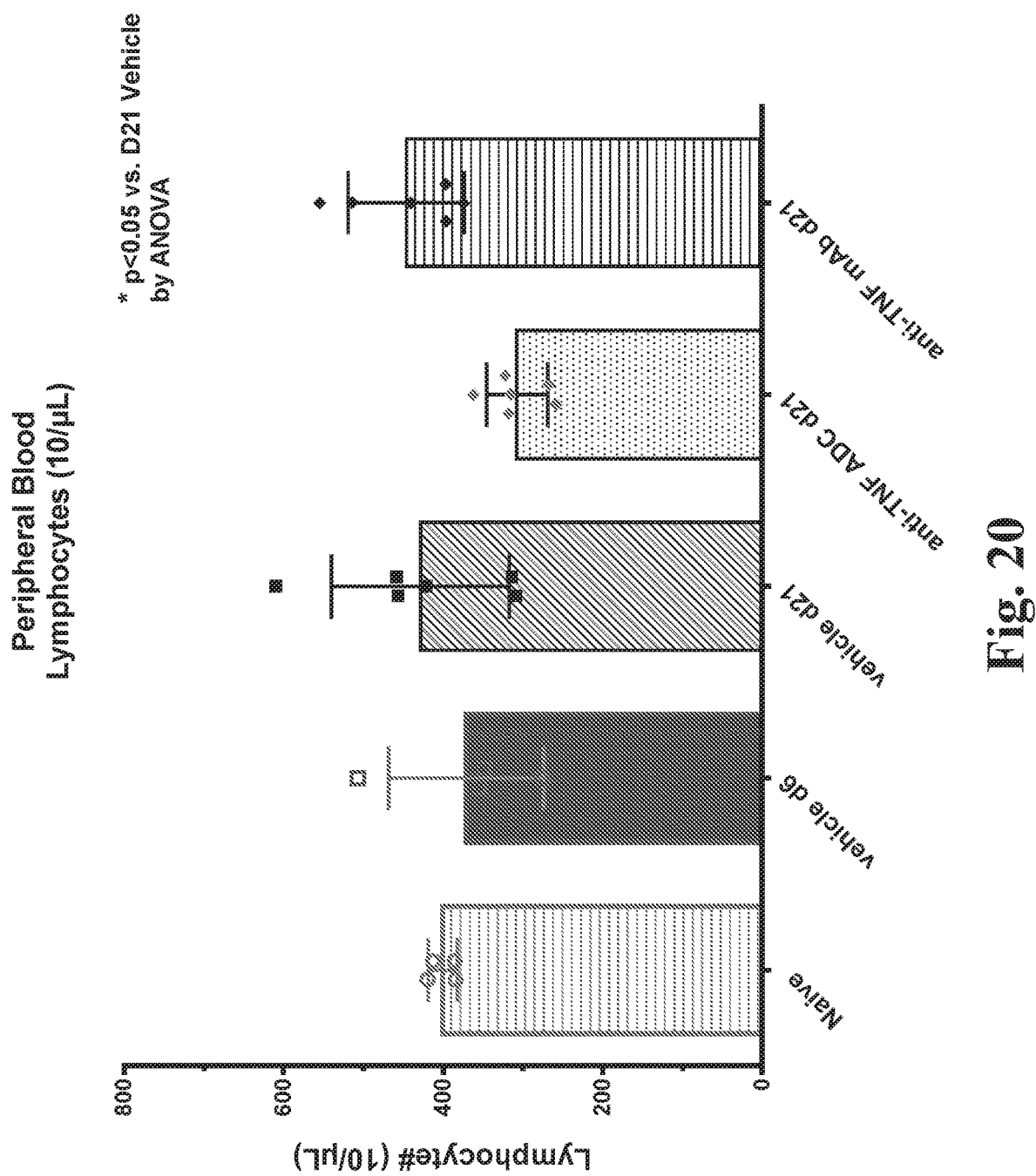

FIG. 20 shows effect of treatment with an anti-TNF steroid ADC on lymphocytes in peripheral blood. (The individual data points (e.g., circles, squares, or diamonds) represent individual animals.) (See Example 88.)

Figure 21:
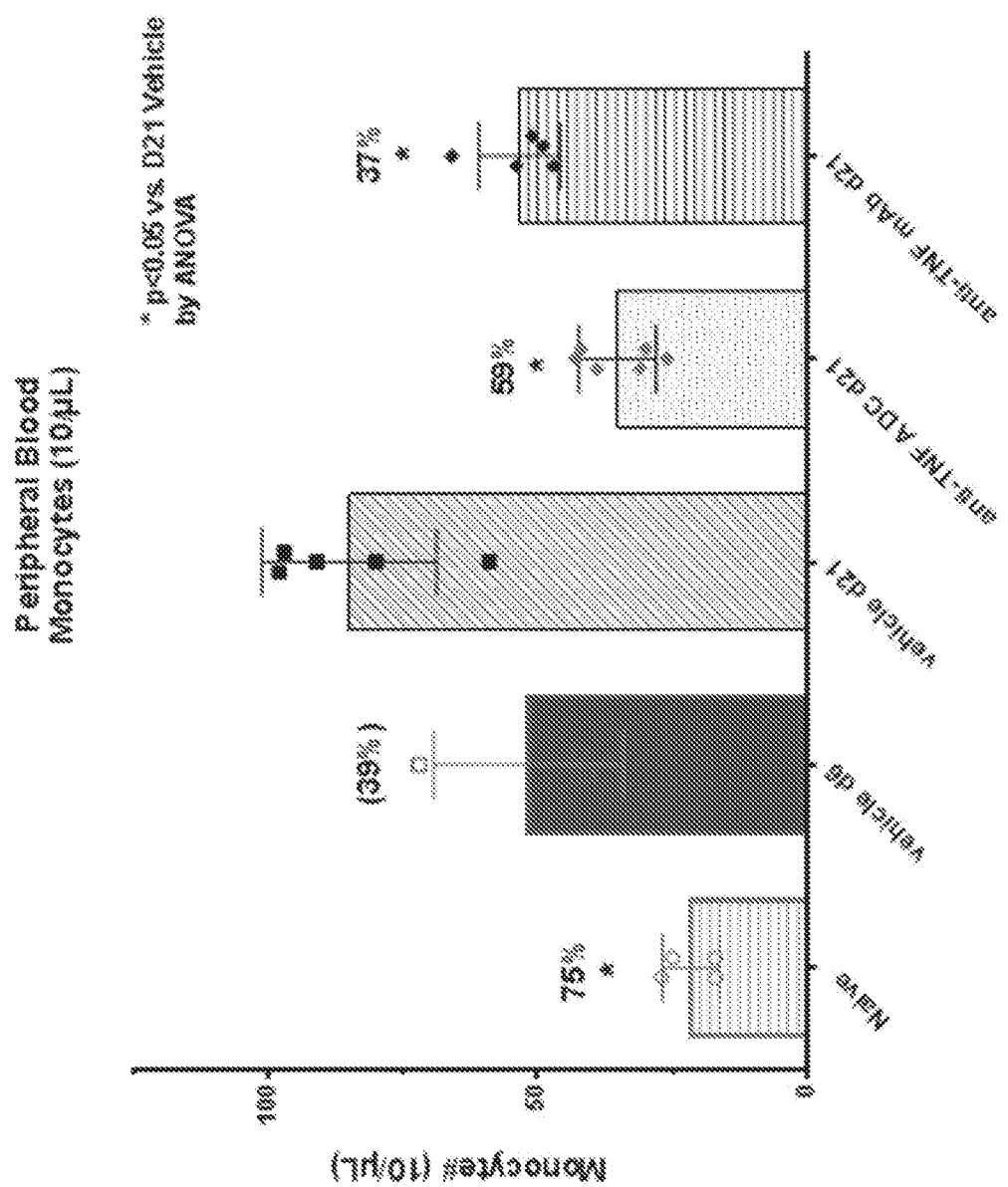

FIG. 21 shows effect of treatment with an anti-TNF steroid ADC on monocytes in peripheral blood. (The individual data points (e.g., circles, squares, or diamonds) represent individual animals.) (See Example 88.)

Figure 22:
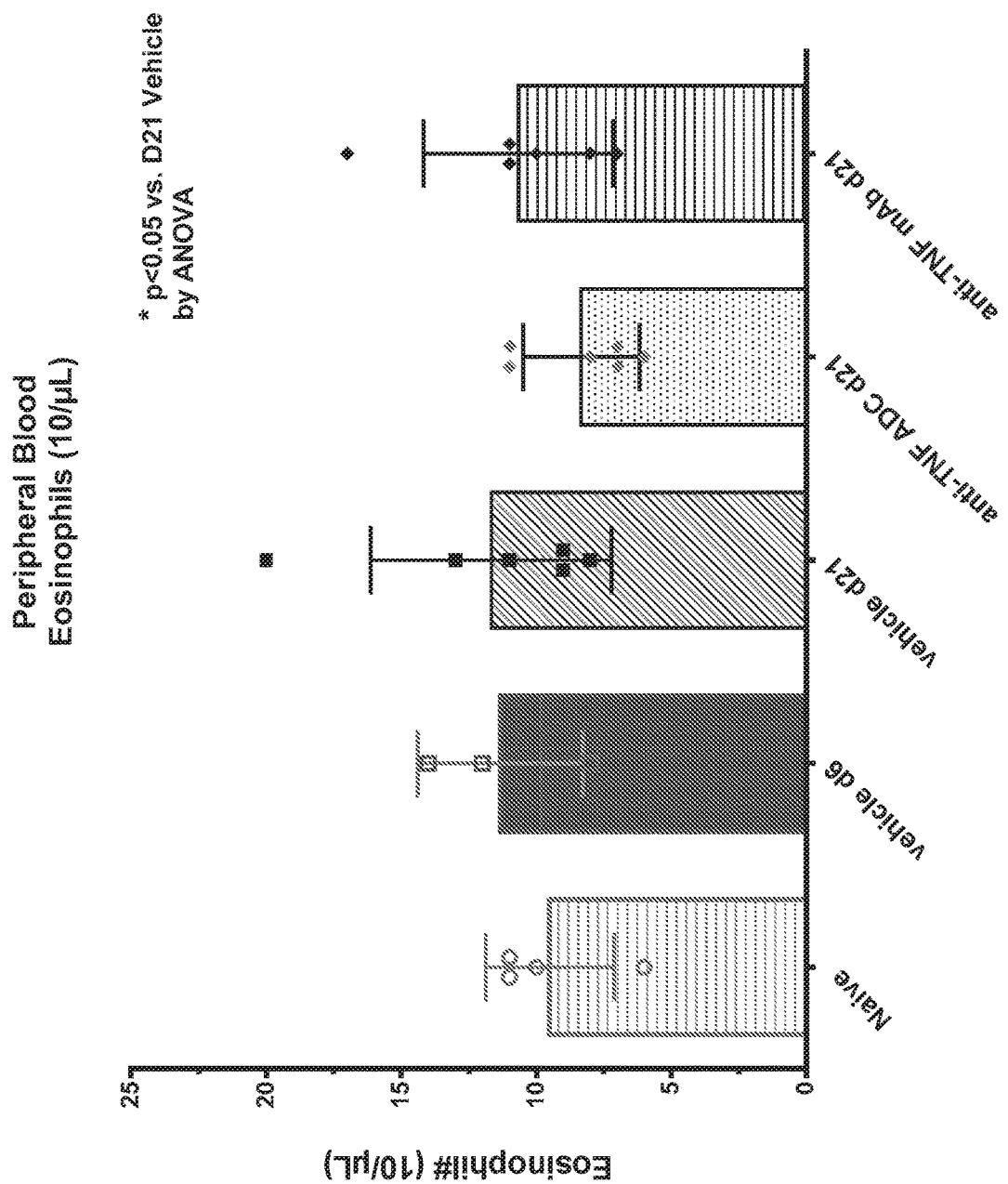

FIG. 22 shows effect of treatment with an anti-TNF steroid ADC on eosinophils in peripheral blood. (See Example 88.)

Figure 23:
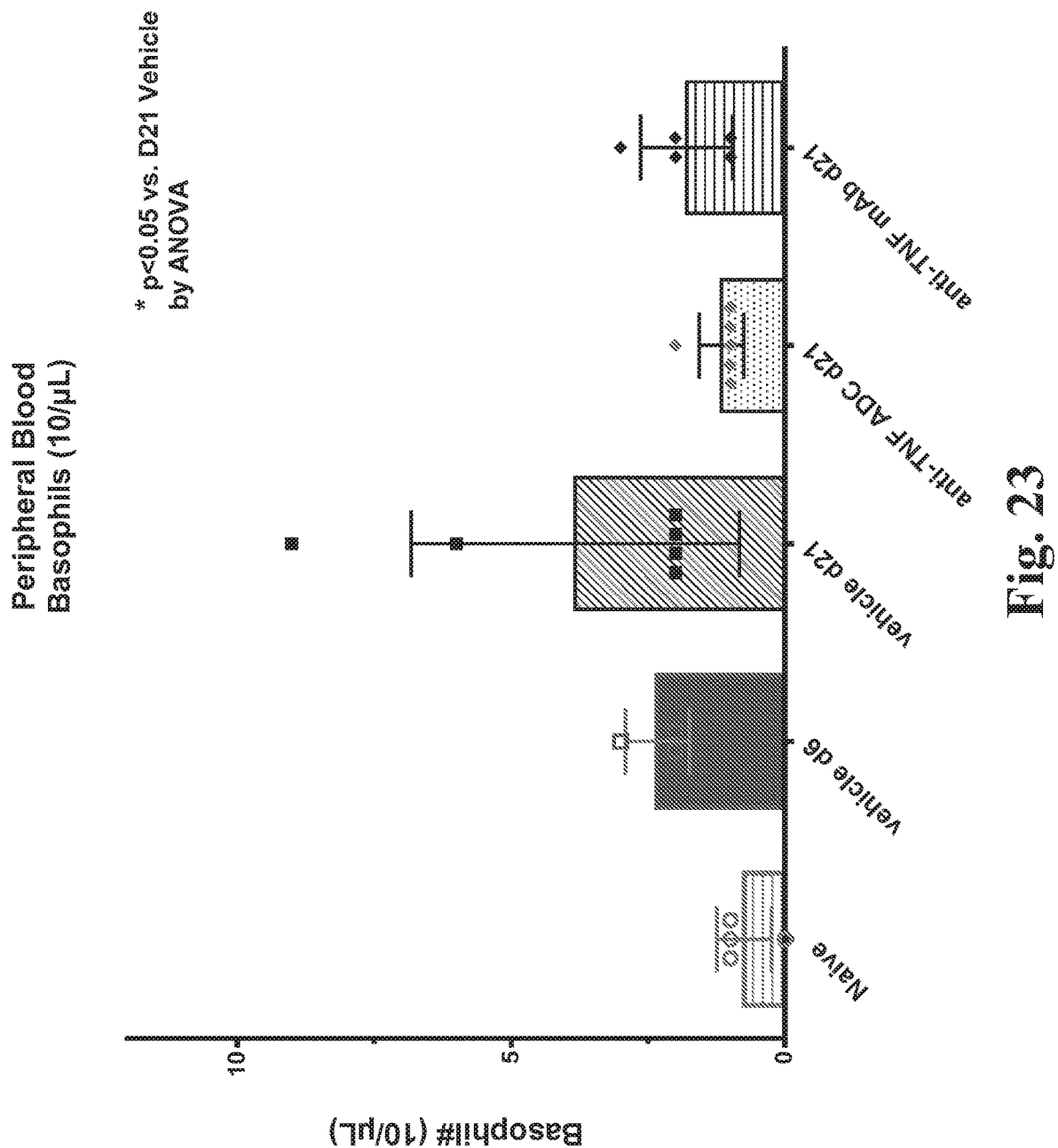

FIG. 23 shows effect of treatment with an anti-TNF steroid ADC on basophils in peripheral blood. (See Example 88.)

Figure 24:
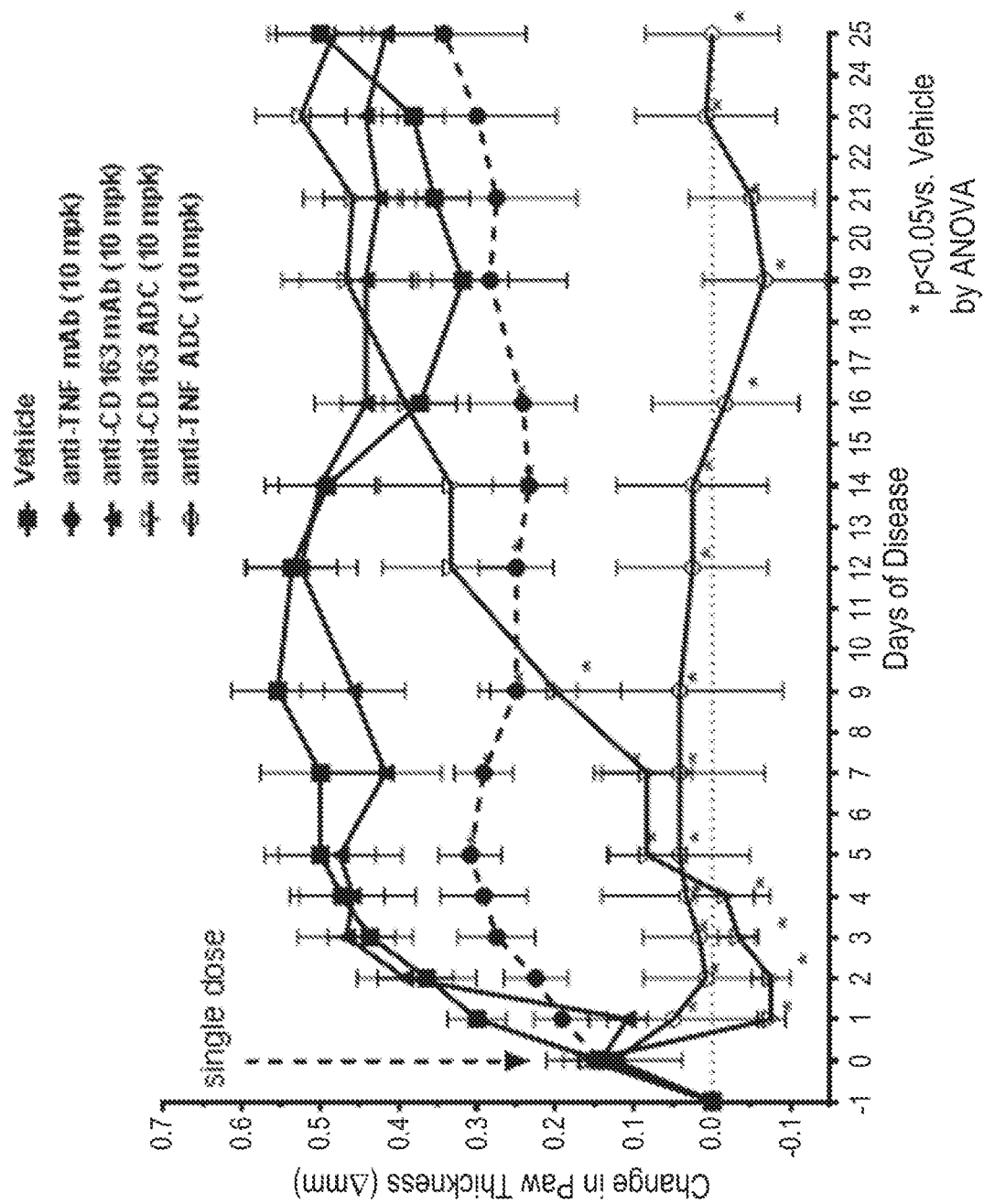

FIG. 24 shows the activity of an anti-TNF steroid ADC and an anti-CD163 steroid ADC in mouse collagen-induced arthritis. (See Example 89.)

DETAILED DESCRIPTION OF THE INVENTION

Provided herein are glucocorticoid receptor agonist immunoconjugates, glucocorticoid receptor agonists, and methods of making and using the same.

I. Definitions

To facilitate an understanding of the present disclosure, a number of terms and phrases are defined below.

The term "anti-TNF alpha protein" refers to proteins that are capable of (i) binding to TNF alpha and (ii) inhibiting binding of soluble TNF-alpha to cell surface TNF receptors (p55 and/or p75) and/or lysing surface TNF alpha or TNF alpha receptor expressing cells in vitro in the presence of complement. Anti-TNF alpha proteins include, for example, anti-TNF antibodies or antigen-binding fragments thereof (e.g., adalimumab or infliximab) as well as soluble TNF receptors (e.g., etanercept).

As used herein, the terms "antibody" and "antibodies" are terms of art and can be used interchangeably herein and refer to a molecule with an antigen-binding site that specifically binds an antigen.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. As used herein, the term "antibody" encompasses bispecific and multispecific antibodies.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies. An "antigen-binding fragment" can be a bispecific or multispecific antigen-binding fragment.

A "blocking" antibody or an "antagonist" antibody is one which inhibits or reduces biological activity of the antigen it binds, such as TNF-alpha. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

The term "anti-TNF-alpha antibody" or "an antibody that binds to TNF-alpha" refers to an antibody that is capable of binding TNF-alpha with sufficient affinity such that the antibody is useful as a diagnostic and/or therapeutic agent in targeting TNF-alpha. The extent of binding of an anti-TNFalpha antibody to an unrelated, non-TNF-alpha protein can be less than about 10% of the binding of the antibody to TNF-alpha as measured, e.g., by a radioimmunoassay (RIA). In certain embodiments, an antibody that binds to TNF-alpha has a dissociation constant (Kd) of ≤1 µM, ≤100 nM, ≤10 nM, ≤1 nM, or ≤0.1 nM.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). Unless explicitly indicated otherwise, the numbering system used herein is the Kabat numbering system.

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a,82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001).

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.).

The term "human" antibody means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric" antibodies refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc.) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if the antibody preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate," "conjugate," "antibody-drug conjugate," or "ADC" as used herein refers to a compound or a derivative thereof that is linked to protein such as a cell binding agent (e.g., an anti-TNF-alpha antibody or fragment thereof) and is defined by a generic formula: $(SM-L-Q)_n$-A, wherein SM=radical derived from a small-molecule glucocorticoid receptor agonist, e.g., a glucocorticosteroid, L=linker, Q=heterobifunctional group, a heterotrifunctional group, or is absent, and A=a protein (e.g., an antibody or antigen-binding fragment thereof, an anti-TNF protein, an anti-TNF-alpha antibody or fragment thereof, a soluble receptor, or a soluble TNF receptor), and n=1-10. Immunoconjugates can also be defined by the generic formula in reverse order: $A-(Q-L-SM)_n$. By way of illustration, the following generic formula shows a immunoconjugate having a dipeptide (Ala-Ala) linker and succinimide thioether-based heterobifunctional group:

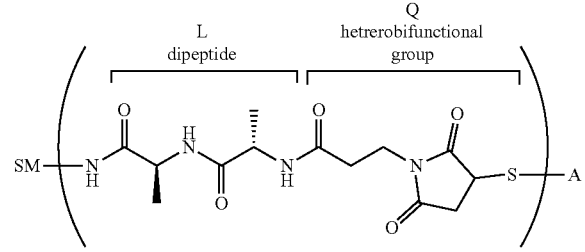

In the present disclosure, the term "linker" refers to any chemical moiety capable of linking a protein, e.g., antibody, antibody fragment (e.g., antigen binding fragments) or functional equivalent to a glucocorticosteroid. Linkers may be susceptible to cleavage (a "cleavable linker") thereby facilitating release of the glucocorticosteroid. For example, such cleavable linkers may be susceptible to acid-induced cleavage, photo-induced cleavage, peptidase-induced cleavage, esterase-induced cleavage, and disulfide bond cleavage, at conditions under which the glucocorticosteroid and/or the antibody remains active. Alternatively, linkers may be substantially resistant to cleavage (a "noncleavable linker").

In the present disclosure, non-cleavable linkers are any chemical moiety capable of linking a glucocorticosteroid to an antibody in a stable, covalent manner and does not fall off under the categories listed above for cleaveable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which a glucocorticosteroid and/or the antibody does not lose its activity.

Some cleavable linkers are cleaved by peptidases ("peptidase cleavable linkers"). Only certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Furthermore, peptides are composed of α-amino acid units and peptidic bonds, which chemically are amide bonds between the carboxylate of one amino acid and the amino group of a second amino acid. Other amide bonds, such as the bond between a carboxylate and the α-amino acid group of lysine, are understood not to be peptidic bonds and are considered non-cleavable.

Some linkers are cleaved by esterases ("esterase cleavable linkers"). Only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

In some embodiments, the cleavable linker component may comprise a peptide comprising one to ten amino acid residues. In these embodiments, the peptide allows for cleavage of the linker by a protease, thereby facilitating release of the glucocorticosteroid upon exposure to intracellular proteases, such as lysosomal enzymes (Doronina et al. (2003) Nat. Biotechnol. 21:778-784). Exemplary peptides include, but are not limited to, dipeptides, tripeptides, tetrapeptides, and pentapeptides. Exemplary dipeptides include, but are not limited to, alanine-alanine (ala-ala), valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly).

A peptide may comprise naturally-occurring and/or non-natural amino acid residues. The term "naturally-occurring amino acid" refer to Ala, Asp, Cys, Glu, Phe, Gly, His, Ile, Lys, Leu, Met, Asn, Pro, Gln, Arg, Ser, Thr, Val, Trp, and Tyr. "Non-natural amino acids" (i.e., amino acids do not occur naturally) include, by way of non-limiting example, homoserine, homoarginine, citrulline, phenylglycine, taurine, iodotyrosine, seleno-cysteine, norleucine ("Nle"), norvaline ("Nva"), beta-alanine, L- or D-naphthalanine, ornithine ("Orn"), and the like. Peptides can be designed and optimized for enzymatic cleavage by a particular enzyme, for example, a tumor-associated protease, cathepsin B, C and D, or a plasmin protease. Amino acids also include the D-forms of natural and non-natural amino acids. "D-" designates an amino acid having the "D" (dextrorotary) configuration, as opposed to the configuration in the naturally occurring ("L-") amino acids. Natural and non-natural amino acids can be purchased commercially (Sigma Chemical Co., Advanced Chemtech) or synthesized using methods known in the art.

In the present disclosure, the term "glucocorticosteroid" refers to naturally-occurring or synthetic steroid hormones that interact with glucocorticoid receptors. Non-limiting exemplary glucocorticosteroids include:

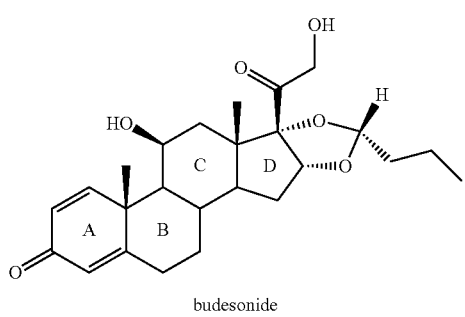

budesonide

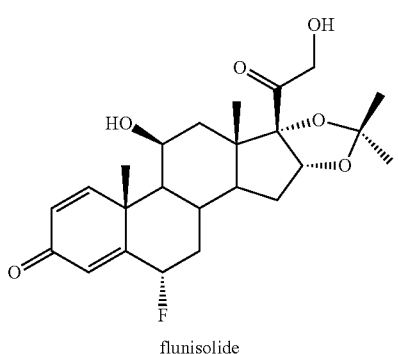

flunisolide

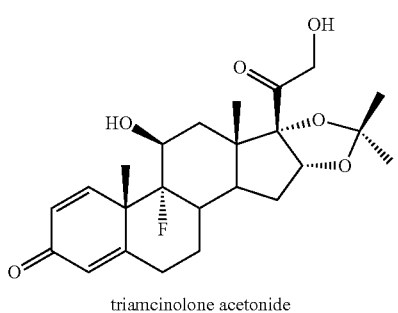

triamcinolone acetonide

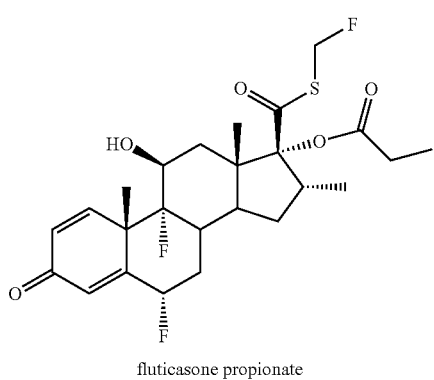

fluticasone propionate

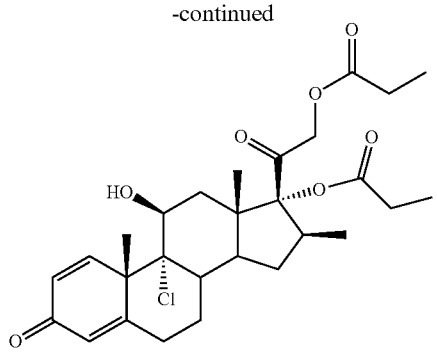

beclomethasone diproprionate

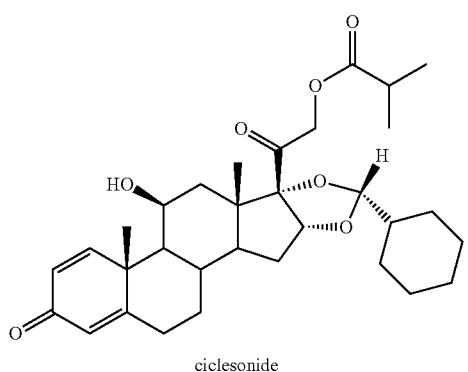 [SMILES: CC(C)C(=O)OCC(=O)[C@@]12O[C@H](C3CCCCC3)O[C@@H]1CC1C3CCC4=CC(=O)C=C[C@]4(C)C3[C@@H](O)C[C@@]12C]

ciclesonide

By way of example, the A-, B-, C-, and D-rings of the steroid skeleton are marked for budesonide. Glucocorticosteroids are described in WO 2009/069032.

A "radical of a glucocorticosteroid" is derived from the removal of one or more hydrogen atoms from a parent glucocorticosteroid. The removal of hydrogen atom(s) facilitates the attachment of the parent glucocorticosteroid to a linker. In one embodiment, the hydrogen atom is removed from any suitable —NH$_2$ group of the parent glucocorticosteroid. In another embodiment, the hydrogen atom is removed from any suitable —OH group of the parent glucocorticosteroid. In another embodiment, the hydrogen atom is removed from any suitable a —SH group of the parent glucocorticosteroid. In another embodiment, the hydrogen atom is removed from any suitable —N(H)— group of the parent glucocorticosteroid. In another embodiment, the hydrogen atom is removed from any suitable —CH$_3$, —CH$_2$— or —CH= group of the parent glucocorticosteroid. In one embodiment, the "radical of a glucocorticosteroid" is a monovalent radical derived from the removal of one hydrogen atom from a parent glucocorticosteroid.

In the present disclosure, the term "heterobifunctional group" or the term "heterotrifunctional group" refers to a chemical moiety that connects a linker and protein, e.g., an antibody. Heterobi- and tri-functional groups are characterized as having different reactive groups at either end of the chemical moiety. Non-limiting exemplary heterobifunctional groups include:

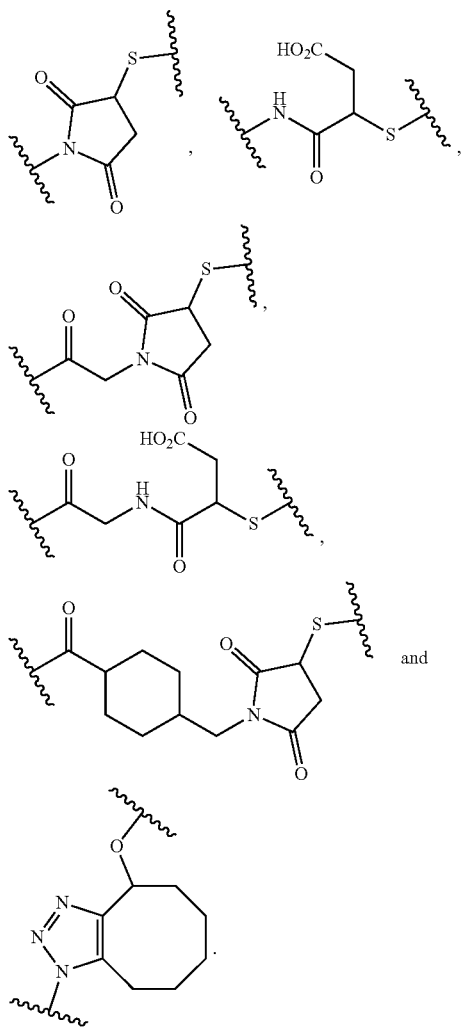

A non-limiting exemplary heterotrifunctional group is:

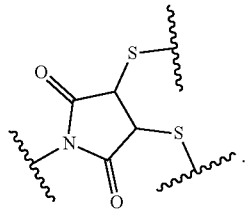 [SMILES: *SC1C(=O)N(*)C(=O)C1S*]

The term "drug antibody ratio" or "DAR" refers to the number of SMs (i.e., radical derived from a small-molecule glucocorticoid receptor agonist, e.g., a glucocorticosteroid) linked to A (i.e., a protein, e.g., an antibody or antigen-binding fragment thereof, an anti-TNF protein, an anti-TNF-alpha antibody or fragment thereof, a soluble receptor, or a soluble TNF receptor). Thus, in the immunoconjugate having the generic formula (SM-L-Q)$_n$-A, the DAR is defined by the variable "n."

When referring to a compound having formula (SM-L-Q)$_n$-A representing an individual immunoconjugate, the DAR refers to the number of SMs linked to the individual A (e.g., n is an integer of 1 to 10).

When referring to a compound having formula (SM-L-Q)$_n$-A representing a plurality of immunoconjugates, the DAR refers to the average number of SMs linked to the As (e.g., n is an integer or fraction of 1 to 10). Thus, by way of an example, a compound having formula (SM-L-Q)$_n$-A comprising a first immunoconjugate with 3 SM per A and a second immunoconjugate with 4 SM per A would have a DAR (i.e., an "n") of 3.5.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an immunoconjugate or glucocorticoid receptor agonist as disclosed herein is an amount sufficient to carry out a specifically stated purpose. An "effective amount" can be determined in relation to the stated purpose.

The term "therapeutically effective amount" refers to an amount of an immunoconjugate or glucocorticoid receptor agonist effective to "treat" a disease or disorder in a subject or mammal. A "prophylactically effective amount" refers to an amount effective to achieve the desired prophylactic result.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. Prophylactic or preventative measures refer to measures that prevent and/or slow the development of a targeted pathological condition or disorder. Thus, those in need of prophylactic or preventative measures include those prone to have the disorder and those in whom the disorder is to be prevented.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST can be used as described in Altschul et al., *Nucleic Acids Res.* 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman (*Advances in Applied Mathematics* 2: 482 489 (1981)) to find the best segment of homology between two sequences. When using Bestfit or any other sequence alignment program to determine whether a particular sequence is, for instance, 95% identical to a reference sequence according to the present disclosure, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the disclosure do not abrogate the binding of the antibody containing the amino acid sequence, to the antigen(s), e.g., the TNF-alpha to which the antibody binds. Methods of identifying nucleotide and amino acid conservative substitutions which do not eliminate antigen binding are well-known in the art (see, e.g., Brummell et al., *Biochem.* 32: 1180-1187 (1993); Kobayashi et al., *Protein Eng.* 12(10):879-884 (1999); and Burks et al., *Proc. Natl. Acad. Sci. USA* 94: 412-417 (1997)).

In the present disclosure, the term "halo" as used by itself or as part of another group refers to —Cl, —F, —Br, or —I. In one embodiment, the halo is —Cl or —F.

In the present disclosure, the term "hydroxy" as used by itself or as part of another group refers to —OH.

In the present disclosure, the term "thiol" or the term "sulfhydryl" as used by itself or as part of another group refers to —SH.

In the present disclosure, the term "alkyl" as used by itself or as part of another group refers to unsubstituted straight- or branched-chain aliphatic hydrocarbons containing from one to twelve carbon atoms, i.e., $C_{1-2}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "optionally substituted alkyl" as used by itself or as part of another group refers to an alkyl that is either unsubstituted or substituted with one, two, or three substituents independently selected from the group consisting of nitro, hydroxy, cyano, haloalkoxy, aryloxy, alkylthio, sulfonamido, alkylcarbonyl, arylcarbonyl, alkylsulfonyl, arylsulfonyl, carboxy, carboxamido, alkoxycarbonyl, thiol, —N(H)C(=O)NH$_2$, and —N(H)C(=NH)NH$_2$, optionally substituted aryl, and optionally substituted heteroaryl. In one embodiment, the optionally substituted alkyl is substituted with two substituents. In another embodiment, the optionally substituted alkyl is substituted with one substituent. In another embodiment, the optionally substituted alkyl is unsubstituted. Non-limiting exemplary substituted alkyl groups include —CH$_2$OH, —CH$_2$SH, —CH$_2$Ph, —CH$_2$(4-OH)Ph, —CH$_2$(imidazolyl), —CH$_2$CH$_2$CO$_2$H, —CH$_2$CH$_2$SO$_2$CH$_3$, —CH$_2$CH$_2$COPh, and —CH$_2$OC(=O)CH$_3$.

In the present disclosure, the term "cycloalkyl" as used by itself or as part of another group refers to unsubstituted saturated or partially unsaturated, e.g., containing one or two double bonds, cyclic aliphatic hydrocarbons containing one to three rings having from three to twelve carbon atoms, i.e., $C_{3-12}$ cycloalkyl, or the number of carbons designated. In one embodiment, the cycloalkyl has two rings. In another embodiment, the cycloalkyl has one ring. In another embodiment, the cycloalkyl is saturated. In another embodiment, the cycloalkyl is unsaturated. In another embodiment, the cycloalkyl is a $C_{3-8}$ cycloalkyl. In another embodiment, the cycloalkyl is a $C_{3-6}$ cycloalkyl. The term "cycloalkyl" is meant to include groups wherein a ring —CH$_2$— is replaced with a —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclopentanone.

In the present disclosure, the term "optionally substituted cycloalkyl" as used by itself or as part of another group refers to a cycloalkyl that is either unsubstituted or substituted with one, two, or three substituents independently selected from the group consisting of halo, nitro, cyano, hydroxy, alkylcarbonyloxy, cycloalkylcarbonyloxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, (heterocyclo)alkyl, and —OC(=O)-amino, The term optionally substituted cycloalkyl includes cycloalkyl groups having a fused optionally substituted aryl, e.g., phenyl, or fused optionally substituted heteroaryl, e.g., pyridyl. An optionally substituted cycloalkyl having a fused optionally substituted aryl or fused optionally substituted heteroaryl group may be attached to the remainder of the molecule at any available carbon atom on the cycloalkyl ring. In one embodiment, the optionally substituted cycloalkyl is substituted with two substituents. In another embodiment, the optionally substituted cycloalkyl is substituted with one substituent. In another embodiment, the optionally substituted cycloalkyl is unsubstituted.

In the present disclosure, the term "aryl" as used by itself or as part of another group refers to unsubstituted monocyclic or bicyclic aromatic ring systems having from six to fourteen carbon atoms, i.e., a $C_{6-14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl.

In the present disclosure, the term "optionally substituted aryl" as used herein by itself or as part of another group refers to an aryl that is either unsubstituted or substituted with one to five substituents independently selected from the group consisting of halo, nitro, cyano, hydroxy, thiol, amino, alkylamino, dialkylamino, optionally substituted alkyl, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, haloalkylsulfonyl cycloalkylsulfonyl, (cycloalkyl)alkylsulfonyl, arylsulfonyl, heteroarylsulfonyl, heterocyclosulfonyl, carboxy, carboxyalkyl, optionally substituted cycloalkyl, alkenyl, alkynyl, optionally substituted aryl, optionally substituted heteroaryl, optionally substituted heterocyclo, alkoxycarbonyl, alkoxyalkyl, (amino)alkyl, (carboxamido)alkyl, and (heterocyclo)alkyl.

In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. In another embodiment, the optionally substituted phenyl is unsubstituted. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, 4-(pyridin-4-ylsulfonyl) phenyl The term optionally substituted aryl includes phenyl groups having a fused optionally substituted cycloalkyl or fused optionally substituted heterocyclo group. An optionally substituted phenyl having a fused optionally substituted cycloalkyl or fused optionally substituted heterocyclo group may be attached to the remainder of the molecule at any available carbon atom on the phenyl ring.

In the present disclosure, the term "alkenyl" as used by itself or as part of another group refers to an alkyl containing one, two or three carbon-to-carbon double bonds. In one embodiment, the alkenyl has one carbon-to-carbon double bond. In another embodiment, the alkenyl is a $C_{2-6}$ alkenyl. In another embodiment, the alkenyl is a $C_{2-4}$ alkenyl. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group refers to an alkenyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, heteroaryl, and optionally substituted heterocyclo.

In the present disclosure, the term "alkynyl" as used by itself or as part of another group refers to an alkyl containing one to three carbon-to-carbon triple bonds. In one embodiment, the alkynyl has one carbon-to-carbon triple bond. In another embodiment, the alkynyl is a $C_{2-6}$ alkynyl. In another embodiment, the alkynyl is a $C_{2-4}$ alkynyl. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part refers to an alkynyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, cycloalkyl, alkenyl, alkynyl, optionally substituted aryl, optionally substituted heteroaryl, and heterocyclo.

In the present disclosure, the term "haloalkyl" as used by itself or as part of another group refers to an alkyl substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "alkoxy" as used by itself or as part of another group refers to an optionally substituted alkyl, optionally substituted cycloalkyl, optionally substituted alkenyl, or optionally substituted alkynyl attached to a terminal oxygen atom. In one embodiment, the alkoxy is an optionally substituted alkyl attached to a terminal oxygen atom. In one embodiment, the alkoxy group is a $C_{1-6}$ alkyl attached to a terminal oxygen atom. In another embodiment, the alkoxy group is a $C_{1-4}$ alkyl attached to a terminal oxygen atom. Non-limiting exemplary alkoxy groups include methoxy, ethoxy, and tert-butoxy.

In the present disclosure, the term "alkylthio" as used by itself or as part of another group refers to an optionally substituted alkyl attached to a terminal sulfur atom. In one embodiment, the alkylthio group is a $C_{1-4}$ alkylthio group. Non-limiting exemplary alkylthio groups include —$SCH_3$ and —$SCH_2CH_3$.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "heteroaryl" refers to unsubstituted monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl is a 5- or 6-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, f3-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is selected from the group consisting of thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl. In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group refers to a heteroaryl that is either unsubstituted or substituted with one two, three, or four substituents, independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, haloalkylsulfonyl cycloalkylsulfonyl, (cycloalkyl)alkylsulfonyl, arylsulfonyl, heteroarylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, and (heterocyclo)alkyl. In one embodiment, the optionally substituted heteroaryl has one substituent. In another embodiment, the optionally substituted heteroaryl is unsubstituted. Any available carbon or nitrogen atom can be substituted. The term optionally substituted heteroaryl includes heteroaryl groups having a fused optionally substituted cycloalkyl or fused optionally substituted heterocyclo group. An optionally substituted heteroaryl having a fused optionally substituted cycloalkyl or fused optionally substituted heterocyclo group may be attached to the remainder of the molecule at any available carbon atom on the heteroaryl ring.

In the present disclosure, the term "heterocyclo" as used by itself or as part of another group refers to unsubstituted saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" includes groups wherein a ring —$CH_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" also includes groups having fused optionally substituted aryl groups, e.g., indolinyl or chroman-4-yl. In one embodiment, the heterocyclo group is a $C_{4-6}$ heterocyclo, i.e., a 4-, 5- or 6-membered cyclic group, containing one ring and one or two oxygen and/or nitrogen atoms. In one embodiment, the heterocyclo group is a $C_{4-6}$ heterocyclo containing one ring and one nitrogen atom. The heterocyclo can be optionally linked to the rest of the molecule through any available carbon or nitrogen atom. Non-limiting exemplary heterocyclo groups include azetidinyl, dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group refers to a heterocyclo that is either unsubstituted or substituted with one, two, three, or four substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, cycloalkylcarbonyl, alkoxycarbonyl, $CF_3C(=O)$—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino) alkyl, (carboxamido)alkyl, or (heterocyclo)alkyl. Substitution may occur on any available carbon or nitrogen atom, or both.

In the present disclosure, the term "amino" as used by itself or as part of another group refers to a radical of the formula —$NR^{22a}R^{22b}$, wherein $R^{22a}$ and $R^{22b}$ are each independently selected from the group consisting of hydrogen, optionally substituted alkyl, and aralkyl, or $R^{22a}$ and $R^{22b}$ are taken together to form a 3- to 8-membered optionally substituted heterocyclo. Non-limiting exemplary amino groups include —$NH_2$ and —$N(H)(CH_3)$.

In the present disclosure, the term "carboxamido" as used by itself or as part of another group refers to a radical of formula —$C(=O)NR^{23a}R^{23b}$, wherein $R^{23a}$ and $R^{23b}$ are each independently selected from the group consisting of hydrogen, optionally substituted alkyl, hydroxyalkyl, and optionally substituted aryl, optionally substituted heterocyclo, and optionally substituted heteroaryl, or $R^{23a}$ and $R^{23b}$ taken together with the nitrogen to which they are attached form a 3- to 8-membered optionally substituted heterocyclo group. In one embodiment, $R^{23a}$ and $R^{23b}$ are each independently hydrogen or optionally substituted alkyl. In one embodiment, $R^{23a}$ and $R^{23b}$ are taken together to taken together with the nitrogen to which they are attached form a 3- to 8-membered optionally substituted heterocyclo group. Non-limiting exemplary carboxamido groups include —CONH$_2$, —CON(H)CH$_3$, and —CON(CH$_3$)$_2$.

In the present disclosure, the term "alkoxycarbonyl" as used by itself or as part of another group refers to a carbonyl group, i.e., —C(═O)—, substituted with an alkoxy. In one embodiment, the alkoxy is a C$_{1-4}$ alkoxy. Non-limiting exemplary alkoxycarbonyl groups include —C(═O)OMe, —C(═O)OEt, and —C(═O)OtBu.

In the present disclosure, the term "carboxy" as used by itself or as part of another group refers to a radical of the formula —CO$_2$H.

In the present disclosure, the term "maleimide" as used by itself or as part of another group refers to:

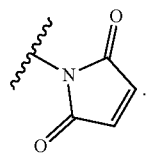 [SMILES: *N1C(=O)C=CC1=O]

In the present disclosure, the term "succinimide" as used as part of a cleavable linker refers to:

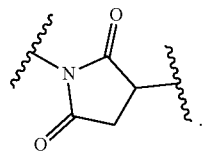 [SMILES: *C1CC(=O)N(*)C1=O]

In the present disclosure, the term "hydrolyzed succinimide" as used as part of a cleavable linker refers to:

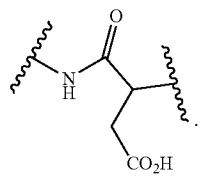

In the present disclosure, the term "amide" as used as part of a cleavable linker refers to:

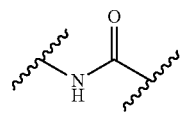

In the present disclosure, the term "thiourea" as used as part of a cleavable linker refers to:

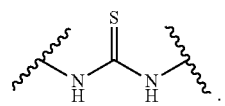 [SMILES: *NC(=S)N*]

In the present disclosure, the term "thioether" as used as part of a cleavable linker refers to:

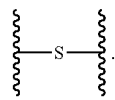

In the present disclosure, the term "oxime" as used as part of a cleavable linker refers to:

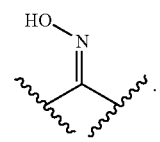 [SMILES: *C(*)=NO]

In the present disclosure, the term "self-immolative group" as used as part of a cleavable linker refers to bifunctional chemical moiety that is capable of covalentlyl inking two spaced chemical moieties into a normally stable tripartite molecule, can release one of the spaced chemical moieties from the tripartite molecule by means of enzymatic cleavage; and following enzymatic cleavage, can spontaneously cleave from the remainder of the molecule to release the other of the spaced chemical moieties, e.g., a glucocorticosteroid. In some embodiments, a self-immolative group comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the self-immolative group is p-aminobenzyloxycarbonyl (PAB).

In the present disclosure, the term "protecting group" or "PG" refers to group that blocks, i.e., protects, the amine functionality while reactions are carried out on other functional groups or parts of the molecule. Those skilled in the art will be familiar with the selection, attachment, and cleavage of amine protecting groups, and will appreciate that many different protective groups are known in the art, the suitability of one protective group or another being dependent on the particular the synthetic scheme planned. Treatises on the subject are available for consultation, such as Wuts, P. G. M.; Greene, T. W., "Greene's Protective Groups in Organic Synthesis", 4th Ed., J. Wiley & Sons, N Y, 2007. Suitable protecting groups include the carbobenzyloxy (Cbz), tert-butyloxycarbonyl (BOC), 9-fluorenylmethyloxycarbonyl (FMOC), and benzyl (Bn) group. In one embodiment, the protecting group is the BOC group.

The compounds disclosed herein contain asymmetric centers and thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also intended to be encompassed by the present disclosure.

The present disclosure encompasses the preparation and use of solvates of the compounds disclosed herein. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds disclosed herein can be present as solvated forms with a pharmaceutically acceptable solvent, such as water, methanol, ethanol, and the like, and it is intended that the disclosure includes both solvated and unsolvated forms of compounds disclosed herein. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a compound disclosed herein in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure encompasses the preparation and use of salts of the compounds disclosed herein, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound disclosed with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Proteins for Linkage to Glucocorticoid Receptor Agonists

The present disclosure provides agents immunoconjugates containing glucocorticoid receptor agonists linked to proteins, for example, antibodies or antigen-binding fragments thereof and soluble receptor proteins. In some embodiments, the antibody or antigen-binding fragment thereof is human, humanized, chimeric, or murine. In some embodiments, the protein, e.g., antibody, antigen-binding fragment thereof, or soluble receptor protein, can bind to a target on the surface of a cell and become internalized.

The present disclosure also provides immunoconjugates containing glucocorticoid receptor agonists linked to anti-TNF alpha proteins. In certain embodiments, the anti-TNF alpha proteins are antibodies or antigen-binding fragments thereof. In certain embodiments, the anti-TNF alpha proteins are antibodies or antigen-binding fragments thereof that bind to TNF alpha (e.g., soluble TNF alpha and/or membrane bound TNF alpha). In certain embodiments, the anti-TNF alpha proteins are soluble TNF receptor proteins, e.g., soluble TNF receptor proteins fused to a heavy chain constant domain or fragment thereof such as an Fc. In some embodiments, the anti-TNF alpha protein, e.g., anti-TNF antibody, antigen-binding fragment thereof, or soluble TNF receptorcan bind to TNF alpha on the surface of a cell and become internalized. For example, US 2014/0294813, which is herein incorporated by referece in its entirety, discloses anti-TNF proteins that exhibit cellular internalization upon binding to cell surface human TNF.

In certain embodiments, the antibodies or antigen-binding fragments thereof bind to human and/or mouse TNF-alpha. Antibodies and antigen-binding fragments that bind to TNF-alpha are known in the art.

The full-length amino acid sequence for membrane bound human TNF alpha is:
MSTESMIRDVELAEEALPKKTGGPQGSRRCL-FLSLFSFLIVAGATTLFCLLHFGVIGPQ REEF-PRDLSLISPLAQAVRSSSRTPSDKPVAHVVANPQAE-GQLQWLNRRANALLANGVELRDNQ LVVPSEGLYLIYSQVLFKGQGCPSTHVLLTHTISRIA-VSYQTKVNLLSAIKSPCQRETPEGAEAKP WYEPI-YLGGVFQLEKGDRLSAEINRPDYLDFAESGQVYFGI-IAL (SEQ ID NO:1). Soluble human TNF alpha contains amino acids 77-233 of SEQ ID NO:1. The full-length amino acid sequence for membrane bound murine TNF-alpha is:
MSTESMIRDVELAEEALPQKMGGFQN SRRCL-CLSLFSFLLVAGATTLFCLLNFGVIGPQRDEKFPN GLPLISSMAQTLTLRSSSQNSSDKPVAHVVANHQVE- EQLEWLSQRANALLANGMDLKDNQLVV PADGLYL-VYSQVLFKGQGCPDYVLLTHTVSRFAISYQEKVNLL-SAVKSPCPKDTPEGAELKPWY EPIYLGGVFQLEKGDQLSAEVNLPKYLDFAESGQVY-FGVIAL (SEQ ID NO:2). Soluble murine TNF alpha contains amino acids 80-235 of SEQ ID NO:2.

In some embodiments, the anti-TNF-alpha antibody or antigen-binding fragment thereof binds to human TNF-alpha. In some embodiments, the anti-TNF-alpha antibody or antigen-binding fragment thereof is human, humanized, or chimeric.

In some embodiments, the anti-TNF-alpha antibody or antigen-binding fragment thereof binds to murine TNF-alpha. In some embodiments, the anti-TNF-alpha antibody or antigen-binding fragment thereof is murine.

In certain embodiments, the anti-TNF-alpha antibody or antigen-binding fragment has one or more of the following effects: neutralizes human TNF-alpha cytotoxicity in a in vitro L929 assay with an IC50 of $1\times10^{-7}$ M or less; blocks the interaction of TNF-alpha with p55 and p75 cell surface receptors; and/or lyses surface TNF expressing cells in vitro in the presence of complement.

In certain embodiments, the anti-TNF-alpha antibody or antigen-binding fragment does not bind to TNF-beta.

Anti-TNF-alpha antibodies and antigen-binding fragments thereof include, for example, adalimumab, infliximab, certolizumab pegol, afelimomab, nerelimomab, ozoralizumab, placulumab, and golimumab. Additional anti-TNF-alpha antibodies and antigen-binding fragments are provided, for example, in WO 2013/087912, WO 2014/152247 and WO 2015/073884, each of which is herein incorporated by reference in its entirety.

Adalimumab is described in U.S. Pat. No. 6,258,562, which is herein incorporated by reference in its entirety. Infliximab is described in U.S. Pat. No. 5,656,272, which is herein incorporated by reference in its entirety. Certolizumab is discussed in WO 01/94585, which is herein incorporated by reference in its entirety. Afelimomab (also known as MAK195) is discussed in Vincent, *Int. J. Clin. Pract.* 54: 190-193 (2000), which is herein incorporated by reference in its entirety. Ozoralizumab (also known as ATN-103) is a nanobody. It contains three heavy chain variable regions fused by GlySer linkers. Variable regions 1 and 3 are identical, and ozoralizumab does not contain a heavy chain. Ozoralizumab is discussed in WO 2012/131053, which is herein incorporated by reference in its entirety. Placulumab (also known as CEP-37247) is a domain antibody consisting of a dimer of VL-pCH1-CH2-CH3 or [V-kappa]2-Fc and is discussed in Gay et al., *Mabs* 2: 625-638 (2010), which is herein incorporated by reference in its entirety. Golimumab (also known as CNTO 148) is discussed in WO2013/087912, and sequences are provided in GenBank: D1496971.1 and GenBank DI 496970.1, each of which is herein incorporated by reference in its entirety.

Anti-TNF-alpha antibodies and antigen-binding fragments thereof also include antibodies and antigen-binding fragments thereof that competitively inhibit binding of adalimumab, infliximab, certolizumab pegol, afelimomab, nerelimomab, ozoralizumab, placulumab, or golimumab to TNF-alpha. Anti-TNF-alpha antibodies and antigen-binding fragments thereof also include antibodies and antigen-binding fragments that bind to the same TNF-alpha epitope as adalimumab, infliximab, certolizumab pegol, afelimomab, nerelimomab, ozoralizumab, placulumab, or golimumab.

In certain embodiments, the anti-TNF-alpha antibody or antigen-binding fragment thereof competitively inhibits binding of adalimumab to TNF-alpha. In certain embodiments, the anti-TNF-alpha antibody or antigen-binding fragment thereof binds to the same TNF-alpha epitope as adalimumab. In certain embodiments, the anti-TNF-alpha antibody or antigen-binding fragment thereof is adalimumab or an antigen-binding fragment thereof. In certain embodiments, the anti-TNF-alpha antibody or antigen-binding fragment thereof is adalimumab.

In certain embodiments, an anti-TNF-alpha antibody or antigen-binding fragment thereof comprises sequences of adalimumab, infliximab, certolizumab pegol, afelimomab, nerelimomab, ozoralizumab, placulumab, or golimumab, e.g., the complementarity-determining regions (CDRs), the variable heavy domain (VH), and/or the variable light domain (VL). Sequences of exemplary anti-TNF-alpha antibodies or antigen-binding fragments thereof are provided in Tables 1-6.

TABLE 1

Variable heavy chain CDR amino acid sequences:

| Antibody | VH-CDR1 | VH-CDR2 | VH-CDR3 |
|---|---|---|---|
| adalimumab | DYAMH (SEQ ID NO: 3) or GFTFDDYAMH (SEQ ID NO: 6) | AITWNSGHIDYADSVEG (SEQ ID NO: 4) | VSYLSTASS (SEQ ID NO: 5) VSYLSTASSLDY (SEQ ID NO: 94) |
| infliximab | GFIFSNHWMN (SEQ ID NO: 7) | EIRSKSINSATHYAESV KG (SEQ ID NO: 8) | NYYGSTYDY (SEQ ID NO: 9) |
| certolizumab | DYGMN (SEQ ID NO: 10) or GYVFTDYGMN (SEQ ID NO: 13) | WINTYIGEPIYADSVKG (SEQ ID NO: 11) | GYRSYAMDY (SEQ ID NO: 12) |
| afelimomab | DYGVN (SEQ ID NO: 14) | MIWGDGSTDYDSTLKS (SEQ ID NO: 15) | EWHHGPVAY (SEQ ID NO: 16) |
| nerelimomab | DYNVD (SEQ ID NO: 17) | NINPNNGGTIYNQKFKG (SEQ ID NO: 18) | SAFYNNYEYFDV (SEQ ID NO: 19) |
| ozoralizumab | V1: DYWMY (SEQ ID NO: 20) V2: SFGMS (SEQ ID NO: 23) | V1: EINTNGLITKYPDSVKG (SEQ ID NO: 21) V2: | V1: SPSGFNR (SEQ ID NO: 22) V2: GGSLSRSS (SEQ ID NO: 25) |

TABLE 1 -continued

Variable heavy chain CDR amino acid sequences:

| Antibody | VH-CDR1 | VH-CDR2 | VH-CDR3 |
|---|---|---|---|
|  | V3: DYWMY (SEQ ID NO: 26) V3: EINTNGLITKY PDSVKG (SEQ ID NO: 27) | SISGSGSDTLYADSVKG (SEQ ID NO: 24) | V3: SPSGFNR (SEQ ID NO: 28) |
| golimumab | GFIFSSYAMH (SEQ ID NO: 29) | FMSYDGSNKKYADSVKG (SEQ ID NO: 30) | DRGIAAGGNYYYYGMDV (SEQ ID NO: 31) |
| placulumab | RASQAIDSYLH (SEQ ID NO: 88) | SASNLET (SEQ ID NO: 89) | QQVVWRPFT (SEQ ID NO: 90) |

TABLE 2

Variable light chain CDR amino acid sequences

| Antibody | VL-CDR1 | VL-CDR2 | VL-CDR3 |
|---|---|---|---|
| adalimumab | RASQGIRNYLA (SEQ ID NO: 32) | AASTLQS (SEQ ID NO: 33) | QRYNRAPYT (SEQ ID NO: 34) |
| infliximab | RASQFVGSSIH (SEQ ID NO: 35) | YASESMS (SEQ ID NO: 36) | QQSHSWPFT (SEQ ID NO: 37) |
| certolizumab | KASQNVGTNVA (SEQ ID NO: 38) | SASFLYS (SEQ ID NO: 39) | QQYNIYPLT (SEQ ID NO: 40) |
| afelimomab | KASQAVSSAVA (SEQ ID NO: 41) | WASTRHT (SEQ ID NO: 42) | QQHYSTPFT (SEQ ID NO: 43) |
| nerelimomab | KSSQSLLYSNNQKNYLA (SEQ ID NO: 44) | WASTRES (SEQ ID NO: 45) | QQYYDYPWT (SEQ ID NO: 46) |
| ozoralizumab | N/A | N/A | N/A |
| golimumab | RASQSVYSYLA (SEQ ID NO: 47) | DASNRAT (SEQ ID NO: 48) | QQRSNWPPFT (SEQ ID NO: 49) |

TABLE 3

Variable heavy chain amino acid sequences

| Antibody | VH Amino Acid Sequence (SEQ ID NO) |
|---|---|
| adalimumab | EVQLVESGGGLVQPGRSLRLSCAASGFTFDDYAMHWVRQAPGKGLEWVSAITWNSGHIDYADSVEGRFTISRDNAKNSLYLQMNSLRAEDTAVYYCAKVSYLSTASSLDYWGQGTLVTVSS (SEQ ID NO: 50) |
| infliximab | EVKLEESGGGLVQPGGSMKLSCVASGFIFSNHWMNWVRQSPEKGLEWVAEIRSKSINSATHYAESVKGRFTISRDDSKSAVYLQMTDLRTEDTGVYYCSRNYYGSTYDYWGQGTLTVSS (SEQ ID NO: 51) EVKLEESGGGLVQPGGSMKLSCVASGFIFSNHWMNWVRQSPEKGLEWVAEIRSKSINSATHYAESVKGRFTISRDDSKSAVYLQMNSLRTEDTGVYYCSRNYYGSTYDYWGQGTLTVS (SEQ ID NO: 91) |
| certolizumab | EVQLVESGGGLVQPGGSLRLSCAASGYVFTDYGMNWVRQAPGKGLEWMGWINTYIGEPIYADSVKGRFTFSLDTSKSTAYLQMNSLRAEDTAVYYCARGYRSYAMDYWGQGTLVTVSS (SEQ ID NO: 52) |
| afelimomab | QVQLKESGPGLVAPSQSLSITCTVSGFSLTDYGVNWVRQPPGKGLEWLGMIWGDGSTDYDSTLKSRLSISKDNSKSQIFLKNNSLQTDDTARYYCAREWHHGPVAYWGQGTLVTVSA (SEQ ID NO: 53) |
| nerelimomab | QVQLVQSGAEVVKPGSSVKVSCKASGYTFTDYNVDWVKQAPGQGLQWIGNINPNNGGTIYNQKFKGKGTLTVDKSTSTAYMELSSLTSEDTAVYYCARSAFYNNYEYFDVWGQGTTVTVSS (SEQ ID NO: 54) |
| ozoralizumab | V1: EVQLVESGGGLVQPGGSLRLSCAASGFTFSDYWMYWVRQAPGKGLEWVSEINTNGLITKYPDSVKGRFTISRDNAKNTLYLQMNSLRPEDTAVYYCARSPSGFNRGQGTLVTVSS (SEQ ID NO: 55) V2: EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS (SEQ ID NO: 56) V3: EVQLVESGGGLVQPGGSLRLSCAASGFTFSDYWMYWVRQAPGKGLEWVSEINTNGLITKYPDSVKGRFTISRDNAKNTLYLQMNSLRPEDTAVYYCARSPSGFNRGQGTLVTVSS (SEQ ID NO: 57) |
| golimumab | QVQLVESGGGVVQPGRSLRLSCAASGFIFSSYAMHWVRQAPGNGLEWVAFMSYDGSNKKYADSVKGRFTISRDNSKNTLYLQMNSLRAEDTAVYYCARDRGIAAGGNYYYYGMDVWGQGTTVTVSS (SEQ ID NO: 58) |

TABLE 4

Variable light chain amino acid sequences

| Antibody | VL Amino Acid Sequence (SEQ ID NO) |
|---|---|
| adalimumab | DIQMTQSPSSLSASVGDRVTITCRASQGIRNYLAWYQQKPGKAPKLLIYAASTLQSGVPSRFSGSGSGTDFTLTISSLQPEDVATYYCQRYNRAPYTFGQGTKVEIK (SEQ ID NO: 59) |
| infliximab | DILLTQSPAILSVSPGERVSFSCRASQFVGSSIHWYQQRTNGSPRLLIKYASESMSGIPSRFSGSGSGTDFTLSINTVESEDIADYYCQQSHSWPFTFGSGTNLEVK (SEQ ID NO: 60) |
| certolizumab | DIQMTQSPSSLSASVGDRVTITCKASQNVGTNVAWYQQKPGKAPKALIYSASFLYSGVPYRFSGSGSGTDFTLTISSLQPEDFATYYCQQYNIYPLTFGQGTKVEIK (SEQ ID NO: 61) |
| afelimomab | DIVMTQSHKFMSTTVGDRVSITCKASQAVSSAVAWYQQKPGQSPKLLIYWASTRHTGVPDRFTGSGSVTDFTLTIHNLQAEDLALYYCQQHYSTPFTFGSGTKLEIK (SEQ ID NO: 62) |

TABLE 4 -continued

Variable light chain amino acid sequences

| Antibody | VL Amino Acid Sequence (SEQ ID NO) |
|---|---|
| nerelimomab | DIMMTQSPSTLSASVGDRVTITCKSSQSLLYSNNQKN YLAWYQQKPGQAPKLLISWASTRESGVPSRFIGSGSG TEFTLTISSLQPDDVATYYCQQYYDYPWTFGQGTKVE IK (SEQ ID NO: 92)<br>DIMMTQSPSTLSASVGDRVTITCKSSQSLLYSNNQKN YLAWYQQKPGQAPKLLISWASTRESGVPSRFIGSGSG TEFTLTISSLQPDDVATYYCQQYYDYPWTFGQGTKVE IKR (SEQ ID NO: 63) |
| placulumab | DIQMTQSPSSLSASVGDRVTITCRASQAIDSYLHWYQ QKPGKAPKLLIYSASNLETGVPSRFSGSGSGTDFTLT ISSLLPEDFATYYCQQVVWRPFTFGQGTKVEIK (SEQ ID NO: 64) |
| golimumab | EIVLTQSPATLSLSPGERATLSCRASQSVYSYLAWYQ QKPGQAPRLLIYDASNRATGIPARFSGSGSGTDFTLT ISSLEPEDFAVYYCQQRSNWPPFTFGPGTKVDIK (SEQ ID NO: 65) |

TABLE 5

Full-length heavy chain amino acid sequences

| Antibody | Full-Length Heavy Chain Amino Acid Sequence (SEQ ID NO) |
|---|---|
| Adalimumab (D2E7) | EVQLVESGGGLVQPGRSLRLSCAASGFTFDDYAMHWVRQAPGKGLEWVSA ITWNSGHIDYADSVEGRFTISRDNAKNSLYLQMNSLRAEDTAVYYCAKVSY LSTASSLDYWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFLY SKLTVDKSRWQQGNVFSCSVMHEALHNHYTQKSLSLSPGK (SEQ ID NO: 66) |
| infliximab | EVKLEESGGGLVQPGGSMKLSCVASGFIFSNHWMNWVRQSPEKGLEWVAE IRSKSINSATHYAESVKGRFTISRDDSKSAVYLQMTDLRTEDTGVYYCSRNY YGSTYDYWGQGTTLTVSSASTKGPSVFPLAPSSKSTSGGTAALGCLVKDYFP EPVTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKL TVDKSRWQQGNVFSCSVMHEALHNHYTQKSLSLSPGK (SEQ ID NO: 67) |
| certolizumab | EVQLVESGGGLVQPGGSLRLSCAASGYVFTDYGMNWVRQAPGKGLEWMG WINTYIGEPIYADSVKGRFTFSLDTSKSTAYLQMNSLRAEDTAVYYCARGY RSYAMDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCAA (SEQ ID NO: 68) |
| afelimomab | QVQLKESGPGLVAPSQSLSITCTVSGFSLTDYGVNWVRQPPGKGLEWLGMI WGDGSTDYDSTLKSRLSISKDNSKSQIFLKNNSLQTDDTARYYCAREWHHG PVAYWGQGTLVTVSAATTTAPSVYPLVPGCSDTSGSSVTLGCLVKGYFPEP VTVKWNYGALSSGVRTVSSVLQSGFYSLSSLVTVPSSTWPSQTVICNVAHPA SKTELIKRIEPRIPKPSTPPGSSCPPGNILGGPSVFIFPPKPKDALMISLTPKVTC VVVDVSEDDPDVHVSWFVDNKEVHTAWTQPREAQYNSTFRVVSALPIQHQ DWMRGKEFKCKVNNKALPAPIERTISKPKGRAQTPQVYTIPPPREQMSKKK VSLTCLVTNFFSEAISVEWERNGELEQDYKNTPPILDSDGTYFLYSKLTVDT DSWLQGEIFTCSVVHEALHNHHTQKNLSRSPGK (SEQ ID NO: 69) |
| ozoralizumab | EVQLVESGGGLVQPGGSLRLSCAASGFTFSDYWMYWVRQAPGKGLEWVSE INTNGLITKYPDSVKGRFTISRDNAKNTLYLQMNSLRPEDTAVYYCARSPSG FNRGQGTLVTVSSggggsggggsEVQLVESGGGLVQPGNSLRLSCAASGFTFSSF GMSWVRQAPGKGLEWVSSISGSGSDTLYADSVKGRFTISRDNAKTTLYLQM NSLRPEDTAVYYCTIGGSLSRSSQGTLVTVSSggggsggggsEVQLVESGGGLVQP GGSLRLSCAASGFTFSDYWMYWVRQAPGKGLEWVSEINTNGLITKYPDSV KGRFTISRDNAKNTLYLQMNSLRPEDTAVYYCARSPSGFNRGQGTLVTVSS (SEQ ID NO: 70) |
| placulumab | VEPKSSDKTHTCPPCPAPELLGGPSVFLFPPKPKDTLMISRTPEVTCVV VDVSHEDPEVKFNWYVDGVEVHNAKTKPREEQYNSTYRVVSVLTV LHQDWLNGKEYKCKVSNKALPAPIEKTISKAKGQPREPQVYTLPPSR DELTKNQVSLTCLVKGFYPSDIAVEWESNGQPENNYKTTPPVLDSDG SFFLYSKLTVDKSRWQQGNVFSCSVMHEALHNHYTQKSLSLSPGK (SEQ ID NO: 93)<br>RVEPKSSDKTHTCPPCPAPELLGGPSVFLFPPKPKDTLMISRTPEVTCV VVDVSHEDPEVKFNWYVDGVEVHNAKTKPREEQYNSTYRVVSVLT VLHQDWLNGKEYKCKVSNKALPAPIEKTISKAKGQPREPQVYTLPPS |

TABLE 5 -continued

Full-length heavy chain amino acid sequences

| Antibody | Full-Length Heavy Chain Amino Acid Sequence (SEQ ID NO) |
|---|---|
| | RDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGK<br>(SEQ ID NO: 71) |
| golimumab | QVQLVESGGGVVQPGRSLRLSCAASGFIFSSYAMHWVRQAPGNGLE<br>WVAFMSYDGSNKKYADSVKGRFTISRDNSKNTLYLQMNSLRAEDTA<br>VYYCARDRGIAAGGNYYYYGMDVWGQGTTVTVSSASTKGPSVFPL<br>APSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKT<br>HTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGK<br>EYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTV<br>DKSRWQQGNVFSCSVMHEALHNHYTQKSLSLSPGK (SEQ ID NO: 72) |

TABLE 6

Full-length light chain amino acid sequences

| Antibody | Full-length Light Chain Amino Acid Sequence (SEQ ID NO) |
|---|---|
| Adalimumab (D2E7) | DIQMTQSPSSLSASVGDRVTITCRASQGIRNYLAWYQQKPGKAPKLLIYAAS<br>TLQSGVPSRFSGSGSGTDFTLTISSLQPEDVATYYCQRYNRAPYTFGQGTKV<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC (SEQ ID NO: 73) |
| infliximab | DILLTQSPAILSVSPGERVSFSCRASQFVGSSIHWYQQRTNGSPRLLIKYASES<br>MSGIPSRFSGSGSGTDFTLSINTVESEDIADYYCQQSHSWPFTFGSGTNLEVK<br>RTVAAPSVFIFPPSDEQLKSGTASVVCLLNNFYPREAKVQWKVDNALQSGN<br>SQESVTEQDSKDSTYSLSSTLTLSKADYEKHKVYACEVTHQGLSSPVTKSFN<br>RGEC (SEQ ID NO: 74) |
| certolizumab | DIQMTQSPSSLSASVGDRVTITCKASQNVGTNVAWYQQKPGKAPKALIYSA<br>SFLYSGVPYRFSGSGSGTDFTLTISSLQPEDFATYYCQQYNIYPLTFGQGTKV<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC (SEQ ID NO: 75) |
| afelimomab | DIVMTQSHKFMSTTVGDRVSITCKASQAVSSAVAWYQQKPGQSPKLLIYWA<br>STRHTGVPDRFTGSGSVTDFTLTIHNLQAEDLALYYCQQHYSTPFTFGSGTK<br>LEIKRADAAPTVSIFPPSSEQLTSGGASVVCFLNNFYPKDINVKWKIDGSERQ<br>NGVLNSWTDQDSKDSTYSMSSTLTLTKDEYERHNSYTCEATHKTSTSPIVKS<br>FNRNEC (SEQ ID NO: 76) |
| placulumab | DIQMTQSPSSLSASVGDRVTITCRASQAIDSYLHWYQQKPGKAPKLLIYSAS<br>NLETGVPSRFSGSGSGTDFTLTISSLLPEDFATYYCQQVVWRPFTFGQGTKV<br>EIKR (SEQ ID NO: 77) |
| golimumab | EIVLTQSPATLSLSPGERATLSCRASQSVYSYLAWYQQKPGQAPRLLIYDAS<br>NRATGIPARFSGSGSGTDFTLTISSLEPEDFAVYYCQQRSNWPPFTFGPGTKV<br>DIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC (SEQ ID NO: 78) |

Also provided are antibodies or antigen-binding fragments that comprise a VH and a VL having at least 80% sequence identity to SEQ ID NOs: 50 and 59, 51 and 60, 52 and 61, 53 and 62, 54 and 63, or 58 and 65, respectively. or Also provided are antibodies or antigen-binding fragments that comprise a VH and a VL having at least 85% sequence identity to SEQ ID NOs: 50 and 59, 51 and 60, 52 and 61, 53 and 62, 54 and 63, or 58 and 65, respectively. Also provided are antibodies or antigen-binding fragments that comprise a VH and a VL having at least 85% sequence identity to SEQ ID NOs: 91 and 60, or 54 and 92, respectively. Also provided are antibodies or antigen-binding fragments that comprise a VH and a VL having at least 90% sequence identity to SEQ ID NOs: 50 and 59, 51 and 60, 52 and 61, 53 and 62, 54 and 63, or 58 and 65, respectively. Also provided are antibodies or antigen-binding fragments that comprise a VH and a VL having at least 90% sequence identity to SEQ ID NOs: 91 and 60, or 54 and 92, respectively. Also provided are antibodies or antigen-binding fragments that comprise a VH and a VL having at least 95% sequence identity to SEQ ID NOs: 50 and 59, 51 and 60, 52 and 61, 53 and 62, 54 and 63, or 58 and 65, respectively. Also provided are antibodies or antigen-binding fragments that comprise a VH and a VL having at least 95% sequence identity to SEQ ID NOs: 91 and 60, or 54 and 92, respectively. Also provided are antibodies or antigen-binding fragments that comprise a VH and a VL having at least 96% sequence identity to SEQ ID NOs: 50 and 59, 51 and 60, 52 and 61, 53 and 62, 54 and 63, or 58 and 65, respectively. Also provided are antibodies or antigen-binding fragments that comprise a VH and a VL having at least 96% sequence identity to SEQ ID NOs: 91 and 60, or 54 and 92, respectively. Also provided are antibodies or antigen-binding fragments that comprise a VH and a VL having at least 97% sequence identity to SEQ ID NOs: 50 and 59, 51 and 60, 52 and 61, 53 and 62, 54 and 63, or 58 and 65, respectively. Also provided are antibodies or antigen-binding fragments that comprise a VH and a VL having at least 97% sequence identity to SEQ ID NOs: 91 and 60, or 54 and 92, respectively. Also provided are antibodies or antigen-binding fragments that comprise a VH and a VL having at least 98% sequence identity to SEQ ID NOs: 50 and 59, 51 and 60, 52 and 61, 53 and 62, 54 and 63, or 58 and 65, respectively. Also provided are antibodies or antigen-binding fragments that comprise a VH and a VL having at least 98% sequence identity to SEQ ID NOs: 91 and 60, or 54 and 92, respectively. Also provided are antibodies or antigen-binding fragments that comprise a VH and a VL having at least 99% sequence identity to SEQ ID NOs: 50 and 59, 51 and 60, 52 and 61, 53 and 62, 54 and 63, or 58 and 65, respectively. Also provided are antibodies or antigen-binding fragments that comprise a VH and a VL having at least 99% sequence identity to SEQ ID NOs: 91 and 60, or 54 and 92, respectively.

Also provided are antibodies or antigen-binding fragments that comprise a VH and a VL having at least 80% sequence identity to SEQ ID NOs: 50 and 59, 51 and 60, 52 and 61, 53 and 62, 54 and 63, or 58 and 65, respectively, and contain the CDRs of SEQ ID NOs: 3 or 6, 4, 5, and 32-34; 7-9 and 35-37; 10 or 13, 11, 12, and 38-40; 14-16, and 41-43; 17-19 and 44-46; or 29-31 and 47-49, respectively.

Also provided are antibodies or antigen-binding fragments that comprise a VH and a VL having at least 80% sequence identity to SEQ ID NOs: 50 and 59, 91 and 60, or 54 and 92 respectively, and contain the CDRs of SEQ ID NOs: 3 or 6, 4, 94, and 32-34; 7-9 and 35-37; or 17-19 and 44-46, respectively. Also provided are antibodies or antigen-binding fragments that comprise a VH and a VL having at least 85% sequence identity to SEQ ID NOs: 50 and 59, 51 and 60, 52 and 61, 53 and 62, 54 and 63, or 58 and 65, respectively and contain the CDRs of SEQ ID NOs: 3 or 6, 4, 5, and 32-34; 7-9 and 35-37; 10 or 13, 11, 12, and 38-40; 14-16, and 41-43; 17-19 and 44-46; or 29-31 and 47-49, respectively. Also provided are antibodies or antigen-binding fragments that comprise a VH and a VL having at least 85% sequence identity to SEQ ID NOs: 50 and 59, 91 and 60, or 54 and 92 respectively, and contain the CDRs of SEQ ID NOs: 3 or 6, 4, 94, and 32-34; 7-9 and 35-37; or 17-19 and 44-46, respectively. Also provided are antibodies or antigen-binding fragments that comprise a VH and a VL having at least 90% sequence identity to SEQ ID NOs: 50 and 59, 51 and 60, 52 and 61, 53 and 62, 54 and 63, or 58 and 65, respectively and contain the CDRs of SEQ ID NOs: 3 or 6, 4, 5, and 32-34; 7-9 and 35-37; 10 or 13, 11, 12, and 38-40; 14-16, and 41-43; 17-19 and 44-46; or 29-31 and 47-49, respectively. Also provided are antibodies or antigen-binding fragments that comprise a VH and a VL having at least 90% sequence identity to SEQ ID NOs: 50 and 59, 91 and 60, or 54 and 92 respectively, and contain the CDRs of SEQ ID NOs: 3 or 6, 4, 94, and 32-34; 7-9 and 35-37; or 17-19 and 44-46, respectively. Also provided are antibodies or antigen-binding fragments that comprise a VH and a VL having at least 95% sequence identity to SEQ ID NOs: 50 and 59, 51 and 60, 52 and 61, 53 and 62, 54 and 63, or 58 and 65, respectively and contain the CDRs of SEQ ID NOs: 3 or 6, 4, 5, and 32-34; 7-9 and 35-37; 10 or 13, 11, 12, and 38-40; 14-16, and 41-43; 17-19 and 44-46; or 29-31 and 47-49, respectively. Also provided are antibodies or antigen-binding fragments that comprise a VH and a VL having at least 95% sequence identity to SEQ ID NOs: 50 and 59, 91 and 60, or 54 and 92 respectively, and contain the CDRs of SEQ ID NOs: 3 or 6, 4, 94, and 32-34; 7-9 and 35-37; or 17-19 and 44-46, respectively. Also provided are antibodies or antigen-binding fragments that comprise a VH and a VL having at least 96% sequence identity to SEQ ID NOs: 50 and 59, 51 and 60, 52 and 61, 53 and 62, 54 and 63, or 58 and 65, respectively and contain the CDRs of SEQ ID NOs: 3 or 6, 4, 5, and 32-34; 7-9 and 35-37; 10 or 13, 11, 12, and 38-40; 14-16, and 41-43; 17-19 and 44-46; or 29-31 and 47-49, respectively. Also provided are antibodies or antigen-binding fragments that comprise a VH and a VL having at least 96% sequence identity to SEQ ID NOs: 50 and 59, 91 and 60, or 54 and 92 respectively, and contain the CDRs of SEQ ID NOs: 3 or 6, 4, 94, and 32-34; 7-9 and 35-37; or 17-19 and 44-46, respectively. Also provided are antibodies or antigen-binding fragments that comprise a VH and a VL having at least 97% sequence identity to SEQ ID NOs: 50 and 59, 51 and 60, 52 and 61, 53 and 62, 54 and 63, or 58 and 65, respectively and contain the CDRs of SEQ ID NOs: 50 and 59, 51 and 60, 52 and 61, 53 and 62, 54 and 63, or 58 and 65, respectively. Also provided are antibodies or antigen-binding fragments that comprise a VH and a VL having at least 97% sequence identity to SEQ ID NOs: 50 and 59, 91 and 60, or 54 and 92 respectively, and contain the CDRs of SEQ ID NOs: 3 or 6, 4, 94, and 32-34; 7-9 and 35-37; or 17-19 and 44-46, respectively. Also provided are antibodies or antigen-binding fragments that comprise a VH and a VL having at least 98% sequence identity to SEQ ID NOs: 50 and 59, 51 and 60, 52 and 61, 53 and 62, 54 and 63, or 58 and 65, respectively and contain the CDRs of SEQ ID NOs: 3 or 6, 4, 5, and 32-34; 7-9 and 35-37; 10 or 13, 11, 12, and 38-40; 14-16, and 41-43; 17-19 and 44-46; or 29-31 and 47-49, respectively. Also provided are antibodies or antigen-binding fragments that comprise a VH and a VL having at least 98% sequence identity to SEQ ID NOs: 50 and 59, 91 and 60, or 54 and 92 respectively, and contain the CDRs of SEQ ID NOs: 3 or 6, 4, 94, and 32-34; 7-9 and 35-37; or 17-19 and 44-46, respectively. Also provided are antibodies or antigen-binding fragments that comprise a VH and a VL having at least 99% sequence identity to SEQ ID NOs: 50 and 59, 51 and 60, 52 and 61, 53 and 62, 54 and 63, or 58 and 65, respectively and contain the CDRs of SEQ ID NOs: 3 or 6, 4, 5, and 32-34; 7-9 and 35-37; 10 or 13, 11, 12, and 38-40; 14-16, and 41-43; 17-19 and 44-46; or 29-31 and 47-49, respectively. Also provided are antibodies or antigen-binding fragments that comprise a VH and a VL having at least 99% sequence identity to SEQ ID NOs: 50 and 59, 91 and 60, or 54 and 92 respectively, and contain the CDRs of SEQ ID NOs: 3 or 6, 4, 94, and 32-34; 7-9 and 35-37; or 17-19 and 44-46, respectively.

In certain embodiments, the anti-TNF alpha antibody or antigen-binding fragment thereof comprises the CDRs of SEQ ID NOs: 3-5 and 32-34 or of SEQ ID NOs: 6, 4, 5, and 32-34. In certain embodiments, the anti-TNF alpha antibody or antigen-binding fragment thereof comprises the CDRs of SEQ ID NOs: 3, 4, 94 and 32-34 or of SEQ ID NOs: 6, 4, 94, and 32-34. In certain embodiments, the anti-TNF alpha antibody or antigen-binding fragment thereof comprises the VH of SEQ ID NO:50 and/or the VL of SEQ ID NO:59. In certain embodiments, the anti-TNF alpha antibody comprises the heavy chain of SEQ ID NO: 66 and/or the light chain of SEQ ID NO:75.

F alpha antibody comprises the heavy chain of SEQ ID NO:74 and/or the light chain of SEQ ID NO:82.

In certain aspects, provided herein are antibodies or antigen-binding fragments thereof that specifically bind to TNF-alpha and comprise the Chothia VL CDRs of a VL of adalimumab, infliximab, certolizumab pegol, afelimomab, nerelimomab, ozoralizumab, placulumab, or golimumab. In certain aspects, provided herein are antibodies or antigen-binding fragments thereof that specifically bind to TNF-alpha and comprise the Chothia VH CDRs of a VH of adalimumab, infliximab, certolizumab pegol, afelimomab, nerelimomab, ozoralizumab, placulumab, or golimumab. In certain aspects, provided herein are antibodies or antigen-binding fragments thereof that specifically bind to TNF-alpha and comprise the Chothia VL CDRs of a VL of adalimumab, infliximab, certolizumab pegol, afelimomab, nerelimomab, ozoralizumab, placulumab, or golimumab and comprise the Chothia VH CDRs of a VH of adalimumab, infliximab, certolizumab pegol, afelimomab, nerelimomab, ozoralizumab, placulumab, or golimumab. In certain embodiments, antibodies or antigen-binding fragments that specifically bind to TNF-alpha comprise one or more CDRs, in which the Chothia and Kabat CDRs have the same amino acid sequence. In certain embodiments, provided herein are antibodies and antigen-binding fragments thereof that specifically bind to TNF-alpha and comprise combinations of Kabat CDRs and Chothia CDRs.

In a particular embodiment, provided herein are antibodies or antigen-binding fragments thereof that specifically bind to TNF-alpha and comprise CDRs of adalimumab, infliximab, certolizumab pegol, afelimomab, nerelimomab, ozoralizumab, placulumab, or golimumab as determined by the IMGT numbering system, for example, as described in Lefranc M-P (1999) supra and Lefranc M-P et al., (1999) supra).

In a particular embodiment, provided herein are antibodies that specifically bind to TNF-alpha and comprise CDRs of adalimumab, infliximab, certolizumab pegol, afelimomab, nerelimomab, ozoralizumab, placulumab, or golimumab as determined by the method in MacCallum R M et al.

In a particular embodiment, provided herein are antibodies or antigen-binding fragments thereof that specifically bind to TNF-alpha and comprise CDRs of adalimumab, infliximab, certolizumab pegol, afelimomab, nerelimomab, ozoralizumab, placulumab, or golimumab as determined by the AbM numbering scheme.

In a particular embodiment, provided herein are antibodies or antigen-binding fragments thereof that specifically bind to CD163.

Monoclonal antibodies can be prepared using hybridoma methods, such as those described by Kohler and Milstein (1975) Nature 256:495. Using the hybridoma method, a mouse, hamster, or other appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA); enzyme-linked immunosorbent assay (ELISA)) can then be propagated either in vitro culture using standard methods (God-ing, Monoclonal Antibodies: Principles and Practice, Academic Press, 1986) or in vivo as ascites tumors in an animal. The monoclonal antibodies can then be purified from the culture medium or ascites fluid as described for polyclonal antibodies.

Alternatively monoclonal antibodies can also be made using recombinant DNA methods as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the TNF-alpha is a humanized antibody. In certain embodiments, such antibodies are used therapeutically to reduce antigenicity and HAMA (human anti-mouse antibody) responses when administered to a human subject.

Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing TNF-alpha binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen e.g., TNF-alpha, and other favorable biological properties. To achieve this goal, humanized (or human) or engineered antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as TNF-alpha. In this way, framework (FR) residues can be selected and combined from the consensus and import sequences so that the desired antibody characteristic, such as increased affinity for the target antigen(s), is achieved.

Humanization, resurfacing or engineering of antibodies of the present disclosure can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; PCT/: US98/16280; US96/18978; US91/09630; US91/05939; US94/01234; GB89/01334; GB91/01134; GB92/01755; WO90/14443; WO90/14424; WO90/14430; EP 229246; 7,557,189; 7,538,195; and 7,342,110, each of which is entirely incorporated herein by reference, including the references cited therein.

In certain alternative embodiments, the antibody (e.g., an anti-TNFalpha antibody) is a human antibody. Human antibodies can be directly prepared using various techniques known in the art.

Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from E. coli or other host cells, thus allowing the production of large amounts of these fragments. Such antibody fragments can also be isolated from antibody phage libraries. The antibody fragment can also be linear antibodies as described in U.S. Pat. No. 5,641,870. Other techniques for the production of antibody fragments will be apparent to the skilled practitioner.

For the purposes of the present disclosure, it should be appreciated that modified antibodies can comprise any type of variable region that provides for the association of the antibody with the antigen (e.g., TNF alpha). In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g., cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present disclosure can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It may not be necessary to replace all of the CDRs with the complete CDRs from the donor variable region to transfer the antigen-binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Anti-TNF alpha proteins include soluble TNF receptor proteins. The anti-TNF alpha protein can be a soluble p75 TNF receptor. The anti-TNF alpha protein can be a soluble p55 TNF receptor.

The soluble TNF receptor can bind to both TNF alpha and TNF beta. The soluble TNF receptor can bind to TNF alpha, but not to TNF beta.

The soluble TNF receptor can inhibit binding of TNF alpha (and optionally TNF beta) to cell surface TNF receptors.

The soluble TNF receptor can be etanercept.

An anti-TNF alpha protein, e.g., a soluble TNF receptor, can be fused to a heavy chain constant domain or fragment thereof or an Fc region or fragment thereof. The heavy chain constant domain fragment or Fc fragment can be a portion of the constant domain or Fc that is capable of binding to Fc receptor. The heavy chain constant domain fragment or Fc fragment can be a portion of the constant domain or Fc that is capable of inducing cell lysis in vitro in the presence of complement. The heavy chain constant domain fragment or Fc fragment can be a portion of the constant domain or Fc that is capable of inducing ADCC.

The heavy chain constant domain or fragment thereof or Fc region or fragment thereof can be a human heavy chain constant domain or fragment thereof or human Fc region or fragment thereof. The heavy chain constant domain or fragment thereof or Fc region or fragment thereof can be an IgG1 heavy chain constant domain or fragment thereof or an IgG1 Fc region or fragment thereof. The heavy chain constant domain or fragment thereof or Fc region or fragment thereof can be a human IgG1 heavy chain constant domain or fragment thereof or human IgG1 Fc region or fragment thereof.

Those skilled in the art will appreciate that the antibodies and antigen-binding fragments thereof of this disclosure and the anti-TNF proteins of this disclosure include antibodies, antigen-binding fragments thereof, and anti-TNF proteins (e.g., full-length antibodies, antigen-binding fragments of antibodies, or soluble TNF receptor proteins) comprising one or more of constant region domains, including domains that have been altered so as to provide desired biochemical characteristics such as reduced serum half-life when compared with an antibody, antigen-binding fragment thereof, or anti-TNF protein of approximately the same immunogenicity comprising a native or unaltered constant region. In some embodiments, the constant region of the antibody, antigen-binding fragment thereof, or anti-TNF protein (e.g., full-length antibodies, antigen-binding fragments of antibodies, or soluble TNF receptor proteins) will comprise a human constant region. Modifications to the constant region compatible with this disclosure comprise additions, deletions, or substitutions of one or more amino acids in one or more domains. That is, the antibody, antigen-binding fragment thereof, or anti-TNF proteins (e.g., full-length antibodies, antigen-binding fragments of antibodies, or soluble TNF receptor proteins) disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the antibodies, antigen-binding fragments thereof, or anti-TNF proteins (e.g., full-length antibodies, antigen-binding fragments of antibodies, or soluble TNF receptor proteins) will comprise domain deleted constructs or variants wherein the entire CH2 domain has been removed (ΔCH2 constructs). In some embodiments, the omitted constant region domain will be replaced by a short amino acid spacer (e.g., 10 residues) that provides some of the molecular flexibility typically imparted by the absent constant region.

It will be noted that in certain embodiments, the antibodies, antigen-binding fragments thereof, or anti-TNF proteins (e.g., full-length antibodies, antigen-binding fragments of antibodies, or soluble TNF receptor proteins) can be engineered to fuse the CH3 domain directly to the hinge region of the respective antibodies, antigen-binding fragments thereof, or anti-TNF proteins (e.g., full-length antibodies, antigen-binding fragments of antibodies, or soluble TNF receptor proteins). In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the antibodies, antigen-binding fragments thereof, or anti-TNF proteins (e.g., full-length antibodies, antigen-binding fragments of antibodies, or soluble TNF receptor proteins).

It will be appreciated that the antibodies, antigen-binding fragments therof, and anti-TNF proteins (e.g., full-length antibodies, antigen-binding fragments of antibodies, or soluble TNF receptor proteins) of the present disclosure can be provided by the partial deletion or substitution of a few or even a single amino acid. For example, the mutation of a single amino acid in selected areas of the CH2 domain can be enough to substantially reduce Fc binding and thereby increase tumor localization. Similarly, it may be desirable to simply delete that part of one or more constant region domains that control the effector function (e.g., complement C1Q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies, antigen-binding fragments therof, and anti-TNF proteins (e.g., full-length antibodies, antigen-binding fragments of antibodies, or soluble TNF receptor proteins) can be modified through the mutation or substitution of one or more amino acids that enhances the profile of the resulting construct. In this respect it can be possible to disrupt the activity provided by a conserved binding site (e.g., Fc binding) while substantially maintaining the configuration and immunogenic profile of the antibodies, antigen-binding fragments therof, and anti-TNF proteins (e.g., full-length antibodies, antigen-binding fragments of antibodies, or soluble TNF receptor proteins). Certain embodiments can comprise the addition of one or more amino acids to the constant region to enhance desirable characteristics such as decreasing or increasing effector function or provide for more glucocorticoid receptor agonist attachment. In such embodiments it can be desirable to insert or replicate specific sequences derived from selected constant region domains.

It will be appreciated that the antibodies, antigen-binding fragments therof, and anti-TNF proteins (e.g., full-length antibodies, antigen-binding fragments of antibodies, or soluble TNF receptor proteins) of the present disclosure can be modified to reduce immunogenicity, i.e., to reduce the anti-drug immune response (ADA). Methods of doing so are disclosed, for example, in WO 2015/073884, which is herein incorporated by reference in its entirety.

The present disclosure further embraces variants and equivalents which are substantially homologous to antibodies, antigen-binding fragments therof, and anti-TNF proteins (e.g., full-length antibodies, antigen-binding fragments of antibodies, or soluble TNF receptor proteins) set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present disclosure can be recombinant polypeptides, natural polypeptides, or synthetic polypeptides of an antibody, antigen-binding fragment thereof, or anti-TNF protein. It will be recognized in the art that some amino acid sequences of the disclosure can be varied without significant effect of the structure or function of the protein. Thus, the disclosure further includes variations of the polypeptides which show substantial activity or which include regions of an antibody, antigen-binding fragment thereof, or anti-TNF alpha protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operativelyl inked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, antigen-binding fragments thereof, or anti-TNF proteins (e.g., full-length antibodies, antigen-binding fragments of antibodies, or soluble TNF receptor proteins). Recombinant expression vectors are replicable DNA constructs which have synthetic or cDNA-derived DNA fragments encoding a polypeptide chain of an antibody, antigen-binding fragment thereof, or anti-TNF protein (e.g., full-length antibodies, antigen-binding fragments of antibodies, or soluble TNF receptor proteins), operativelyl inked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operativelyl inked when they are functionally related to each other. For example, DNA for a signal peptide (secretory leader) is operativelyl inked to DNA for a polypeptide if it is expressed as a precursor which participates in the secretion of the polypeptide; a promoter is operativelyl inked to a coding sequence if it controls the transcription of the sequence; or a ribosome binding site is operativelyl inked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of antibodies, antigen-binding fragments thereof, and anti-TNF proteins (e.g., full-length antibodies, antigen-binding fragments of antibodies, or soluble TNF receptor proteins) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify anti-TNF proteins (e.g., full-length antibodies, antigen-binding fragments of antibodies, or soluble TNF receptor proteins). Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies, antigen-binding fragments thereof, and anti-TNF alpha proteins also include, for example, those described in U.S. Patent Publication Nos. 2008/0312425, 2008/0177048, and 2009/0187005, each of which is hereby incorporated by reference herein in its entirety.

III. Immunoconjugates Containing Glucocorticoid Receptor Agonists

Immunoconjugates containing glucocorticoid receptor agonists are provided herein. In some embodiments, an immunoconjugate provided herein binds to Fc gamma receptor. In some embodiments, an immunoconjugate provided herein is active in the GRE transmembrane TNF-alpha reporter assay (as used herein the "GRE transmembrane TNF-alpha reporter assay" refers to the assay used in Example 79 below). In some embodiments, an immunoconjugate provided herein is active in the L929 assay (as used herein, the "L929 assay" refers to the assay used in Example 82 below). In some embodiments, an immunoconjugate provided herein shows reduced immunogenicity (reduced anti-drug immune response (ADA)) as compared to the protein in the immunoconjugate (e.g., the antibody, antigen-binding fragment thereof, or soluble receptor) alone.

In one embodiment, disclosed herein is a compound having Formula I-a:

$$(SM-L-Q)_n-A^1 \qquad \text{I-a}$$

or a pharmaceutically acceptable salt thereof, wherein:

$A^1$ is an anti-tumor necrosis factor (TNF) alpha protein;

L is a linker;

Q is a heterobifunctional group or heterotrifunctional group; or

Q is absent;

n is 1-10; and

SM is a radical of a glucocorticosteroid.

In one embodiment, disclosed herein is a compound having Formula I-a:

$$(SM-L-Q)_n-A^1 \qquad \text{I-a}$$

or a pharmaceutically acceptable salt thereof, wherein:

$A^1$ is an anti-tumor necrosis factor (TNF) alpha antibody, an anti-TNF alpha monoclonal antibody, or adalimumab;

L is a linker;

Q is a heterobifunctional group or heterotrifunctional group; or

Q is absent;

n is 1-10; and

SM is a radical of a glucocorticosteroid.

In another embodiment, disclosed herein is a compound having Formula I-a, or a pharmaceutically acceptable salt thereof, wherein SM is a monovalent radical of a glucocorticosteroid.

In another embodiment, disclosed herein is a compound having Formula I-a, or a pharmaceutically acceptable salt thereof, wherein SM is a monovalent radical of a glucocorticosteroid selected from the group consisting of:

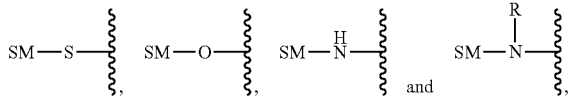

wherein the sulfur, oxygen, or nitrogen atom is attached directly or indirectly to the C- or D-ring of the glucocorticosteroid, and R is $C_{1-4}$ alkyl. In another embodiment, the sulfur, oxygen, or nitrogen atom is attached directly or indirectly to the D-ring of the glucocorticosteroid.

In another embodiment, disclosed herein is a compound having Formula I-a, or a pharmaceutically acceptable salt thereof, wherein SM is a monovalent radical of a glucocorticosteroid having Formula II-a:

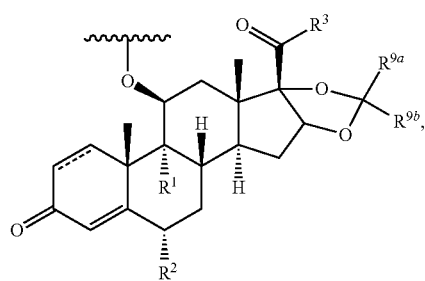

II-a wherein:

$R^1$ is selected from the group consisting of hydrogen and halo;

$R^2$ is selected from the group consisting of hydrogen, halo, and hydroxy;

$R^3$ is selected from the group consisting of —CH$_2$OH, —CH$_2$SH, —CH$_2$Cl, —SCH$_2$Cl, —SCH$_2$F, —SCH$_2$CF$_3$, —OH (or hydroxy), —OCH$_2$CN, —OCH$_2$Cl, —OCH$_2$F, —OCH$_3$, —OCH$_2$CH$_3$, —SCH$_2$CN,

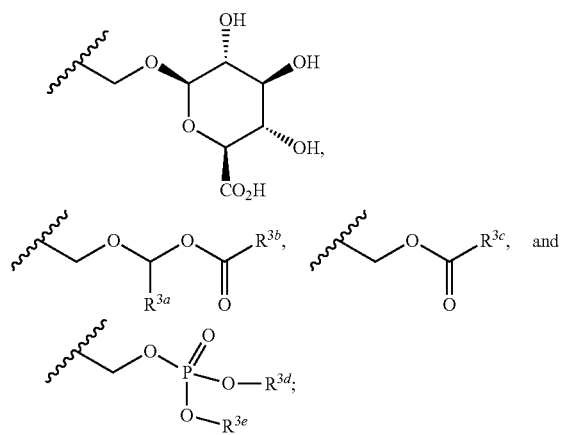

$R^{3a}$ is selected from the group consisting of hydrogen and $C_{1-4}$ alkyl;

$R^{3b}$ is selected from the group consisting of $C_{1-4}$ alkyl and $C_{1-4}$ alkoxy;

$R^{3c}$ is selected from the group consisting of hydrogen, $C_{1-4}$ alkyl, —CH$_2$OH, and $C_{1-4}$ alkoxy;

$R^{3d}$ and $R^{3e}$ are independently selected from hydrogen and $C_{1-4}$ alkyl;

$R^{9a}$ is selected from the group consisting of optionally substituted alkyl, optionally substituted cycloalkyl, optionally substituted aryl, and optionally substituted heteroaryl;

$R^{9b}$ is selected from the group consisting of hydrogen and alkyl; or $R^{9a}$ is:

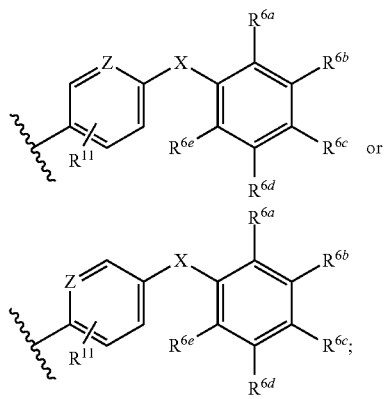

and $R^{9b}$ is hydrogen or methyl;

X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent;

t is 1 or 2;

Z is selected from the group consisting of =CH—, =C(OH)—, and =N—;

each $R^{4a}$ and $R^{4b}$ are independently selected from the group consisting of hydrogen and $C_{1-4}$ alkyl; or $R^{4a}$ and $R^{4b}$ taken together with the carbon atom to which they are attached form a 3- to 6-membered cycloalkyl;

$R^{4c}$ and $R^{4d}$ are independently selected from the group consisting of hydrogen and $C_{1-4}$ alkyl;

$R^5$ is selected from the group consisting of hydrogen and $C_{1-4}$ alkyl;

$R^{6a}$, $R^{6b}$, $R^{6c}$, $R^{6d}$, and $R^{6e}$ are each independently selected from the group consisting of hydrogen, halo, $C_{1-4}$ alkyl, $C_{1-4}$ haloalkyl, cyano, hydroxy, thiol, amino, alkylthio, and alkoxy;

$R^{8a}$ and $R^{8b}$ are independently selected from the group consisting of hydrogen and $C_{1-4}$ alkyl;

$R^{11}$ is selected from the group consisting of hydrogen, halo, $C_{1-4}$ alkyl, hydroxy, thiol, amino, alkylthio, and alkoxy; and ═══ represents a single or double bond.

In another embodiment, disclosed herein is a compound having Formula I-a, wherein SM is a monovalent radical of a glucocorticosteroid having Formula II-a, wherein $R^{9a}$ is:

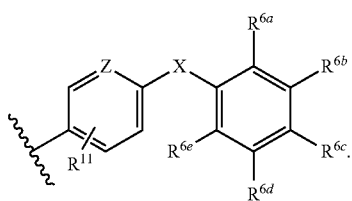

In another embodiment, disclosed herein is a compound having Formula I-a, wherein SM is a monovalent radical of a glucocorticosteroid having Formula II-a':

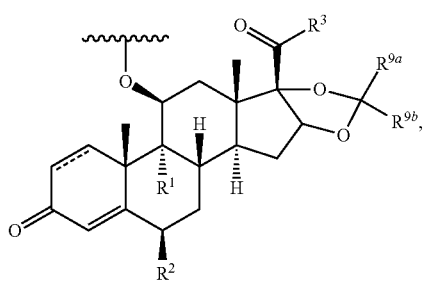

II-a' wherein $R^1$, $R^2$, $R^3$, $R^{9a}$, $R^{9b}$ and $===$ are as defined in connection with Formula II-a.

In another embodiment, disclosed herein is a compound having Formula I-a, wherein SM is a monovalent radical of a glucocorticosteroid having Formula II-b:

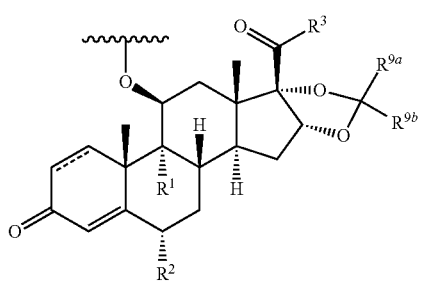

II-b wherein $R^1$, $R^2$, $R^3$, $R^{9a}$, $R^{9b}$, and $===$ are as defined in connection with Formula II-a.

In another embodiment, disclosed herein is a compound having Formula I-a, wherein SM is a monovalent radical of a glucocorticosteroid having Formula II-b':

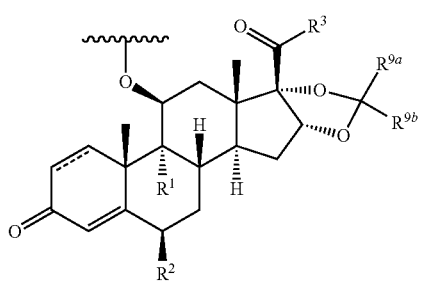

II-b' wherein $R^1$, $R^2$, $R^3$, $R^{9a}$, $R^{9b}$, and $===$ are as defined in connection with Formula II-a.

In another embodiment, iscjosedA herein is a compound having Formula I-a, or a pharmaceutically acceptable salt thereof, wherein SM is a monovalent radical of a glucocorticosteroid having Formula II-c:

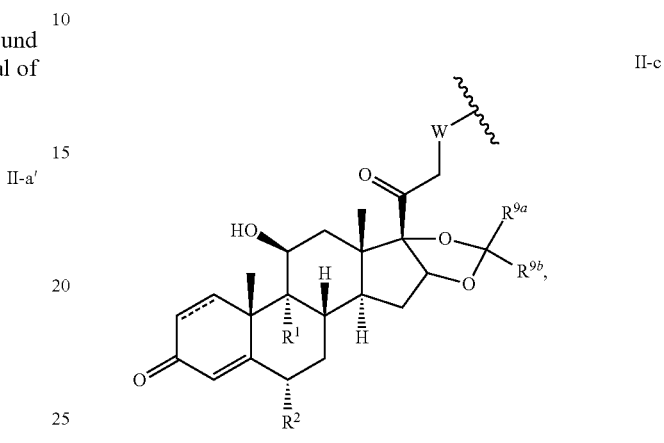

II-c wherein $R^1$, $R^2$, $R^{9a}$, $R^{9b}$, and $===$ are as defined in connection with Formula II-a; and W is selected from the group consisting of —O— and —S—. In another embodiment, W is —O—. In another embodiment, W is —S—.

In another embodiment, disclosed herein is a compound having Formula I-a, wherein SM is a monovalent radical of a glucocorticosteroid having Formula II-c':

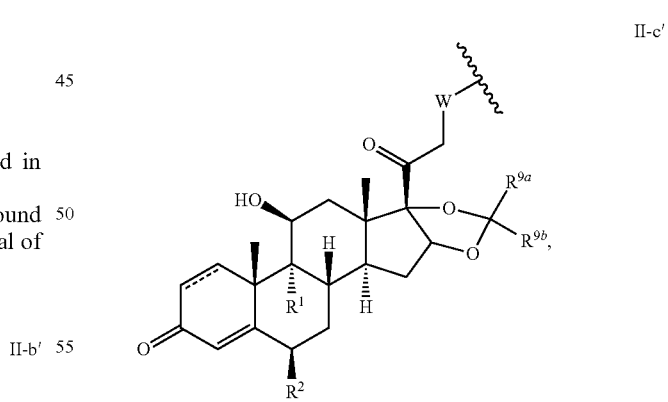

II-c' wherein $R^1$, $R^2$, $R^{9a}$, $R^{9b}$, W, and $===$ are as defined in connection with Formula II-c.

In another embodiment, disclosed herein is a compound having Formula I-a, or a pharmaceutically acceptable salt thereof, wherein SM is a monovalent radical of a glucocorticosteroid having Formula II-d:

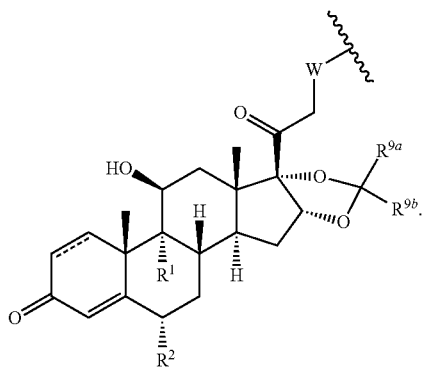

II-d wherein $R^1$, $R^2$, $R^{9a}$, $R^{9b}$, W, and === are as defined in connection with Formula II-c.

In another embodiment, disclosed herein is a compound having Formula I-a, wherein SM is a monovalent radical of a glucocorticosteroid having Formula II-d':

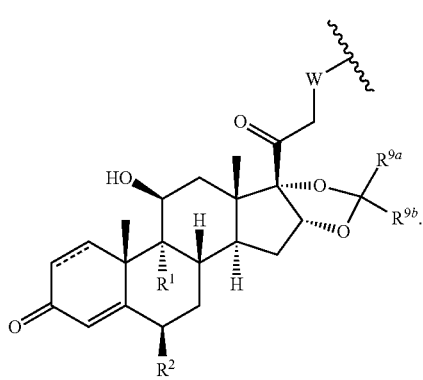

II-d' wherein $R^1$, $R^2$, $R^{9a}$, $R^{9b}$, W === and, are as defined in connection with Formula II-c.

In another embodiment, disclosed herein is a compound having Formula I-a, or a pharmaceutically acceptable salt thereof, wherein SM is a monovalent radical of a glucocorticosteroid having Formula II-e:

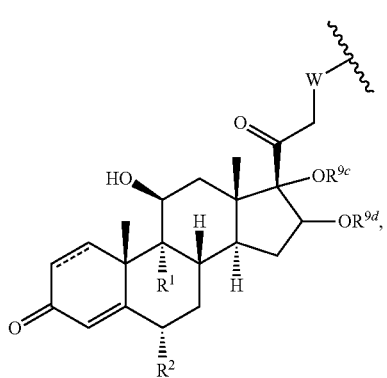

II-e wherein:
$R^1$, $R^2$, W, and === are as defined in connection with Formula II-c;

$R^{9c}$ is selected from the group consisting of hydrogen, $C_{1-4}$ alkyl, and —C(=O)$R^{9e}$;

$R^{9d}$ is selected from the group consisting of hydrogen, optionally substituted alkyl, optionally substituted cycloalkyl, optionally substituted aryl, and optionally substituted heteroaryl; and $R^{9e}$ is selected from the group consisting of hydrogen, optionally substituted alkyl, optionally substituted cycloalkyl, optionally substituted aryl, and optionally substituted heteroaryl.

In another embodiment, disclosed herein is a compound having Formula I-a, wherein SM is a monovalent radical of a glucocorticosteroid having Formula II-e':

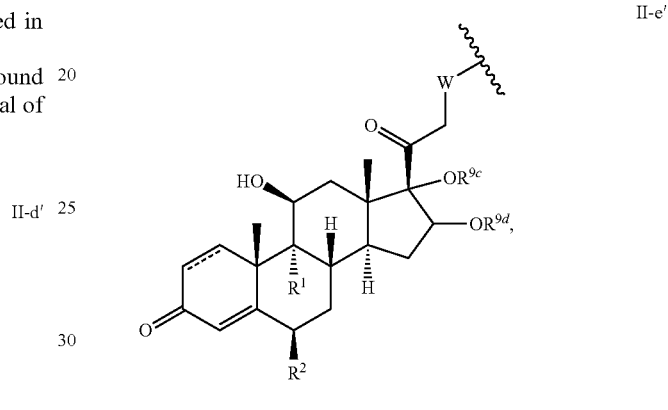

II-e' wherein $R^1$, $R^2$, W, $R^{9c}$, $R^{9d}$, and === are as defined in connection with Formula II-e.

In another embodiment, disclosed herein is a compound having Formula I-a, or a pharmaceutically acceptable salt thereof, wherein SM is a monovalent radical of a glucocorticosteroid having Formula II-f:

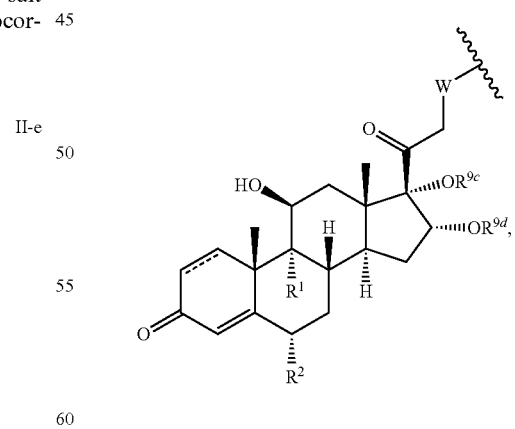

II-f wherein:
$R^1$, $R^2$, $R^{9c}$, $R^{9d}$, W, and === are as deed in connection with Formula II-e.

In another embodiment, disclosed herein is a compound having Formula I-a, wherein SM is a monovalent radical of a glucocorticosteroid having Formula II-f':

II-f'

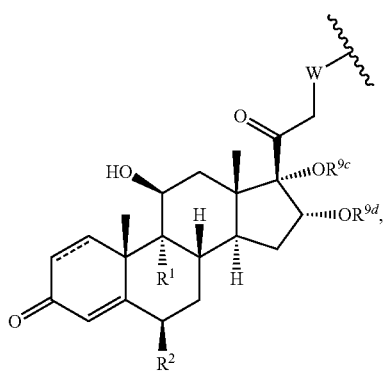

wherein $R^1$, $R^2$, $R^{9c}$, $R^{9d}$, W, and ⹀ are as defined in connection with Formula II-e.

In another embodiment, disclosed herein is a compound having Formula I-b:

$$(SM-L-Q)_n-A^2 \qquad \text{I-b}$$

or a pharmaceutically acceptable salt thereof, wherein:

$A^2$ is a protein;

L is a linker;

Q is a heterobifunctional group or heterotrifunctional group; or

Q is absent;

n is 1-10; and

SM is a monovalent radical of a glucocorticosteroid having any one of:

(1) Formula II-l:

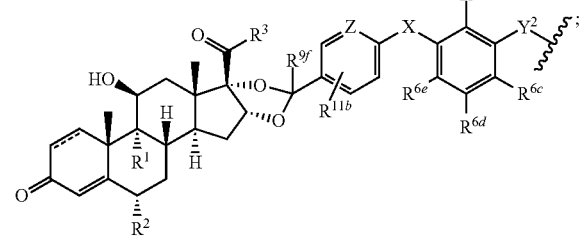

II-l (2) Formula II-m:

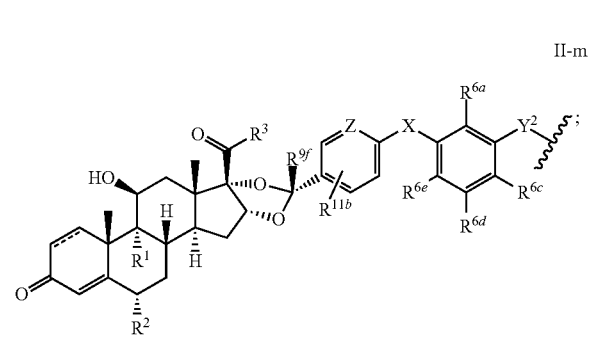

II-m (3) Formula II-n:

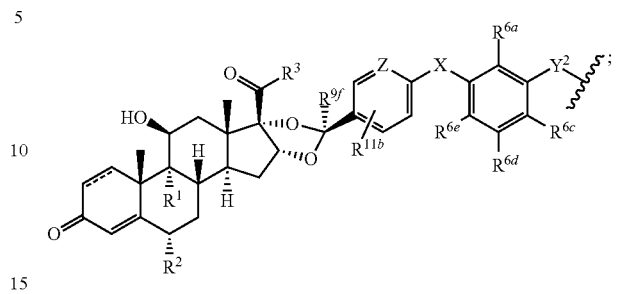

II-n (4) Formula II-o:

II-o (5) Formula II-p:

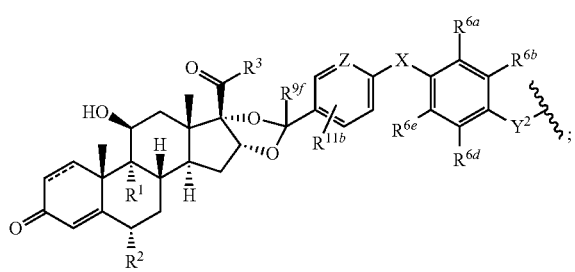

II-p (6) Formula II-q:

II-q wherein:

$R^1$ is selected from the group consisting of hydrogen and halo;

$R^2$ is selected from the group consisting of hydrogen, halo, and hydroxy;

$R^3$ is selected from the group consisting of —CH$_2$OH, —CH$_2$SH, —CH$_2$Cl, —SCH$_2$Cl, —SCH$_2$F, —SCH$_2$CF$_3$, —OH, —OCH$_2$CN, —OCH$_2$Cl, —OCH$_2$F, —OCH$_3$, —OCH$_2$CH$_3$, —SCH$_2$CN,

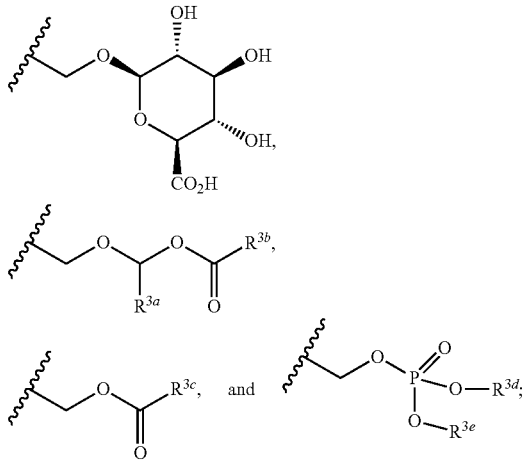

$R^{3a}$ is selected from the group consisting of hydrogen and C$_{1-4}$ alkyl;
$R^{3b}$ is selected from the group consisting of C$_{1-4}$ alkyl and C$_{1-4}$ alkoxy;
$R^{3c}$ is selected from the group consisting of hydrogen, C$_{1-4}$ alkyl, —CH$_2$OH, and C$_{1-4}$ alkoxy;
$R^{3d}$ and $R^{3e}$ are independently selected from hydrogen and C$_{1-4}$ alkyl;
$R^{6a}$, $R^{6b}$, $R^{6c}$, $R^{6d}$, and $R^{6e}$ are each independently selected from the group consisting of hydrogen, halo, C$_{1-4}$ alkyl, C$_{1-4}$ haloalkyl, cyano, hydroxy, thiol, amino, alkylthio, and alkoxy;
X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$— (including both E and Z isomers), and —C≡C—; (wherein when X is —CH$_2$S—, —CH$_2$O—, or —N(H)C(R$^{8a}$)(R$^{8b}$)—, the hetereoatom of —CH$_2$S—, —CH$_2$O—, or —N(H)C(R$^{8a}$)(R$^{8b}$)— can be attached to either 6-membered ring, i.e., —CH$_2$S— is equivalent to —SCH$_2$—, —CH$_2$O— is equivalent to —OCH$_2$—, and —N(H)C(R$^{8a}$)(R$^{8b}$)— is equivalent to —C(R$^{8a}$)(R$^{8b}$)N(H)—); or
X is absent, i.e., X represents a chemical bond;
$Y^2$ is selected from the group consisting of —O—, —S—, and —N(R$^{7a}$)—; or
$Y^2$ is absent, i.e., $Y^2$ represents a chemical bond;
t is 1 or 2;
Z is selected from the group consisting of =CR$^{11a}$— and =N—;
each $R^{4a}$ and $R^{4b}$ are independently selected from the group consisting of hydrogen and C$_{1-4}$ alkyl; or
$R^{4a}$ and $R^{4b}$ taken together with the carbon atom to which they are attached form a 3- to 6-membered cycloalkyl;
$R^{4c}$ and $R^{4d}$ are independently selected from the group consisting of hydrogen and C$_{1-4}$ alkyl;
$R^5$ is selected from the group consisting of hydrogen and C$_{1-4}$ alkyl;
$R^{7a}$ is selected from the group consisting of hydrogen and C$_{1-4}$ alkyl;
$R^{8a}$ and $R^{8b}$ are independently selected from the group consisting of hydrogen and C$_{1-4}$ alkyl;

$R^{9f}$ is selected from the group consisting of hydrogen and C$_{1-4}$ alkyl;
$R^{11a}$ and $R^{11b}$ are independently selected from the group consisting of hydrogen, halo, C$_{1-4}$ alkyl, C$_{1-4}$ haloalkyl, cyano, hydroxy, thiol, amino, alkylthio, and alkoxy; and
═ represents a single or double bond.

In another embodiment, disclosed herein is a compound having Formula I-b:

wherein:
$A^2$ is a protein;
L is a linker;
Q is a heterobifunctional group or heterotrifunctional group; or
Q is absent;
n is 1-10; and
SM is a monovalent radical having any one of:
(1) Formula II-l':

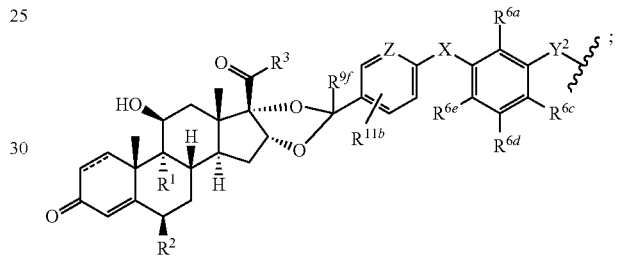

(2) Formula II-m':

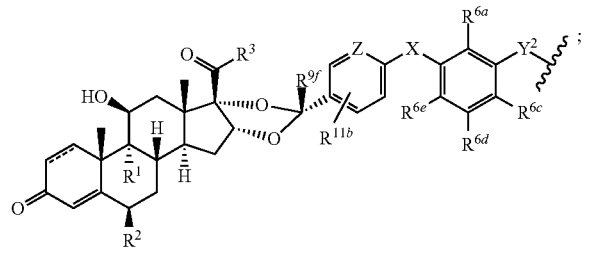

(3) Formula II-n':

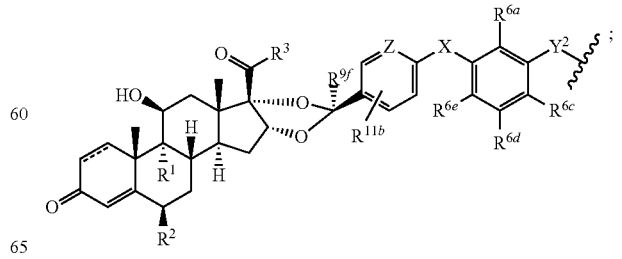

(4) Formula II-o':

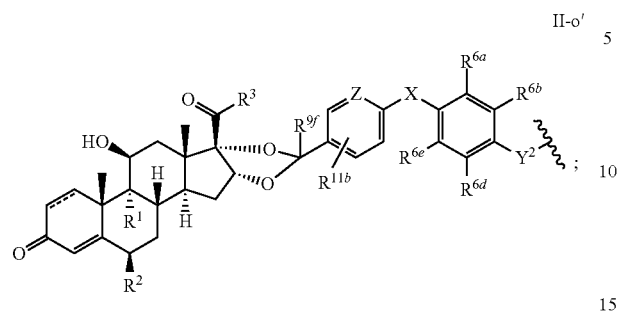

(5) Formula II-p':

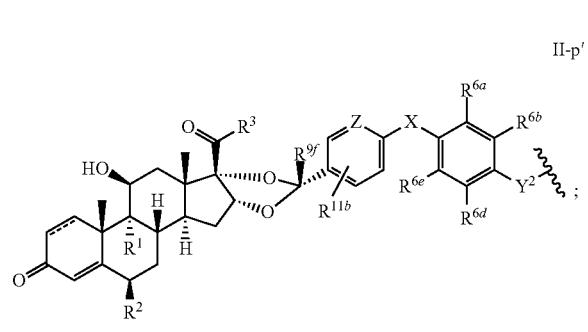

(6) Formula II-q':

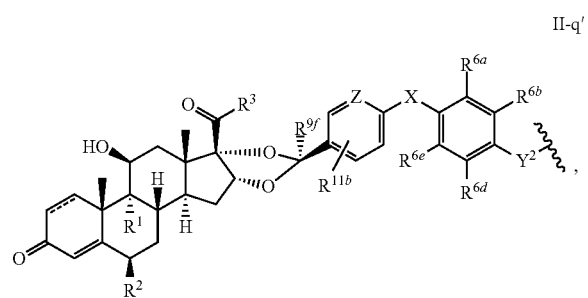

wherein $R^1$, $R^2$, $R^3$, ===, $R^{6a}$, $R^{6c}$, $R^{6d}$, $R^{6e}$, $R^{9f}$, $R^{11b}$, $Y^2$, X, and Z are as defined in connection with Formula II-l.

In another embodiment, disclosed herein is a compound having Formula I-b:

$(SM-L-Q)_n-A^2$  I-b, wherein:

$A^2$ is a protein;

L is a linker;

Q is a heterobifunctional group or heterotrifunctional group; or

Q is absent;

n is 1-10; and

SM is a monovalent radical having any one of:

(1) Formula II-l":

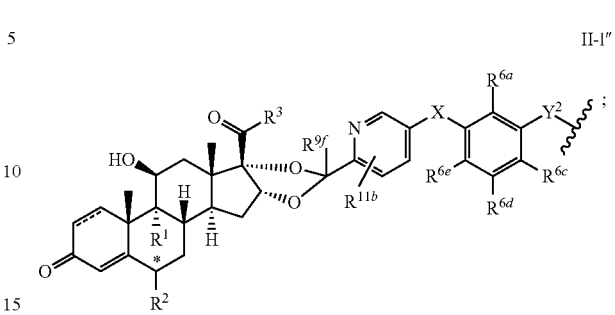

(2) Formula II-m":

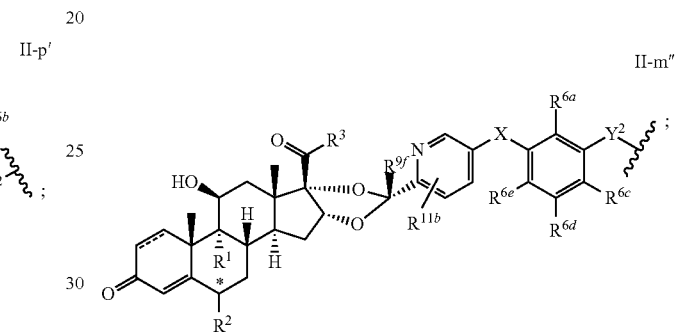

(3) Formula II-n":

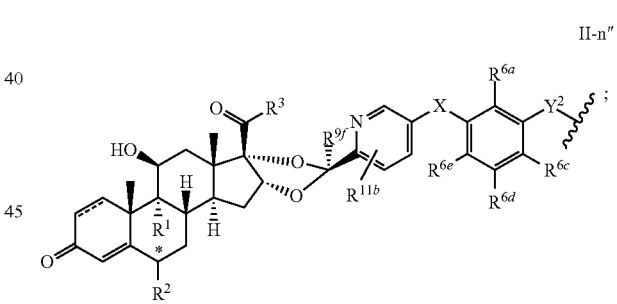

(4) Formula II-o":

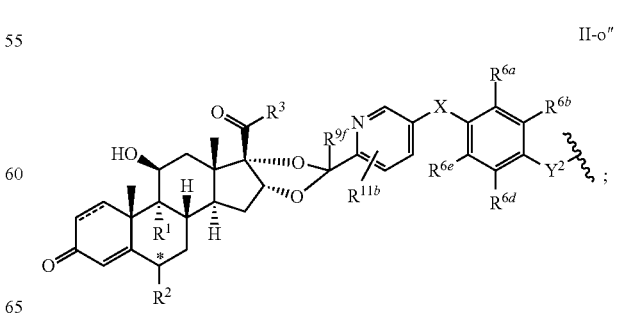

(5) Formula II-p":

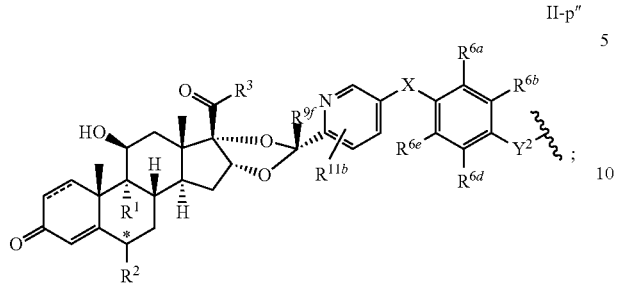

(6) Formula II-q":

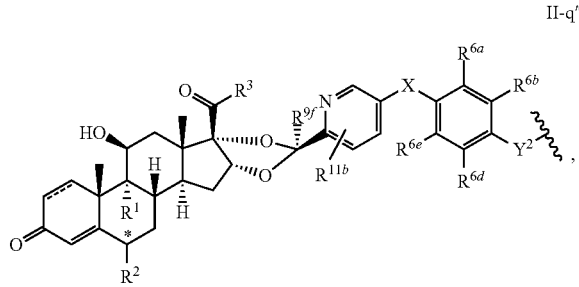

wherein $R^1$, $R^2$, $R^3$, ===, $R^{6a}$, $R^{6c}$, $R^{6d}$, $R^{6e}$, $R^{9f}$, $R^{11b}$, $Y^2$, and X are as defined in connection with Formula II-l, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having Formula I-a or I-b, or a pharmaceutically acceptable salt thereof, wherein SM is a monovalent radical of a glucocorticosteroid having Formula II-l:

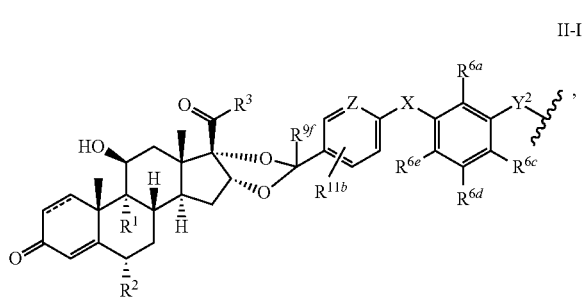

wherein:

$R^1$ is selected from the group consisting of hydrogen and halo;

$R^2$ is selected from the group consisting of hydrogen, halo, and hydroxy;

$R^3$ is selected from the group consisting of —CH$_2$OH, —CH$_2$SH, —CH$_2$Cl, —SCH$_2$Cl, —SCH$_2$F, —SCH$_2$CF$_3$, —OH, —OCH$_2$CN, —OCH$_2$Cl, —OCH$_2$F, —OCH$_3$, —OCH$_2$CH$_3$, —SCH$_2$CN,

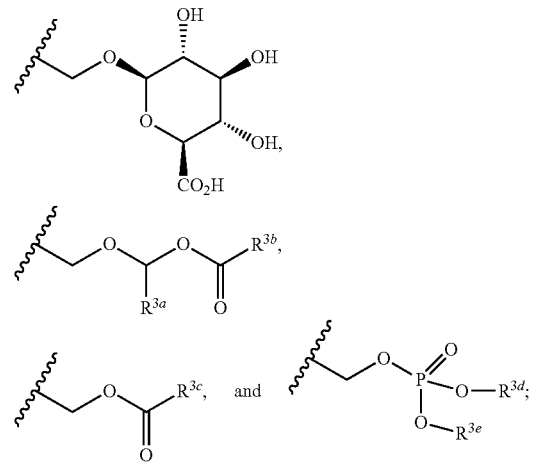

$R^{3a}$ is selected from the group consisting of hydrogen and $C_{1-4}$ alkyl;

$R^{3b}$ is selected from the group consisting of $C_{1-4}$ alkyl and $C_{1-4}$ alkoxy;

$R^{3c}$ is selected from the group consisting of hydrogen, $C_{1-4}$ alkyl, —CH$_2$OH, and $C_{1-4}$ alkoxy;

$R^{3d}$ and $R^{3e}$ are independently selected from hydrogen and $C_{1-4}$ alkyl;

X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent;

t is 1 or 2;

Z is selected from the group consisting of =CR$^{11a}$— and =N—;

each $R^{4a}$ and $R^{4b}$ are independently selected from the group consisting of hydrogen and $C_{1-4}$ alkyl; or $R^{4a}$ and $R^{4b}$ taken together with the carbon atom to which they are attached form a 3- to 6-membered cycloalkyl;

$R^{4c}$ and $R^{4d}$ are independently selected from the group consisting of hydrogen and $C_{1-4}$ alkyl;

$R^5$ is selected from the group consisting of hydrogen and $C_{1-4}$ alkyl;

$R^{6a}$, $R^{6c}$, $R^{6d}$, and $R^{6e}$ are each independently selected from the group consisting of hydrogen, halo, $C_{1-4}$ alkyl, $C_{1-4}$ haloalkyl, cyano, hydroxy, thiol, amino, alkylthio, and alkoxy;

$Y^2$ is selected from the group consisting of —O—, —S—, and —N(R$^{7a}$)—; or $Y^2$ is absent;

$R^{7a}$ is selected from the group consisting of hydrogen and $C_{1-4}$ alkyl;

$R^{8a}$ and $R^{8b}$ are independently selected from the group consisting of hydrogen and $C_{1-4}$ alkyl;

$R^{9f}$ is selected from the group consisting of hydrogen and $C_{1-4}$ alkyl;

$R^{11a}$ and $R^{11b}$ are independently selected from the group consisting of hydrogen, halo, $C_{1-4}$ alkyl, $C_{1-4}$ haloalkyl, cyano, hydroxy, thiol, amino, alkylthio, and alkoxy; and === represents a single or double bond.

In another embodiment, disclosed herein is a compound having Formula I-a or I-b, or a pharmaceutically acceptable salt thereof, wherein SM is a monovalent radical of a glucocorticosteroid having Formula II-m:

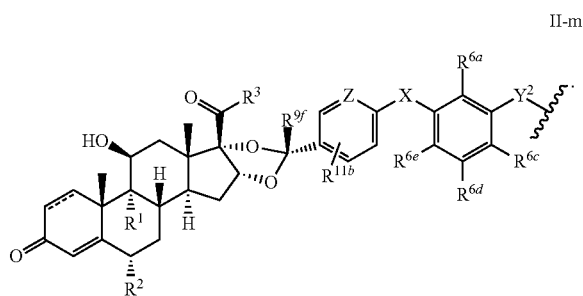

II-m

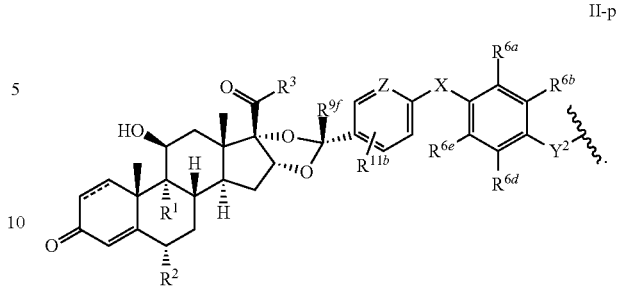

II-p wherein $R^1$, $R^2$, $R^3$, ===, $R^{6a}$, $R^{6c}$, $R^{6d}$, $R^{6e}$, $R^{9f}$, $R^{11b}$, $Y^2$, X, and Z are as defined in connection with Formula II-l.

In another embodiment, disclosed herein is a compound having Formula I-a or Ib, or a pharmaceutically acceptable salt thereof, wherein SM is a monovalent radical of a glucocorticosteroid having Formula II-n:

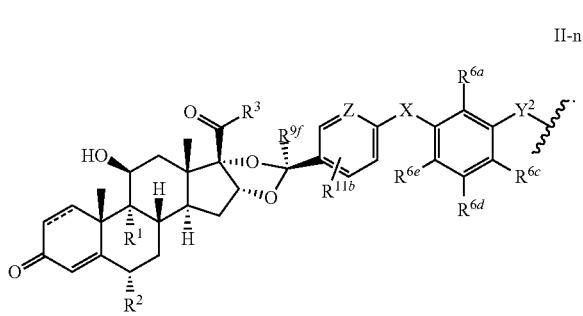

II-n wherein $R^1$, $R^2$, $R^3$, ===, $R^{6a}$, $R^{6c}$, $R^{6d}$, $R^{6e}$, $R^{9f}$, $R^{11b}$, $y^2$, X, and Z are as defined in connection with Formula II-l.

In another embodiment, disclosed herein is a compound having Formula I-a or I-b, or a pharmaceutically acceptable salt thereof, wherein SM is a monovalent radical of a glucocorticosteroid having Formula II-o:

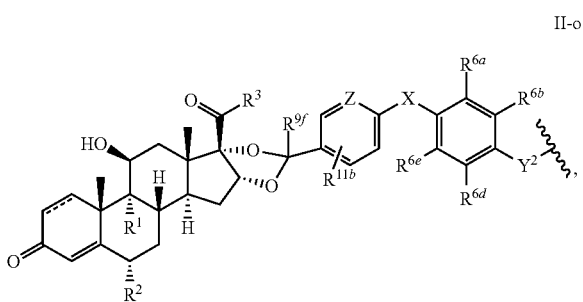

II-o wherein $R^1$, $R^2$, $R^3$, ===, $R^{6a}$, $R^{6d}$, $R^{6e}$, $R^{9f}$, $R^{11b}$, $Y^2$, X, and Z are as defined in connection with Formula II-l; and $R^{6b}$ is selected from the group consisting of hydrogen, halo, $C_{1-4}$ alkyl, $C_{1-4}$ haloalkyl, cyano, hydroxy, thiol, amino, alkylthio, and alkoxy.

In another embodiment, disclosed herein is a compound having Formula I-a or I-b, or a pharmaceutically acceptable salt thereof, wherein SM is a monovalent radical of a glucocorticosteroid having Formula II-p:

wherein $R^1$, $R^2$, $R^3$, ===, $R^{6a}$, $R^{6b}$, $R^{6d}$, $R^{6e}$, $R^{9f}$, $R^{11b}$ $Y^2$, X, and Z are as defined in connection with Formula II-o.

In another embodiment, disclosed herein is a compound having Formula I-a or I-b, or a pharmaceutically acceptable salt thereof, wherein SM is a monovalent radical of a glucocorticosteroid having Formula II-q:

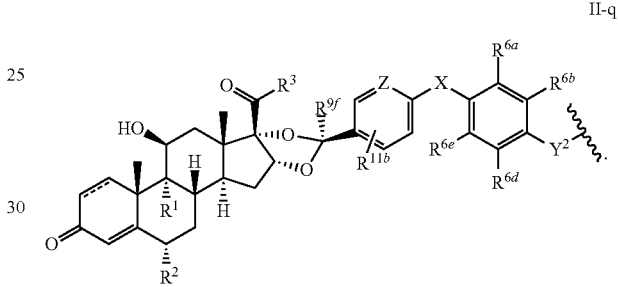

II-q wherein $R^1$, $R^2$, $R^3$, ===, $R^{6a}$, $R^{6b}$, $R^{6d}$, $R^{6e}$, $R^{9f}$, $R^{11b}$, $Y^2$, X, and Z are as defined in connection with Formula II-o.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein === represents a double bond.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein === is selected from the group consisting of hydrogen and fluoro.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein $R^2$ is selected from the group consisting of hydrogen and fluoro.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-l, II-m, II-n, II-o, II-p, or II-q, or any one of Formulae II-a', II-b', II-l', II-m', II-n', II-o', II-p', II-q', II-l", II-m", II-n", II-o", II-p", or II-q", wherein R³ is selected from the group consisting of —CH₂OH, —CH₂Cl, —SCH₂Cl, —SCH₂F, and —OH.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-l, II-m, II-n, II-o, II-p, or II-q, or any one of Formulae II-a', II-b', II-l', II-m', II-n', II-o', II-p', II-q', II-l", II-m", II-n", II-o", II-p", or II-q", wherein:

R³ is selected from the group consisting of:

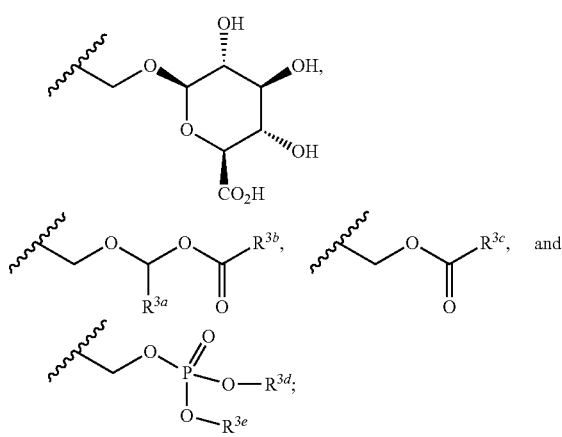

R$^{3a}$ is selected from the group consisting of hydrogen and methyl;

R$^{3b}$ is selected from the group consisting of methyl, ethyl, isopropyl, isobutyl, methoxy, ethoxy, isopropoxy, and isobutoxy;

R$^{3c}$ is selected from the group consisting of hydrogen, methyl, ethyl, —CH₂OH, methoxy, ethoxy, and isopropoxy;

R$^{3d}$ and R$^{3e}$ are independently selected from the group consisting of hydrogen, methyl, and ethyl.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-l, II-m, II-n, II-o, II-p, or II-q, or any one of Formulae II-a', II-b', II-c', II-d', II-l', II-m', II-n', II-o', II-p', II-q', II-l", II-m", II-n", II-o", II-p", or II-q", wherein R⁵ and R$^{8a}$ are independently selected from the group consisting of hydrogen and methyl.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-l, II-m, II-n, II-o, II-p, or II-q, or any one of Formulae II-a', II-b', II-c', II-d', II-l', II-m', II-n', II-o', II-p', II-q', II-l", II-m", II-n", II-o", II-p", or II-q", wherein Z is =CH—.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-l, II-m, II-n, II-o, II-p, or II-q, or any one of Formulae II-a', II-b', II-c', II-d', II-l', II-m', II-n', II-o', II-p', II-q', II-l", II-m", II-n", II-o", II-p", or II-q", wherein Z is =N—.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-l, II-m, II-n, II-o, II-p, or II-q, or any one of Formulae II-a', II-b', II-c', II-d', II-l', II-m', II-n', II-o', II-p', II-q', II-l", II-m", II-n", II-o", II-p", or II-q", wherein R$^{6a}$, R$^{6d}$, and R$^{6e}$ are hydrogen.

In another embodiment, disclosed herein is a compound having Formula I-a or I-b, or a pharmaceutically acceptable salt thereof, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein Y² is —N(R$^{7a}$)—. In another embodiment, R$^{7'}$ is selected from the group consisting of hydrogen and methyl. In another embodiment, R$^{7'}$ is hydrogen. In another embodiment, R$^{7'}$ is methyl.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-l, II-m, II-n, II-o, II-p, or II-q, or any one of Formulae II-a', II-b', II-c', II-d', II-l', II-m', II-n', II-o', II-p', II-q', II-l", II-m", II-n", II-o", II-p", or II-q", wherein:

X is selected from the group consisting of —(CR$^{4a}$R$^{4b}$)$_t$—, —O—, —S—, —S(=O)—, —S(=O)₂—, —CH₂S—, and —N(H)CH(R$^{8a}$)—;

t is 1;

R$^{4a}$ and R$^{4b}$ are independently selected from the group consisting of hydrogen and methyl; or R$^{4a}$ and R$^{4b}$ taken together with the carbon atom to which they are attached form a 3-membered cycloalkyl; and R$^{8a}$ is selected from the group consisting of hydrogen and methyl. In another embodiment, X is —CH₂—. In another embodiment, X is selected from the group consisting of:

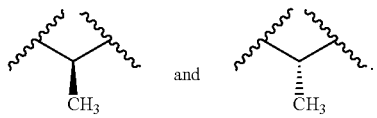

In another embodiment, X is —O—. In another embodiment, X is —S—. In another embodiment, X is —CH₂S—. In another embodiment, X is —N(H)CH₂—. In another embodiment, X is selected from the group consisting of:

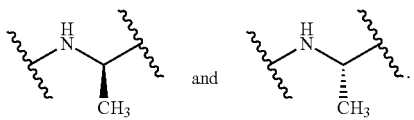

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-l, II-m, or II-n, or any one of Formulae II-a', II-b', II-c', II-d', II-l', II-m', II-n', II-l", II-m", or II-n", wherein R$^{6c}$ is selected from the group consisting of hydrogen, —Cl, —OMe (or —OCH₃), and —OH.

In another embodiment, disclosed herein is a compound having Formula I-a or I-b, or a pharmaceutically acceptable salt thereof, wherein SM is a monovalent radical of a glucocorticosteroid having any one of Formulae II-a, II-b, II-c, II-d, II-o, II-p, or II-q, or any one of Formulae II-a', II-b', II-c', II-d', II-o', II-p', II-q', II-o", II-p", or II-q" wherein $R^{6b}$ is selected from the group consisting of hydrogen, —Cl, —OMe (or —OCH$_3$), and —OH.

In another embodiment, disclosed herein is a compound having Formula I-a or I-b, or a pharmaceutically acceptable salt thereof, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $R^{9f}$ is hydrogen.

In another embodiment, disclosed herein is a compound having Formula I-a or I-b, or a pharmaceutically acceptable salt thereof, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $R^{9f}$ is methyl.

In another embodiment, disclosed herein is a compound having Formula I-a or I-b, or a pharmaceutically acceptable salt thereof, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $R^{11a}$ is selected from the group consisting of hydrogen and —OH.

In another embodiment, disclosed herein is a compound having Formula I-a or I-b, or a pharmaceutically acceptable salt thereof, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $R^{11b}$ is hydrogen.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein L is a cleavable linker. In another embodiment, the cleavable linker comprises a succinimide, amide, thiourea, thioether, oxime, or self-immolative group, or a combination thereof. In another embodiment, the cleavable linker comprises a peptide. In another embodiment, the cleavable linker comprises a tripeptide. In another embodiment, the cleavable linker comprises a dipeptide. In another embodiment, the cleavable linker comprises phosphate ester. In another embodiment, the cleavable linker comprises a pyrophosphate diester.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein Q is absent.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein Q is a heterobifunctional group.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein Q is a heterobifunctional group selected from the group consisting of:

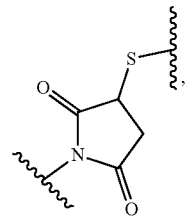

Q-1

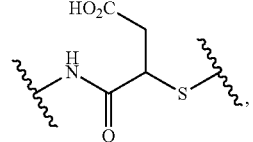

Q-2

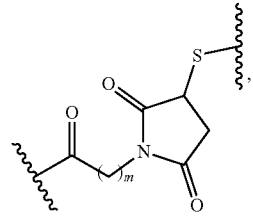

Q-3

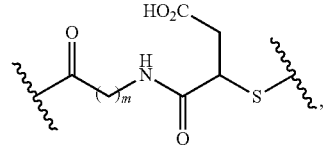

Q-4

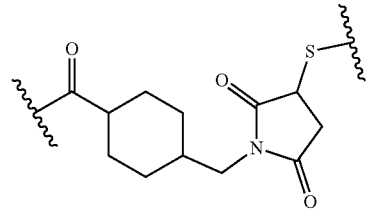

Q-5 and

-continued

Q-6

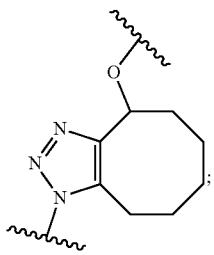

wherein m is 1, 2, 3, 4, 5, or 6. In another embodiment, Q is selected from the group consisting of Q-1, Q-2, Q-3, and Q-4. In another embodiment, Q is selected from the group consisting of Q-3 and Q-4. In another embodiment, m is 2.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein Q is a heterotrifunctional group.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein Q is a heterotrifunctional group that is:

Q-7

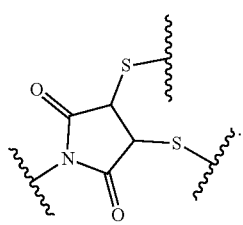

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein -L-Q- is:

LQ-1

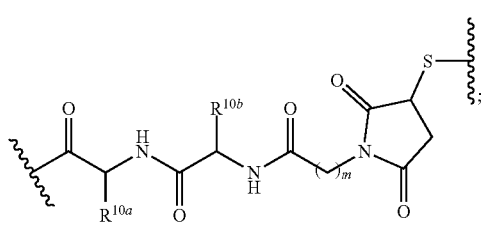

m is 2 or 3; and $R^{10a}$ and $R^{10b}$ are independently selected from the group consisting of hydrogen and optionally substituted $C_{1-6}$ alkyl.

In another embodiment, m is 2. In another embodiment, m is 1. In another embodiment, -L-Q- is:

LQ-2

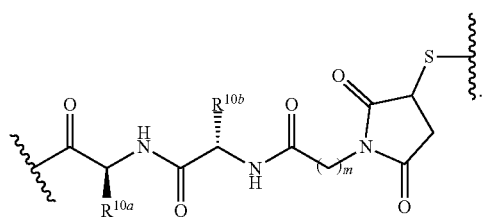

In another embodiment, -L-Q- is:

LQ-3

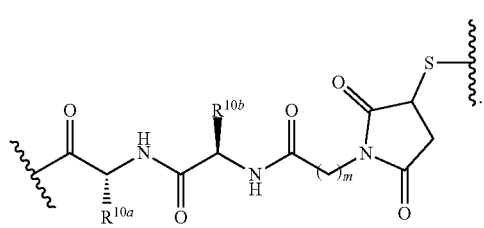

In another embodiment, -L-Q- is:

LQ-4

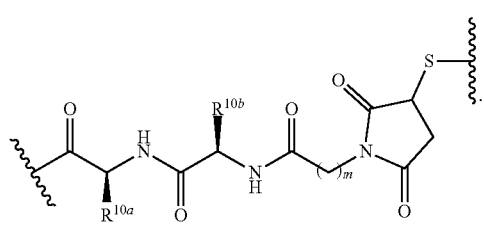

In another embodiment, -L-Q- is:

LQ-5

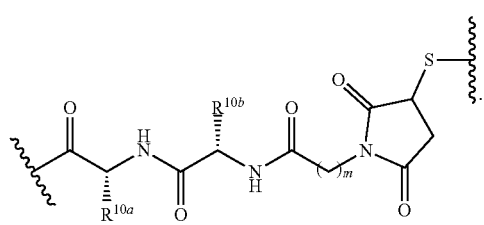

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein -L-Q- is:

LQ-6

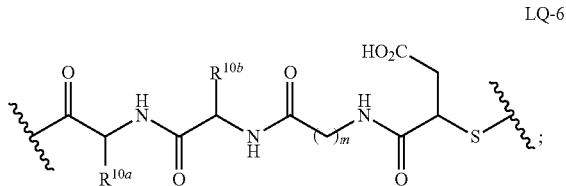

m is 2 or 3; and

R$^{10a}$ and R$^{10b}$ are independently selected from the group consisting of hydrogen and optionally substituted C$_{1-6}$ alkyl. In another embodiment, m is 2. In another embodiment, -L-Q- is:

LQ-7

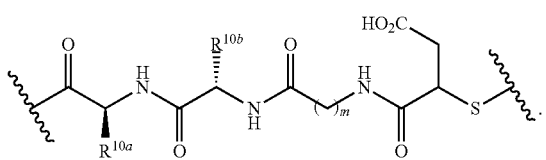

In another embodiment, -L-Q- is:

LQ-8

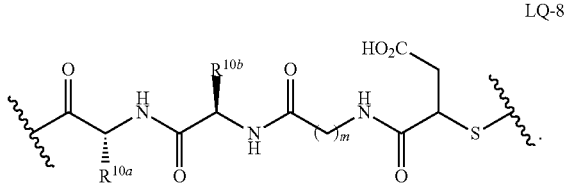

In another embodiment, -L-Q- is:

LQ-9

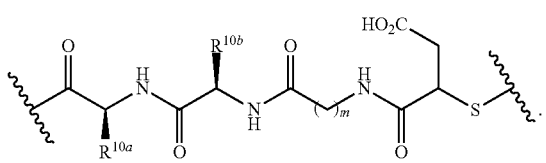

In another embodiment, -L-Q- is:

LQ-10

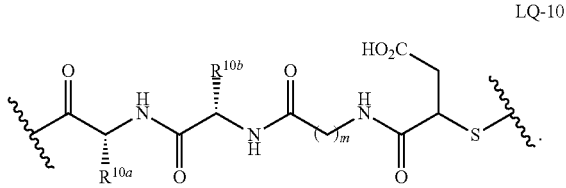

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein L is a noncleavable linker. In another embodiment, the linker comprises one or more polyethylene glycol units.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein -L-Q- is:

LQ-11

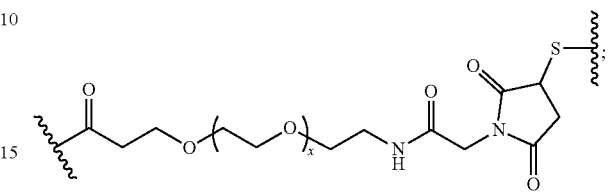

m is 2 or 3; and x is 0, 1, 2, 3, 4, 5, 6, 7, 8, 9, 10, 11, 12, 13, 14, or 15. In another embodiment, m is 2.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein -L-Q- is:

LQ-12

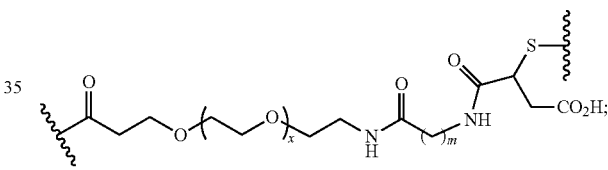

m is 2 or 3; and x is 0, 1, 2, 3, 4, 5, 6, 7, 8, 9, 10, 11, 12, 13, 14, or 15. In another embodiment, m is 2.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein -L-Q- is:

LQ-13

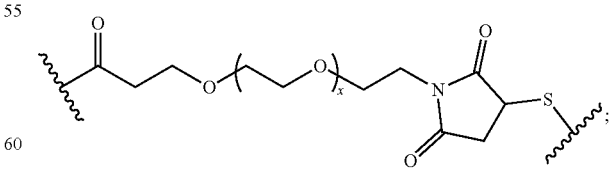

and x is 0, 1, 2, 3, 4, 5, 6, 7, 8, 9, 10, 11, 12, 13, 14, or 15.

The compound of any one of claims 1-47, or a pharmaceutically acceptable salt or solvate thereof, wherein -L-Q- is:

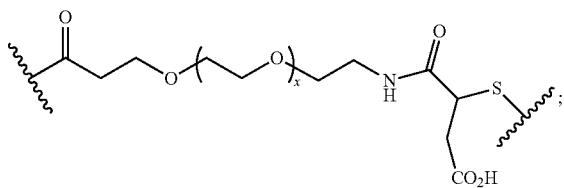

LQ-29 and x is 0, 1, 2, 3, 4, 5, 6, 7, 8, 9, 10, 11, 12, 13, 14, or 15.

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', wherein -L-Q- is:

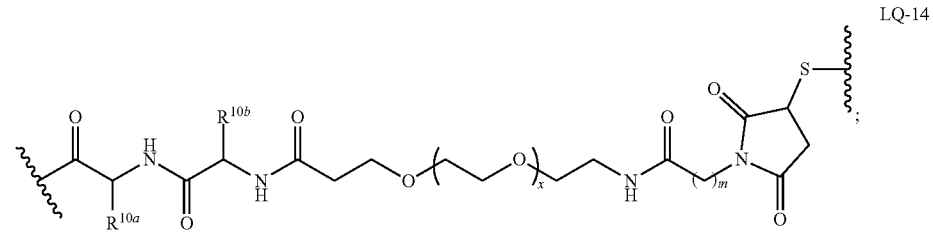

LQ-14 m is 1 or 2;
x is 0, 1, 2, 3, 4, 5, 6, 7, 8, 9, 10, 11, 12, 13, 14, or 15; and
$R^{10a}$ and $R^{10b}$ are independently selected from the group consisting of hydrogen and optionally substituted $C_{1-6}$ alkyl.

In another embodiment, -L-Q- is:

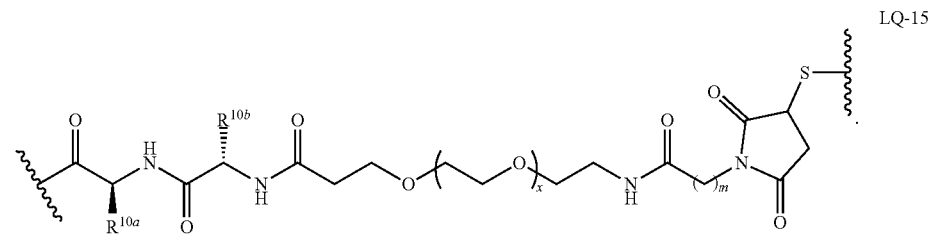

LQ-15

In another embodiment, -L-Q- is:

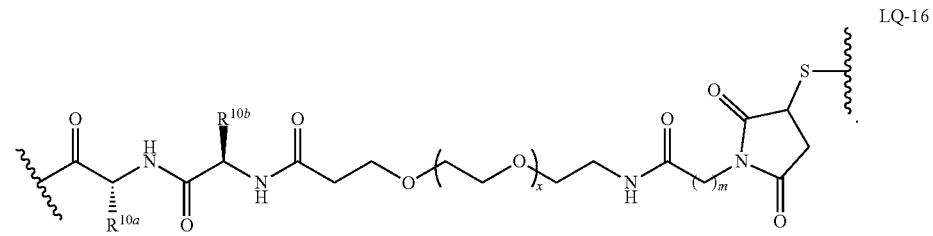

LQ-16

In another embodiment, -L-Q- is:

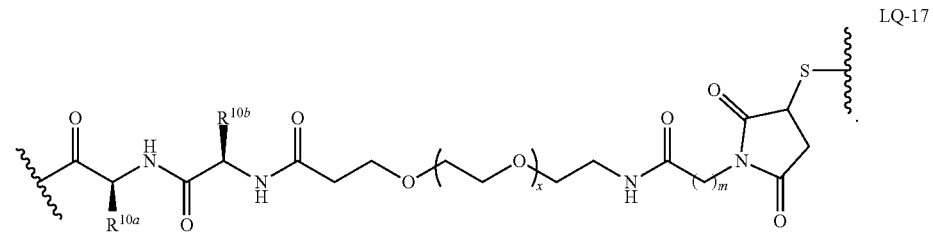

LQ-17

In another embodiment, -L-Q- is:

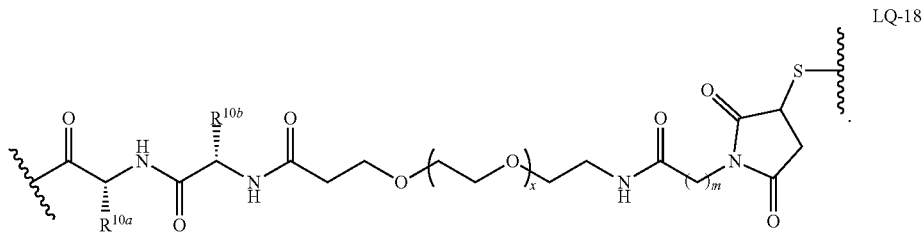

LQ-18

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', wherein -L-Q- is:

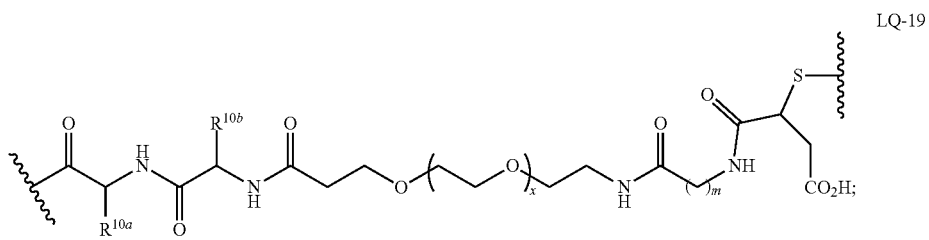

LQ-19 m is 1 or 2;
x is 0, 1, 2, 3, 4, 5, 6, 7, 8, 9, 10, 11, 12, 13, 14, or 15; and
$R^{10a}$ and $R^{10b}$ are independently selected from the group consisting of hydrogen and optionally substituted $C_{1-6}$ alkyl.
In another embodiment, -L-Q- is:

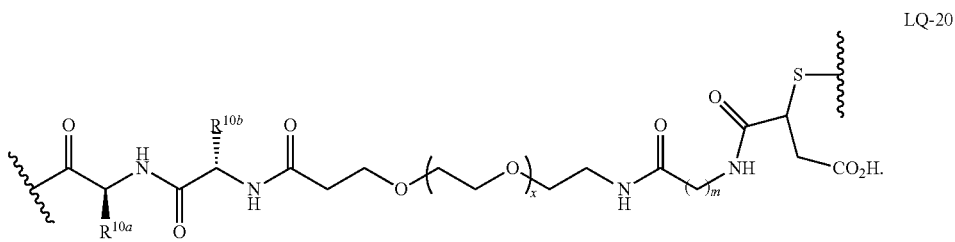

LQ-20

In another embodiment, -L-Q- is:

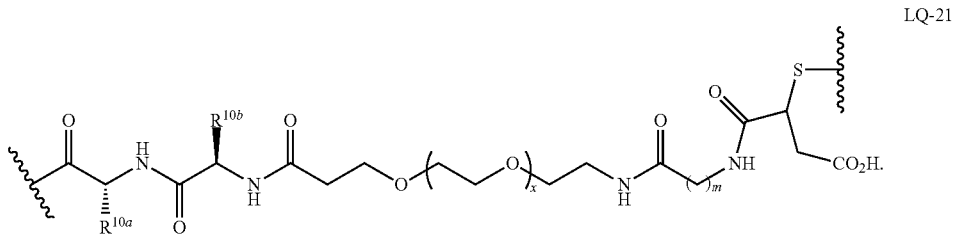

LQ-21

In another embodiment, -L-Q- is:

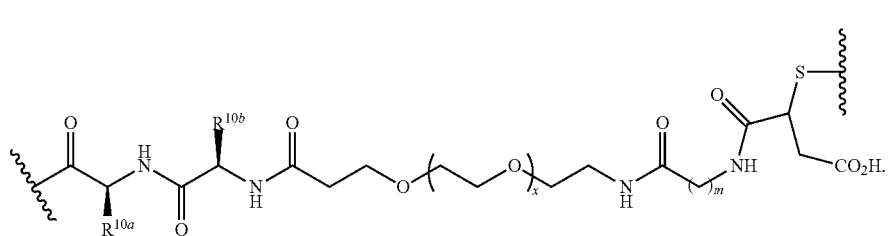

LQ-22

In another embodiment, -L-Q- is:

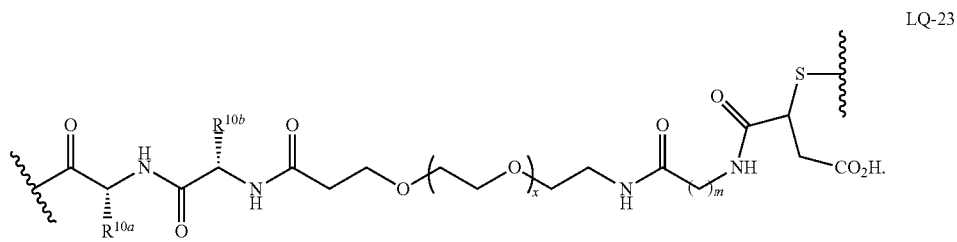

LQ-23

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein -L-Q- is:

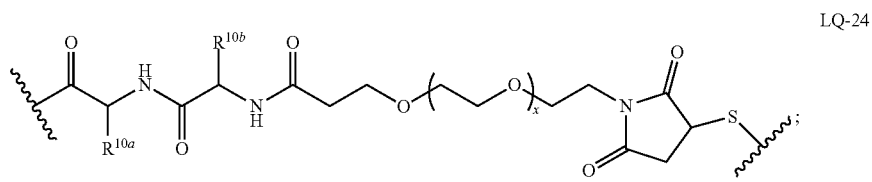

LQ-24 x is 0, 1, 2, 3, 4, 5, 6, 7, 8, 9, 10, 11, 12, 13, 14, or 15; and $R^{10a}$ and $R^{10b}$ are independently selected from the group consisting of hydrogen and optionally substituted $C_{1-6}$ alkyl.

In another embodiment, -L-Q- is:

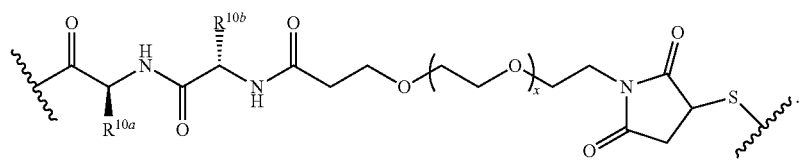

LQ-25

In another embodiment, -L-Q- is:

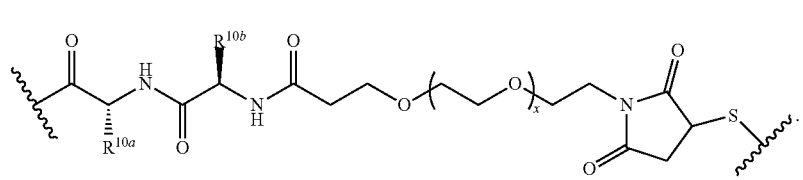

LQ-26

In another embodiment, -L-Q- is:

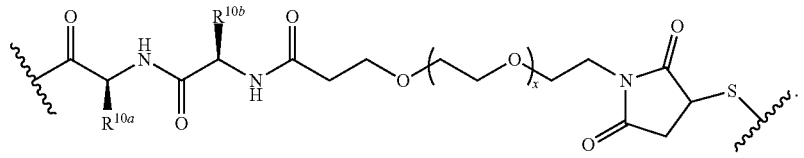

LQ-27

In another embodiment, -L-Q- is:

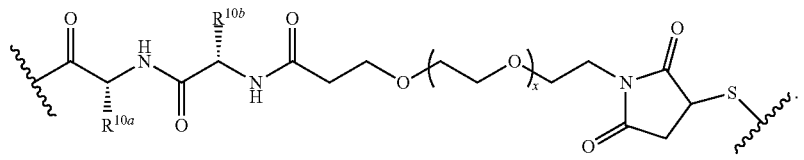

LQ-28

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein -L-Q- is:

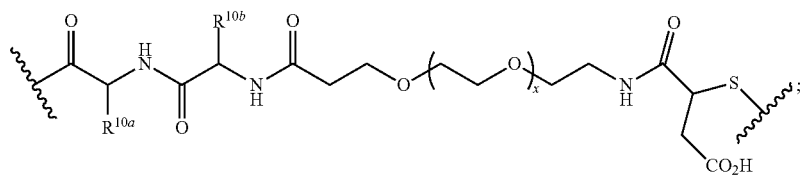

LQ-30 x is 0, 1, 2, 3, 4, 5, 6, 7, 8, 9, 10, 11, 12, 13, 14, or 15; and $R^{10a}$ and $R^{10b}$ are independently selected from the group consisting of hydrogen and optionally substituted $C_{1-6}$ alkyl.

In another embodiment, -L-Q- is:

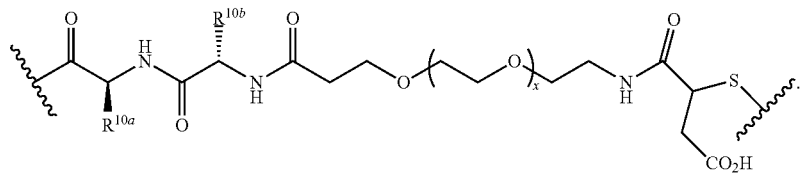

LQ-31

In another embodiment, -L-Q- is:

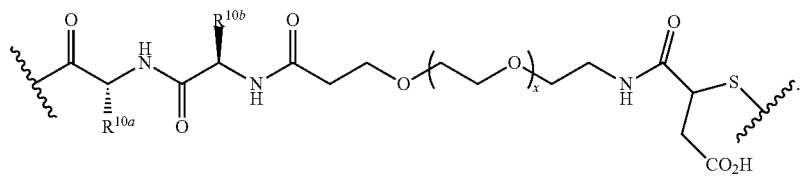

LQ-32

In another embodiment, -L-Q- is:

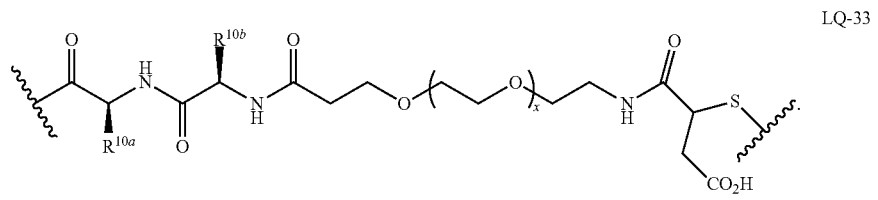

LQ-33

In another embodiment, -L-Q- is:

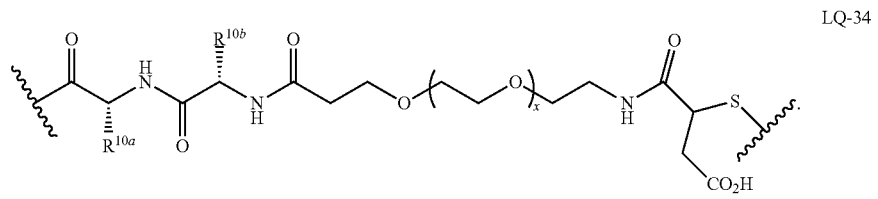

LQ-34

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', wherein -L-Q- is any one of the chemical structures of Table I:

TABLE I

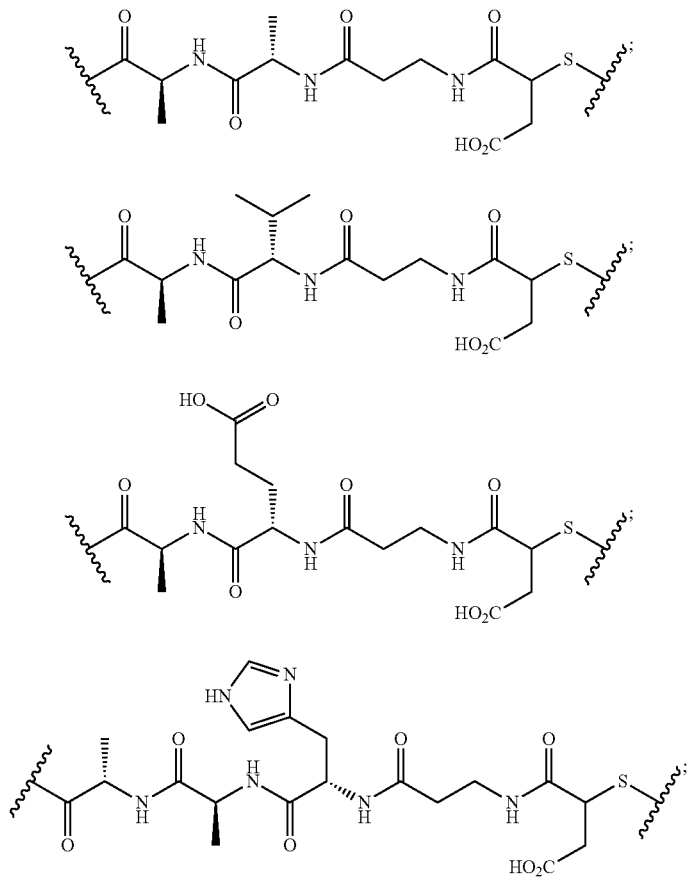

TABLE I-continued
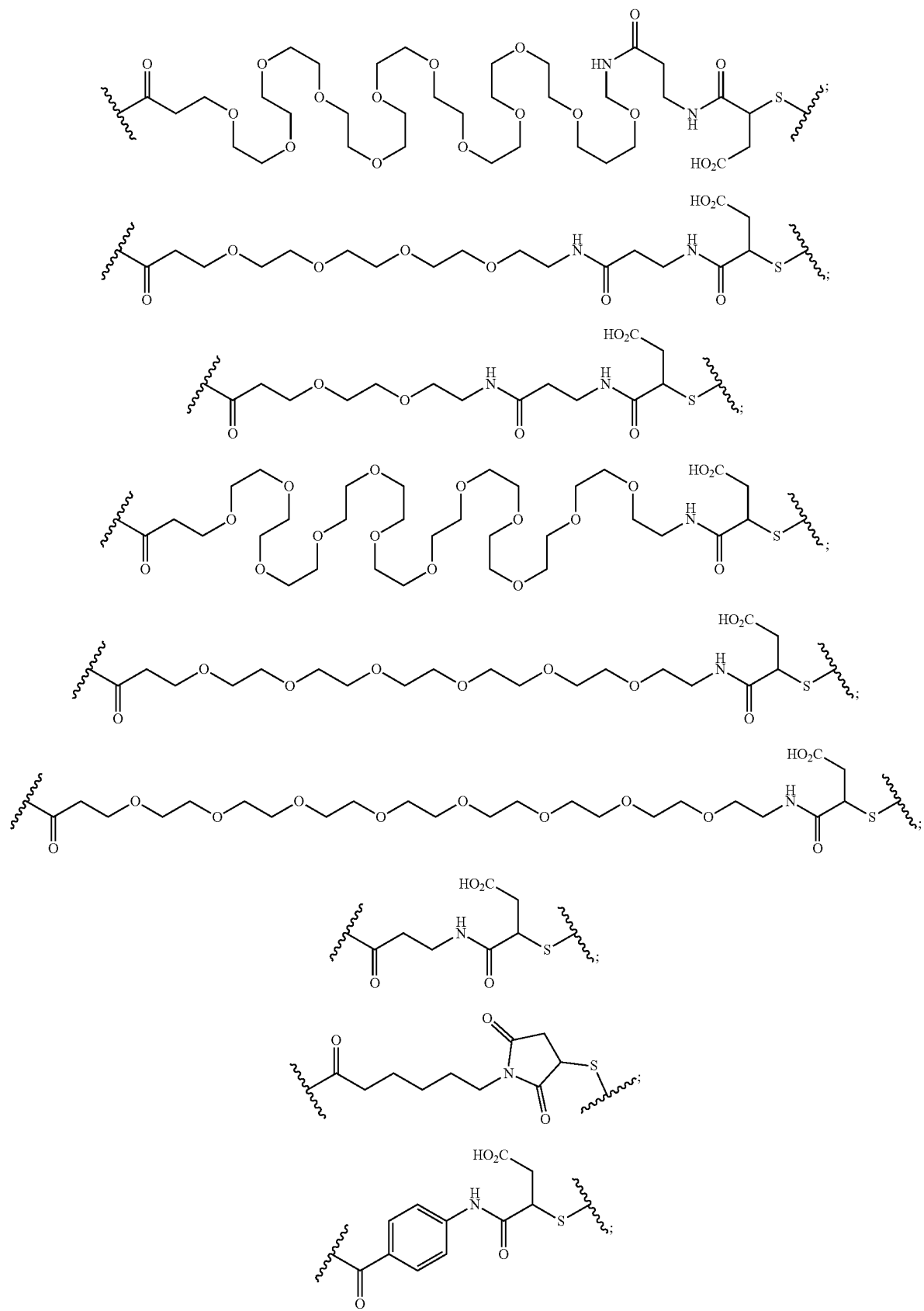

TABLE I-continued

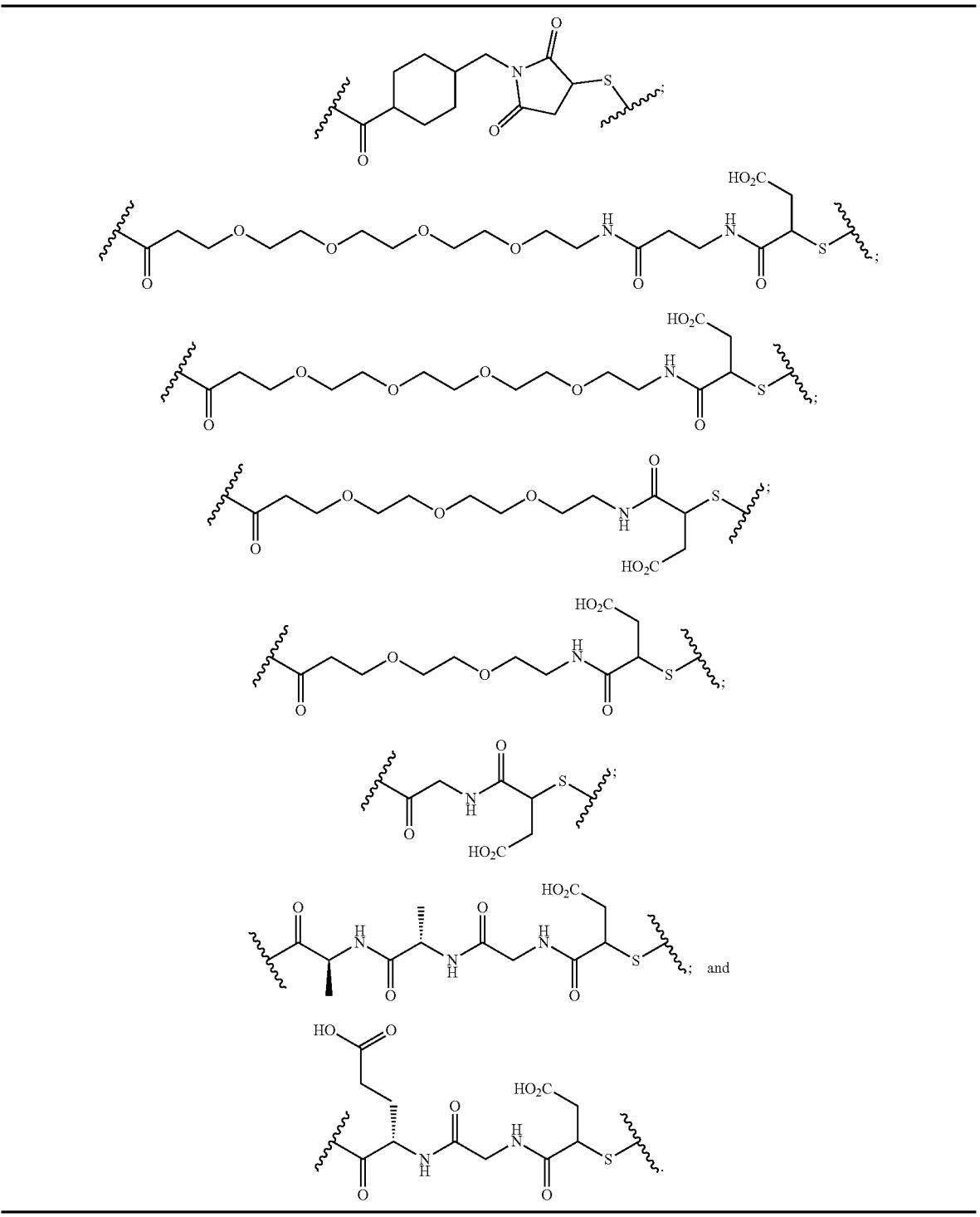

In another embodiment, disclosed herein is a compound having Formula I-a or I-b, or a pharmaceutically acceptable salt thereof, e.g. a compound having Formula I-a or I-b wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", wherein n is 2-8. In another embodiment, n is 1-5. In another embodiment, n is 2-5. In another embodiment, n is 1. In another embodiment, n is 2. In another embodiment n is 3. In another embodiment, n is 4. In another embodiment, n is 5. In another embodiment, n is 6. In another embodiment, n is 7. In another embodiment, n is 8.

In another embodiment, disclosed herein is a compound having Formula I-a or I-b, or a pharmaceutically acceptable salt thereof, wherein SM is a monovalent radical of a glucocorticosteroid which is any one of the chemical structures of Table II.

TABLE II
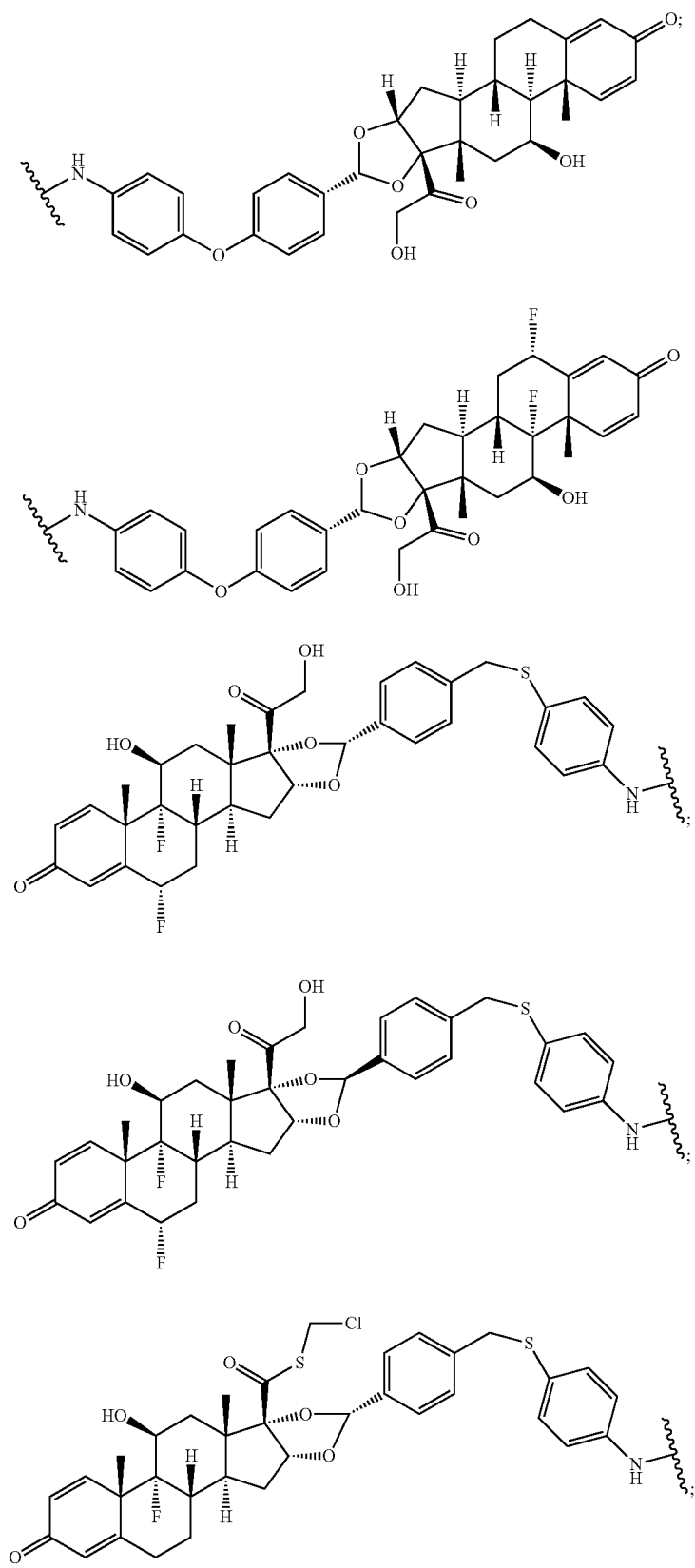

TABLE II-continued
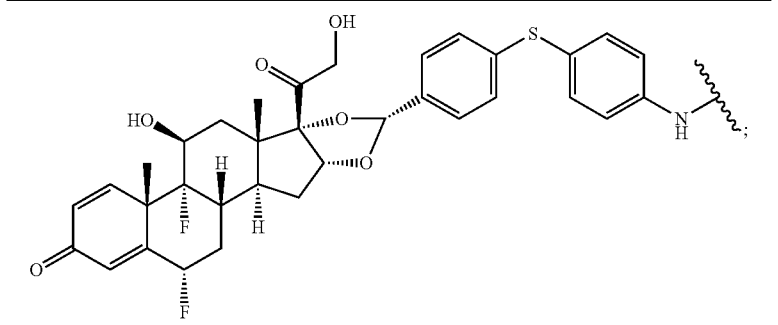
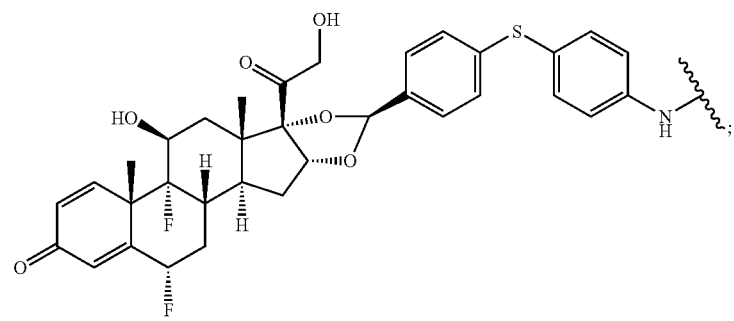
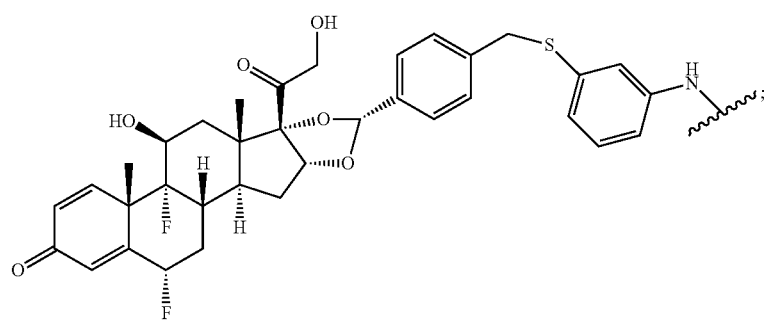
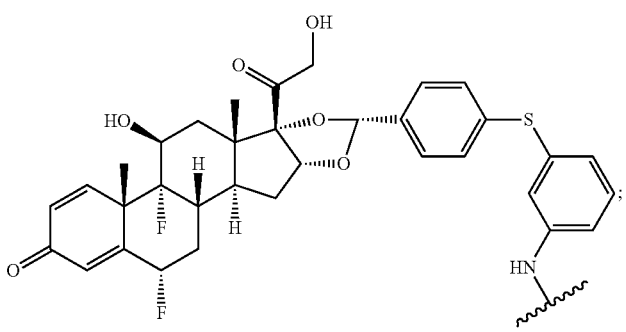
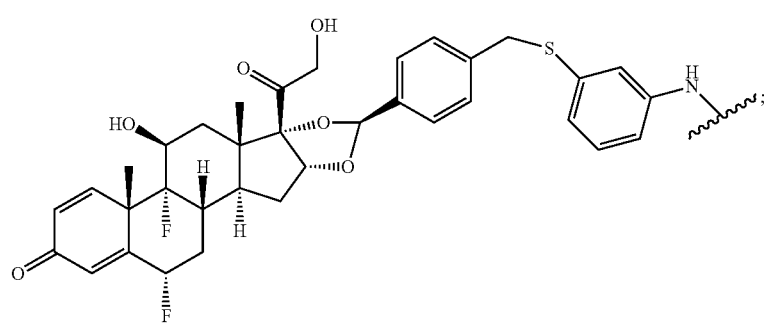

TABLE II-continued
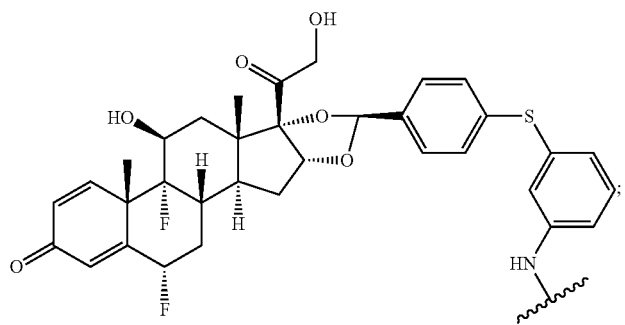
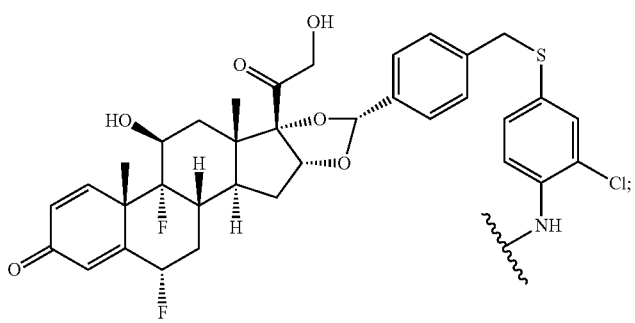
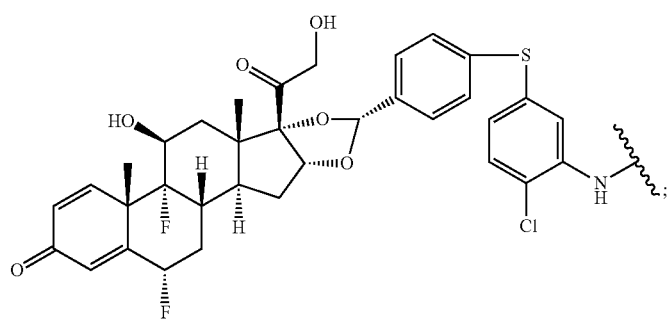
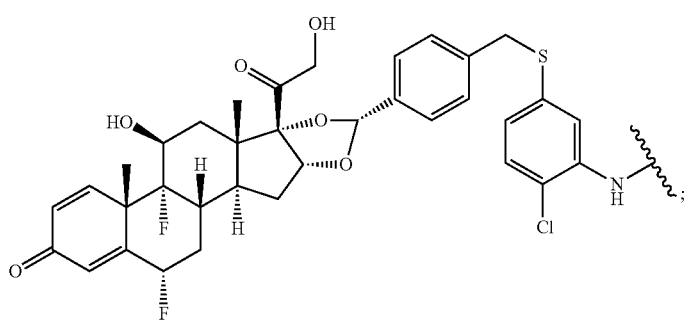
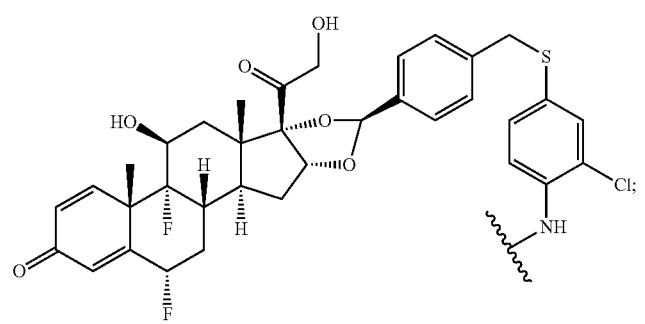

TABLE II-continued
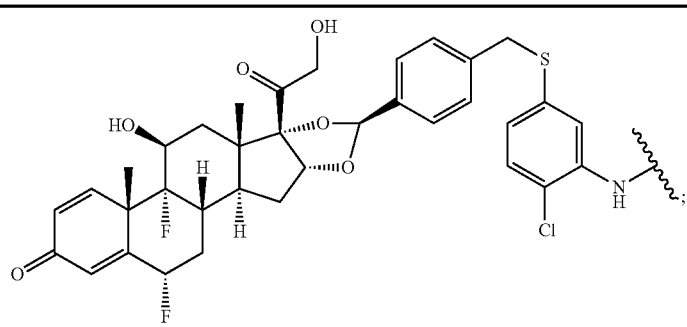
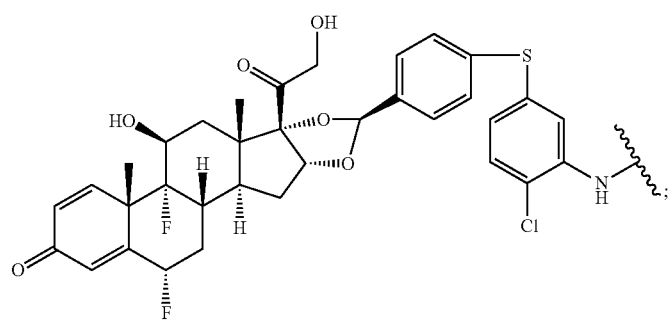
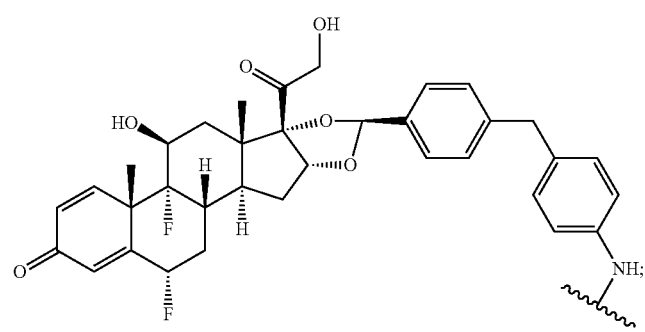
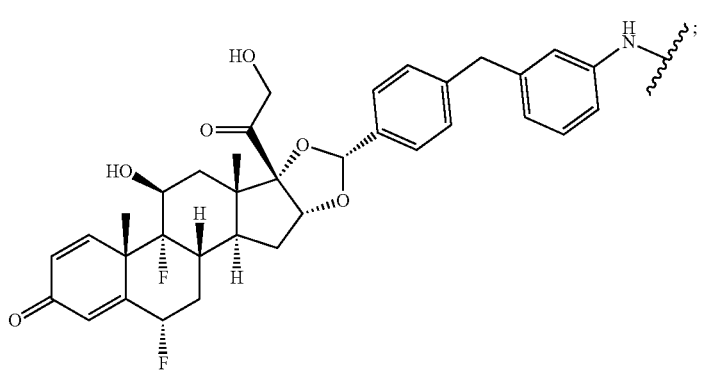
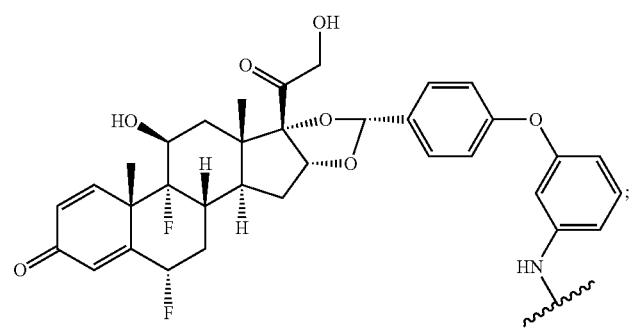

TABLE II-continued
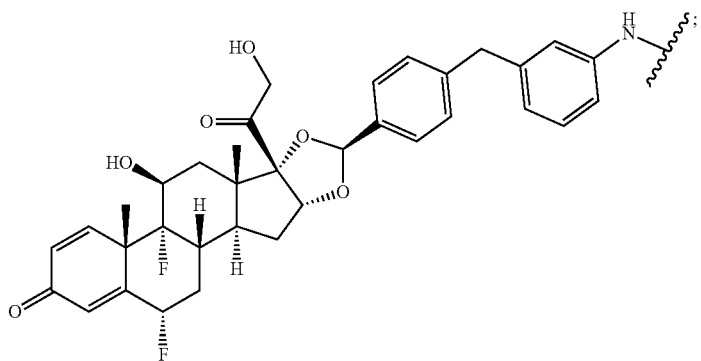
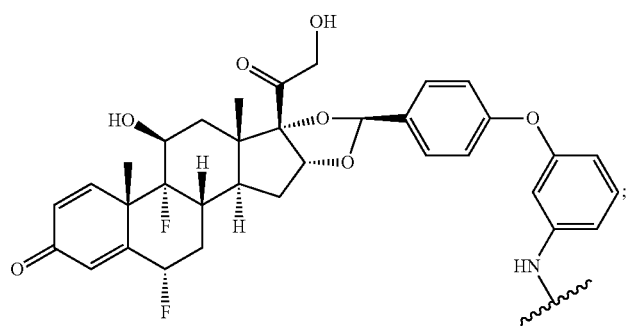
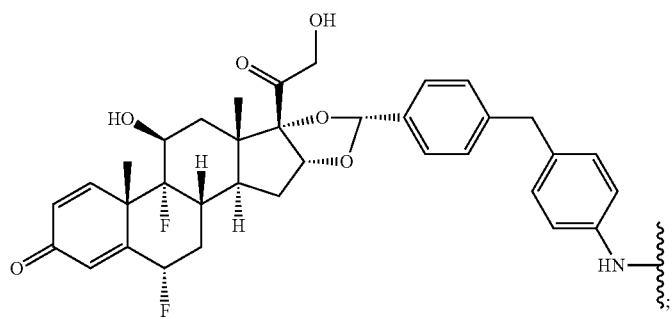
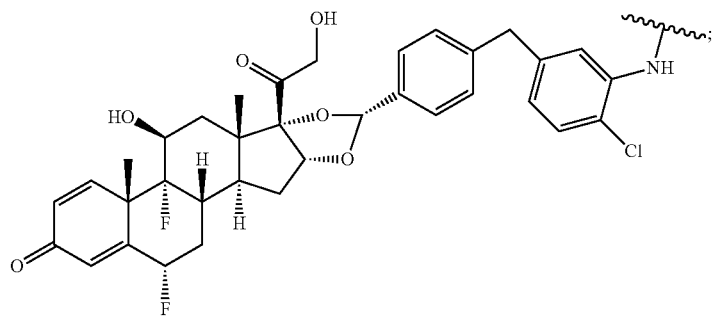

TABLE II-continued
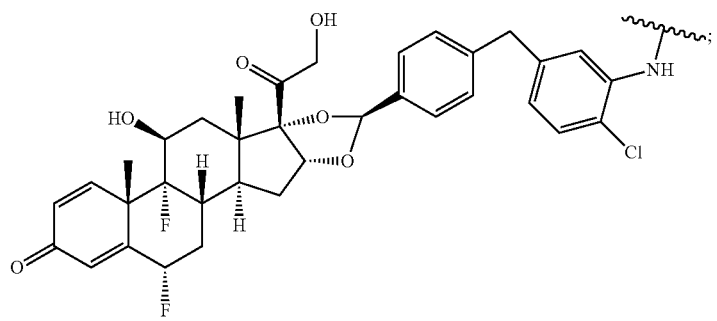
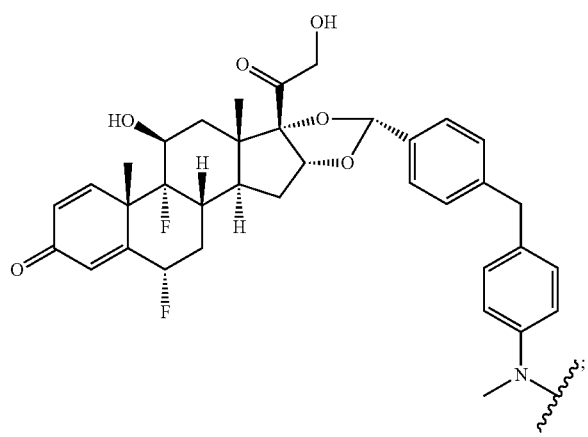
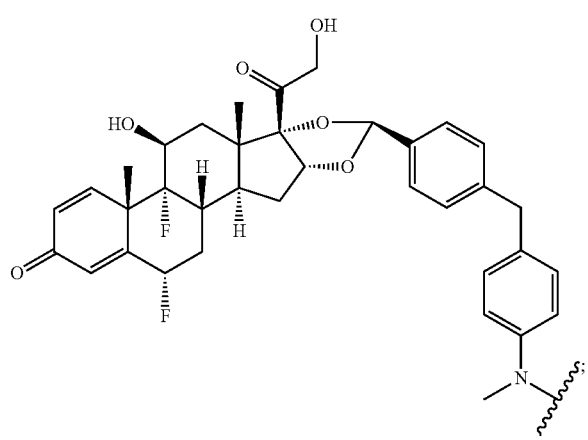
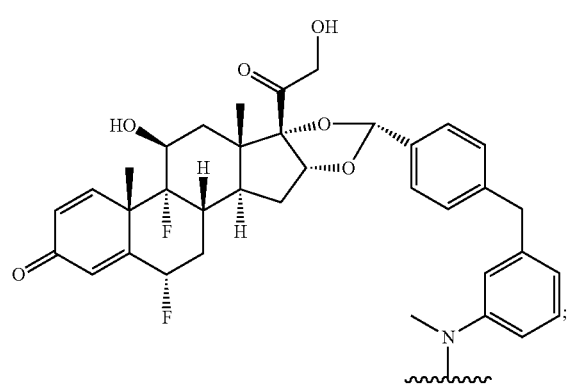

TABLE II-continued
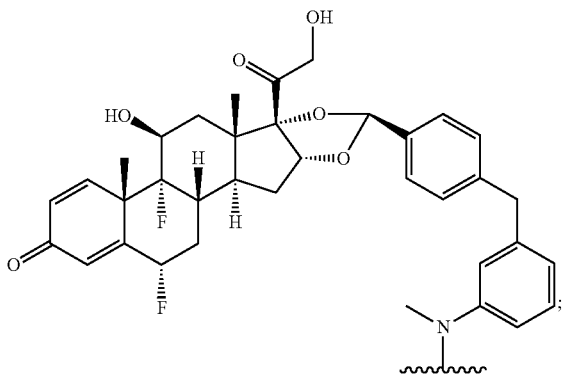
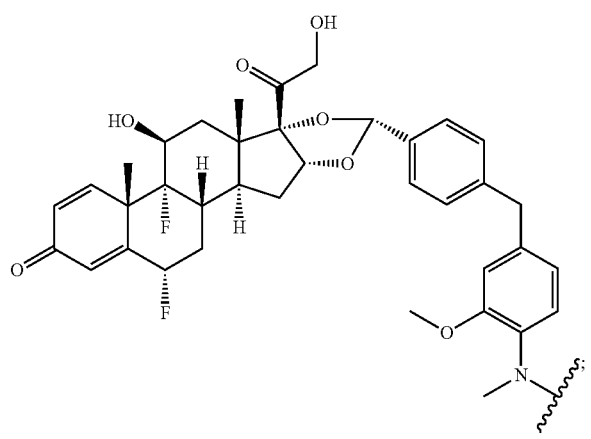
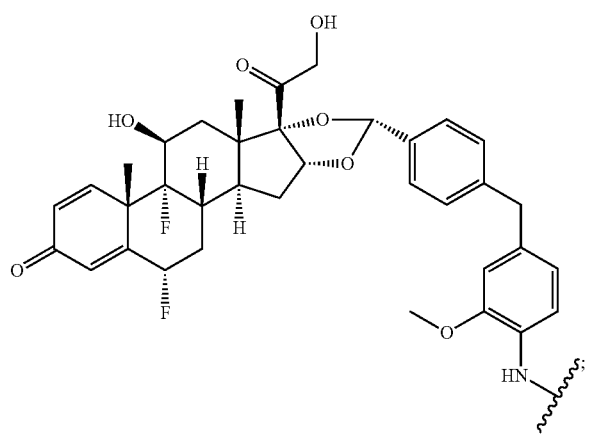

TABLE II-continued
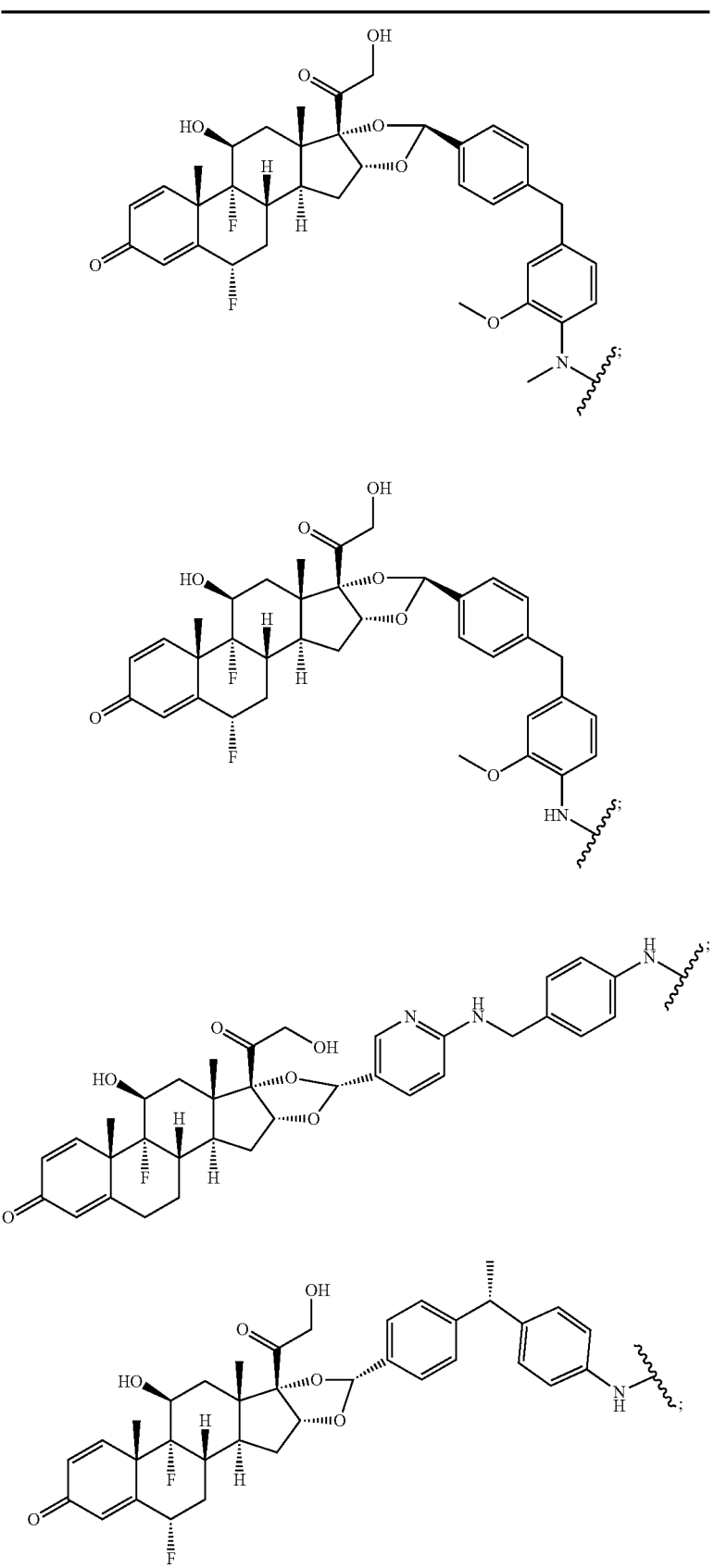

TABLE II-continued
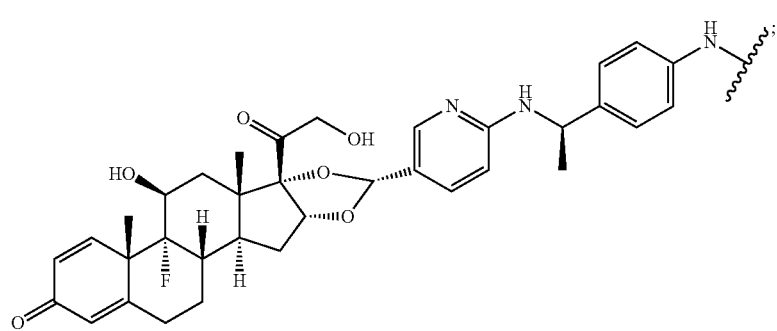
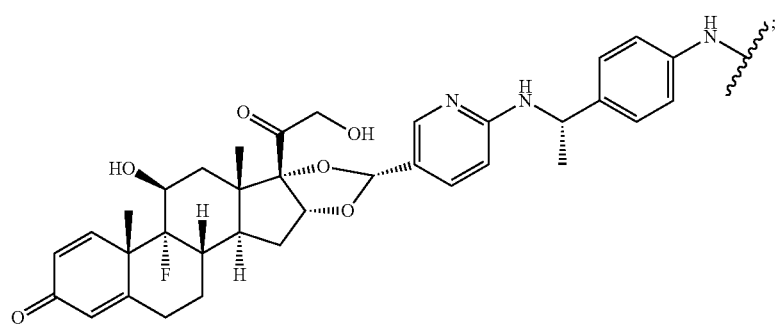
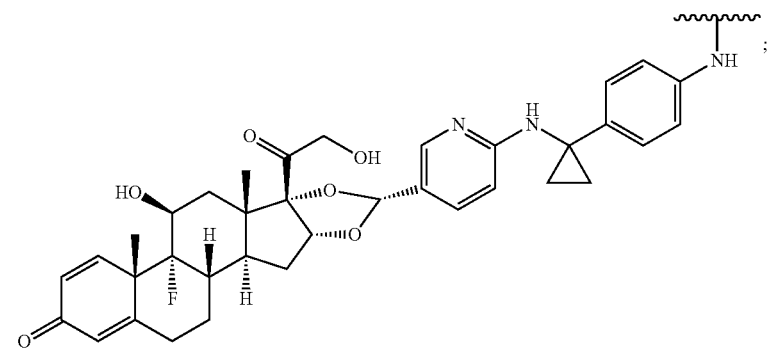
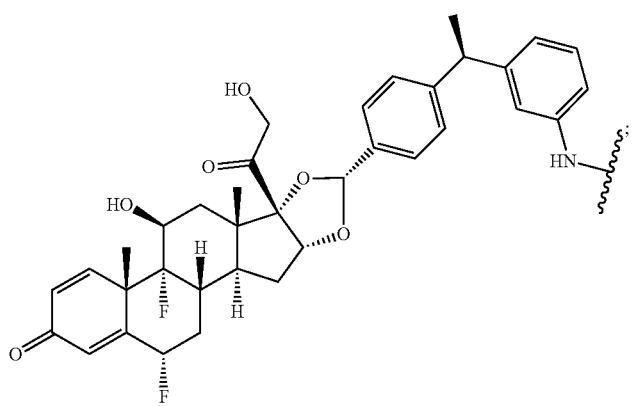

TABLE II-continued
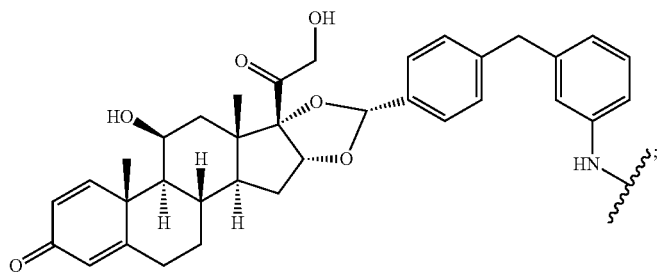
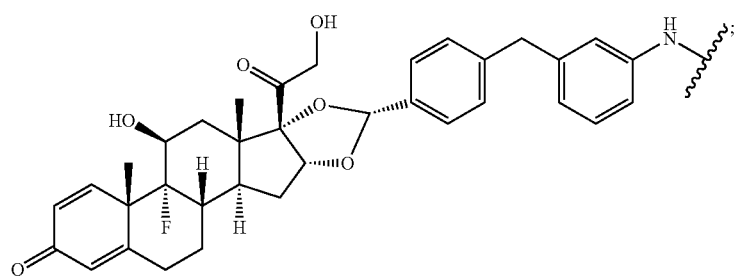
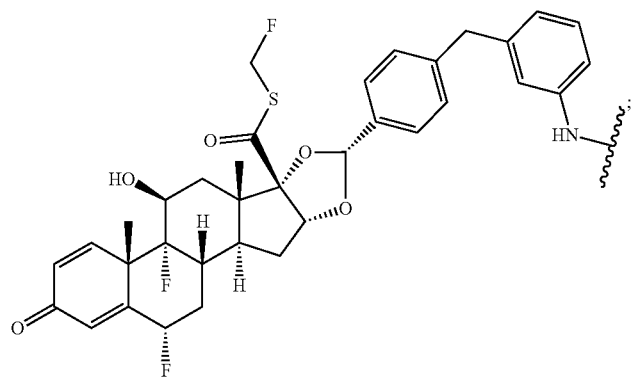
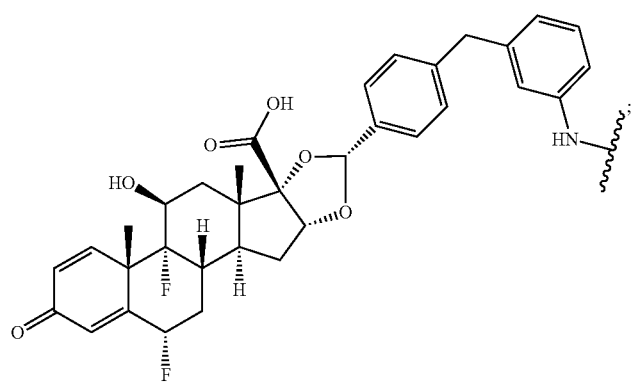

TABLE II-continued
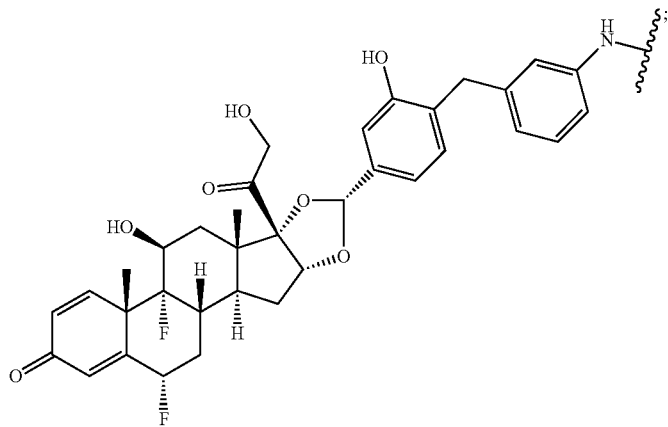
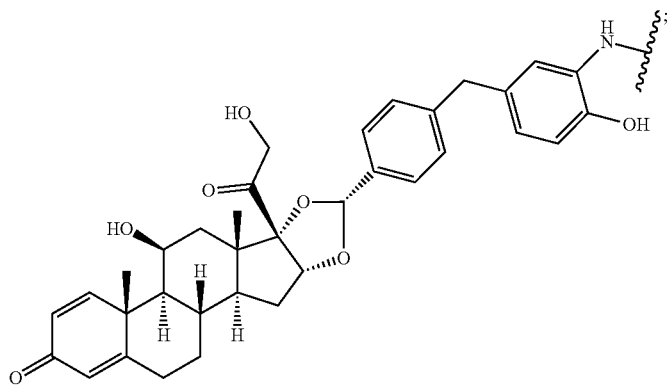
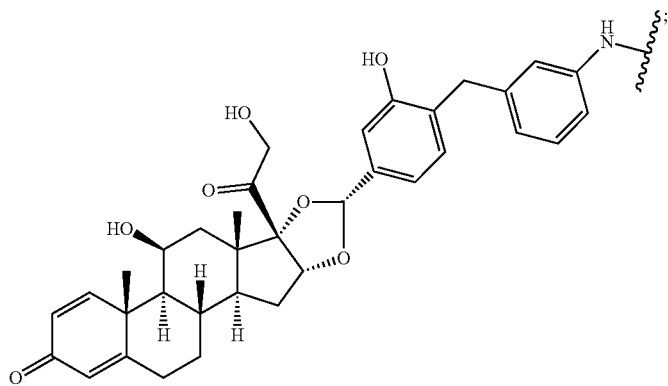
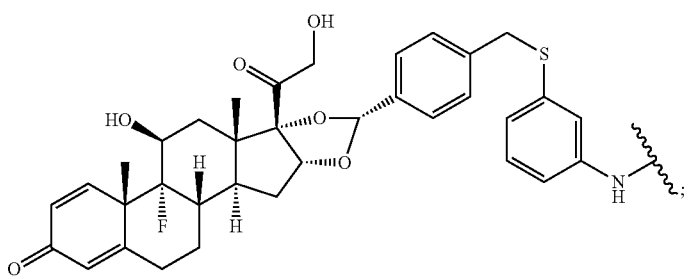

TABLE II-continued
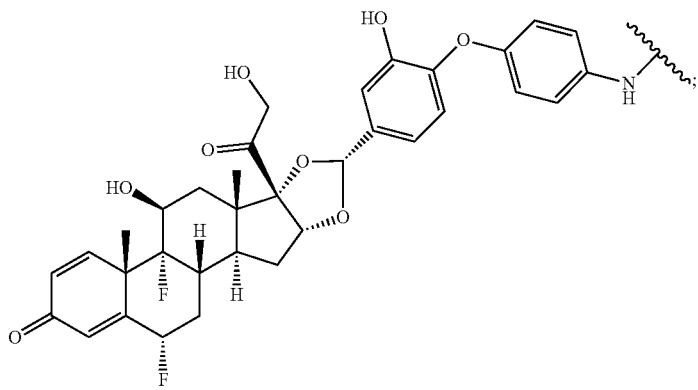
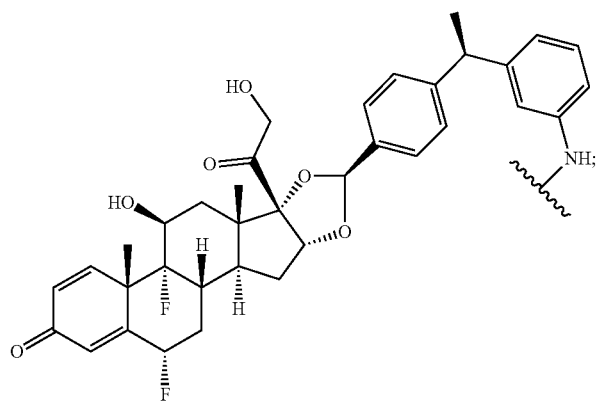
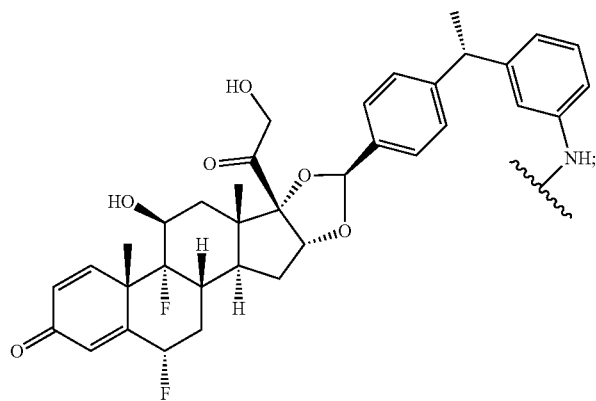
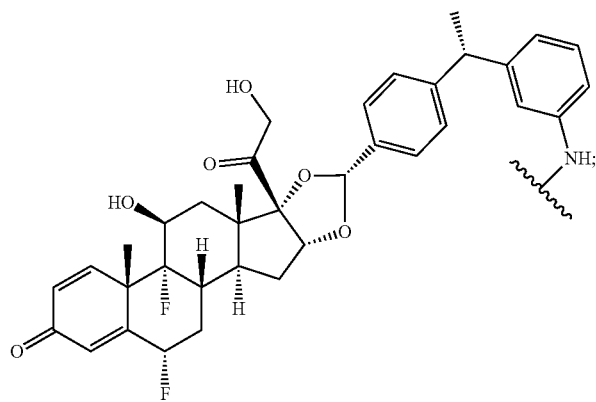

TABLE II-continued
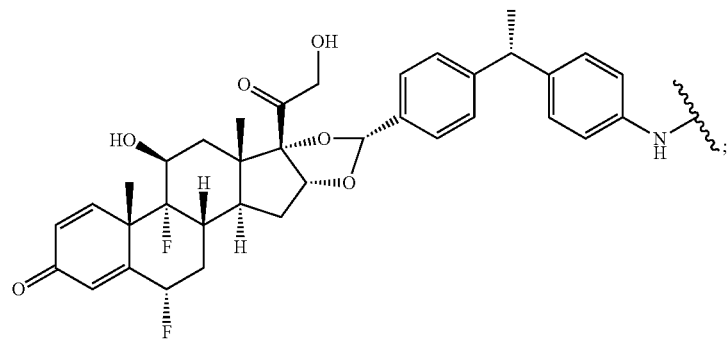
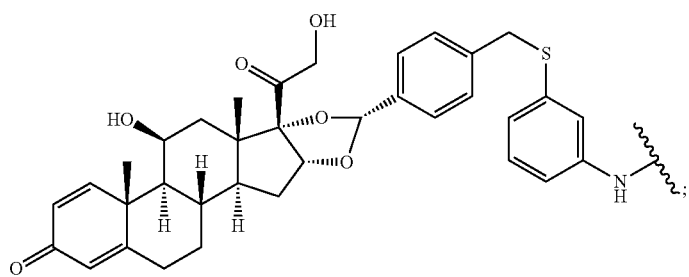
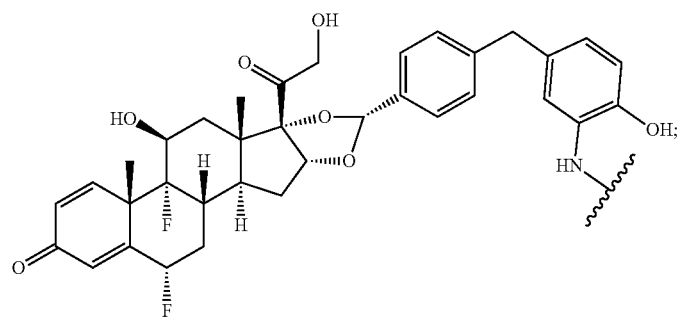
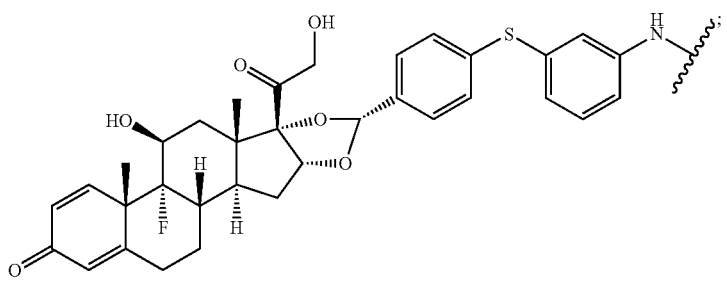
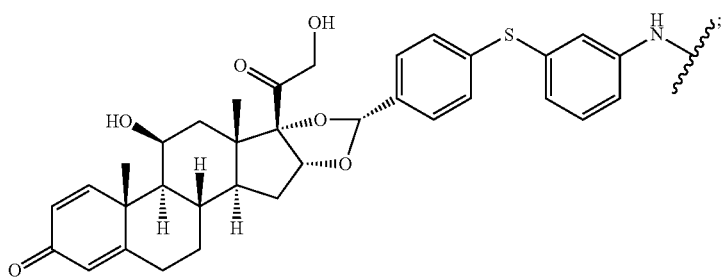

TABLE II-continued
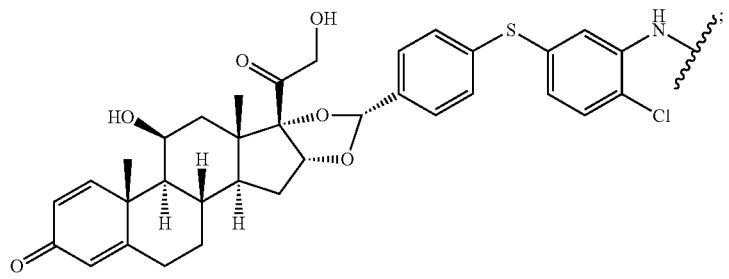
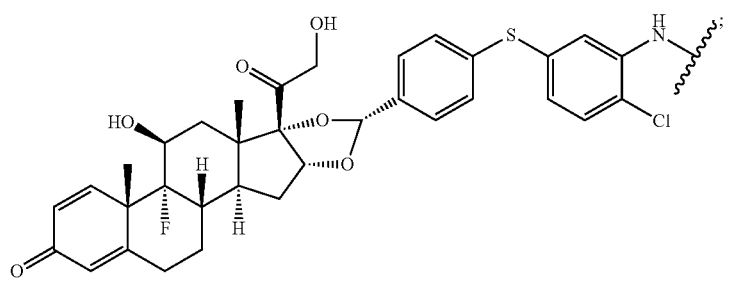
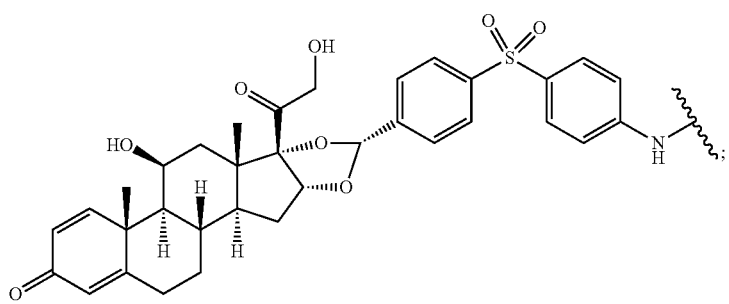
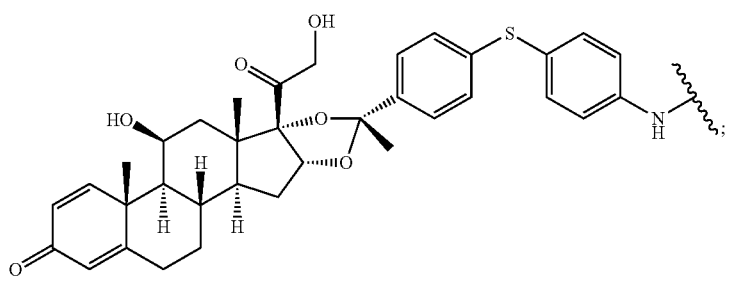
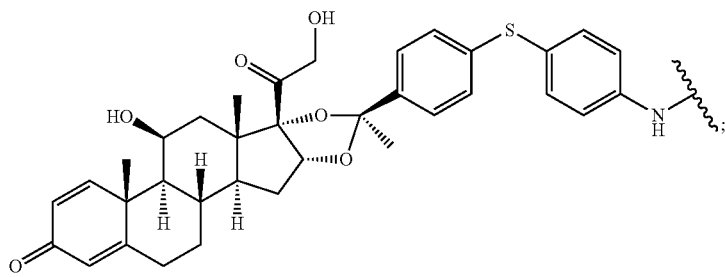

TABLE II-continued
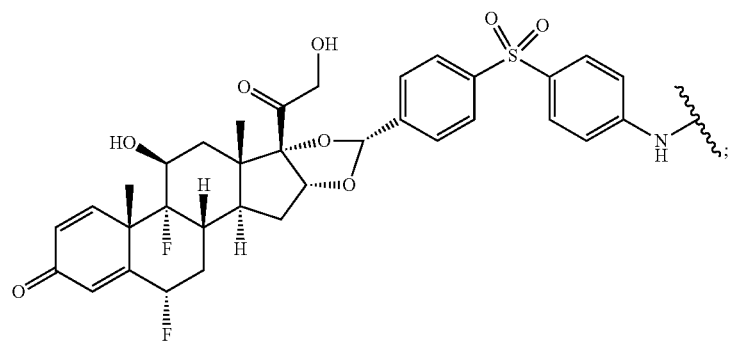
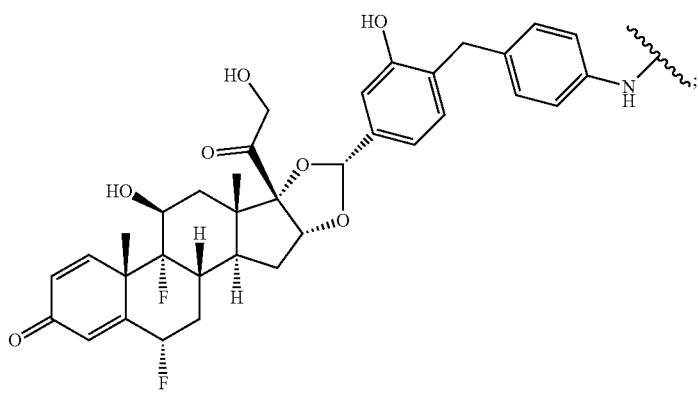
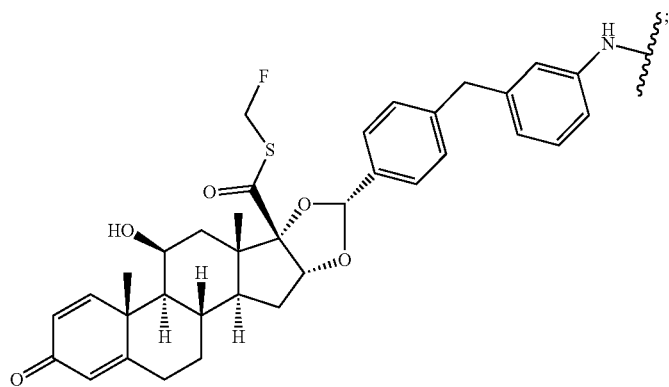
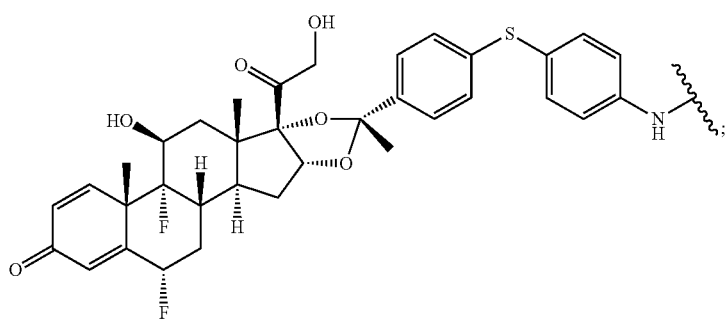

TABLE II-continued

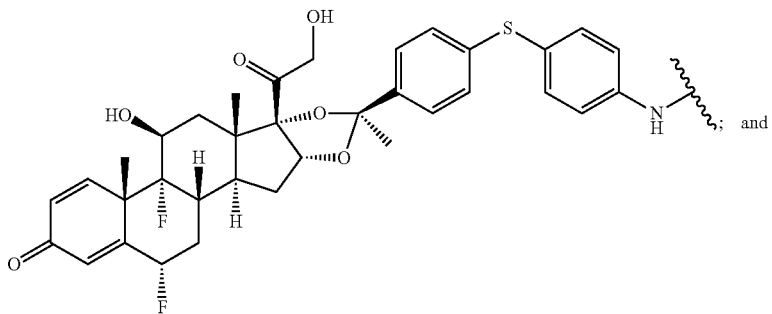

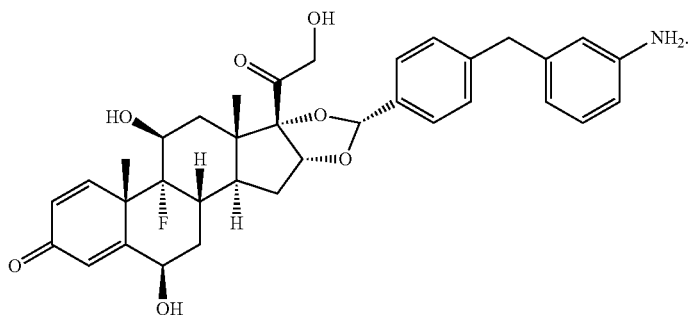

In another embodiment, disclosed herein is a compound having Formula I-a or I-b, or a pharmaceutically acceptable salt thereof, wherein SM is a monovalent radical of a glucocorticosteroid selected from the group consisting of:

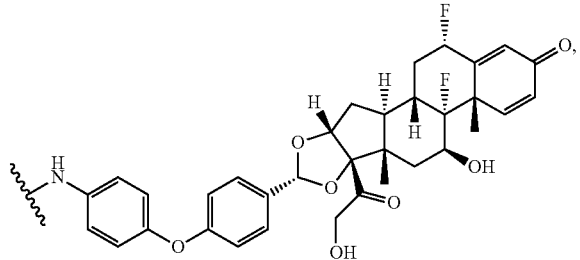

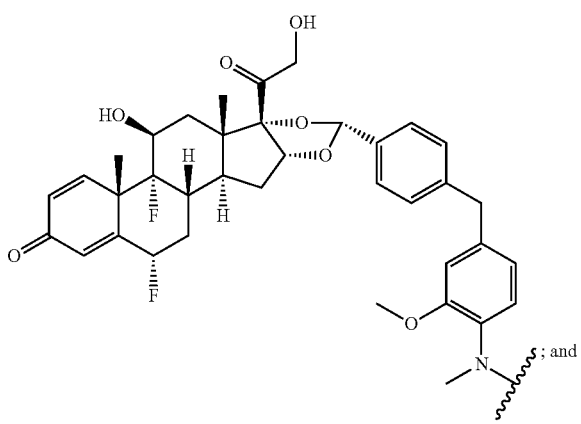

-continued

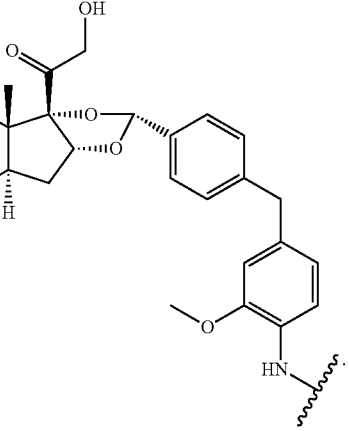

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ is an antibody or antigen-binding fragment thereof or wherein $A^2$ is an antibody or antigen-binding fragment thereof.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $A^1$ is an anti-tumor necrosis factor (TNF) alpha protein that binds to human TNF alpha and/or murine TNF alpha or wherein $A^2$ is protein that binds to human TNF alpha and/or murine TNF alpha.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $A^1$ is an anti-tumor necrosis factor (TNF) alpha protein that binds to soluble TNF alpha or wherein $A^2$ is protein that binds to soluble TNF alpha.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $A^1$ is an anti-tumor necrosis factor (TNF) alpha protein that binds to membrane-bound TNF alpha or wherein $A^2$ is a protein that binds to membrane-bound TNF alpha.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $A^1$ is an anti-tumor necrosis factor (TNF) alpha protein comprising an anti-TNF antibody or wherein $A^2$ is protein comprising an anti-TNF antibody.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $A^1$ is an anti-tumor necrosis factor (TNF) alpha protein comprising an anti-TNF receptor antibody or wherein $A^2$ is a protein comprising an anti-TNF receptor antibody.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $A^1$ is an anti-tumor necrosis factor (TNF) alpha protein comprising an antigen-binding fragment of an anti-TNF antibody or wherein $A^2$ is a protein comprising an antigen-binding fragment of an anti-TNF antibody.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein $A^1$ is an anti-tumor necrosis factor (TNF) alpha protein comprising an antigen-binding fragment of an anti-TNF receptor antibody or wherein $A^2$ is an anti-tumor necrosis factor (TNF) alpha protein comprising an antigen-binding fragment of an anti-TNF receptor antibody.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein the antigen-binding fragment is selected from the group consisting of Fab, Fab', F(ab')2, single chain Fv or scFv, disulfide linked Fv, V-NAR domain, IgNar, intrabody, IgGACH2, minibody, F(ab')3, tetrabody, triabody, diabody, single-domain antibody, DVD-Ig, Fcab, mAb2, (scFv)2, or scFv-Fc.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein the antibody or antigen-binding fragment thereof is murine, chimeric, humanized, or human.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ is an anti-tumor necrosis factor (TNF) alpha protein comprising a soluble TNF receptor or wherein $A^2$ is a protein comprising a soluble TNF receptor. In another embodiment, the soluble TNF receptor is a soluble p75 TNF receptor.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ comprises a heavy chain constant domain or a fragment thereof or wherein or $A^2$ comprises a heavy chain constant domain or a fragment thereof. In another embodiment, the heavy chain constant domain or fragment thereof comprises a constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain or is a fragment thereof. In another embodiment, the heavy chain constant domain comprises a human IgG1 heavy chain constant domain or fragment thereof. In another embodiment, the heavy chain constant domain comprises a human IgG1 Fc domain.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, wherein $A^1$ comprises a light chain constant domain or a fragment thereof or wherein $A^2$ comprises a light chain constant domain or a fragment thereof. In another embodiment, the light chain constant domain or fragment thereof comprises a constant domain selected group consisting of (a) an Ig kappa constant domain and (b) an Ig lambda constant domain or is a fragment thereof.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ competitively inhibits binding of an antibody selected from the group consisting of adalimumab, infliximab, certolizumab pegol, and golimumab to TNF-alpha or wherein $A^2$ competitively inhibits binding of an antibody selected from the group consisting of adalimumab, infliximab, certolizumab pegol, and golimumab to TNF-alpha.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ binds to the same TNF-alpha epitope as an antibody selected from the group consisting of adalimumab, infliximab, certolizumab pegol, afelimomab, nerelimomab, ozoralizumab, placulumab, and golimumab or wherein $A^2$ binds to the same TNF-alpha epitope as an antibody selected from the group consisting of adalimumab, infliximab, certolizumab pegol, afelimomab, nerelimomab, ozoralizumab, placulumab, and golimumab.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein the anti-TNF alpha protein is selected from the group consisting of adalimumab, infliximab, certolizumab pegol, afelimomab, nerelimomab, ozoralizumab, placulumab, and golimumab.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ comprises the variable heavy chain CDR1, CDR2, and CDR3 sequences of SEQ ID NO:3 or 6, SEQ ID NO:4, and SEQ ID NO:5, respectively and the variable light chain CDR1, CDR2, and CDR3 sequences of SEQ ID NO:32, SEQ ID NO:33, and SEQ ID NO:34, respectively or wherein $A^2$ comprises the variable heavy chain CDR1, CDR2, and CDR3 sequences of SEQ ID NO:3 or 6, SEQ ID NO:4, and SEQ ID NO:5 respectively and the variable light chain CDR1, CDR2, and CDR3 sequences of SEQ ID NO:32, SEQ ID NO:33, and SEQ ID NO:34, respectively.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ comprises the variable heavy chain sequence of SEQ ID NO:50 and the variable light chain sequence of SEQ ID NO:59 or wherein $A^2$ comprises the variable heavy chain sequence of SEQ ID NO:50 and the variable light chain sequence of SEQ ID NO:59.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ does not bind to TNF beta or wherein $A^2$ does not bind to TNF beta.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ binds to TNF beta or wherein $A^1$ binds to TNF beta.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ neutralizes human TNF-alpha cytotoxicity in a in vitro L929 assay with an IC50 of $1 \times 10^{-7}$ M or less or wherein $A^2$ neutralizes human TNF-alpha cytotoxicity in a in vitro L929 assay with an IC50 of $1 \times 10^{-7}$ M or less.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ blocks the interaction of TNF-alpha with p55 and p75 cell surface receptors or wherein $A^2$ blocks the interaction of TNF-alpha with p55 and p75 cell surface receptors.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l'', II-m'', II-n'', II-o'', II-p'', or II-q'', wherein $A^1$ lyses surface TNF expressing cells in vitro in the presence of complement or wherein $A^2$ lyses surface TNF expressing cells in vitro in the presence of complement.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l'', II-m'', II-n'', II-o'', II-p'', or II-q'', or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein the soluble p75 TNF receptor is etanercept.

In another embodiment, disclosed herein is a compound having Formula I-a, or a pharmaceutically acceptable salt thereof, e.g., a compound having Formula I-a, wherein SM is a monovalent radical of a glucocorticosteroid having any one of Formulae II-a, II-b, II-c, II-d, II-e, II-f, II-l, II-m, II-n, II-o, II-p, or II-q, or any one of Formulae II-a', II-b', II-c', II-d', II-e', II-f', II-l', II-m', II-n', II-o', II-p', II-q', II-l", II-m", II-n", II-o", II-p", or II-q", or a compound having Formula I-b, or a pharmaceutically acceptable salt thereof, e.g., a compound having Formula I-b, wherein SM is a monovalent radical of a glucocorticosteroid having any one of Formulae II-l, II-m, II-n, II-o, II-p, or II-q, or any one of Formulae II-l', II-m', II-n', II-o', II-p', II-q', II-l", II-m", II-n", II-o", II-p", or II-q", wherein the antibody is adalimumab.

In another embodiment, disclosed herein is a compound having Formula I-a, or a pharmaceutically acceptable salt thereof, or a compound having Formula I-b, or a pharmaceutically acceptable salt thereof, which is any one of the chemical structures of Table III:

TABLE III

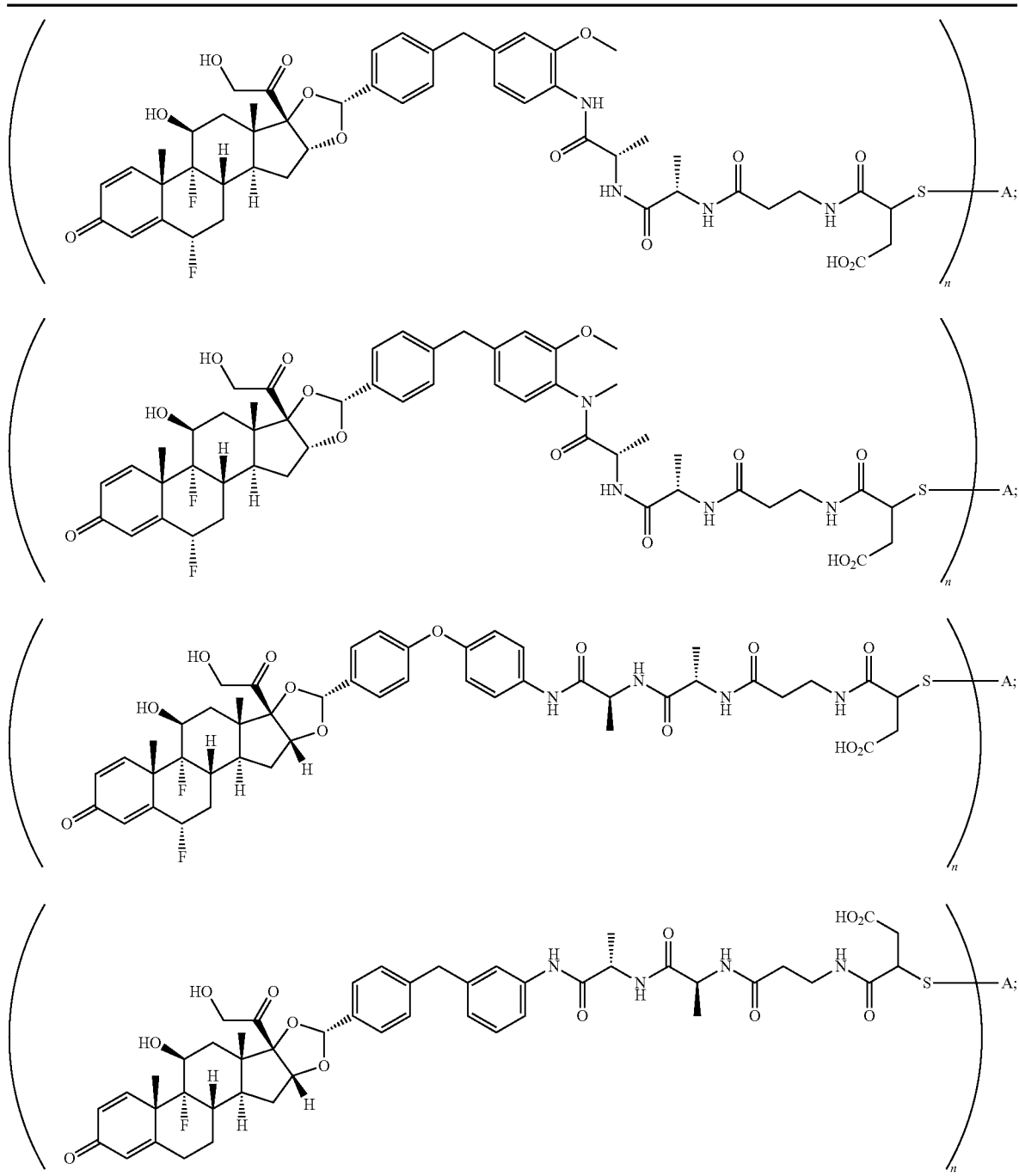

TABLE III-continued
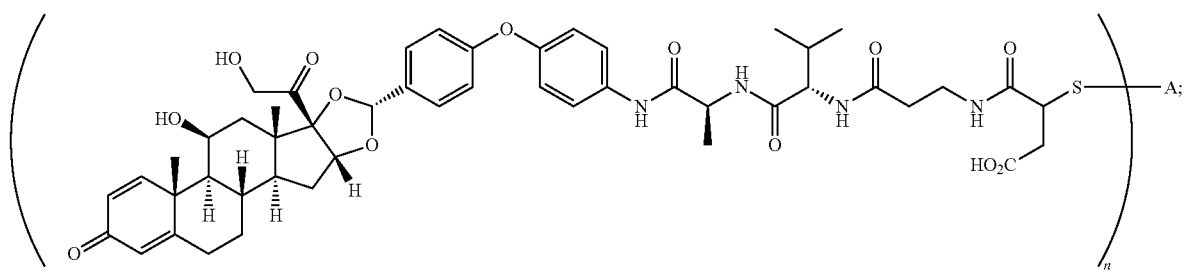
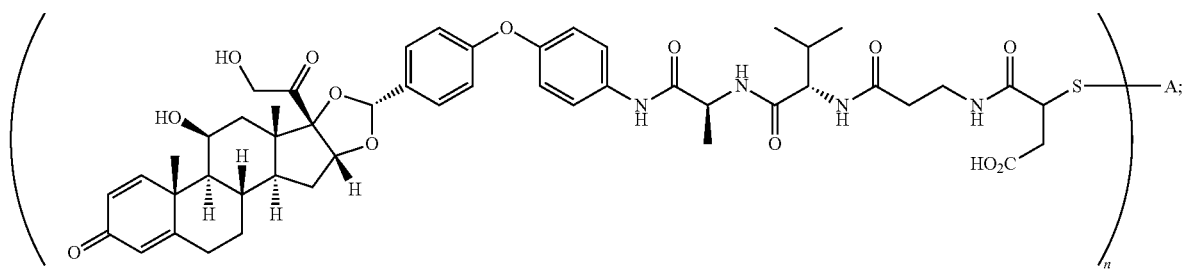
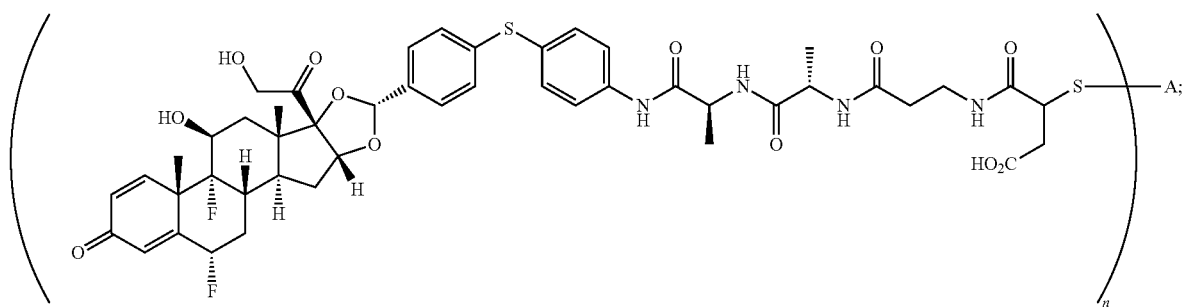
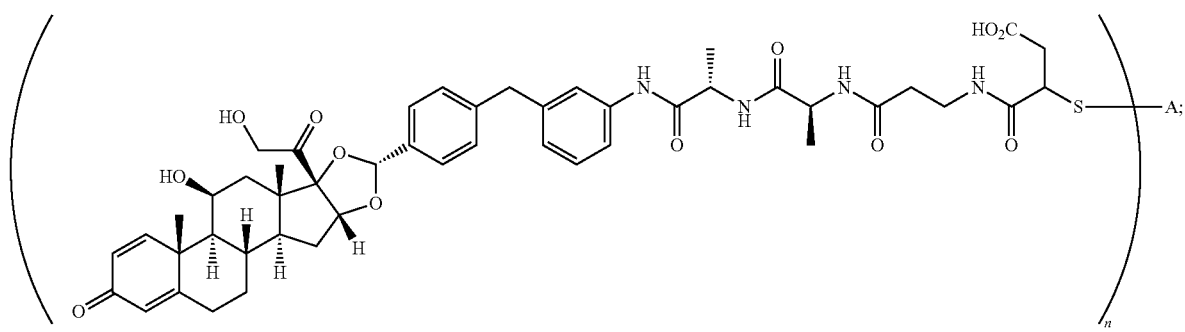
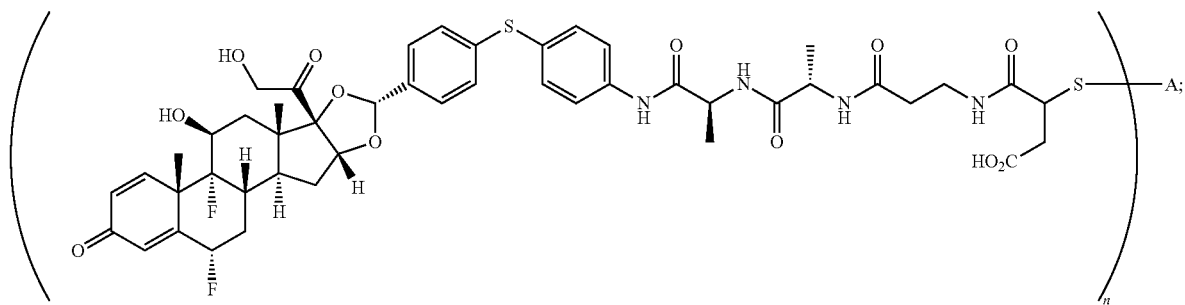

TABLE III-continued
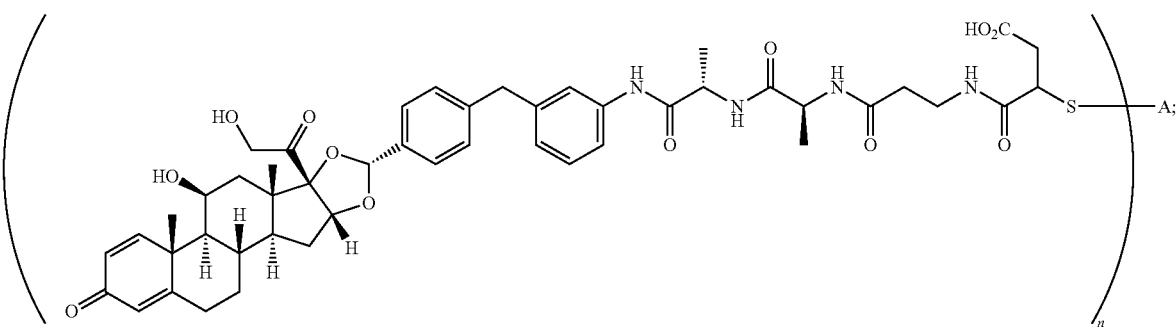
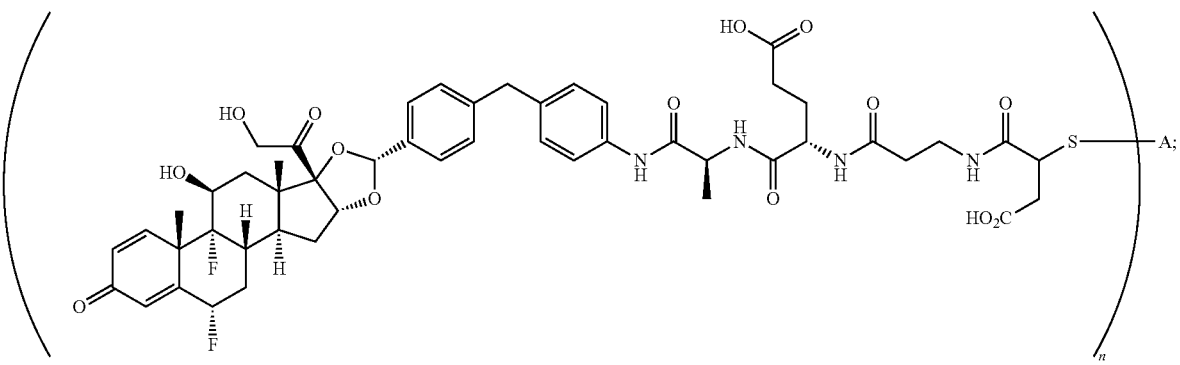
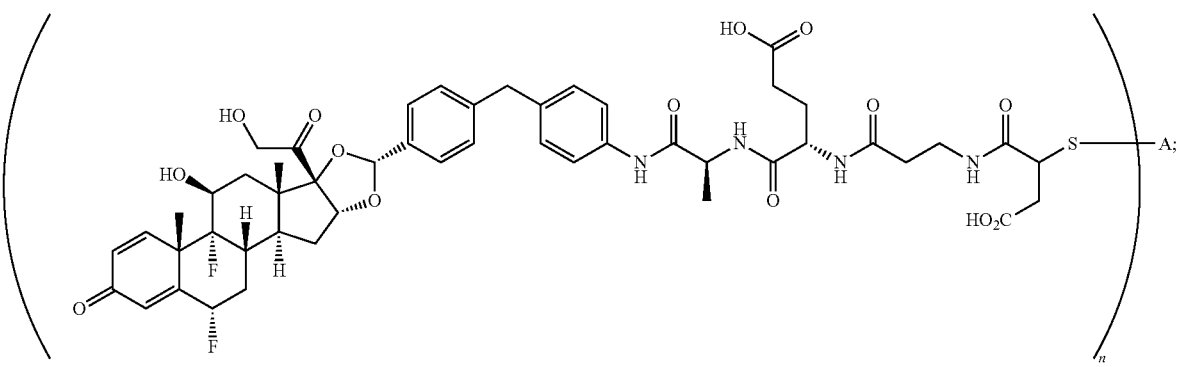
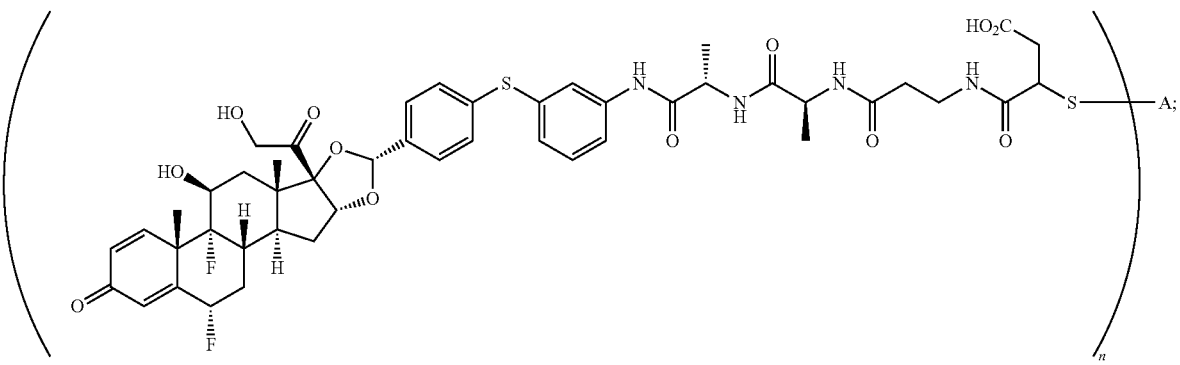

TABLE III-continued
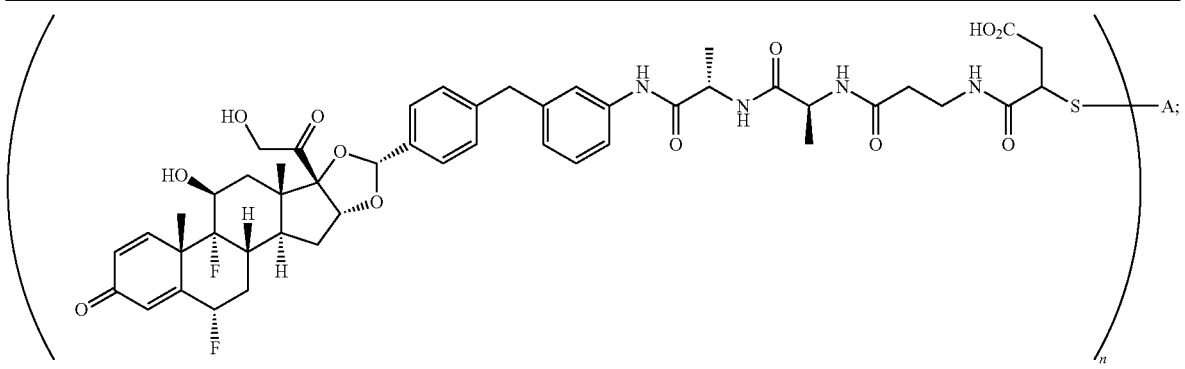
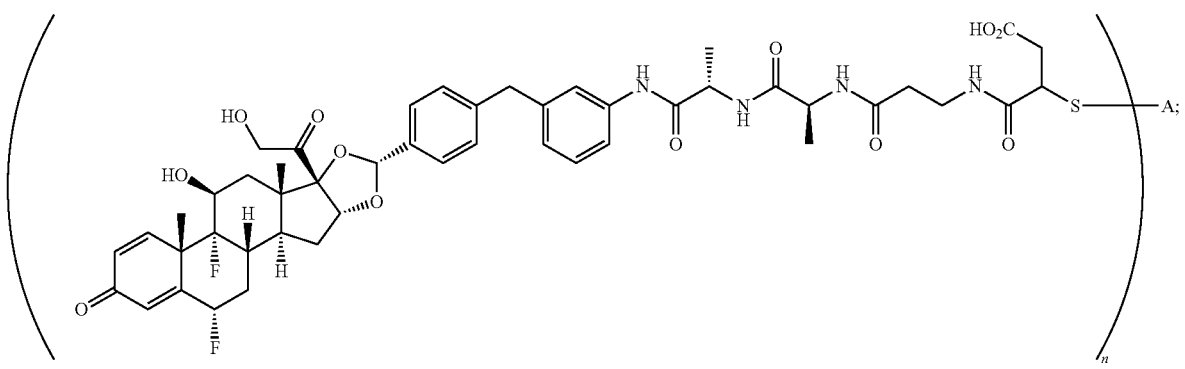
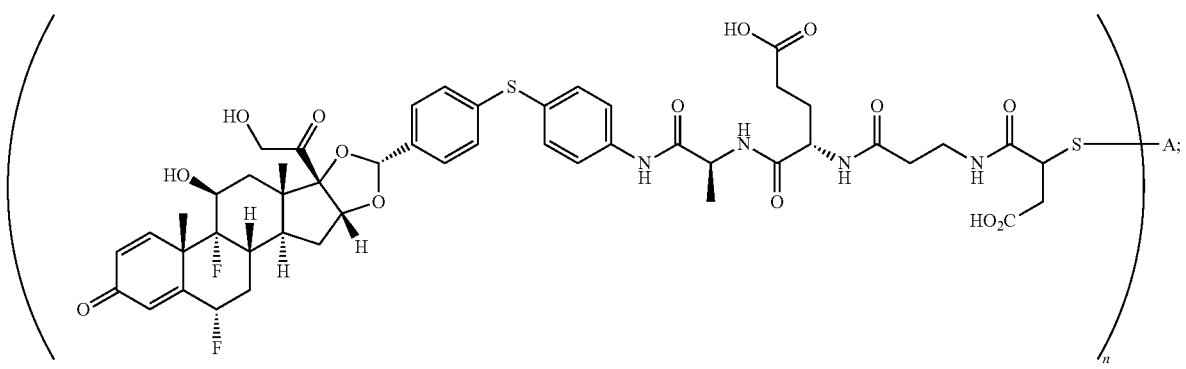
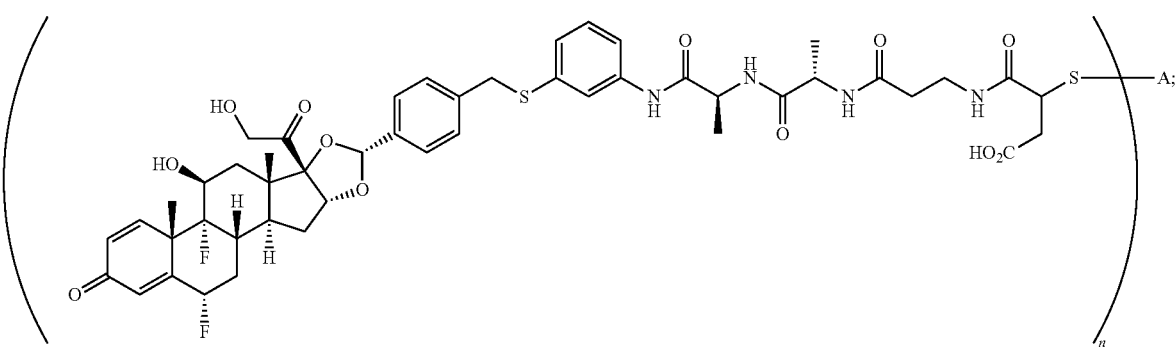

TABLE III-continued
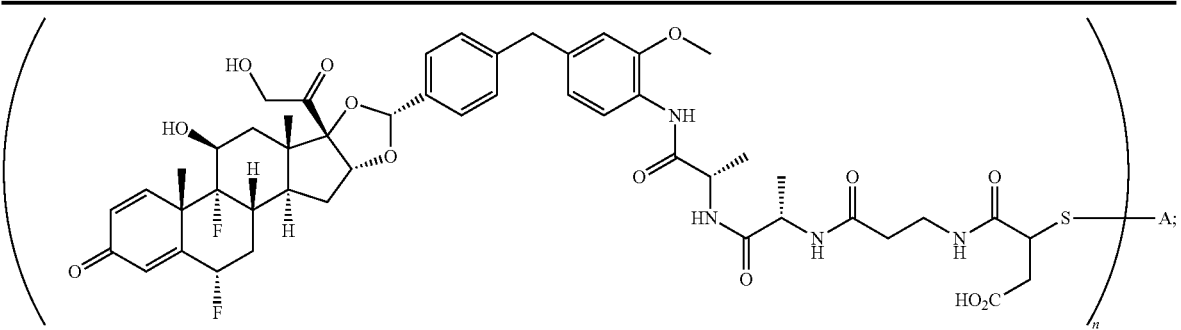
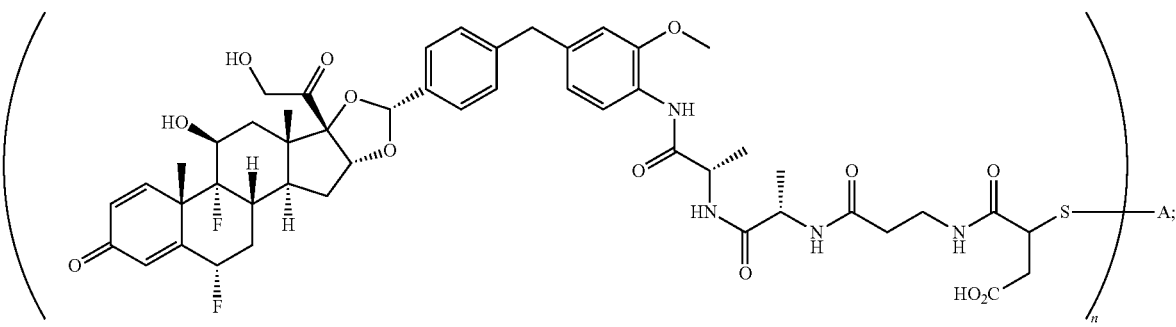
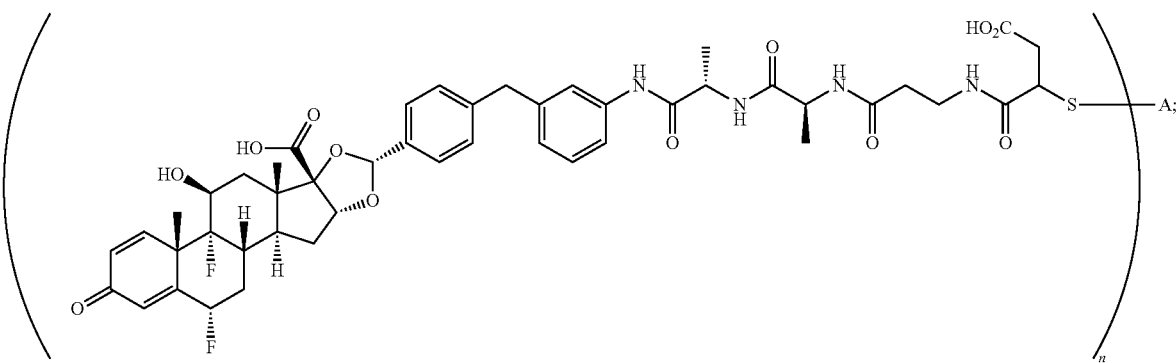
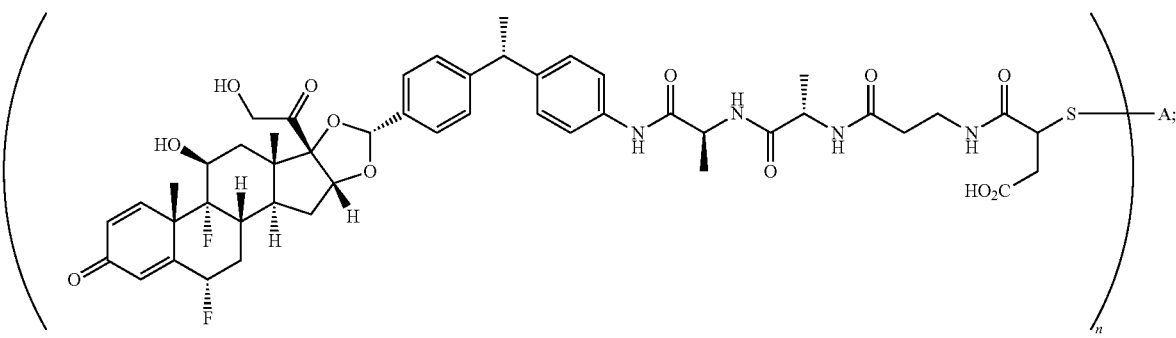

TABLE III-continued
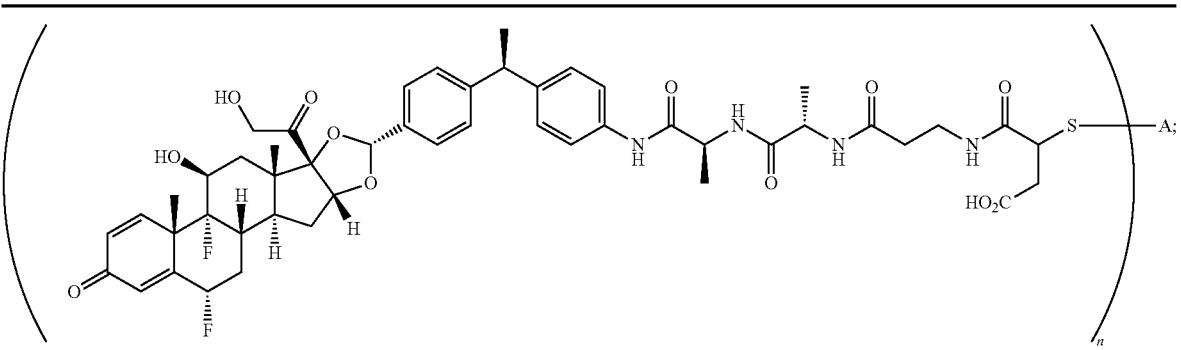
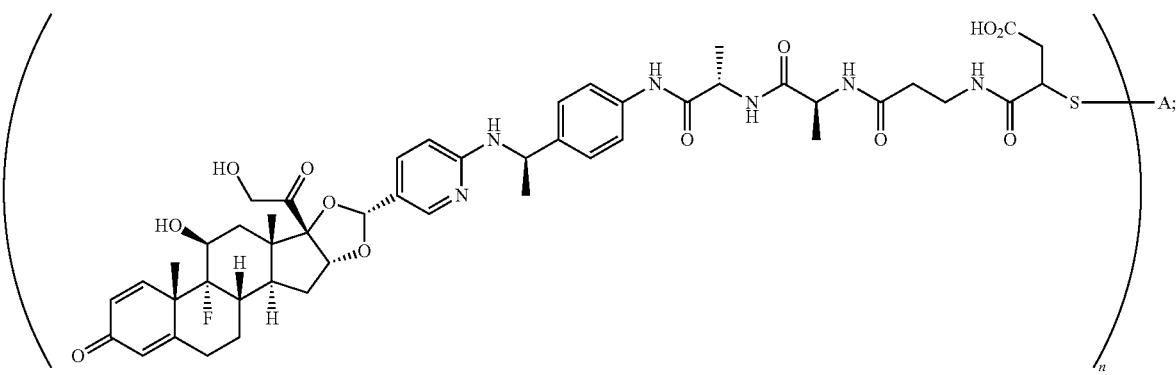
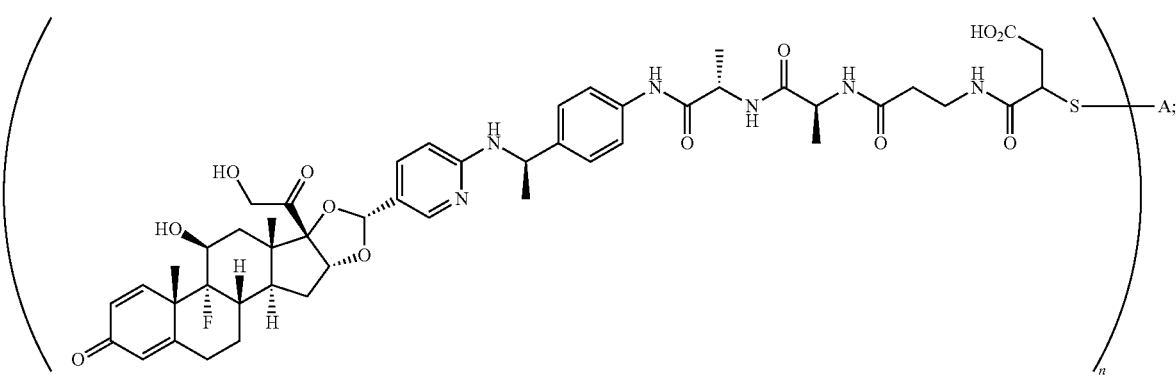
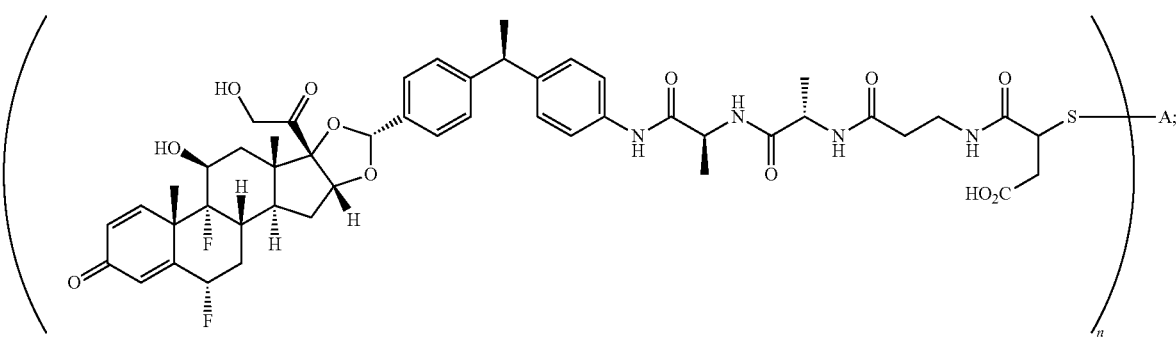

TABLE III-continued
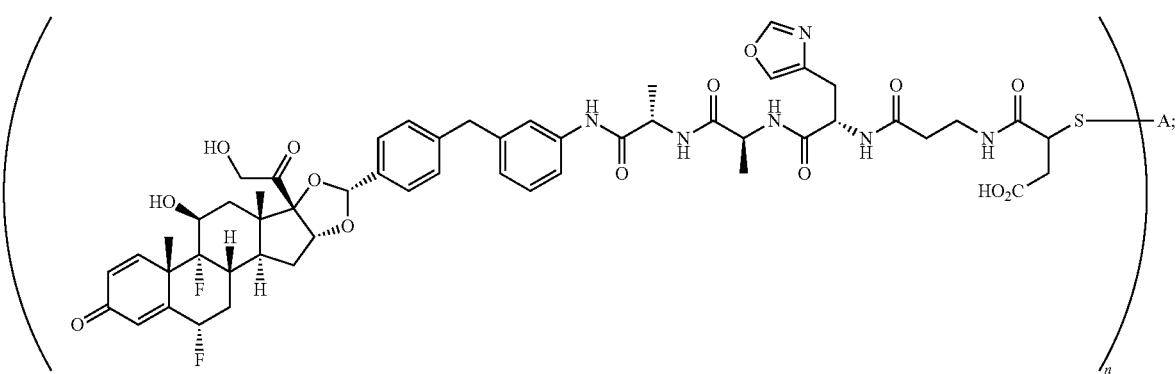
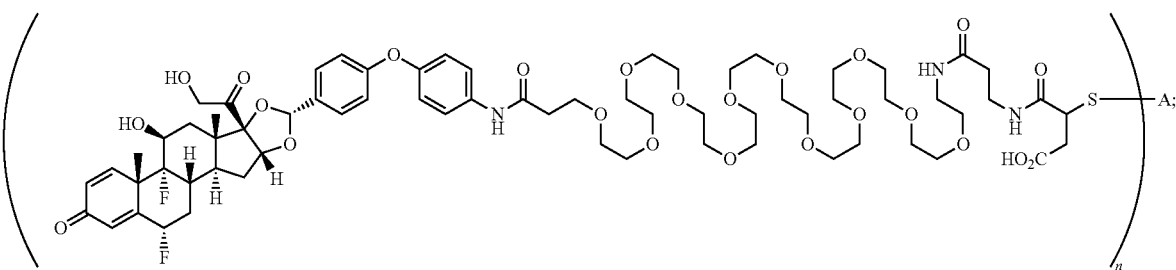
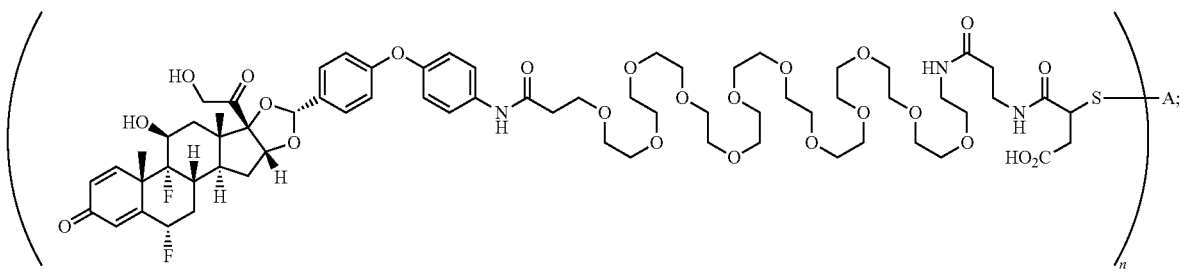
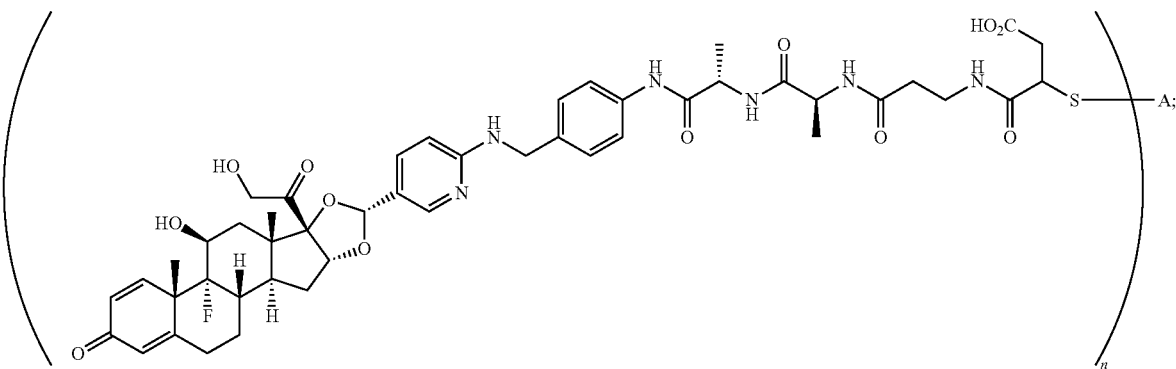

TABLE III-continued
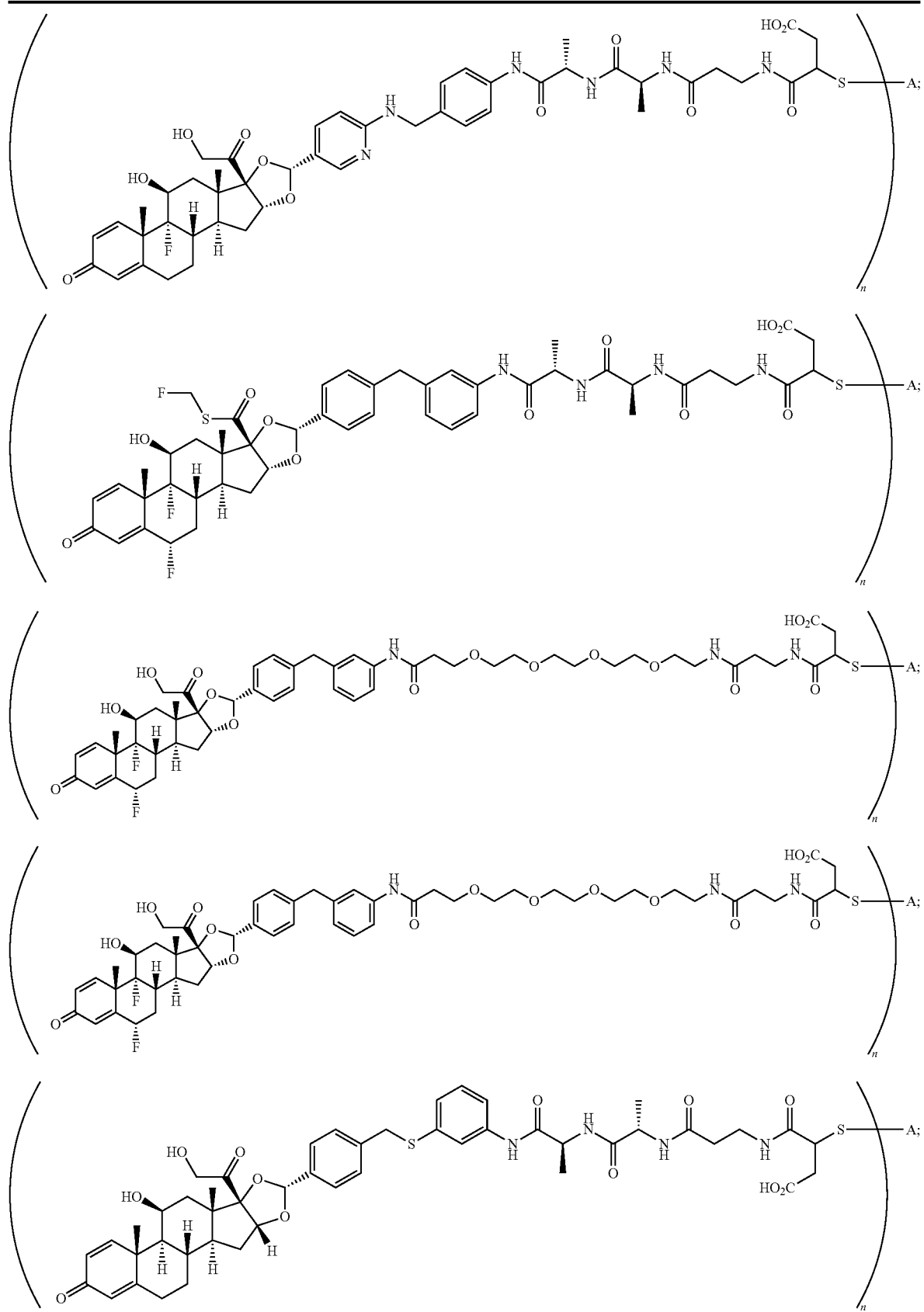

TABLE III-continued
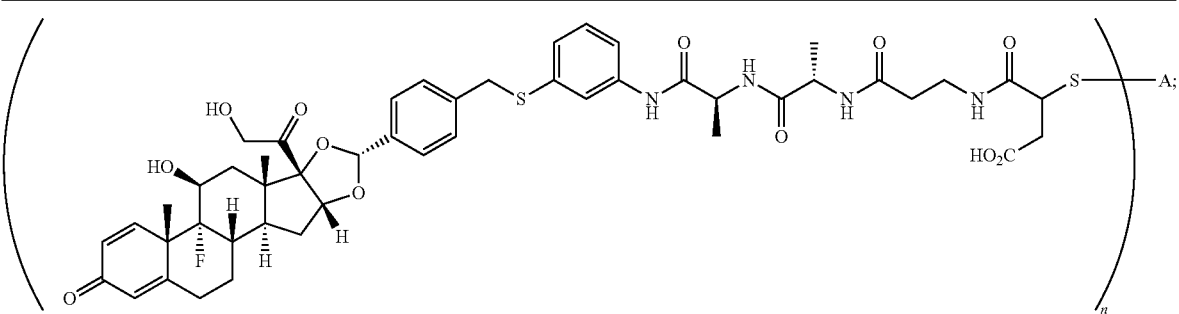
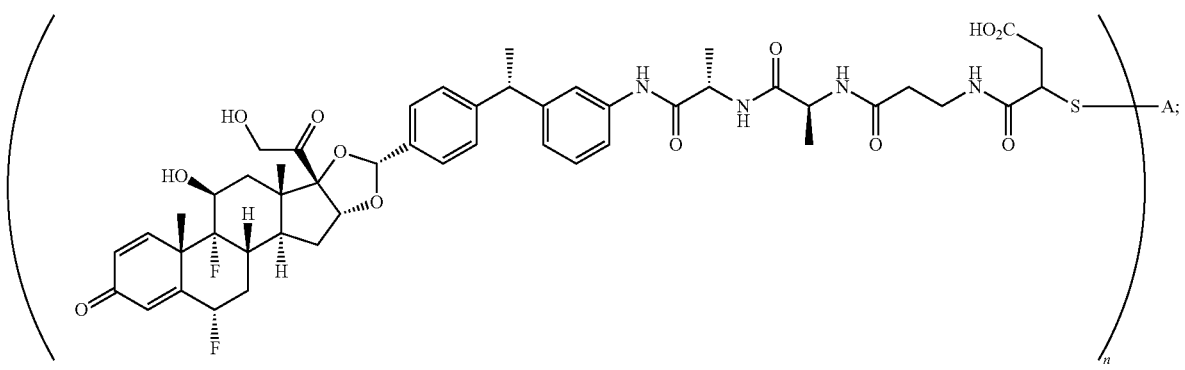
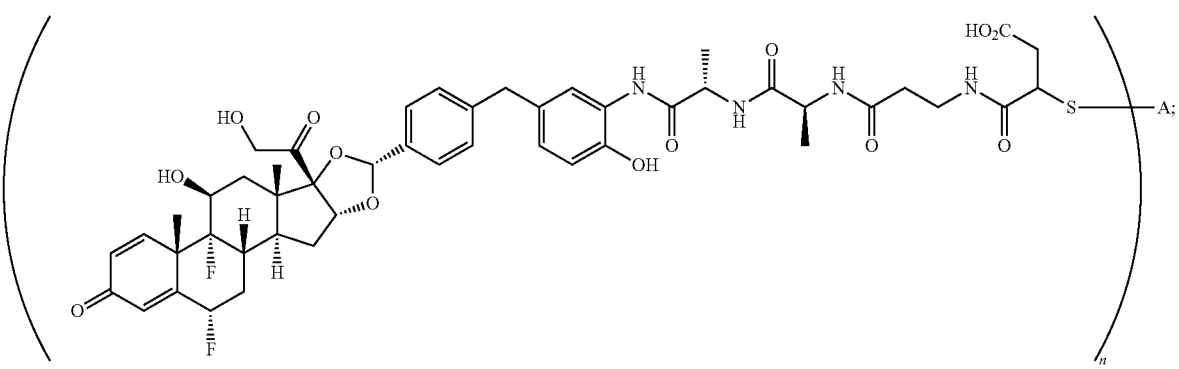
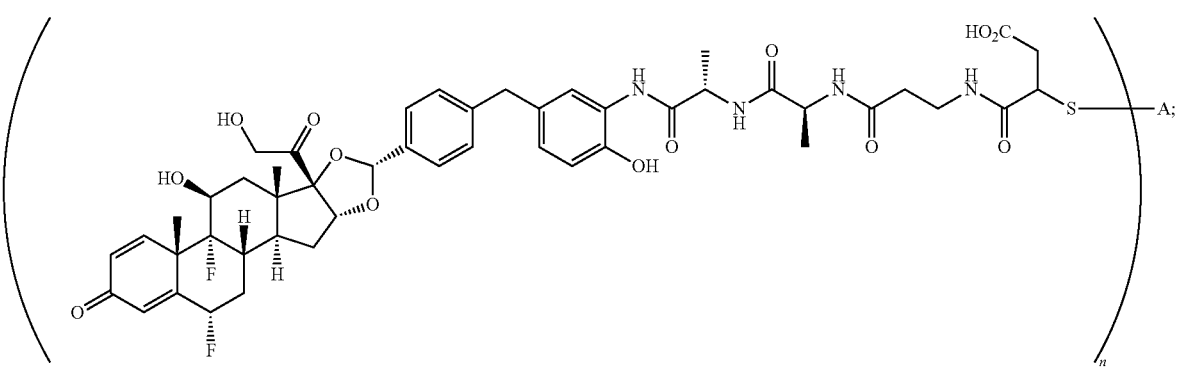

TABLE III-continued
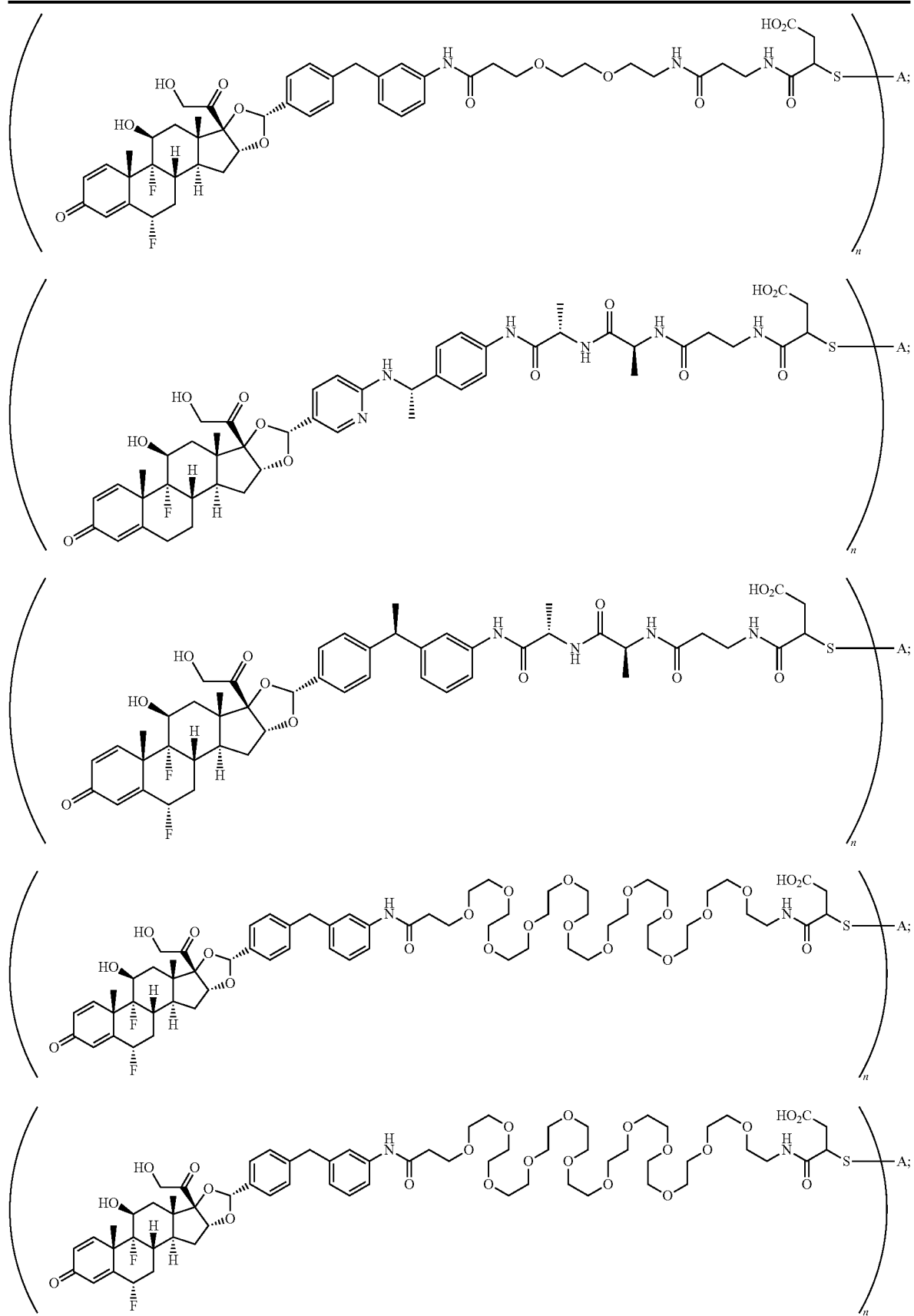

TABLE III-continued
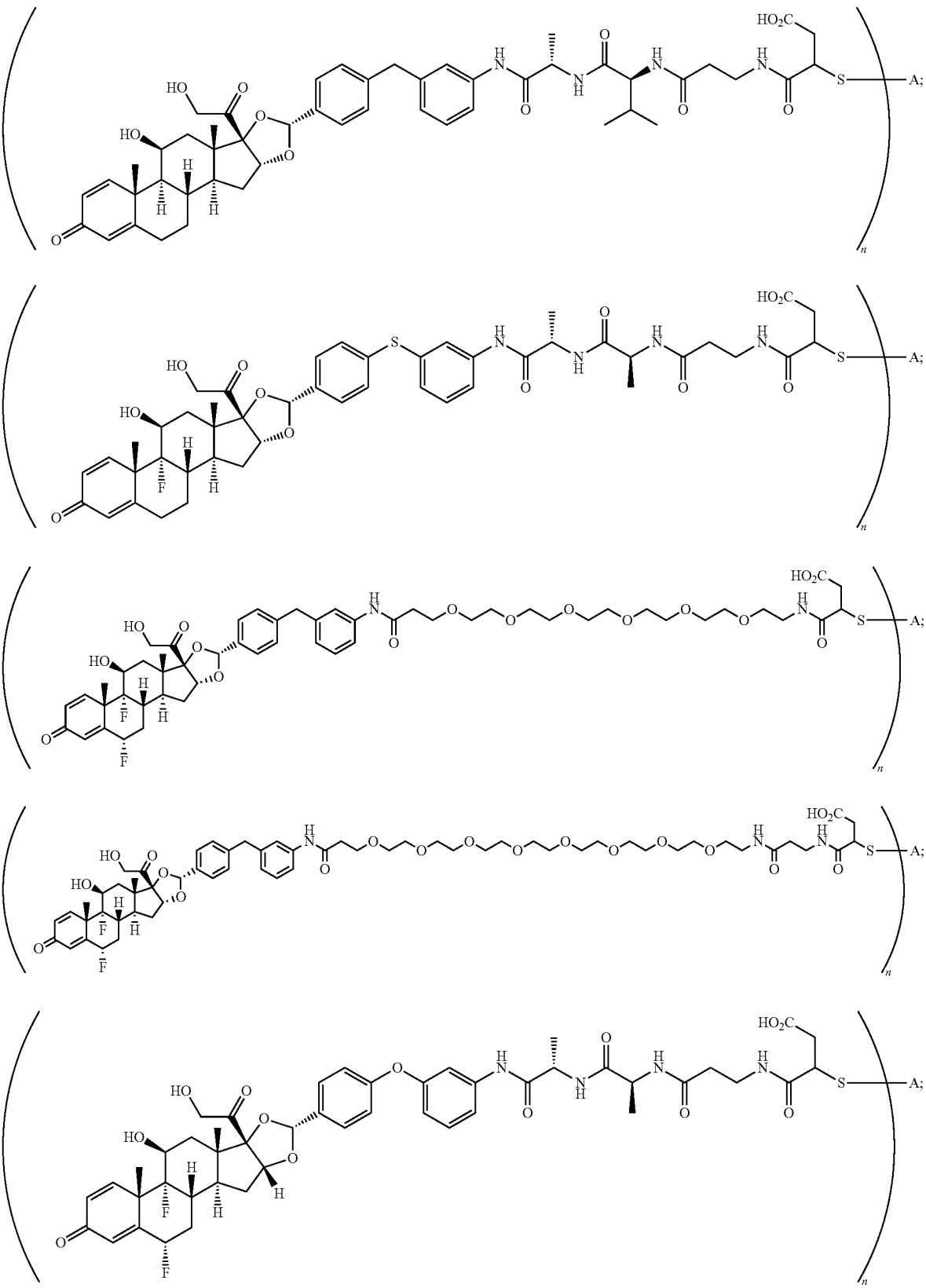

TABLE III-continued
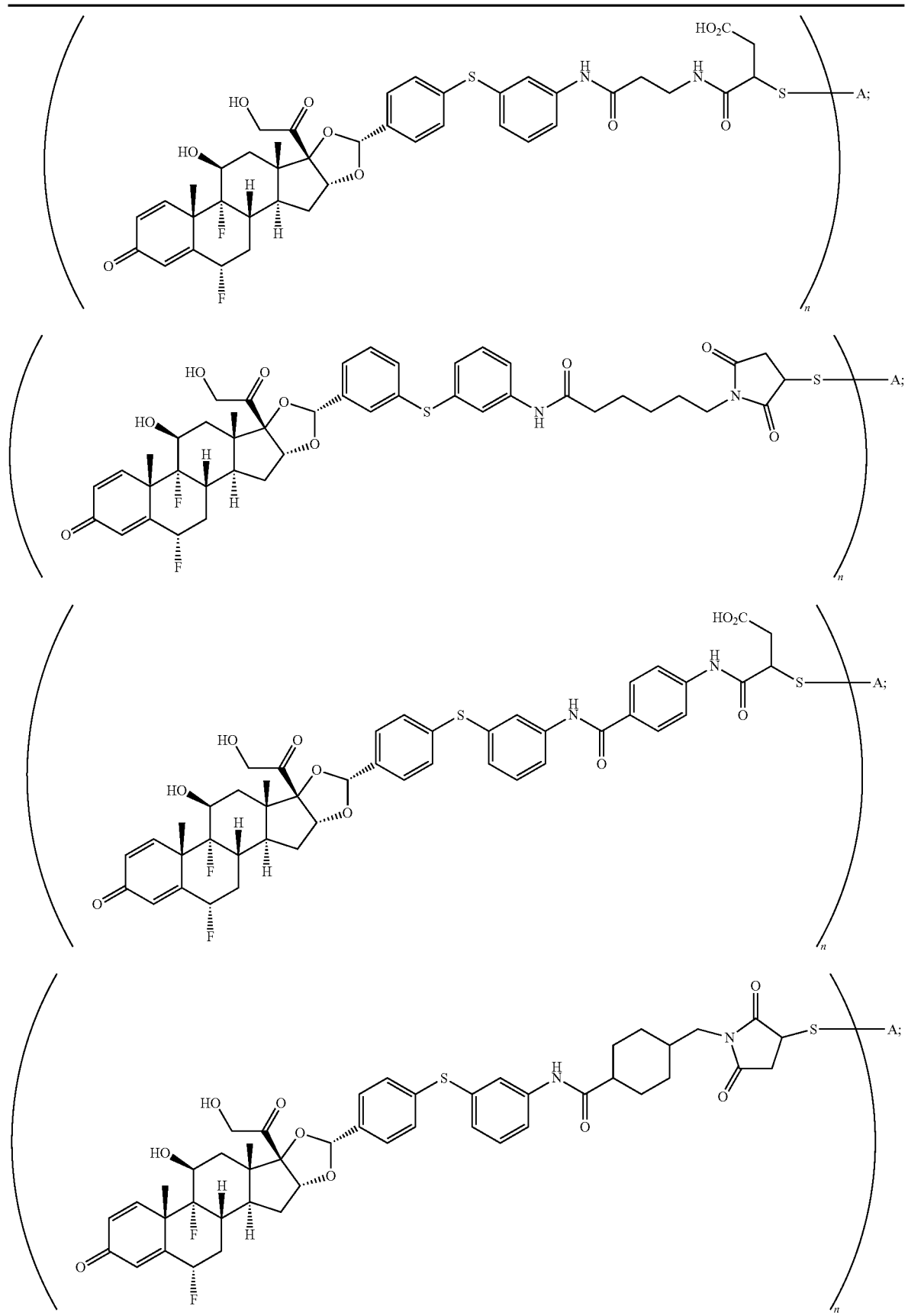

TABLE III-continued
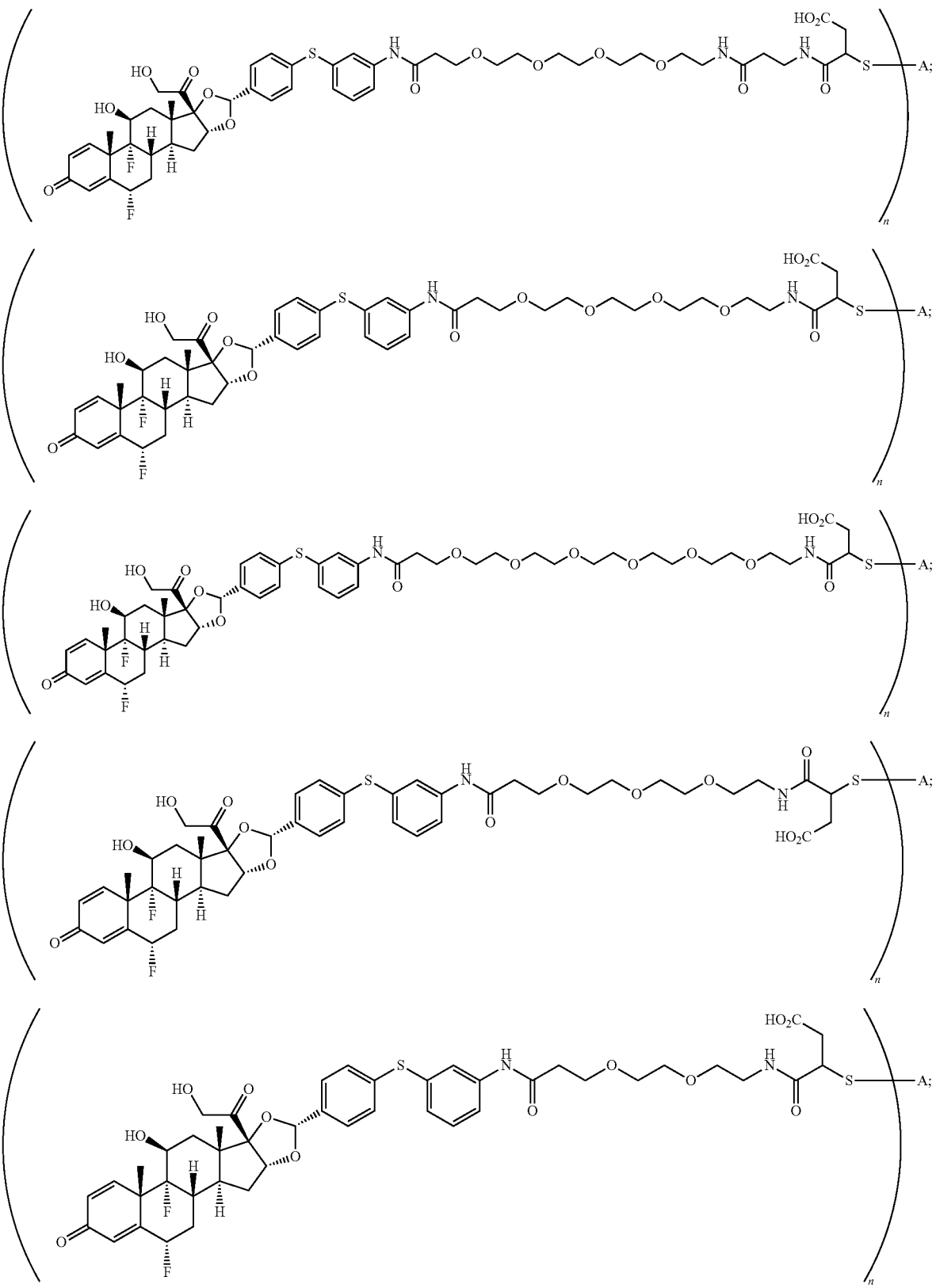
and

TABLE III-continued

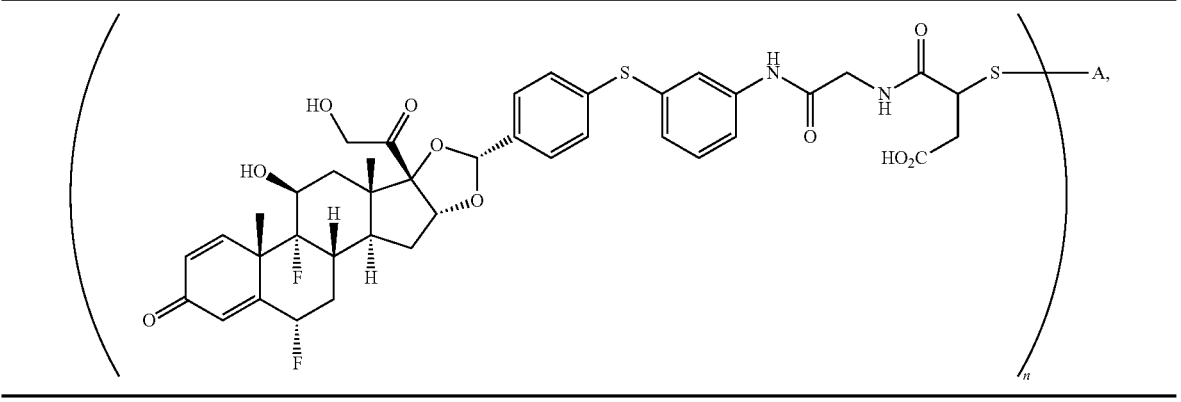

wherein n is 1-5 and A is $A^1$ or $A^2$. In another embodiment, A is adalimumab.

In another embodiment, disclosed herein is a compound having Formula I-a, or a pharmaceutically acceptable salt thereof, or a compound having Formula I-b, or a pharmaceutically acceptable salt thereof, which is any one of the chemical structures of Table IV:

TABLE IV

| Structure | n |
|---|---|

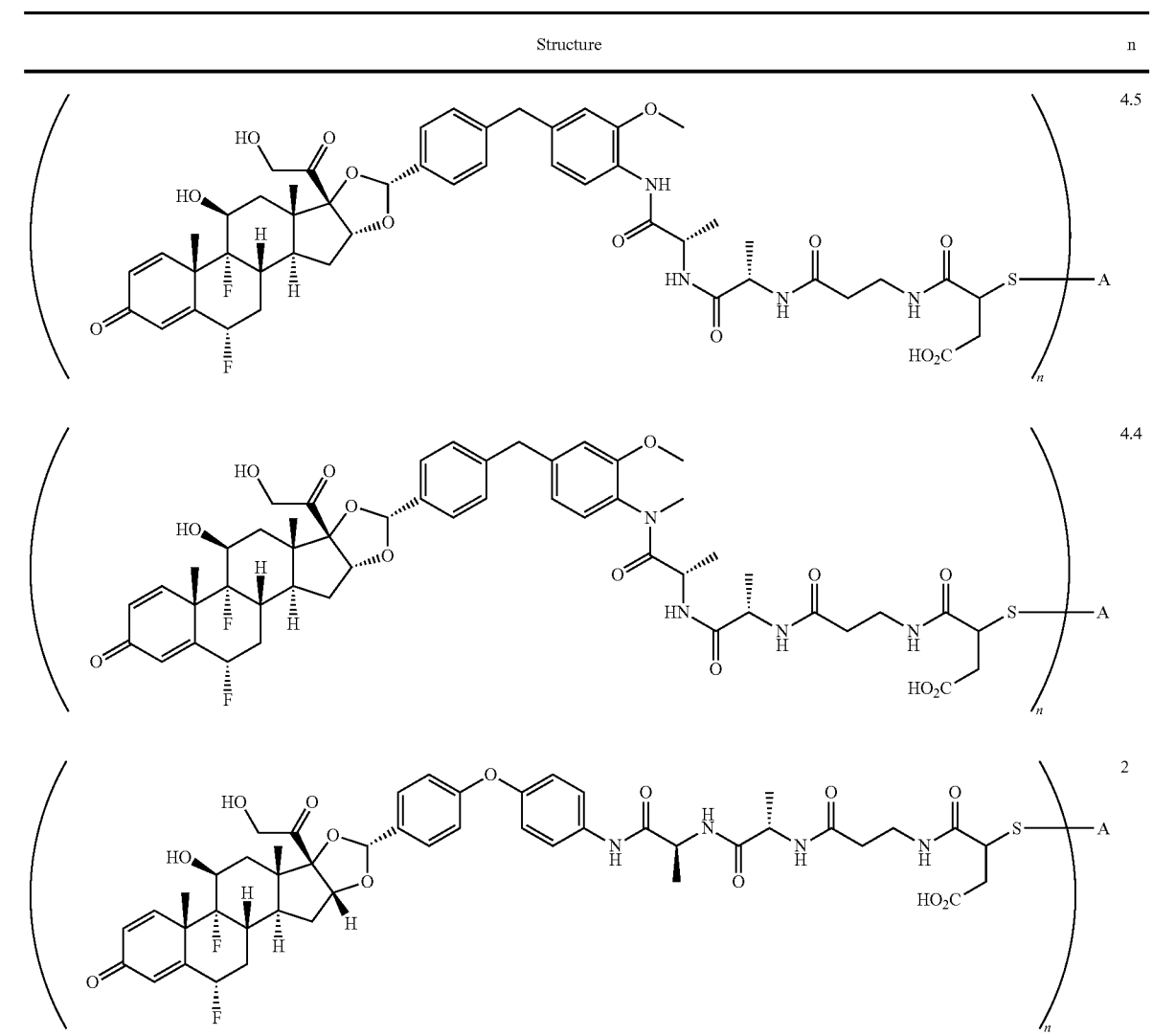

TABLE IV-continued

| Structure | n |
|---|---|
| | 4 |
| | 2 |
| | 4 |
| | 2 |
| | 4 |

TABLE IV-continued

| Structure | n |
|---|---|
| | 2 |
| | 2 |
| | 4 |
| | 4 |
| | 2 |

TABLE IV-continued

| Structure | n |
|---|---|
| | 4 |
| | 2 |
| | 4 |
| | 2 |

TABLE IV-continued

| Structure | n |
|---|---|
| | 4 |
| | 2 |
| | 4 |
| | 2 |

TABLE IV-continued

| Structure | n |
|---|---|
| | 4 |
| | 2 |
| | 4 |
| | 2 |

TABLE IV-continued

| Structure | n |
|---|---|
| | 4 |
| 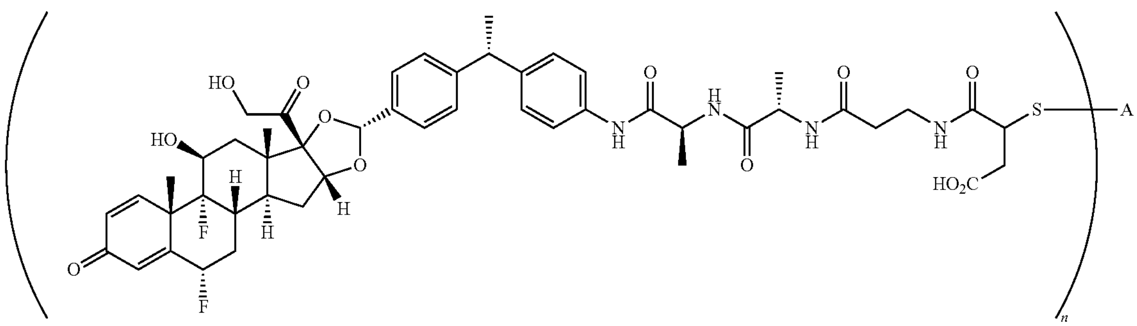 | 2 |
| | 4 |
| | 4 |

TABLE IV-continued

| Structure | n |
|---|---|
| | 2 |
| 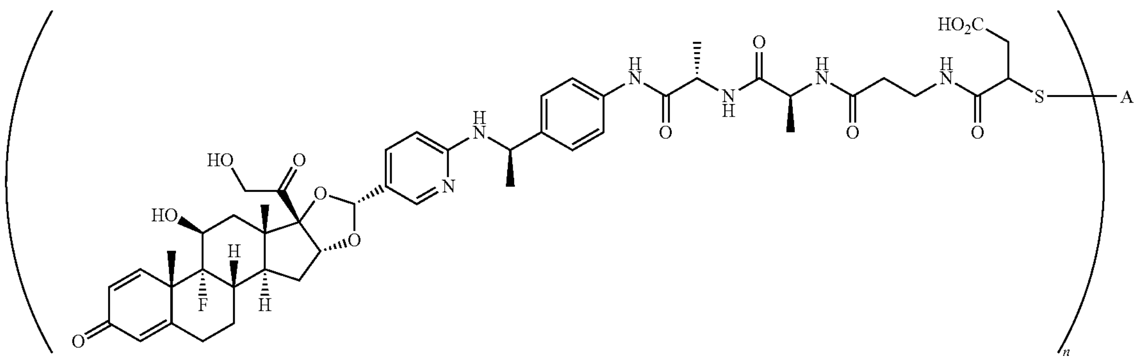 | 4 |
| | 2 |
| | 2 |

TABLE IV-continued
| Structure | n |
|---|---|
| 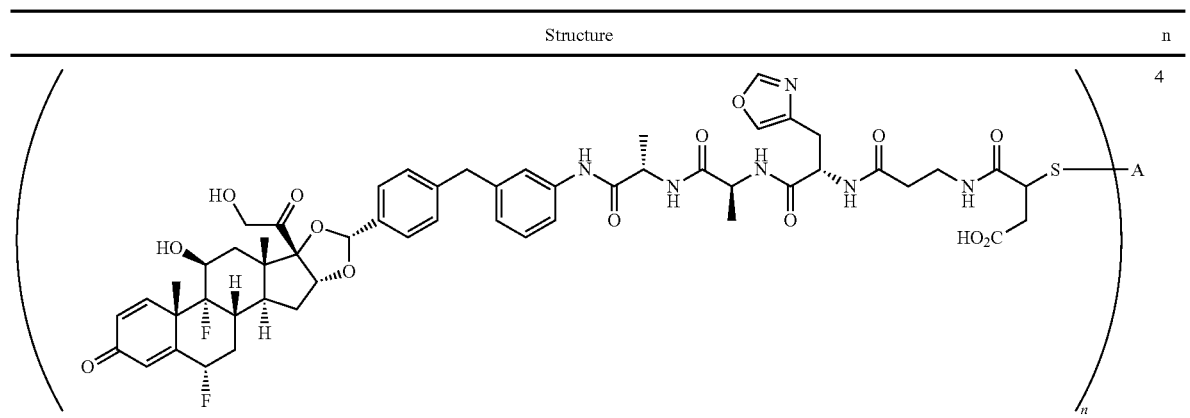 | 4 |
| 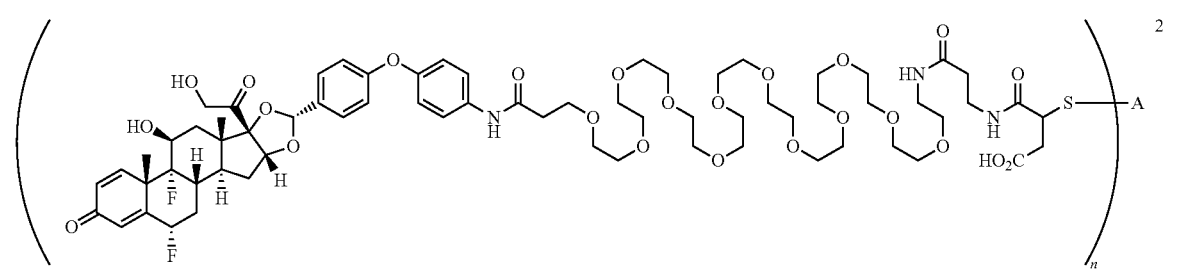 | 2 |
| 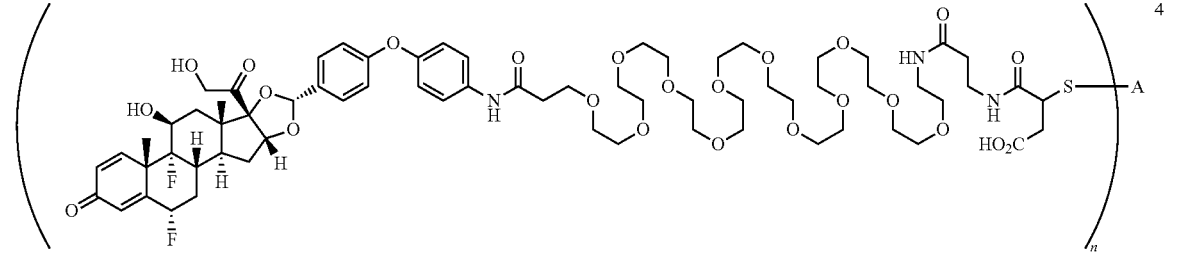 | 4 |
| 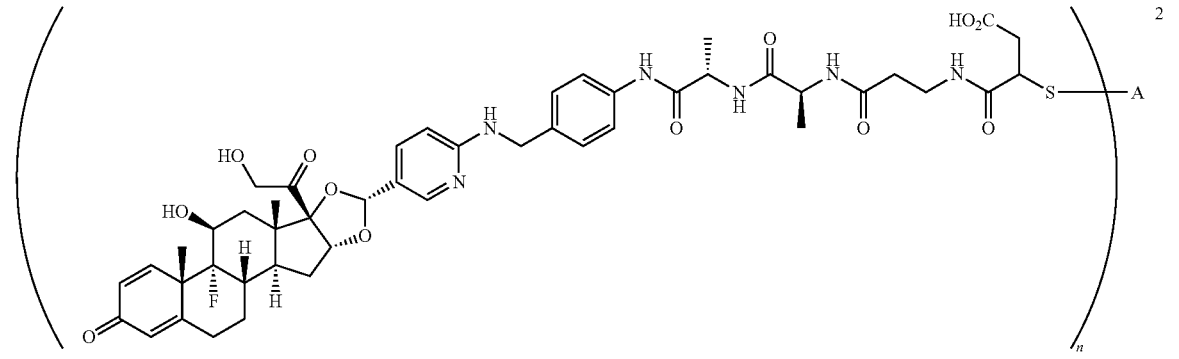 | 2 |
| 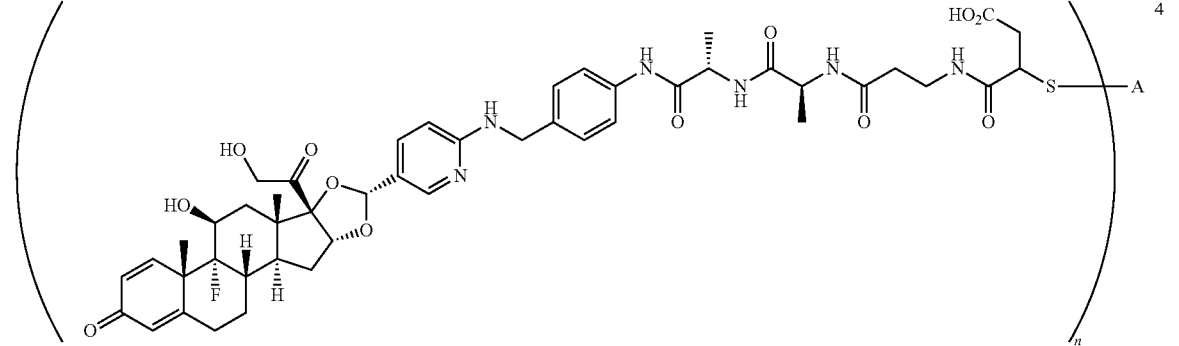 | 4 |

TABLE IV-continued

| Structure | n |
|---|---|
| (structure) | 4 |
| (structure) | 1.3 |
| (structure) | 2 |
| (structure) | 4 |
| (structure) | 4 |

TABLE IV-continued

| Structure | n |
|---|---|
| (structure) | 4 |
| (structure) | 4 |
| (structure) | 2 |
| (structure) | 4 |

TABLE IV-continued

| Structure | n |
|---|---|
| (structure) | 4 |
| (structure) | 4 |
| (structure) | 4 |
| (structure) | 2 |
| (structure) | 4 |

TABLE IV-continued

| Structure | n |
|---|---|
| (chemical structure) | 4 |
| (chemical structure) | 4 |
| (chemical structure) | 4 |
| (chemical structure) | 4 |
| (chemical structure) | 4 |

TABLE IV-continued

| Structure | n |
|---|---|
| 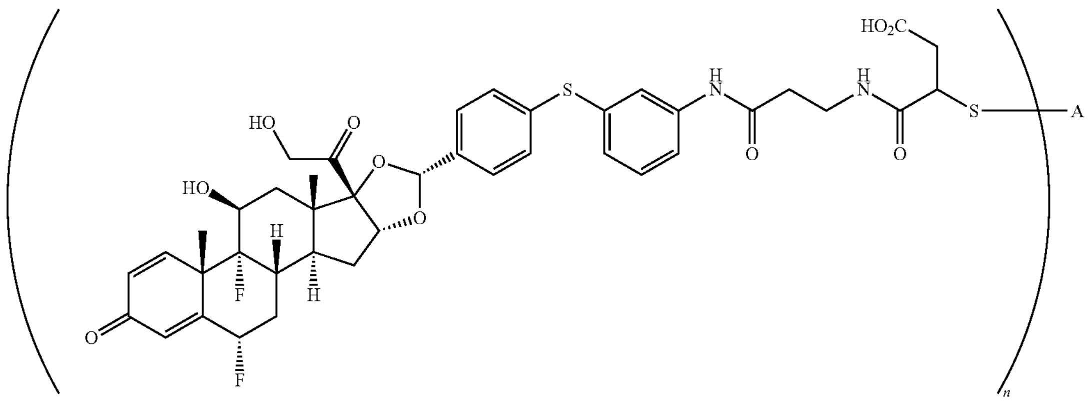 | 3.7 |
| 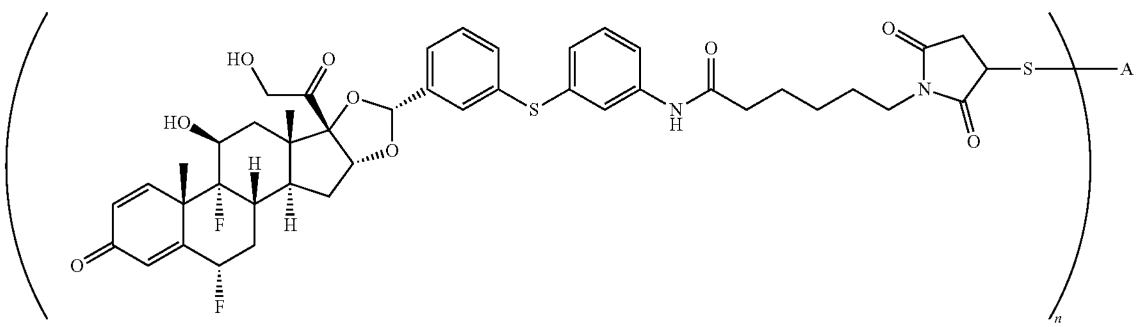 | 4.1 |
| 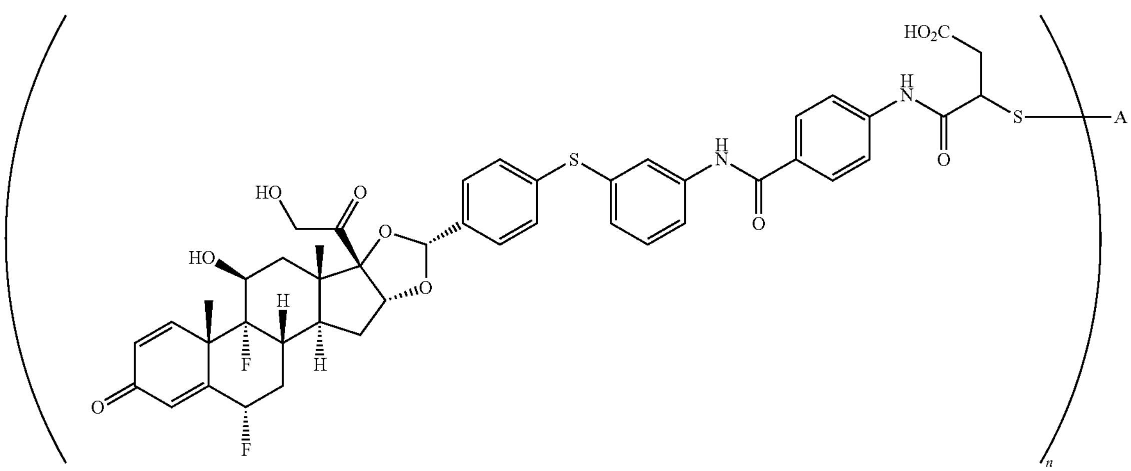 | 3.9 |

TABLE IV-continued

| Structure | n |
|---|---|
| 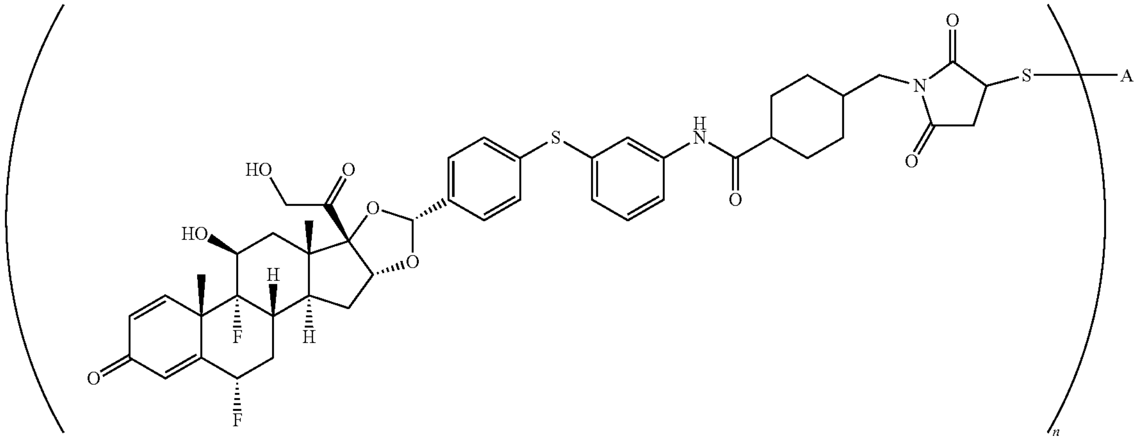 | 3.9 |
| | 3.5 |
| | 3.5 |
| | 3.6 |
| | 3.6 |

TABLE IV-continued

| Structure | n |
|---|---|
| [chemical structure] | 3.5 |
| [chemical structure] | 3.8 | wherein A is $A^1$ or $A^2$. In another embodiment, A is adalimumab.

In another embodiment, disclosed herein is a compound having Formula I-a, or a pharmaceutically acceptable salt thereof, or a compound having Formula I-b, or a pharmaceutically acceptable salt thereof, which is any one of the chemical structures of Table IV-A:

TABLE IV-A

| Structure | n |
|---|---|
| [chemical structure] | 2 |
| [chemical structure] | 4 |

TABLE IV-A-continued
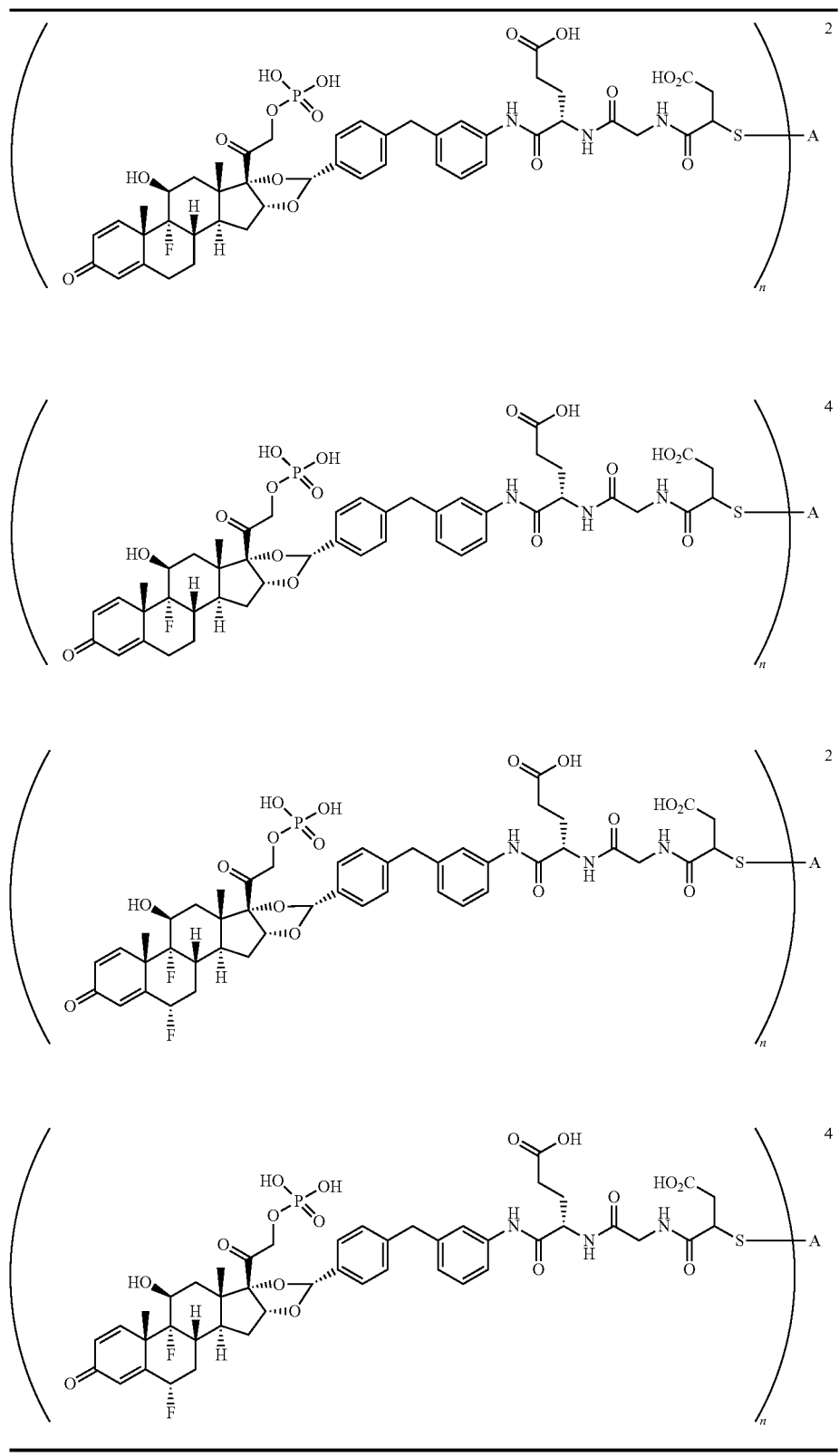
wherein A is $A^1$ or $A^2$. In another embodiment, A is adalimumab.
In another embodiment, disclosed herein is a compound having Formula I-a, or a pharmaceutically acceptable salt thereof, or a compound having Formula I-b, or a pharmaceutically acceptable salt thereof, which is any one of the chemical structures of Table V:

TABLE V
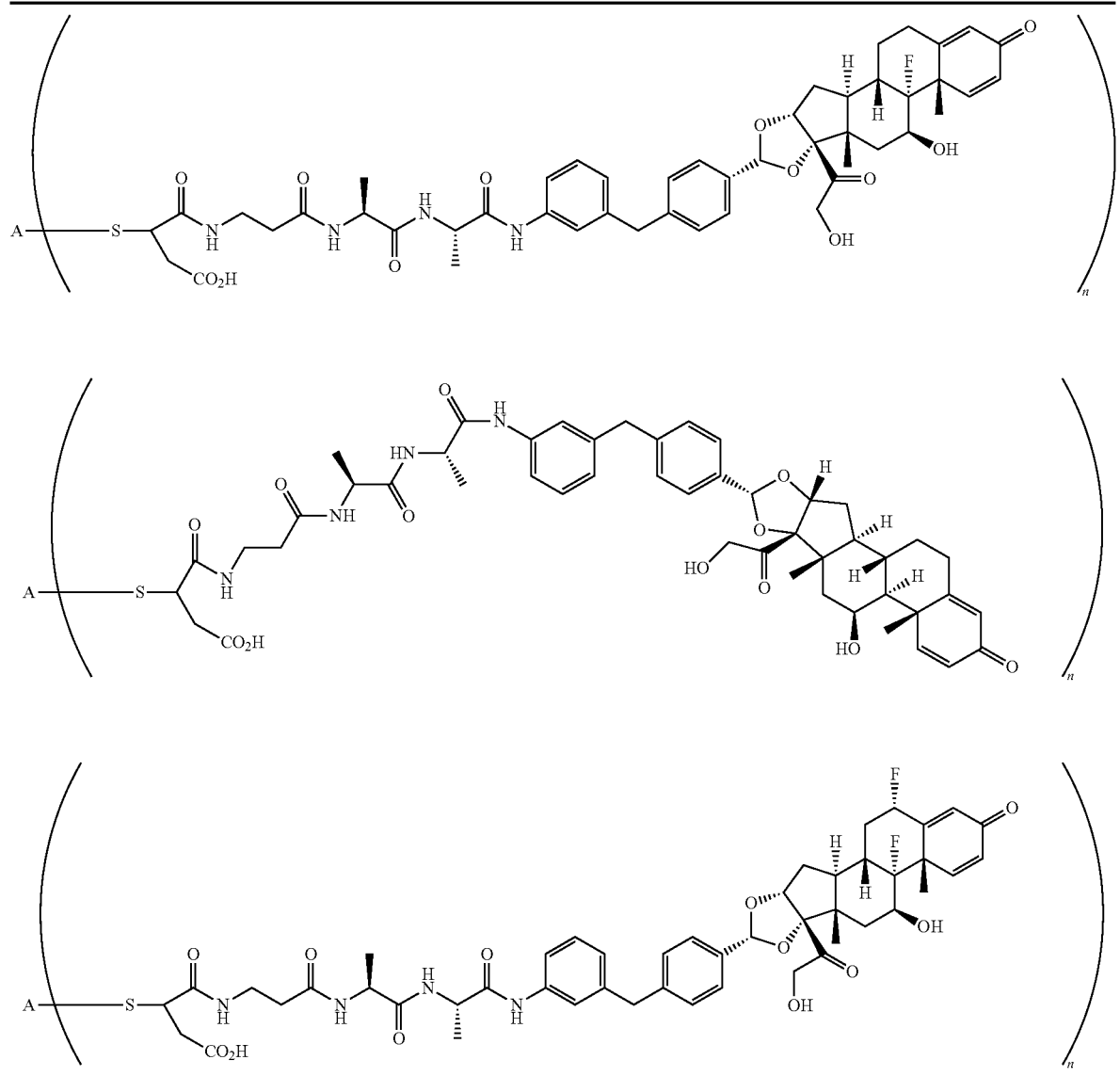
wherein n is 1-5 and A is $A^1$ or $A^2$. In another embodiment, A is adalimumab.
In another embodiment, disclosed herein is a compound having Formula I-a, or a pharmaceutically acceptable salt thereof, or a compound having Formula I-b, or a pharmaceutically acceptable salt thereof, selected from the group consisting of:
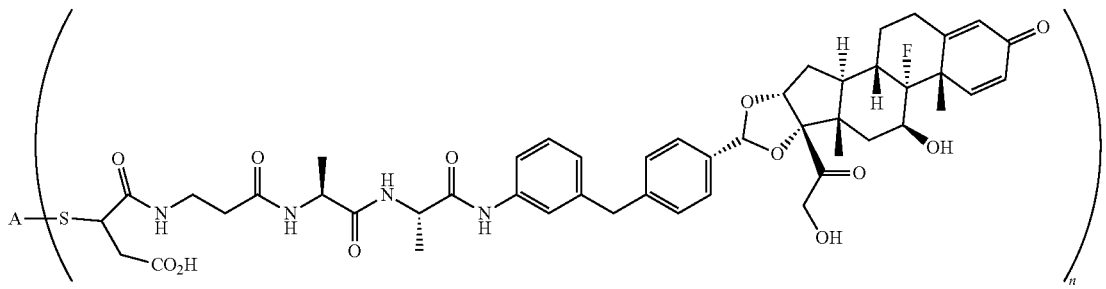

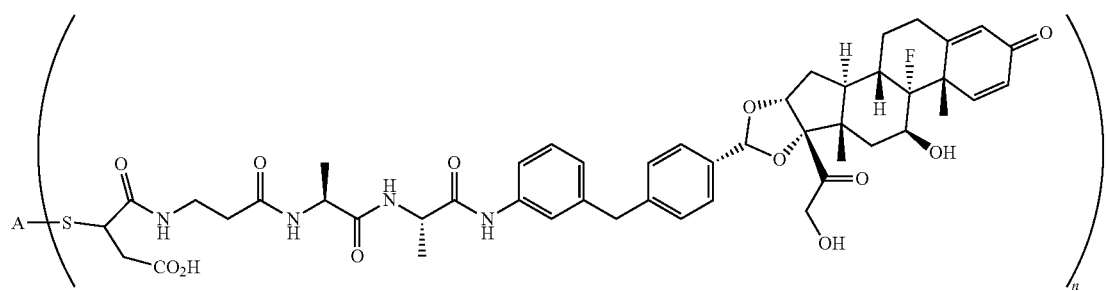
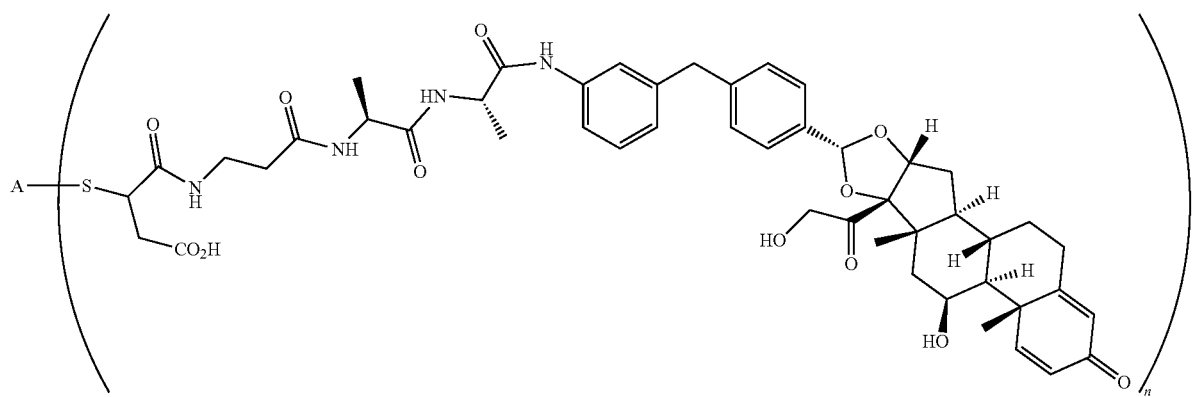
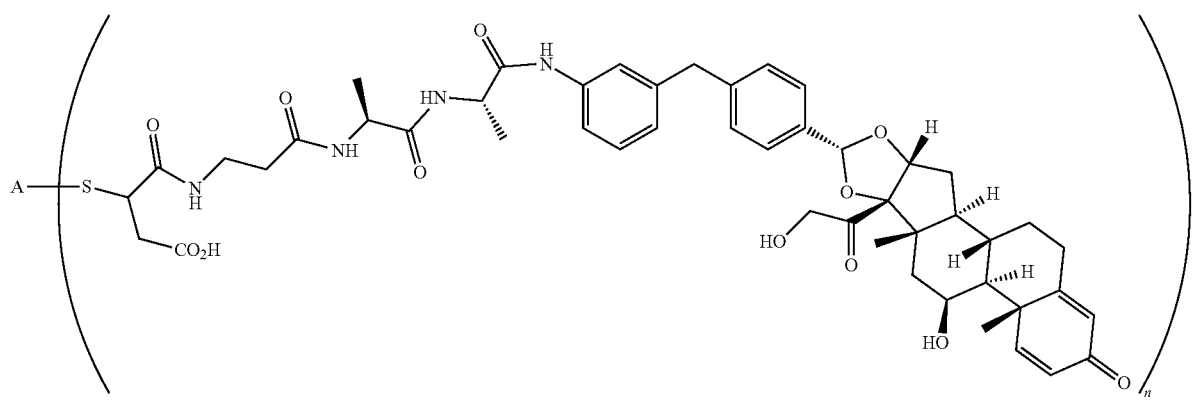
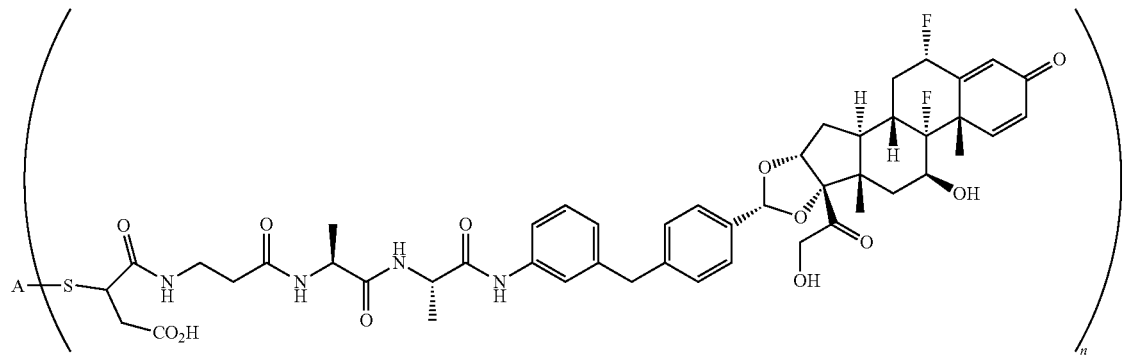

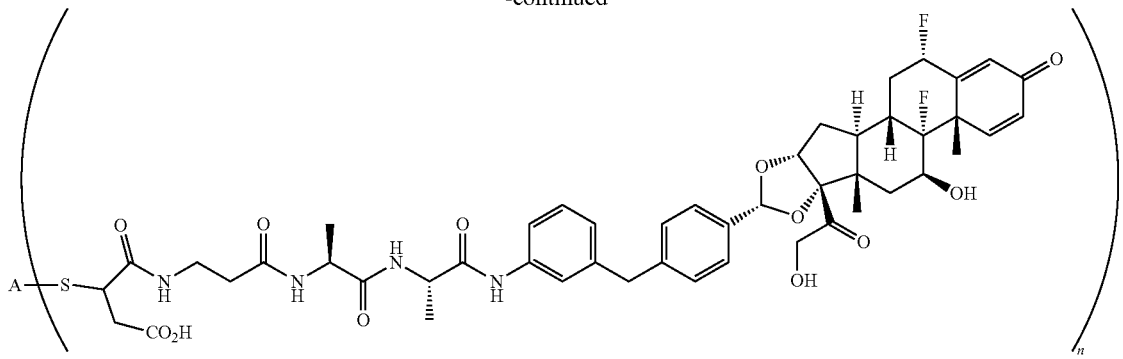

wherein n is 2-4, A is $A^1$ or $A^2$. In another embodiment, A is adalimumab. In another embodiment, n is 2 or 4. In another embodiment, n is 2. In another embodiment, n is 4.

IV. Glucocorticoid Receptor Agonists

In another embodiment, disclosed herein is a compound having Formula VII:

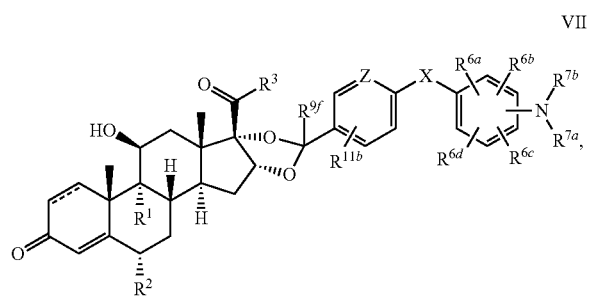

or a pharmaceutically acceptable salt thereof, wherein:

$R^1$ is selected from the group consisting of hydrogen and halo;

$R^2$ is selected from the group consisting of hydrogen, halo, and hydroxy;

$R^3$ is selected from the group consisting of —$CH_2OH$, —$CH_2SH$, —$CH_2Cl$, —$SCH_2Cl$, —$SCH_2F$, —$SCH_2CF_3$, —$CH_2OS(=O)_2OH$, —OH, —$OCH_2CN$, —$OCH_2Cl$, —$OCH_2F$, —$OCH_3$, —$OCH_2CH_3$, —$SCH_2CN$,

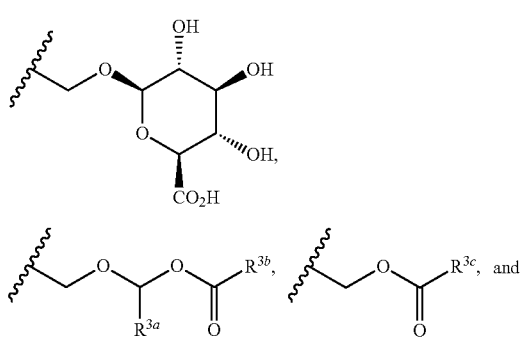

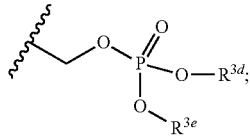

$R^{3a}$ is selected from the group consisting of hydrogen and $C_{1-4}$ alkyl;

$R^{3b}$ is selected from the group consisting of $C_{1-4}$ alkyl and $C_{1-4}$ alkoxy;

$R^{3c}$ is selected from the group consisting of hydrogen, $C_{1-4}$ alkyl, —$CH_2H$, $C_{1-4}$ alkoxy, —$CH_2$(amino), and —$CH_2CH_2C(=O)OR^{3f}$;

$R^{3d}$ and $R^{3e}$ are independently selected from the group consisting of hydrogen and $C_{1-4}$ alkyl;

$R^{3f}$ is selected from the group consisting of hydrogen and $C_{1-4}$ alkyl;

X is selected from the group consisting of —($CR^{4a}R^{4b})_t$—, —O—, —S—, —S(=O)—, —S(=O)$_2$—, —$NR^5$—, —$CH_2S$—, —$CH_2O$—, —N(H)C($R^{8a}$)($R^{8b}$)—, —$CR^{4c}$=$CR^{4d}$— (including both E and Z isomers), —C≡C—, —N($R^5$)C(=O)—, and —OC(=O)—; (wherein when X is —$CH_2S$—, —$CH_2O$—, —N(H)C($R^{8a}$)($R^{8b}$)—, —N($R^5$)C(=O)—, or —OC(=O)—; the hetereoatom of —$CH_2S$—, —$CH_2O$—, —N(H)C($R^{8a}$)($R^{8b}$)—, —N($R^5$)C(=O)—, or —OC(=O)—; can be attached to either 6-membered ring, i.e., —$CH_2S$— is equivalent to —$SCH_2$—, —$CH_2O$— is equivalent to —$OCH_2$—, —N(H)C($R^{8a}$)($R^{8b}$)— is equivalent to —C($R^{8a}$)($R^{8b}$)N(H)—), —N($R^5$)C(=O)— is equivalent to —C(=O)N($R^5$) C=O)— and —OC(=O)— is equivalent to —C(=O)O—; or X is absent, i.e., X represents a chemical bond;

t is 1 or 2;

Z is selected from the group consisting of =$CR^{11a}$— and =N—;

each $R^{4a}$ and $R^{4b}$ are independently selected from the group consisting of hydrogen and $C_{1-4}$ alkyl; or $R^{4a}$ and $R^{4b}$ taken together with the carbon atom to which they are attached form a 3- to 6-membered cycloalkyl;

$R^{4c}$ and $R^{4d}$ are independently selected from the group consisting of hydrogen and $C_{1-4}$ alkyl;

$R^5$ is selected from the group consisting of hydrogen and $C_{1-4}$ alkyl;

$R^{6a}$, $R^{6b}$, $R^{6c}$, and $R^{6d}$ are each independently selected from the group consisting of hydrogen, halo, $C_{1-4}$ alkyl, haloalkyl, cyano, hydroxy, thiol, amino, alkylthio, and alkoxy;

$R^{7a}$ is selected from the group consisting of hydrogen and $C_{1-4}$ alkyl;
$R^{7b}$ is selected from the group consisting of hydrogen, -L-H, -L-PG,

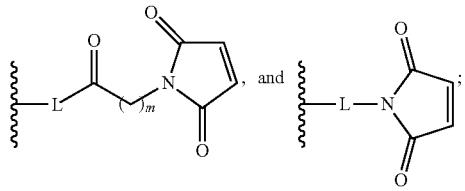

$R^{7a}$ and $R^{7b}$ taken together with the nitrogen atom to which they are attached form:

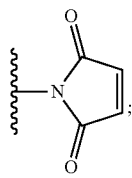

$R^{7a}$ and $R^{7b}$ taken together with the nitrogen atom to which they are attached form a nitro ($—NO_2$) group;
m is 1, 2, 3, 4, 5, or 6;
L is a linker;
PG is a protecting group, e.g., Boc, FMOC;
$R^{9f}$ is selected from the group consisting of hydrogen and $C_{1-4}$ alkyl;
$R^{8a}$ and $R^{8b}$ are independently selected from the group consisting of hydrogen and $C_{1-4}$ alkyl;
$R^{11a}$ and $R^{11b}$ are independently selected from the group consisting of hydrogen, halo, $C_{1-4}$ alkyl, $C_{1-4}$ haloalkyl, cyano, hydroxy, thiol, amino, alkylthio, and alkoxy; and
=== represents a single or double bond. In another embodiment, $R^{7b}$ is hydrogen. In another embodiment, $R^{7b}$ is selected from the group consisting of:

$R^{7b}$-1

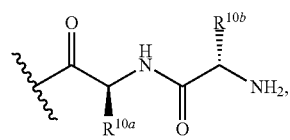

$R^{7b}$-2

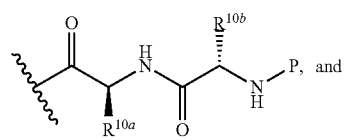

$R^{7b}$-3

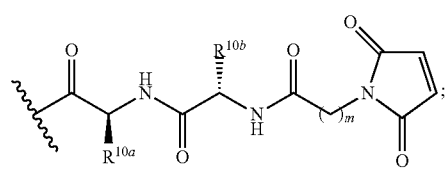

m is 1, 2, 3, 4, 5, or 6; and
$R^{10a}$ and $R^{10b}$ are each independently selected from the group consisting of hydrogen and optionally substituted $C_{1-6}$ alkyl.

In another embodiment, disclosed herein is a compound having Formula VII':

VII'

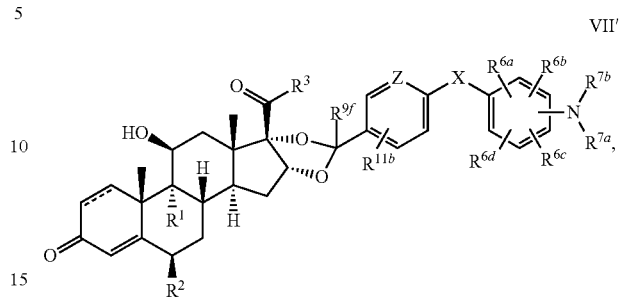

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula VII":

VII"

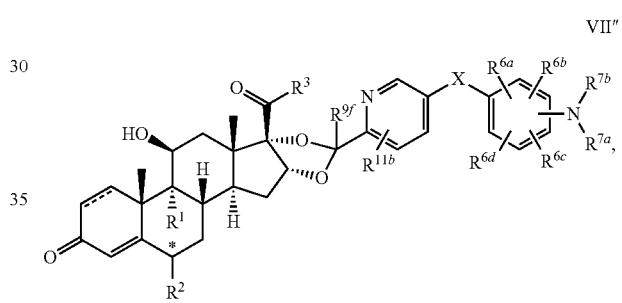

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, === and X are as defined in connection with Formula VII, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having Formula VII-A or Formula VII-B:

VII-A

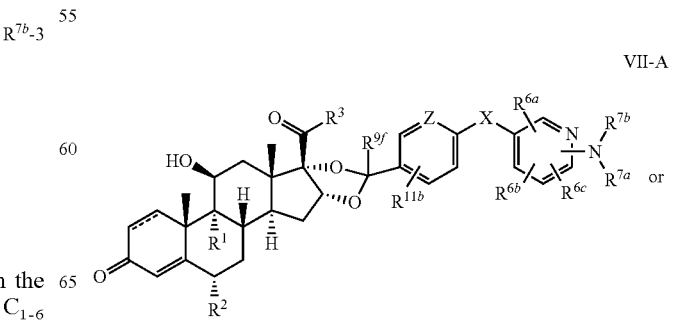

or

-continued

VII-B

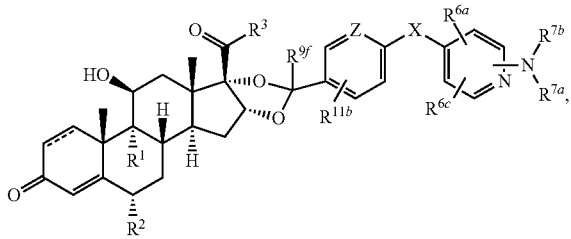

or a pharmaceutically acceptable salt or solvate thereof, wherein:

$R^1$ is selected from the group consisting of hydrogen and halo;

$R^2$ is selected from the group consisting of hydrogen, halo, and hydroxy;

$R^3$ is selected from the group consisting of —CH$_2$OH, —CH$_2$SH, —CH$_2$Cl, —SCH$_2$Cl, —SCH$_2$F, —SCH$_2$CF$_3$, —CH$_2$OS(=O)$_2$OH, hydroxy, —OCH$_2$CN, —OCH$_2$Cl, —OCH$_2$F, —OCH$_3$, —OCH$_2$CH$_3$, —SCH$_2$CN,

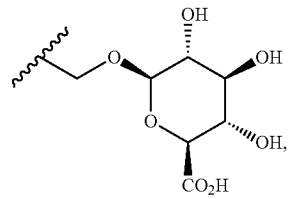

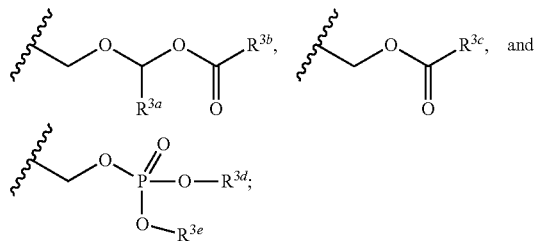

$R^{3a}$ is selected from the group consisting of hydrogen and C$_{1-4}$ alkyl;

$R^{3b}$ is selected from the group consisting of C$_{1-4}$ alkyl and C$_{1-4}$ alkoxy;

$R^{3C}$ is selected from the group consisting of hydrogen, C$_{1-4}$ alkyl, —CH$_2$OH, C$_{1-4}$ alkoxy, —CH—$_2$(amino), and —CH$_2$CH$_2$C(=O)OR$^{3f}$;

$R^{3d}$ and $R^{3e}$ are independently selected from the group consisting of hydrogen and C$_{1-4}$ alkyl;

$R^{3f}$ is selected from the group consisting of hydrogen and C$_{1-4}$ alkyl; X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, —C≡C—, —N(R$^5$)C(=O)—, and —OC(=O)—; or X is absent;

t is 1 or 2;

Z is selected from the group consisting of =CR$^{11a}$— and =N—;

each R$^{4a}$ and R$^{4b}$ are independently selected from the group consisting of hydrogen and C$_{1-4}$ alkyl; or R$^{4a}$ and R$^{4b}$ taken together with the carbon atom to which they are attached form a 3- to 6-membered cycloalkyl;

R$^{4c}$ and R$^{4d}$ are independently selected from the group consisting of hydrogen and C$_{1-4}$ alkyl;

R$^5$ is selected from the group consisting of hydrogen and C$_{1-4}$ alkyl;

R$^{6a}$, R$^{6b}$, and R$^{6c}$ are each independently selected from the group consisting of hydrogen, halo, C$_{1-4}$ alkyl, haloalkyl, cyano, hydroxy, thiol, amino, alkylthio, and alkoxy;

R$^{7a}$ is selected from the group consisting of hydrogen and C$_{1-4}$ alkyl;

R$^{7b}$ is selected from the group consisting of hydrogen, -L-H, -L-PG,

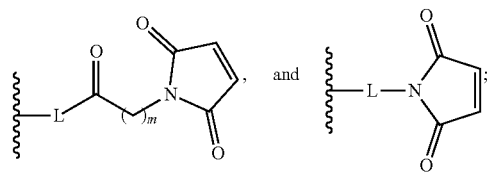

or

R$^{7a}$ and R$^{7b}$ taken together with the nitrogen atom to which they are attached form:

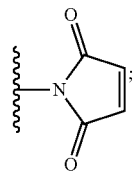 [SMILES: *N1C(=O)C=CC1=O]

or

R$^{7a}$ and R$^{7b}$ taken together with the nitrogen atom to which they are attached form a nitro (—NO$_2$) group;

m is 1, 2, 3, 4, 5, or 6;

L is a linker;

PG is a protecting group;

R$^{9f}$ is selected from the group consisting of hydrogen and C$_{1-4}$ alkyl;

R$^{8a}$ and R$^{8b}$ are independently selected from the group consisting of hydrogen and C$_{1-4}$ alkyl;

R$^{11a}$ and R$^{11b}$ are independently selected from the group consisting of hydrogen, halo, C$_{1-4}$ alkyl, C$_{1-4}$ haloalkyl, cyano, hydroxy, thiol, amino, alkylthio, and alkoxy; and === represents A single or double bond. In another embodiment, R$^{7b}$ is hydrogen. In another embodiment, R$^{7b}$ is selected from the group consisting of:

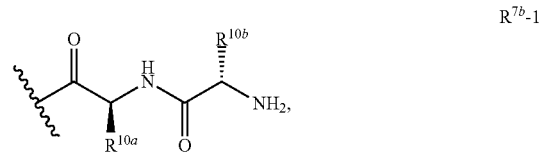

R$^{7b}$-1

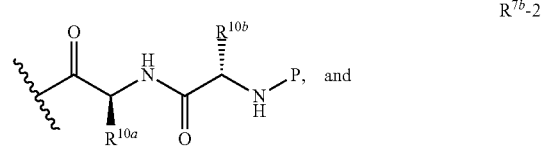

R$^{7b}$-2

-continued

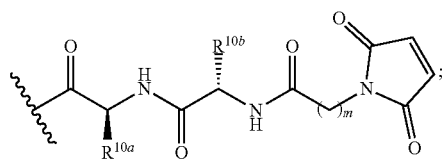

m is 1, 2, 3, 4, 5, or 6; and $R^{10a}$ and $R^{10b}$ are each independently selected from the group consisting of hydrogen and optionally substituted $C_{1-6}$ alkyl.

In another embodiment, disclosed herein is a compound having Formula VII-A' or Formula VII-B':

VII-A'

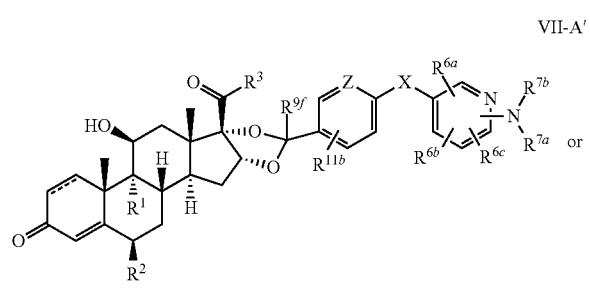

VII-B'

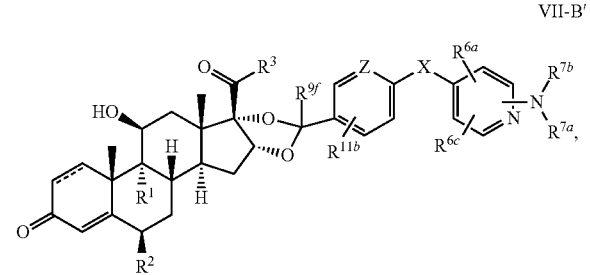

or a pharmaceutically acceptable salt thereof, wherein $R^1$, $R^2$, $R^3$, ===, $R^{6a}$, $R^{6b}$, $R^{6c}$, $R^{7a}$, $R^{7b}$, $R^{9f}$, $R^{11b}$, X, and Z are as defined in connection with Formula VII-A.

In another embodiment, disclosed herein is a compound having Formula VII-A" or Formula VII-B":

VII-A"

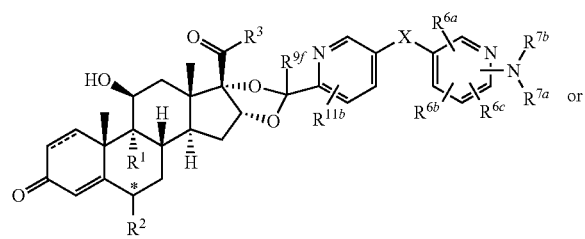

VII-B"

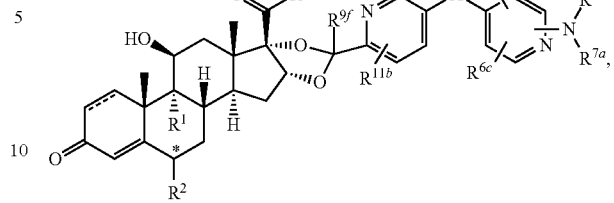

or a pharmaceutically acceptable salt thereof, wherein $R^1$, $R^2$, $R^3$, ===, $R^{6a}$, $R^{6b}$, $R^{6c}$, $R^{7a}$, $R^{7b}$, $R^{9f}$, $R^{11b}$, and X, are as defined in connection with Formula VII-A, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having Formula VIII:

VIII

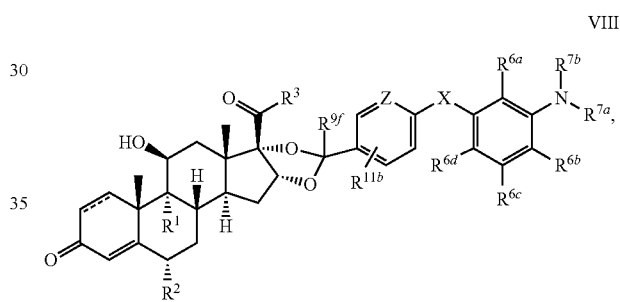

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula VIII':

VIII'

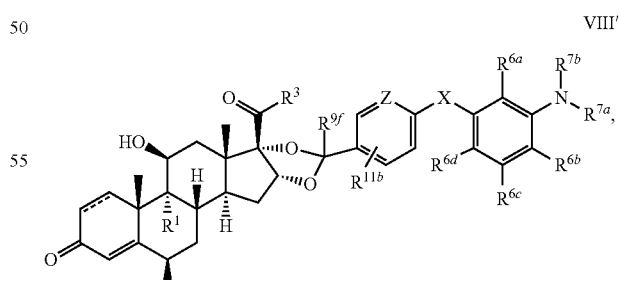

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula VIII":

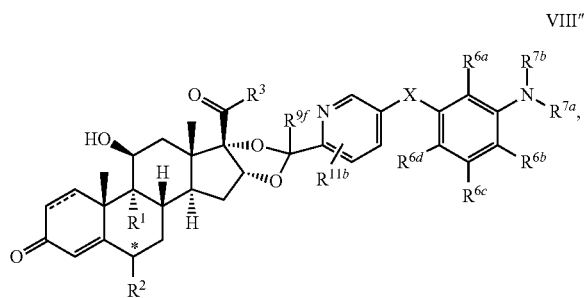

VIII″ or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, and X are as defined in connection with Formula VII, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having Formula VIII-a:

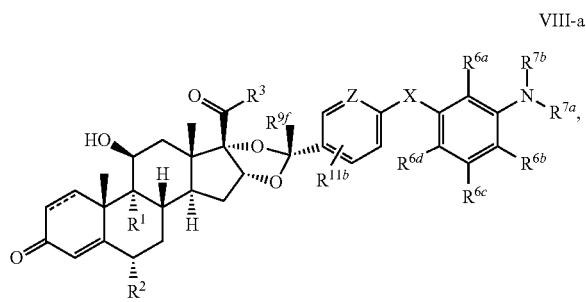

VIII-a or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula VIII-a':

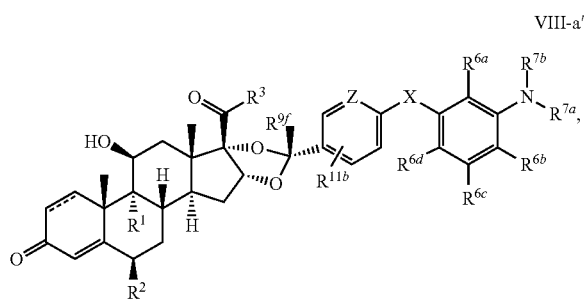

VIII-a' or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula VIII-a":

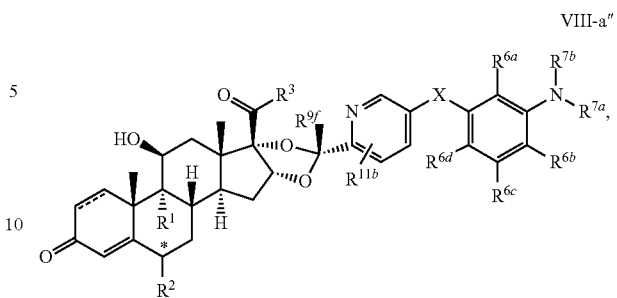

VIII-a″ or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, and X are as defined in connection with Formula VII, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having Formula VIII-b:

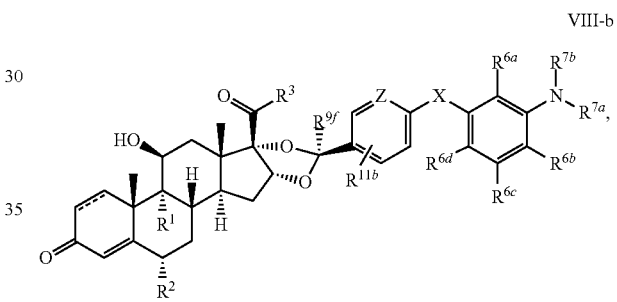

VIII-b or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula VIII-b':

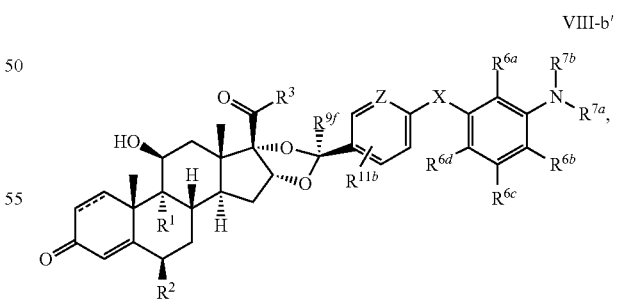

VIII-b' or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula VIII-b":

VIII-b″

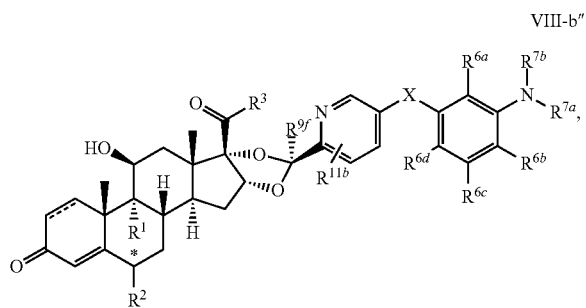

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, and X are as defined in connection with Formula VII, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having Formula IX:

IX

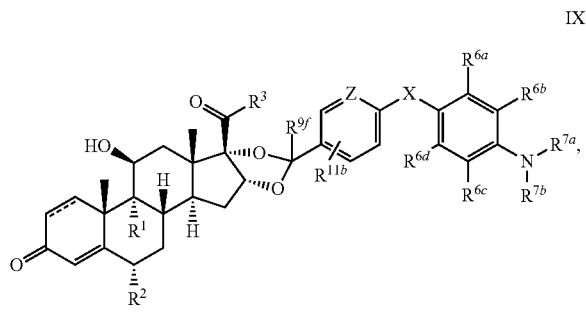

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula IX':

IX'

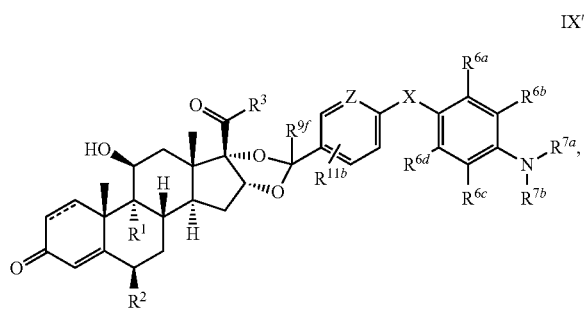

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula IX":

IX″

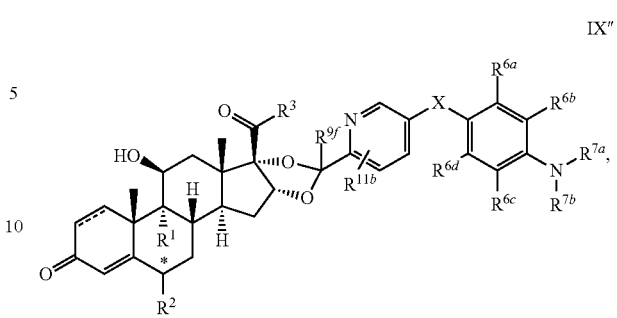

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, and X are as defined in connection with Formula VII, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having Formula IX-a:

IX-a

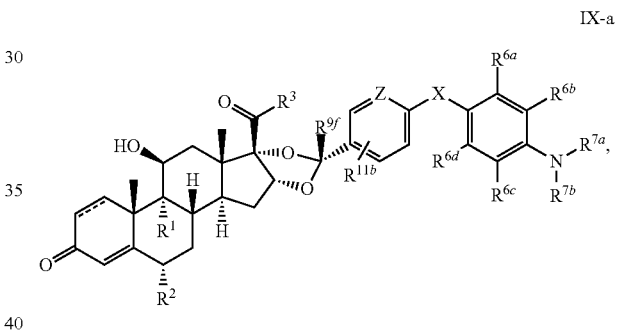

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula IX-a':

IX-a'

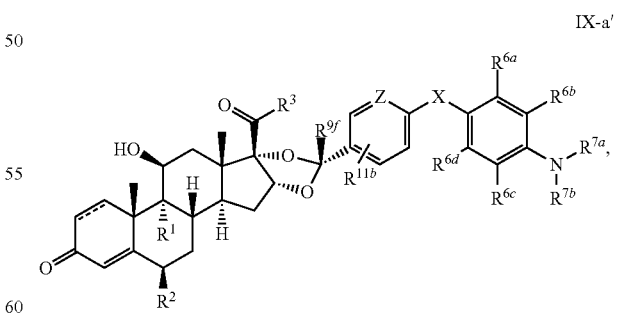

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula IX-a":

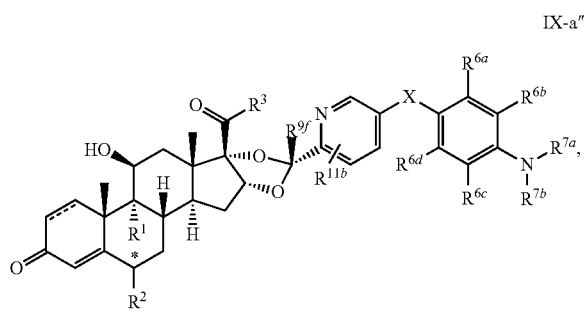

IX-a''

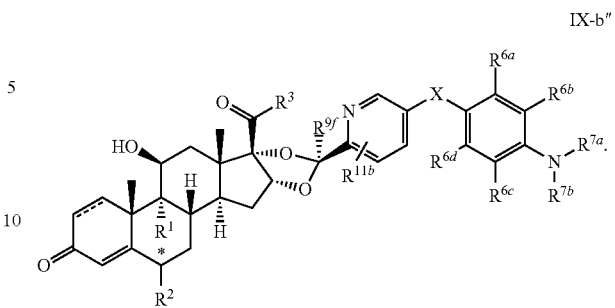

IX-b'' or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, and X are as defined in connection with Formula VII, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having Formula IX-b:

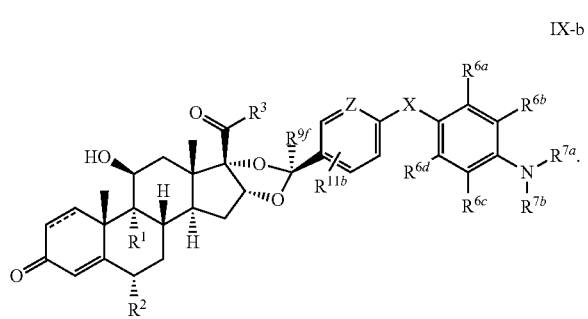

IX-b or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula IX-b':

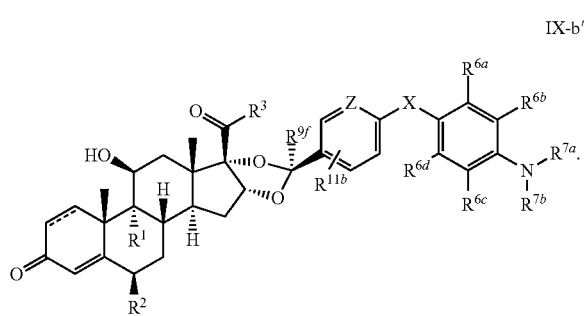

IX-b' or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, X, and Z are as defined in connection with Formula VII.

In another embodiment, disclosed herein is a compound having Formula IX-b'':

or a pharmaceutically acceptable salt thereof, wherein $R^1$, $R^2$, $R^3$, ===, $R^{6a}$, $R^{6b}$, $R^{6c}$, $R^{6d}$, $R^{7a}$, $R^{7b}$, $R^{9f}$, $R^{11b}$, and X are as defined in connection with Formula VII, and the carbon atom marked with an "*" is either the R-isomer or the S-isomer when $R^2$ is halo or hydroxyl. In one embodiment, the carbon atom marked with an "*" is the R-isomer. In another embodiment, the carbon atom marked with an "*" is the S-isomer.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein === represents a single or double bond. In another embodiment, === represents a double bond.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^1$ is selected from the group consisting of hydrogen and fluoro.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^2$ is selected from the group consisting of hydrogen and fluoro.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^3$ is selected from the group consisting of —CH$_2$OH, —CH$_2$Cl, —SCH$_2$Cl, —SCH$_2$F, and —OH.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein:

$R^3$ is selected from the group consisting of:

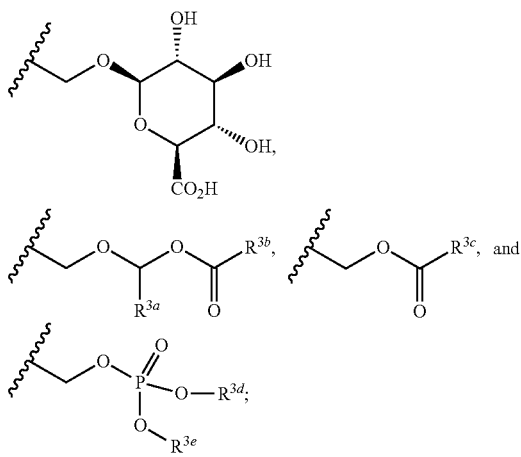

$R^{3a}$ is selected from the group consisting of hydrogen and methyl;

$R^{3b}$ is selected from the group consisting of methyl, ethyl, isopropyl, isobutyl, methoxy, ethoxy, isopropoxy, and isobutoxy;

$R^{3c}$ is selected from the group consisting of hydrogen, methyl, ethyl, —CH$_2$OH, methoxy, ethoxy, and isopropoxy;

$R^{3d}$ and $R^{3e}$ are independently selected from the group consisting of hydrogen, methyl, and ethyl.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, wherein $R^5$ and $R^{8a}$ are independently selected from the group consisting of hydrogen and methyl.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', or IX-b', or a pharmaceutically acceptable salt thereof, wherein Z is =CH—.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', or a pharmaceutically acceptable salt thereof, wherein Z is =N—.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, wherein $R^{7a}$ is selected from the group consisting of hydrogen and methyl. In another embodiment, $R^{7a}$ is hydrogen. In another embodiment, $R^{7a}$ is methyl.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, wherein:

X is selected from the group consisting of —(CR$^{4a}$R$^{4b}$)$_t$—, —O—, —S—, —S(=O)—, —S(=O)$_2$—, —CH$_2$S—, and —N(H)CH(R$^{8a}$)—;

t is 1; and $R^{4a}$ and $R^{4b}$ are independently selected from the group consisting of hydrogen and methyl; or $R^{4a}$ and $R^{4b}$ taken together with the carbon atom to which they are attached form a 3-membered cycloalkyl. In another embodiment, X is —CH$_2$—. In another embodiment, X is selected from the group consisting of:

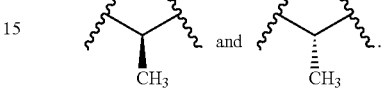

In another embodiment, X is —O—. In another embodiment, X is —S—. In another embodiment, X is —CH$_2$S—. In another embodiment, X is —N(H)CH$_2$—. In another embodiment, X is selected from the group consisting of:

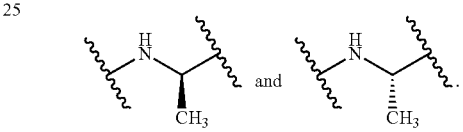

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, wherein $R^{11b}$ is hydrogen.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, wherein $R^{7b}$ is hydrogen.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, wherein $R^{7a}$ and $R^{7b}$ are hydrogen.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, $R^{6b}$ is selected from the group consisting of hydrogen, —Cl, —OMe (or —OCH$_3$), and —OH.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, wherein $R^{9f}$ is hydrogen.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^{9f}$ is methyl.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^{11a}$ is selected from the group consisting of hydrogen and —OH.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^{11b}$ is hydrogen.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^{7b}$ is $R^{7b}$-1. In another embodiment, $R^{10a}$ and $R^{10b}$ are independently optionally substituted $C_{1-6}$ alkyl. In another embodiment, $R^{10a}$ and $R^{10b}$ are independently optionally substituted $C_{1-4}$ alkyl.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^{7b}$ is $R^{7b}$-2, and PG is BOC. In another embodiment, $R^{10a}$ and $R^{10b}$ are independently optionally substituted $C_{1-6}$ alkyl. In another embodiment, $R^{10a}$ and $R^{10b}$ are independently optionally substituted $C_{1-4}$ alkyl.

In another embodiment, disclosed herein is a compound having any one of Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a pharmaceutically acceptable salt thereof, wherein $R^{7b}$ is $R^{7b}$-3. In another embodiment, m is 2 or 3, and $R^{10a}$ and $R^{10b}$ are each optionally substituted $C_{1-6}$ alkyl. In another embodiment, m is 2. In another embodiment, $R^{10a}$ and $R^{10b}$ are independently optionally substituted $C_{1-4}$ alkyl.

In another embodiment, disclosed herein is a compound having Formulae VIII, or a pharmaceutically acceptable salt thereof, which is any one of the compounds of Table VI.

TABLE VI

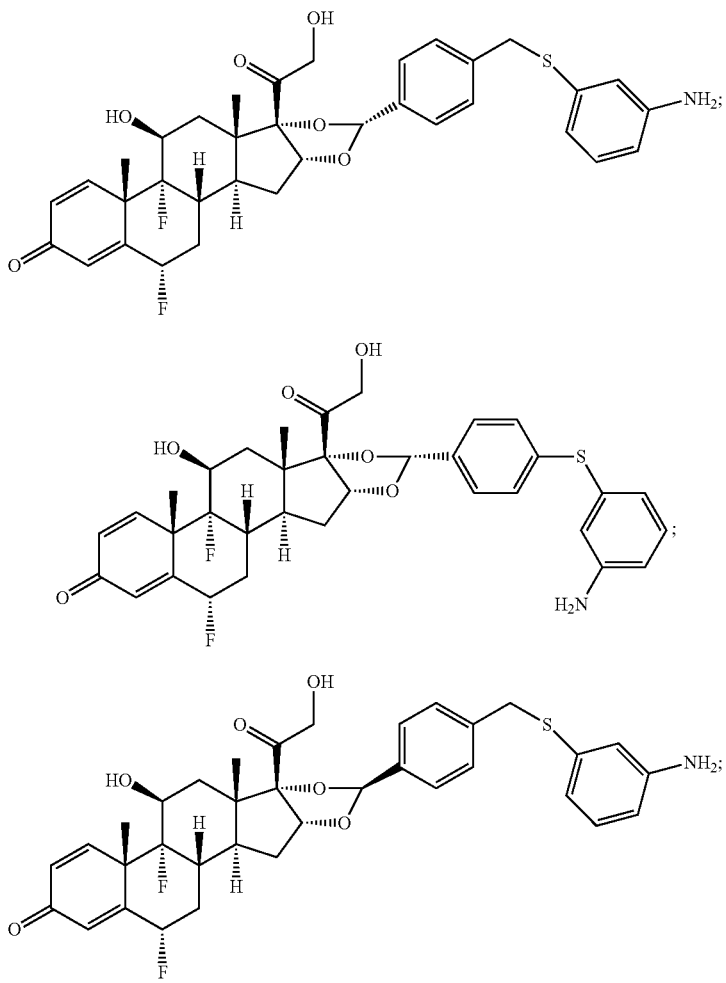

TABLE VI-continued
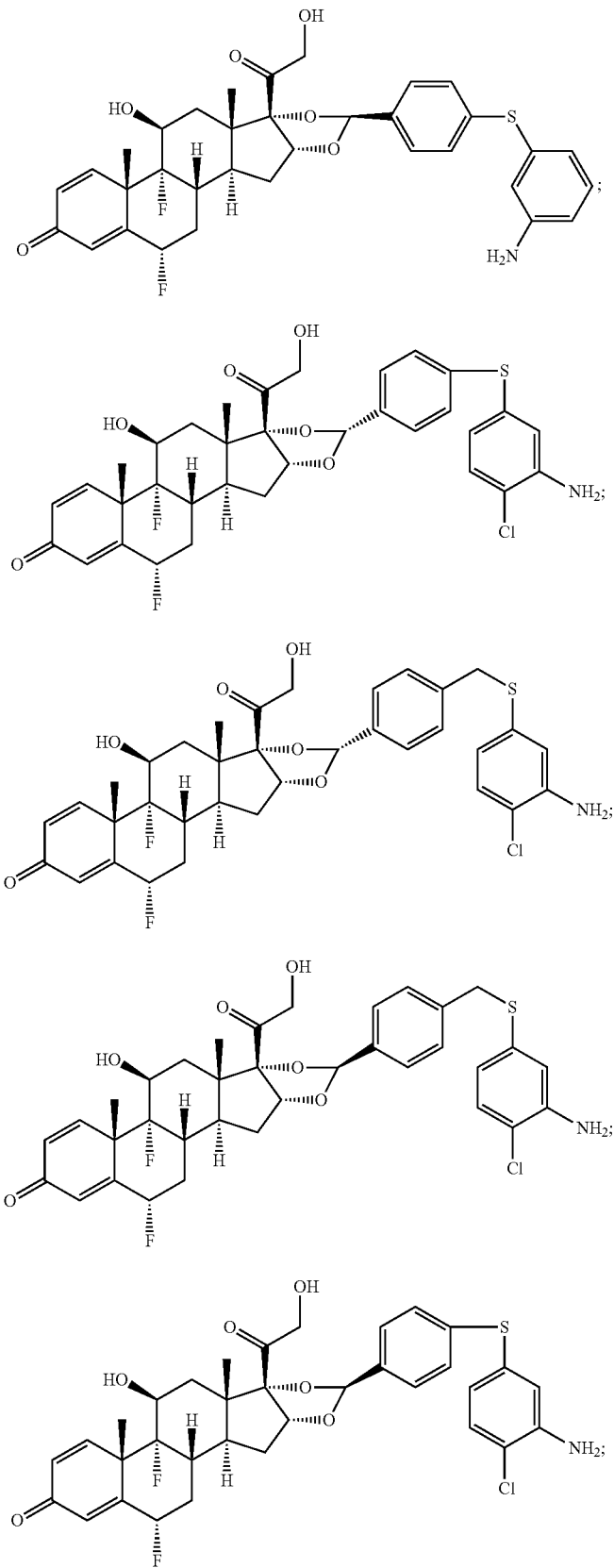

TABLE VI-continued
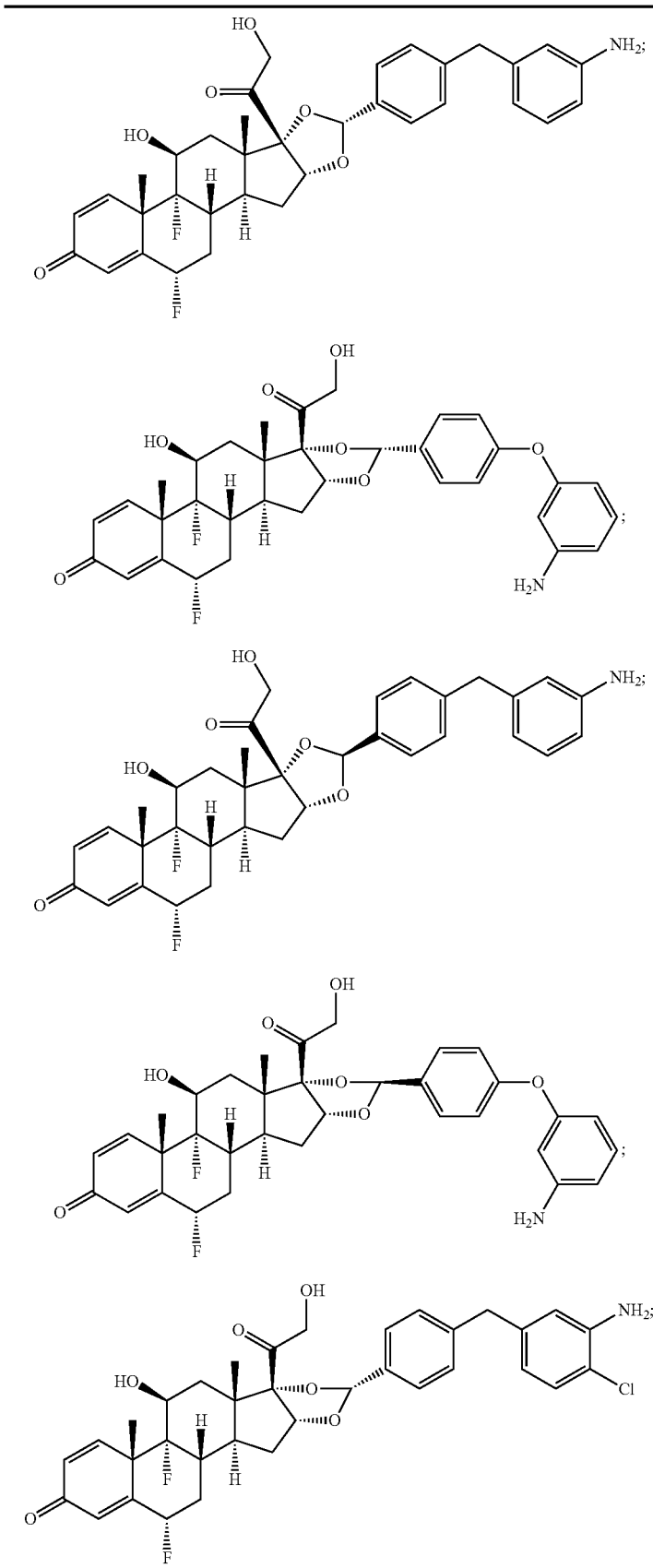

TABLE VI-continued
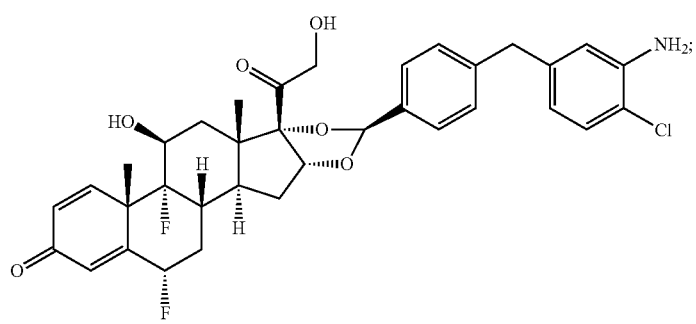
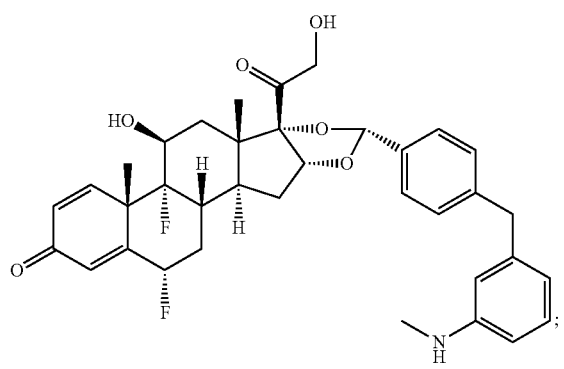
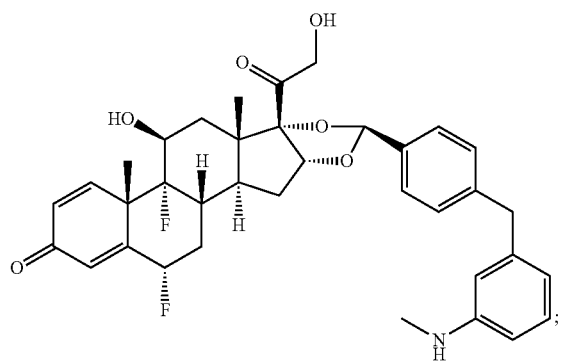
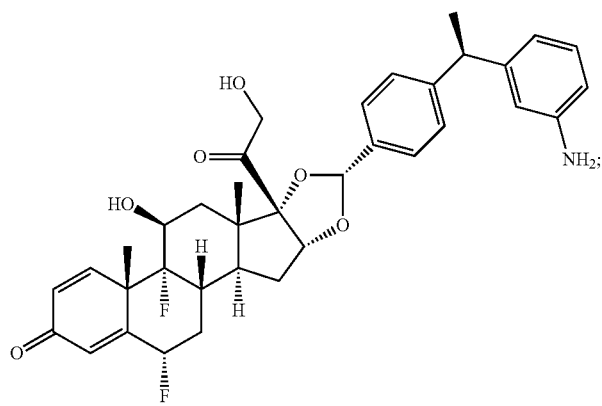

TABLE VI-continued
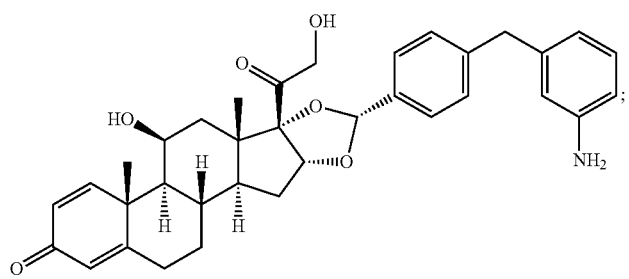
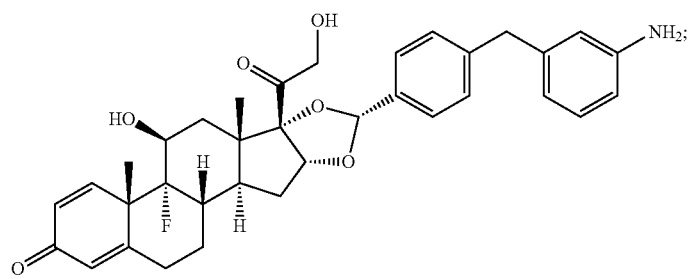
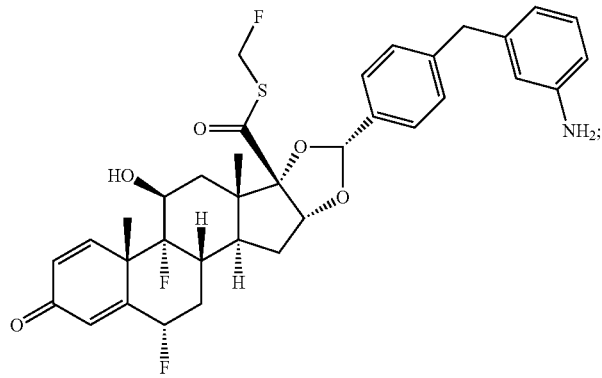
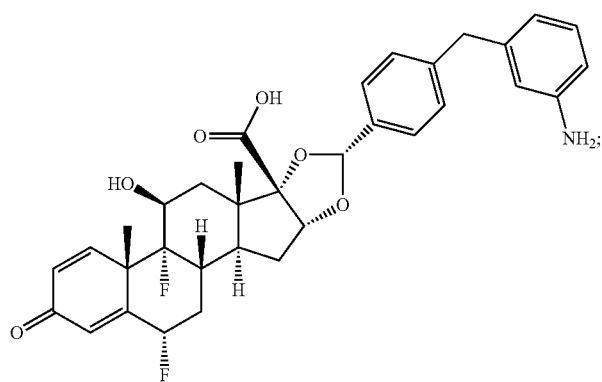

TABLE VI-continued
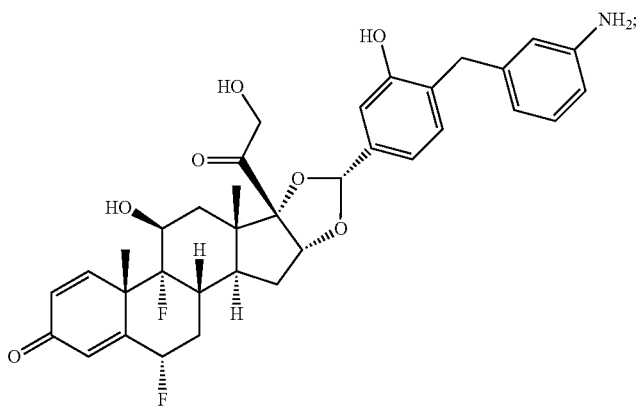
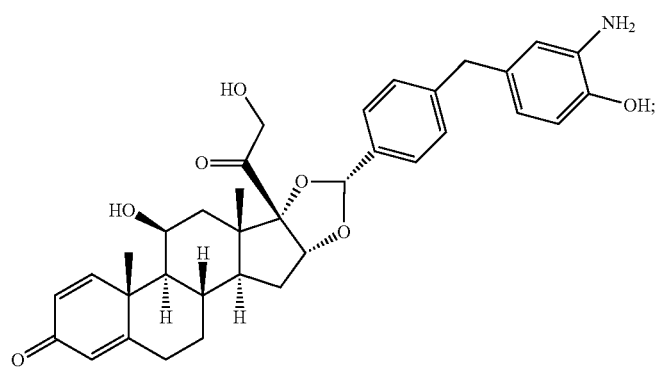
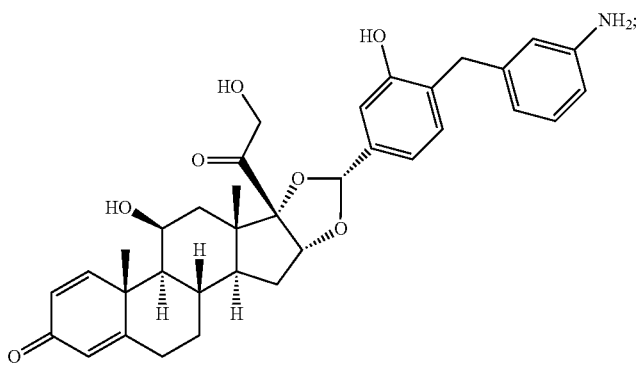
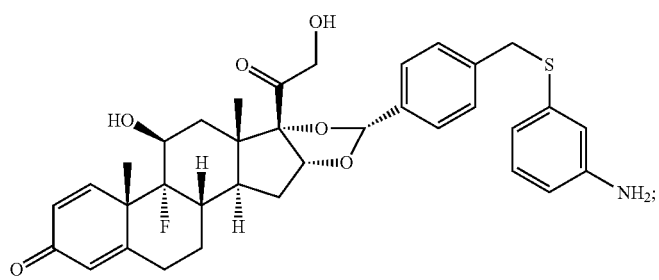

TABLE VI-continued
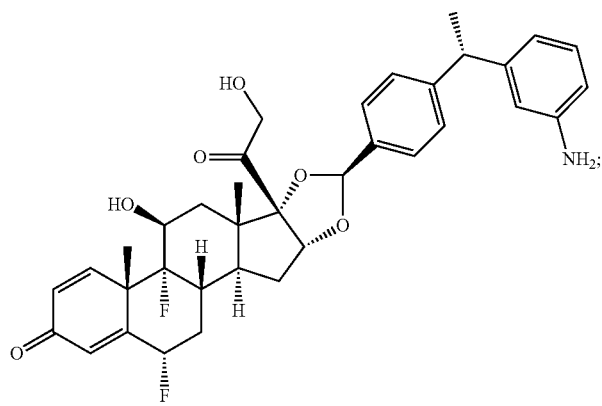
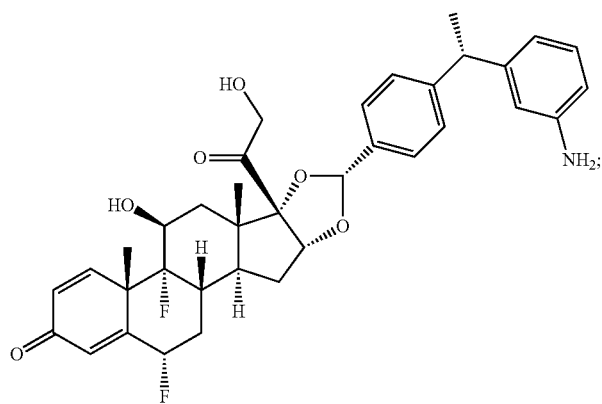
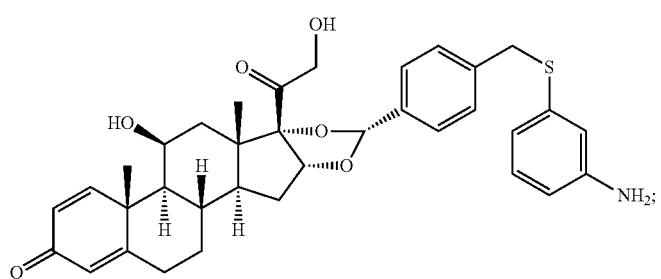
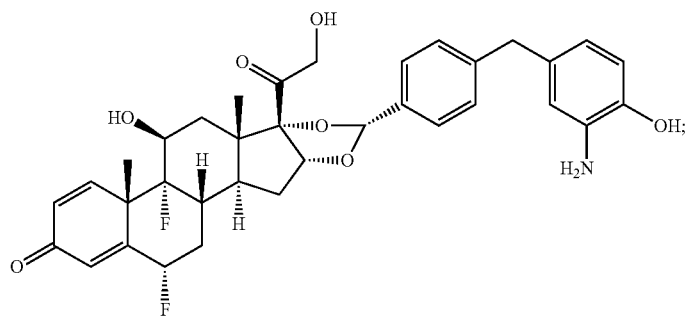

TABLE VI-continued
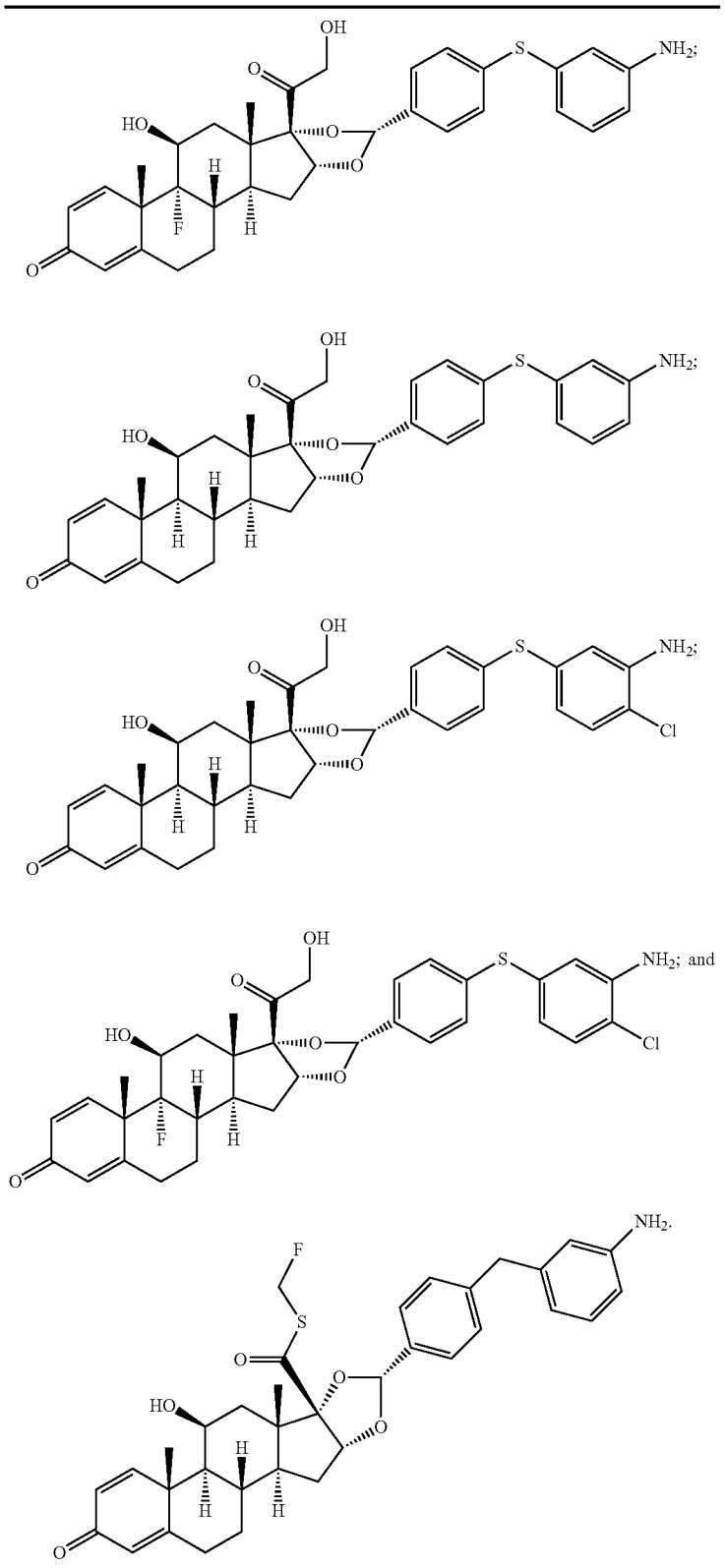
In another embodiment, disclosed herein is a compound having Formulae VIII, or a pharmaceutically acceptable salt thereof, which is any one of the compounds of Table VI-A.

TABLE VI-A
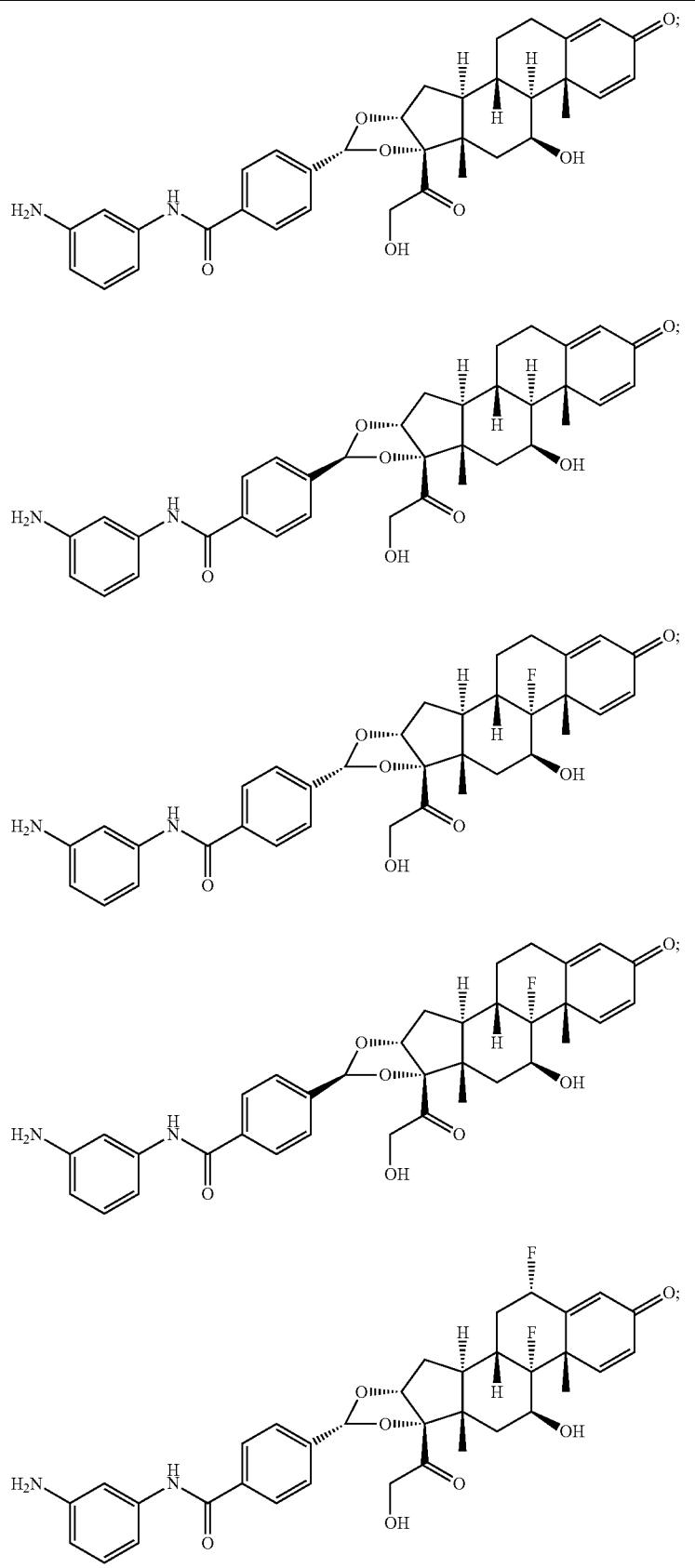

TABLE VI-A-continued
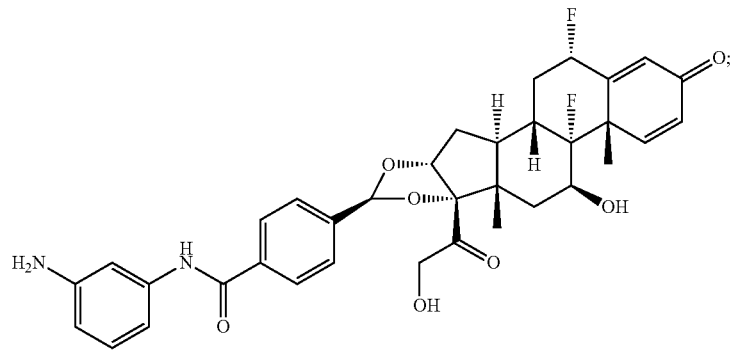
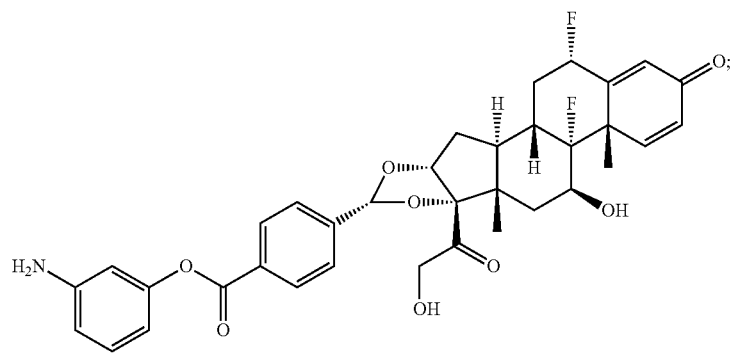
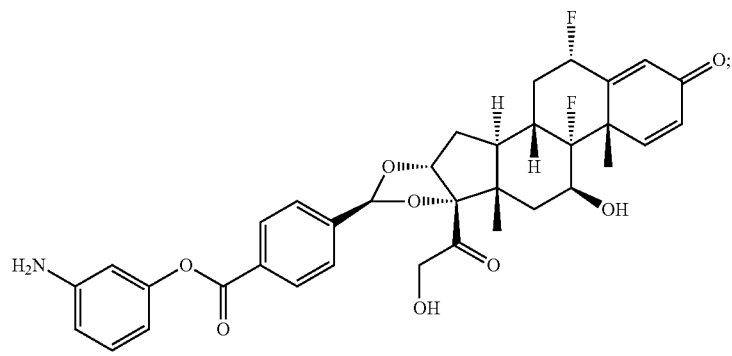
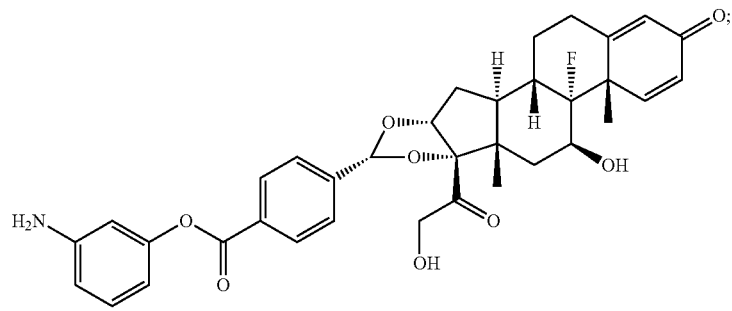

TABLE VI-A-continued
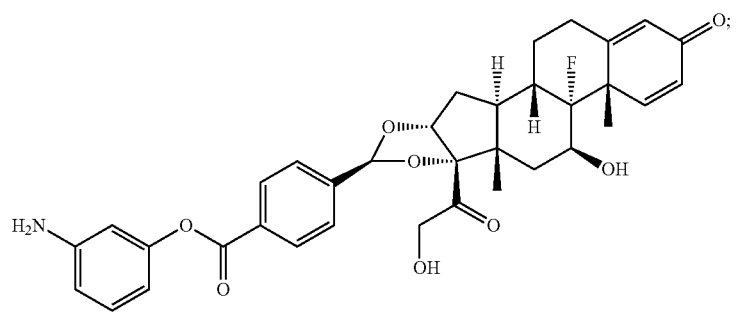
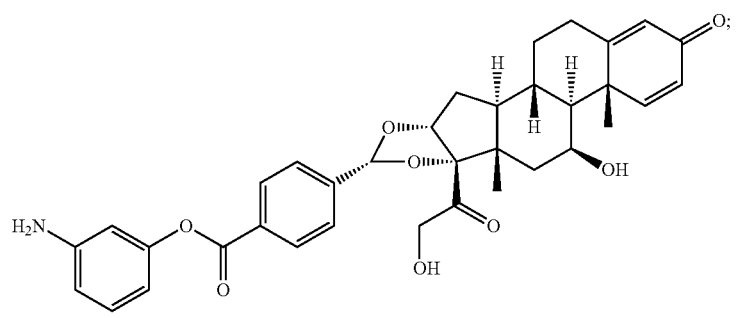
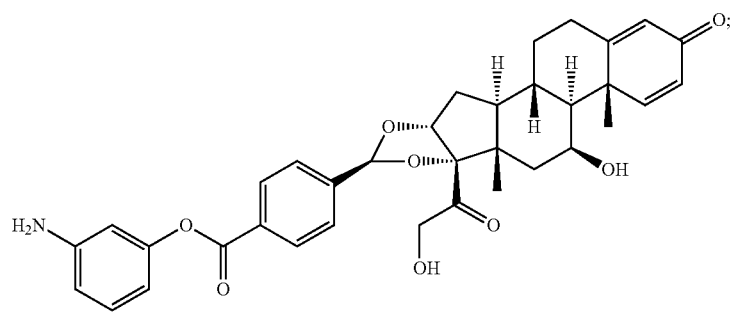
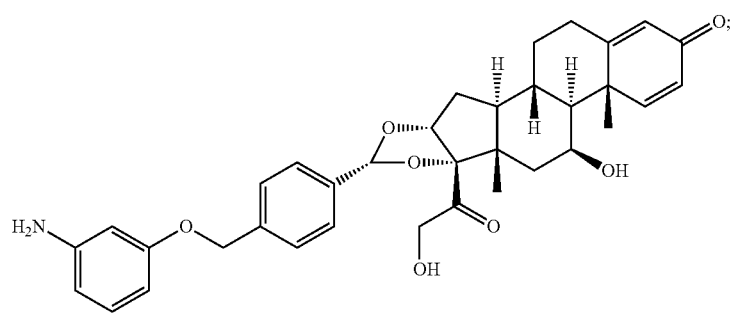
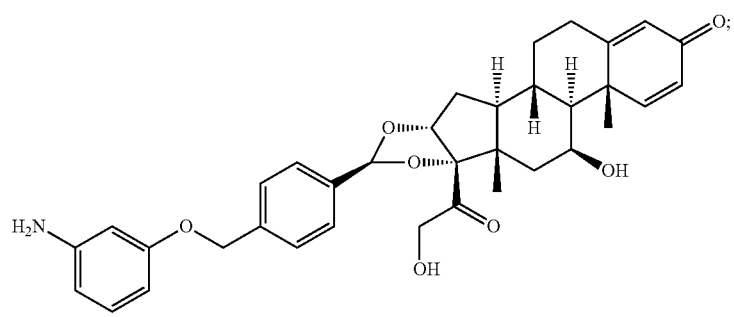

TABLE VI-A-continued
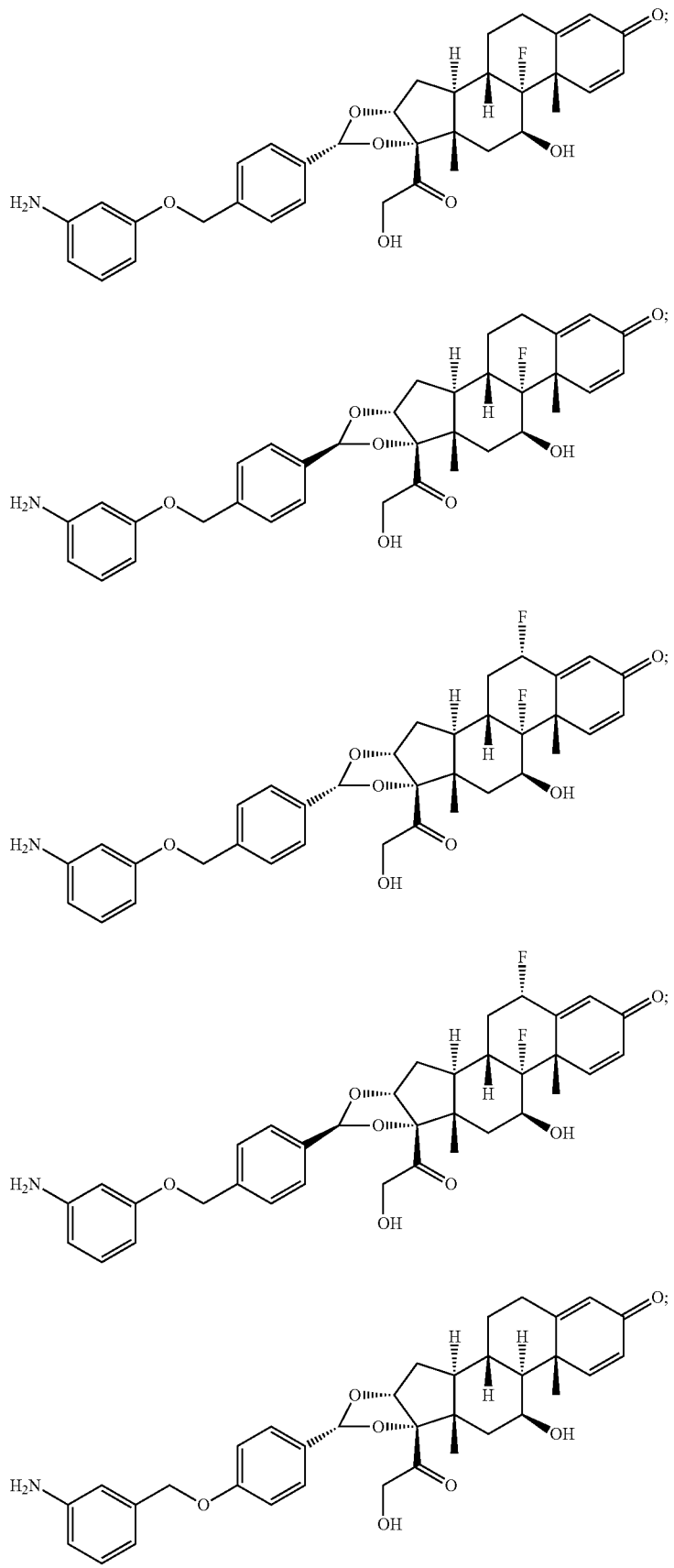

TABLE VI-A-continued
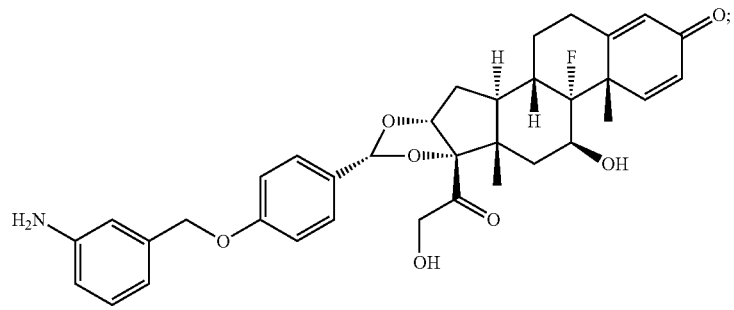
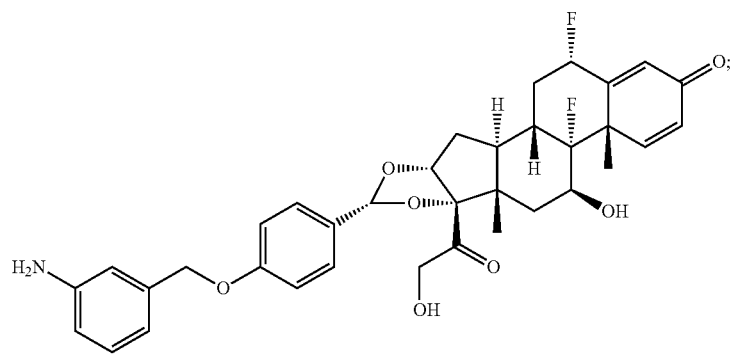
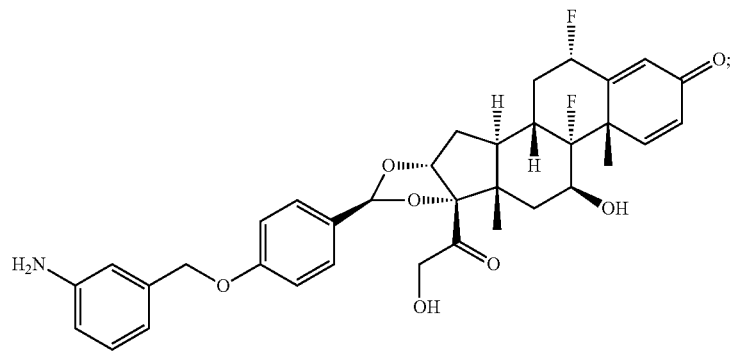
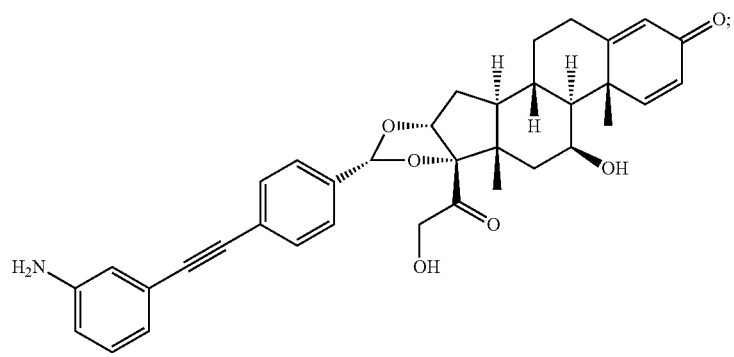

TABLE VI-A-continued
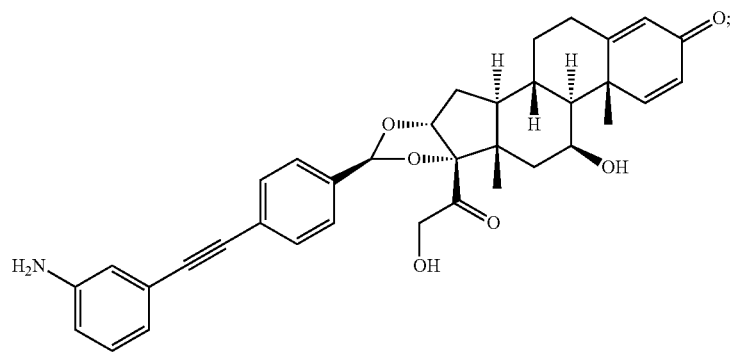
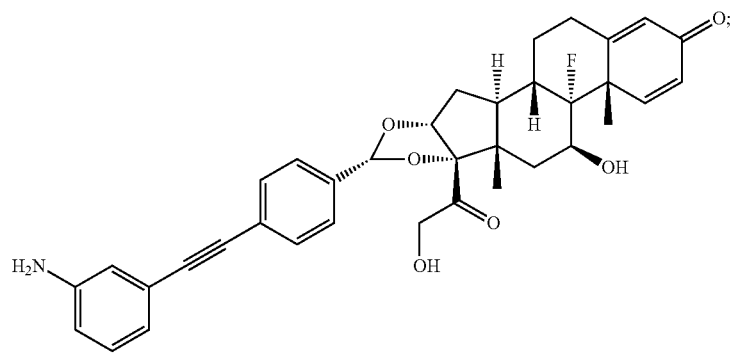
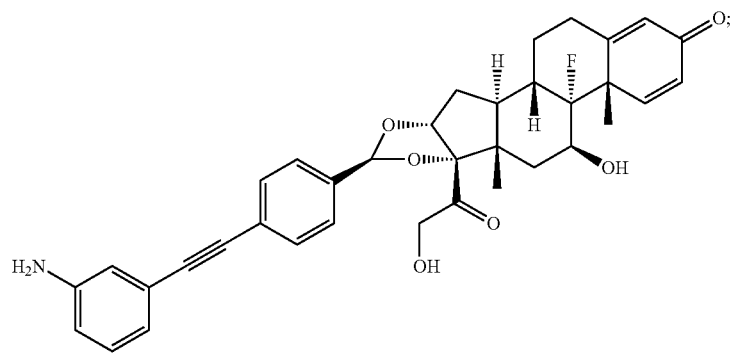
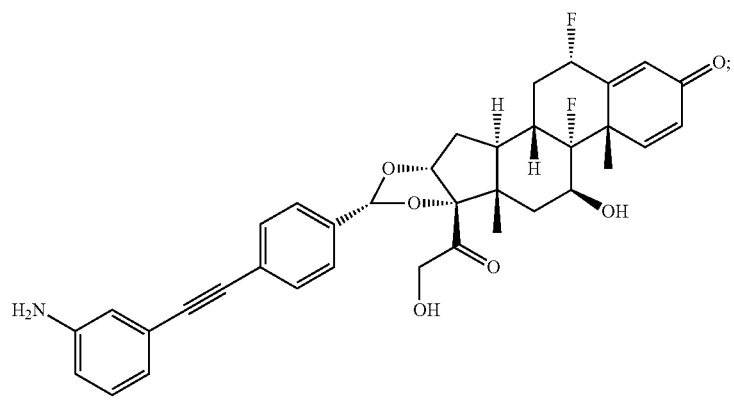

TABLE VI-A-continued
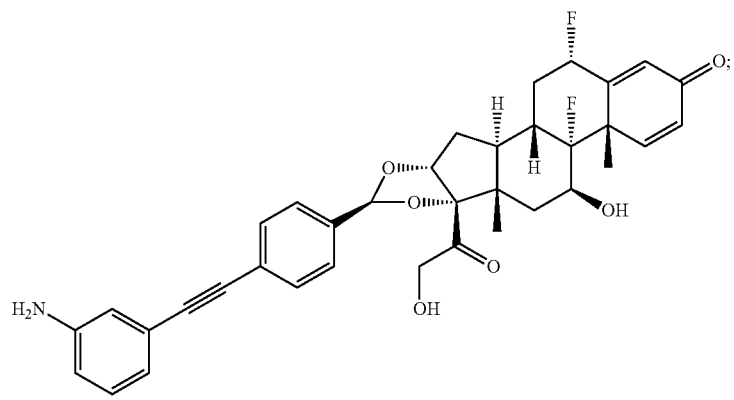
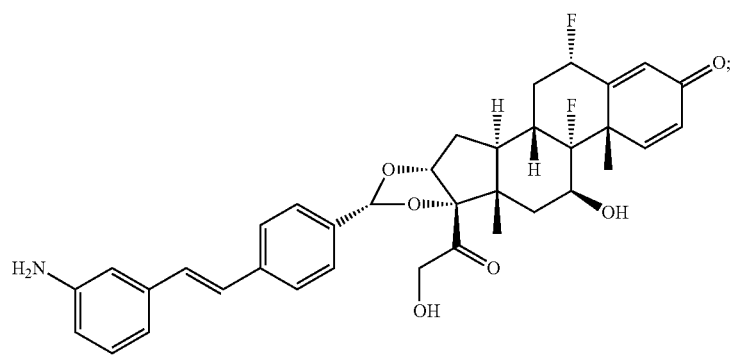
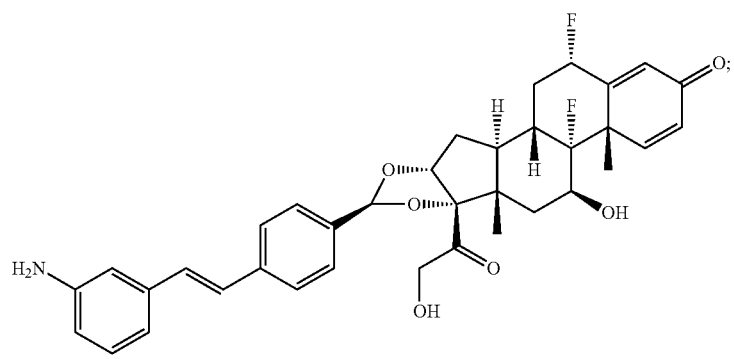
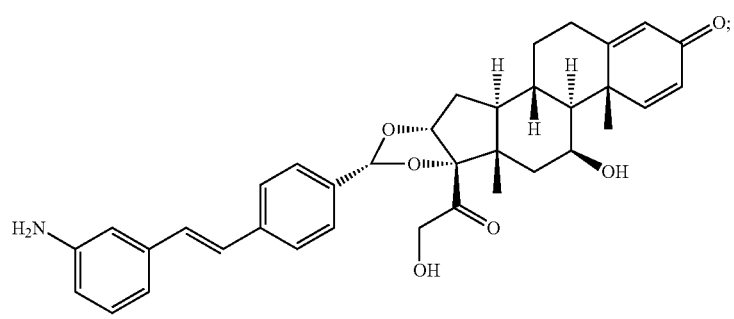

TABLE VI-A-continued
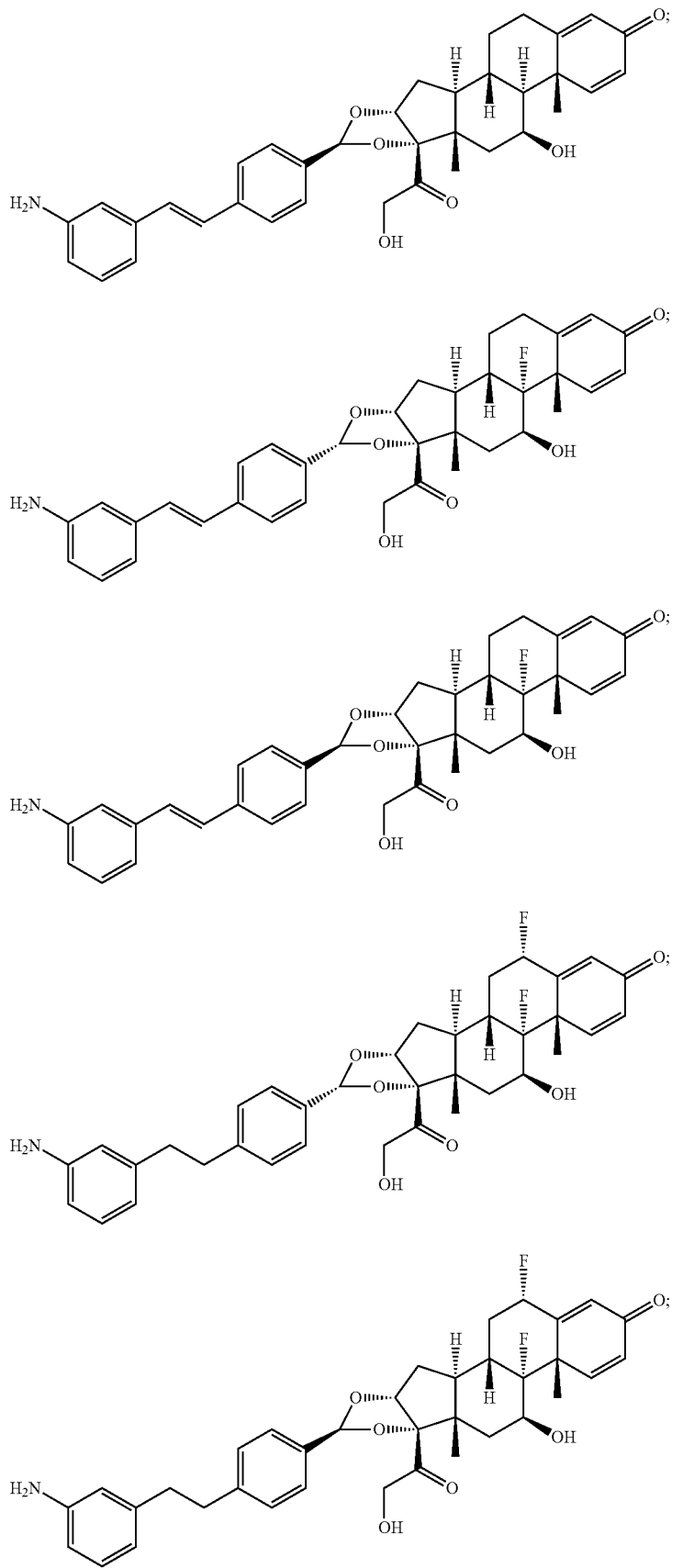

TABLE VI-A-continued
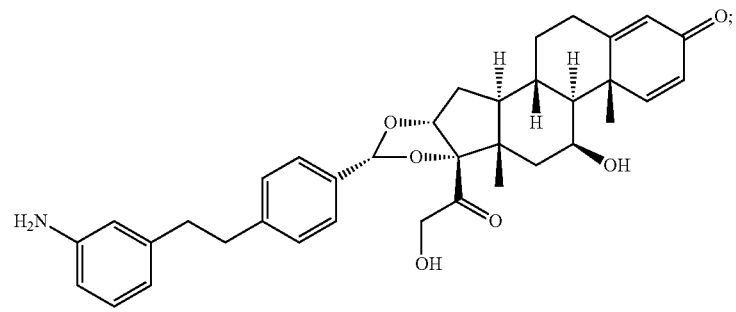
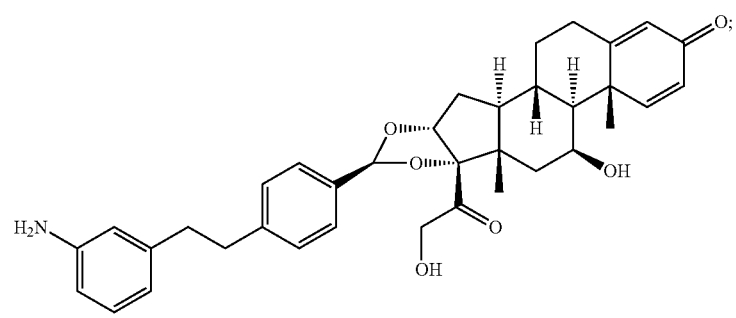
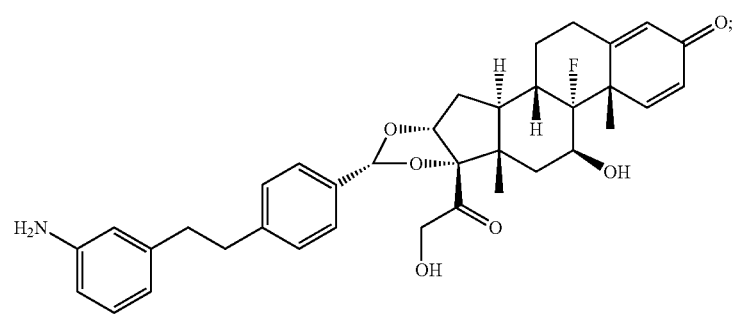
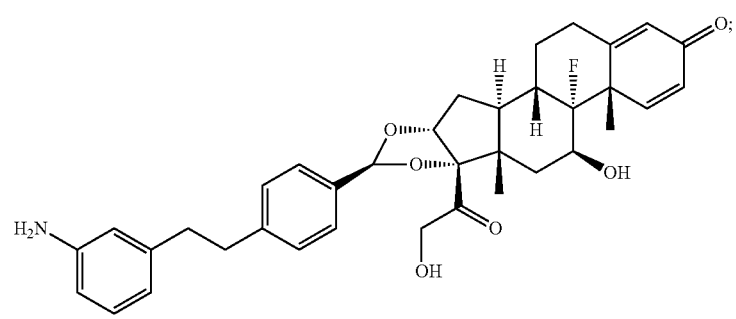
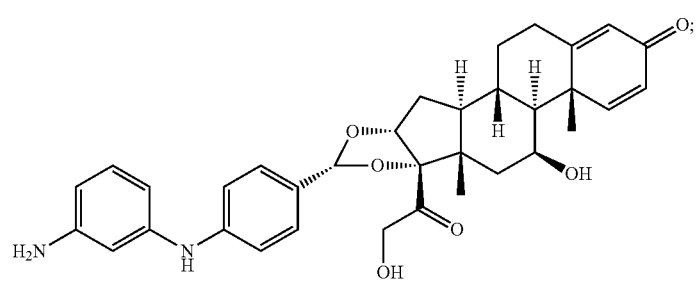

TABLE VI-A-continued
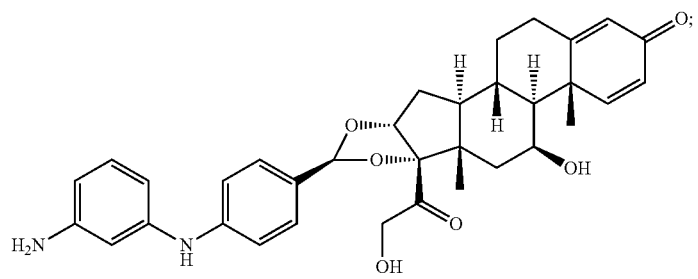
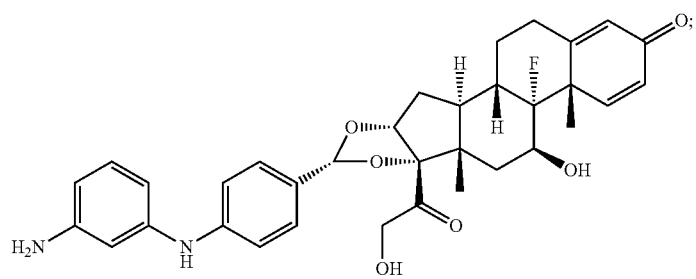
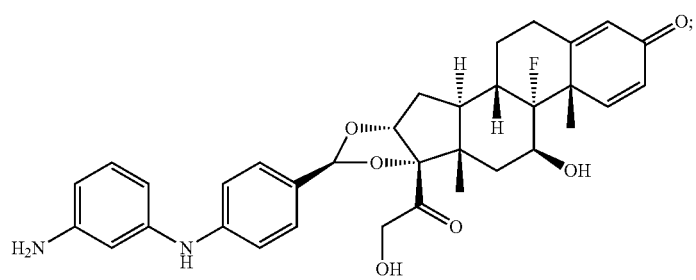
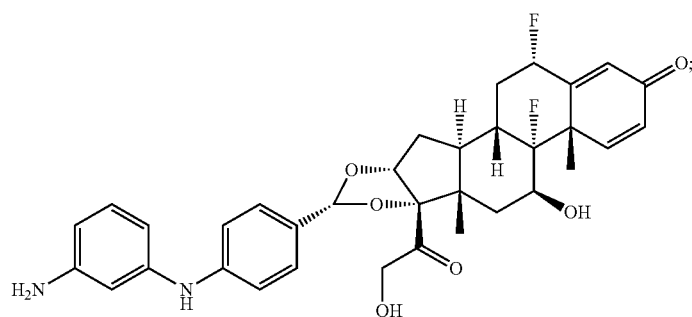
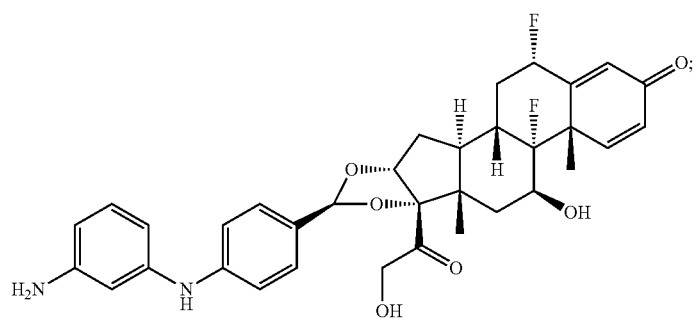

TABLE VI-A-continued
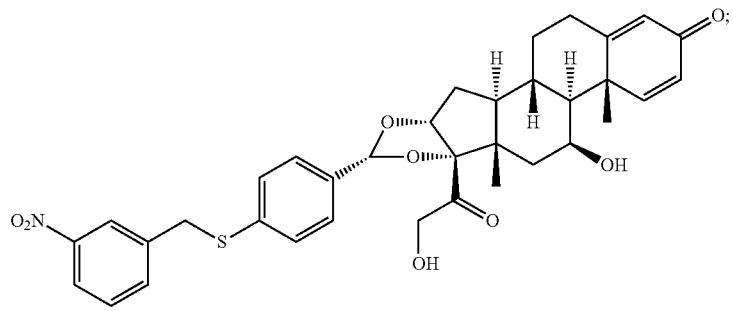
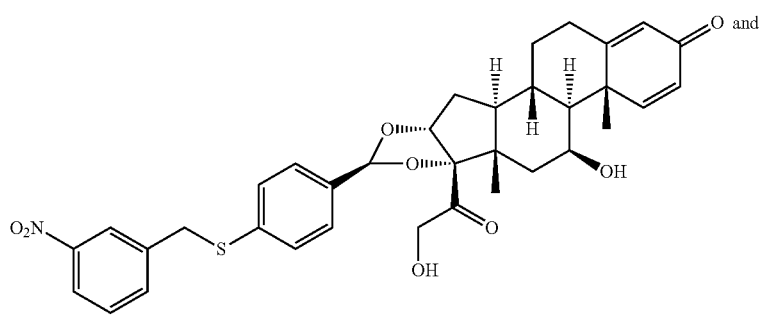
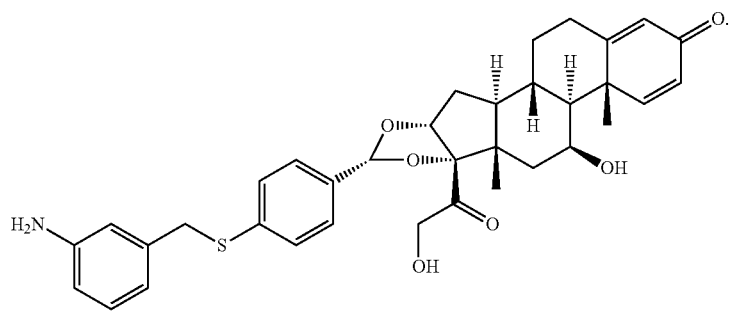
In another embodiment, disclosed herein is a compound having Formula VII-A or Formula VII-B, or a pharmaceutically acceptable salt thereof, which is any one of the compounds of Table VI-B.
TABLE VI-B
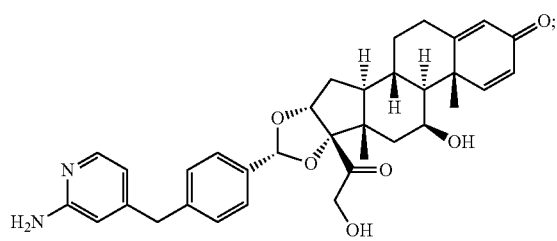
TABLE VI-B-continued
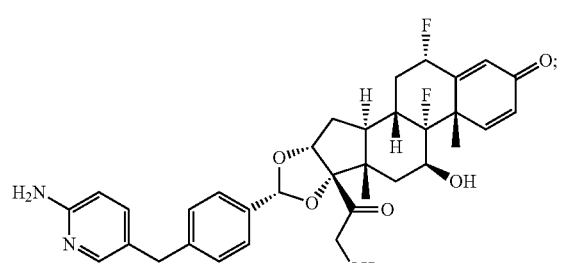
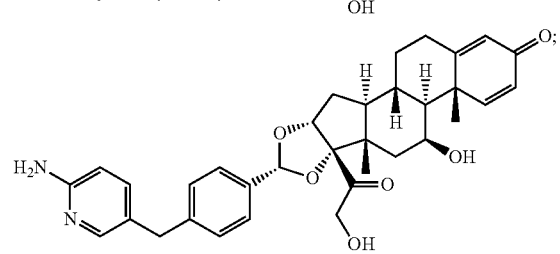

TABLE VI-B-continued
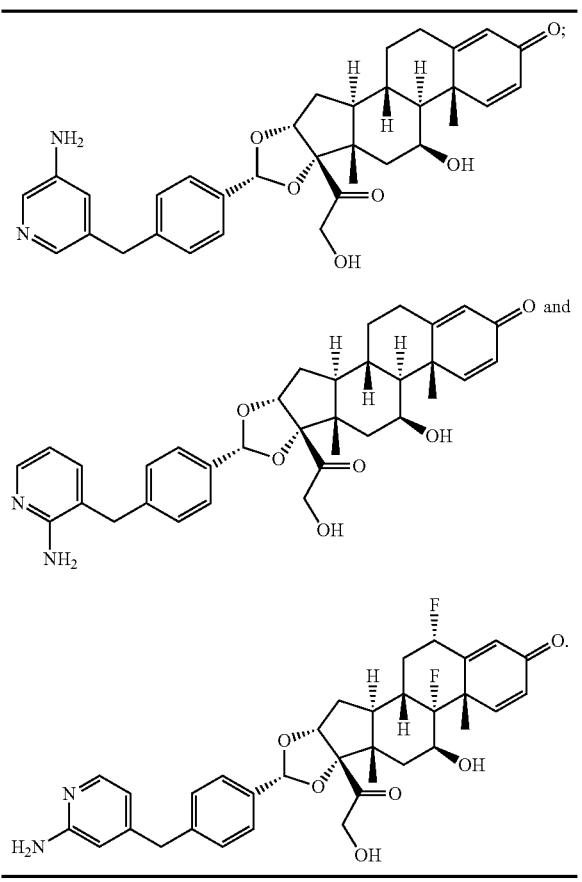
In another embodiment, disclosed herein is a compound having Formulae VIII, or a pharmaceutically acceptable salt thereof, selected from the group consisting of:
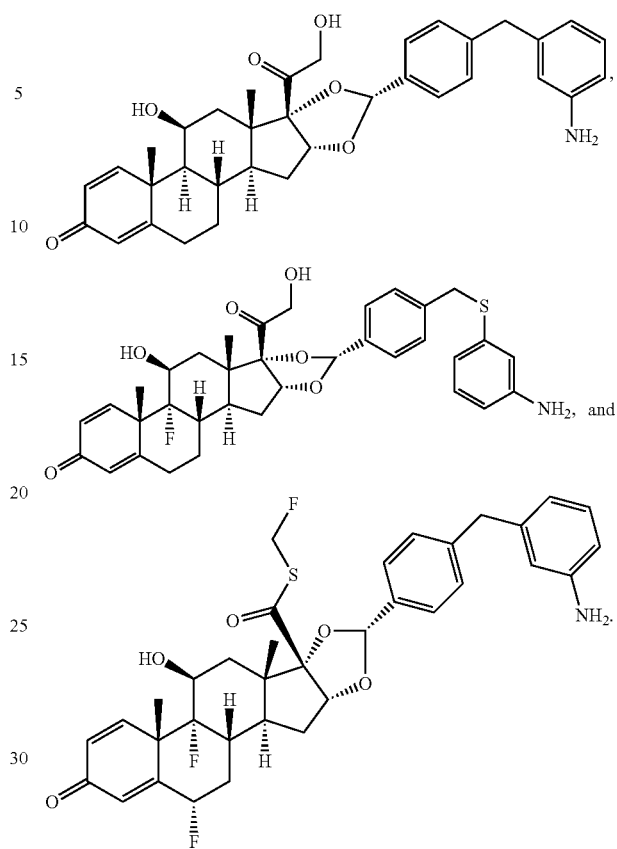
In another embodiment, disclosed herein is a compound having Formula IX, or a pharmaceutically acceptable salt thereof, which is any one of the compounds of Table VII.
TABLE VII
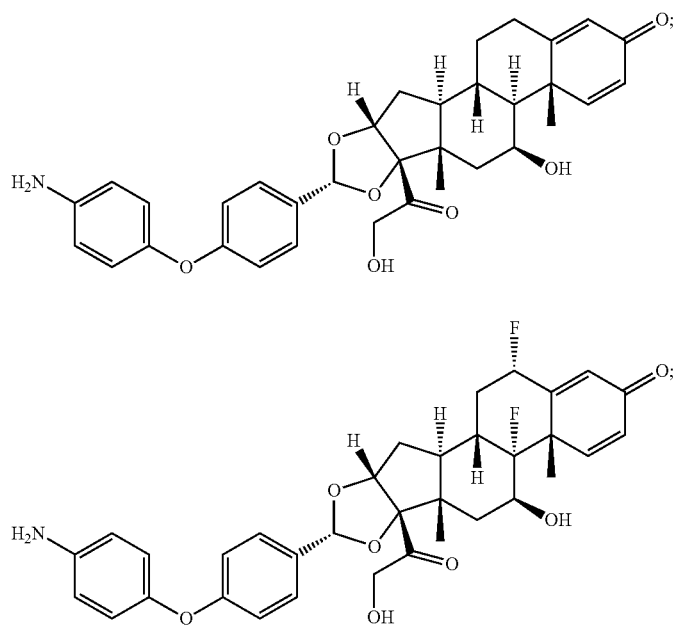

TABLE VII-continued
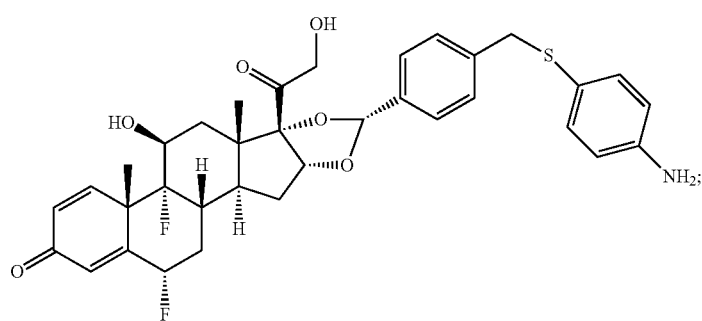
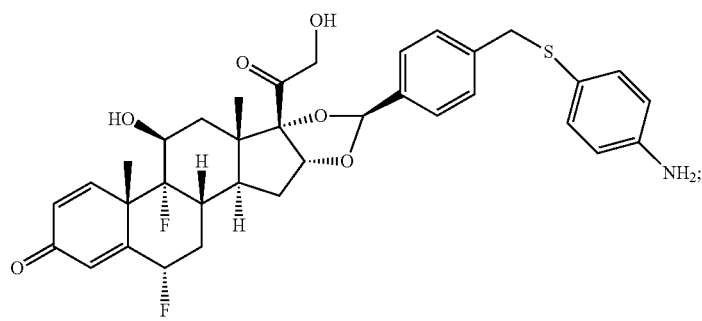
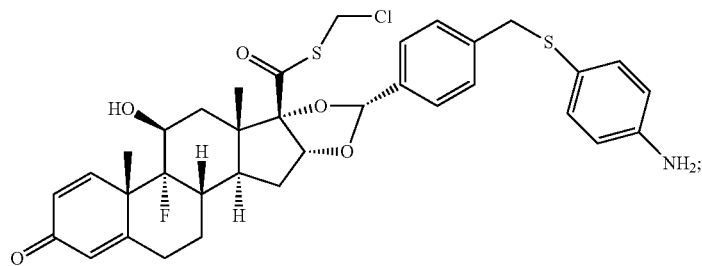
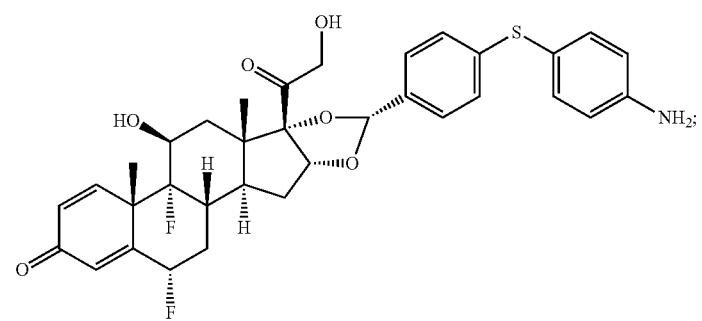
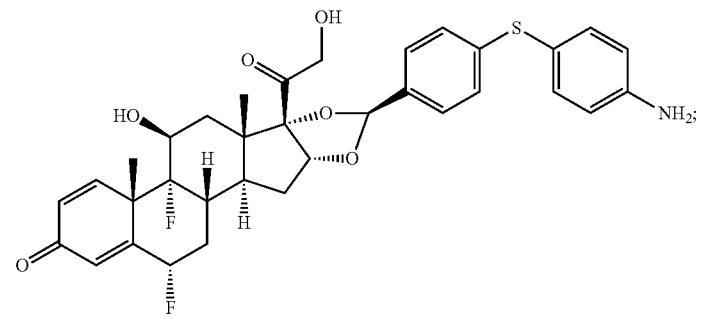

TABLE VII-continued
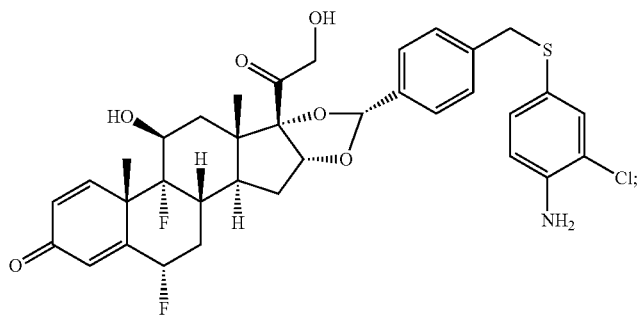
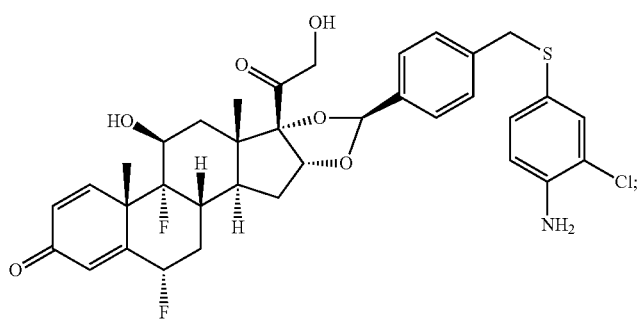
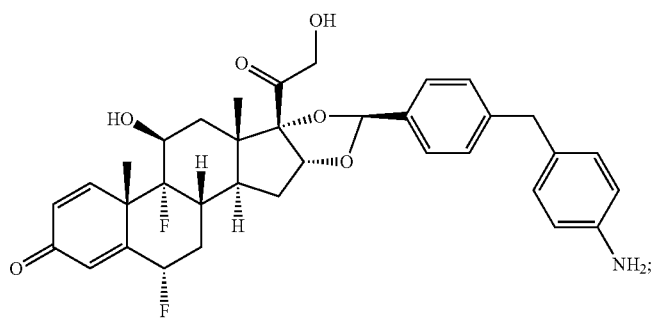
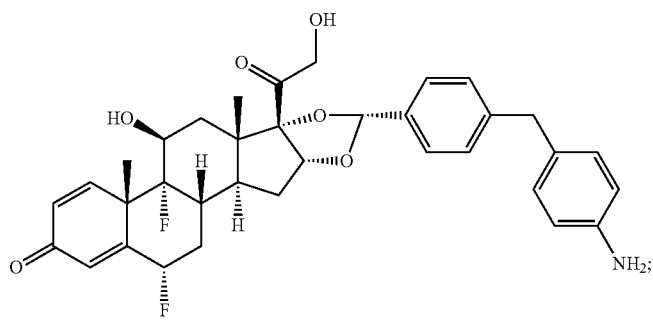

TABLE VII-continued
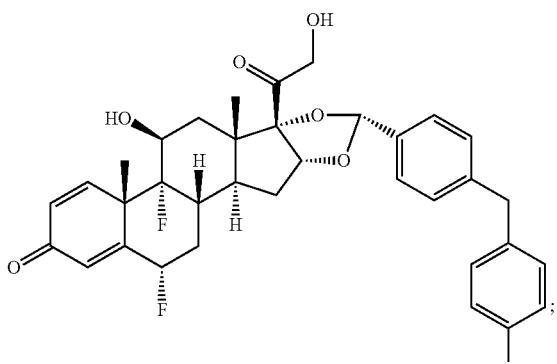
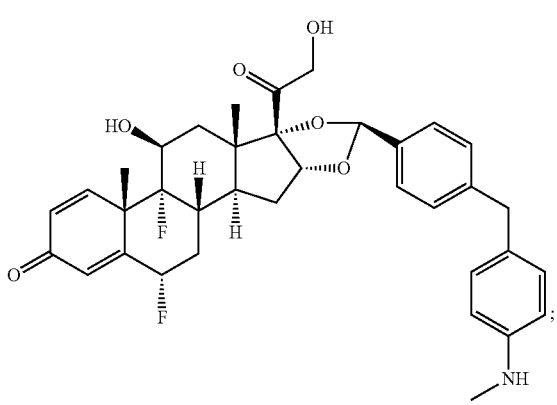
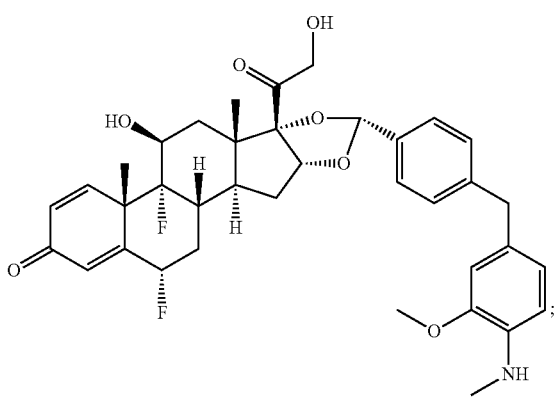
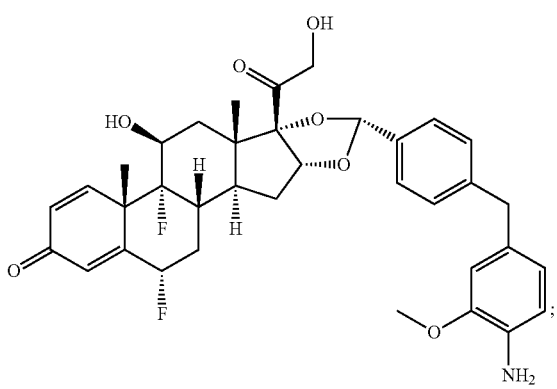

TABLE VII-continued
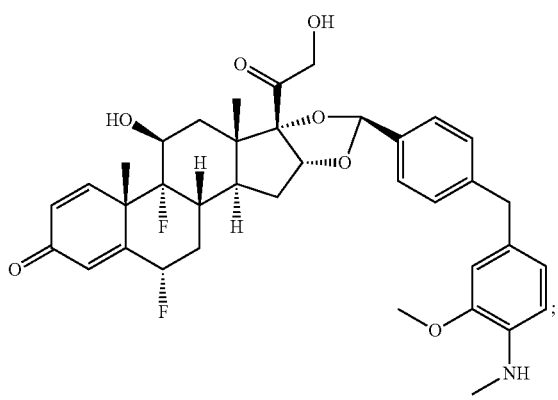
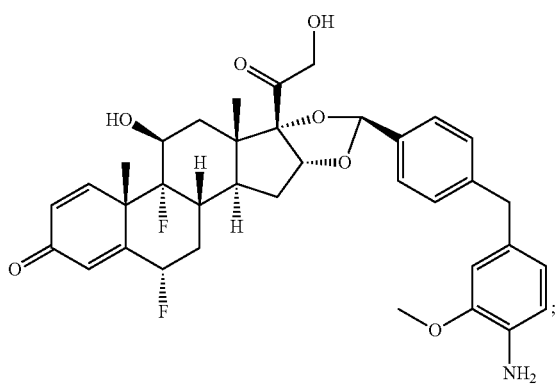
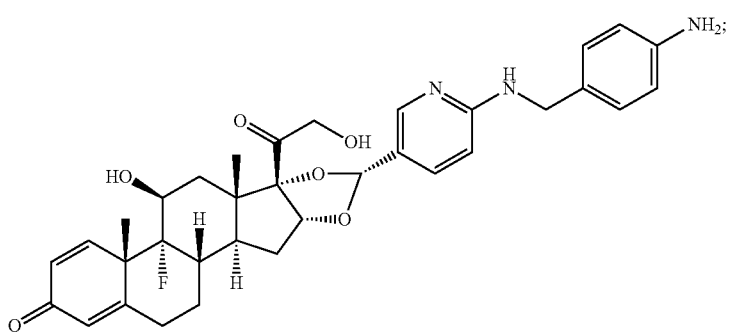
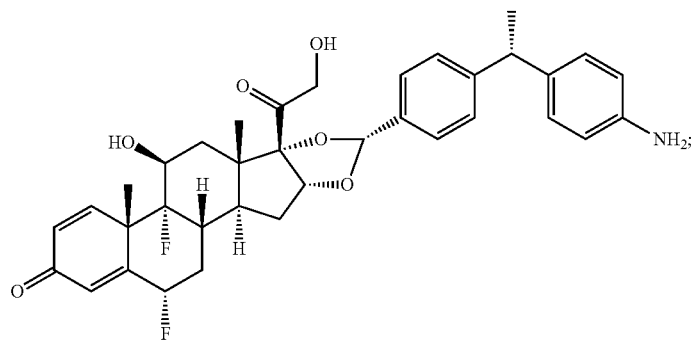

TABLE VII-continued
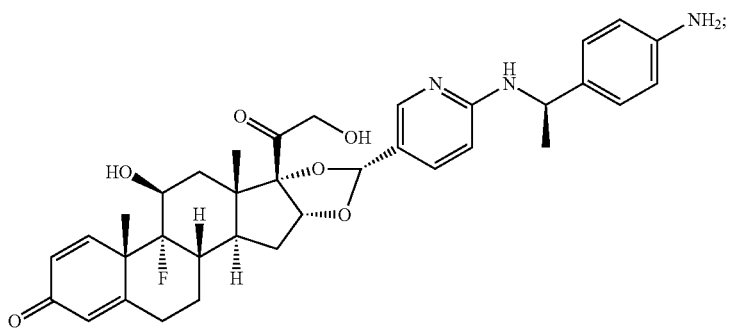
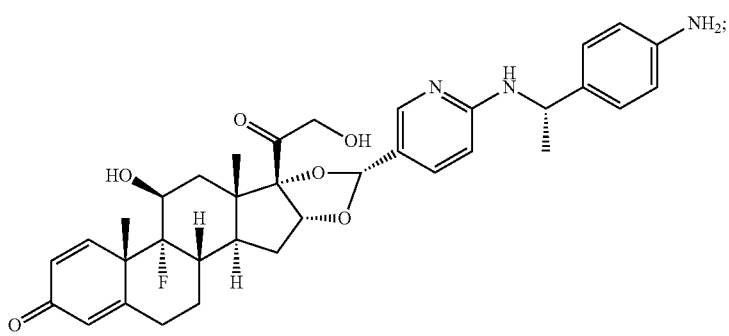
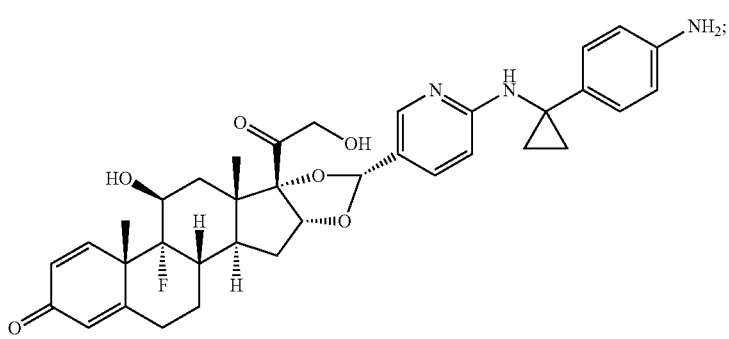
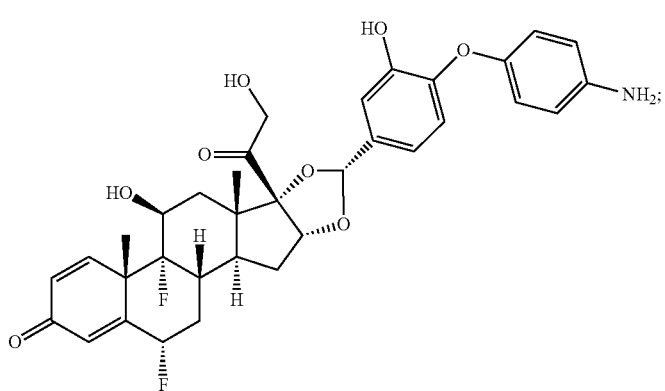

TABLE VII-continued
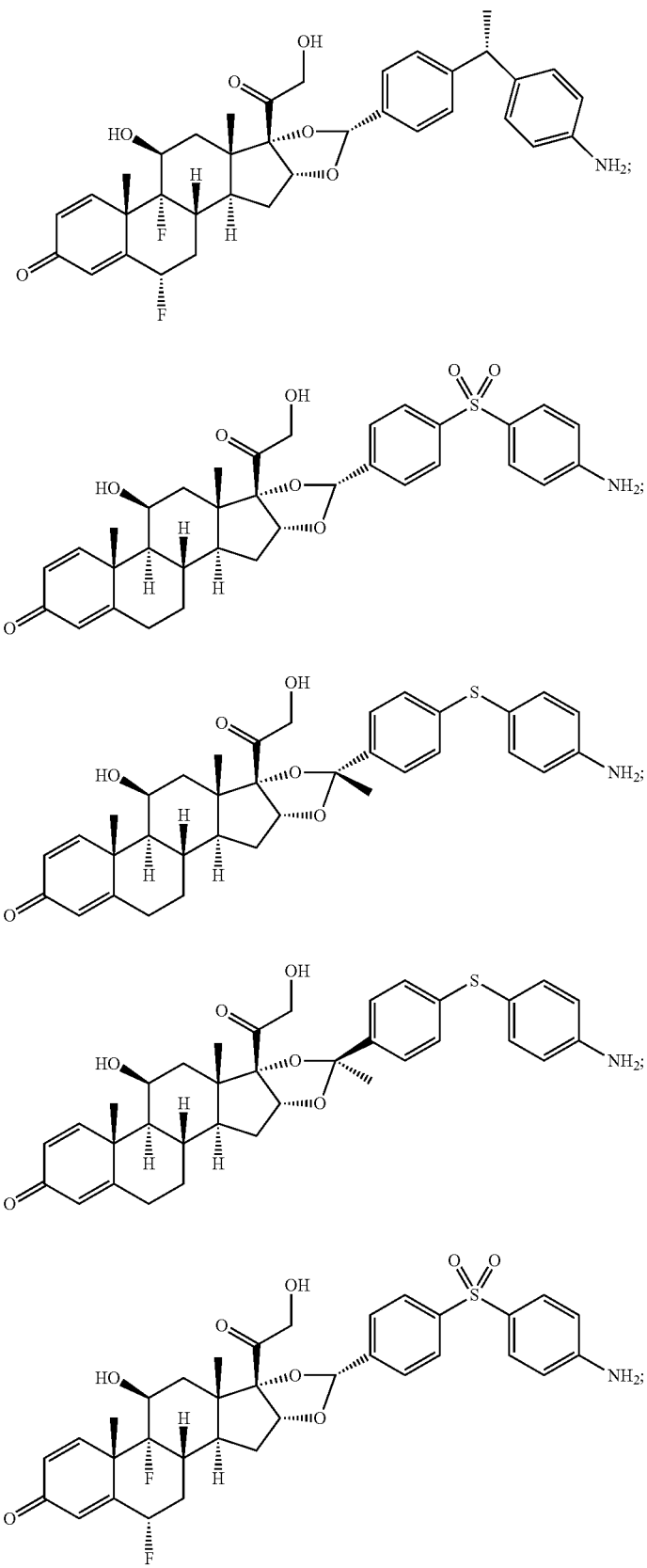

TABLE VII-continued
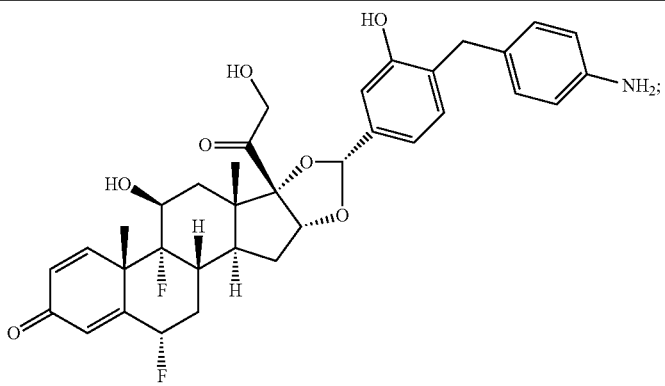
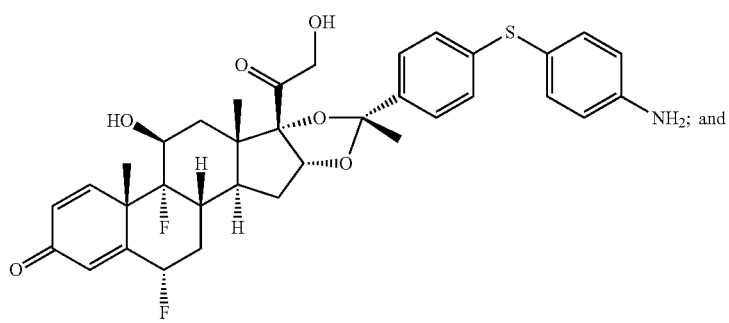
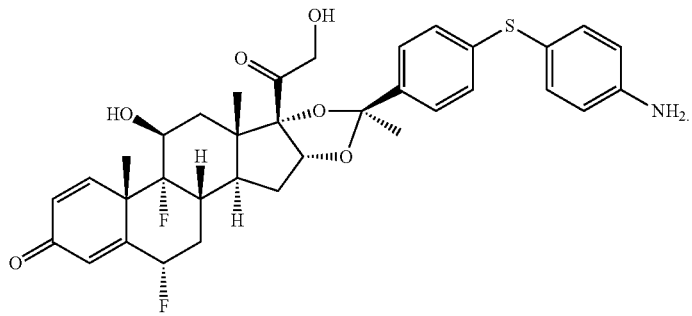
In another embodiment, disclosed herein is a compound having Formula IX-a, or a pharmaceutically acceptable salt thereof, selected from the group consisting of:
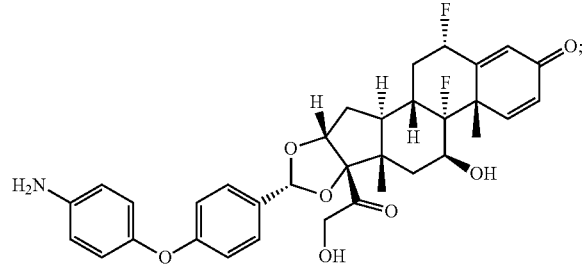
-continued
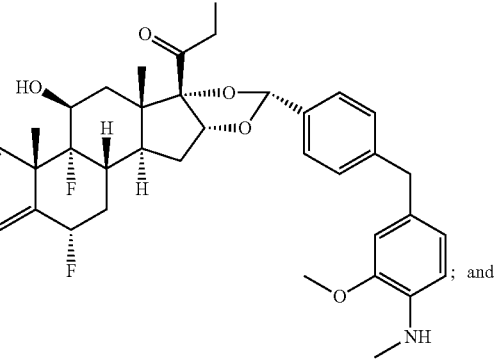

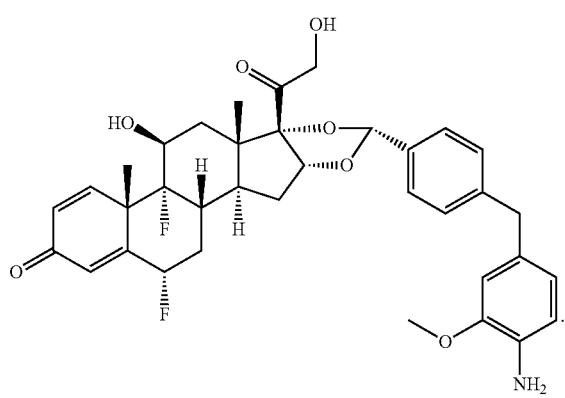

V. Methods of Making Immunoconjugates and Synthetic Intermediates

The general synthesis of the immunoconjugates of the disclosure is described in General Scheme 1.

General Scheme 1

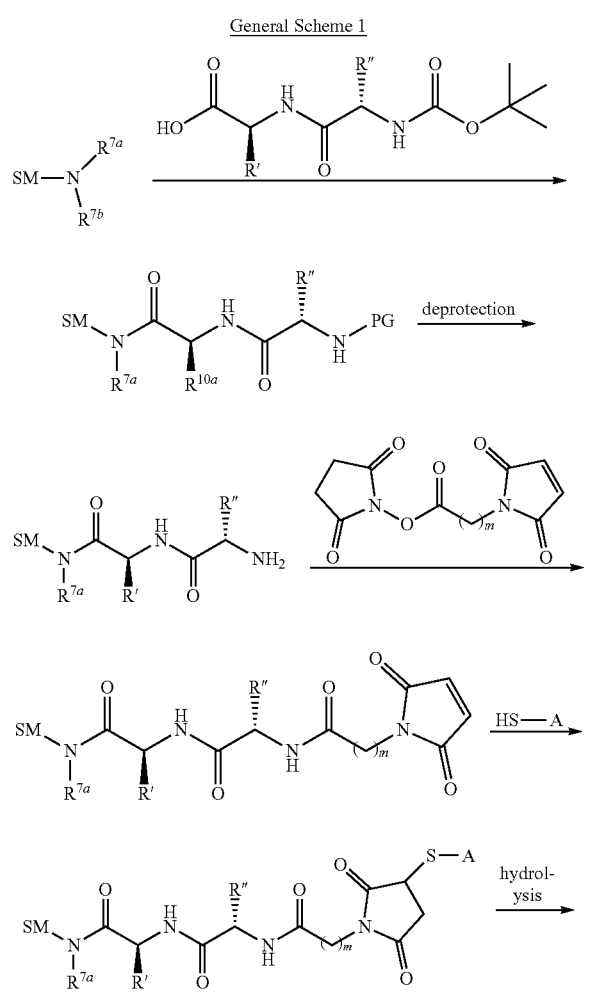

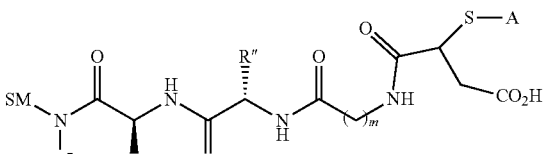

In General Scheme 1, SM-N($R^{7a}$)($R^{7b}$) is a glucocorticosteroid having an —NH($R^{7a}$) group (wherein $R^{7a}$ is hydrogen or $C_{1-4}$ alky), or a compound having any one of Formulae VII, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'', or a compound of Table 9; HS-A is an antibody or antigen binding fragment having a limited number of reduced interchain disulfide bonds, R' and R'' are independently any side chain found in a naturally-occurring, e.g., methyl, isopropyl, and/or non-natural amino acid, e.g., —$CH_2CH_2CH_2N(H)C(=O)NH_2$, m is 1, 2, 3, 4, 5, or 6, and PG is a protecting group, e.g., BOC. For the purpose of illustration, General Scheme 1 shows only one sulfhydryl as being available for conjugation in the antibody or antigen binding fragment.

In another embodiment, disclosed herein is a method of making a compound having Formula I-c:

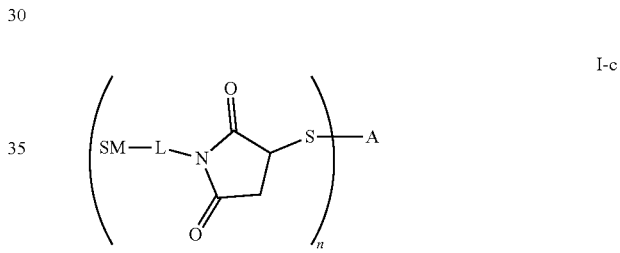

or a pharmaceutically acceptable salt thereof, wherein:
A is $A^1$ or $A^2$;
$A^1$ is an anti-tumor necrosis factor (TNF) alpha protein;
$A^2$ is a protein;
L is a linker;
n is 1-10; and
SM is a radical of a glucocorticosteroid, e.g., a compound having any one of Formulae II-a-q; the method comprising:
a) conjugating a compound having Formula X:

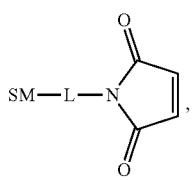

with an anti-tumor necrosis factor (TNF) alpha protein or a protein; and
b) isolating the compound having Formula I-c, or a pharmaceutically acceptable salt thereof. In another embodiment, the method further comprises hydrolyzing the compound having Formula I-c to give a compound having Formula I-d:

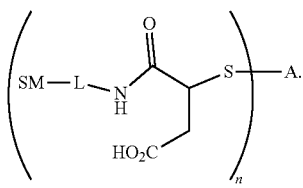

I-d

In another embodiment, disclosed herein is a method of making a compound having Formula I-e:

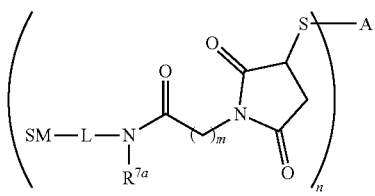

I-e or a pharmaceutically acceptable salt thereof, wherein:
A is $A^1$ or $A^2$;
$A^1$ is an anti-tumor necrosis factor (TNF) alpha protein;
$A^2$ is a protein;
L is a linker;
$R^{7a}$ is selected from the group consisting of hydrogen and $C_{1-4}$ alkyl;
n is 1-10;
m is 1, 2, 3, 4, 5, or 6; and SM is a radical of a glucocorticosteroid, e.g., a compound having any one of Formulae II-a-e or I-q;
the method comprising:
a) conjugating a compound having Formula XI:

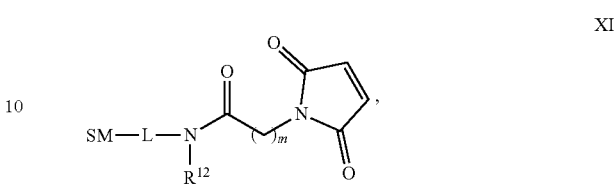

XI with an anti-tumor necrosis factor (TNF) alpha protein or a protein; and
b) isolating the compound having Formula I-e, or a pharmaceutically acceptable salt thereof. In another embodiment, the method further comprises hydrolyzing the compound having Formula I-e to give a compound having Formula I-f:

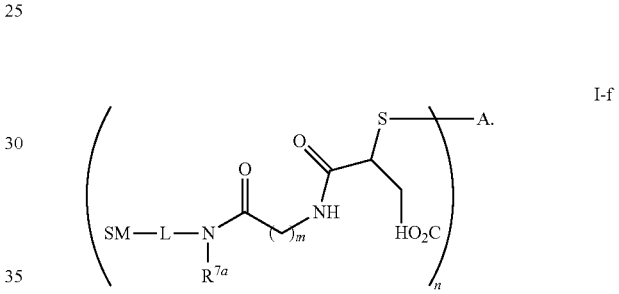

I-f

In another embodiment, disclosed herein is a method of making a compound having Formula I-G:

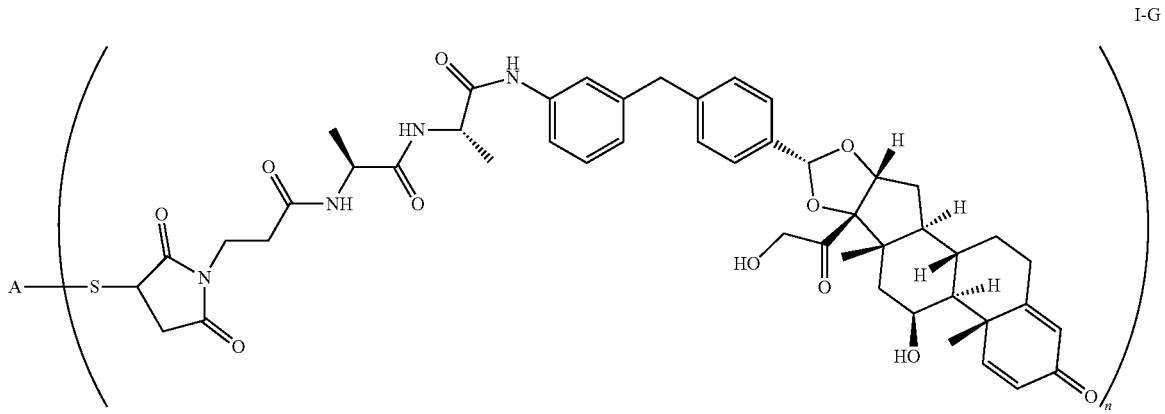

I-G wherein:
  A is adalimumab; and
  n is 1-10,
the method comprising:
  a) conjugating Cpd. No. 88:

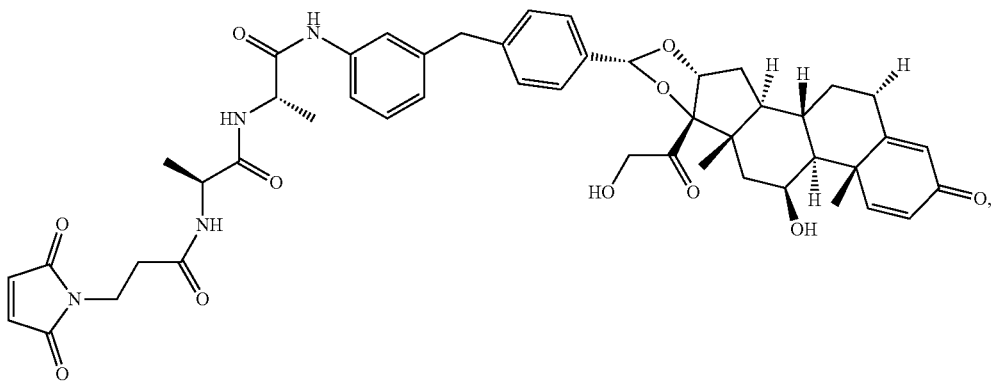

Cpd. No. 88 with partially-reduced adalimumab; and
  b) isolating, e.g., by chromatography, the compound having Formula I-G.

In another embodiment, disclosed herein is a method of making a compound having Formula I-H:

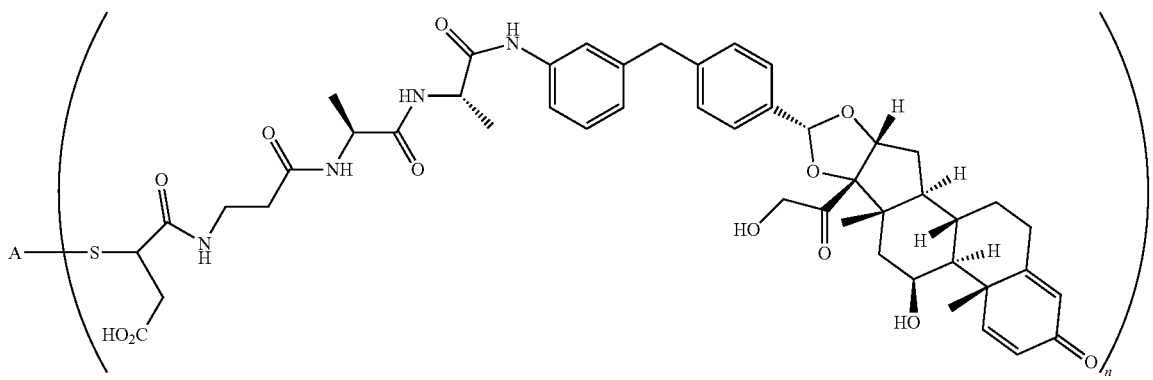

I-H wherein:
  A is adalimumab; and
  n is 1-10,
the method comprising hydrolyzing the compound having Formula I-G to give Formula I-H.

In another embodiment, disclosed herein is a method of making a compound having Formula I-G or Formula I-H, wherein n is 1-7. In another embodiment, n is 1-5. In another embodiment, n is 2-4. In another embodiment, n is 1. In another embodiment, n is 1.5. In another embodiment, n is 2. In another embodiment, n is 2.5. In another embodiment, n is 3. In another embodiment, n is 3.5. In another embodiment, n is 4. In another embodiment, n is 4.5. In another embodiment, n is 5.

In another embodiment, disclosed herein is a compound having Formula I-H:

I-H

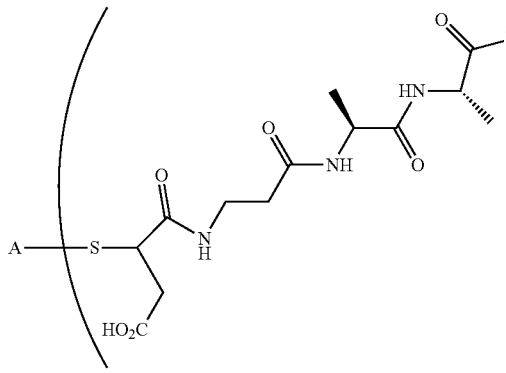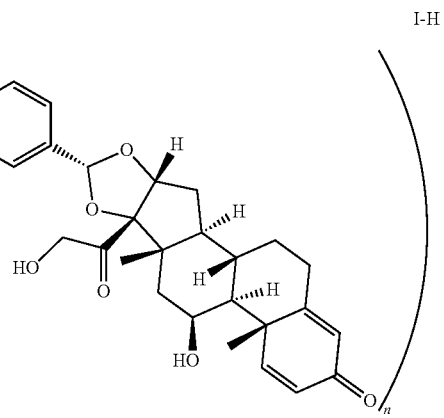

wherein:
A is adalimumab; and
n is 1-10.

In another embodiment, disclosed herein is a compound having Formula I-H, wherein n is 1-7. In another embodiment, n is 1-5. In another embodiment, n is 2-4. In another embodiment, n is 1. In another embodiment, n is 1.5. In another embodiment, n is 2. In another embodiment, n is 2.5. In another embodiment, n is 3. In another embodiment, n is 3.5. In another embodiment, n is 4. In another embodiment, n is 4.5. In another embodiment, n is 5. In another embodiment, n is 5.5. In another embodiment, n is 6. In another embodiment, n is 6.5. In another embodiment, n is 7. In another embodiment, n is 7.5. In another embodiment, n is 8.

According to the present disclosure, glucorticoid receptor agonists can be linked to the antibody, antigen-binding fragment thereof, or anti-TNF alpha proteins via any method and at any location that does not prevent the antibody, antigen-binding fragment thereof, or anti-TNF alpha protein from binding antigen (e.g., TNF alpha) or prevent activity of the glucorticoid receptor agonist. Methods for achieving such a linkage have been discussed, for example, in Panowski et al., mAbs 6: 34-45 (2014), Jain et al., Pharm. Res. 32: 3526-3540 (2015), Mack et al., Seminars in Oncology 41: 637-652 (2014), U.S. Published Application No. 2008/0305044, and U.S. Published Application No. 2011/0097322 each of which is herein incorporated by reference in its entirety.

The glucorticoid receptor agonists can be linked to the antibodies, antigen-binding fragments thereof, or anti-TNF alpha proteins via a natural amino acid, e.g., an amino acid that has a side-chain with a nucleophilic group.

For example, the glucorticoid receptor agonist can be linked to a lysine residue. Methods for conjugation via lysine are known. Such methods include a two-step process in which a linker is attached to the antibody, antigen-binding fragment thereof, or anti-TNF alpha protein in a first chemical reaction and then the linker is reacted with the glucocorticoid receptor agonist in a second chemical reaction. In another method, a one-step reaction with a preformed linker-glucocorticoid receptor agonist to form the conjugate containing the glucocorticoid receptor agonist linked to the antibody, antigen-binding fragment thereof, or anti-TNF alpha protein.

The glucorticoid receptor agonist can also be linked to a cysteine residue. Methods for conjugation via cysteine are know. IgG1 antibodies contain four inter-chain disulfide bonds, and conjugation via cysteine can occur after reduction of these bonds creates sulfhydryls available for conjugation.

The glucorticoid receptor agonists can be linked to the antibody, antigen-binding fragment thereof, or anti-TNF alpha proteins via site-specific conjugation.

One method of site-specific conjugation is cysteine-based site-specific conjugation. An example of this method has been reported by Junutula et al., Nat. Biotechnol 26: 925-935 (2008); see also Junutula et al., J. Immunol. Methods 332: 41-52 (2008), each of which is herein incorporated by reference in its entirety. Using this method, antibodies, antigen-binding fragments thereof or anti-TNF alpha proteins can be engineered with additional cysteines that provide reactive thiol groups to conjugate glucocorticoid receptor agonist. These publications also provide guidance regarding the selection of reactive cysteins that do not interfere with antigen binding.

Another method of site-specific conjugation makes use of selenocysteine. Selenocysteine is similar to cysteine but contains a more reactive selenium atom in place of the sulfur atom in cysteine. Conditions can be used in which selenocysteines are selectively activated. Hofer et al., Biochemistry 48: 12047-12057 (2009), which is herein incorporated by reference in its entirety, has exemplified this technique.

Another method of site-specific conjugation makes use of unnatural amino acids, e.g., acetylphenylalanine (pAcPhe) or para-azido phenylalanine (pAF). Wang et al. Proc. Natl. Acad Sci. 100: 56-61 (2003), Axup et al., Proc. Natl. Acad Sci. 109:16101-16106 (2012), and Kern et al., JACS 138: 1430-1445 (2016), each of which is herein incorporated by reference in its entirety, have exemplified this technique.

Another method of site-specific conjugation makes use of enzymatic approaches, e.g., via glycotransferases or transglutaminases. Mutant glycotransferases can be used to attach a chemically active sugar moiety to a glycosylation site on an antibody, antigen-binding fragment thereof, or anti-TNF alpha protein. Human IgG antibodies contain an N-glycosylation site at residue Asn-297 of the Fc fragment. The glycans attached at this residue can be degalactosylated so that a mutant glycotransferase is capable of transferring thereto. Boeggeman et al., Bioconjug. Chem. 20: 1228-1236 (2009), which is herein incorporated by reference in its entirety, has exemplified this technique. Transglutaminases, e.g., from Streptoverticillium mobaranse, recognize a glutamine tag, e.g., LLQG, that can be engineered into an anti-TNF alpha protein. Jeger et al., Angew Chem. Int. Ed.

Engl. 49: 9995-9997 (2010), which is herein incorporated by reference in its entirety, has exemplified this technique.

C-terminal attachment via expressed protein ligation can also be used. For example, intein mediated C-terminal thioester formation can be used for chemoselective ligation with an anti-TNF alpha protein containing an N-temrinal cysteine peptide. Chiang et al., *J. Am. Chem. Soc.* 136: 3370-3373 (2014), which is herein incorporated by reference in its entirety, has exemplified this technique.

Also provided herein are synthetic intermediates, e.g., compounds having Formula X and XI, that useful for the preparation of immunoconjugates.

In one embodiment, the synthetic intermediate disclosed herein is a compound having any one of Formulae VII, VIII, VIII-a, VIII-b, IX, IX-a, or IX-b, or any one of Formulae VII', VII-A', VII-B', VIII', VIII-a', VIII-b', IX', IX-a', IX-b', VII", VII-A", VII-B", VIII", VIII-a", VIII-b", IX", IX-a", or IX-b", or a pharmaceutically acceptable salt thereof, wherein $R^{7b}$ is selected from the group consisting of -L-H, -L-PG,

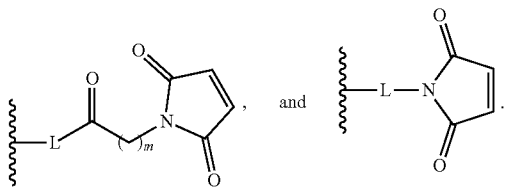

In another embodiment, the synthetic intermediate disclosed herein is a compound having Formula VIII, or a pharmaceutically acceptable salt thereof, which is any one or more of the compounds of Table VIII:

TABLE VIII

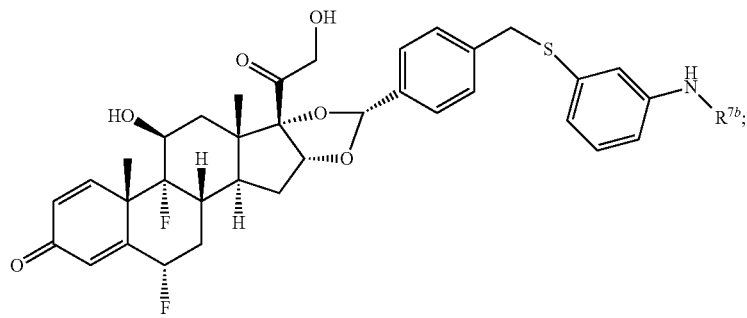

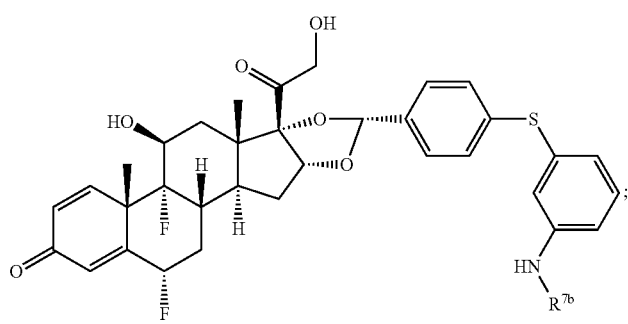

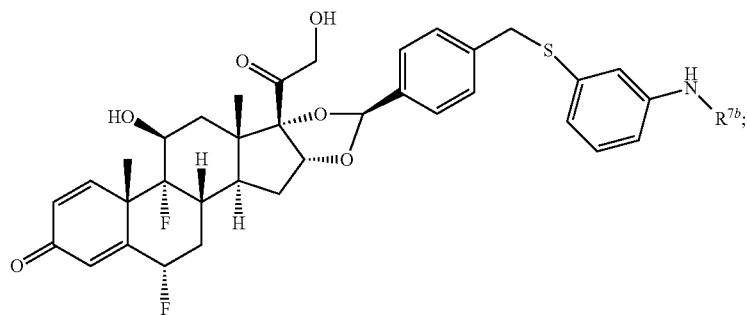

TABLE VIII-continued
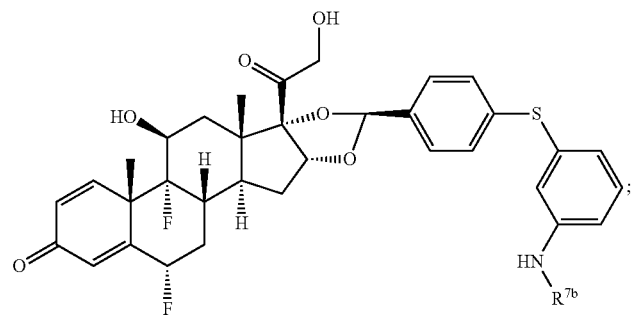
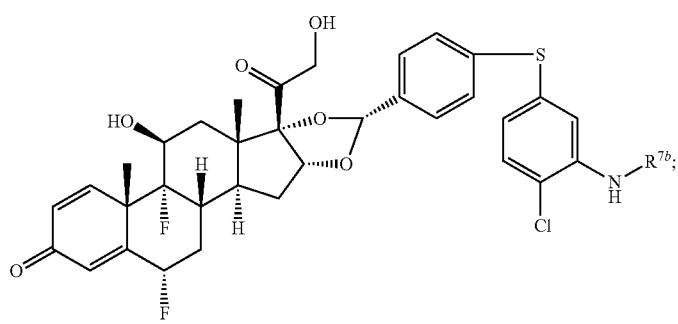
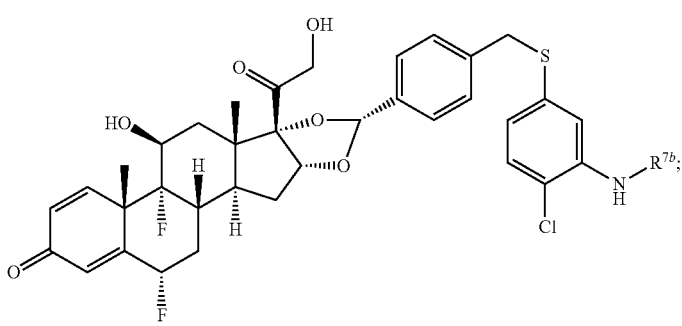
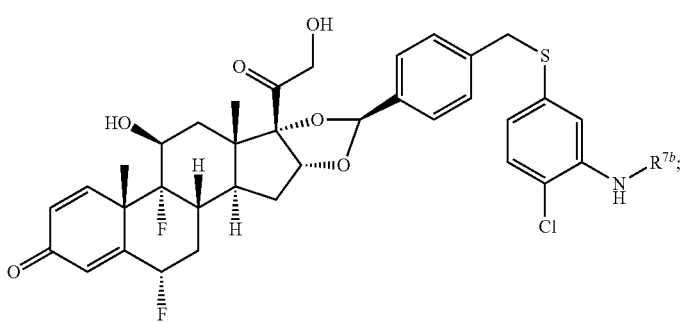
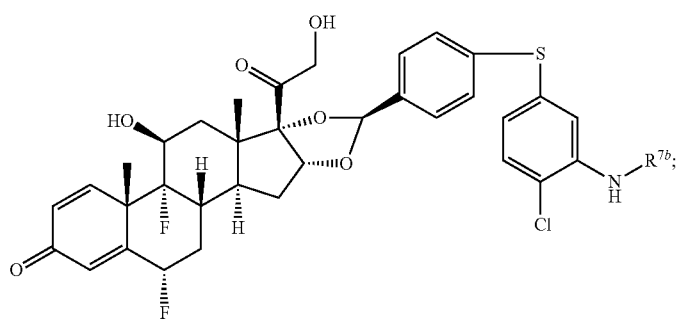

TABLE VIII-continued
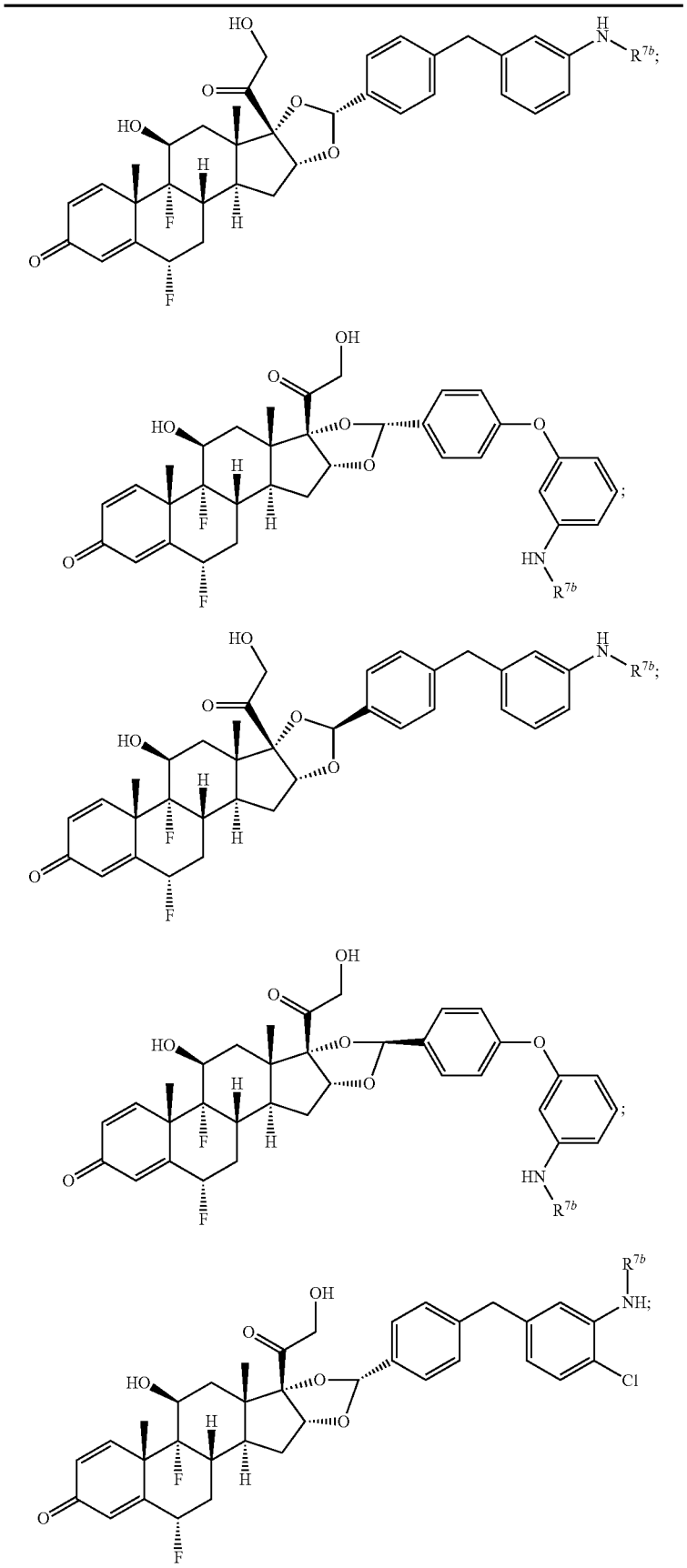

TABLE VIII-continued
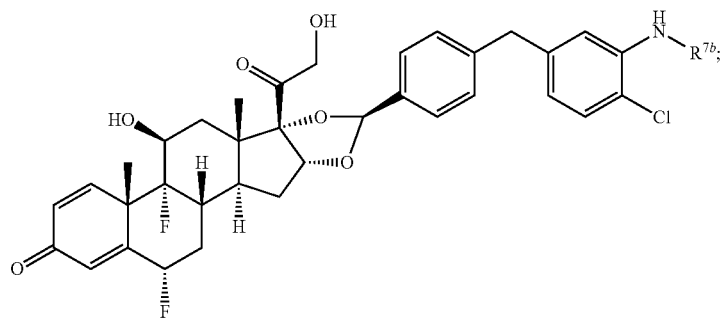
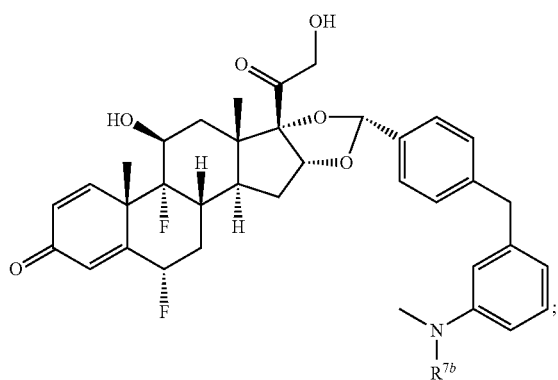
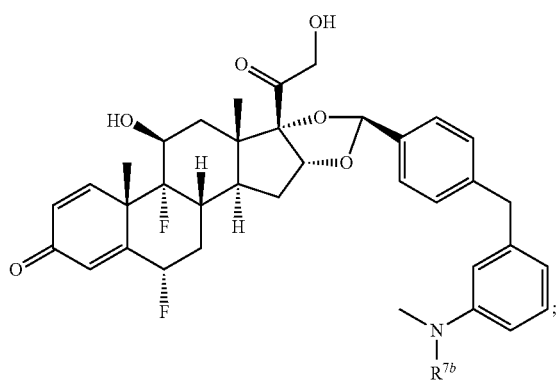
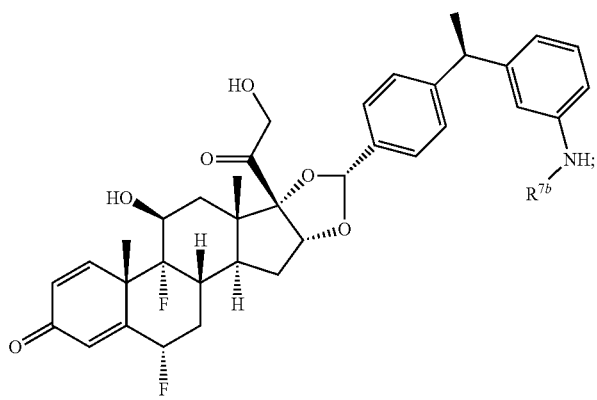

TABLE VIII-continued
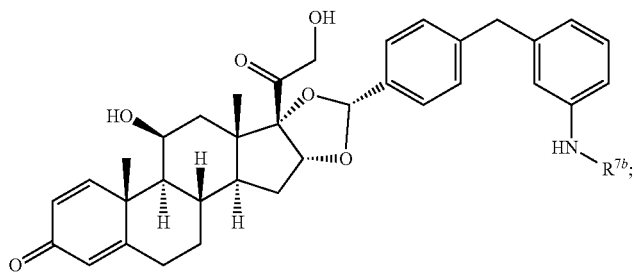
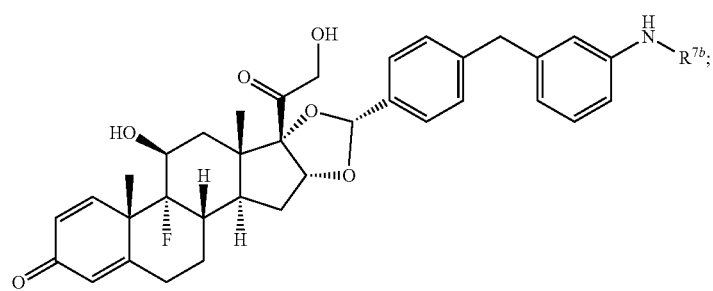
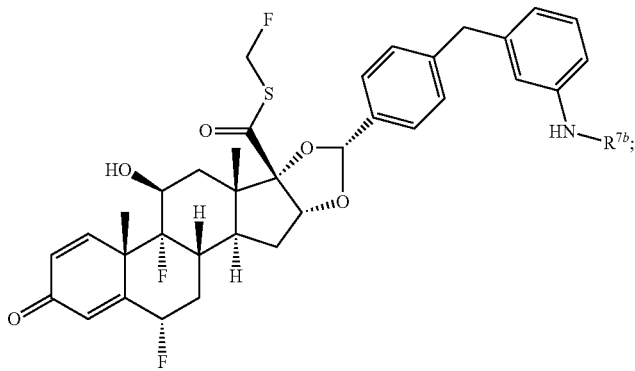
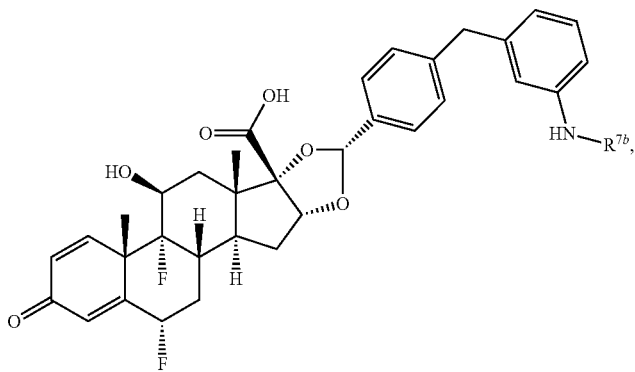

TABLE VIII-continued
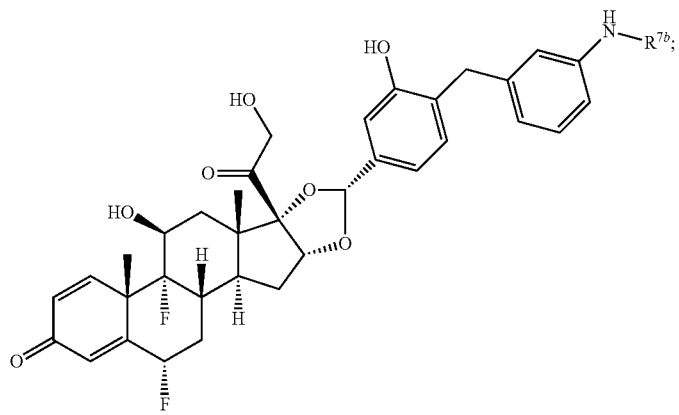
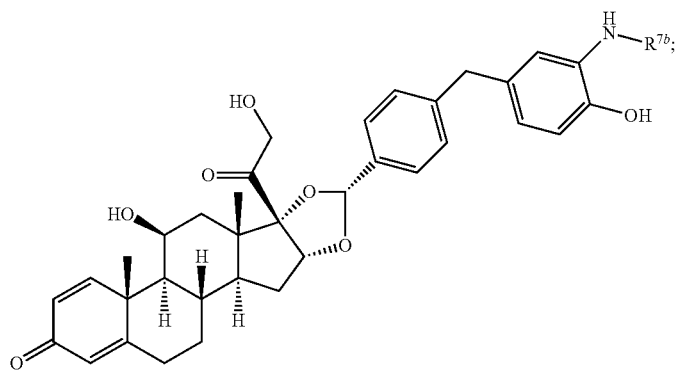
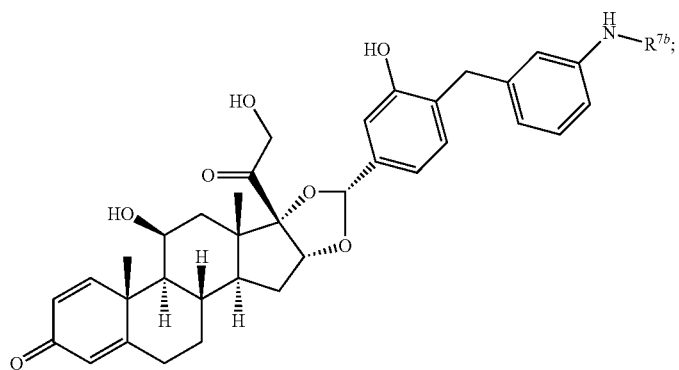
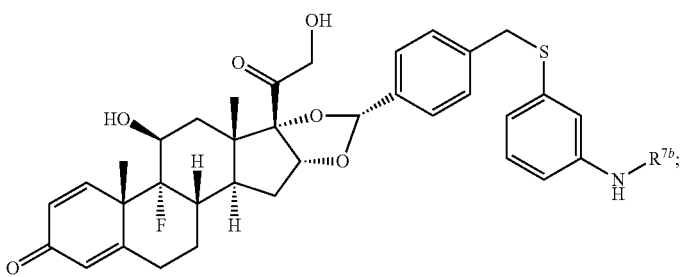

TABLE VIII-continued
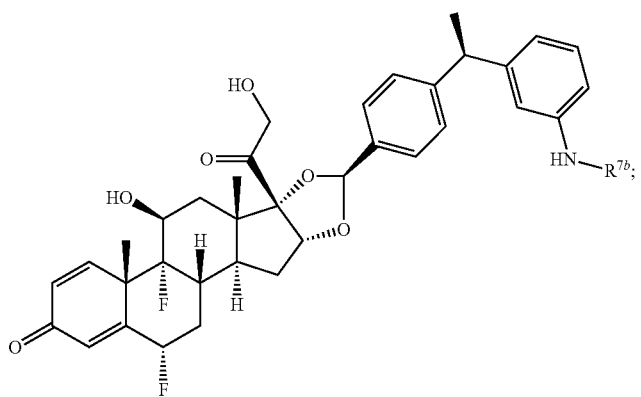
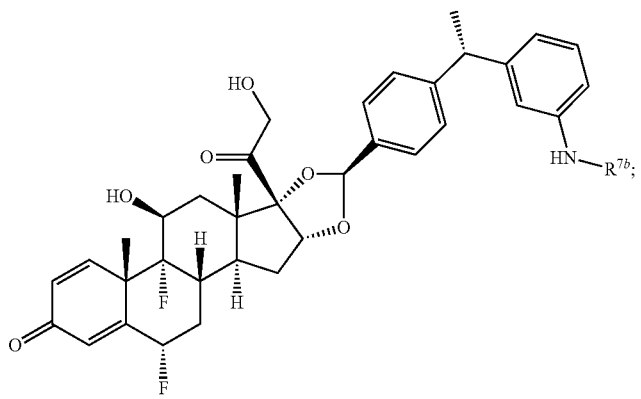
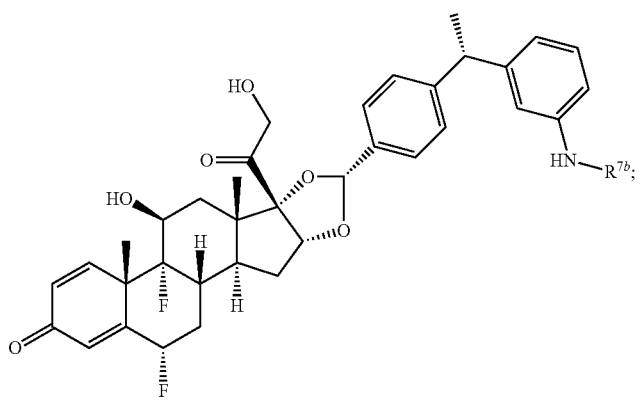
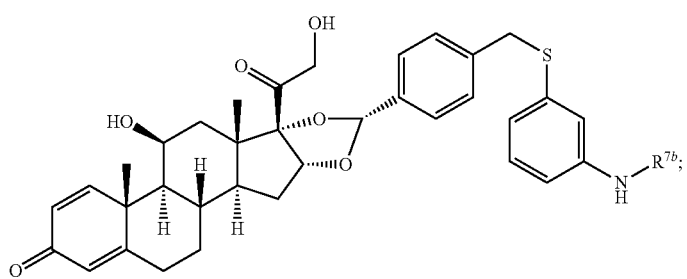

TABLE VIII-continued
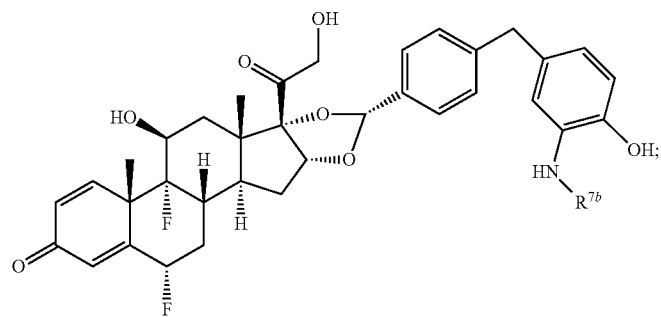
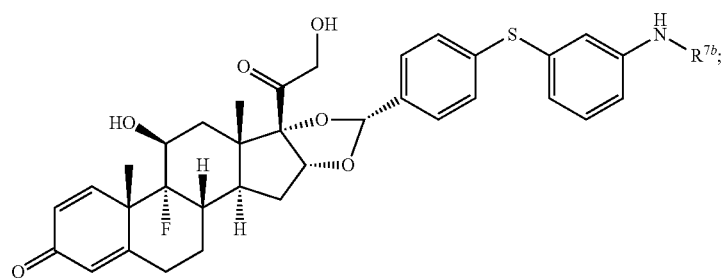
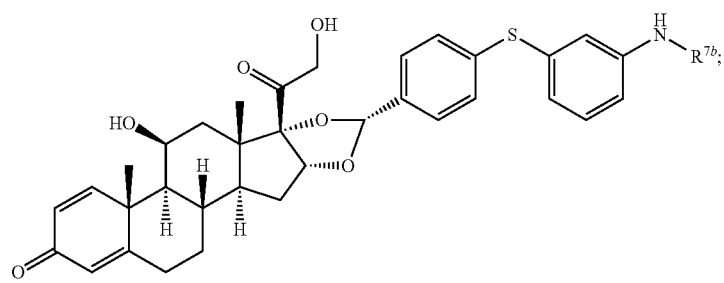
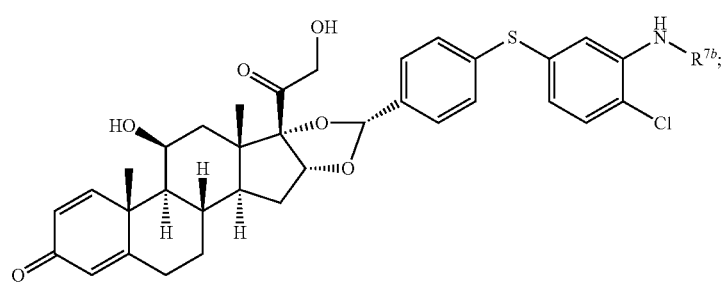
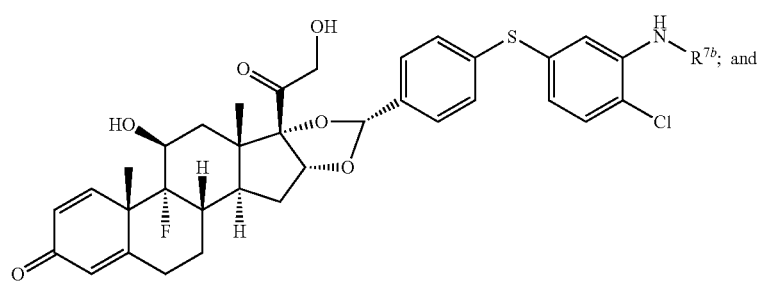

TABLE VIII-continued

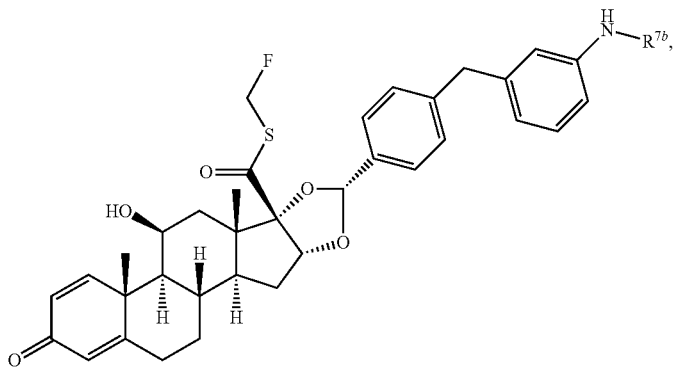

wherein $R^{7b}$ is selected from the group consisting of -L-H, -L-PG,

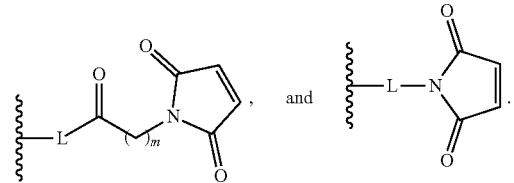

In another embodiment, $R^{7b}$ is selected from the group consisting of:

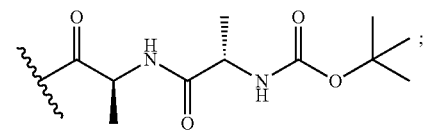

$R^{7b}$-4

-continued

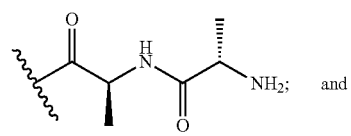

$R^{7b}$-5

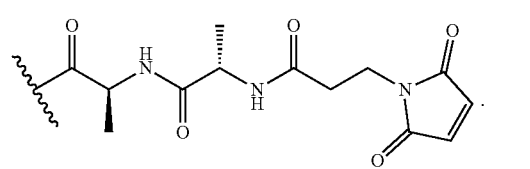

$R^{7b}$-6

In another embodiment, $R^{7b}$ is $R^{7b}$-4. In another embodiment, $R^{7b}$ is $R^{7b}$-5. In another embodiment, $R^{7b}$ is $R^{7b}$-6. In another embodiment, $R^{7b}$ is any one of the structures of Table IX.

TABLE IX

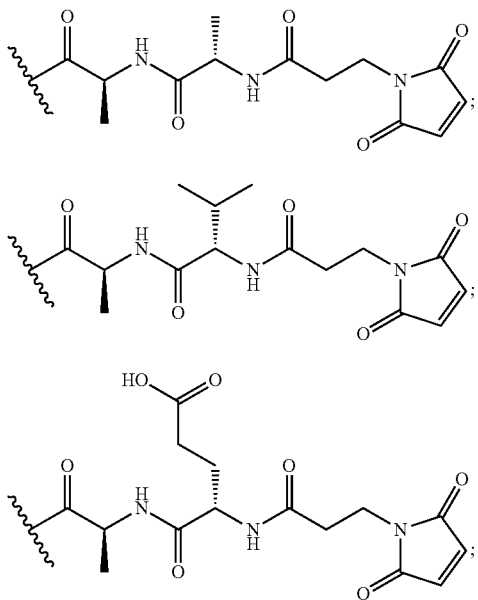

TABLE IX-continued
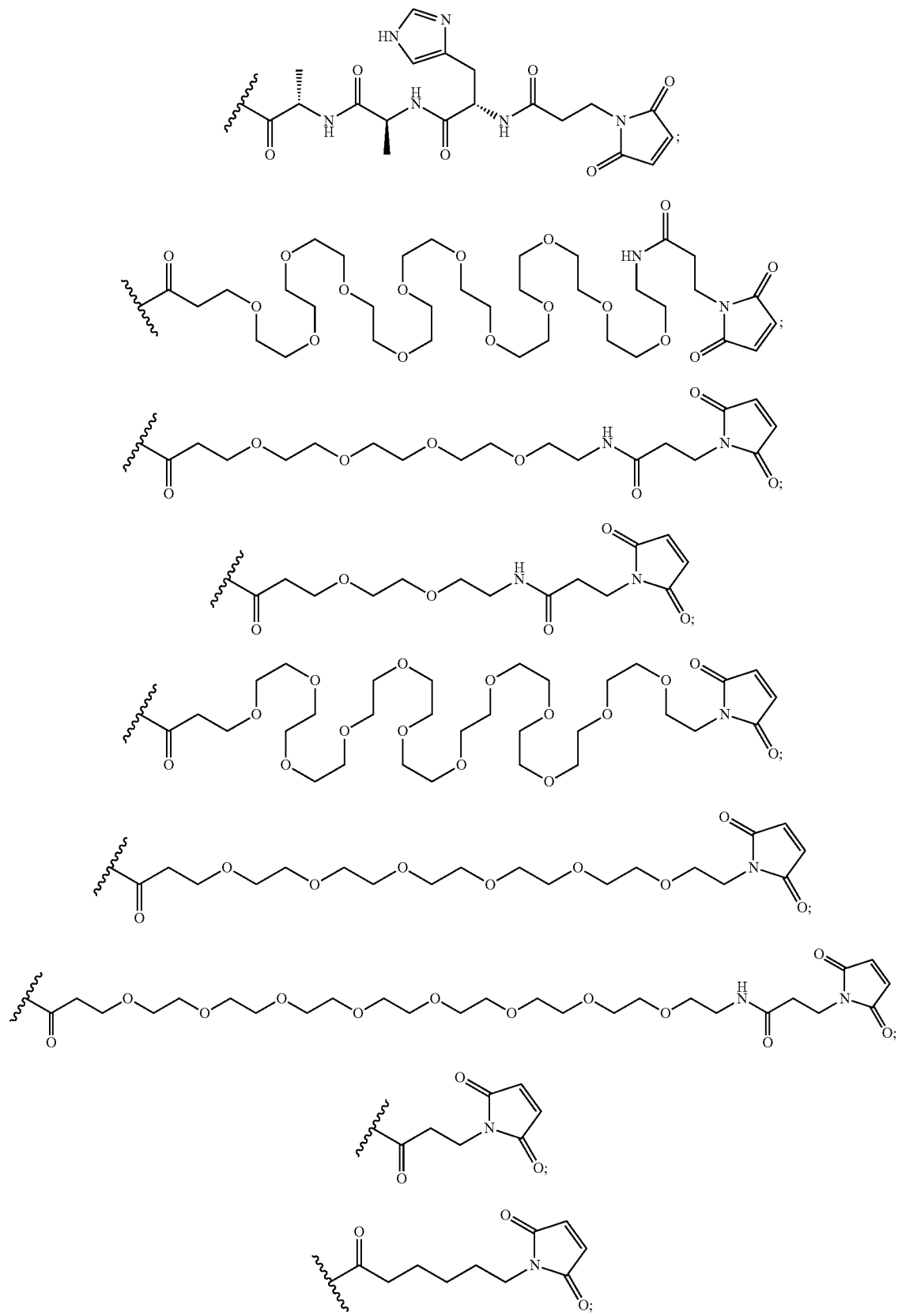

TABLE IX-continued
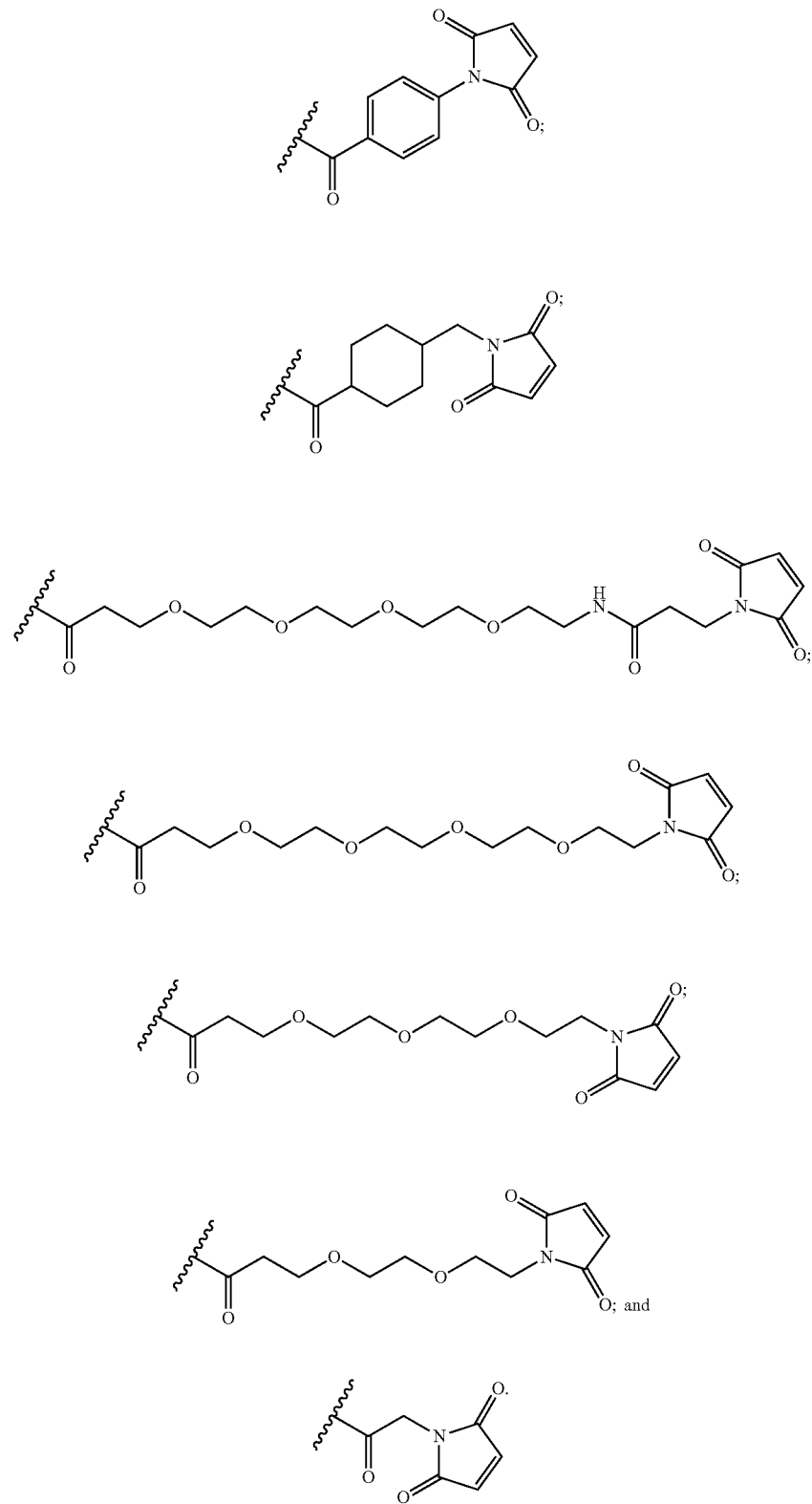
In another embodiment, the synthetic intermediate disclosed herein is a compound having Formulae VIII, or a pharmaceutically acceptable salt thereof, which is any one of the compounds of Table X.

TABLE X
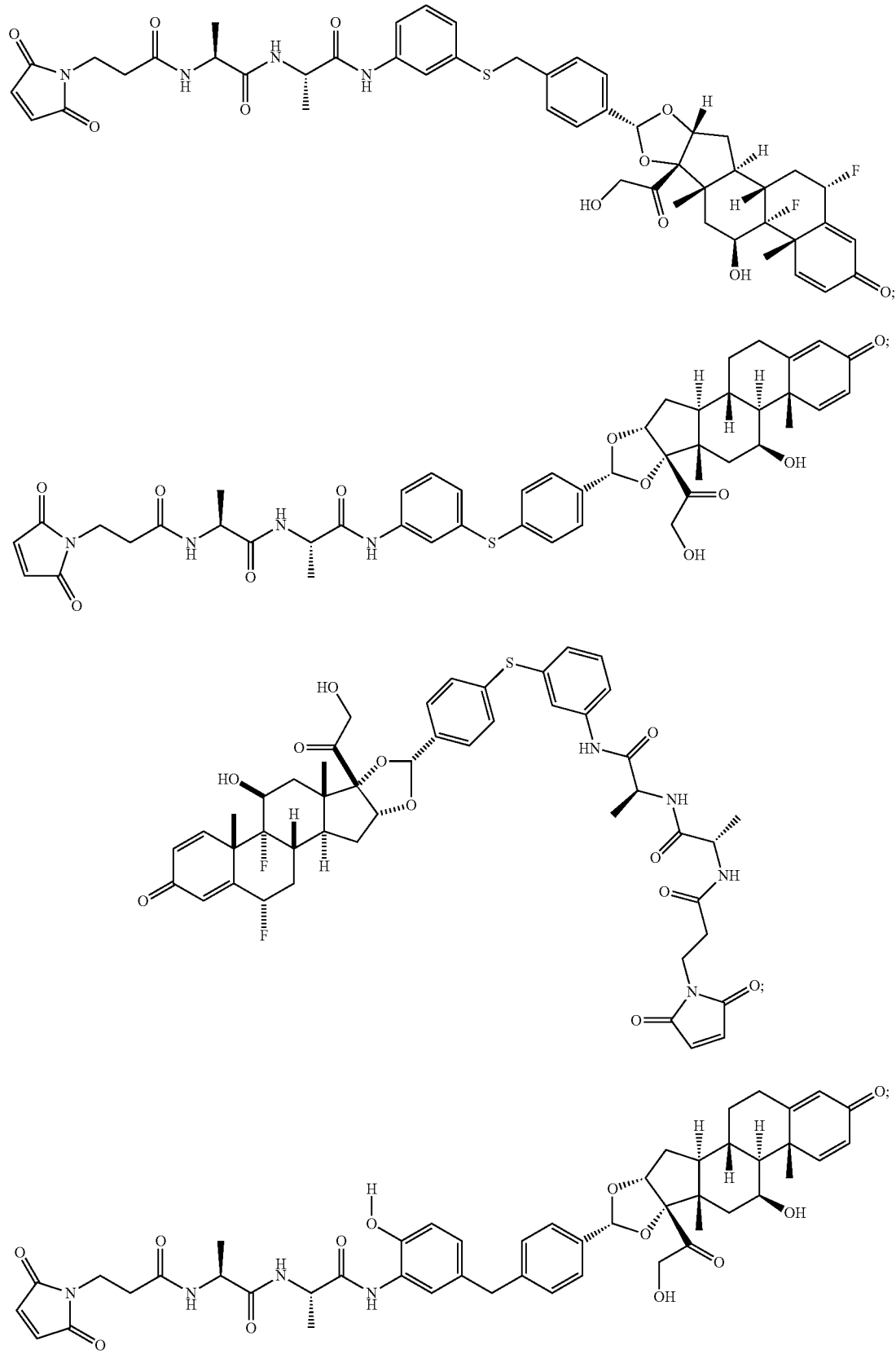

TABLE X-continued
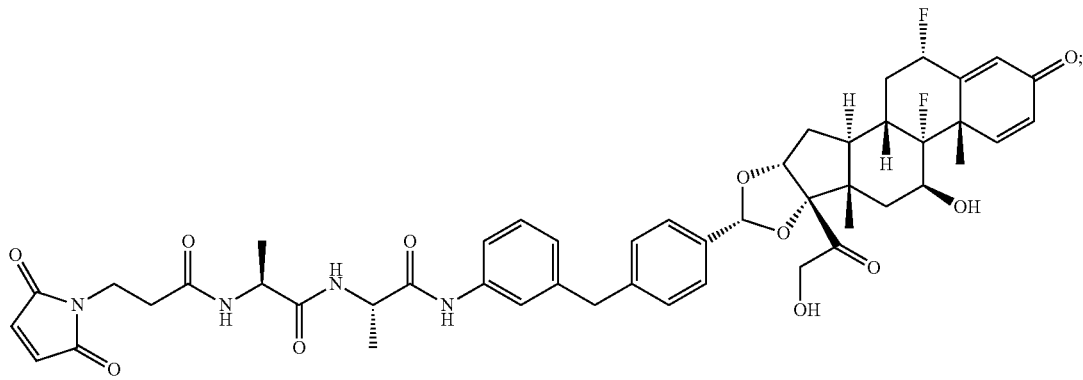
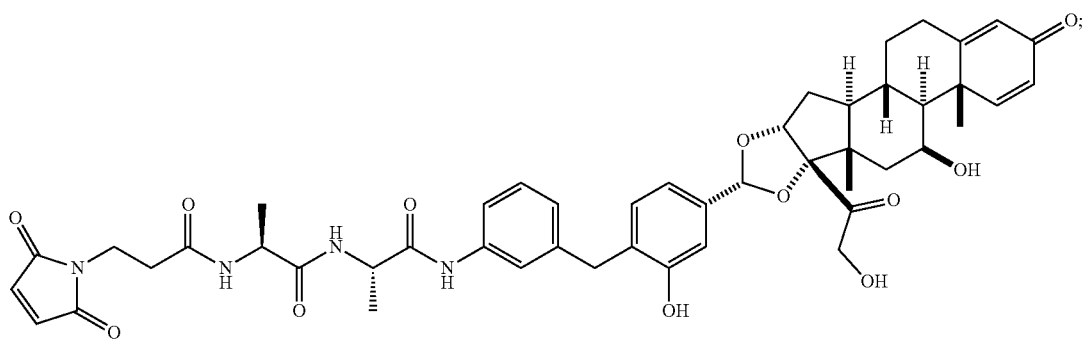
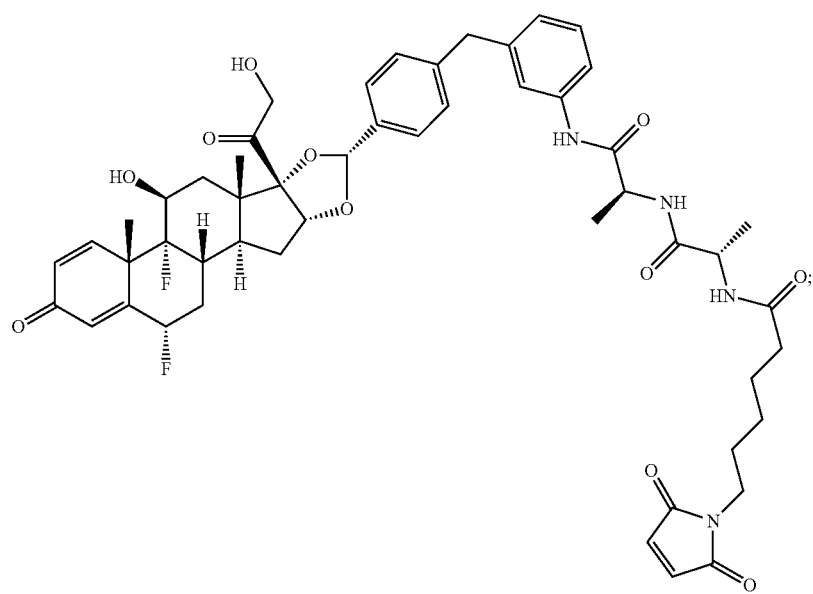

TABLE X-continued
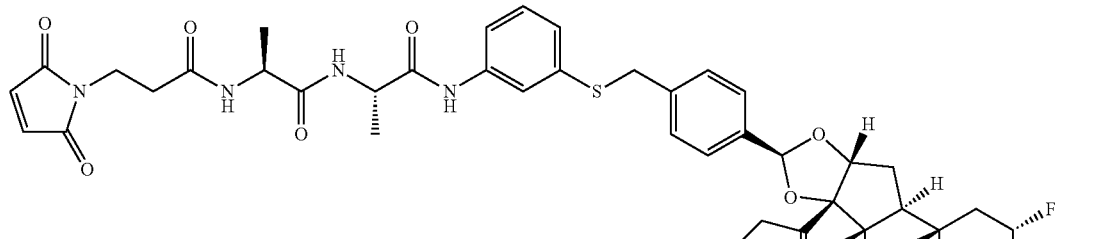
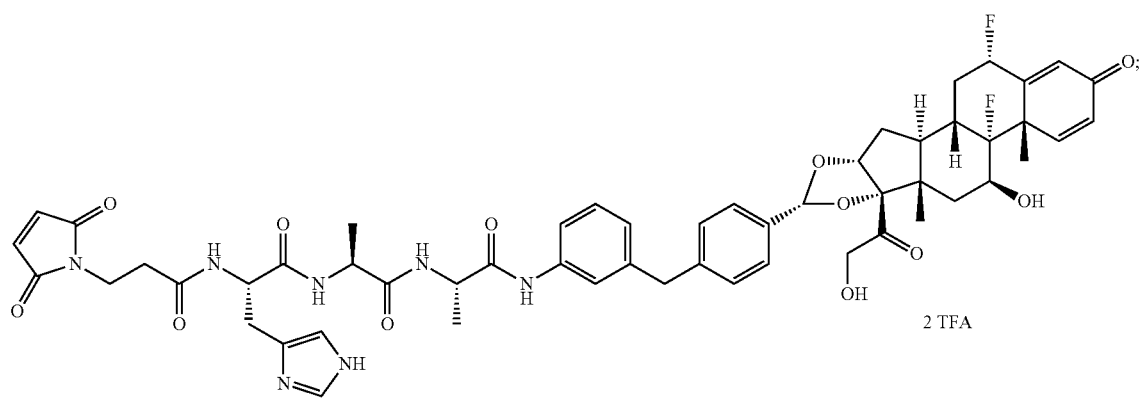
2 TFA
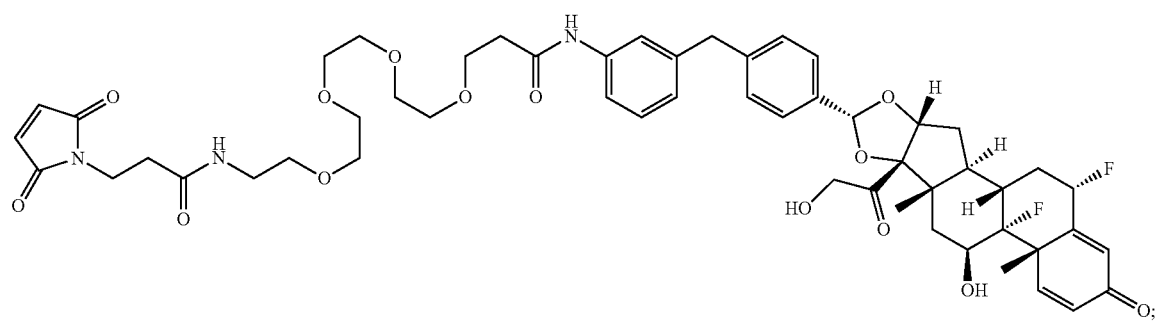
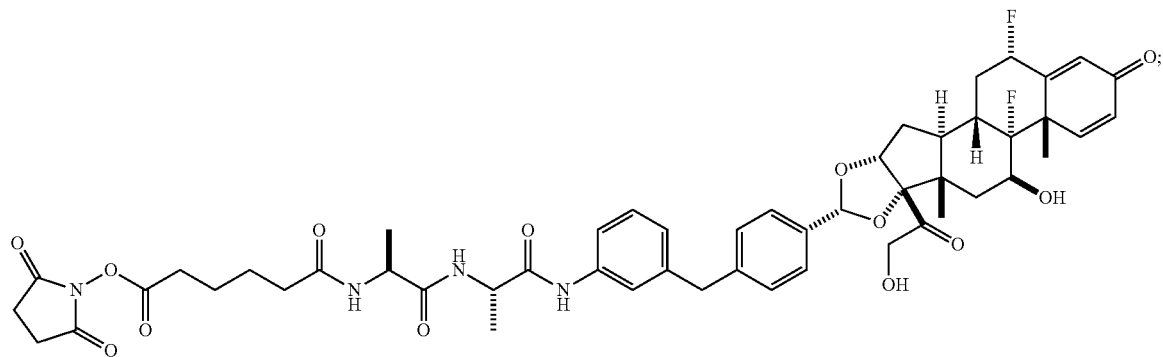

TABLE X-continued
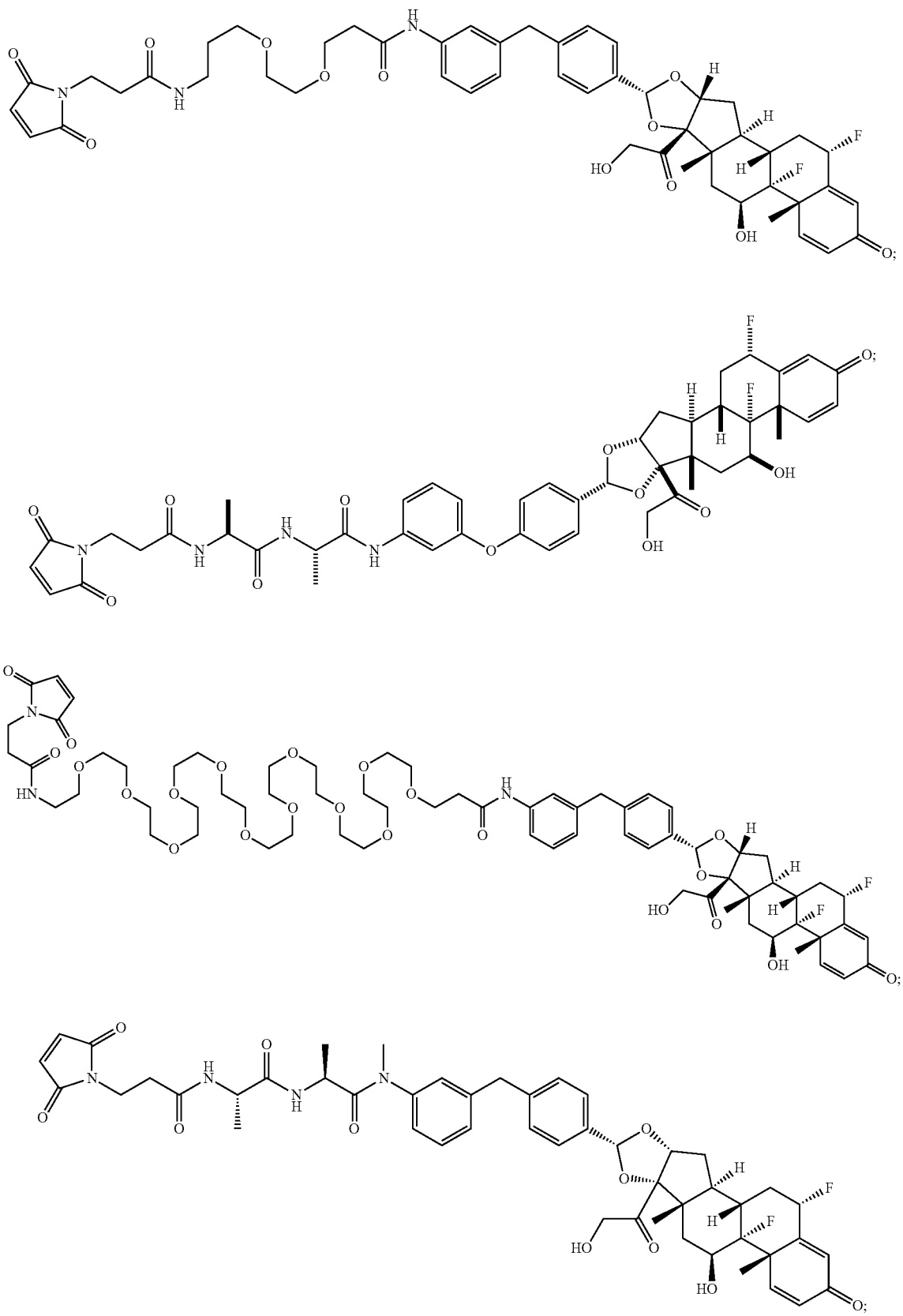

TABLE X-continued
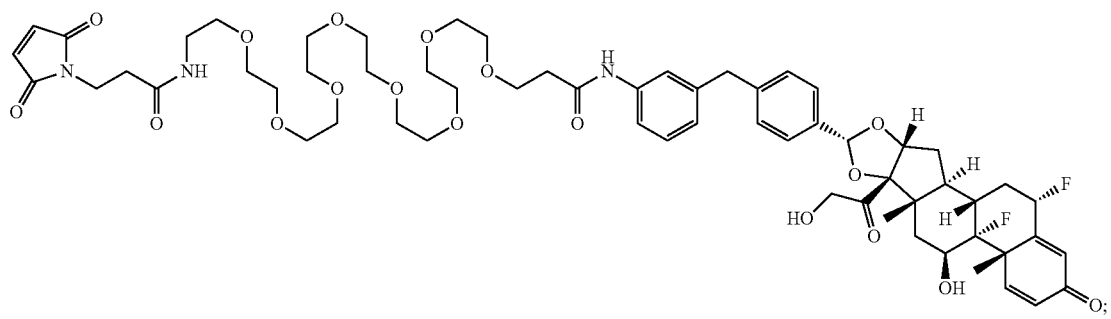
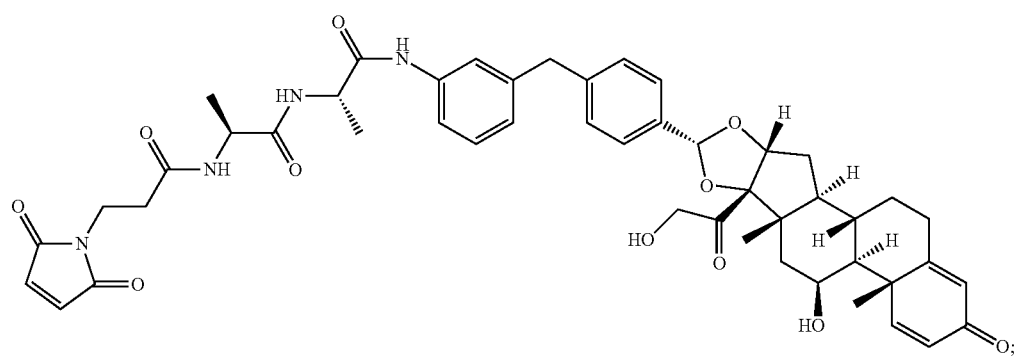
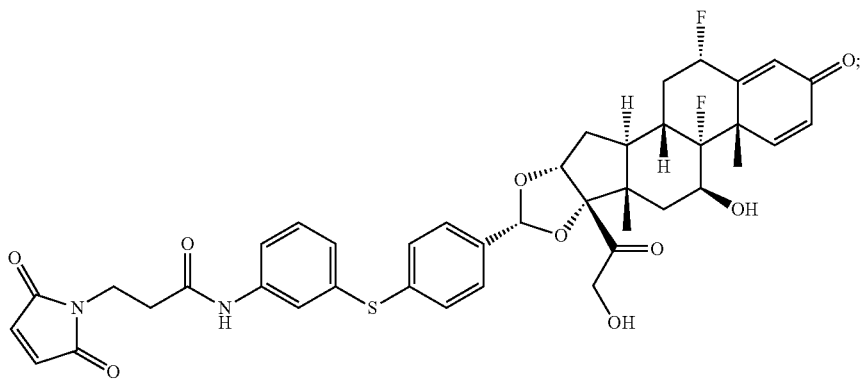
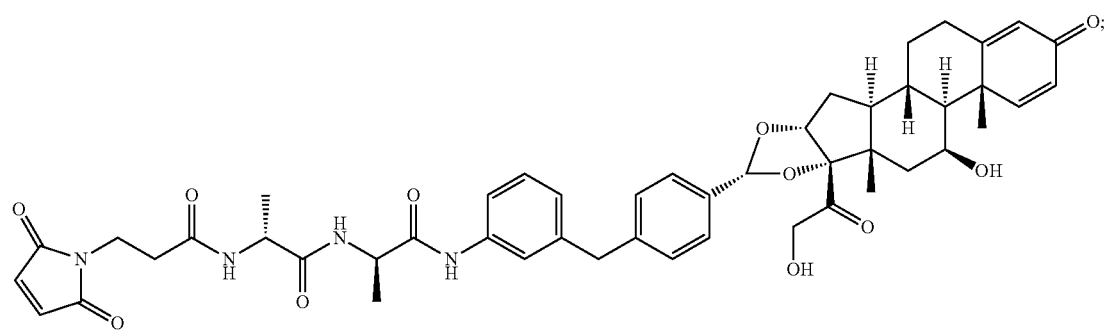

TABLE X-continued
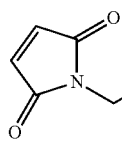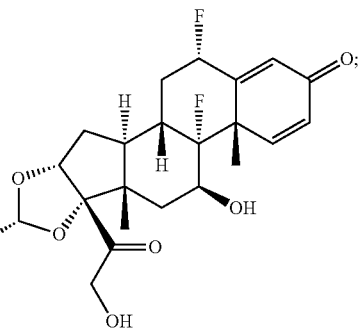
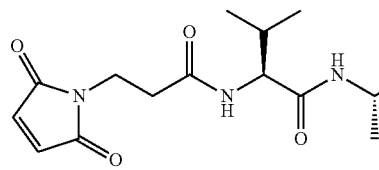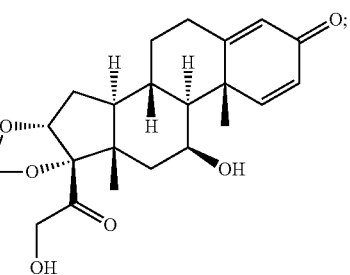
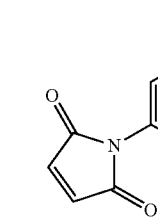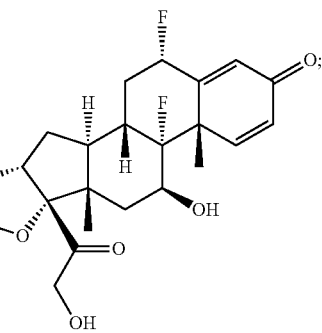
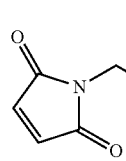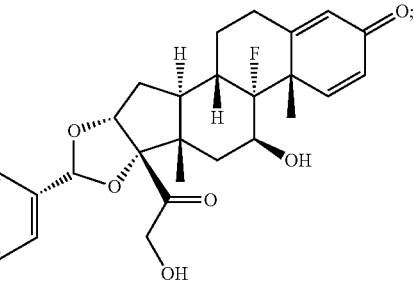

TABLE X-continued
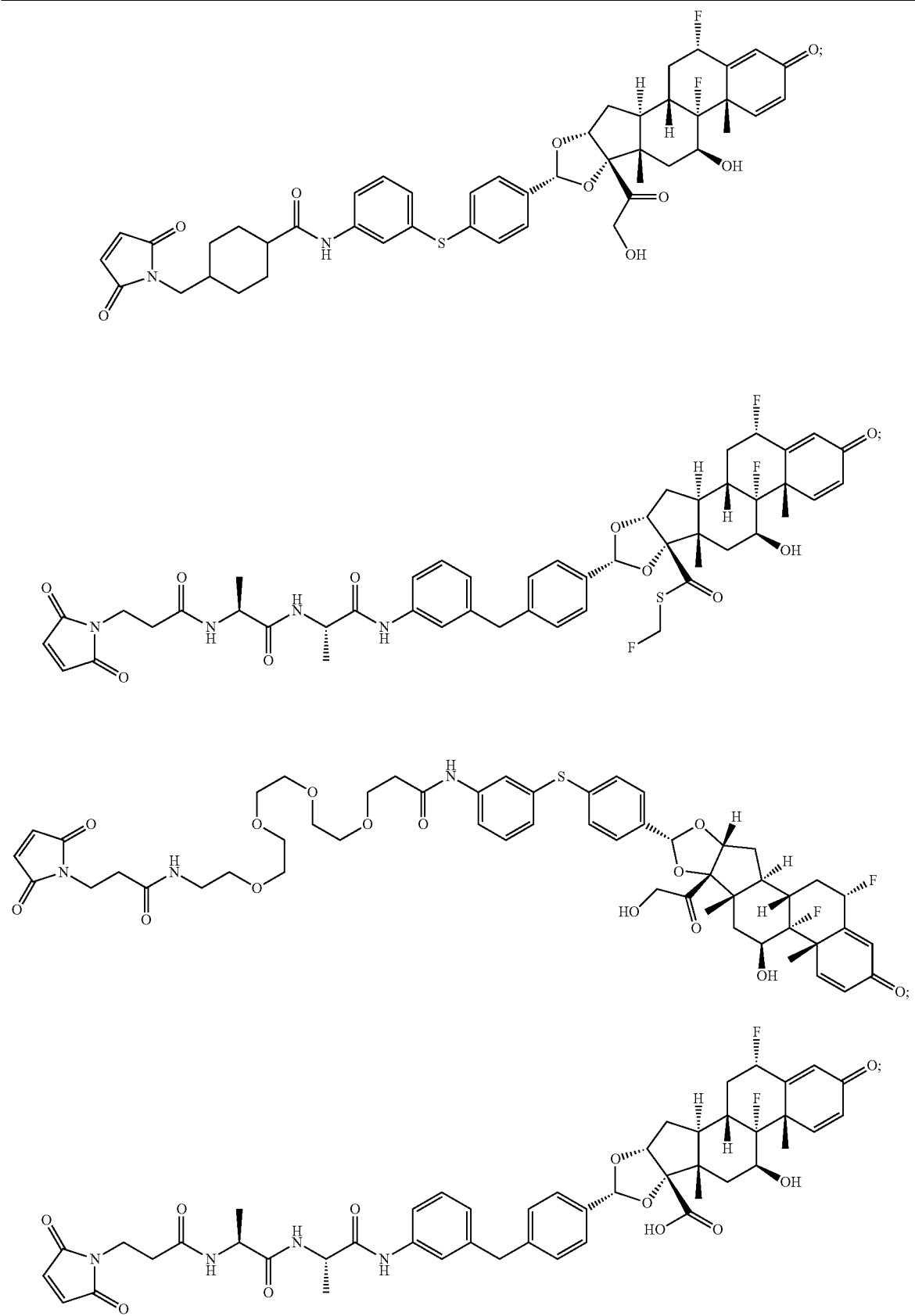

TABLE X-continued
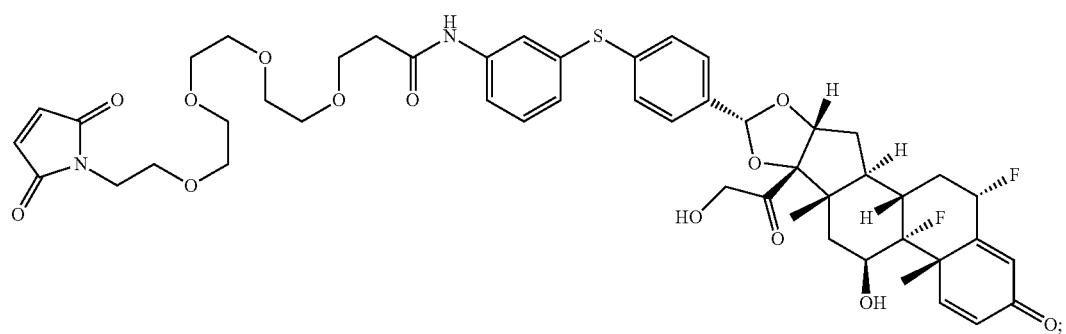
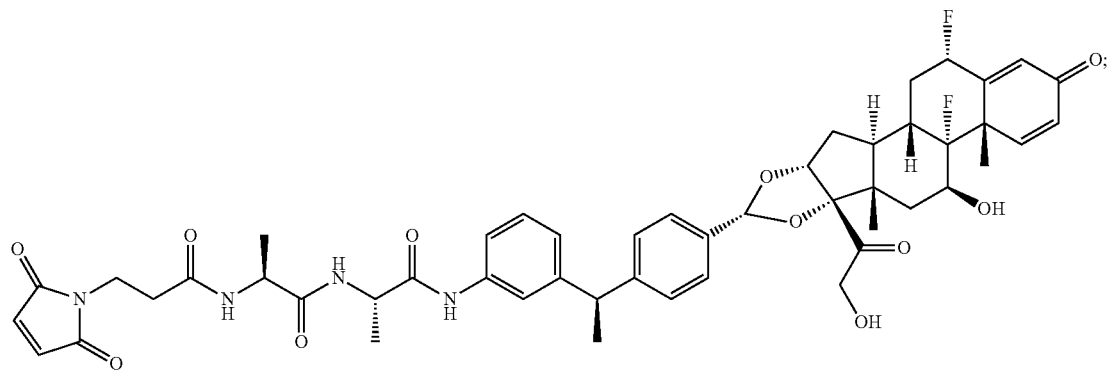
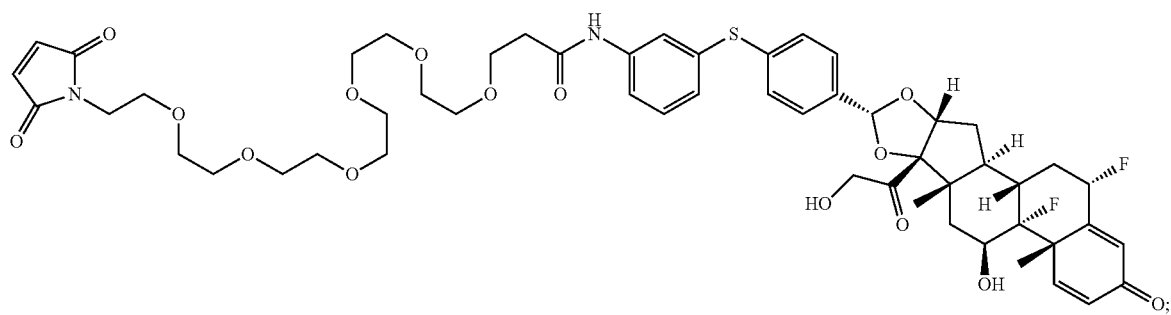
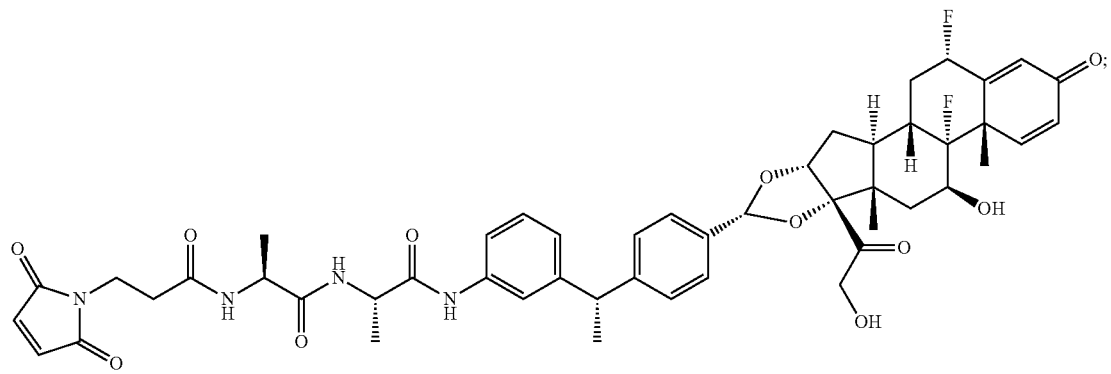

TABLE X-continued
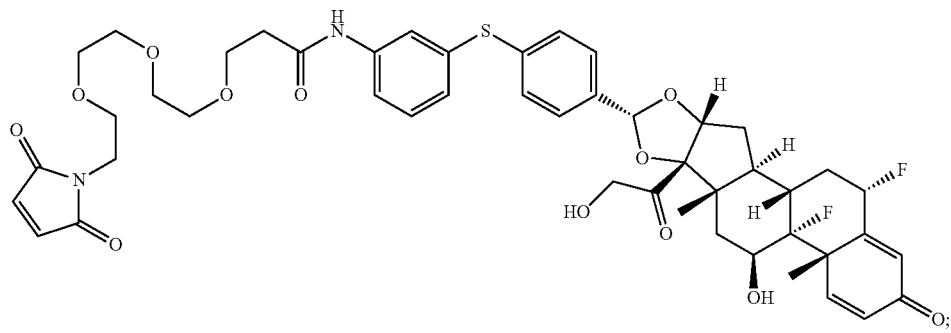
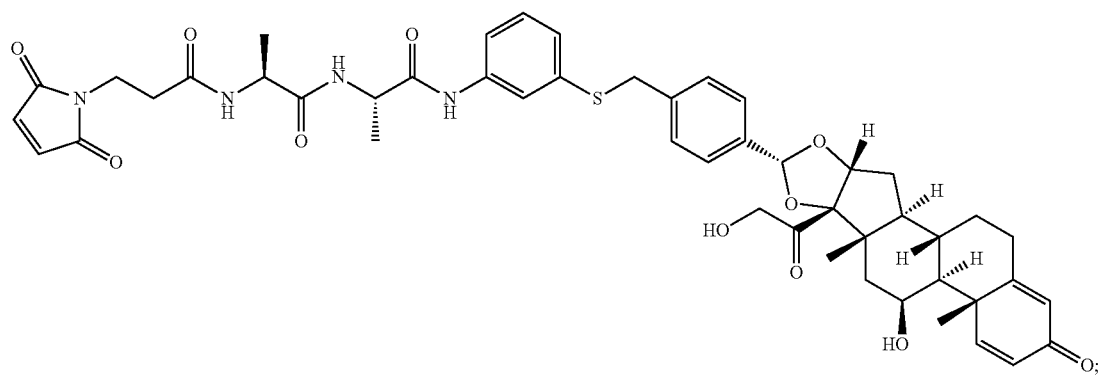
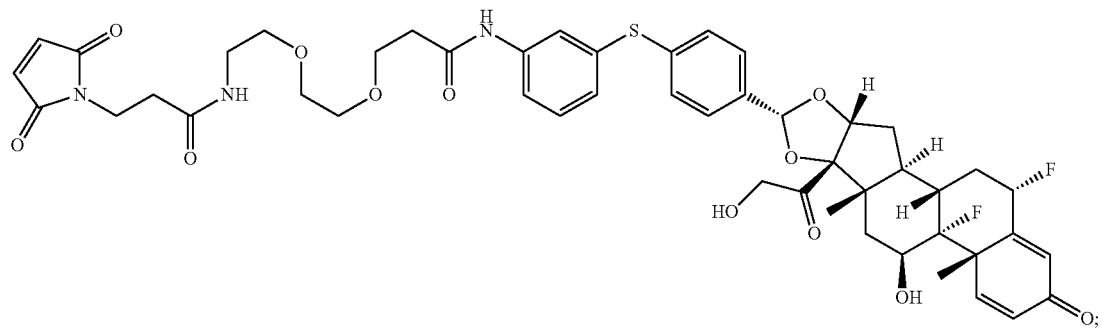
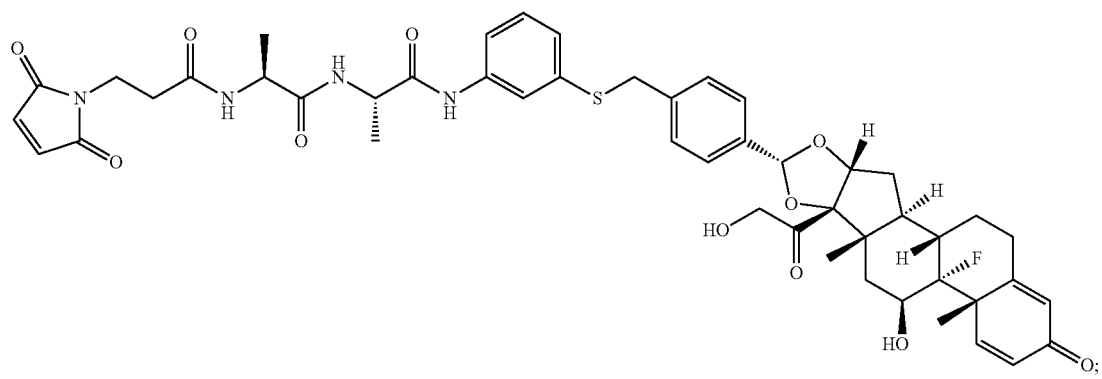

TABLE X-continued
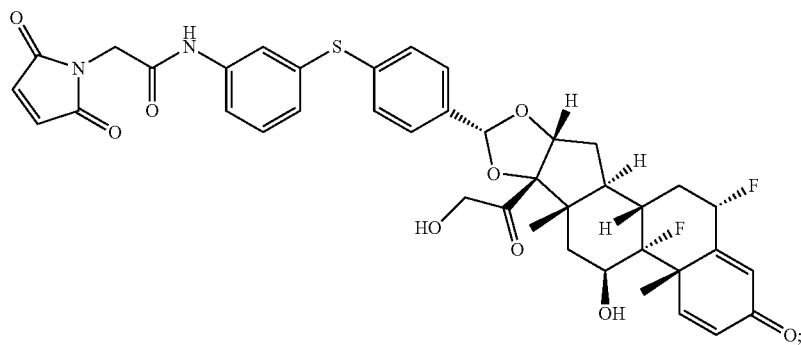
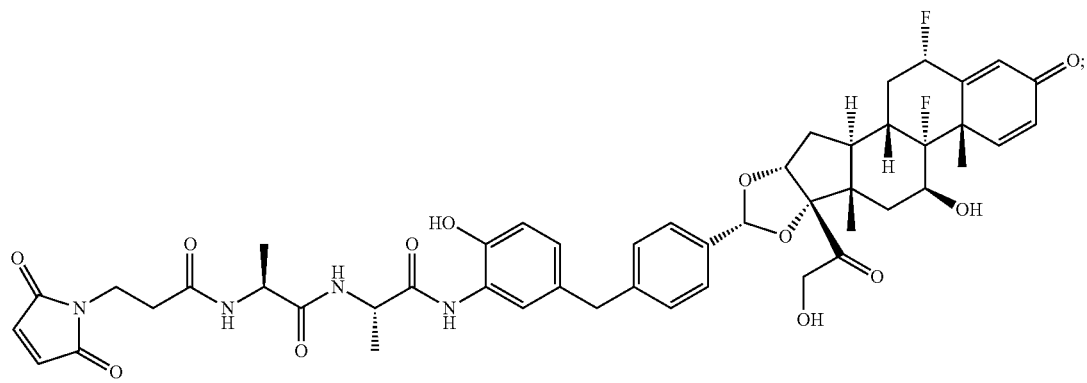
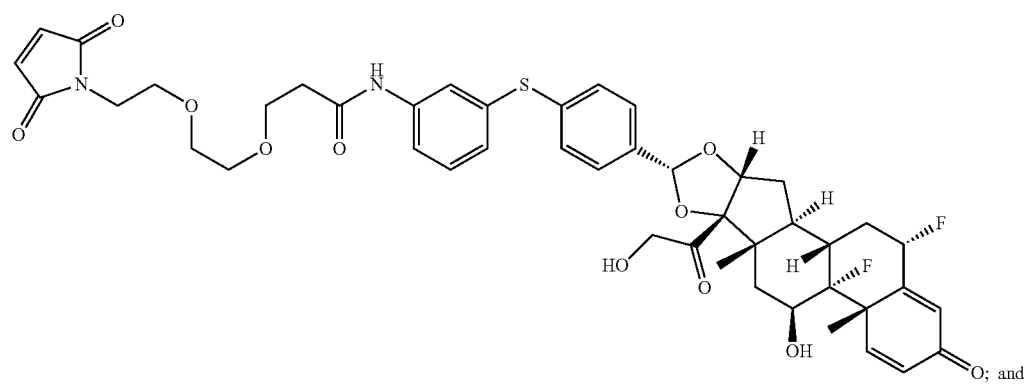
; and
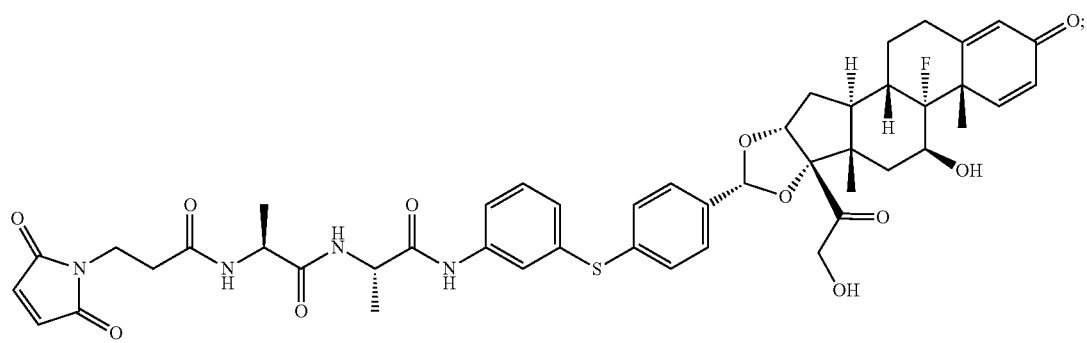

TABLE X-continued
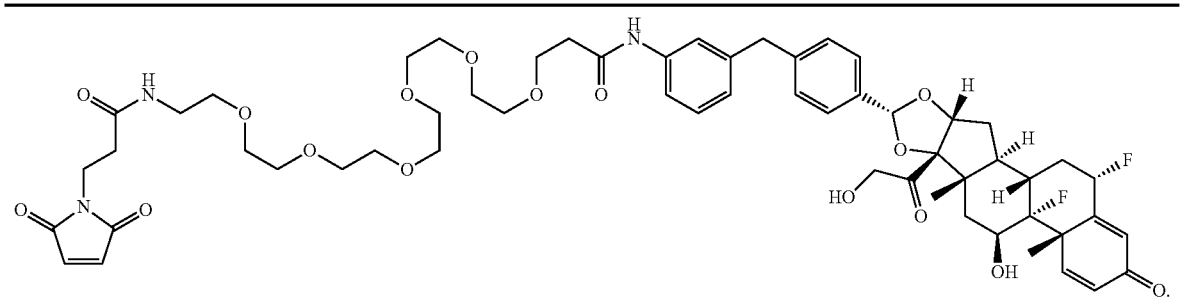
In another embodiment, the synthetic intermediate disclosed herein is a compound having Formulae VIII, or a pharmaceutically acceptable salt thereof, which is any one of the compounds of Table X-A.
TABLE X-A
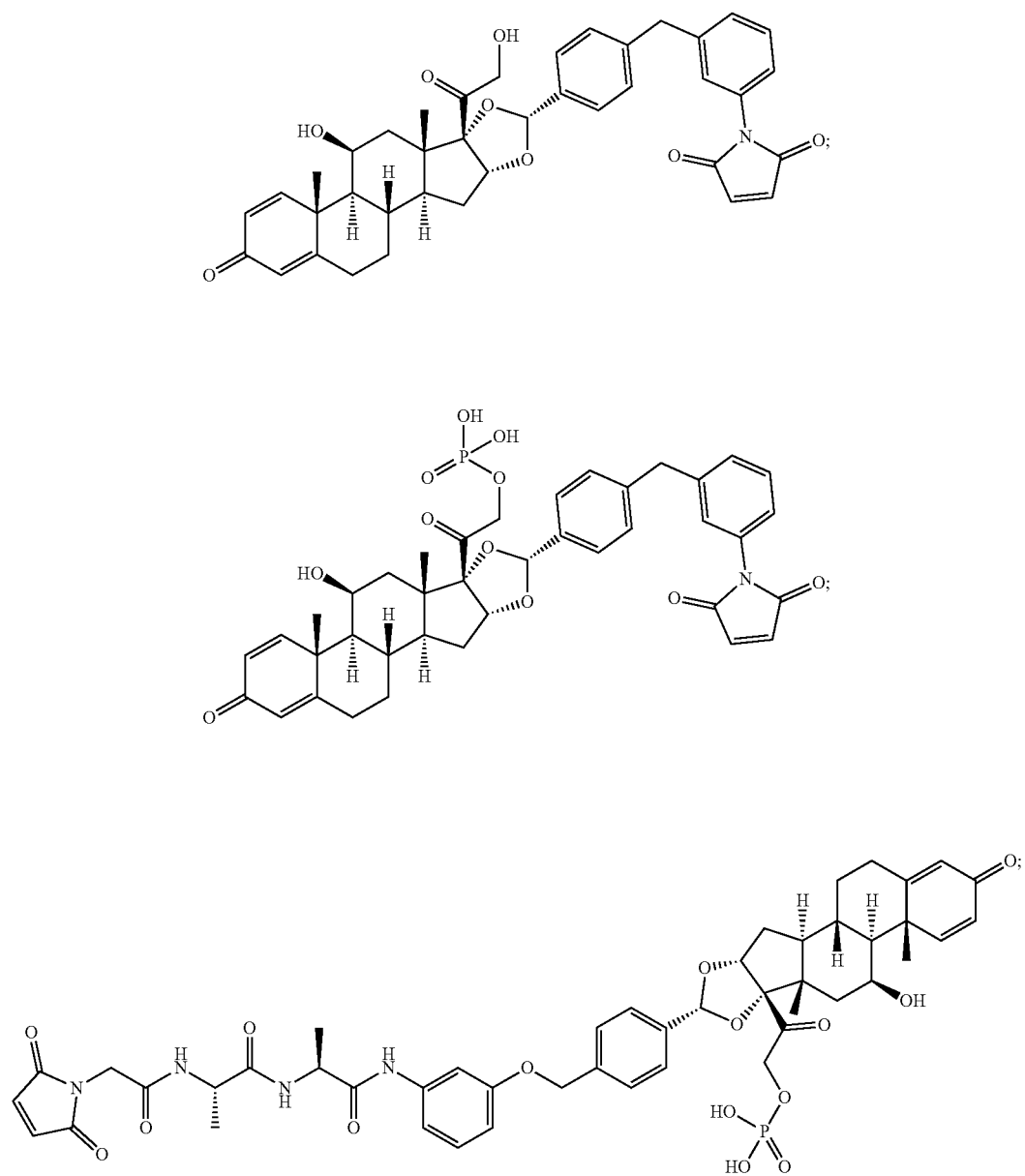

TABLE X-A-continued
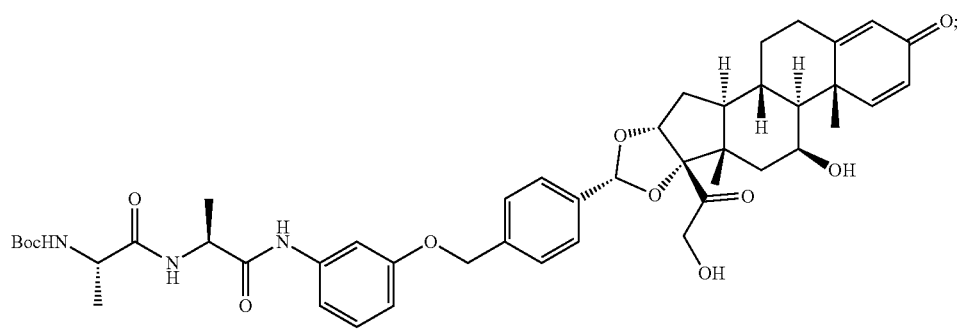
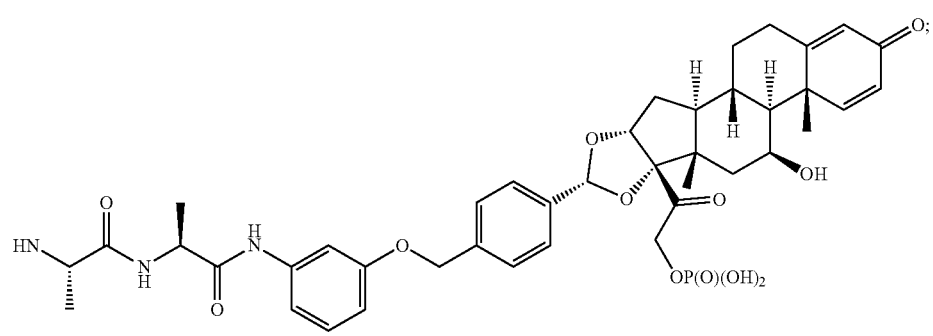
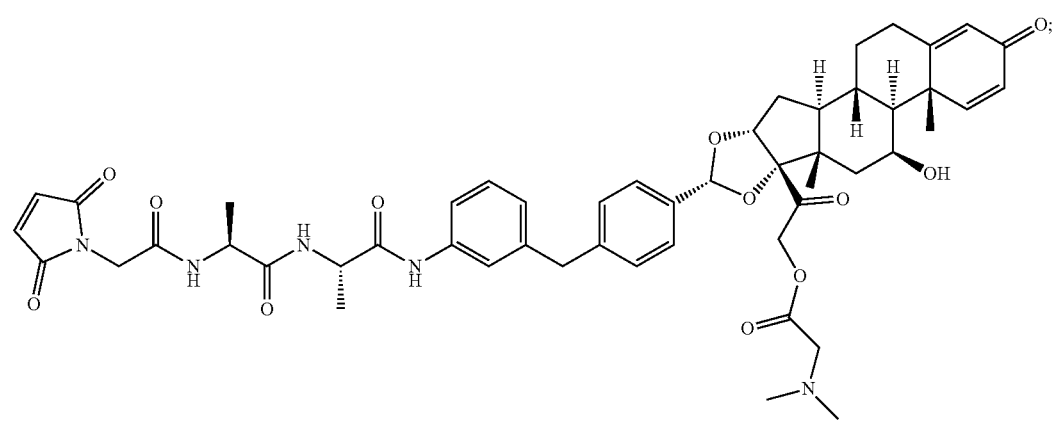
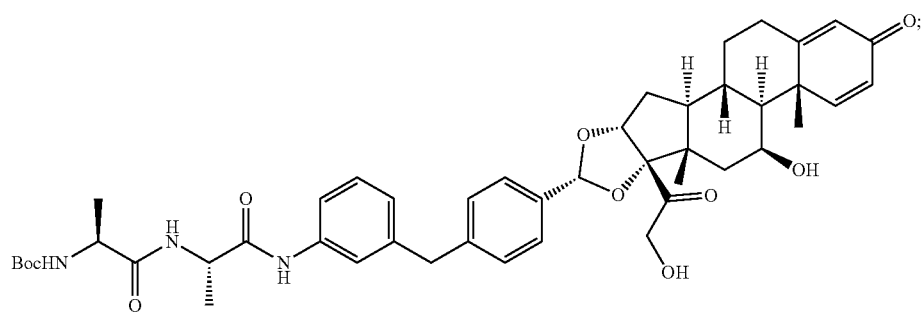

TABLE X-A-continued
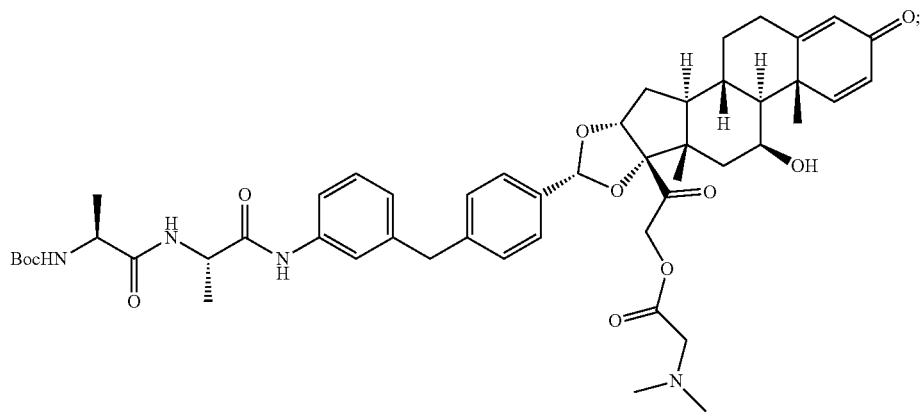
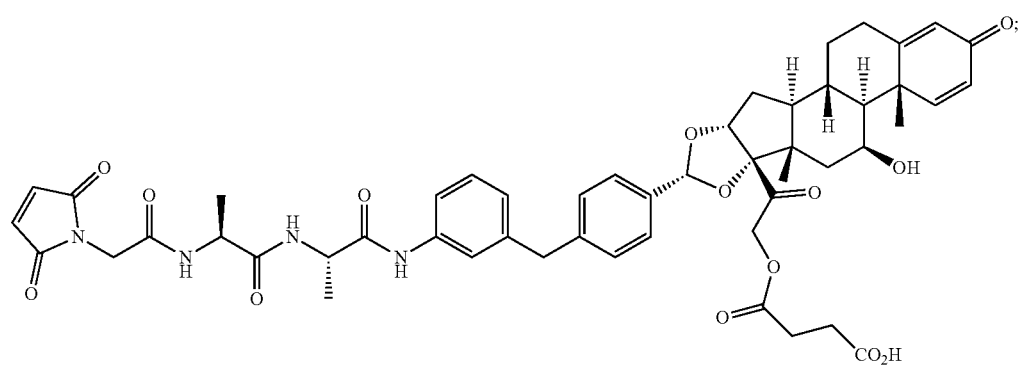
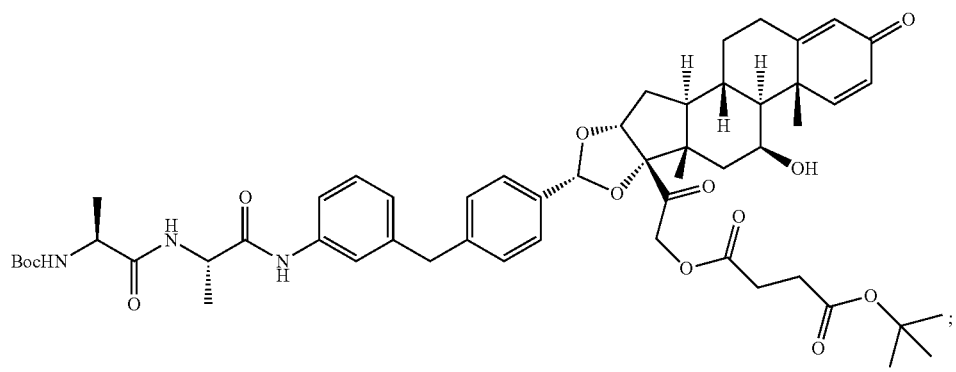
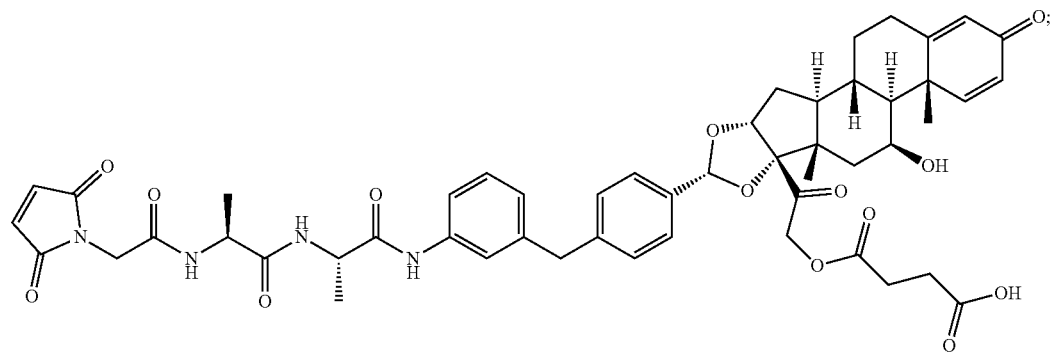

TABLE X-A-continued
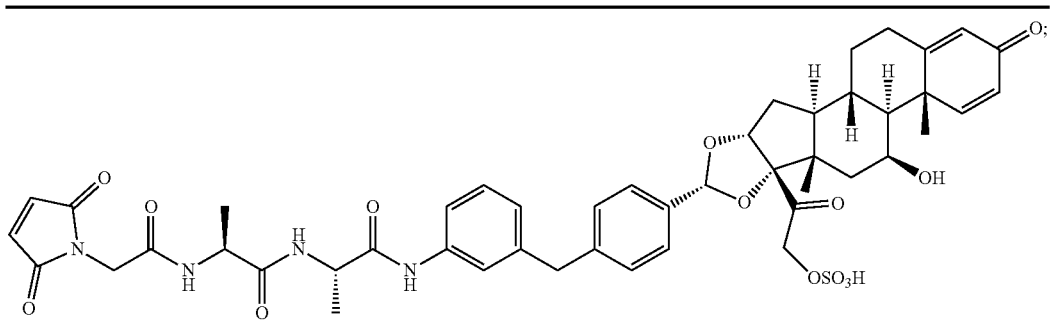
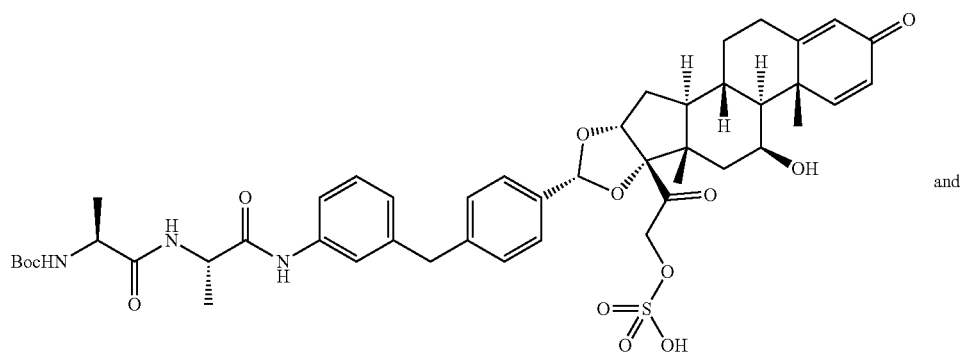
and
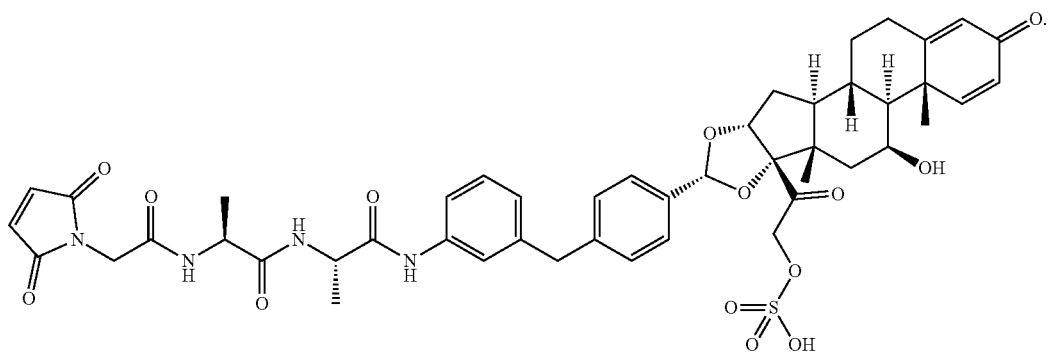
In another embodiment, the synthetic intermediate disclosed herein is a compound having Formula IX, or a pharmaceutically acceptable salt thereof, which is any one of the chemical structures of Table XI.
TABLE XI
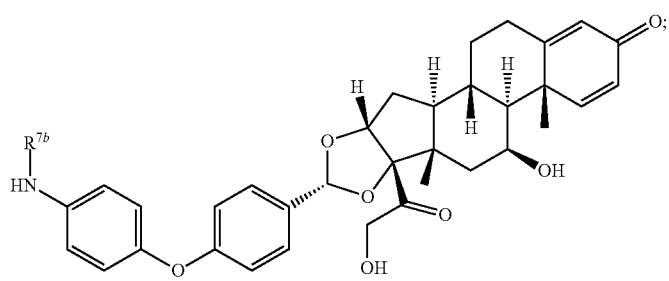

TABLE XI-continued
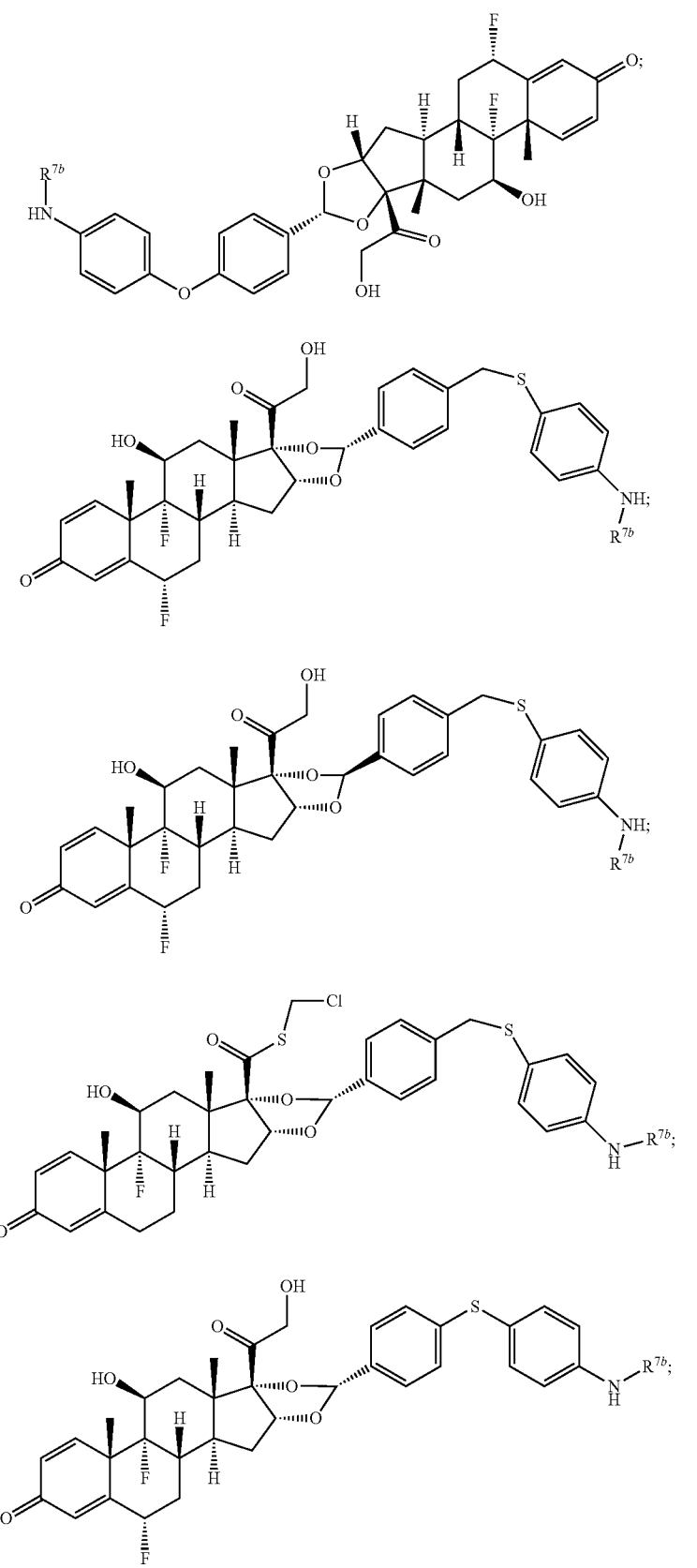

TABLE XI-continued
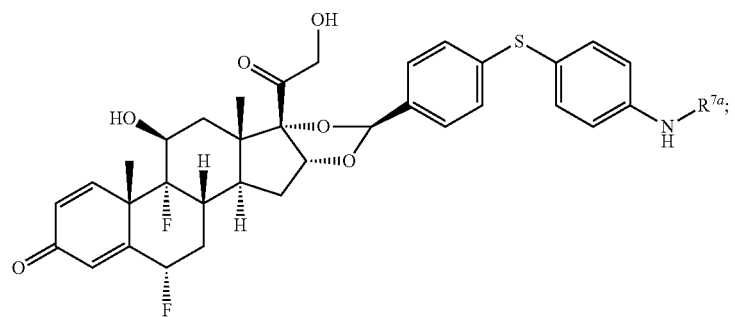
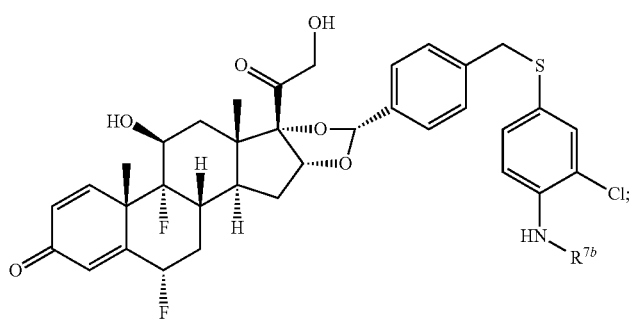
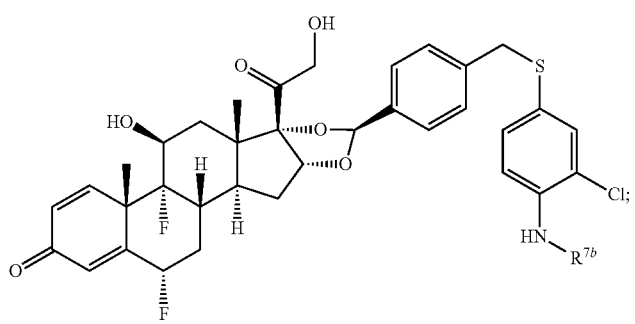
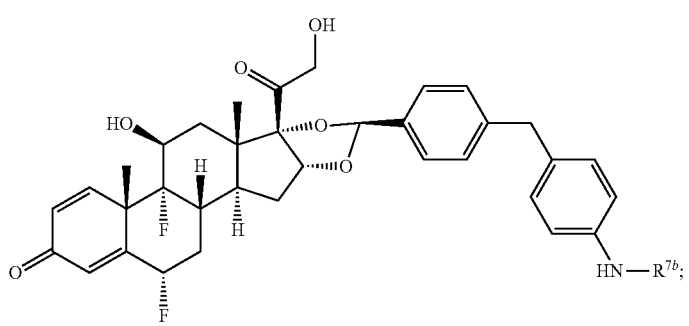
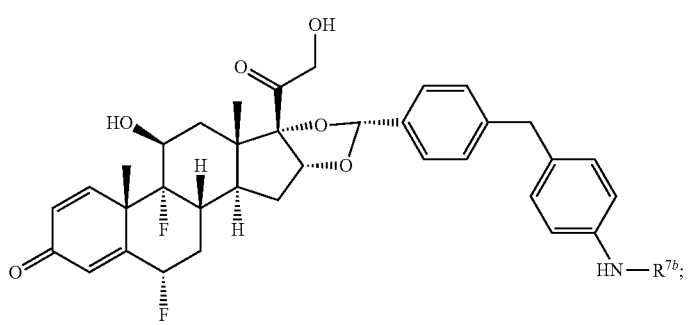

TABLE XI-continued
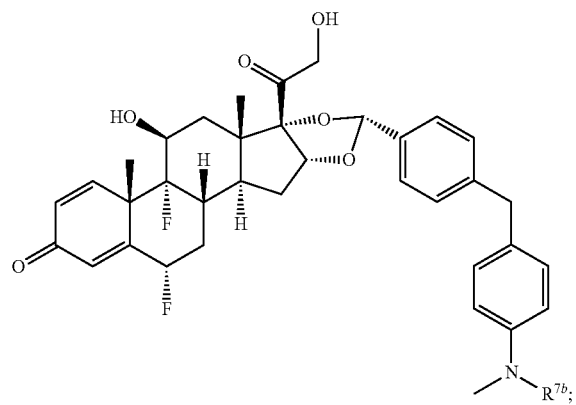
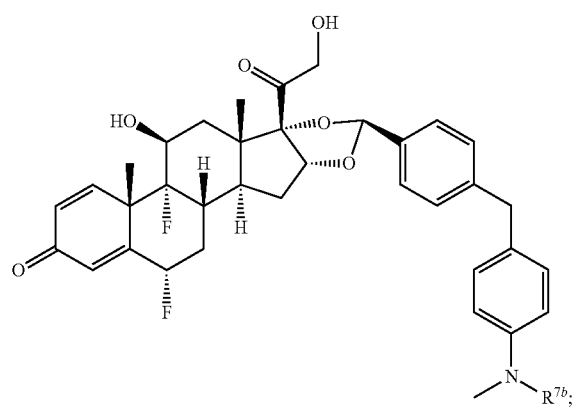
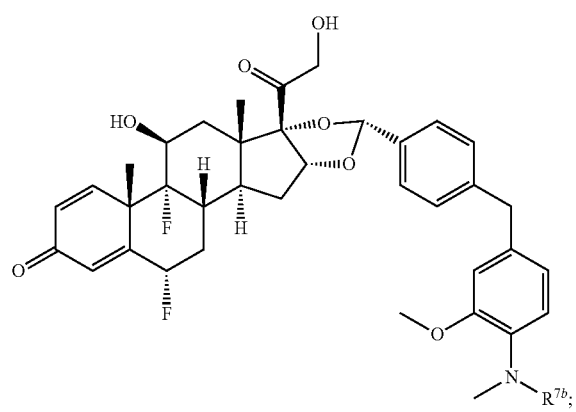
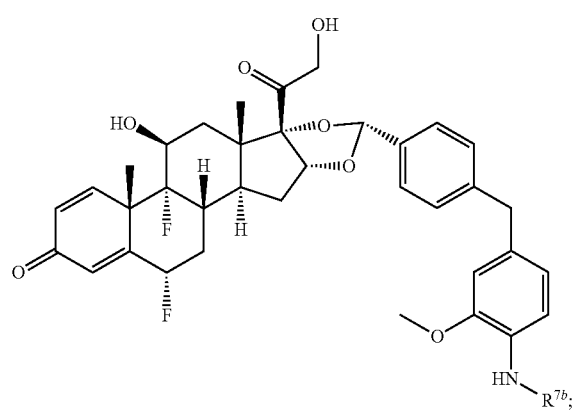

TABLE XI-continued
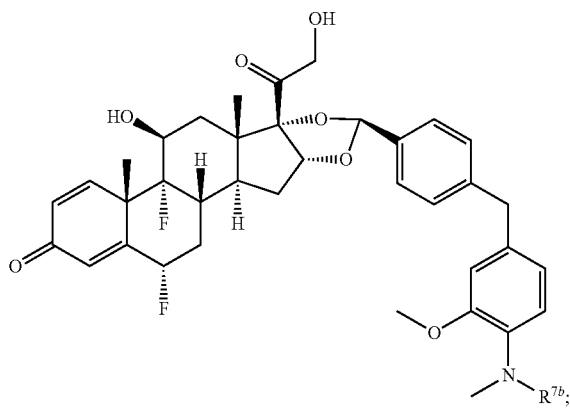
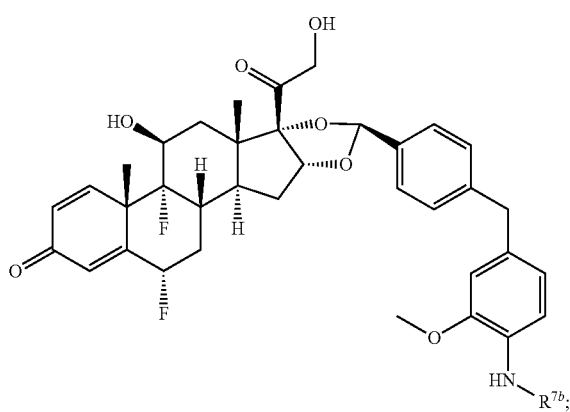
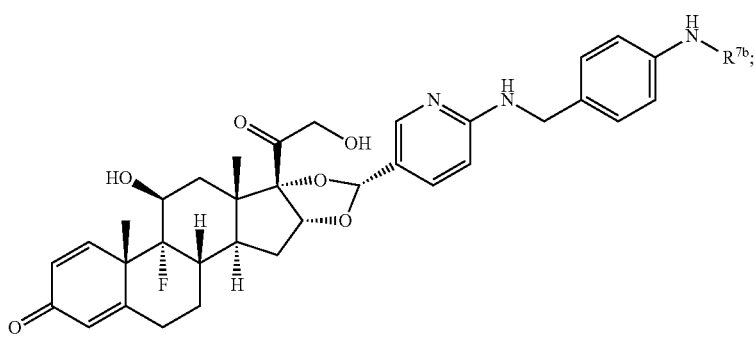
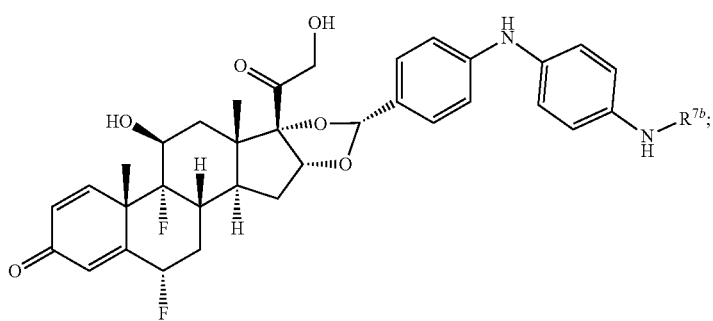

TABLE XI-continued
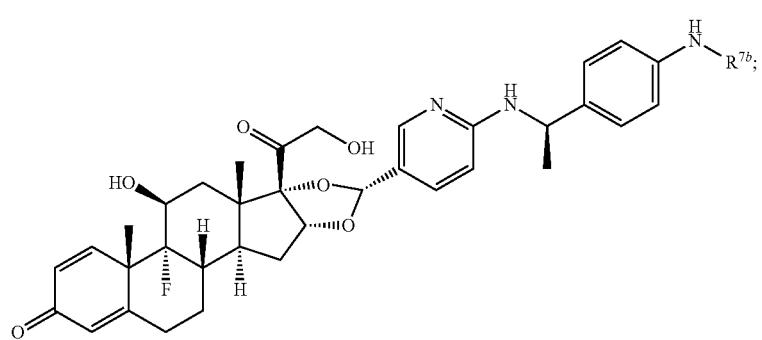
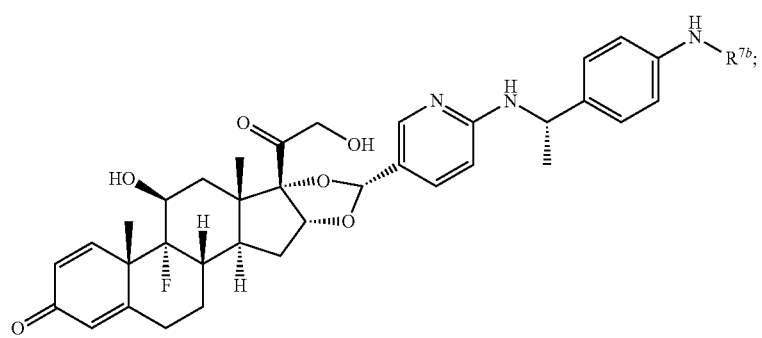
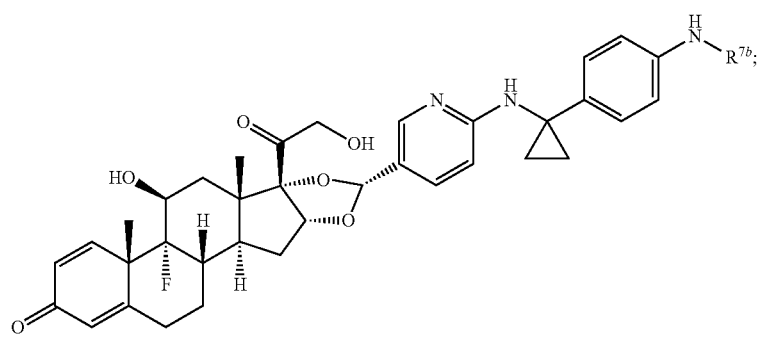
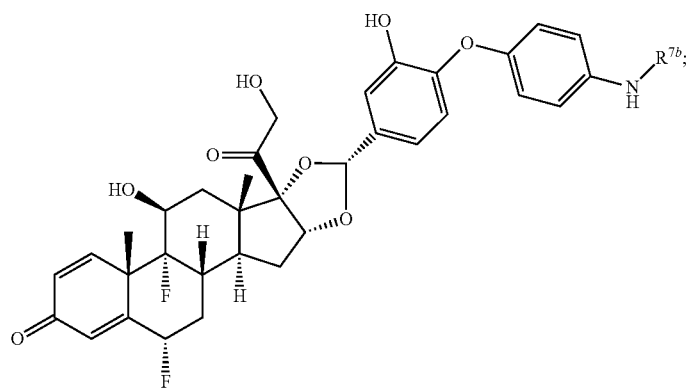

TABLE XI-continued
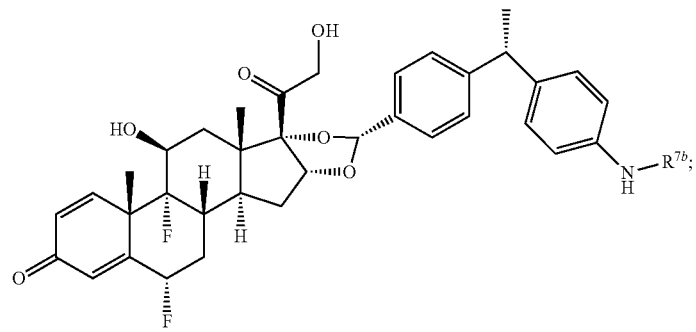
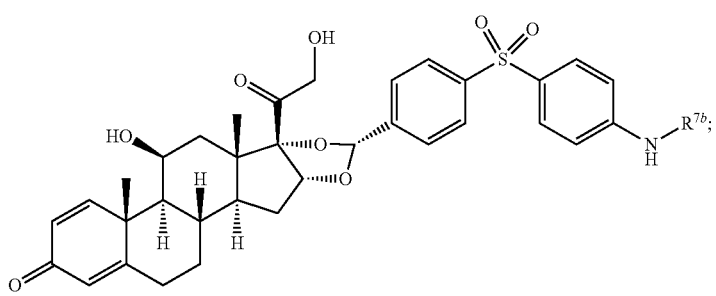
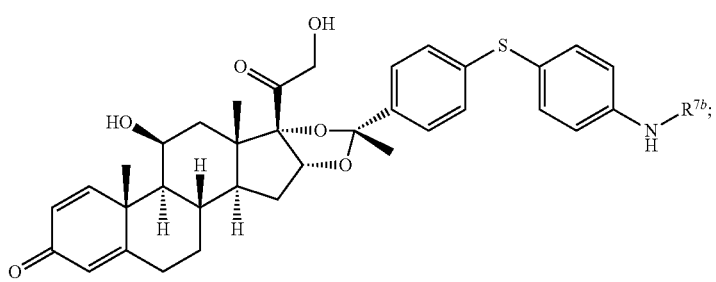
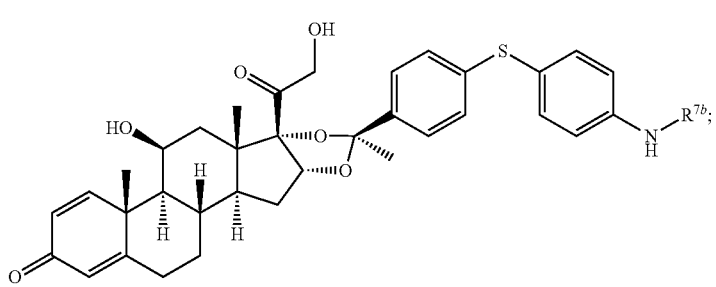
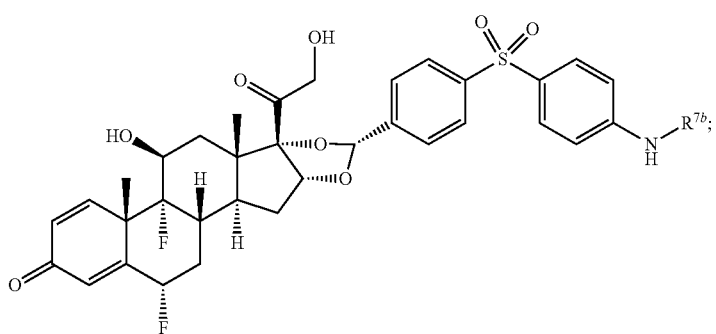

TABLE XI-continued

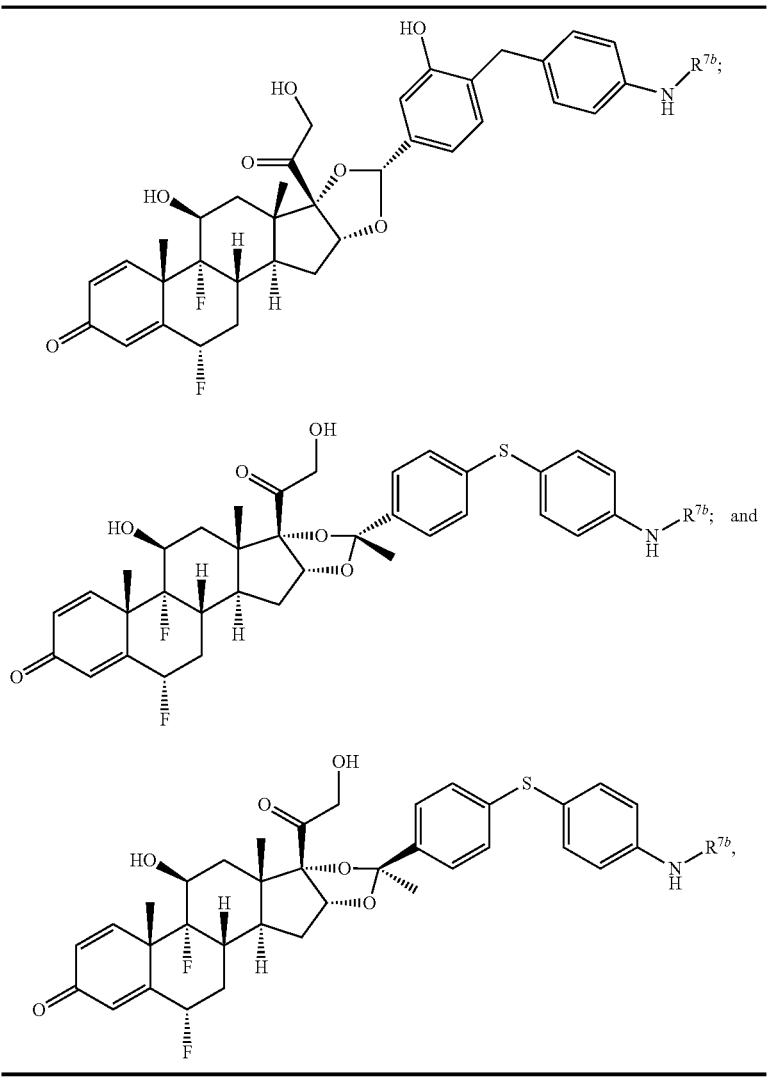

wherein $R^{7b}$ is selected from the group consisting of -L-H, -L-PG,

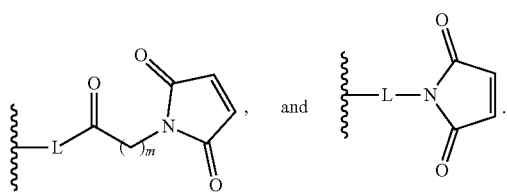

In another embodiment, R is selected from the group consisting of:

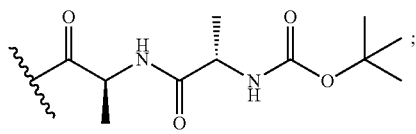

R$^{7b}$-4

-continued

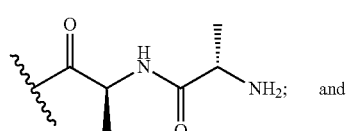

R$^{7b}$-5

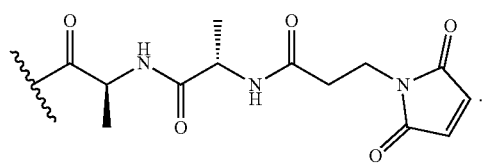

R$^{7b}$-6

In another embodiment, $R^{7b}$ is $R^{7b}$-4. In another embodiment, $R^{7b}$ is $R^{7b}$-5. In another embodiment, $R^{7b}$ is $R^{7b}$-6. In another embodiment, $R^{7b}$ any one of the chemical structures of Table IX.

In another embodiment, the synthetic intermediate disclosed herein is a compound having Formula IX, or a pharmaceutically acceptable salt thereof, which is any one of the compounds of Table XII.

TABLE XII
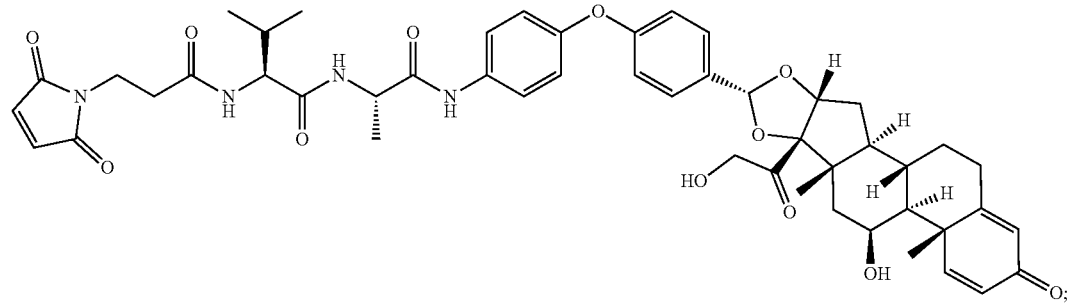
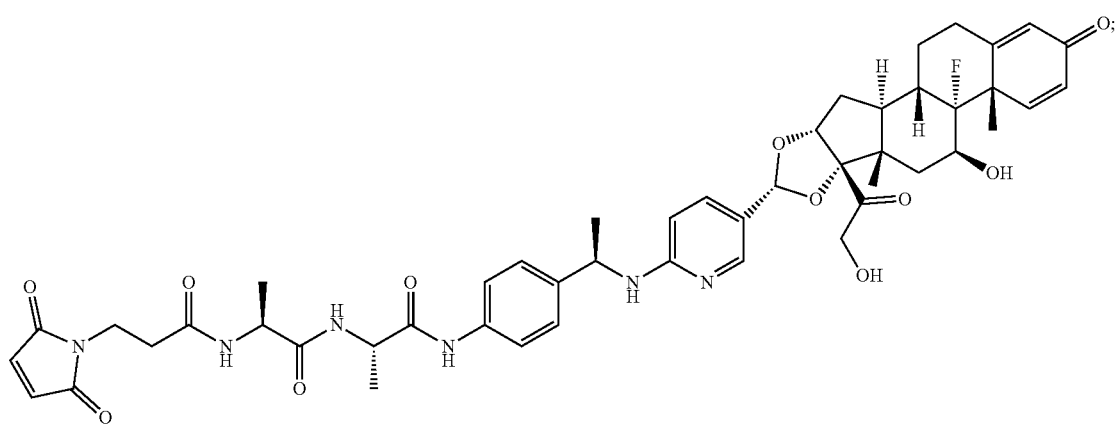
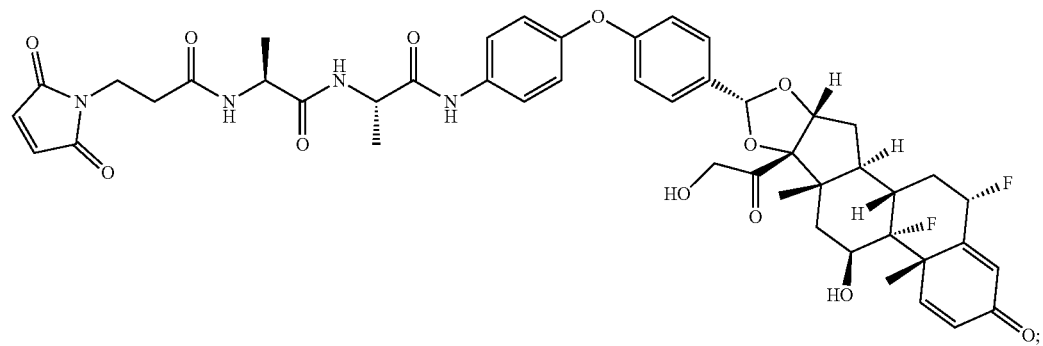
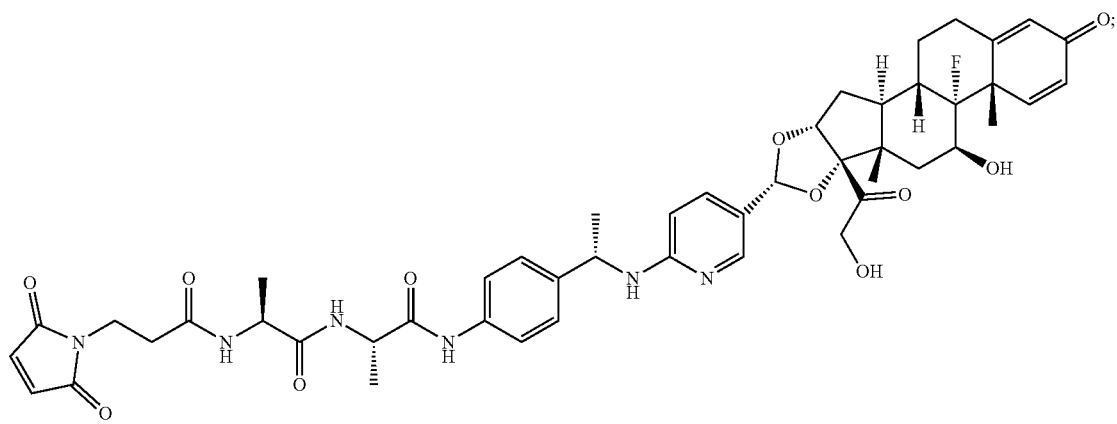

TABLE XII-continued
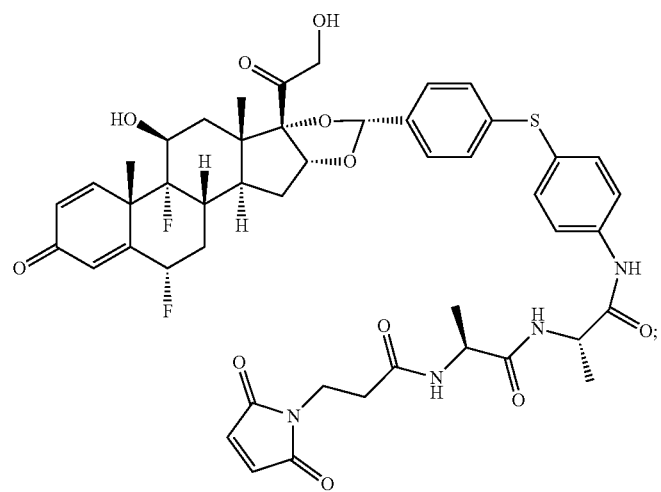
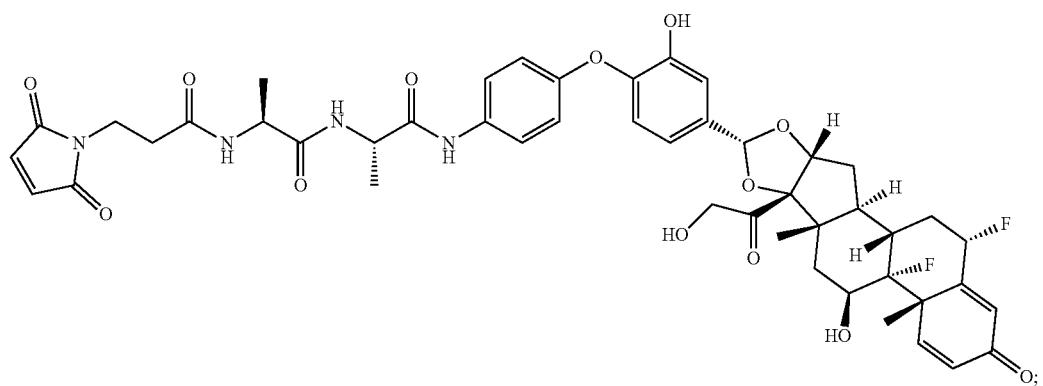
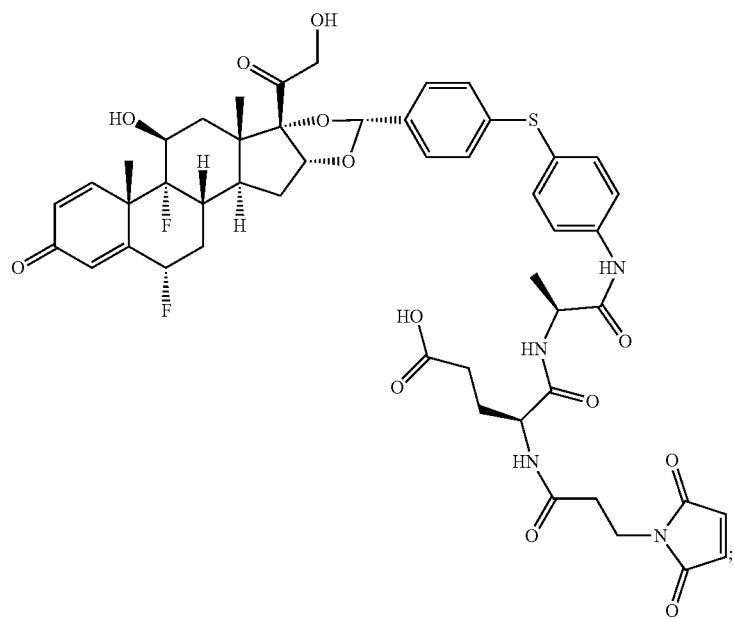

TABLE XII-continued
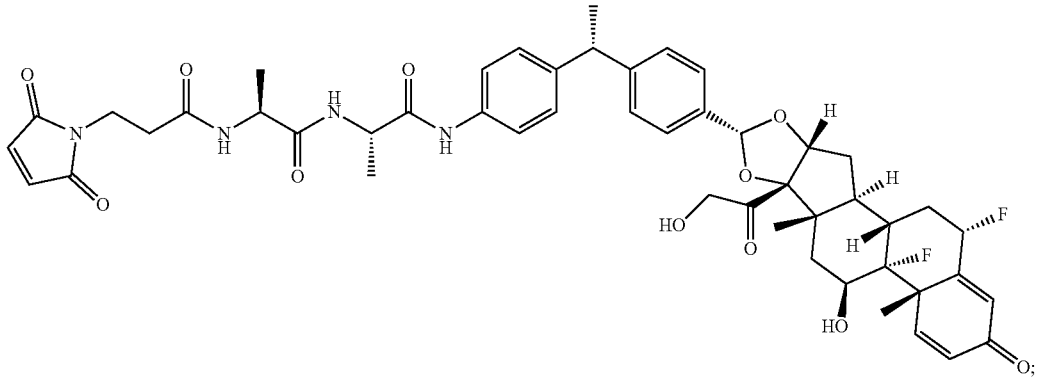
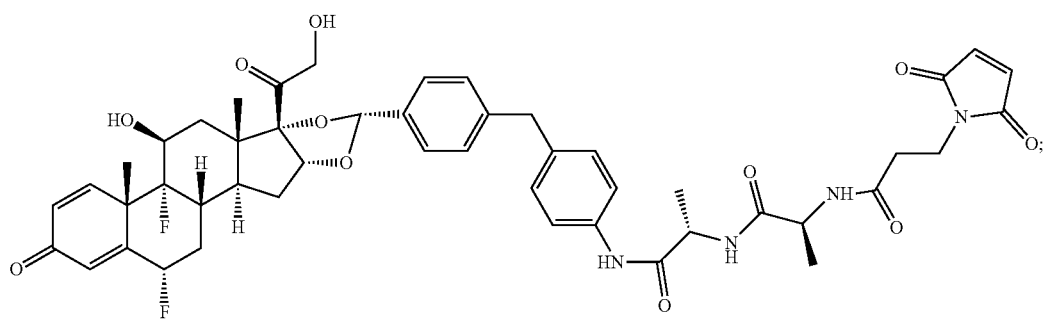
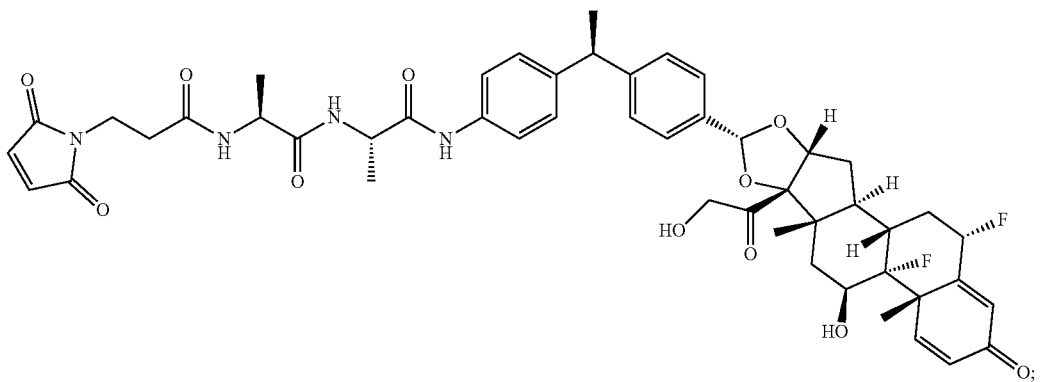

TABLE XII-continued
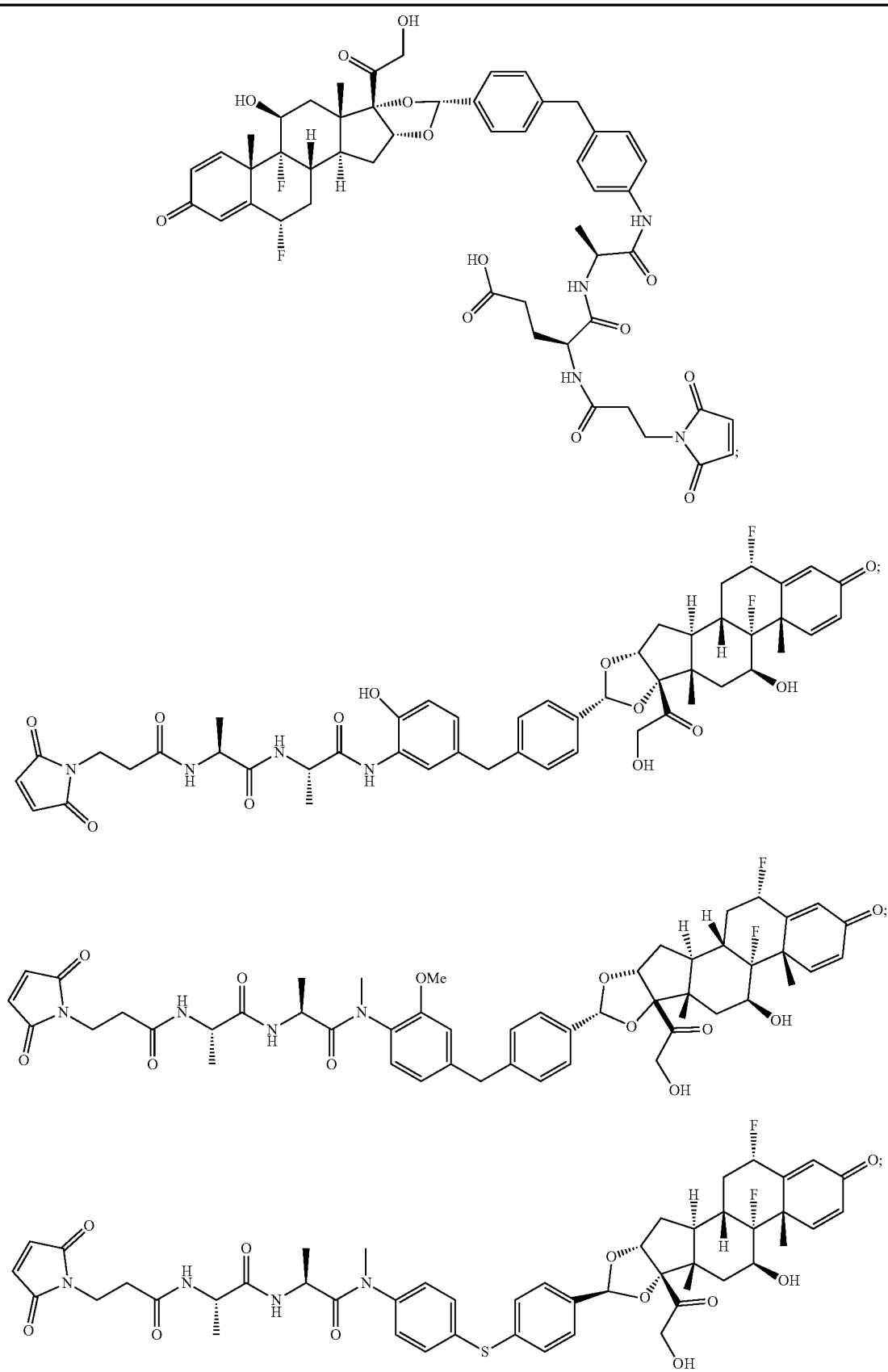

TABLE XII-continued

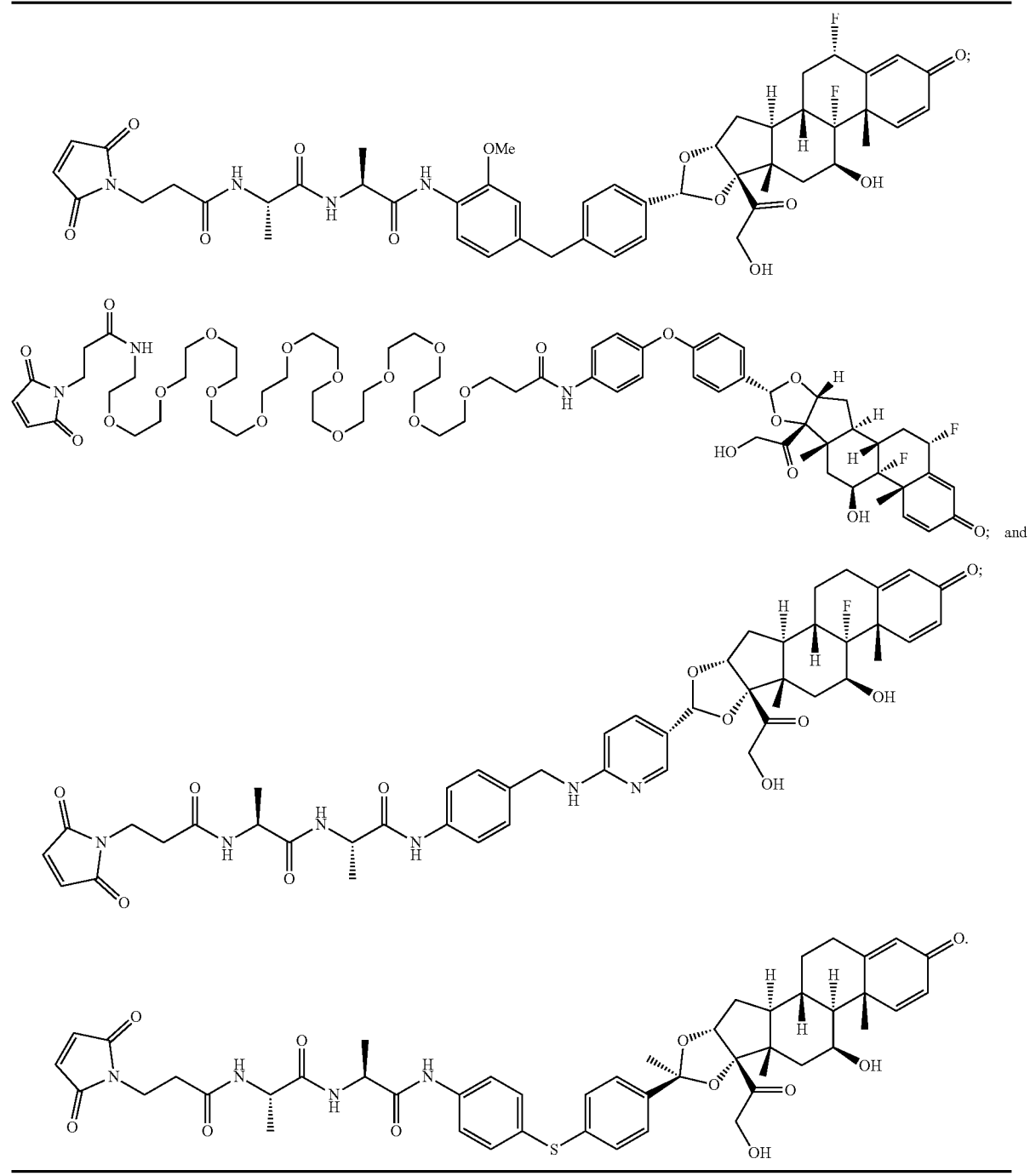

VI. Methods of Use and Pharmaceutical Compositions

Provided herein are conjugates having Formulae I-a and I-b, and glucocorticoid receptor agonists having Formulae VII, VII-A, VII-B, VIII, VIII-a, VIII-b, IX, IX-a, or IX-b, or any one of Formulae VII', VII-A', VII-B', VIII', VIII-a', VIII-b', IX', IX-a', IX-b', VII'', VII-A'', VII-B'', VIII'', VIII-a'', VIII-b'', IX'', IX-a'', or IX-b'' (wherein $R^{7b}$ is hydrogen) that can be used in vitro or in vivo. Accordingly, also provided herein are compositions, e.g., pharmaceutical compositions for certain in vivo uses, comprising a conjugate or a glucocorticoid receptor agonist described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

The compositions (e.g., pharmaceutical compositions) to be used for in vivo administration can be sterile. This is readily accomplished by filtration through, e.g., sterile filtration membranes. The compositions (e.g., pharmaceutical compositions) to be used for in vivo administration can comprise a preservative.

A pharmaceutical composition comprising a glucocorticoid receptor agonist provided herein can be formulated, for example, as a nasal spray, an inhalation aerosol (e.g., for oral inhalation), or a capsule, tablet, or pill (e.g., for oral administration).

The glucocorticoid receptor agonists provided herein (e.g., an anti-TNF ADC) are compounds, wherein the average number of glucocorticosteroids per antibody (DAR) in the composition is about 1 to about 10. In some embodiments, the average number of glucocorticosteroids per antibody (DAR) in the composition is about 2 to about 6. In some embodiments, the average number of glucocorticosteroids per antibody (DAR) in the composition is about 3 to about 4. In some embodiments, the average number of glucocorticosteroids per antibody (DAR) in the composition is about 3.1. In some embodiments, the average number of glucocorticosteroids per antibody (DAR) in the composition is about 3.2. In some embodiments, the average number of glucocorticosteroids per antibody (DAR) in the composition is about 3.3. In some embodiments, the average number of glucocorticosteroids per antibody (DAR) in the composition is about 3.4. In some embodiments, the average number of glucocorticosteroids per antibody (DAR) in the composition is about 3.5. In some embodiments, the average number of glucocorticosteroids per antibody (DAR) in the composition is about 3.6. In some embodiments, the average number of glucocorticosteroids per antibody (DAR) in the composition is about 3.7. In some embodiments, the average number of glucocorticosteroids per antibody (DAR) in the composition is about 3.8. In some embodiments, the average number of glucocorticosteroids per antibody (DAR) in the composition is about 3.9.

Glucocorticoid receptor agonists and pharmaceutical compositions comprising a glucocorticoid receptor agonist described herein can be useful in inhibiting cytokine release (in vitro or in vivo) and/or for the treatment of autoimmune or inflammatory diseases. Glucocorticoid receptor agonists and pharmaceutical compositions comprising a glucocorticoid receptor agonist described herein can be used for the treatment of asthma (e.g., bronchial asthma), Crohn's disease (e.g., mild to moderate active Crohn's disease involving the ileum and/or the ascending colon and/or the maintenance of clinical remission of mild to moderate Crohn's disease involving the ileum and/or the ascending colon for up to 3 months), ulcerative colitis (e.g., for the induction of remission in patients with active, mild to moderate ulcerative colitis), allergic rhinitis (e.g. nasal symptoms associated with seasonal allergic rhinitis and/or perennial allergic rhinitis).

For administration to human patients, the total daily dose of glucocorticoid receptor agonists provided herein is typically in the range of 0.001 mg to 5000 mg, or in the range of 0.01 mg to 1000 mg, depending on the mode of administration. For example, oral administration or intravenous, intramuscular, intra-articular, or peri-articular administration can require a total daily dose of from 0.01 mg to 1000 mg, or from 0.1 mg to 100 mg. The total daily dose can be administered in single or divided doses.

A pharmaceutical composition comprising a conjugate provided herein can be formulated, for example, for intravenous administration or infusion.

Conjugates and pharmaceutical compositions comprising conjugates described herein can be useful in lysing a cell expressing surface TNF-alpha (in vitro or in vivo), for the treatment of diseases or disorders characterized by increased TNF-alpha (e.g., increasead TNF-alpha in synovial fluid), and/or for the treatment of an autoimmune or inflammatory disease.

A pharmaceutical composition comprising a glucocortic receptor agonist or a conjugate described herein is used for the treatment of rheumatoid arthritis (RA), juvenile idiopathic arthritis (JIA), psoriatic arthritis (PsA), a spondyloarthropathy such as ankylosing spondylitis (AS) or axial spondyloarthritis (axSpA), adult Crohns' disease (CD), pediatric Crohn's disease, ulcerative colitis (UC), plaque psoriasis (Ps), hidradenitis suppurativa (HS), uveitis, Behcets disease, or psoriasis, including plaque psoriasis.

For administration to human patients, the total daily dose of conjugate provided herein is typically in the range of from 0.01 µg to 100 mg per kg of body weight, and can be given once or more daily, weekly, monthly or yearly.

The disclosure also provides Embodiments (Embs) 1-209 as particular embodiments. The Formulae and Tables referred to these particular embodiments that are not shown in the embodiment are set forth in the description above.

Embodiment (Emb) 1. A compound having Formula I-a:

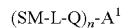

(SM-L-Q)$_n$-A$^1$   I-a or a pharmaceutically acceptable salt or solvate thereof, wherein:

A$^1$ is an anti-tumor necrosis factor (TNF) alpha protein; L is a linker; Q is a heterobifunctional group or heterotrifunctional group; or Q is absent; n is 1-10; and SM is a radical of a glucocorticosteroid.

Emb 2. The compound of Emb 1, or a pharmaceutically acceptable salt or solvate thereof, wherein SM is a monovalent radical of a glucocorticosteroid.

Emb 3. The compound of Emb 2, or a pharmaceutically acceptable salt or solvate thereof, wherein SM is a monovalent radical of a glucocorticosteroid selected from the group consisting of:

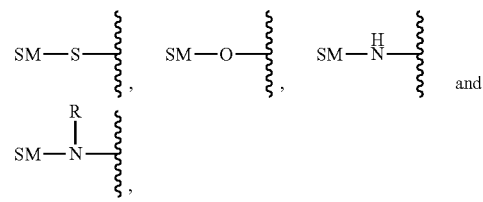

wherein the sulfur, oxygen, or nitrogen atom is attached directly or indirectly to the C- or D-ring of the glucocorticosteroid, and R is $C_{1-4}$ alkyl.

Emb 4. The compound of Emb 3, or a pharmaceutically acceptable salt or solvate thereof, wherein the sulfur, oxygen, or nitrogen atom is attached directly or indirectly to the D-ring of the glucocorticosteroid.

Emb 5. The compound of Emb 2 or Emb 3, or a pharmaceutically acceptable salt or solvate thereof, wherein SM is a monovalent radical of a glucocorticosteroid having Formula II-a, wherein:

R$^1$ is selected from the group consisting of hydrogen and halo; R$^2$ is selected from the group consisting of hydrogen, halo, and hydroxy; R$^3$ is selected from the group consisting of —CH$_2$OH, —CH$_2$SH, —CH$_2$Cl, —SCH$_2$Cl, —SCH$_2$F, —SCH$_2$CF$_3$, hydroxy, —OCH$_2$CN, —OCH$_2$Cl, —OCH$_2$F, —OCH$_3$, —OCH$_2$CH$_3$, —SCH$_2$CN.

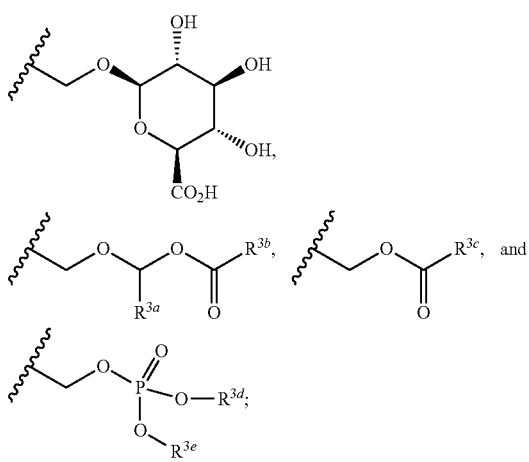

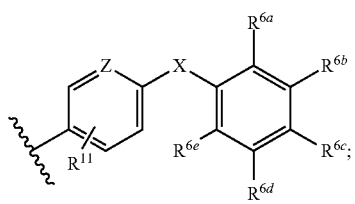

and
R$^{9b}$ is hydrogen or methyl;

X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent; t is 1 or 2;

Z is selected from the group consisting of =CH—, =C(OH)—, and =N—; each R$^{4a}$ and R$^{4b}$ are independently selected from the group consisting of hydrogen and C$_{1-4}$ alkyl; or R$^{4a}$ and R$^{4b}$ taken together with the carbon atom to which they are attached form a 3- to 6-membered cycloalkyl; R$^{4c}$ and R$^{4d}$ are independently selected from the group consisting of hydrogen and C$_{1-4}$ alkyl; R$^5$ is selected from the group consisting of hydrogen and C$_{1-4}$ alkyl; R$^{6a}$, R$^{6b}$, R$^{6c}$, R$^{6d}$, and R$^{6e}$ are each independently selected from the group consisting of hydrogen, halo, C$_{1-4}$ alkyl, C$_{1-4}$ haloalkyl, cyano, hydroxy, thiol, amino, alkylthio, and alkoxy; R$^{8a}$ and R$^{8b}$ are independently selected from the group consisting of hydrogen and C$_{1-4}$ alkyl; R$^1$ is selected from the group consisting of hydrogen, halo, C$_{1-4}$ alkyl, hydroxy, thiol, amino, alkylthio, and === alkoxy; and represents a single or double bond.

Emb 6. The compound of Emb 5, or a pharmaceutically acceptable salt or solvate thereof, wherein SM is a monovalent radical of a glucocorticosteroid having Formula II-b.

Emb 7. The compound of any one of Embs 2-4, or a pharmaceutically acceptable salt or solvate thereof, wherein SM is a monovalent radical of a glucocorticosteroid having Formula II-c, wherein: R$^1$ is selected from the group consisting of hydrogen and halo;

R$^2$ is selected from the group consisting of hydrogen, halo, and hydroxy; R$^{9a}$ is selected from the group consisting of optionally substituted alkyl, optionally substituted cycloalkyl, optionally substituted aryl, and optionally substituted heteroaryl; and R$^{9b}$ is selected from the group consisting of hydrogen and alkyl; or R$^{9a}$ is:

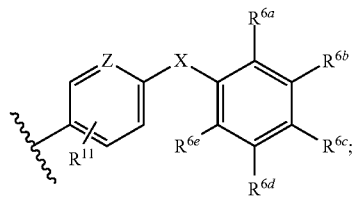

and
R$^{9b}$ is hydrogen;

W is selected from the group consisting of —O— and —S—; X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent; t is 1 or 2; Z is selected from the group consisting of =CH—, =C(OH)—, and =N—; each R$^{4a}$ and R$^{4b}$ are independently selected from the group consisting of hydrogen and C$_{1-4}$ alkyl; or R$^{4a}$ and R$^{4b}$ taken together with the carbon atom to which they are attached form a 3- to 6-membered cycloalkyl; R$^{4c}$ and R$^{4d}$ are independently selected from the group consisting of hydrogen and C$_{1-4}$ alkyl; R$^5$ is selected from the group consisting of hydrogen and C$_{1-4}$ alkyl; R$^{6a}$, R$^{6b}$, R$^{6c}$, R$^{6d}$, and R$^{6e}$ are each independently selected from the group consisting of hydrogen, halo, C$_{1-4}$ alkyl, C$_{1-4}$ haloalkyl, cyano, hydroxy, thiol, amino, alkylthio, and alkoxy; R$^{8a}$ and R$^{8b}$ are independently selected from the group consisting of hydrogen and C$_{1-4}$ alkyl; R$_{11}$ is selected from the group consisting of hydrogen, halo, C$_{1-4}$ alkyl, C$_{1-4}$ haloalkyl, cyano, hydroxy, thiol, amino, alkylthio, and alkoxy; and === represents a single or double bond.

Emb 8. The compound of Emb 7, or a pharmaceutically acceptable salt or solvate thereof, wherein SM is a monovalent radical of a glucocorticosteroid having Formula II-d.

Emb 9. The compound of any one of Embs 2-4, or a pharmaceutically acceptable salt or solvate thereof, wherein SM is a monovalent radical of a glucocorticosteroid having Formula II-e, wherein: R$^1$ is selected from the group consisting of hydrogen and halo; R$^2$ is selected from the group consisting of hydrogen, halo, and hydroxy; R$^{9c}$ is selected from the group consisting of hydrogen, C$_{1-4}$ alkyl, and —C(=O)R$^{9e}$; R$^{9d}$ is selected from the group consisting of hydrogen, optionally substituted alkyl, optionally substituted cycloalkyl, optionally substituted aryl, and optionally substituted heteroaryl; R$^{9e}$ is selected from the group consisting of hydrogen, optionally substituted alkyl, optionally substituted cycloalkyl, optionally substituted aryl, and optionally substituted heteroaryl; W is selected from the group consisting of —O— and —S—; and === represents a single or double bond.

Emb 10. The compound of Emb 9, or a pharmaceutically acceptable salt or solvate thereof, wherein SM is a monovalent radical of a glucocorticosteroid having Formula II-f.

Emb 11. The compound of any one of Embs 7-10, or a pharmaceutically acceptable salt or solvate thereof, wherein W is —S—.

Emb 12. The compound of any one of Embs 7-10, or a pharmaceutically acceptable salt or solvate thereof, wherein W is —O—.

Emb 13. A compound having Formula I-b:

(SM-L-Q)$_n$-A$^2$    I-b, or a pharmaceutically acceptable salt or solvate thereof, wherein: A$^2$ is a protein; L is a linker; Q is a heterobifunctional group or heterotrifunctional group; or Q is absent; n is 1-10; and SM is a monovalent radical of a glucocorticosteroid having any one of: Formula II-l, Formula II-m, Formula II-n, Formula II-o, Formula II-p or Formula II-q, wherein: R$^1$ is selected from the group consisting of hydrogen and halo; R$^2$ is selected from the group consisting of hydrogen, halo, and hydroxy; R$^3$ is selected from the group consisting of —CH$_2$OH, —CH$_2$SH, —CH$_2$Cl, —SCH$_2$Cl, —SCH$_2$F, —SCH$_2$CF$_3$, hydroxy, —OCH$_2$CN, —OCH$_2$Cl, —OCH$_2$F, —OCH$_3$, —OCH$_2$CH$_3$, —SCH$_2$CN,

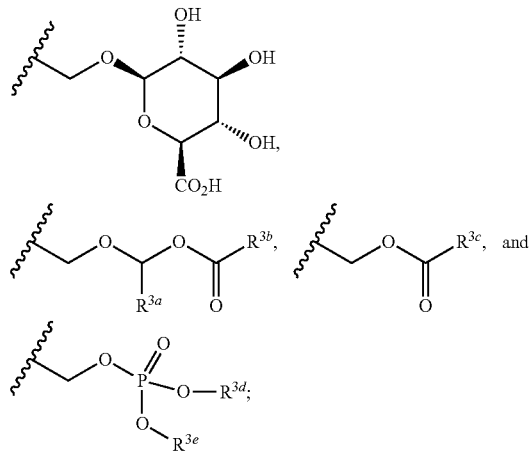

R$^{3a}$ is selected from the group consisting of hydrogen and C$_{1-4}$ alkyl; R$^{3b}$ is selected from the group consisting of C$_{1-4}$ alkyl and C$_{1-4}$ alkoxy; R$^{3c}$ is selected from the group consisting of hydrogen, C$_{1-4}$ alkyl, —CH$_2$OH, and C$_{1-4}$ alkoxy; R$^{3d}$ and R$^{3e}$ are independently selected from hydrogen and C$_{1-4}$ alkyl; R$^{6a}$, R$^{6b}$, R$^{6c}$, R$^{6d}$, and R$^{6e}$ are each independently selected from the group consisting of hydrogen, halo, C$_{1-4}$ alkyl, C$_{1-4}$ haloalkyl, cyano, hydroxy, thiol, amino, alkylthio, and alkoxy; X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent; Y$^2$ is selected from the group consisting of —O—, —S—, and —N(R$^{7a}$)—; or Y$^2$ is absent; t is 1 or 2; Z is selected from the group consisting of =CR$^{11a}$— and =N—; each R$^{4a}$ and R$^{4b}$ are independently selected from the group consisting of hydrogen and C$_{1-4}$ alkyl; or R$^{4a}$ and R$^{4b}$ taken together with the carbon atom to which they are attached form a 3- to 6-membered cycloalkyl; R$^{4c}$ and R$^{4d}$ are independently selected from the group consisting of hydrogen and C$_{1-4}$ alkyl; R$^5$ is selected from the group consisting of hydrogen and C$_{1-4}$ alkyl; R$^{7a}$ is selected from the group consisting of hydrogen and C$_{1-4}$ alkyl; R$^{8a}$ and R$^{8b}$ are independently selected from the group consisting of hydrogen and C$_{1-4}$ alkyl; R$^{9f}$ is selected from the group consisting of hydrogen and C$_{1-4}$ alkyl; R$^{11a}$ and R$^{11b}$ are independently selected from the group consisting of hydrogen, halo, C$_{1-4}$ alkyl, C$_{1-4}$ haloalkyl, cyano, hydroxy, thiol, amino, alkylthio, and alkoxy; and === represents a single or double bond.

Emb 14. The compound of any one of Embs 2-4 or 13, or a pharmaceutically acceptable salt or solvate thereof, wherein SM is a monovalent radical of a glucocorticosteroid having Formula II-l, wherein: R$^1$ is selected from the group consisting of hydrogen and halo; R$^2$ is selected from the group consisting of hydrogen, halo, and hydroxy; R$^3$ is selected from the group consisting of —CH$_2$OH, —CH$_2$SH, —CH$_2$Cl, —SCH$_2$Cl, —SCH$_2$F, —SCH$_2$CF$_3$, hydroxy, —OCH$_2$CN, —OCH$_2$Cl, —OCH$_2$F, —OCH$_3$, —OCH$_2$CH$_3$, —SCH$_2$CN,

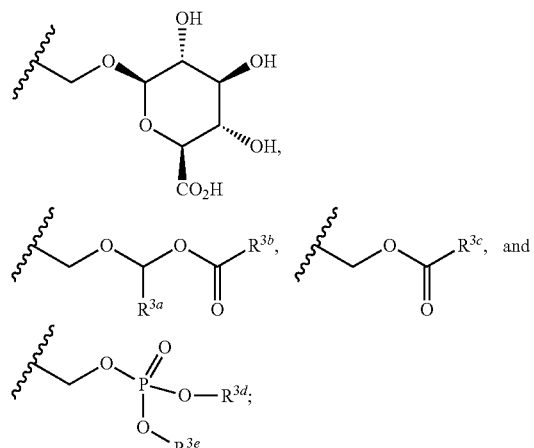

R$^{3a}$ is selected from the group consisting of hydrogen and C$_{1-4}$ alkyl; R$^{3b}$ is selected from the group consisting of C$_{1-4}$ alkyl and C$_{1-4}$ alkoxy; R$^{3c}$ is selected from the group consisting of hydrogen, C$_{1-4}$ alkyl, —CH$_2$OH, and C$_{1-4}$ alkoxy; R$^{3d}$ and R$^{3e}$ are independently selected from hydrogen and C$_{1-4}$ alkyl; X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent; t is 1 or 2; Z is selected from the group consisting of =CR$^{11a}$— and =N—; each R$^{4a}$ and R$^{4b}$ are independently selected from the group consisting of hydrogen and C$_{1-4}$ alkyl; or R$^{4a}$ and R$^{4b}$ taken together with the carbon atom to which they are attached form a 3- to 6-membered cycloalkyl; R$^{4c}$ and R$^{4d}$ are independently selected from the group consisting of hydrogen and C$_{1-4}$ alkyl; R$^5$ is selected from the group consisting of hydrogen and C$_{1-4}$ alkyl; R$^{6a}$, R$^{6c}$, R$^{6d}$, and R$^{6e}$ are each independently selected from the group consisting of hydrogen, halo, C$_{1-4}$ alkyl, C$_{1-4}$ haloalkyl, cyano, hydroxy, thiol, amino, alkylthio, and alkoxy; Y$^2$ is selected from the group consisting of —O—, —S—, and —N(R$^{7a}$)—; or Y$^2$ is absent; R$^{7a}$ is selected from the group consisting of hydrogen and C$_{1-4}$ alkyl; R$^{8a}$ and R$^{8b}$ are independently selected from the group consisting of hydrogen and C$_{1-4}$ alkyl; R$^{9f}$ is selected from the group consisting of hydrogen and C$_{1-4}$ alkyl; R$^{11a}$ and R$^{11b}$ are independently selected from the group consisting of hydrogen, halo, C$_{1-4}$ alkyl, C$_{1-4}$ haloalkyl, cyano, === hydroxy, thiol, amino, alkylthio, and alkoxy; and === represents a single or double bond.

Emb 15. The compound of Emb 14, or a pharmaceutically acceptable salt or solvate thereof, wherein SM is a monovalent radical of a glucocorticosteroid having Formula II-m.

Emb 16. The compound of Emb 14, or a pharmaceutically acceptable salt or solvate thereof, wherein SM is a monovalent radical of a glucocorticosteroid having Formula II-n.

Emb 17. The compound of any one of Embs 2-4 or 13, or a pharmaceutically acceptable salt or solvate thereof, wherein SM is a monovalent radical of a glucocorticosteroid having Formula II-o, wherein: $R^1$ is selected from the group consisting of hydrogen and halo; $R^2$ is selected from the group consisting of hydrogen, halo, and hydroxy; $R^3$ is selected from the group consisting of —$CH_2OH$, —$CH_2SH$, —$CH_2Cl$, —$SCH_2Cl$, —$SCH_2F$, —$SCH_2CF_3$, hydroxy, —$OCH_2CN$, —$OCH_2Cl$, —$OCH_2F$, —$OCH_3$, —$OCH_2CH_3$, —$SCH_2CN$,

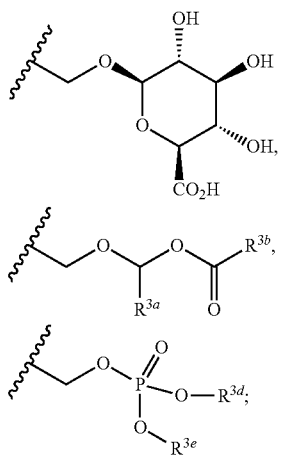

$R^{3a}$ is selected from the group consisting of hydrogen and $C_{1-4}$ alkyl; $R^{3b}$ is selected from the group consisting of $C_{1-4}$ alkyl and $C_{1-4}$ alkoxy; $R^{3c}$ is selected from the group consisting of hydrogen, $C_{1-4}$ alkyl, —$CH_2OH$, and $C_{1-4}$ alkoxy; $R^{3d}$ and $R^{3e}$ are independently selected from hydrogen and $C_{1-4}$ alkyl; X is selected from the group consisting of —$(CR^{4a}R^{4b})_t$—, —O—, —S—, —S(=O)—, —S(=O)$_2$—, —$NR^5$—, —$CH_2S$—, —$CH_2O$—, —N(H)C($R^{8a}$)($R^{8b}$)—, —$CR^{4c}$=$CR^{4d}$—, and —C≡C—; or X is absent; t is 1 or 2; Z is selected from the group consisting of =$CR^{11a}$— and =N—; each $R^{4a}$ and $R^{4b}$ are independently selected from the group consisting of hydrogen and $C_{1-4}$ alkyl; or $R^{4a}$ and $R^{4b}$ taken together with the carbon atom to which they are attached form a 3- to 6-membered cycloalkyl; $R^{4c}$ and $R^{4d}$ are independently selected from the group consisting of hydrogen and $C_{1-4}$ alkyl; $R^5$ is selected from the group consisting of hydrogen and $C_{1-4}$ alkyl; $R^{6a}$, $R^{6b}$, $R^{6d}$, and $R^{6e}$ are each independently selected from the group consisting of hydrogen, halo, $C_{1-4}$ alkyl, $C_{1-4}$ haloalkyl, cyano, hydroxy, thiol, amino, alkylthio, and alkoxy; $Y^2$ is selected from the group consisting of —O—, —S—, and —N($R^{7a}$)—; or $Y^2$ is absent; $R^{7a}$ is selected from the group consisting of hydrogen and $C_{1-4}$ alkyl; $R^{8a}$ and $R^{8b}$ are independently selected from the group consisting of hydrogen and $C_{1-4}$ alkyl; $R^{9f}$ is selected from the group consisting of hydrogen and $C_{1-4}$ alkyl; $R^{11a}$ and $R^{11b}$ are independently selected from the group consisting of hydrogen, halo, $C_{1-4}$ alkyl, $C_{1-4}$ haloalkyl, cyano, hydroxy, thiol, amino, alkylthio, and alkoxy; and = represents a single or double bond.

Emb 18. The compound of Emb 17, or a pharmaceutically acceptable salt or solvate thereof, wherein SM is a monovalent radical of a glucocorticosteroid having Formula II-p.

Emb 19. The compound of Emb 17, or a pharmaceutically acceptable salt or solvate thereof, wherein SM is a monovalent radical of a glucocorticosteroid having Formula II-q.

Emb 20. The compound of any one of Embs 5-19, or a pharmaceutically acceptable salt or solvate thereof, wherein = represents a double bond.

Emb 21. The compound of any one of Embs 5-20, or a pharmaceutically acceptable salt or solvate thereof, wherein $R^1$ is selected from the group consisting of hydrogen and fluoro.

Emb 22. The compound of any one of Embs 5-21, or a pharmaceutically acceptable salt or solvate thereof, wherein $R^2$ is selected from the group consisting of hydrogen and fluoro.

Emb 23. The compound of any one of Embs 5, 6, or 13-22, or a pharmaceutically acceptable salt or solvate thereof, wherein $R^3$ is selected from the group consisting of —$CH_2OH$, —$CH_2Cl$, —$SCH_2Cl$, —$SCH_2F$, and hydroxy.

Emb 24. The compound of any one of Embs 5, 6, or 13-22, or a pharmaceutically acceptable salt or solvate thereof, wherein $R^3$ is selected from the group consisting of:

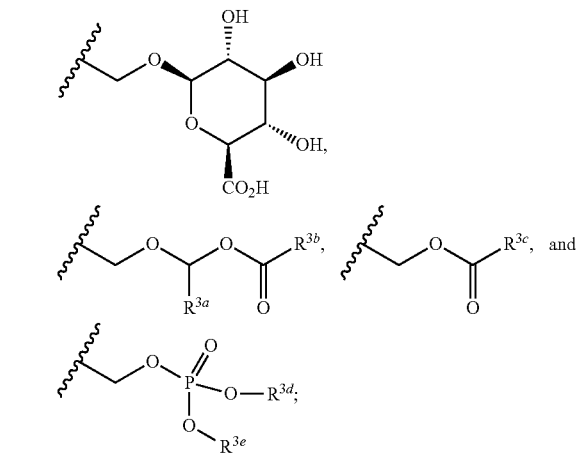

$R^{3a}$ is selected from the group consisting of hydrogen and methyl; $R^{3b}$ is selected from the group consisting of methyl, ethyl, isopropyl, isobutyl, methoxy, ethoxy, isopropoxy, and isobutoxy; $R^{3c}$ is selected from the group consisting of hydrogen, methyl, ethyl, —$CH_2OH$, methoxy, ethoxy, and isopropoxy; $R^{3d}$ and $R^{3e}$ are independently selected from the group consisting of hydrogen, methyl, and ethyl.

Emb 25. The compound of any one of Embs 5-8 or 11-24, or a pharmaceutically acceptable salt or solvate thereof, wherein $R^5$ and $R^{8a}$ are independently selected from the group consisting of hydrogen and methyl.

Emb 26. The compound of any one of Embs 5-8, 11-25, or a pharmaceutically acceptable salt or solvate thereof, wherein Z is =CH—.

Emb 27. The compound of any one of Embs 5-8 or 11-25, or a pharmaceutically acceptable salt or solvate thereof, wherein Z is =N—.

Emb 28. The compound of any one of Embs 5-8 or 11-27, or a pharmaceutically acceptable salt or solvate thereof, wherein $R^{6a}$, $R^{6d}$, and $R^{6e}$ are hydrogen.

Emb 29. The compound of any one of Embs 13-28, or a pharmaceutically acceptable salt or solvate thereof, wherein $Y^2$ is —N($R^{7a}$)—.

Emb 30. The compound of Emb 29, or a pharmaceutically acceptable salt or solvate thereof, wherein $R^{7'}$ is selected from the group consisting of hydrogen and methyl.

Emb 31. The compound of Emb 30, or a pharmaceutically acceptable salt or solvate thereof, wherein $R^7$ is hydrogen.

Emb 32. The compound of Emb 30, or a pharmaceutically acceptable salt or solvate thereof, wherein $R^7$ is methyl.

Emb 33. The compound of any one of Embs 5-8 or 13-32, or a pharmaceutically acceptable salt or solvate thereof, wherein: X is selected from the group consisting of $-(CR^{4a}R^{4b})_t-$, $-O-$, $-S-$, $-S(=O)-$, $-S(=O)_2-$, $-CH_2S-$, and $-N(H)CH(R^{8a})_t-$; t is 1; $R^{4a}$ and $R^{4b}$ are independently selected from the group consisting of hydrogen and methyl; or $R^{4a}$ and $R^{4b}$ taken together with the carbon atom to which they are attached form a 3-membered cycloalkyl; and $R^{8a}$ is selected from the group consisting of hydrogen and methyl.

Emb 34. The compound of Emb 33, or a pharmaceutically acceptable salt or solvate thereof, wherein X is $-CH_2-$.

Emb 35. The compound of Emb 33, or a pharmaceutically acceptable salt or solvate thereof, wherein X is selected from the group consisting of:

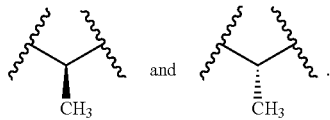

Emb 36. The compound of Emb 33, or a pharmaceutically acceptable salt or solvate thereof, wherein X is $-O-$.

Emb 37. The compound of Emb 33, or a pharmaceutically acceptable salt or solvate thereof, wherein X is $-S-$.

Emb 38. The compound of Emb 33, or a pharmaceutically acceptable salt or solvate thereof, wherein X is $-CH_2S-$.

Emb 39. The compound of Emb 33, or a pharmaceutically acceptable salt or solvate thereof, wherein X is $-N(H)CH_2-$.

Emb 40. The compound of Emb 33, or a pharmaceutically acceptable salt or solvate thereof, wherein X is selected from the group consisting of:

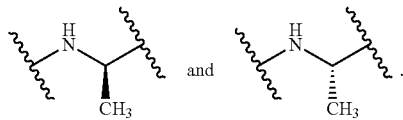

Emb 41. The compound of any one of Embs 13-16 or 20-40, or a pharmaceutically acceptable salt or solvate thereof, wherein $R^{6c}$ is selected from the group consisting of hydrogen, $-Cl$, $-OCH_3$, and hydroxy.

Emb 42. The compound of any one of Embs 13 or 17-40, or a pharmaceutically acceptable salt or solvate thereof, wherein $R^{6b}$ is selected from the group consisting of hydrogen, $-Cl$, $-OCH_3$, and hydroxy.

Emb 43. The compound of any one of Embs 13-42, or a pharmaceutically acceptable salt or solvate thereof, wherein $R^{9f}$ is hydrogen.

Emb 44. The compound of any one of Embs 13-42, or a pharmaceutically acceptable salt or solvate thereof, wherein $R^{9f}$ is methyl.

Emb 45. The compound of any one of Embs 13-44, or a pharmaceutically acceptable salt or solvate thereof, wherein $R^{11}a$ is selected from the group consisting of hydrogen and hydroxy.

Emb 46. The compound of any one of Embs 13-44, or a pharmaceutically acceptable salt or solvate thereof, wherein $R^{11b}$ is hydrogen.

Emb 47. The compound of any one of Embs 1-46, or a pharmaceutically acceptable salt or solvate thereof, wherein L is a cleavable linker.

Emb 48. The compound of any one of Embs 1-47, or a pharmaceutically acceptable salt or solvate thereof, wherein the cleavable linker comprises a succinimide, amide, thiourea, thioether, oxime, or self-immolative group, or a combination thereof.

Emb 49. The compound of any one of Embs 1-48, or a pharmaceutically acceptable salt or solvate thereof, wherein the cleavable linker comprises a peptide.

Emb 50. The compound of Emb 49, or a pharmaceutically acceptable salt or solvate thereof, wherein the cleavable linker comprises a tripeptide.

Emb 51. The compound of Emb 49, or a pharmaceutically acceptable salt or solvate thereof, wherein the cleavable linker comprises a dipeptide.

Emb 52. The compound of any one of Embs 1-47, or a pharmaceutically acceptable salt or solvate thereof, wherein the cleavable linker comprises phosphate ester.

Emb 53. The compound of any one of Embs 1-47, or a pharmaceutically acceptable salt or solvate thereof, wherein the cleavable linker comprises a pyrophosphate diester.

Emb 54. The compound of any one of Embs 1-53, or a pharmaceutically acceptable salt or solvate thereof, wherein Q is absent.

Emb 55. The compound of any one of Embs 1-53, or a pharmaceutically acceptable salt or solvate thereof, wherein Q is a heterobifunctional group selected from the group consisting of Q-1, Q-2, Q-3, Q-4, Q-5, and Q-6, wherein m is 1, 2, 3, 4, 5, or 6.

Emb 56. The compound of any one of Embs 1-53, or a pharmaceutically acceptable salt or solvate thereof, wherein Q is a heterotrifunctional group that is Q-7.

Emb 57. The compound of Emb 55, or a pharmaceutically acceptable salt or solvate thereof, wherein Q is selected from the group consisting of Q-1, Q-2, Q-3, and Q-4.

Emb 58. The compound of Emb 57, or a pharmaceutically acceptable salt or solvate thereof, wherein Q is selected from the group consisting of Q-3 and Q-4.

Emb 59. The compound of any one of Embs 1-47, or a pharmaceutically acceptable salt or solvate thereof, wherein -L-Q- is LQ-1; m is 1 or 2; and $R^{10a}$ and $R^{10b}$ are independently selected from the group consisting of hydrogen and optionally substituted $C_{1-6}$ alkyl.

Emb 60. The compound of Emb 59, or a pharmaceutically acceptable salt or solvate thereof, wherein -L-Q- is LQ-2.

Emb 61. The compound of Emb 59, or a pharmaceutically acceptable salt or solvate thereof, wherein -L-Q- is LQ-3.

Emb 62. The compound of Emb 59, or a pharmaceutically acceptable salt or solvate thereof, wherein -L-Q- is LQ-4.

Emb 63. The compound of Emb 59, or a pharmaceutically acceptable salt or solvate thereof, wherein -L-Q- is LQ-5.

Emb 64. The compound of any one of Embs 1-47, or a pharmaceutically acceptable salt or solvate thereof, wherein -L-Q- is LQ-6; m is 1 or 2; and $R^{10a}$ and $R^{10b}$ are independently selected from the group consisting of hydrogen and optionally substituted $C_{1-6}$ alkyl.

Emb 65. The compound of Emb 64, or a pharmaceutically acceptable salt or solvate thereof, wherein -L-Q- is LQ-7.

Emb 66. The compound of Emb 64, or a pharmaceutically acceptable salt or solvate thereof, wherein -L-Q- is LQ-8.

Emb 67. The compound of Emb 64, or a pharmaceutically acceptable salt or solvate thereof, wherein -L-Q- is LQ-9.

Emb 68. The compound of Emb 64, or a pharmaceutically acceptable salt or solvate thereof, wherein -L-Q- is: LQ-10.

Emb 69. The compound of any one of Embs 1-47, or a pharmaceutically acceptable salt or solvate thereof, wherein L is a noncleavable linker.

Emb 70. The compound of any one of Embs 1-47, or a pharmaceutically acceptable salt or solvate thereof, wherein the linker comprises one or more polyethylene glycol units.

Emb 71. The compound of any one of Embs 1-47, or a pharmaceutically acceptable salt or solvate thereof, wherein -L-Q- is LQ-11; m is 1 or 2; and x is 0, 1, 2, 3, 4, 5, 6, 7, 8, 9, 10, 11, 12, 13, 14, or 15.

Emb 72. The compound of any one of Embs 1-47, or a pharmaceutically acceptable salt or solvate thereof, wherein -L-Q- is LQ-12; m is 1 or 2; and x is 0, 1, 2, 3, 4, 5, 6, 7, 8, 9, 10, 11, 12, 13, 14, or 15.

Emb 73. The compound of any one of Embs 1-47, or a pharmaceutically acceptable salt or solvate thereof, wherein -L-Q- is LQ-14; m is 1 or 2; x is 0, 1, 2, 3, 4, 5, 6, 7, 8, 9, 10, 11, 12, 13, 14, or 15; and $R^{10a}$ and $R^{10b}$ are independently selected from the group consisting of hydrogen and optionally substituted $C_{1-6}$ alkyl.

Emb 74. The compound of Emb 73, or a pharmaceutically acceptable salt or solvate thereof, wherein -L-Q- is LQ-15.

Emb 75. The compound of Emb 73, or a pharmaceutically acceptable salt or solvate thereof, wherein -L-Q- is LQ-16.

Emb 76. The compound of Emb 73, or a pharmaceutically acceptable salt or solvate thereof, wherein -L-Q- is LQ-17.

Emb 77. The compound of Emb 73, or a pharmaceutically acceptable salt or solvate thereof, wherein -L-Q- is LQ-18.

Emb 78. The compound of any one of Embs 1-47, or a pharmaceutically acceptable salt or solvate thereof, wherein -L-Q- is LQ-19; m is 1 or 2; x is 0, 1, 2, 3, 4, 5, 6, 7, 8, 9, 10, 11, 12, 13, 14, or 15; and $R^{10a}$ and $R^{10b}$ are independently selected from the group consisting of hydrogen and optionally substituted $C_{1-6}$ alkyl.

Emb 79. The compound of Emb 78, or a pharmaceutically acceptable salt or solvate thereof, wherein -L-Q- is LQ-20.

Emb 80. The compound of Emb 78, or a pharmaceutically acceptable salt or solvate thereof, wherein -L-Q- is LQ-21.

Emb 81. The compound of Emb 78, or a pharmaceutically acceptable salt or solvate thereof, wherein -L-Q- is LQ-22.

Emb 82. The compound of Emb 78, or a pharmaceutically acceptable salt or solvate thereof, wherein -L-Q- is LQ-23.

Emb 83. The compound of any one of Embs 1-47, or a pharmaceutically acceptable salt or solvate thereof, wherein -L-Q- is LQ-13; and x is 0, 1, 2, 3, 4, 5, 6, 7, 8, 9, 10, 11, 12, 13, 14, or 15.

Emb 84. The compound of any one of Embs 1-47, or a pharmaceutically acceptable salt or solvate thereof, wherein -L-Q- is LQ-29; and x is 0, 1, 2, 3, 4, 5, 6, 7, 8, 9, 10, 11, 12, 13, 14, or 15.

Emb 85. The compound of any one of Embs 1-47, or a pharmaceutically acceptable salt or solvate thereof, wherein -L-Q- is LQ-24; x is 0, 1, 2, 3, 4, 5, 6, 7, 8, 9, 10, 11, 12, 13, 14, or 15; and $R^{10a}$ and $R^{10b}$ are independently selected from the group consisting of hydrogen and optionally substituted $C_{1-6}$ alkyl.

Emb 86. The compound of Emb 85, or a pharmaceutically acceptable salt or solvate thereof, wherein -L-Q- is LQ-25.

Emb 86A. The compound of Emb 85, or a pharmaceutically acceptable salt or solvate thereof, wherein -L-Q- is LQ-26.

Emb 87. The compound of Emb 85, or a pharmaceutically acceptable salt or solvate thereof, wherein -L-Q- is LQ-27.

Emb 88. The compound of Emb 85, or a pharmaceutically acceptable salt or solvate thereof, wherein -L-Q- is LQ-28.

Emb 89. The compound of any one of Embs 1-47, or a pharmaceutically acceptable salt or solvate thereof, wherein -L-Q- is LQ-30; x is 0, 1, 2, 3, 4, 5, 6, 7, 8, 9, 10, 11, 12, 13, 14, or 15; and $R^{10a}$ and $R^{10b}$ are independently selected from the group consisting of hydrogen and optionally substituted $C_{1-6}$ alkyl.

Emb 90. The compound of Emb 89, or a pharmaceutically acceptable salt or solvate thereof, wherein -L-Q- is LQ-31.

Emb 91. The compound of Emb 89, or a pharmaceutically acceptable salt or solvate thereof, wherein -L-Q- is LQ-32.

Emb 92. The compound of Emb 89, or a pharmaceutically acceptable salt or solvate thereof, wherein -L-Q- is LQ-33.

Emb 93. The compound of Emb 89, or a pharmaceutically acceptable salt or solvate thereof, wherein -L-Q- is LQ-34.

Emb 94. The compound of any one of Embs 55, 59-68, or 71-82, or a pharmaceutically acceptable salt or solvate thereof, wherein m is 2.

Emb 95. The compound of any one of Embs 1-47, or a pharmaceutically acceptable salt or solvate thereof, wherein -L-Q- is any one the chemical structures of Table I.

Emb 96. The compound of any one of Embs 1-95, or a pharmaceutically acceptable salt or solvate thereof, wherein n is 2-8.

Emb 97. The compound of Emb 96, or a pharmaceutically acceptable salt or solvate thereof, wherein n is 2-5.

Emb 98. The compound of any one of Embs 1-95, or a pharmaceutically acceptable salt or solvate thereof, wherein n is 2.

Emb 99. The compound of any one of Embs 1-95, or a pharmaceutically acceptable salt or solvate thereof, wherein n is 4.

Emb 100. The compound of any one of Embs 1 or 47-99, or a pharmaceutically acceptable salt or solvate thereof, wherein SM is a monovalent radical of a glucocorticosteroid which is any one of the chemical structures of Table II.

Emb 101. The compound of Emb 100, or a pharmaceutically acceptable salt or solvate thereof, wherein SM is a monovalent radical of a glucocorticosteroid selected from the group consisting of:

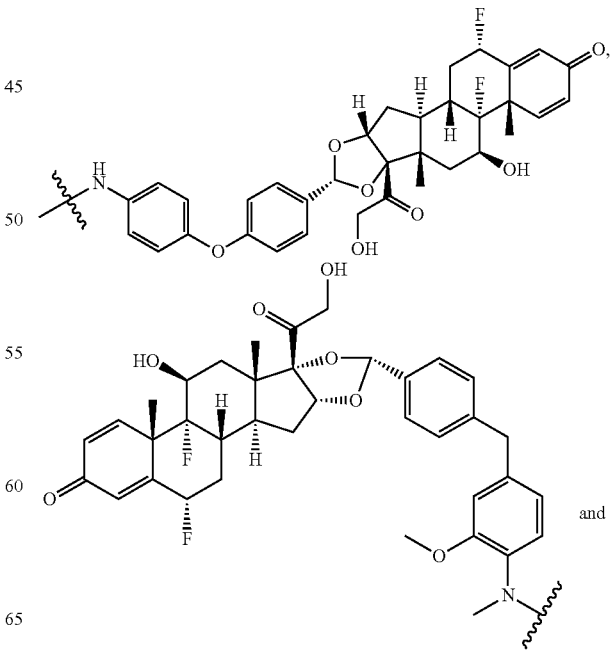

and

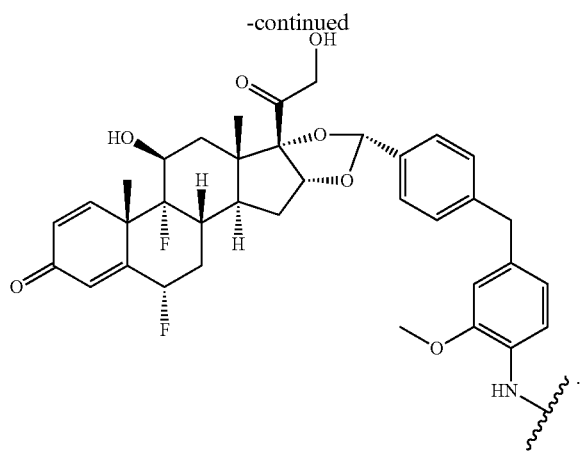

Emb 102. The compound of any one of Embs 1-101, or a pharmaceutically acceptable salt or solvate thereof, wherein $A^1$ is an antibody or antigen-binding fragment thereof or wherein $A^2$ is an antibody or antigen-binding fragment thereof.

Emb 103. The compound of any one of Embs 1-101, or a pharmaceutically acceptable salt or solvate thereof, wherein $A^1$ is an anti-tumor necrosis factor (TNF) alpha protein that binds to human TNF alpha and/or murine TNF alpha or wherein $A^2$ is protein that binds to human TNF alpha and/or murine TNF alpha.

Emb 104. The compound of any one of Embs 1-101, or a pharmaceutically acceptable salt or solvate thereof, wherein $A^1$ is an anti-tumor necrosis factor (TNF) alpha protein that binds to soluble TNF alpha or wherein $A^2$ is a protein that binds to soluble TNF alpha.

Emb 105. The compound of any one of Embs 1-101, or a pharmaceutically acceptable salt or solvate thereof, wherein $A^1$ is an anti-tumor necrosis factor (TNF) alpha protein that binds to membrane-bound TNF alpha or wherein $A^2$ is a protein that binds to membrane-bound TNF alpha.

Emb 106. The compound of any one of Embs 1-101, or a pharmaceutically acceptable salt or solvate thereof, wherein $A^1$ is an anti-tumor necrosis factor (TNF) alpha protein comprising an anti-TNF antibody or wherein $A^2$ is protein comprising an anti-TNF antibody.

Emb 107. The compound of any one of Embs 1-101, or a pharmaceutically acceptable salt or solvate thereof, wherein $A^1$ is an anti-tumor necrosis factor (TNF) alpha protein comprising an antigen-binding fragment of an anti-TNF antibody or wherein $A^2$ is a protein comprising an antigen-binding fragment of an anti-TNF antibody.

Emb 108. The compound of any one of Embs 102-105 or 107, or a pharmaceutically acceptable salt or solvate thereof, wherein the antigen-binding fragment is selected from the group consisting of Fab, Fab', F(ab')2, single chain Fv or scFv, disulfide linked Fv, V-NAR domain, IgNar, intrabody, IgGΔCH$_2$, minibody, F(ab')3, tetrabody, triabody, diabody, single-domain antibody, DVD-Ig, Fcab, mAb2, (scFv)2, or scFv-Fc.

Emb 109. The compound of any one of Embs 1-108, or a pharmaceutically acceptable salt or solvate thereof, wherein the antibody or antigen-binding fragment thereof is murine, chimeric, humanized, or human.

Emb 110. The compound of any one of Embs 1-101, or a pharmaceutically acceptable salt or solvate thereof, wherein $A^1$ is an anti-tumor necrosis factor (TNF) alpha protein comprising a soluble TNF receptor or wherein $A^2$ is a protein comprising a soluble TNF receptor.

Emb 111. The compound of Emb 110, or a pharmaceutically acceptable salt or solvate thereof, wherein the soluble TNF receptor is a soluble p75 TNF receptor.

Emb 112. The compound of any one of Embs 1-101, or a pharmaceutically acceptable salt or solvate thereof, wherein $A^1$ comprises a heavy chain constant domain or a fragment thereof or wherein or $A^2$ comprises a heavy chain constant domain or a fragment thereof.

Emb 113. The compound of Emb 112, or a pharmaceutically acceptable salt or solvate thereof, wherein the heavy chain constant domain or fragment thereof comprises a constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain or is a fragment thereof.

Emb 114. The compound of Emb 113, or a pharmaceutically acceptable salt or solvate thereof, wherein the heavy chain constant domain comprises a human IgG1 heavy chain constant domain or fragment thereof.

Emb 115. The compound of Emb 114, or a pharmaceutically acceptable salt or solvate thereof, wherein the heavy chain constant domain comprises a human IgG1 Fc domain.

Emb 116. The compound of any one of Embs 1-101, or a pharmaceutically acceptable salt or solvate thereof, wherein $A^1$ comprises a light chain constant domain or a fragment thereof or wherein $A^2$ comprises a light chain constant domain or a fragment thereof.

Emb 117. The compound of Emb 116, or a pharmaceutically acceptable salt or solvate thereof, wherein the light chain constant domain or fragment thereof comprises a constant domain selected group consisting of (a) an Ig kappa constant domain and (b) an Ig lambda constant domain or is a fragment thereof.

Emb 118. The compound of any one of Embs 1-101, or a pharmaceutically acceptable salt or solvate thereof, wherein $A^1$ competitively inhibits binding of an antibody selected from the group consisting of adalimumab, infliximab, certolizumab pegol, and golimumab to TNF-alpha or wherein $A^2$ competitively inhibits binding of an antibody selected from the group consisting of adalimumab, infliximab, certolizumab pegol, and golimumab to TNF-alpha.

Emb 119. The compound of any one of Embs 1-101, or a pharmaceutically acceptable salt or solvate thereof, wherein $A^1$ binds to the same TNF-alpha epitope as an antibody selected from the group consisting of adalimumab, infliximab, certolizumab pegol, afelimomab, nerelimomab, ozoralizumab, placulumab, and golimumab or wherein $A^2$ binds to the same TNF-alpha epitope as an antibody selected from the group consisting of adalimumab, infliximab, certolizumab pegol, afelimomab, nerelimomab, ozoralizumab, placulumab, and golimumab.

Emb 120. The compound of any one of Embs 1-101, or a pharmaceutically acceptable salt or solvate thereof, wherein the anti-TNF alpha protein or protein is selected from the group consisting of adalimumab, infliximab, certolizumab pegol, afelimomab, nerelimomab, ozoralizumab, placulumab, and golimumab.

Emb 121. The compound of any one of Embs 1-101, or a pharmaceutically acceptable salt or solvate thereof, wherein $A^1$ comprises the variable heavy chain CDR1, CDR2, and CDR3 sequences of SEQ ID NO:3 or 6, SEQ ID NO:4, and SEQ ID NO:5, respectively and the variable light chain CDR1, CDR2, and CDR3 sequences of SEQ ID NO:32, SEQ ID NO:33, and SEQ ID NO:34, respectively or wherein $A^2$ comprises the variable heavy chain CDR1, CDR2, and CDR3 sequences of SEQ ID NO:3 or 6, SEQ ID NO:4, and SEQ ID NO:5 respectively and the variable light chain CDR1, CDR2, and CDR3 sequences of SEQ ID NO:32, SEQ ID NO:33, and SEQ ID NO:34, respectively.

Emb 122. The compound of any one of Embs 1-101, or a pharmaceutically acceptable salt or solvate thereof, wherein $A^1$ comprises the variable heavy chain sequence of SEQ ID NO:50 and the variable light chain sequence of SEQ ID NO:59 or wherein $A^2$ comprises the variable heavy chain sequence of SEQ ID NO:50 and the variable light chain sequence of SEQ ID NO:59.

Emb 123. The compound of any one of Embs 1-101, or a pharmaceutically acceptable salt or solvate thereof, wherein $A^1$ does not bind to TNF beta or wherein $A^2$ does not bind to TNF beta.

Emb 124. The compound of any one of Embs 1-101, or a pharmaceutically acceptable salt or solvate thereof, wherein $A^1$ binds to TNF beta or wherein $A^2$ binds to TNF beta.

Emb 125. The compound of any one of Embs 1-101, or a pharmaceutically acceptable salt or solvate thereof, wherein $A^1$ neutralizes human TNF-alpha cytotoxicity in a standard in vitro L929 assay with an IC50 of $1\times10^{-7}$ M or less or wherein $A^2$ neutralizes human TNF-alpha cytotoxicity in a standard in vitro L929 assay with an IC50 of $1\times10^{-7}$ M or less.

Emb 126. The compound of any one of Embs 1-101, or a pharmaceutically acceptable salt or solvate thereof, wherein $A^1$ blocks the interaction of TNF-alpha with p55 and p75 cell surface receptors or wherein $A^2$ blocks the interaction of TNF-alpha with p55 and p75 cell surface receptors.

Emb 127. The compound of any one of Embs 1-101, or a pharmaceutically acceptable salt or solvate thereof, wherein $A^1$ lyses surface TNF expressing cells in vitro in the presence of complement or wherein $A^2$ lyses surface TNF expressing cells in vitro in the presence of complement.

Emb 128. The compound of Emb 111, or a pharmaceutically acceptable salt or solvate thereof, wherein the soluble p75 TNF receptor is etanercept.

Emb 129. The compound of Emb 102, or a pharmaceutically acceptable salt or solvate thereof, wherein the antibody is adalimumab.

Emb 130. The compound of any one of Embs 1-101, wherein $A^1$ binds to Fc gamma receptor or wherein $A^2$ binds to Fc gamma receptor.

Emb 131. The compound of any one of Embs 1-101, wherein $A^1$ is active in the GRE transmembrane TNF-alpha reporter assay and/or the L929 assay or wherein $A^2$ is active in the GRE transmembrane TNF-alpha reporter assay and/or the L929 assay.

Emb 132. The compound of any one of Embs 1 or 102-131, or a pharmaceutically acceptable salt or solvate thereof, which is any one of the chemical structures of Table III, wherein n is 1-5 and A is $A^1$ or $A^2$.

Emb 133. The compound of Emb 132, or a pharmaceutically acceptable salt or solvate thereof, which is any one of the chemical structures of Table IV, wherein A is $A^1$ or $A^2$.

Emb 134. The compound of any one of Embs 1 or 102-131, or a pharmaceutically acceptable salt or solvate thereof, which is any one of the chemical structures of Table V, wherein n is 1-5 and A is $A^1$ or $A^2$.

Emb 135. The compound of Emb 134, or a pharmaceutically acceptable salt or solvate thereof, wherein n is 2 or 4.

Emb 136. A pharmaceutical composition comprising the compound of any one of Embs 1-135, or a pharmaceutically acceptable salt or solvate thereof, and a pharmaceutically acceptable carrier.

Emb 137. A pharmaceutical composition comprising a plurality of the compounds of any one of Embs 1-135 or a pharmaceutically salt or solvate thereof, wherein the compounds in the pharmaceutical composition have an average of 1 to 10 SM-L-Q per $A^1$ or $A^2$, i.e., n is 1-10, 2 to 6 SM-L-Q per $A^1$ or $A^2$, 3 to 4 SM-L-Q per $A^1$ or $A^2$, about 2 SM-L-Q per $A^1$ or $A^2$, about 3 SM-L-Q per $A^1$ or $A^2$, or about 4 SM-L-Q per $A^1$ or $A^2$.

Emb 138. A method for lysing a cell expressing surface TNF-alpha comprising contacting the cell with the compound of any one of Embs 1-135 or the pharmaceutical composition of Embs 136 or 137.

Emb 139. A method for treating an autoimmune disease in a patient in need thereof comprising administering to said patient the compound of any one of Embs 1-135 or the pharmaceutical composition of Embs 136 or 137.

Emb 140. The method of Emb 139, wherein said autoimmune disease is rheumatoid arthritis, juvenile idiopathic arthritis, psoriatic arthritis, ankylosing spondylitis, adult Crohn's disease, pediatric Crohn's disease, ulcerative colitis, plaque psoriasis, hidradenitis suppurativa, uveitis, Behcets disease, a spondyloarthropathy, or psoriasis.

Emb 141. A method for treating a disease or disorder characterized by increased TNF-alpha in synovial fluid in a patient in need thereof comprising administering to said patient the compound of any one of Embs 1-135 or the pharmaceutical composition of Embs 136 or 137.

Emb 142. A compound having Formula VII, or a pharmaceutically acceptable salt or solvate thereof, wherein: $R^1$ is selected from the group consisting of hydrogen and halo; $R^2$ is selected from the group consisting of hydrogen, halo, and hydroxy; $R^3$ is selected from the group consisting of —$CH_2OH$, —$CH_2SH$, —$CH_2Cl$, —$SCH_2Cl$, —$SCH_2F$, —$SCH_2CF_3$, hydroxy, —$OCH_2CN$, —$OCH_2Cl$, —$OCH_2F$, —$OCH_3$, —$OCH_2CH_3$, —$SCH_2CN$,

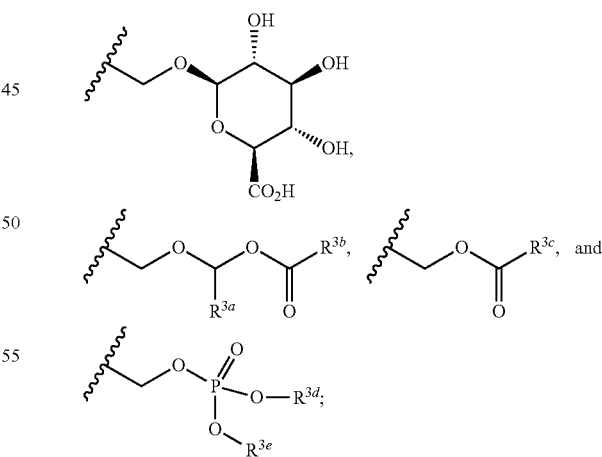

$R^{3a}$ is selected from the group consisting of hydrogen and $C_{1-4}$ alkyl; $R^{3b}$ is selected from the group consisting of $C_{1-4}$ alkyl and $C_{1-4}$ alkoxy; $R^{3c}$ is selected from the group consisting of hydrogen, $C_{1-4}$ alkyl, —$CH_2OH$, and $C_{1-4}$ alkoxy; $R^{3d}$ and $R^{3e}$ are independently selected from hydrogen and $C_{1-4}$ alkyl; X is selected from the group consisting of —$(CR^{4a}R^{4b})_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent; t is 1 or 2; Z is selected from the group consisting of =CR$^{11a}$— and =N—; each R$^{4a}$ and R$^{4b}$ are independently selected from the group consisting of hydrogen and C$_{1-4}$ alkyl; or R$^{4a}$ and R$^{4b}$ taken together with the carbon atom to which they are attached form a 3- to 6-membered cycloalkyl; R$^{4c}$ and R$^{4d}$ are independently selected from the group consisting of hydrogen and C$_{1-4}$ alkyl; R$^5$ is selected from the group consisting of hydrogen and C$_{1-4}$ alkyl; R$^{6a}$, R$^{6b}$, R$^{6c}$, and R$^{6d}$ are each independently selected from the group consisting of hydrogen, halo, C$_{1-4}$ alkyl, v haloalkyl, cyano, hydroxy, thiol, amino, alkylthio, and alkoxy; R$^{7a}$ is selected from the group consisting of hydrogen and C$_{1-4}$ alkyl; R$^{7b}$ is selected from the group consisting of hydrogen, -L-H, -L-PG,

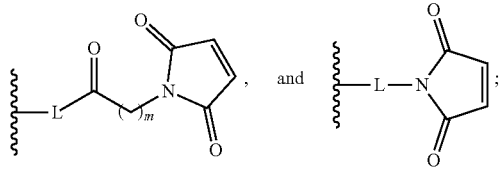

m is 1, 2, 3, 4, 5, or 6; L is a linker; PG is a protecting group; R$^9$ is selected from the group consisting of hydrogen and C$_{1-4}$ alkyl; R$^{8a}$ and R$^{8b}$ are independently selected from the group consisting of hydrogen and C$_{1-4}$ alkyl; R$^{11a}$ and R$^{11b}$ are independently selected from the group consisting of hydrogen, halo, C$_{1-4}$ alkyl, C$_{1-4}$ haloalkyl, cyano, hydroxy, thiol, amino, alkylthio, and alkoxy; and ═══ represents a single or double bond.

Emb 143. The compound of Emb 142, or a pharmaceutically acceptable salt or solvate thereof, wherein R$^{7b}$ is selected from the group consisting of R$^{7b}$-1, R$^{7b}$-2, and R$^{7b}$-3; m is 1, 2, 3, 4, 5, or 6; and R$^{10a}$ and R$^{10b}$ are each independently selected from the group consisting of hydrogen and optionally substituted C$_{1-6}$ alkyl.

Emb 144. The compound of Embs 142 or 143, or a pharmaceutically acceptable salt or solvate thereof, having Formula VIII.

Emb 145. The compound of Emb 144, or a pharmaceutically acceptable salt or solvate thereof, having Formula VIII-a.

Emb 146. The compound of Emb 144, or a pharmaceutically acceptable salt or solvate thereof, having Formula VIII-b.

Emb 147. The compound of Emb 142 or 143, or a pharmaceutically acceptable salt or solvate thereof, having Formula IX.

Emb 148. The compound of Emb 147, or a pharmaceutically acceptable salt or solvate thereof, having Formula IX-a.

Emb 149. The compound of Emb 147, or a pharmaceutically acceptable salt or solvate thereof, having Formula IX-b.

Emb 150. The compound of any one of Embs 142-149, or a pharmaceutically acceptable salt or solvate thereof, wherein ═══ represents a double bond.

Emb 151. The compound of any one of Embs 142-150, or a pharmaceutically acceptable salt or solvate thereof, wherein R$^1$ is selected from the group consisting of hydrogen and fluoro.

Emb 152. The compound of any one of Embs 142-151, or a pharmaceutically acceptable salt or solvate thereof, wherein R$^2$ is selected from the group consisting of hydrogen and fluoro.

Emb 153. The compound of any one of Embs 142-152, or a pharmaceutically acceptable salt or solvate thereof, wherein R$^3$ is selected from the group consisting of —CH$_2$OH, —CH$_2$Cl, —SCH$_2$Cl, —SCH$_2$F, and hydroxy.

Emb 154. The compound of any one of Embs 142-152, or a pharmaceutically acceptable salt or solvate thereof, wherein R$^3$ is selected from the group consisting of:

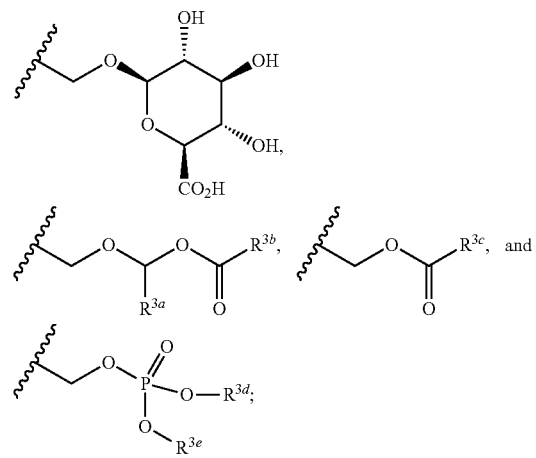

R$^{3a}$ is selected from the group consisting of hydrogen and methyl; R$^{3b}$ is selected from the group consisting of methyl, ethyl, isopropyl, isobutyl, methoxy, ethoxy, isopropoxy, and isobutoxy; R$^{3c}$ is selected from the group consisting of hydrogen, methyl, ethyl, —CH$_2$OH, methoxy, ethoxy, and isopropoxy; R$^{3d}$ and R$^{3e}$ are independently selected from the group consisting of hydrogen, methyl, and ethyl.

Emb 155. The compound of any one of Embs 142-154, or a pharmaceutically acceptable salt or solvate thereof, wherein R$^5$ and R$^{8a}$ are independently selected from the group consisting of hydrogen and methyl.

Emb 156. The compound of any one of Embs 142-155, or a pharmaceutically acceptable salt or solvate thereof, wherein Z is =CH—.

Emb 157. The compound of any one of Embs 142-155, or a pharmaceutically acceptable salt or solvate thereof, wherein Z is =N—.

Emb 158. The compound of any one of Embs 142-155, or a pharmaceutically acceptable salt or solvate thereof, wherein R$^{7a}$ is selected from the group consisting of hydrogen and methyl.

Emb 159. The compound of Emb 158, or a pharmaceutically acceptable salt or solvate thereof, wherein R$^{7a}$ is hydrogen.

Emb 160. The compound of Emb 158, or a pharmaceutically acceptable salt or solvate thereof, wherein R$^{7a}$ is methyl.

Emb 161. The compound of any one of Embs 142-160, or a pharmaceutically acceptable salt or solvate thereof, wherein:

X is selected from the group consisting of —(CR$^{4a}$R$^{4b}$)$_t$—, —O—, —S—, —S(=O)—, —S(=O)$_2$—, —CH$_2$S—, and —N(H)CH(R$^{8a}$)—; t is 1; and R$^{4a}$ and R$^{4b}$ are independently selected from the group consisting of hydrogen and methyl; or $R^{4a}$ and $R^{4b}$ taken together with the carbon atom to which they are attached form a 3-membered cycloalkyl.

Emb 162. The compound of Emb 161, or a pharmaceutically acceptable salt or solvate thereof, wherein X is —$CH_2$—.

Emb 163. The compound of Emb 161, or a pharmaceutically acceptable salt or solvate thereof, wherein X is selected from the group consisting of:

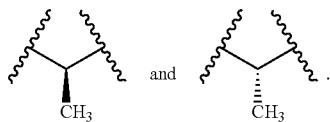

Emb 164. The compound of Emb 161, or a pharmaceutically acceptable salt or solvate thereof, wherein X is —O—.

Emb 165. The compound of Emb 161, or a pharmaceutically acceptable salt or solvate thereof, wherein X is —S—.

Emb 166. The compound of Emb 161, or a pharmaceutically acceptable salt or solvate thereof, wherein X is —$CH_2S$—.

Emb 167. The compound of Emb 161, or a pharmaceutically acceptable salt or solvate thereof, wherein X is —N(H)$CH_2$—.

Emb 168. The compound of Emb 161, or a pharmaceutically acceptable salt or solvate thereof, wherein X is selected from the group consisting of:

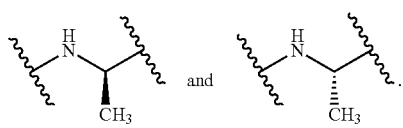

Emb 169. The compound of any one of Embs 142-168, or a pharmaceutically acceptable salt or solvate thereof, wherein $R^{11b}$ is hydrogen.

Emb 170. The compound of any one of Embs 142-169, or a pharmaceutically acceptable salt or solvate thereof, wherein $R^{11b}$ is hydrogen.

Emb 171. The compound of any one of Embs 142-170, or a pharmaceutically acceptable salt or solvate thereof, wherein $R^{6b}$ is selected from the group consisting of hydrogen, —Cl, —$OCH_3$, and hydroxy.

Emb 172. The compound of any one of Embs 142-171, or a pharmaceutically acceptable salt or solvate thereof, wherein $R^{9f}$ is hydrogen.

Emb 173. The compound of any one of Embs 142-171, or a pharmaceutically acceptable salt or solvate thereof, wherein $R^{9f}$ is methyl.

Emb 174. The compound of any one of Embs 142-173, or a pharmaceutically acceptable salt or solvate thereof, wherein $R^{11a}$ is selected from the group consisting of hydrogen and hydroxy.

Emb 175. The compound of any one of Embs 142-174, or a pharmaceutically acceptable salt or solvate thereof, wherein $R^{11b}$ is hydrogen.

Emb 176. The compound of any one of Embs 143-175, or a pharmaceutically acceptable salt or solvate thereof, wherein $R^{7b}$ is $R^{7b}$-1.

Emb 177. The compound of Emb 176, or a pharmaceutically acceptable salt or solvate thereof, wherein $R^{10a}$ and $R^{10b}$ are independently optionally substituted $C_{1-6}$ alkyl.

Emb 178. The compound of any one of Embs 143-175, or a pharmaceutically acceptable salt or solvate thereof, wherein $R^{7b}$ is $R^{7b}$-2, and PG is BOC.

Emb 179. The compound of Emb 178, or a pharmaceutically acceptable salt or solvate thereof, wherein $R^{10a}$ and $R^{10b}$ are independently optionally substituted $C_{1-6}$ alkyl.

Emb 180. The compound of any one of Embs 143-175, or a pharmaceutically acceptable salt or solvate thereof, wherein $R^{7b}$ is $R^{7b}$-3.

Emb 181. The compound of Emb 180, or a pharmaceutically acceptable salt or solvate thereof, wherein m is 1 or 2, and $R^{10a}$ and $R^{10b}$ are each optionally substituted $C_{1-6}$ alkyl.

Emb 182. The compound of Emb 142, or a pharmaceutically acceptable salt or solvate thereof, which is any one or more of the compounds of Table VI.

Emb 183. The compound of Emb 182, or a pharmaceutically acceptable salt or solvate thereof, selected from the group consisting of:

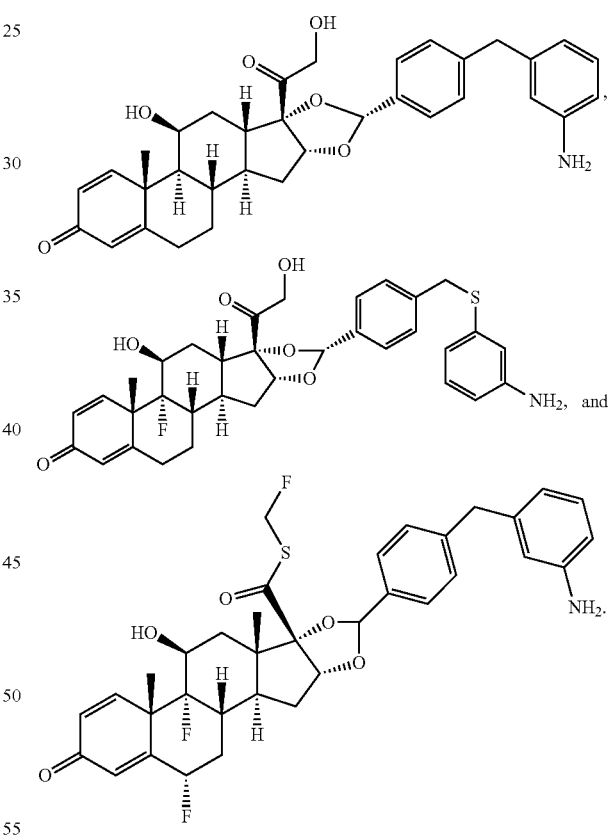

Emb 184. The compound of Emb 142, or a pharmaceutically acceptable salt or solvate thereof, which is any one or more of the chemical structures of Table VIII, wherein $R^{7b}$ is selected from the group consisting of $R^{7b}$-4, $R^{7b}$-5, and $R^{7b}$-6.

Emb 185. The compound of Emb 184, or a pharmaceutically acceptable salt or solvate thereof, wherein $R^{7b}$ is $R^{7b}$-4.

Emb 186. The compound of Emb 184, or a pharmaceutically acceptable salt or solvate thereof, wherein $R^{7b}$ is $R^{7b}$-5.

Emb 187. The compound of Emb 184, or a pharmaceutically acceptable salt or solvate thereof, wherein $R^{7b}$ is $R^{7b}$-6.

Emb 188. The compound of Emb 142, or a pharmaceutically acceptable salt or solvate thereof, which is any one or more of the chemical structures of Table VIII, wherein $R^{7b}$ is any one of the chemical structures of Table IX.

Emb 189. The compound of Emb 142, or a pharmaceutically acceptable salt or solvate thereof, which is any one of the compounds of Table X.

Emb 190. The compound of Emb 142, or a pharmaceutically acceptable salt or solvate thereof, which is any one of the compounds of Table VII.

Emb 191. The compound of Emb 190, or a pharmaceutically acceptable salt or solvate thereof, selected from the group consisting of:

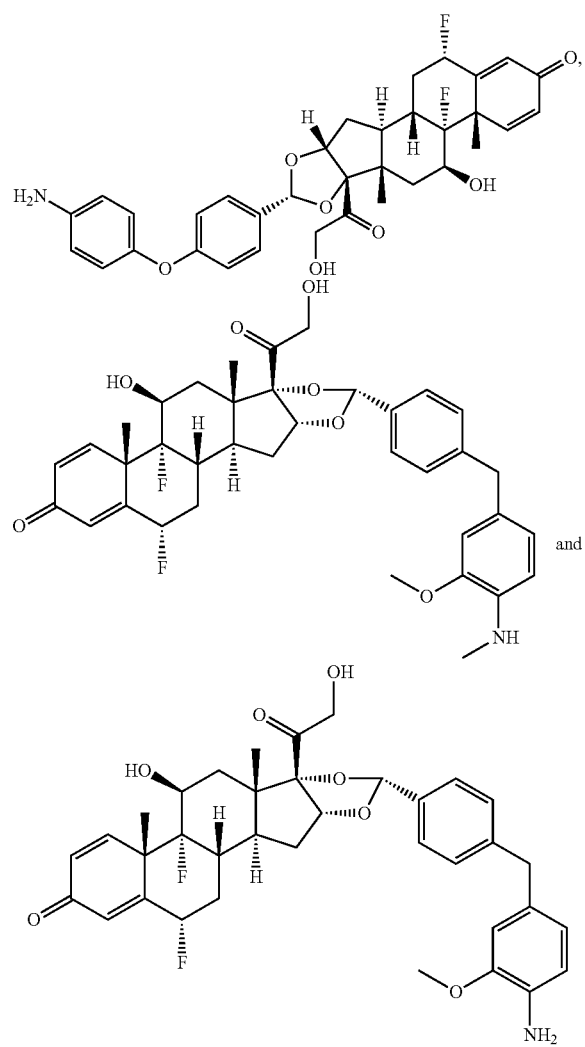

and

Emb 192. The compound of Emb 142, or a pharmaceutically acceptable salt or solvate thereof, which is any one of the compounds of Table XI, wherein $R^{7b}$ is selected from the group consisting of $R^{7b}$-4, $R^{7b}$-5 and $R^{7b}$-6.

Emb 193. The compound of Emb 192, or a pharmaceutically acceptable salt or solvate thereof, wherein $R^{7b}$ is $R^{b}$-4.

Emb 194. The compound of Emb 192, or a pharmaceutically acceptable salt or solvate thereof, wherein $R^{7b}$ is $R^{b}$-5.

Emb 195. The compound of Emb 192, or a pharmaceutically acceptable salt or solvate thereof, wherein $R^{7b}$ is $R^{b}$-6.

Emb 196. The compound of Emb 142, or a pharmaceutically acceptable salt or solvate thereof, which is any one of the chemical structures of Table XI, wherein $R^{7b}$ any one of the structures of Table IX.

Emb 197. The compound of Emb 142, or a pharmaceutically acceptable salt or solvate thereof, which is any one of the compounds of Table XII.

Emb 198. A pharmaceutical composition comprising the compound of any one of Embs 142-197, or a pharmaceutically acceptable salt or solvate thereof, wherein $R^{7b}$ is hydrogen, and a pharmaceutically acceptable carrier.

Emb 199. A method for treating an autoimmune or inflammatory disease in a patient in need thereof, the method comprising administering to said patient the compound of any one of Embs 142-197, or a pharmaceutically acceptable salt or solvate thereof, wherein $R^{7b}$ is hydrogen, or the pharmaceutical composition of Emb 198.

Emb 200. The method of Emb 199, wherein said autoimmune disease is rheumatoid arthritis, juvenile idiopathic arthritis, psoriatic arthritis, ankylosing spondylitis, adult Crohn's disease, pediatric Crohn's disease, ulcerative colitis, plaque psoriasis, or hidradenitis suppurativa.

Emb 201. A method of making a compound having Formula I-c, or a pharmaceutically acceptable salt or solvate thereof, wherein: $A^1$ is an anti-tumor necrosis factor (TNF) alpha protein; L is a linker; n is 1-10; and SM is a radical of a glucocorticosteroid, the method comprising: a) conjugating a compound having Formula X with an anti-tumor necrosis factor (TNF) alpha protein; and b) isolating the compound having Formula I-c, or a pharmaceutically acceptable salt or solvate thereof.

Emb 202. The method of Emb 201 further comprising hydrolyzing the compound having Formula Ic to give a compound having Formula I-d.

Emb 203. A method of making a compound having Formula I-e, or a pharmaceutically acceptable salt or solvate thereof, wherein: $A^1$ is an anti-tumor necrosis factor (TNF) alpha protein; L is a linker; $R^{7a}$ is selected from the group consisting of hydrogen and $C_{1-4}$ alkyl; n is 1-10; m is 1, 2, 3, 4, 5, or 6; and SM is a radical of a glucocorticosteroid, the method comprising: a) conjugating a compound having Formula XI, with an anti-tumor necrosis factor (TNF) alpha protein; and b) isolating the compound having Formula I-e, or a pharmaceutically acceptable salt or solvate thereof.

Emb 204. The method of Emb 203 further comprising hydrolyzing the compound having Formula I-e to give a compound having Formula I-f.

Emb 205. The compound of Emb 182, which is

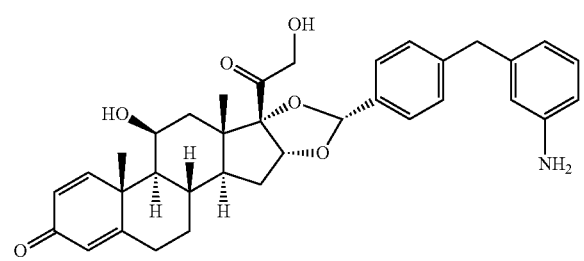

or a pharmaceutically acceptable salt or solvate thereof.

Emb 206. The compound of Emb 182, which is

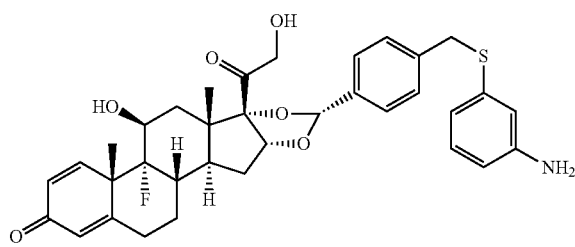

or a pharmaceutically acceptable salt or solvate thereof.

Emb 207. The compound of Emb 182, which is

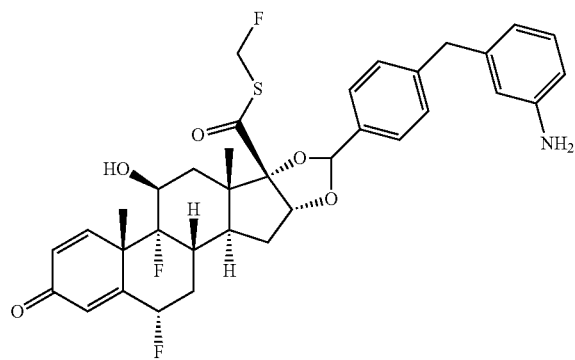

or a pharmaceutically acceptable salt or solvate thereof.

Emb 208. The compound of Emb 189, which is

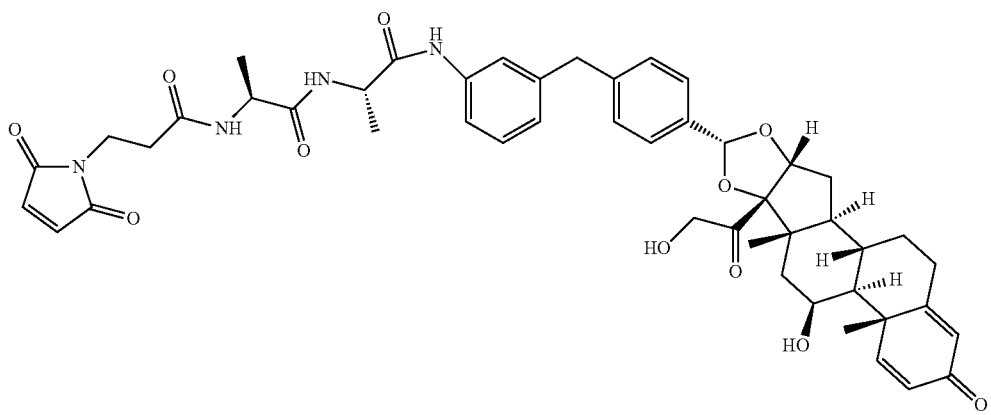

or a pharmaceutically acceptable salt or solvate thereof.

Emb 209. The compound of Emb 132, or a pharmaceutically acceptable salt or solvate thereof, which is any one of the chemical structures of Table IV, wherein A is $A^1$ or $A^2$.

The disclosure also provides Embs I-XXXIII as particular embodiments. The Formulae and Tables referred to these particular embodiments that are not shown in Embs I-XXXII are set forth in the description above.

Emb I. A compound having Formula I-a:

$$(SM-L-Q)_n-A^1 \quad \text{I-a}$$

wherein: $A^1$ is an anti-tumor necrosis factor (TNF) alpha protein; L is a linker; Q is a heterobifunctional group or heterotrifunctional group; or Q is absent; n is 1-10; and SM is a monovalent radical of a glucocorticosteroid.

Emb II. A compound having Formula I-b:

$$(SM-L-Q)_n-A^2 \quad \text{I-b}$$

wherein $A^2$ is a protein; L is a linker; Q is a heterobifunctional group or heterotrifunctional group; or Q is absent; n is 1-10; and SM is a radical of a glucocorticosteroid having Formula II-m or Formula II-p; $R^1$ is selected from the group consisting of hydrogen and halo; $R^2$ is selected from the group consisting of hydrogen, halo, and hydroxy; $R^3$ is selected from the group consisting of —CH$_2$OH, —CH$_2$SH, —CH$_2$Cl, —SCH$_2$Cl, —SCH$_2$F, —SCH$_2$CF$_3$, hydroxy, —OCH$_2$CN, —OCH$_2$Cl, —OCH$_2$F, —OCH$_3$, —OCH$_2$CH$_3$, —SCH$_2$CN,

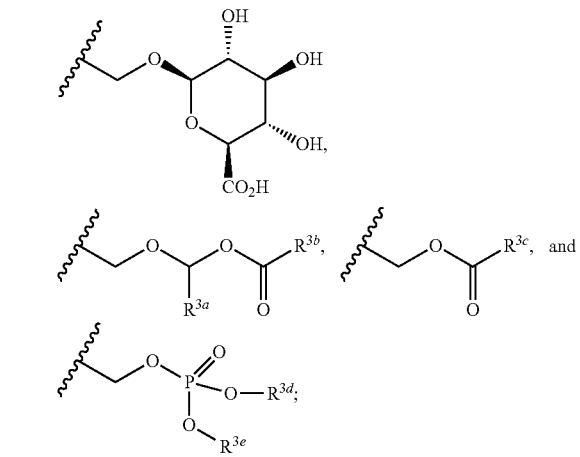

$R^{3a}$ is selected from the group consisting of hydrogen and $C_{1-4}$ alkyl; $R^{3b}$ is selected from the group consisting of $C_{1-4}$ alkyl and $C_{1-4}$ alkoxy; $R^{3c}$ is selected from the group consisting of hydrogen, $C_{1-4}$ alkyl, —CH$_2$OH, and $C_{1-4}$ alkoxy; $R^{3d}$ and $R^{3e}$ are independently selected from hydrogen and $C_{1-4}$ alkyl; $R^{6a}$, $R^{6b}$, $R^{6c}$, $R^{6d}$, and $R^{6e}$ are each independently selected from the group consisting of hydrogen, halo, $C_{1-4}$ alkyl, $C_{1-4}$ haloalkyl, cyano, hydroxy, thiol, amino, alkylthio, and alkoxy; X is selected from the group consisting of —(CR$^{4a}$R$^{4b}$)$_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent; $Y^2$ is selected from the group consisting of —O—, —S—, and —N(R$^{7a}$)—; or Y$^2$ is absent; t is 1 or 2; Z is selected from the group consisting of =CR$^{11a}$— and =N—; each R$^{4a}$ and R$^{4b}$ are independently selected from the group consisting of hydrogen and C$_{1-4}$ alkyl; or R$^{4a}$ and R$^{4b}$ taken together with the carbon atom to which they are attached form a 3- to 6-membered cycloalkyl; R$^{4c}$ and R$^{4d}$ are independently selected from the group consisting of hydrogen and C$_{1-4}$ alkyl; R$^5$ is selected from the group consisting of hydrogen and C$_{1-4}$ alkyl; R$^{7a}$ is selected from the group consisting of hydrogen and C$_{1-4}$ alkyl; R$^{8a}$ and R$^{8b}$ are independently selected from the group consisting of hydrogen and C$_{1-4}$ alkyl; R$^{9f}$ is selected from the group consisting of hydrogen and C$_{1-4}$ alkyl; R$^{11a}$ and R$^{11b}$ are independently selected from the group consisting of hydrogen, halo, C$_{1-4}$ alkyl, C$_{1-4}$ haloalkyl, cyano, hydroxy, thiol, amino, alkylthio, and alkoxy; and === represents a single or double bond.

Emb III. The compound of Embs I or II, wherein SM is a radical of a glucocorticosteroid having Formula II-m; R$^1$ is selected from the group consisting of hydrogen and halo; R$^2$ is selected from the group consisting of hydrogen, halo, and hydroxy; R$^3$ is selected from the group consisting of —CH$_2$OH, —CH$_2$SH, —CH$_2$Cl, —SCH$_2$Cl, —SCH$_2$F, —SCH$_2$CF$_3$, hydroxy, —OCH$_2$CN, —OCH$_2$Cl, —OCH$_2$F, —OCH$_3$, —OCH$_2$CH$_3$, —SCH$_2$CN,

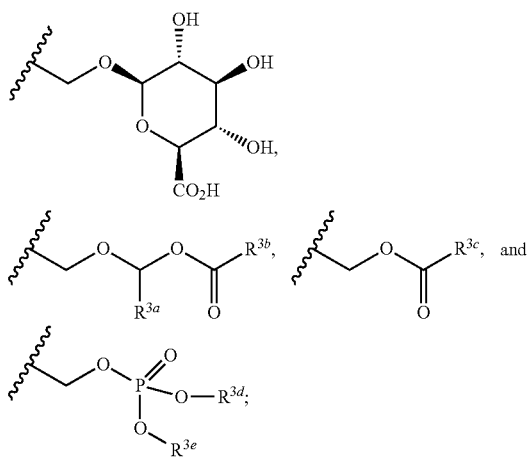

R$^{3a}$ is selected from the group consisting of hydrogen and C$_{1-4}$ alkyl; R$^{3b}$ is selected from the group consisting of C$_{1-4}$ alkyl and C$_{1-4}$ alkoxy; R$^{3c}$ is selected from the group consisting of hydrogen, C$_{1-4}$ alkyl, —CH$_2$OH, and C$_{1-4}$ alkoxy; R$^{3d}$ and R$^{3e}$ are independently selected from hydrogen and C$_{1-4}$ alkyl; R$^{6a}$, R$^{6c}$, R$^{6d}$, and R$^{6e}$ are each independently selected from the group consisting of hydrogen, halo, C$_{1-4}$ alkyl, C$_{1-4}$ haloalkyl, cyano, hydroxy, thiol, amino, alkylthio, and alkoxy; X is selected from the group consisting of —(CR$^{4a}$R$^{4b}$)$_t$—, —O—, —O—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, and —C≡C—; or X is absent; Y$^2$ is selected from the group consisting of —O—, —S—, and —N(R$^{7a}$)—; or Y$^2$ is absent; t is 1 or 2; Z is =CH—; each R$^{4a}$ and R$^{4b}$ are independently selected from the group consisting of hydrogen and C$_{1-4}$ alkyl; or R$^{4a}$ and R$^{4b}$ taken together with the carbon atom to which they are attached form a 3- to 6-membered cycloalkyl; R$^{4c}$ and R$^{4d}$ are independently selected from the group consisting of hydrogen and C$_{1-4}$ alkyl; R$^5$ is selected from the group consisting of hydrogen and C$_{1-4}$ alkyl; R$^{7a}$ is selected from the group consisting of hydrogen and C$_{1-4}$ alkyl; R$^{8a}$ and R$^{8b}$ are independently selected from the group consisting of hydrogen and C$_{1-4}$ alkyl; R$^{9f}$ is selected from the group consisting of hydrogen and C$_{1-4}$ alkyl; R$^{11b}$ is selected from the group consisting of hydrogen, halo, C$_{1-4}$ alkyl, C$_{1-4}$ haloalkyl, cyano, hydroxy, thiol, amino, alkylthio, and alkoxy; and === represents a single or double bond.

Emb IV. The compound of Embs II or III, wherein === represents a double bond; R$^1$ is selected from the group consisting of hydrogen and fluoro; R$^2$ is selected from the group consisting of hydrogen and fluoro; R$^3$ is selected from the group consisting of —CH$_2$OH, —CH$_2$Cl, —SCH$_2$Cl, —SCH$_2$F, and

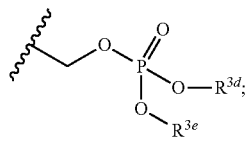

R$^{3d}$ and R$^{3e}$ are independently selected from the group consisting of hydrogen, methyl, and ethyl; R$^{6a}$, R$^{6c}$, R$^{6d}$, and R$^{6e}$ are hydrogen; X is selected from the group consisting of —CH$_2$—, —O—, —S—, —S(=O)—, —S(=O)$_2$—, —CH$_2$S—, and —N(H)CH$_2$—; Y$^2$ is —N(H)—; Z is =CH—; R$^{9f}$ is hydrogen; and R$^{11b}$ is hydrogen.

Emb V. The compound of any one of Embs I-IV, wherein L is a linker comprising a dipeptide.

Emb VI. The compound of any one of Embs I-V, wherein Q is a heterobifunctional group selected from the group consisting of Q-3 and Q-4 and m is 1, 2, 3, or 4.

Emb VII. The compound of any one of Embs I-VII, wherein -L-Q- is LQ-7; m is 2 or 3; and R$^{10a}$ and R$^{10b}$ are independently selected from the group consisting of hydrogen and C$_{1-4}$ alkyl.

Emb VIII. The compound of any one of Embs I-VII, wherein n is 2-5.

Emb IX. The compound of Embs I or II, wherein SM is a monovalent radical of a glucocorticosteroid which is any one of the compounds of Table II.

Emb X. The compound of any one of Embs I or III-IX, wherein A$^1$ is (i) an antibody or antigen-binding fragment thereof that binds to human TNF alpha or (ii) a soluble TNF receptor.

Emb XI. The compound of any one of Embs I or III-X, wherein A$^1$ is selected from the group consisting of adalimumab, infliximab, certolizumab pegol, afelimomab, nerelimomab, ozoralizumab, placulumab, and golimumab.

Emb XII. The compound of Emb I, which is any one or more of the compounds of Table III, wherein n is 1-5; A is A$^1$; and A$^1$ is selected from the group consisting of adalimumab, infliximab, certolizumab pegol, afelimomab, nerelimomab, ozoralizumab, placulumab, and golimumab.

Emb XIII. The compound of Emb II, which is any one or more of the compounds of Table III, wherein n is 1-5; A is A$^2$; and A$^2$ is selected from the group consisting of antibody, an antigen-binding fragment thereof, or a soluble receptor protein.

Emb XIV. A compound selected from the group consisting of:

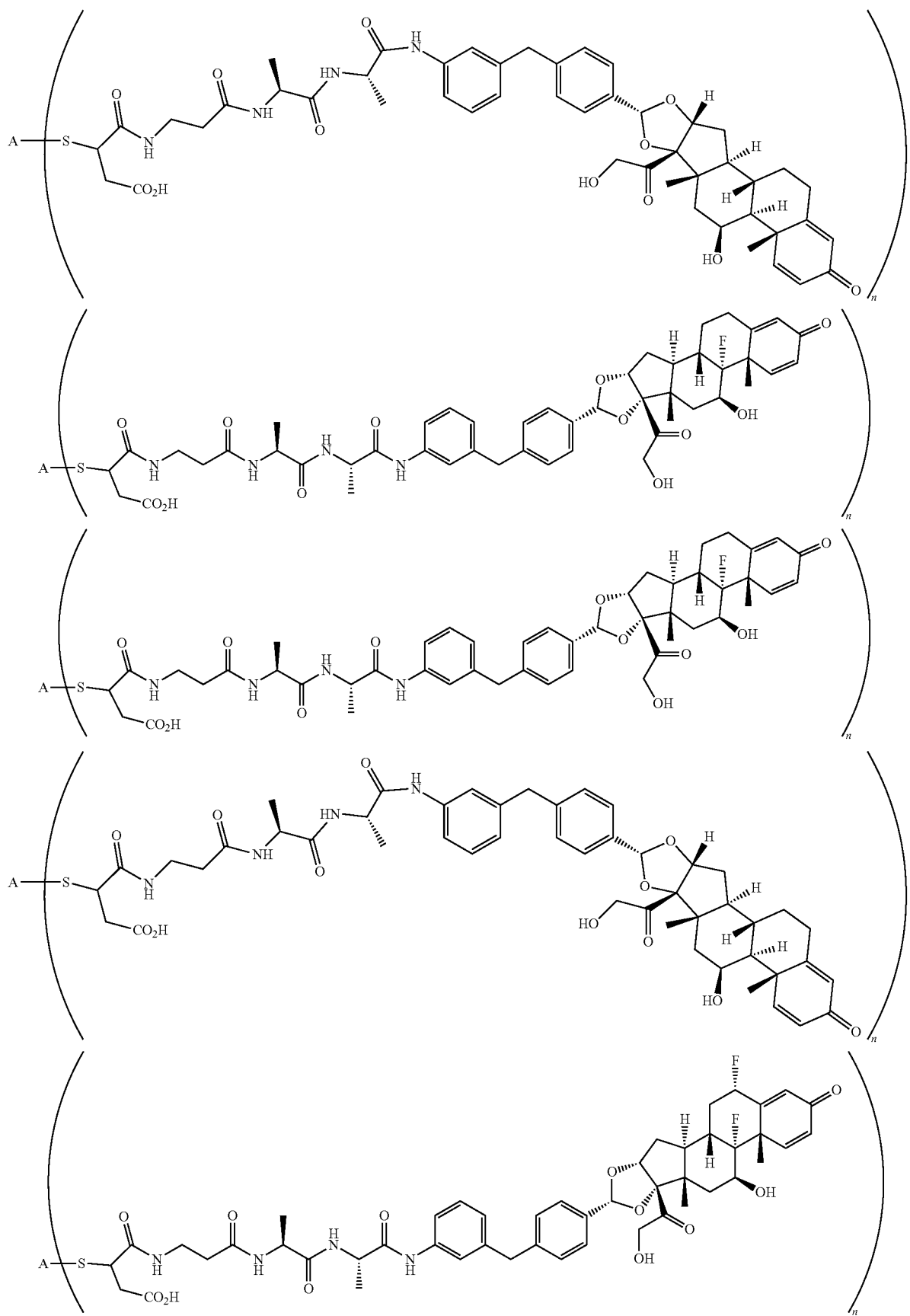

-continued
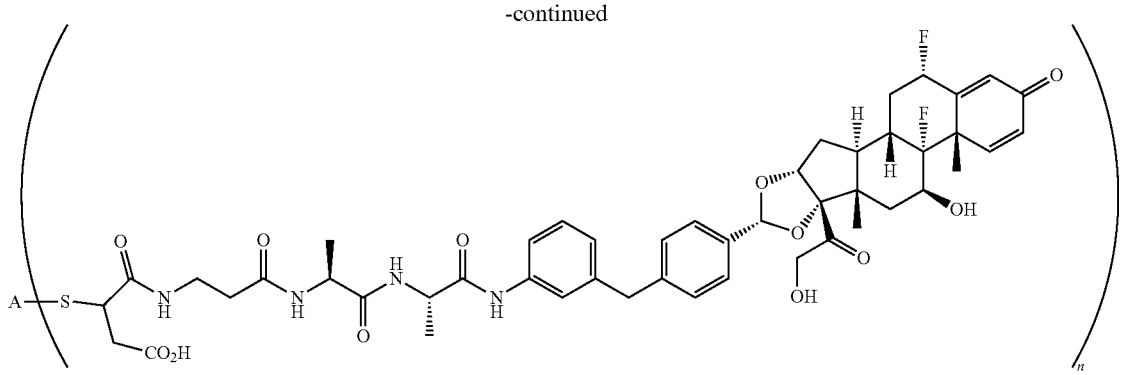
wherein n is 1-5 and A is an antibody comprising the heavy and light chain sequences of SEQ ID NO:66 and SEQ ID NO:73, respectively.
Emb XV. The compound of Emb XIV selected from the group consisting of:
| Structure | n |
|---|---|
| | 4 |
| 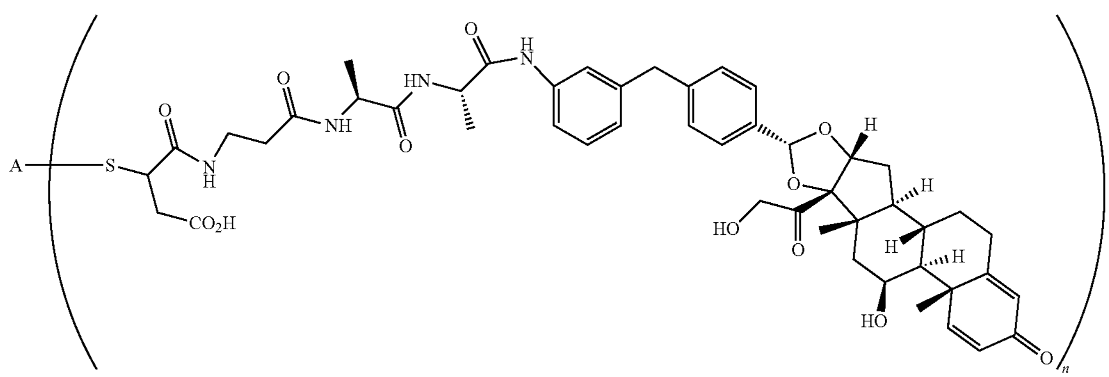 | 2 |
| | 4 |

| Structure | n |
|---|---|
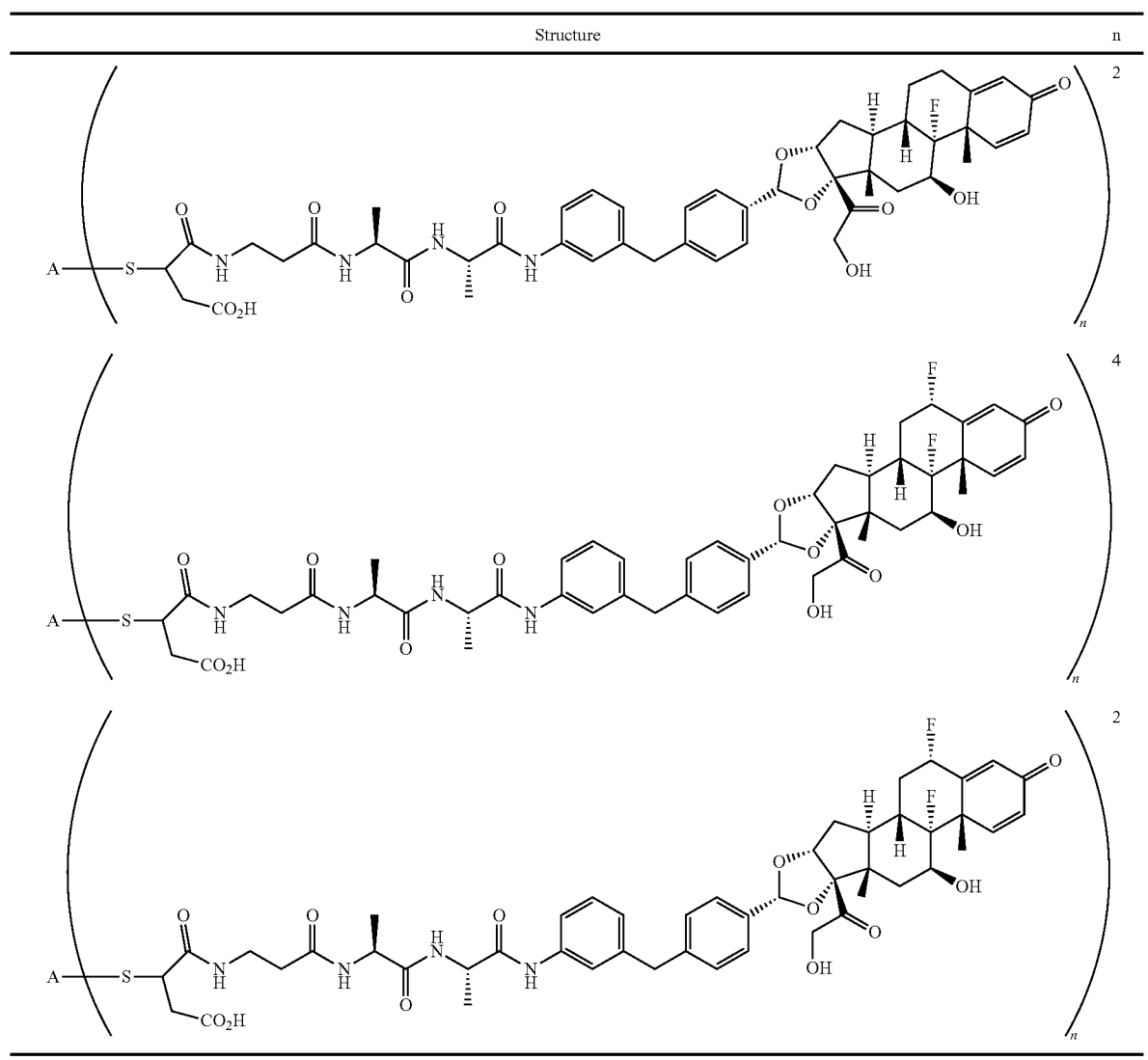
Emb XVI. The compound of Emb XIV, wherein the compound is
| Structure | n |
|---|---|
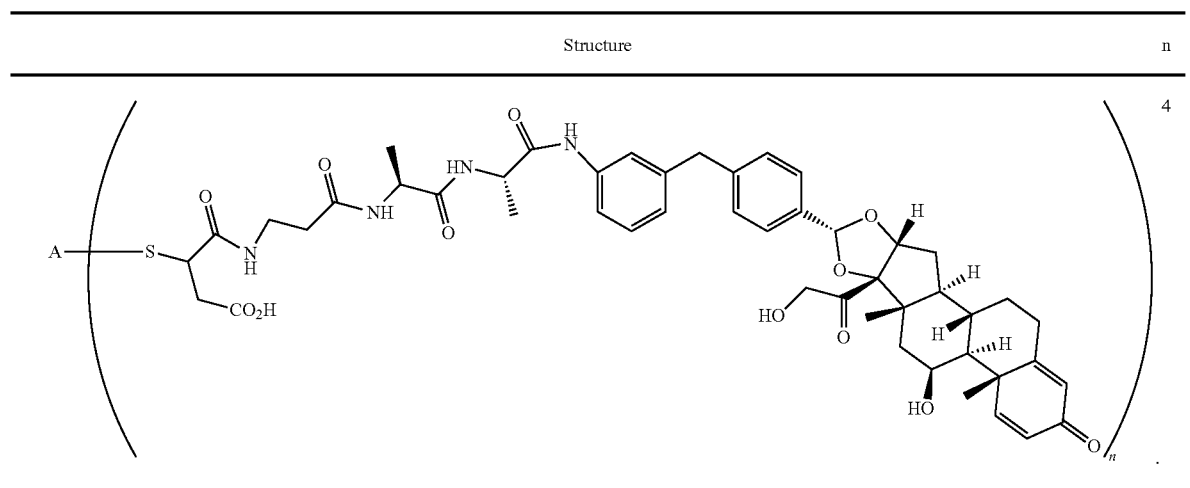

Emb XVII. The compound of Emb XIV, wherein the compound is
| Structure | n |
|---|---|
| 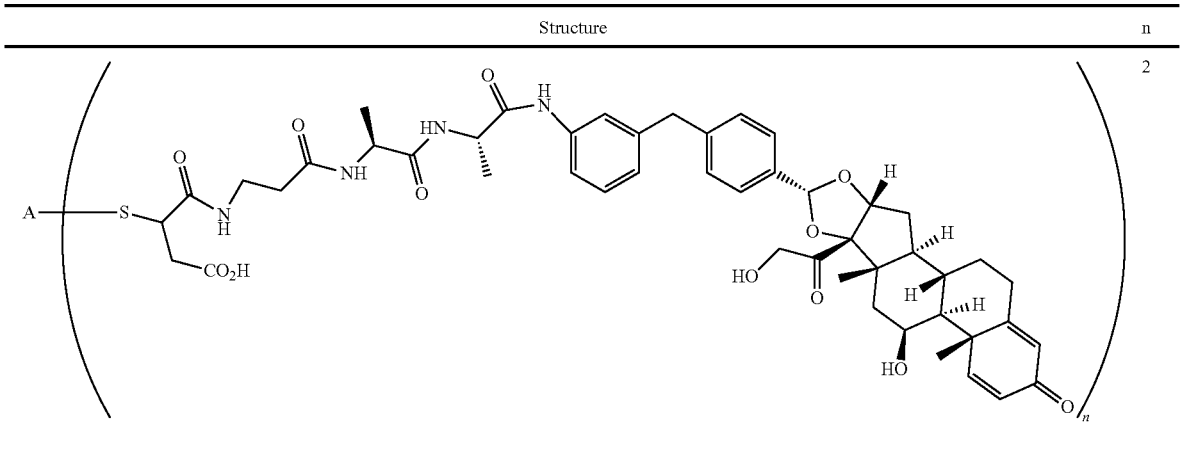 | 2 |
Emb XVIII. The compound of Emb XIV, wherein the compound is
| Structure | n |
|---|---|
| 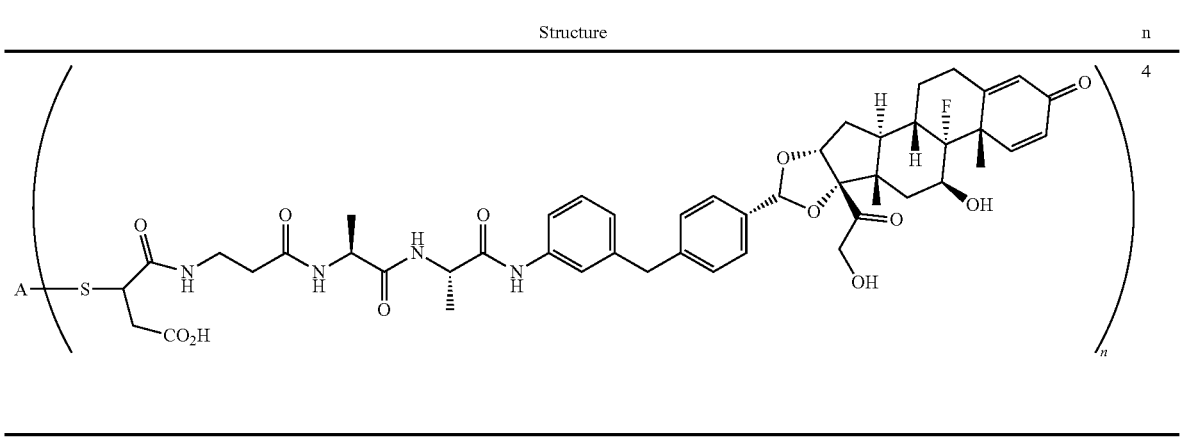 | 4 |
Emb XIX. The compound of Emb XIV, wherein the compound is
| Structure | n |
|---|---|
| 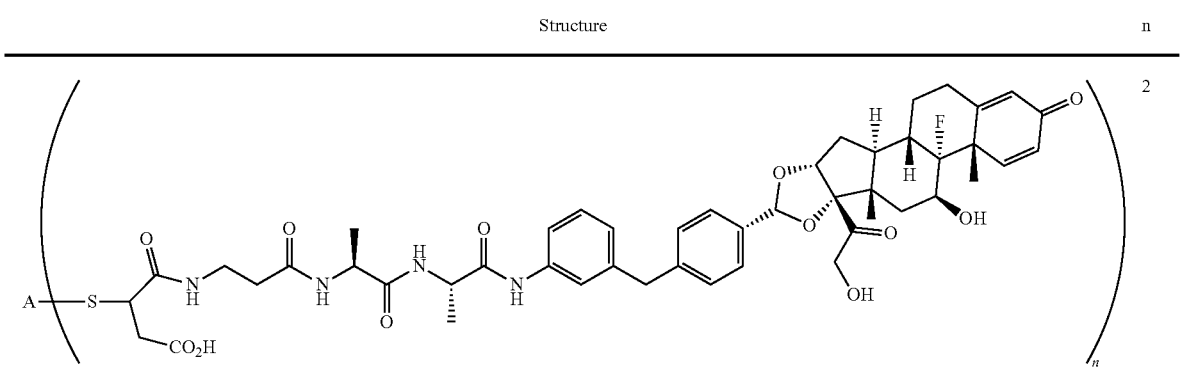 | 2 |

Emb. XX. The compound of Emb XIV, wherein the compound is

| Structure | n |
|---|---|
| 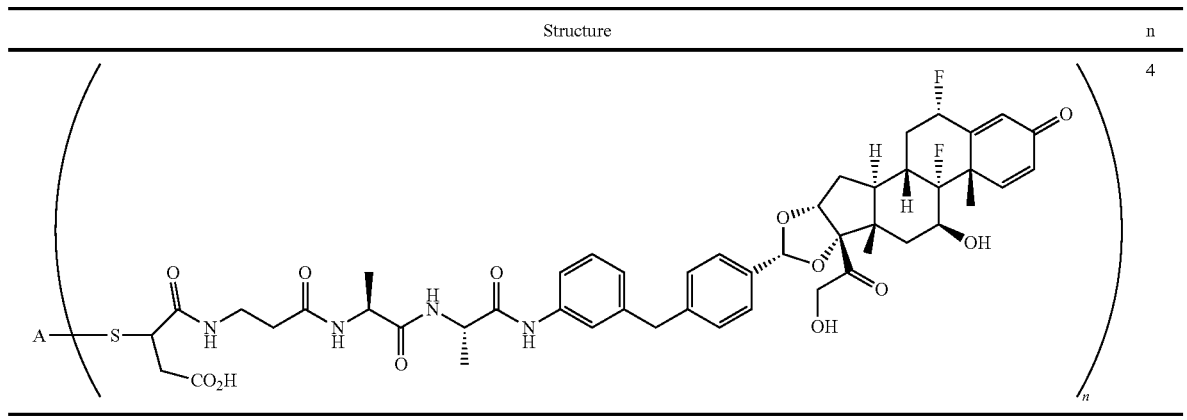 | 4 |

Emb. XXI. The compound of Emb XIV, wherein the compound is

| Structure | n |
|---|---|
| 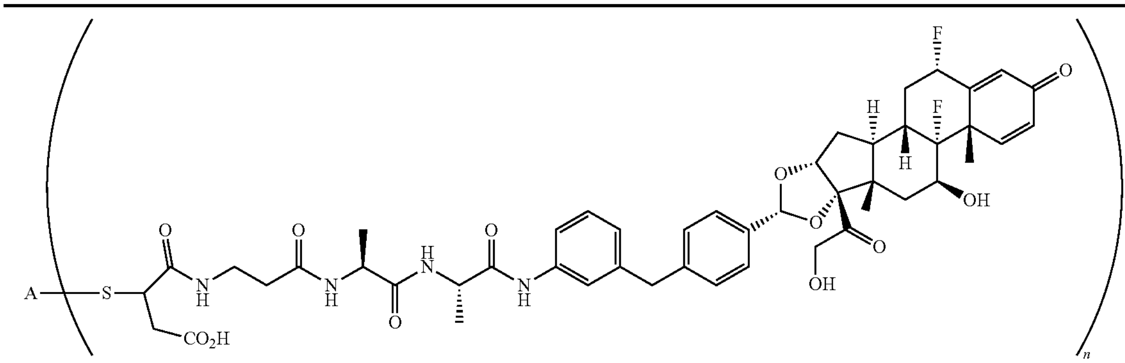 | 2 |

Emb XXII. A pharmaceutical composition comprising the compound of any one of Embs I-XXI, and a pharmaceutically acceptable carrier.

Emb XXIII. A method for treating an autoimmune disease in a patient in need thereof comprising administering to said patient the compound of any one of Embs I-XXI or the pharmaceutical composition of Emb XXII, optionally wherein said autoimmune disease is rheumatoid arthritis, juvenile idiopathic arthritis, psoriatic arthritis, ankylosing spondylitis, adult Crohn's disease, pediatric Crohn's disease, ulcerative colitis, plaque psoriasis, hidradenitis suppurativa, uveitis, Behcets disease, a spondyloarthropathy, or psoriasis.

Emb XXIV. A compound having Formula VII, or a pharmaceutically acceptable salt or solvate thereof, wherein $R^1$ is selected from the group consisting of hydrogen and halo; $R^2$ is selected from the group consisting of hydrogen, halo, and hydroxy; $R^3$ is selected from the group consisting of —$CH_2OH$, —$CH_2SH$, —$CH_2Cl$, —$SCH_2Cl$, —$SCH_2F$, —$SCH_2CF_3$, —$CH_2OS(=O)_2OH$, hydroxy, —$OCH_2CN$, —$OCH_2Cl$, —$OCH_2F$, —$OCH_3$, —$OCH_2CH_3$, —$SCH_2CN$,

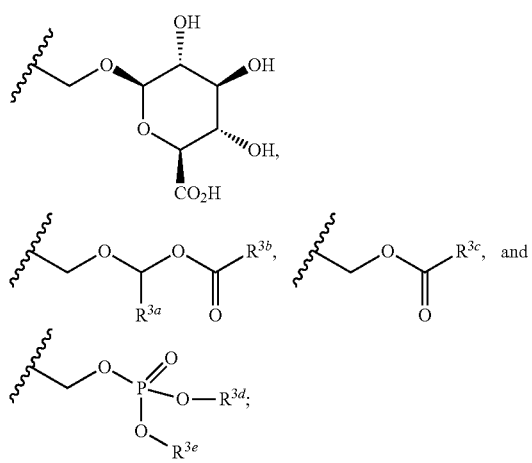

$R^{3a}$ is selected from the group consisting of hydrogen and $C_{1-4}$ alkyl; $R^{3b}$ is selected from the group consisting of $C_{1-4}$ alkyl and $C_{1-4}$ alkoxy; $R^{3C}$ is selected from the group consisting of hydrogen, $C_{1-4}$ alkyl, —$CH_2OH$, $C_{1-4}$ alkoxy, —$CH_2$(amino), and —$CH_2CH_2C(=O)OR^{3f}$; $R^{3d}$ and $R^{3e}$ are independently selected from the group consisting of hydrogen and $C_{1-4}$ alkyl; $R^{3f}$ is selected from the group consisting of hydrogen and $C_{1-4}$ alkyl; X is selected from the group consisting of —$(CR^{4a}R^{4b})_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, —C≡C—, —N(R$^5$)C(=O)—, and —OC(=O)—; or X is absent; t is 1 or 2; Z is selected from the group consisting of =CR$^{11a}$— and =N—; each R$^{4a}$ and R$^{4b}$ are independently selected from the group consisting of hydrogen and $C_{1-4}$ alkyl; or R$^{4a}$ and R$^{4b}$ taken together with the carbon atom to which they are attached form a 3- to 6-membered cycloalkyl; R$^{4c}$ and R$^{4d}$ are independently selected from the group consisting of hydrogen and $C_{1-4}$ alkyl; R$^5$ is selected from the group consisting of hydrogen and $C_{1-4}$ alkyl; R$^{6a}$, R$^{6b}$, R$^{6c}$, and R$^{6d}$ are each independently selected from the group consisting of hydrogen, halo, $C_{1-4}$ alkyl, haloalkyl, cyano, hydroxy, thiol, amino, alkylthio, and alkoxy; R$^{7a}$ is selected from the group consisting of hydrogen and $C_{1-4}$ alkyl; R$^{7b}$ is selected from the group consisting of hydrogen, -L-H, -L-PG,

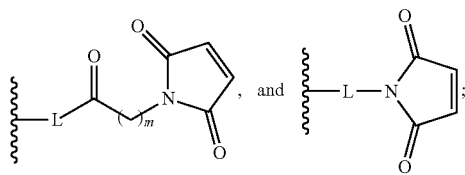, and or R$^{7a}$ and R$^{7b}$ taken together with the nitrogen atom to which they are attached form:

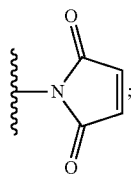 [SMILES: *N1C(=O)C=CC1=O];

or R$^{7a}$ and R$^{7b}$ taken together with the nitrogen atom to which they are attached form a nitro (—NO$_2$) group; m is 1, 2, 3, 4, 5, or 6; L is a linker; PG is a protecting group; R$^{9f}$ is selected from the group consisting of hydrogen and $C_{1-4}$ alkyl; R$^{8a}$ and R$^{8b}$ are independently selected from the group consisting of hydrogen and $C_{1-4}$ alkyl; R$^{11a}$ and R$^{11b}$ are independently selected from the group consisting of hydrogen, halo, $C_{1-4}$ alkyl, $C_{1-4}$ haloalkyl, cyano, hydroxy, thiol, amino, alkylthio, and alkoxy; and === represents a single or double bond Emb XXV. A compound having Formula VII-A or Formula VII-B:

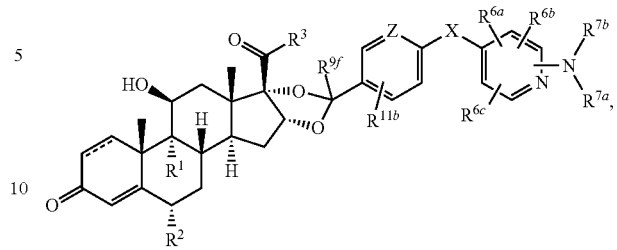

VII-A

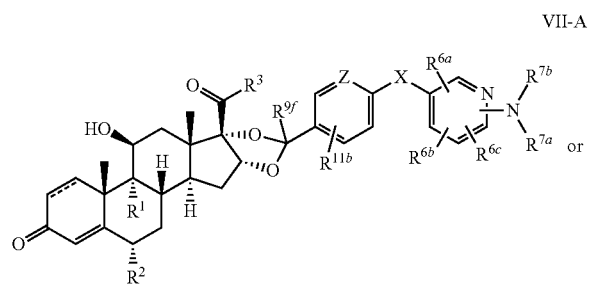

VII-B or a pharmaceutically acceptable salt or solvate thereof, wherein:

R$^1$ is selected from the group consisting of hydrogen and halo;

R$^2$ is selected from the group consisting of hydrogen, halo, and hydroxy;

R$^3$ is selected from the group consisting of —CH$_2$OH, —CH$_2$SH, —CH$_2$Cl, —SCH$_2$Cl, —SCH$_2$F, —SCH$_2$CF$_3$, —CH$_2$OS(=O)$_2$OH, hydroxy, —OCH$_2$CN, —OCH$_2$Cl, —OCH$_2$F, —OCH$_3$, —OCH$_2$CH$_3$, —SCH$_2$CN,

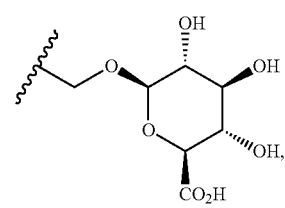

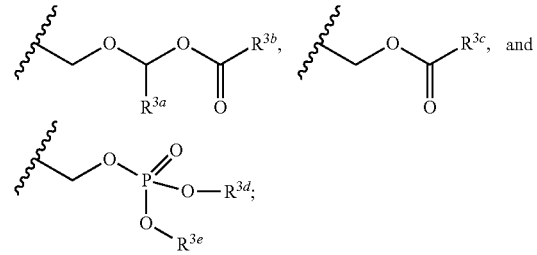, and

R$^{3a}$ is selected from the group consisting of hydrogen and $C_{1-4}$ alkyl;

R$^{3b}$ is selected from the group consisting of $C_{1-4}$ alkyl and $C_{1-4}$ alkoxy;

R$^{3c}$ is selected from the group consisting of hydrogen, $C_{1-4}$ alkyl, —CH$_2$OH, $C_{1-4}$ alkoxy, —CH$_2$(amino), and —CH$_2$CH$_2$C(=O)OR$^3$;

R$^{3d}$ and R$^{3e}$ are independently selected from the group consisting of hydrogen and $C_{1-4}$ alkyl;

R$^{3f}$ is selected from the group consisting of hydrogen and $C_{1-4}$ alkyl; X is selected from the group consisting of —$(CR^{4a}R^{4b})_t$—, —O—, —S—, —S(=O)—, —S(=O)$_2$—, —NR$^5$—, —CH$_2$S—, —CH$_2$O—, —N(H)C(R$^{8a}$)(R$^{8b}$)—, —CR$^{4c}$=CR$^{4d}$—, —C≡C—, —N(R$^5$)C(=O)—, and —OC(=O)—; or X is absent;

t is 1 or 2;

Z is selected from the group consisting of =CR$^{11a}$— and =N—;

each R$^{4a}$ and R$^{4b}$ are independently selected from the group consisting of hydrogen and $C_{1-4}$ alkyl; or R$^{4a}$ and R$^{4b}$ taken together with the carbon atom to which they are attached form a 3- to 6-membered cycloalkyl;

$R^{4c}$ and $R^{4d}$ are independently selected from the group consisting of hydrogen and $C_{1-4}$ alkyl;

$R^5$ is selected from the group consisting of hydrogen and $C_{1-4}$ alkyl;

$R^{6a}$, $R^{6b}$, and $R^{6c}$ are each independently selected from the group consisting of hydrogen, halo, $C_{1-4}$ alkyl, haloalkyl, cyano, hydroxy, thiol, amino, alkylthio, and alkoxy;

$R^{7a}$ is selected from the group consisting of hydrogen and $C_{1-4}$ alkyl;

$R^{7b}$ is selected from the group consisting of hydrogen, -L-H, -L-PG,

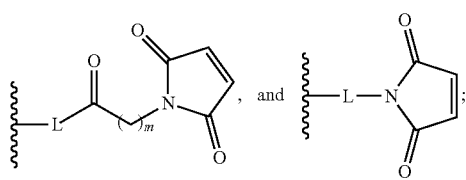

or $R^{7a}$ and $R^{7b}$ taken together with the nitrogen atom to which they are attached form:

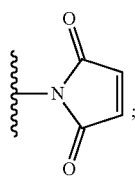

m is 1, 2, 3, 4, 5, or 6;
L is a linker;
PG is a protecting group;
$R^{9f}$ is selected from the group consisting of hydrogen and $C_{1-4}$ alkyl;
$R^{8a}$ and $R^{8b}$ are independently selected from the group consisting of hydrogen and $C_{1-4}$ alkyl;
$R^{11a}$ and $R^{1b}$ are independently selected from the group consisting of hydrogen, halo, $C_{1-4}$ alkyl, $C_{1-4}$ haloalkyl, cyano, hydroxy, thiol, amino, alkylthio, and alkoxy; and
=== represents a single or double bond.

Emb XXVI. The compound of Embs XXIV or XXV, or a pharmaceutically acceptable salt or solvate thereof, wherein $R^{7b}$ is selected from the group consisting of $R^{7b}$-1, $R^{7b}$-2, and $R^{7b}$-_3; m is 1, 2, 3, 4, 5, or 6; and $R^{10a}$ and $R^{10b}$ are each independently selected from the group consisting of hydrogen and optionally substituted $C_{1-6}$ alkyl.

Emb XXVII. The compound of Embs XXIV or XXVI, or a pharmaceutically acceptable salt or solvate thereof, having Formula VIII-a.

Emb XXVIII. The compound of any one of Embs XXIV-XXVII, or a pharmaceutically acceptable salt or solvate thereof, wherein === represents a double bond; $R^1$ is selected from the group consisting of hydrogen and fluoro; $R^2$ is selected from the group consisting of hydrogen and fluoro; $R^3$ is selected from the group consisting of —$CH_2OH$, —$CH_2Cl$, —$SCH_2Cl$, —$SCH_2F$, and

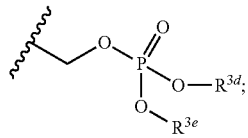

$R^{3d}$ and $R^{3e}$ are independently selected from the group consisting of hydrogen, methyl, and ethyl; Z is =CH—; $R^{6a}$, $R^{6b}$, $R^{6c}$, and $R^{6d}$ are hydrogen; $R^{7a}$ is hydrogen; X is selected from the group consisting of —$CH_2$—, —O—, —S—, —S(=O)—, —S(=O)$_2$—, —$CH_2S$—, and —N(H)$CH_2$—; $R^{9f}$ is hydrogen; and $R^{1b}$ is hydrogen.

Emb XXIX. The compound of any one of Embs XXIV-XXVIII, or a pharmaceutically acceptable salt or solvate thereof, wherein $R^{7b}$ is hydrogen.

Emb XXX. The compound of any one of Embs XXIV-XXVIII, or a pharmaceutically acceptable salt or solvate thereof, wherein $R^{7b}$ is $R^{7b}$-1.

Emb XXXI. The compound of any one of Embs XXIV-XXVIII, or a pharmaceutically acceptable salt or solvate thereof, wherein $R^{7b}$ is $R^{7b}$-_2, and PG is BOC.

Emb XXXII. The compound of any one of Embs XXIV-XXVIII, or a pharmaceutically acceptable salt or solvate thereof, wherein $R^{7b}$ is $R^{7b}$-3.

Emb XXXIII. The compound of Emb XXIX, or a pharmaceutically acceptable salt or solvate thereof, which is any one or more of the compounds of Table VI.

Emb XXXIV. The compound of Emb XXIX, or a pharmaceutically acceptable salt or solvate thereof, which is any one of the compounds of Table VII.

Emb XXXV. The compound of Emb XXXIII, or a pharmaceutically acceptable salt or solvate thereof, which is:

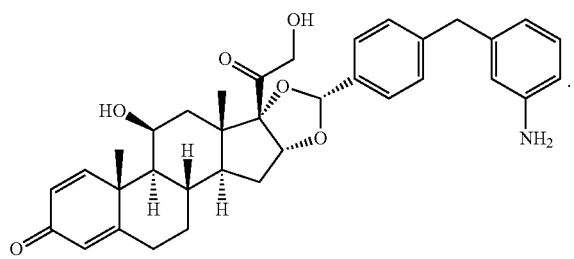

Emb XXXVI. The compound of Emb XXIV, or a pharmaceutically acceptable salt or solvate thereof, which is any one or more of the compounds of Table VIII, wherein $R^{7b}$ is selected from the group consisting of $R^{7b}$-4, $R^{7b}$-5, and $R^{7b}$-6.

Emb XXXVII. The compound of Emb XXIV, or a pharmaceutically acceptable salt or solvate thereof, which is any one or more of the compounds of Table X.

Emb XXXVIII. The compound of Emb XXXVII, or a pharmaceutically acceptable salt or solvate thereof, which is:

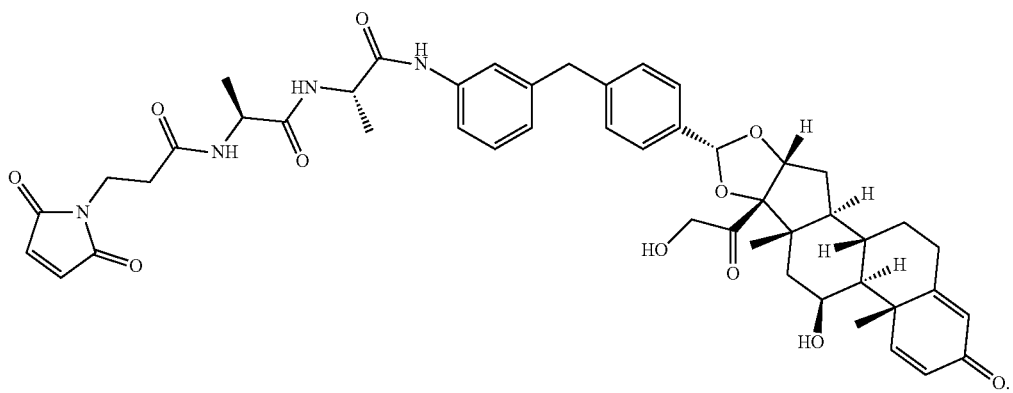

Emb XXXIX. A method of making a compound having Formula I-e:

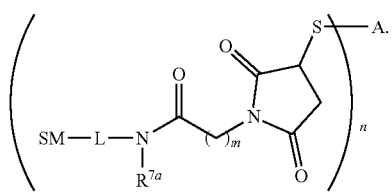

or a pharmaceutically acceptable salt or solvate thereof, wherein A is $A^1$ or $A^2$; $A^1$ is an anti-tumor necrosis factor (TNF) alpha protein; $A^2$ is a protein; L is a linker; $R^{7a}$ is selected from the group consisting of hydrogen and $C_{1-4}$ alkyl; n is 1-10; m is 1, 2, 3, 4, 5, or 6; and SM is a radical of a glucocorticosteroid,
the method comprising:
a) conjugating a compound having Formula XI:

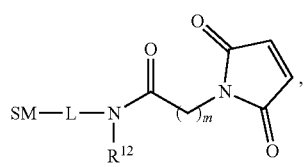

with an anti-tumor necrosis factor (TNF) alpha protein or a protein; and
b) isolating the compound having Formula I-e, or a pharmaceutically acceptable salt or solvate thereof.

Emb XL. The method of Emb XXXIV further comprising hydrolyzing the compound having Formula I-e to give a compound having Formula I-f:

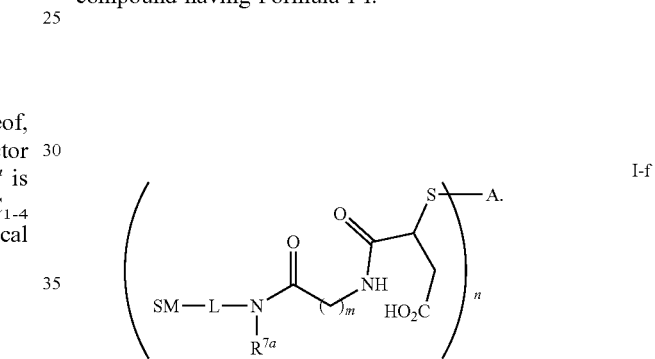

or a pharmaceutically acceptable salt or solvate thereof.
Emb XLI. A compound which is:

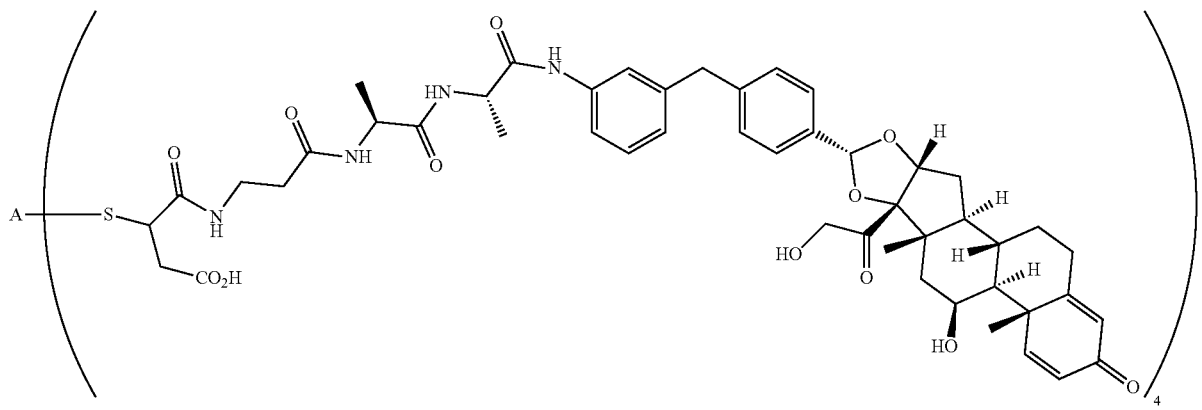

wherein A is adalimumab.
Emb XLII. A composition comprising the compound of Emb XLI.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

Examples

It is understood that the examples and embodiments described herein are for illustrative purposes only and that various modifications or changes in light thereof will be suggested to persons skilled in the art and are to be included within the spirit and purview of this disclosure.

Analytical Methods for Compound Synthesis and Characterization

Analytical data is included within the procedures below, in the illustrations of the general procedures, or in the tables of examples. Unless otherwise stated, all $^1$H and $^{13}$C NMR data were collected on a Varian Mercury Plus 400 MHz or a Bruker AVIII 300 MHz instrument; chemical shifts are quoted in parts per million (ppm). HPLC analytical data are either detailed within the experimental or referenced to the table of LC/MS and HPLC conditions, using the method provided in Table 7.

TABLE 7

List of LC/MS and GC/MS Methods

| Method | Conditions |
|---|---|
| a | The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% trifluoroactic acid in water, mobile phase B was 0.018% TFA in MeCN. The column used for the chromatography was a 2.0 × 50 mm phenomenex Luna-C18 column (5 µm particles). Detection methods are diode array (DAD) and evaporative light scattering (ELSD) detection as well as positive electrospray ionization(MS). |
| b | The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0 × 50 mm phenomenex Luna-C18 column (5 µm particles). Detection methods are diode array (DAD) and evaporative light scattering (ELSD) detection as well as positive electrospray ionization (MS). |
| c | The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% $CF_3CO_2H$ in water, mobile phase B was 0.018% $CF_3CO_2H$ in $CH_3CN$. The column used for the chromatography was a 2.0 × 50 mm phenomenex Luna-C18 column (5 µm particles). Detection methods are diode array (DAD) and evaporative light scattering (ELSD) detection as well as positive electrospray ionization (MS). |
| d | The gradient was 5% B for 0.2 min, and to 95% B within 1.7 min then with a hold at 95% B for 1.3 min, back to 5% B within 0.01 min (2.3 mL/min flow rate). Mobile phase A was 0.01% TFA in water, and mobile phase B was 0.01% TFA in HPLC grade MeCN. The column used for the chromatography was an XBridge C18 column (4.6 × 50 mm, 3.5 µm particles). Detection methods are diode array (DAD) and evaporative light scattering (ELSD) detection as well as positive/negative electrospray ionization |
| e | The gradient was 5% B to 95% B within 1.5 min then with a hold at 95% B for 1.5 min, back to 5% B within 0.01 min (2.3 mL/min flow rate). Mobile phase A was 10 mM $NH_4HCO_3$ in water, and mobile phase B was HPLC grade MeCN. The column used for the chromatography was a XBridge C18 column (4.6 × 50 mm, 3.5 µm particles). Detection methods are diode array (DAD) and evaporative light scattering (ELSD) detection as well as positive/negative electrospray ionization. |
| f | Mobile Phase: A: Water (0.01% TFA); B: MeCN (0.01% TFA). Gradient: 5% B increase to 95% B within 1.2 min, 95% B for 1.3 min, back to 5% B within 0.01 min, at a flow rate of 2.0 mL/min. Column: SunFire C18 (4.6 × 50 mm, 3.5 □m). Column Temp: 50° C. Detection: UV (214, 254 nm) and MS (ESI, Pos mode, 110 to 1000 amu) |
| g | The gradient was 5% B for 0.1 min, and to 95% B within 1.0 min then with a hold at 95% B for 0.9 min, back to 5% B within 0.01 min (3.0 mL/min flow rate). Mobile phase A was 0.05% TFA in water, and mobile phase B was 0.05% TFA in HPLC grade MeCN. The column used for the chromatography was a Zorbax SB-C18 Rapid Resolution HT column (4.6 × 30 mm, 1.8 µm particles). Detection methods are diode array (DAD) and evaporative light scattering (ELSD) detection as well as positive/negative electrospray ionization. |
| h | Mobile Phase: A: water (0.1% TFA); B: MeCN (0.1% TFA). Gradient: 5% B increase to 95% B within 1.3 min, 95% B for 1.5 min, back to 5% B within 0.01 min, at a flow rate of 2 mL/min. Column: Sunfire C18 (4.6 × 50 mm, 3.5 µm). Column Temperature: 50° C. |
| i | Mobile Phase: A: water (0.01% TFA); B: MeCN (0.01% TFA). Gradient: 5% B for 0.2 min, increase to 95% B within 1.5 min, 95% B for 1.5 min, back to 5% B within 0.01 min, at a flow rate of 2 mL/min. Column: Sunfire (50 × 4.6 mm, 3.5 µm). Column Temperature: 50° C. |
| j | Mobile phase: A: water (0.05% TFA); B: MeCn (0.05% TFA). Gradient: 5% increase to 100% of B in 1.3 min, at a flow rate of 2 mL/min. Column: SunFire C18 (4.6 × 50 mm, 3.5 µm). Detection: UV (214, 254 nm) and MS (ESI, Pos mode, 110 to 1000 amu). Column Temperature: 50° C. |
| k | Mobile Phase: A: water (10 mM $NH_4HCO_3$); B: MeCN. Gradient: 5% increase to 95% B in 1.5 min, at a flow rate of 1.8 mL/min. Column: XBridge C18 (4.6 × 50 mm, 3.5 µm). Column Temperature: 50° C. |

TABLE 7-continued

List of LC/MS and GC/MS Methods

| Method | Conditions |
|---|---|
| l | Mobile phase: A: water (10 mM NH₄HCO₃); B: MeCN. Gradient: 10% increase to 95% of B in 1.5 min, at a flow rate of 1.8 mL/min. Column: Xbridge C18(2) (4.6 × 50 mm, 3.5 µm). Column Temperature: 50° C. Detection: UV (214, 254 nm) and MS (ESI, Pos mode, 103 to 800 amu) |
| m | Mobile Phase: A: Water (0.01% TFA) B: MeCN (0.01% TFA). 5% B increase to 95% B within 1.2 min, 95% B for 1.3 min, back to 5% B within 0.01 min. Flow Rate: 2.0 mL/min. Column: SunFire C18, 4.6*50 mm, 3.5 □m. Column Temperature: 50° C. Detection: UV (214, 4 nm) and MS (ESI, Pos mode, 110 to 1000 amu). |
| n | The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% TFA in water. Mobile phase B was 0.018% TFA in CH₃CN. The column used for the chromatography was a Phenomenex Luna-C18 column (2.0 × 50 mm, 5 µm particles). Detection methods are diode array (DAD) and evaporative light scattering (ELSD) detection as well as positive electrospray ionization (MS). |
| o | A gradient of 5-100% MeCN (A) and 10 mM ammonium acetate in water (B) was used, at a flow rate of 1.5 mL/min (0-0.05 min 5% A, 0.05-1.2 min 5-100% A, 1.2-1.4 min 100% A, 1.4-1.5 min 100-5% A. 0.25 min post-run delay). |
| q | 2-coupled C8 5 um 100 Å Waters Sunfire columns (30 mm × 75 mm each). A gradient of MeCN (A) and 10 mM ammonium acetate in water (B) was used, at a flow rate of 50 mL/min (0-0.5 min 5% A, 0.5-8.5 min linear gradient X to Y % A, 8.7-10.7 min 100% A, 10.7-11 min linear gradient 100-05% A). Linear gradient is stated in the synthetic procedure of the compound. |
| r | A gradient of 5-100% MeCN (A) and 0.1% TFA in water (B) was used, at a flow rate of 1.5 mL/min (0-0.05 min 5% A, 0.05-1.2 min 5-100% A, 1.2-1.4 min 100% A, 1.4-1.5 min 100-5% A. 0.25 min post-run delay). |
| s | Analytical UPLC-MS was performed on a Waters SQD mass spectrometer and Acquity UPLC system running MassLynx 4.1 and Openlynx 4.1 software. The SQD mass spectrometer was operated under positive APCI ionization conditions. The column used was a Waters BEH C8, 1.7 µm (2.1 mm × 30 mm) at a temperature of 55° C. A gradient of 10-100% acetonitrile (A) and 10 mM ammonium acetate in water (B) was used, at a flow rate of 1.0 mL/min (0-0.1 min 10% A, 0.1-1.1 min 10-100% A, 1.1-1.3 min 100% A, 1.3-1.4 min 100-10% A). |

Abbreviations used in the examples that follow are:

| | |
|---|---|
| APCI | Atmospheric pressure chemical ionization |
| Bn | Benzyl |
| BOC | tert-butyloxycarbonyl |
| BSA | Bovine serum albumin |
| Cbz | Carbobenzyloxy |
| CuCN | Copper cyanide |
| D₂O | Deuterated water |
| DAD | Diode array |
| DCM | Dichloromethane |
| DIAD | Diisopropyl azodicarboxylate |
| DIPEA | N,N-Diisopropylethylamine |
| DMA | Dimethylacetamide |
| DMF | Dimethyl formamide |
| DMSO | Dimethyl sulfoxide |
| EIC | Extracted ion chromatogram |
| ELSD | Evaporative light scattering detector |
| Eq | Equivalent |
| Et₂O | Diethyl ether |
| EtOAc | Ethyl acetate |
| FMOC | 9-Fluorenylmethyloxycarbonyl |
| H | Hour(s) |
| H₂SO₄ | Sulfuric acid |
| HATU | 1-[Bis(dimethylamino)methylene]-1H-1,2,3-triazolo[4,5-b]pyridinium 3-oxid hexafluorophosphate |
| HCl | Hydrochloric acid |
| HEPES | 4-(2-hydroxyethyl)-1-piperazineethanesulfonic acid |
| HIC | Hydrophobic Interaction Chromatography |
| HPLC | High performance liquid chromatography |
| IBX | 2-Iodoxybenzoic acid |
| MeCN | Acetonitrile |
| MeOH | Methanol |
| MgSO₄ | Magnesium sulfate |
| Min | Minute(s) |
| MP-NaCNBH₃ | Sodium cyanoborohydride on solid support |
| MTBE | Dimethyl methyl tert-butyl ether |
| NaCN | Sodium cyanide |
| NaHCO₃ | Sodium hydrogen carbonate |
| NaHSO₃ | Sodium hydrogen sulfate |
| Na₂SO₄ | Sodium sulfate |
| NMR | Nuclear magnetic resonance |
| Pd₂dba₃ | tris(dibenzylideneacetone)dipalladium(0) |
| PBST | Phosphate Buffered Saline with Tween 20 |
| PE | Petroleum ether |
| PPh₃ | Triphenyl phosphine |
| RP | Reverse phase |
| R_t | Retention time |
| TBAF | Tetrabutylammonium flouride |
| TBS-Cl | tert-Butylchlorodimethylsilane |
| TFA | Trifluoroacetic acid |
| TLC | Thin layer chromatography |

Example 1: Synthesis of (2S,6aS,6bR,7S,8aS,8bS,10R,11aR,12aS,12bS)-10-(4-(4-aminophenoxy)phenyl)-2,6b-difluoro-7-hydroxy-8b-(2-hydroxyacetyl)-6a,8a-dimethyl-1,2,6a,6b,7,8,8a,8b, 11a,12,12a,12b-dodecahydro-4H-naphtho[2',1':4,5]indeno[1,2-d][1,3]dioxol-4-one Step 1: Synthesis of tert-butyl (4-(4-formylphenoxy)phenyl)carbamate

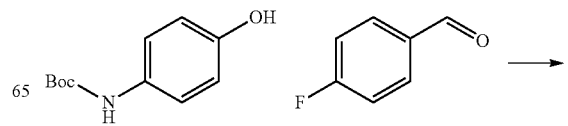

-continued

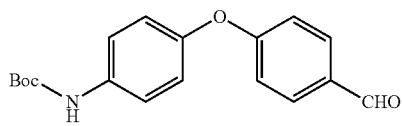

To a solution of tert-butyl (4-hydroxyphenyl)carbamate (10 g, 47.8 mmol) and 4-fluorobenzaldehyde (11.86 g, 96 mmol) in N,N-dimethylformamide (100 mL) was added potassium carbonate (39.6 g, 287 mmol). The mixture was stirred at 90° C. for 5 hours. One additional vial was set up as described above. All two reaction mixtures were combined and diluted with DCM (300 mL), then extracted with water (3×100 mL). The organic layer was washed with brine (100 mL) and dried over $Na_2SO_4$, filtered and concentrated under reduced pressure. The residue was purified by column chromatography (eluted with PE:EtOAc=30:1 to 5:1) to obtain the target compound (20 g, 63.8 mmol, 66.7% yield) as a yellow solid. $^1$H NMR (400 MHz, DMSO-$d_6$) δ 9.91 (s, 1H), 9.45 (s, 1H), 7.90 (d, J=8.6 Hz, 2H), 7.54 (d, J=8.8 Hz, 2H), 7.11-7.02 (m, 4H), 1.48 (s, 9H).

Step 2: Synthesis of (2S,6aS,6bR,7S,8aS,8bS,10R, 11aR,12aS,12bS)-10-(4-(4-aminophenoxy)phenyl)-2,6b-difluoro-7-hydroxy-8b-(2-hydroxyacetyl)-6a, 8a-dimethyl-1,2,6a,6b,7,8,8a,8b, 11a,12,12a,12b-dodecahydro-4H-naphtho[2',1':4,5]indeno[1,2-d][1, 3]dioxol-4-one

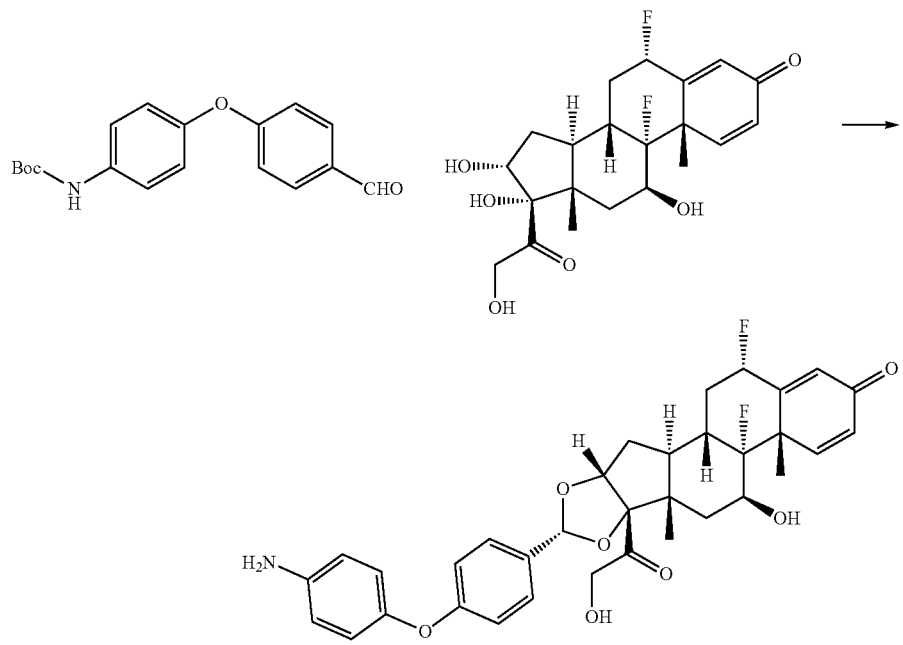

A suspension of (6S,8S,9R,10S,11S,13S,14S,16R,17S)-6, 9-difluoro-11,16,17-trihydroxy-17-(2-hydroxyacetyl)-10, 13-dimethyl-6,7,8,9,10,11,12,13,14,15,16,17-dodecahydro-3H-cyclopenta[a]phenanthren-3-one (4.5 g, 10.91 mmol) and magnesium sulfate (6.57 g, 54.6 mmol) in MeCN (100 mL) was allowed to stir at 20° C. for 1 hours A solution of tert-butyl (4-(4-formylphenoxy)phenyl)carbamate (3.42 g, 10.91 mmol) in MeCN (100 mL) was added in one portion. Trifluoromethanesulfonic acid (4.84 mL, 54.6 mmol) was added dropwise via syringe while maintaining an internal temperature of 25° C. using an ice bath. After the addition, the mixture was stirred at 20° C. for 2 hours. Three additional vials were set up as described above. All four reaction mixtures were combined and filtered, the filtrate was concentrated under reduced pressure to give a residue, which was purified by Prep-HPLC to obtain the target compound (7.5 g, 12.34 mmol, 28.8% yield) as a yellow solid. LCMS (Method a, Table 7) $R_t$=2.21 min; MS m/z=608.3 (M+H)+; $^1$H NMR (400 MHz, DMSO-$d_6$) δ 7.36 (d, J=8.6 Hz, 2H), 7.27 (d, J=10.1 Hz, 1H), 6.85 (d, J=8.6 Hz, 2H), 6.75 (d, J=8.6 Hz, 2H), 6.58 (d, J=8.6 Hz, 2H), 6.29 (dd, J=1.3, 10.1 Hz, 1H), 6.13 (s, 1H), 5.76-5.65 (m, 1H), 5.62-5.57 (m, 1H), 5.54 (d, J=3.1 Hz, 1H), 5.44 (s, 1H), 5.12 (t, J=5.8 Hz, 1H), 5.00 (s, 2H), 4.94 (d, J=4.9 Hz, 1H), 4.53 (dd, J=6.4, 19.4 Hz, 1H), 4.26-4.14 (m, 2H), 2.72-2.58 (m, 1H), 2.34-2.17 (m, 2H), 2.04 (d, J=13.7 Hz, 1H), 1.77-1.62 (m, 3H), 1.49 (s, 3H), 0.86 (s, 3H). Prep-HPLC Method: Instrument: Gilson 281 semi-preparative HPLC system, Mobile phase: A: $CF_3CO_2H/H_2O$=0.075% v/v; B: $CH_3OH$; Column: Phenomenex Luna C18 250*50 mm*10 um; Flow rate: 80 mL/min; Monitor wavelength: 220 & 254 nm.

| | Time | | | | | | |
|---|---|---|---|---|---|---|---|
| | 0.0 | 20.0 | 20.1 | 20.2 | 30.2 | 30.3 | 31.5 |
| B % | 28 | 58 | 58 | 100 | 100 | 28 | 28 |

389

Example 2: Synthesis of (2S,6aS,6bR,7S,8aS,8bS,10S,11aR,12aS,12bS)-10-(4-(3-aminobenzyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one Step 1: Synthesis of 4-(bromomethyl)benzaldehyde

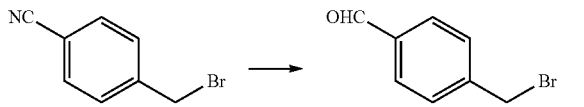 [SMILES: N#Cc1ccc(CBr)cc1 ; O=Cc1ccc(CBr)cc1]

Diisobutylaluminum hydride (153 mL, 153 mmol, 1 M in toluene) was added drop-wise to a 0° C. solution of 4-(bromomethyl)benzonitrile (20 g, 102 mmol) in toluene (400 mL over 1 hour Two additional vials were set up as described above. All three reaction mixtures were combined. The mixture solution was added 10% aqueous HCl (1.5 L). The mixture was extracted with DCM (3×500 mL). The organic layer was dried over $Na_2SO_4$, filtered and concentrated under reduced pressure. The residue was purified by column chromatography on silica gel (eluted with PE/EtOAc=10/1) to obtain the target compound (50 g, yield 82%) as white solid. $^1$H NMR (400 MHz, chloroform-d) δ 10.02 (s, 1H), 7.91-7.82 (m, 2H), 7.56 (d, J=7.9 Hz, 2H), 4.55-4.45 (m, 2H).

Step 2: Synthesis of 3-(4,4,5,5-Tetramethyl-1,3,2-dioxaborolan-2-yl)aniline

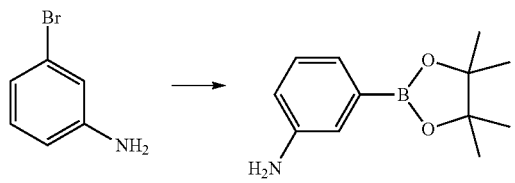 [SMILES: Nc1cccc(Br)c1 ; CC1(C)OB(c2cccc(N)c2)OC1(C)C]

To a solution of 3-bromoaniline (40 g, 233 mmol) in 1,4-dioxane (480 mL) was added 4,4,4',4',5,5,5',5'-octamethyl-2,2'-bi(1,3,2-dioxaborolane) (94 g, 372 mmol), potassium acetate (45.6 g, 465 mmol), 2-dicyclohexylphosphino-2',4',6'-tri-i-propyl-1,1'-biphenyl (X-phos) (8.07 g, 13.95 mmol), tris(dibenzylideneacetone)dipalladium(0) (8.52 g, 9.30 mmol). Then the mixture was heated at 80° C. for 4 hours under nitrogen. Another additional vial was set up as described above. Two reaction mixtures were combined, concentrated and the residue was purified by column chromatography on silica gel (eluted with PE/EtOAc=10/1) to obtain the target compound (60 g, yield 55.4%) as light yellow solid. $^1$H NMR (400 MHz, chloroform-d) δ 7.23-7.13 (m, 3H), 6.80 (d, J=7.5 Hz, 1H), 3.82-3.38 (m, 2H), 1.34 (s, 12H).

390

Step 3: Synthesis of tert-butyl (3-(4,4,5,5-tetramethyl-1,3,2-dioxaborolan-2-yl)phenyl) carbamate

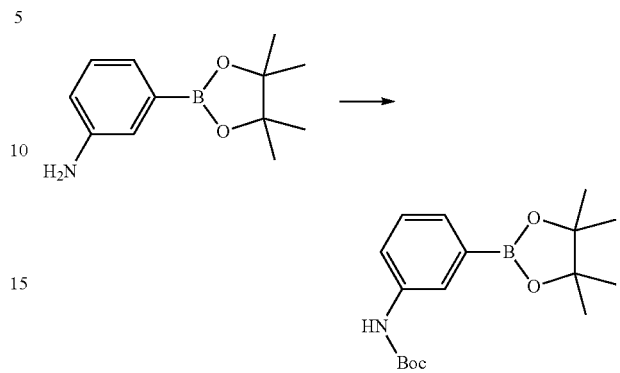

3-(4,4,5,5-Tetramethyl-1,3,2-dioxaborolan-2-yl)aniline (30 g, 137 mmol) and di-tert-butyl dicarbonate (38.9 g, 178 mmol) were mixed in toluene (600 mL) at 100° C. for 24 hours. Another additional vial was set up as described above. Two reaction mixtures were combined. The brown mixture was evaporated, dissolved in EtOAc (1.5 L), washed with 0.1 N HCl (3×2 L) and brine (3 L), dried over $Na_2SO_4$, filtered and concentrated under reduced pressure to give the title compound (50 g, yield 57%) as red solid. $^1$H NMR (400 MHz, chloroform-d) δ 7.63 (br. s., 2H), 7.48 (d, J=7.1 Hz, 1H), 7.37-7.28 (m, 1H), 1.52 (s, 9H), 1.34 (s, 12H).

Step 4: Synthesis of tert-butyl (3-(4-formylbenzyl)phenyl)carbamate

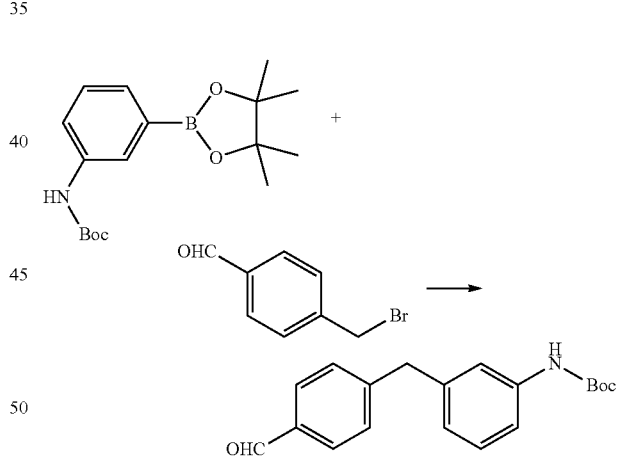

A mixture of 4-(bromomethyl)benzaldehyde (24.94 g, 125 mmol), 1,1'-bis(diphenylphosphino) ferrocenedichloro palladium(II) DCM complex (13.75 g, 18.80 mmol), tert-butyl (3-(4,4,5,5-tetramethyl-1,3,2-dioxaborolan-2-yl)phenyl)carbamate (20 g, 62.7 mmol) and potassium carbonate (43.3 g, 313 mmol) in tetrahydrofuran (400 mL) was heated to 80° C. for 12 hours. Another additional vial was set up as described above. Two reaction mixtures were combined. The reaction mixture was diluted with water (500 mL). The aqueous layer was extracted with EtOAc (3×500 mL). The organic layer was dried over $Na_2SO_4$, filtered and concentrated under reduced pressure. The residue was purified by column chromatography on silica gel (eluted with PE/EtOAc=10/1) to obtain the title compound (15 g, yield 38.4%) as white solid. ¹H NMR (400 MHz, chloroform-d) δ 9.95 (s, 1H), 7.78 (d, J=7.9 Hz, 2H), 7.33 (d, J=7.9 Hz, 2H), 7.27-7.13 (m, 3H), 6.82 (d, J=7.1 Hz, 1H), 6.47 (br. s., 1H), 4.00 (s, 2H), 1.48 (s, 9H).

Step 5: Synthesis of (6S,8S,9R,10S,11S,13S,14S, 16R,17S)-6,9-difluoro-11,16,17-trihydroxy-17-(2-hydroxyacetyl)-10,13-dimethyl-6,7,8,9,10,11,12,13, 14,15,16,17-dodecahydro-3H-cyclopenta[a]phenanthren-3-one

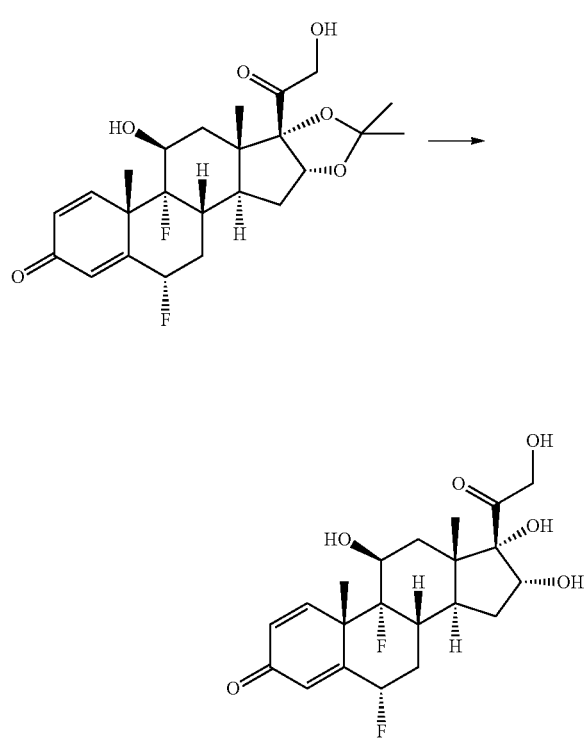

(2S,6aS,6bR,7S,8aS,8bS,11aR,12aS,12bS)-2,6b-difluoro-7-hydroxy-8b-(2-hydroxyacetyl)-6a,8a,10,10-tetramethyl-1,2,6a,6b,7,8,8a,8b,11a,12,12a,12b-dodecahydro-4H-naphtho[2',1':4,5]indeno[1,2-d][1,3]dioxol-4-one (20 g, 44.2 mmol) was suspended in 40% aqueous HBF₄ (440 mL) and the mixture was stirred at 25° C. for 48 hours. After the reaction was complete, 2 L of H₂O was added and the solid was collected by filtration to give a white solid. This solid was washed with H₂O (1 L) and then MeOH (200 mL) to give the title compound (11 g, yield 60.3%) as a white solid. ¹H NMR (400 MHz, DMSO-d6) δ 7.25 (d, J=10.1 Hz, 1H), 6.28 (d, J=10.1 Hz, 1H), 6.10 (s, 1H), 5.73-5.50 (m, 1H), 5.39 (br. s., 1H), 4.85-4.60 (m, 2H), 4.50 (d, J=19.4 Hz, 1H), 4.20-4.04 (m, 2H), 2.46-2.06 (m, 6H), 1.87-1.75 (m, 1H), 1.56-1.30 (m, 6H), 0.83 (s, 3H).

Step 6: Synthesis of (2S,6aS,6bR,7S,8aS,8bS,10S, 11aR,12aS,12bS)-10-(4-(3-aminobenzyl)phenyl)-2, 6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1, 3]dioxol-4-one

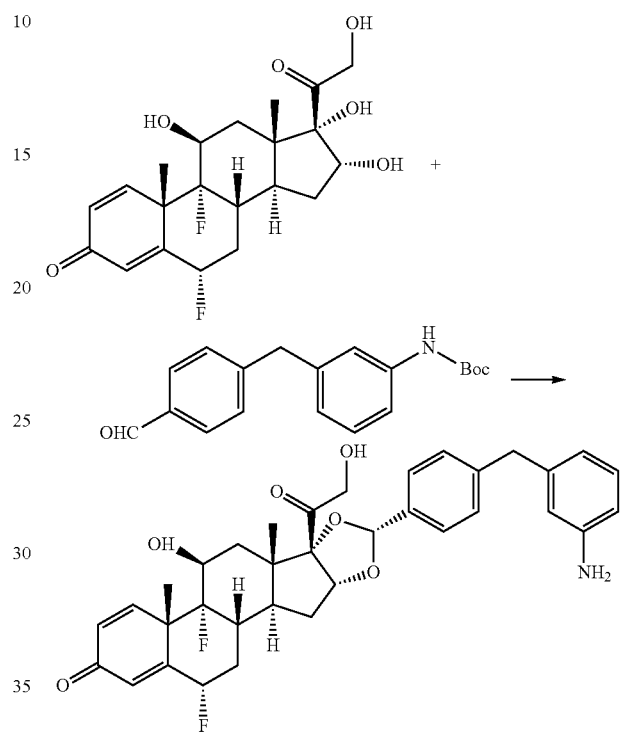

A suspension of (6S,8S,9R,10S,11S,13S,14S,16R,17S)-6, 9-difluoro-11,16,17-trihydroxy-17-(2-hydroxyacetyl)-10, 13-dimethyl-6,7,8,9,10,11,12,13,14,15,16,17-dodecahydro-3H-cyclopenta[a]phenanthren-3-one (4.4 g, 10.67 mmol) and magnesium sulfate (6.42 g, 53.3 mmol) in MeCN (100 mL) was allowed to stirred at 20° C. for 1 hour A solution of tert-butyl (3-(4-formylbenzyl)phenyl)carbamate (3.65 g, 11.74 mmol) in MeCN (100 mL) was added in one portion. Trifluoromethanesulfonic acid (9.01 mL, 53.3 mmol) was added drop wise while maintaining an internal temperature below 25° C. using an ice bath. After the addition, the mixture was stirred at 20° C. for 2 hours. Three additional vials were set up as described above. All four reaction mixtures were combined. The mixture solution was concentrated and the residue was purification by Prep-HPLC to give the title compound (4.5 g, yield 14.2%) as yellow solid. LCMS (Method b, Table 7) R$_t$=2.65 min; MS m/z=606.2 (M+H)+; ¹H NMR (400 MHz, DMSO-d6) δ 7.44-7.17 (m, 5H), 6.89 (t, J=7.7 Hz, 1H), 6.44-6.25 (m, 4H), 6.13 (br. s., 1H), 5.79-5.52 (m, 2H), 5.44 (s, 1H), 5.17-4.89 (m, 3H), 4.51 (d, J=19.4 Hz, 1H), 4.25-4.05 (m, 2H), 3.73 (s, 2H), 3.17 (br. s., 1H), 2.75-2.55 (m, 1H), 2.36-1.97 (m, 3H), 1.76-1.64 (m, 3H), 1.59-1.39 (m, 4H), 0.94-0.78 (m, 3H). Prep-HPLC Method: Instrument: Gilson 281 semi-preparative HPLC system; Mobile phase: A: Formic Acid/H₂O=0.01% v/v; B: CH₃CN; Column: Luna C18 150*25 5 micron; Flow rate: 25 mL/min; Monitor wavelength: 220 and 254 nm.

| | Time | | | | | |
|---|---|---|---|---|---|---|
| | 0.0 | 10.5 | 10.6 | 10.7 | 13.7 | 13.8 | 15.0 |
| B % | 15 | 35 | 35 | 100 | 100 | 10 | 10 |

Example 2A: Synthesis of (6aR,6bS,7S,8aS,8bS,10R,11aR,12aS,12bS)-10-(4-(3-aminobenzyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (Cpd. No. 41)

Step 1: Synthesis of 4-(bromomethyl)benzaldehyde

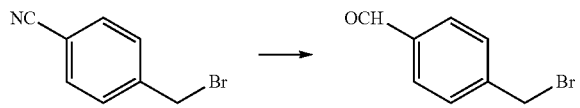

To a solution of 4-(bromomethyl)benzonitrile (50 g, 255 mmol) in toluene (1 L) was added diisobutylaluminum hydride (383 mL, 383 mmol, 1 M in toluene) dropwise at 0° C. The mixture was stirred for 1 hour Two additional vials were set up as described above. All three reaction mixtures were combined. 10% aqueous HCl (1.5 L) was added and then extracted with DCM (3×1.5 L). The organic layer was dried over Na$_2$SO$_4$, filtered and concentrated under reduced pressure. The residue was purified by column chromatography on silica gel (eluted with petroleum ether/ethyl acetate=10/1) to afford the title compound (120 g, 82%) as a white solid. $^1$H NMR (400 MHz, CDCl$_3$) δ 10.01 (s, 1H), 7.86 (d, J=8.4 Hz, 2H), 7.55 (d, J=7.9 Hz, 2H), 4.51 (s, 2H).

Step 2: Synthesis of 3-(4,4,5,5-tetramethyl-1,3,2-dioxaborolan-2-yl)aniline

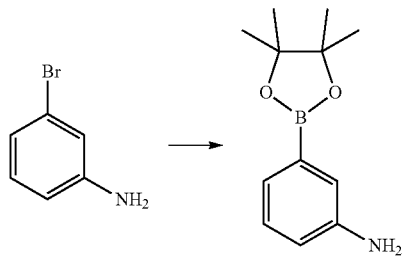 [SMILES: Nc1cccc(Br)c1 ; CC1(C)OB(c2cccc(N)c2)OC1(C)C]

To a solution of 3-bromoaniline (80 g, 465 mmol) in 1,4-dioxane (960 mL) was added 4,4,4',4',5,5,5',5'-octamethyl-2,2'-bi(1,3,2-dioxaborolane) (177 g, 698 mmol), potassium acetate (91 g, 930 mmol), 2-dicyclohexylphosphino-2',4',6'-tri-i-propyl-1,1'-biphenyl (13.45 g, 23.25 mmol) and tris(dibenzylideneacetone)dipalladium(0) (17.03 g, 18.60 mmol). The mixture was heated at 80° C. for 4 hours under nitrogen. Two additional vials were set up as described above. Three reaction mixtures were combined, concentrated and the residue purified by column chromatography on silica gel (eluted with petroleum ether/ethyl acetate=10/1) to afford the title compound (150 g, 46.6%) as a light yellow solid.

$^1$H NMR (400 MHz, CDCl$_3$) δ 7.23-7.13 (m, 3H), 6.80 (d, J=7.5 Hz, 1H), 3.82-3.38 (m, 2H), 1.34 (s, 12H).

Step 3: Synthesis of tert-butyl (3-(4,4,5,5-tetramethyl-1,3,2-dioxaborolan-2-yl)phenyl)carbamate

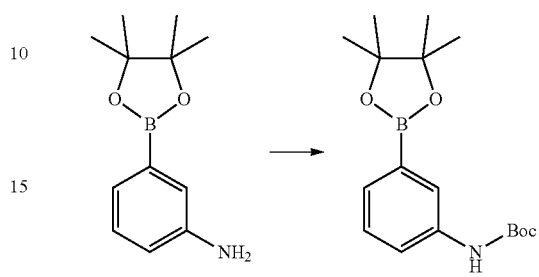

3-(4,4,5,5-Tetramethyl-1,3,2-dioxaborolan-2-yl)aniline (50 g, 228 mmol) and di-tert-butyl dicarbonate (64.8 g, 297 mmol) were mixed in toluene (500 mL) and the mixture stirred at 100° C. for 24 hours. Two additional vials were set up as described above. The three reaction mixtures were combined. The brown mixture was concentrated and the residue was washed with PE to afford the title compound (120 g, 49.5%) as a white solid. $^1$H NMR (400 MHz, CDCl$_3$) δ 7.62 (s, 2H), 7.48 (d, J=7.5 Hz, 1H), 7.35-7.29 (m, 1H), 6.46 (br. s., 1H), 1.52 (s, 9H), 1.34 (s, 12H).

Step 4: Synthesis of tert-butyl (3-(4-formylbenzyl)phenyl)carbamate

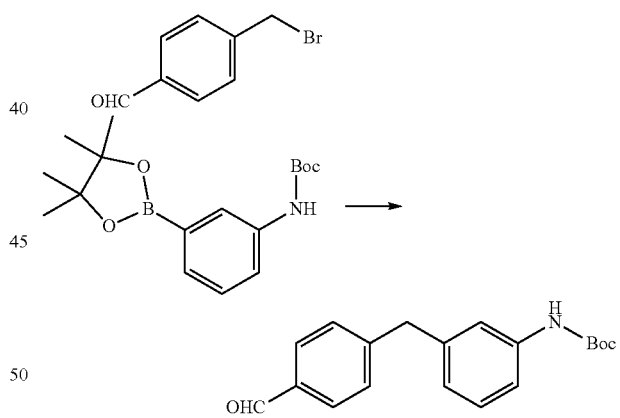

A mixture of 4-(bromomethyl)benzaldehyde (29.9 g, 150 mmol), 1,1'-bis(diphenylphosphino) ferrocenedichloro palladium(II) (20.63 g, 28.2 mmol), tert-butyl (3-(4,4,5,5-tetramethyl-1,3,2-dioxaborolan-2-yl)phenyl)carbamate (30 g, 94 mmol) and potassium carbonate (64.9 g, 470 mmol) in THF (600 mL) was heated to 80° C. for 12 hours. Three additional vials were set up as described above. All four reaction mixtures were combined. The reaction mixture was diluted with water (1 L). The aqueous layer was extracted with EtOAc (3×800 mL). The organic layer was dried over Na$_2$SO$_4$, filtered and concentrated under reduced pressure. The residue was purified by column chromatography on silica gel (eluted with PE/EtOAc=10/1) to afford the title compound (35.5 g, 27.3%) as a white solid.

$^1$H NMR (400 MHz, CDCl$_3$) δ 9.97 (s, 1H), 7.80 (d, J=7.9 Hz, 2H), 7.35 (d, J=7.9 Hz, 2H), 7.26 (s, 2H), 7.24-7.13 (m, 2H), 6.84 (d, J=7.1 Hz, 1H), 6.43 (br. s., 1H), 4.02 (s, 2H), 1.50 (s, 9H).

Step 5: Synthesis of (6aR,6bS,7S,8aS,8bS,10R, 11aR,12aS,12bS)-10-(4-(3-aminobenzyl)phenyl)-7-hydroxy-8b-(2-hydroxyacetyl)-6a,8a-dimethyl-1,2, 6a,6b,7,8,8a,8b,11a,12,12a,12b-dodecahydro-4H-naphtho[2',1':4,5]indeno[1,2-d][1,3]dioxol-4-one

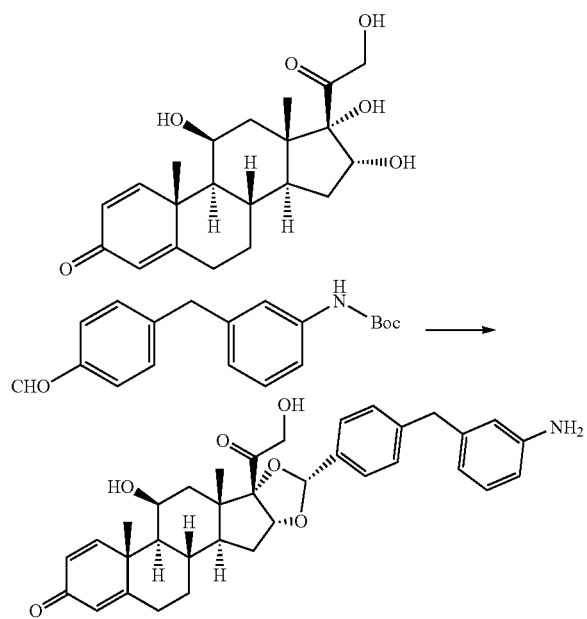

To a solution of (8S,9S,10R,11S,13S,14S,16R,17S)-11, 16,17-trihydroxy-17-(2-hydroxyacetyl)-10,13-dimethyl-6,7, 8,9,10,11,12,13,14,15,16,17-dodecahydro-3H-cyclopenta [a]phenanthren-3-one (6 g, 15.94 mmol) and tert-butyl (3-(4-formylbenzyl)phenyl)carbamate (4.96 g, 15.94 mmol) in MeCN (50 mL) was added perchloric acid (4.79 mL, 80 mmol) dropwise while maintaining an internal temperature below 25° C. using an ice bath. After the addition, the mixture was stirred at 20° C. for 2 hours. Three additional vials were set up as described above. All four reaction mixtures were combined. The reaction mixture was quenched with saturated NaHCO$_3$ aqueous (500 mL) and extracted with dichloromethane (3×800 mL). The organic phase was concentrated and the residue was purified by Prep-HPLC to afford the title compound (10 g, 27.0%) as a yellow solid. $^1$H NMR (400 MHz, DMSO-d$_6$) δ 7.36 (d, J=7.9 Hz, 2H), 7.31 (d, J=10.1 Hz, 1H), 7.20 (d, J=7.9 Hz, 2H), 6.89 (t, J=7.9 Hz, 1H), 6.39-6.28 (m, 3H), 6.16 (dd, J=1.5, 9.9 Hz, 1H), 5.93 (s, 1H), 5.39 (s, 1H), 5.08 (t, J=5.7 Hz, 1H), 4.98-4.87 (m, 3H), 4.78 (d, J=3.1 Hz, 1H), 4.49 (dd, J=6.2, 19.4 Hz, 1H), 4.29 (br. s., 1H), 4.17 (dd, J=5.5, 19.6 Hz, 1H), 3.74 (s, 2H), 2.61-2.53 (m, 1H), 2.36-2.26 (m, 1H), 2.11 (d, J=11.0 Hz, 1H), 2.07 (s, 1H), 2.02 (d, J=12.8 Hz, 1H), 1.83-1.54 (m, 5H), 1.39 (s, 3H), 1.16-0.96 (m, 2H), 0.85 (s, 3H). LCMS: t$_R$=2.365 min, 98% purity, m/z=570.2 (M+H)$^+$ LC/MS (Table 7, method a)

Method of Prep-HPLC: Instrument: Gilson 281 semi-preparative HPLC system, Mobile phase: A: CF$_3$COOH/ H$_2$O=0.075% v/v; B: CH$_3$CN, Column: Phenomenex Luna (2) C18 250*50 10u, Flow rate: 80 mL/min, Monitor wavelength: 220&254 nm, Time B %, 0.0 28, 20.0 45, 20.1 45, 20.2 100, 30.2 100, 0.3 28, 31.5 28.

Example 2B

Synthesis of (2R,6aS,6bR,7S,8aS,8bS,10R,11aR, 12aS,12bS)-10-(4-(3-Aminobenzyl)phenyl)-6b-fluoro-2,7-dihydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4 (2H)-one

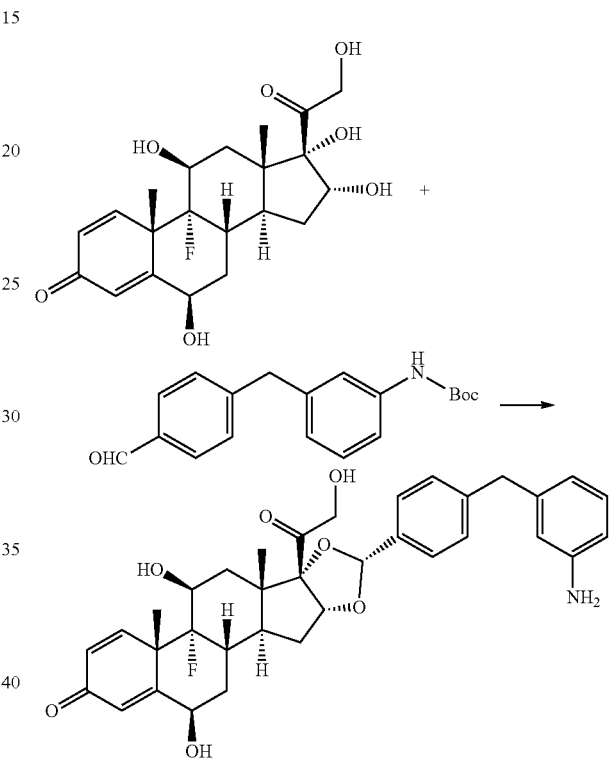

Trifluoromethane sulfonic acid (1.34 ml, 15.11 mmol) was added drop-wise to a −10° C. suspension of (6R,8S, 9R,10S,11S,13S,14S,16R,17S)-9-fluoro-6,11,16,17-tetra-hydroxy-17-(2-hydroxyacetyl)-10,13-dimethyl-6,7,8,9,10, 11,12,13,14,15,16,17-dodecahydro-3H-cyclopenta[a] phenanthren-3-one (1.55 g, 3.78 mmol), tert-butyl (3-(4-formylbenzyl)phenyl)carbamate (from Example 2, step 4) (1.176 g, 3.78 mmol), and MgSO$_4$ (2.273 g, 18.89 mmol) in MeCN (15.1 mL). After 20 min, the reaction was quenched by addition of a saturated aqueous solution of NaHCO$_3$ (15 mL), followed by water (60 mL) and EtOAc (100 mL). The organic layer was washed sequentially with water (60 mL), brine (60 mL), dried (Na$_2$SO$_4$), and solvent was removed under reduced pressure. Purification by chromatography (silica, 40 g) eluting with a gradient of 40-100% EtOAc/ heptanes provided the title compound as a foam (880 mg, 1.458 mmol, 39% yield) in 90% purity. The product could be further purified by reverse phase HPLC on a Waters XBridge™ RP18 5 micron column (30×100 mm). A gradient of MeCN (A) and 0.1 mM NH$_4$CO$_3$ in water (B) was used, at a flow rate of 40 mL/min (0-5.0 min 5% A, 5.0-19.0 min linear gradient 15-55% A). LC-MS (Method r, Table 7) Rt=0.72 min, m/z=604.3 [M+H+]. $^1$H NMR (500 MHz, DMSO-d$_6$) δ 7.37-7.31 (m, 2H), 7.28 (d, J=10.1 Hz, 1H), 7.24-7.19 (m, 2H), 6.93-6.85 (m, 1H), 6.36 (d, J=2.1 Hz, 2H), 6.35 (p, J=1.1 Hz, 1H), 6.23 (dd, J=10.1, 1.9 Hz, 1H), 6.10 (d, J=1.9 Hz, 1H), 5.45 (s, 1H), 5.38 (s, 1H), 5.10 (s, 1H), 4.96-4.91 (m, 3H), 4.51 (d, J=19.4 Hz, 1H), 4.38 (s, 1H), 4.28-4.16 (m, 2H), 3.74 (s, 2H), 2.76-2.60 (m, 1H), 2.20 (td, J=12.5, 6.3 Hz, 1H), 2.08 (s, 2H), 1.86 (d, J=11.8 Hz, 1H), 1.75-1.58 (m, 7H), 0.89 (s, 3H).

Example 3: Synthesis of (6aS,6bR,7S,8aS,8bS,10R,11aR,12aS,12bS)-10-(4-((3-aminophenyl)thio)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one Step 1: Synthesis of tert-butyl (3-mercaptophenyl)carbamate

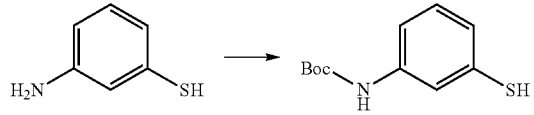 [SMILES: Nc1cccc(S)c1 ; CC(C)(C)OC(=O)Nc1cccc(S)c1]

To a mixture of zinc perchlorate (0.422 g, 1.598 mmol) and 3-aminobenzenethiol (10 g, 80 mmol) was added di-tert-butyl dicarbonate (22.66 g, 104 mmol) drop wise. The solution was stirred at 25° C. for 12 hours. Three additional vials were set up as described above. Four reaction mixtures were combined. The mixture was dissolved in EtOAc (200 mL) and washed with water (500 mL). The organic layer was dried over Na$_2$SO$_4$, filtered and concentrated under reduced pressure to give a residue. The residue was purified by column chromatography on silica gel (eluted with PE/EtOAc=5/1) to obtain the target compound (50 g, yield 69.4%) as white solid. $^1$H NMR (400 MHz, CDCl$_3$) δ 7.45 (br. s., 1H), 7.16-7.09 (m, 1H), 7.06-7.01 (m, 1H), 6.92 (d, J=7.4 Hz, 1H), 6.55 (br. s., 1H), 3.46 (s, 1H), 1.52 (s, 9H).

Step 2: Synthesis of tert-butyl (3-((4-formylphenyl)thio)phenyl)carbamate

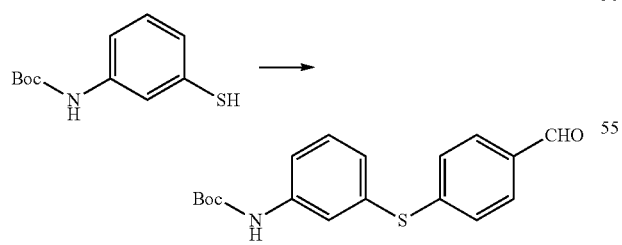

To a solution of tert-butyl (3-((4-formylphenyl)thio)phenyl)carbamate (10 g, 44.4 mmol) in DMF (300 mL) was added triphenylphosphine (11.64 g, 44.4 mmol) and N-ethyl-N-isopropylpropan-2-amine (11.47 g, 89 mmol) at 25° C. The reaction mixture was stirred at 25° C. for 30 minutes under N$_2$. The mixture was added 4-fluorobenzaldehyde (8.26 g, 66.6 mmol) at 100° C. and the mixture was stirred at 100° C. for 12 hours. Four additional vials were set up as described above. The five reaction mixtures were combined. The mixture was diluted with water (2 L) and extracted with EtOAc (3×1 L). The organic layer was dried over Na$_2$SO$_4$, filtered and concentrated under reduced pressure. The residue was purified by column chromatography on silica gel (eluted with PE/EtOAc=10/1) to obtain the target compound (55 g, yield 75%) as yellow oil. $^1$H NMR (400 MHz, CDCl$_3$) δ 9.90 (s, 1H), 7.71 (d, J=8.4 Hz, 2H), 7.58 (s, 1H), 7.48-7.41 (m, 1H), 7.33 (t, J=7.9 Hz, 1H), 7.25 (d, J=8.4 Hz, 2H), 7.17 (d, J=7.9 Hz, 1H), 6.72 (br. s., 1H), 1.50 (s, 9H).45 (br. s., 1H), 7.16-7.09 (m, 1H), 7.06-7.01 (m, 1H), 6.92 (d, J=7.4 Hz, 1H), 6.55 (br. s., 1H), 3.46 (s, 1H), 1.52 (s, 9H).

Step 3: Synthesis of sodium (4-((3-((tert-butoxycarbonyl)amino)phenyl)thio)phenyl) (hydroxy)methanesulfonate

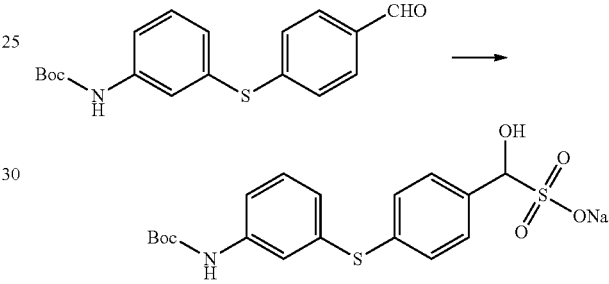

To a solution of the aldehyde (15 g, 45.5 mmol) in CH$_3$CN (30 mL) was added a solution of sodium metabisulfite (11.25 g, 59.2 mmol) in water (90 mL) at 25° C. The mixture was stirred at 25° C. for 48 hours. Another additional vial was set up as described above. Two reaction mixtures were combined. The solution was filtered and the solid was washed with water (150 mL), CH$_3$CN (150 mL) and dried under reduced pressure to give the target compound (32 g, yield 81%) as white solid. $^1$H NMR (400 MHz, DMSO-d6) δ 9.45 (br. s., 1H), 7.54-7.49 (m, 1H), 7.47-7.35 (m, 3H), 7.33-7.17 (m, 3H), 6.85 (d, J=7.9 Hz, 1H), 5.97 (d, J=4.9 Hz, 1H), 4.98 (d, J=4.9 Hz, 1H), 1.45 (s, 9H).

Step 4: Synthesis of (6aS,6bR,7S,8aS,8bS,10R,11aR,12aS,12bS)-10-(4-((3-aminophenyl)thio)phenyl)-6b-fluoro-7-hydroxy-8b-(2-hydroxyacetyl)-6a,8a-dimethyl-1,2,6a,6b,7,8,8a,8b, 11a,12,12a,12b-dodecahydro-4H-naphtho[2',1':4,5]indeno[1,2-d][1,3]dioxol-4-one

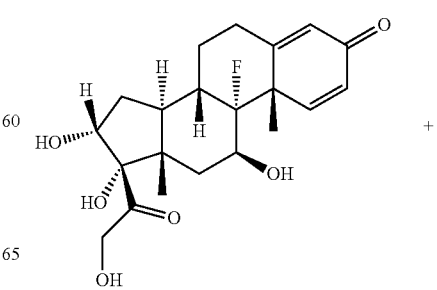

-continued

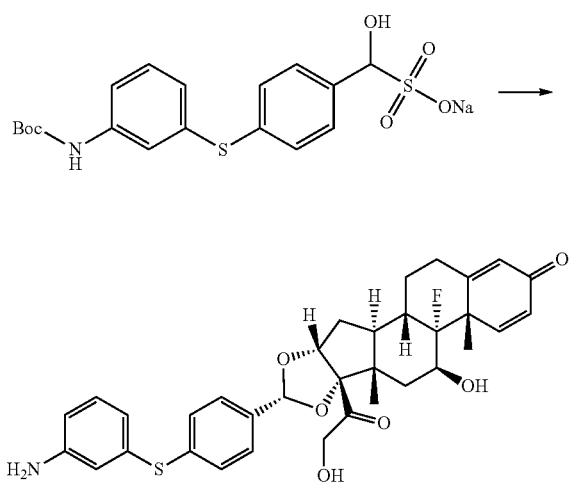

To a solution of (8S,9R,10S,11S,13S,14S,16R,17S)-9-fluoro-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (6 g, 15.21 mmol) and sodium (4-((3-((tert-butoxycarbonyl)amino)phenyl)thio)phenyl)(hydroxy)methanesulfonate (4.74 g, 15.21 mmol) in THF (50 mL) was added perchloric acid (4.58 mL, 76 mmol) drop wise while maintaining an internal temperature below 25° C. using an ice bath. After the addition, the mixture was stirred at 20° C. for 2 hours. Three additional vials were set up as described above. All four reaction mixtures were combined. The reaction mixture was quenched with sat. NaHCO$_3$ aqueous (500 mL) and extracted with DCM (3×800 mL). The organic phase was concentrated and the residue was purification by Prep-HPLC to give the target compound (9.5 g, 25.8%) as yellow solid. LCMS (Method b, Table 7) R$_t$=2.68 min, m/z=588.1 (M+H)+; $^1$H NMR (400 MHz, DMSO-d6) δ 7.37-7.26 (m, 3H), 7.21 (d, J=7.9 Hz, 2H), 6.89 (t, J=7.7 Hz, 1H), 6.43-6.30 (m, 3H), 6.23 (d, J=10.1 Hz, 1H), 6.04 (s, 1H), 5.75 (s, 1H), 5.44 (s, 2H), 5.09 (t, J=5.7 Hz, 1H), 4.93 (br. s., 3H), 4.50 (dd, J=6.2, 19.4 Hz, 1H), 4.28-4.09 (m, 2H), 3.74 (s, 2H), 2.73-2.54 (m, 2H), 2.35 (d, J=13.2 Hz, 1H), 2.25-2.12 (m, 1H), 2.05 (d, J=15.0 Hz, 1H), 1.92-1.77 (m, 1H), 1.74-1.58 (m, 3H), 1.50 (s, 3H), 1.45-1.30 (m, 1H), 0.87 (s, 3H). Prep-HPLC Method: Instrument: Gilson 281 semi-preparative HPLC system; Mobile phase: A: CF$_3$CO$_2$H/H$_2$O=0.075% v/v; B: CH$_3$CN; Column: Phenomenex Luna C18 250x*50 mm*10 micron; Flow rate: 80 mL/min; Monitor wavelength: 220 and 254 nm.

| | Time | | | | | | |
|---|---|---|---|---|---|---|---|
| | 0.0 | 20.0 | 20.1 | 20.2 | 30.2 | 30.3 | 31.5 |
| B % | 10 | 42 | 42 | 100 | 100 | 10 | 10 |

Example 4: Synthesis of (6aR,6bS,7S,8aS,8bS,10R,11aR,12aS,12bS)-10-(4-((3-aminophenyl)thio)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

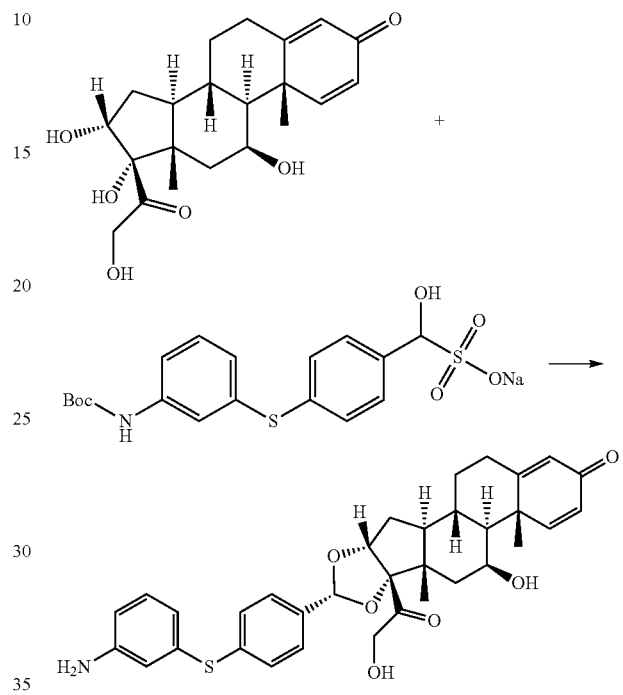

To a solution of (8S,9S,10R,11S,13S,14S,16R,17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (6 g, 15.94 mmol) and sodium (4-((3-((tert-butoxycarbonyl)amino)phenyl)thio)phenyl)(hydroxy)methanesulfonate (4.96 g, 15.94 mmol) in MeCN (50 mL) was added perchloric acid (4.79 mL, 80 mmol) drop wise while maintaining an internal temperature below 25° C. using an ice bath. After the addition, the mixture was stirred at 20° C. for 2 hours. Three additional vials were set up as described above. All four reaction mixtures were combined. The reaction mixture was quenched with sat. aqueous NaHCO$_3$ (500 mL) and extracted with DCM (3×800 mL). The organic phase was concentrated and the residue was purification by Prep-HPLC to give the target compound (10 g, 27.0%) as yellow solid. LCMS (Method b, Table 7) R$_t$=2.36 min, m/z=570.2 (M+H)+; $^1$H NMR (400 MHz, DMSO-d6) δ 7.36 (d, J=7.9 Hz, 2H), 7.31 (d, J=10.1 Hz, 1H), 7.20 (d, J=7.9 Hz, 2H), 6.89 (t, J=7.9 Hz, 1H), 6.39-6.28 (m, 3H), 6.16 (dd, J=1.5, 9.9 Hz, 1H), 5.93 (s, 1H), 5.39 (s, 1H), 5.08 (t, J=5.7 Hz, 1H), 4.98-4.87 (m, 3H), 4.78 (d, J=3.1 Hz, 1H), 4.49 (dd, J=6.2, 19.4 Hz, 1H), 4.29 (br. s., 1H), 4.17 (dd, J=5.5, 19.6 Hz, 1H), 3.74 (s, 2H), 2.61-2.53 (m, 1H), 2.36-2.26 (m, 1H), 2.11 (d, J=11.0 Hz, 1H), 2.07 (s, 1H), 2.02 (d, J=12.8 Hz, 1H), 1.83-1.54 (m, 5H), 1.39 (s, 3H), 1.16-0.96 (m, 2H), 0.85 (s, 3H). Prep-HPLC Method: Instrument: Gilson 281 semi-preparative HPLC system; Mobile phase: A: CF$_3$CO$_2$H/H$_2$O=0.075% v/v; B: CH$_3$CN; Column: Phenomenex Luna C18 250x*50 mm*10 micron; Flow rate: 80 mL/min; Monitor wavelength: 220 and 254 nm.

| Time | | | | | | |
|---|---|---|---|---|---|---|
| 0.0 | 20.0 | 20.1 | 20.2 | 30.2 | 30.3 | 31.5 |
| B % 28 | 45 | 45 | 100 | 100 | 28 | 28 |

Example 5: Synthesis of (2S,6aS,6bR,7S,8aS,8bS, 10R,11aR,12aS,12bS)-10-(4-((3-aminophenyl) thio) phenyl)-2,6b-difluoro-7-hydroxy-8b-(2-hydroxy-acetyl)-6a,8a-dimethyl-1,2,6a,6b,7,8,8a,8b,11a,12, 12a,12b-dodecahydro-4H-naphtho[2',1':4,5]indeno [1,2-d][1,3]dioxol-4-one

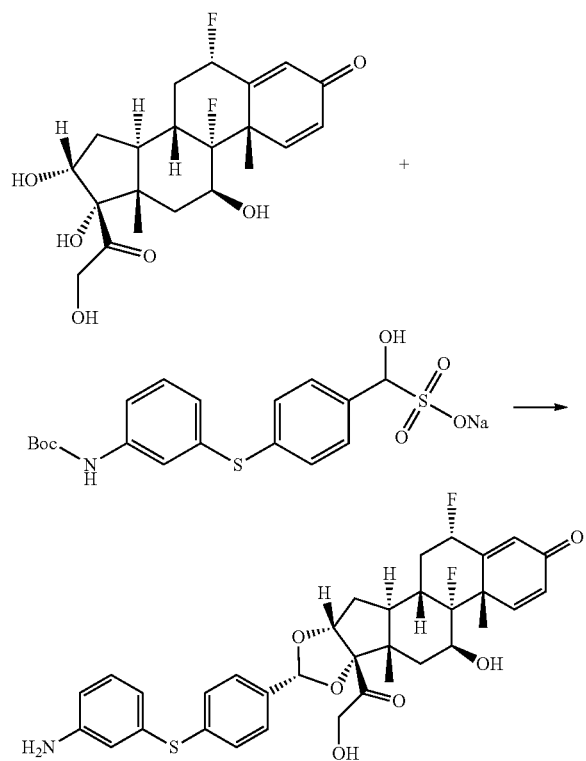

To a solution of steroid (10 g, 24.25 mmol) in CH$_3$CN (200 mL) was added magnesium sulfate (10.21 g, 85 mmol) at 25° C. The mixture was stirred at 25° C. for 4 hours. Then to the above solution was added sodium (4-((3-((tert-bu-toxycarbonyl)amino)phenyl)thio) phenyl)(hydroxy)meth-anesulfonate (10.51 g, 24.25 mmol) and trifluoromethane-sulfonic acid (20.48 mL, 121 mmol) at 0° C. The resulting mixture was stirred at 25° C. for 1 hour. Two additional vials were set up as described above. Three reaction mixtures were combined. The mixture was diluted with 1 N NaOH (300 mL) and extracted with EtOAc (3×600 mL). The organic layer was concentrated under reduced pressure to give a residue. The residue was dissolve in EtOAc (60 mL) and added 2-butanone (180 mL). After stirring for 30 minutes, the solid was collected by filtration and purified by Prep-HPLC to give the title compound (8.4 g, yield 17.52%) as yellow solid. LCMS (Method c, Table 7) R$_f$=2.66 min; MS m/z=624.1 (M+H)+; $^1$H NMR (400 MHz, DMSO-d6) δ 7.39 (d, J=8.4 Hz, 2H), 7.25 (d, J=8.4 Hz, 3H), 7.03 (t, J=7.7 Hz, 1H), 6.61 (s, 1H), 6.53 (t, J=8.2 Hz, 2H), 6.29 (dd, J=1.5, 9.9 Hz, 1H), 6.12 (s, 1H), 5.76-5.49 (m, 2H), 5.46 (s, 1H), 4.96 (d, J=4.9 Hz, 1H), 4.52 (d, J=19.4 Hz, 1H), 4.21 (d, J=19.4 Hz, 2H), 2.74-2.53 (m, 2H), 2.34-2.13 (m, 2H), 2.09-1.96 (m, 1H), 1.79-1.62 (m, 3H), 1.57-1.43 (m, 4H), 0.86 (s, 3H). Prep-HPLC method: Instrument: Shimadzu LC-8A preparative HPLC; Column: Phenomenex Luna C18 250×*50 mm*10 micron; Mobile phase: A for H$_2$O (0.09% CF$_3$CO$_2$H) and B for CH$_3$CN; Gradient: B from 22% to 52% in 20 min; Flow rate: 80 mL/min; Wavelength: 220&254 nm.

Example 6: Synthesis of (6aR,6bS,7S,8aS,8bS,10R, 11aR,12aS,12bS)-10-(4-(3-Amino-4-hydroxybenzyl) phenyl)-7-hydroxy-8b-(2-hydroxyacetyl)-6a,8a-dim-ethyl-6a,6b,7,8,8a,8b,11a,12,12a,12b-decahydro-1H-naphtho[2',1':4,5]indeno[1,2-d][1,3]dioxol-4(2H)-one

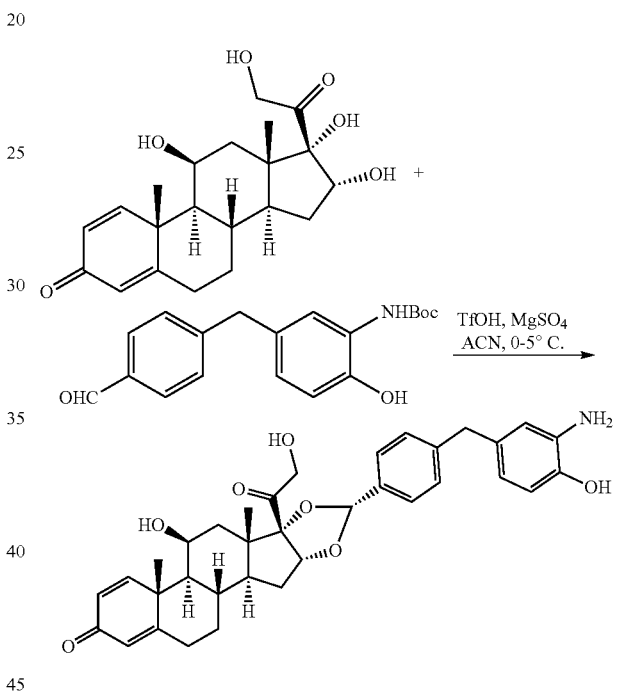

Triflic acid (0.2 mL, 2.183 mmol) was added drop-wise to a 0° C. slurry of (8S,9S,10R,11S,13S,14S,16R,17S)-11,16,17-trihydroxy-17-(2-hydroxyacetyl)-10,13-dimethyl-6,7,8,9, 10,11,12,13,14,15,16,17-dodecahydro-3H-cyclopenta[a] phenanthren-3-one (0.164 g, 0.437 mmol), tert-butyl (2-((tert-butyldimethylsilyl)oxy)-5-(4-formylbenzyl)phenyl) carbamate (0.193 g, 0.437 mmol) and MgSO$_4$ (0.189 g, 1.572 mmol) in MeCN (1.8 mL). After 40 min the reaction was diluted with EtOAc (15 mL), and then washed sequentially with a saturated aqueous solution of NaHCO$_3$ (10 mL×2), and with a saturated aqueous solution of brine (5 mL). The organic phase was dried (Na$_2$SO$_4$) and solvent was removed under reduced pressure. Purification by chromatography (silica, 12 g) eluting with a gradient of 0-10% MeOH/DCM gave the title compound (163 mg, 0.278 mmol, 64% yield) as a waxy solid. A portion of this material (ca. 48.9 mg) was further purified by reverse phase HPLC on a Phenomenex C18(2) 10 micron column (250×50 mm column). A gradient of MeCN (A) and 0.1% TFA in water (B) was used, at a flow rate of 90 mL/min (0-5.0 min 15% A, 5.0-20 min linear gradient 15-70% A, hold 2 min). Combined fractions were concentrated under reduced pressure to remove volatile solvents, and the resulting solution was frozen and lyophilized to give a off-white solid (11.9 mg). LCMS (Method r, Table 7) $R_t$=0.75 min, m/z=586.26 [M+H+]. $^1$H NMR (400 MHz, DMSO-d6) δ 10.27 (s, 1H), 9.04 (s, 2H), 7.34 (d, J=8.0 Hz, 2H), 7.28 (d, J=10.1 Hz, 1H), 7.18 (d, J=8.0 Hz, 2H), 6.94 (dd, J=8.1, 2.1 Hz, 1H), 6.90 (d, J=2.1 Hz, 1H), 6.82 (d, J=8.2 Hz, 1H), 6.17-6.07 (m, 1H), 5.90 (d, J=1.6 Hz, 1H), 5.37 (s, 1H), 4.89 (d, J=4.9 Hz, 1H), 4.75 (s, 1H), 4.46 (d, J=19.4 Hz, 1H), 4.26 (q, J=3.3 Hz, 1H), 4.14 (d, J=19.5 Hz, 1H), 3.80 (s, 2H), 2.58-2.46 (m, 1H), 2.36-1.92 (m, 3H), 1.76-1.56 (m, 4H), 1.36 (s, 3H), 1.10-0.90 (m, 2H), 0.83 (s, 3H).

Example 7: Synthesis of (2S,6aS,6bR,7S,8aS,8bS, 10R,11aR,12aS,12bS)-10-(4-(3-Aminobenzyl)-3-hydroxyphenyl)-2,6b-difluoro-7-hydroxy-8b-(2-hydroxyacetyl)-6a,8a-dimethyl-6a,6b,7,8,8a,8b,11a, 12,12a,12b-decahydro-1H-naphtho[2',1':4,5]indeno[1,2-d][1,3]dioxol-4(2H)-one Step 1: Synthesis of 4-((3-bromophenyl)(hydroxy)methyl)-3-methoxybenzonitrile

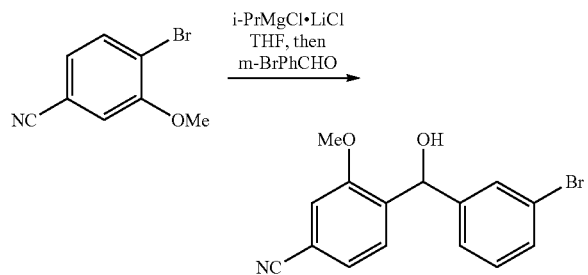

Isopropylmagnesium chloride lithium chloride complex (1.3 M in THF, 8.34 mL, 10.85 mmol) was added drop-wise to a 0-5° C. solution of 4-bromo-3-methoxybenzonitrile (2 g, 9.43 mmol) in THF (21 mL). The reaction was stirred for 5 h, whereupon a solution of 3-bromobenzaldehyde (1.979 g, 10.38 mmol) in THF (10.5 mL) was added drop-wise, maintaining a temperature of <10° C. The reaction was permitted to slowly warm to room temperature overnight. The reaction quenched with a saturated aqueous solution of NH$_4$Cl (25 mL) and extracted with MTBE (50 mL×3). The combined organics were washed with brine (20 mL), dried (Na$_2$SO$_4$), and solvents were removed under reduced pressure. Purification by chromatography (80 g silica) eluting with a gradient of 0-10% MTBE/heptanes gave the title compound (1.77 g, 5.56 mmol, 59% yield) as a beige syrup/oil. LCMS (Method r, Table 7) $R_t$=0.86 min; MS (ESI-) m/z=315.7 [M–H+]. $^1$H NMR (501 MHz, DMSO-d6) δ 7.67 (d, J=7.8 Hz, 1H), 7.47 (t, J=1.8 Hz, 1H), 7.43 (dd, J=7.8, 1.5 Hz, 1H), 7.41 (d, J=1.4 Hz, 1H), 7.40-7.36 (m, 1H), 7.28 (dt, J=7.8, 1.5 Hz, 1H), 7.23 (d, J=7.8 Hz, 1H), 6.10 (d, J=4.4 Hz, 1H), 5.94 (d, J=4.1 Hz, 1H), 3.80 (s, 3H).

Step 2: Synthesis of 4-(3-bromobenzyl)-3-methoxybenzonitrile

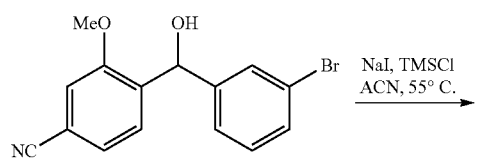

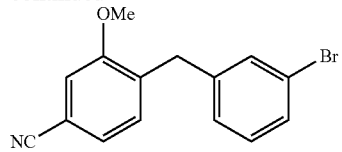

Chlorotrimethylsilane (3.63 g, 33.4 mmol) was added to a room temperature solution of sodium iodide (5.00 g, 33.4 mmol) in MeCN (18.5 mL), which resulted in the immediate precipitation of a white solid. A solution of 4-((3-bromophenyl)(hydroxy)methyl)-3-methoxybenzonitrile (1.77 g, 5.56 mmol) in MeCN (18.5 mL) was then added, whereupon the reaction mixture was heated to 55° C. for 60 min. After cooling to room temperature the reaction was partitioned between MTBE (50 mL) and water (50 mL). After separating the layers the aqueous phase was extracted with MTBE (50 mL×2). The combined organics were washed sequentially with a 1 M aqueous solution of Na$_2$S$_2$O$_3$ (50 mL×2), followed by a saturated aqueous solution of brine (30 mL), dried (Na$_2$SO$_4$), and solvents were removed under reduced pressure. Purification by chromatography (silica, 80 g) eluting with a gradient of 5-40% MTBE/heptanes gave the title compound (1.58 g, 5.23 mmol, 94% yield) as an off-white solid. LCMS (Method r, Table 7) $R_t$=1.02 min; MS m/z=not observed. $^1$H NMR (501 MHz, DMSO-d6) δ 7.42 (d, J=1.5 Hz, 1H), 7.39-7.30 (m, 4H), 7.22 (td, J=7.6, 0.6 Hz, 1H), 7.18 (dt, J=7.7, 1.4 Hz, 1H), 3.94 (s, 2H), 3.82 (s, 3H).

Step 3: Synthesis of 4-(3-bromobenzyl)-3-methoxybenzaldehyde

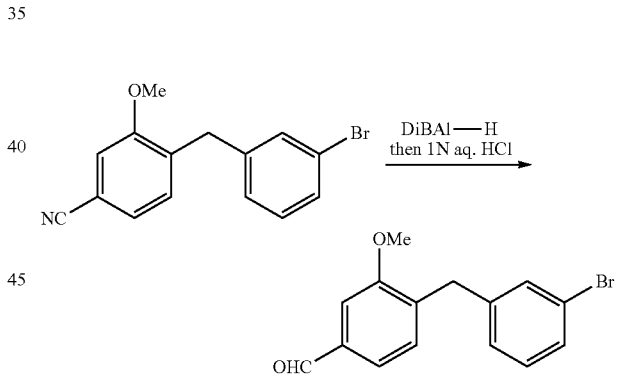

Diisobutylaluminum hydride (4.9 mL, 1.0 M solution in hexanes, 4.9 mmol) was added drop-wise over 5 min to a 0° C. solution of 4-(3-bromobenzyl)-3-methoxybenzonitrile (0.99 g, 3.28 mmol) in toluene (16 mL), maintaining a temperature of <6° C. After 10 min the reaction was quenched by careful addition of a 1 N aqueous solution of HCl (100 mL) at 0° C. It was then extracted with DCM (50 mL×4), washed with a saturated aqueous solution of brine (30 mL), and solvent was removed under reduced pressure. Purification by chromatography (silica, 40 g) eluting with a gradient of 0-40% MTBE/heptanes gave the title compound (780 mg, 2.56 mmol, 78% yield) as a colorless oil. LCMS (Method r, Table 7) $R_t$=0.95 min, MS (DCI+) m/z=303.9, 305.9 (M+). $^1$H NMR (400 MHz, DMSO-d6) δ 9.93 (s, 1H), 7.47 (dd, J=7.5, 1.5 Hz, 1H), 7.44 (d, J=1.5 Hz, 1H), 7.42-7.33 (m, 3H), 7.25-7.17 (m, 2H), 3.96 (s, 2H), 3.85 (s, 3H).

Step 4: Synthesis of 4-(3-bromobenzyl)-3-hydroxybenzaldehyde

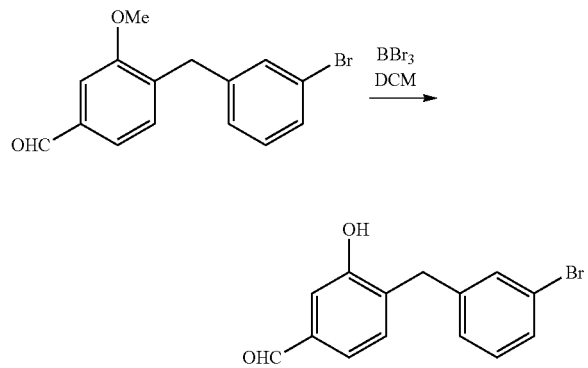

Boron tribromide (1.0 M in methylene chloride, 6.4 mL, 6.4 mmol) was added drop-wise to a 0-3° C. solution of 4-(3-bromobenzyl)-3-methoxybenzaldehyde (0.78 g, 2.56 mmol) in DCM (7.8 mL). The reaction was stirred at 0° C. for 30 min; then was stirred for 90 min at room temperature. Solvent was removed under reduced pressure and the resulting dark oil was treated with MeOH (20 mL) and water (15 mL), which gave a heterogeneous mixture. MeCN was added until a homogeneous solution was obtained (ca. 10 mL) and the solution was stirred overnight. Volatile solvents were removed under reduced pressure and the resulting aqueous suspension was extracted with DCM (25 mL×3). The combined organics were washed with brine (20 mL), dried over $Na_2SO_4$ and solvent was removed under reduced pressure. Purification by chromatography (silica, 40 g) eluting with a gradient of 10-50% MTBE/heptanes gave 4-(3-bromobenzyl)-3-hydroxybenzaldehyde (660 mg, 2.267 mmol, 89% yield) as a white solid. LCMS (Method r, Table 7) $R_t$=0.85 min; MS (DCI+) m/z=307.98, 309.97 [M+$NH_4$+]. $^1$H NMR (400 MHz, DMSO-d6) δ 10.07 (s, 1H), 9.83 (s, 1H), 7.39 (q, J=1.3 Hz, 1H), 7.33 (ddt, J=6.5, 4.4, 2.0 Hz, 1H), 7.30 (d, J=0.9 Hz, 2H), 7.25 (s, 1H), 7.25-7.15 (m, 2H), 3.92 (s, 2H).

Step 5: Synthesis of 4-(3-bromobenzyl)-3-((tert-butyldimethylsilyl)oxy)benzaldehyde

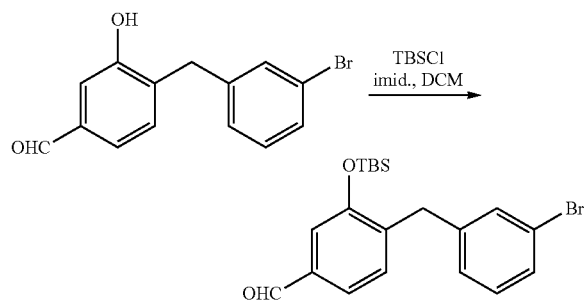

Imidazole (0.231 g, 3.40 mmol) and tert-butyldimethylchlorosilane (0.410 g, 2.72 mmol) were added to a room temperature suspension of 4-(3-bromobenzyl)-3-hydroxybenzaldehyde (0.660 g, 2.267 mmol) in DCM (7.6 mL), which was stirred for 3 h. MeOH (0.5 mL) was added and stirring continued for 10 min, whereupon the reaction was diluted with DCM (100 mL), washed sequentially with water (25 mL), a 1 N aqueous solution of HCl (25 mL), and with a saturated aqueous solution of brine (20 mL). The organic phase was dried ($Na_2SO_4$) and solvent was removed under reduced pressure to give a syrup. Purification by chromatography (silica, 40 g) eluting with a gradient of 0-10% MTBE/heptanes gave the target compound (820 mg, 2.023 mmol, 89% yield) as a colorless oil. LCMS (Method r, Table 7) $R_t$=1.18 min, MS (DCI+) m/z=422.07, 424.09 [M+$NH_4$+]. $^1$H NMR (500 MHz, DMSO-d6) δ 9.94 (s, 1H), 7.50 (dd, J=7.7, 1.6 Hz, 1H), 7.42-7.36 (m, 2H), 7.36-7.32 (m, 2H), 7.25 (t, J=7.8 Hz, 1H), 7.17 (ddd, J=7.7, 1.7, 1.0 Hz, 1H), 4.01 (s, 2H), 0.92 (s, 9H), 0.26 (s, 6H).

Step 6: Synthesis of tert-butyl (3-(4-formyl-2-hydroxybenzyl)phenyl)carbamate

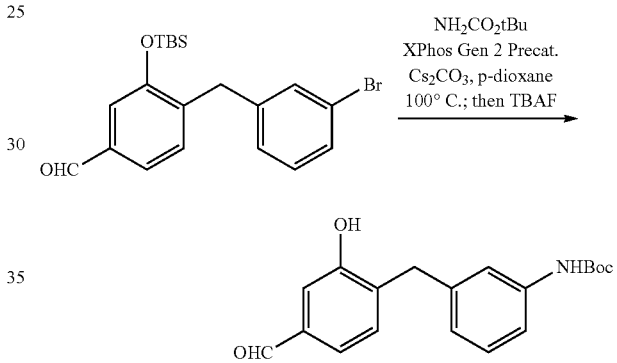

Nitrogen was sparged through a mixture of 4-(3-bromobenzyl)-3-((tert-butyldimethylsilyl)oxy)benzaldehyde (0.820 g, 2.023 mmol), tert-butyl carbamate (0.3027 g, 2.58 mmol), $Cs_2CO_3$ (1.006 g, 3.09 mmol) in p-dioxane (16 mL) for 30 min. Added the 2nd generation XPhos precatalyst (0.0937 g, 0.119 mmol) and continued sparging for 5 min, whereupon the reaction was heated to 100° C. for 4 h. The reaction was cooled to room temperature, treated with a 1 N aqueous solution of HCl (25 mL), and was extracted with MTBE (25 mL×3). The combined organics were washed with brine (30 mL), dried over $Na_2SO_4$ and solvent was removed under reduced pressure. The residue was redissolved in THF (16 mL, 0.125 M) and treated with TBAF/$SiO_2$ (1.0-1.5 mmol/g, 4.1338 g, 4.13-6.2 mmol) for 45 min, whereupon solvent was removed under reduced pressure. Purification by chromatography (silica, 40 g) eluting with a gradient of 0-75% MTBE/heptanes gave tert-butyl (3-(4-formyl-2-hydroxybenzyl)phenyl)carbamate (380 mg, 1.161 mmol, 57% yield) was isolated as a gummy foam. LCMS (Method r, Table 7) $R_t$=0.85 min; MS (DCI+) m/z=345.0 [M+$NH_4$+]. $^1$H NMR (500 MHz, DMSO-d6) δ 10.04 (s, 1H), 9.86 (s, 1H), 9.25 (s, 1H), 7.37 (s, 1H), 7.34-7.28 (m, 2H), 7.27-7.20 (m, 2H), 7.14 (t, J=7.8 Hz, 1H), 6.82 (dt, J=7.7, 1.2 Hz, 1H), 3.89 (s, 2H), 1.45 (s, 9H).

Step 7: Synthesis of (2S,6aS,6bR,7S,8aS,8bS,10R, 11aR,12aS,12bS)-10-(4-(3-aminobenzyl)-3-hydroxyphenyl)-2,6-difluoro-7-hydroxy-8b-(2-hydroxyacetyl)-6a,8a-dimethyl-6a,6b,7,8,8a,8b,11a,12,12a, 12b-decahydro-1H-naphtho[2',1':4,5]indeno[1,2-d][1,3]dioxol-4(2H)-one

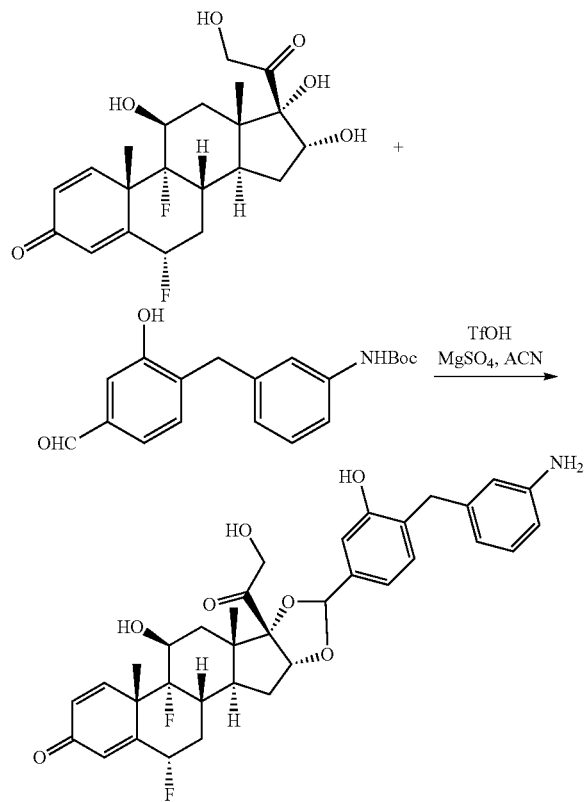

Triflic acid (0.060 mL, 0.680 mmol) was added drop-wise to a 0° C. slurry of (6S,8S,9R,10 S,11S,13S,14S,16R,17S)-6,9-difluoro-11,16,17-trihydroxy-17-(2-hydroxyacetyl)-10, 13-dimethyl-6,7,8,9,10,11,12,13,14,15,16,17-dodecahydro-3H-cyclopenta[a]phenanthren-3-one (0.056 g, 0.136 mmol), tert-butyl (3-(4-formyl-2-hydroxybenzyl)phenyl)carbamate (0.049 g, 0.150 mmol) and MgSO₄ (0.049 g, 0.408 mmol) in MeCN (1.5 mL), maintaining a reaction temperature of <5° C. After 30 min the reaction mixture was diluted with EtOAc (15 mL), and was washed sequentially with a saturated aqueous solution of NaHCO₃ (5 mL×2), and then with a saturated aqueous solution of brine (3 mL). The organic phase was dried (Na₂SO₄) and solvent was removed under reduced pressure. Purification by reverse phase HPLC on a Phenomenex C18(2) 10 micron column (250×30 mm column). A gradient of MeCN (A) and 0.1% formic acid in water (B) was used, at a flow rate of 60 mL/min (0-5.0 min 15% A, 5.0-20.0 min linear gradient 15-80% A, hold 5 min). Combined fractions were concentrated under reduced pressure to remove volatile solvents, and were then lyophilized to give the title compound as a white amorphous solid (6.7 mg). LCMS (Method r, Table 7) $R_t$=0.70 min; MS m/z=622.39 [M+H⁺].

¹H NMR (501 MHz, DMSO-d6) δ 9.51 (s, 1H), 7.25 (d, J=10.2 Hz, 1H), 6.96 (d, J=7.7 Hz, 1H), 6.89-6.81 (m, 2H), 6.75 (d, J=7.7 Hz, 1H), 6.37-6.24 (m, 4H), 6.11 (s, 1H), 5.63 (ddd, J=49.2, 11.2, 6.4 Hz, 1H), 5.50 (d, J=4.3 Hz, 1H), 5.30 (s, 1H), 5.07 (s, 1H), 4.91 (d, J=4.8 Hz, 1H), 4.85 (s, 2H), 4.47 (d, J=19.3 Hz, 1H), 4.21-4.14 (m, 2H), 3.70-3.60 (m, 2H), 2.69-2.50 (m, 1H), 2.26 (s, 1H), 2.31-2.16 (m, 1H), 2.07-1.94 (m, 1H), 1.68 (q, J=10.2, 8.9 Hz, 2H), 1.64-1.50 (m, 1H), 1.48 (s, 3H), 0.84 (s, 3H).

Example 8: Synthesis of (6aR,6bS,7S,8aS,8bS,10R, 11aR,12aS,12bS)-10-(4-(3-aminobenzyl)-3-hydroxyphenyl)-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one

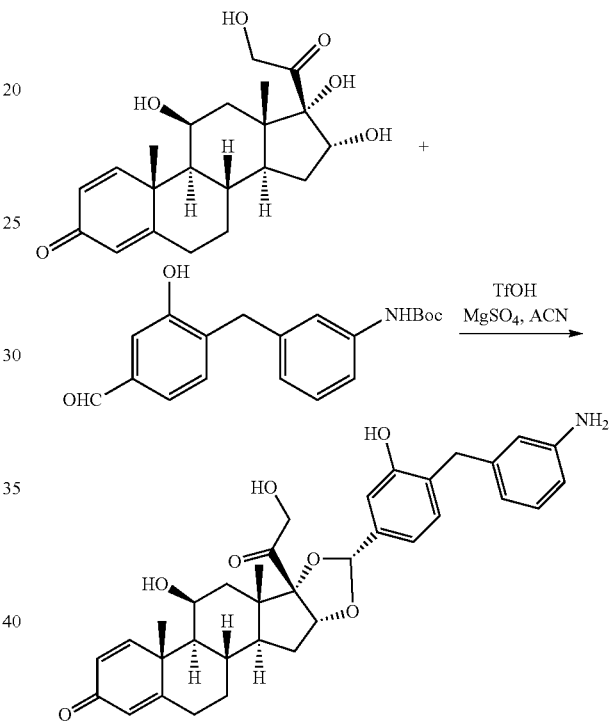

Triflic acid (0.35 mL1, 3.83 mmol) was added drop-wise to a 0° C. slurry of (8S,9S,10R,11S,13S,14S,16R,17S)-11, 16,17-trihydroxy-17-(2-hydroxyacetyl)-10,13-dimethyl-6,7, 8,9,10,11,12,13,14,15,16,17-dodecahydro-3H-cyclopenta [a]phenanthren-3-one (0.296 g, 0.786 mmol), tert-butyl (3-(4-formyl-2-hydroxybenzyl)phenyl)carbamate (0.251 g, 0.767 mmol) and MgSO₄ (0.332 g, 2.76 mmol) in MeCN (3.0 mL), maintaining a reaction temperature of <5° C. After 40 min the reaction was diluted with EtOAc (15 mL), and was washed sequentially with a saturated aqueous solution of NaHCO₃ (10 mL×2), and then with a saturated aqueous solution of brine (5 mL). The organic layer was dried over Na₂SO₄ and solvent was removed under reduced pressure. Purification by chromatography (silica, 12 g) eluting with a gradient of 0-10% MeOH/DCM gave the title compound (238.4 mg, 0.407 mmol, 53% yield) as a white solid. A portion of this material (ca. 79.1 mg) was further purified by reverse phase HPLC on a Phenomenex C18(2) 10 micron column (250×30 mm column). A gradient of MeCN (A) and 0.1% TFA in water (B) was used, at a flow rate of 60 mL/min (0-5.0 min 15% A, 5.0-20 min linear gradient 15-60% A, hold 2 min). Combined fractions were concentrated under reduced pressure to remove volatile solvents, and the resulting solution was frozen and lyophilized to give the title compound as an off-white solid (43.4 mg). LCMS (Method r, Table 7) R$_f$=0.73 min; MS m/z=586.2 [M+H$^+$]. $^1$H NMR (501 MHz, DMSO-d6) δ 9.61 (s, 1H), 7.30 (d, J=10.1 Hz, 1H), 7.27-7.20 (m, 1H), 7.04 (dd, J=7.7, 2.9 Hz, 2H), 6.95-6.91 (m, 2H), 6.90 (d, J=1.6 Hz, 1H), 6.79 (dd, J=7.7, 1.6 Hz, 1H), 6.15 (dd, J=10.1, 1.9 Hz, 1H), 5.92 (d, J=1.6 Hz, 1H), 5.29 (s, 1H), 4.88 (d, J=5.1 Hz, 1H), 4.79 (s, 1H), 4.45 (d, J=19.4 Hz, 1H), 4.28 (q, J=3.3 Hz, 1H), 4.15 (d, J=19.4 Hz, 1H), 3.82 (s, 2H), 2.59-2.49 (m, 1H), 2.30 (dt, J=13.0, 3.8 Hz, 1H), 2.16-2.05 (m, 1H), 2.07-1.98 (m, 1H), 1.75 (d, J=3.0 Hz, 2H), 1.73-1.54 (m, 3H), 1.38 (s, 3H), 1.05 (qd, J=12.9, 4.8 Hz, 1H), 0.97 (dd, J=11.2, 3.6 Hz, 1H), 0.84 (s, 3H).

Example 9: Synthesis of (S)—N-(3-(4-((2S,6aS,6bR,7S,8aS,8bS,10R,11aR,12aS,12bS)-2,6b-Difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)-2-((S)-2-(3-(2,5-dioxo-2,5-dihydro-1H-pyrrol-1-yl)propanamido)propanamido)propanamide Step 1: Synthesis of (9H-Fluoren-9-yl)methyl ((S)-1-(((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate HATU (1.3 g, 3.41 mmol) and 2,6-lutidine (0.4 mL, 3.43 mmol) were added to a room temperature suspension of (2S,6aS,6bR,7S,8aS,8bS,10R,11aR,12aS,12bS)-10-(4-(3-aminobenzyl)phenyl)-2,6b-difluoro-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one (1.0327 g, 1.705 mmol), and (S)-2-((S)-2-((((9H-fluoren-9-yl)methoxy)carbonyl)amino)propanamido)propanoic acid (0.782 g, 2.046 mmol) in THF (11.5 mL). After 3 hours at room temperature, the reaction was diluted with EtOAc (16 mL), then washed sequentially with a 1N aqueous solution of HCl (4 mL×3), and a saturated aqueous solution of brine (4 mL). Purification by chromatography (silica, 40 g) eluting with a gradient of 75-100% EtOAc/heptanes gave the title compound (0.926 g, 0.955 mmol, 56% yield). LC-MS (Method r, Table 7) Rt=1.01 min, m/z=970.18 [M+H$^+$]. $^1$H NMR (500 MHz, DMSO-d6) δ 9.85 (d, J=5.6 Hz, 1H), 8.08 (d, J=7.3 Hz, 1H), 7.89 (dd, J=7.5, 1.0 Hz, 2H), 7.76-7.69 (m, 2H), 7.55 (d, J=7.4 Hz, 1H), 7.49-7.16 (m, 13H), 6.94-6.88 (m, 1H), 6.30 (ddd, J=10.1, 3.7, 1.9 Hz, 1H), 6.14 (dt, J=2.6, 1.2 Hz, 1H), 5.74-5.55 (m, 1H), 5.53 (dt, J=5.0, 2.5 Hz, 1H), 5.12 (t, J=6.0 Hz, 1H), 4.95 (d, J=5.1 Hz, 1H), 4.52 (dd, J=19.4, 6.2 Hz, 1H), 4.38 (p, J=7.0 Hz, 1H), 4.32-4.16 (m, 5H), 4.09 (p, J=6.9 Hz, 1H), 3.88 (d, J=10.9 Hz, 2H), 2.65-2.60 (m, 1H), 2.33-2.20 (m, 1H), 2.05 (d, J=13.5 Hz, 1H), 1.77-1.63 (m, 3H), 1.50 (s, 3H), 1.28 (d, J=7.1 Hz, 3H), 1.23 (d, J=7.1 Hz, 4H), 0.88 (d, J=12.6 Hz, 3H).

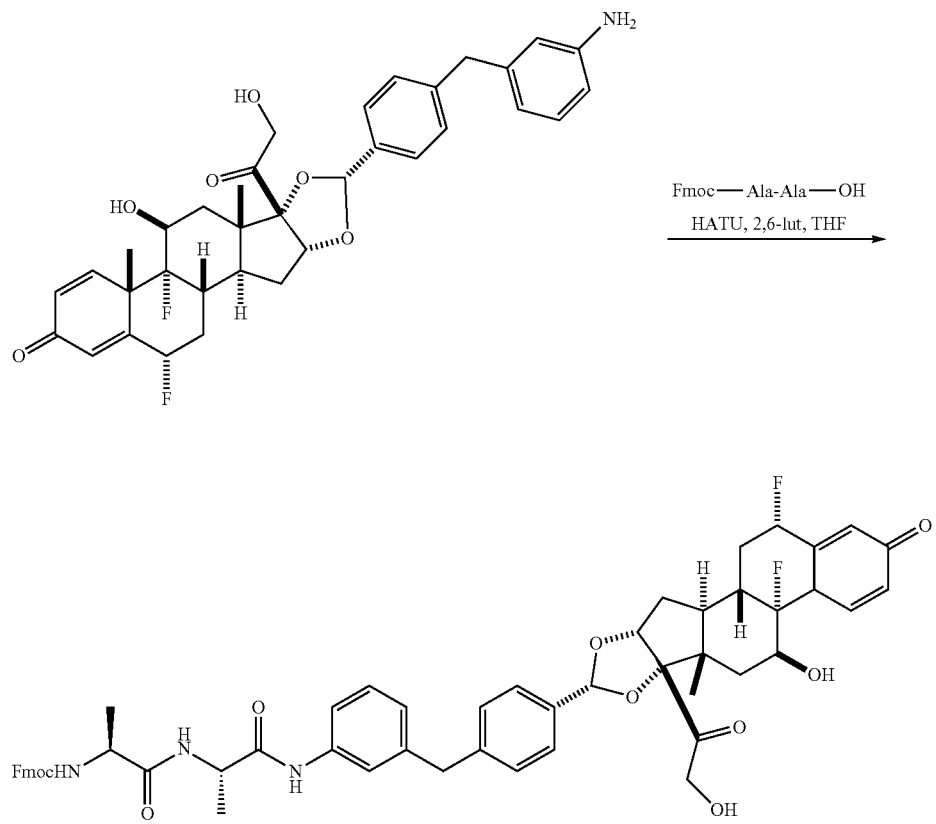

Step 2: Synthesis of (S)-2-amino-N—((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)propanamide dioxol-10-yl)benzyl)phenyl)amino)-1-oxopropan-2-yl)amino)-1-oxopropan-2-yl)carbamate (1.18 g, 1.216 mmol) in THF (6.0 mL). After 2 h, MTBE (10 mL) was added, which resulted in the immediate precipitation of a yellow solid. This slurry was stirred for 90 min, filtered, and washed with MTBE (5 mL×3) to give a yellow solid (802.7 mg). This material was purified further by reverse phase HPLC on

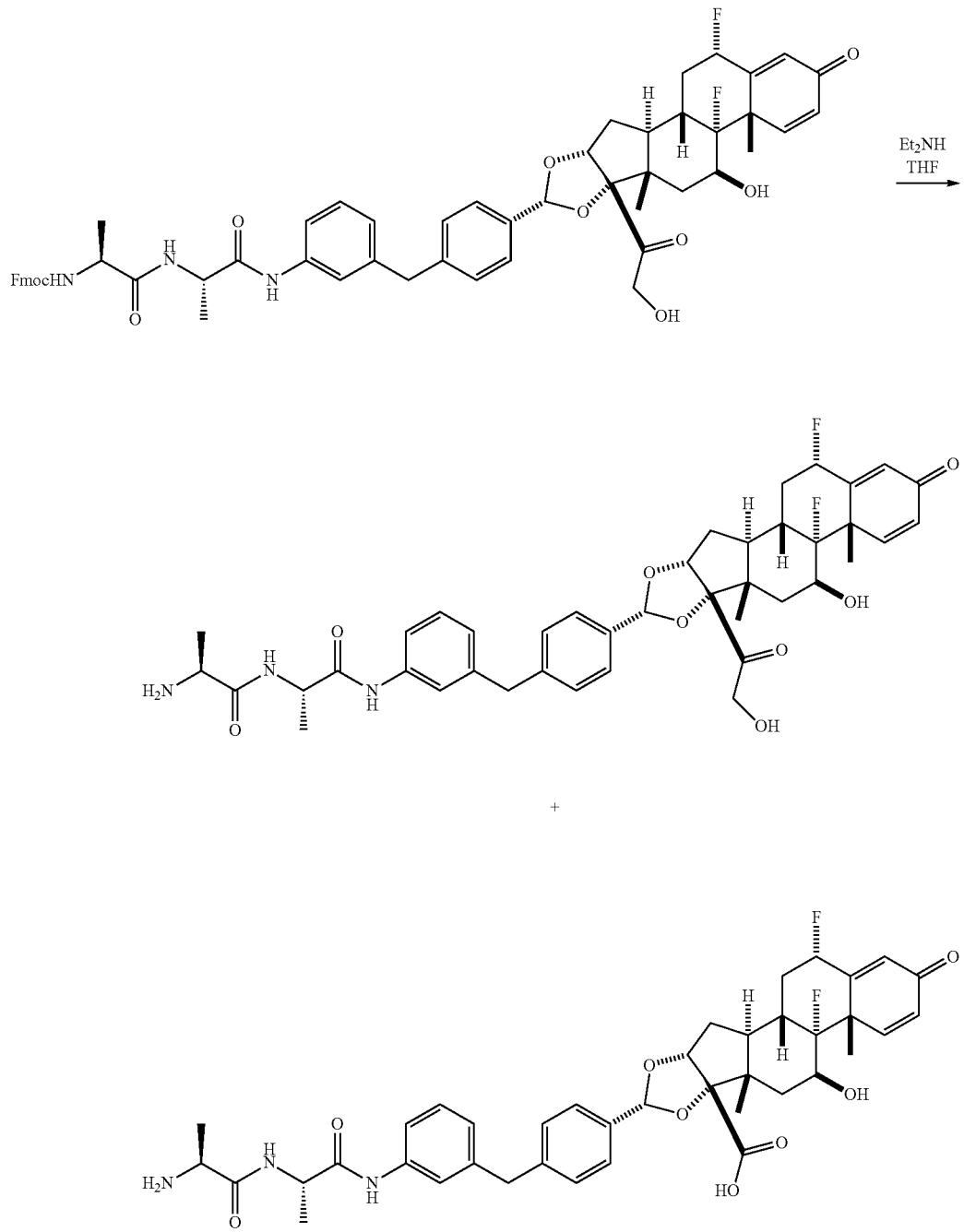

Diethylamine (0.5 mL, 4.79 mmol) was added to a room temperature solution of (9H-fluoren-9-yl)methyl ((S)-1-(((S)-1-(3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]

a Phenomenex C18(2) 10 micron column (250×50 mm column). A gradient of MeCN (A) and 0.1% formic acid in water (B) was used, at a flow rate of 90 mL/min (0-5.0 min 15% A, 5.0-20.0 min linear gradient 15-75% A, hold 2 min, 22.0-22.5 min linear gradient from 75-95%, hold for 4 min). Combined fractions were concentrated under reduced pressure to dryness and then dried overnight in the vacuum oven at 50° C. LC-MS (Method r, Table 7) $R_t$=0.76 min, m/z=748.5 [M+H$^+$]. $^1$H NMR indicates that the title compound is an approximately 1:1 mixture with (2S,6aS,6bR,7S,8aS,8bS,10R,11aR,12aS,12bS)-10-(4-(3-((S)-2-((S)-2-aminopropanamido)propanamido)benzyl)phenyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxole-8b-carboxylic acid. (0.170 g total, 0.115 mol and 10% yield of each compound). $^1$H NMR (500 MHz, DMSO-d$_6$) δ 10.00 (d, J=3.3 Hz, 2H), 8.42 (d, J=34.2 Hz, 2H), 8.30 (s, 1H), 7.48-7.37 (m, 3H), 7.38-7.29 (m, 5H), 7.31-7.15 (m, 8H), 6.92 (d, J=7.6 Hz, 2H), 6.28 (ddd, J=10.3, 6.6, 1.9 Hz, 3H), 6.12 (d, J=3.7 Hz, 3H), 5.77-5.53 (m, 3H), 5.45 (d, J=7.7 Hz, 3H), 5.04-4.99 (m, 1H), 4.94 (d, J=5.1 Hz, 1H), 4.50 (d, J=19.4 Hz, 1H), 4.40 (s, 3H), 4.23-4.12 (m, 2H), 3.54 (dq, J=17.6, 6.9 Hz, 1H), 2.71-2.56 (m, 1H), 2.30-2.15 (m, 1H), 2.03 (d, J=14.2 Hz, 2H), 1.94 (d, J=14.3 Hz, 1H), 1.84 (d, J=14.1 Hz, 1H), 1.76-1.59 (m, 7H), 1.49 (d, J=2.6 Hz, 8H), 1.39-1.10 (m, 13H), 1.00 (s, 4H), 0.86 (s, 3H).

Step 3: Synthesis of (S)—N-(3-(4-((2S,6aS,6bR,7S,8aS,8bS,10R,11aR,12aS,12bS)-2,6b-Difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)-2-((S)-2-(3-(2,5-dioxo-2,5-dihydro-1H-pyrrol-1-yl)propanamido)propanamido)propanamide propanamide (0.170 g, 0.227 mmol) and N-succinimidyl 3-maleimidopropionate (0.0691 g, 0.260 mmol) in DMF (2.5 mL). After 30 min, the pH of the reaction mixture was adjusted to 4-5 by drop-wise addition of a 7% solution of TFA in water (1.2 mL). The crude mixture was purified by reverse phase HPLC on a Phenomenex C18(2) 10 micron column (250×50 mm column). A gradient of MeCN (A) and 0.1% TFA in water (B) was used, at a flow rate of 90 mL/min (0-5.0 min 15% A, 5.0-20 min linear gradient 15-85% A, hold 2 min). Combined fractions were concentrated under reduced pressure to remove volatile solvents, and the resulting solution was frozen and lyophilized to give a white solid (85.2 mg, 0.0473 mmol, 21% yield). LC-MS (Method R, Table 7) $R_t$=0.82 min, m/z=899.92 [M+H$^+$]. $^1$H NMR data was consistent with a 1:1 mixture of the title compound (2S,6aS,6bR,7S,8aS,8bS,10R,11aR,12aS,12bS)-10-(4-(3-((S)-2-((S)-2-(3-(2,5-dioxo-2,5-dihydro-1H-pyrrol-1-yl)propanamido)propanamido)propanamido)benzyl)phenyl)-2,6b-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxole-8b-carboxylic acid (see example 10 for an alternative preparation of the title compound, which avoids this mixture). MS analysis confirms that this material is a mixture of two compounds with m/z=899.1 [M+H$^+$] and m/z=885.0 [M+H$^+$]. $^1$H NMR (400 MHz, DMSO-d$_6$) δ 9.71 (s, 2H), 8.16 (d, J=7.1 Hz, 2H), 8.03 (d, J=7.3 Hz, 2H), 7.49-7.29 (m, 9H), 7.30-7.13 (m, 9H), 6.96 (s, 3H), 6.92-6.85 (m, 2H), 6.27 (dt, J=10.1, 1.9 Hz, 2H), 6.11 (d, J=2.3 Hz, 2H), 5.74-5.53 (m, 2H), 5.46 (d, J=23.9

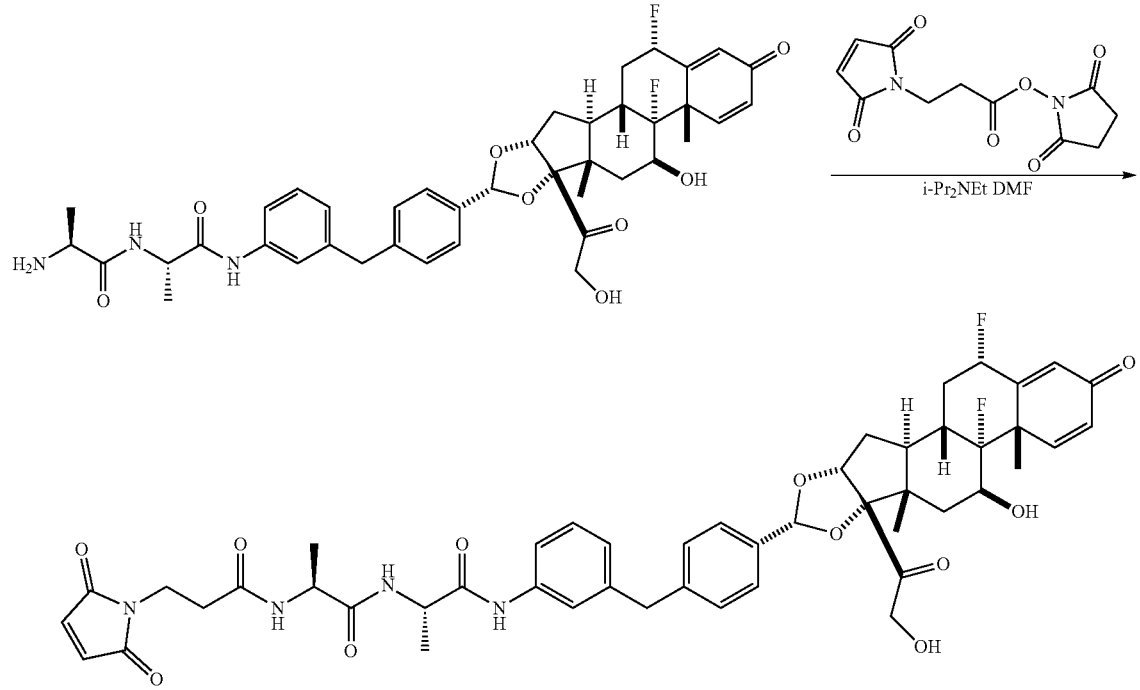

Diisopropylethylamine (0.1 mL, 0.573 mmol) was added to a room temperature solution of (S)-2-amino-N—((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,1a,12,12a,12b-dodecahydro-1H-naphtho[2',1': 4,5]indeno[1,2-d][1,3]dioxol-10-yl)benzyl)phenyl)amino)-1-oxopropan-2-yl)

Hz, 4H), 4.93 (d, J=5.0 Hz, 1H), 4.32 (p, J=7.1 Hz, 2H), 4.27-4.13 (m, 3H), 4.17 (s, 3H), 3.59 (t, J=7.3 Hz, 4H), 2.69-2.53 (m, 2H), 2.38 (t, J=7.3 Hz, 4H), 2.28 (s, 3H), 2.22 (s, 1H), 2.08-1.98 (m, 1H), 1.98-1.90 (m, 1H), 1.83-1.68 (m, 2H), 1.69 (s, 2H), 1.66 (s, 2H), 1.48 (d, J=3.7 Hz, 8H), 1.25 (d, J=7.0 Hz, 6H), 1.15 (d, J=7.1 Hz, 6H), 0.99 (s, 3H), 0.84 (s, 3H).

Example 10: Synthesis of (S)—N-(3-(4-((2S,6aS, 6bR,7S,8aS,8bS,10R,11aR,12aS,12bS)-2,6b-Difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)-2-((S)-2-(3-(2,5-dioxo-2,5-dihydro-1H-pyrrol-1-yl)propanamido)propanamido)propanamide Step 1: Synthesis of tert-butyl ((S)-1-(((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate

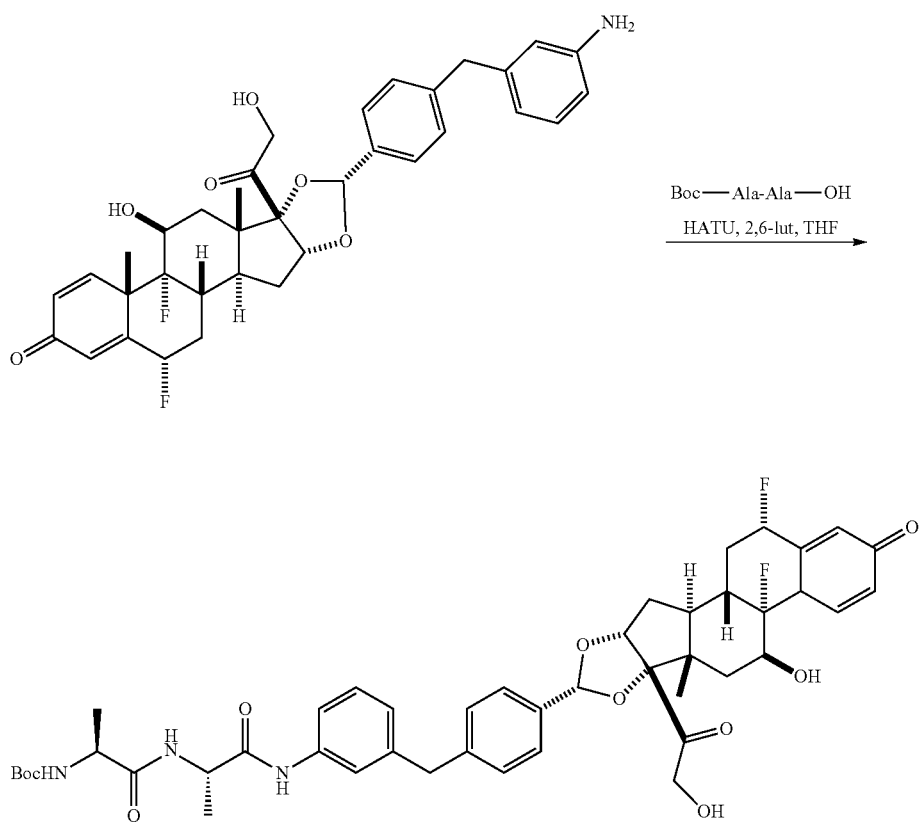

HATU (610 mg, 1.605 mmol) and 2,6-lutidine (0.3 mL, 2.58 mmol) were added to a room temperature mixture of (2S,6aS,6bR,7S,8aS,8bS,10R,11aR,12aS,12bS)-10-(4-(3-aminobenzyl)phenyl)-2,6b-difluoro-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one (648.1 mg, 1.070 mmol), and (S)-2-((S)-2-((tert-butoxycarbonyl)amino)propanamido)propanoic acid (334 mg, 1.284 mmol) in THF (11.5 mL). After 9 hours the reaction was diluted with EtOAc (16 mL), then washed with a 1N aqueous solution of HCl (4 mL×3), followed by a saturated aqueous solution of brine (4 mL). Purification by chromatography (silica, 40 g) eluting with a gradient of 0-10% MeOH/DCM gave the title compound as a yellow foam (773.7 mg, 0.912 mmol, 85% yield). LC-MS (Method r, Table 7) $R_t$=0.92 min, m/z=848.53 [M+H$^+$].

Step 2: Synthesis of (S)-2-amino-N—((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)propanamide

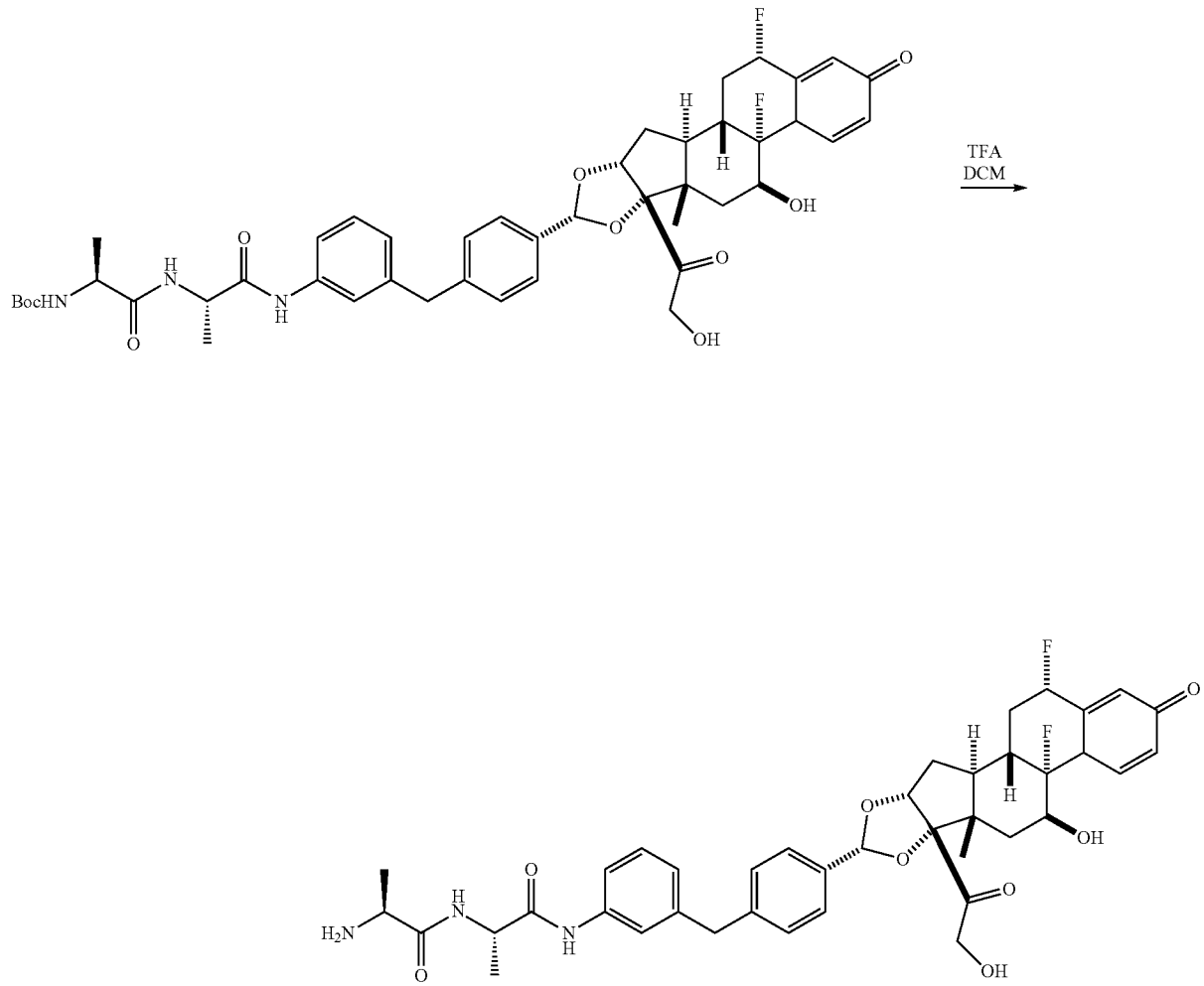

TFA (1.97 mL, 25.6 mmol) was added drop-wise to a room temperature solution of tert-butyl ((S)-1-(((S)-1-((3-(4-((2S,6aS,6bR,7S,8aS,8bS,10R,11 aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate (0.7683 g, 0.906 mmol) in DCM (6.0 mL). After 50 min solvent was removed under reduced pressure to give a brown syrup. The residue was dissolved in 1:1 DMSO:MeOH (12 mL) and purified by reverse phase HPLC on a Phenomenex C18(2) 10 micron column (250×50 mm column). A gradient of MeCN (A) and 0.1% TFA in water (B) was used, at a flow rate of 90 mL/min (0-5.0 min 15% A, 5.0-20 min linear gradient 15-75% A, hold 2 min, 22.0-22.5 min linear gradient 75-95% A, hold 4 min). Combined fractions were concentrated under reduced pressure to dryness and the residue was dried overnight in the vacuum oven at 50° C. to give the title compound (230 mg, 0.308 mmol, 34% yield. LC-MS (Method r, Table 7) major acetal isomer $R_t$=0.73 min, m/z=748.78 [M+H$^+$]. $^1$H NMR (400 MHz, DMSO-d$_6$) δ 10.01 (s, 1H), 8.62 (d, J=7.2 Hz, 1H), 8.04 (d, J=5.4 Hz, 3H), 7.46-7.31 (m, 4H), 7.31-7.13 (m, 4H), 6.91 (d, J=7.6 Hz, 1H), 6.27 (dd, J=10.2, 1.9 Hz, 1H), 6.11 (s, 1H), 5.76-5.47 (m, 2H), 5.43 (s, 1H), 4.93 (d, J=4.6 Hz, 1H), 4.49 (d, J=19.5 Hz, 1H), 4.42 (q, J=7.1 Hz, 1H), 4.23-4.13 (m, 2H), 2.72-2.54 (m, 1H), 2.33-2.16 (m, 2H), 2.02 (dt, J=13.6, 3.6 Hz, 1H), 1.69 (h, J=5.9, 5.1 Hz, 3H), 1.48 (s, 4H), 1.33 (d, J=7.0 Hz, 3H), 1.30 (d, J=7.1 Hz, 3H), 0.85 (s, 3H).

Step 3: Synthesis of (S)—N-(3-(4-((2S,6aS,6bR,7S, 8aS,8bS,10R,11aR,12aS,12bS)-2,6b-Difluoro-7-hydroxy-8b-(2-hydroxyacetyl)-6a,8a-dimethyl-4-oxo-2,4,6a,6b,7,8,8a,8b, 11a,12,12a,12b-dodecahydro-1H-naphtho[2',1':4,5]indeno[1,2-d][1,3]dioxol-10-yl)benzyl)phenyl)-2-((S)-2-(3-(2,5-dioxo-2,5-dihydro-1H-pyrrol-1-yl)propanamido)propanamido)propanamide 5.72-5.51 (m, 1H), 5.48 (s, 1H), 5.41 (s, 1H), 4.91 (d, J=4.9 Hz, 1H), 4.47 (d, J=19.4 Hz, 1H), 4.30 (p, J=7.1 Hz, 1H), 4.25-4.11 (m, 3H), 3.85 (s, 2H), 3.57 (t, J=7.3 Hz, 2H), 2.71-2.48 (m, 1H), 2.36 (dd, J=8.0, 6.7 Hz, 2H), 2.23 (ddt, J=25.1, 12.2, 6.6 Hz, 2H), 2.01 (dt, J=13.7, 3.7 Hz, 1H), 1.75-1.57 (m, 3H), 1.48 (p, J=11.9 Hz, 1H), 1.46 (s, 3H), 1.24 (d, J=7.2 Hz, 3H), 1.13 (d, J=7.2 Hz, 3H), 0.83 (s, 3H).

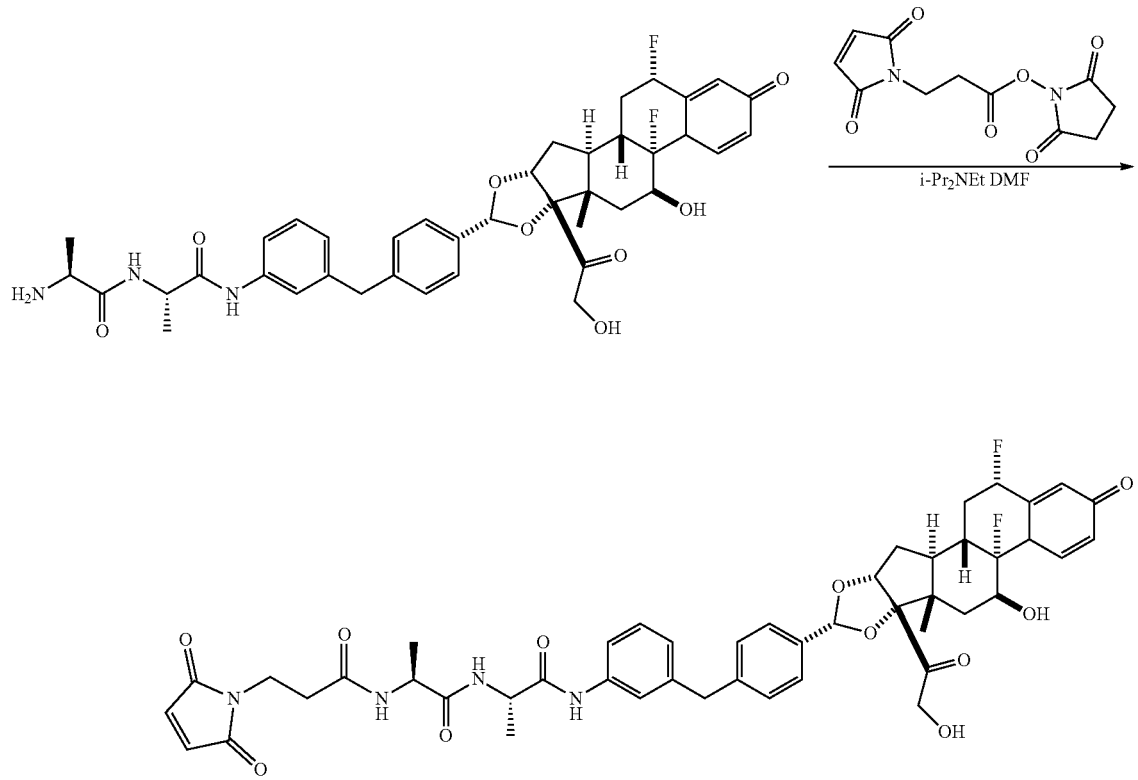

Diisopropylethylamine (0.1 mL, 0.573 mmol) was added to a room temperature solution of (S)-2-amino-N—((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1': 4,5]indeno[1,2-d][1,3]dioxol-10-yl)benzyl)phenyl)amino)-1-oxopropan-2-yl)propanamide (0.220 g, 0.294 mmol) and N-succinimidyl 3-maleimidopropionate (0.086 g, 0.324 mmol) in DMF (2.8 mL). After 30 min the pH of the reaction mixture was adjusted to 4-5 by drop-wise addition of a 7% solution of TFA in water (1.0 mL). The crude mixture was purified by reverse phase HPLC on a Phenomenex C18(2) 10 micron column (250×50 mm column). A gradient of MeCN (A) and 0.1% TFA in water (B) was used, at a flow rate of 90 mL/min (0-5.0 min 15% A, 5.0-20 min linear gradient 15-85% A, hold 2 min). Combined fractions were concentrated under reduced pressure to remove volatile solvents, and the resulting solution was frozen and lyophilized to give a white solid (175.2 mg, 0.195 mmol, 66% yield). LC-MS (Method r, Table 7) R$_t$=0.82 min, m/z=899.87 [M+H$^+$]. $^1$H NMR (400 MHz, DMSO-d$_6$) δ 9.70 (s, 1H), 8.14 (d, J=7.0 Hz, 1H), 8.01 (d, J=7.2 Hz, 1H), 7.47-7.35 (m, 2H), 7.32 (d, J=8.1 Hz, 2H), 7.26-7.10 (m, 4H), 6.95 (s, 1H), 6.87 (dt, J=7.6, 1.3 Hz, 1H), 6.26 (dd, J=10.2, 1.9 Hz, 1H), 6.09 (d, J=2.0 Hz, 1H), Example 11: Synthesis of (S)—N—((S)-1-(((S)-1-((3-(4-((2S,6aS,6bR,7S,8aS,8bS,10R,11aR,12aS, 12bS)-2,6b-difluoro-7-hydroxy-8b-(2-hydroxyacetyl)-6a,8a-dimethyl-4-oxo-2,4,6a,6b,7,8,8a,8b, 11a,12,12a,12b-dodecahydro-1H-naphtho[2',1':4,5] indeno[1,2-d][1,3]dioxol-10-yl)benzyl)phenyl) amino)-1-oxopropan-2-yl)amino)-1-oxopropan-2-yl)-2-(3-(2,5-dioxo-2,5-dihydro-1H-pyrrol-1-yl) propanamido)-3-(1H-imidazol-4-yl)propanamide Step1: Synthesis of (S)-2-((tert-Butoxycarbonyl) amino)-3-(1H-imidazol-5-yl)propanoic acid, 2 hydrochloric Acid

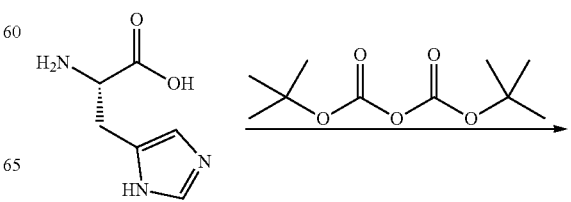

421
-continued

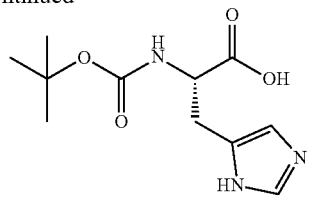

To a solution of (S)-2-amino-3-(1H-imidazol-5-yl)propanoic acid (1.55 g, 9.99 mmol) in water (40 mL) and 1,4-dioxane (10 mL) at 0° C. were added NaOH (10 mL, 19.98 mmol) and BOC-anhydride (2.319 mL, 9.99 mmol). The resulting mixture was stirred at 23° C. for 4 h. Then the mixture was acidified with HCl solution to pH 5, and washed with EtOAc (3×30 mL). Then the inorganic layer was freeze-dried to give the title compound (including NaCl)) (4.449 g, 9.90 mmol, 99% yield) as a white solid. LCMS (Method m, Table 7) $R_t$=1.22 min, m/z 256.2 (M+1)+.

Step 2: Synthesis of tert-butyl ((S)-1-(((S)-1-(((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)amino)-3-(1H-imidazol-5-yl)-1-oxopropan-2-yl)carbamate To a solution of (S)-2-((tert-butoxycarbonyl)amino)-3-(1H-imidazol-5-yl)propanoic acid, 2hydrochloric acid (170 mg, 0.197 mmol), (S)-2-((tert-butoxycarbonyl)amino)-3-(1H-imidazol-5-yl)propanoic acid, 2 hydrochloric acid (443 mg, 0.986 mmol) in THF (20 mL) at 0° C. were added DIPEA (0.345 mL, 1.973 mmol) and HATU (90 mg, 0.237 mmol), DMAP (31.3 mg, 0.256 mmol) and the resulting mixture was stirred at 0° C. for 10 min, and gradually warmed to 25° C. for 16 h. After that, the mixture was concentrated to give the residue, which was purified by DCM/MeOH(10:1) by silica gel to obtain the title compound (194 mg, 0.138 mmol, 69.9% yield) as a yellow solid. LCMS (Method m, Table 7) $R_t$=1.72 min, m/z 985.3 (M+1)+; $^1$H NMR: (400 MHz, DMSO-d6) δ ppm: 0.82-0.89 (m, 10H), 1.12-1.18 (m, 9H), 1.23 (s, 9H), 1.68-1.71 (m, 2H), 2.20-2.33 (m, 2H), 3.86-3.88 (m, 2H), 4.18-4.29 (m, 4H), 4.36-4.39 (m, 1H), 4.49-4.54 (m, 1H), 4.94 (d, J=4.4 Hz, 1H), 5.13 (bs, 1H), 5.45 (s, 1H), 5.57-5.74 (m, 2H), 6.12 (s, 1H), 6.29 (d, J=10.0 Hz, 1H), 6.91 (d, J=8.0 Hz, 1H), 7.01 (d, J=8.0 Hz, 1H), 7.10-7.25 (m, 4H), 7.29-7.37 (m, 3H), 7.44-7.49 (m, 2H), 8.06 (d, J=6.0 Hz, 1H).

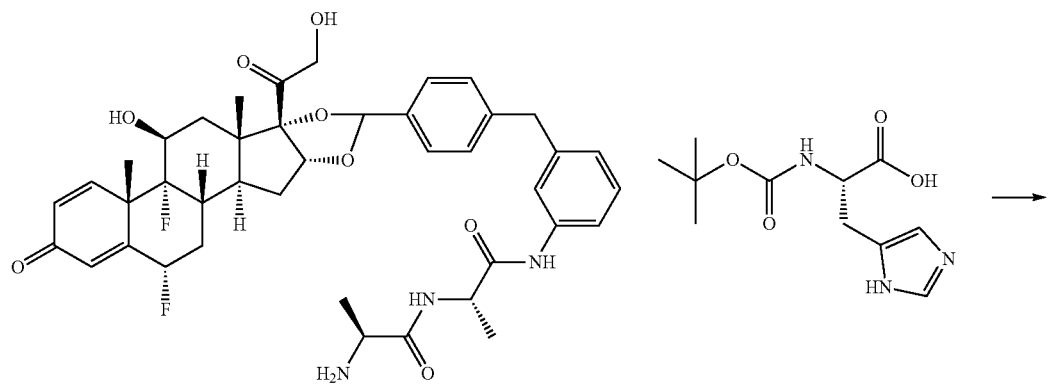

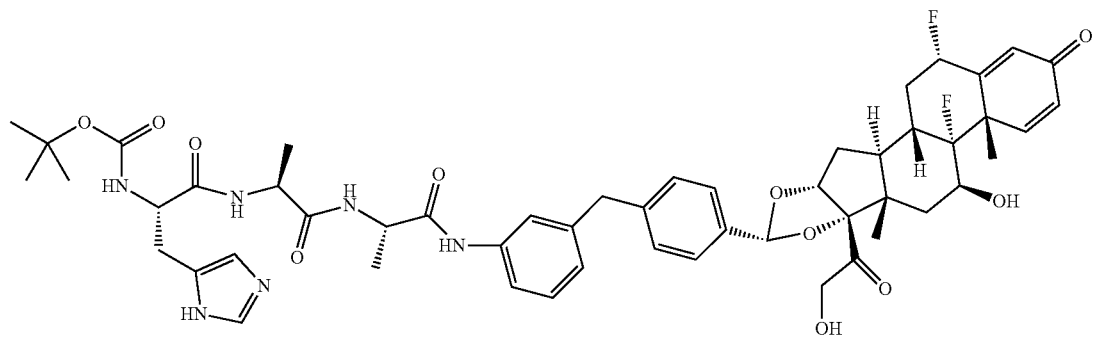

Step 3: Synthesis of (S)-2-amino-N—((S)-1-(((S)-1-((3-(4-((2S,6aS,6bR,7S,8aS,8bS, 10R,11aR,12aS, 12bS)-2,6b-difluoro-7-hydroxy-8b-(2-hydroxy-acetyl)-6a,8a-dimethyl-4-oxo-2,4,6a,6b,7,8,8a,8b, 11a,12,12a,12b-dodecahydro-1H-naphtho[2',1':4,5] indeno[1,2-d][1,3]dioxol-10-yl)benzyl)phenyl) amino)-1-oxopropan-2-yl)amino)-1-oxopropan-2-yl)-3-(1H-imidazol-5-yl)propanamide, 3trifluoroacetic Acid

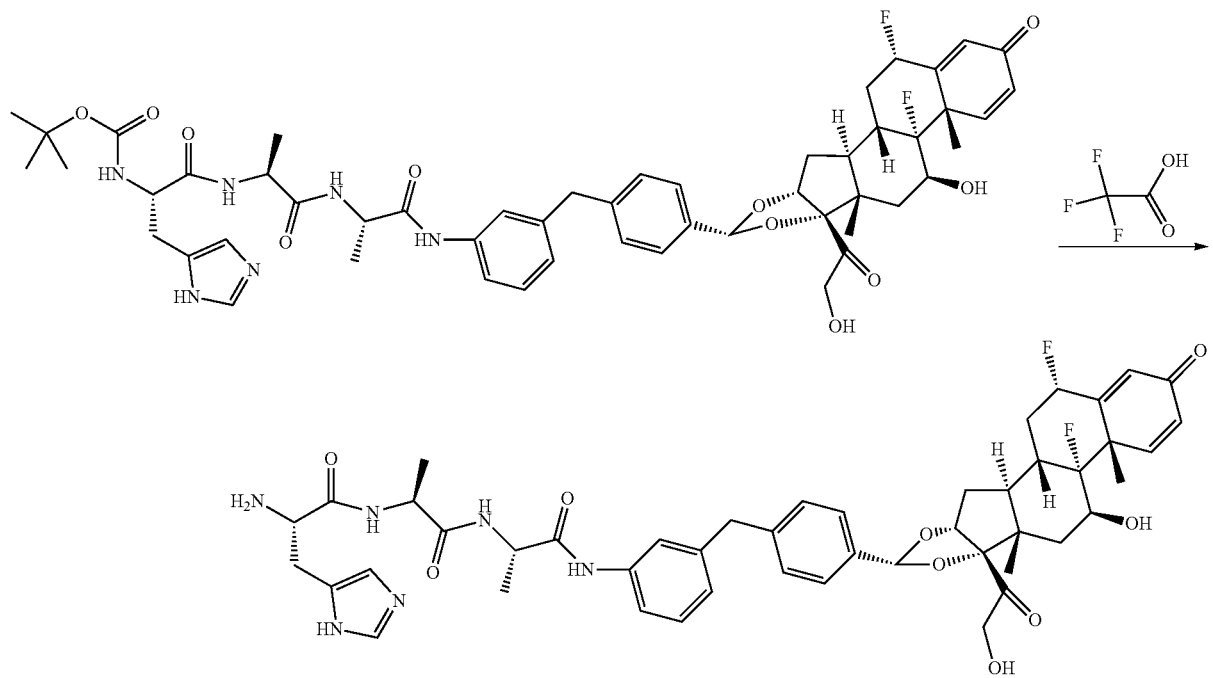

To a solution of tert-butyl-(((S)-1-(((S)-1-((3-(4-((2S,6aS, 6bR,7S,8aS,8bS,10R,11aR,12aS,12bS)-2,6b-difluoro-7-hy-droxy-8b-(2-hydroxyacetyl)-6a,8a-dimethyl-4-oxo-2,4,6a, 6b,7,8,8a,8b,1a,12,12a,12b-dodecahydro-1H-naphtho[2',1': 4,5]indeno[1,2-d][1,3]dioxol-10-yl)benzyl)phenyl)amino)-1-oxopropan-2-yl)amino)-1-oxopropan-2-yl)amino)-3-(1H-imidazol-5-yl)-1-oxopropan-2-yl)carbamate (120 mg, 0.122 mmol) in DCM (3 mL) was added TFA (0.6 mL, 7.79 mmol), and the reaction mixture was stirred at 20° C. for 1 hour. After that, the mixture was diluted with DCM, concentrated in vacuo at about 25° C. to give the title compound (149 mg, 0.103 mmol, 84.90% yield) as a yellow solid.

LCMS (Method m, Table 7) $R_f$=1.64 min, m/z 885.3 (M+1)$^+$.

Step 4: Synthesis of (S)—N—((S)-1-(((S)-1-((3-(4-((2S,6aS,6bR,7S,8aS,8bS,10R,11 aR,12aS,12bS)-2, 6b-difluoro-7-hydroxy-8b-(2-hydroxyacetyl)-6a,8a-dimethyl-4-oxo-2,4,6a,6b,7,8,8a,8b,1a,12,12a,12b-dodecahydro-1H-naphtho[2',1':4,5]indeno[1,2-d][1, 3]dioxol-10-yl)benzyl)phenyl)amino)-1-oxopropan-2-yl)amino)-1-oxopropan-2-yl)-2-(3-(2,5-dioxo-2,5-dihydro-1H-pyrrol-1-yl)propanamido)-3-(1H-imidazol-4-yl)propanamid

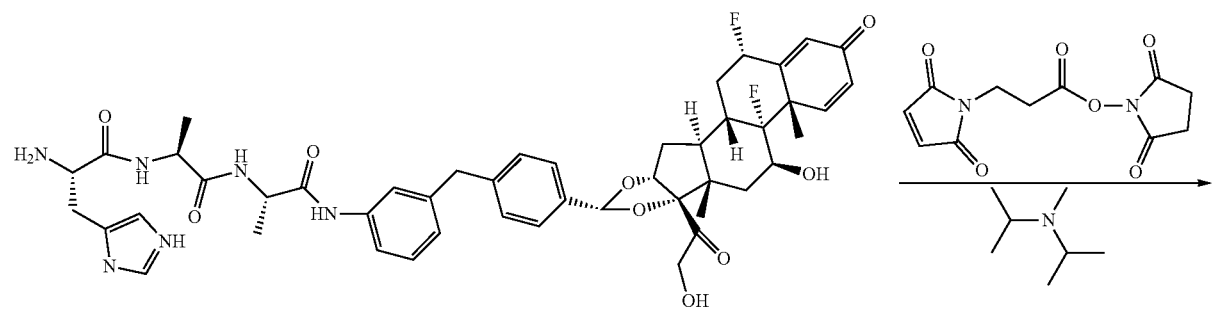

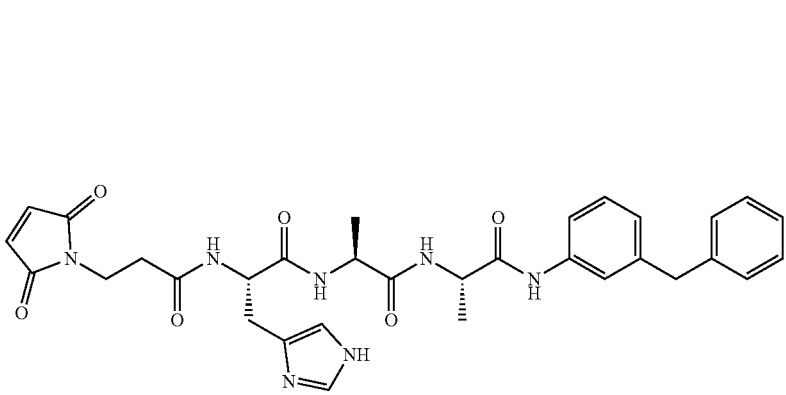
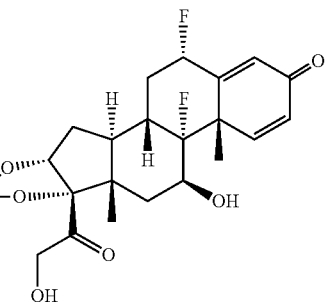

DIPEA (0.106 mL, 0.607 mmol) was added to the solution of (S)-2-amino-N—((S)-1-(((S)-1-((3-(4-((2S,6aS,6bR,7S,8aS,8bS,10R,11aR,12aS,12bS)-2,6b-difluoro-7-hydroxy-8b-(2-hydroxy acetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)-3-(1H-imidazol-5-yl)propanamide, 3trifluoroacetic acid (149 mg, 0.121 mmol) and 2,5-dioxopyrrolidin-1-yl 3-(2,5-dioxo-2,5-dihydro-1H-pyrrol-1-yl)propanoate (48.5 mg, 0.182 mmol) in DMF (2 mL) at 0° C., and then the mixture was stirred at room temperature for 2 h. The reaction mixture was purified by prep-HPLC (Mobile Phase:A=0.05% TFA in water, B=MeCN; Flow Rate: 2 mL/min) to afford the title compound (11.4 mg, 9.02 mmol, 7.43% yield) as a white solid. LCMS (Method m, Table 7) RT=1.62 min, m/z 1058.3 (M+Na)$^+$; $^1$H NMR: (400 MHz, DMSO-d) δ ppm: 0.86 (s, 3H), 1.24-1.29 (m, 9H), 1.46-1.54 (m, 3H), 1.68-1.76 (m, 2H), 1.98-2.06 (m, 2H), 2.20-2.33 (m, 2H), 2.40-2.44 (m, 2H), 2.60-2.68 (m, 1H), 2.88-2.94 (m, 1H), 3.00-3.05 (m, 1H), 3.57 (t, J=7.4 Hz, 2H), 3.89 (s, 2H), 4.18-4.39 (m, 4H), 4.49-4.60 (m, 2H), 4.95 (d, J=4.8 Hz, 1H), 5.46 (s, 1H), 5.54-5.74 (m, 2H), 6.13 (s, 1H), 6.30 (d, J=10.4 Hz, 1H), 6.92 (d, J=7.6 Hz, 1H), 7.00 (s, 2H), 7.20-7.28 (m, 4H), 7.35-7.46 (m, 5H), 8.16 (d, J=6.4 Hz, 1H), 8.23 (d, J=7.2 Hz, 1H), 8.31 (d, J=8.4 Hz, 1H), 8.96 (s, 1H), 9.89 (s, 1H).

Example 12: Synthesis of (S)-5-(((S)-1-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)amino)-1-oxopropan-2-yl)amino)-4-(3-(2,5-dioxo-2,5-dihydro-1H-pyrrol-1-yl)propanamido)-5-oxopentanoic acid (Cpd. No. 81)

Step 1: Synthesis of (2S,6aS,6bR,7S,8aS,8bS,10R,11aR,12aS,12bS)-10-(4-((4-Aminophenyl)thio)phenyl)-8b-(2-((tert-buty dimethylsilyl)oxy)acetyl)-2,6b-difluoro-7-hydroxy-6a,8a-dimethyl-6a,6b,7,8,8a,8b,11a,12,12a,12b-decahydro-1H-naphtho[2',1':4,5]indeno[1,2-d][1,3]dioxol-4(2H)-one

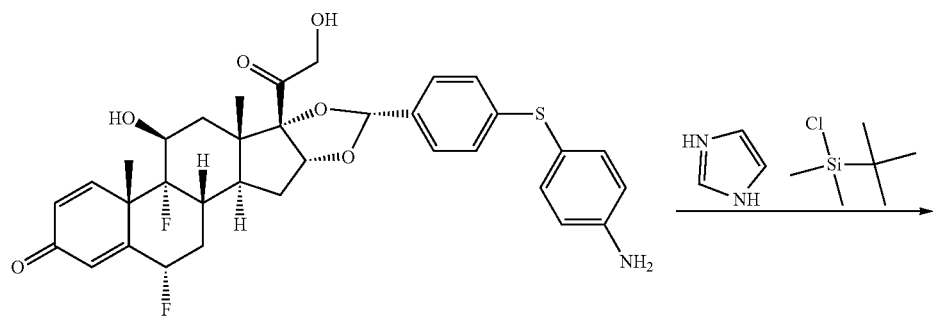

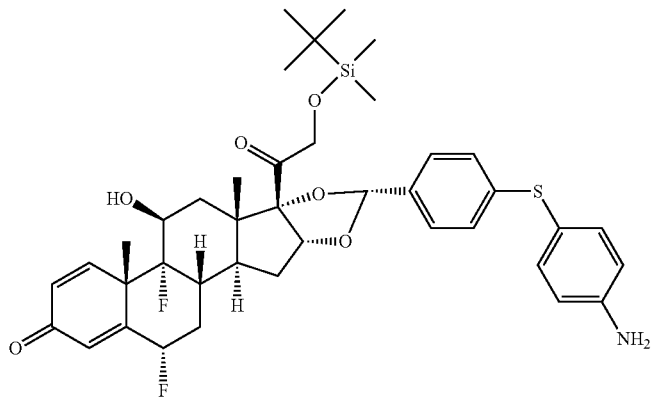

To a stirred solution of (2S,6aS,6bR,7S,8aS,8bS,10R,11aR,12aS,12bS)-10-(4-((4-aminophenyl)thio)phenyl)-2,6b-difluoro-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one (62.4 mg, 0.1 mmol) and imidazole (34.0 mg, 0.500 mmol) in DCM was added TBS-Cl (45.2 mg, 0.300 mmol) at 0° C., After stirring was continued for 30 min at the same temperature, the mixture was allowed to warm to room temperature and stirred for 2 h. the reaction mixture was diluted with EtOAc (10 mL), washed with water (2×10 mL) and brine (1×10 mL), dried over Na$_2$SO$_4$, filtered and concentrated in vacuo. The residue was purified by column (EA:PE=1:10-1:1) to give the product (2S,6aS,6bR,7S,8aS,8bS,10R,11aR,12aS,12bS)-10-(4-((4-aminophenyl)thio)phenyl)-8b-(2-((tert-butyldimethylsilyl)oxy)acetyl)-2,6b-difluoro-7-hydroxy-6a,8a-dimethyl-6a,6b,7,8,8a,8b,11a,12,12a,12b-decahydro-1H-naphtho[2',1':4,5]indeno[1,2-d][1,3]dioxol-4(2H)-one (50 mg, 0.068 mmol, 67.8% yield). LCMS (Method m, Table 7) R$_t$=2.144 min, m/z 738 (M+H).

Step 2: Synthesis of tert-butyl ((S)-1-((4-((4-((2S,6aS,6bR,7S,8aS,8bS,10R,11aR,12aS,12bS)-8b-(2-((tert-butyldimethylsilyl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)amino)-1-oxopropan-2-yl)carbamate

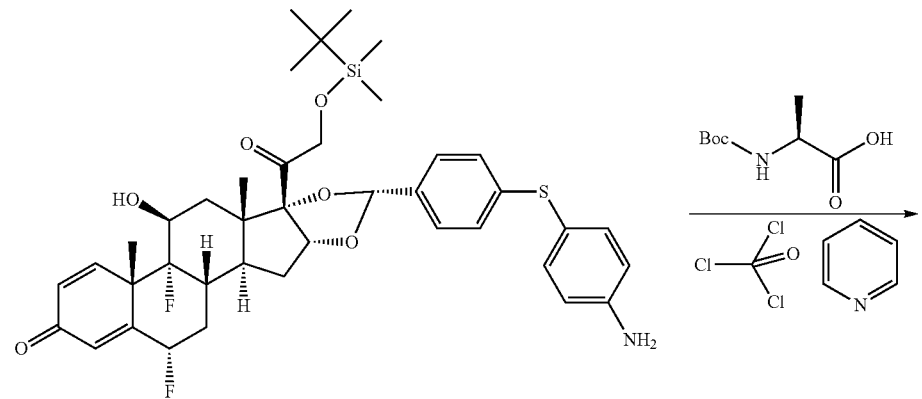

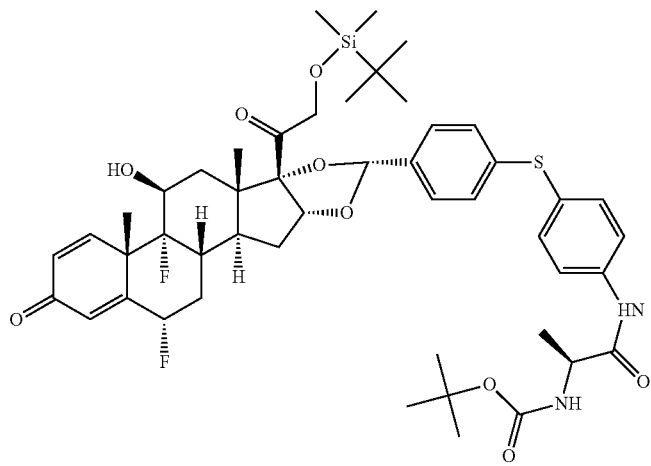

To a stirred solution of (2S,6aS,6bR,7S,8aS,8bS,10R,11aR,12aS,12bS)-10-(4-((4-aminophenyl)thio)phenyl)-8b-(2-((tert-butyldimethylsilyl)oxy)acetyl)-2,6b-difluoro-7-hydroxy-6a,8a-dimethyl-6a,6b,7,8,8a,8b,11a,12,12a,12b-decahydro-1H-naphtho[2',1':4,5]indeno[1,2-d][1,3]dioxol-4(2H)-one (0.148 g, 0.2 mmol) and (S)-2-((tert-butoxycarbonyl) amino)propanoic acid (0.076 g, 0.400 mmol) in DCM (3 mL) was added pyridine (0.162 mL, 2.000 mmol), followed by POCl₃ (0.075 mL, 0.800 mmol) in dropwise. The reaction mixture was stirred for 1 hour at ambient temperature, then concentrated in vacuo, and the residue was purified by column (EA:PE=1:10-9:1) to give tert-butyl ((S)-1-((4-((4-((2S,6aS,6bR,7S,8aS,8bS,10R,11aR,12aS,12bS)-8b-(2-((tert-butyldimethylsilyl) oxy) acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)amino)-1-oxopropan-2-yl)carbamate (0.073 g, 0.080 mmol, 40% yield) as a semi-solid. LCMS (Method m, Table 7) $R_f$=2.156 min, m/z 909 (M+H).

Step 3: Synthesis of (S)-2-amino-N-(4-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)propanamide

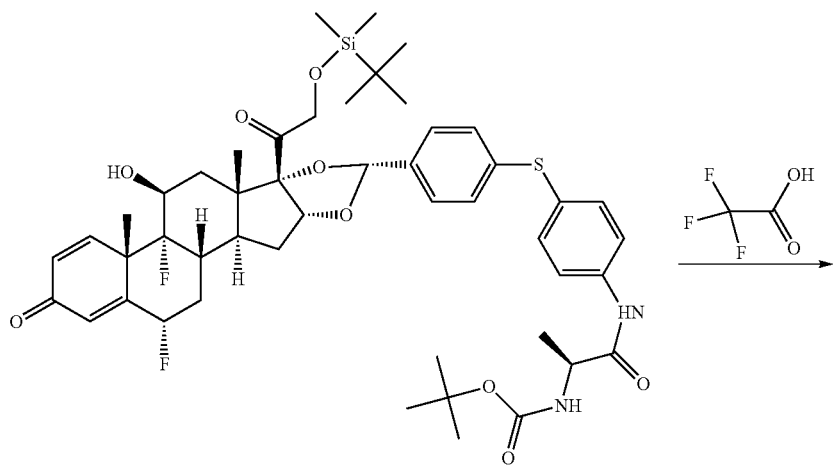

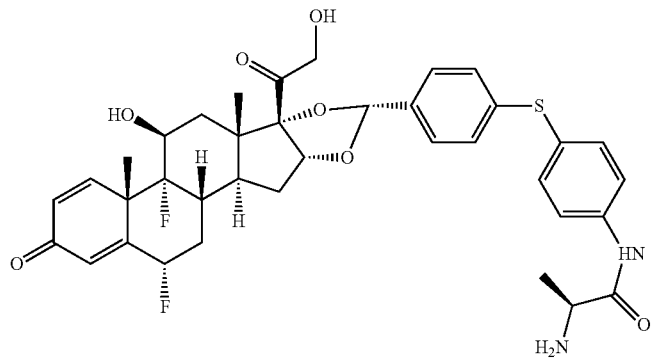

To a stirred solution of tert-butyl ((S)-1-((4-((4-((2S,6aS, 6bR,7S,8aS,8bS,10R,11aR, 12aS,12bS)-8b-(2-((tert-butyldimethylsilyl)oxy)acetyl)-2,6b-difluoro-7-hydroxy-6a, 8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)amino)-1-oxopropan-2-yl)carbamate (0.091 g, 0.1 mmol) in methylene chloride (1 mL) was added TFA (1 mL, 12.98 mmol), and the solution was stirred for 2 hours at ambient temperature, then concentrated in vacuo to give the product (S)-2-amino-N-(4-((4-((2S,6aS, 6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a, 6b,7,8,8a,8b,11a,12,12a,12b-dodecahydro-1H-naphtho[2', 1':4,5]indeno[1,2-d][1,3]dioxol-10-yl)phenyl)thio)phenyl) propanamide (7.21 g, 10.38 mmol, 80% yield). LCMS (Method m, Table 7) R$_t$=1.653 min, m/z 695 (M+H).

Step 4: Synthesis of (S)-5-(tert-Butoxy)-2-(3-(2,5-dioxo-2,5-dihydro-1H-pyrrol-1-yl)propanamido)-5-oxopentanoic Acid

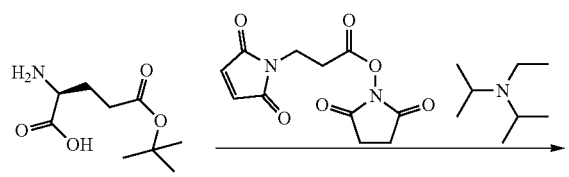

To a stirred solution of (S)-2-amino-5-(tert-butoxy)-5-oxopentanoic acid (406 mg, 2 mmol) and 2,5-dioxopyrrolidin-1-yl 3-(2,5-dioxo-2,5-dihydro-1H-pyrrol-1-yl)propanoate (532 mg, 2.000 mmol) in dimethyl formamide (2 mL) was added DIPEA (0.524 mL, 3.00 mmol). After stirring was continued for 2 h at room temperature, the reaction mixture was diluted with EtOAc (10 mL), washed with water (2×10 mL) and brine (1×10 mL), dried over Na$_2$SO$_4$, filtered and concentrated in vacuo, and the residue was purified by column (MeOH/DCM=0:10-1:10) to give the title compound (209 mg, 0.590 mmol, 29.5% yield) as a yellow oil. LCMS (Method m, Table 7) R$_t$=1.490 min, m/z 377 (M+Na).

Step 5: Synthesis of (S)-tert-butyl 5-(((S)-1-((4-((4-((2S,6aS,6bR,7S,8aS, 8bS,10R,11aR,12aS,12bS)-2, 6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1, 3]dioxol-10-yl)phenyl)thio)phenyl)amino)-1-oxopropan-2-yl)amino)-4-(3-(2,5-dioxo-2,5-dihydro-H-pyrrol-1-yl)propanamido)-5-oxopentanoate

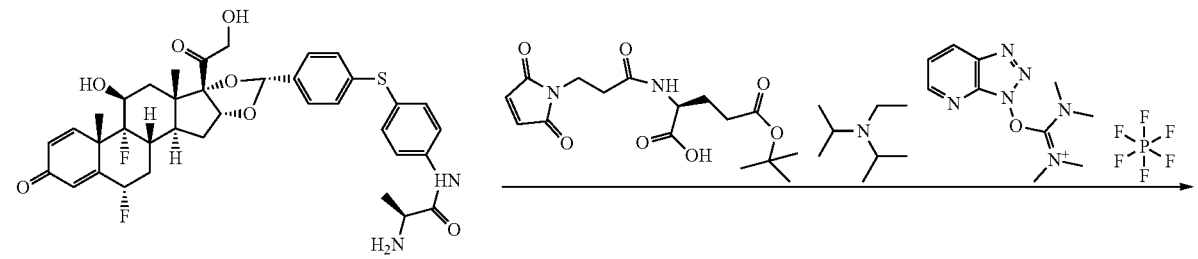

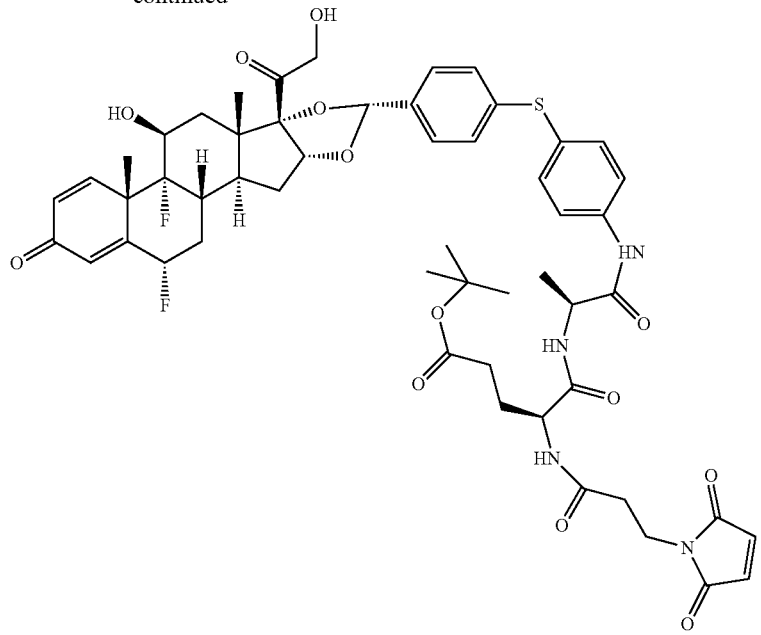

A solution of (S)-2-amino-N-(4-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl) thio)phenyl)propanamide (40 mg, 0.058 mmol), (S)-5-(tert-butoxy)-2-(3-(2,5-dioxo-2,5-dihydro-H-pyrrol-1-yl)propanamido)-5-oxopentanoic acid (30.6 mg, 0.086 mmol), HATU (32.8 mg, 0.086 mmol) and DIPEA (0.030 mL, 0.173 mmol) in dimethyl formamide (2 mL) was stirred overnight at room temperature, and diluted with EtOAc (10 mL), washed with water (2×10 mL) and brine (1×10 mL), dried over Na₂SO₄, filtered and evaporated in reduced pressure. The residue was purified by column chromatography (MeOH/DCM=0:10; 1:10) to give the title compound (30 mg, 0.029 mmol, 50.5% yield). LCMS (Method m, Table 7) $R_t$=2.051 min, m/z 1031 (M+H).

Step 6: Synthesis of (S)-5-(((S)-1-((4-((4-((2S,6aS,6bR,7S,8aS,8bS,10R,11aR,12aS,12bS)-2,6b-Difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)amino)-1-oxopropan-2-yl)amino)-4-(3-(2,5-dioxo-2,5-dihydro-1H-pyrrol-1-yl)propanamido)-5-oxopentanoic Acid

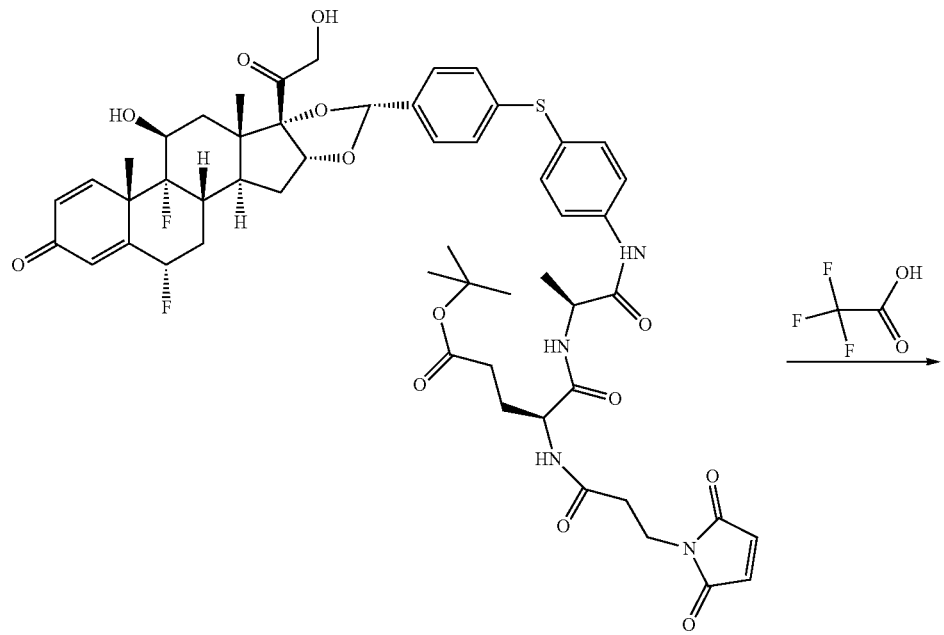

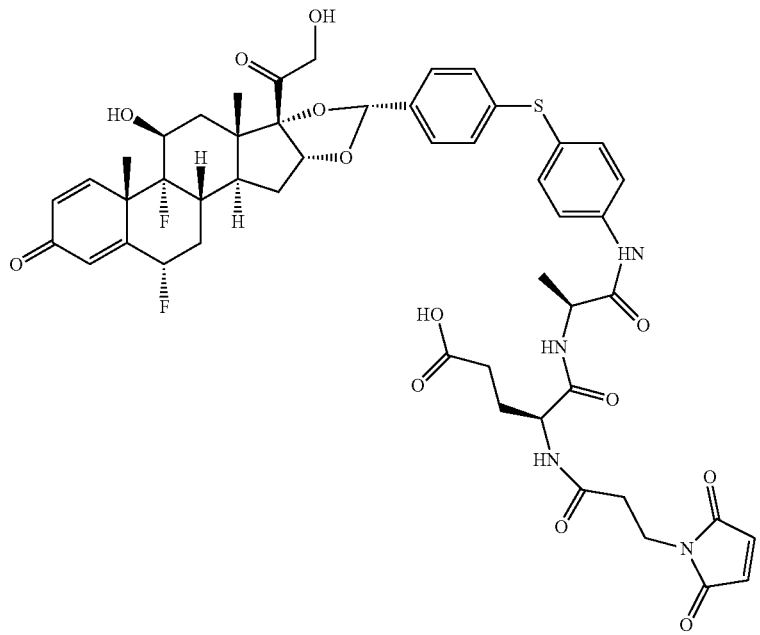

To a stirred solution of (S)-tert-butyl 5-(((S)-1-((4-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)amino)-1-oxopropan-2-yl)amino)-4-(3-(2,5-dioxo-2,5-dihydro-H-pyrrol-1-yl)propanamido)-5-oxopentanoate (10.31 mg, 0.01 mmol) in DCM (0.5 mL) was added TFA (0.5 mL, 6.49 mmol). After stirring was continued for 2 h, the reaction mixture was concentrated in vacuo to give the title compound (6.83 mg, 7.00 gmol, 70% yield). LCMS (Method m, Table 7) $R_t$=1.875 min, m/z 975 (M+H).

Example 13: Synthesis of N-(4-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenoxy)phenyl)-1-(3-(2,5-dioxo-2,5-dihydro-H-pyrrol-1-yl)propanamido)-3,6,9,12,15,18,21,24,27,30,33,36-dodecaoxanonatriacontan-39-amide Step 1: Synthesis of (2S,6aS,6bR,7S,8aS,8bS,10R,11aR,12aS,12bS)-10-(4-(4-Aminophenoxy)phenyl)-8b-(2-((tert-buty dimethylsilyl)oxy)acetyl)-2,6b-difluoro-7-hydroxy-6a,8a-dimethyl-6a,6b,7,8,8a,8b,11a,12,12a,12b-decahydro-1H-naphtho[2',1':4,5]indeno[1,2-d][1,3]dioxol-4(2H)-one

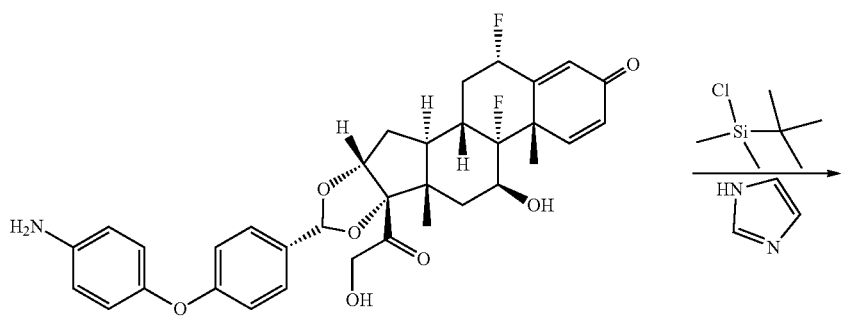

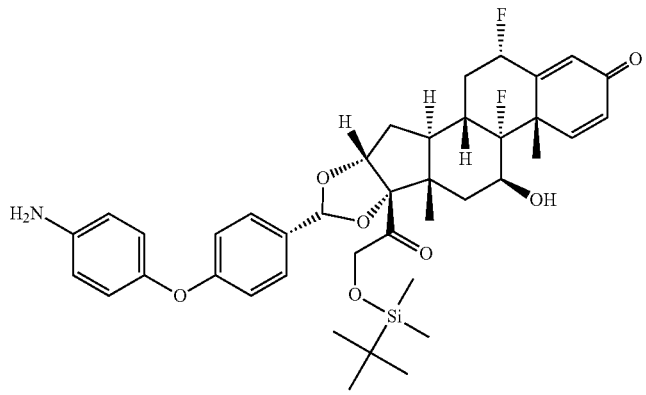

To a stirred solution of (2S,6aS,6bR,7S,8aS,8bS,10R,11aR,12aS,12bS)-10-(4-(4-aminophenoxy)phenyl)-2,6b-difluoro-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one (290 mg, 0.477 mmol) and imidazole (162 mg, 2.386 mmol) in $CH_2Cl_2$ (10 mL) was added TBS-Cl (216 mg, 1.432 mmol) at 0° C., After stirring was continued for 30 min at the same temperature, the mixture was allowed to warm to room temperature and stirred for 2 h. the reaction mixture was diluted with EtOAc (10 mL), washed with water (2×10 mL) and brine (1×10 mL), dried over $Na_2SO_4$, filtered and concentrated in vacuo. The residue was purified by column (EA: PE=1:10-9:1) to give title compound (300 mg, 0.416 mmol, 87% yield). LCMS (Method m, Table 7) $R_t$=1.812 min, m/z 722 (M+H).

Step 2: Synthesis of tert-butyl (39-((4-(4-(((2S,6aS,6bR,7S,8aS,8bS,11aR,12aS,12bS)-8b-(2-(((tert-Butyldimethylsilyl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenoxy)phenyl)amino)-39-oxo-3,6,9,12,15,18,21,24,27,30,33,36-dodecaoxanonatriacontyl)carbamate

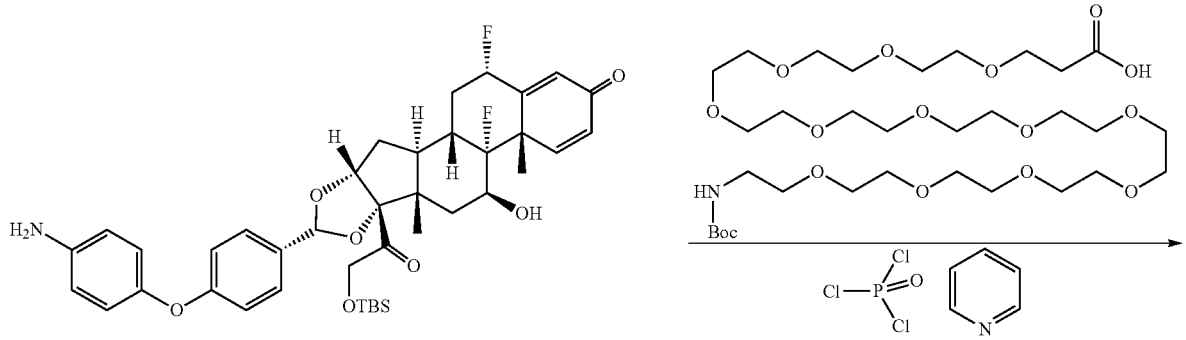

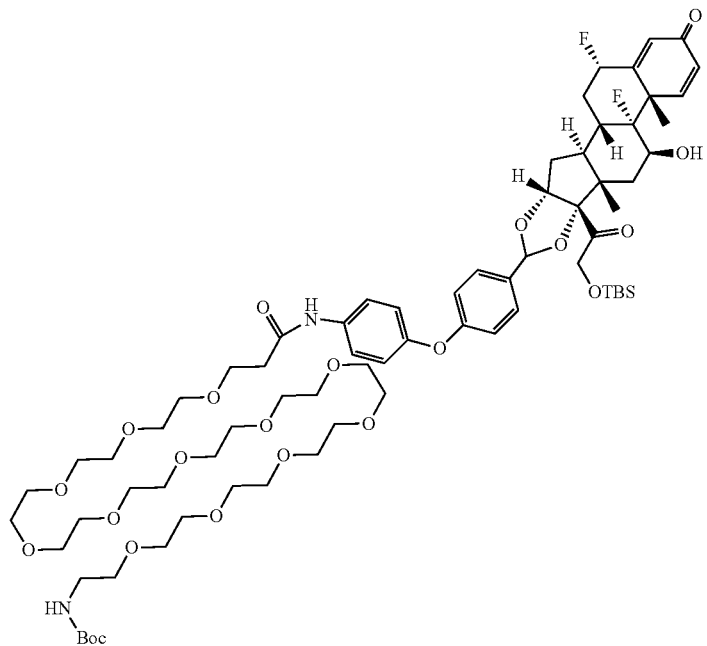

To a stirred solution of (2S,6aS,6bR,7S,8aS,8bS,11aR, 12aS,12bS)-10-(4-(4-aminophenoxy)phenyl)-8b-(2-((tert-butyldimethylsilyl)oxy)acetyl)-2,6b-difluoro-7-hydroxy-6a, 8a-dimethyl-6a,6b,7,8,8a,8b,11a,12,12a,12b-decahydro-1H-naphtho[2',1':4,5]indeno[1,2-d][1,3]dioxol-4(2H)-one (144 mg, 0.2 mmol) and 2,2-dimethyl-4-oxo-3,8,11,14,17, 20,23,26,29,32,35,38,41-tridecaoxa-5-azatetratetracontan-44-oic acid (144 mg, 0.200 mmol) in CH$_2$Cl$_2$ (3 mL) was added pyridine (0.162 mL, 2.000 mmol), followed by POCl$_3$ (0.037 mL, 0.400 mmol) in dropwise. The reaction mixture was stirred for 1 hour at ambient temperature, then concentrated in vacuo, and the residue was purified by column chromatography (MeOD:DCM=0:10-1:10) to give the title compound (120 mg, 0.084 mmol, 42.2% yield) as a semi-solid. LCMS (Method m, Table 7) R$_t$=2.065 min, m/z 1422 (M+H-100).

Step 3: Synthesis of 1-amino-N-(4-(4-((2S,6aS,6bR, 7S,8aS,8bS,11aR,12aS,12bS)-2,6b-Difluoro-7-hydroxy-8b-(2-hydroxyacetyl)-6a,8a-dimethyl-4-oxo-2, 4,6a,6b,7,8,8a,8b,11a,12,12a,12b-dodecahydro-1H-naphtho[2',1':4,5]indeno[1,2-d][1,3]dioxol-10-yl) phenoxy)phenyl)-3,6,9,12,15,18,21,24,27,30,33,36-dodecaoxanonatriacontan-39-amide

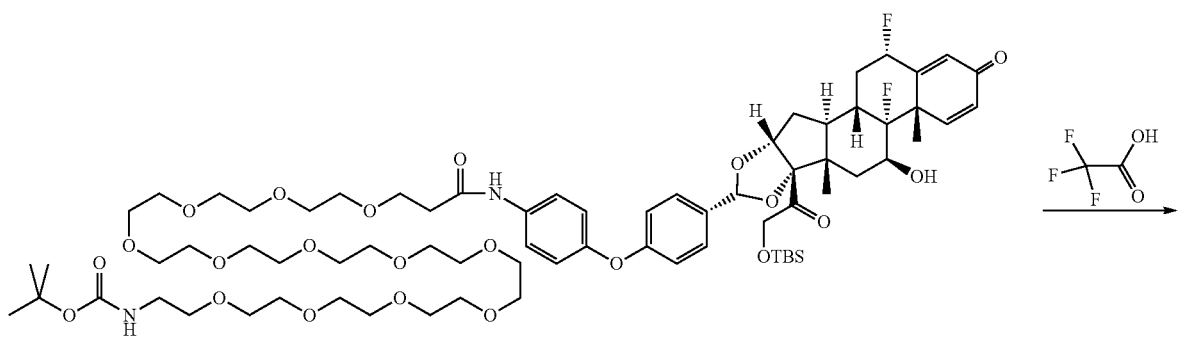

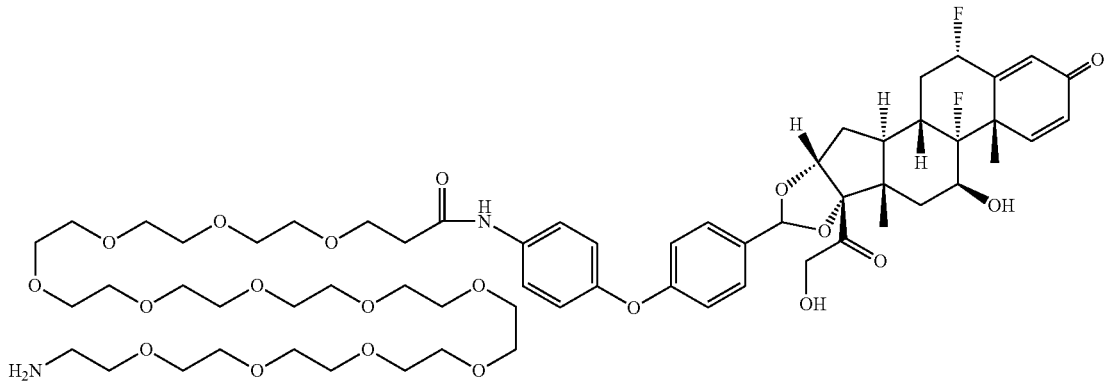

To a stirred solution of tert-butyl (39-((4-(4-((2S,6aS,6bR,7S,8aS,8bS,10R,11aR,12aS, 12bS)-8b-(2((tert-butyldimethylsilyl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenoxy)phenyl)amino)-39-oxo-3,6,9,12,15,18,21,24,27,30,33,36-dodecaoxanonatriacontyl)carbamate (190 mg, 0.134 mmol) in methylene chloride (0.5 mL) was added TFA (0.1 mL, 1.298 mmol), and the solution was stirred for 2 hours at ambient temperature, then concentrated in vacuo to give the title compound (100 mg, 0.083 mmol, 62.0% yield). LCMS (Method m, Table 7) $R_f$=1.521 min, m/z 1208 (M+H).

Step 4: Synthesis of N-(4-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenoxy)phenyl)-1-(3-(2,5-dioxo-2,5-dihydro-1H-pyrrol-1-yl)propanamido)-3,6,9,12,15,18,21,24,27,30,33,36-dodecaoxanonatriacontan-39-amide

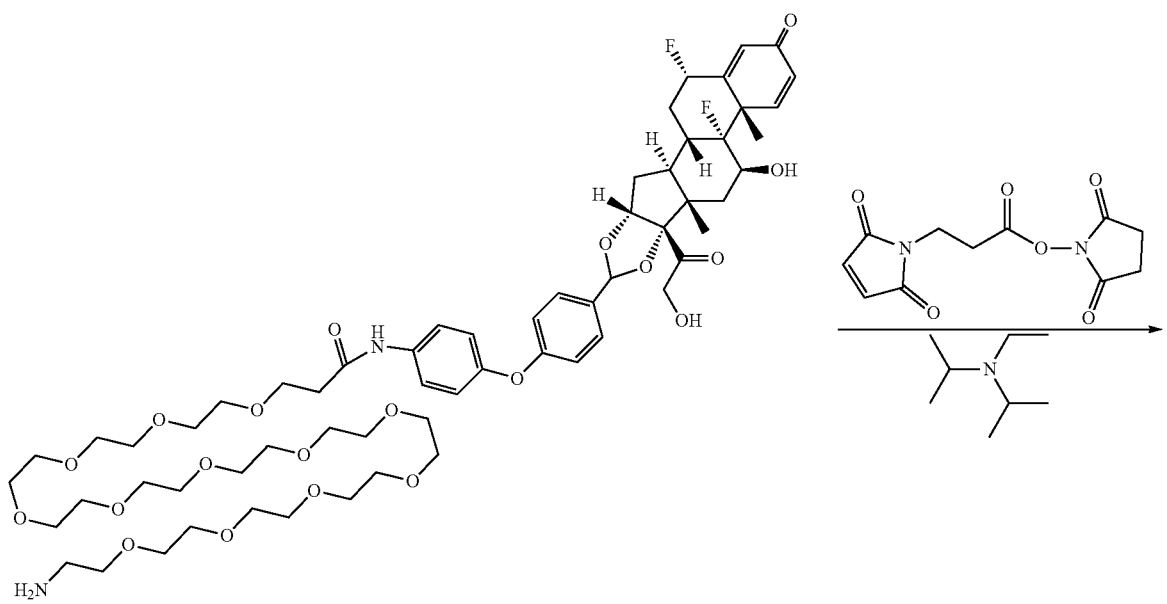

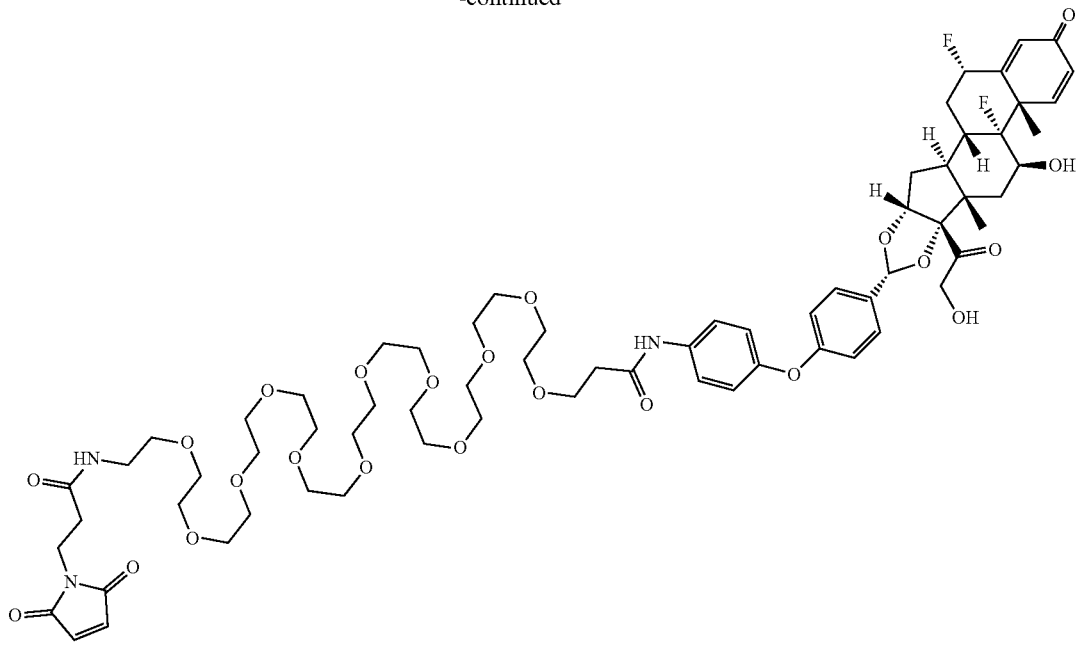

DIPEA (6.99 µL, 0.040 mmol) was added to a solution of 1-amino-N-(4-(4-(4-(((2S,6aS,6bR,7S,8aS,8bS,11aR,12aS,12bS)-2,6b-difluoro-7-hydroxy-8b-(2-hydroxyacet yl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenoxy)phenyl)-3,6,9,12,15,18,21,24,27,30,33,36-dodecaoxanonatriacontan-39-amide (0.024 g, 0.02 mmol) and 2,5-dioxopyrrolidin-1-yl 3-(2,5-dioxo-2,5-dihydro-1H-pyrrol-1-yl)propanoate (7.99 mg, 0.030 mmol) in N,N-dimethylformamide (1 mL), and the mixture was stirred at room temperature for 2 h. The reaction mixture was diluted with EtOAc (10 mL) and washed with water (2×10 mL), brine (1×10 mL), dried over Na₂SO₄, filtered and concentrated in vacuo. The residue was purified by column chromatography (MeOH/DCM=0:100-10:100) to give the title compound (0.011 g, 8.20 µmol, 41% yield). LCMS (Method m, Table 7) R$_t$=1.679 min, m/z 1359 (M+H).

Example 14: Synthesis of 2,5-Dioxopyrrolidin-1-yl 6-(((S)-1-(((S)-1-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,1a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)amino)-6-oxohexanoate (Cpd. No. 78)

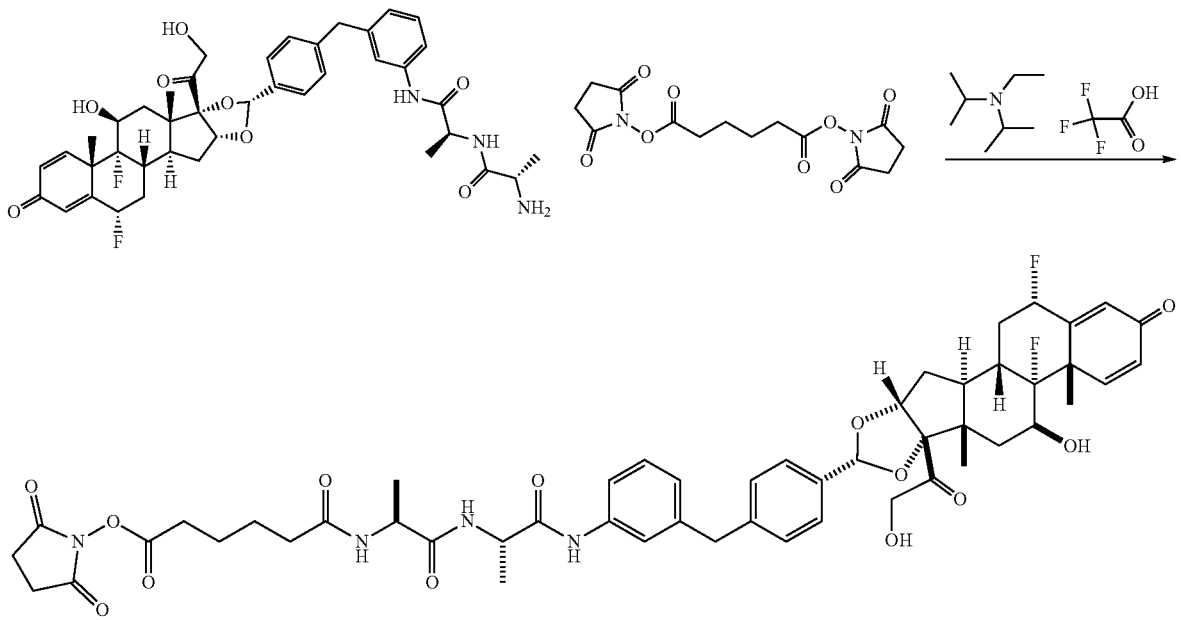

A solution of (S)-2-amino-N—((S)-1-((3-(4-((2S,6aS, 6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a, 6b,7,8,8a,8b,11a,12,12a,12b-dodecahydro-1H-naphtho[2', 1':4,5]indeno[1,2-d][1,3]dioxol-10-yl)benzyl)phenyl) amino)-1-oxopropan-2-yl)propanamide (0.060 g, 0.080 mmol) and N,N-diisopropylethylamine (0.14 mL, 0.802 mmol) in DMSO (1 mL) was added drop-wise to a room temperature solution of bis(2,5-dioxopyrrolidin-1-yl) adipate (0.273 g, 0.802 mmol) in DMSO (3.5 mL). After 60 min the reaction was quenched by addition of a 7 wt % solution of TFA in water to bring the reaction mixture to a pH of 4-5. The crude reaction mixture was purified by reverse phase HPLC on a Phenomenex C18(2) 5 micron column (250×21 mm column). A gradient of MeCN (A) and 0.1% formic acid in water (B) was used, at a flow rate of 30 mL/min (0-1.0 min 15% A, 1.0-11 min linear gradient 15-80% A, hold 1 min). Combined fractions were concentrated under reduced pressure to remove volatile solvents, and the resulting solution was frozen and lyophilized to give the title compound as a white solid (21.2 mg, 0.022 mmol, 27% yield). LCMS (Method r, Table 7) $R_f$=0.80 min, m/z=1005.1 [M+MeOH+H$^+$]. $^1$H NMR (DMSO) δ 0.84 (s, 3H), 1.17 (d, J=7.1 Hz, 3H), 1.25 (d, J=7.1 Hz, 3H), 1.48 (s, 4H), 1.57 (q, J=6.2 Hz, 4H), 1.68 (dq, J=13.7, 6.3 Hz, 3H), 1.99-2.06 (m, 1H), 2.09-2.18 (m, 2H), 2.18-2.36 (m, 2H), 2.55-2.72 (m, 3H), 2.78 (s, 4H), 3.87 (s, 2H), 4.14-4.22 (m, 2H), 4.26 (p, J=7.1 Hz, 1H), 4.33 (p, J=7.1 Hz, 1H), 4.49 (d, J=19.4 Hz, 1H), 4.93 (d, J=5.1 Hz, 1H), 5.43 (s, 1H), 5.49 (d, J=5.4 Hz, 1H), 5.54-5.75 (m, 1H), 6.11 (s, 1H), 6.28 (dd, J=10.2, 2.0 Hz, 1H), 6.89 (d, J=7.6 Hz, 1H), 7.17 (t, J=7.9 Hz, 1H), 7.23 (t, J=9.7 Hz, 3H), 7.34 (d, J=7.8 Hz, 2H), 7.39 (s, 1H), 7.44 (d, J=8.1 Hz, 1H), 7.99 (d, J=7.2 Hz, 1H), 8.02 (d, J=7.3 Hz, 1H), 9.77 (s, 1H); MS (ESI-) m/z=971.

Example 15: Synthesis of tert-butyl ((S)-1-(((S)-1-((3-(4-((2S,6aS,6bR,7S,8aS,8bS,10R,11aR,12aS, 12bS)-2,6b-difluoro-7-hydroxy-8b-(2-hydroxyacetyl)-6a,8a-dimethyl-4-oxo-2,4,6a,6b,7,8,8a,8b, 11a,12,12a,12b-dodecahydro-1H-naphtho[2',1':4,5] indeno[1,2-d][1,3]dioxol-10-yl)benzyl)phenyl) amino)-1-oxopropan-2-yl)amino)-3-methyl-1-oxobutan-2-yl)carbamate HATU (106 mg, 0.280 mmol) and 2,6-lutidine (0.1 mL, 0.859 mmol) were added to a room temperature suspension of (2S,6aS,6bR,7S,8aS,8bS,10R,11aR,12aS,12bS)-10-(4-(3-aminobenzyl)phenyl)-2,6b-difluoro-7-hydroxy-8b-(2-hydroxyacetyl)-6a,8a-dimethyl-6a,6b,7,8,8a,8b,11a,12,12a, 12b-decahydro-1H-naphtho[2',1':4,5]indeno[1,2-d][1,3] dioxol-4(2H)-one (113 mg, 0.187 mmol) and (tert-butoxycarbonyl)-L-valyl-L-alanine (53.8 mg, 0.187 mmol) in THF (1.25 mL). After 8 h the reaction was diluted with EtOAc (16 mL), then washed sequentially with a 1M aqueous solution of HCl (4 mL×3), a saturated aqueous solution of NaHCO$_3$ (4 mL), and then a saturated aqueous solution of brine (4 mL). Solvent was removed under reduced pressure and the product was purified by chromatography (12 g silica), eluting with a gradient of 0-10% MeOH/DCM to give the title compound (148.6 mg, 0.170 mmol, 91% yield). LCMS (Method r, Table 7) $R_f$=0.94 min, m/z=875.9 [M+H$^+$]. $^1$H NMR (DMSO-d$_6$) δ 9.85 (s, 1H), 7.99 (d, J=7.1 Hz, 1H), 7.43 (dd, J=8.0, 1.7 Hz, 1H), 7.36-7.31 (m, 3H), 7.27-7.15 (m, 5H), 6.89 (d, J=7.5 Hz, 1H), 6.67 (d, J=8.8 Hz, 1H), 6.27 (dd, J=10.2, 1.9 Hz, 1H), 6.11 (s, 1H), 5.73-5.52 (m, 1H), 5.50 (dd, J=4.5, 1.7 Hz, 1H), 5.43 (s, 1H), 5.07 (t, J=5.9 Hz, 1H), 4.93 (d, J=4.8 Hz, 1H), 4.49 (dd, J=19.5, 6.4 Hz, 1H), 4.37 (t, J=7.0 Hz, 1H), 4.25-4.12 (m, 2H), 3.87 (s, 2H), 3.80 (t, J=7.7 Hz, 1H), 2.73-2.53 (m, 1H), 2.23 (ddd, J=18.7, 11.9, 6.0 Hz, 2H), 2.08-1.99 (m, 1H), 1.93 (q, J=7.0 Hz, 1H), 1.77-1.59 (m, 3H), 1.48 (s, 3H), 1.35 (s, 9H), 1.25 (d, J=7.0 Hz, 3H), 0.89-0.74 (m, 9H).

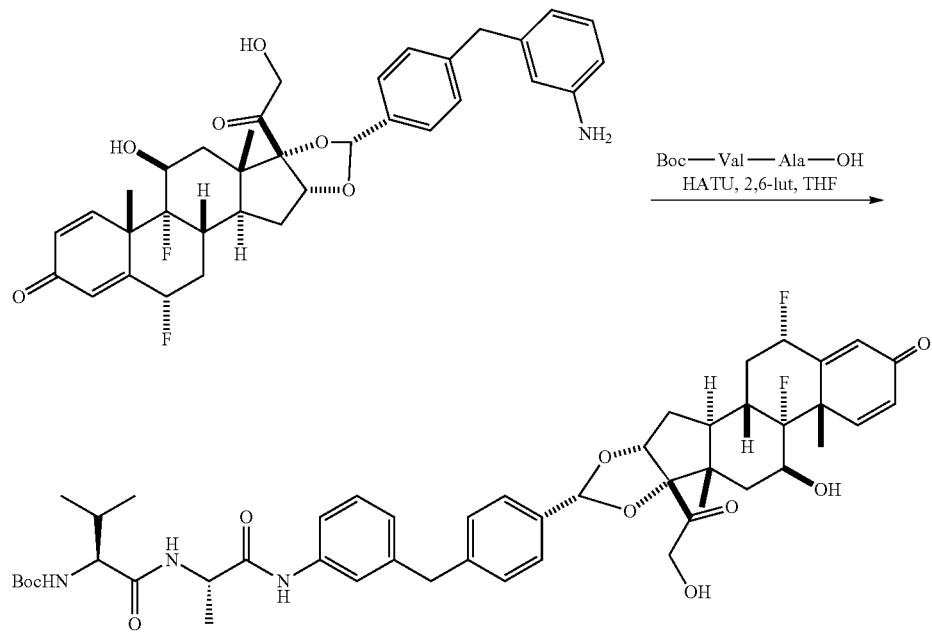

Example 16: Synthesis of (2S,6aS,6bR,7S,8aS,8bS, 10R,11aR,12aS,12bS)-10-(4-((4-Aminophenyl)thio) phenyl)-2,6b-difluoro-7-hydroxy-8b-(2-hydroxy-acetyl)-6a,8a,10-trimethyl-6a,6b,7,8,8a,8b,11a,12, 12a,12b-decahydro-1H-naphtho[2',1':4,5]indeno[1,2-d][1,3]dioxol-4(2H)-one and (2S,6aS,6bR,7S,8aS, 8bS,10S,11aR,12aS,12bS)-10-(4-((4-Aminophenyl) thio)phenyl)-2,6b-difluoro-7-hydroxy-8b-(2-hydroxyacetyl)-6a,8a,10-trimethyl-6a,6b, 7,8,8a,8b, 11a,12,12a,12b-decahydro-1H-naphtho[2',1':4,5] indeno[1,2-d][1,3]dioxol-4(2H)-one Step 1: Synthesis of
1-(4-((4-bromophenyl)thio)phenyl)ethanone

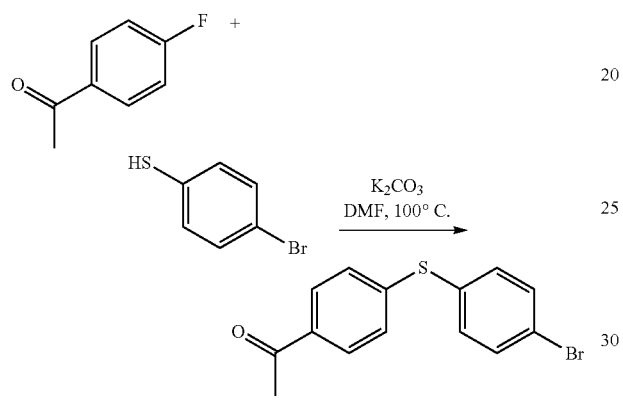

1-(4-Fluorophenyl)ethanone (2.19 mL, 18.04 mmol) was added to a stirred solution of 4-bromobenzenethiol (3.1 g, 16.40 mmol) and $K_2CO_3$ (2.72 g, 19.67 mmol) in DMF (45 mL), whereupon the reaction was heated to 100° C. for 20 min. The reaction was cooled to ambient temperature, diluted with water (50 mL) and extracted with EtOAc (3×50 mL). The combined organics were dried ($MgSO_4$) and solvents were removed under reduced pressure. Purification by chromatography (silica, 120 g) eluting with a gradient of 0-60% EtOAc/heptanes gave the title compound (3.24 g, 10.55 mmol, 64% yield) as a yellow solid. LCMS (Method r, Table 7) $R_t$=0.95 min; m/z=307.0 [M+H$^+$]. $^1$H NMR (400 MHz, DMSO-d6) δ 7.87 (d, J=8.7 Hz, 2H), 7.62 (d, J=8.6 Hz, 2H), 7.38 (d, J=8.6 Hz, 2H), 7.28 (d, J=8.7 Hz, 2H), 2.50 (s, 3H).

Step 2: Synthesis of tert-butyl
(4-((4-acetylphenyl)thio)phenyl)carbamate

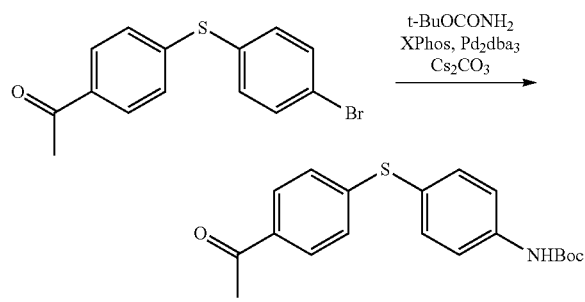

Nitrogen was sparged through a mixture of 1-(4-((4-bromophenyl)thio)phenyl)ethanone (3.24 g, 10.55 mmol), tert-butyl carbamate (1.483 g, 12.66 mmol), $Cs_2CO_3$ (5.15 g, 15.82 mmol), and dicyclohexyl(2',4',6'-triisopropyl-[1,1'-biphenyl]-2-yl)phosphine (0.503 g, 1.055 mmol) in 1,4-dioxane for 30 min. The flask was evacuated and back filled with $N_2$ (3×). $Pd_2dba_3$ (0.290 g, 0.316 mmol) was added and the reaction was evacuated and back filled with $N_2$ (3×). The reaction mixture was heated to 100° C. for 18 h. The reaction was cooled to ambient temperature, treated with water (75 mL), then extracted with EtOAc (3×50 mL), dried ($MgSO_4$), and solvents were removed under reduced pressure. Purification by chromatography (silica, 120 g) eluting with a gradient of 0-60% EtOAc/heptanes gave the title compound (2.0 g, 5.82 mmol, 55% yield) as a yellow solid. LCMS (Method r, Table 7) $R_t$=0.96 min; m/z=344.0 [M+H$^+$]. $^1$H NMR (501 MHz, DMSO-d6) δ 9.62 (s, 1H), 7.82 (d, J=8.7 Hz, 2H), 7.58 (d, J=8.7 Hz, 2H), 7.43 (d, J=6.7 Hz, 2H), 7.11 (d, J=8.7 Hz, 2H), 2.49 (s, 3H), 1.47 (s, 9H).

Step 3: Synthesis of (2S,6aS,6bR,7S,8aS,8bS,10R, 11aR,12aS,12bS)-10-(4-((4-Aminophenyl)thio)phenyl)-2,6b-difluoro-7-hydroxy-8b-(2-hydroxyacetyl)-6a,8a,10-trimethyl-6a,6b,7,8,8a,8b,11a,12,12a,12b-decahydro-1H-naphtho[2',1':4,5]indeno[1,2-d][1,3] dioxol-4(2H)-one and (2S,6aS,6bR,7S,8aS,8bS,10S, 11aR,12aS,12bS)-10-(4-((4-Aminophenyl)thio) phenyl)-2,6b-difluoro-7-hydroxy-8b-(2-hydroxyacetyl)-6a,8a,10-trimethyl-6a,6b, 7,8,8a,8b, 11a,12,12a,12b-decahydro-1H-naphtho[2',1':4,5] indeno[1,2-d][1,3]dioxol-4(2H)-one

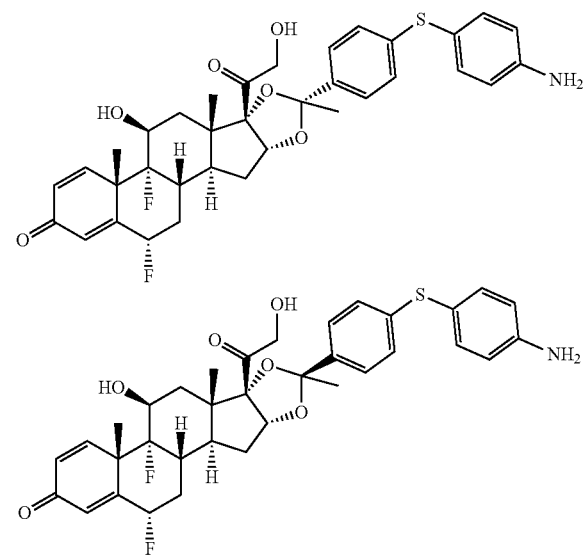

Triflic acid (0.431 mL, 4.85 mmol) was added drop-wise to a 0° C. slurry of (6S,8S,9R,10S,11S,13S,14S,16R,17S)-6,9-difluoro-11,16,17-trihydroxy-17-(2-hydroxyacetyl)-10, 13-dimethyl-6,7,8,9,10,11,12,13,14,15,16,17-dodecahydro-3H-cyclopenta[a]phenanthren-3-one (0.400 g, 0.970 mmol), tert-butyl (4-((4-acetylphenyl)thio)phenyl)carbamate (0.366 g, 1.067 mmol), and $MgSO_4$ (0.350 g, 2.91 mmol) in MeCN (4.0 mL). After 30 min the reaction was diluted with EtOAc (25 mL), washed sequentially with a saturated aqueous solution of $NaHCO_3$ (20 mL), with a saturated aqueous solution of brine (25 mL), dried ($MgSO_4$), and then solvent was removed under reduced pressure to give a yellow foam. Purification by chromatography (silica, 40 g) eluting with a gradient of 0-10% MeOH/DCM gave the product as a mixture of the ketal isomers (460 mg, 0.721 mmol, 74% yield). A portion of this material was purified by reverse phase HPLC on a Phenomenex C18(2) 10 micron column (250×50 mm). A gradient of MeCN (A) and 0.1% TFA in water (B) was used, at a flow rate of 90 mL/min (0-5.0 min 15% A, 5.0-18 min linear gradient 15-75% A, then hold 5 min). Combined fractions were concentrated to remove volatile solvents under reduced pressure, and the resulting solutions were frozen and lyophilized to give the ketal isomers as yellow solids. Minor ketal isomer: (2S,6aS,6bR, 7S,8aS,8bS,10R,11aR,12aS,12bS)-10-(4-((4-aminophenyl) thio)phenyl)-2,6b-difluoro-7-hydroxy-8b-(2-hydroxyacetyl)-6a,8a,10-trimethyl-6a,6b, 7,8,8a,8b,11a,12,12a,12b-decahydro-1H-naphtho[2',1':4,5]indeno[1,2-d][1,3]dioxol-4 (2H)-one. Yellow powder (10.0 mg). LCMS (Method r, Table 7) $R_t$=0.80 min; m/z=638.2 [M+H$^+$]. $^1$H NMR (500 MHz, DMSO-d$_6$) δ 7.33 (d, J=8.5 Hz, 2H), 7.23 (dd, J=10.1, 1.5 Hz, 1H), 7.19-7.12 (m, 2H), 6.96 (d, J=8.5 Hz, 2H), 6.76-6.63 (m, 2H), 6.29 (dd, J=10.2, 1.9 Hz, 1H), 6.10 (s, 1H), 5.66-5.45 (m, 2H), 5.14 (d, J=5.8 Hz, 1H), 4.65 (d, J=19.3 Hz, 1H), 4.22-4.07 (m, 2H), 2.48-2.35 (m, 1H), 2.14-2.04 (m, 1H), 2.02-1.91 (m, 1H), 1.77-1.64 (m, 2H), 1.63-1.56 (m, 1H), 1.50 (dd, J=13.2, 6.3 Hz, 1H), 1.44 (s, 3H), 1.36 (s, 3H), 1.14-0.98 (m, 1H), 0.80 (s, 3H). Major ketal isomer: (2S,6aS,6bR,7S,8aS,8bS,10S,11aR,12aS, 12bS)-10-(4-((4-aminophenyl)thio)phenyl)-2,6b-difluoro-7-hydroxy-8b-(2-hydroxyacetyl)-6a,8a,10-trimethyl-6a,6b, 7,8,8a,8b,11a,12,12a,12b-decahydro-1H-naphtho[2',1':4,5] indeno[1,2-d][1,3]dioxol-4(2H)-one. Yellow powder (18.1 mg). LCMS (Method r, Table 7) $R_t$=0.85 min; m/z=638.2 [M+H$^+$]. $^1$H NMR (500 MHz, DMSO-d$_6$) δ 7.28 (d, J=10.2 Hz, 1H), 7.20 (dd, J=8.4, 7.2 Hz, 4H), 6.95 (d, J=8.4 Hz, 2H), 6.73 (d, J=8.5 Hz, 2H), 6.31 (d, J=12.0 Hz, 1H), 6.13 (s, 1H), 5.75-5.57 (m, 1H), 5.53 (s, 1H), 5.00 (d, J=5.1 Hz, 1H), 4.22 (d, J=7.2 Hz, 1H), 4.06-3.80 (m, 4H), 2.72-2.55 (m, 1H), 2.39-2.27 (m, 1H), 2.17-2.02 (m, 2H), 1.79-1.56 (m, 3H), 1.50 (d, J=12.4 Hz, 6H), 0.73 (s, 3H).

Example 17: Synthesis of (6aR,6bS,7S,8aS,8bS, 10R,11aR,12aS,12bS)-10-(4-((4-aminophenyl)thio) phenyl)-7-hydroxy-8b-(2-hydroxyacetyl)-6a,8a,10-trimethyl-6a,6b,7,8,8a,8b,11a,12,12a,12b-decahydro-1H-naphtho[2',1':4,5]indeno[1,2-d][1,3]dioxol-4 (2H)-one and (6aR,6bS,7S,8aS,8bS,10S,11aR,12aS, 12bS)-10-(4-((4-aminophenyl)thio)phenyl)-7-hydroxy-8b-(2-hydroxyacetyl)-6a,8a,10-trimethyl-6a,6b,7,8,8a,8b,11a,12,12a,12b-decahydro-1H-naphtho[2',1':4,5]indeno[1,2-d][1,3]dioxol-4(2H)-one

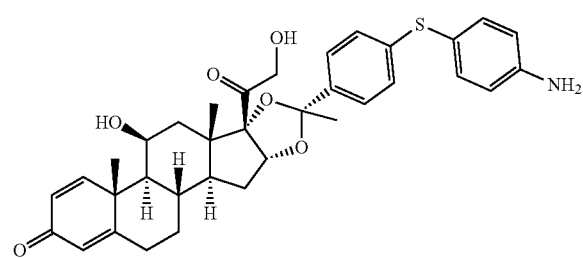

-continued

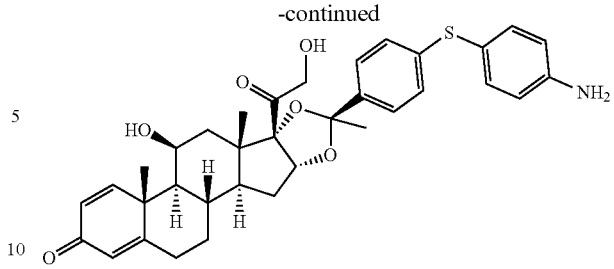

Triflic acid (0.24 mL, 2.66 mmol) was added drop-wise to a 0° C. slurry of (8S,9S,10R,11S,13S,14S,16R,17S)-11,16, 17-trihydroxy-17-(2-hydroxyacetyl)-10,13-dimethyl-6,7,8, 9,10,11,12,13,14,15,16,17-dodecahydro-3H-cyclopenta[a] phenanthren-3-one (0.200 g, 0.531 mmol), tert-butyl (4-((4-acetylphenyl)thio)phenyl)carbamate (0.201 g, 0.584 mmol), and MgSO$_4$ (0.192 g, 1.59 mmol) in MeCN (2.0 mL). After 30 min the reaction was diluted with EtOAc (15 mL), washed sequentially with a saturated aqueous solution of NaHCO$_3$ (10 mL), and then with a saturated aqueous solution of brine (10 mL), dried (MgSO$_4$), and solvent was removed under reduced pressure to give a yellow foam. Purification by chromatography (silica, 24 g) eluting with a gradient of 0-10% MeOH/DCM gave the product as a mixture of the ketal isomers (198 mg, 0.329 mmol, 62% yield). A portion of this material was purified by reverse phase HPLC on a Phenomenex C18(2) 10 micron column (250×50 mm). A gradient of MeCN (A) and 0.1% TFA in water (B) was used, at a flow rate of 90 mL/min (0-5.0 min 15% A, 5.0-18 min linear gradient 15-75% A, then hold 5 min). Combined fractions were concentrated to remove volatile solvents under reduced pressure, and the resulting solution was frozen and lyophilized to give both ketal isomers as white solids. Major ketal isomer: (6aR,6bS,7S, 8aS,8bS,10S,11aR,12aS,12bS)-10-(4-((4-aminophenyl) thio)phenyl)-7-hydroxy-8b-(2-hydroxyacetyl)-6a,8a,10-trimethyl-6a,6b,7,8,8a,8b,11a,12,12a,12b-decahydro-1H-naphtho[2',1':4,5]indeno[1,2-d][1,3]dioxol-4(2H)-one. White powder (14.6 mg). LCMS (Method r; Table 7) $R_t$=0.83 min; m/z=602.1 [M+H$^+$]. $^1$H NMR (501 MHz, DMSO-d6) δ 7.30 (d, J=10.1 Hz, 1H), 7.22-7.12 (m, 4H), 6.91 (d, J=8.5 Hz, 2H), 6.68 (d, J=8.5 Hz, 2H), 6.16 (dd, J=10.1, 1.9 Hz, 1H), 5.91 (s, 1H), 4.93 (d, J=4.6 Hz, 1H), 4.74 (brs, 2H), 4.30 (d, J=2.9 Hz, 1H), 4.02-3.79 (m, 4H), 2.53 (dt, J=14.7, 7.6 Hz, 1H), 2.30 (d, J=14.8 Hz, 1H), 2.16-1.95 (m, 2H), 1.85 (d, J=3.6 Hz, 1H), 1.78-1.67 (m, 2H), 1.55 (td, J=15.2, 13.3, 7.7 Hz, 2H), 1.50 (s, 3H), 1.37 (s, 3H), 1.13-0.97 (m, 2H), 0.70 (s, 3H). Minor ketal isomer: (6aR,6bS,7S,8aS,8bS,10R,11aR,12aS,12bS)-10-(4-((4-aminophenyl)thio)phenyl)-7-hydroxy-8b-(2-hydroxyacetyl)-6a,8a,10-trimethyl-6a,6b,7,8,8a,8b,11a,12,12a,12b-decahydro-1H-naphtho[2',1':4,5]indeno[1,2-d][1,3]dioxol-4 (2H)-one. White powder (12.0 mg). LCMS (Method r, Table 7) $R_t$=0.80 min; m/z=602.1[M+H$^+$]. $^1$H NMR (501 MHz, DMSO-d6) 7.32 (d, J=6.8 Hz, 2H), 7.25 (d, J=10.1 Hz, 1H), 7.13 (d, J=8.5 Hz, 2H), 6.95 (d, J=8.5 Hz, 2H), 6.66 (d, J=8.5 Hz, 2H), 6.13 (dd, J=10.1, 1.9 Hz, 1H), 5.87 (s, 1H), 5.09 (d, J=6.1 Hz, 1H), 4.71 (brs, 1H), 4.62 (d, J=19.3 Hz, 1H), 4.22 (d, J=2.9 Hz, 1H), 4.11 (d, J=19.2 Hz, 2H), 2.47-2.37 (m, 1H), 2.25-2.07 (m, 1H), 1.94 (qd, J=11.3, 3.8 Hz, 1H), 1.87-1.75 (m, 1H), 1.70 (s, 2H), 1.59-1.44 (m, 2H), 1.32 (d, J=5.1 Hz, 6H), 1.18-1.03 (m, 1H), 0.78 (s, 3H), 0.61 (dd, J=11.2, 3.5 Hz, 1H), 0.50 (qd, J=12.9, 4.8 Hz, 1H).

Example 18: Synthesis of 2S,6aS,6bR,7S,8aS,8bS, 10R,11aR,12aS,12bS)-10-(4-(4-Aminophenoxy)-3-hydroxyphenyl)-2,6b-difluoro-7-hydroxy-8b-(2-hydroxyacetyl)-6a,8a-dimethyl-6a,6b,7,8,8a,8b,11a, 12,12a,12b-decahydro-1H-naphtho[2',1':4,5]indeno[1,2-d][1,3]dioxol-4(2H)-one Step 1: Synthesis of
3-Methoxy-4-(4-nitrophenoxy)benzaldehyde

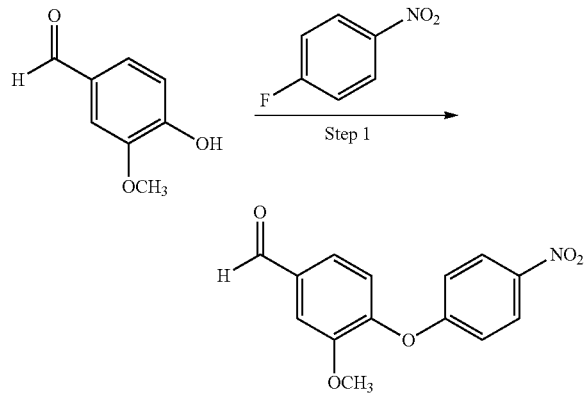

Vanillin (2.5 g, 16.43 mmol), 4-Fluoronitrobenzene (2.61 mL, 24.65 mmol), and potassium carbonate (4.54 g, 32.9 mmol) were dissolved in DMF (15 mL) and stirred at 80° C. overnight. After cooling, the mixture was treated with water, and extracted with EtOAc (×2). The combined organic layers were washed with water and brine, dried (Na$_2$SO$_4$), and concentrated. Purification by chromatography (silica, 120 g) eluting with a gradient of 0-40% EtOAc in heptanes afforded the title compound as a slightly yellow solid (3.37 g, 75%). LCMS (Method r, Table 7) R$_t$=0.88 min; m/z not observed. $^1$H NMR (400 MHz, DMSO-d$_6$) δ 10.00 (s, 1H), 8.26-8.17 (m, 2H), 7.72-7.60 (m, 2H), 7.42 (d, J=8.1 Hz, 1H), 7.12-7.03 (m, 2H), 3.82 (s, 3H).

Step 2: Synthesis of
3-hydroxy-4-(4-nitrophenoxy)benzaldehyde

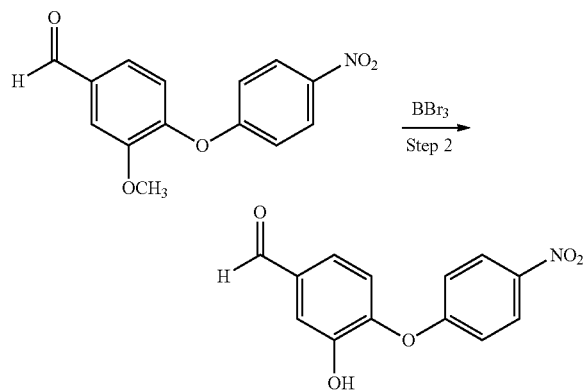

Tribromoborane (110 mL, 110 mmol) was added to a −78° C. solution of 3-methoxy-4-(4-nitrophenoxy)benzaldehyde (6.02 g, 22.03 mmol) in DCM (100 mL). The reaction was stirred at −78° C. for 1 h, then stirred at 0° C. for 5 hours. The mixture was mixed with ice, and extracted with DCM. The combined organic layers were washed with water and brine, dried (Na$_2$SO$_4$), and concentrated. Purification by chromatography (silica, 120 g) eluting with a gradient of 0-30% EtOAc in heptanes afforded the title compound as a purplish oil (5.55 g, 97% yield). LCMS (Method r, Table 7) R$_t$=0.80 min; m/z not observed. $^1$H NMR (400 MHz, DMSO-d6) δ 10.24 (s, 1H), 8.22-8.14 (m, 2H), 7.36 (s, 1H), 7.30 (d, J=2.1 Hz, 1H), 7.15-7.07 (m, 2H), 7.02-6.96 (m, 2H).

Step 3: Synthesis of
4-(4-aminophenoxy)-3-hydroxybenzaldehyde

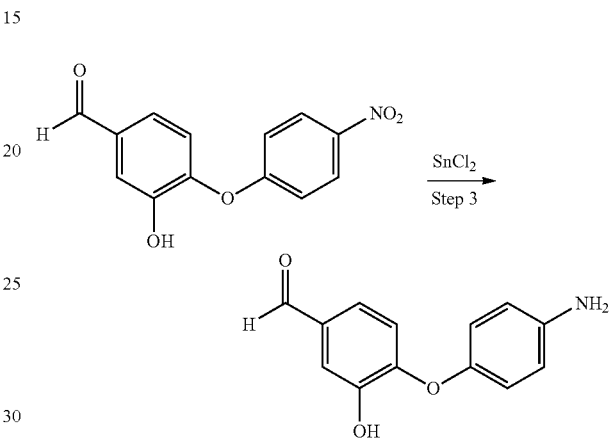

Stannous chloride (18.29 g, 96 mmol) was added to a solution of added 3-hydroxy-4-(4-nitrophenoxy)benzaldehyde (5.g, 19.29 mmol), stannous chloride (18.29 g, 96 mmol) in ethanol (60 mL), which was heated to 80° C. for 2 h. The mixture was cooled and mixed carefully with ice, and saturated sodium bicarbonate aqueous solution, then extracted with EtOAc multiple times. The combined organic layers were washed with brine, dried (Na$_2$SO$_4$), filtered through Celite®, and the filtrate was concentrated to afford the title compound as a yellow solid (1.18 g, 27% yield). LCMS (Method r, Table 7) R$_t$=0.48 min; m/z=not observed. $^1$H NMR (400 MHz, DMSO-d6) δ 9.90-9.87 (m, 1H), 10.90-9.26 (m, 2H), 8.66-8.56 (m, 1H), 7.66-7.61 (m, 1H), 7.50-7.46 (m, 1H), 7.46-7.38 (m, 2H), 7.38-7.29 (m, 4H), 7.16-6.99 (m, 6H); MS(ESI-) m/z=227.9 (M−H).

Step 4: Synthesis of (2S,6aS,6bR,7S,8aS,8bS,10R, 11aR,12aS,12bS)-10-(4-(4-Aminophenoxy)-3-hydroxyphenyl)-2,6b-difluoro-7-hydroxy-8b-(2-hydroxyacetyl)-6a,8a-dimethyl-6a,6b,7,8,8a,8b,11a,12, 12a,12b-decahydro-1H-naphtho[2',1':4,5]indeno[1,2-d][1,3]dioxol-4(2H)-one

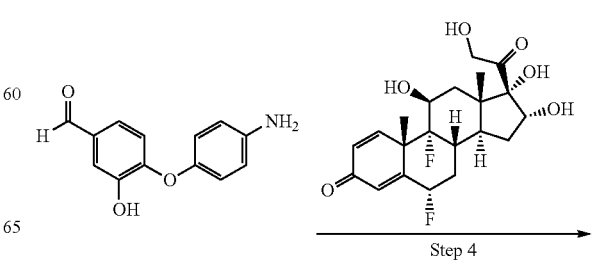

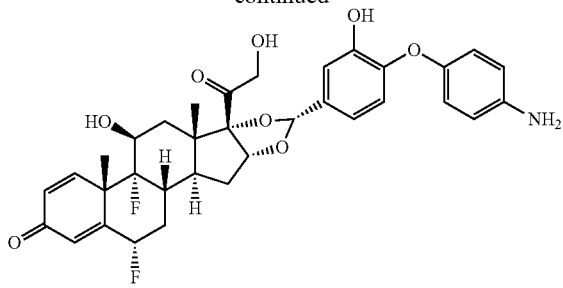

Perchloric acid (2.64 mL, 24.25 mmol) was added to a room temperature solution of 4-(4-aminophenoxy)-3-hydroxybenzaldehyde (0.611 g, 2.67 mmol) and (6S,8S,9R,10S,11S,13S,14S,16R,17S)-6,9-difluoro-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (1 g, 2.425 mmol) in THF (70 mL). After 16 hours the reaction was treated with water and extracted twice with EtOAc. The combined organic layers were washed with a saturated aqueous solution of sodium bicarbonate, a saturated aqueous solution of sodium thiosulfate solution, then a saturated aqueous solution of brine, dried ($Na_2SO_4$), and solvent was removed under reduced pressure. The material was purified by reverse phase HPLC on a Phenomenex C18(2) 5 micron column (250×21 mm column). A gradient of MeCN (A) and 0.1% TFA in water (B) was used at a flow rated of 30 mL/min (0.0-1.0 min 15% A, 1.0-10 min linear gradient to 65% A, hold 1 min). Combined fractions were concentrated under reduced pressure to remove volatile solvents, and the resulting solution frozen and lyophilized to give the title product as a yellow solid (338.9 mg, 23% yield). LCMS (Method r, Table 7) $R_t$=0.72 min; MS (ESI+) 624.2 (M+H); $^1$H NMR (400 MHz, DMSO-d6) δ 9.88 (s, 2H), 7.28 (dd, 1H), 7.27-7.22 (m, 2H), 7.07 (d, 1H), 7.00 (d, 1H), 6.96-6.88 (m, 3H), 6.30 (dd, 1H), 6.18-6.08 (m, 1H), 5.78-5.67 (m, 1H), 5.65-5.52 (m, 1H), 5.42 (s, 1H), 5.00-4.95 (m, 1H), 4.53 (d, 1H), 4.27-4.18 (m, 2H), 2.79-2.57 (m, 1H), 2.36-2.28 (m, 1H), 2.24 (td, 1H), 2.13-2.01 (m, 1H), 1.80-1.66 (m, 3H), 1.65-1.52 (m, 1H), 1.51 (s, 3H), 0.88 (s, 3H).

Example 19: Synthesis of (6aR,6bS,7S,8aS,8bS,10R,11aR,12aS,12bS)-10-(4-((4-Aminophenyl)sulfonyl)phenyl)-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one Step 1: Synthesis of 4-((4-Bromophenyl)thio)benzonitrile

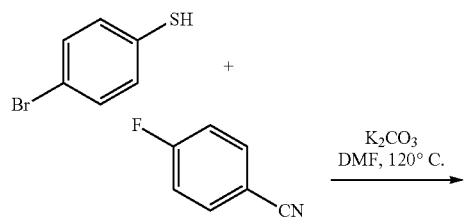

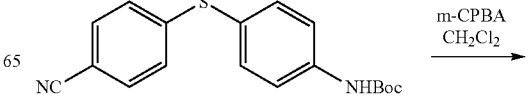

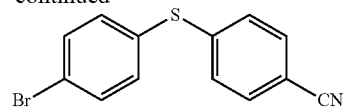

Potassium carbonate (4.39 g, 31.7 mmol) was added to a solution of 4-bromobenzenethiol (5.0 g, 26.4 mmol) and 4-fluorobenzonitrile (3.20 g, 26.4 mmol) in DMF (50 mL), which was heated to 120° C. for 3 h. The reaction was cooled to 0° C. water was added (100 mL) and the mixture was extracted with EtOAc (3×50 mL). The combined organics were dried ($MgSO_4$) and solvent was removed under reduced pressure. Purification by chromatography (80 g silica) eluting with a gradient of 0-60% EtOAc/heptanes gave the title compound (6.82 g, 23.5 mmol, 89% yield) as a yellow solid. LCMS (Method r, Table 7) $R_t$=0.95 min; m/z=291.2 [M+H$^+$]. $^1$H NMR (400 MHz, DMSO-d6) δ 7.72 (d, J=8.7 Hz, 2H), 7.65 (d, J=8.5 Hz, 2H), 7.43 (d, J=8.5 Hz, 2H), 7.26 (d, J=8.7 Hz, 2H).

Step 2: Synthesis of tert-butyl (4-((4-cyanophenyl)thio)phenyl)carbamate

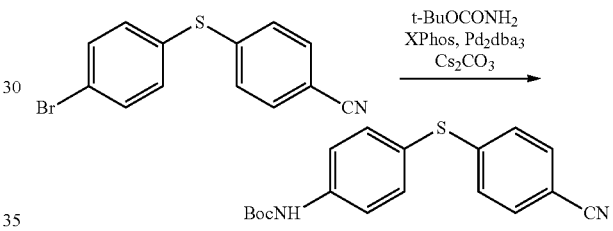

Nitrogen was sparged through a mixture of 4-((4-bromophenyl)thio)benzonitrile (6.0 g, 20.68 mmol), tert-butyl carbamate (2.91 g, 24.81 mmol), diisopropyl(2',4',5'-triisopropyl-[1,1'-biphenyl]-2-yl)phosphine (0.820 g, 2.068 mmol), and $Cs_2CO_3$ (10.11 g, 31.0 mmol) in 1,4-dioxane (207 mL) for 30 min. The flask was evacuated and back filled with $N_2$ (3×). $Pd_2dba_3$ (0.568 g, 0.620 mmol) was added and the reaction was evacuated and back filled with $N_2$ (3×) times. The reaction mixture was heated to 100° C. for 28 h. The reaction was cooled to room temperature, whereupon it was treated with water (200 mL), extracted with EtOAc (3×75 mL), dried ($MgSO_4$) and solvents were removed under reduced pressure. Purification by chromatography (silica, 120 g) eluting with a gradient of 0-30% EtOAc/heptanes gave the title compound (3.20 g, 9.80 mmol, 47% yield) as a yellow solid. LCMS (Method r, Table 7) $R_t$=1.0 min; m/z=344.1 [M+NH$_4$+]. $^1$H NMR (400 MHz, DMSO-d6) δ 9.67 (s, 1H), 7.69 (d, J=8.7 Hz, 2H), 7.61 (d, J=8.7 Hz, 2H), 7.47 (d, J=8.7 Hz, 2H), 7.14 (d, J=8.6 Hz, 2H), 1.49 (s, 9H).

Step 3: Synthesis of tert-butyl (4-((4-cyanophenyl)sulfonyl)phenyl)carbamate

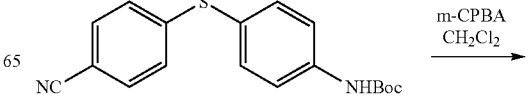

-continued

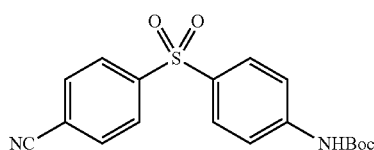

3-Chloroperoxybenzoic acid (639 mg, 3.71 mmol) was added portion-wise to a room temperature solution of tert-butyl (4-((4-cyanophenyl)thio)phenyl)carbamate (480 mg, 1.471 mmol) in $CH_2Cl_2$ (15 mL). After 30 min, the reaction was portioned between water (20 mL) and EtOAc (10 mL). The layers were separated and the aqueous phase was extracted with EtOAc (2×25 mL). The combined organics were washed with a saturated aqueous solution of brine (50 mL), dried over $MgSO_4$, and solvents were removed under reduced pressure. Purification by chromatography (silica, 40 g) eluting with a gradient of 0-60% EtOAc/heptanes gave the title compound (372 mg, 1.04 mmol, 71% yield) as a yellow solid. LCMS (Method r, Table 7) $R_t$=0.86 min; m/z=376.0 [M+$NH_4^+$]. $^1$H NMR (400 MHz, DMSO-d6) 9.92 (s, 1H), 8.06 (s, 4H), 7.87 (d, J=8.9 Hz, 2H), 7.66 (d, J=9.0 Hz, 2H), 1.45 (s, 9H).

Step 4: Synthesis of tert-butyl (4-((4-formylphenyl)sulfonyl)phenyl)carbamate

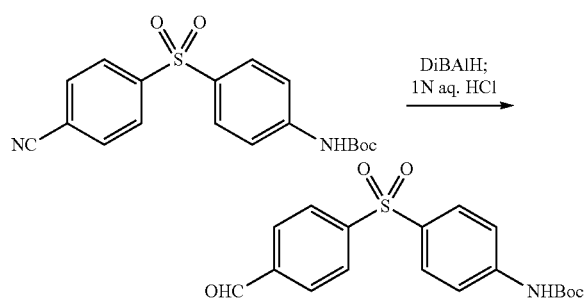

Diisobutylaluminum hydride (6.53 mL, 1.0 M in toluene, 6.53 mmol) was added drop-wise over 5 minutes to a 0° C. solution of tert-butyl (4-((4-cyanophenyl)sulfonyl)phenyl) carbamate (0.780 g, 2.176 mmol) in THF (20 mL). After 30 min diisobutylaluminum hydride (1.0 M in toluene) (2.176 mL, 2.176 mmol) was added and the reaction was stirred at 0° C. for an additional 1 h. The reaction was quenched at 0° C. by slow addition of al N aqueous solution of HCl (120 mL) and the aqueous phase was extracted with EtOAc (2×75 mL). The combined organics were washed with a saturated aqueous solution of brine (50 mL), dried over $MgSO_4$ and solvents were removed under reduced pressure. Purification by chromatography (silica, 80 g) eluting with a gradient of 0-10% $CH_2Cl_2$/MeOH gave the title compound (0.275 g, 0.761 mmol, 35% yield) as a yellow oil. LCMS (Method r, Table 7) $R_t$=0.83 min; m/z=359.9 [M−H$^-$]. $^1$H NMR (400 MHz, DMSO-d6) δ 10.04 (s, 1H), 9.89 (s, 1H), 8.18-7.97 (m, 4H), 7.85 (d, J=8.9 Hz, 2H), 7.64 (d, J=8.9 Hz, 2H), 1.43 (s, 9H).

Step 5: Synthesis of (6aR,6bS,7S,8aS,8bS,10R,11aR,12aS,12bS)-10-(4-((4-Aminophenyl)sulfonyl) phenyl)-7-hydroxy-8b-(2-hydroxyacetyl)-6a,8a-dimethyl-11a,12,12a,12b-decahydro-1H-naphtho[2',1':4,5]indeno[1,2-d][1,3]dioxol-4(2H)-one

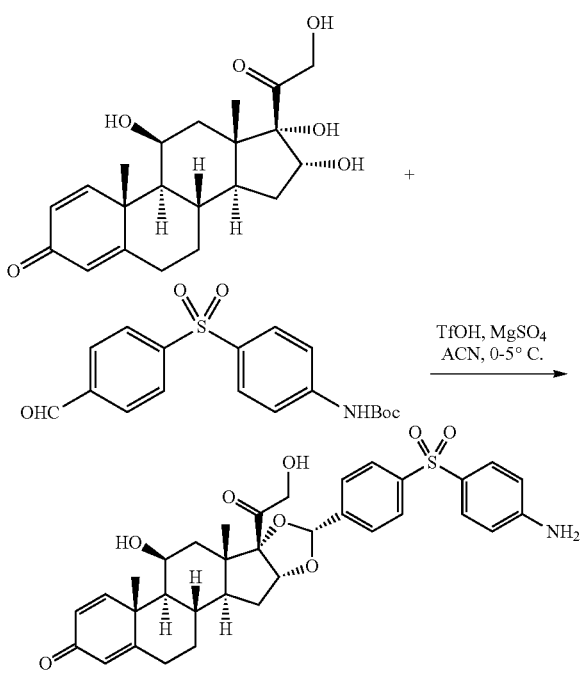

Triflic acid (0.12 mL, 1,328 mmol) was added drop-wise to a 0° C. slurry of (8S,9S,10R,11S,13S,14S,16R,17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (0.100 g, 0.266 mmol), tert-butyl (4-((4-formylphenyl)sulfonyl)phenyl)carbamate (0.106 g, 0.292 mmol), and $MgSO_4$ (0.096 g, 0.797 mmol) in MeCN (1.0 mL). After 30 minutes the reaction was diluted with EtOAc (15 mL), and then washed with a saturated aqueous solution of $NaHCO_3$ (10 mL) followed by a saturated aqueous solution of brine (10 mL), and dried ($MgSO_4$). Removal of solvent under reduced pressure gave a light yellow foam, which was purified by chromatography (silica, 24 g) eluting with a gradient of 0-10% $CH_2Cl_2$/MeOH to give a colorless glass. The acetal isomers were separated by preparative reverse phase HPLC on a Phenomenex C18 (2) 10 micron column, (250×30 mm). A gradient of MeCN (A) and 0.1% TFA in water (B) was used, at a flow rate of 60 mL/min (0-3.0 min 15% A, 3.0-18 min linear gradient 15-80% A, then hold 5 min). Combined fractions were concentrated to remove volatile solvents under reduced pressure, and the resulting solution was frozen and lyophilized to give the title compound as a white solid (8.0 mg, 18% yield). LCMS (Method r, Table 7) $R_t$=0.76 min; MS m/z=620.0 [M+H$^+$]. $^1$H NMR (400 MHz, DMSO-d6) δ 7.81 (d, J=8.4 Hz, 2H), 7.61 (d, J=8.4 Hz, 2H), 7.49 (d, J=8.8 Hz, 2H), 7.27 (d, J=10.0 Hz, 1H), 6.56 (d, J=8.8 Hz, 2H), 6.12 (dd, J=10.1, 1.9 Hz, 1H), 5.89 (s, 1H), 5.47 (s, 1H), 4.91 (d, J=4.6 Hz, 1H), 4.73 (s, 1H), 4.48 (d, J=19.4 Hz, 1H), 4.24 (s, 1H), 4.13 (d, J=19.5 Hz, 1H), 2.51 (s, 2H), 2.32-2.22 (m, 1H), 2.13-2.01 (m, 1H), 2.02-1.88 (m, 1H), 1.78-1.56 (m, 5H), 1.35 (s, 3H), 1.11-0.96 (m, 2H), 0.82 (s, 3H).

Example 20: N-(3-(4-((2S,6aS,6bR,7S,8aS,8bS,10R, 11aR,12aS,12bS)-2,6b-Difluoro-7-hydroxy-8b-(2-hydroxyacetyl)-6a,8a-dimethyl-4-oxo-2,4,6a,6b,7,8, 8a,8b,11a,12,12a,12b-dodecahydro-1H-naphtho[2', 1':4,5]indeno[1,2-d][1,3]dioxol-10-yl)benzyl) phenyl)-3-(2-(2-(3-(2,5-dioxo-2,5-dihydro-1H-pyrrol-1-yl)propanamido)ethoxy)ethoxy) propanamide Step 1: Synthesis of tert-butyl (2-(2-(3-((3-(4-((2S, 6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1, 3]dioxol-10-yl)benzyl)phenyl)amino)-3-oxopropoxy)ethoxy)ethyl)carbamate was purified by chromatography (silica, 24 g) eluting with a gradient of 0-10% MeOH/CH$_2$Cl$_2$ to give the title compound as a light yellow foam (226 mg, 0.261 mmol, 80% yield). LCMS (Method r, Table 7) R$_t$=0.91 min, m/z=865.5 [M+H$^+$]. $^1$H NMR (DMSO-d$_6$) δ 0.86 (s, 3H), 1.36 (s, 9H), 1.50 (s, 4H), 1.71 (ddt, J=17.9, 13.3, 5.8 Hz, 3H), 1.94-2.14 (m, 2H), 2.18-2.39 (m, 1H), 2.55-2.74 (m, 1H), 3.03 (q, J=6.0 Hz, 2H), 3.48 (hept, J=3.1, 2.7 Hz, 4H), 3.66 (t, J=6.3 Hz, 2H), 3.88 (s, 2H), 4.13-4.26 (m, 2H), 4.51 (d, J=19.4 Hz, 1H), 4.94 (d, J=5.1 Hz, 1H), 5.45 (s, 1H), 5.52 (dd, J=4.3, 1.7 Hz, 1H), 5.65 (dddd, J=48.5, 11.4, 6.7, 2.0 Hz, 1H), 6.13 (d, J=2.1 Hz, 1H), 6.73 (t, J=5.8 Hz, 1H), 6.80-6.97 (m, 1H), 7.18 (t, J=7.8 Hz, 1H), 7.25 (td, J=9.1, 8.2, 1.6 Hz, 3H), 7.32-7.39 (m, 3H), 7.45 (dd, J=8.4, 2.0 Hz, 1H), 7.63 (d, J=7.8 Hz, 1H), 8.11-8.85 (m, 1H), 9.83 (s, 1H).

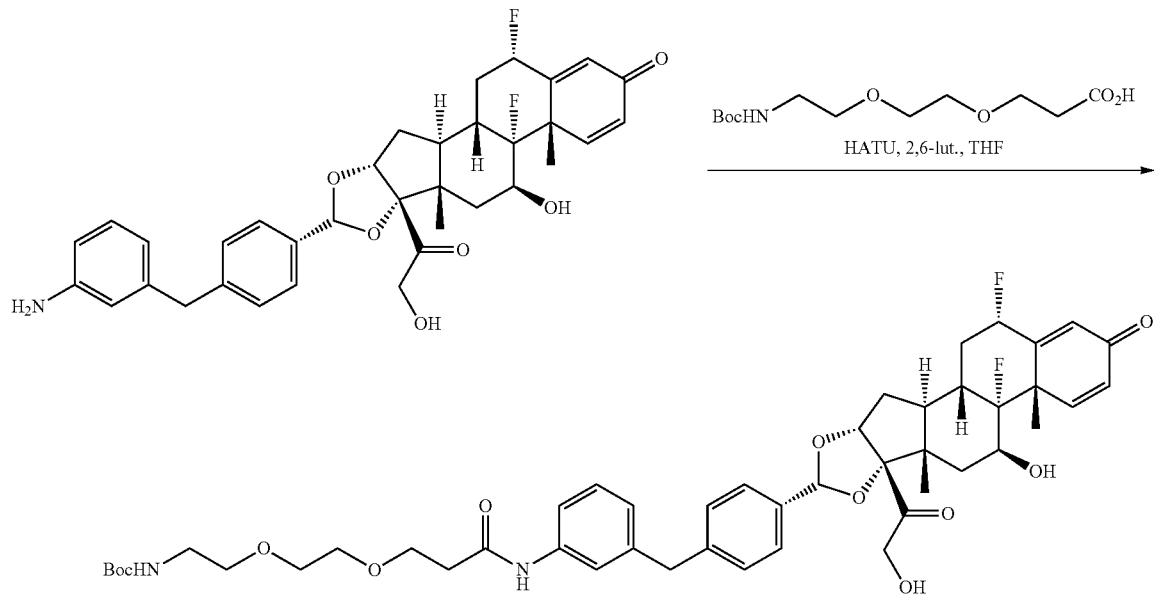

HATU (0.125 g, 0.328 mmol) was added to a room temperature solution of 2,2-dimethyl-4-oxo-3,8,11-trioxa-5-azatetradecan-14-oic acid (0.100 g, 0.361 mmol), (2S,6aS, 6bR,7S,8aS,8bS,10R,11aR,12aS,12bS)-10-(4-(3-aminobenzyl)phenyl)-2,6b-difluoro-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one (0.199 g, 0.328 mmol) and 2,6-dimethylpyridine (0.12 mL, 0.983 mmol) in THF (2.0 mL). After 24 hours solvents were removed under reduced pressure and the reaction mixture Step 2: 3-(2-(2-Aminoethoxy)ethoxy)-N-(3-(4-((2S,6aS,6bR,7S,8aS,8bS,10R,11aR, 12aS,12bS)-2,6b-difluoro-7-hydroxy-8b-(2-hydroxyacetyl)-6a,8a-dimethyl-4-oxo-2,4,6a6b,7,8,8a,8b, 11a,12,12a,12b-dodecahydro-1H-naphtho[2',1':4,5] indeno[1,2-d][1,3]dioxol-10-yl)benzyl)phenyl)propanamide

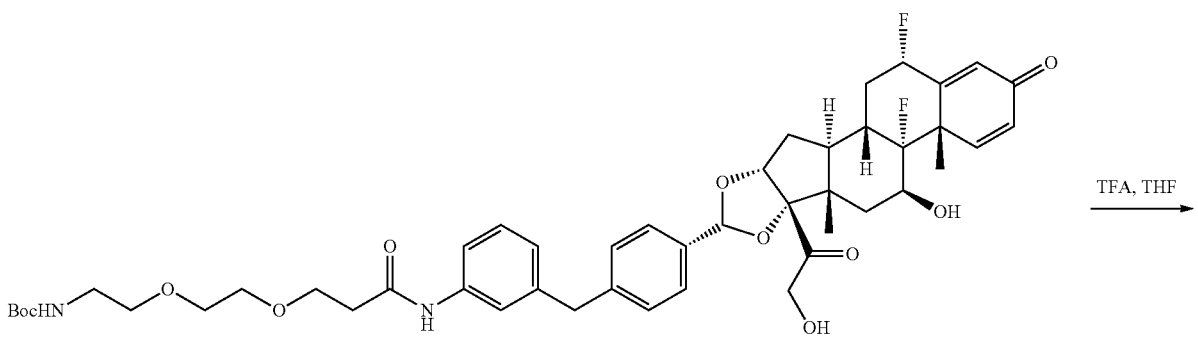

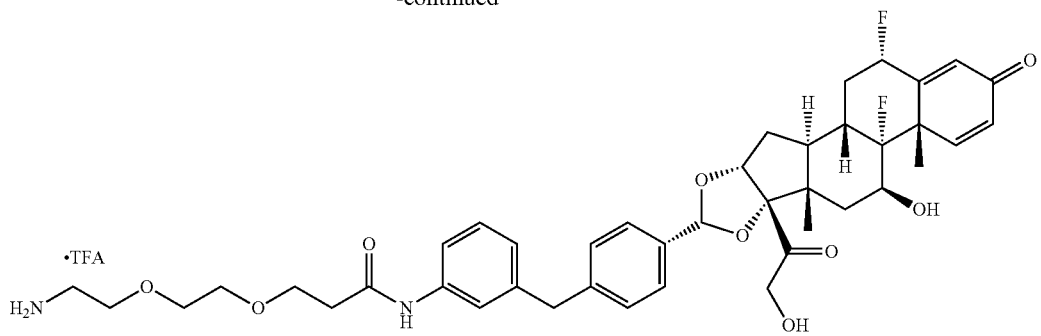

TFA (1.0 mL, 12.98 mmol) was added to a room temperature solution of tert-butyl (2-(2-(3-(((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-3-oxopropoxy)ethoxy)ethyl)carbamate (226 mg, 0.261 mmol) in CH$_2$Cl$_2$ (3.0 mL). After 45 min volatiles were removed under vacuum and the crude product was carried on to the next step without further purification, assuming 100% yield. LCMS (Method r, Table 7) R$_t$=0.80 min, m/z=765.4 [M+H$^+$].

Step 3: Synthesis of N-(3-(4-((2S,6aS,6bR,7S,8aS, 8bS,10R,11aR,12aS,12bS)-2,6b-Difluoro-7-hydroxy-8b-(2-hydroxyacetyl)-6a,8a-dimethyl-4-oxo-2, 4,6a,6b,7,8,8a,8b,11a,12,12a,12b-dodecahydro-1H-naphtho[2',1':4,5]indeno[1,2-d][1,3]dioxol-10-yl) benzyl)phenyl)-3-(2-(2-(3-(2,5-dioxo-2,5-dihydro-1H-pyrrol-1-yl)propanamido)ethoxy)ethoxy) propanamide 12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)propanamide (0.226 g, 0.295 mmol) and 2,5-dioxopyrrolidin-1-yl 3-(2,5-dioxo-2,5-dihydro-1H-pyrrol-1-yl)propanoate (0.087 g, 0.325 mmol) in DMF (2.0 mL). After 45 min, the crude reaction mixture was purified by reverse phase HPLC on a Phenomenex C18(2) 10 micron column (250×50 mm column). A gradient of MeCN (A) and 0.1% formic acid in water (B) was used, at a flow rate of 80 mL/min (0-5.0 min 18% A, 5.0-25.0 min linear gradient 15-80% A, hold 5 min). Combined fractions were concentrated under reduced pressure to remove volatile solvents, and the resulting solution was frozen and lyophilized to give the title compound as a white solid (48 mg, 0.052 mmol, 18% yield). LCMS (Method r, Table 7) R$_t$=0.84 min, m/z=916.4 [M+H$^+$]. $^1$H NMR (DMSO-d$_6$) δ 0.84 (s, 3H), 1.48 (s, 4H), 1.59-1.76 (m, 3H), 2.03 (d, J=13.9 Hz, 1H), 2.17-2.38 (m, 4H), 2.54-2.72 (m, 1H), 3.11 (q, J=5.8 Hz, 2H), 3.31-3.35 (m, 4H), 3.42-3.51 (m, 4H), 3.57

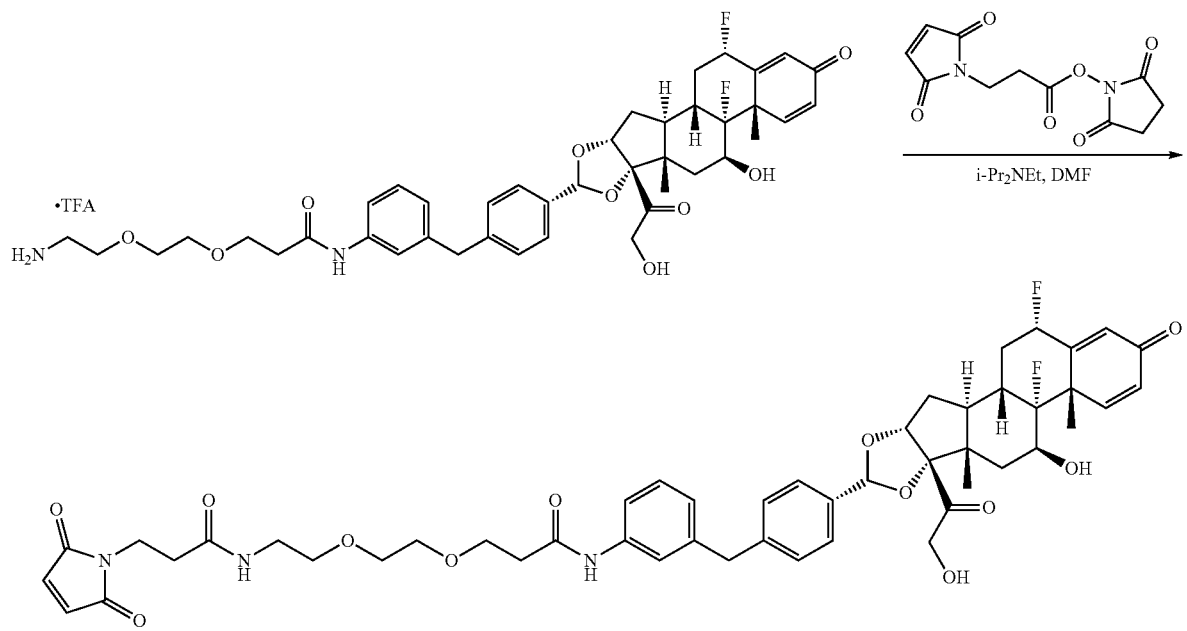

N,N-Diisopropylethylamine (0.155 mL, 0.88 mmol) was added to a room temperature solution of 3-(2-(2-aminoethoxy)ethoxy)-N-(3-(4-((2S,6aS,6bR,7S,8aS,8bS,10R,11aR, (dd, J=7.8, 6.8 Hz, 2H), 3.64 (t, J=6.3 Hz, 2H), 3.86 (s, 2H), 4.10-4.25 (m, 2H), 4.49 (dd, J=19.5, 6.0 Hz, 1H), 4.93 (d, J=5.1 Hz, 1H), 5.07 (t, J=5.9 Hz, 1H), 5.43 (s, 1H), 5.51 (s, 1H), 5.53-5.74 (m, 1H), 6.11 (s, 1H), 6.28 (dd, J=10.2, 1.9 Hz, 1H), 6.88 (d, J=7.5 Hz, 1H), 6.97 (s, 2H), 7.16 (t, J=7.8 Hz, 1H), 7.20-7.28 (m, 3H), 7.30-7.39 (m, 3H), 7.38-7.48 (m, 1H), 7.96 (t, J=5.6 Hz, 1H), 9.81 (s, 1H).

Example 21: N-(3-(4-((2S,6aS,6bR,7S,8aS,8bS,10R,11aR,12aS,12bS)-2,6b-Difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)-1-(3-(2,5-dioxo-2,5-dihydro-1H-pyrrol-1-yl)propanamido)-3,6,9,12-tetraoxapentadecan-15-amide Prepared by the same procedure as Example 20. White solid (23.2 mg, 0.021 mmol, 22% yield). LCMS (Method r, Table 7) $R_t$=0.83 min, m/z=1092.3 [M+H⁺]. ¹H NMR (DMSO-d₆) δ 0.84 (s, 3H), 1.48 (s, 4H), 1.58-1.76 (m, 3H), 2.02 (dt, J=14.0, 3.6 Hz, 1H), 2.17-2.37 (m, 4H), 2.62 (dtd, J=24.1, 11.9, 4.4 Hz, 1H), 3.12 (q, J=5.8 Hz, 2H), 3.40-3.52 (m, 23H), 3.57 (t, J=7.3 Hz, 2H), 3.64 (t, J=6.3 Hz, 2H), 3.86 (s, 2H), 4.10-4.25 (m, 2H), 4.49 (d, J=19.4 Hz, 1H), 4.92 (d, J=5.0 Hz, 1H), 5.08 (s, 1H), 5.43 (s, 1H), 5.49-5.73 (m, 2H), 6.11 (s, 1H), 6.27 (dd, J=10.1, 1.9 Hz, 1H), 6.87 (d, J=7.6 Hz, 1H), 6.97 (s, 2H), 7.16 (t, J=7.8 Hz, 1H), 7.23 (dd, J=13.9, 9.0 Hz, 3H), 7.30-7.38 (m, 3H), 7.43 (d, J=8.1 Hz, 1H), 7.98 (t, J=5.6 Hz, 1H), 9.81 (s, 1H).

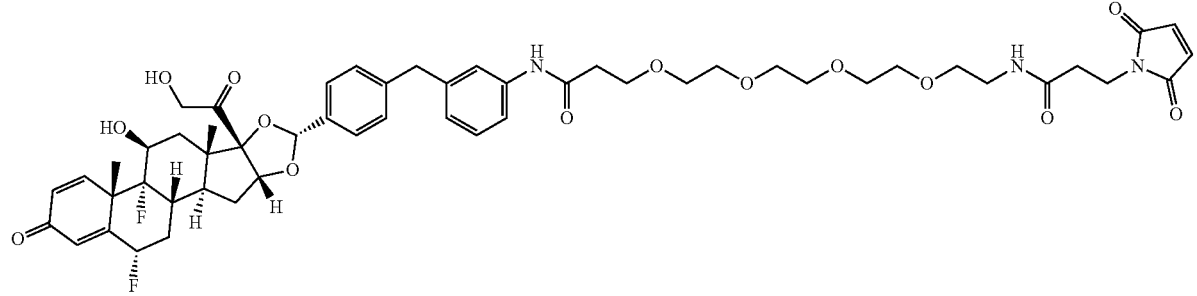

Prepared by the same procedure as Example 20. White solid (17 mg, 0.017 mmol, 9% yield). LCMS (Method r, Table 7) $R_t$=0.82 min, m/z=1026 [M+Na+]. ¹H NMR (DMSO-d₆) δ 0.85 (s, 3H), 1.22 (s, 8H), 1.49 (s, 3H), 1.61-1.77 (m, 2H), 2.03 (d, J=13.9 Hz, 1H), 2.12-2.40 (m, 3H), 2.55-2.66 (m, 1H), 3.12 (q, J=5.8 Hz, 2H), 3.33 (s, 1H), 3.41-3.51 (m, 11H), 3.58 (t, J=7.3 Hz, 2H), 3.65 (t, J=6.3 Hz, 2H), 3.87 (s, 2H), 4.18 (d, J=14.1 Hz, 2H), 4.42-4.61 (m, 1H), 4.93 (d, J=5.2 Hz, 1H), 5.07 (s, 1H), 5.44 (s, 1H), 5.50 (s, 1H), 5.6-5.7 (m, 1H), 6.28 (dd, J=10.2, 1.9 Hz, 1H), 6.88 (d, J=7.8 Hz, 1H), 6.98 (s, 2H), 7.17 (t, J=7.9 Hz, 1H), 7.24 (t, J=9.8 Hz, 3H), 7.32-7.38 (m, 3H), 7.43 (d, J=8.3 Hz, 1H), 7.98 (s, 1H), 9.81 (s, 1H).

Example 22: N-(3-(4-((2S,6aS,6bR,7S,8aS,8bS,10R,11aR,12aS,12bS)-2,6b-Difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)-1-(3-(2,5-dioxo-2,5-dihydro-1H-pyrrol-1-yl)propanamido)-3,6,9,12,15,18-hexaoxahenicosan-21-amide

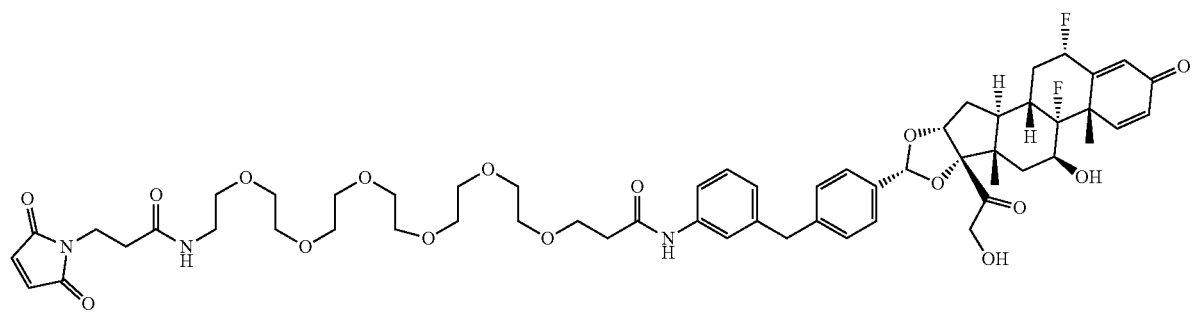

Example 23: N-(3-(4-((2S,6aS,6bR,7S,8aS,8bS,10R,11aR,12aS,12bS)-2,6b-Difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)-1-(3-(2,5-dioxo-2,5-dihydro-1H-pyrrol-1-yl)propanamido)-3,6,9,12,15,18,21,24,27,30,33,36-dodecaoxanonatriacontan-39-amide

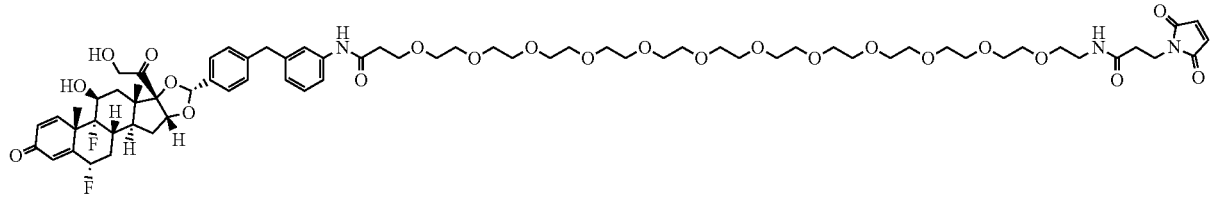

Prepared by the same procedure as Example 20. Isolated as a colorless glass (20 mg, 0.015 mmol, 18% yield). LCMS (Method r, Table 7) $R_t$=0.85 min, m/z=1356.4 [M+H$^+$]. $^1$H NMR (DMSO-d$_6$) δ 0.84 (s, 3H), 1.48 (s, 4H), 1.67 (d, J=14.3 Hz, 3H), 2.03 (d, J=14.0 Hz, 1H), 2.30 (q, J=9.8, 8.5 Hz, 4H), 2.65 (s, 1H), 3.13 (q, J=5.8 Hz, 2H), 3.34 (t, J=6.2 Hz, 2H), 3.39-3.54 (m, 46H), 3.57 (t, J=7.3 Hz, 2H), 3.64 (t, J=6.2 Hz, 2H), 3.86 (s, 2H), 4.18 (d, J=14.6 Hz, 2H), 4.49 (d, J=19.2 Hz, 1H), 4.93 (d, J=4.8 Hz, 1H), 5.07 (s, 1H), 5.43 (s, 1H), 5.50 (s, 1H), 5.62 (d, J=41.1 Hz, 1H), 6.11 (s, 1H), 6.20-6.36 (m, 1H), 6.87 (d, J=7.5 Hz, 1H), 6.98 (s, 2H), 7.16 (t, J=7.8 Hz, 1H), 7.23 (t, J=9.0 Hz, 3H), 7.34 (d, J=8.4 Hz, 3H), 7.43 (d, J=8.4 Hz, 1H), 7.97 (s, 1H), 9.80 (s, 1H).

Example 24: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-3-(2,5-dioxo-2,5-dihydro-1H-pyrrol-1-yl)propanamide

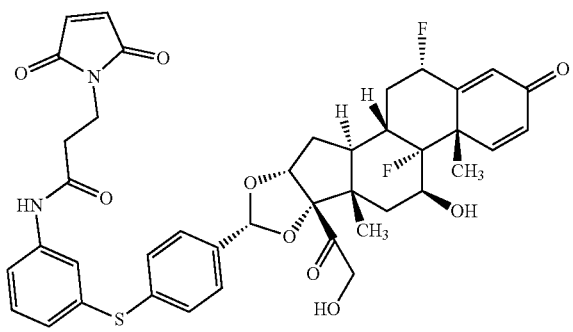

In a 4 mL vial 3-(2,5-dioxo-2,5-dihydro-1H-pyrrol-1-yl)propanoic acid was added (43.5 mg, 0.26 mmol), followed by HATU (148 mg, 0.39 mmol) dissolved in DMA (1.0 mL), followed by N,N-Diisopropylethylamine neat (67 ul, 0.39 mmol). Then a solution of (2S,6aS,6bR,7S,8aS,8bS,10R,11aR,12aS,12bS)-10-(4-((3-aminophenyl)thio)phenyl)-2,6b-difluoro-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one (80.83 mg, 0.13 mmol)(80.83 mg, 0.13 mmol) dissolved in DMA (0.5 mL) was added. The reaction was shaken at room temperature for 2 hours. The reaction was checked by LC/MS and purified by reverse phase HPLC (Method q, linear gradient 45-75%), to provide the title compound. LCMS (Method s, Table 7) $R_t$=0.78 min; MS m/z=775.3 (M+H)+; $^1$H NMR (400 MHz, DMSO-d6/D$_2$O, Temp=27° C.) δ 7.61-7.57 (m, 1H), 7.49-7.44 (m, 1H), 7.43-7.37 (m, 2H), 7.34-7.22 (m, 4H), 7.06-7.02 (m, 1H), 6.92 (s, 2H), 6.29 (dd, J=10.2, 1.9 Hz, 1H), 6.14-6.09 (m, 1H), 5.72-5.52 (m, 1H), 5.46 (s, 1H), 4.98-4.93 (m, 1H), 4.52 (d, J=19.4 Hz, 1H), 4.26-4.14 (m, 2H), 3.73-3.71 (m, 2H), 3.69-3.65 (m, 2H), 2.73-2.55 (m, 1H), 2.35-2.26 (m, 1H), 2.25-2.12 (m, 1H), 2.03-1.95 (m, 1H), 1.79-1.62 (m, 3H), 1.55-1.39 (m, 4H), 0.85 (s, 3H).

Example 25: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-6-(2,5-dioxo-2,5-dihydro-1H-pyrrol-1-yl)hexanamide

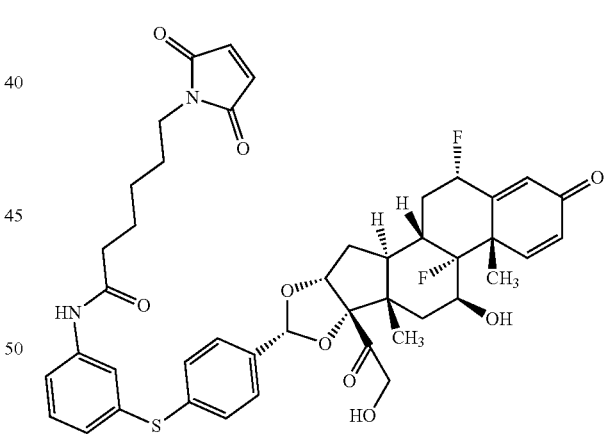

Prepared as described in example 24 from 6-(2,5-dioxo-2,5-dihydro-1H-pyrrol-1-yl)hexanoic acid. Purified by reverse phase HPLC (Method s, linear gradient 50-80%). LCMS (Method c, Table 7) $R_t$=0.82 min; MS m/z=817.3 (M+H)+; $^1$H NMR (400 MHz, DMSO-d6/D$_2$O, Temp=27° C.) δ 7.68-7.65 (m, 1H), 7.53-7.49 (m, 1H), 7.42-7.38 (m, 2H), 7.33-7.24 (m, 4H), 7.04-7.01 (m, 1H), 6.91 (s, 2H), 6.29 (dd, J=10.1, 1.9 Hz, 1H), 6.14-6.10 (m, 1H), 5.72-5.53 (m, 1H), 5.46 (s, 1H), 4.96-4.92 (m, 1H), 4.51 (d, J=19.4 Hz, 1H), 4.24-4.15 (m, 2H), 3.38 (t, J=7.0 Hz, 2H), 2.70-2.54 (m, 1H), 2.35-2.11 (m, 5H), 2.03-1.96 (m, 1H), 1.76-1.61 (m, 3H), 1.59-1.41 (m, 8H), 1.24-1.13 (m, 2H), 0.85 (s, 3H).

Example 26: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-4-(2,5-dioxo-2,5-dihydro-1H-pyrrol-1-yl)benzamide

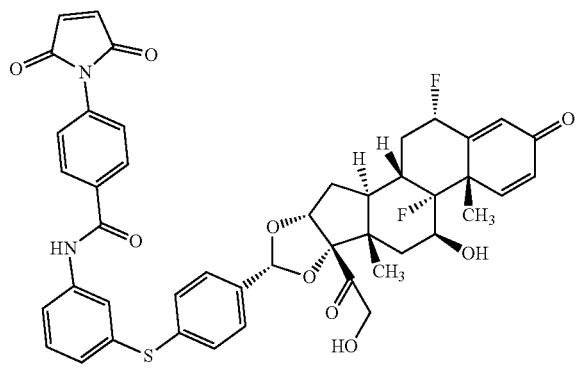

Prepared as described in example 24 from 4-(2,5-dioxo-2,5-dihydro-1H-pyrrol-1-yl)benzoic acid. Purified by reverse phase HPLC (Method s, linear gradient 50-80%). LCMS (Method c, Table 7) $R_t$=0.83 min; MS m/z=823.2 (M+H)+; $^1$H NMR (400 MHz, DMSO-d6/D$_2$O, Temp=27° C.) δ 8.02-7.97 (m, 2H), 7.88-7.85 (m, 1H), 7.77-7.73 (m, 1H), 7.52-7.47 (m, 2H), 7.44-7.36 (m, 3H), 7.35-7.30 (m, 2H), 7.29-7.23 (m, 1H), 7.15 (s, 2H), 7.14-7.10 (m, 1H), 6.29 (dd, J=10.2, 1.9 Hz, 1H), 6.15-6.09 (m, 1H), 5.71-5.54 (m, 1H), 5.47 (s, 1H), 4.97-4.94 (m, 1H), 4.52 (d, J=19.4 Hz, 1H), 4.24-4.14 (m, 2H), 2.70-2.57 (m, 1H), 2.37-2.27 (m, 1H), 2.24-2.12 (m, 1H), 2.03-1.97 (m, 1H), 1.75-1.64 (m, 3H), 1.54-1.42 (m, 4H), 0.85 (s, 3H).

Example 27: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-4-((2,5-dioxo-2,5-dihydro-1H-pyrrol-1-yl)methyl)cyclohexanecarboxamide

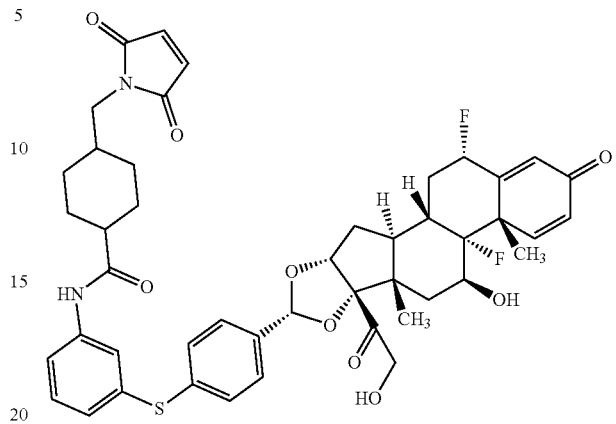

Prepared as described in example 24 from 4-((2,5-dioxo-2,5-dihydro-1H-pyrrol-1-yl)methyl)cyclohexane-1-carboxylic acid. Purified by reverse phase HPLC (Method q, linear gradient 50-80%). LCMS (Method s, Table 7) $R_t$=0.85 min; MS m/z=843.3 (M+H)+; $^1$H NMR (400 MHz, DMSO-d6/D$_2$O, Temp=27° C.) δ 7.68 (t, J=2.0 Hz, 1H), 7.54-7.49 (m, 1H), 7.42-7.37 (m, 2H), 7.35-7.22 (m, 4H), 7.04-7.01 (m, 1H), 6.95 (s, 2H), 6.29 (dd, J=10.1, 1.9 Hz, 1H), 6.12 (s, 1H), 5.71-5.53 (m, 1H), 5.46 (s, 1H), 4.99-4.93 (m, 1H), 4.51 (d, J=19.4 Hz, 1H), 4.25-4.15 (m, 2H), 3.26 (d, J=7.0 Hz, 2H), 2.73-2.58 (m, 1H), 2.35-2.14 (m, 3H), 2.03-1.96 (m, 1H), 1.83-1.62 (m, 7H), 1.59-1.40 (m, 5H), 1.37-1.24 (m, 2H), 0.98-0.87 (m, 2H), 0.85 (s, 3H).

Example 28: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-1-(3-(2,5-dioxo-2,5-dihydro-1H-pyrrol-1-yl)propanamido)-3,6,9,12-tetraoxapentadecan-15-amide

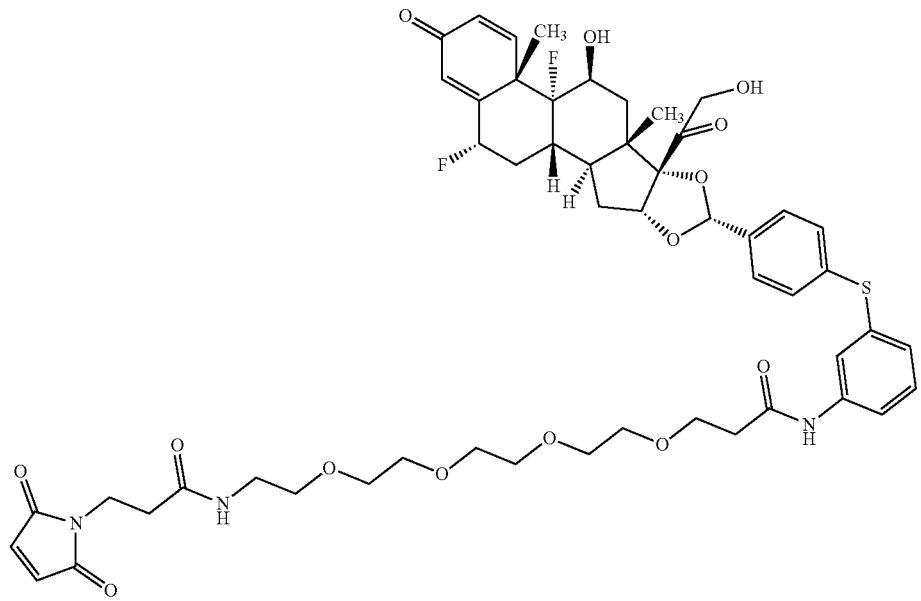 [SMILES: C[C@]12C=CC(=O)C=C1[C@@H](F)C[C@H]1[C@@H]3C[C@H]4O[C@@H](c5ccc(Sc6cccc(NC(=O)CCOCCOCCOCCOCCNC(=O)CCN7C(=O)C=CC7=O)c6)cc5)O[C@@]4(C(=O)CO)[C@@]3(C)C[C@H](O)[C@@]12F]

Prepared as described in example 24 from 1-(2,5-dioxo-2,5-dihydro-1H-pyrrol-1-yl)-3-oxo-7,10,13,16-tetraoxa-4-azanonadecan-19-oic acid. Purified by reverse phase HPLC (Method s, linear gradient 45-75%). LCMS (Method c, Table 7) $R_t$=0.76 min; MS m/z=1022.4 (M+H)$^+$; $^1$H NMR (400 MHz, DMSO-d6/D$_2$O, Temp=27° C.) δ 7.70-7.66 (m, 1H), 7.55-7.50 (m, 1H), 7.43-7.37 (m, 2H), 7.34-7.23 (m, 4H), 7.06-7.01 (m, 1H), 6.92 (s, 2H), 6.29 (dd, J=10.2, 1.9 Hz, 1H), 6.14-6.11 (m, 1H), 5.72-5.53 (m, 1H), 5.46 (s, 1H), 5.00-4.92 (m, 1H), 4.51 (d, J=19.4 Hz, 1H), 4.26-4.15 (m, 2H), 3.66 (t, J=6.1 Hz, 2H), 3.59 (t, J=7.2 Hz, 2H), 3.51-3.40 (m, 11H), 3.33 (t, J=5.8 Hz, 2H), 3.12 (t, J=5.8 Hz, 2H), 2.70-2.58 (m, 1H), 2.51-2.47 (m, 3H), 2.36-2.25 (m, 3H), 2.24-2.13 (m, 1H), 2.04-1.97 (m, 1H), 1.75-1.65 (m, 3H), 1.56-1.42 (m, 4H), 0.85 (s, 3H).

Example 29: N-(3-((4-(((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-1-(2,5-dioxo-2,5-dihydro-H-pyrrol-1-yl)-3,6,9,12-tetraoxapentadecan-15-amide

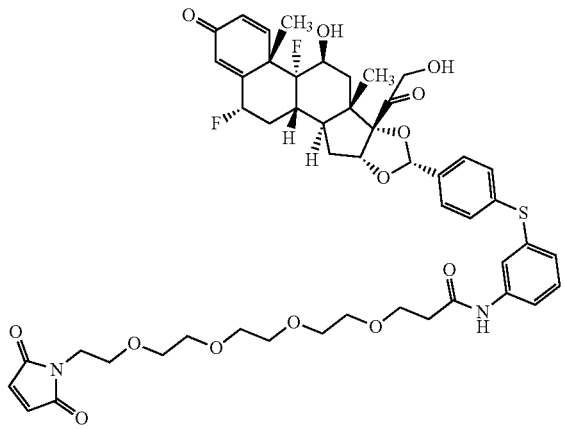 [SMILES: C[C@]12C=CC(=O)C=C1[C@@H](F)C[C@H]1[C@@H]3C[C@H]4O[C@@H](c5ccc(Sc6cccc(NC(=O)CCOCCOCCOCCOCCN7C(=O)C=CC7=O)c6)cc5)O[C@@]4(C(=O)CO)[C@@]3(C)C[C@H](O)[C@@]12F]

Prepared as described in example 24 from 1-(2,5-dioxo-2,5-dihydro-1H-pyrrol-1-yl)-3,6,9,12-tetraoxapentadecan-15-oic acid. Purified by reverse phase HPLC (Method s, linear gradient 45-75%). LCMS (Method c, Table 7) $R_t$=0.80 min; MS m/z=951.3 (M+H)$^+$; $^1$H NMR (400 MHz, DMSO-d6/D$_2$O, Temp=27° C.) δ 7.69-7.66 (m, 1H), 7.54-7.49 (m, 1H), 7.42-7.37 (m, 2H), 7.35-7.24 (m, 4H), 7.06-7.01 (m, 1H), 6.93 (s, 2H), 6.29 (dd, J=10.2, 1.9 Hz, 1H), 6.17-6.10 (m, 1H), 5.71-5.55 (m, 1H), 5.46 (s, 1H), 4.98-4.93 (m, 1H), 4.51 (d, J=19.4 Hz, 1H), 4.24-4.16 (m, 2H), 3.66 (t, J=6.1 Hz, 2H), 3.56-3.51 (m, 2H), 3.50-3.36 (m, 14H), 2.71-2.60 (m, 1H), 2.51-2.48 (m, 2H), 2.33-2.27 (m, 1H), 2.18 (q, J=10.5 Hz, 1H), 2.03-1.94 (m, 1H), 1.74-1.66 (m, 3H), 1.56-1.44 (m, 4H), 0.85 (s, 3H).

Example 30: N-(3-((4-(((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-1-(2,5-dioxo-2,5-dihydro-1H-pyrrol-1-yl)-3,6,9,12,15,18-hexaoxa-henicosan-21-amide

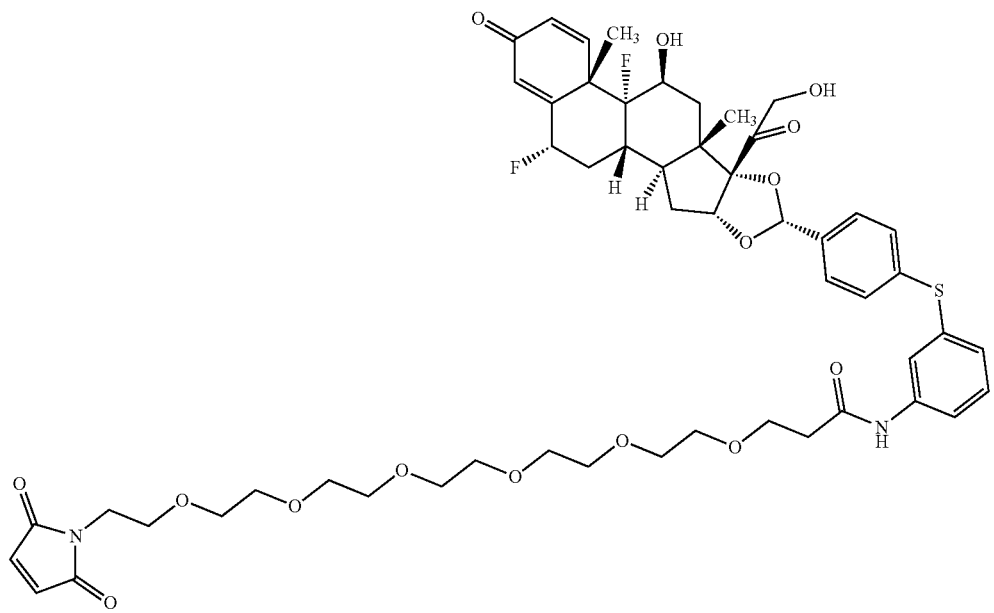 [SMILES: C[C@]12C=CC(=O)C=C1[C@@H](F)C[C@H]1[C@@H]3C[C@H]4O[C@@H](c5ccc(Sc6cccc(NC(=O)CCOCCOCCOCCOCCOCCOCCN7C(=O)C=CC7=O)c6)cc5)O[C@@]4(C(=O)CO)[C@@]3(C)C[C@H](O)[C@@]12F]

Prepared as described in example 24 from 1-(2,5-dioxo-2,5-dihydro-1H-pyrrol-1-yl)-3,6,9,12,15,18-hexaoxahenicosan-21-oic acid. Purified by reverse phase HPLC (Method q, linear gradient 10-100%). LCMS (Method s, Table 7) R$_t$=0.80 min; MS m/z did not ionize; $^1$H NMR (400 MHz, DMSO-d$_6$/D$_2$O, Temp=27° C.) δ 7.69-7.66 (m, 1H), 7.55-7.50 (m, 1H), 7.44-7.37 (m, 2H), 7.34-7.24 (m, 4H), 7.06-7.01 (m, 1H), 6.94 (s, 2H), 6.29 (dd, J=10.2, 1.9 Hz, 1H), 6.13 (s, 1H), 5.69-5.55 (m, 1H), 5.46 (s, 1H), 4.97-4.93 (m, 1H), 4.51 (d, J=19.4 Hz, 1H), 4.23-4.16 (m, 2H), 3.66 (t, J=6.1 Hz, 2H), 3.56-3.38 (m, 22H), 2.70-2.63 (m, 1H), 2.54-2.53 (m, 2H), 2.51-2.48 (m, 2H), 2.33-2.26 (m, 1H), 2.18 (q, J=10.3 Hz, 1H), 2.03-1.97 (m, 1H), 1.73-1.65 (m, 3H), 1.55-1.44 (m, 4H), 0.85 (s, 3H).

Example 31: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-3-(2-(2-(2-(2,5-dioxo-2,5-dihydro-1H-pyrrol-1-yl)ethoxy)ethoxy)ethoxy)propanamide

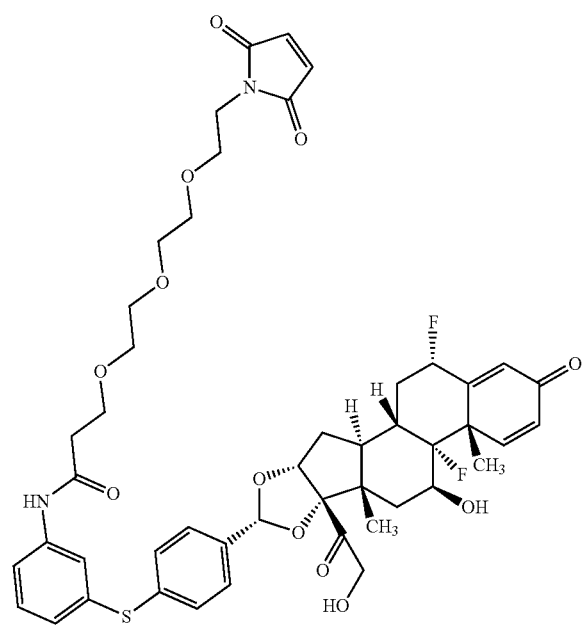 [SMILES: C[C@]12C=CC(=O)C=C1[C@@H](F)C[C@H]1[C@@H]3C[C@H]4O[C@@H](c5ccc(Sc6cccc(NC(=O)CCOCCOCCOCCN7C(=O)C=CC7=O)c6)cc5)O[C@@]4(C(=O)CO)[C@@]3(C)C[C@H](O)[C@@]12F]

Prepared as described in example 24 from 3-(2-(2-(2-(2,5-dioxo-2,5-dihydro-1H-pyrrol-1-yl)ethoxy)ethoxy)ethoxy)propanoic acid. Purified by reverse phase HPLC (Method q, linear gradient 45-75%). LCMS (Method s, Table 7) R$_t$=0.80 min; MS m/z=908.1 (M+H)$^+$; $^1$H NMR (400 MHz, DMSO-d$_6$/D$_2$O, Temp=27° C.) δ 7.69-7.66 (m, 1H), 7.54-7.51 (m, 1H), 7.42-7.38 (m, 2H), 7.34-7.24 (m, 4H), 7.06-7.02 (m, 1H), 6.93 (s, 2H), 6.29 (dd, J=10.2, 1.9 Hz, 1H), 6.12 (s, 1H), 5.68-5.55 (m, 1H), 5.46 (s, 1H), 4.98-4.94 (m, 1H), 4.51 (d, J=19.4 Hz, 1H), 4.24-4.16 (m, 2H), 3.64 (t, J=6.1 Hz, 2H), 3.55-3.50 (m, 2H), 3.47-3.37 (m, 9H), 2.69-2.66 (m, 1H), 2.54-2.53 (m, 1H), 2.50-2.47 (m, 2H), 2.32-2.25 (m, 1H), 2.21-2.14 (m, 1H), 2.03-1.97 (m, 1H), 1.74-1.65 (m, 3H), 1.54-1.43 (m, 4H), 0.85 (s, 3H).

Example 32: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-3-(2-(2-(3-(2,5-dioxo-2,5-dihydro-1H-pyrrol-1-yl)propanamido)ethoxy)ethoxy)propanamide

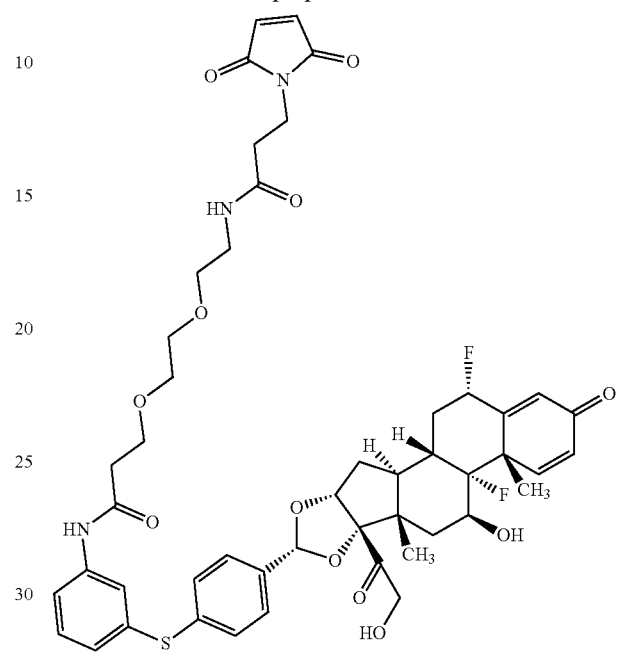

Prepared as described in example 24 from 3-(2-(2-(3-(2,5-dioxo-2,5-dihydro-1H-pyrrol-1-yl)propanamido)ethoxy)ethoxy)propanoic acid. Purified by reverse phase HPLC (Method q, linear gradient 45-75%). LCMS (Method s, Table 7) R$_t$=0.76 min; MS m/z=934.4 (M+H)$^+$; $^1$H NMR (400 MHz, DMSO-d$_6$/D$_2$O, Temp=27° C.) δ 7.69-7.66 (m, 1H), 7.54-7.49 (m, 1H), 7.42-7.38 (m, 2H), 7.34-7.23 (m, 4H), 7.05-7.01 (m, 1H), 6.91 (s, 2H), 6.29 (dd, J=10.2, 1.9 Hz, 1H), 6.13 (s, 1H), 5.68-5.56 (m, 1H), 5.46 (s, 1H), 4.97-4.93 (m, 1H), 4.51 (d, J=19.4 Hz, 1H), 4.24-4.15 (m, 2H), 3.66 (t, J=6.2 Hz, 2H), 3.58 (t, J=7.2 Hz, 2H), 3.51-3.43 (m, 4H), 3.33 (t, J=5.8 Hz, 2H), 3.10 (t, J=5.7 Hz, 2H), 2.63-2.58 (m, 1H), 2.55-2.53 (m, 1H), 2.50-2.49 (m, 2H), 2.32-2.27 (m, 2H), 2.18 (q, J=10.3 Hz, 1H), 2.03-1.97 (m, 1H), 1.73-1.63 (m, 3H), 1.54-1.42 (m, 4H), 0.85 (s, 3H).

Example 33: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-2-(2,5-dioxo-2,5-dihydro-1H-pyrrol-1-yl)acetamide

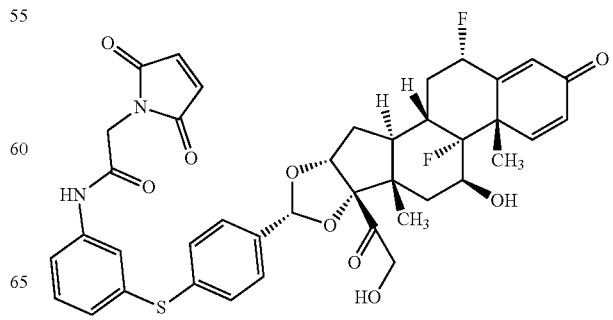

Prepared as described in example 24 from 2-(2,5-dioxo-2,5-dihydro-1H-pyrrol-1-yl)acetic acid. Purified by reverse phase HPLC (Method s, linear gradient 45-75%). LCMS (Method c, Table 7) $R_t$=0.95 min; MS m/z=761.7 (M+H)$^+$; $^1$H NMR (400 MHz, DMSO-d6/D$_2$O, Temp=27° C.) δ 7.65-7.61 (m, 1H), 7.52-7.47 (m, 1H), 7.44-7.39 (m, 2H), 7.36 (t, J=7.9 Hz, 1H), 7.33-7.25 (m, 3H), 7.11-7.08 (m, 1H), 7.07 (s, 2H), 6.32 (dd, J=10.1, 1.9 Hz, 1H), 6.15 (s, 1H), 5.72-5.55 (m, 1H), 5.47 (s, 1H), 5.00-4.92 (m, 1H), 4.53 (d, J=19.5 Hz, 1H), 4.30-4.17 (m, 4H), 2.72-2.61 (m, 1H), 2.38-2.28 (m, 1H), 2.19 (q, J=10.3 Hz, 1H), 2.05-1.98 (m, 1H), 1.78-1.64 (m, 3H), 1.60-1.42 (m, 4H), 0.87 (s, 3H).

Example 34: N-(3-((4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)phenyl)thio)phenyl)-3-(2-(2-(2,5-dioxo-2,5-dihydro-1H-pyrrol-1-yl)ethoxy)ethoxy)propanamide

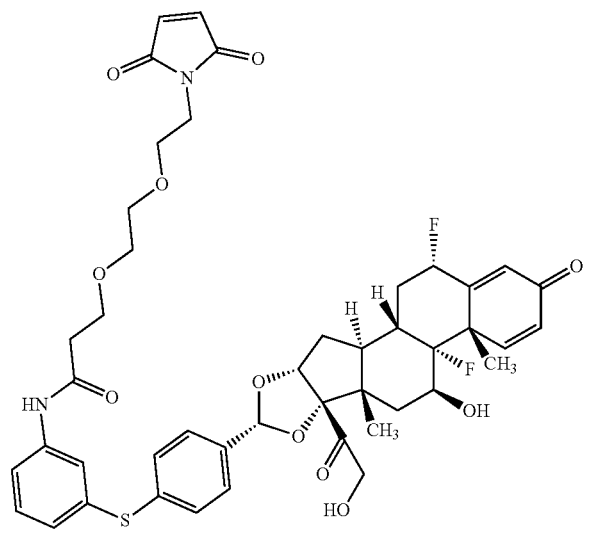 [SMILES: C[C@]12C=CC(=O)C=C1[C@@H](F)C[C@H]1[C@@H]3C[C@H]4O[C@@H](c5ccc(Sc6cccc(NC(=O)CCOCCOCCN7C(=O)C=CC7=O)c6)cc5)O[C@@]4(C(=O)CO)[C@@]3(C)C[C@H](O)[C@@]12F]

Prepared as described in example 24 from 3-(2-(2-(2,5-dioxo-2,5-dihydro-1H-pyrrol-1-yl)ethoxy)ethoxy)propanoic acid. Purified by reverse phase HPLC (Method q, linear gradient 40-75%). LCMS (Method c, Table 7) $R_t$=0.95 min; MS m/z=863.9 (M+H)$^+$; $^1$H NMR (400 MHz, DMSO-d6/D$_2$O, Temp=27° C.) δ 7.71-7.66 (m, 1H), 7.55-7.51 (m, 1H), 7.44-7.38 (m, 2H), 7.36-7.25 (m, 4H), 7.08-7.03 (m, 1H), 6.91 (s, 2H), 6.31 (dd, J=10.1, 1.9 Hz, 1H), 6.14 (s, 1H), 5.72-5.55 (m, 1H), 5.47 (s, 1H), 4.98-4.94 (m, 1H), 4.53 (d, J=19.4 Hz, 1H), 4.27-4.14 (m, 2H), 3.63 (t, J=6.1 Hz, 2H), 3.53-3.43 (m, 8H), 2.72-2.61 (m, 1H), 2.48 (t, J=6.2 Hz, 2H), 2.35-2.24 (m, 1H), 2.20 (q, J=10.4 Hz, 1H), 2.05-1.96 (m, 1H), 1.76-1.65 (m, 3H), 1.57-1.41 (m, 4H), 0.87 (s, 3H).

Example 34A: Synthesis of 3-(2,5-dioxo-2,5-dihydro-1H-pyrrol-1-yl)-N-((S)-1-(((S)-1-((3-(4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)propanamide Step 1: Synthesis of (S)-2-amino-N—((S)-1-((3-(4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)propanamide

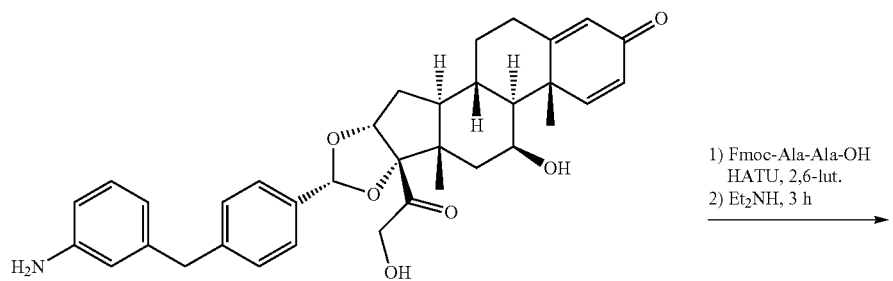

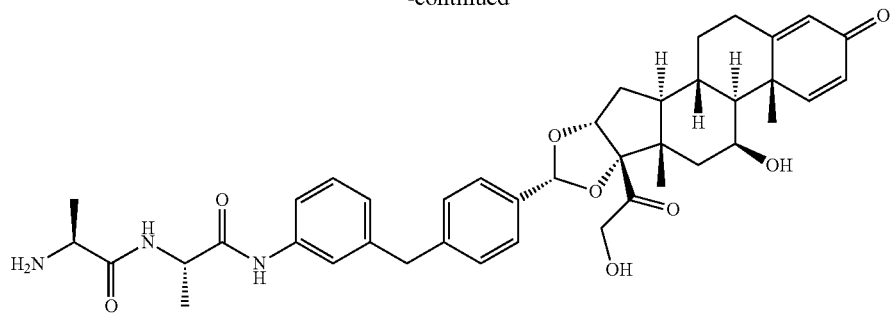

HATU (601 mg, 1.580 mmol) and 2,6-lutidine (0.37 mL, 3.16 mmol) were added to a 0° C. solution of (S)-2-((S)-2-((((9H-fluoren-9-yl)methoxy)carbonyl)amino)propanamido)propanoic acid (765 mg, 2.00 mmol), (6aR,6bS,7S,8aS,8bS,10R,11aR,12aS,12bS)-10-(4-(3-aminobenzyl)phenyl)-7-hydroxy-8b-(2-hydroxyacetyl)-6a,8a-dimethyl-6a,6b,7,8,8a,8b,11a,12,12a,12b-decahydro-1H-naphtho[2',1':4,5]indeno[1,2-d][1,3]dioxol-4(2H)-one (600 mg, 1.053 mmol) in DCM (6 mL) and DMF (12 mL). After 30 min, the mixture was warmed to room temperature and stirred overnight. Diethylamine (2.18 mL, 21.06 mmol) was added to the reaction mixture, and stirring continued at room temp for 3 h, whereupon volatile solvents were removed under reduced pressure. The residue was dissolved in 1:1 DMSO:MeOH (12 mL) and purified by reverse phase HPLC on a Phenomenex C18(2) 10 micron column (250×50 mm column). A gradient of MeCN (A) and 0.1% TFA in water (B) was used, at a flow rate of 90 mL/min (0-5.0 min 15% A, 5.0-20 min linear gradient 15-85% A, hold 5 min). Combined product fractions were lyophilized to give the title compound as an off-white solid (447 mg, 0.628 mmol, 60% yield). LC-MS (Method r, Table 7) Rt=0.78 min, m/z=711.9 [M+H]. $^1$H NMR (501 MHz, DMSO-$d_6$) δ 10.03 (s, 1H), 8.63 (d, J=7.2 Hz, 1H), 8.07 (d, J=5.4 Hz, 3H), 7.44-7.38 (m, 2H), 7.38-7.34 (m, 2H), 7.29 (d, J=10.1 Hz, 1H), 7.23-7.16 (m, 3H), 6.90 (dt, J=7.7, 1.3 Hz, 1H), 6.14 (dd, J=10.1, 1.9 Hz, 1H), 5.90 (t, J=1.6 Hz, 1H), 5.38 (s, 1H), 4.90 (d, J=5.3 Hz, 1H), 4.52-4.37 (m, 2H), 4.27 (q, J=3.3 Hz, 1H), 4.16 (d, J=19.4 Hz, 1H), 3.87 (s, 2H), 2.58-2.49 (m, 1H), 2.28 (ddd, J=13.4, 4.5, 2.1 Hz, 1H), 2.09 (dtd, J=17.0, 10.6, 5.0 Hz, 1H), 2.00 (dd, J=12.2, 5.7 Hz, 1H), 1.78-1.54 (m, 5H), 1.37 (s, 3H), 1.35 (s, 3H), 1.30 (d, J=7.1 Hz, 3H), 1.01 (ddd, J=22.1, 11.9, 4.2 Hz, 2H), 0.84 (s, 3H).

Step 2: Synthesis of 3-(2,5-dioxo-2,5-dihydro-1H-pyrrol-1-yl)-N—((S)-1-(((S)-1-((3-(4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)propanamide

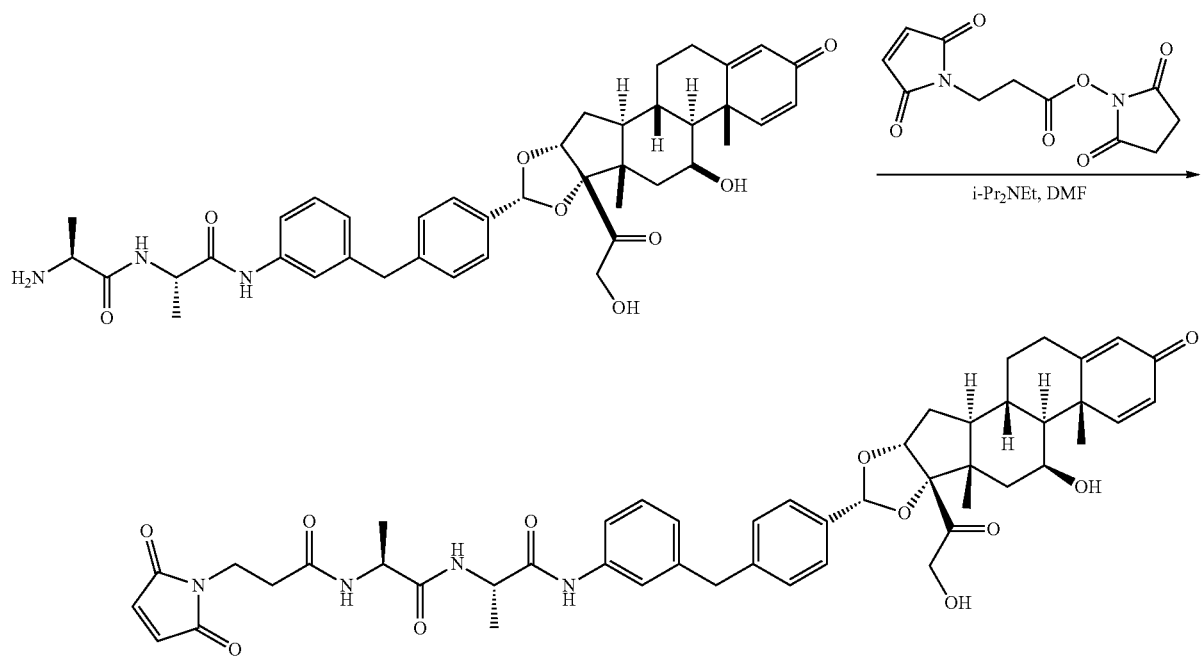

Cpd. No. 88

N,N-Diisopropylethylamine (0.33 mL, 1.875 mmol) was added to a room temperature solution of N-succinimidyl 3-maleimidopropionate (250 mg, 0.938 mmol) and (S)-2-amino-N—((S)-1-((3-(4-(((6aR,6bS,7S,8aS,8bS,10R,11aR, 12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)propanamide (445 mg, 0.625 mmol) in DMF (12 mL). After 30 min at room temperature, the volatile solvents were removed under reduced pressure. The residue was diluted with 1:1 DMSO:MeOH (12 mL) and purified by reverse phase HPLC on a Phenomenex C18(2) 10 micron column (250×50 mm column). A gradient of MeCN (A) and 0.1% TFA in water (B) was used, at a flow rate of 90 mL/min (0-5.0 min 25% A, 5.0-20 min linear gradient 25-90% A, hold 5 min). Combined product fractions were lyophilized to give the title compound as an off-white solid (295.1 mg, 0.342 mmol, 55% yield). LC-MS (Method r, Table 7) Rt=0.85 min, m/z=863.4 [M+H]. $^1$H NMR (501 MHz, DMSO-d$_6$) δ 9.71 (s, 1H), 8.17 (d, J=7.0 Hz, 1H), 8.03 (d, J=7.3 Hz, 1H), 7.43 (dd, J=7.8, 1.1 Hz, 2H), 7.38-7.32 (m, 2H), 7.29 (d, J=10.1 Hz, 1H), 7.22-7.15 (m, 3H), 6.96 (s, 2H), 6.88 (dt, J=7.8, 1.3 Hz, 1H), 6.13 (dd, J=10.1, 1.9 Hz, 1H), 5.90 (t, J=1.6 Hz, 1H), 5.37 (s, 1H), 4.90 (d, J=5.4 Hz, 1H), 4.48 (d, J=19.4 Hz, 1H), 4.32 (p, J=7.1 Hz, 1H), 4.27 (q, J=3.3 Hz, 1H), 4.21 (p, J=7.1 Hz, 1H), 4.16 (d, J=19.4 Hz, 1H), 3.87 (s, 2H), 3.59 (t, J=7.3 Hz, 2H), 2.57-2.49 (m, 1H), 2.38 (dd, J=8.0, 6.6 Hz, 2H), 2.32-2.24 (m, 1H), 2.15-2.04 (m, 1H), 2.04-1.95 (m, 1H), 1.80-1.54 (m, 5H), 1.37 (s, 3H), 1.26 (d, J=7.1 Hz, 3H), 1.15 (d, J=7.1 Hz, 3H), 1.02 (ddd, J=21.2, 12.1, 4.2 Hz, 2H), 0.84 (s, 3H).

Example 35

The following compounds were prepared using the methods described above.

| Cpd. No. | Structure |
|---|---|
| 70 | 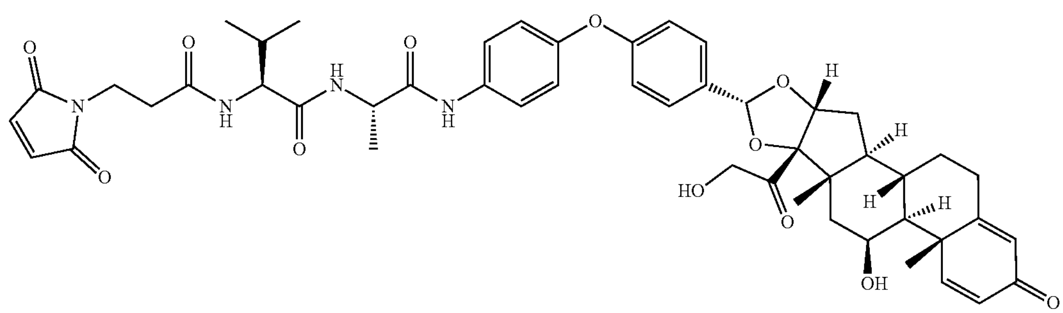 |
| 71 | 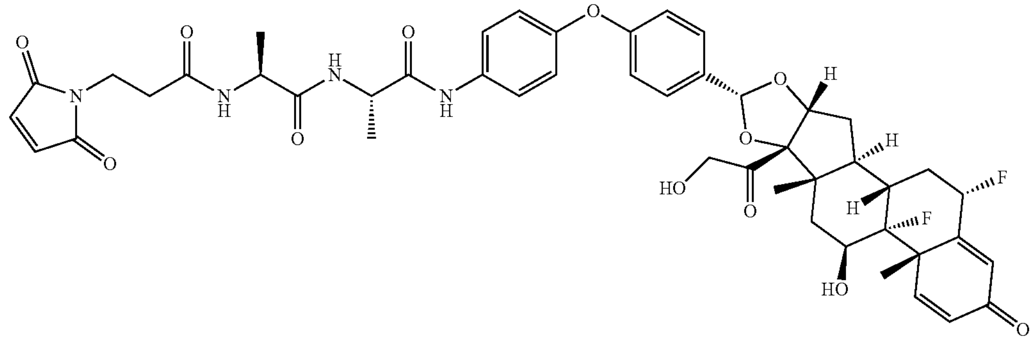 |

| Cpd. No. | Structure |
|---|---|
| 72 | |
| 72 | |
| 73 | 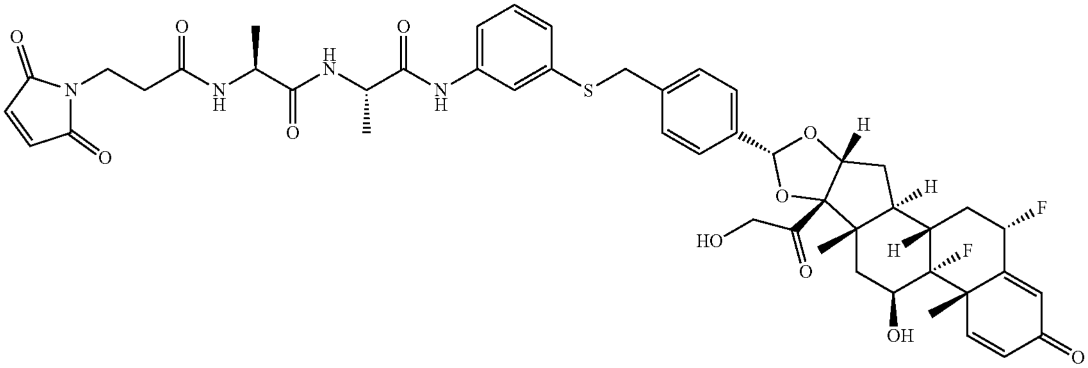 |

| Cpd. No. | Structure |
|---|---|
| 74 | 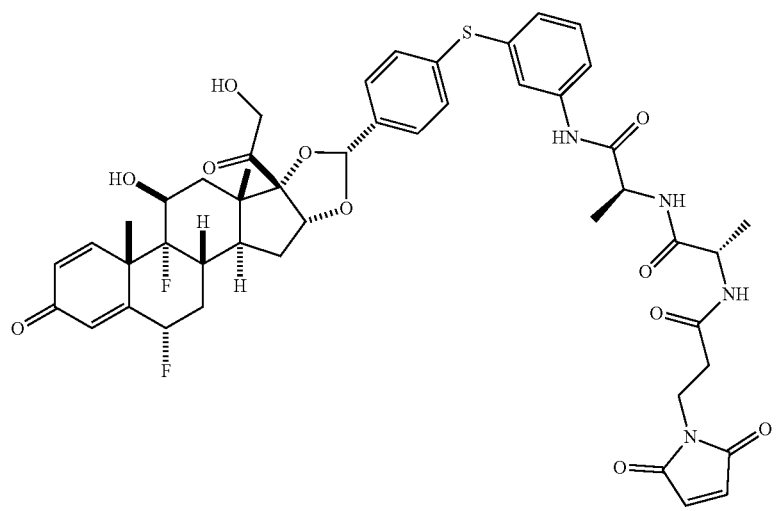 |
| 75 | 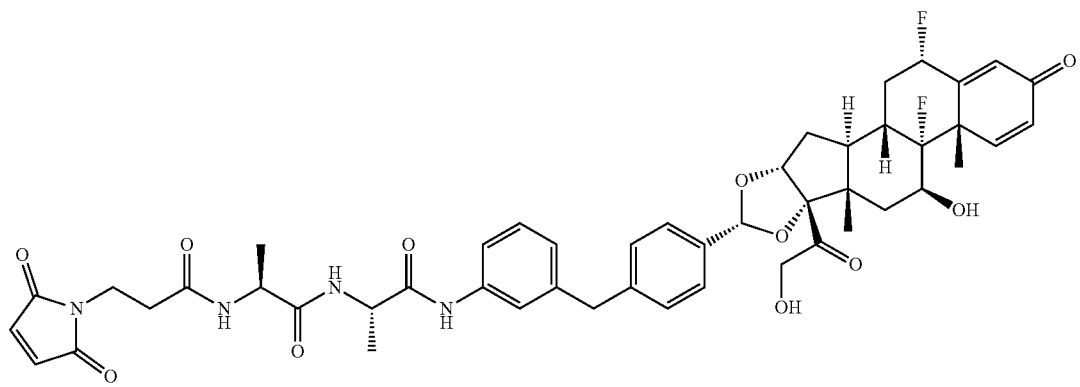 |
| 76 | 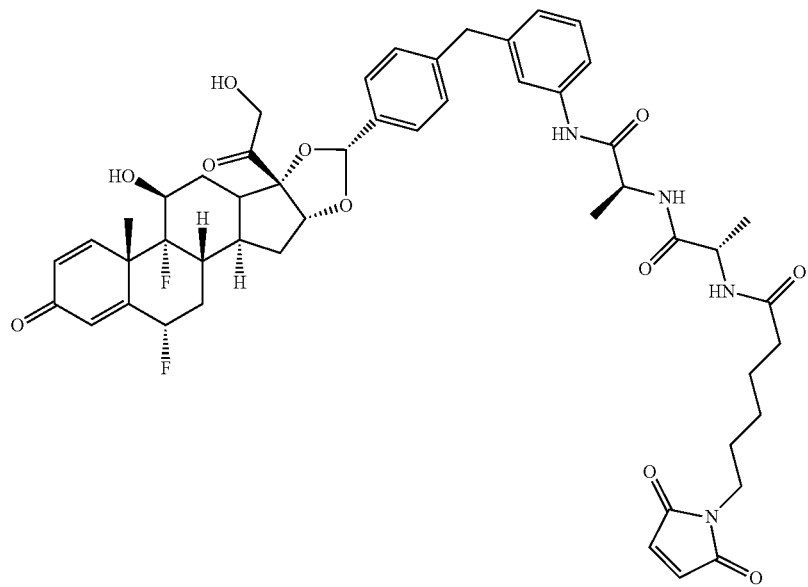 |

| Cpd. No. | Structure |
|---|---|
| 77 | (structure shown) 2 TFA |
| 78 | (structure shown) |
| 79 | (structure shown) |
| 80 | (structure shown) |

| Cpd. No. | Structure |
|---|---|
| 81 | 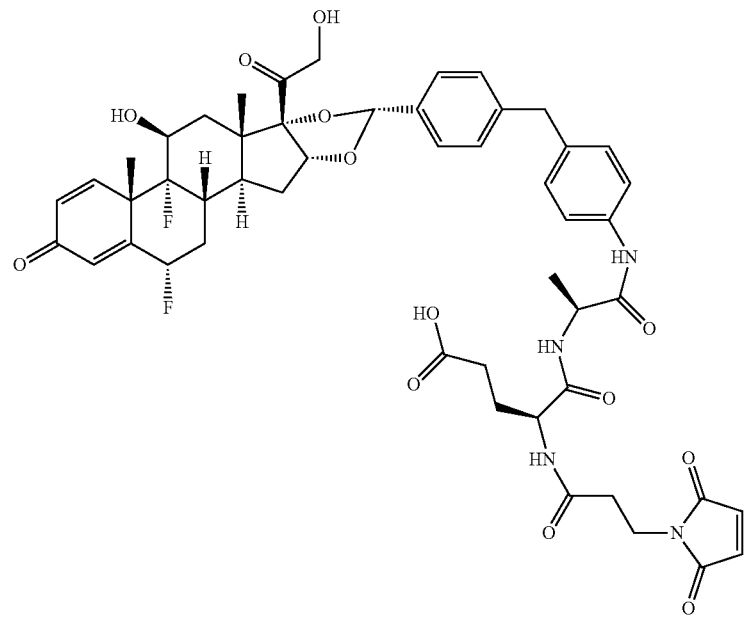 |
| 82 | 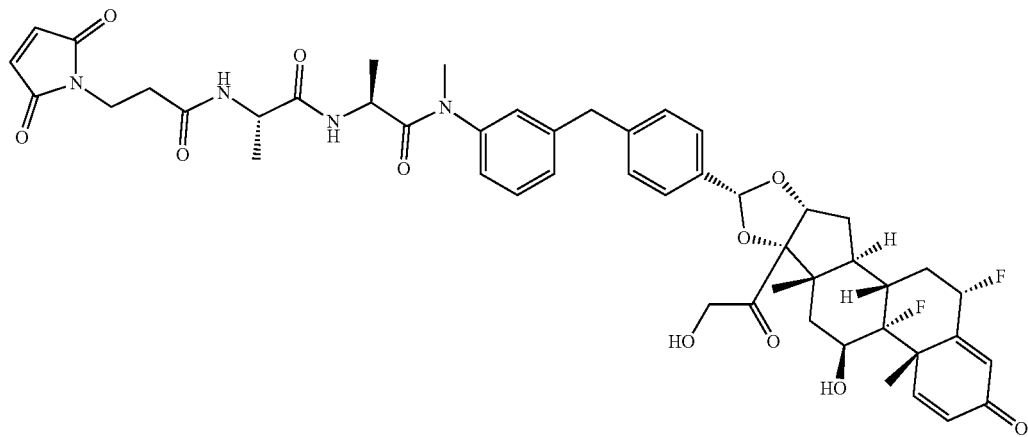 |
| 83 | 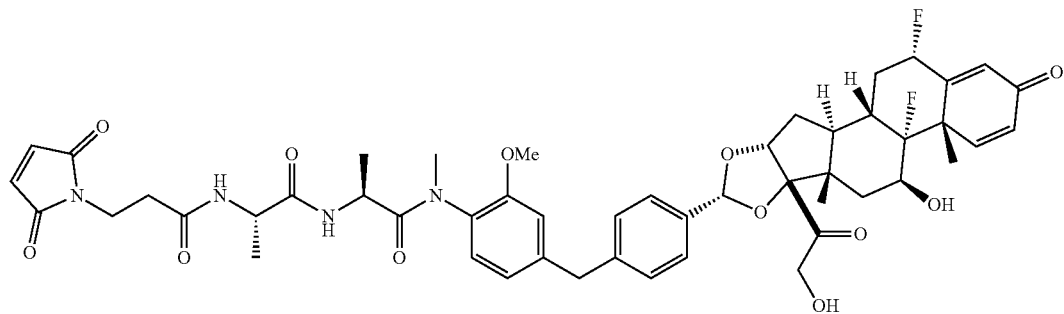 |

| Cpd. No. | Structure |
|---|---|
| 84 | 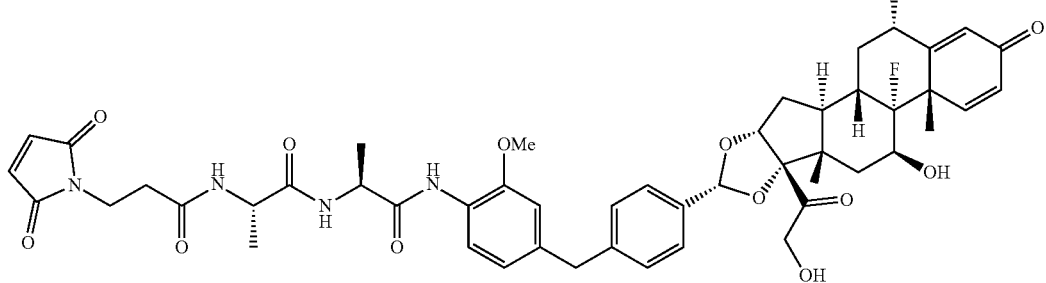 |
| 85 | 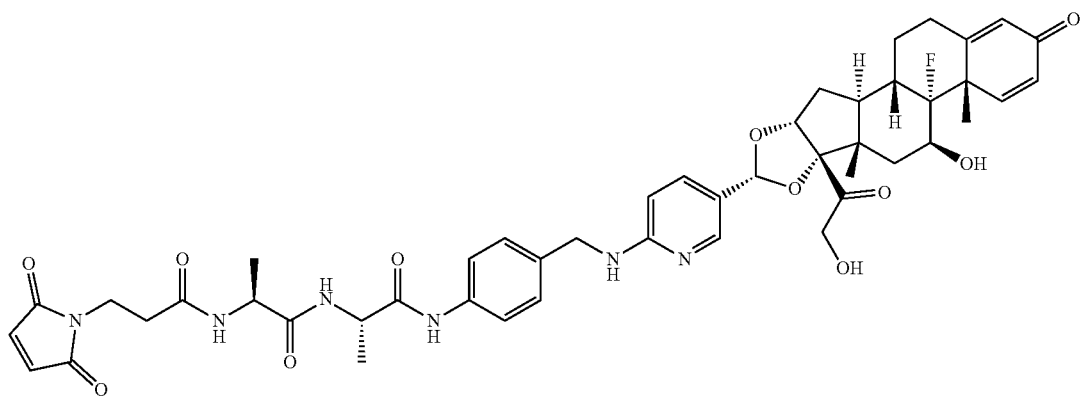 |
| 86 | 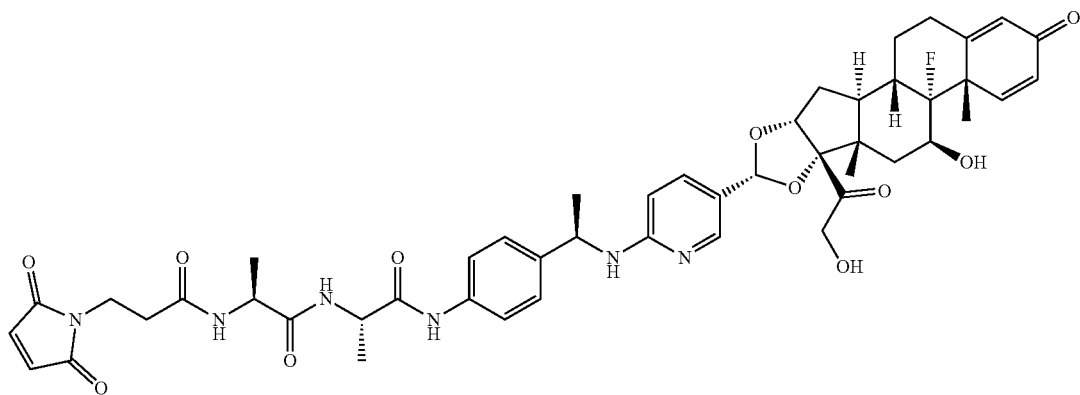 |
| 87 | 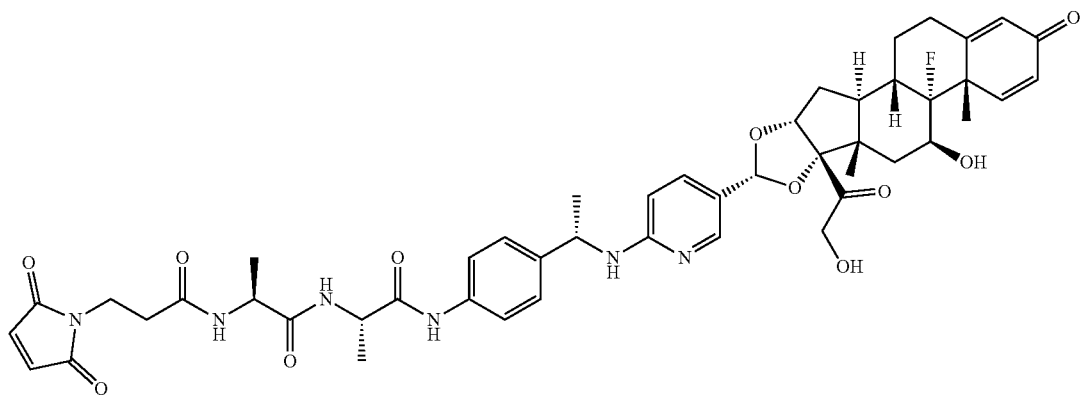 |

| Cpd. No. | Structure |
|---|---|
| 89 | 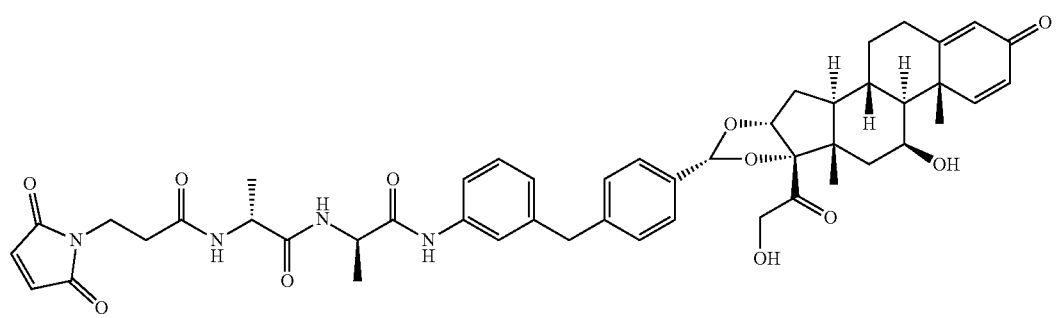 |
| 90 | 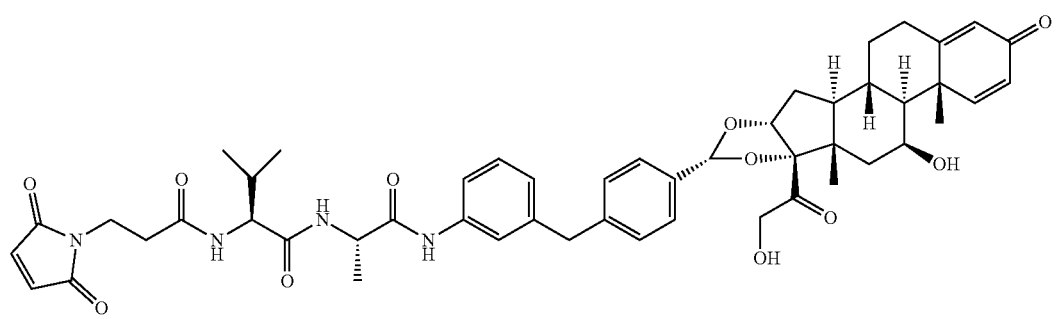 |
| 99 | 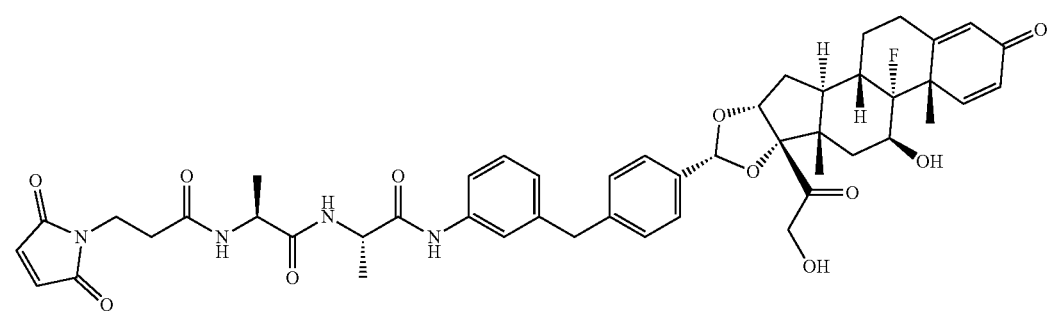 |
| 100 | 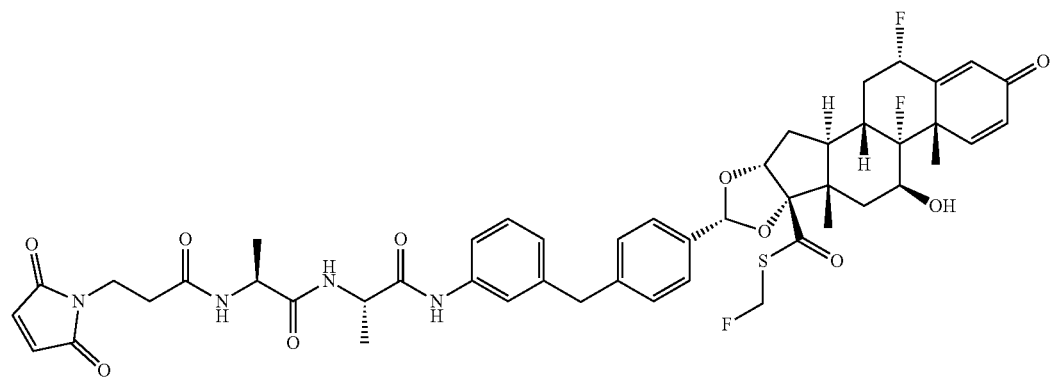 |

| Cpd. No. | Structure |
|---|---|
| 101 | 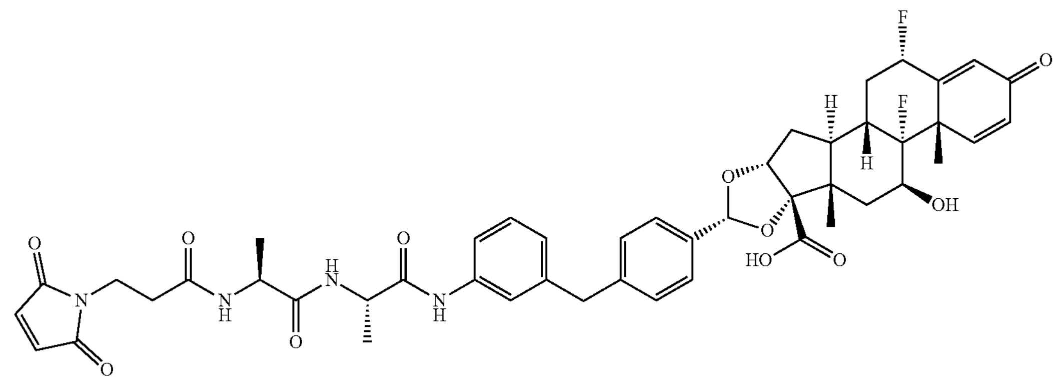 |
| 102 | 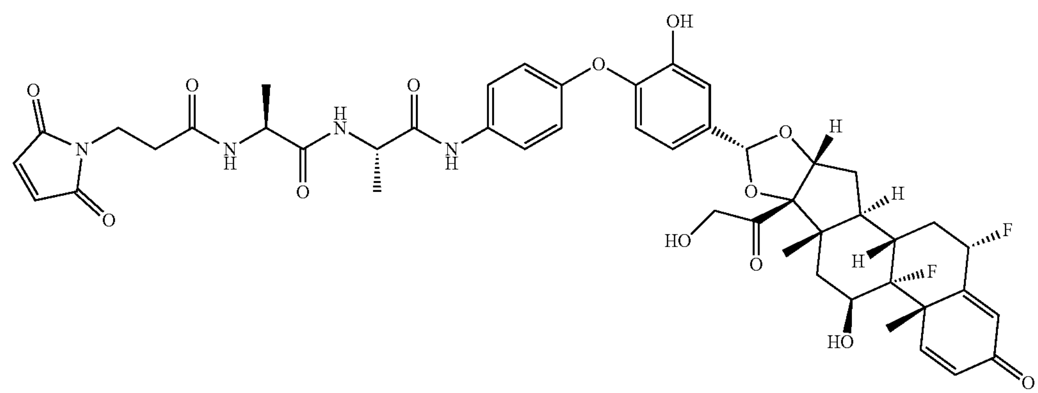 |
| 103 | 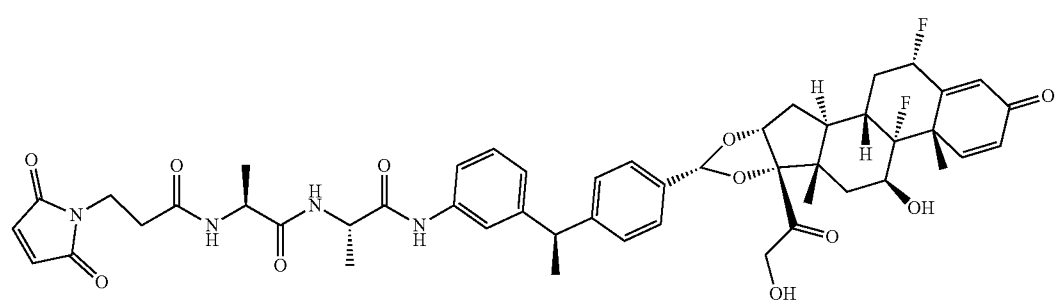 |
| 104 | 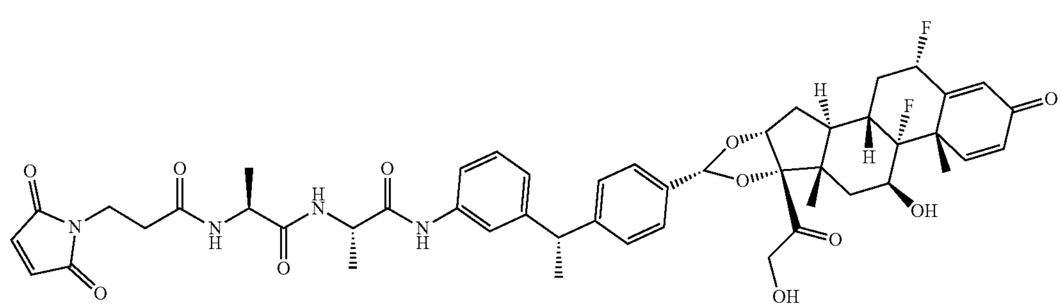 |

| Cpd. No. | Structure |
|---|---|
| 105 | 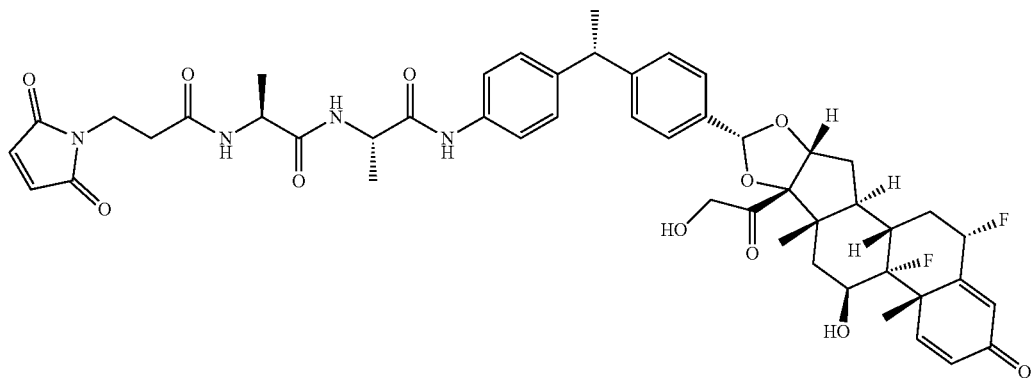 |
| 106 | 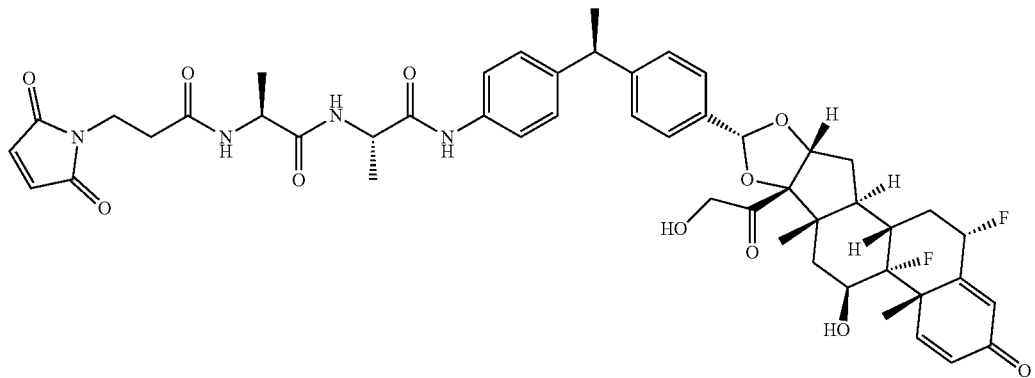 |
| 107 | 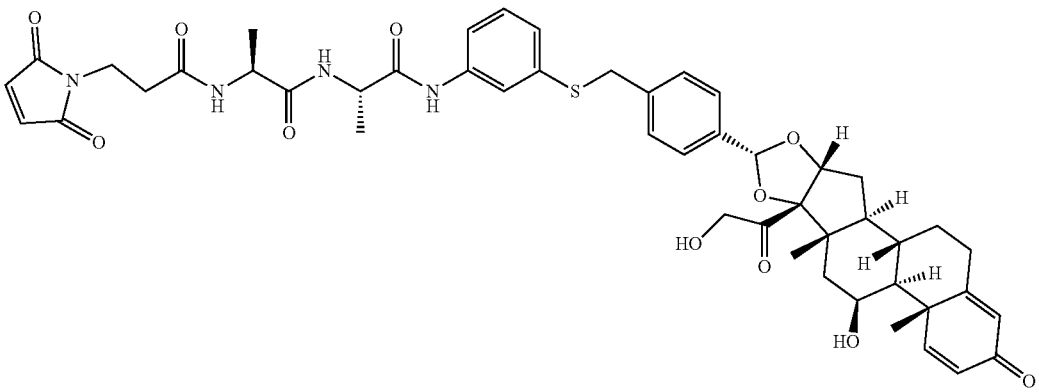 |
| 108 | 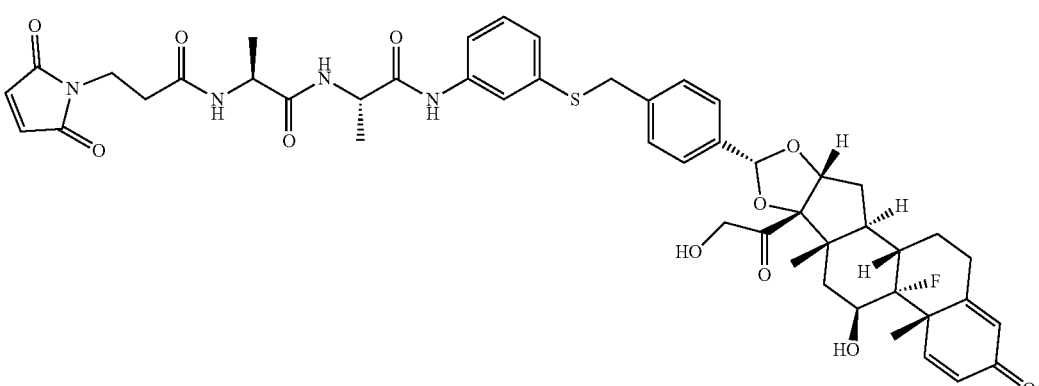 |

| Cpd. No. | Structure |
|---|---|
| 109 | 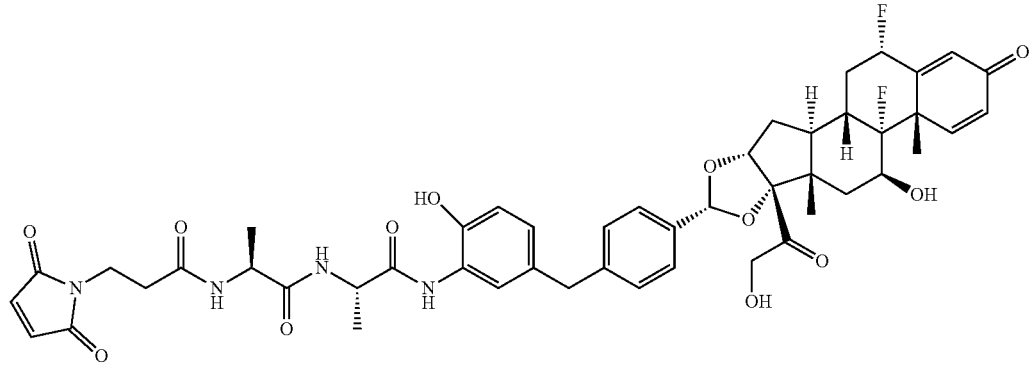 |
| 110 | 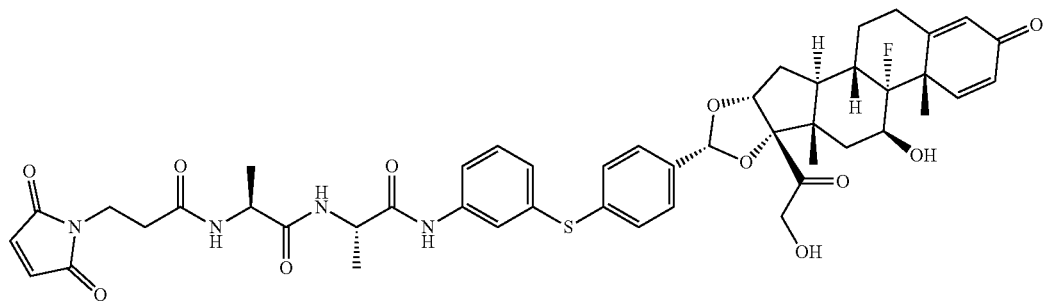 |
| 111 | 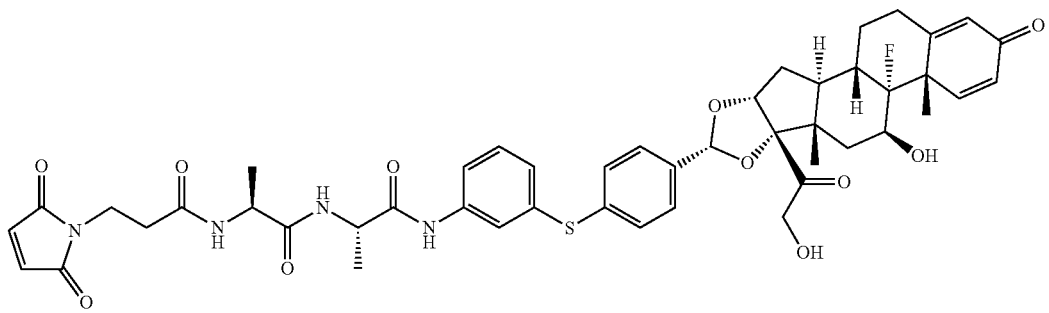 |
| 112 | 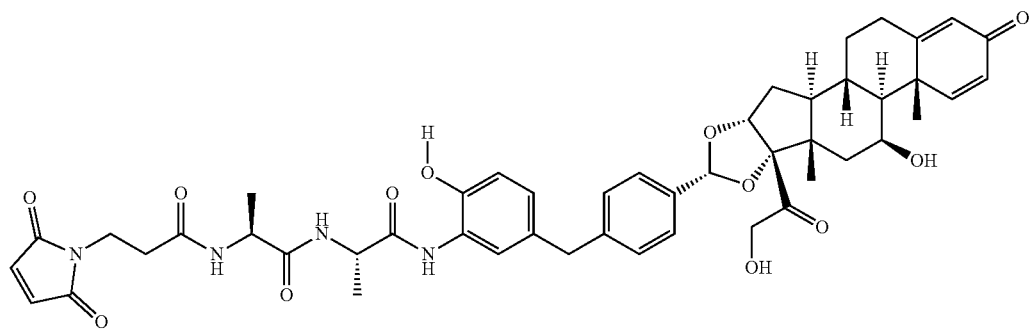 |

-continued
| Cpd. No. | Structure |
|---|---|
| 113 | 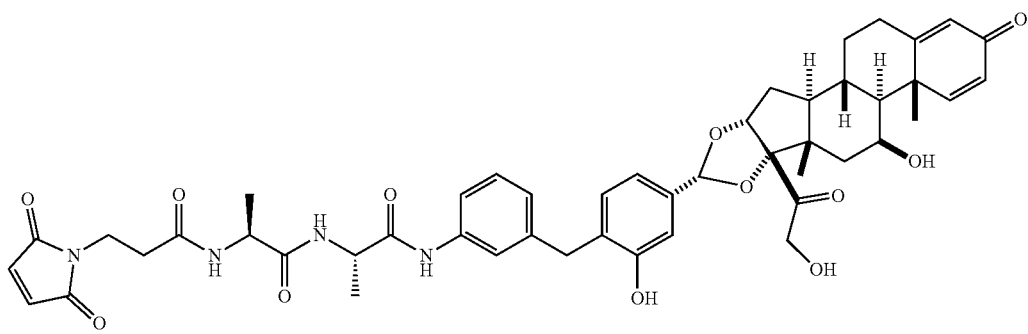 |
| 114 | 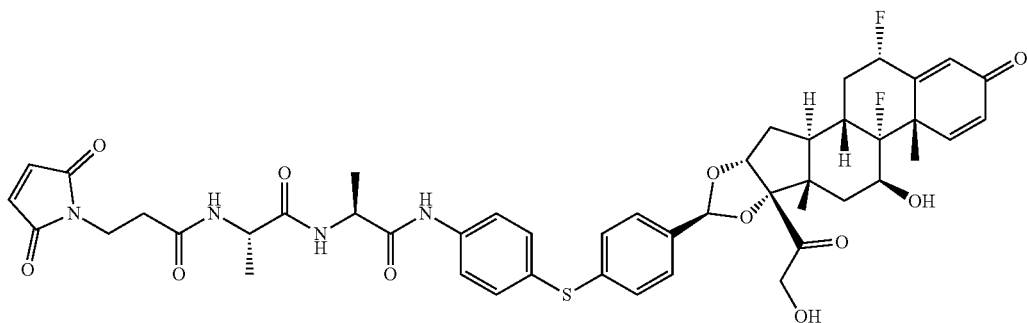 |
| 115 | 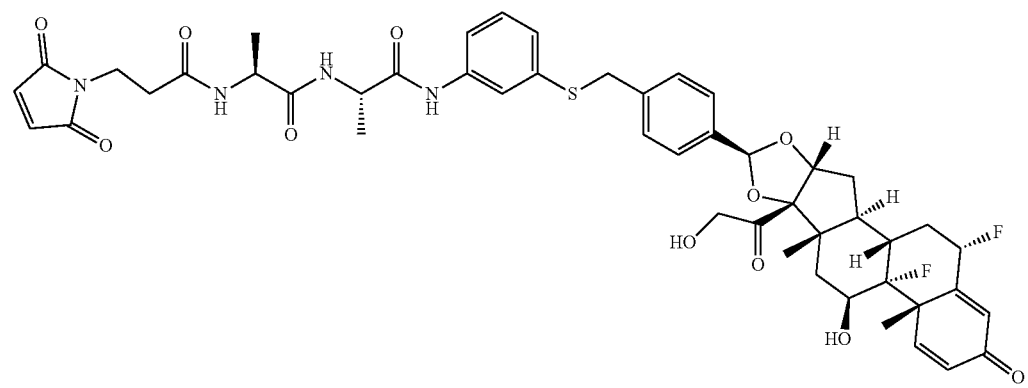 |
| 116 | 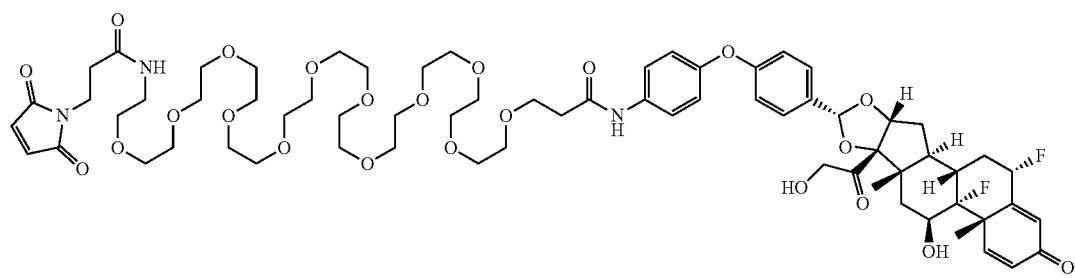 |

-continued
| Cpd. No. | Structure |
|---|---|
| 117 | 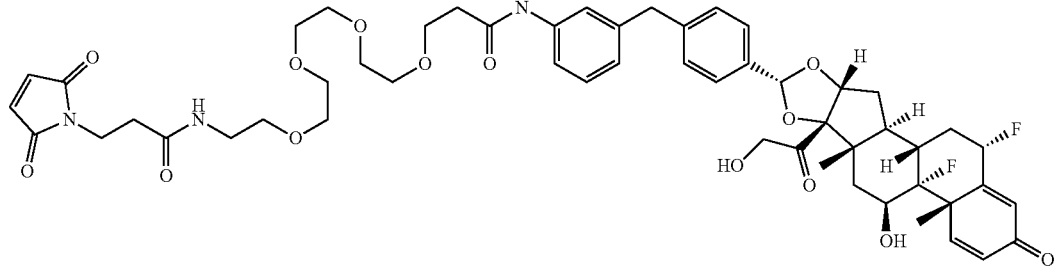 |
| 118 | 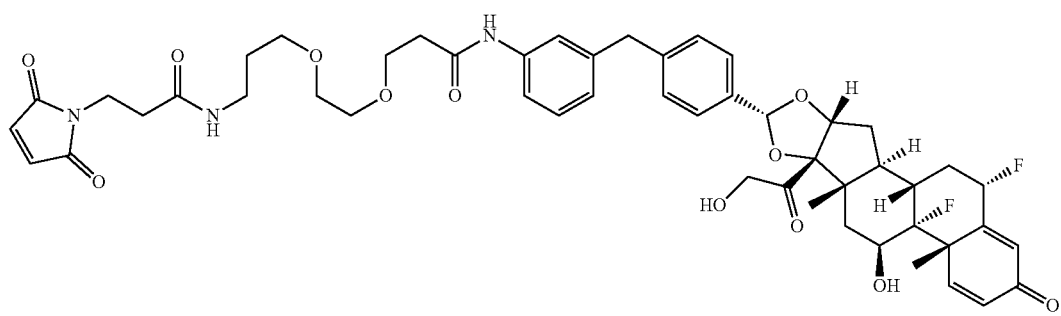 |
| 119 | 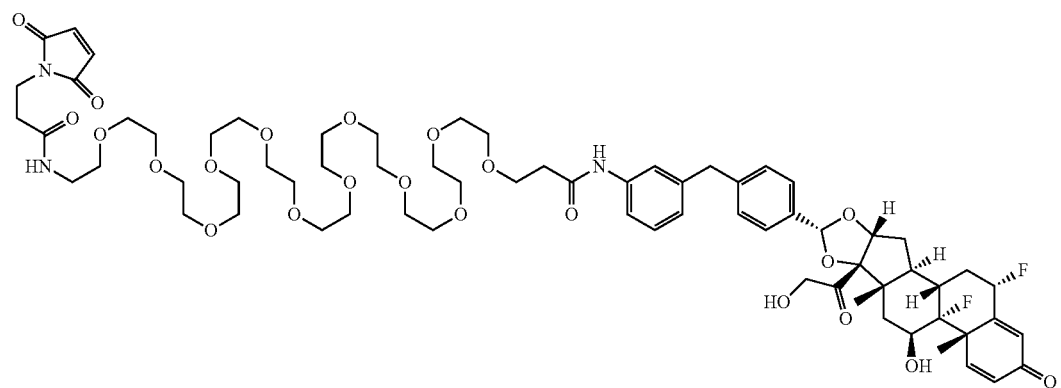 |
| 120 | 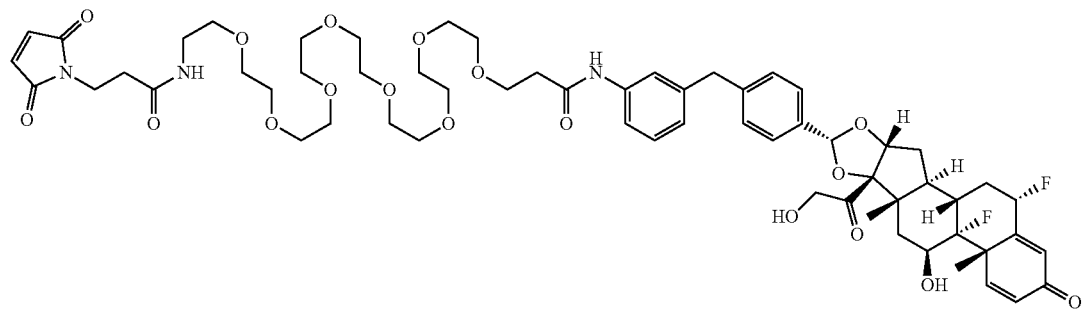 |

| Cpd. No. | Structure |
|---|---|
| 121 | 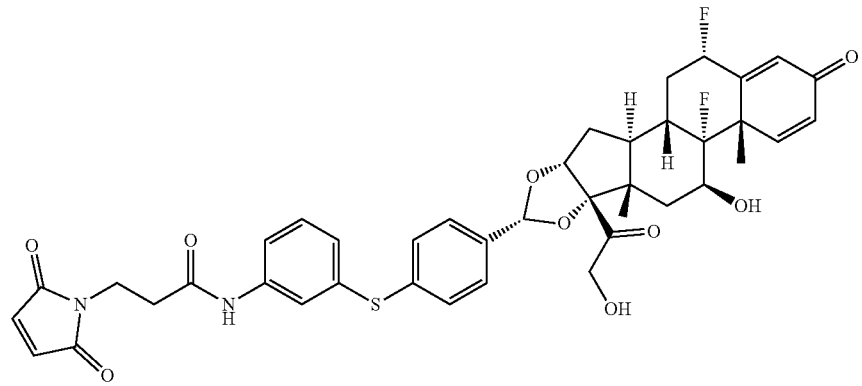 |
| 122 | 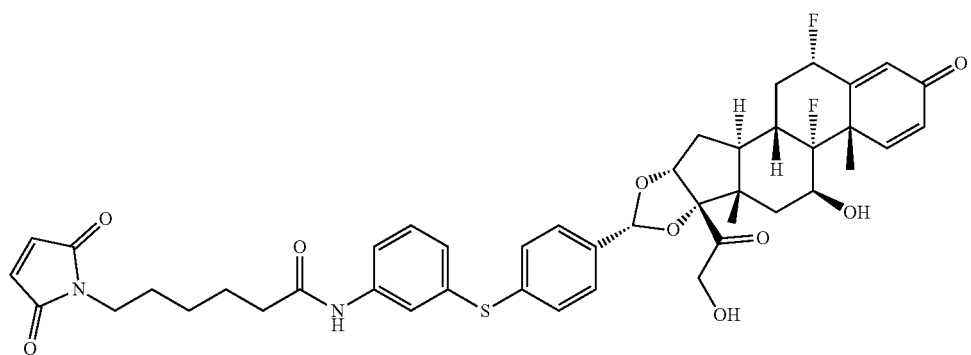 |
| 123 | 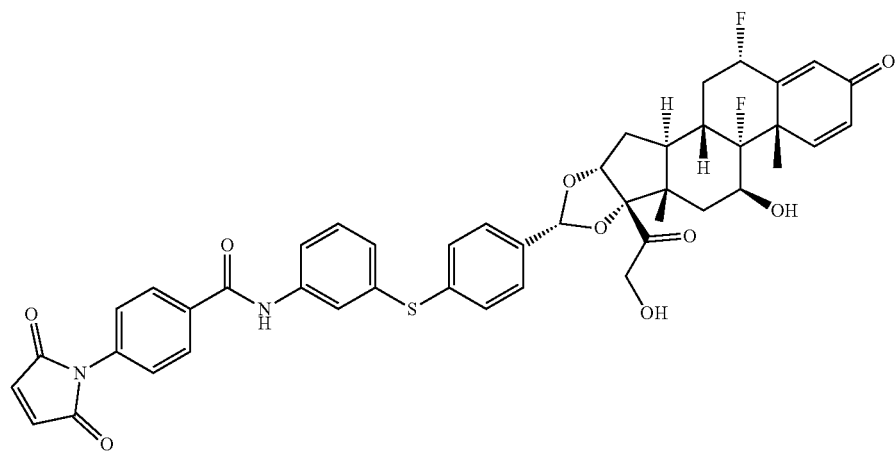 |

-continued
| Cpd. No. | Structure |
|---|---|
| 124 | 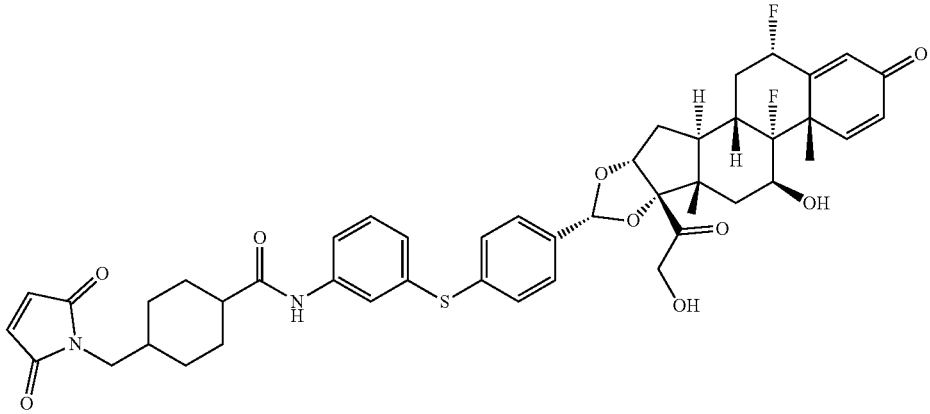 |
| 125 | 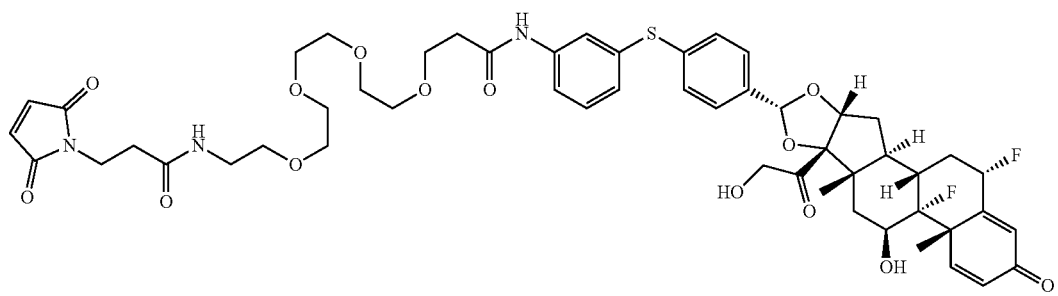 |
| 126 | 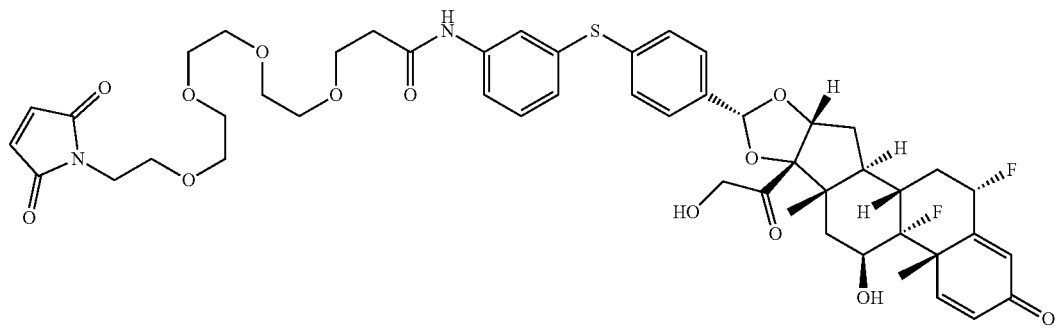 |
| 127 | 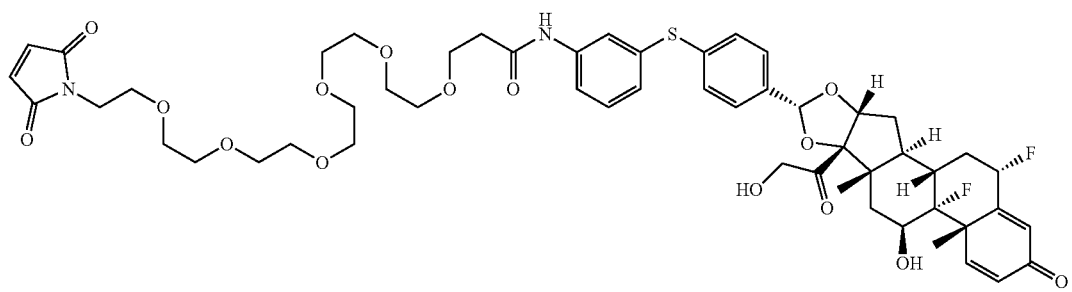 |

| Cpd. No. | Structure |
|---|---|
| 128 | 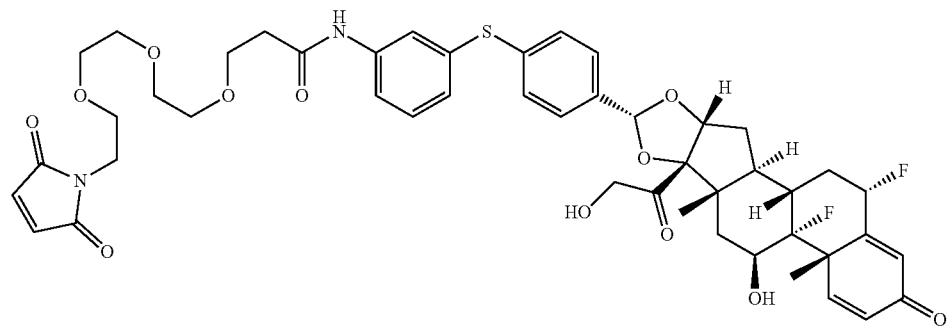 |
| 129 | 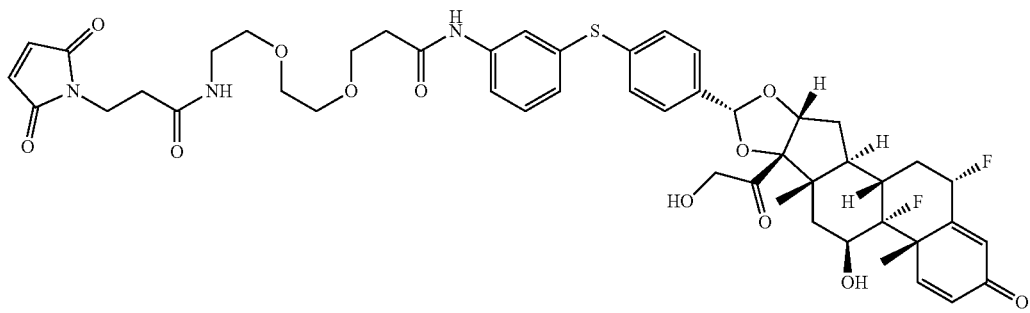 |
| 130 | 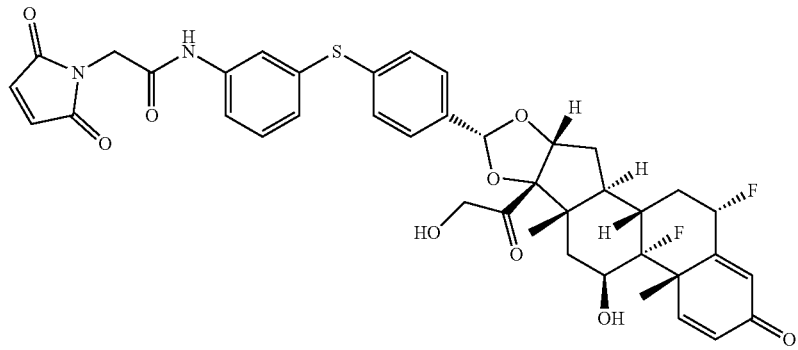 |
| 131 | 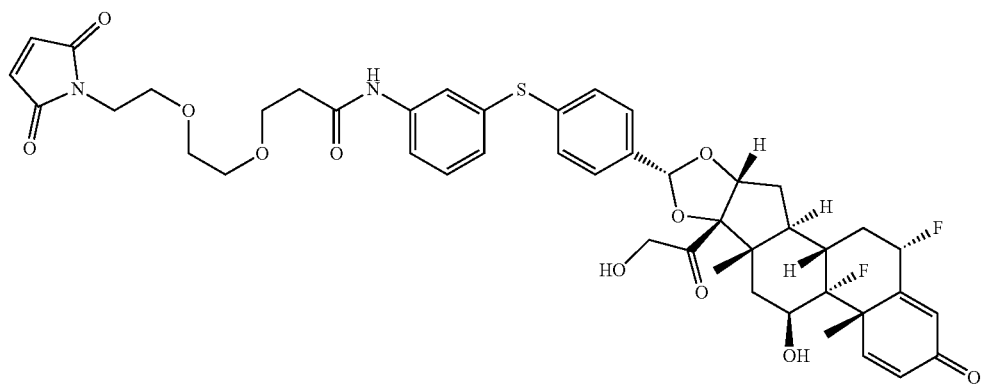 |

| Cpd. No. | Structure |
|---|---|
| 132 | 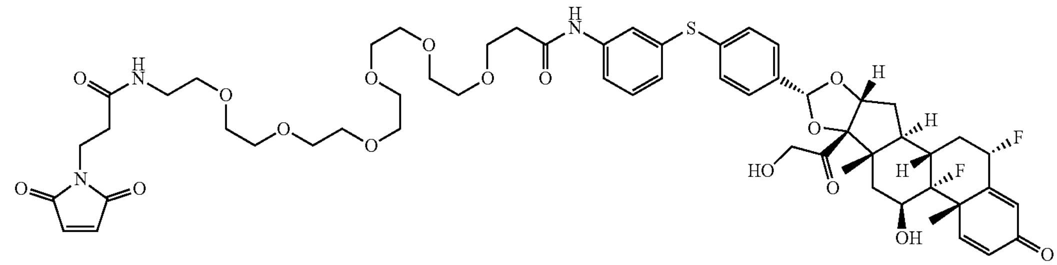 |
| 133 | 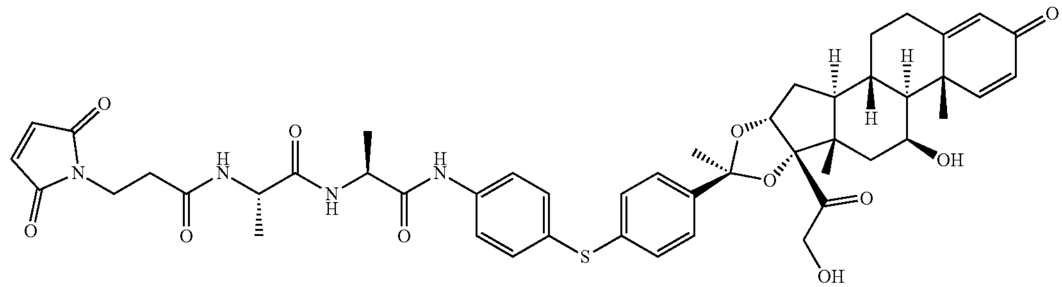 |

| Cpd. No. | LC-MS Data | ¹H NMR Data |
|---|---|---|
| 70 | Method a LC-MS, Table 7 $R_t$ = 1.28 min; m/z = 894.0 [M + H⁺] | ¹H NMR (DMSO-d₆) δ: 0.79-0.87 (m, 10H), 0.95-1.13 (m, 1H), 1.29 (d, J = 7.1 Hz, 3H), 1.38 (s, 3H), 1.57-1.76 (m, 2H), 1.76 (s, 2H), 1.90-2.01 (m, 2H), 2.05 (s, 2H), 2.28 (s, 2H), 2.43 (dd, J = 14.4, 7.0 Hz, 2H), 3.58 (p, J = 6.8 Hz, 2H), 4.11 (dd, J = 8.4, 6.7 Hz, 1H), 4.16 (d, J = 19.4 Hz, 1H), 4.28 (s, 1H), 4.36 (q, J = 6.7 Hz, 1H), 4.49 (d, J = 19.4 Hz, 1H), 4.75 (s, 1H), 4.90 (d, J = 5.1 Hz, 1H), 5.40 (s, 1H), 5.90 (s, 1H), 6.14 (dd, J = 10.1, 1.9 Hz, 1H), 6.89-7.02 (m, 6H), 7.29 (d, J = 10.1 Hz, 1H), 7.42 (d, J = 8.7 Hz, 2H), 7.56-7.63 (m, 2H), 7.98 (d, J = 8.4 Hz, 1H), 8.13 (d, J = 6.9 Hz, 1H), 9.86 (s, 1H) |
| 71 | Method r, Table 7 $R_t$ = 0.79 min; m/z = 900.91 [M + H⁺] | ¹H NMR (DMSO-d₆) δ: 0.85 (s, 3H), 1.16 (d, J = 7.1 Hz, 3H), 1.29 (d, J = 7.1 Hz, 3H), 1.48 (s, 3H), 1.53 (d, J = 12.6 Hz, 1H), 1.60-1.77 (m, 3H), 1.98-2.09 (m, 1H), 2.24 (dd, J = 21.2, 8.6 Hz, 2H), 2.39 (dd, J = 8.0, 6.5 Hz, 2H), 2.53-2.72 (m, 1H), 3.59 (dd, J = 8.1, 6.5 Hz, 2H), 4.13-4.27 (m, 2H), 4.34 (p, J = 7.1 Hz, 1H), 4.51 (dd, J = 19.5, 6.4 Hz, 1H), 4.93 (d, J = 5.0 Hz, 1H), 5.07 (t, J = 6.0 Hz, 1H), 5.45 (s, 1H), 5.50 (dd, J = 4.5, 1.7 Hz, 1H), 5.53-5.75 (m, 1H), 6.07-6.12 (m, 1H), 6.27 (dd, J = 10.2, 1.9 Hz, 1H), 6.92-7.00 (m, 6H), 7.24 (dd, J = 10.2, 1.4 Hz, 1H), 7.36-7.43 (m, 2H), 7.58-7.66 (m, 2H), 8.08 (d, J = 7.3 Hz, 1H), 8.18 (d, J = 7.0 Hz, 1H), 9.83 (s, 1H) |
| 72 | Method m LC-MS, Table 7 $R_t$ = 1.71 min; m/z = 917 [M + H⁺] | ¹H NMR (MeOH-d₄) δ: 1.00 (s, 3H), 1.37 (dd, J = 12.2, 7.1 Hz, 3H), 1.48 (t, J = 7.2 Hz, 3H), 1.59 (s, 4H), 1.69 (dd, J = 27.0, 13.1 Hz, 2H), 1.79 (dd, J = 13.7, 5.8 Hz, 2H), 2.26 (d, J = 13.6 Hz, 1H), 2.38 (d, J = 8.0 Hz, 3H), 2.56 (td, J = 12.5, 11.2, 6.8 Hz, 3H), 2.60-2.81 (m, 1H), 3.80 (dt, J = 12.7, 6.8 Hz, 2H), 4.24 (dd, J = 11.9, 7.0 Hz, 1H), 4.32 (s, 2H), 4.43-4.51 (m, 1H), 4.64 (d, J = 19.4 Hz, 1H), 5.07 (d, J = 4.6 Hz, 1H), 5.47 (s, 1H), 5.57 (d, J = 42.9 Hz, 1H), 6.27-6.38 (m, 3H), 6.73 (d, J = 3.0 Hz, 2H), 7.16-7.25 (m, 2H), 7.36 (dt, J = 16.7, 8.0 Hz, 6H), 7.70 (dd, J = 22.7, 8.4 Hz, 2H) |
| 72 | Method m LC-MS, Table 7 $R_t$ = 1.88 min; m/z = 975 [M + H⁺] | ¹H NMR (MeOH-d₄) δ: 1.00 (s, 3H), 1.49 (d, J = 7.2 Hz, 3H), 1.59 (s, 3H), 1.60-1.89 (m, 3H), 2.04 (d, J = 52.2 Hz, 1H), 2.27 (d, J = 13.5 Hz, 1H), 2.31-2.52 (m, 4H), 2.58 (t, J = 6.7 Hz, 2H), 3.81 (t, J = 6.7 Hz, 2H), 4.34 (d, J = 19.7 Hz, 3H), 4.42-4.53 (m, 1H), 4.64 (d, J = 19.4 Hz, 1H), 5.07 (d, J = 4.6 Hz, 1H), 5.47 (s, 1H), 5.58 (d, J = 40.9 Hz, 1H), 6.25-6.47 (m, 2H), 6.76 (s, 2H), 7.20 (d, J = 8.1 Hz, 2H), 7.28-7.44 (m, 5H), 7.67 (d, J = 8.5 Hz, 2H) |
| 73 | Method a LC-MS, Table 7 $R_t$ = 2.08 min; m/z = 931.30 [M + H⁺] | ¹H NMR (DMSO-d₆) δ: 0.84 (s, 3H), 1.16 (d, J = 7.1 Hz, 3H), 1.27 (d, J = 7.1 Hz, 3H), 1.48 (s, 4H), 1.59-1.77 (m, 3H), 1.96-2.08 (m, 1H), 2.13-2.33 (m, 2H), 2.39 (dd, J = 7.9, 6.7 Hz, 2H), 2.52 (s, 1H), 2.53-2.72 (m, 1H), 3.59 (t, J = 7.3 Hz, 2H), 4.08-4.26 (m, 5H), 4.32 (p, J = 7.0 Hz, 1H), 4.50 (d, J = 19.4 Hz, 1H), 4.93 (d, J = 5.0 Hz, 1H), 5.44 (s, 1H), |

| Cpd. No. | LC-MS Data | $^1$H NMR Data |
|---|---|---|
| | | 5.45-5.51 (m, 1H), 5.63 (dt, J = 48.4, 9.3 Hz, 1H), 6.11 (d, J = 2.1 Hz, 1H), 6.28 (dd, J = 10.2, 1.9 Hz, 1H), 6.93-7.02 (m, 3H), 7.19 (t, J = 8.0 Hz, 1H), 7.24 (dd, J = 10.1, 1.4 Hz, 1H), 7.30-7.44 (m, 5H), 7.65 (t, J = 1.9 Hz, 1H), 8.05 (d, J = 7.2 Hz, 1H), 8.16 (d, J = 7.0 Hz, 1H), 9.77 (s, 1H) |
| 74 | Method r, Table 7 $R_t$ = 0.82 min; m/z = 918.60 [M + H$^+$] | $^1$H NMR (DMSO-d$_6$) δ: 0.84 (s, 3H), 1.15 (d, J = 7.1 Hz, 3H), 1.26 (d, J = 7.2 Hz, 4H), 1.48 (s, 4H), 1.59-1.79 (m, 3H), 1.94-2.10 (m, 1H), 2.10-2.31 (m, 2H), 2.37 (t, J = 7.3 Hz, 2H), 2.51-2.77 (m, 1H), 3.58 (t, J = 7.3 Hz, 2H), 4.10-4.25 (m, 3H), 4.31 (p, J = 7.1 Hz, 1H), 4.51 (d, J = 19.4 Hz, 1H), 4.94 (d, J = 5.0 Hz, 1H), 5.45 (s, 1H), 5.50 (s, 1H), 5.62 (dt, J = 48.6, 9.4 Hz, 1H), 6.10 (s, 1H), 6.27 (dd, J = 10.1, 1.9 Hz, 1H), 6.96 (s, 2H), 7.02 (dd, J = 7.3, 1.7 Hz, 1H), 7.20-7.34 (m, 4H), 7.40 (d, J = 8.3 Hz, 2H), 7.58 (dd, J = 7.9, 2.1 Hz, 1H), 7.69 (d, J = 2.1 Hz, 1H), 8.07 (d, J = 7.2 Hz, 1H), 8.16 (d, J = 7.0 Hz, 1H), 9.89 (s, 1H) |
| 75 | Method r, Table 7 $R_t$ = 0.82 min; m/z = 899.87 [M + H$^+$] | $^1$H NMR (DMSO-d$_6$) δ: 0.83 (s, 3H), 1.13 (d, J = 7.1 Hz, 3H), 1.24 (d, J = 7.2 Hz, 3H), 1.46 (s, 4H), 1.57-1.77 (m, 3H), 2.01 (dt, J = 13.9, 3.7 Hz, 1H), 2.13-2.32 (m, 2H), 2.36 (dd, J = 8.0, 6.7 Hz, 2H), 2.51-2.73 (m, 1H), 3.56 (d, J = 7.3 Hz, 2H), 3.85 (s, 2H), 4.10-4.25 (m, 3H), 4.30 (p, J = 7.1 Hz, 1H), 4.47 (d, J = 19.4 Hz, 1H), 4.91 (d, J = 4.9 Hz, 1H), 5.41 (s, 1H), 5.48 (s, 1H), 5.51-5.71 (m, 1H), 6.09 (d, J = 2.0 Hz, 1H), 6.26 (dd, J = 10.2, 1.9 Hz, 1H), 6.87 (dt, J = 7.6, 1.3 Hz, 1H), 6.95 (s, 2H), 7.16 (t, J = 7.8 Hz, 1H), 7.18-7.27 (m, 3H), 7.32 (d, J = 8.1 Hz, 2H), 7.39 (d, J = 1.9 Hz, 1H), 7.43 (dd, J = 8.5, 1.9 Hz, 1H), 8.01 (d, J = 7.2 Hz, 1H), 8.14 (d, J = 7.0 Hz, 1H), 9.70 (s, 1H) |
| 76 | Method r, Table 7 $R_t$ = 1.00 min; m/z = not observed | $^1$H NMR (DMSO-d$_6$) δ: 0.88 (d, J = 7.4 Hz, 3H), 1.19 (dt, J = 33.9, 7.1 Hz, 11H), 1.35-1.63 (m, 10H), 1.61-1.85 (m, 2H), 2.06 (q, J = 7.4 Hz, 3H), 2.16-2.35 (m, 1H), 2.38 (t, J = 7.3 Hz, 1H), 3.87 (d, J = 8.1 Hz, 2H), 4.10-4.42 (m, 3H), 4.67-5.15 (m, 3H), 5.51-5.73 (m, 3H), 6.11 (s, 1H), 6.28 (dd, J = 10.1, 2.1 Hz, 1H), 6.89 (d, J = 7.3 Hz, 1H), 6.92-7.02 (m, 3H), 7.13-7.29 (m, 5H), 7.30-7.41 (m, 2H), 7.42-7.57 (m, 1H), 7.88-8.34 (m, 2H), 9.74 (s, 1H) |
| 77 | Method m, Table 7 $R_t$ = 1.62 min; m/z = 1058.3 [M + Na$^+$] | $^1$H NMR (DMSO-d$_6$) δ: 0.86 (s, 3H), 1.26 (dd, J = 15.9, 6.5 Hz, 9H), 1.50 (s, 4H), 1.70 (t, J = 8.4 Hz, 3H), 1.90-2.10 (m, 2H), 2.14-2.35 (m, 1H), 2.35-2.45 (m, 1H), 2.54-2.77 (m, 1H), 2.96 (ddd, J = 47.6, 15.3, 6.6 Hz, 2H), 3.57 (t, J = 7.3 Hz, 2H), 3.89 (s, 2H), 4.20 (d, J = 19.0 Hz, 1H), 4.32 (dt, J = 27.9, 7.0 Hz, 2H), 4.45-4.64 (m, 2H), 4.94 (d, J = 4.7 Hz, 1H), 5.07 (d, J = 39.6 Hz, 1H), 5.45 (s, 1H), 5.49-5.79 (m, 2H), 6.12 (s, 1H), 6.29 (dd, J = 10.2, 1.8 Hz, 1H), 6.92 (d, J = 7.6 Hz, 1H), 6.99 (s, 2H), 7.20 (t, J = 7.9 Hz, 1H), 7.25 (t, J = 8.6 Hz, 3H), 7.33-7.42 (m, 4H), 7.45 (d, J = 8.1 Hz, 1H), 8.31 (d, J = 8.0 Hz, 1H), 8.95 (s, 1H), 9.88 (s, 1H), 14.10 (s, 2H) |
| 78 | Method r, Table 7 $R_t$ = 0.80 min; m/z = 1005.1 [M + MeOH + H$^+$] | $^1$H NMR (DMSO-d$_6$) δ: 0.84 (s, 3H), 1.17 (d, J = 7.1 Hz, 3H), 1.25 (d, J = 7.1 Hz, 3H), 1.48 (s, 4H), 1.57 (q, J = 6.2 Hz, 4H), 1.68 (dq, J = 13.7, 6.3, 5.6 Hz, 3H), 1.99-2.06 (m, 1H), 2.09-2.18 (m, 2H), 2.18-2.36 (m, 2H), 2.55-2.72 (m, 3H), 2.78 (s, 4H), 3.87 (s, 2H), 4.14-4.22 (m, 2H), 4.26 (p, J = 7.1 Hz, 1H), 4.33 (p, J = 7.1 Hz, 1H), 4.49 (d, J = 19.4 Hz, 1H), 4.93 (d, J = 5.1 Hz, 1H), 5.43 (s, 1H), 5.49 (d, J = 5.4 Hz, 1H), 5.54-5.75 (m, 1H), 6.11 (s, 1H), 6.28 (dd, J = 10.2, 2.0 Hz, 1H), 6.89 (d, J = 7.6 Hz, 1H), 7.17 (t, J = 7.9 Hz, 1H), 7.23 (t, J = 9.7 Hz, 3H), 7.34 (d, J = 7.8 Hz, 2H), 7.39 (s, 1H), 7.44 (d, J = 8.1 Hz, 1H), 7.99 (d, J = 7.2 Hz, 1H), 8.02 (d, JJ = 7.3 Hz, 1H), 9.77 (s, 1H) |
| 79 | Method r, Table 7 $R_t$ = 0.80 min; m/z = 901.81 [M + H$^+$] | $^1$H NMR (DMSO-d$_6$) δ: 0.85 (s, 3H), 1.14 (d, J = 7.1 Hz, 3H), 1.26 (d, J = 7.1 Hz, 3H), 1.48 (s, 4H), 1.61-1.80 (m, 3H), 2.04 (d, J = 13.1 Hz, 1H), 2.25 (ddd, J = 18.6, 14.9, 8.4 Hz, 2H), 2.37 (dd, J = 8.0, 6.5 Hz, 2H), 2.53-2.74 (m, 1H), 3.57 (t, J = 7.3 Hz, 2H), 4.09-4.24 (m, 2H), 4.30 (p, J = 7.1 Hz, 1H), 4.52 (dd, J = 19.5, 6.4 Hz, 1H), 4.94 (d, J = 5.0 Hz, 1H), 5.08 (t, J = 5.9 Hz, 1H), 5.46 (s, 1H), 5.48-5.53 (m, 1H), 5.63 (dt, J = 48.9, 9.1 Hz, 1H), 6.10 (s, 1H), 6.27 (dd, J = 10.1, 1.9 Hz, 1H), 6.69 (ddd, J = 7.9, 2.6, 1.1 Hz, 1H), 6.96 (s, 2H), 6.98-7.06 (m, 2H), 7.22-7.32 (m, 2H), 7.32-7.40 (m, 2H), 7.39-7.51 (m, 2H), 8.06 (d, J = 7.2 Hz, 1H), 8.15 (d, J = 7.0 Hz, 1H), 9.87 (s, 1H) |
| 80 | Method m, Table 7 $R_t$ = 1.64 min; m/z = 899 [M + H$^+$] | $^1$H NMR (MeOH-d$_4$) δ: 1.00 (s, 3H), 1.36 (dd, J = 11.5, 7.1 Hz, 4H), 1.46 (t, J = 6.9 Hz, 3H), 1.53-1.76 (m, 5H), 1.75-1.89 (m, 2H), 2.28 (d, J = 13.8 Hz, 1H), 2.33-2.48 (m, 1H), 2.48-2.62 (m, 2H), 2.61-2.84 (m, 1H), 3.72-3.88 (m, 2H), 3.95 (s, 2H), 4.18-4.40 (m, 3H), 4.46 (q, J = 6.9 Hz, 1H), 4.65 (d, J = 19.4 Hz, 1H), 5.07 (d, J = 4.6 Hz, 1H), 5.43-5.69 (m, 2H), 6.30-6.39 (m, 2H), 6.69 (s, 2H), 7.14 (dd, J = 8.2, 5.6 Hz, 2H), 7.23 (dd, J = 7.9, 3.4 Hz, 3H), 7.34 (d, J = 10.1 Hz, 1H), 7.38 (d, J = 7.8 Hz, 2H), 7.51 (d, J = 8.2 Hz, 2H), 7.55 (d, J = 8.2 Hz, 1H), 8.55 (s, 1H) |
| 81 | Method m, Table 7 $R_t$ = 1.526 min; m/z = 957 [M + H$^+$] | $^1$H NMR (MeOH-d$_4$) δ: 0.88 (s, 3H), 1.21 (d, J = 11.6 Hz, 3H), 1.35 (d, J = 7.1 Hz, 3H), 1.48 (s, 3H), 1.57 (dd, J = 25.8, 13.5 Hz, 2H), 1.68 (dd, J = 13.4, 5.5 Hz, 2H), 1.83 (dd, J = 14.4, 7.5 Hz, 1H), 1.88-2.05 (m, 1H), 2.12-2.21 (m, 1H), 2.30 (q, J = 12.7, 10.3 Hz, 3H), 2.44 (t, J = 6.7 Hz, 2H), 2.49-2.73 (m, 1H), 3.68 (t, J = 6.7 Hz, 2H), 3.82 (s, 2H), 4.11-4.28 (m, 3H), 4.34 (q, J = 7.1 Hz, 1H), 4.53 (d, J = 19.4 Hz, 1H), 4.95 (d, J = 4.6 Hz, 1H), 5.30-5.59 (m, 2H), 6.23 (dd, J = 13.2, 3.0 Hz, 2H), |

| Cpd. No. | LC-MS Data | ¹H NMR Data |
|---|---|---|
| | | 6.60 (s, 2H), 7.02 (d, J = 8.2 Hz, 2H), 7.10 (d, J = 7.9 Hz, 2H), 7.24 (dd, J = 15.1, 8.9 Hz, 3H), 7.37 (d, J = 8.2 Hz, 2H) |
| 82 | Method r, Table 7 $R_t$ = 0.77 min; 913.27 [M + H$^+$] | ¹H NMR (DMSO-d$_6$) δ: 0.84 (s, 3H), 0.96 (s, 2H), 1.01-1.19 (m, 4H), 1.19-1.35 (m, 2H), 1.48 (s, 3H), 1.67 (d, J = 14.3 Hz, 2H), 2.03 (d, J = 19.7 Hz, 1H), 2.13-2.42 (m, 5H), 2.64 (d, J = 8.4 Hz, 2H), 3.08 (s, 3H), 3.38-3.61 (m, 1H), 3.93 (s, 2H), 4.17 (d, J = 18.9 Hz, 3H), 4.49 (d, J = 19.3 Hz, 1H), 4.92 (d, J = 4.8 Hz, 1H), 5.43 (s, 1H), 5.49 (s, 1H), 5.53-5.77 (m, 1H), 6.11 (s, 1H), 6.28 (dd, J = 10.2, 1.8 Hz, 1H), 6.96 (d, J = 6.1 Hz, 1H), 7.10-7.41 (m, 8H), 7.83-8.20 (m, 1H) |
| 83 | Method r, Table 7 $R_t$ = 0.88 min; m/z = 943.52 [M + H$^+$] | ¹H NMR (DMSO-d$_6$) δ: 0.84 (s, 3H), 0.93 (dd, J = 23.5, 6.9 Hz, 3H), 1.04-1.16 (m, 3H), 1.48 (s, 4H), 1.60-1.76 (m, 3H), 2.03 (d, J = 20.7 Hz, 1H), 2.17-2.26 (m, 1H), 2.24-2.40 (m, 2H), 2.55-2.72 (m, 2H), 2.96 (d, J = 13.0 Hz, 3H), 3.55 (t, J = 7.3 Hz, 1H), 3.72 (d, J = 57.6 Hz, 3H), 3.93 (d, J = 4.7 Hz, 2H), 4.10-4.28 (m, 4H), 4.49 (d, J = 19.5 Hz, 1H), 4.93 (d, J = 5.0 Hz, 1H), 5.44 (d, J = 2.9 Hz, 1H), 5.50 (d, J = 4.2 Hz, 1H), 5.63 (dt, J = 48.7, 9.8 Hz, 1H), 6.11 (s, 1H), 6.28 (dd, J = 10.2, 1.9 Hz, 1H), 6.82 (t, J = 7.1 Hz, 1H), 6.93-7.00 (m, 1H), 7.02-7.07 (m, 1H), 7.19 (d, J = 7.9 Hz, 1H), 7.24 (d, J = 10.0 Hz, 1H), 7.29-7.41 (m, 4H), 7.93 (d, J = 7.1 Hz, 1H) |
| 84 | Method r, Table 7 $R_t$ = 0.82 min; m/z = 929.45 [M + H$^+$] | ¹H NMR (DMSO-d$_6$) δ: 0.83 (s, 3H), 1.17 (d, J = 7.1 Hz, 3H), 1.25 (d, J = 7.1 Hz, 3H), 1.46 (s, 4H), 1.58-1.77 (m, 3H), 2.01 (dt, J = 13.8, 4.1 Hz, 1H), 2.23 (dtd, J = 25.2, 12.3, 10.9, 5.8 Hz, 2H), 2.31-2.40 (m, 2H), 2.49-2.73 (m, 1H), 3.56 (t, J = 7.3 Hz, 2H), 3.74 (s, 3H), 3.84 (s, 2H), 4.11-4.20 (m, 2H), 4.27 (p, J = 7.1 Hz, 1H), 4.39 (p, J = 7.2 Hz, 1H), 4.47 (d, J = 19.4 Hz, 1H), 4.91 (d, J = 4.8 Hz, 1H), 5.41 (s, 1H), 5.42-5.50 (m, 1H), 5.50-5.78 (m, 1H), 6.09 (s, 1H), 6.26 (dd, J = 10.1, 1.9 Hz, 1H), 6.70 (dd, J = 8.3, 1.8 Hz, 1H), 6.89 (d, J = 1.8 Hz, 1H), 6.95 (s, 2H), 7.23 (d, J = 8.5 Hz, 3H), 7.31 (d, J = 7.9 Hz, 2H), 7.87 (d, J = 8.2 Hz, 1H), 8.14 (d, J = 7.5 Hz, 1H), 8.23 (d, J = 7.2 Hz, 1H), 8.81 (s, 1H) |
| 85 | Method r, Table 7 $R_t$ = 0.73 min; m/z = 897.3 [M + H$^+$] | ¹H NMR (DMSO-d$_6$) δ: 0.84 (s, 3H), 1.16 (d, J = 7.1 Hz, 3H), 1.27 (d, J = 7.1 Hz, 3H), 1.39 (qd, J = 13.1, 5.2 Hz, 1H), 1.48 (s, 3H), 1.55-1.72 (m, 3H), 1.78-1.90 (m, 1H), 2.03 (d, J = 25.4 Hz, 1H), 2.13 (td, J = 12.2, 6.8 Hz, 1H), 2.29-2.41 (m, 3H), 2.48 (p, J = 1.9 Hz, 1H), 2.58-2.69 (m, 1H), 3.59 (t, J = 7.3 Hz, 2H), 4.09-4.26 (m, 3H), 4.29-4.44 (m, 3H), 4.47 (d, J = 19.4 Hz, 1H), 4.82-4.91 (m, 1H), 5.32 (s, 1H), 5.41 (s, 1H), 6.02 (d, J = 1.7 Hz, 1H), 6.22 (dd, J = 10.1, 1.9 Hz, 1H), 6.47 (d, J = 8.7 Hz, 1H), 6.97 (s, 2H), 7.18-7.21 (m, 2H), 7.23 (t, J = 6.2 Hz, 1H), 7.27 (d, J = 10.1 Hz, 1H), 7.33 (dd, J = 8.7, 2.3 Hz, 1H), 7.44-7.57 (m, 2H), 7.95 (d, J = 2.3 Hz, 1H), 8.04 (d, J = 7.3 Hz, 1H), 8.10-8.23 (m, 2H), 9.73 (s, 1H) |
| 86 | Method r, Table 7 $R_t$ = 0.73 min; m/z = 911.46 [M + H$^+$] | ¹H NMR (DMSO-d$_6$) δ: 0.83 (s, 3H), 1.15 (d, J = 7.2 Hz, 3H), 1.26 (d, J = 7.1 Hz, 3H), 1.36 (d, J = 6.7 Hz, 4H), 1.48 (s, 3H), 1.63 (t, J = 11.1 Hz, 3H), 1.74-1.90 (m, 1H), 1.93-2.19 (m, 2H), 2.26-2.41 (m, 3H), 2.48 (p, J = 1.8 Hz, 1H), 2.58-2.70 (m, 1H), 3.59 (t, J = 7.3 Hz, 2H), 4.09-4.27 (m, 3H), 4.33 (p, J = 7.2 Hz, 1H), 4.46 (d, J = 19.4 Hz, 1H), 4.85 (d, J = 4.1 Hz, 1H), 4.93 (t, J = 6.9 Hz, 1H), 5.04 (s, 1H), 5.30 (s, 1H), 5.40 (dd, J = 4.5, 1.7 Hz, 1H), 6.02 (s, 1H), 6.21 (dd, J = 10.1, 1.9 Hz, 1H), 6.48 (s, 1H), 6.97 (s, 2H), 7.26 (t, J = 9.3 Hz, 3H), 7.32 (d, J = 8.0 Hz, 1H), 7.48 (d, J = 8.3 Hz, 2H), 7.90 (d, J = 2.2 Hz, 1H), 8.03 (d, J = 7.3 Hz, 1H), 8.16 (d, J = 7.0 Hz, 1H), 9.71 (s, 1H) |
| 87 | Method r, Table 7 $R_t$ = 0.72 min; m/z = 911.64 [M + H$^+$] | ¹H NMR (DMSO-d$_6$) δ: 0.83 (s, 3H), 1.15 (d, J = 7.1 Hz, 3H), 1.27 (d, J = 7.1 Hz, 3H), 1.35 (d, J = 6.8 Hz, 4H), 1.48 (s, 3H), 1.55-1.70 (m, 3H), 1.77-1.88 (m, 1H), 1.99 (d, J = 13.5 Hz, 1H), 2.12 (td, J = 12.3, 6.6 Hz, 1H), 2.28-2.40 (m, 3H), 2.48 (p, J = 1.8 Hz, 1H), 2.56-2.69 (m, 1H), 3.59 (t, J = 7.3 Hz, 2H), 4.06-4.28 (m, 3H), 4.33 (p, J = 7.2 Hz, 1H), 4.45 (dd, J = 19.4, 6.4 Hz, 1H), 4.85 (d, J = 4.9 Hz, 1H), 4.93 (t, J = 7.2 Hz, 1H), 5.03 (t, J = 6.0 Hz, 1H), 5.28 (s, 1H), 5.40 (dd, J = 4.4, 1.9 Hz, 1H), 6.02 (d, J = 2.1 Hz, 1H), 6.22 (dd, J = 10.1, 1.9 Hz, 1H), 6.43 (d, J = 8.6 Hz, 1H), 6.97 (s, 2H), 7.16 (d, J = 7.8 Hz, 1H), 7.20-7.33 (m, 4H), 7.44-7.49 (m, 2H), 7.90 (d, J = 2.3 Hz, 1H), 8.03 (d, J = 7.3 Hz, 1H), 8.17 (d, J = 7.1 Hz, 1H), 9.71 (s, 1H) |
| 88 | Method r, Table 7 $R_t$ = 0.87 min; m/z = 863.32 [M + H$^+$] | ¹H NMR (DMSO-d$_6$) δ: 0.84 (s, 3H), 1.02 (ddd, J = 21.3, 12.1, 4.2 Hz, 2H), 1.15 (d, J = 7.1 Hz, 3H), 1.26 (d, J = 7.1 Hz, 3H), 1.37 (s, 3H), 1.53-1.81 (m, 4H), 2.00 (dd, J = 12.2, 5.5 Hz, 1H), 2.04-2.15 (m, 1H), 2.23-2.33 (m, 1H), 2.38 (dd, J = 8.0, 6.6 Hz, 2H), 2.51 (d, J = 18.2 Hz, 1H), 3.59 (t, J = 7.3 Hz, 2H), 3.87 (s, 2H), 4.16 (d, J = 19.4 Hz, 1H), 4.21 (p, J = 7.1 Hz, 1H), 4.27 (q, J = 3.3 Hz, 1H), 4.32 (p, J = 7.1 Hz, 1H), 4.48 (d, J = 19.4 Hz, 1H), 4.72 (s, 2H), 4.90 (d, J = 5.4 Hz, 1H), 5.37 (s, 1H), 5.90 (t, J = 1.6 Hz, 1H), 6.13 (dd, J = 10.1, 1.8 Hz, 1H), 6.88 (dt, J = 7.9, 1.3 Hz, 1H), 6.96 (s, 2H), 7.14-7.22 (m, 3H), 7.29 (d, J = 10.1 Hz, 1H), 7.33-7.38 (m, 2H), 7.43 (dd, J = 7.8, 1.1 Hz, 2H), 8.03 (d, J = 7.2 Hz, 1H), 8.17 (d, J = 7.0 Hz, 1H), 9.71 (s, 1H) |
| 89 | Method m, Table 7 $R_t$ = 1.99 min; | ¹H NMR (MeOH-d$_4$) δ: 1.01 (d, J = 8.5 Hz, 3H), 1.10-1.30 (m, 2H), 1.34 (dd, J = 10.5, 7.1 Hz, 3H), 1.45 (dd, J = 7.2, 3.6 Hz, 3H), 1.52 (s, 3H), 1.80 (t, J = 13.0 Hz, 1H), 1.90 (p, J = 8.3, 7.3 Hz, 1H), 2.04 (d, J = 12.4 Hz, |

| Cpd. No. | LC-MS Data | ¹H NMR Data |
|---|---|---|
| | m/z = 863 [M + H]⁺ | 1H), 2.12-2.32 (m, 2H), 2.42 (d, J = 11.2 Hz, 1H), 2.46-2.58 (m, 2H), 2.60-2.78 (m, 1H), 3.68-3.84 (m, 2H), 3.96 (d, J = 6.0 Hz, 2H), 4.12 (d, J = 19.3 Hz, 1H), 4.16-4.27 (m, 1H), 4.27-4.38 (m, 1H), 4.43 (d, J = 6.2 Hz, 2H), 5.40 (d, J = 6.3 Hz, 1H), 6.05 (s, 1H), 6.12 (d, J = 4.4 Hz, 1H), 6.28 (dd, J = 9.9, 1.8 Hz, 1H), 6.75 (d, J = 3.3 Hz, 2H), 6.96 (d, J = 7.7 Hz, 1H), 7.15-7.30 (m, 5H), 7.43 (d, J = 18.7 Hz, 3H), 7.56 (d, J = 8.2 Hz, 3H) |
| 90 | Method r, Table 7 $R_t$ = 0.91 min; m/z = 891.36 [M + H]⁺ | ¹H NMR (DMSO-$d_6$) δ: 0.79 (d, J = 6.8 Hz, 3H), 0.82 (d, J = 6.8 Hz, 3H), 0.84 (s, 2H), 0.95-1.12 (m, 2H), 1.26 (d, J = 7.1 Hz, 3H), 1.38 (d, J = 4.7 Hz, 3H), 1.54-1.77 (m, 4H), 1.91 (h, J = 6.8 Hz, 1H), 1.96-2.05 (m, 1H), 2.04-2.17 (m, 1H), 2.23-2.34 (m, 1H), 2.37-2.47 (m, 2H), 2.49-2.58 (m, 1H), 3.51-3.67 (m, 2H), 3.87 (s, 2H), 4.11 (s, 1H), 4.16 (d, J = 19.4 Hz, 1H), 4.27 (q, J = 3.4 Hz, 1H), 4.32 (p, J = 7.1 Hz, 1H), 4.48 (d, J = 19.4 Hz, 1H), 4.73 (s, 1H), 4.90 (d, J = 5.3 Hz, 1H), 5.38 (s, 1H), 5.90 (d, J = 1.6 Hz, 1H), 6.13 (dt, J = 10.1, 1.8 Hz, 1H), 6.88 (dt, J = 7.7, 1.3 Hz, 1H), 6.96 (s, 2H), 7.18 (dd, J = 16.7, 8.1 Hz, 3H), 7.29 (d, J = 10.1 Hz, 1H), 7.32-7.40 (m, 3H), 7.43 (ddd, J = 8.1, 2.2, 1.0 Hz, 1H), 7.99 (d, J = 8.4 Hz, 1H), 8.10 (d, J = 7.0 Hz, 1H), 9.74 (s, 1H) |
| 99 | Method r, Table 7 $R_t$ = 0.85 min; m/z = 881.46 [M + H]⁺ | ¹H NMR (DMSO-$d_6$) δ: 0.83 (s, 3H), 1.13 (d, J = 7.1 Hz, 3H), 1.24 (d, J = 7.1 Hz, 3H), 1.35 (qd, J = 13.3, 12.8, 5.1 Hz, 1H), 1.46 (s, 3H), 1.63 (q, J = 9.7, 8.5 Hz, 3H), 1.73-1.88 (m, 1H), 2.01 (dt, J = 13.7, 3.5 Hz, 1H), 2.14 (td, J = 11.8, 7.2 Hz, 1H), 2.26-2.40 (m, 3H), 2.48-2.69 (m, 2H), 3.57 (t, J = 7.3 Hz, 2H), 3.85 (s, 2H), 4.17 (ddd, J = 17.5, 11.7, 6.2 Hz, 3H), 4.30 (p, J = 7.2 Hz, 1H), 4.47 (d, J = 19.4 Hz, 1H), 4.83-4.95 (m, 1H), 5.40 (s, 2H), 5.99 (d, J = 1.6 Hz, 1H), 6.20 (dd, J = 10.1, 1.9 Hz, 1H), 6.87 (d, J = 7.5 Hz, 1H), 6.95 (s, 2H), 7.16 (t, J = 7.9 Hz, 1H), 7.20 (d, J = 8.1 Hz, 2H), 7.25 (d, J = 10.1 Hz, 1H), 7.31 (d, J = 8.0 Hz, 2H), 7.38 (d, J = 1.9 Hz, 1H), 7.43 (dd, J = 8.0, 2.0 Hz, 1H), 8.01 (d, J = 7.3 Hz, 1H), 8.14 (d, J = 7.1 Hz, 1H), 9.70 (s, 1H) |
| 100 | Method r, Table 7 $R_t$ = 0.87 min; m/z = 933.0 [M + H]⁺ | ¹H NMR (DMSO-$d_6$) δ: 0.93 (s, 3H), 1.15 (d, J = 7.2 Hz, 3H), 1.26 (d, J = 7.1 Hz, 3H), 1.48 (s, 4H), 1.73 (dd, J = 25.4, 11.3 Hz, 3H), 2.00 (d, J = 14.1 Hz, 1H), 2.12-2.26 (m, 1H), 2.27 (s, 1H), 2.37 (q, J = 8.3, 7.8 Hz, 2H), 2.65 (d, J = 33.3 Hz, 1H), 3.59 (t, J = 7.3 Hz, 2H), 3.88 (s, 2H), 4.14-4.27 (m, 2H), 4.32 (t, J = 7.2 Hz, 1H), 4.92 (d, J = 3.5 Hz, 1H), 5.50 (s, 1H), 5.55 (s, 1H), 5.54-5.72 (m, 1H), 5.79-6.04 (m, 2H), 6.11 (s, 1H), 6.28 (dd, J = 10.1, 1.9 Hz, 1H), 6.90 (d, J = 7.7 Hz, 1H), 6.97 (s, 2H), 7.18 (t, J = 7.8 Hz, 1H), 7.24 (t, J = 9.5 Hz, 3H), 7.34 (d, J = 7.8 Hz, 2H), 7.40 (s, 1H), 7.46 (d, J = 8.2 Hz, 1H), 8.03 (d, J = 7.3 Hz, 1H), 8.16 (d, J = 7.1 Hz, 1H), 9.72 (s, 1H) |
| 101 | Method r, Table 7 $R_t$ = 0.84 min; m/z = 885.41 [M + H]⁺ | ¹H NMR (DMSO-$d_6$) δ: 0.99 (s, 3H), 1.15 (d, J = 7.1 Hz, 3H), 1.25 (d, J = 7.1 Hz, 3H), 1.49 (s, 4H), 1.60-1.75 (m, 2H), 1.79 (d, J = 14.0 Hz, 1H), 1.94 (dt, J = 14.4, 3.5 Hz, 1H), 2.20 (q, J = 10.4 Hz, 1H), 2.24-2.33 (m, 1H), 2.38 (dd, J = 8.0, 6.5 Hz, 2H), 2.62 (dtd, J = 30.0, 12.0, 11.5, 4.1 Hz, 1H), 3.59 (t, J = 7.3 Hz, 2H), 3.87 (s, 2H), 4.16 (d, J = 9.1 Hz, 1H), 4.21 (p, J = 7.2 Hz, 1H), 4.32 (p, J = 7.2 Hz, 1H), 5.00 (t, J = 2.9 Hz, 1H), 5.40-5.47 (m, 1H), 5.48 (s, 1H), 5.54-5.72 (m, 1H), 6.11 (s, 1H), 6.27 (dd, J = 10.2, 1.9 Hz, 1H), 6.89 (d, J = 7.6 Hz, 1H), 6.96 (s, 2H), 7.17 (t, J = 7.9 Hz, 1H), 7.21 (d, J = 8.0 Hz, 2H), 7.24 (dd, J = 10.3, 1.5 Hz, 1H), 7.32 (d, J = 7.9 Hz, 2H), 7.39 (t, J = 1.9 Hz, 1H), 7.46 (dd, J = 8.1, 2.1 Hz, 1H), 8.04 (d, J = 7.3 Hz, 1H), 8.16 (d, J = 7.1 Hz, 1H), 9.73 (s, 1H) |
| 102 | Method r, Table 7 $R_t$ = 0.77 min; m/z = 917.22 [M + H]⁺ | ¹H NMR (DMSO-$d_6$) δ: 0.85 (s, 3H), 1.16 (d, J = 7.1 Hz, 3H), 1.28 (d, J = 7.1 Hz, 3H), 1.48 (s, 3H), 1.56 (p, J = 12.4, 12.0 Hz, 1H), 1.62-1.76 (m, 3H), 1.98-2.10 (m, 1H), 2.22 (td, J = 12.3, 6.6 Hz, 1H), 2.24-2.33 (m, 1H), 2.38 (td, J = 7.0, 1.0 Hz, 2H), 2.54-2.72 (m, 1H), 3.59 (t, J = 7.3 Hz, 2H), 4.15-4.25 (m, 3H), 4.33 (p, J = 7.1 Hz, 1H), 4.50 (d, J = 19.4 Hz, 1H), 4.93 (d, J = 5.0 Hz, 1H), 5.36 (s, 1H), 5.50 (s, 1H), 5.55-5.73 (m, 1H), 6.11 (q, J = 1.5 Hz, 1H), 6.27 (dd, J = 10.2, 1.9 Hz, 1H), 6.78-6.83 (m, 2H), 6.84 (d, J = 1.8 Hz, 2H), 6.97 (s, 2H), 7.01 (d, J = 1.6 Hz, 1H), 7.25 (dd, J = 10.1, 1.5 Hz, 1H), 7.45-7.61 (m, 3H), 8.04 (d, J = 7.3 Hz, 1H), 8.17 (d, J = 7.0 Hz, 1H), 9.73 (s, 1H) |
| 103 | Method r, Table 7 $R_t$ = 0.84 min; m/z = 935.4 [M + Na]⁺ | ¹H NMR (DMSO-$d_6$) δ: 0.84 (s, 3H), 1.15 (d, J = 7.3 Hz, 3H), 1.25 (d, J = 7.1 Hz, 3H), 1.48 (s, 3H), 1.51 (d, J = 7.3 Hz, 4H), 1.67 (d, J = 14.2 Hz, 2H), 2.02 (d, J = 13.7 Hz, 1H), 2.13-2.34 (m, 2H), 2.38 (t, J = 7.3 Hz, 2H), 2.65 (s, 1H), 3.59 (t, J = 7.3 Hz, 2H), 4.08 (d, J = 7.1 Hz, 1H), 4.12-4.24 (m, 2H), 4.32 (p, J = 7.2 Hz, 1H), 4.48 (dd, J = 19.6, 6.3 Hz, 1H), 4.92 (d, J = 4.8 Hz, 1H), 5.07 (t, J = 5.8 Hz, 1H), 5.72-5.54 (m, 1H), 5.41 (s, 1H), 5.49 (s, 1H), 6.11 (s, 1H), 6.28 (d, J = 9.9 Hz, 1H), 6.88-6.95 (m, 1H), 6.97 (s, 2H), 7.17 (t, J = 7.9 Hz, 1H), 7.25 (d, J = 8.1 Hz, 3H), 7.33 (d, J = 7.9 Hz, 2H), 7.45 (d, J = 12.0 Hz, 2H), 8.03 (d, J = 7.2 Hz, 1H), 8.16 (d, J = 6.9 Hz, 1H), 9.71 (s, 1H) |
| 104 | Method r, Table 7 $R_t$ = 0.84 min; m/z = 935.4 [M + Na]⁺ | ¹H NMR (DMSO-$d_6$) δ: 0.85 (s, 3H), 1.16 (d, J = 7.1 Hz, 3H), 1.26 (d, J = 7.1 Hz, 3H), 1.49 (s, 3H), 1.52 (d, J = 7.3 Hz, 3H), 1.69 (t, J = 12.7 Hz, 3H), 2.04 (d, J = 13.9 Hz, 1H), 2.18-2.33 (m, 2H), 2.33-2.42 (m, 2H), 2.56-2.74 (m, 1H), 3.60 (t, J = 7.3 Hz, 2H), 4.09 (q, J = 7.2 Hz, 1H), 4.20 (tq, J = 13.0, 6.3, 5.6 Hz, 3H), 4.32 (p, J = 7.1 Hz, 1H), 4.49 (dd, J = 19.5, 6.3 Hz, 1H), 4.93 (d, J = 5.1 Hz, 1H), 5.08 (t, J = 6.0 Hz, 1H), |

| Cpd. No. | LC-MS Data | ¹H NMR Data |
|---|---|---|
| | | 5.42 (s, 1H), 5.51 (d, J = 4.2 Hz, 1H), 5.64 (dt, J = 48.9, 8.9 Hz, 1H), 6.12 (s, 1H), 6.29 (dd, J = 10.0, 1.9 Hz, 1H), 6.93 (d, J = 7.6 Hz, 1H), 6.97 (s, 2H), 7.18 (t, J = 7.9 Hz, 1H), 7.23-7.29 (m, 3H), 7.34 (d, J = 8.2 Hz, 2H), 7.44 (d, J = 2.1 Hz, 1H), 7.44-7.49 (m, 1H), 8.03 (d, J = 7.3 Hz, 1H), 8.17 (d, J = 7.1 Hz, 1H), 9.72 (s, 1H) |
| 105 | Method r, Table 7 $R_t$ = 0.80 min; m/z = 913.75 [M + H⁺] | ¹H NMR (DMSO-$d_6$) δ: 0.84 (s, 3H), 1.15 (d, J = 7.2 Hz, 3H), 1.26 (d, J = 7.1 Hz, 3H), 1.44-1.58 (m, 7H), 1.67 (d, J = 13.8 Hz, 2H), 2.03 (d, J = 14.0 Hz, 1H), 2.18-2.34 (m, 2H), 2.38 (t, J = 7.3 Hz, 2H), 2.50-2.72 (m, 1H), 3.58 (t, J = 7.3 Hz, 2H), 4.07 (p, J = 7.3 Hz, 1H), 4.11-4.26 (m, 2H), 4.33 (d, J = 7.2 Hz, 1H), 4.48 (d, J = 19.3 Hz, 1H), 4.92 (d, J = 4.8 Hz, 1H), 5.41 (s, 1H), 5.45-5.53 (m, 1H), 5.62 (dd, J = 48.5, 9.8 Hz, 1H), 6.11 (s, 1H), 6.28 (d, J = 10.0 Hz, 1H), 6.97 (s, 2H), 7.11-7.20 (m, 2H), 7.20-7.29 (m, 3H), 7.32 (d, J = 8.0 Hz, 2H), 7.47 (d, J = 8.3 Hz, 2H), 8.03 (d, J = 7.2 Hz, 1H), 8.16 (d, J = 7.0 Hz, 1H), 9.71 (s, 1H) |
| 106 | Method r, Table 7 $R_t$ = 0.84 min; m/z = 913.46 [M + H⁺] | ¹H NMR (DMSO-$d_6$) δ: 0.84 (s, 3H), 1.15 (d, J = 7.1 Hz, 3H), 1.26 (d, J = 7.1 Hz, 3H), 1.48 (s, 3H), 1.48-1.54 (m, 4H), 1.60-1.75 (m, 2H), 2.03 (dt, J = 13.8, 3.6 Hz, 1H), 2.08-2.18 (m, 1H), 2.18-2.25 (m, 1H), 2.25-2.32 (m, 1H), 2.38 (dd, J = 8.1, 6.4 Hz, 2H), 2.54-2.72 (m, 1H), 3.59 (t, J = 7.3 Hz, 2H), 4.06 (dq, J = 14.9, 7.0 Hz, 1H), 4.11-4.28 (m, 3H), 4.33 (p, J = 7.1 Hz, 1H), 4.48 (d, J = 19.6 Hz, 1H), 4.92 (d, J = 5.0 Hz, 1H), 5.42 (s, 1H), 5.45-5.54 (m, 1H), 5.54-5.73 (m, 1H), 6.12 (d, J = 2.2 Hz, 1H), 6.26-6.33 (m, 1H), 6.97 (d, J = 1.3 Hz, 2H), 7.10-7.18 (m, 3H), 7.20-7.28 (m, 3H), 7.29-7.36 (m, 2H), 7.47 (dd, J = 8.6, 4.4 Hz, 2H), 8.04 (d, J = 7.3 Hz, 1H), 8.17 (d, J = 7.1 Hz, 1H), 9.71 (d, J = 2.9 Hz, 1H) |
| 107 | Method r, Table 7 $R_t$ = 0.88 min; m/z = 895.30 [M + H⁺] | ¹H NMR (DMSO-$d_6$) δ: 0.84 (s, 3H), 0.94-1.11 (m, 2H), 1.16 (d, J = 7.1 Hz, 3H), 1.27 (d, J = 7.1 Hz, 3H), 1.37 (s, 3H), 1.51-1.82 (m, 5H), 1.94-2.03 (m, 1H), 2.08 (d, J = 19.3 Hz, 1H), 2.30 (t, J = 8.2 Hz, 1H), 2.38 (t, J = 7.3 Hz, 2H), 2.48-2.59 (m, 1H), 3.60 (t, J = 7.3 Hz, 2H), 4.11-4.25 (m, 4H), 4.27 (d, J = 3.6 Hz, 1H), 4.32 (p, J = 7.2 Hz, 1H), 4.48 (d, J = 19.5 Hz, 1H), 4.90 (d, J = 5.0 Hz, 1H), 5.38 (s, 1H), 5.91 (d, J = 1.6 Hz, 1H), 6.14 (dd, J = 10.1, 1.8 Hz, 1H), 6.97 (s, 2H), 6.94-7.01 (m, 1H), 7.19 (t, J = 8.0 Hz, 1H), 7.25-7.37 (m, 2H), 7.37 (s, 4H), 7.66 (t, J = 1.9 Hz, 1H), 8.10 (d, J = 7.2 Hz, 1H), 8.20 (d, J = 6.9 Hz, 1H), 9.80 (s, 1H) |
| 108 | Method r, Table 7 $R_t$ = 0.83 min; m/z = 913.0 [M + H⁺] | ¹H NMR (DMSO-$d_6$) δ: 0.85 (s, 3H), 1.16 (d, J = 7.1 Hz, 3H), 1.27 (d, J = 7.1 Hz, 3H), 1.37 (qd, J = 12.8, 5.2 Hz, 1H), 1.48 (s, 3H), 1.57-1.71 (m, 3H), 1.83 (dt, J = 11.7, 5.4 Hz, 1H), 2.03 (dt, J = 13.8, 3.6 Hz, 1H), 2.14 (td, J = 12.1, 6.8 Hz, 1H), 2.30-2.36 (m, 1H), 2.38 (t, J = 7.3 Hz, 2H), 2.42-2.57 (m, 1H), 2.63 (td, J = 13.3, 5.8 Hz, 1H), 3.59 (t, J = 7.3 Hz, 2H), 4.13-4.26 (m, 5H), 4.32 (p, J = 7.2 Hz, 1H), 4.49 (d, J = 19.4 Hz, 1H), 4.91 (d, J = 4.7 Hz, 1H), 5.42 (s, 2H), 6.02 (s, 1H), 6.21 (dd, J = 10.1, 1.9 Hz, 1H), 6.98 (dd, J = 7.9, 1.8 Hz, 1H), 7.19 (t, J = 8.0 Hz, 1H), 7.27 (d, J = 10.2 Hz, 1H), 7.29-7.44 (m, 5H), 7.61-7.70 (m, 1H), 8.07 (d, J = 7.2 Hz, 1H), 8.18 (d, J = 7.0 Hz, 1H), 9.79 (s, 1H) |
| 109 | Method r, Table 7 $R_t$ = 0.80 min; m/z = 915.54 [M + H⁺] | ¹H NMR (DMSO-$d_6$) δ: 0.85 (s, 3H), 1.19 (d, J = 7.1 Hz, 3H), 1.28 (d, J = 7.1 Hz, 3H), 1.49 (s, 4H), 1.61-1.78 (m, 3H), 2.04 (d, J = 13.7 Hz, 1H), 2.22 (dd, J = 12.3, 6.3 Hz, 1H), 2.26-2.32 (m, 1H), 2.37 (td, J = 7.0, 2.0 Hz, 2H), 2.55-2.73 (m, 1H), 3.58 (t, J = 7.3 Hz, 2H), 3.78 (s, 2H), 4.18 (d, J = 19.4 Hz, 1H), 4.29 (p, J = 7.1 Hz, 1H), 4.39 (p, J = 7.1 Hz, 1H), 4.50 (d, J = 19.4 Hz, 1H), 4.93 (d, J = 5.2 Hz, 1H), 5.43 (s, 1H), 5.51 (dd, J = 4.5, 1.7 Hz, 1H), 5.54-5.75 (m, 1H), 6.12 (s, 1H), 6.29 (dd, J = 10.1, 1.9 Hz, 1H), 6.72-6.78 (m, 2H), 6.98 (s, 2H), 7.19 (d, J = 7.9 Hz, 2H), 7.25 (dd, J = 10.1, 1.5 Hz, 1H), 7.29-7.37 (m, 2H), 7.76 (d, J = 1.8 Hz, 1H), 8.18 (d, J = 7.5 Hz, 1H), 8.30 (d, J = 7.1 Hz, 1H), 8.92 (s, 1H), 9.72 (s, 1H) |
| 110 | Method r, Table 7 $R_t$ = 0.84 min; m/z = 899.0 [M + H⁺] | ¹H NMR (DMSO-$d_6$) δ: 0.83 (s, 3H), 1.13 (d, J = 7.2 Hz, 3H), 1.25 (d, J = 7.2 Hz, 3H), 1.36 (qd, J = 12.7, 5.4 Hz, 1H), 1.46 (s, 3H), 1.55-1.72 (m, 3H), 1.75-1.87 (m, 1H), 1.93-2.05 (m, 1H), 2.05-2.18 (m, 1H), 2.25-2.40 (m, 3H), 2.47 (p, J = 1.9 Hz, 1H), 2.53-2.69 (m, 1H), 3.56 (t, J = 7.3 Hz, 2H), 4.09-4.23 (m, 3H), 4.29 (p, J = 7.1 Hz, 1H), 4.49 (d, J = 19.5 Hz, 1H), 4.87-4.95 (m, 1H), 5.40 (s, 1H), 5.43 (s, 1H), 5.99 (d, J = 1.7 Hz, 1H), 6.19 (dd, J = 10.1, 1.9 Hz, 1H), 6.95 (s, 2H), 7.00 (dt, J = 7.8, 1.3 Hz, 1H), 7.21-7.33 (m, 4H), 7.33-7.41 (m, 2H), 7.56 (ddd, J = 8.2, 2.1, 1.0 Hz, 1H), 7.67 (t, J = 2.0 Hz, 1H), 8.05 (d, J = 7.1 Hz, 1H), 8.14 (d, J = 7.0 Hz, 1H), 9.87 (s, 1H) |
| 111 | Method r, Table 7 $R_t$ = 0.86 min; m/z = 881.38 [M + H⁺] | ¹H NMR (DMSO-$d_6$) δ: 0.84 (s, 3H), 1.04 (ddd, J = 14.7, 11.7, 4.1 Hz, 2H), 1.14 (d, J = 7.1 Hz, 3H), 1.26 (d, J = 7.1 Hz, 3H), 1.37 (s, 3H), 1.54-1.85 (m, 4H), 1.93-2.03 (m, 1H), 2.09 (d, J = 11.6 Hz, 1H), 2.23-2.33 (m, 1H), 2.36 (q, J = 6.4, 5.5 Hz, 2H), 2.50 (d, J = 9.7 Hz, 1H), 3.57 (t, J = 7.3 Hz, 2H), 4.12-4.24 (m, 2H), 4.24-4.34 (m, 2H), 4.48 (d, J = 19.5 Hz, 1H), 4.76 (s, 1H), 4.90 (d, J = 5.1 Hz, 1H), 5.39 (s, 1H), 5.89 (s, 1H), 6.14 (dd, J = 10.1, 1.9 Hz, 1H), 6.97 (s, 2H), 7.03 (d, J = 7.7 Hz, 1H), 7.22-7.35 (m, 4H), 7.42 (d, J = 8.2 Hz, 2H), 7.57 (dd, J = 8.2, 2.0 Hz, 1H), 7.71 (d, J = 2.0 Hz, 1H), 8.09 (d, J = 7.1 Hz, 1H), 8.17 (d, J = 6.9 Hz, 1H), 9.89 (s, 1H) |

| Cpd. No. | LC-MS Data | $^1$H NMR Data |
|---|---|---|
| 112 | Method r, Table 7 $R_t$ = 0.85 min; m/z = 879.30 [M + H$^+$] | $^1$H NMR (DMSO-d$_6$) δ: 0.84 (s, 3H), 1.02 (ddd, J = 21.5, 11.7, 4.1 Hz, 2H), 1.18 (d, J = 7.1 Hz, 3H), 1.27 (d, J = 7.1 Hz, 3H), 1.37 (s, 3H), 1.54-1.81 (m, 5H), 1.95-2.03 (m, 1H), 2.09 (dd, J = 11.1, 4.0 Hz, 1H), 2.29 (d, J = 12.8 Hz, 1H), 2.36 (td, J = 7.1, 2.0 Hz, 2H), 2.49-2.59 (m, 1H), 3.57 (d, J = 7.3 Hz, 2H), 3.77 (s, 2H), 4.15 (d, J = 19.4 Hz, 1H), 4.23-4.34 (m, 2H), 4.38 (p, J = 7.1 Hz, 1H), 4.47 (d, J = 19.5 Hz, 1H), 4.74 (s, 1H), 4.89 (d, J = 5.3 Hz, 1H), 5.37 (s, 1H), 5.90 (t, J = 1.6 Hz, 1H), 6.13 (dd, J = 10.1, 1.9 Hz, 1H), 6.73 (d, J = 1.8 Hz, 2H), 6.97 (s, 2H), 7.17 (d, 2H), 7.28 (d, J = 10.1 Hz, 1H), 7.31-7.36 (m, 2H), 7.76 (d, J = 1.5 Hz, 1H), 8.17 (d, J = 7.6 Hz, 1H), 8.29 (d, J = 7.1 Hz, 1H), 8.90 (s, 1H), 9.72 (s, 1H) |
| 113 | Method r, Table 7 $R_t$ = 0.80 min; m/z = 880.26 [M + H$^+$] | $^1$H NMR (DMSO-d$_6$) δ: 0.84 (s, 3H), 1.04 (ddd, J = 34.7, 11.8, 4.1 Hz, 2H), 1.14 (d, J = 7.1 Hz, 3H), 1.25 (d, J = 7.1 Hz, 3H), 1.38 (s, 3H), 1.54-1.81 (m, 4H), 1.95-2.04 (m, 1H), 2.10 (tt, J = 10.9, 5.9 Hz, 1H), 2.25-2.33 (m, 1H), 2.37 (dd, J = 8.0, 6.5 Hz, 2H), 2.49-2.59 (m, 1H), 3.58 (t, J = 7.3 Hz, 2H), 3.78 (s, 2H), 4.15 (d, J = 19.4 Hz, 1H), 4.21 (p, J = 7.1 Hz, 1H), 4.25-4.36 (m, 2H), 4.45 (d, J = 19.4 Hz, 1H), 4.76 (s, 1H), 4.87 (d, J = 5.3 Hz, 1H), 5.27 (s, 1H), 5.92 (t, J = 1.6 Hz, 1H), 6.14 (dd, J = 10.1, 1.9 Hz, 1H), 6.77 (dd, J = 7.7, 1.6 Hz, 1H), 6.84-6.91 (m, 2H), 6.97 (s, 2H), 6.99 (d, J = 7.7 Hz, 1H), 7.11-7.17 (m, 1H), 7.30 (d, J = 10.1 Hz, 1H), 7.39-7.45 (m, 2H), 8.03 (d, J = 7.3 Hz, 1H), 8.16 (d, J = 7.2 Hz, 1H), 9.55 (s, 1H), 9.72 (s, 1H) |

Example 36: Synthesis of N-(3-Aminophenyl)-4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzamide

Step 1: Synthesis of 4-Formylbenzoyl Chloride

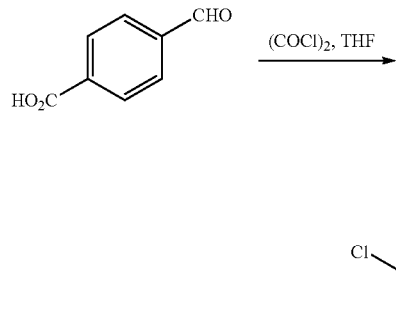

Oxalyl chloride (17.51 mL, 200 mmol) was added drop-wise to a 0° C. solution of 4-formylbenzoic acid (15.01 g, 100 mmol) in THF (100 mL), followed by N,N-dimethylformamide (0.387 mL, 5.00 mmol) in drop-wise addition. The mixture was allowed to warm to room temperature and then stirred for an additional 2 h. The mixture was concentrated in vacuo to give 4-formylbenzoyl chloride (16.86 g, 100 mmol, 100% yield), which was used without further purification.

Step 2: Synthesis of tert-Butyl (3-(4-formylbenzamido)phenyl)carbamate

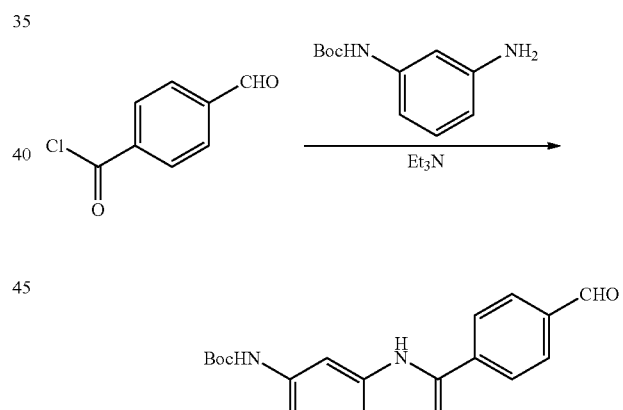

Triethylamine (63.4 mL, 455 mmol) was added drop-wise to a 0° C. solution of 4-formylbenzoyl chloride (16.86 g, 100 mmol) in THF (100 mL), followed by addition of tert-butyl (3-aminophenyl)carbamate (18.93 g, 91 mmol). After stirring at room temperature for 2 h, the mixture was diluted with EtOAc (200 mL), washed with water (2×100 mL) and brine (100 mL), dried over Na$_2$SO$_4$, and concentrated in vacuo. The residue was triturated in 20 mL of EtOAc/PE (1:1), and the resulting precipitate was collected to give tert-butyl (3-(4-formylbenzamido)phenyl)carbamate (27.8 g, 82 mmol, 90% yield) as a yellow solid. LCMS (Method e Table 7) R$_t$=2.00 min; MS m/z=285 [M-t-Bu].

Step 3: Synthesis of N-(3-Aminophenyl)-4-((6aR, 6bS,7S,8aS,8bS,10R,11aR,12aS, 12bS)-7-hydroxy-8b-(2-hydroxyacetyl)-6a,8a-dimethyl-4-oxo-2,4,6a, 6b,7,8,8a,8b,11a,12,12a,12b-dodecahydro-1H-naphtho[2',1':4,5]indeno[1,2-d][1,3]dioxol-10-yl) benzamide

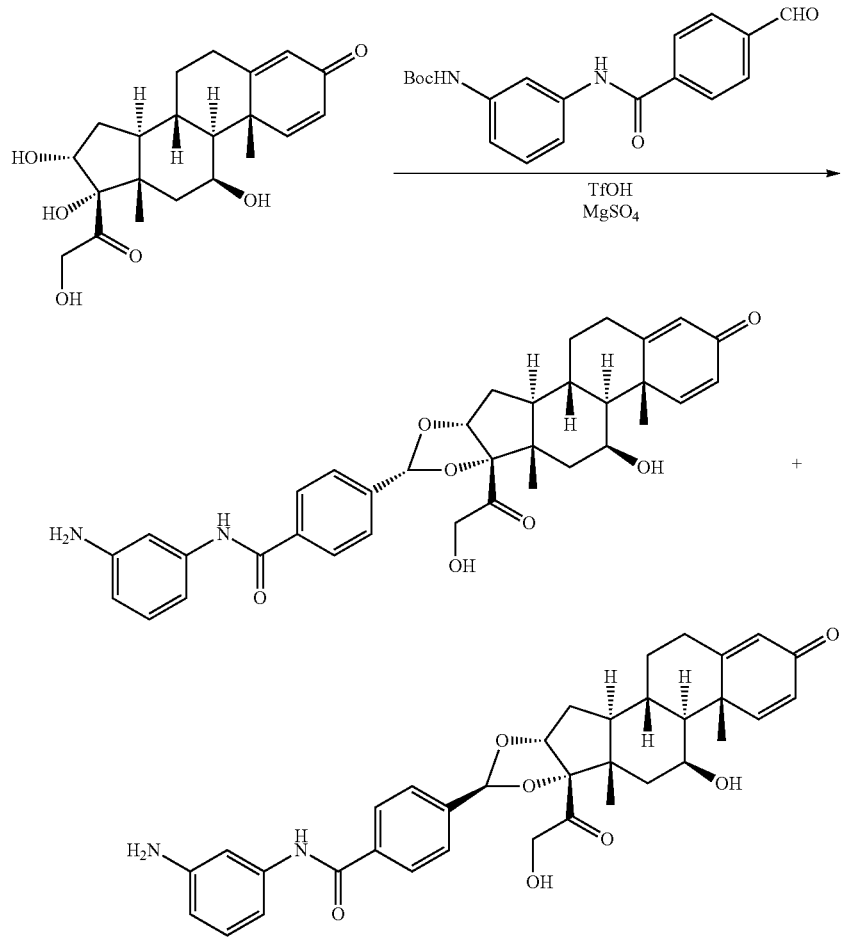

To a stirred solution of (8S,9S,10R,11S,13S,14S,16R, 17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (9.42 g, 25.02 mmol), tert-butyl (3-(4-formylbenzamido)phenyl) carbamate, made in a manner similar to Example 2, Step 5, (8.515 g, 25.02 mmol and MgSO₄ (12.04 g, 100 mmol) in MeCN (250 mL) was added drop-wise trifluoromethanesulfonic acid (11.11 ml, 125 mmol) at 0° C. The mixture was stirred at 0° C. for 2 hours and then warmed to room temperature and stirred for additional 16 h. The mixture was filtered and washed with THF, and the filtrate was concentrated in vacuo. The residue was dissolved in THF (100 mL) and then neutralized with 1 M NaOH aqueous solution to pH=8. The mixture was extracted with EtOAc (200 mL), washed with water (2×100 mL) and brine (100 mL), dried over Na₂SO₄, and concentrated in vacuo. Purification by chromatography (silica) eluting with 5% MeOH/DCM gave crude product, which was further purified by reverse phase HPLC on a Sunfire C18 10 micron (250×19 mm column). A gradient of MeCN (A) and 0.05% TFA in water (B) was used, at a flow rate of 30 mL/min (0-10.0 min linear gradient22-32%, hold 5 min). Combined fractions were frozen and lyophilized to give N-(3-aminophenyl)-4-((6aR,6bS,7S,8aS,8bS,10R,11aR, 12aS,12bS)-7-hydroxy-8b-(2-hydroxyacetyl)-6a,8a-dimethyl-4-oxo-2,4,6a,6b,7,8,8a,8b,11a, 12,12a,12b-dodecahydro-1H-naphtho[2',1':4,5]indeno[1,2-d][1,3]dioxol-10-yl) benzamide (1.972 g, 3.29 mmol, 13% yield) as a white solid. LCMS (Method f, Table 7) R$_t$=1.37 min; MS m/z=599 [M+H⁺]. ¹H NMR (400 MHz, Methanol-d₄) δ 8.01-7.92 (m, 3H), 7.64 (d, J=8.0 Hz, 2H), 7.55-7.40 (m, 3H), 7.05 (d, J=7.8 Hz, 1H), 6.27 (dd, J=10.2, 1.8 Hz, 1H), 6.03 (s, 1H), 5.60 (s, 1H), 5.13 (d, J=4.1 Hz, 1H), 4.68 (d, J=19.4 Hz, 1H), 4.45 (d, J=3.3 Hz, 1H), 4.37 (d, J=19.4 Hz, 1H), 2.68 (dt, J=14.5, 7.0 Hz, 1H), 2.41 (dd, J=13.7, 10.2 Hz, 1H), 2.29 (d, J=10.5 Hz, 1H), 2.18 (d, J=12.8 Hz, 1H), 1.99 (dd, J=13.8, 3.5 Hz, 1H), 1.94-1.80 (m, 2H), 1.82-1.69 (m, 2H), 1.52 (s, 3H), 1.14 (m, J=16.8, 8.0 Hz, 2H), 1.02 (s, 3H).

Minor acetal isomer: N-(3-Aminophenyl)-4-((6aR,6bS, 7S,8aS,8bS,10S,11aR,12aS,12bS)-7-hydroxy-8b-(2-hydroxyacetyl)-6a,8a-dimethyl-4-oxo-2,4,6a,6b,7,8,8a,8b,11a, 12,12a,12b-dodecahydro-1H-naphtho[2',1':4,5]indeno[1,2-d][1,3]dioxol-10-yl)benzamide (112 mg, 0.176 mmol, 0.9% yield) as a yellow solid. LCMS (Method e, Table 7) R$_t$=1.53 min; MS m/z=599 [M+H⁺]. ¹H NMR (400 MHz, MeOH-d₄) δ 7.90 (d, J=7.9 Hz, 2H), 7.48 (dd, J=8.1, 3.5 Hz, 3H), 7.15 (d, J=2.2 Hz, 1H), 7.09 (t, J=8.0 Hz, 1H), 6.96 (d, J=8.1 Hz, 1H), 6.59-6.51 (m, 1H), 6.28 (dd, J=10.1, 1.9 Hz, 1H), 6.25

(s, 1H), 6.05 (s, 1H), 5.51-5.37 (m, 1H), 4.45 (s, 1H), 4.30 (d, J=19.2 Hz, 1H), 4.14 (d, J=19.2 Hz, 1H), 2.70 (t, J=13.6 Hz, 1H), 2.43 (d, J=13.3 Hz, 1H), 2.22 (dd, J=23.3, 12.5 Hz, 2H), 2.07 (d, J=13.5 Hz, 1H), 1.93 (q, J=5.1, 3.5 Hz, 2H), 1.80 (d, J=14.0 Hz, 2H), 1.53 (d, J=1.7 Hz, 3H), 1.21 (dd, J=41.7, 12.1 Hz, 2H), 1.03 (s, 3H).

Example 37: Synthesis of N-(3-Aminophenyl)-4-((6aS,6bR,7S,8aS,8bS,10R,11aR,12aS,12bS)-6b-fluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzamide

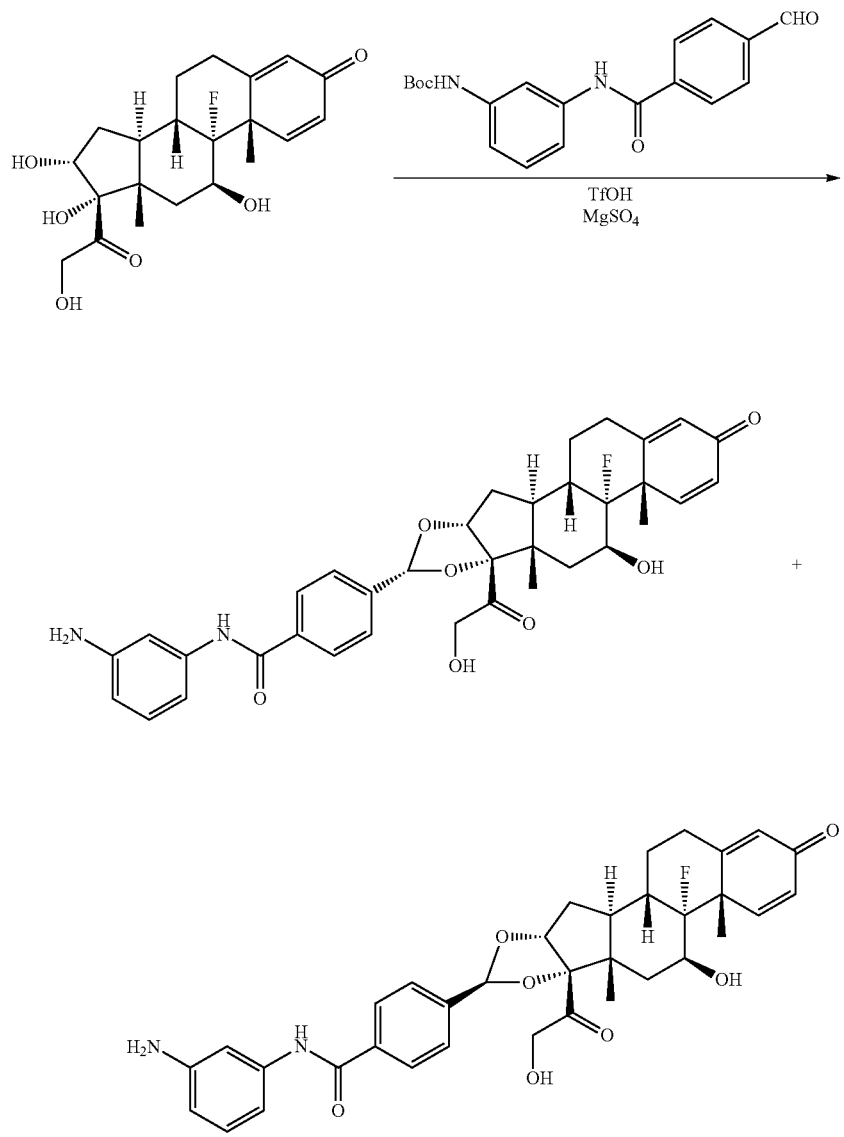

Synthesized using the same procedure as Example 36 above. Major acetal isomer: N-(3-Aminophenyl)-4-((6aS,6bR,7S,8aS,8bS,10R,11aR,12aS,12bS)-6b-fluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzamide. LCMS (Method f, Table 7) $R_t$=1.35 min; MS m/z=617 [M+H$^+$]. $^1$H NMR (400 MHz, DMSO-d$_6$) δ 10.29 (d, J=7.4 Hz, 1H), 8.00-7.93 (m, 2H), 7.73 (s, 1H), 7.59 (d, J=8.1 Hz, 2H), 7.43 (s, OH), 7.38 (s, 1H), 7.29 (dd, J=10.0, 5.3 Hz, 2H), 6.81 (s, 1H), 6.24 (dd, J=10.1, 1.9 Hz, 1H), 6.05 (d, J=1.6 Hz, 1H), 5.62 (s, 1H), 5.49 (s, 1H), 5.03-4.96 (m, 1H), 4.58 (d, J=19.5 Hz, 1H), 4.23 (d, J=19.6 Hz, 1H), 2.73-2.52 (m, 1H), 2.40-2.32 (m, 1H), 2.25-2.12 (m, 1H), 2.11-2.02 (m, 1H), 1.92-1.84 (m, 1H), 1.76-1.67 (m, 3H), 1.51 (s, 3H), 1.40 (tt, J=14.3, 7.1 Hz, 1H), 0.90 (s, 3H).

Minor acetal isomer: N-(3-Aminophenyl)-4-((6aS,6bR,7S,8aS,8bS,10S,11aR,12aS,12bS)-6b-fluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzamide. LCMS (Method B, Table 7) $R_t$=1.45 min; MS m/z=617 [M+H$^+$]. $^1$H NMR (400 MHz, DMSO-d$_6$) δ ppm: 8.06 (s, 1H), 7.95 (d, J=8.4 Hz, 2H), 7.54-7.41 (m, 5H), 7.09 (d, J=6.8 Hz, 1H), 6.34 (d, J=10 Hz, 1H), 6.28 (s, 1H), 6.13 (s, 1H), 5.49 (d, J=6.4 Hz, 1H), 4.34-4.13 (m, 3H), 2.79-2.24 (m, 5H), 1.74-1.63 (m, 2H), 1.60 (s, 3H), 1.04 (s, 3H).

Example 38: Synthesis of N-(3-Aminophenyl)-4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzamide

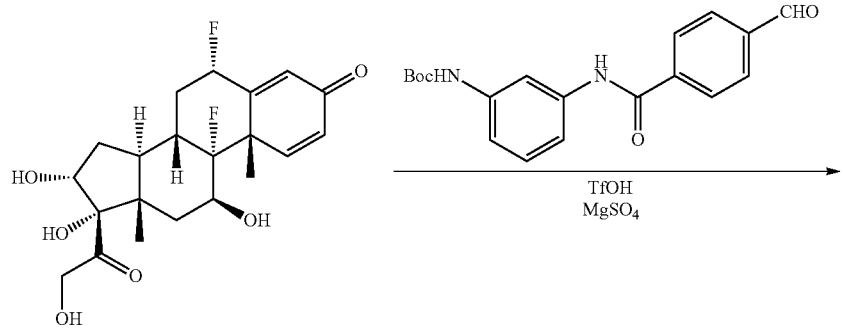

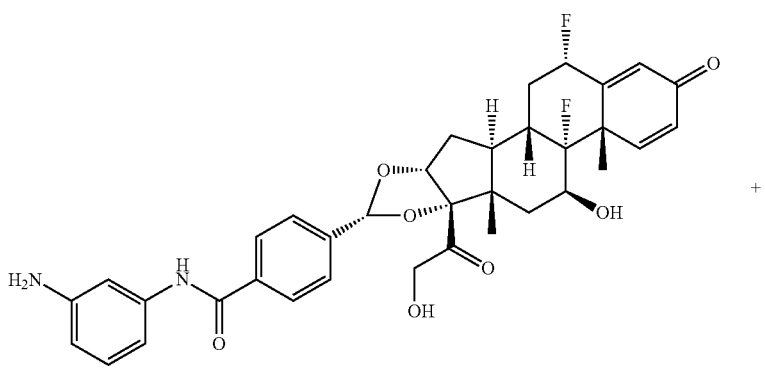

+

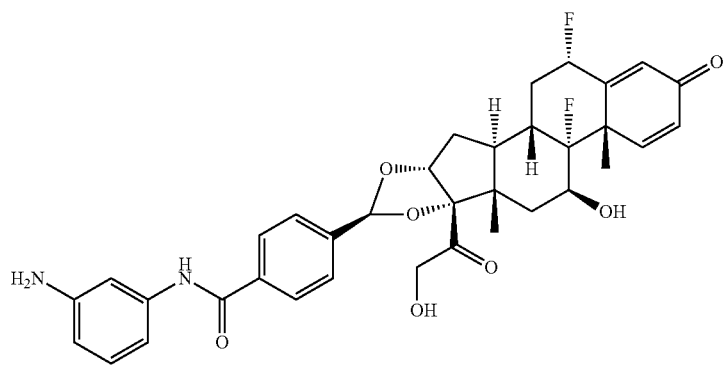

Synthesized using the same procedure as Example 36 above. Major acetal isomer: N-(3-Aminophenyl)-4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzamide. LCMS (Method f, Table 7) $R_f$=1.376 min, MS m/z=635 [M+H$^+$]. $^1$H NMR (400 MHz, MeOH-d$_4$) δ 7.96 (d, J=8.0 Hz, 2H), 7.88 (d, J=2.1 Hz, 1H), 7.64 (dd, J=8.3, 1.5 Hz, 2H), 7.48-7.42 (m, 1H), 7.39 (t, J=7.9 Hz, 1H), 7.34 (d, J=10.0 Hz, 1H), 6.98 (dt, J=7.7, 1.6 Hz, 1H), 6.41-6.26 (m, 2H), 5.71-5.45 (m, 2H), 5.14 (d, J=4.1 Hz, 1H), 4.69 (d, J=19.4 Hz, 1H), 4.44-4.28 (m, 2H), 2.73 (dt, J=25.9, 12.1 Hz, 1H), 2.41 (td, J=11.7, 6.9 Hz, 2H), 2.29 (dt, J=14.0, 3.6 Hz, 1H), 1.91-1.67 (m, 4H), 1.60 (s, 4H), 1.02 (s, 3H).

Minor acetal isomer: N-(3-Aminophenyl)-4-((2S,6aS,6bR,7S,8aS,8bS,10S,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzamide. LCMS (Method e, Table 7) $R_f$=1.506 min, MS m/z=635 [M+H$^+$]. $^1$H NMR (400 MHz, MeOH-d$_4$) δ 7.90 (d, J=8.0 Hz, 2H), 7.49 (d, J=7.9 Hz, 2H), 7.35 (d, J=10.0 Hz, 1H), 7.16 (d, J=2.2 Hz, 1H), 7.09 (t, J=8.0 Hz, 1H), 6.96 (d, J=8.2 Hz, 1H), 6.65-6.48 (m, 1H), 6.41-6.27 (m, 3H), 5.76-5.39 (m, 2H), 4.42-4.22 (m, 2H), 4.15 (d, J=19.4 Hz, 1H), 2.66 (dd, J=27.8, 13.4 Hz, 1H), 2.47-2.24 (m, 3H), 2.08-1.85 (m, 2H), 1.75 (t, J=14.9 Hz, 2H), 1.61 (s, 3H), 1.03 (s, 3H).

Example 39: Synthesis of 3-Aminophenyl 4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzoate

Step 1: Synthesis of tert-Butyl (3-hydroxyphenyl)carbamate

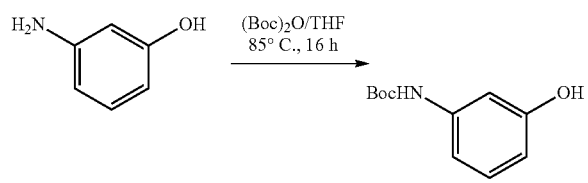

To a solution of 3-aminophenol (10 g, 92 mmol) in THF (450 mL) was added Boc anhydride (23.40 mL, 101 mmol). The mixture was heated at 85° C. for 16 h, monitored by LCMS. After that, the mixture was concentrated to obtain a residue, which was dissolved in EtOAc (150 mL) and washed with water (100 mL), saturated NaHCO$_3$ (100 mL) and brine (100 mL), dried over Na$_2$SO$_4$, and concentrated in vacuo. The crude material was washed with PE (50 mL×2) to give the title compound (16.5 g, 76 mmol, 82% yield) as a white solid. LCMS (Method g, Table 7) R$_t$=1.66 min, MS m/z=232.1 [M+Na$^+$].

Step 2: Synthesis of 3-((tert-Butoxycarbonyl)amino)phenyl 4-formylbenzoate

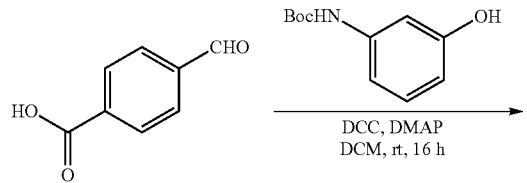

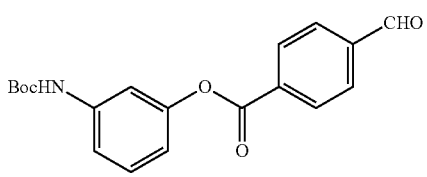

To a solution of tert-butyl (3-hydroxyphenyl)carbamate (5 g, 23.90 mmol) in DCM (60 mL) at 0° C. was added 4-formylbenzoic acid (3.59 g, 23.90 mmol), N,N'-dicyclohexylcarbodiimide (7.40 g, 35.8 mmol) and 4-dimethylaminopyridine (0.584 g, 4.78 mmol). The resulting mixture was stirred at that temperature for 10 min under an atmosphere of argon. Then the mixture was warmed to room temperature and stirring was continued for 16 h. The mixture was cooled in an ice bath. The side product N,N'-dicyclohexylurea was filtered off as a precipitate and the clear filtrate was concentrated under vacuum. The crude material was purified by silica gel chromatography eluting with DCM/EtOAc (100%-30:1) to give the title compound (7.0 g, 18.54 mmol, 78% yield) as a white solid. LCMS (Method d, Table 7) R$_t$=2.17 min, MS m/z=364.0 [M+Na$^+$].

Step 3: Synthesis of 3-Aminophenyl 4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzoate

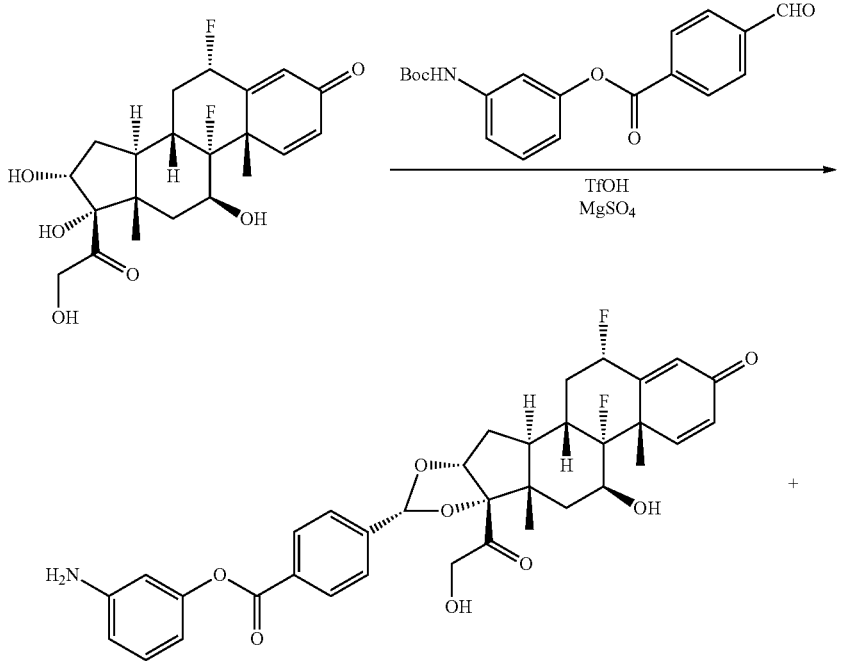

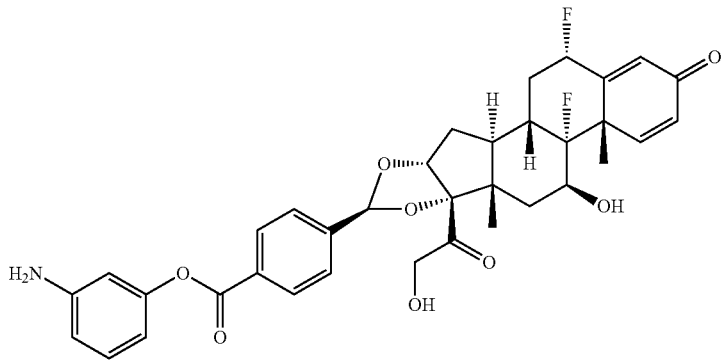

To a stirred solution of (6S,8S,9R,10S,11S,13S,14S,16R,17S)-6,9-difluoro-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (Step 5, Example 2) (7.248 g, 17.58 mmol) and 3-((tert-butoxycarbonyl)amino)phenyl 4-formylbenzoate (6 g, 17.58 mmol) in anhydrous MeCN (40 mL) and THF (40 mL) at 0° C. under nitrogen was added drop-wise trifluoromethanesulfonic acid (7.8 mL, 87.9 mmol). The mixture was stirred at 0° C. for 1 h, then poured onto ice water (30 mL) and extracted with EtOAc (2×45 mL). The combined organic layers were washed with cooled water (2×30 mL), brine (30 mL), saturated NaHCO₃ (30 mL) and additional water (30 mL), concentrated in vacuo affording a yellow solid. The crude material was purified by silica gel column chromatography (200-300 mesh), eluting with DCM/MmeOH (100%-40:1) and then further purified by prep HPLC to give the title compound (major acetal isomer) (2.166 g, 3.32 mmol, 19% yield) as a white solid. LCMS (Method d, Table 7) $R_t$=1.54 min; MS m/z=636.3 [M+H⁺]. ¹H NMR (400 MHz, DMSO-d₆) δ 8.13 (d, J=8.2 Hz, 2H), 7.66 (d, J=8.2 Hz, 2H), 7.27 (dd, J=10.1, 1.4 Hz, 1H), 7.06 (t, J=8.0 Hz, 1H), 6.48 (dd, J=8.3, 2.1 Hz, 1H), 6.40 (t, J=2.2 Hz, 1H), 6.34 (dd, J=7.8, 2.2 Hz, 1H), 6.30 (dd, J=10.1, 1.9 Hz, 1H), 6.12 (s, 1H), 5.82-5.47 (m, 3H), 5.31 (s, 2H), 5.15 (t, J=5.9 Hz, 1H), 5.03 (d, J=5.1 Hz, 1H), 4.60 (dd, J=19.5, 6.4 Hz, 1H), 4.33-4.12 (m, 2H), 2.66 (ddd, J=26.2, 13.7, 9.3 Hz, 1H), 2.31 (d, J=10.9 Hz, 1H), 2.21 (td, J=12.4, 6.3 Hz, 1H), 2.12-1.98 (m, 1H), 1.84-1.64 (m, 3H), 1.50 (s, 4H), 0.89 (s, 3H).

3-Aminophenyl 4-((2S,6aS,6bR,7S,8aS,8bS,10S,11aR,12aS,12bS)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzoate, the minor acetal isomer was also isolated (1.073 g, 1.676 mmol, 10% yield) as a white solid. LCMS (Method d, Table 7) $R_t$=1.58 min; MS m/z=636.3 [M+H⁺]. ¹H NMR (400 MHz, DMSO-d₆) δ 8.13-8.06 (m, 2H), 7.51 (d, J=8.2 Hz, 2H), 7.28 (dd, J=10.1, 1.4 Hz, 1H), 7.06 (t, J=8.0 Hz, 1H), 6.52-6.44 (m, 1H), 6.43-6.28 (m, 4H), 6.14 (s, 1H), 5.80-5.48 (m, 2H), 5.39 (d, J=6.8 Hz, 1H), 5.31 (s, 2H), 5.04 (t, J=6.1 Hz, 1H), 4.26-4.15 (m, 2H), 4.05 (dd, J=19.2, 5.9 Hz, 1H), 2.67-2.51 (m, 1H), 2.29 (d, J=6.9 Hz, 1H), 2.27-2.14 (m, 1H), 2.11 (d, J=13.5 Hz, 1H), 1.96-1.59 (m, 4H), 1.51 (s, 3H), 0.90 (s, 3H).

Example 40: Synthesis of 3-Aminophenyl 4-((6aS,6bR,7S,8aS,8bS,10R,11aR,12aS,12bS)-6b-fluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzoate

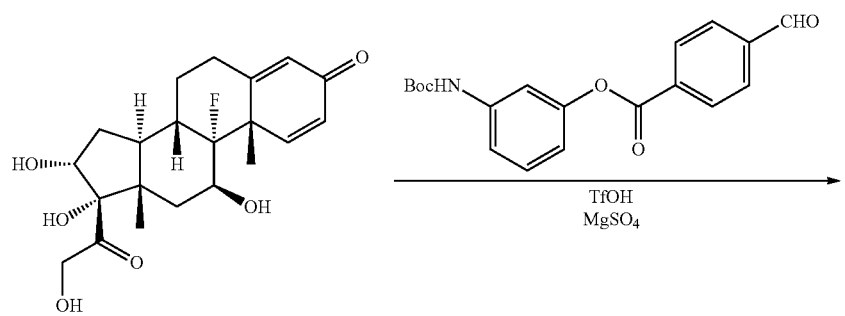

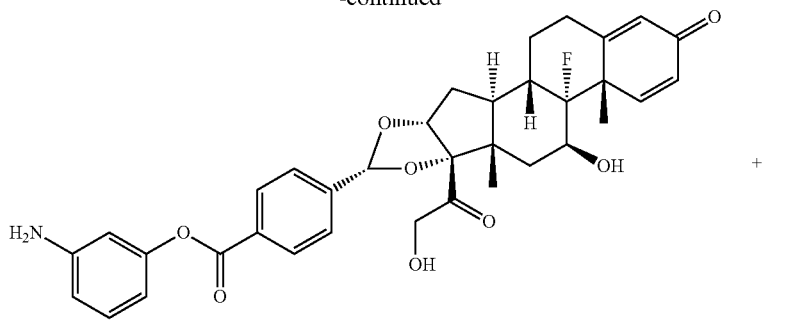

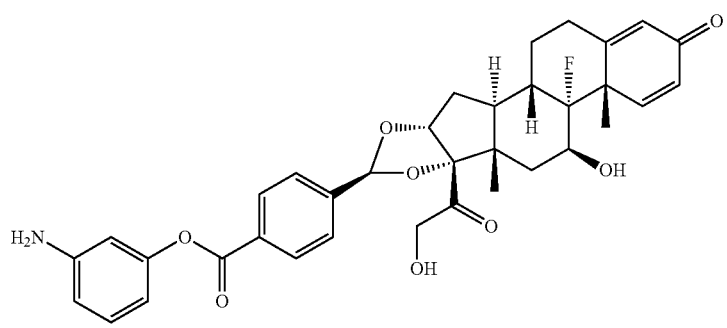

Synthesized using the same procedure as Example 39 above. Major acetal isomer: 3-aminophenyl 4-(((6aS,6bR,7S,8aS,8bS,10R,11aR,12aS,12bS)-6b-fluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzoate. LCMS (Method d, Table 7) $R_t$=1.54 min; MS m/z=618.3 [M+H$^+$]. $^1$H NMR (400 MHz, MeOH-d$_4$) δ 8.19 (dd, J=7.8, 1.9 Hz, 2H), 7.67 (d, J=8.0 Hz, 2H), 7.41 (d, J=10.1 Hz, 1H), 7.35 (t, J=8.0 Hz, 1H), 6.97-6.84 (m, 3H), 6.32 (dd, J=10.1, 1.9 Hz, 1H), 6.12 (s, 1H), 5.63 (s, 1H), 5.13 (d, J=5.0 Hz, 1H), 4.69 (d, J=19.4 Hz, 1H), 4.43-4.30 (m, 2H), 2.76 (td, J=13.6, 5.8 Hz, 1H), 2.70-2.54 (m, 1H), 2.43 (d, J=13.6 Hz, 1H), 2.31 (ddd, J=14.9, 11.6, 4.5 Hz, 2H), 2.01-1.92 (m, 1H), 1.89-1.69 (m, 3H), 1.62 (s, 4H), 1.03 (s, 3H).

Minor acetal isomer: 3-aminophenyl 4-(((6aS,6bR,7S,8aS,8bS,10S,11aR,12aS,12bS)-6b-fluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzoate. LCMS (Method d, Table 7) $R_t$=1.58 min; MS m/z=618.2 [M+H$^+$]. $^1$H NMR (400 MHz, DMSO-d$_6$) δ 8.10 (d, J=8.1 Hz, 2H), 7.52 (d, J=8.1 Hz, 2H), 7.30 (d, J=10.1 Hz, 1H), 7.16 (dd, J=9.8, 6.0 Hz, 1H), 6.64 (d, J=8.2 Hz, 1H), 6.61-6.51 (m, 2H), 6.31-6.19 (m, 2H), 6.05 (s, 1H), 5.47 (s, 1H), 5.38 (d, J=6.7 Hz, 1H), 4.19 (d, J=18.7 Hz, 2H), 4.04 (d, J=19.2 Hz, 1H), 2.66 (td, J=13.9, 6.3 Hz, 1H), 2.48-2.33 (m, 1H), 2.17-2.05 (m, 2H), 1.87 (dt, J=13.8, 7.0 Hz, 2H), 1.84-1.69 (m, 2H), 1.51 (s, 4H), 0.90 (s, 3H).

Example 41: Synthesis of 3-Aminophenyl 4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzoate

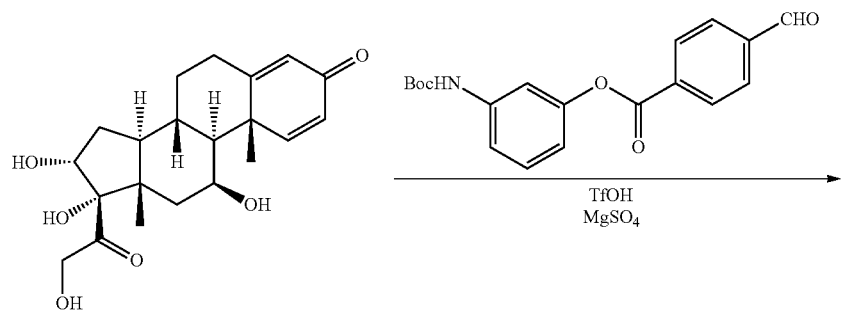

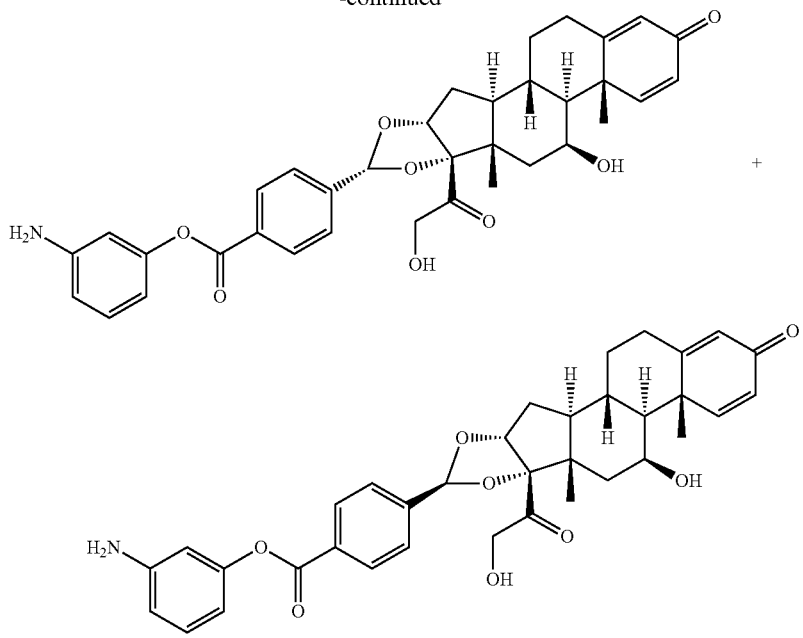

Synthesized using the same procedure as Example 39 above. Major acetal isomer: 3-aminophenyl 4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,1a,12,12a,12b-dodecahydro-1H-naphtho[2′,1′:4,5]indeno[1,2-d][1,3]dioxol-10-yl)benzoate. LCMS (Method d, Table 7) $R_t$=1.86 min; MS m/z=599.8 [M+H$^+$]. $^1$H NMR (400 MHz, MeOH-d$_4$) δ 8.14 (d, J=8.2 Hz, 2H), 7.64 (d, J=8.1 Hz, 2H), 7.44 (d, J=10.0 Hz, 1H), 7.14 (t, J=8.0 Hz, 1H), 6.63 (dd, J=8.1, 2.2 Hz, 1H), 6.54 (q, J=2.6 Hz, 1H), 6.48 (dd, J=8.1, 2.2 Hz, 1H), 6.24 (dd, J=10.0, 2.0 Hz, 1H), 6.00 (s, 1H), 5.59 (s, 1H), 5.13 (d, J=4.4 Hz, 1H), 4.69 (d, J=19.4 Hz, 1H), 4.43 (q, J=3.3 Hz, 1H), 4.37 (d, J=19.4 Hz, 1H), 2.66 (td, J=13.4, 5.3 Hz, 1H), 2.38 (dd, J=13.7, 4.1 Hz, 1H), 2.32-2.19 (m, 1H), 2.14 (d, J=12.7 Hz, 1H), 2.06-1.93 (m, 1H), 1.94-1.85 (m, 1H), 1.89-1.68 (m, 3H), 1.50 (s, 3H), 1.22-1.01 (m, 2H), 1.02 (s, 3H).

Minor acetal isomer: 3-aminophenyl 4-((6aR,6bS,7S,8aS,8bS,10S,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2′,1′:4,5]indeno[1,2-d][1,3]dioxol-10-yl)benzoate. LCMS (Method d, Table 7) $R_t$=1.89 min; MS m/z=599.8 [M+H$^+$]. $^1$H NMR (400 MHz, MeOH-d$_4$) δ 8.22-8.11 (m, 2H), 7.53 (d, J=8.2 Hz, 2H), 7.49 (d, J=10.0 Hz, 1H), 7.14 (t, J=8.0 Hz, 1H), 6.63 (dd, J=8.1, 2.1 Hz, 1H), 6.55 (t, J=2.2 Hz, 1H), 6.53-6.45 (m, 1H), 6.33-6.24 (m, 2H), 6.05 (t, J=1.6 Hz, 1H), 5.46 (t, J=3.8 Hz, 1H), 4.46 (q, J=3.3 Hz, 1H), 4.30 (d, J=19.2 Hz, 1H), 4.15 (d, J=19.2 Hz, 1H), 2.70 (td, J=13.5, 5.4 Hz, 1H), 2.48-2.38 (m, 1H), 2.23 (ddd, J=24.3, 12.6, 6.6 Hz, 2H), 2.12-2.03 (m, 1H), 2.02-1.89 (m, 2H), 1.89-1.77 (m, 2H), 1.53 (s, 3H), 1.26 (tt, J=12.4, 6.3 Hz, 1H), 1.17 (dd, J=11.1, 3.6 Hz, 1H), 1.03 (s, 3H).

Example 42: Synthesis of (6aR,6bS,7S,8aS,8bS,10R,11aR,12aS,12bS)-10-(4-((3-Aminophenoxy)methyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2′,1′:4,5]indeno[1,2-d][1,3]dioxol-4-one Step 1: Synthesis of tert-Butyl (3-((4-formylbenzyl)oxy)phenyl)carbamate

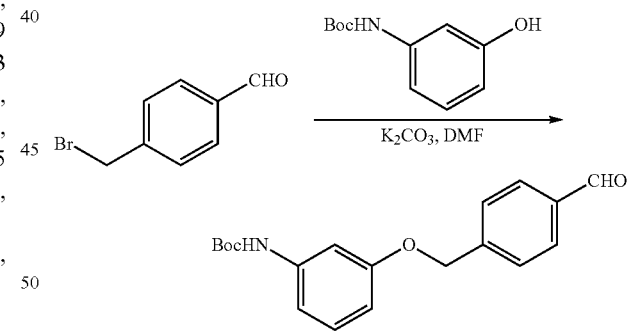

K$_2$CO$_3$ (47.8 g, 346 mmol) and tert-butyl (3-hydroxyphenyl)carbamate (36.2 g, 173 mmol) were added sequentially to a solution of 4-(bromomethyl)benzaldehyde (34.4 g, 173 mmol) in dimethyl formamide (200 mL). The yellow suspension was then heated at 80° C. in an oil bath for 2 h. The reaction was quenched with water (200 mL) and extracted with EtOAc (2×200 mL). The combined organic layers were washed with brine (100 mL), dried over Na$_2$SO$_4$, and were concentrated under reduced pressure. The residue obtained was purified by chromatography (silica gel; petroleum ether to 80:20 PE/EtOAc; gradient elution) to provide tert-butyl (3-((4-formylbenzyl)oxy)phenyl)carbamate (47.27 g, 144 mmol, 83% yield) as a white solid. LCMS (Method h Table 7) $R_t$=1.92 min; MS m/z=272 [M-t-Bu+H$^+$].

Step 2: Synthesis of (6aR,6bS,7S,8aS,8bS,10R, 11aR,12aS,12bS)-10-(4-((3-Aminophenoxy)methyl) phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

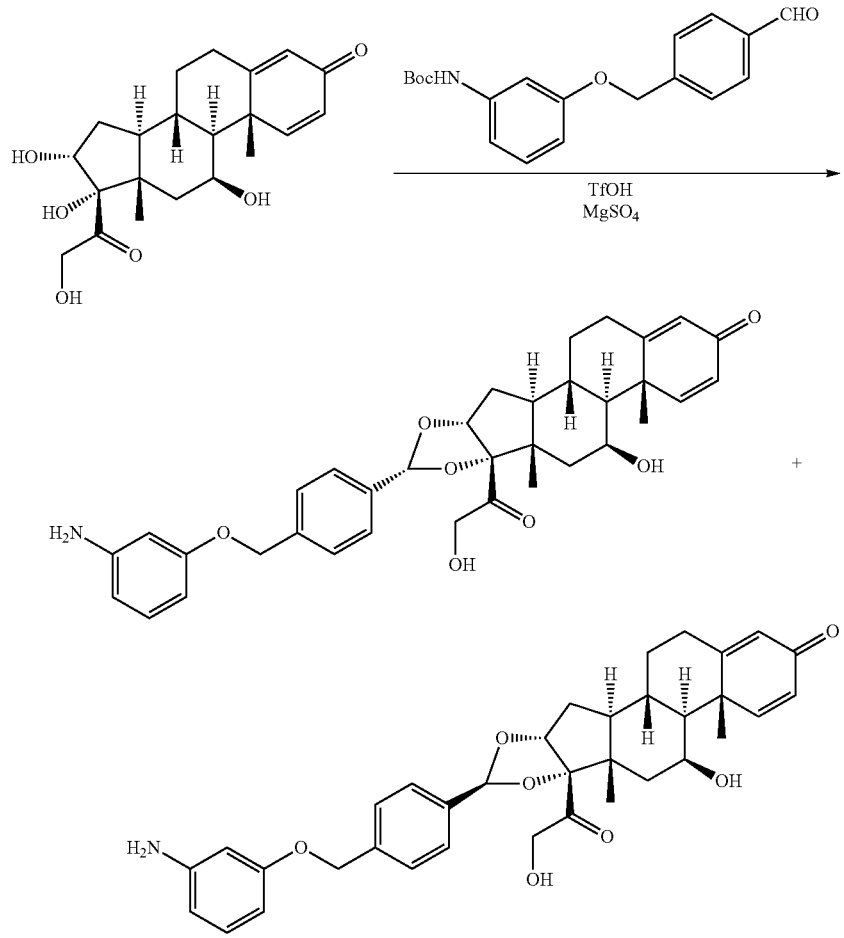

Trifluoromethanesulfonic acid (17.76 mL, 200 mmol) was added drop-wise to a stirred 0° C. suspension of (8S,9S,10R,11S,13S,14S,16R,17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (15.06 g, 40 mmol) and tert-butyl (3-((4-formylbenzyl)oxy) phenyl) carbamate (13.75 g, 42.0 mmol), and MgSO₄ (19.26 g, 160 mmol) in MeCN (400 mL). The reaction mixture was then warmed to 20° C. and stirred for an additional 2 h. The mixture was filtered and washed with THF, and the filtrate was concentrated in vacuo. The residue was dissolved in THF (100 mL), neutralized with 1 M aqueous NaOH to pH 8, diluted with EtOAc (200 mL), washed with water (2×200 mL) and brine (200 mL), dried (Na₂SO₄), and concentrated in vacuo. The residue was purified by flash column (MeOH: DCM=1:20). The resulting material was purified further by prep HPLC on a Sunfire C18 10 micron (250×19 mm column). A gradient of MeCN (A) and 0.05% TFA in water (B) was used, at a flow rate of 30 mL/min (0-10.0 min linear gradient 22-32% A, hold 5 min) to give the title compound (7.338 g, 12.15 mmol, 30% yield) as a yellow solid. LCMS (Method i, Table 7) $R_t$=1.47 min; MS m/z=586 [M+H⁺]. ¹H NMR (400 MHz, MeOD-d₄) δ 7.502-7.446 (m, 5H), 7.389-7.349 (m, 1H), 7.009, 6.988 (dd, J1=2 Hz, J2=8.4 Hz, 1H), 6.890-6.859 (m, 2H), 6.275, 6.250 (dd, J1=1.2 Hz, J2=8.8 Hz, 1H), 6.027 (s, 1H), 5.501 (s, 1H), 5.147 (s, 2H), 5.107, 5.078 (dd, J1=6.8 Hz, J2=11.6 Hz, 1H), 4.672 (d, J=19.6 Hz, 1H), 4.436 (s, 1H), 4.370 (d, J=19.2 Hz, 1H), 2.706-2.671 (m, 1H), 2.652-2.265 (m, 3H), 2.002-1.700 (m, 5H), 1.512 (s, 3H), 1.151-1.112 (m, 1H), 1.054-1.009 (m, 4H).

Minor acetal isomer: (6aR,6bS,7S,8aS,8bS,10S,11aR,12aS,12bS)-10-(4-((3-aminophenoxy)methyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one, the minor acetal isomer was also isolated (354 mg, 0.604 mmol, 2% yield) as a yellow solid. LCMS (Method i, Table 7) $R_t$=1.51 min; MS m/z=586 [M+H⁺]. ¹H NMR (400 MHz, DMSO-d₆) δ 7.416 (d, J=8 Hz, 2H), 7.332-7.276 (m, 3H), 6.879 (t, J=8 Hz, 1H), 6.185-6.115 (m, 5H), 5.948 (s, 1H), 5.319 (d, J=6.8 Hz, 1H), 5.041-5.014 (m, 3H), 4.980 (s, 2H), 4.791 (d, J=3.2 Hz, 1H), 4.302-4.239 (m, 2H), 4.056, 4.008 (dd, J1=6 Hz, J2=19.6 Hz, 1H), 2.552-2.540 (m, 1H), 2.337-2.304 (m, 1H), 2.075-2.005 (m, 2H), 1.884-1.736 (m, 5H), 1.395 (s, 3H), 1.219-1.045 (m, 2H), 0.892 (s, 3H).

Example 43: Synthesis of (6aS,6bR,7S,8aS,8bS, 10R,11aR,12aS,12bS)-10-(4-((3-aminophenoxy) methyl)phenyl)-6b-fluoro-7-hydroxy-8b-(2-hydroxy-acetyl)-6a,8a-dimethyl-1,2,6a,6b,7,8,8a,8b,11a,12, 12a,12b-dodecahydro-4H-naphtho[2',1':4,5]indeno [1,2-d][1,3]dioxol-4-one

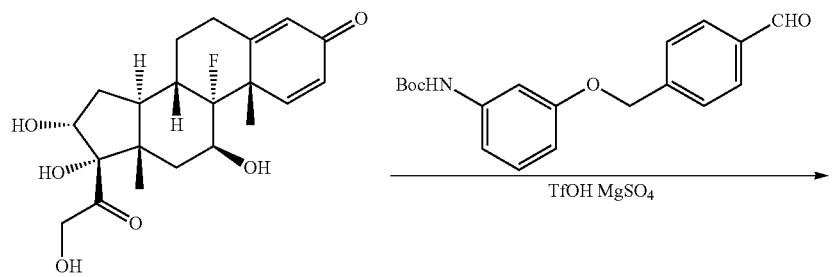

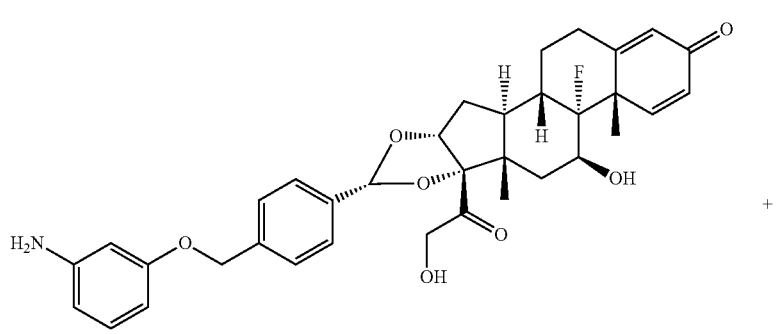

+

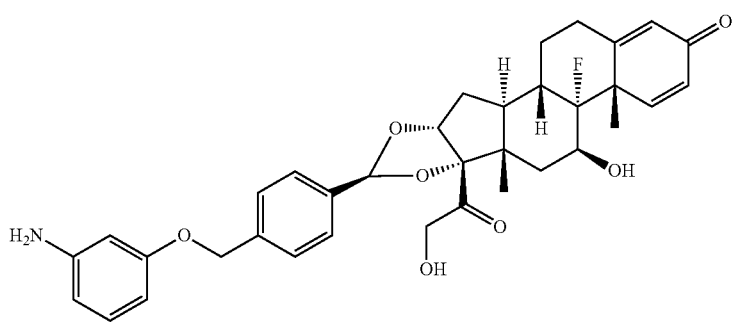

Synthesized using the same procedure as Example 42 above. Major acetal isomer: (6aS,6bR,7S,8aS,8bS,10R, 11aR,12aS,12bS)-10-(4-((3-aminophenoxy)methyl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method i, Table 7) R$_t$=1.74 min; MS m/z=604 [M+H$^+$]. $^1$H NMR (400 MHz, CD$_3$OD) δ 7.48-7.49 (m, 4H), 7.44-7.33 (m, 2H), 7.02 (dd, J=8.3, 1.9 Hz, 1H), 6.96-6.84 (m, 2H), 6.32 (dd, J=10.1, 1.8 Hz, 1H), 6.13 (s, 1H), 5.52 (s, 1H), 5.16 (s, 2H), 5.08 (d, J=4.9 Hz, 1H), 4.65 (d, J=19.4 Hz, 1H), 4.46-4.27 (m, 2H), 2.84-2.50 (m, 2H), 2.45-2.27 (m, 3H), 2.01-1.90 (m, 1H), 1.80-1.70 (m, 3H), 1.62 (s, 3H), 1.55 (dd, J=12.8, 4.8 Hz, 1H), 1.02 (s, 3H).

Minor acetal isomer: (6aS,6bR,7S,8aS,8bS,10S,11aR, 12aS,12bS)-10-(4-((3-aminophenoxy)methyl)phenyl)-6b-fluoro-7-hydroxy-8b-(2-hydroxyacetyl)-6a,8a-dimethyl-1, 2,6a,6b,7,8,8a,8b,11a,12,12a,12b-dodecahydro-4H-naphtho [2',1':4,5]indeno[1,2-d][1,3]dioxol-4-one. LCMS (Method i, Table 7) R$_t$=1.77 min; MS m/z=604 [M+H$^+$]. $^1$H NMR (400 MHz, DMSO) δ 7.42 (d, J=8.1 Hz, 2H), 7.36-7.25 (m, 3H), 7.01 (t, J=8.1 Hz, 1H), 6.43-6.30 (m, 3H), 6.24 (dd, J=10.1, 1.5 Hz, 1H), 6.12 (s, 1H), 6.04 (s, 1H), 5.47 (s, 1H), 5.35 (d, J=7.1 Hz, 1H), 5.02 (s, 2H), 4.31-4.14 (m, 2H), 4.04 (d, J=19.2 Hz, 1H), 2.72-2.58 (m, 1H), 2.18-1.98 (m, 2H), 1.85 (d, J=6.9 Hz, 2H), 1.77-1.63 (m, 2H), 1.58-1.40 (m, 4H), 0.90 (s, 3H).

Example 44: Synthesis of (2S,6aS,6bR,7S,8aS,8bS, 10R,11aR,12aS,12bS)-10-(4-((3-Aminophenoxy) methyl)phenyl)-2,6b-difluoro-7-hydroxy-8b-(2-hydroxyacetyl)-6a,8a-dimethyl-1,2,6a,6b,7,8,8a,8b,11a, 12,12a,12b-dodecahydro-4H-naphtho[2',1':4,5] indeno[1,2-d][1,3]dioxol-4-one

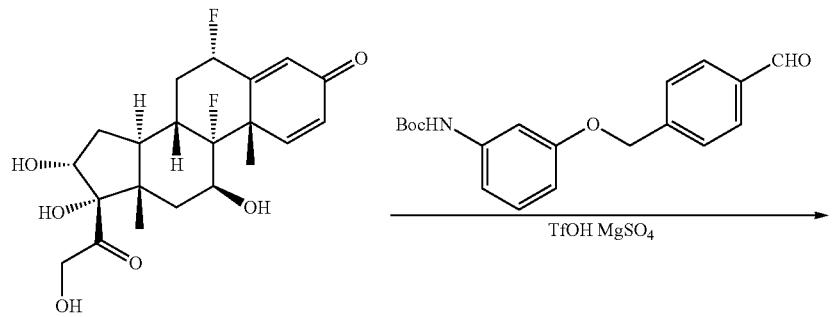

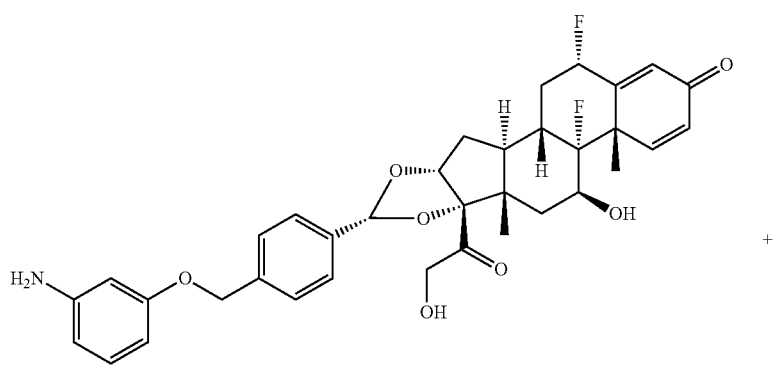

+

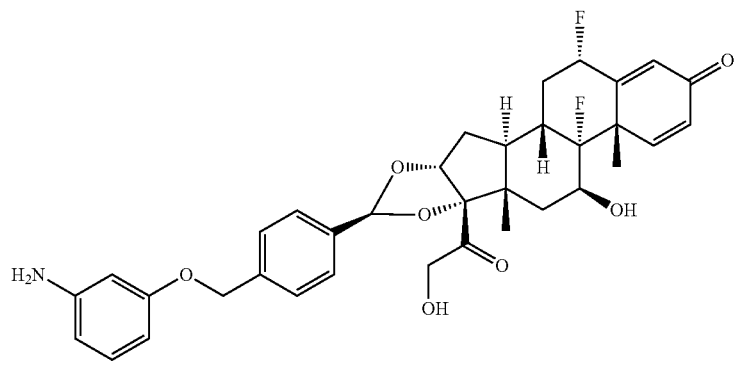

Synthesized using the same procedure as Example 42 above. Major acetal isomer: (2S,6aS,6bR,7S,8aS,8bS,10R, 11aR,12aS,12bS)-10-(4-((3-aminophenoxy)methyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method f, Table 7) $R_t$=1.45 min; MS m/z=622 [M+H$^+$]. $^1$H NMR (400 MHz, DMSO) δ 7.44 (s, 4H), 7.27 (d, J=10.1 Hz, 1H), 6.87 (t, J=8.0 Hz, 1H), 6.30 (dd, J=10.1, 1.5 Hz, 1H), 6.24-6.04 (m, 4H), 5.81-5.39 (m, 3H), 5.13 (t, J=5.9 Hz, 1H), 5.09-4.91 (m, 5H), 4.55 (dd, J=19.5, 6.4 Hz, 1H), 4.32-4.09 (m, 2H), 3.60 (t, J=6.3 Hz, 2H), 2.81-2.55 (m, 1H), 2.40-2.14 (m, 2H), 2.06 (d, J=13.6 Hz, 1H), 1.85-1.63 (m, 6H), 1.58-1.43 (m, 4H), 0.88 (s, 3H).

Minor acetal isomer: (2S,6aS,6bR,7S,8aS,8bS,10S,11aR, 12aS,12bS)-10-(4-((3-aminophenoxy)methyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method f, Table 7) $R_t$=1.49 min; MS m/z=622 [M+H$^+$]. $^1$H NMR (400 MHz, DMSO) δ 7.41 (d, J=8.1 Hz, 3H), 7.35-7.20 (m, 3H), 6.88 (t, J=8.0 Hz, 1H), 6.31 (dd, J=10.1, 1.6 Hz, 1H), 6.16 (dd, J=13.9, 5.0 Hz, 6H), 5.77-5.45 (m, 2H), 5.36 (d, J=7.1 Hz, 1H), 4.35-4.13 (m, 2H), 4.05 (dd, J=18.9, 4.9 Hz, 1H), 2.70-2.53 (m, 1H), 2.29 (s, 1H), 2.24-2.13 (m, 1H), 2.12-2.04 (m, 1H), 1.96-1.81 (m, 1H), 1.81-1.63 (m, 3H), 1.50 (s, 4H), 0.89 (s, 3H).

Example 45: Synthesis of (6aR,6bS,7S,8aS,8bS, 10R,11aR,12aS,12bS)-10-(4-((3-Aminobenzyl)oxy) phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one Step 1: Synthesis of tert-Butyl (3-(hydroxymethyl)phenyl)carbamate

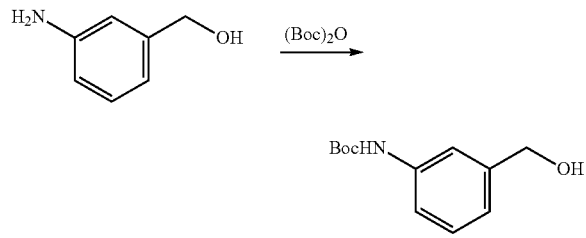

To a solution of (3-aminophenyl)methanol (88.5 g, 719 mmol) in THF (80 mL) was added di-tert-butyl dicarbonate (184 mL, 790 mmol). The mixture was stirred at 25° C. overnight. The mixture was then concentrated to dryness and the residue was purified by silica gel column chromatography (eluted with EtOAc/hexanes=1:9, v/v) to afford the title compound (161.1 g, 722 mmol, 100% yield), as a white solid. LCMS (Method j, Table 7) $R_t$=1.77 min; MS m/z=246 [M+Na⁻]. Step 2: Synthesis of tert-Butyl (3-(bromomethyl) phenyl)carbamate

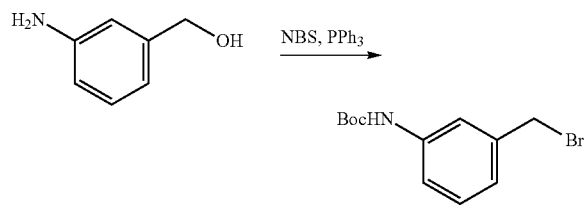

To a solution of tert-butyl (3-(hydroxymethyl)phenyl) carbamate (120 g, 484 mmol) in THF (50 mL) at −20° C. was added triphenylphosphine (254 g, 967 mmol) followed by N-bromosuccinimide (103 g, 580 mmol). After stirring for 3 h, the solvent was removed in vacuo, and the residue was purified by silica gel column chromatography (eluted with hexane:EtOAc=100:1) to provide the title compound (125 g, 437 mmol, 90% yield) as a white solid. LCMS (Method j, Table 7) $R_t$=2.10 min; MS m/z=230, 232 [M-t-Bu+H⁺].

Step 3: Synthesis of tert-Butyl (3-((4-formylphenoxy)methyl)phenyl)carbamate

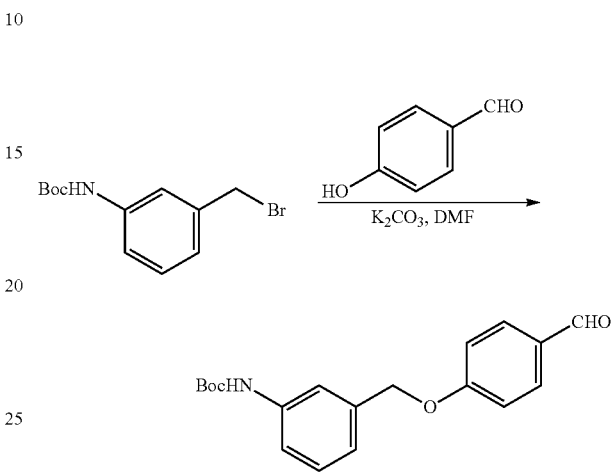

A mixture of 4-hydroxybenzaldehyde (25.6 g, 210 mmol) and potassium carbonate (29.0 g, 210 mmol) in dimethyl formamide (300 mL) was stirred for 15 min. Then tert-butyl (3-(bromomethyl)phenyl)carbamate (60 g, 210 mmol) was added. The mixture was heated to 60° C. and stirred for 2 hours at this temperature. The mixture was poured into 50 mL of water, extracted with EtOAc (3×50 mL). The combined organic layers was washed with water (1×100 mL) and brine (1×100 mL), concentrated in vacuum. The crude material was purified by silica gel column chromatography (eluted with dichloromethane/methanol=500:1) to afford the title compound (72 g, 209 mmol, 100% yield) as a white solid. LCMS (Method j, Table 7) $R_t$=2.08 min; MS m/z=272 [M-t-Bu+H⁺].

Step 4: Synthesis of (6aR,6bS,7S,8aS,8bS,10R, 11aR,12aS,12bS)-10-(4-((3-aminobenzyl)oxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

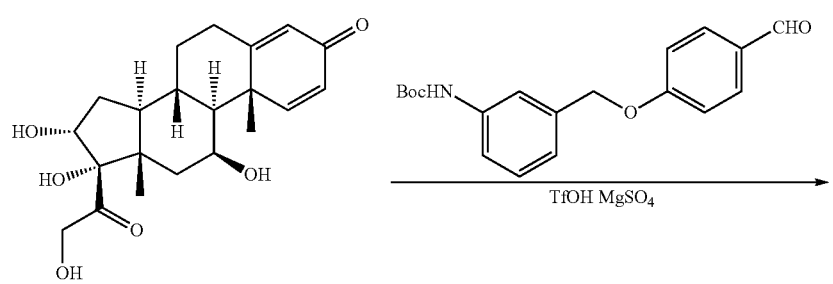

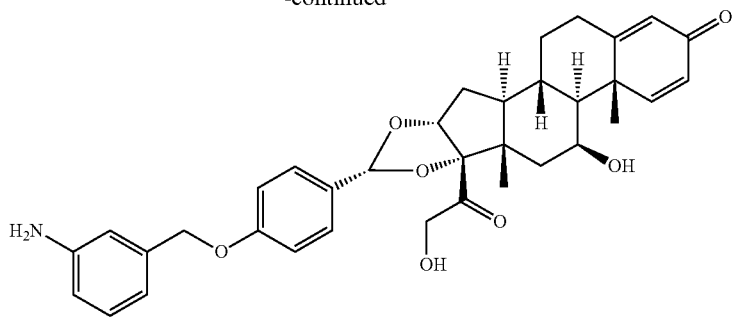

Trifluoromethanesulfonic acid (12.38 mL, 139 mmol) was added drop-wise to a mixture of magnesium sulfate (13.43 g, 112 mmol), tert-butyl (3-((4-formylphenoxy)methyl)phenyl)carbamate (10.96 g, 33.5 mmol) and (8S,9S,10R,11S,13S,14S,16R,17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (10.5 g, 27.9 mmol) in MeCN (150 mL) at 0° C. The mixture was warmed to room temperature and stirred for 2 hours at this temperature. The mixture was filtered and the filtrate was poured into 500 mL of saturated sodium bicarbonate solution, extracted with EtOAc (250 mL). The organic layer was washed with brine (200 mL) and water (200 mL), concentrated in vacuo. The crude material was purified by silica gel column chromatography (eluted with DCM-MeOH=50:1, v/v), and the resulting product was purified further by prep-HPLC to afford the title compound (6.04 g, 10.31 mmol, 37% yield) as a white solid. LCMS (Method k, Table 7) R$_t$=1.91 min; MS m/z=586 [M+H$^+$]. $^1$H NMR (400 MHz, DMSO-d$_6$) δ 7.35 (dd, J=19.6, 9.4 Hz, 3H), 6.61-6.33 (m, 3H), 6.18 (dd, J=10.1, 1.7 Hz, 1H), 5.95 (s, 1H), 5.38 (s, 1H), 5.16-5.01 (m, 3H), 5.02-4.85 (m, 3H), 4.80 (d, J=3.0 Hz, 1H), 4.50 (dd, J=19.5, 6.3 Hz, 1H), 4.31 (s, 1H), 4.18 (dd, J=19.4, 5.5 Hz, 1H), 2.33 (d, J=10.5 Hz, 1H), 2.17-1.98 (m, 2H), 1.90-1.53 (m, 5H), 1.40 (s, 3H), 1.13-0.96 (m, 2H), 0.87 (s, 3H).

Example 46: Synthesis of (6aS,6bR,7S,8aS,8bS,10R,11aR,12aS,12bS)-10-(4-((3-aminobenzyl)oxy)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

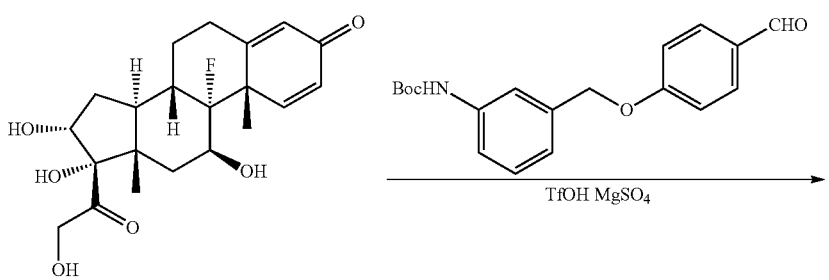

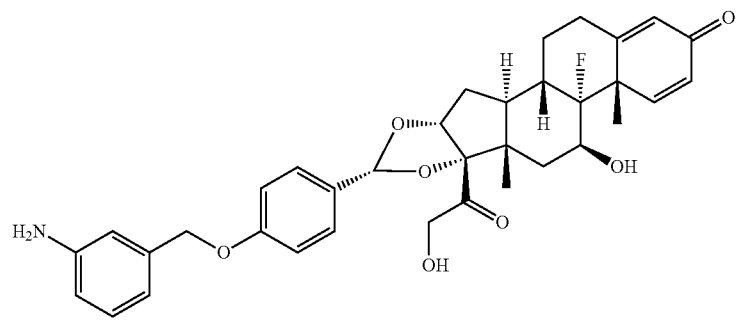

Synthesized using the same procedure as Example 45 above. LCMS (Method k, Table 7) R$_t$=1.89 min; MS m/z=604 [M+H$^+$]. $^1$H NMR (400 MHz, DMSO-d$_6$) δ 7.32 (dd, J=17.3, 9.4 Hz, 3H), 7.10-6.94 (m, 3H), 6.65-6.35 (m, 3H), 6.25 (dd, J=10.1, 1.7 Hz, 1H), 6.05 (s, 1H), 5.58-5.32 (m, 2H), 5.22-5.03 (m, 3H), 5.01-4.86 (m, 3H), 4.52 (dd, J=19.5, 6.4 Hz, 1H), 4.20 (dd, J=19.4, 5.5 Hz, 2H), 2.78-2.56 (m, 1H), 2.44-2.31 (m, 1H), 2.19 (td, J=12.0, 6.8 Hz, 1H), 2.06 (d, J=13.7 Hz, 1H), 1.95-1.81 (m, 1H), 1.68 (dd, J=15.4, 9.7 Hz, 3H), 1.57-1.30 (m, 4H), 0.88 (s, 3H).

Example 47: Synthesis of (2S,6aS,6bR,7S,8aS,8bS, 10R,11aR,12aS,12bS)-10-(4-((3-aminobenzyl)oxy) phenyl)-2,6b-difluoro-7-hydroxy-8b-(2-hydroxy-acetyl)-6a,8a-dimethyl-1,2,6a,6b,7,8,8a,8b,11a,12, 12a,12b-dodecahydro-4H-naphtho[2',1':4,5]indeno [1,2-d][1,3]dioxol-4-one

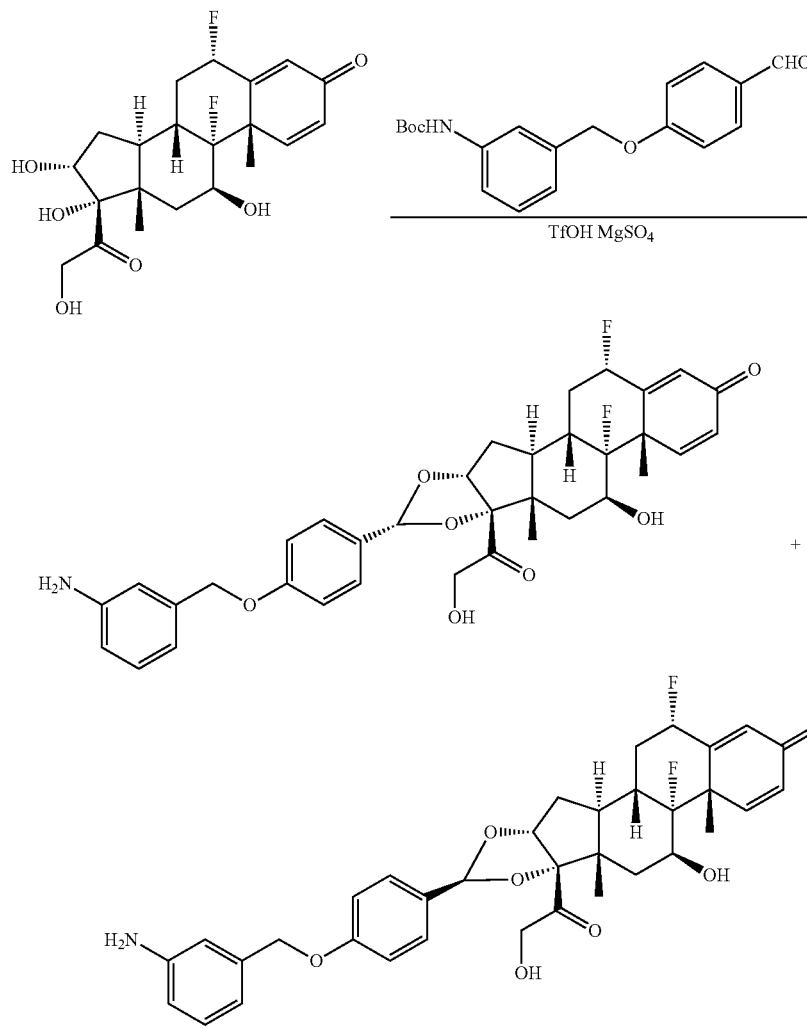

Synthesized using the same procedure as Example 45 above. LCMS (Method C, Table 7) R$_t$=1.45 min; MS m/z=622 [M+H$^+$]. $^1$H NMR (400 MHz, CD$_3$OD) δ 7.57-7.29 (m, 6H), 7.24 (d, J=7.7 Hz, 1H), 7.02 (d, J=8.6 Hz, 2H), 6.45-6.23 (m, 2H), 5.69-5.49 (m, 1H), 5.46 (s, 1H), 5.16 (s, 2H), 5.06 (d, J=3.7 Hz, 1H), 4.64 (d, J=19.5 Hz, 1H), 4.43-4.15 (m, 2H), 2.89-2.56 (m, 1H), 2.52-2.32 (m, 2H), 2.28 (d, J=13.8 Hz, 1H), 1.87-1.62 (m, 4H), 1.60 (s, 3H), 1.00 (s, 3H).

Minor acetal isomer: (2S,6aS,6bR,7S,8aS,8bS,10S,11aR, 12aS,12bS)-10-(4-((3-aminobenzyl)oxy)phenyl)-2,6b-difluoro-7-hydroxy-8b-(2-hydroxyacetyl)-6a,8a-dimethyl-1,2, 6a,6b,7,8,8a,8b,11a,12,12a,12b-dodecahydro-4H-naphtho [2',1':4,5]indeno[1,2-d][1,3]dioxol-4-one. LCMS (Method C, Table 7) R$_t$=1.48 min; MS m/z=622 [M+H$^+$]. $^1$H NMR (400 MHz, DMSO) δ 7.41-7.13 (m, 3H), 7.08-6.90 (m, 3H), 6.61 (s, 1H), 6.52 (dd, J=17.3, 7.5 Hz, 2H), 6.31 (d, J=10.2 Hz, 1H), 6.11 (d, J=18.4 Hz, 2H), 5.79-5.56 (m, 1H), 5.53 (d, J=3.3 Hz, 1H), 5.34 (d, J=7.2 Hz, 1H), 5.18-5.00 (m, 3H), 4.93 (s, 2H), 4.28 (dd, J=19.1, 6.2 Hz, 1H), 4.19 (d, J=5.9 Hz, 1H), 4.05 (dd, J=19.1, 5.9 Hz, 1H), 3.60 (t, J=6.2 Hz, 3H), 2.72-2.51 (m, 1H), 2.29 (s, 1H), 2.22-2.11 (m, 1H), 2.06 (d, J=13.4 Hz, 1H), 1.93-1.80 (m, 1H), 1.80-1.60 (m, 6H), 1.50 (s, 3H), 1.36 (s, 1H), 0.89 (s, 3H).

Example 48: Synthesis of (6aR,6bS,7S,8aS,8bS, 10R,11aR,12aS,12bS)-10-(4-((3-Aminophenyl)ethynyl)phenyl)-7-hydroxy-8b-(2-hydroxyacetyl)-6a,8a-dimethyl-1,2,6a,6b,7,8,8a,8b, 11a,12,12a,12b-dodecahydro-4H-naphtho[2',1':4,5]indeno[1,2-d][1, 3]dioxol-4-one Step 1: Synthesis of tert-Butyl (3-ethynylphenyl)carbamate

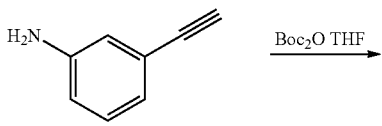

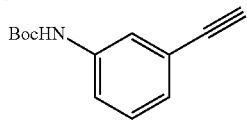

Di-tert-butyl dicarbonate (123 ml, 531 mmol) was added to a stirred solution of 3-ethynylaniline (56.6 g, 483 mmol) in THF (300 mL). The mixture was heated to reflux for overnight. The mixture was then cooled to ambient temperature and taken up in ethyl acetate (500 mL) and washed sequentially with 1N aqueous HCl (200 mL), saturated aqueous $Na_2CO_3$ (200 mL) and brine (200 mL). The organic layer was dried over $Na_2SO_4$, concentrated in vacuo, and purified by silica gel column chromatography (eluted with 15% EtOAc/PE) to give tert-butyl (3-ethynylphenyl)carbamate (94 g, 435 mmol, 90% yield). LCMS (Method f, Table 7) $R_t$=1.80 min; MS m/z=162 [M-t-Bu+H$^+$].

Step 2: Synthesis of tert-Butyl (3-((4-formylphenyl)ethynyl)phenyl)carbamate

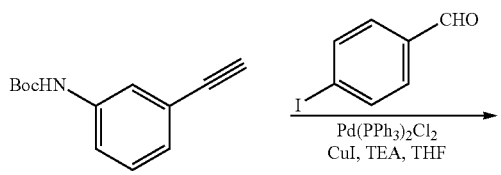

In a 500 mL of round bottom flask 4-iodobenzaldehyde (30.2 g, 130 mmol), bis(triphenylphosphine)palladium(II) chloride (4.56 g, 6.50 mmol), copper(I) iodide (2.476 g, 13.00 mmol) and triphenylphosphine (3.41 g, 13.00 mmol) were dissolved in THF (200 mL) and triethylamine (181 mL, 1300 mmol) followed by addition of tert-butyl (3-ethynylphenyl)carbamate (28.2 g, 130 mmol). The mixture was stirred at 75° C. under nitrogen atmosphere for 16 h. After completion of the reaction, the volatile solvents were completely removed. The crude material was purified by silica gel column chromatography (eluted with PE/$CH_2Cl_2$=1:3) to obtain tert-butyl (3-((4-formylphenyl)ethynyl)phenyl)carbamate (35.5 g, 111 mmol, 85% yield) as an off-white solid. LCMS (Method f, Table 7) $R_t$=2.08 min; MS m/z=322 [M+H$^+$].

Step 3: Synthesis of (6aR,6bS,7S,8aS,8bS,10R, 11aR,12aS,12bS)-10-(4-((3-Aminophenyl)ethynyl) phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

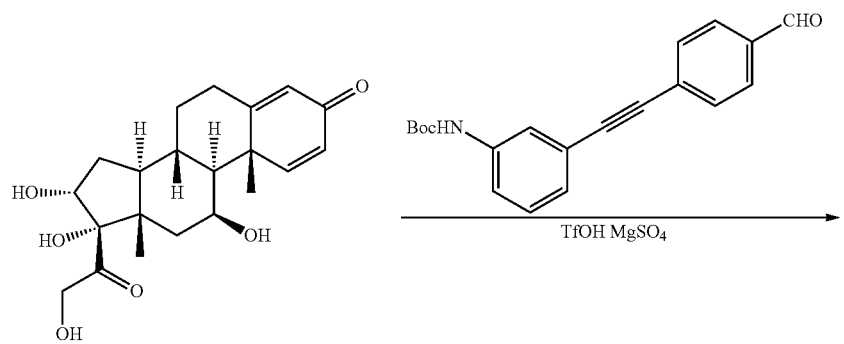

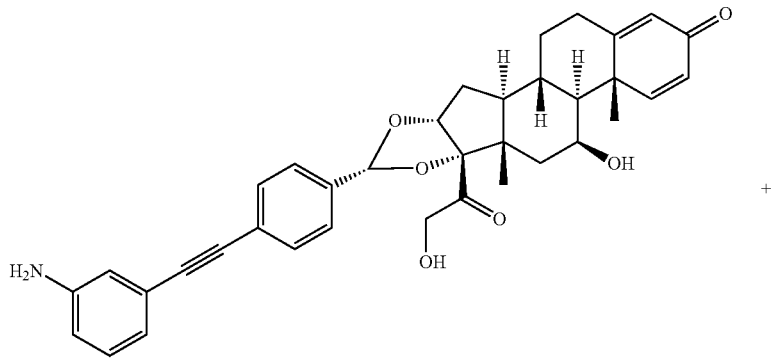

-continued

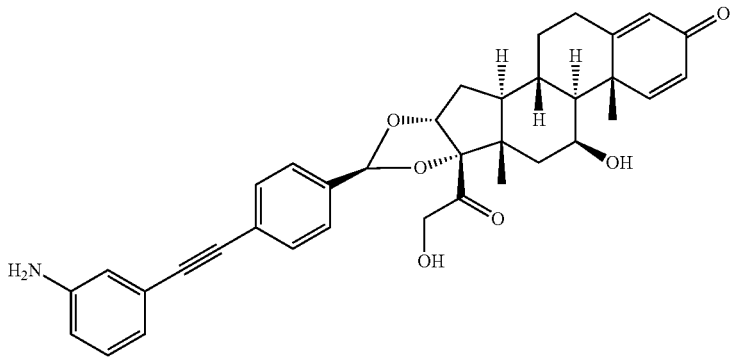

Trifluoromethanesulfonic acid (4.44 ml, 50.0 mmol) was added drop-wise to a 0° C. suspension of (8S,9S,10R,11S,13S,14S,16R,17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (3.76 g, 10.00 mmol), tert-butyl (3-((4-formylphenyl)ethynyl)phenyl) carbamate (3.21 g, 10 mmol) and MgSO$_4$ (4.81 g, 40.0 mmol) in MeCN (100 ml). The mixture was stirred for additional 2 h. The mixture was filtered and washed with THF. The filtrate was concentrated in vacuo. The residue was dissolved in THF (50 mL), neutralized with 1 M aqueous NaOH aqueous solution to pH=8, extracted with EtOAc (200 mL), washed with water (2×100 mL) and brine (100 mL), dried over (Na$_2$SO$_4$), and concentrated in vacuo. The residue was purified by column chromatography (silica gel, eluted with MeOH:DCM=1:40) to give 2.5 g of the crude product which was further purified by prep-HPLC to afford the title compound (1.449 g, 2.500 mmol, 25% yield) as a yellow solid. LCMS (Method 1, Table 7) R$_t$=1.86 min; MS m/z=580 [M+H$^+$]. $^1$H NMR (400 MHz, DMSO-d$_6$) δ 7.65-7.41 (m, 4H), 7.32 (d, J=9.9 Hz, 2H), 7.05 (dd, J=9.8, 5.7 Hz, 1H), 6.85-6.49 (m, 4H), 6.29-6.05 (m, 1H), 6.01-5.83 (m, 1H), 5.63-5.40 (m, 1H), 5.26 (s, 2H), 5.12 (t, J=5.8 Hz, 1H), 4.96 (d, J=4.3 Hz, 1H), 4.82 (d, J=3.0 Hz, 1H), 4.63-4.41 (m, 1H), 4.37-4.08 (m, 2H), 2.40-1.91 (m, 5H), 1.87-1.52 (m, 6H), 1.40 (s, 4H), 1.14-0.95 (m, 2H), 0.88 (s, 3H).

The minor acetal isomer, (6aR,6bS,7S,8aS,8bS,10S,11aR,12aS,12bS)-10-(4-((3-aminophenyl)ethynyl)phenyl)-7-hydroxy-8b-(2-hydroxyacetyl)-6a,8a-dimethyl-6a,6b,7,8,8a,8b,11a, 12,12a,12b-decahydro-1H-naphtho[2',1':4,5]indeno[1,2-d][1,3]dioxol-4(2H)-one, also was isolated (85 mg, 0.147 mmol, 1.5% yield) as a yellow solid. LCMS (Method i, Table 7) R$_t$=1.93 min; MS m/z=580 [M+H$^+$]. $^1$H NMR (400 MHz, DMSO-d$_6$) δ 7.51 (d, J=7.6 Hz, 2H), 7.42-7.21 (m, 3H), 7.05 (t, J=7.7 Hz, 1H), 6.83-6.45 (m, 3H), 6.29-6.07 (m, 2H), 5.95 (s, 1H), 5.47-5.14 (m, 3H), 4.82 (s, 1H), 4.38-4.14 (m, 2H), 4.03 (d, J=19.3 Hz, 1H), 2.33 (d, J=10.3 Hz, 2H), 2.15-1.96 (m, 1H), 1.93-1.68 (m, 5H), 1.40 (s, 3H), 1.33-0.97 (m, 3H), 0.89 (s, 3H).

Example 49: Synthesis of (6aS,6bR,7S,8aS,8bS,10R,11aR,12aS,12bS)-10-(4-((3-Aminophenyl)ethynyl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

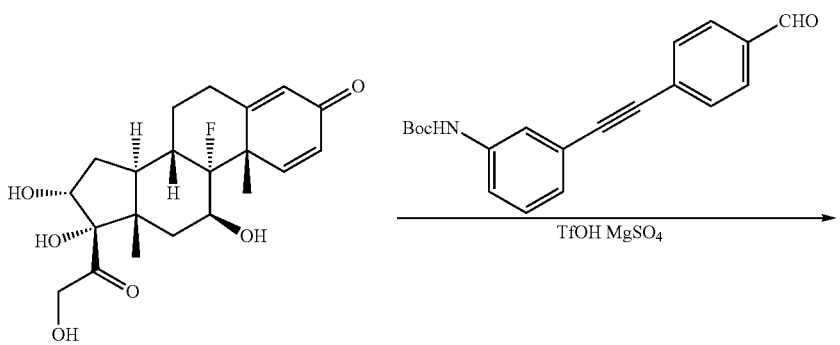

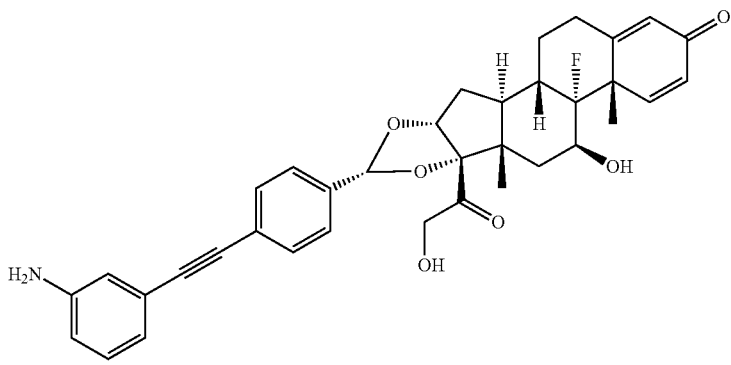

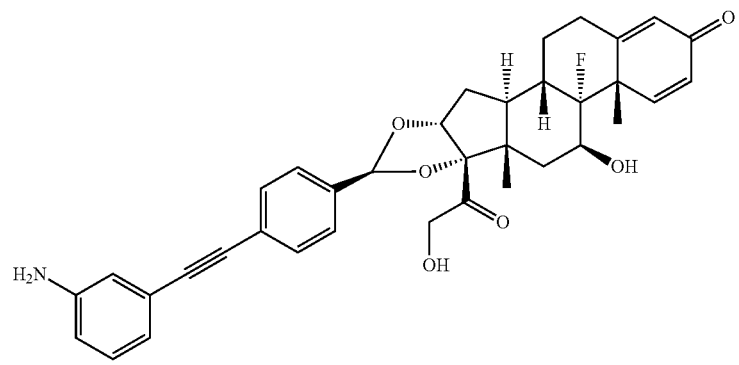

Synthesized using the same procedure as Example 48 above. Major acetal isomer: (6aS,6bR,7S,8aS,8b S,10R,11aR,12aS,12bS)-10-(4-((3-aminophenyl)ethynyl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method f, Table 7) $R_t$=1.57 min; MS m/z=598 [M+H$^+$]. $^1$H NMR (400 MHz, DMSO-d$_6$) δ 7.55 (d, J=8.1 Hz, 2H), 7.46 (d, J=8.1 Hz, 2H), 7.30 (d, J=10.1 Hz, 1H), 7.05 (t, J=7.8 Hz, 1H), 6.71 (s, 1H), 6.66 (d, J=7.5 Hz, 1H), 6.60 (d, J=7.8 Hz, 1H), 6.24 (d, J=8.9 Hz, 1H), 6.04 (s, 1H), 5.51 (d, J=15.2 Hz, 2H), 5.26 (s, 2H), 4.97 (d, J=4.4 Hz, 1H), 4.55 (d, J=19.5 Hz, 1H), 4.22 (d, J=19.5 Hz, 2H), 2.74-2.56 (m, 1H), 2.36 (d, J=9.7 Hz, 1H), 2.24-2.10 (m, 1H), 2.06 (d, J=14.5 Hz, 1H), 1.92-1.78 (m, 1H), 1.78-1.58 (m, 3H), 1.50 (s, 3H), 1.45-1.31 (m, 1H), 0.88 (s, 3H).

Minor acetal isomer: (6aS,6bR,7S,8aS,8bS,10S,11aR,12aS,12bS)-10-(4-((3-aminophenyl)ethynyl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one.

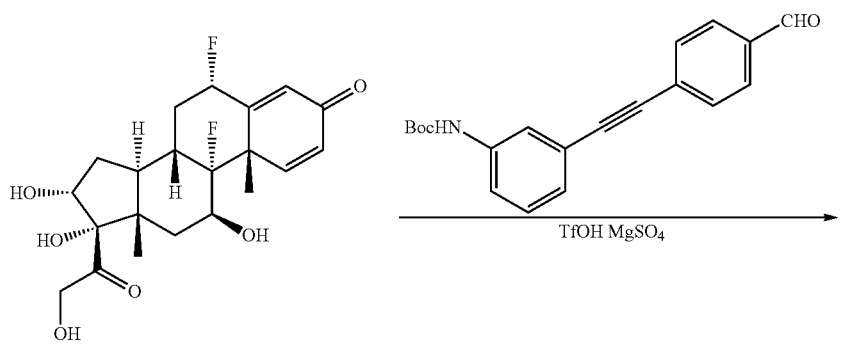

-continued

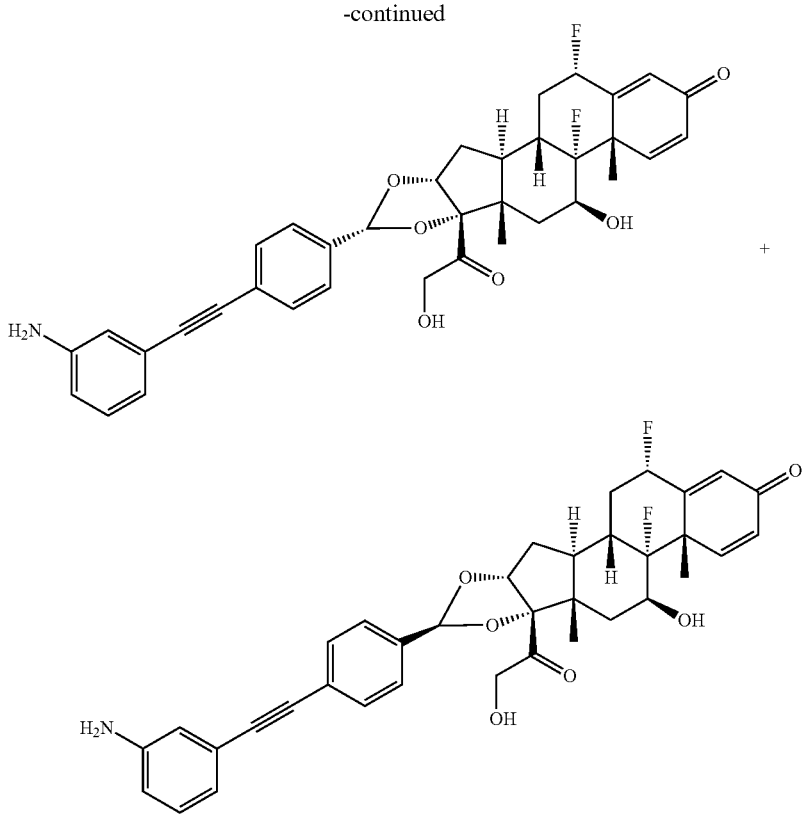

Synthesized using the same procedure as Example 48 above. Major acetal isomer: (2S,6aS,6bR,7S,8aS,8bS,10R,11aR,12aS,12bS)-10-(4-((3-aminophenyl)ethynyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method f, Table 7) $R_f$=1.57 min; MS m/z=616 [M+H$^+$]. $^1$H NMR (400 MHz, DMSO-d$_6$) δ 7.55 (d, J=8.1 Hz, 2H), 7.47 (d, J=8.2 Hz, 2H), 7.27 (d, J=10.1 Hz, 1H), 7.05 (t, J=7.8 Hz, 1H), 6.71 (s, 1H), 6.66 (d, J=7.6 Hz, 1H), 6.60 (d, J=8.1 Hz, 1H), 6.30 (dd, J=10.1, 1.4 Hz, 1H), 6.13 (s, 1H), 5.80-5.58 (m, 1H), 5.55 (d, J=7.1 Hz, 2H), 5.26 (s, 2H), 5.14 (t, J=5.9 Hz, 1H), 4.99 (d, J=5.1 Hz, 1H), 4.56 (dd, J=19.5, 6.4 Hz, 1H), 4.23 (dd, J=19.5, 5.4 Hz, 2H), 2.79-2.56 (m, 1H), 2.31 (s, 1H), 2.26-2.14 (m, 1H), 2.12-1.99 (m, 1H), 1.83-1.62 (m, 3H), 1.61-1.40 (m, 4H), 0.88 (s, 3H).

Minor acetal isomer: (2S,6aS,6bR,7S,8aS,8bS,10S,11aR,12aS,12bS)-10-(4-((3-aminophenyl)ethynyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method f, Table 7) $R_f$=1.61 min; MS m/z=616 [M+H$^+$]. $^1$H NMR (400 MHz, DMSO-d$_6$) δ 7.52 (d, J=8.3 Hz, 2H), 7.33 (d, J=8.2 Hz, 2H), 7.28 (d, J=10.0 Hz, 1H), 7.05 (t, J=7.8 Hz, 1H), 6.73 (s, 1H), 6.68 (d, J=7.5 Hz, 1H), 6.61 (d, J=8.1 Hz, 1H), 6.32 (dd, J=10.1, 1.7 Hz, 1H), 6.21 (s, 1H), 6.15 (s, 1H), 5.78-5.58 (m, 1H), 5.55 (d, J=2.7 Hz, 1H), 5.36 (t, J=7.9 Hz, 1H), 5.27 (s, 2H), 5.08 (t, J=5.8 Hz, 1H), 4.33-4.12 (m, 2H), 4.06 (dd, J=19.1, 5.0 Hz, 1H), 2.72-2.53 (m, 1H), 2.29 (s, 1H), 2.23-2.02 (m, 2H), 1.92-1.82 (m, 1H), 1.82-1.61 (m, 3H), 1.51 (s, 4H), 0.90 (s, 3H).

Example 51: Synthesis of (2S,6aS,6bR,7S,8aS,8bS,10R,11aR,12aS,12bS)-10-(4-((E)-3-Aminostyryl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one Step 1: Synthesis of tert-Butyl (E)-(3-(2-(4,4,5,5-tetramethyl-1,3,2-dioxaborolan-2-yl)vinyl)phenyl)carbamate

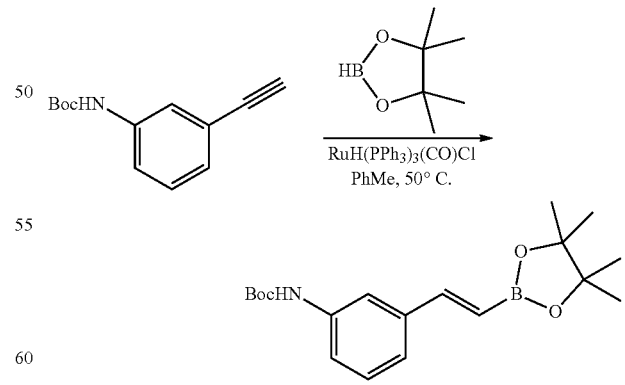

4,4,5,5-Tetramethyl-1,3,2-dioxaborolane (16.70 mL, 115 mmol) and carbonylchlorohydridotris(triphenylphosphine)ruthenium(II) (2.63 g, 2.76 mmol) were added to a nitrogen-purged solution of tert-butyl (3-ethynylphenyl)carbamate (10 g, 46.0 mmol) in toluene (150 mL). The mixture was heated at 50° C. for 16 h, whereupon it was concentrated under reduced pressure. Purification by chromatography (silica) eluting with PE/EtOAc (100%-10:1) gave the title compound (13.25 g, 36.8 mmol, 80% yield) as a white solid. LCMS (Method d Table 7) $R_t$=2.19 min; MS m/z=290.1 [M-tBu]$^+$. $^1$H NMR (400 MHz, CDCl$_3$) δ 1.33 (s, 12H), 1.54 (s, 9H), 6.17 (d, J=18.4 Hz, 1H), 6.49 (bs, 1H), 7.18 (d, J=7.6 Hz, 1H), 7.26-7.29 (m, 1H), 7.35-7.40 (m, 2H), 7.47 (s, 1H).

Step 2: Synthesis of tert-Butyl (E)-(3-(4-formylstyryl)phenyl)carbamate

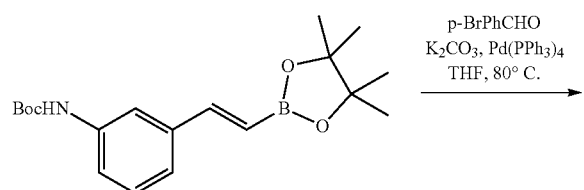

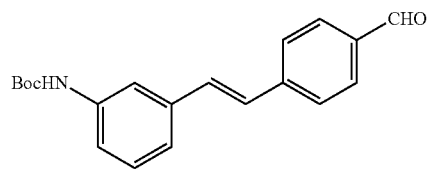

To a solution of tert-Butyl (E)-(3-(2-(4,4,5,5-tetramethyl-1,3,2-dioxaborolan-2-yl)vinyl)phenyl)carbamate (6 g, 17.38 mmol) and 4-bromobenzaldehyde (3.38 g, 18.25 mmol) in THF (85 mL) at 20° C. under N$_2$ were added K$_2$CO$_3$ (4.80 g, 34.8 mmol) and Pd(Ph$_3$P)$_4$ (1.607 g, 1.390 mmol). The mixture was stirred at 80° C. for 32 h. The mixture was concentrated to give the residue, which was dissolved with EtOAc (50 mL) and filtered. The filtrate was concentrated. The residue was purified by silica gel column chromatography eluting with PE/EtOAc (10:1-6:1) to give the product, which was further washed with PE (10 mL) to obtain the title compound (3.43 g, 10.49 mmol, 60% yield) as a green solid. LCMS (Method d, Table 7) $R_t$=2.08 min; MS m/z=324.1 [M+H$^+$].

Step 3: Synthesis of (2S,6aS,6bR,7S,8aS,8bS,10R,11aR,12aS,12bS)-10-(4-((E)-3-Aminostyryl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

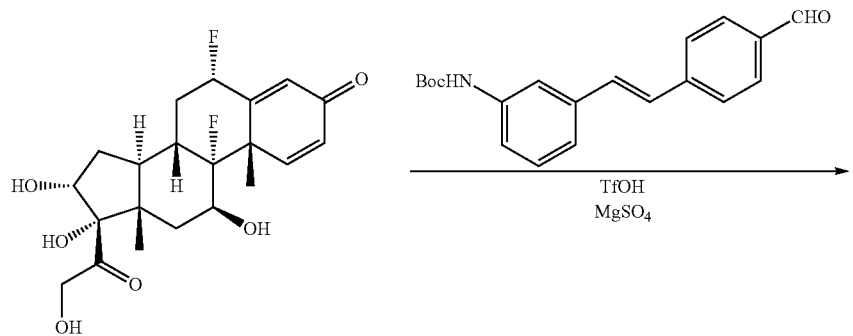

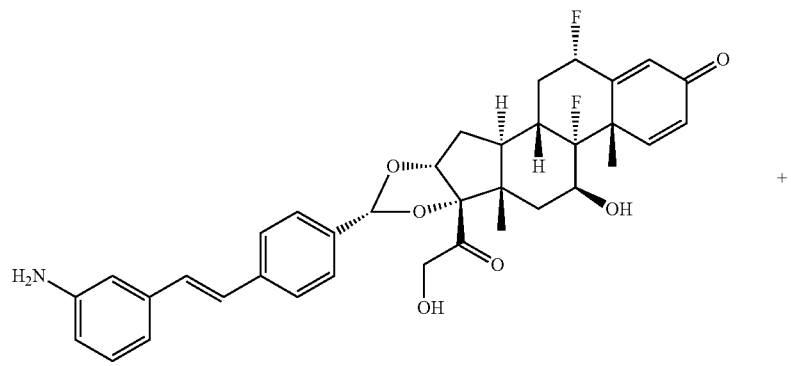

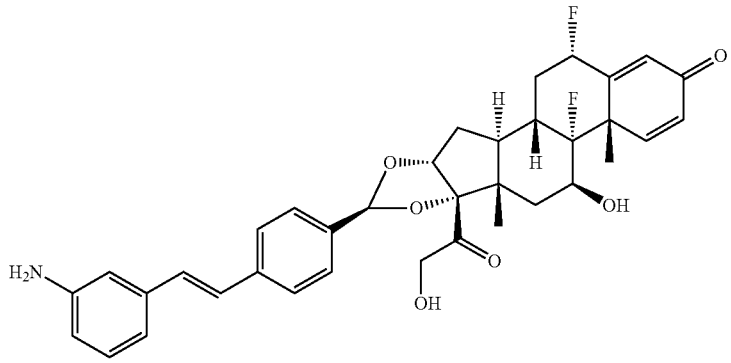

Trifluoromethanesulfonic acid (5.38 mL, 60.6 mmol) was added drop-wise to a 0° C. stirred suspension of (6S,8S,9R,10S,11S,13S,14S,16R,17S)-6,9-difluoro-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (Example 2, Step 5) (5.0 g, 12.12 mmol) and (E)-tert-butyl (3-(4-formylstyryl)phenyl)carbamate (4.612 g, 12.12 mmol) in anhydrous MeCN (30 mL) and THF (30 mL) under nitrogen. The mixture was stirred at 0° C. for 1 h, then poured onto ice water (30 mL) and extracted with EtOAc (2×50 mL). The combined organic layers were washed with cooled water (30 mL), brine (30 mL), saturated NaHCO₃ (30 mL) and water (30 mL) again, and concentrated in vacuo affording a yellow solid. The crude material was purified by silica gel column chromatography (200-300 mesh), eluting with DCM/MeOH (100%-40:1) and then further purified by prep-HPLC to give the title compound (1.45 g, 2.328 mmol, 19% yield). LCMS (Method d, Table 7) $R_t$=1.47 min; MS m/z=618.3 [M+H⁺]. ¹H NMR (400 MHz, DMSO-d₆) δ 7.61 (d, J=8.2 Hz, 2H), 7.43 (d, J=8.3 Hz, 2H), 7.28 (d, J=10.9 Hz, 1H), 7.15 (d, J=16.4 Hz, 1H), 7.03 (dd, J=15.5, 7.6 Hz, 2H), 6.75 (dd, J=8.0, 4.7 Hz, 2H), 6.50 (dd, J=7.9, 1.3 Hz, 1H), 6.31 (dd, J=10.1, 1.8 Hz, 1H), 6.15 (s, 1H), 5.79-5.46 (m, 3H), 5.13 (dd, J=14.7, 8.7 Hz, 3H), 4.97 (d, J=5.1 Hz, 1H), 4.55 (dd, J=19.5, 6.4 Hz, 1H), 4.23 (dd, J=19.4, 5.5 Hz, 2H), 2.73-2.56 (m, 1H), 2.40-2.21 (m, 2H), 2.15-2.02 (m, 1H), 1.82-1.64 (m, 3H), 1.61-1.44 (m, 4H), 0.88 (s, 3H).

The minor acetal isomer, (2S,6aS,6bR,7S,8aS,8bS,10S,11aR,12aS,12bS)-10-(4-((E)-3-aminostyryl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (0.30 g, 0.456 mmol, 4% yield), also was isolated as a white solid. LCMS (Method d, Table 7) $R_t$=1.51 min; MS m/z=618.3 [M+H⁺]. ¹H NMR (400 MHz, DMSO-d₆) δ 7.57 (d, J=8.2 Hz, 2H), 7.27 (d, J=7.9 Hz, 3H), 7.18-6.97 (m, 3H), 6.75 (d, J=7.8 Hz, 2H), 6.50 (d, J=7.4 Hz, 1H), 6.31 (dd, J=10.2, 1.6 Hz, 1H), 6.15 (d, J=10.3 Hz, 2H), 5.78-5.67 (m, 1H), 5.63-5.49 (m, 2H), 5.37 (d, J=7.0 Hz, 1H), 5.07 (dd, J=12.0, 5.8 Hz, 3H), 4.33-4.15 (m, 2H), 4.06 (dd, J=19.2, 5.7 Hz, 1H), 2.69-2.54 (m, 1H), 2.36-2.08 (m, 3H), 1.94-1.60 (m, 4H), 1.50 (s, 3H), 0.90 (s, 3H).

Example 52: Synthesis of (6aR,6bS,7S,8aS,8bS,10R,11aR,12aS,12bS)-10-(4-((E)-3-Aminostyryl)phenyl)-7-hydroxy-8b-(2-hydroxyacetyl)-6a,8a-dimethyl-1,2,6a,6b,7,8,8a,8b, 11a,12,12a,12b-dodecahydro-4H-naphtho[2',1':4,5]indeno[1,2-d][1,3]dioxol-4-one

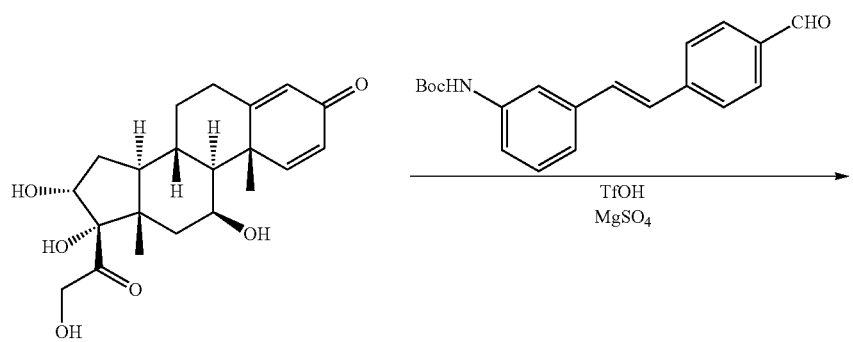

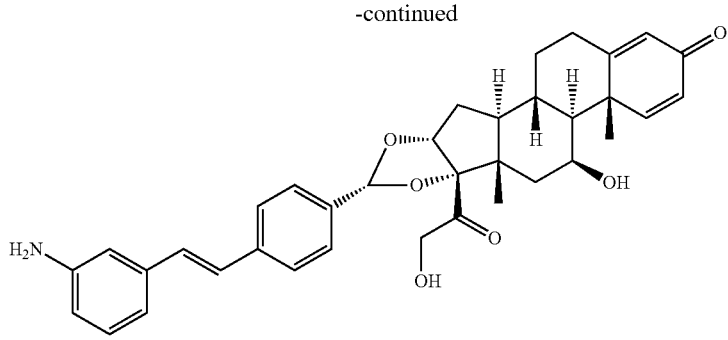

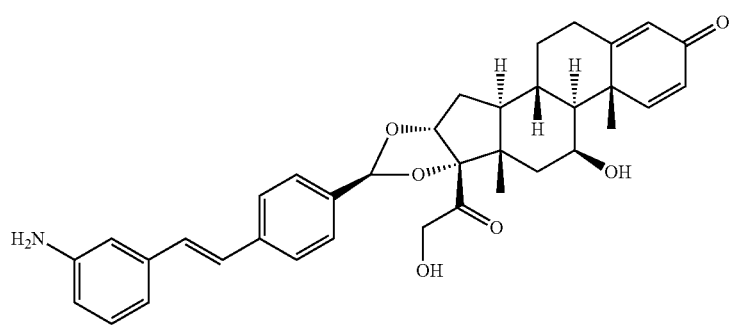

Synthesized using the same procedure as Example 51 above. Major acetal isomer: (6aR,6bS,7S,8aS,8bS,10R,11aR,12aS,12bS)-10-(4-((E)-3-aminostyryl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method d, Table 7) $R_t$=1.48 min; MS m/z=582.3 [M+H$^+$]. $^1$H NMR (400 MHz, DMSO-d$_6$) δ 0.88 (s, 3H), 1.00-1.09 (m, 2H), 1.40 (s, 3H), 1.63-1.79 (m, 5H), 2.04-2.15 (m, 2H), 2.32-2.34 (m, 1H), 2.55-2.60 (m, 1H), 4.20 (dd, J=20.2 Hz, 5.0 Hz, 1H), 4.31 (s, 1H), 4.54 (dd, J=19.2 Hz, 6.0 Hz, 1H), 4.82 (s, 1H), 4.94-4.95 (m, 1H), 5.10-5.14 (m, 3H), 5.46 (s, 1H), 5.95 (s, 1H), 6.18 (d, J=10.0 Hz, 1H), 6.50 (d, J=7.6 Hz, 1H), 6.73-6.76 (m, 2H), 7.00-7.14 (m, 3H), 7.32 (d, J=10.0 Hz, 1H), 7.45 (d, J=8.4 Hz, 2H), 7.59 (d, J=8.0 Hz, 2H).

Minor acetal isomer: (6aR,6bS,7S,8aS,8bS,10S,11aR,12aS,12bS)-10-(4-((E)-3-aminostyryl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method d, Table 7) $R_t$=1.52 min; MS m/z=582.3 [M+H$^+$]. $^1$H NMR (400 MHz, DMSO-d$_6$) δ 0.89 (s, 3H), 1.05-1.31 (m, 3H), 1.40 (s, 3H), 1.74-1.89 (m, 5H), 2.05-2.07 (m, 2H), 2.31-2.34 (m, 1H), 2.54-2.59 (m, 1H), 4.00-4.06 (m, 1H), 4.23-4.31 (m, 2H), 4.80 (s, 1H), 5.05-5.09 (m, 3H), 5.31-5.32 (m, 1H), 5.95 (s, 1H), 6.12 (s, 1H), 6.18 (d, J=9.6 Hz, 1H), 6.49-6.50 (m, 1H), 6.74-6.76 (m, 2H), 7.00-7.14 (m, 3H), 7.26 (d, J=7.6 Hz, 2H), 7.32 (d, J=10.0 Hz, 1H), 7.57 (d, J=7.6 Hz, 2H).

Example 53: Synthesis of (6aS,6bR,7S,8aS,8bS,10R,11aR,12aS,12bS)-10-(4-((E)-3-aminostyryl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

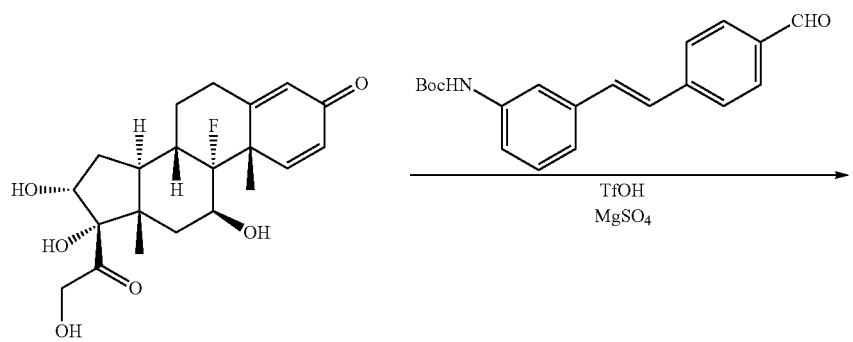

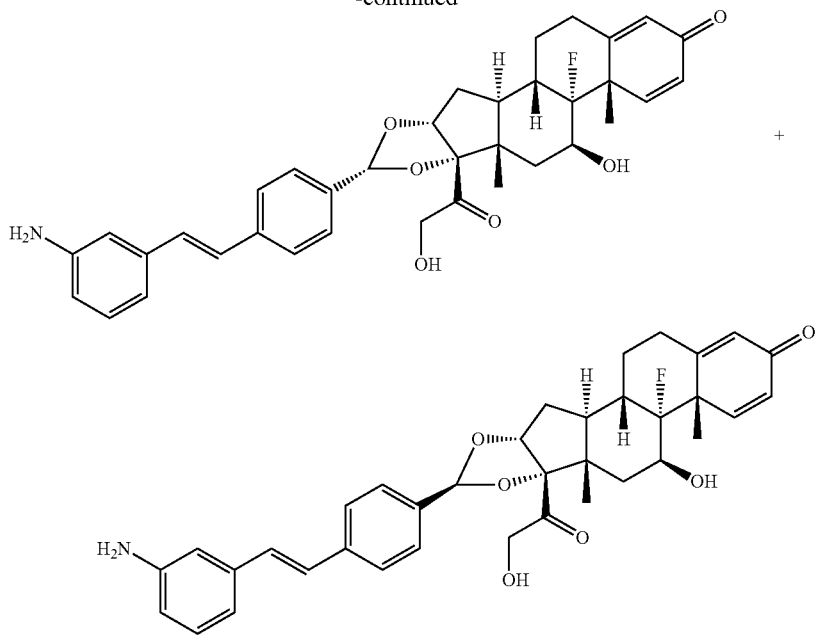

Synthesized using the same procedure as Example 51 above. Major acetal isomer: (6aS,6bR,7S,8aS,8bS,10R,11aR,12aS,12bS)-10-(4-((E)-3-aminostyryl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one. LCMS (Method d, Table 7) $R_t$=1.45 min; MS m/z=600.3 [M+H$^+$]. $^1$H NMR (400 MHz, DMSO-d$_6$) δ 7.61 (d, J=8.1 Hz, 2H), 7.42 (d, J=8.1 Hz, 2H), 7.30 (d, J=10.1 Hz, 1H), 7.15 (d, J=16.4 Hz, 1H), 7.03 (dd, J=15.6, 7.6 Hz, 2H), 6.79-6.70 (m, 2H), 6.50 (d, J=7.7 Hz, 1H), 6.25 (dd, J=10.1, 1.4 Hz, 1H), 6.06 (s, 1H), 5.54-5.43 (m, 2H), 5.13 (t, J=6.0 Hz, 3H), 4.95 (d, J=4.5 Hz, 1H), 4.55 (dd, J=19.5, 6.4 Hz, 1H), 4.22 (dd, J=19.3, 5.4 Hz, 2H), 2.62 (m, 2H), 2.42-2.02 (m, 3H), 1.92-1.80 (m, 1H), 1.77-1.61 (m, 3H), 1.51 (s, 3H), 1.47-1.32 (m, 1H), 0.89 (s, 3H).

Minor acetal isomer: (6aS,6bR,7S,8aS,8bS,10S,11aR,12aS,12bS)-10-(4-((E)-3-aminostyryl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one.

LCMS (Method d, Table 7) $R_t$=1.48 min; MS m/z=600.3 [M+H$^+$]. $^1$H NMR (400 MHz, DMSO-d$_6$) δ 7.57 (d, J=8.1 Hz, 2H), 7.28 (dd, J=12.2, 9.3 Hz, 3H), 7.18-6.97 (m, 3H), 6.75 (d, J=7.7 Hz, 2H), 6.50 (d, J=7.3 Hz, 1H), 6.25 (dd, J=10.1, 1.2 Hz, 1H), 6.13 (s, 1H), 6.05 (s, 1H), 5.46 (d, J=2.8 Hz, 1H), 5.35 (d, J=6.9 Hz, 1H), 5.06 (dd, J=14.0, 7.9 Hz, 3H), 4.24 (dd, J=19.3, 6.3 Hz, 2H), 4.05 (dd, J=19.1, 5.8 Hz, 1H), 2.73-2.58 (m, 1H), 2.47-2.30 (m, 2H), 2.09 (d, J=10.1 Hz, 2H), 1.85 (d, J=6.5 Hz, 2H), 1.78-1.65 (m, 2H), 1.50 (s, 4H), 0.90 (s, 3H).

Example 54: Synthesis of (2S,6aS,6bR,7S,8aS,8bS,10R,11aR,12aS,12bS)-10-(4-(3-aminophenethyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one Step 1: Synthesis of tert-Butyl (E)-(3-(4-(hydroxymethyl)styryl)phenyl)carbamate

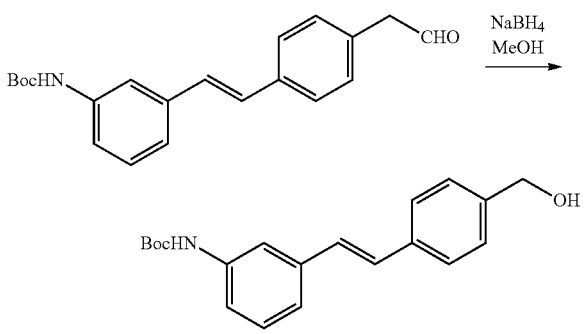

NaBH$_4$ (0.936 g, 24.74 mmol) was added to a 0° C. solution of (E)-tert-butyl (3-(4-formylstyryl)phenyl)carbamate) Step 2, Example. 51)(4.0 g, 12.37 mmol) in MeOH (60 mL) and THF (60 mL) and stirred at 0° C. for 1 h. The mixture was quenched with saturated aqueous NH$_4$Cl (20 mL), concentrated to obtain a residue, which was partitioned between EtOAc (100 mL) and water (100 mL). The organic layer was concentrated under reduced pressure, and was purified by silica gel column chromatography, eluting with DCM/EtOAc (10:1-5:1) to give the title compound (3.23 g, 7.08 mmol, 57% yield) as a light red solid. LCMS (Method d, Table 7) $R_t$=1.98 min; MS m/z=348.1 [M+Na$^+$].

Step 2: Synthesis of tert-Butyl (3-(4-(hydroxymethyl)phenethyl)phenyl)carbamate

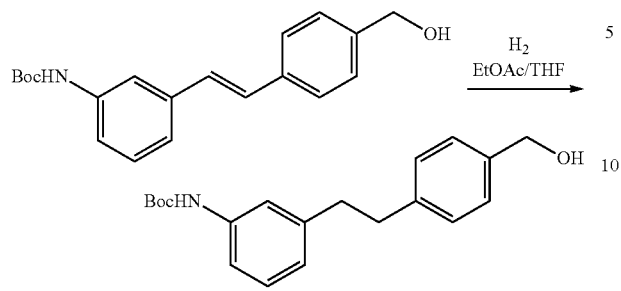

A suspension of Pd/C (0.657 g, 0.618 mmol) and (E)-tert-butyl (3-(4-(hydroxymethyl)styryl) phenyl)carbamate (pure) 7 (3.35 g, 10.29 mmol) in EtOAc (50 mL) and THF (50 mL) was treated with hydrogen balloon and stirred at 0° C. for 1.5 h, monitored by LCMS. The mixture was filtered. Additional Pd/C (0.657 g, 0.618 mmol) was added to the filtrate. The mixture was stirred for additional 1 h under an atmosphere of hydrogen and monitored by LCMS. The mixture was filtered and washed with EtOAc (15 mL). The filtrate was concentrated to give a residue, which was purified by silica gel column chromatography, eluting with PE/EtOAc (10:1-2:1) to give the title compound (1.2 g, 3.49 mmol, 34% yield) as a white solid. LCMS (Method d, Table 7) $R_t$=2.0 min; MS m/z=350.0 [M+Na$^+$].

Step 3: Synthesis of tert-Butyl (3-(4-formylphenethyl)phenyl)carbamate

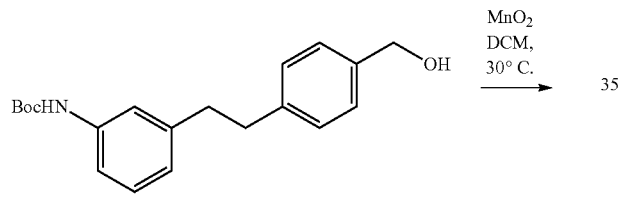

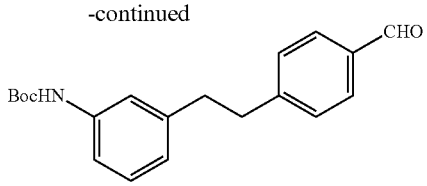

A suspension of MnO$_2$ (9.24 g, 106 mmol) and tert-butyl (3-(4-(hydroxymethyl)phenethyl) phenyl)carbamate (2.9 g, 8.86 mmol) in DCM (40 mL) was treated with nitrogen balloon and stirred at 30° C. for 2 h, monitored by LCMS. Additional MnO$_2$ (0.8 g, 9.2 mmol) was added to the above mixture, stirred at 30° C. for additional 1 h. The mixture was filtered and washed with DCM (20 mL). The filtrate was concentrated to obtain the title compound (2.9 g, 8.58 mmol, 97% yield) as a yellow solid. LCMS (Method d, Table 7) $R_t$=2.14 min; MS m/z=226.0 [M-Boc]$^+$. $^1$H NMR (400 MHz, CDCl$_3$) δ 9.90 (s, 1H), 7.71 (d, J=7.8 Hz, 2H), 7.25 (s, 2H), 7.19-6.97 (m, 3H), 6.73 (d, J=7.3 Hz, 1H), 6.48 (s, 1H), 2.98-2.87 (m, 2H), 2.86-2.78 (m, 2H), 1.44 (s, 9H).

Step 4: Synthesis of (2S,6aS,6bR,7S,8aS,8bS,10R,11aR,12aS,12bS)-10-(4-(3-Aminophenethyl)phenyl)-2,6b-difluoro-7-hydroxy-8b-(2-hydroxyacetyl)-6a,8a-dimethyl-1,2,6a,6b,7,8,8a,8b, 11a,12,12a,12b-dodecahydro-4H-naphtho[2',1':4,5]indeno[1,2-d][1,3]dioxol-4-one

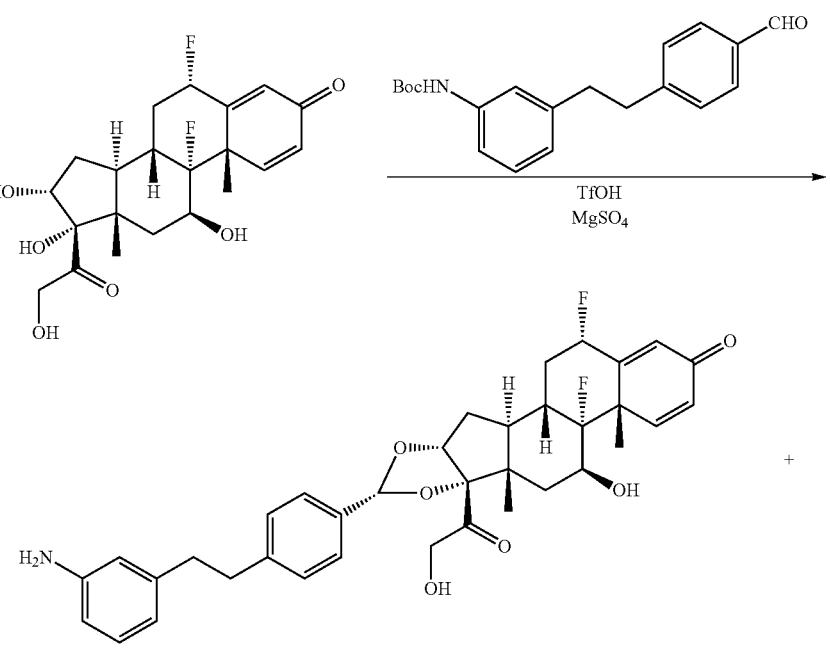

-continued

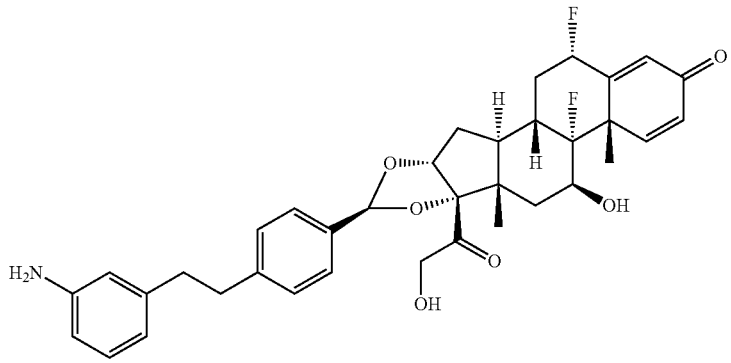

Trifluoromethanesulfonic acid (5.61 mL, 64.2 mmol) was added drop-wise to a stirred 0° C. suspension of tert-butyl (3-(4-formylphenethyl)phenyl)carbamate (4.18 g, 12.85 mmol) and (6S,8S,9R,10S,11S,13S,14S,16R,17S)-6,9-difluoro-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (5.3 g, 12.85 mmol) in anhydrous MeCN (30 mL) and THF (30 mL) under. The resulting mixture was stirred at 0° C. for 1 h, then poured onto ice water (20 mL) and extracted with EtOAc (2×25 mL). The combined organic layers were washed with cooled water (20 mL), brine (10 mL), saturated aqueous NaHCO$_3$ (20 mL) and water (20 mL), concentrated in vacuo affording a yellow solid. The crude material was purified by silica gel column chromatography (200-300 mesh), eluting with dichloromethane/methanol (100%0/40:1) to obtain the product, which was further purified by prep-HPLC to give the title compound (2.21 g, 3.57 mmol, 28% yield) as a white solid. LCMS (Method d, Table 7) R$_t$=1.75 min; MS m/z=619.8 [M+H$^+$]. $^1$H NMR (400 MHz, DMSO-d$_6$) δ 7.34 (d, J=8.1 Hz, 2H), 7.27 (t, J=8.0 Hz, 3H), 6.89 (t, J=7.7 Hz, 1H), 6.43 (s, 1H), 6.36 (d, J=7.9 Hz, 2H), 6.31 (dd, J=10.2, 1.8 Hz, 1H), 6.14 (s, 1H), 5.75-5.56 (m, 1H), 5.54 (d, J=2.9 Hz, 1H), 5.46 (s, 1H), 5.12 (t, J=6.0 Hz, 1H), 4.95 (d, J=5.1 Hz, 1H), 4.92 (s, 2H), 4.53 (dd, J=19.5, 6.4 Hz, 1H), 4.21 (dd, J=19.4, 5.6 Hz, 2H), 2.83-2.79 (m, 2H), 2.73-2.57 (m, 3H), 2.275-2.25 (m, 2H), 2.08-2.04 (m, 1H), 1.79-1.62 (m, 3H), 1.67-1.50 (m, 4H), 0.87 (s, 3H).

The minor acetal isomer, (2S,6aS,6bR,7S,8aS,8bS,10S,11aR,12aS,12bS)-10-(4-(3-aminophenethyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (0.45 g, 0.667 mmol, 5% yield) also was isolated as a white solid. LCMS (Method d, Table 7) R$_t$=1.79 min; MS m/z=619.8 [M+H$^+$]. $^1$H NMR (400 MHz, DMSO-d$_6$) δ 7.33-7.17 (m, 5H), 6.89 (t, J=7.7 Hz, 1H), 6.46-6.27 (m, 4H), 6.12 (d, J=8.8 Hz, 2H), 5.75-5.55 (m, 1H), 5.53 (s, 1H), 5.34 (d, J=7.1 Hz, 1H), 5.06 (t, J=5.9 Hz, 1H), 4.92 (s, 2H), 4.31-4.15 (m, 2H), 4.05 (dd, J=19.2, 5.6 Hz, 1H), 2.83-2.79 (m, 2H), 2.72-2.54 (m, 3H), 2.29 (s, 1H), 2.21-2.13 (m, 1H), 2.09-2.05 (m, 1H), 1.93-1.81 (m, 1H), 1.79-1.60 (m, 3H), 1.50 (s, 3H), 0.88 (s, 3H).

Example 55: Synthesis of (6aR,6bS,7S,8aS,8bS,10R,11aR,12aS,12bS)-10-(4-(3-aminophenethyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

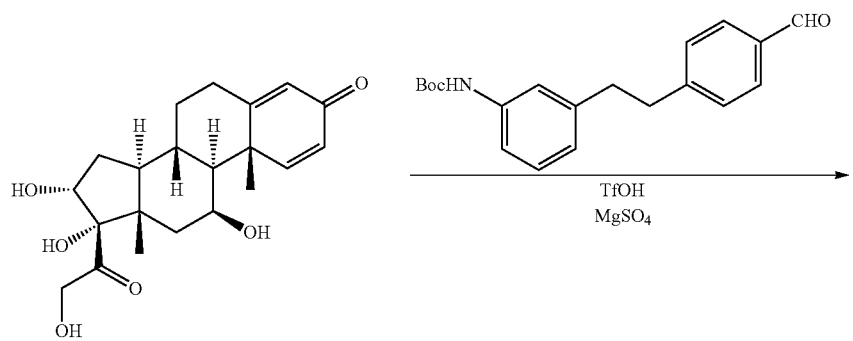

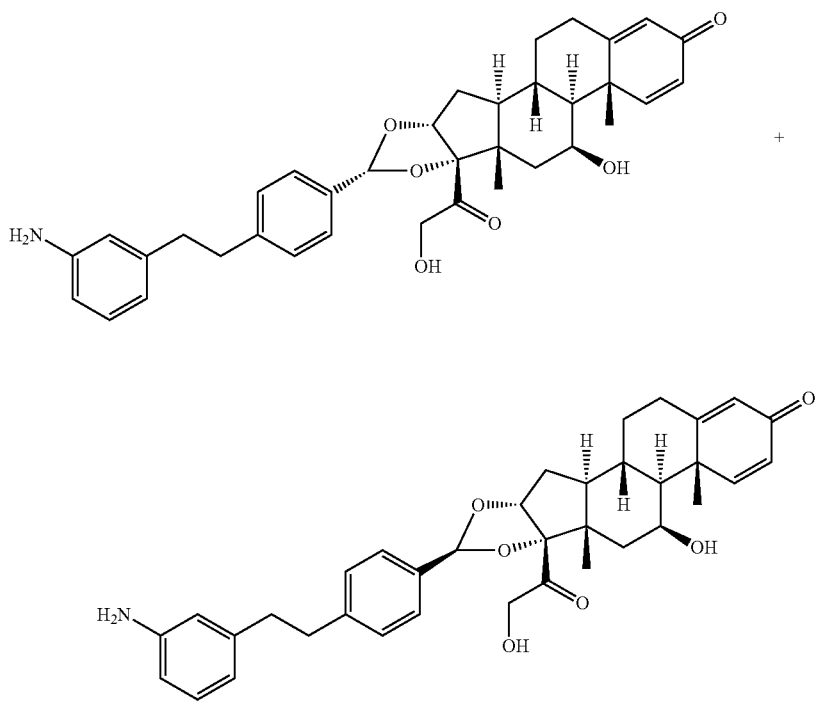

Synthesized using the same procedure as Example 54 above. Major acetal isomer: LCMS (Method d, Table 7) R$_t$=1.74 min; MS m/z=583.8 [M+H$^+$]. $^1$H NMR (400 MHz, DMSO-d$_6$) δ 7.34 (dd, J=16.7, 9.1 Hz, 3H), 7.24 (d, J=8.0 Hz, 2H), 6.89 (t, J=7.7 Hz, 1H), 6.42 (s, 1H), 6.36 (dd, J=7.7, 1.6 Hz, 2H), 6.17 (dd, J=10.1, 1.7 Hz, 1H), 5.95 (s, 1H), 5.41 (s, 1H), 5.11 (t, J=5.9 Hz, 1H), 4.93 (d, J=5.4 Hz, 3H), 4.81 (d, J=3.0 Hz, 1H), 4.52 (dd, J=19.5, 6.4 Hz, 1H), 4.30 (s, 1H), 4.19 (dd, J=19.5, 5.6 Hz, 1H), 2.87-2.77 (m, 2H), 2.73-2.64 (m, 2H), 2.62-2.52 (m, 1H), 2.32 (d, J=11.0 Hz, 1H), 2.18-1.98 (m, 2H), 1.83-1.58 (m, 5H), 1.40 (s, 3H), 1.24-0.97 (m, 2H), 0.87 (s, 3H).

Minor acetal isomer, (6aR,6bS,7S,8aS,8bS,10S,11aR,12aS,12bS)-10-(4-(3-aminophenethyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one: LCMS (Method d, Table 7) R$_t$=1.77 min; MS m/z=583.9 [M+H$^+$]. $^1$H NMR (400 MHz, DMSO-d$_6$) δ 7.32 (d, J=10.1 Hz, 1H), 7.19 (q, J=8.2 Hz, 4H), 6.89 (t, J=7.7 Hz, 1H), 6.44-6.29 (m, 3H), 6.17 (dd, J=10.1, 1.8 Hz, 1H), 6.07 (s, 1H), 5.95 (s, 1H), 5.29 (d, J=6.9 Hz, 1H), 5.03 (t, J=6.1 Hz, 1H), 4.92 (s, 2H), 4.78 (d, J=3.1 Hz, 1H), 4.34-4.19 (m, 2H), 4.02 (dd, J=19.2, 5.9 Hz, 1H), 2.81 (dd, J=9.5, 6.1 Hz, 2H), 2.68 (dd, J=9.6, 6.0 Hz, 2H), 2.61-2.52 (m, 1H), 2.32 (d, J=10.4 Hz, 1H), 2.03 (d, J=7.8 Hz, 2H), 1.91-1.67 (m, 5H), 1.39 (s, 3H), 1.27-1.01 (m, 2H), 0.89 (s, 3H).

Example 56: Synthesis of (6aS,6bR,7S,8aS,8bS,10R,11aR,12aS,12bS)-10-(4-(3-Aminophenethyl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

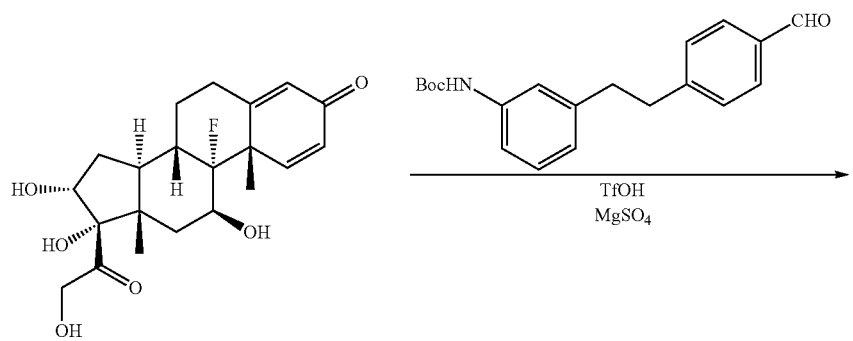

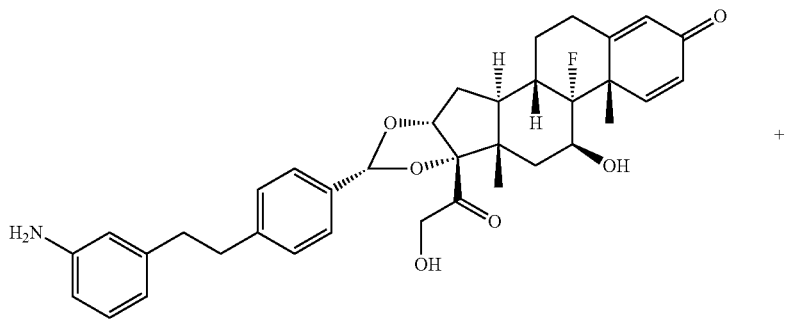

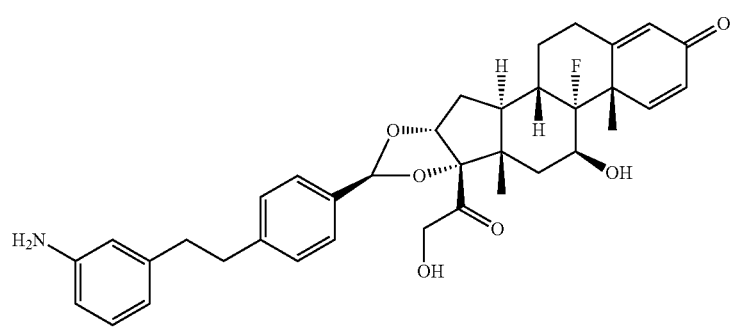

Synthesized using the same procedure as Example 54 above. Major acetal isomer: LCMS (Method d, Table 7) $R_t$=1.74 min; MS m/z=601.9 [M+H⁺]. ¹H NMR (400 MHz, DMSO-$d_6$) δ 7.32 (t, J=7.2 Hz, 2H), 7.26 (t, J=8.0 Hz, 2H), 6.89 (t, J=7.7 Hz, 1H), 6.43 (s, 1H), 6.36 (d, J=7.7 Hz, 2H), 6.24 (dd, J=10.1, 1.7 Hz, 1H), 6.05 (s, 1H), 5.45 (s, 2H), 5.10 (t, J=5.9 Hz, 1H), 4.97-4.85 (m, 3H), 4.52 (dd, J=19.5, 6.4 Hz, 1H), 4.20 (dd, J=19.2, 5.6 Hz, 2H), 2.85-2.76 (m, 2H), 2.72-2.54 (m, 3H), 2.36 (d, J=10.4 Hz, 1H), 2.20-2.18 (m, 1H), 2.04 (s, 1H), 1.91-1.80 (m, 1H), 1.73-1.61 (m, 3H), 1.50 (s, 3H), 1.40-1.38 (m, 1H), 0.87 (s, 3H).

Minor acetal isomer, (6aS,6bR,7S,8aS,8bS,10S,11aR,12aS,12bS)-10-(4-(3-aminophenethyl)phenyl)-6b-fluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one: LCMS (Method d, Table 7) $R_t$=1.77 min; MS m/z=601.9 [M+H⁺]. ¹H NMR (400 MHz, DMSO-$d_6$) δ 7.35-7.13 (m, 5H), 6.89 (t, J=7.7 Hz, 1H), 6.41 (s, 1H), 6.36 (d, J=7.6 Hz, 2H), 6.24 (dd, J=10.1, 1.7 Hz, 1H), 6.06 (d, J=13.8 Hz, 2H), 5.44 (d, J=2.6 Hz, 1H), 5.33 (d, J=7.0 Hz, 1H), 5.04 (t, J=6.0 Hz, 1H), 4.91 (s, 2H), 4.27-4.21 (m, 2H), 4.04 (dd, J=19.2, 5.9 Hz, 1H), 2.85-2.76 (m, 2H), 2.70-2.66 (m, 3H), 2.37-2.35 (m, 2H), 2.07-2.06 (m, 2H), 1.84 (d, J=7.1 Hz, 2H), 1.71 (t, J=10.3 Hz, 2H), 1.50 (s, 4H), 0.90 (s, 3H).

Example 57: Synthesis of (6aR,6bS,7S,8aS,8bS,10R,11aR,12aS,12bS)-10-(4-((3-Aminophenyl)amino)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one Step 1: Synthesis of tert-Butyl (3-((4-formylphenyl)amino)phenyl)carbamate

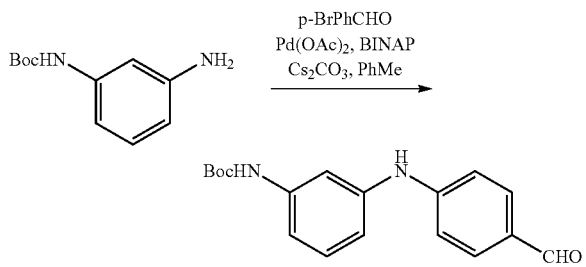

A mixture tert-butyl (3-aminophenyl)carbamate (31.2 g, 150 mmol), 4-bromobenzaldehyde (33.3 g, 180 mmol), Pd(OAc)₂ (1.684 g, 7.50 mmol), BINAP ((RS)2,2'-bis(diphenylphosphino)-1,1'-binaphthyl) (9.34 g, 15.00 mmol), Cs₂CO₃ (98 g, 300 mmol) was refluxed in toluene (300 mL)

under nitrogen for 16 h. After cooling to room temperature, the mixture was partitioned between water and EtOAc. The organic layer was concentrated and purified by column chromatography eluting with PE:EtOAc (5:1) to give the title compound (32.8 g, 105 mmol, 70% yield) as a yellow oil. LCMS (Method j, Table 7) $R_t$=1.94 min; MS m/z=313 [M+H$^+$].

Step 2: Synthesis of (6aR,6bS,7S,8aS,8bS,10R, 11aR,12aS,12bS)-10-(4-((3-Aminophenyl)amino) phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one DCM=1:40), and the resulting material was purified further by prep-HPLC to afford the title compound (1.729 g, 3.03 mmol, 10% yield) as a white solid. LCMS (Method k, Table 7) $R_t$=1.50 min; MS m/z=571[M+H$^+$]. $^1$H NMR (400 MHz, DMSO) δ 8.01 (s, 1H), 7.33 (d, J=10.1 Hz, 1H), 7.27 (d, J=8.5 Hz, 2H), 7.00 (d, J=8.5 Hz, 2H), 6.87 (t, J=7.9 Hz, 1H), 6.36 (s, 1H), 5.94 (s, 1H), 5.32 (s, 1H), 5.10 (s, 1H), 5.02-4.87 (m, 3H), 4.80 (d, J=2.8 Hz, 1H), 4.51 (d, J=16.4 Hz, 1H), 4.31 (s, 1H), 4.20 (d, J=17.8 Hz, 1H), 2.62-2.52 (m, 1H), 2.32 (d, J=11.0 Hz, 1H), 2.20-1.98 (m, 2H), 1.86-1.69 (m, 4H), 1.69-1.55 (m, 1H), 1.41 (s, 3H), 1.18-0.97 (m, 2H), 0.87 (s, 3H).

The minor acetal isomer, (6aR,6bS,7S,8aS,8bS,10S,11aR, 12aS,12bS)-10-(4-((3-aminophenyl)amino)phenyl)-7-hy-

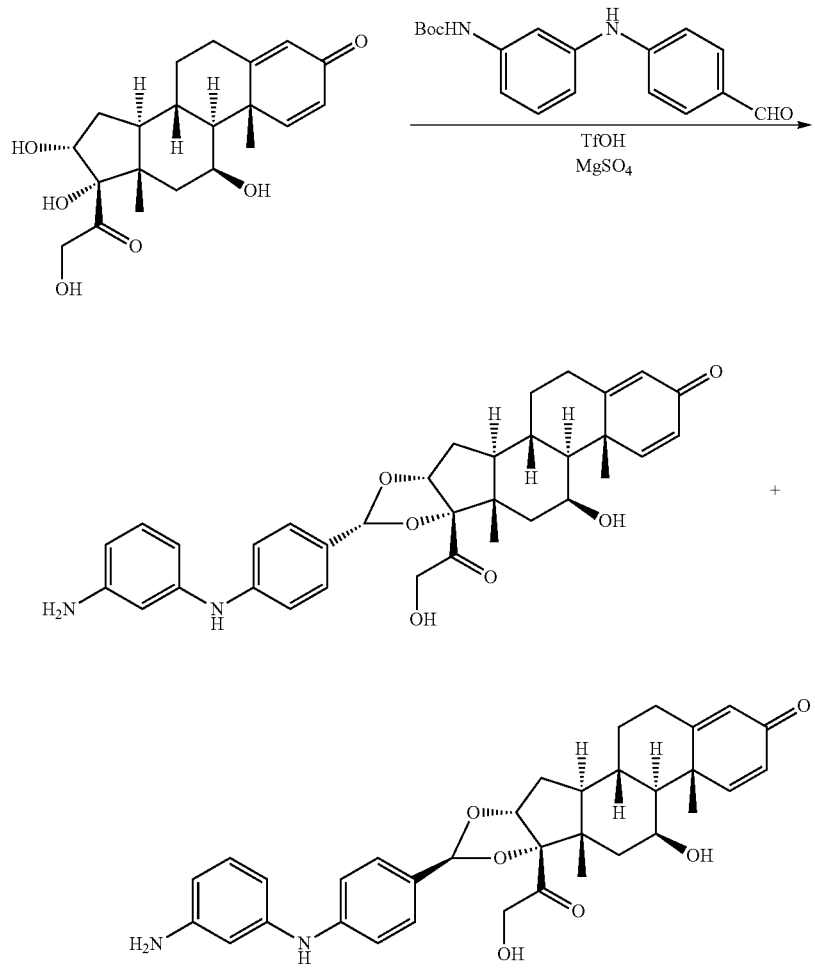

Trifluoromethanesulfonic acid (14.21 ml, 160 mmol) was added drop-wise to a 0° C. suspension of (8S,9S,10R,11S, 13S,14S,16R,17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (12.05 g, 32.0 mmol) and tert-butyl (3-((4-formylphenyl)amino)phenyl)carbamate (10 g, 32.0 mmol) in THF (50.00 ml) and MeCN (50 ml). The reaction mixture was stirred for additional 2 hours at the same temperature. The mixture was diluted with EtOAc (200 mL), washed with water (100 mL), saturated NaHCO$_3$ solution (lx 100 mL), and brine (1×100 mL), dried over Na$_2$SO$_4$, and concentrated in vacuo. The residue was purified by column chromatography (MeOH:

droxy-8b-(2-hydroxyacetyl)-6a,8a-dimethyl-1,2,6a,6b,7,8, 8a,8b,11a,12,12a,12b-dodecahydro-4H-naphtho[2',1':4,5] indeno[1,2-d][1,3]dioxol-4-one (78 mg, 0.137 mmol, 0.4% yield) as a white solid. LCMS (Method k, Table 7) $R_t$=1.53 min; MS m/z=571[M+H$^+$]. $^1$H NMR (400 MHz, DMSO) δ 8.00 (s, 1H), 7.32 (d, J=10.1 Hz, 1H), 7.07 (d, J=8.5 Hz, 2H), 6.96 (d, J=8.5 Hz, 2H), 6.87 (t, J=7.9 Hz, 1H), 6.35 (s, 1H), 6.24 (d, J=7.9 Hz, 1H), 6.17 (d, J=10.0 Hz, 1H), 6.10 (d, J=7.9 Hz, 1H), 6.00 (s, 1H), 5.95 (s, 1H), 5.27 (d, J=7.0 Hz, 1H), 5.02 (t, J=5.9 Hz, 1H), 4.97 (s, 2H), 4.78 (d, J=2.7 Hz, 1H), 4.30 (s, 2H), 4.03 (dd, J=19.1, 5.8 Hz, 1H), 2.65-2.52 (m, 1H), 2.32 (d, J=10.2 Hz, 1H), 2.14-1.95 (m, 2H), 1.89-1.63 (m, 5H), 1.39 (s, 3H), 1.28-1.11 (m, 1H), 1.05 (d, J=10.7 Hz, 1H), 0.89 (s, 3H).

Example 58: Synthesis of (6aS,6bR,7S,8aS,8bS, 10R,11aR,12aS,12bS)-10-(4-((3-Aminophenyl) amino)phenyl)-6b-fluoro-7-hydroxy-8b-(2-hydroxy-acetyl)-6a,8a-dimethyl-1,2,6a,6b,7,8,8a,8b, 11a,12, 12a,12b-dodecahydro-4H-naphtho[2',1':4,5]indeno [1,2-d][1,3]dioxol-4-one

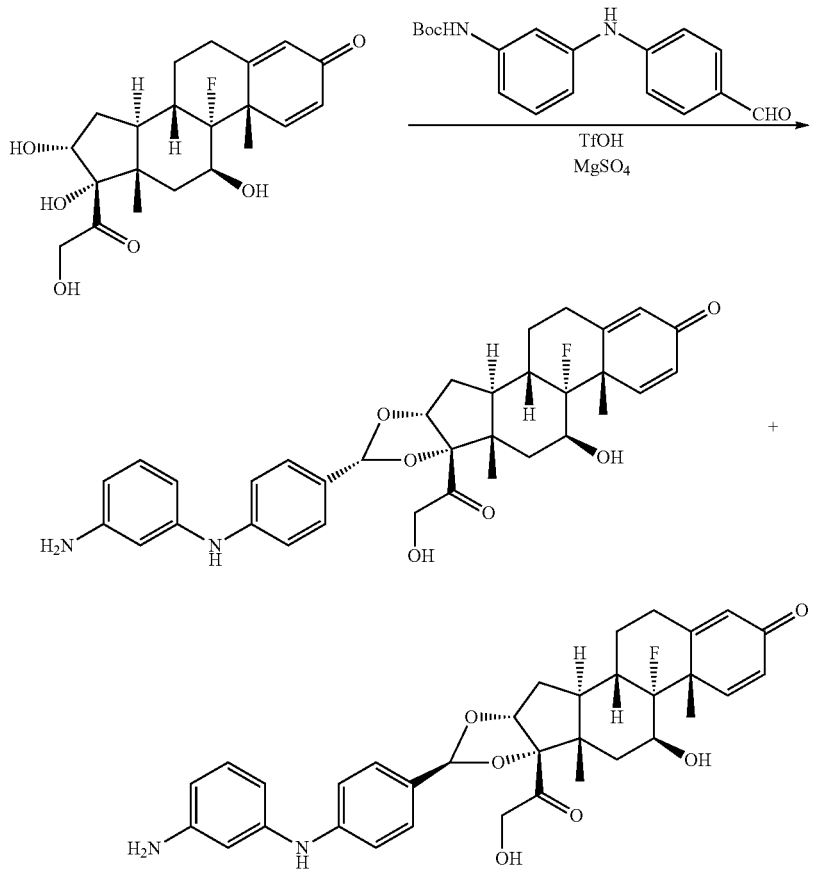

Synthesized using the same procedure as Example 57 above. Major acetal isomer: LCMS (Method k, Table 7) $R_t$=1.49 min; MS m/z=589 [M+H$^+$]. $^1$H NMR (400 MHz, DMSO) δ 8.02 (s, 1H), 7.30 (d, J=10.1 Hz, 1H), 7.23 (d, J=8.5 Hz, 2H), 6.99 (d, J=8.5 Hz, 2H), 6.87 (t, J=7.9 Hz, 1H), 6.36 (s, 1H), 6.31-6.16 (m, 2H), 6.10 (d, J=7.8 Hz, 1H), 6.04 (s, 1H), 5.45 (d, J=2.6 Hz, 1H), 5.35 (s, 1H), 5.11 (t, J=5.9 Hz, 1H), 4.97 (s, 2H), 4.91 (d, J=4.6 Hz, 1H), 4.51 (dd, J=19.5, 6.3 Hz, 1H), 4.20 (dd, J=19.2, 5.5 Hz, 2H), 2.74-2.58 (m, 1H), 2.36 (d, J=10.2 Hz, 1H), 2.27-2.13 (m, 1H), 2.06 (d, J=9.5 Hz, 2H), 1.93-1.78 (m, 1H), 1.78-1.57 (m, 3H), 1.51 (s, 3H), 1.42 (dd, J=12.4, 4.5 Hz, 1H), 0.87 (s, 3H).

Minor acetal isomer, (6aS,6bR,7S,8aS,8bS,10S,11aR, 12aS,12bS)-10-(4-((3-aminophenyl)amino)phenyl)-6b-fluoro-7-hydroxy-8b-(2-hydroxyacetyl)-6a,8a-dimethyl-1, 2,6a,6b,7,8,8a,8b,11a,12,12a,12b-dodecahydro-4H-naphtho [2',1':4,5]indeno[1,2-d][1,3]dioxol-4-one

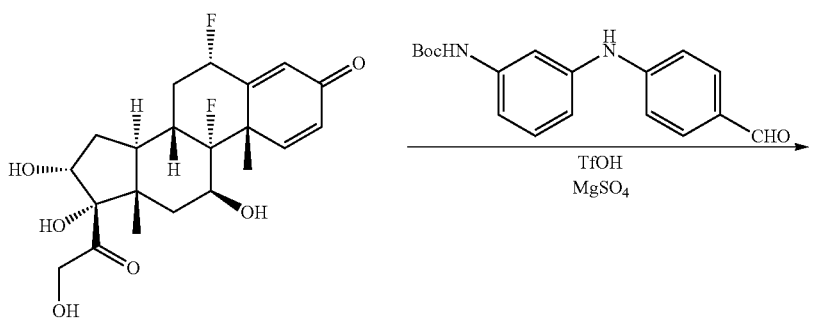

-continued

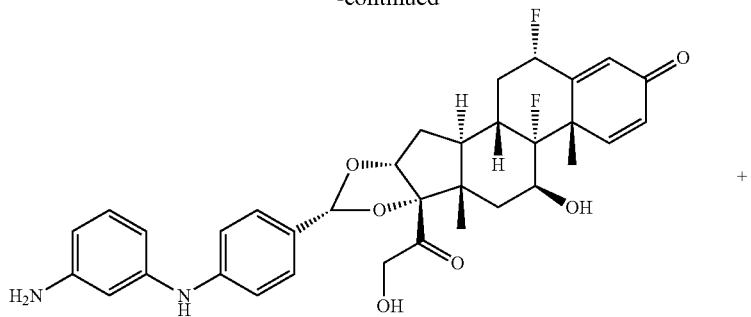

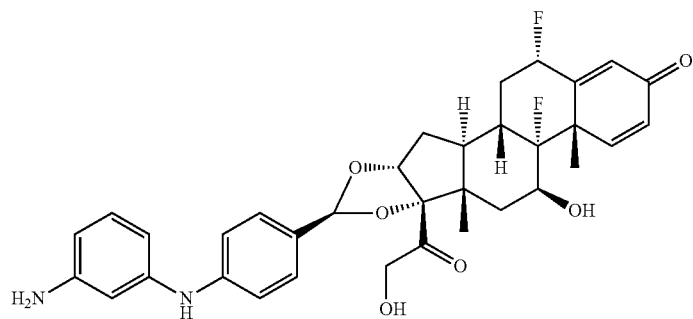

Synthesized using the same procedure as Example 57 above. Major acetal isomer: LCMS (Method 1, Table 7) $R_t$=1.62 min; MS m/z=607 [M+H$^+$]. $^1$H NMR (400 MHz, DMSO) δ 8.02 (s, 1H), 7.25 (dd, J=18.2, 9.4 Hz, 3H), 6.99 (d, J=8.6 Hz, 2H), 6.87 (t, J=7.9 Hz, 1H), 6.36 (t, J=1.9 Hz, 1H), 6.30 (dd, J=10.1, 1.8 Hz, 1H), 6.25-6.19 (m, 1H), 6.14 (s, 1H), 6.09 (dd, J=7.9, 1.3 Hz, 1H), 5.77-5.55 (m, 1H), 5.53 (d, J=2.8 Hz, 1H), 5.35 (s, 1H), 5.11 (t, J=6.0 Hz, 1H), 4.96 (s, 2H), 4.92 (d, J=5.1 Hz, 1H), 4.51 (dd, J=19.5, 6.4 Hz, 1H), 4.21 (dd, J=19.3, 5.6 Hz, 2H), 2.76-2.53 (m, 1H), 2.28 (dd, J=12.6, 5.9 Hz, 2H), 2.06 (d, J=12.0 Hz, 3H), 1.70 (dt, J=20.2, 6.0 Hz, 3H), 1.60-1.40 (m, 4H), 0.86 (s, 3H).

Minor acetal isomer, (2S,6aS,6bR,7S,8aS,8bS,10S,11aR,12aS,12bS)-10-(4-((3-aminophenyl)amino)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one: LCMS (Method 1, Table 7) $R_t$=1.65 min; MS m/z=607 [M+H$^+$]. $^1$H NMR (400 MHz, DMSO) δ 8.01 (s, 1H), 7.27 (d, J=9.8 Hz, 1H), 7.09 (d, J=7.9 Hz, 2H), 6.97 (d, J=8.0 Hz, 2H), 6.88 (t, J=7.7 Hz, 1H), 6.41-6.19 (m, 3H), 6.20-6.07 (m, 2H), 6.03 (s, 1H), 5.65 (d, J=46.4 Hz, 1H), 5.52 (s, 1H), 5.32 (d, J=6.8 Hz, 1H), 5.06 (s, 1H), 4.97 (s, 2H), 4.32 (dd, J=19.1, 5.3 Hz, 1H), 4.19 (s, 1H), 4.06 (dd, J=18.7, 4.8 Hz, 1H), 2.59 (d, J=13.8 Hz, 1H), 2.29 (s, 1H), 2.17 (d, J=7.2 Hz, 1H), 2.07 (s, 1H), 1.87 (d, J=6.7 Hz, 1H), 1.69 (dd, J=23.7, 12.4 Hz, 3H), 1.50 (s, 4H), 0.89 (s, 3H).

Example 60: Synthesis of (6aR,6bS,7S,8aS,8bS,10R,11aR,12aS,12bS)-10-(4-((3-Aminobenzyl)thio)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one Step 1: Synthesis of 4-((3-Nitrobenzyl)thio)benzaldehyde

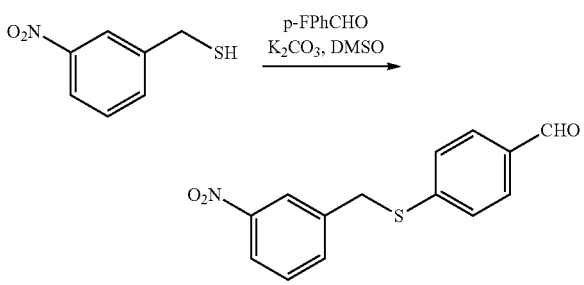

To a solution of (3-nitrophenyl)methanethiol (35 g, 282 mmol) and 4-fluorobenzaldehyde (52.5 g, 310 mmol) in dry dimethyl sulfoxide (220 mL) was added potassium carbonate (78 g, 564 mmol). The reaction mixture was heated to 100° C. for 4 hours. One additional vial was set up as described above. The two reactions were combined and diluted with water (2 L) and then extracted with EtOAc (3×600 mL). The combined organic layer was dried over Na$_2$SO$_4$, and concentrated to give a residue, which was purified by column chromatography (eluted with PE/EtOAc=20/1 to 5/1) to give the title compound (62 g, 80% yield) as slight brown solid. $^1$H NMR (400 MHz, DMSO-d$_6$) δ 4.54 (s, 2H) 7.51 (d, J=8.33 Hz, 2H) 7.59 (s, 1H) 7.77 (d, J=8.33 Hz, 2H) 7.87 (d, J=7.89 Hz, 1H) 8.05-8.10 (m, 1H) 8.30 (s, 1H) 9.87 (s, 1H).

Step 2: Synthesis of (6aR,6bS,7S,8aS,8bS,10R,11aR,12aS,12bS)-7-Hydroxy-8b-(2-hydroxyacetyl)-6a,8a-dimethyl-10-(4-((3-nitrobenzyl)thio)phenyl)-1,2,6a,6b,7,8,8a,8b,11a,12,12a,12b-dodecahydro-4H-naphtho[2',1':4,5]indeno[1,2-d][1,3]dioxol-4-one

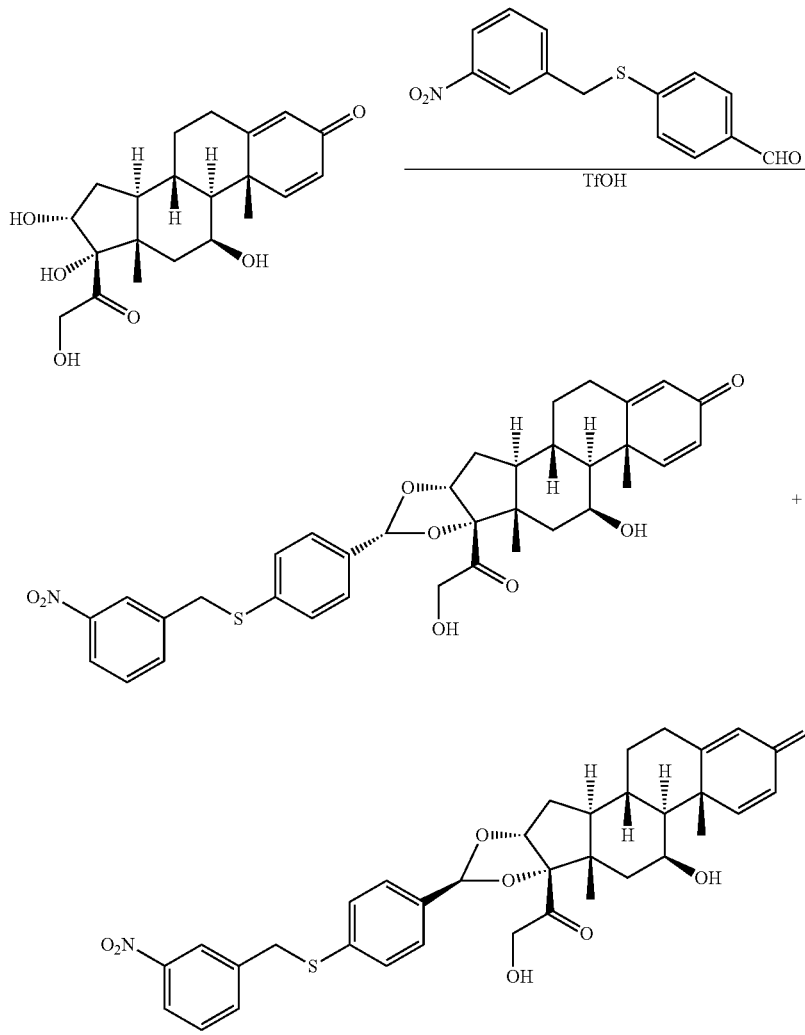

Trifluoromethanesulfonic acid (21.23 mL, 239 mmol) was added drop-wise to a 0 OC solution of (8S,9S,1R,11S,13S,14S,16R,17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (9 g, 23.91 mmol) and 4-((3-nitrobenzyl)thio)benzaldehyde (7.19 g, 26.3 mmol) in MeCN (500 mL). The reaction was stirred for 1 hour at 0° C. Two additional vials were set up as described above. All three reactions were combined and poured into water (2 L). The resulting mixture was extracted with EtOAc (3×500 mL). The combined organic layer was dried over $Na_2SO_4$, and concentrated to give a residue, which was purified by prep-HPLC to give the title compound (5.57 g, 16% yield) as white solid. LCMS (Method n Table 7): $R_t$=3.20 min; m/z=632.0 [M+H$^+$]. $^1$H NMR (400 MHz, DMSO-$d_6$) δ 0.84 (s, 3H) 0.93-1.08 (m, 2H) 1.37 (s, 3H) 1.52-1.76 (m, 5H) 1.94-2.15 (m, 2H) 2.29 (br d, J=11.91 Hz, 1H) 2.50-2.58 (m, 1H) 4.15 (dd, J=19.40, 5.51 Hz, 1H) 4.27 (br d, J=2.87 Hz, 1H) 4.39 (s, 2H) 4.48 (dd, J=19.40, 6.39 Hz, 1H) 4.77 (d, J=3.09 Hz, 1H) 4.89 (d, J=4.63 Hz, 1H) 5.07 (t, J=5.95 Hz, 1H) 5.38 (s, 1H) 5.91 (s, 1H) 6.15 (dd, J=10.14, 1.76 Hz, 1H) 7.25-7.38 (m, 5H) 7.55 (t, J=7.94 Hz, 1H) 7.79 (d, J=7.72 Hz, 1H) 8.04 (dd, J=8.16, 1.54 Hz, 1H) 8.19 (d, J=1.76 Hz, 1H)

The minor acetal isomer, (6aR,6bS,7S,8aS,8bS,10S,11aR,12aS,12bS)-7-hydroxy-8b-(2-hydroxyacetyl)-6a,8a-dimethyl-10-(4-((3-nitrobenzyl)thio)phenyl)-1,2,6a,6b,7,8,8a,8b,11a,12,12a,12b-dodecahydro-4H-naphtho[2',1':4,5]indeno[1,2-d][1,3]dioxol-4-one (0.34 g, 1% yield) also was obtained as a white solid. LCMS (Method n, Table 7): $R_t$=3.28 min; MS m/z=631.8 [M+H$^+$]. $^1$H NMR (400 MHz, DMSO-$d_6$) δ 0.86 (s, 3H) 0.98-1.05 (m, 1H) 1.10-1.21 (m, 1H) 1.37 (s, 3H) 1.66-1.88 (m, 5H) 1.94-2.08 (m, 2H) 2.29 (br dd, J=13.23, 2.87 Hz, 1H) 2.50-2.56 (m, 1H) 3.99 (dd, J=19.18, 5.95 Hz, 1H) 4.20 (dd, J=19.07, 6.28 Hz, 1H) 4.27 (br s, 1H) 4.39 (s, 2H) 4.77 (d, J=3.09 Hz, 1H) 4.99 (s, 1H) 5.26 (d, J=6.84 Hz, 1H) 5.92 (s, 1H) 6.04 (s, 1H) 6.15 (dd, J=10.03, 1.87 Hz, 1H) 7.16 (d, J=8.38 Hz, 2H) 7.26-7.34 (m, 3H) 7.55 (t, J=7.94 Hz, 1H) 7.75 (d, J=7.72 Hz, 1H) 8.05 (dd, J=8.16, 1.54 Hz, 1H) 8.21 (t, J=1.76 Hz, 1H).

Step 3: Synthesis of (6aR,6bS,7S,8aS,8bS,10R, 11aR,12aS,12bS)-10-(4-((3-Aminobenzyl)thio)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

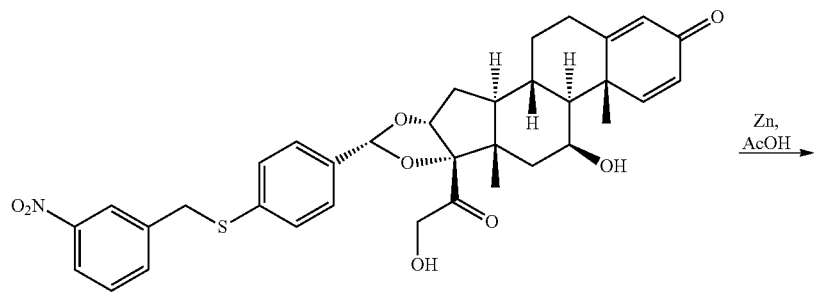

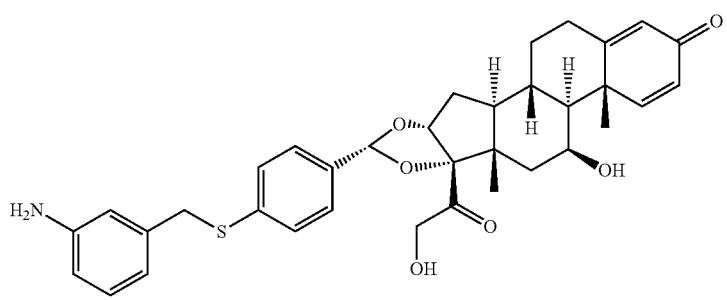

A mixture of (6aR,6bS,7S,8aS,8bS,10R,11aR,12aS, 12bS)-7-hydroxy-8b-(2-hydroxyacetyl)-6a,8a-dimethyl-10-(4-((3-nitrobenzyl)thio)phenyl)-1,2,6a,6b,7,8,8a,8b,11a,12, 12a,12b-dodecahydro-4H-naphtho[2',1':4,5]indeno[1,2-d] [1,3]dioxol-4-one (138 mg, 0.22 mmol), zinc (214 mg, 3.28 mmol), and acetic acid (0.4 ml, 6.99 mmol) in EtOAc (2 mL) was stirred at 40° C. for 2 hours. LCMS showed partial conversion to the desired aniline product. Added more zinc (71 mg, 1.09 mml) and stirred at 40° C. for an additional 2 hours. The solution was cooled to room temperature and partitioned between saturated aqueous $NaHCO_3$ and EtOAc (3×). The combined organic layers were dried over $Na_2SO_4$ and purified by chromatography (silica gel) eluting with 0-5% MeOH in DCM to give the title compound (64 mg, 0.106 mmol, 49% yield). LCMS (Method r, Table 7) $R_f$=0.77 min; MS m/z=601.9 [M+H$^+$]. $^1$H NMR (400 MHz, DMSO-$d_6$) δ 7.35 (d, J=8.5 Hz, 2H), 7.32-7.24 (m, 3H), 6.89 (t, J=7.7 Hz, 1H), 6.56 (q, J=2.3 Hz, 1H), 6.47 (d, J=7.4 Hz, 1H), 6.40 (ddd, J=7.6, 2.6, 1.4 Hz, 1H), 6.15 (dd, J=10.1, 1.8 Hz, 1H), 5.95-5.89 (m, 1H), 5.38 (s, 1H), 5.03 (d, J=14.0 Hz, 3H), 4.90 (d, J=4.8 Hz, 1H), 4.77 (d, J=3.5 Hz, 1H), 4.54-4.44 (m, 1H), 4.28 (s, 1H), 4.16 (d, J=20.6 Hz, 1H), 4.06 (d, J=2.3 Hz, 2H), 2.59-2.50 (m, 1H), 2.30 (d, J=11.5 Hz, 1H), 2.14-2.03 (m, 1H), 1.97 (s, 2H), 1.88-1.67 (m, 4H), 1.63 (td, J=11.9, 10.4, 5.1 Hz, 1H), 1.37 (d, J=1.9 Hz, 3H), 1.10-0.92 (m, 2H), 0.84 (s, 3H).

Example 61: Synthesis of (6aR,6bS,7S,8aS,8bS, 10R,11aR,12aS,12bS)-10-(4-((2-Aminopyridin-4-yl) methyl)phenyl)-7-hydroxy-8b-(2-hydroxyacetyl)-6a, 8a-dimethyl-1,2,6a,6b, 7,8,8a,8b,11a,12,12a,12b-dodecahydro-4H-naphtho[2',1':4,5]indeno[1,2-d][1, 3]dioxol-4-one Step 1: Synthesis of (6aR,6bS,7S,8aS,8bS,10R, 11aR,12aS,12bS)-10-(4-(Bromomethyl)phenyl)-7-hydroxy-8b-(2-hydroxyacetyl)-6a,8a-dimethyl-6a, 6b,7,8,8a,8b,11a,12,12a,12b-decahydro-1H-naphtho [2',1':4,5]indeno[1,2-d][1,3]dioxol-4(2H)-one

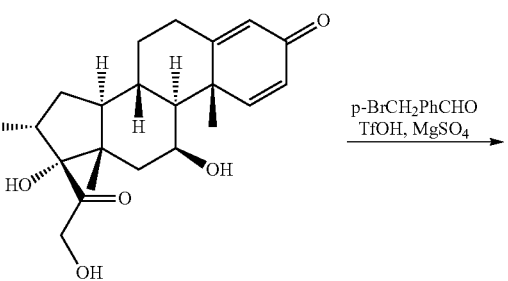

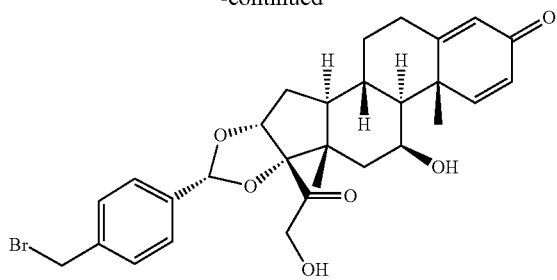

4-(Bromomethyl)benzaldehyde (0.539 g, 2.71 mmol) was added to a 0 OC suspension of (8S,9S,10R,11S,13S,14S,16R,17S)-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one (1.0738 g, 2.85 mmol), 4-(bromomethyl)benzaldehyde (0.539 g, 2.71 mmol), and MgSO$_4$ (1.33 g, 11.05 mmol) in MeCN (18 ml). Trifluoromethanesulfonic acid (2.0 g, 13.5 mmol) was added in a drop-wise manner, so as to maintain a temperature of less than 7° C. The reaction was stirred for 4 min, whereupon it was quenched by addition of saturated aqueous NaHCO$_3$ (20 mL) and extracted with EtOAc (60 mL). The combined organics were washed with brine (10 mL) and solvent was removed under reduced pressure. Purification by chromatography (silica, 40 g) eluting with a gradient of 0-5% MeOH/DCM gave the title compound (1.59 g, 2.85 mmol, 100% yield) as an off-white foam (9:1 mixture of acetal diastereomers. Characterization is provided for the major acetal isomer: LCMS (Method r, Table 7) R$_t$=1.04 min; MS m/z=557.2, 559.2 [M+H]. 1H NMR (501 MHz, DMSO-d6) δ 7.44 (s, 4H), 7.30 (dd, J=10.1, 2.2 Hz, 1H), 6.15 (ddd, J=10.1, 4.8, 1.9 Hz, 1H), 5.91 (t, J=1.7 Hz, 1H), 5.43 (s, 1H), 5.07 (s, 1H), 4.93 (d, J=5.1 Hz, 1H), 4.77 (dd, J=3.6, 0.9 Hz, 1H), 4.67 (s, 2H), 4.51 (dd, J=19.4, 4.1 Hz, 1H), 4.31-4.26 (m, 1H), 4.17 (d, J=19.5 Hz, 1H), 2.58-2.49 (m, 1H), 2.30 (dd, J=12.9, 4.7 Hz, 1H), 2.16-2.05 (m, 1H), 1.99 (d, J=23.9 Hz, 1H), 1.89-1.71 (m, 2H), 1.75-1.65 (m, 1H), 1.67-1.57 (m, 1H), 1.38 (s, 3H), 1.11-0.91 (m, 2H), 0.85 (s, 3H).

Step 2: Synthesis of (6aR,6bS,7S,8aS,8bS,10R,11aR,12aS,12bS)-10-(4-((2-Aminopyridin-4-yl)methyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

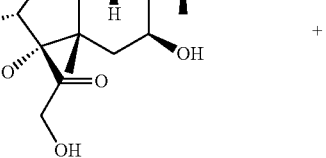

+

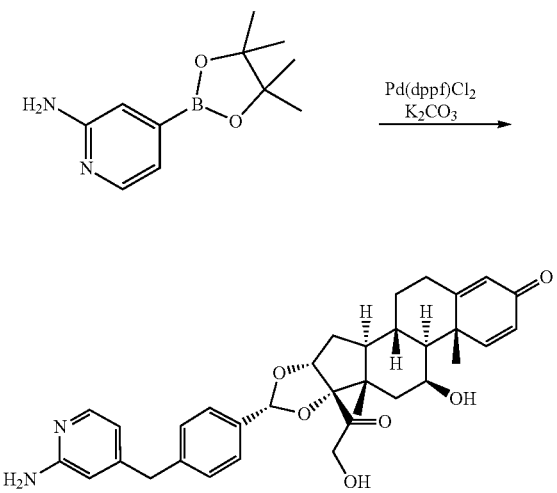

A 20 mL vial was charged with (6aR,6bS,7S,8aS,8bS,10R,11aR,12aS,12bS)-10-(4-(bromomethyl)phenyl)-7-hydroxy-8b-(2-hydroxyacetyl)-6a,8a-dimethyl-6a,6b,7,8,8a,8b, 11a,12,12a,12b-decahydro-1H-naphtho[2',1':4,5]indeno[1,2-d][1,3]dioxol-4(2H)-one (0.100 g, 0.179 mmol), 4-(4,4,5,5-tetramethyl-1,3,2-dioxaborolan-2-yl)pyridin-2-amine (0.039 g, 0.179 mmol), and K$_2$CO$_3$ (0.099 g, 0.718 mmol) in degassed dioxane (2.0 ml)/water (0.200 mL) solution. The suspension was evacuated and back filled with dry N$_2$ (3×). Pd(dppf)Cl$_2$ (0.012 g, 0.016 mmol) was added and the vial was once again evacuated and back filled with dry N2. The reaction mixture was heated to 90° C. After 1.5 hours the starting material was consumed. The reaction was allowed to cool to room temperature, diluted with EtOAc (20 mL) and washed with water (25 mL) then brine (25 mL), dried over MgSO$_4$, and solvent was removed under reduced pressure. Purification by chromatography (silica, 40 g) eluting with a gradient of 0-10% MeOH/CH$_2$Cl$_2$ gave a light tan solid. Further purification by reverse phase prep HPLC on a Phenomenex C18(2) 10 micron column (250×50 mm). A gradient of MeCN (A) and 0.1% TFA in water (B) was used, at a flow rate of 80 mL/min (0-5.0 min 15% A, 5.0-20 min linear gradient 15-85% A, 20-25 min hold). Combined fractions were frozen and lyophilized to give the title compound (27 mg, 0.047 mmol, 26% yield) as a white solid. LCMS (Method r, Table 7) R$_t$=0.90 min; MS m/z=571.3 [M+H$^+$]. 1H NMR (501 MHz, DMSO-d6) δ 7.93 (s, 2H), 7.82 (d, J=6.6 Hz, 1H), 7.44 (d, J=8.1 Hz, 2H), 7.39-7.22 (m, 3H), 6.73 (d, J=8.1 Hz, 1H), 6.69 (s, 1H), 6.24-6.09 (m, 1H), 5.93 (s, 1H), 5.44 (s, 1H), 4.94 (d, J=5.1 Hz, 1H), 4.80 (s, 1H), 4.50 (d, J=19.4 Hz, 1H), 4.30 (s, 1H), 4.19 (d, J=19.4 Hz, 1H), 3.99 (s, 2H), 2.61-2.51 (m, 1H), 2.35-2.27 (m, 1H), 2.19-2.08 (m, 1H), 2.08-1.99 (m, 1H), 1.82-1.59 (m, 5H), 1.40 (s, 3H), 1.02 (ddd, J=27.9, 11.7, 3.2 Hz, 2H), 0.87 (s, 3H).

The following examples were synthesized using the same procedure as Example 61 (above).

TABLE 8

| Example | Structure and Name | LCMS and ¹H NMR |
|---|---|---|
| 62 | 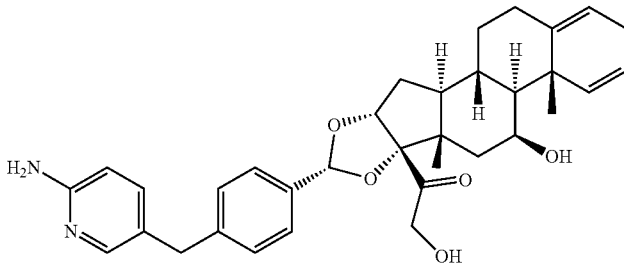<br>(6aR,6bS,7S,8aS,8bS,10R,11aR,12aS,12bS)-10-(4-((6-aminopyridin-3-yl)methyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one | LCMS (Method r, Table 7) $R_t$ = 0.87 min; MS m/z = 571.4 [M + H].<br>¹H NMR (500 MHz, DMSO-d$_6$) δ 7.84 (d, J = 2.1 Hz, 2H), 7.75 (dd, J = 9.1, 2.1 Hz, 1H), 7.44-7.37 (m, 2H), 7.31 (d, J = 10.1 Hz, 1H), 7.26 (d, J = 8.2 Hz, 2H), 6.90 (d, J = 9.0 Hz, 1H), 6.17 (dd, J = 10.1, 1.9 Hz, 1H), 5.93 (t, J = 1.6 Hz, 1H), 5.42 (s, 1H), 5.10 (s, 1H), 4.92 (d, J = 4.9 Hz, 1H), 4.80 (d, J = 3.4 Hz, 1H), 4.50 (d, J = 19.4 Hz, 1H), 4.29 (s, 1H), 4.17 (d, J = 19.5 Hz, 1H), 3.84 (s, 2H), 2.61-2.52 (m, 2H), 2.31 (d, J = 12.3 Hz, 1H), 2.13 (d, J = 10.9 Hz, 1H), 2.08-1.98 (m, 1H), 1.81-1.58 (m, 5H), 1.40 (s, 3H), 1.00 (ddd, J = 32.4, 11.7, 4.1 Hz, 2H), 0.86 (s, 3H). |
| 63 | 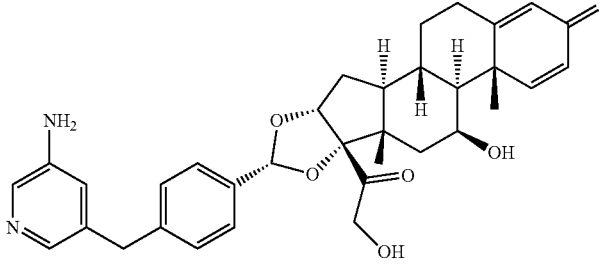<br>(6aR,6bS,7S,8aS,8bS,10R,11aR,12aS,12bS)-10-(4-((5-aminopyridin-3-yl)methyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one | LCMS (Method r, Table 7) $R_t$ = 0.87 min; MS m/z = 571.4 [M + H].<br>¹H NMR (400 MHz, DMSO-d6) δ 7.88 (s, 1H), 7.81 (d, J = 2.2 Hz, 1H), 7.36 (d, J = 8.1 Hz, 2H), 7.32-7.18 (m, 3H), 6.10 (dd, J = 10.1, 1.8 Hz, 1H), 5.87 (s, 1H), 5.36 (s, 1H), 4.86 (d, J = 4.8 Hz, 1H), 4.74 (s, 1H), 4.43 (d, J = 19.5 Hz, 1H), 4.23 (s, 1H), 4.11 (d, J = 19.4 Hz, 1H), 3.93 (s, 2H), 2.54-2.45 (m, 1H), 2.31-2.17 (m, 1H), 2.14-1.90 (m, 2H), 1.76-1.50 (m, 5H), 1.33 (s, 3H), 1.05-0.85 (m, 2H), 0.80 (s, 3H) |
| 64 | 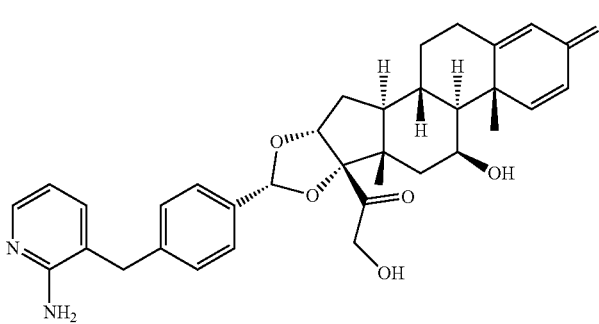<br>(6aR,6bS,7S,8aS,8bS,10R,11aR,12aS,12bS)-10-(4-((2-aminopyridin-3-yl)methyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one | LCMS (Method r, Table 7) $R_t$ = 0.86 min; MS m/z = 571.3 [M + H].<br>¹H NMR (501 MHz, DMSO-d6) δ 7.89 (s, 2H), 7.82 (d, J = 6.2 Hz, 1H), 7.58 (d, J = 6.1 Hz, 1H), 7.36 (d, J = 8.1 Hz, 2H), 7.23 (dd, J = 20.2, 9.1 Hz, 3H), 6.85-6.71 (m, 1H), 6.10 (d, J = 11.9 Hz, 1H), 5.86 (s, 1H), 5.36 (s, 1H), 4.87 (d, J = 5.0 Hz, 1H), 4.75 (s, 1H), 4.44 (d, J = 19.4 Hz, 1H), 4.23 (s, 1H), 4.12 (d, J = 19.4 Hz, 1H), 3.87 (s, 2H), 2.55-2.45 (m, 1H), 2.24 (d, J = 11.0 Hz, 1H), 2.05 (d, J = 22.0 Hz, 1H), 2.01-1.91 (m, 1H), 1.77-1.49 (m, 5H), 1.33 (s, 3H), 1.04-0.87 (m, 2H), 0.80 (s, 3H). |
| 65 | 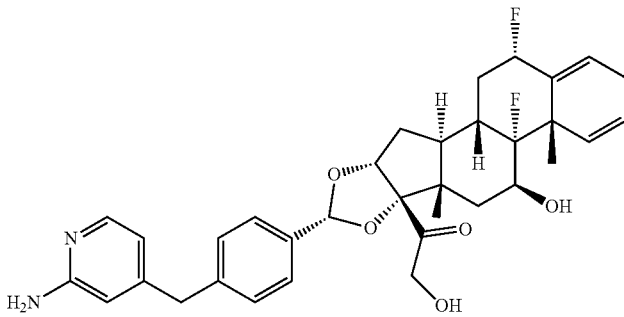<br>(2S,6aS,6bR,7S,8aS,8bS,10R,11aR,12aS,12bS)-10-(4-((2-aminopyridin-4-yl)methyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one | LCMS (Method r, Table 7) $R_t$ = 0.85 min; MS m/z = 607.4 [M + H].<br>¹H NMR (500 MHz, DMSO-d6) δ 7.80 (d, J = 6.5 Hz, 1H), 7.59 (s, 2H), 7.41 (d, J = 8.2 Hz, 2H), 7.31 (d, J = 7.9 Hz, 2H), 7.27 (d, J = 10.8 Hz, 1H), 6.69 (d, J = 6.8 Hz, 1H), 6.64 (s, 1H), 6.30 (dd, J = 10.2, 1.9 Hz, 1H), 6.13 (s, 1H), 5.55 (d, J = 5.8 Hz, 1H), 5.49 (s, 1H), 5.13 (s, 1H), 4.96 (d, J = 4.5 Hz, 1H), 4.26-4.13 (m, 2H), 3.95 (s, 2H), 2.62-2.53 (m, 1H), 2.35-2.28 (m, 1H), 2.28-2.18 (m, 1H), 2.09-1.99 (m, 1H), 1.77-1.66 (m, 3H), 1.50 (s, 4H), 0.87 (s,3H). |

TABLE 8-continued

| Example | Structure and Name | LCMS and $^1$H NMR |
|---|---|---|
| 66 | 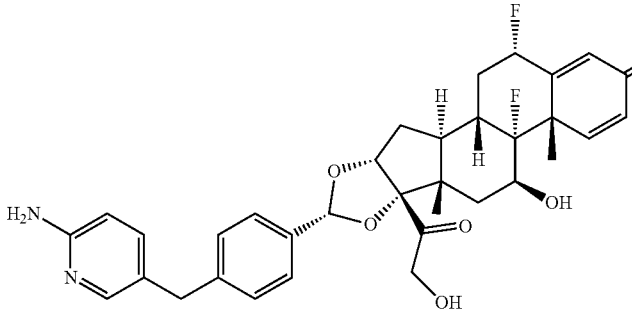<br>(2S,6aS,6bR,7S,8aS,8bS,10R,11aR,12aS,12bS)-10-(4-((6-aminopyridin-3-yl)methyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one | LCMS (Method r, Table 7) $R_t$ = 0.85 min; MS m/z = 607.4 [M + H].<br>$^1$H NMR (400 MHz, DMSO-d6) δ 7.76 (s, 1H), 7.65 (d, J = 9.5 Hz, 1H), 7.59 (s, 1H), 7.31 (d, J = 8.2 Hz, 2H), 7.25-7.15 (m, 3H), 6.79 (d, J = 9.2 Hz, 1H), 6.23 (d, J = 10.2 Hz, 1H), 6.06 (s, 1H), 5.69-5.49 (m, 1H), 5.46 (d, J = 4.0 Hz, 1H), 5.40 (s, 1H), 5.03 (s, 1H), 4.88 (d, J = 4.2 Hz, 1H), 4.44 (d, J = 19.4 Hz, 1H), 4.21-4.05 (m, 2H), 3.76 (s, 2H), 2.67-2.51 (m, 1H), 2.32-2.09 (m, 2H), 1.96 (d, J = 13.1 Hz, 1H), 1.71-1.57 (m, 3H), 1.50-1.35 (m, 4H), 0.80 (s, 3H). |

Example 67

Synthesis of 1-(3-(4-((6aR,6bS,7S,8aS,8bS,10R,11aR,12aS,12bS)-7-Hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)-1H-pyrrole-2,5-dione

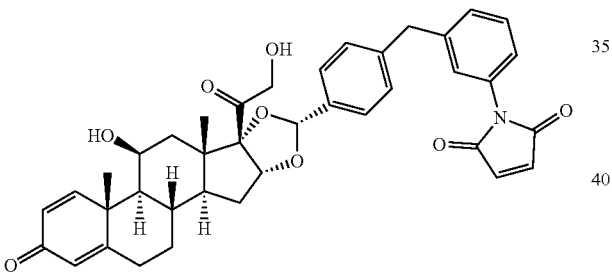

Step 1: Synthesis of (Z)-4-((3-(4-((6aR,6bS,7S,8aS,8bS,10R,11aR,12aS,12bS)-7-Hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-4-oxobut-2-enoic Acid

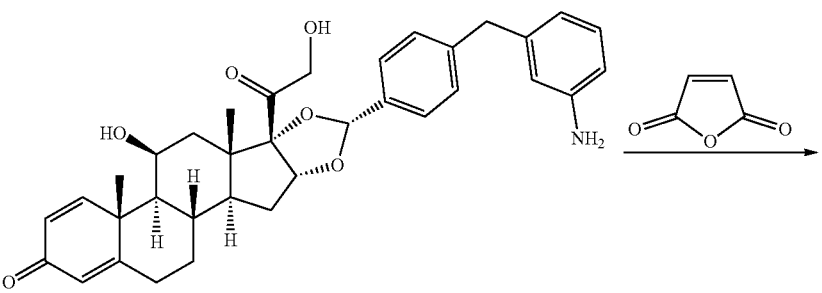

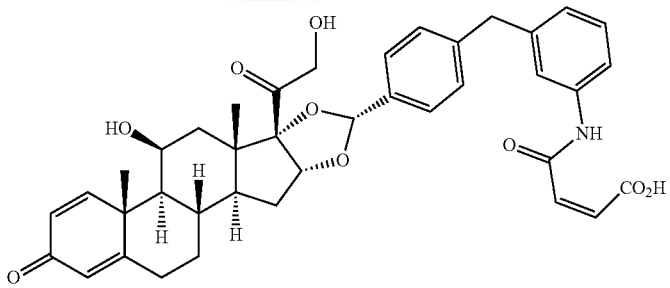

Maleic anhydride (46.5 mg, 0.474 mmol) was added to a room temperature solution of (6aR,6bS,7S,8aS,8bS,10R,11aR,12aS,12bS)-10-(4-(3-aminobenzyl)phenyl)-7-hydroxy-8b-(2-hydroxyacetyl)-6a,8a-dimethyl-6a,6b,7,8,8a,8b, 11a,12,12a,12b-decahydro-1H-naphtho[2',1':4,5]indeno[1,2-d][1,3]dioxol-4(2H)-one (239 mg, 0.420 mmol) in THF (3.0 mL). After 75 min, solvent was removed under reduced pressure to give the title compound as an off-white foam. This was used without further purification in the next step (100% yield was assumed). LCMS (Method o, Table 7) $R_t$=0.86 min; MS m/z=668.5 [M+H$^+$]. $^1$H NMR (400 MHz, DMSO-d6) δ 12.99 (s, 1H), 10.29 (s, 1H), 7.45-7.38 (m, 2H), 7.38-7.31 (m, 2H), 7.27 (d, J=10.1 Hz, 1H), 7.24-7.15 (m, 3H), 6.92 (dt, J=7.8, 1.3 Hz, 1H), 6.38 (d, J=12.1 Hz, 1H), 6.25 (d, J=12.0 Hz, 1H), 6.12 (dd, J=10.1, 1.9 Hz, 1H), 5.89 (d, J=1.5 Hz, 1H), 5.36 (s, 1H), 5.03 (s, 1H), 4.88 (d, J=5.1 Hz, 1H), 4.73 (d, J=3.3 Hz, 1H), 4.46 (d, J=19.4 Hz, 1H), 4.26 (p, J=3.2 Hz, 1H), 4.14 (d, J=19.4 Hz, 1H), 3.87 (s, 2H), 2.52 (dd, J=13.6, 5.3 Hz, 1H), 2.32-2.23 (m, 1H), 2.07 (tt, J=10.8, 6.2 Hz, 1H), 2.02-1.94 (m, 1H), 1.84-1.51 (m, 5H), 1.36 (s, 3H), 1.09 0.93 (m, 2H), 0.82 (s, 3H).

Step 2: Synthesis of 1-(3-(4-((6aR,6bS,7S,8aS,8bS,10R,11aR,12aS,12bS)-7-Hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)-1H-pyrrole-2,5-dione Bis(trimethylsilyl)amine (HMDS) (63.4 μL, 0.306 mmol) was added to a solution of zinc bromide (75.0 mg, 0.333 mmol) and (Z)-4-((3-(4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-4-oxobut-2-enoic acid (171 mg, 0.256 mmol) in tetrahydrofuran (2.0 mL). The mixture was heated to 50° C. for 2.5 h. LCMS indicated incomplete conversion, so another aliquot of bis(trimethylsilyl)amine (HMDS) (63.4 μL, 0.306 mmol) was added. The reaction was complete after an additional 90 min at 50° C. The mixture was cooled to room temperature, diluted with EtOAc (20 mL), then washed sequentially with 1 N aqueous HCl (2×10 mL), saturated aqueous NaHCO$_3$ (10 mL), brine (10 mL), dried over Na$_2$SO$_4$, and solvent was removed under reduced pressure. Purification by chromatography (silica, 12 g) eluting with a gradient of 0-10% MeOH/DCM gave the title compound (82.6 mg, 0.127 mmol, 50% yield) as an off-white solid. LCMS (Method r, Table 7) $R_t$=1.02 min; MS m/z=650.5 [M+H$^+$]. $^1$H NMR (400 MHz, DMSO-d6) δ 7.27 (dt, J=7.8, 3.7 Hz, 3H), 7.19 (d, J=10.1 Hz, 1H), 7.17-7.06 (m, 4H), 7.06-7.01 (m, 3H), 6.04 (dd, J=10.1, 1.9 Hz, 1H), 5.81 (t, J=1.5 Hz, 1H), 5.64 (s, 1H), 5.29 (s, 1H), 4.95 (t, J=5.9 Hz, 1H), 4.80 (d, J=5.1 Hz, 1H), 4.65 (d, J=3.2 Hz, 1H), 4.38 (dd, J=19.4, 6.4 Hz, 1H), 4.18 (t, J=3.4 Hz, 1H), 4.06 (dd, J=19.5, 5.7 Hz, 1H), 3.86 (s, 2H), 2.45 (dd, J=13.5, 5.4 Hz, 1H), 2.30-2.11 (m, 1H), 2.11-1.81 (m, 1H), 1.76-1.44 (m, 4H), 1.28 (s, 3H), 1.02-0.83 (m, 2H), 0.75 (s, 3H).

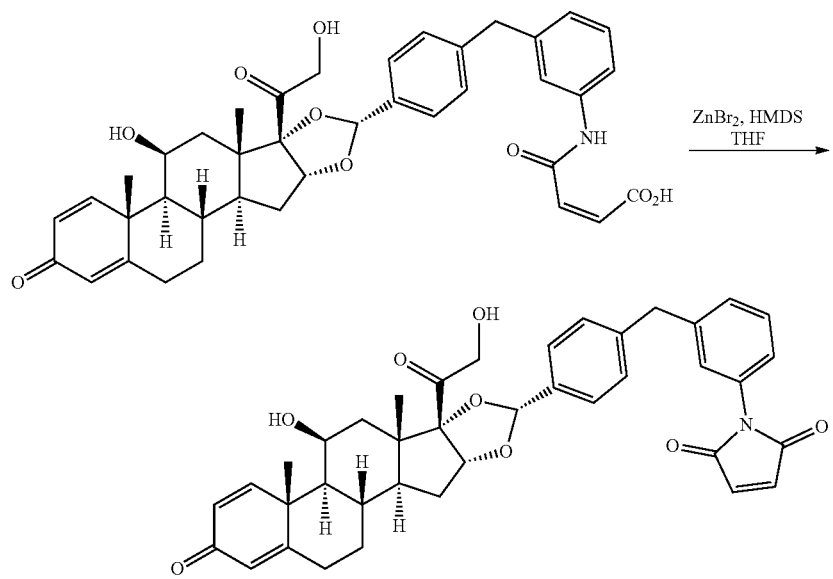

Example 68: Synthesis of 2-((6aR,6bS,7S,8aS,8bS, 10R,11aR,12aS,12bS)-10-(4-(3-(2,5-Dioxo-2,5-di-hydro-1H-pyrrol-1-yl)benzyl)phenyl)-7-hydroxy-6a, 8a-dimethyl-4-oxo-2,4,6a,6b,7,8,8a,8b,11a,12,12a, 12b-dodecahydro-1H-naphtho[2',1':4,5]indeno[1,2-d][1,3]dioxol-8b-yl)-2-oxoethyl dihydrogen phosphate

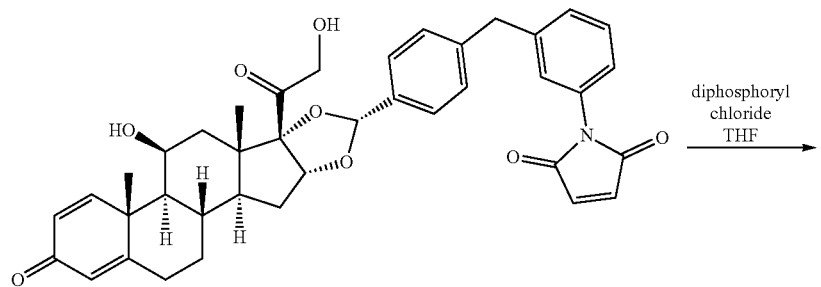

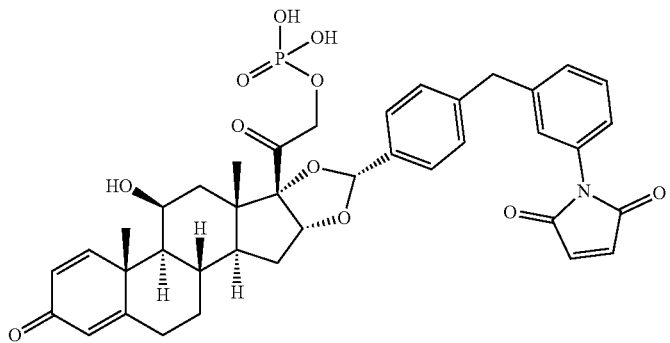

Diphosphoryl chloride (158 mg, 0.609 mmol) was added drop-wise to a −51° C. solution of 1-(3-(4-(((6aR,6bS,7S, 8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12, 12a,12b-dodecahydro-1H-naphtho[2',1':4,5]indeno[1,2-d][1,3]dioxol-10-yl)benzyl)phenyl)-1H-pyrrole-2,5-dione (82 mg, 0.126 mmol) in tetrahydrofuran (0.5 mL). The reaction was slowly warmed to −10 OC over an hour then quenched with water at −5° C. The mixture was treated with a saturated aqueous solution of NaHCO₃ to give a solution with a pH of 8. Treatment with EtOAc (5 mL) gave a milky emulsion. Adjusting the pH to 1 by addition of 1 N aqueous HCl improved the emulsion. Extracted with EtOAc (4×5 mL), then washed the combined organics with brine (5 mL), dried (Na₂SO₄), and removed solvent under reduced pressure. The product was purified by reverse phase prep HPLC on a Phenomenex C18(2) 10 micron column (250×50 mm). A gradient of MeCN (A) and 0.1% TFA in water (B) was used, at a flow rate of 90 mL/min (0-5.0 min 15% A, 5.0-20.0 min linear gradient 15-95% A). Combined fractions were frozen and lyophilized to give the title compound (3.6 mg, 4.93 mmol, 4% yield) as a white solid. LCMS (Method r, Table 7) R$_t$=0.95 min; MS m/z=730.5 [M+H⁺]. ¹H NMR (501 MHz, DMSO-d6) δ 7.38 (dt, J=7.8, 3.7 Hz, 3H), 7.31 (d, J=10.1 Hz, 1H), 7.29-7.26 (m, 2H), 7.25-7.22 (m, 1H), 7.19 (t, J=1.9 Hz, 1H), 7.17-7.12 (m, 3H), 6.16 (dd, J=10.1, 1.9 Hz, 1H), 5.93 (t, J=1.6 Hz, 1H), 5.48 (s, 1H), 4.96-4.86 (m, 2H), 4.84 (s, 1H), 4.56 (dd, J=18.1, 8.1 Hz, 1H), 4.30 (q, J=3.3 Hz, 1H), 3.97 (s, 2H), 2.59-2.52 (m, 1H), 2.31 (d, J=12.0 Hz, 1H), 2.17-2.07 (m, 1H), 2.05-1.98 (m, 1H), 1.85-1.56 (m, 5H), 1.39 (s, 3H), 1.03 (ddd, J=18.5, 11.8, 4.1 Hz, 2H), 0.88 (s, 3H).

Example 69: Synthesis of 2-(((6aR,6bS,7S,8aS,8bS,10R,11aR,12aS,12bS)-10-(4-(((3-((S)-2-((S)-2-(2-(2,5-Dioxo-2,5-dihydro-1H-pyrrol-1-yl)acetamido)propanamido)propanamido)phenoxy)methyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethyl dihydrogen phosphate dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)oxy)phenyl)amino)-1-oxopropan-2-yl)amino)-1-oxopropan-2-yl)carbamate (463 mg, 0.559 mmol) and 1H-tetrazole (0.45 M in MeCN, 4.97 ml, 2.237 mmol) in dimethyl acetamide (2 ml). Additional di-tert-butyl N,N-diethylphosphoramidite (0.2 mL) was charged after 4.5 hours and stirring was continued overnight. The reaction

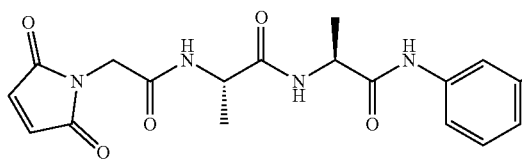
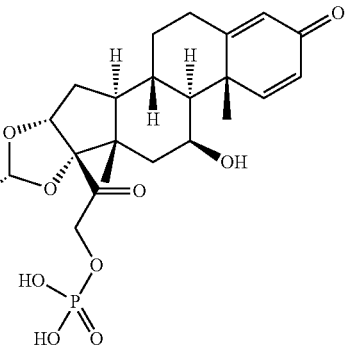

Step 1: Synthesis of tert-Butyl ((S)-1-(((S)-1-((3-((4-((6aR,6bS,7S,8aS,8bS,10R,11aR,12aS,12bS)-8b-(2-((di-tert-butoxyphosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)oxy)phenyl)amino)-1-oxopropan-2-yl)amino)-1-oxopropan-2-yl)carbamate was cooled to 0° C., whereupon a 30% solution of hydrogen peroxide in water (0.17 mL, 1.67 mmol) was added dropwise. Oxidation to the phosphate was complete within 1.5. The reaction was cooled to 0° C., and the reaction was quenched by addition of a 1M aq. solution of Na$_2$S$_2$O$_3$ (8 mL). The mixture was extracted with EtOAc (2×30 mL), the combined organic layers were washed with brine, dried over Na$_2$SO$_4$, and solvent removed under reduced pressure. Puri-

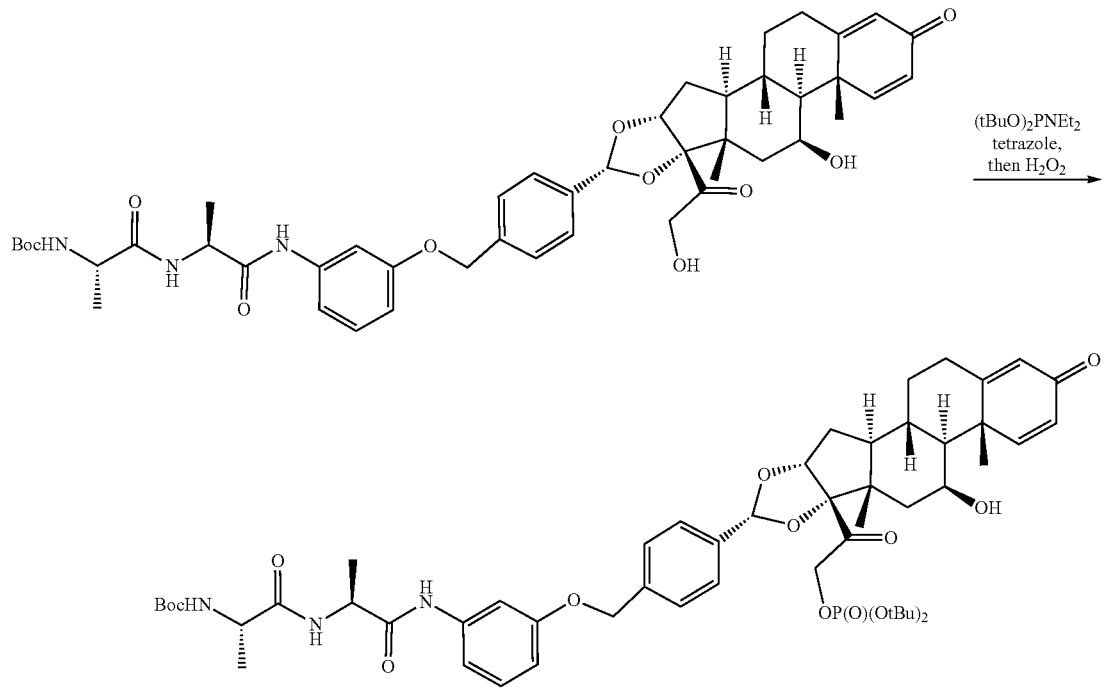

Di-tert-butyl N,N-diethylphosphoramidite (0.226 ml, 0.811 mmol) was added to a room temperature solution of tert-butyl ((S)-1-(((S)-1-((3-((4-((6aR,6bS,7S,8aS,8bS,10R,11aR,12aS,12bS)-7-hydroxy-8b-(2-hydroxyacetyl)-6a,8a- fication by chromatography (silica) using 100% EtOAc as eluent provided the title compound (366 mg, 0.359 mmol, 64% yield) as white solid. LCMS (Method r, Table 7) R$_t$=1.08 min; MS m/z=1020.5 [M+H$^+$].

Step 2: Synthesis of 2-((6aR,6bS,7S,8aS,8bS,10R,11aR,12aS,12bS)-10-(4-((3-((S)-2-((S)-2-Aminopropanamido)propanamido)phenoxy)methyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethyl dihydrogen phosphate

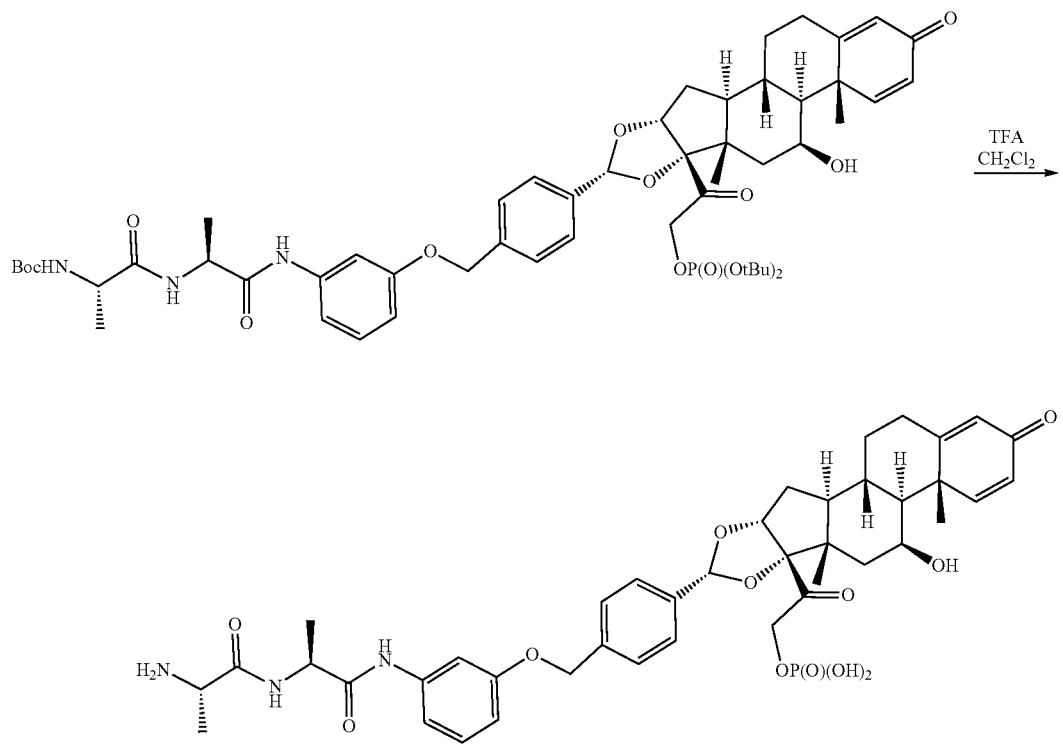

TFA (0.95 mL) was added to a room temperature solution of tert-butyl ((S)-1-(((S)-1-((3-((4-((6aR,6bS,7S,8aS,8bS,10R,11aR,12aS,12bS)-8b-(2-((di-tert-butoxyphosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)oxy)phenyl)amino)-1-oxopropan-2-yl)amino)-1-oxopropan-2-yl)carbamate (364 mg, 0.357 mmol) in DCM (2 mL). The reaction was complete within 2 h, whereupon solvent was removed under reduced pressure. The title compound was obtained as a foamy light yellow solid and was used without further purification. LCMS (Method r, Table 7) major acetal isomer: $R_t$=0.77 min; MS m/z=808.3 [M+H$^+$], minor acetal isomer: $R_t$=0.79 min; MS m/z=808.3 [M+H$^+$].

Step 3: Synthesis of 2-((6aR,6bS,7S,8aS,8bS,10R,11aR,12aS,12bS)-10-(4-((3-((S)-2-((S)-2-(2-(2,5-Dioxo-2,5-dihydro-1H-pyrrol-1-yl)acetamido)propanamido)propanamido)phenoxy)methyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethyl dihydrogen phosphate

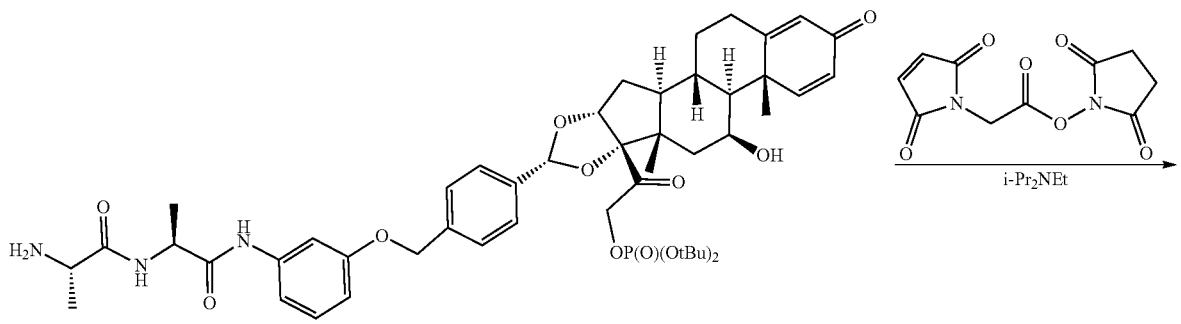

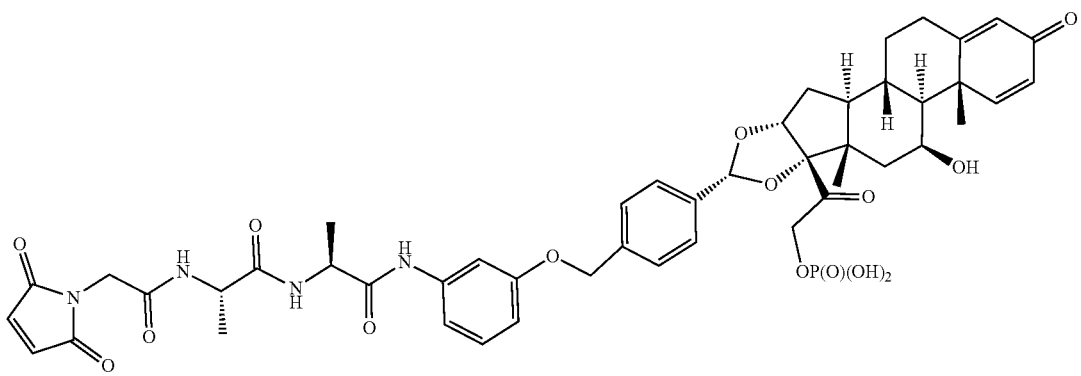

N,N-Diisopropylethylamine (0.37 mL, 2.12 mmol) and maleimidoacetic acid N-hydroxysuccinimide ester (89 mg, 0.353 mmol) were added sequentially to a room temperature solution of 2-((6aR,6bS,7S,8aS,8bS,10R,11aR,12aS,12bS)-10-(4-((3-((S)-2-((S)-2-aminopropanamido)propanamido)phenoxy)methyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethyl dihydrogen phosphate (285 mg, 0.353 mmol) in dimethyl formamide (1.5 mL) and was stirred overnight. The reaction mixture was diluted with DMSO and was purified by preparative reverse phase HPLC on a Phenomenex C18(2) 10 micron column (250×50 mm). A gradient of MeCN (A) and 0.1% TFA in water (B) was used, at a flow rate of 30 mL/min (0-3.0 min 15% A, 3.0-19.0 min linear gradient 15-60% A, then 19.0-23.0 min linear gradient to 85% A). Combined fractions were concentrated to remove volatile solvents under reduced pressure, and the resulting solution was frozen and lyophilized to give the title compound (93 mg, 0.098 mmol, 28% yield) as a white solid. Major acetal isomer: LCMS (Method r, Table 7) Rt=0.83 min; MS m/z=945.4 [M+H⁺]. 1H NMR (400 MHz, DMSO-d6) δ 9.78 (s, 1H), 8.39 (d, J=7.2 Hz, 1H), 8.13 (d, J=7.2 Hz, 1H), 7.49-7.37 (m, 4H), 7.33 (t, J=2.2 Hz, 1H), 7.28 (d, J=10.1 Hz, 1H), 7.14 (t, J=8.1 Hz, 1H), 7.10-7.05 (m, 1H), 7.03 (s, 2H), 6.64 (dd, J=8.0, 2.4 Hz, 1H), 6.13 (dd, J=10.1, 1.9 Hz, 1H), 5.89 (d, J=1.5 Hz, 1H), 5.50 (s, 1H), 5.04 (s, 2H), 4.96-4.85 (m, 2H), 4.81 (s, 1H), 4.55 (dd, J=18.1, 8.2 Hz, 1H), 4.38-4.21 (m, 3H), 4.13-3.98 (m, 2H), 2.53 (dd, J=13.2, 5.2 Hz, 1H), 2.28 (d, J=16.1 Hz, 1H), 2.09 (d, J=11.2 Hz, 1H), 2.08-1.95 (m, 1H), 1.70 (dddd, J=29.9, 25.9, 14.4, 6.4 Hz, 5H), 1.36 (s, 3H), 1.26 (d, J=7.0 Hz, 3H), 1.18 (d, J=7.1 Hz, 3H), 1.02 (ddd, J=14.7, 11.6, 4.0 Hz, 2H), 0.86 (s, 3H).

Example 70: Synthesis of 2-((6aR,6bS,7S,8aS,8bS,10R,11aR,12aS,12bS)-10-(4-(3-((S)-2-((S)-2-(2-(2,5-Dioxo-2,5-dihydro-1H-pyrrol-1-yl)acetamido)propanamido)propanamido)benzyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethyl 2-(dimethylamino)acetate 2,2,2-trifluoroacetate

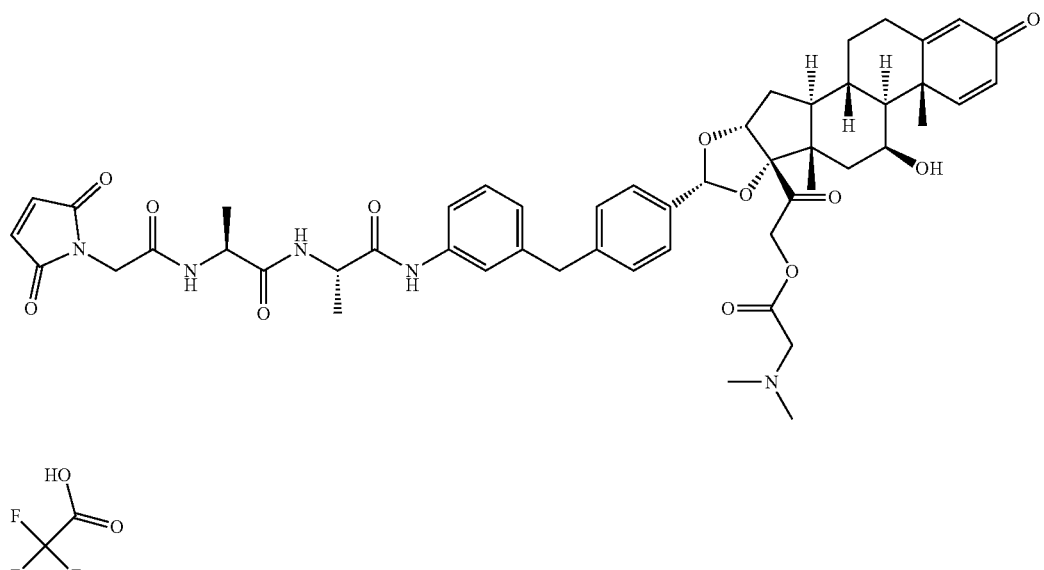

Step 1: Synthesis of 2-((6aR,6bS,7S,8aS,8bS,10R, 11aR,12aS,12bS)-10-(4-(3-((S)-2-((S)-2-((tert-Butoxycarbonyl)amino)propanamido)propanamido)benzyl)phenyl)-7-hydroxy-6a,8a-dimethyl-4-oxo-2, 4,6a,6b,7,8,8a,8b,11a,12,12a,12b-dodecahydro-1H-naphtho[2',1':4,5]indeno[1,2-d][1,3]dioxol-8b-yl)-2-oxoethyl 2-(dimethylamino)acetate 2,2,2-trifluoroacetate

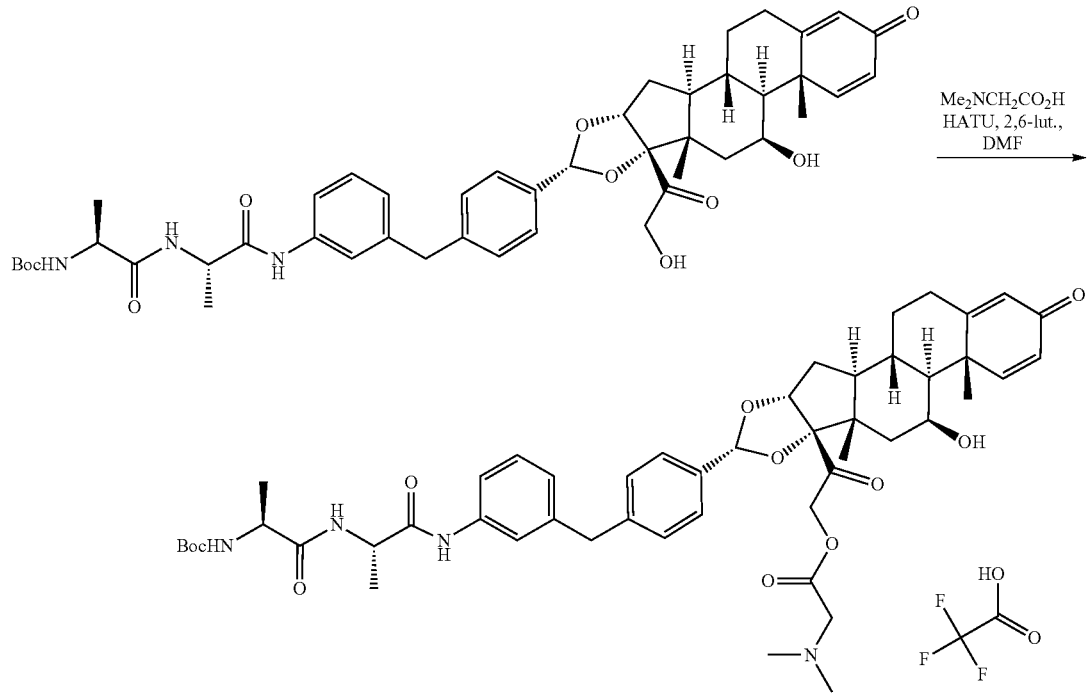

To a solution of tert-butyl ((2S)-1-(((2S)-1-((3-(4-((6aR, 7S,8aS,8bS, OR, 1 aR,12aS,12bS)-7-hydroxy-8b-(2-hydroxyacetyl)-6a,8a-dimethyl-4-oxo-2,4,6a,6b,7,8,8a,8b,11a, 12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate (Prepared in same manner as Example 10, Step 1)(78 mg, 0.096 mmol), 2-(dimethylamino)acetic acid (10.9 mg, 0.106 mmol), and 2,6-dimethylpyridine (0.022 mL, 0.192 mmol) in anhydrous N,N-dimethylformamide (2.0 mL) was added HATU (43.8 mg, 0.115 mmol), and the resulting solution was stirred at room temperature for 45 minutes. The crude product was purified by C18 HPLC, eluting with a solvent gradient of 5-95% MeCN in 0.1M aqueous TFA. Fractions containing the pure product were concentrated bylyophilization to afford the title compound (82 mg, 89% yield). LCMS (Method r, Table 7) R$_t$=0.80 min, MS m/z=898.2 [M+H$^+$].

Step 2: Synthesis of 2-((6aR,6bS,7S,8aS,8bS,10R, 11aR,12aS,12bS)-10-(4-(3-((S)-2-((S)-2-(2-(2,5-Dioxo-2,5-dihydro-1H-pyrrol-1-yl)acetamido)propanamido)propanamido)benzyl)phenyl)-7-hydroxy-6a,8a-dimethyl-4-oxo-2,4,6a,6b,7,8,8a,8b,11a,12, 12a,12b-dodecahydro-1H-naphtho[2',1':4,5]indeno[1,2-d][1,3]dioxol-8b-yl)-2-oxoethyl 2-(dimethylamino)acetate 2,2,2-trifluoroacetate

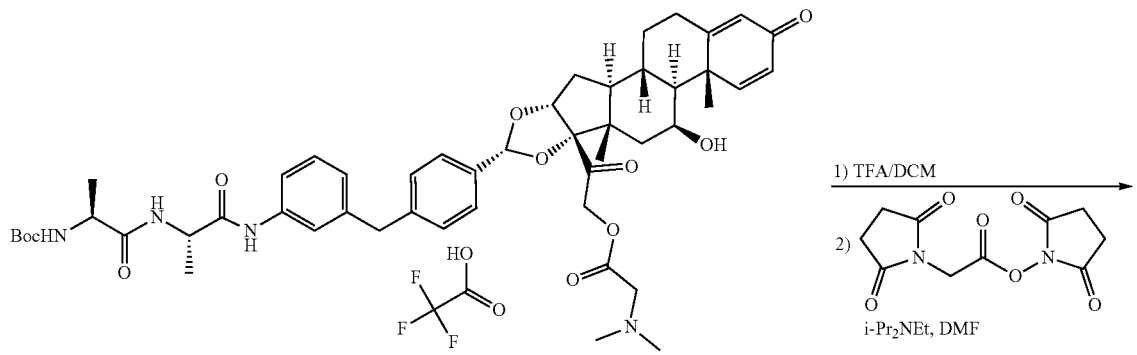

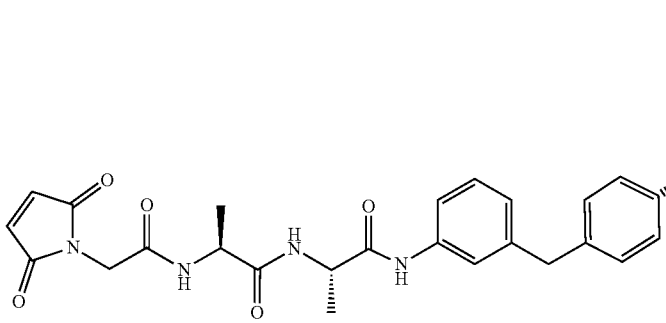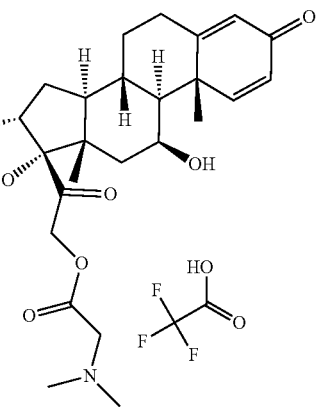

A solution of 2-((6aR,7S,8aS,8bS,10R,11aR,12aS,12bS)-10-(4-(3-((S)-2-((S)-2-((tert-butoxycarbonyl)amino)propanamido)propanamido)benzyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethyl 2-(dimethylamino)acetate (82 mg, 0.074 mmol) in DCM (4 mL) and TFA (1 mL) was stirred at room temperature for 20 minutes, and then concentrated in vacuo. To a solution of this compound in anhydrous N,N-dimethylformamide (1 mL) was added Hunig's base (0.20 mL, 1.15 mmol) and 2,5-dioxopyrrolidin-1-yl 2-(2,5-dioxo-2,5-dihydro-1H-pyrrol-1-yl)acetate (27.8 mg, 0.11 mmol). The resulting mixture was stirred at room temperature for 15 minutes, and TFA (0.106 mL, 1.376 mmol) was added. The crude product was purified by C18 HPLC, eluting with a solvent gradient of 5-95% MeCN in 0.1M aqueous TFA. Fractions containing the pure product were concentrated bylyophilization to afford the title compound as a colorless solid (46 mg, 0.0439 mmol, 59% yield). LCMS (Method r, Table 7) major acetal isomer R$_t$=0.82 min, MS m/z=934 [M+H$^+$]; minor acetal isomer R$_t$=0.81 min, MS m/z=934 [M+H$^+$]. $^1$H NMR (501 MHz, DMSO-d$_6$) δ 10.12 (s, 2H), 9.75 (s, 1H), 8.40 (d, J=7.3 Hz, 1H), 8.11 (d, J=7.1 Hz, 1H), 7.45-7.42 (m, 1H), 7.38 (dd, J=8.2, 2.0 Hz, 2H), 7.31 (d, J=10.1 Hz, 1H), 7.22 (d, J=8.2 Hz, 2H), 7.17 (t, J=7.8 Hz, 1H), 7.06 (s, 1H), 6.89 (d, J=7.7 Hz, 1H), 6.50 (s, 1H), 6.15 (dd, J=10.1, 1.9 Hz, 1H), 5.93-5.90 (m, 1H), 5.52 (s, 1H), 5.30 (d, J=17.7 Hz, 1H), 5.00 (d, J=17.7 Hz, 1H), 4.86 (t, J=5.0 Hz, 2H), 4.36-4.25 (m, 4H), 4.12-4.02 (m, 2H), 3.87 (s, 1H), 2.82 (s, 3H), 2.56-2.51 (m, 1H), 2.50 (s, OH), 2.50 (d, J=1.8 Hz, 0H), 2.33-2.26 (m, 2H), 2.15-2.06 (m, 2H), 2.04-1.97 (m, 2H), 1.84-1.80 (m, 1H), 1.77-1.60 (m, 4H), 1.37 (s, 3H), 1.26 (d, J=7.1 Hz, 3H), 1.19 (d, J=7.1 Hz, 3H), 1.10-0.98 (m, 3H), 0.89 (s, 3H).

Example 71

Synthesis of 4-(2-(((6aR,6bS,7S,8aS,8bS,10R,11aR,12aS,12bS)-10-(4-(3-((S)-2-((S)-2-(2-(2,5-Dioxo-2,5-dihydro-1H-pyrrol-1-yl)acetamido)propanamido)propanamido)benzyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethoxy)-4-oxobutanoic Acid

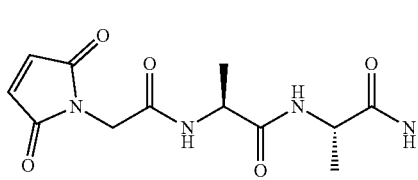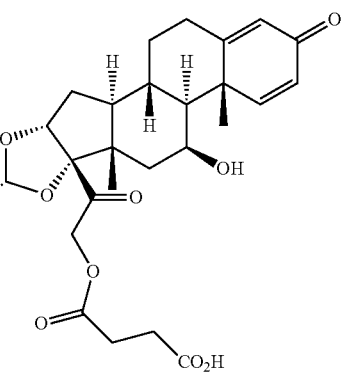

Step 1: Synthesis of 2-((6aR,6bS,7S,8aS,8bS,10R,11aR,12aS,12bS)-10-(4-(3-((S)-2-((S)-2-((tert-butoxycarbonyl)amino)propanamido)propanamido)benzyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethyl tert-butyl succinate

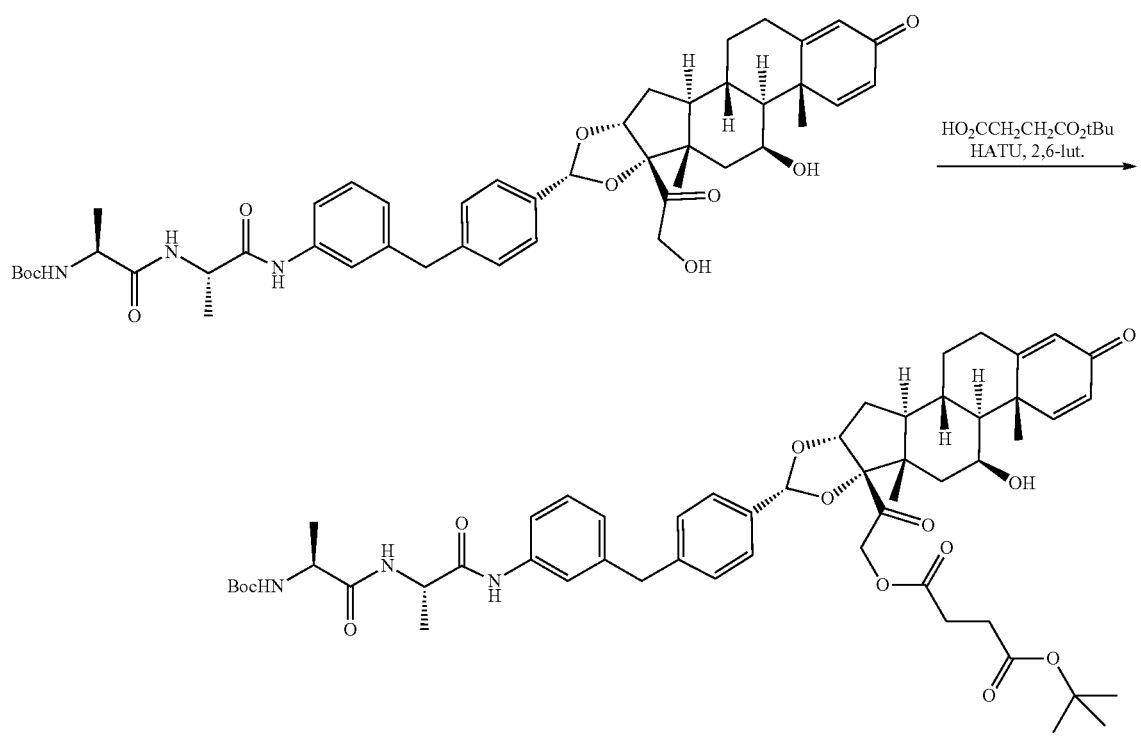

The title compound was prepared using the method described for Example 70, substituting 4-(tert-butoxy)-4-oxobutanoic acid for 2-(dimethylamino)acetic acid. LCMS (Method r, Table 7) $R_t$=1.03 min; MS m/z=968 [M+H$^+$].

Step 2: Synthesis of 4-(2-((6aR,6bS,7S,8aS,8bS,10R,11aR,12aS,12bS)-10-(4-(3-((S)-2-((S)-2-(2-(2,5-Dioxo-2,5-dihydro-H-pyrrol-1-yl)acetamido)propanamido)propanamido)benzyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethoxy)-4-oxobutanoic Acid

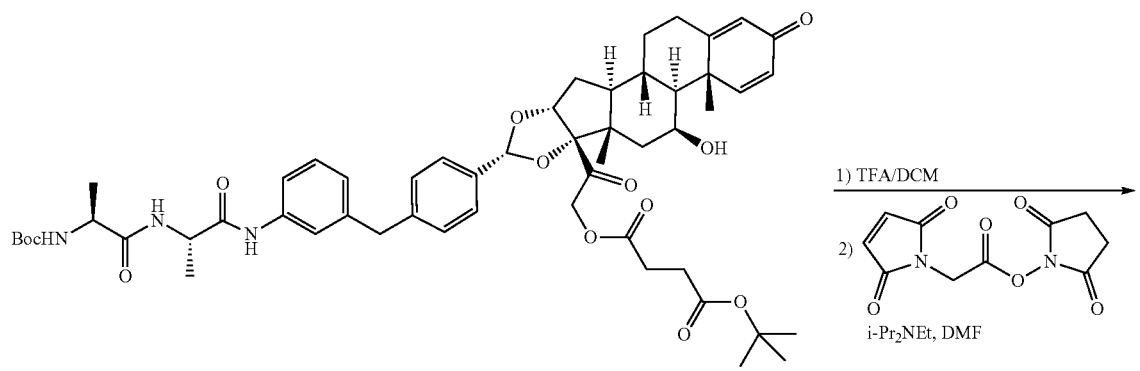

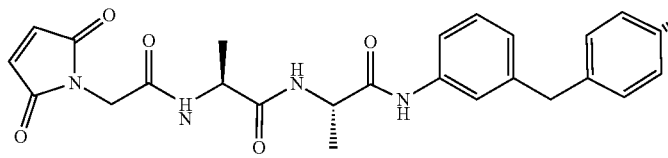

The title compound was prepared using the method described in Step 2, Example 69. It was isolated as a colorless solid (49 mg, 43%). LCMS (Method r, Table 7) R$_t$=0.88 min; MS m/z=948.9 [M+H$^+$]. $^1$H NMR (400 MHz, DMSO-d$_6$) δ 12.23 (s, 1H), 9.74 (s, 1H), 8.37 (d, J=7.3 Hz, 1H), 8.09 (d, J=7.2 Hz, 1H), 7.42-7.33 (m, 3H), 7.31-7.25 (m, 1H), 7.17 (dd, J=20.7, 7.9 Hz, 3H), 6.90-6.84 (m, 1H), 6.15-6.09 (m, 1H), 5.90-5.87 (m, 1H), 5.48 (s, 1H), 5.07 (d, J=17.7 Hz, 1H), 4.86-4.79 (m, 2H), 4.37-4.23 (m, 3H), 4.12-3.98 (m, 2H), 3.85 (s, 2H), 2.65-2.58 (m, 2H), 2.52-2.47 (m, 2H), 2.32-2.24 (m, 2H), 2.09 (d, J=10.8 Hz, 2H), 2.02-1.94 (m, 2H), 1.85-1.56 (m, 6H), 1.36 (s, 3H), 1.24 (d, J=7.1 Hz, 3H), 1.17 (d, J=7.1 Hz, 3H), 1.10-0.95 (m, 3H), 0.85 (s, 3H).

Example 72

Synthesis of 2-((6aR,6bS,7S,8aS,8bS,10R,11aR, 12aS,12bS)-10-(4-(3-((S)-2-((S)-2-(2-(2,5-Dioxo-2, 5-dihydro-1H-pyrrol-1-yl)acetamido)propanamido) propanamido)benzyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1, 3]dioxol-8b-yl)-2-oxoethyl hydrogen sulfate

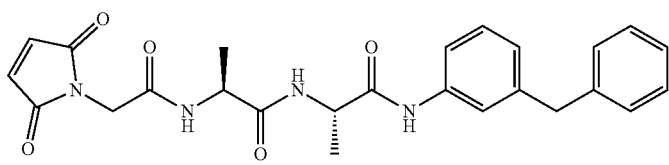

Step 1: Synthesis of 2-((6aR,6bS,7S,8aS,8bS,10R, 11aR,12aS,12bS)-10-(4-(3-((S)-2-((S)-2-((tert-Butoxycarbonyl)amino)propanamido)propanamido) benzyl)phenyl)-7-hydroxy-6a,8a-dimethyl-4-oxo-2, 4,6a,6b,7,8,8a,8b, 11a,12,12a,12b-dodecahydro-1H-naphtho[2',1':4,5]indeno[1,2-d][1,3]dioxol-8b-yl)-2-oxoethyl hydrogen sulfate

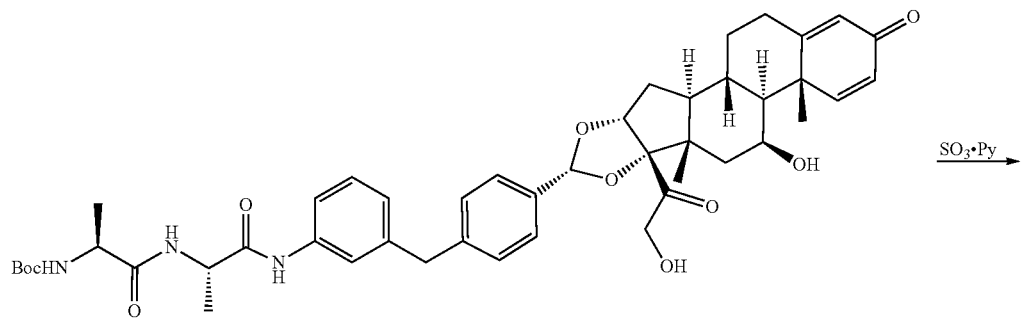

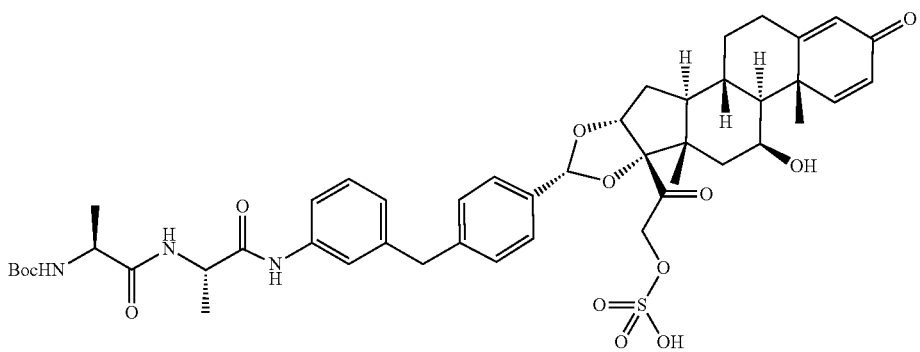

To a solution of tert-butyl ((S)-1-(((S)-1-((3-(4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)amino)-1-oxopropan-2-yl)carbamate, prepared in a similar manner to Example 10, Step 1, (53 mg, 0.065 mmol) in MeCN (2 mL) was added pyridine sulfur trioxide complex (42 mg, 0.26 mmol). The rmixture was stirred at room temperature for 2 hours. The crude product was purified by C18 HPLC, eluting with a solvent gradient of 5-95% MeCN in 0.1M aqueous TFA. Fractions containing the pure product were concentrated bylyophilization to afford the title compound. LCMS (Method r, Table 7) $R_f$=0.83 min; MS m/z=892.0 [M+H$^+$].

Step 2: Synthesis of 2-((6aR,6bS,7S,8aS,8bS,10R,11aR,12aS,12bS)-10-(4-(3-((S)-2-((S)-2-(2-(2,5-dioxo-2,5-dihydro-1H-pyrrol-1-yl)acetamido)propanamido)propanamido)benzyl)phenyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-8b-yl)-2-oxoethyl hydrogen sulfate

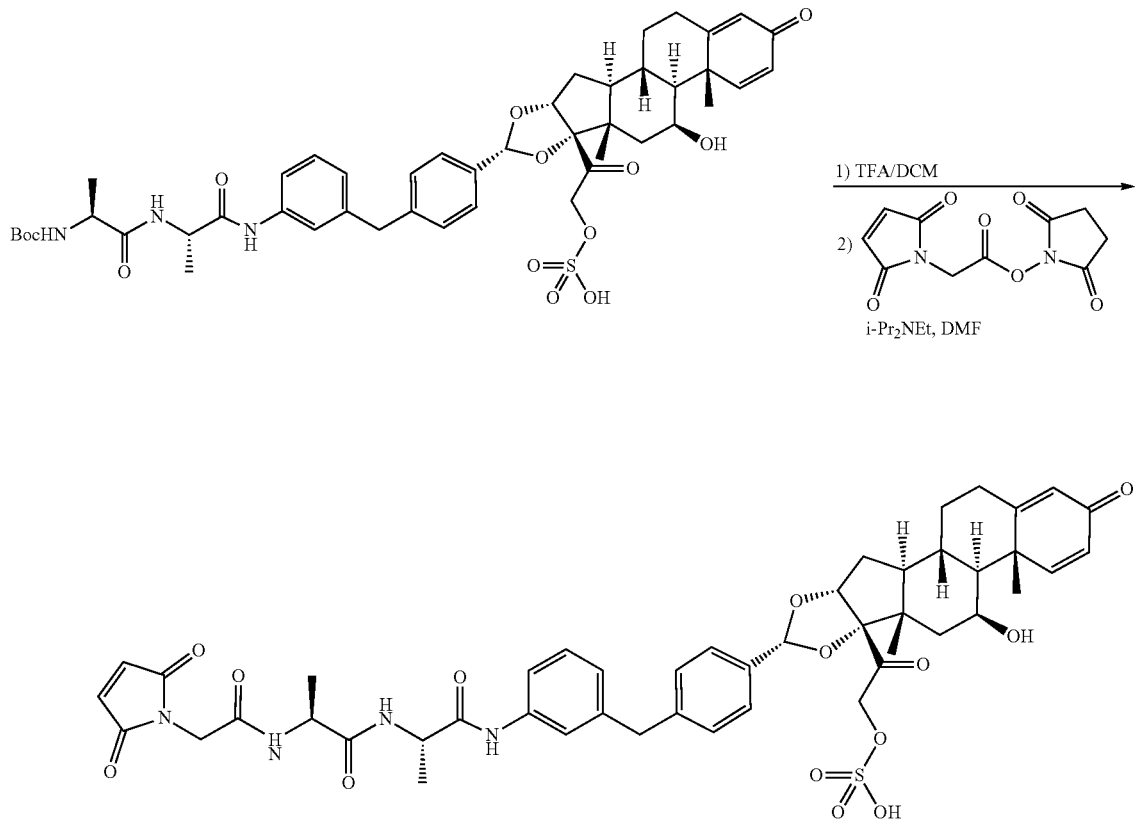

The title compound was prepared using the method described in Step 2, Example 69. It was isolated as a colorless solid (27 mg, 28% yield). LCMS (Method r, Table 7) $R_t$=0.77 min; MS m/z=928.9 [M+H$^+$]. $^1$H NMR (400 MHz, DMSO-d$_6$) δ 9.75 (s, 1H), 8.37 (d, J=7.3 Hz, 1H), 8.10 (d, J=7.2 Hz, 1H), 7.44 (d, J=8.3 Hz, 1H), 7.40-7.32 (m, 2H), 7.33-7.29 (m, 1H), 7.27 (d, J=10.1 Hz, 1H), 7.23-7.12 (m, 3H), 7.04 (s, 1H), 6.93-6.83 (m, 2H), 6.12 (dd, J=10.1, 1.9 Hz, 1H), 5.91-5.86 (m, 1H), 5.42 (s, 1H), 4.87 (d, J=5.1 Hz, 1H), 4.84 (s, 1H), 4.74 (d, J=18.3 Hz, 1H), 4.45 (d, J=18.3 Hz, 1H), 4.36-4.24 (m, 3H), 4.11-3.99 (m, 2H), 3.86 (s, 2H), 2.58-2.48 (m, 1H), 2.32-2.22 (m, 1H), 2.08 (d, J=11.1 Hz, 1H), 1.98 (s, 1H), 1.77 (s, 2H), 1.75-1.56 (m, 4H), 1.36 (s, 3H), 1.24 (d, J=7.1 Hz, 3H), 1.17 (d, J=7.0 Hz, 3H), 1.10-0.95 (m, 2H), 0.83 (s, 3H).

Example 73: Conjugation Protocols

General Cysteine Conjugation Protocol

An approximate 10 mg/mL solution of the desired antibody was prepared in PBS buffer, pH 7.4 as well as a 10 mM TCEP solution in PBS (Pierce Bond-Breaker, cat. 77720). Antibodies (anti-hTNF hIgG1 (D2E7) or anti-mTNF mIgG2a (8C11; McRae B L et al. *J Crohns Colitis* 10 (1): 69-76 (2016)) were then partially reduced by adding approximately two molar eq of 10 mM TCEP, briefly mixing, and incubating for 60 min at 37° C. DMSO was then added to the partially reduced antibodies in sufficient quantity to 15% total DMSO. For the conjugations, 8 molar eq of a 10 mM D-L-maleimide solution (wherein SM is a radical of a glucocorticosteroid and L is a linker) were then added and incubated for 30 min at room temperature. Excess combo and DMSO were then removed using NAP-5 desalting columns (GE Healthcare, cat. 17-0853-02) previously equilibrated with PBS buffer, pH 7.4. Desalted samples were then analyzed by size exclusion chromatography (SEC), hydrophobic interaction chromatography (HIC), and reduced mass spectrometry.

Thiosuccinimide Hydrolysis

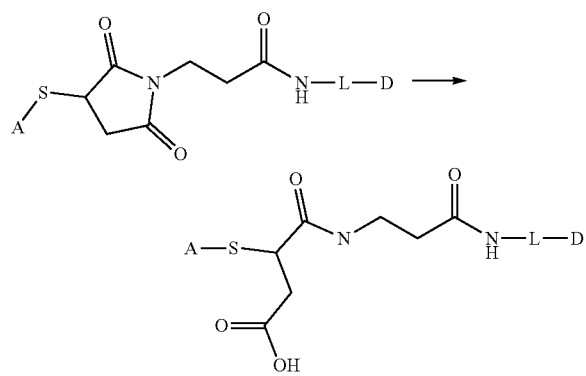

Hydrolysis of the thiosuccinimide ring of ADCs of the disclosure was accomplished by incubating the ADCs at an elevated pH. Briefly, a 0.7 M arginine, pH 9.0 solution was prepared and added to each ADC in PBS buffer to bring the total arginine concentration to 50 mM (pH~8.9). The material was then incubated at 25° C. for 72 hours. Hydrolysis of the succinimide ring was then confirmed by reduced mass spectrometry, after which, hydrolysis was quenched with the addition of a 0.1 M acetic acid solution to 12.5 mM total acetic acid (pH~7.1).

General Lysine Conjugation Protocol

An approximate 10 mg/mL solution of the desired antibody was initially prepared in PBS buffer, pH 7.4. Eight molar eq of the D-L-N-hydroxysuccinimide (wherein SM is a radical of a glucocorticosteroid and L is a linker) was then added to the antibody and incubated at 23° C. for up to 24 hours in the presence of 15% DMSO. Conjugated samples were then desalted to remove excess combo and DMSO using NAP-5 desalting columns (GE Healthcare, cat. 17-0853-02) equilibrated with PBS buffer, pH 7.4. Desalted samples were then analyzed by size exclusion chromatography (SEC), hydrophobic interaction chromatography (HIC), and reduced mass spectrometry.

ADC Analytical Procedures

Hydrophobic Interaction Chromatography. ADCs were profiled by hydrophobic interaction chromatography (HIC) to determine degree of conjugation and to calculate approximate drug to antibody drug ratios (DARs). Briefly, 100 Cpg of the ADCs were loaded onto an Ultimate 3000 Dual LC system (Thermo Scientific) equipped with a 4.6×35 mm butyl-NPR column (Tosoh Bioscience, cat. 14947). ADCs were loaded onto the column equilibrated in 100% buffer A and eluted using a linear gradient from 100% buffer A to 100% buffer B over 12 min at 0.8 mL/min, where buffer A is 25 mM sodium phosphate, 1.5 M ammonium sulfate, pH 7.25 and buffer B is 25 mM sodium phosphate, 20% isopropanol, pH 7.25. The DAR was determined by taking the sum of each peak percent area multiplied by their corresponding drug load and dividing the weighted sum by 100.

Size Exclusion Chromatography. Size distributions of the ADCs were profiled by size exclusion chromatography (SEC) using an Ultimate 3000 Dual LC system (Thermo Scientific) equipped with a 7.8×300 mm TSK-gel 3000SW$_{XL}$ column (Tosoh Bioscience, cat. 08541). 20 ug of each of the ADCs were loaded onto the column and eluted over 17 min using an isocratic gradient at 1mL/min of 100 mM sodium sulfate, 100 mM sodium phosphate, pH 6.8 at 0.8 mL/min.

Example 74: Preparation of Adalimumab Conjugated with a Glucocorticosteroid to Give an ADC Adalimumab MP-ala-ala steroid ADC having an average DAR 3.5 was prepared by a two-step chemical process: disulfide reduction of adalimumab followed by alkylation (conjugation) with maleimidopropyl alanine-alanine steroid Cpd. No. 88.

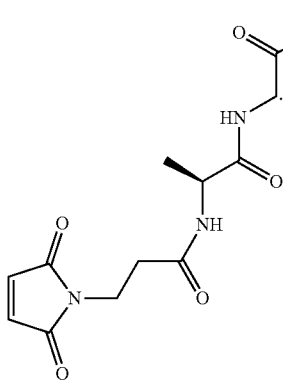
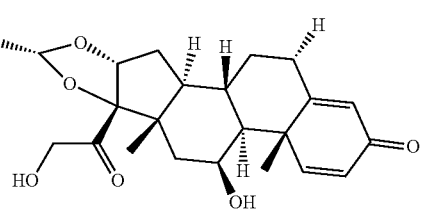

Cpd. No. 88

In the first step, a limited number of interchain disulfide bonds of adalimumab are reduced with tris(2-carboxyethyl)phosphine ("TCEP") (>1.8 equiv). Partially-reduced adalimumab is then conjugated to Cpd. No. 88 (≥5 equiv) in DMSO.

Referring to FIG. 5 which shows a chromatographic resolution of the resultant ADC preparation, the ADC is a heterogenous mixture containing antibodies having zero drug linker molecules attached ("E0" peak), two drug linker molecules attached ("E2" peak), four drug linker molecules attached ("E4" peak), six drug linker molecules attached ("E6" peak) and eight drug linker molecules attached ("E8" peak), depending upon the number of interchain disulfide bonds reduced. Methods of chromatographically separating and isolating the homogenous E2 and E4 peaks are described by Hamblett et al., Clin Cancer Res 2004; 10:7063-7070. The HIC conditions used in FIG. 5 were as follows:

The column was TOSOH Tskgel Butyl-NPR, 4.6 mm×3.5 cm, 2.5 g and the column temperature was 30° C. Wavelength was 280 nm, run time was 22 minutes, injection, volume was 40 μL, flow rate was 0.5 mL/minute. Mobile Phase A: 25 mM $Na_2HPO_4$, pH 7.0 and 1.5M $(NH_4)_2SO_4$, Mobile Phase B: 25 mM $Na_2HPO_4$, pH 7.0/IPA=75/25. Gradient Profile:

| Time (minutes) | Mobile Phase A | Mobile Phase B |
|---|---|---|
| 0 | 90 | 10 |
| 2 | 85 | 15 |
| 18 | 5 | 95 |
| 18.1 | 90 | 10 |
| 22 | 90 | 10 |

Methods of chromatographically separating and isolating the homogenous E2 and E4 peaks are described by Hamblett et al., Clin Cancer Res 2004; 10:7063-7070. Briefly, after hydrolysis and adjustment to pH<7.4, the broad distribution mixture was treated with 3 M ammonium sulfate/50 mM phosphate buffer to bring the overall solution concentration of ammonium sulfate to approximately 0.8 M. A pre-packed Hydrophobic Interaction Chromatography (HIC) column (resin butyl sepharose HP) was prepared by sanitizing with 0.5 N NaOH solution (4 CV), rinsing with water for injection (WFI, 0.5 CV) and equilibration with 0.8 M ammonium sulfate/25 mM phosphate buffer (4 CV). The broad distribution/ammonium sulfate buffered solution was loaded on the HIC column (approximate loading, 30 mg protein per mL of resin) followed by a wash with 0.8 M ammonium sulfate/25 mM phosphate buffer (2.5 CV). Elution of the product was as follows: 0.72 M ammonium sulfate/25 mM phosphate buffer (3 CV), unconjugated mAb; 0.56 M ammonium sulfate/25 mM phosphate buffer (4.5 CV), DAR2 ADC; 0.32 M ammonium sulfate/25 mM phosphate buffer (6.5 CV), DAR4 ADC. The DAR 2 and DAR4 product fractions were then separately concentrated to approximately 30 mg/mL via ultrafiltration (Millipore Ultracel, 30 kD cutoff) followed by diafiltration into WFI (8 CV).

The succinimide of the purified E4 conjugate was hydrolyzed to provide the stabilized attachment by adjusting the pH of the product solution to ≥9 using an arginine buffer. The solution was held at ambient temperature for ≥2 days at which time LC-MS analysis determined the hydrolysis was >90% complete. See FIG. 6 for a portion of the LC-MS chromatogram. The SEC conditions used in FIG. 6 were as follows:

The column was TOSOH TSK-gel $G3000SW_{xL}$, 5μ, 250 Å, 7.8×300 mm, the column was ambient temperature, Wavelength was 214 nm, Run Time was 55 minutes, Injection Volume was 10 μL, Flow Rate was 0.25 mL/minute, Autosampler Temp. was 4° C. Mobile Phase: 100 mM $Na_2HPO_4$ & 100 mM $Na_2SO_4$, pH 6.8/IPA=90/10.

Raw (FIG. 7) and deconvoluted (FIG. 8) MS data of adalimumab conjugated with MP-ala-ala-steroid Cpd. No. 88. Black square and circle represent the ADC with succinimide hydrolyzed and unhydrolyzed, respectively. The relative abundance of hydrolyzed and unhydrolyzed ADC is used to determine hydrolysis conversion.

Hydrolysis

Hydrolysis of succinimide ring after conjugation was conducted with borate buffer at pH 8.0, pH 8.5 and pH 9.0 and arginine buffer at pH 8.0 and pH 9.0 to study the rate of ring hydrolysis. The results are shown in Table 9 below.

TABLE 9

Succinimide ring hydrolysis

| | Hydrolysis after 1 day/% (pH) | | | | | Hydrolysis after 2 days/% (pH) | | | | | Hydrolysis after 3 days/% (pH) | | | | |
|---|---|---|---|---|---|---|---|---|---|---|---|---|---|---|---|
| Cpd. No. | Borate (8.0) | Borate (8.5) | Borate (9.0) | Arg. (8.0) | Arg. (9.0) | Borate (8.0) | Borate (8.5) | Borate (9.0) | Arg. (8.0) | Arg. (9.0) | Borate (8.0) | Borate (8.5) | Borate (9.0) | Arg. (8.0) | Arg. (9.0) |
| 121 | 28 | 37.6 | 49.7 | 24.5 | 63.4 | 42.6 | 55.9 | 71.8 | 33.8 | 84.4 | 56 | 72.1 | 85.4 | 46.5 | 100 |
| 122 | — | — | — | — | — | — | — | — | — | — | — | — | — | — | — |
| 123 | 100 | 100 | 100 | 100 | 100 | 100 | 100 | 100 | 100 | 100 | 100 | 100 | 100 | 100 | 100 |
| 124 | — | — | — | — | — | — | — | — | — | — | — | — | — | — | — |
| 125 | 38.2 | 49.8 | 64.5 | 29.8 | 75.7 | 56.4 | 71.5 | 88.6 | 42.2 | 100 | 73.6 | 86.2 | 100 | 58 | 100 |
| 126 | 30.5 | 37.7 | 50.3 | 23.5 | 59.3 | 44.5 | 57.1 | 72.2 | 33.4 | 82.4 | 58.7 | 74.9 | 90.3 | 45.8 | 100 |
| 127 | 32.2 | 40.8 | 53.9 | 24.6 | 63 | 46.4 | 60.1 | 75.1 | 33.7 | 84.7 | 61.2 | 77 | 90.3 | 48.5 | 100 |
| 128 | 28.6 | 35.6 | 48.4 | 20.7 | 56.9 | 40.8 | 53.6 | 69.9 | 30.1 | 82.5 | 54.9 | 71.5 | 88.9 | 42.6 | 100 |
| 129 | 39.1 | 49.6 | 65.7 | 30 | 76.6 | 57.5 | 71.9 | 88.4 | 42.1 | 100 | 73.9 | 100 | 100 | 58.7 | 100 |
| 130 | 84.3 | 100 | 100 | 74.4 | 100 | 100 | 100 | 100 | 94.2 | 100 | 100 | 100 | 100 | 100 | 100 |
| 131 | 28.6 | 35.2 | 49.5 | 23.9 | 55.4 | 40.9 | 51.4 | 67.7 | 29.8 | 79.2 | 53.4 | 68.1 | 85.6 | 41.7 | 100 |

Example 75: In Vitro Activity of Small Molecule Steroids

Glucocorticoid Receptor Binding Assay

Small molecules were tested for glucocorticoid receptor (GR) binding using the Polarscreen™ Glucocorticoid Receptor Assay Kit, Red (ThermoFisher A15898) according to the manufacturer's protocol. Briefly, compounds were serially diluted in DMSO then transferred into assay kit buffer at a 1:10 dilution. Compounds were further diluted 1:5 in assay kit buffer, and 10 µl was transferred to a 384 well low volume black walled plate (Corning 4514). 5 µl of 4×Fluormone GS Red stock solution and 5 ul of 4×GR full length stock solution were added to each well containing test compound, and plates were incubated protected from light at room temperature for 4 hours. Fluorescence Polarization (mP) was measured for each plate using an EnVision Multilabel Plate Reader (Perkinelmer #2104-0010), and data were analyzed using a four parameter curve fit to generate EC50 values. The results are shown in Table 10 below.

Mineralcorticoid Receptor Cell Assay

Small molecules were tested for mineralcorticoid receptor (MR) agonist activity using the PathHunter® NHRPRO CHO-K1 MR cell line (DiscoveRx cat #93-0451C₂) according to the manufacturer's protocol. Briefly, 20,000 cells/well in culture medium were plated in a 96 half-well plate (Costar cat #3885) overnight at 37° C. Media was removed and replaced with serially diluted small molecules in assay medium (30 µl; 0.3% DMSO final). Plates were incubated overnight at 37° C. Media was removed, replaced with detection reagent (DiscoveRx cat #93-0001; 12 µl/well), and incubated at room temperature (RT) for 60 minutes. Luminescence was measured for each plate using an EnVision Multilabel Plate Reader (Perkinelmer #2104-0010), and data were analyzed using a four parameter curve fit to generate EC50 values. The results are shown in Table 10 below.

Progesterone Receptor Binding Assay

Small molecules were tested for progersterone receptor (PR) binding using a modification of the LanthaScreen® TR-FRET Progesterone Receptor Coactivator Assay (Thermofisher cat # A15903) where the fluorescein-labeled coactivator peptide was replaced with Fluormone AL-Red (Thermofisher cat # PV4294) to improve assay signal. Briefly, compounds were serially diluted in DMSO, then transferred into assay buffer (Thermofisher cat # PV4301+5 mM DTT) at a 1:10 dilution. 10 µl of compound was transferred to a 96 half-area black well plate (Corning cat #3694) in duplicate. 5 µl of PR-LBD protein (4 nM stock in assay buffer; Thermofisher cat # P2899) was added to each well. In addition 5 µl of a prepared mixture of Fluormone AL-Red (12 nM) and terbium-labeled anti-GST monoclonal antibody (mAb) (20 nM; Thermofisher cat # PV3550) in assay buffer was also added to each well. Plates were incubated at room temperature (RT) for 2 hours, and then TR-FRET emission ratio was measured using an EnVision Multilabel Plate Reader (Perkinelmer #2104-0010). Data were analyzed using a four parameter curve fit to generate EC50 values. The results are shown in Table 10 below.

Androgen Receptor Binding Assay

Small molecules were tested for androgen receptor (AR) binding using a modification of the LanthaScreen® TR-FRET Androgen Receptor Coactivator Assay (Thermofisher cat # A15878) where the fluorescein-labeled coactivator peptide was replaced with Fluormone AL-Red (Thermofisher cat #PV4294) to improve assay signal. Briefly, compounds were serially diluted in DMSO then transferred into assay buffer (Thermofisher cat # PV4295+5 mM DTT) at a 1:10 dilution. 10 µl of compound was transferred to a 96 half-area black well plate (Corning cat #3694) in duplicate. 5 µl of AR-LBD protein (5 nM stock in assay buffer; Thermofisher cat #3009) was added to each well. In addition 5 µl of a prepared stock of Fluormone AL-Red (20 nM) and terbium-labeled anti-GST monoclonal antibody (mAb) (30 nM; Thermofisher cat # PV3550) in assay buffer was also added to each well. Plates were incubated at room temperature (RT) for 6 hours then TR-FRET emission ratio was measured using an EnVision Multilabel Plate Reader (Perkinelmer #2104-0010). Data were analyzed using a four parameter curve fit to generate EC50 values. The results are shown in Table 10 below.

GRE Reporter Assay

K562 parental GRE (pGL4.36[luc2P/MMTV/Hygro]) cells described in Example 78 were plated onto 96 well tissue culture treated white plates (Costar: 3917) at 50,000 cells per well in 50 µL of assay medium (RPMI, 1% CSFBS, 1% L-glutamine, 1% Na Pyruvate and 1% MEAA). Small molecule GR agonist compounds were serial diluted at a starting concentration of 100 µM and serial diluted 4 fold in 100% DMSO. The small molecule compounds were diluted further in assay medium by transferring 2 µl of serial diluted compounds into 248 µl assay medium into a secondary dilution plate (1:125 dilution). The cells were then treated with 25 µL of 1:125 diluted GR agonist compound for a final starting concentration of 266.7 nM (1:3) or media alone and incubated for 24 hours at 37°, 5% $CO_2$. After 24 hours incubation, cells were treated with 75 µL of Dual-Glo Luciferase Assay System (Promega-E2920) for 10 minutes and analyzed for luminescence using the TopCount or MicroBeta2 (PerkinElmer).

Estrogen Receptor Binding Assay

Small molecules were tested for estrogen receptor (ER) alpha binding using a modification of the LanthaScreen® TR-FRET Estrogen Receptor Alpha Coactivator Assay (Thermofisher cat # A15885) where the fluorescein-labeled coactivator peptide was replaced with Fluormone ES2 Green (Thermofisher cat # PV6045) to improve assay signal. Briefly, compounds were serially diluted in DMSO then transferred into assay buffer (Thermofisher cat # PV4295+5 mM DTT) at a 1:10 dilution. 10 µl of compound was transferred to a 96 half-area black well plate (Corning cat #3694) in duplicate. 5 µl of ER-LBD protein (5 nM stock in assay buffer; Thermofisher cat #4542) was added to each well. In addition 5 µl of a prepared stock of Fluormone ES2 Green (12 nM) and terbium-labeled anti-GST monoclonal antibody (mAb) (8 nM; Thermofisher cat # PV3550) in assay buffer was also added to each well. Plates were incubated at room temperature (RT) for 4 hours, and then TR-FRET emission ratio was measured using an EnVision Multilabel Plate Reader (Perkinelmer #2104-0010). Data were analyzed using a four parameter curve fit to generate EC50 values. The results are shown in Table 10 below.

TABLE 10

| | | in vitro activity | | | | | |
|---|---|---|---|---|---|---|---|
| Cpd. No. | Chemical Structure | GR binding $IC_{50}$ (µM) | GRE Reporter $EC_{50}$ (µM) | MR (Agonist) $EC_{50}$ (µM) | PR Binding $IC_{50}$ (µM) | ER Binding $IC_{50}$ (µM) | AR Binding $IC_{50}$ (µM) |
| 2 (TFA) | | 0.0066 | NT | NT | NT | NT | NT |
| 3 | | 0.0036 | 0.0002 | 0.0846 | 0.0026 | 30++ | >30 |
| 4 (TFA) | | 0.0095 | 0.0003 | 0.836 0.957 | 0.0198 | >30 | 3.99 |
| 5 | | 0.0120 | 0.0184 | NT | NT | NT | NT |

TABLE 10-continued

| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 6 (TFA) | | 0.0641 | 0.0396 | NT | NT | NT | NT |
| 7 | | 0.0155 | 0.0005 | 0.515 0.300 | 0.0157 | >30 | >30 |
| 8 | | 0.0201 | 0.0151 | NT | NT | NT | NT |
| 9 | | 0.0094 | 0.0001 | 2.61 | 0.0116 | 30++ | >30 |
| 10 | | 0.0156 | 0.0001 | 0.305 | 0.0105 | 5.13 | >30 |

TABLE 10-continued in vitro activity

| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
|---|---|---|---|---|---|---|---|
| 11 | | 0.0139 | 0.0185 | NT | NT | NT | NT |
| 12 | | 0.0247 | 0.0161 | NT | NT | NT | NT |
| 13 | | 0.0157 | 0.0009 | 10.1 >30 | 0.0154 | >30 | >30 |
| 14 | | 0.0255 | 0.0001 | 0.119 | 0.0222 | 2.71 | >30 |

TABLE 10-continued

| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 15 | | 0.0149 | 0.0006 | 0.141 | 0.0165 | 3.77 | >30 |
| 16 | | 0.0537 | 0.0188 | NT | NT | NT | NT |
| 17 | | 0.0278 | 0.0656 | NT | NT | NT | NT |
| 18 | | 0.0437 | 0.0299 | NT | NT | NT | NT |
| 19 (TFA) | | 0.0101 | 0.0152 | NT | NT | NT | NT |

TABLE 10-continued
| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 20 | 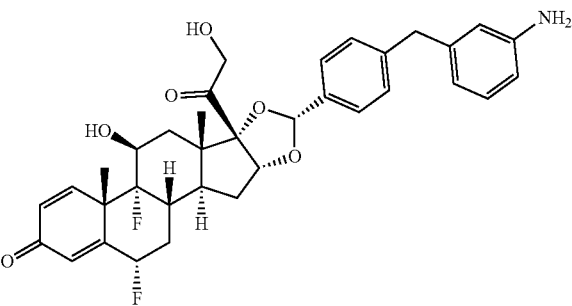 | 0.0194 | 0.0002 | 0.521 | 0.0186 | 0.814 | >30 |
| 20 (TFA) | 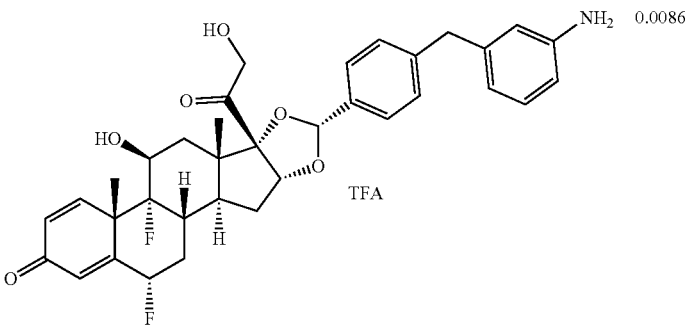 | 0.0086 | 0.0003 | 1.64 1.64 | 0.0171 | 30++ | >30 |
| 21 | 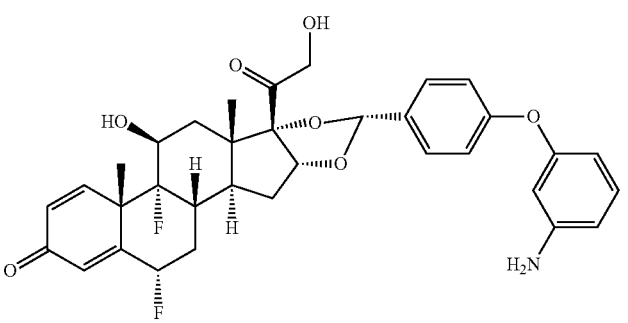 | 0.0094 | 0.0002 | 0.149 4.42 | 0.0073 | >30 | >30 |
| 22 | 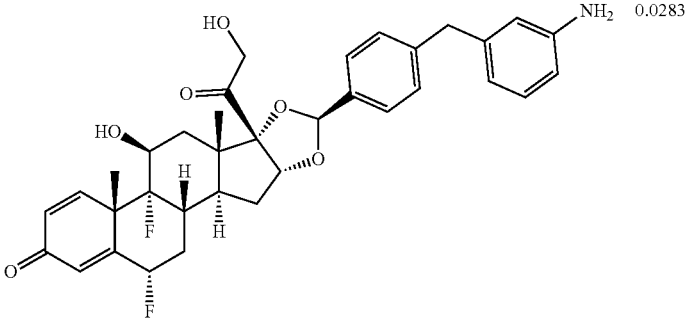 | 0.0283 | 0.0075 | NT | NT | NT | NT |

TABLE 10-continued

| | | in vitro activity | | | | | |
|---|---|---|---|---|---|---|---|
| Cpd. No. | Chemical Structure | GR binding $IC_{50}$ (μM) | GRE Reporter $EC_{50}$ (μM) | MR (Agonist) $EC_{50}$ (μM) | PR Binding $IC_{50}$ (μM) | ER Binding $IC_{50}$ (μM) | AR Binding $IC_{50}$ (μM) |
| 22 (TFA) | | 0.0082 | 0.0233 | NT | NT | NT | NT |
| 23 | | 0.0108 | 0.0051 | NT | NT | NT | NT |
| 24 (TFA) | | 0.0138 | 0.0023 | 1.06 | 0.0089 | 30++ | >30 |
| 25 | | 0.0216 | 0.0002 | 3.09 | 0.0133 | 30++ | >30 |

TABLE 10-continued

| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 26 | | 0.0256 | 0.0167 | NT | NT | NT | NT |
| 27 | | 0.0102 | NV | NT | NT | NT | NT |
| 28 | | 0.0146 | 0.0419 | NT | NT | NT | NT |
| 29 | | 0.0132 | 0.0011 | NT | NT | NT | NT |

TABLE 10-continued

| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 30 | | 0.0177 | 0.0078 | NT | NT | NT | NT |
| 31 | | 0.0107 | 0.0003 | NT | NT | NT | NT |
| 32 | | 0.0074 | 0.0001 | 3.56 | 0.013 | 30++ | >30 |

TABLE 10-continued

| | | in vitro activity | | | | | |
|---|---|---|---|---|---|---|---|
| Cpd. No. | Chemical Structure | GR binding $IC_{50}$ (μM) | GRE Reporter $EC_{50}$ (μM) | MR (Agonist) $EC_{50}$ (μM) | PR Binding $IC_{50}$ (μM) | ER Binding $IC_{50}$ (μM) | AR Binding $IC_{50}$ (μM) |
| 33 | | 0.0169 | 0.0306 | NT | NT | NT | NT |
| 34 | | 0.0122 | 0.0034 | NT | NT | NT | NT |
| 35 | | 0.0034 | 0.0214 | NT | NT | NT | NT |
| 35 (TFA) | | 0.0067 | 0.0178 | 0.407 0.407+ | 0.256 | 30++ | >30 |

TABLE 10-continued

| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 36 (TFA) | | 0.0034 | 0.0002 | 0.129 >30 | 0.052 | >30 | >30 |
| 37 | | 0.0131 | 0.1320 | 2.12 5.05 | 1.09 | >30 | >30 |
| 38 | | 0.0128 | 0.266++ | 0.876 1.47 | 1.19 | >30 | 9.28 |
| 39 | | 0.0156 | 0.0322 | 0.422 | 0.137 | 30++ | >30 |
| 40 | | 0.0111 | 0.0007 | >30 >30 | 0.106 | >30 | >30 |

TABLE 10-continued

| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 41 | | 0.0028 | 0.0014 | 30++ | 0.076 | 30++ | >30 |
| 42 | | 0.0124 | 0.0004 | 10.1 | 0.0873 | 9.75 | >30 |
| 45 (TFA) | | 0.0661 | 0.0013 | 30++ >10 | 0.08 | 6.48 | >14.42 |
| 46 (TFA) | | 0.0267 | 0.0541 | 30++ | 2.13 | 30++ | >30 |

TABLE 10-continued in vitro activity

| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
|---|---|---|---|---|---|---|---|
| 47 | 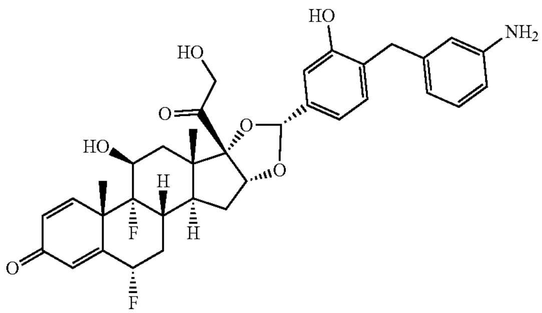 | 0.0065 | 0.0042 | 3.86 | 0.171 | >30 | NT |
| 48 | 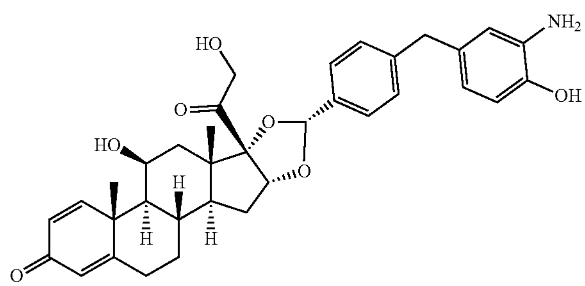 | 0.0118 | 0.0871 | >30 | 0.108 | >30 | NT |
| 49 | 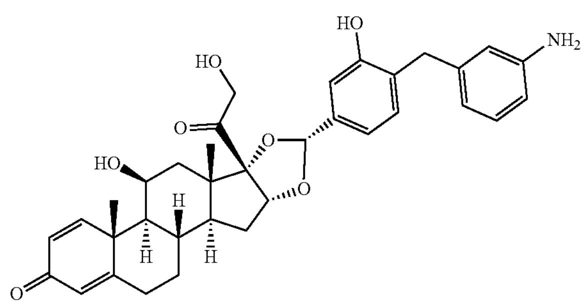 | 0.0056 | 0.0183 | >30 | 2.7 | >30 | NT |
| 50 | 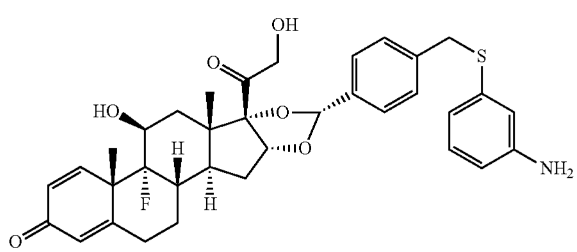 | 0.0080 | 0.0009 | 10.1<br>0.751 | 0.0345 | 30++ | >30 |
| 51 (TFA) | 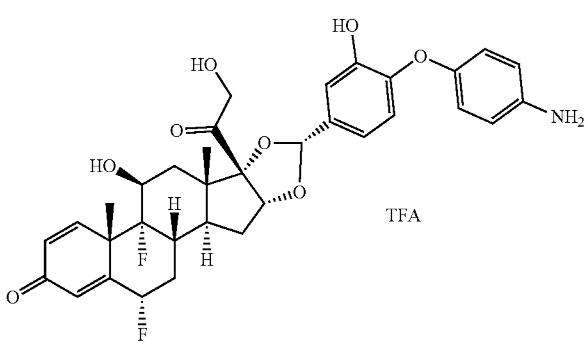 | 0.0042 | 0.0006 | 4.98 | 0.0136 | 30++ | >30 |

TABLE 10-continued

| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 52 | | NT | NT | NT | NT | NT | NT |
| 53 | | 0.0065 | 0.0009 | NT | NT | NT | NT |
| 54 | | 0.0095 | 0.0003 | 0.269<br>6.23 | 0.0527 | >30 | >30 |
| 55 (TFA) | | 0.0114 | 0.0004 | 10.5<br>>30 | 0.0933 | >30 | >30 |

TABLE 10-continued

| | | in vitro activity | | | | | |
|---|---|---|---|---|---|---|---|
| Cpd. No. | Chemical Structure | GR binding IC$_{50}$ (μM) | GRE Reporter EC$_{50}$ (μM) | MR (Agonist) EC$_{50}$ (μM) | PR Binding IC$_{50}$ (μM) | ER Binding IC$_{50}$ (μM) | AR Binding IC$_{50}$ (μM) |
| 57 | | 0.0063 | 0.0015 | 10.1 | 0.0914 | 30++ | >30 |
| 58 | | 0.0078 | 0.0013 | 0.830 | 0.0341 | 5.98 | NT |
| 59 | | 0.0127 | 0.0004 | 0.179 | 0.0134 | >30 | NT |
| 60 | | 0.0121 | 0.0017 | >30 | 0.0699 | >30 | NT |
| 61 | | 0.0302 | 0.0191 | >30 | 0.839 | >30 | NT |
| 62 | | 0.0210 | 0.0030 | 0.475 | 0.0248 | >30 | NT |

TABLE 10-continued

| | | in vitro activity | | | | | |
|---|---|---|---|---|---|---|---|
| Cpd. No. | Chemical Structure | GR binding $IC_{50}$ (μM) | GRE Reporter $EC_{50}$ (μM) | MR (Agonist) $EC_{50}$ (μM) | PR Binding $IC_{50}$ (μM) | ER Binding $IC_{50}$ (μM) | AR Binding $IC_{50}$ (μM) |
| 63 | | 0.0038 | 0.0067 | >30 | 0.447 | >30 | NT |
| 64 | | 0.0116 | 0.0215 | 30++ | 0.121 | >30 | NT |
| 65 | | NT | NT | NT | NT | NT | NT |
| 66 | | NT | NT | NT | NT | NT | NT |
| 67 | | 0.00749 | 0.00313 | 30++ | 0.181 | 30++ | NT |

TABLE 10-continued in vitro activity

| Cpd. No. | Chemical Structure | GR binding IC$_{50}$ (µM) | GRE Reporter EC$_{50}$ (µM) | MR (Agonist) EC$_{50}$ (µM) | PR Binding IC$_{50}$ (µM) | ER Binding IC$_{50}$ (µM) | AR Binding IC$_{50}$ (µM) |
|---|---|---|---|---|---|---|---|
| 68 | (structure) | NT | NT | NT | NT | NT | NT |
| 69 | (structure) | 0.012 | 0.00244 | 30++ | 0.0096 | 30++ | NT |
| 70 | (structure) | 0.0198 | 0.00932 | NT | NT | NT | NT |

++ indicates that the reported data is an average of multiple data points and the reported data can be read as "greater than" the reported data
NT indicates Not Tested

Example 76: Stability of anti-TNF-alpha immunoconjugates

Matrix Stability

Anti-TNFα steroid ADCs were tested for their susceptibility to prematurely release small molecule payload under physiological conditions. In these experiments, ADCs were diluted in plasma (human, monkey, mouse, or rat) or buffer in duplicate and incubated for 6 days at 37° C., 5% $CO_2$. Each sample was quenched at time 0 minutes and at various time points over the 6-day period. Samples were then analyzed using LC/MS/MS and compared with standard curves for the corresponding small molecule. The % maximum release of small molecule payload over time was calculated. The results are summarized in Table 11 below.

TABLE 11

Stability of anti-TNFα steroid ADCs

| | Matrix stability (% max SM release) | | | |
|---|---|---|---|---|
| Cpd. No. | PBS buffer | Human plasma | Cynomolgous Monkey Plasma | Mouse plasma |
| 136 | 0.00864 | 8.34E−04 | 0.0165 | 0.0327 |
| 137 | 0 | 0 | 0 | 0 |
| 138 | 0.00954 | 0.00471 | 0.00444 | 0.0215 |
| 139 | 0 | 0 | 0 | 0 |
| 142 | 0.00306 | 0 | 0.00766 | 0.0564 |
| 144 | 0 | 0 | 0 | 0 |
| 145 | 0.00451 | 0 | 0 | 0 |
| 146 | 0.031 | 0.016 | 0.0306 | 0.0744 |
| 147 | 0 | 0 | 0 | 0.00565 |
| 148 | 4.51E−04 | 0.0032 | 0.0188 | 0.0162 |

TABLE 11-continued

Stability of anti-TNFα steroid ADCs

Matrix stability (% max SM release)

| Cpd. No. | PBS buffer | Human plasma | Cynomolgous Monkey Plasma | Mouse plasma |
|---|---|---|---|---|
| 149 | 0 | 0 | 0 | 0.00648 |
| 150 | 0.00809 | 0 | 0.0153 | 0.074 |
| 152 | 0.00513 | 0 | 5.42E−04 | 0.0392 |
| 153 | 0 | 4.01E−04 | 0 | 0.132 |
| 154 | 0.00E+00 | 0 | 0 | 0 |
| 155 | 0 | 0 | 0 | 0 |
| 156 | 0 | 0 | 0 | 0.152 |
| 157 | 0.0134 | 0.00559 | 0 | 0.026 |

These results demonstrate that anti-TNFα steroid ADCs are stable in buffer and plasma of multiple species and that minimal small molecule release is observed.

Proteolytic Stability

The susceptibility of steroid ADCs to release their payload through protease treatment was compared with an ADC generated using the vcmcMMAE drug linker conjugated to a murine CD-19 antibody. ADCs (average DAR of 4) were incubated with either cathepsin B or proteinase K, and payload release was analyzed by LC-MS at various timepoints (0, 1, 4, 7 and 24 hours).

Figure 1:
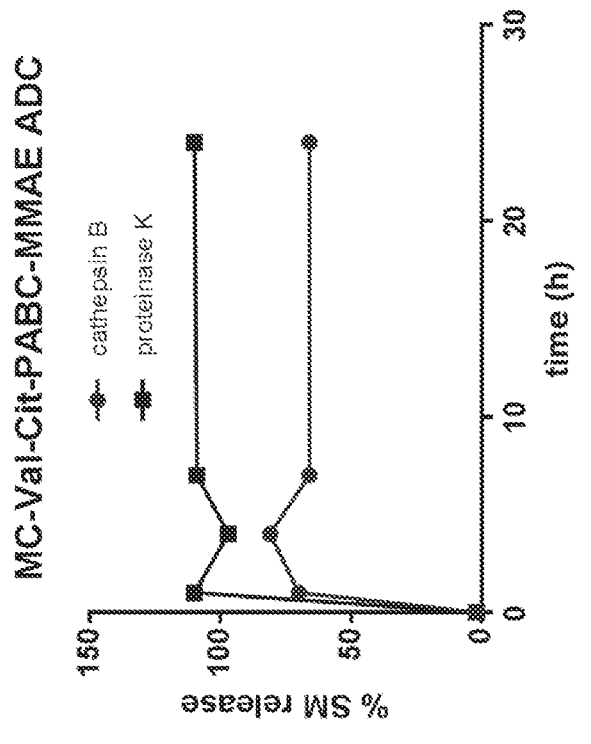
FIG. 1 shows the proteolytic stability of an ADC containing a steroid and an ADC containing MMAE (monomethyl auristatin E). (See Example 76.)
Figure 1:
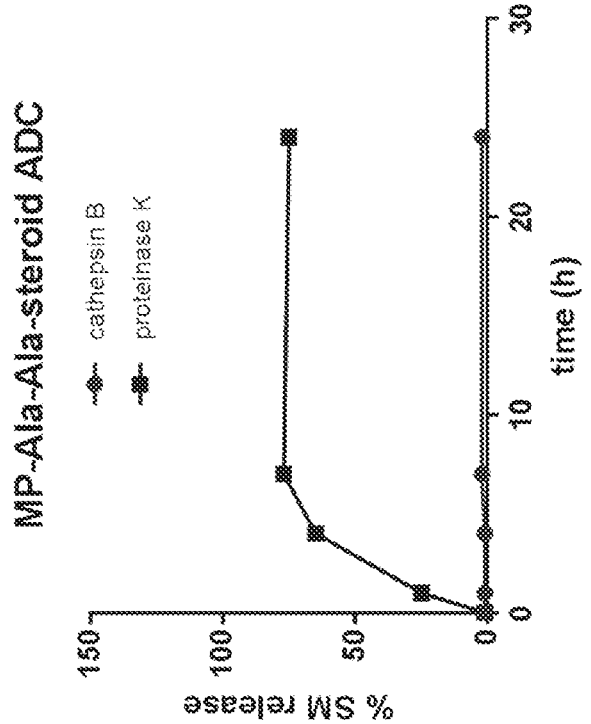

The results are shown in FIG. 1 and demonstrate that the steroid ADCs are resistant to exogenous cathepsin-mediated release of payload from the ADC. This is in contrast to a known payload linker (mcvcMMAE) ADC, where MMAE is released in significant amounts upon cathepsin treatment. This data indicates that steroid ADCs are much less susceptible to premature payload release that results from cathepsin activity in circulation than known ADCs. Indeed, steroid release is only observed with proteinase K, a serine protease that displays broad cleavage specificity. This indicates that the antibody portion of the steroid ADC needs to be significantly catabolized prior to steroid linker cleavage and that payload release can be restricted to an environment where digestion of the antibody scaffold of the ADC can occur, such as the lysosome.

Cathepsin B Digestion

A 0.2 mg/mL stock solution of cathepsin B (Sigma) was prepared in buffer (25 mM Tris, 50 mM NaCl and 5% glycerol). To generate a 10 μg/mL working solution of cathepsin B, 5 μl of 0.2 mg/mL cathepsin B stock was mixed with 95 μl of activation buffer (50 mM sodium acetate pH5, 1 mM EDTA, and 5 mM DTT) and incubated at 37° C. for 15 minutes. For ADC digestion, 20 μl of 100 ug/mL ADC and 20 μl of cathepsin B working solution were mixed with 160 μl dilution buffer (50 mM sodium acetate, 1 mM EDTA). The sample was incubated at 37° C. with shaking, and 40 μl aliquots were removed after 0, 1, 4, 7, and 24 hours. To each aliquot was added 160 μl of quench solution (0.1% formic acid; 1:1 MeOH:MeCN; 100 nM carbutamide), and released small molecule was detected by LC-MS/MS as previously described.

Proteinase K Digestion

A 5 mg/mL stock of proteinase K (Sigma) was prepared in deionized (DI) water. A 0.25 mg/mL working solution of proteinase K was prepared by mixing 50 μL of 5 mg/mL proteinase K with 950 μl dilution buffer (1×HBSS and 1 mM EDTA). For ADC digestion, 20 μL of 100 ug/mL ADC and 40 μl of proteinase K working solution were mixed with 140 μl dilution buffer. The sample was incubated at 37° C. with shaking, and 40 μL aliquots were removed after 0, 1, 4, 7, and 24 hours. To each aliquot was added 160 μl of quench solution (0.1% formic acid; 1:1 MeOH:MeCN; 100 nM carbutamide), and released small molecule was detected by LC-MS/MS as previously described.

Example 77: In Vivo Stability of Anti-TNF-Alpha Immunoconjugates

The susceptibility of the steroid ADC to undergo drug linker loss was assessed in mice. MP-Ala-Ala-steroid was conjugated to human IgG1 mAb (av. DAR 4) and incubated at pH 9 to catalyze ring-opening hydrolysis of the thiosuccinimide ring. After neutralization, the steroid ADC was injected in mice, and the kinetics of drug linker loss were monitored over 7 days by LC-MS.

In these experiments, ADC formulated in phosphate buffer saline was dosed intravenously to 15 male DBA/1 mice at 5 mg/kg. Three mice were sacrificed at 1 hr, 24 hr, 72 hr, 168 hr and 240 hr post-dose. EDTA whole blood was collected and serum was prepared for in vivo DAR analysis by mass spectrometry.

Serum Sample Pre-Dilution

Serum samples were diluted in horse serum (Life technologies, 16050-122) based on total antibody concentrations of ADC measured by total antibodyligand binding assay. Dilutions were based on estimations of final concentration to a range of 10-30 μg/mL, which is suitable for the magnetic beads upper limit of binding capacity.

Immunoaffinity Affinity Purification

In a protein LoBind tube (Eppendorf North America), 350 μL horse serum was added to 100 μL of each pre-diluted ADC serum sample to a total volume of 450 μL, followed by addition of 4 μg of biotin-anti-human Fc antibody (2 μL of biotin-anti human at 2 mg/mL solution). Samples were incubated for 2 hours (hr) at room temperature by shaking at 900 rpm on an orbital shaker. For each serum sample, 50 μL slurry of streptavidin coated magnetic beads (Pierce, Cat #88817) was equilibrated with 0.1% Tween in PBS buffer (PBST) in a LoBind tube. Phosphate Buffered Saline with Tween 20 (PBST) buffer was removed by a pipette after pulling the magnetic beads to the side of the LoBind tube by placing the LoBind tube on a magnetic rack. Serum samples after 2 hr incubation with anti-human capturing reagent were transferred to the LoBind tubes containing equilibrated magnetic beads, and incubated at room temperature for 1 hr at 900 rpm on an orbital shaker. Serum was removed after magnetic bead incubation, and the magnetic bead was washed thoroughly with 500 μL PBST (3 times) followed by 500 μL 5% MeOH in MilliQ water (3 times). Magnetic bead bound ADC was released by incubating the magnetic beads with 100 μL 0.5% formic acid in 50% MeOH/MilliQ water for 15 minutes.

Reduction of Purified ADC

Released ADC was reduced by adding 10 μL reducing reagent (10 mM TCEP freshly prepared from powder purchased from Thermo Scientific, with 10 mM EDTA in 2M pH7.5 Tris buffer) to 100 μL of sample and incubated at 37° C. for 30 minutes.

LC/MS Analysis

Reduced samples (10 μL) were injected into an Agilent 6550 QT of LC/MS system through a temperature controlled (5° C.) CTC autosampler. Sample elution was achieved on a Waters C-4, 3.5 μm, 300 Å, 2.1×50 mm i.d. HPLC column. The mobile phases were: A: 0.1% formic acid in water, and B: 0.1% formic acid in MeCN; the flow rate was 0.45 mL/min; and the column compartment was maintained at 40° C.

The HPLC gradient was as follows:

| Time (min) | % A | % B |
|---|---|---|
| 0 | 95 | 5 |
| 0.6 | 95 | 5 |
| 1.1 | 10 | 90 |
| 2.2 | 10 | 90 |
| 2.4 | 95 | 5 |
| 3.5 | 95 | 5 |

High resolution MS analysis of reduced ADC was performed on an Agilent 6550 quadruple time-of-flight (Agilent Technology, San Clara, Calif.) equipped with a Dual Agilent Jet Stream electrospray ionization (ESI) source operated in the positive ion mode. Mass spectrometer was operated in the extended dynamic range (2G Hz) mode with a MS range up to 3,200 m/z. The primary ESI source was used for LC/MS analysis, and the secondary ESI probe was used for infusing calibration solution at 922.009798 m/z to achieve real time MS calibration. The mass spectrometer was calibrated on a daily basis. Typical mass errors of analytes relative to theoretical masses were less than +5 parts per million in daily operations. MS data were processed using MassHunter Qual Browser Build 5.0.

MS Spectrum Deconvolution

Maximum entropy method in the MassHunter Bioconfirm software package was used to deconvolute the multiple charged ion mass spectra to derive neutral molecular weight spectra. The intensity of the deconvoluted peak was used to calculate DAR.

DAR Value Calculation from De-convoluted MS Spectrum

DAR values were calculated using de-convoluted MS peak intensity based on the following equations:

DAR value from light chain (LC): LC DAR=(2× peak intensity of LC^)/((peak intensity of LC+peak intensity of LC^))

LC and LC^ are light chains with zero and one drug linker, respectively.

DAR value from heavy chain (HC):

HC DAR=2×(peak intensity of HC^+2×peak intensity of HC^^+3×peak intensity of HC^^^)/(peak intensity of HC+peak intensity of HC^+peak intensity of HC^^+peak intensity of HC^^^)

HC, HC^, HC^^ and HC^^^ are heavy chains with zero, one, two and three drug linkers, respectively.

Total DAR=LC DAR+HC DAR

Results

Figure 2:
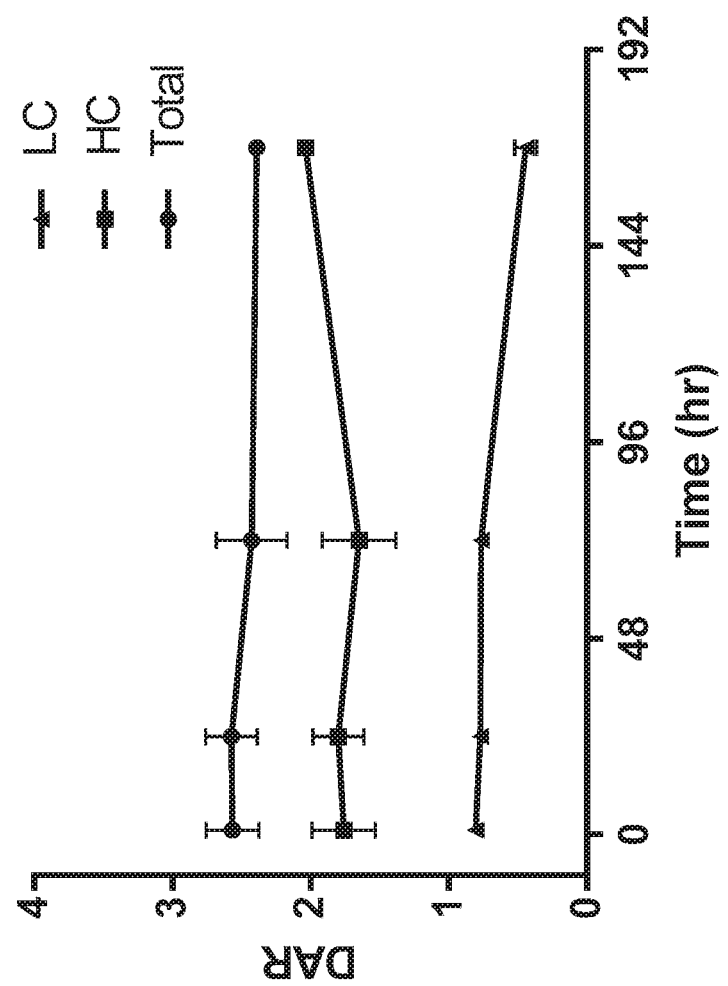
FIG. 2 shows the kinetics of drug linker loss of steroid ADC in mice. (See Example 77.)

The results are shown in FIG. 2. This example demonstrates that minimal loss of drug linker is observed from steroid ADC over 7 days.

Example 78: Generation of Human and Mouse Transmembrane TNF-Alpha GRE Reporter Cell Lines In order to create a parental cell line, K562 cells were seeded onto a 6 well dish (Costar: 3516) with 2 mL of complete growth medium (RPMI,10% FBS, 1% L-glutamine, 1% Na Pyruvate and 1% MEM NEAA) at 500,000 cells per well for 24 hours at 37°, 5% $CO_2$. The next day, 1.5 µg of pGL4.36[Luc2P/MMTV/Hygro] (Promega: E316), 1.5 ug pG14.75 [hRLuc/CMV] (Promega: E639A), and 3 µl of PLUS reagent (Invitrogen: 10964-021) were diluted into 244 uL Opti-MEM (Gibco: 31985-070) and incubated at room temperature for 15 minutes. The pGL4.36[luc2P/MMTV/Hygro] vector contains MMTV LTR (Murine Mammary Tumor Virus Long Terminal Repeat) that drives the transcription of the luciferase reporter gene luc2P in response to activation of several nuclear receptors such as glucocorticoid receptor and androgen receptor. The pGL4.75 [hRluc/CMV] Vector encodes the luciferase reporter gene hRluc (Renilla reniformis) and is designed for high expression and reduced anomalous transcription. After incubation, diluted DNA solution was pre-incubated with 1:1 Lipofectamine LTX solution (Invitrogen: 94756) (13.2 µl+256.8 µl Opti-MEM) and incubated at room temperature for 25 minutes to form DNA-Lipofectamine LTX complexes. After incubation, 500 1 of DNA-Lipofectamine complexes were added directly to the well containing cells. K562 cells were transfected for 24 hours at 37°, 5% $CO_2$. After incubation, cells were washed with 3 mL of PBS and selected with complete growth medium containing 125 µg/mL of hygromycin B (Invitrogen: 10687-010) for two weeks. "K562 pGL4.36[Luc2P/MMTV/Hygro]_pGL4.75 [hRLuc/CMV]" cells were produced.

In order to create a murine transmembrane TNF-alpha GRE reporter cell line, the parental cells, K562 pGL4.36 [Luc2P/MMTV/Hygro]_pGL4.75[hRLuc/CMV], were seeded onto 6 well dish (Costar: 3516) with 2 mL of complete growth medium (RPMI, 10% FBS, 1% L-glutamine, 1% Na Pyruvate and 1% MEM NEAA) at 500,000 cells per well for 24 hours at 37°, 5% $CO_2$. The next day, 3 µg of mFL_TNFa DNA (Origene: MC208048), which encodes untagged mouse TNF, and 3 µl of PLUS reagent (Invitrogen: 10964-021) were diluted into 244 uL Opti-MEM (Gibco: 31985-070) and incubated at room temperature for 15 minutes. After incubation, diluted DNA solution was pre-incubated with 1:1 Lipofectamine LTX solution (Invitrogen: 94756) (13.2 uL+256.8 uL Opti-MEM) and incubated at room temperature for 25 minutes to form DNA-Lipofectamine LTX complexes. After incubation, 500 µl of DNA-Lipofectamine complexes were added directly to the well containing cells. The parental K562 pGL4.36 [Luc2P/MMTV/Hygro]_pGL4.75[hRLuc/CMV] cells were transfected for 24 hours at 37°, 5% $CO_2$. After incubation, cells were washed with 3 mL of PBS and selected with complete growth medium containing 125 µg/mL of hygromycin B (Invitrogen: 10687-010) and 250 µg/mL G418 (Gibco: 10131-027) for two weeks. "K562 mouse FL-TNFa GRE (pGL4.36[luc2P/MMTV/Hygro])" cells were produced.

In order to create a human transmembrane TNF-alpha GRE reporter cell line, the parental cells, K562 pGL4.36 [Luc2P/MMTV/Hygro]_pGL4.75[hRLuc/CMV], were transfected with the plasmid hTNF delta 1-12 C-Myc pcDNA3.1(−) plasmid construct. This plasmid is pcDNA 3.1 (Thermofisher cat # V79020) encoding tace resistant transmembrane TNF (i.e., SEQ ID NO:1 lacking amino acids 77-88). (See Perez C et al. Cell 63 (2): 251-8 (1990) discussing tace resistant transmembrane TNF.) These cell lines were then used in the TNF-alpha reporter assays described in the subsequent examples.

Example 79: Activity of Anti-TNF-Alpha Immunoconjugates in GRE Transmembrane TNF-Alpha Reporter Assays K562 parental GRE (pGL4.36[luc2P/MMTV/Hygro]) cells and K562 mFL-TNF-α or hTNF delta 1-12 GRE (pGL4.36[luc2P/MMTV/Hygro]) cells were plated onto 96 well tissue culture treated white plates (Costar: 3917) at 50,000 cells per well in 50 µL of assay medium (RPMI, 1% CSFBS, 1% L-glutamine, 1% Na Pyruvate and 1% MEAA). The cells were treated with 25 µL of 3× serial diluted murine or human anti-TNF-α antibody drug conjugates in assay medium, steroid compound, or media alone and incubated for 48 hours at 37°, 5% $CO_2$. After 48 hours of incubation, cells were treated with 75 µL of Dual-Glo Luciferase Assay System (Promega-E2920) for 10 minutes and analyzed for luminescence using the TopCount (PerkinElmer). Data were analyzed using a four parameter curve fit to generate EC50 values. % maximum activation was normalized to 100 nM dexamethasone, which was considered maximum activation. The results using the murine TNF-alpha cell line are shown in Table 12 below, and the results using the human TNF-alpha cell line are shown in Table 13 below. In Table 12 below, A refers to 8C11. In Table 13 below, A refers to adalimumab (SEQ ID NOs: 66 and 73). Percent (%) monomer was determined by SEC as previously described (see ADC analytical procedures).

TABLE 12

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 134 | 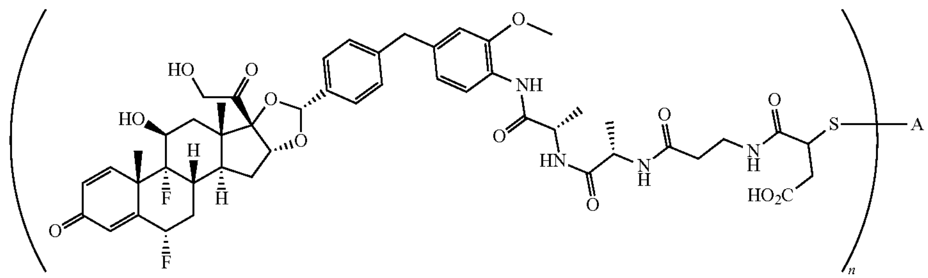 | 4.5 | 91.4 | 0.00519 | 118 | 1.61 | 74 |
| 135 | 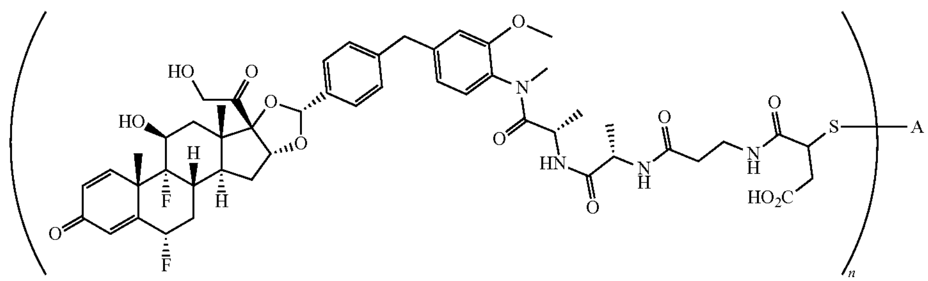 | 4.4 | 95.4 | 1.27 | 106 | 36.3 | 68 |
| 136 | 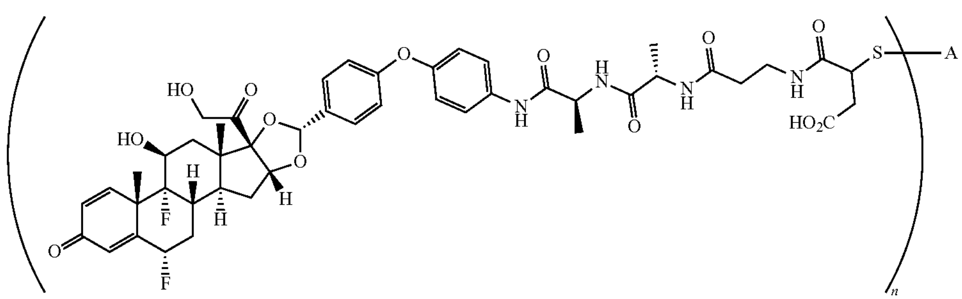 | 2 | 99.9 | 0.0108 | 95 | 9.3 | 46 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 137 | 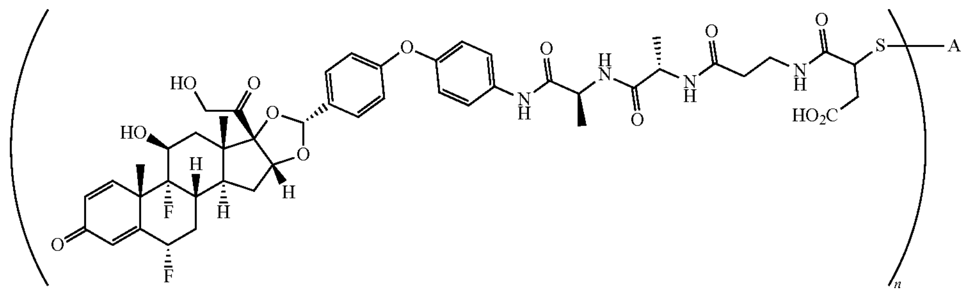 | 4 | 99.9 | 0.0105 | 114 | 5.27 | 93 |
| 138 | 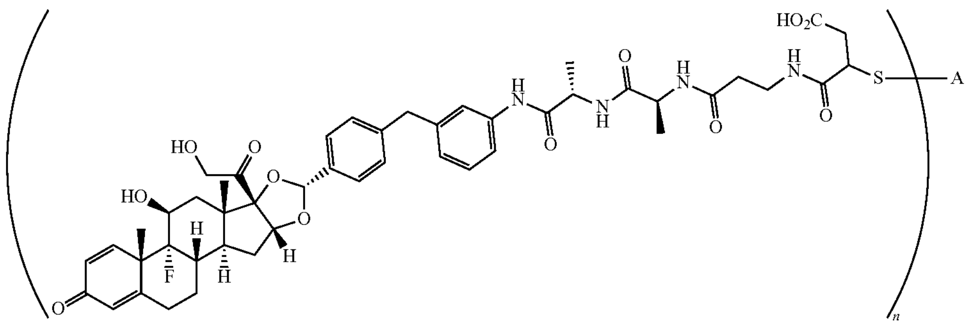 | 2 | 98.02 | 00297 | 108 | 28.7 | 53 |
| 139 | 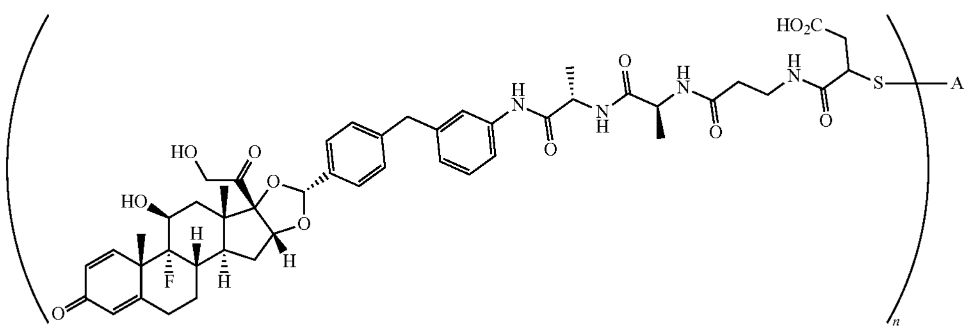 | 4 | 96.6 | 0.0239 | 92 | 15.2 | 61 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 140 | 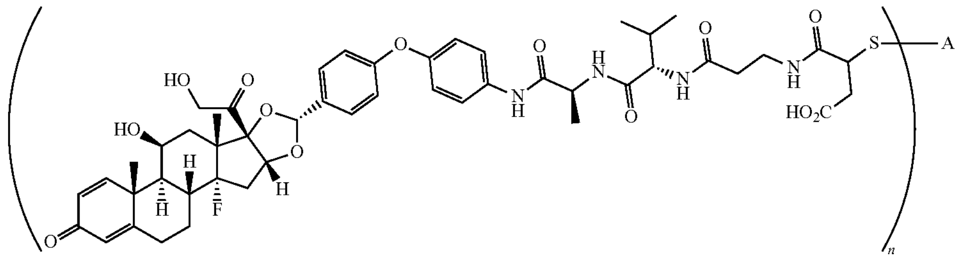 | 2 | 98.8 | 0.179 | 112 | 50 | 23 |
| 141 | 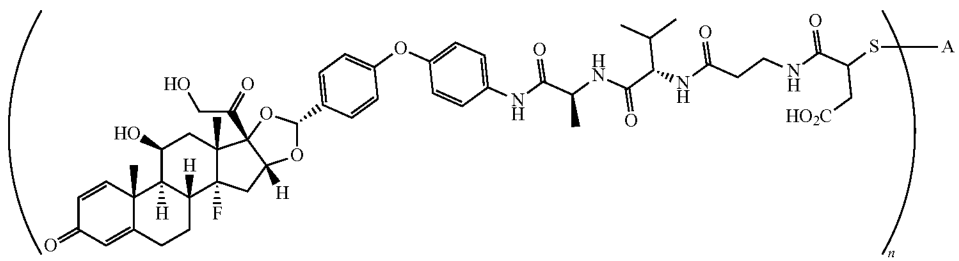 | 4 | 98 | 0.144 | 96 | >50 | 43 |
| 142 | 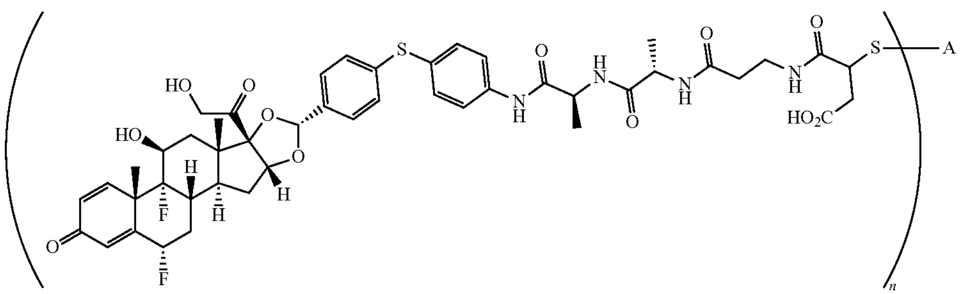 | 2 | 99.1 | 0.0515 | 96 | >50 | 57 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 143 | 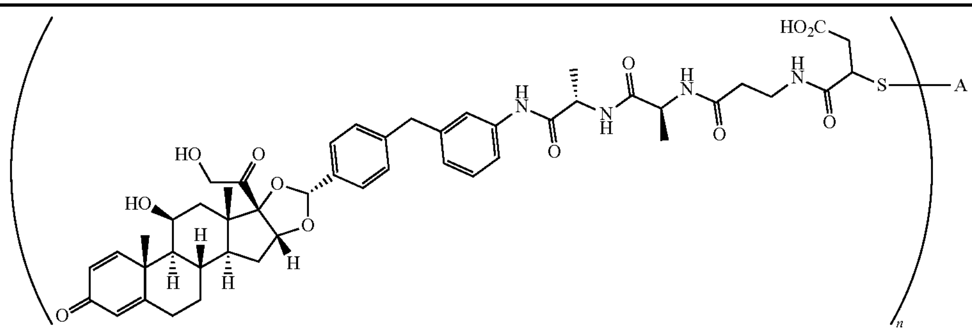 | 2 | 97.7 | 0.0795 | 82 | >50 | 24 |
| 144 | 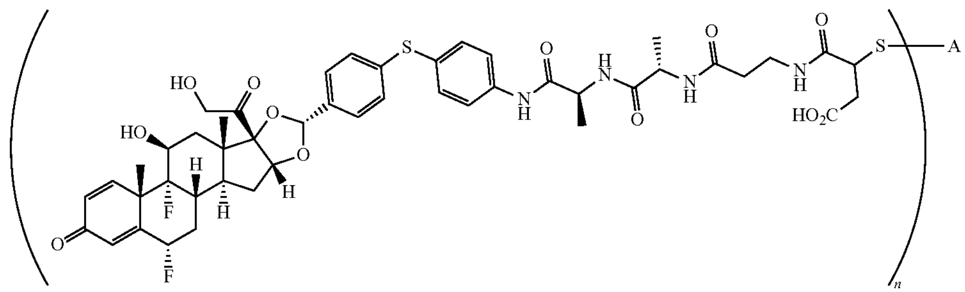 | 4 | 94.25 | 0.0406 | 116 | 14.7 | 74 |
| 145 | 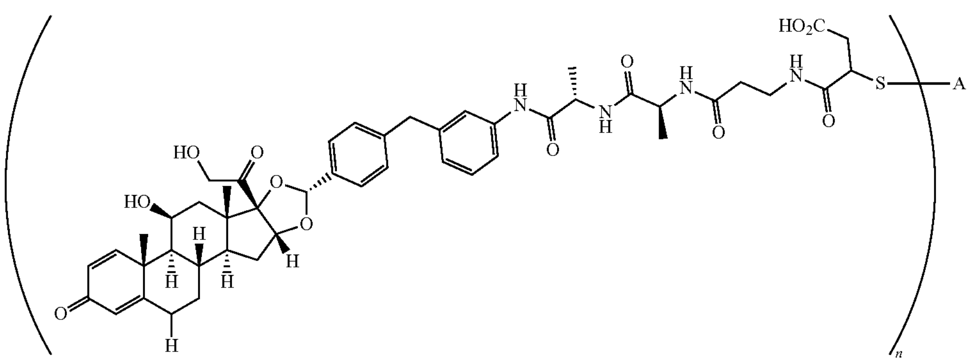 | 4 | 98 | 0.0393 | 95 | 24.7 | 36 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 146 | 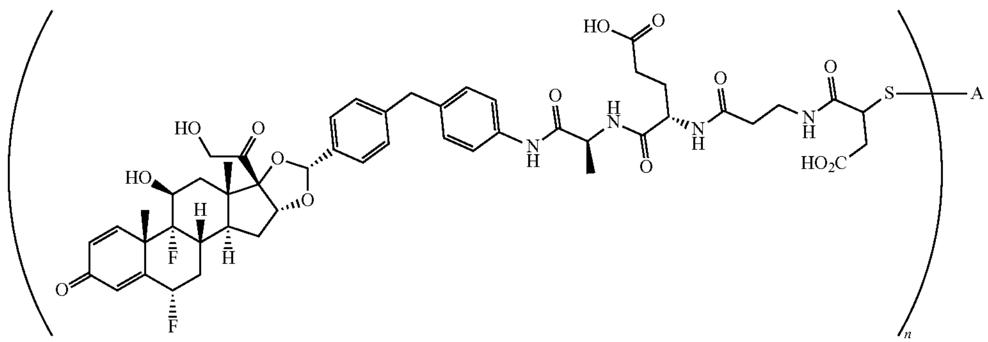 | 2 | 98.5 | 0.0399 | 118 | 27.5 | 73 |
| 147 | 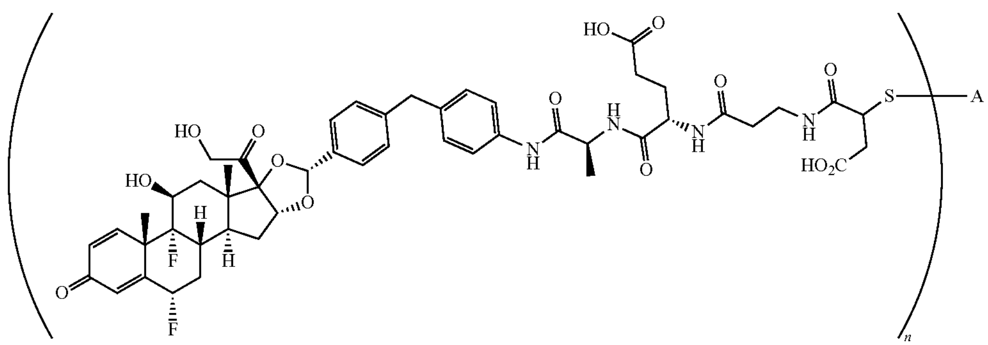 | 4 | 97.6 | 0.0259 | 113 | 7.89 | 80 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 148 | 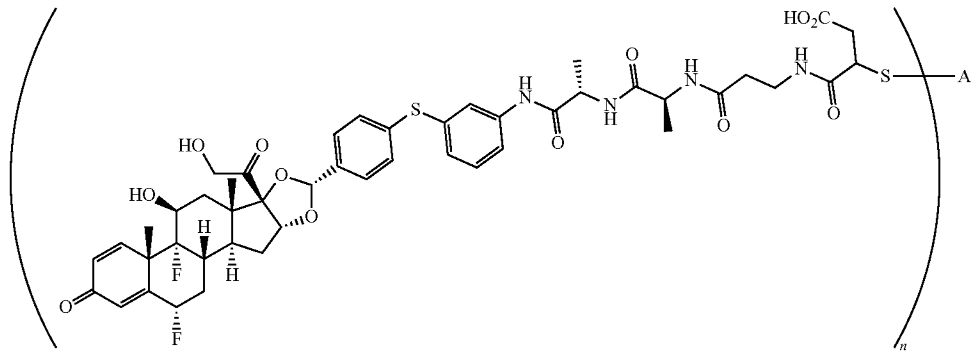 | 2 | 97.8 | 0.0384 | 120 | 23.6 | 77 |
| 149 | 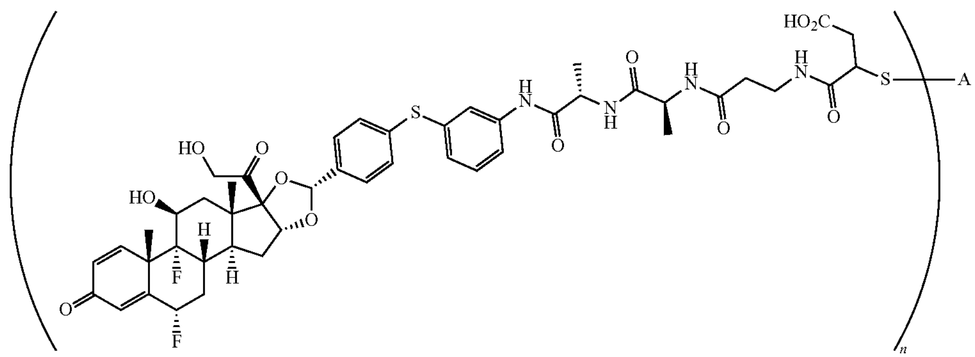 | 4 | 91.8 | 0.0314 | 113 | 10.7 | 78 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 150 | 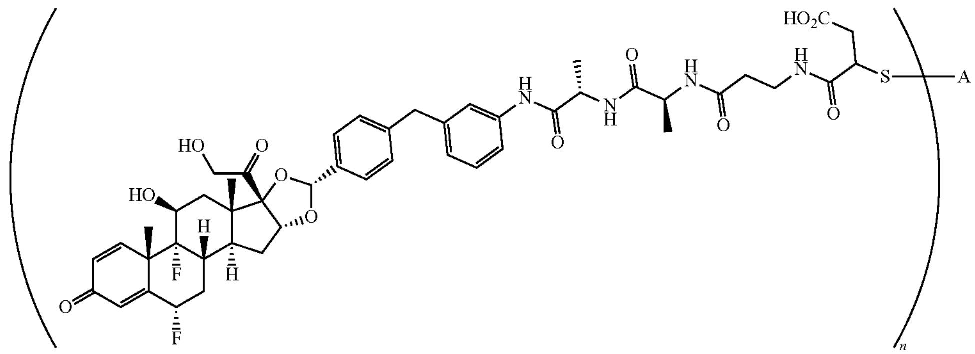 | 2 | 98 | 0.02092 | 102 | 10.99 | 84 |
| 151 | 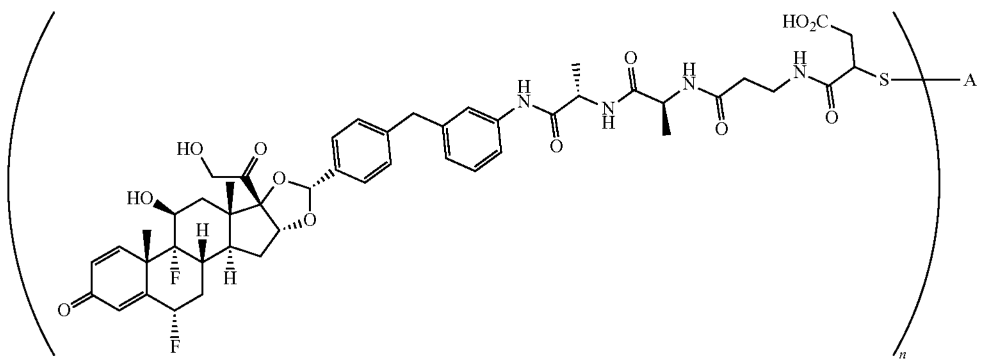 | 4 | 90.1 | 0.0098 | 104 | 2.85 | 87 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 152 | 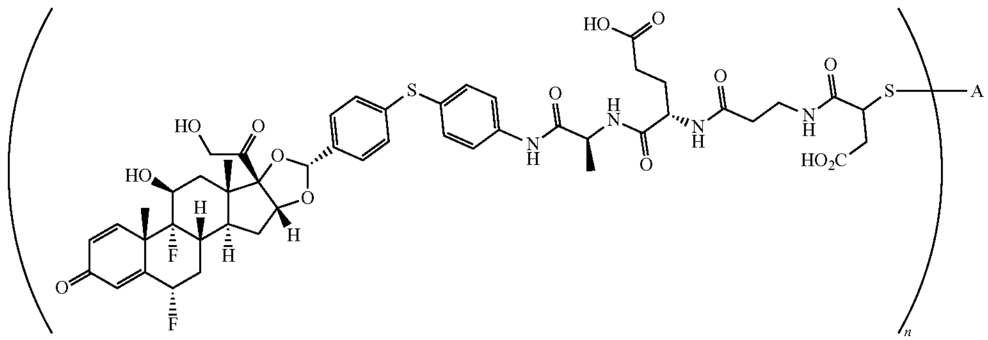 | 2 | 98.3 | 0.0247 | 96 | 3.44 | 70 |
| 153 | 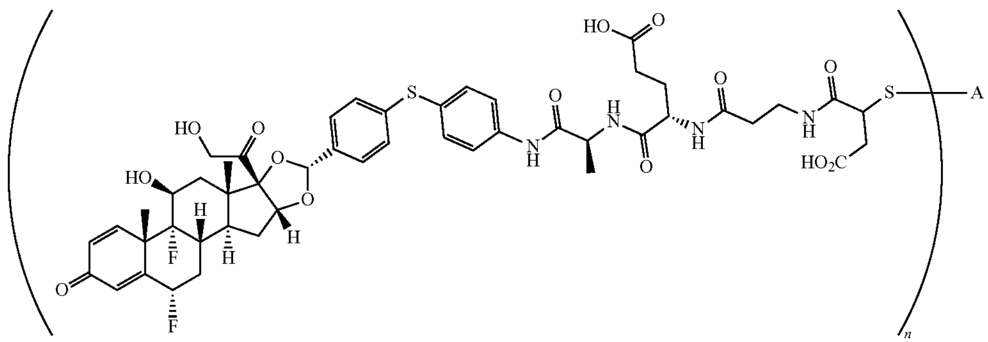 | 4 | 93.8 | 0.0185 | 75 | 2.77 | 94 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 154 | 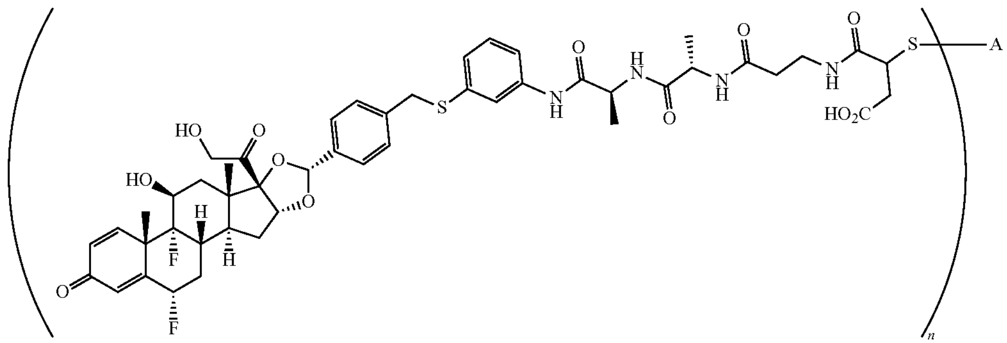 | 2 | 96.6 | 2.00E-04 | 104 | 12.1 | 91 |
| 155 | 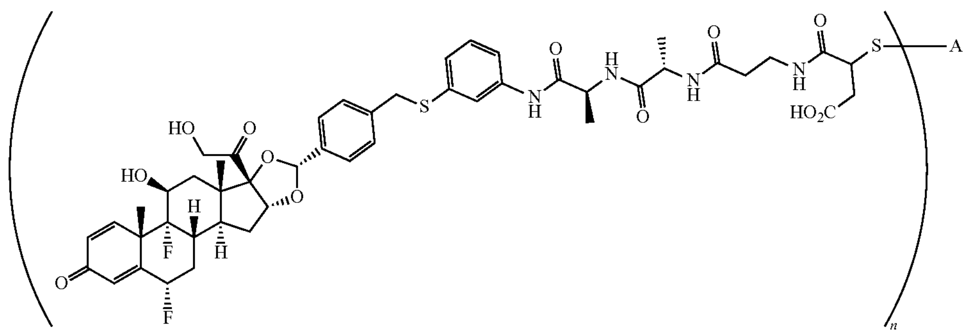 | 4 | 96 | 0.0171 | 94 | 2.8 | 79 |
| 156 | 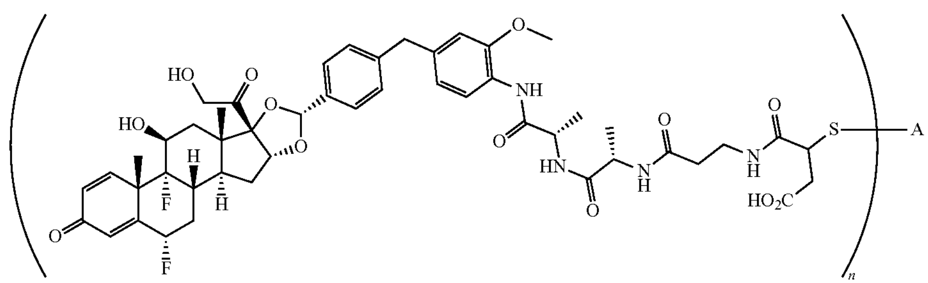 | 2 | 98.2 | 0.039 | 107 | 15.8 | 73 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
| --- | --- | --- | --- | --- | --- | --- | --- |
| 157 | 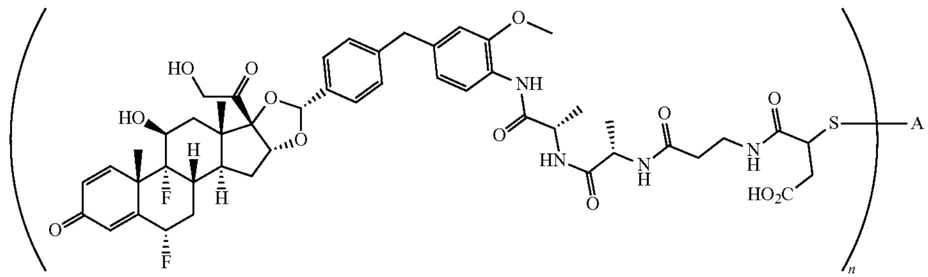 | 4 | 92.5 | 0.0198 | 115 | 3.63 | 83 |
| 158 | 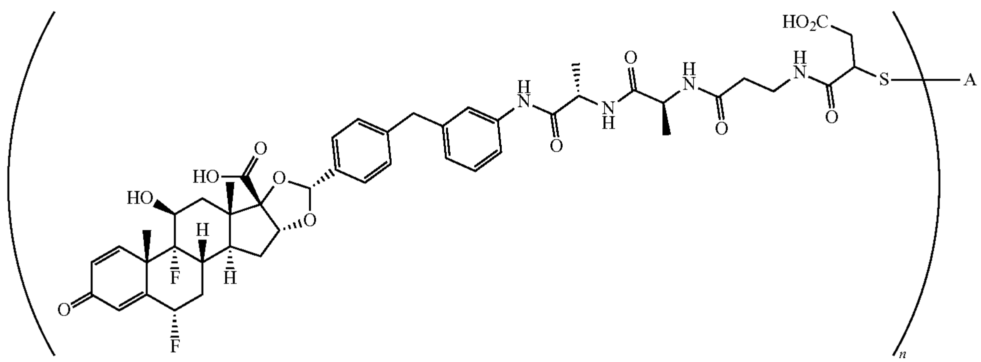 | 2 | 99.4 | >50 | 0.05 | >50 | 0.2 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 159 | 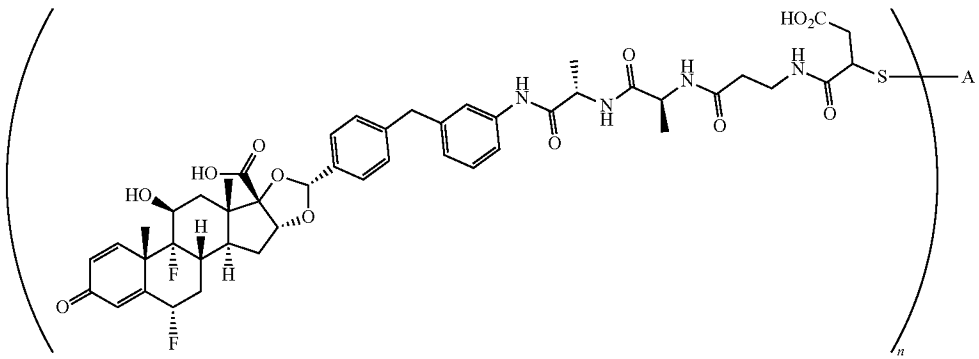 | 4 | 98.4 | >50 | 0.075 | >50 | 0.7 |
| 160 | 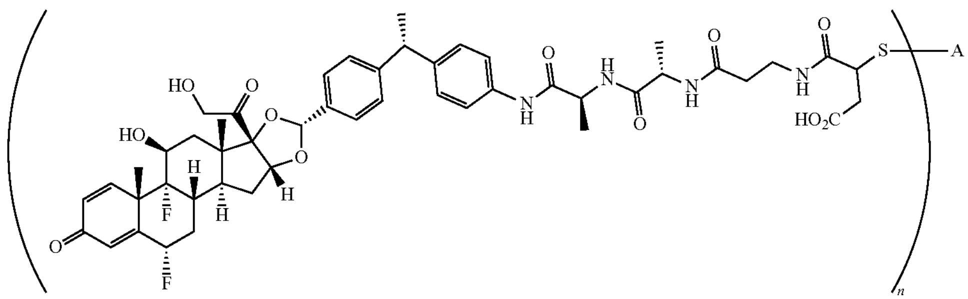 | 2 | 98.2 | 0.0242 | 91 | >50 | 63 |
| 161 | 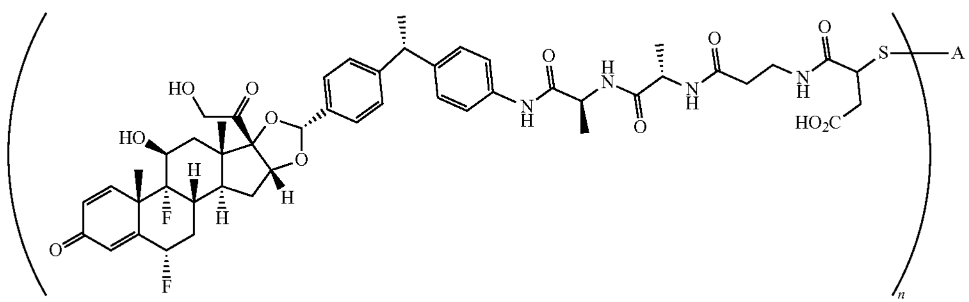 | 4 | 95.8 | 0.0203 | 94 | 16.9 | 77 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 162 | 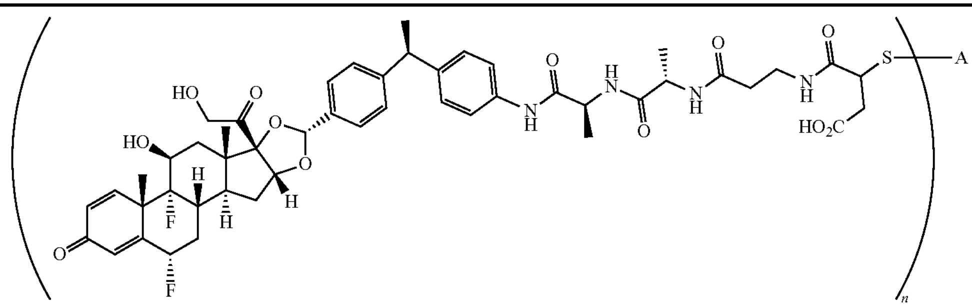 | 4 | 95 | 0.0072 | 119 | 12.4 | 88 |
| 163 | 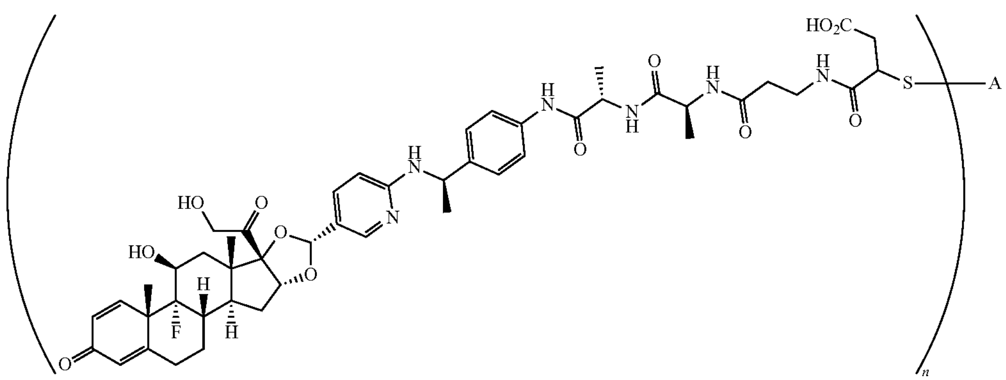 | 2 | 97.7 | >50 | 6 | >50 | 0.4 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 164 | 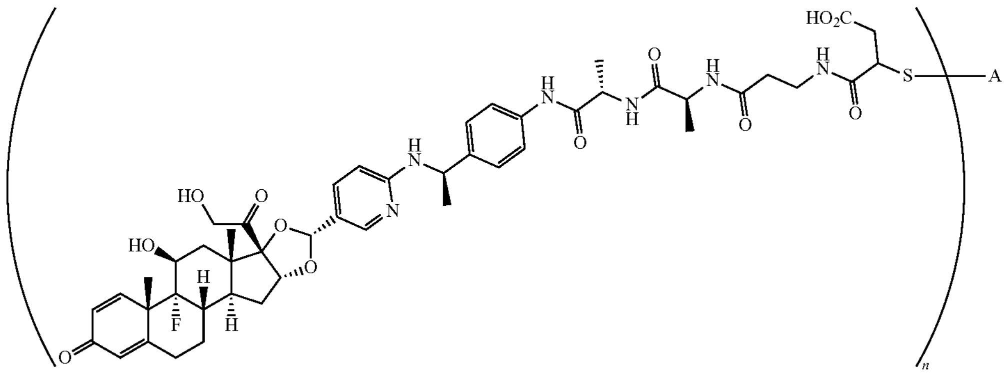 | 4 | 97.8 | >50 | 24 | >50 | 0.8 |
| 165 | 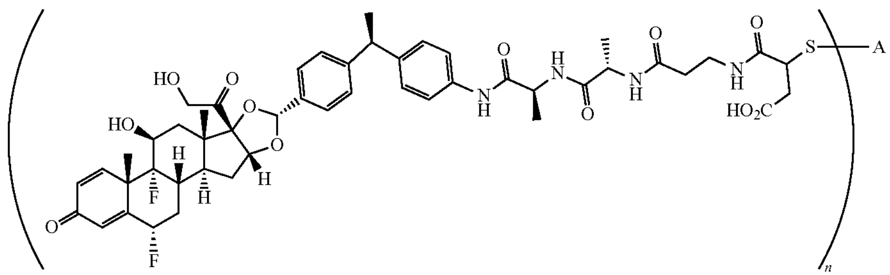 | 2 | 96.3 | 0.0179 | 93.6 | >50 | 94 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 166 | 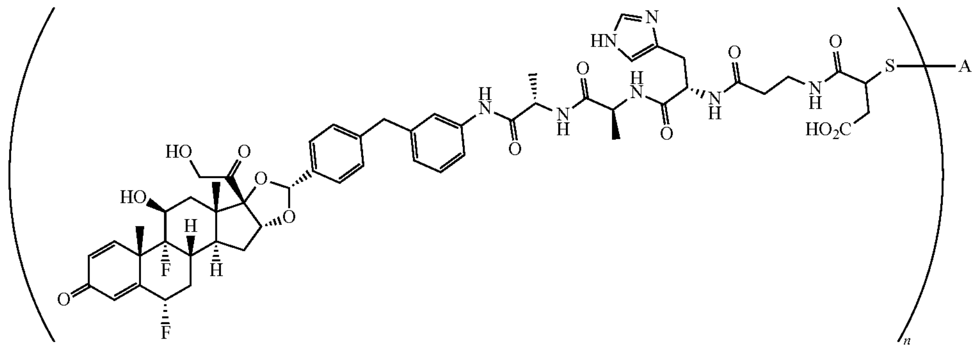 | 2 | 98 | 0.0136 | 107 | 14.6 | 75 |
| 167 | 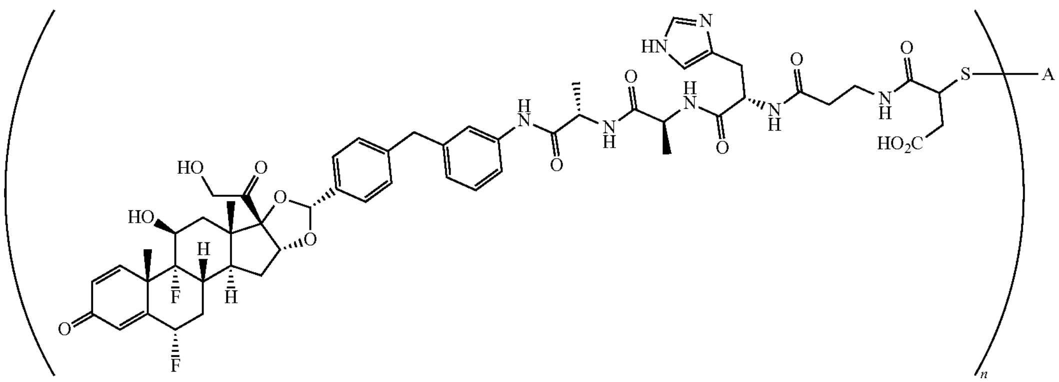 | 4 | 94.4 | 0.0108 | 97 | 11.4 | 73 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 168 | 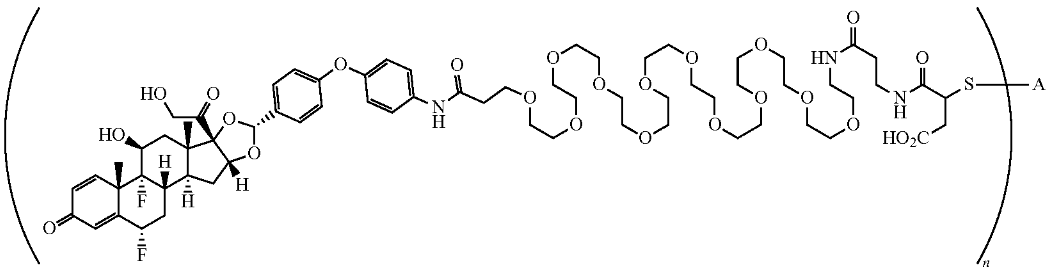 | 2 | 97.9 | 0.146 | 81 | 50 | 71 |
| 169 | 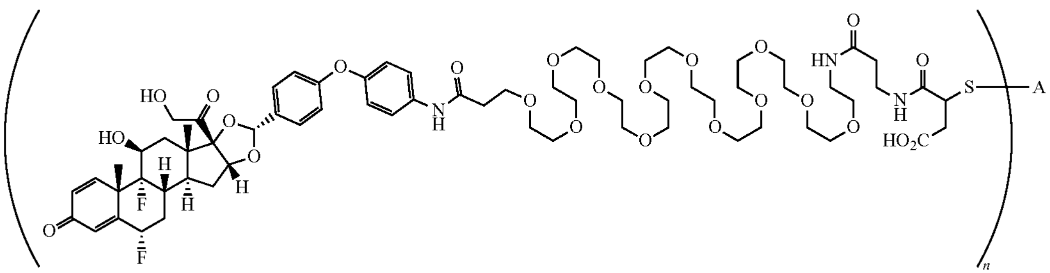 | 4 | 92.25 | 0.0551 | 117 | 18.4 | 88 |
| 170 | 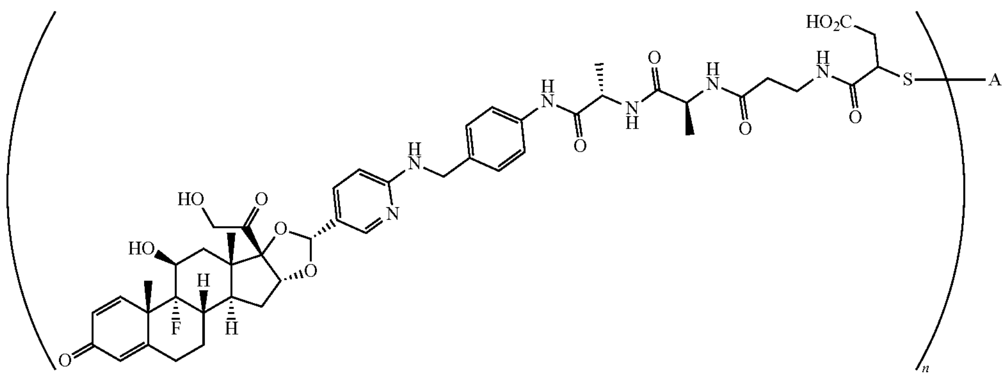 | 2 | 99.5 | 0.463 | 18.4 | >50 | 0.5 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 171 | 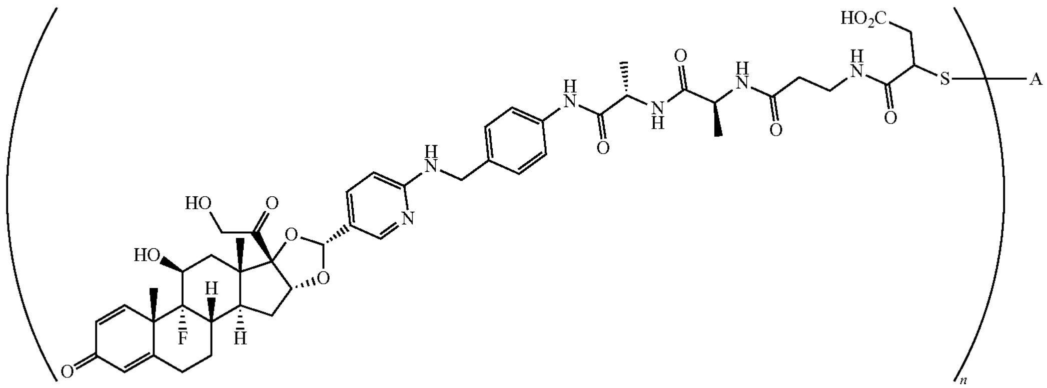 | 4 | 97.6 | 0.276 | 35 | >50 | 5 |
| 172 | 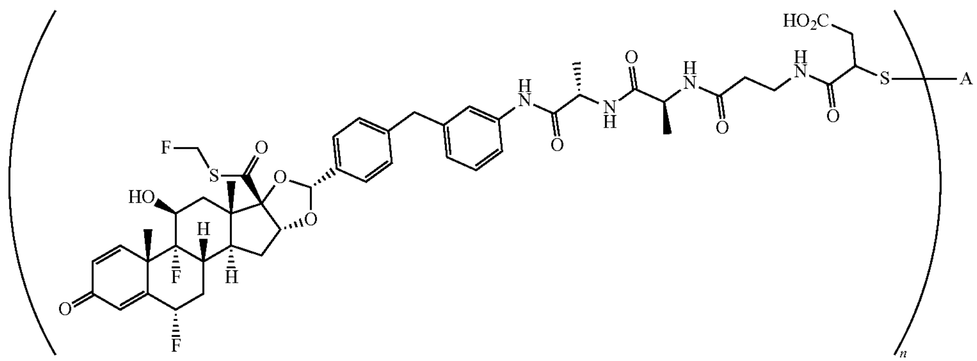 | 4 | 94.6 | 0.0319 | 89 | 2.9 | 64 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 173 | 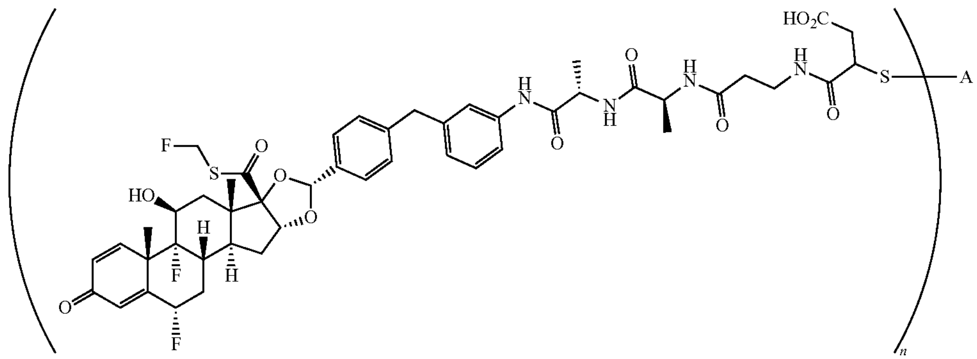 | 1.3 | 98 | 0.0959 | 78 | >50 | 35 |
| 174 | 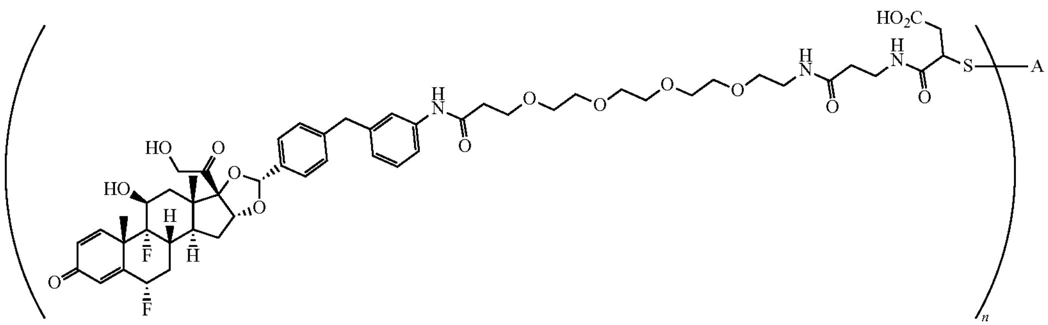 | 2 | 98 | 0.0607 | 143 | 4.23 | 14 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 175 | 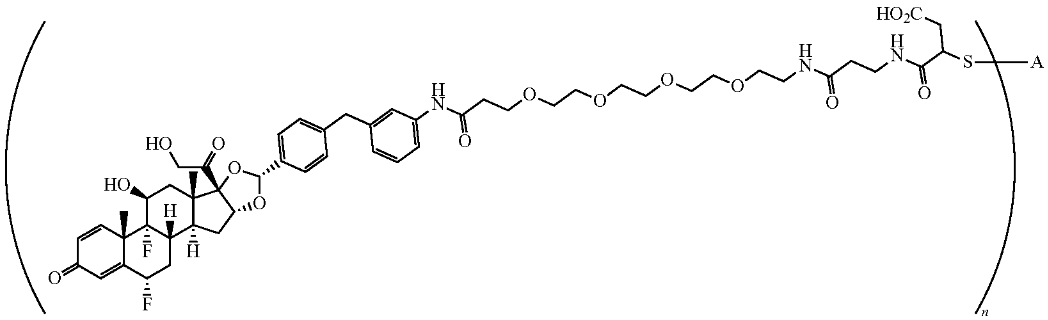 | 4 | 93.4 | 0.0464 | 92 | >50 | 55 |
| 176 | 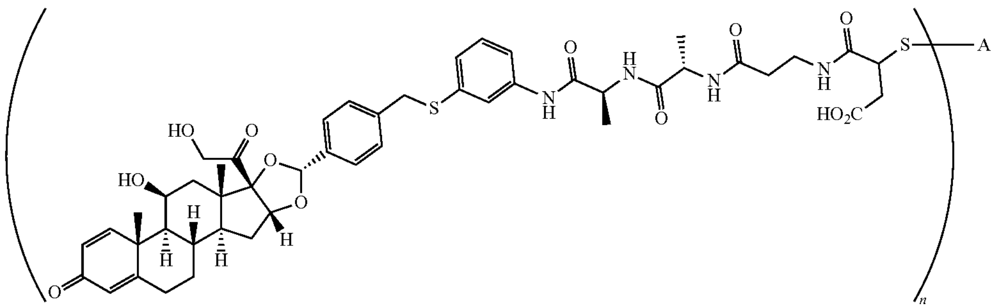 | 4 | 97.4 | 0.0262 | 113 | 41.4 | 60 |
| 177 | 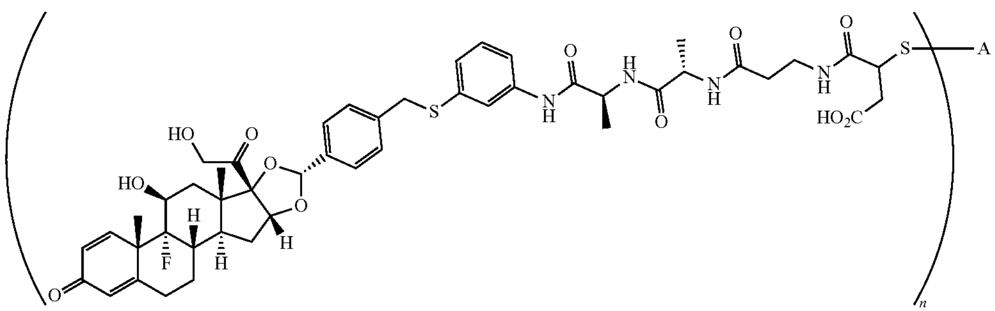 | 4 | 95.6 | 0.00998 | 105 | 7.94 | 66 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 178 | 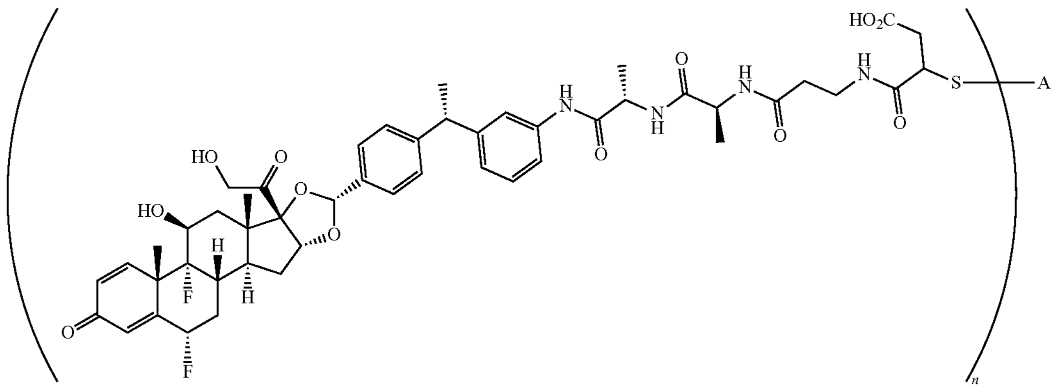 | 4 | 88.3 | 8.00E-04 | 93 | 3.88 | 48 |
| 179 | 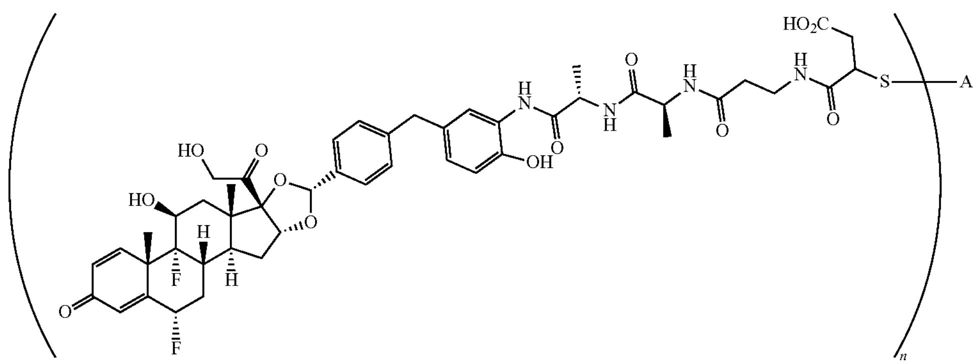 | 2 | 97.7 | 0.0249 | 89 | 11.7 | 84 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 180 | 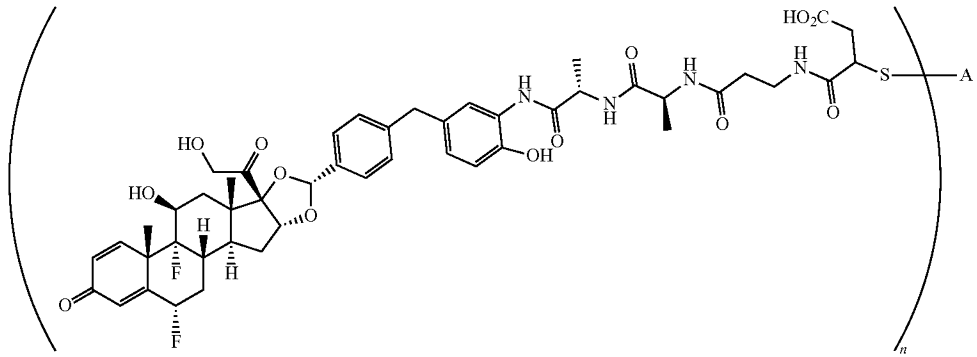 | 4 | 96.8 | 0.0118 | 84 | 2.75 | 78 |
| 181 | 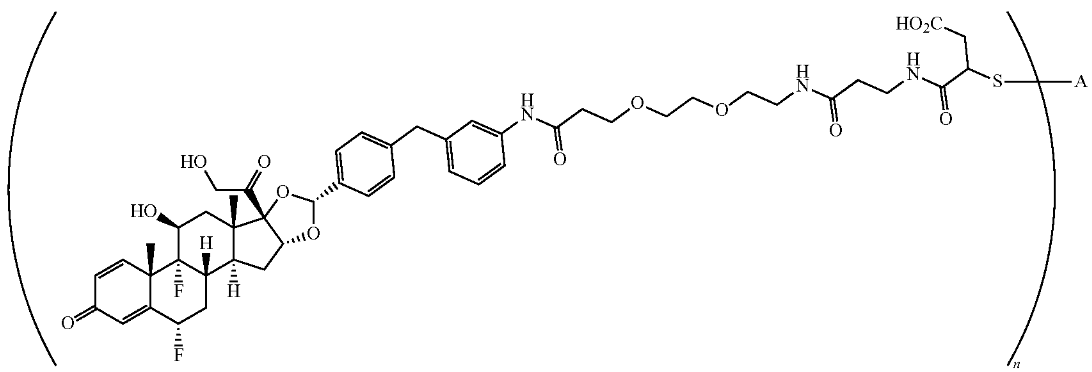 | 4 | 95.3 | 0.0593 | 83.8 | 50 | 35 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC50 (ug/mL) | K562 GRE (% max) |
|---|---|---|---|---|---|---|---|
| 182 | 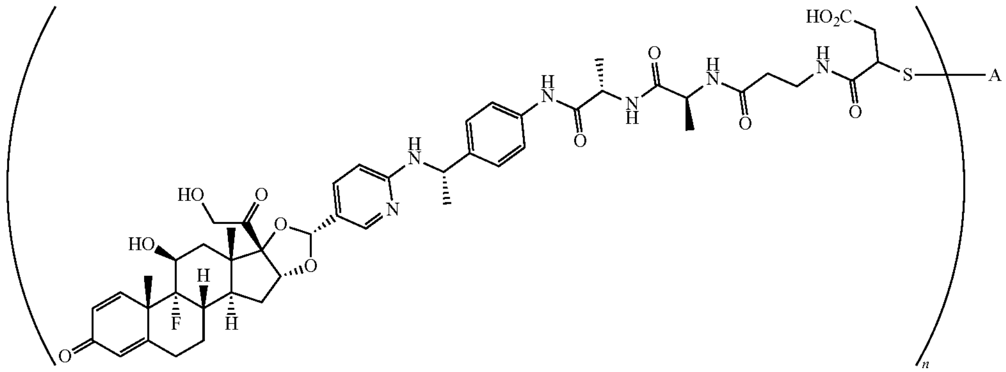 | 4 | 97.6 | >50 | 8 | >50 | 4 |
| 183 | 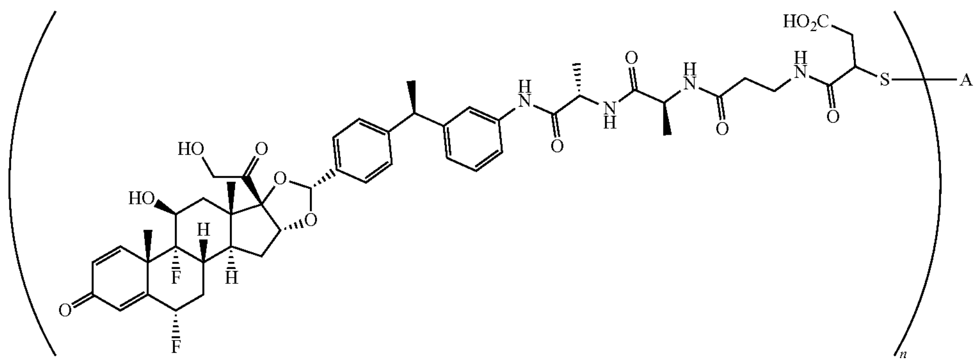 | 4 | 94.7 | 0.0144 | 87 | 12 | 49 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 184 | 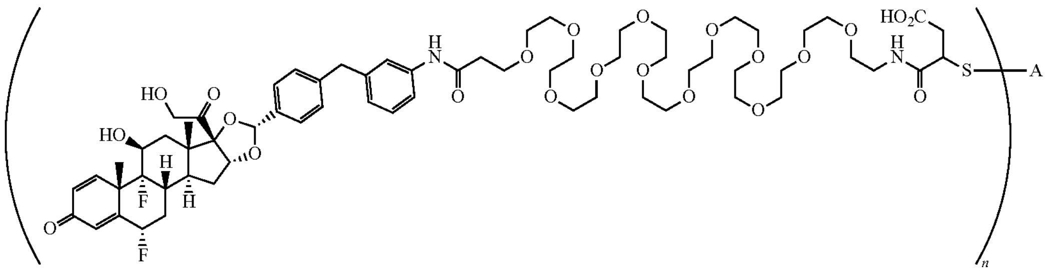 | 2 | 98.9 | 0.0525 | 75 | 46.7 | 36 |
| 185 | 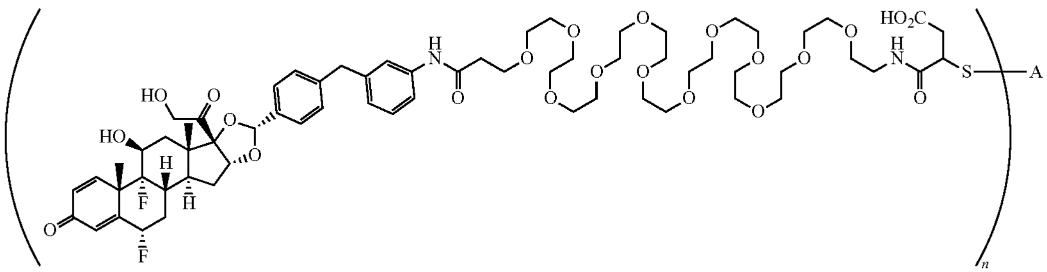 | 4 | 96.6 | 0.0294 | 64 | 5.02 | 76 |
| 186 | 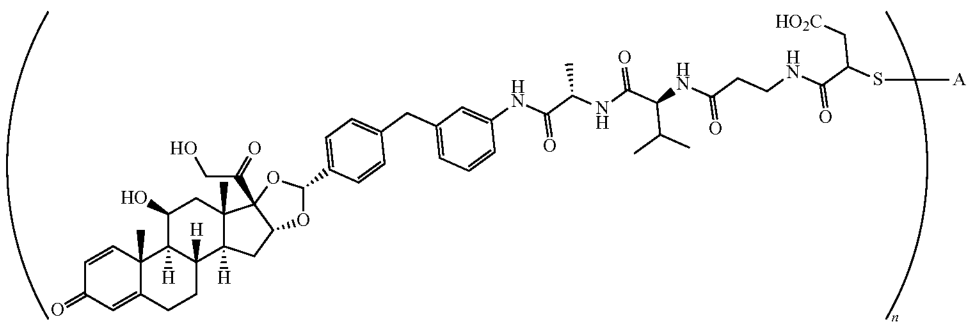 | 4 | 97.5 | 0.0479 | 143 | >50 | 31 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 187 | 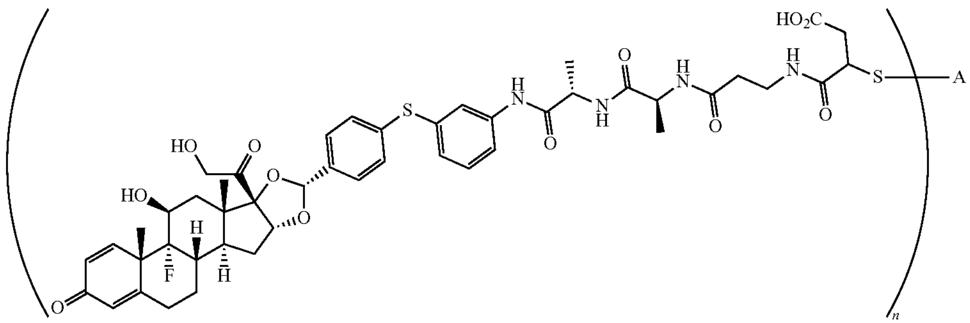 | 4 | 91.8 | 0.0185 | 103 | >50 | 73 |
| 188 | 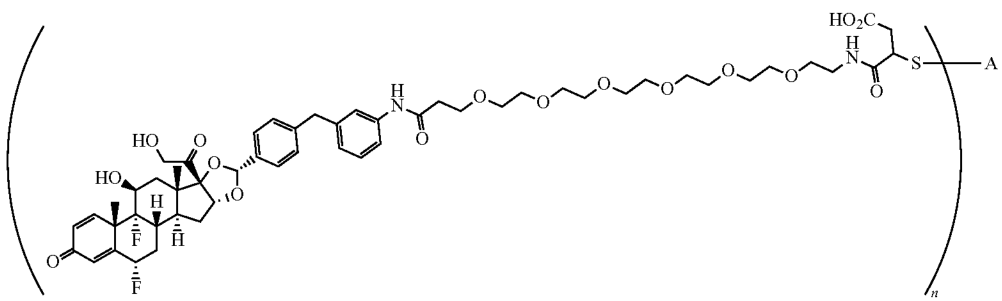 | 4 | 94 | 0.0107 | 126 | >50 | 43 |
| 189 | 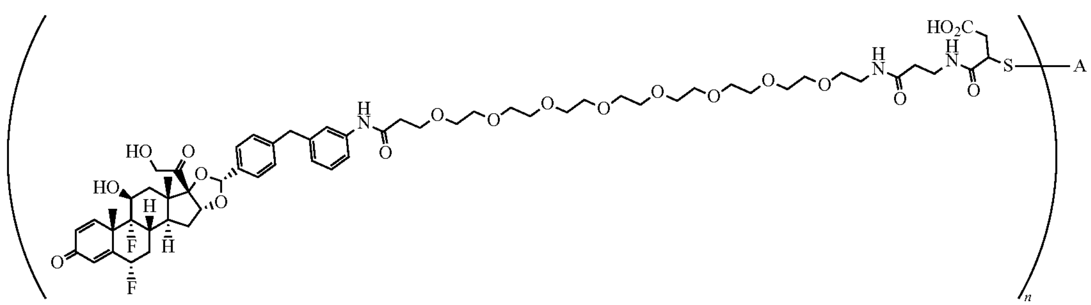 | 4 | 99.9 | 0.0215 | 149 | >50 | 59 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 190 | 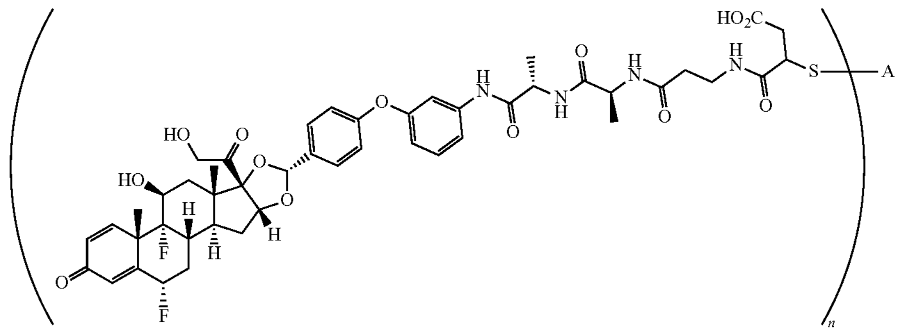 | 4 | 99.9 | 0.0112 | 109 | >50 | 90 |
| 191 | 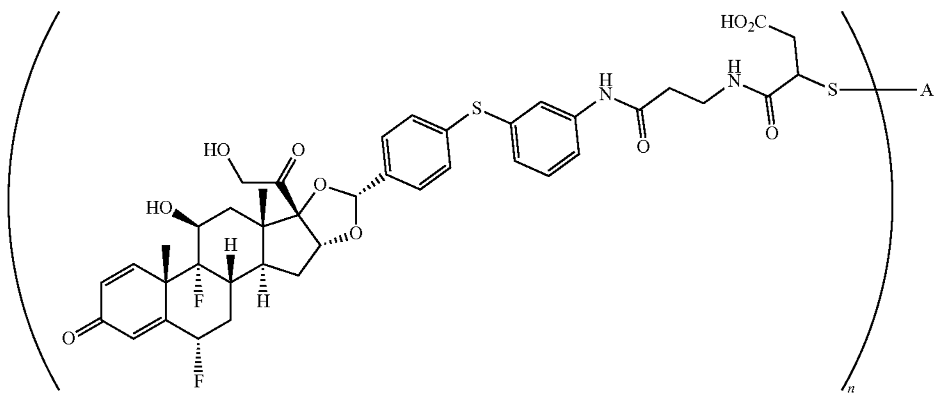 | 3.7 | 88.6 | 0.0692 | 122 | 14.4 | 90 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 192 | 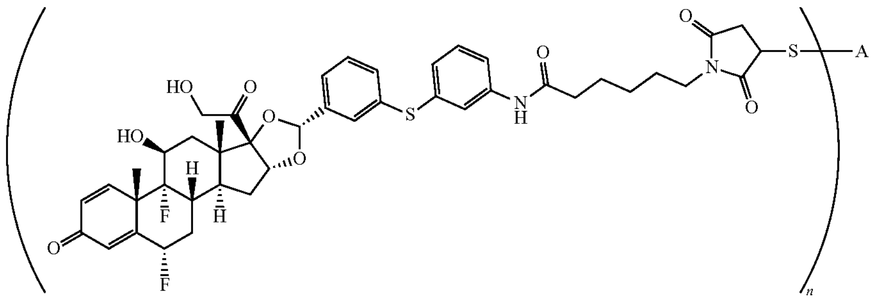 | 4.1 | 74.4 | 0.0225 | 98 | 1.23 | 99 |
| 193 | 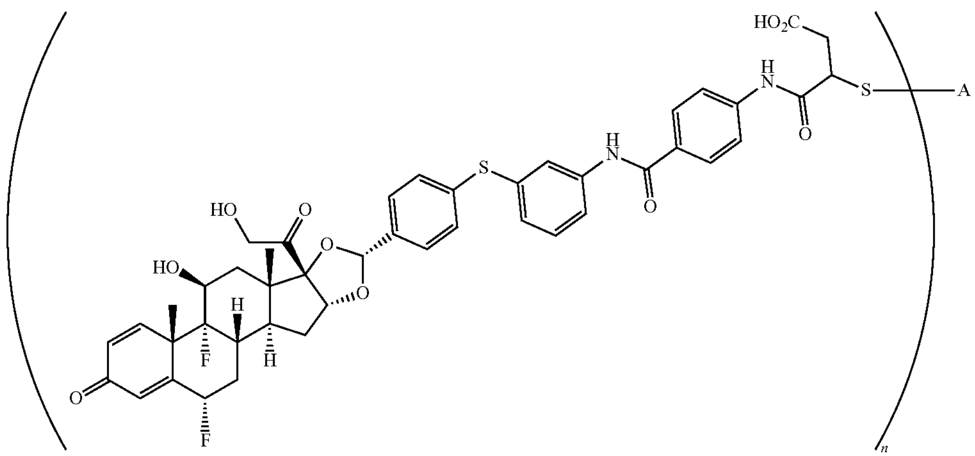 | 3.9 | 68 | 0.149 | 124 | 6.4 | 104 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 194 | 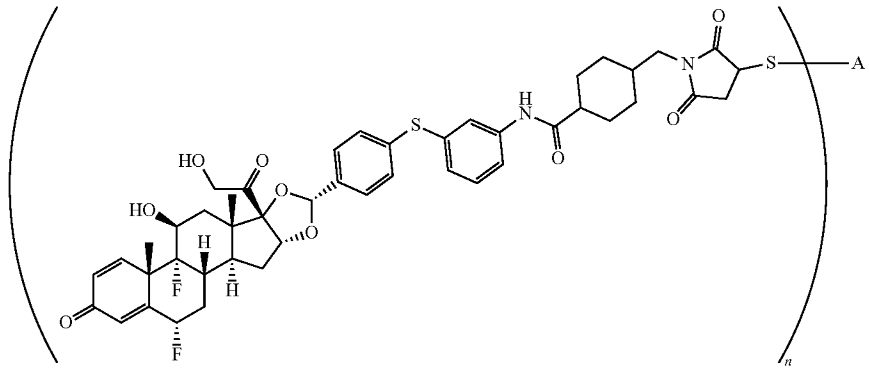 | 3.9 | 67.7 | 0.0517 | 95.3 | 5.01 | 85 |
| 195 | 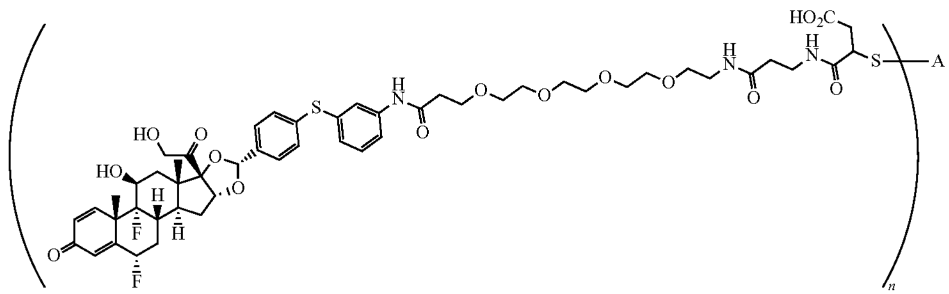 | 3.5 | 92.2 | 0.123 | 156 | 23.6 | 75 |
| 196 | 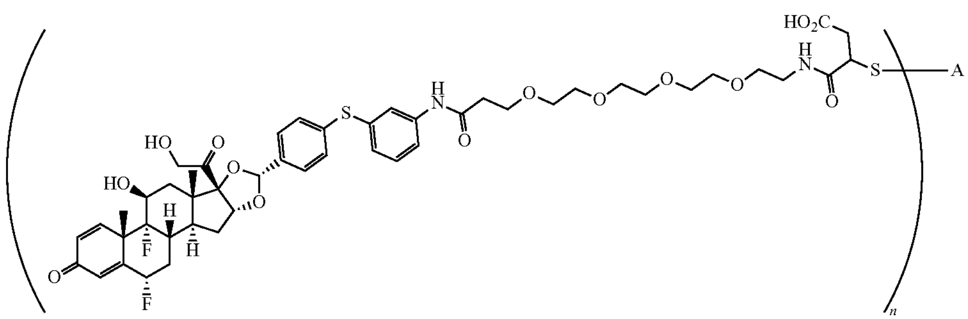 | 3.5 | 92.9 | 0.0331 | 96 | 24.2 | 63 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 197 | 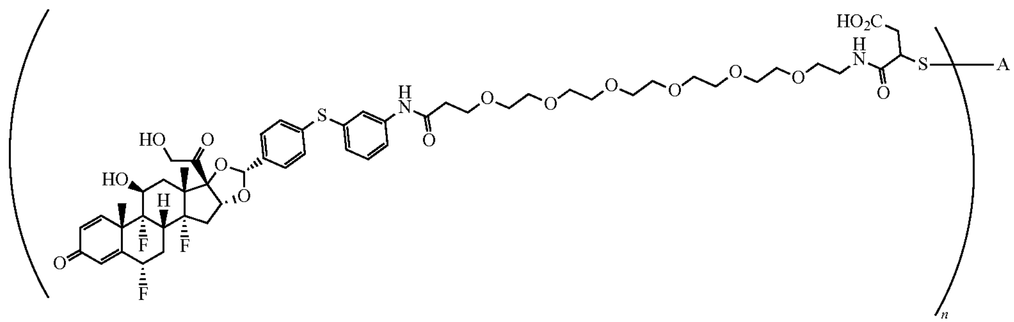 | 3.6 | 94.1 | 0.0626 | 143 | 39.3 | 60 |
| 198 | 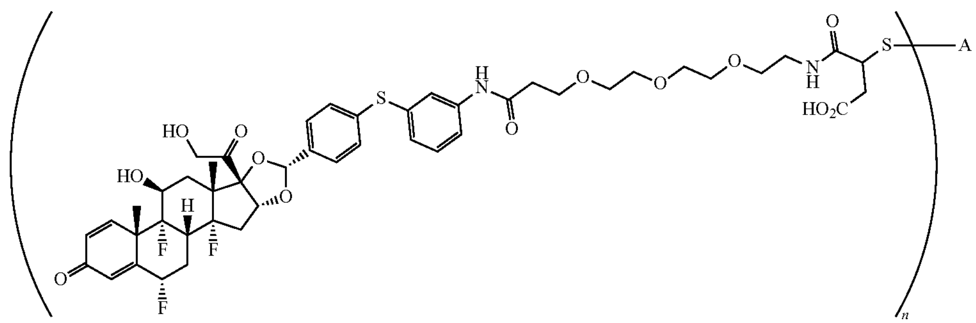 | 3.6 | 93 | 0.0614 | 96 | 12.7 | 91 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 199 | 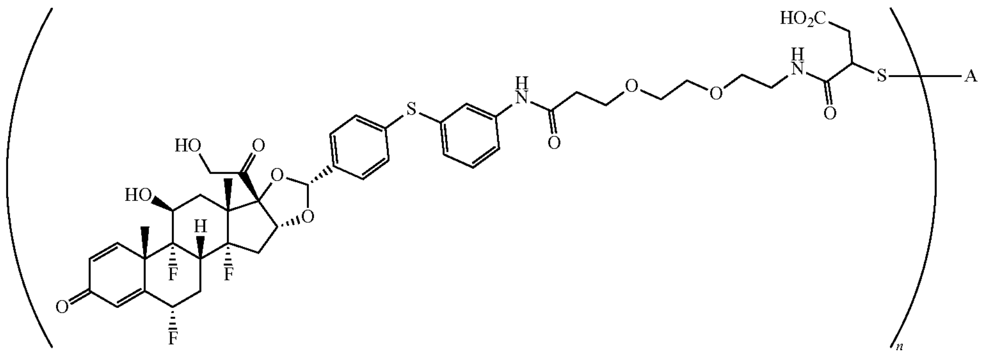 | 3.5 | 93 | 0.0654 | 93 | 23.3 | 73 |
| 200 | 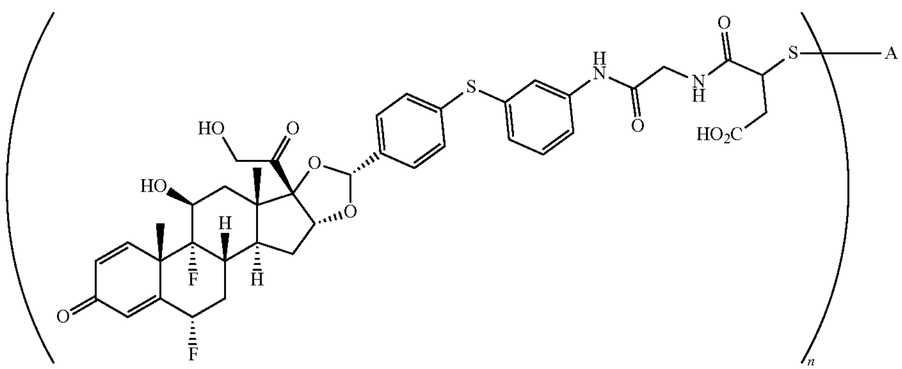 | 3.8 | 90.1 | 0.0114 | 114 | 4.76 | 92 |
| 207 | 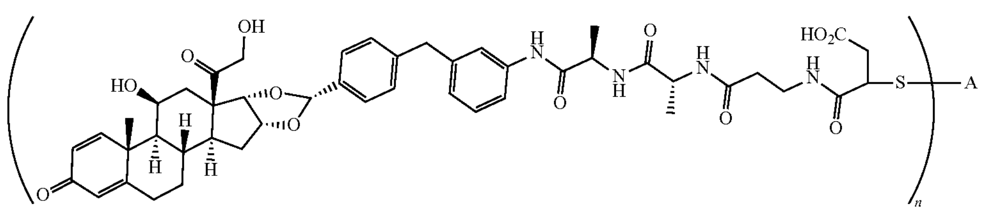 | 4 | | | | | |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 208 | 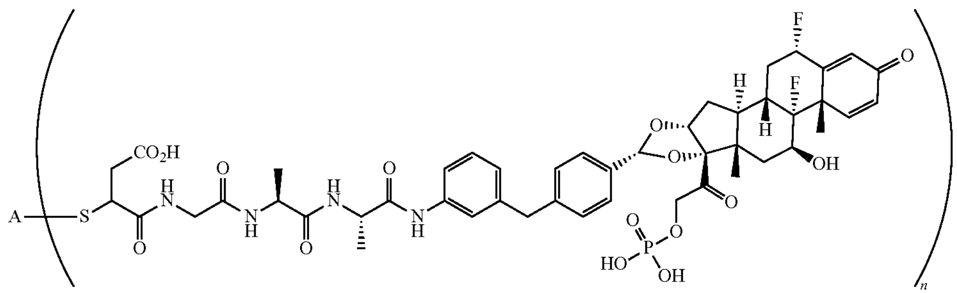 | 4 | 99.3 | 0.0154 | 123 | 50.0 | 98.7 |
| 209 | 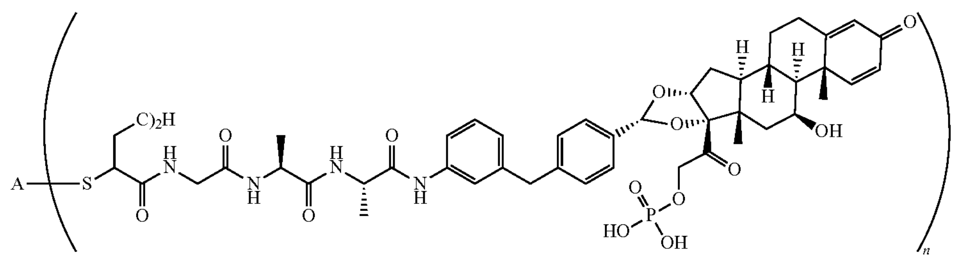 | 3.84 | 99.5 | 0.16 | 116 | 50.0 | 70.0 |
| 210 | 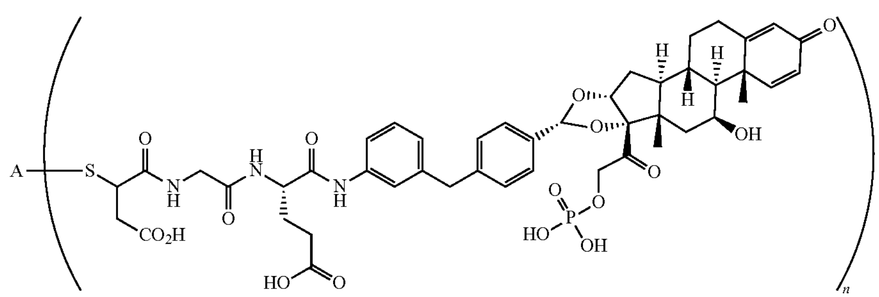 | 4 | 100 | 0.154 | 129 | 50.0 | 61.7 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 211 | 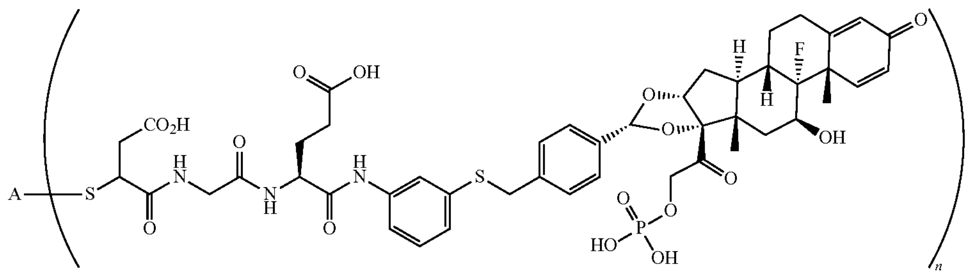 | 4 | 99.4 | 0.0341 | 130 | 18.7 | 91.7 |
| 212 | 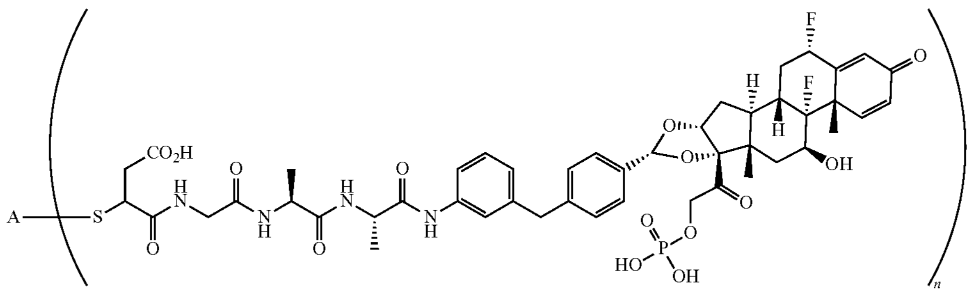 | 3.99 | 99.2 | 0.00633 | 101 | 1.9 | 348 |
| 213 | 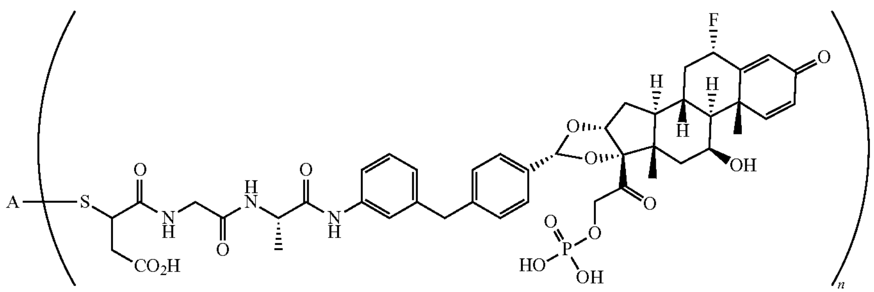 | 4.08 | 99.2 | 0.0267 | 140 | 27.6 | 146 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 214 | 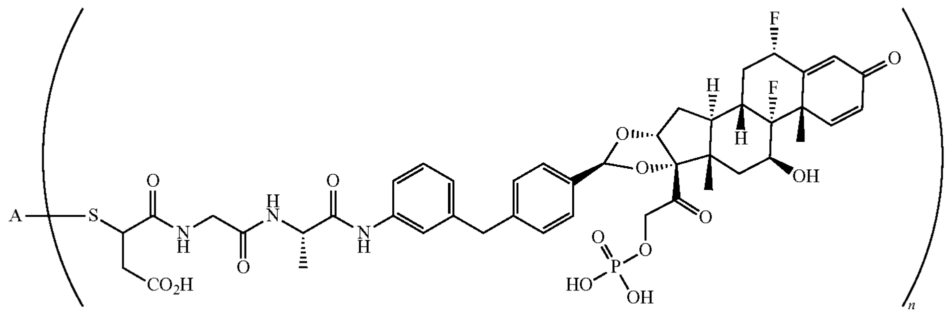 | 3.8 | 99.2 | 0.362 | 248 | 50.0 | 97.1 |
| 215 | 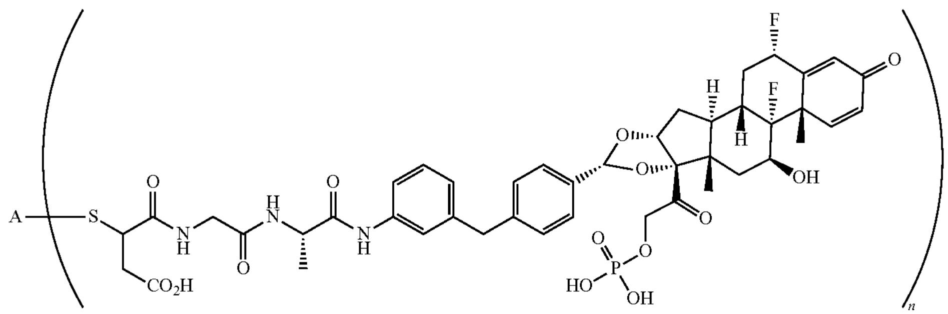 | 3.8 | 99.3 | 0.0166 | 126 | 1.93 | 103 |
| 216 | 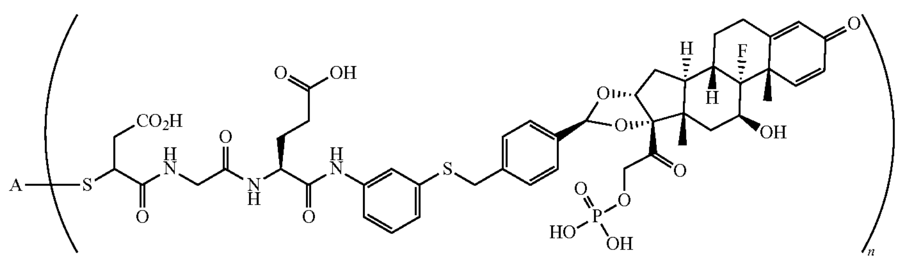 | 3.74 | 99.4 | 0.351 | 108 | 50.0 | 27.9 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 217 | 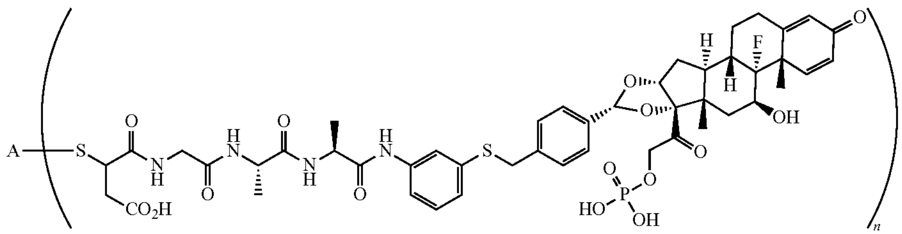 | 3.7 | 98.8 | 0.0147 | 101 | 18.3 | 97.2 |
| 218 | 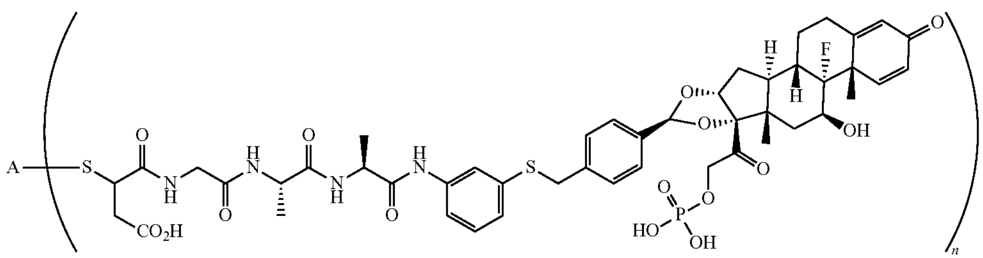 | 3.7 | 98.9 | 0.023 | 96.0 | 22.9 | 102 |
| 219 | 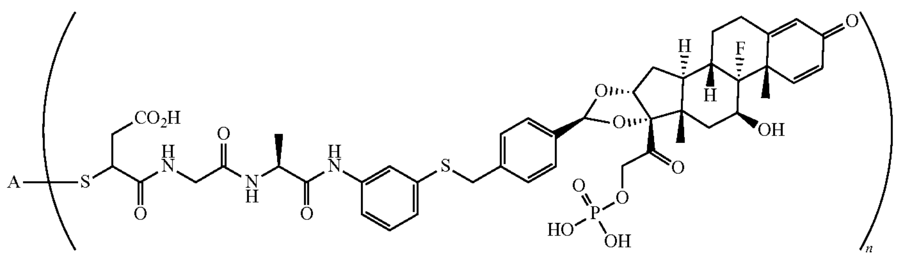 | 4.03 | 99.1 | 0.0371 | 140 | 50.0 | 91.2 |

TABLE 12-continued

In vitro activity of anti-murine TNFa antibody drug conjugates in mouse transmembrane TNFa GRE reporter assay (A refers to the anti-murine TNFa antibody 8C11)

| Cpd. No. | Structure | n | % monomer | mTNFa GRE EC50 (ug/mL) | mTNFa GRE (% max) | K562 GRE EC$_{50}$ (ug/mL) | K562 GRE (% max) |
|---|---|---|---|---|---|---|---|
| 220 | 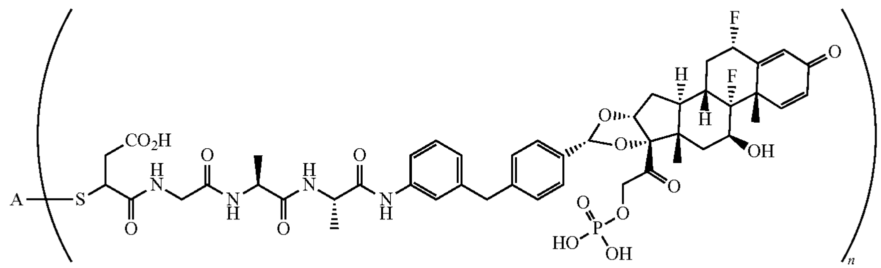 | 1.7 | 99.5 | 0.00329 | 97.7 | 9.96 | 112 |
| 221 | 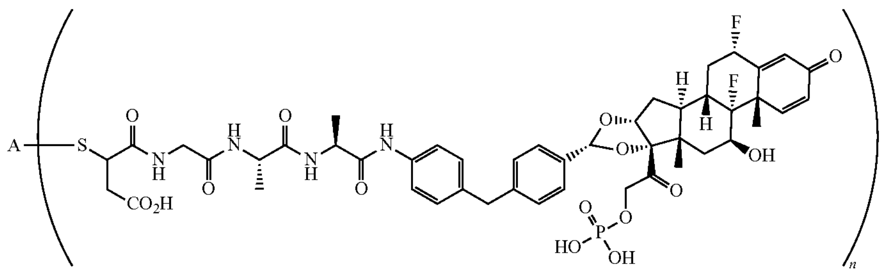 | 3.6 | 99 | 0.011 | 131 | 4.28 | 112 |
| 222 | 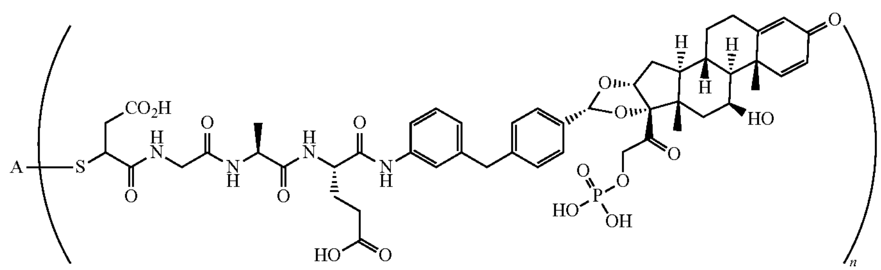 | 3.8 | 99 | 0.114 | 102 | 43.4 | 86.6 |

TABLE 13

In vitro activity of anti-human TNFa antibody drug conjugates in human transmembrane TNFa GRE reporter assay
(A refers to the anti-human TNFa antibody adalimumab (SEQ ID NOs: 66 and 73))

| Cpd. No. | Structure |
|---|---|
| 201 | 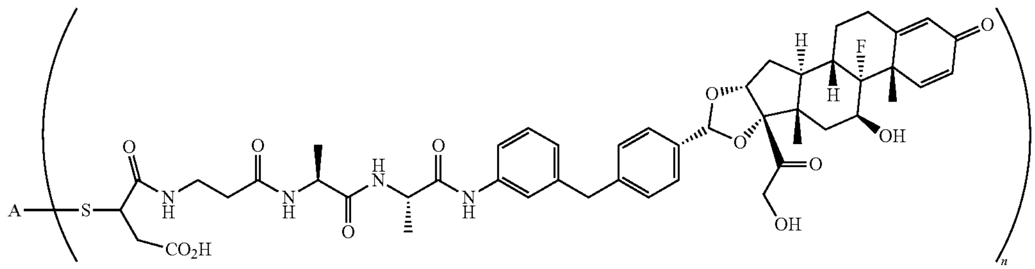 |
| 202 | 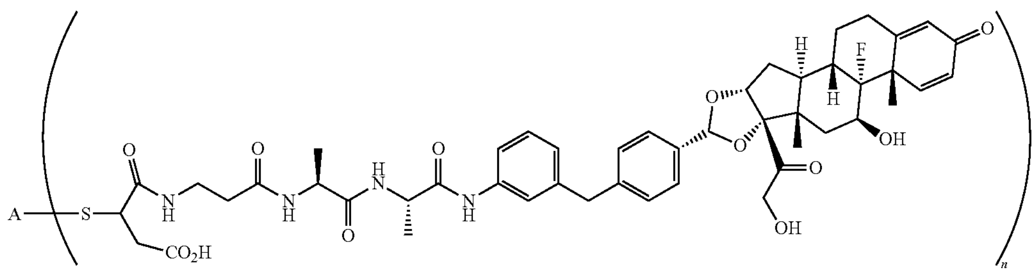 |
| 203 | 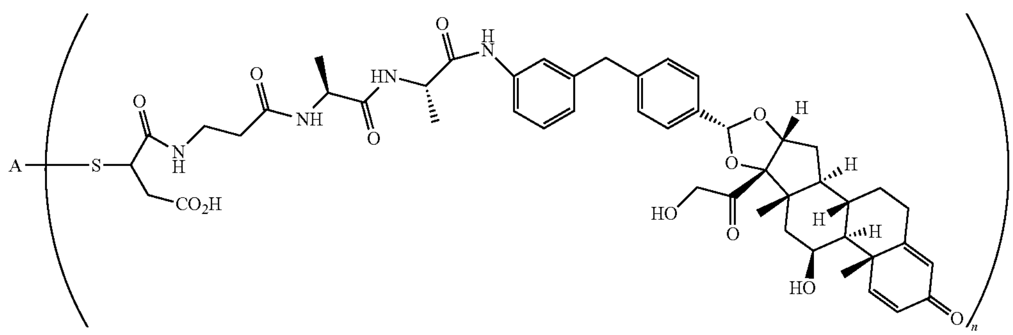 |
| 204 | 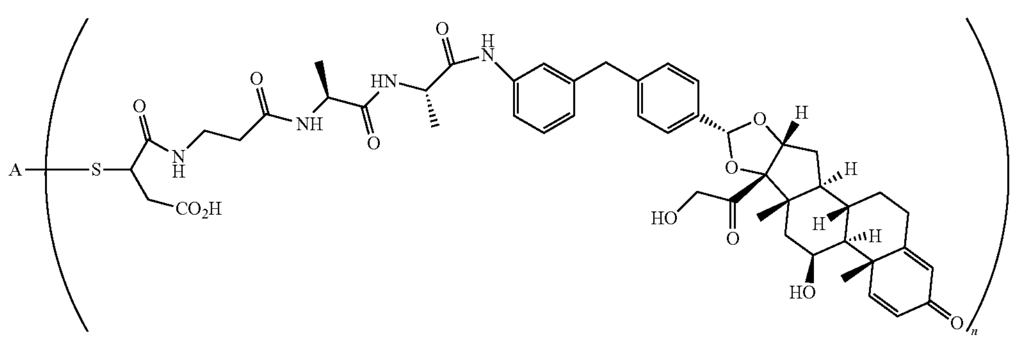 |

TABLE 13-continued

In vitro activity of anti-human TNFa antibody drug conjugates in human transmembrane TNFa GRE reporter assay
(A refers to the anti-human TNFa antibody adalimumab (SEQ ID NOs: 66 and 73)

205
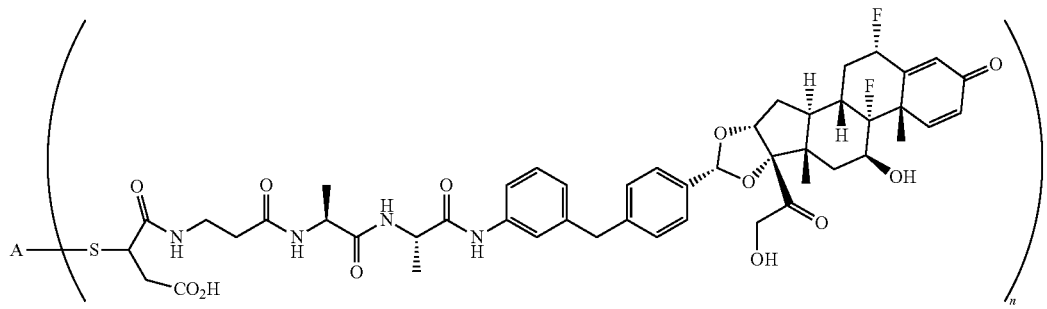

206
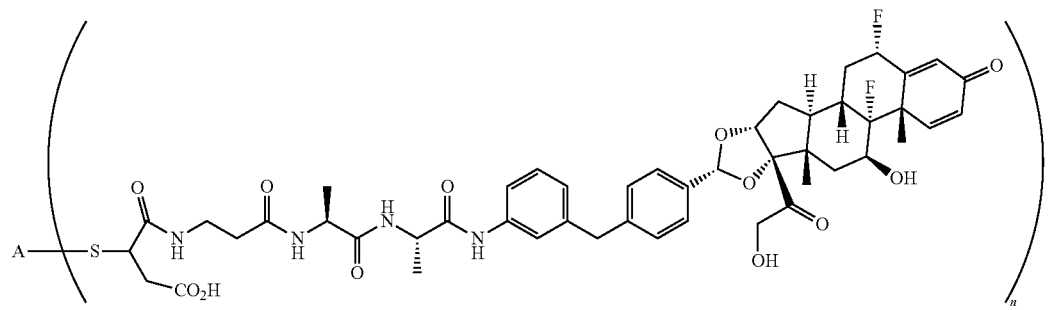

| Cpd. No. | n | hTNFa % monomer | hTNFa GRE EC$_{50}$ (ug/mL) | GRE (% max) | K562 GRE EC$_{50}$ (ug/mL) | K562 GRE (% max) |
|---|---|---|---|---|---|---|
| 201 | 4 | 97.6 | 0.0179 | 100 | 43 | 66 |
| 202 | 2 | 99.1 | 0.0318 | 121 | >50 | 51 |
| 203 | 4 | 98.2 | 0.0482 | 118 | >50 | 35 |
| 204 | 2 | 99.4 | 0.0767 | 103 | >50 | 21 |
| 205 | 4 | 96.9 | 0.0035 | 97 | 17.5 | 103 |
| 206 | 2 | 99.4 | 0.0082 | 101 | >50 | 97 |

Example 80: Activity of Various Anti-Human TNF-Alpha Immunoconjugates in GRE Transmembrane TNF-Alpha Reporter Assays Preparation of Anti-Human TNF Alpha Immunoconjugates All proteins were conjugated to Cpd. No. 99 using conditions highlighted under the general cysteine conjugation protocol in Example 36. Where indicated in Table 14 below, a cysteine addition (underlined) was engineered into the anti-TNF sequence to allow conjugation.

TABLE 14

| Amino acid sequences of anti-human TNF alpha antibodies used in immunoconjugates | |
|---|---|
| Antibody | Sequence (SEQ ID NO) |
| Infliximab HC | SEQ ID NO: 67 |
| Infliximab LC | SEQ ID NO: 74 |
| Golimumab HC | SEQ ID NO: 72 |
| Golimumab LC | SEQ ID NO: 78 |
| etanercept | LPAQVAFTPYAPEPGSTCRLREYYD QTAQMCCSKCSPGQHAKVFCTKTSD TVCDSCEDSTYTQLWNWVPECLSCG SRCSSDQVETQACTREQNRICTCRP GWYCALSKQEGCRLCAPLRKCRPGF GVARPGTETSDVVCKPCAPGTFSNT TSSTDICRPHQICNVVAIPGNASMD AVCTSTSPTRSMAPGAVHLPQPVST RSQHTQPTPEPSTAPSTSFLLPMGP SPPAEGSTGDEPKSCDKTHTCPPCP APELLGGPSVFLFPPKPKDTLMISR TPEVTCVVVDVSHEDPEVKFNWYVD GVEVHNAKTKPREEQYNSTYRVVSV LTVLIIQDWLNGKEYKCKVSNKALP APIEKTISKAKGQPREPQVYTLPPS REEMTKNQVSLTCLVKGFYPSDIAV EWESNGQPENNYKTTPPVLDSDGSF FLYSKLTVDKSRWQQGNVFSCSVMH EALHNHYTQKSLSLSPGK (SEQ ID NO: 79) |
| ABT-122 HC | EVQLVESGGGLVQPGRSLRLSCAAS GFTFDDYAMHWVRQAPGKGLEWVSA |

TABLE 14-continued

Amino acid sequences of anti-human TNF alpha antibodies used in immunoconjugates

| Antibody | Sequence (SEQ ID NO) |
|---|---|
| | ITWNSGHIDYADSVEGRFTISRDNA KNSLYLQMNSLRAEDTAVYYCAKVS YLSTASSLDYWGQGTLVTVSSGGGG SGGGGSEVQLVQSGAEVKKPGSSVK VSCKASGGSFGGYGIGWVRQAPGQG LEWMGGITPFFGFADYAQKFQGRVT ITADESTTTAYMELSGLTSDDTAVY YCARDPNEFWNGYYSTHDFDSWGQG TTVTVSSASTKGPSVFPLAPSSKST SGGTAALGCLVKDYFPEPVTVSWNS GALTSGVHTFPAVLQSSGLYSLSSV VTVPSSSLGTQTYICNVNHKPSNTK VDKKVEPKSCDKTHTCPPCPAPELL GGPSVFLFPPKPKDTLMISRTPEVT CVVVDVSHEDPEVKFNWYVDGVEVH NAKTKPREEQYNSTYRVVSVLTVLH QDWLNGKEYKCKVSNKALPAPIEKT ISKAKGQPREPQVYTLPPSRDELTK NQVSLTCLVKGFYPSDIAVEWESNG QPENNYKTTPPVLDSDGSFFLYSKL TVDKSRWQQGNVFSCSVMHEALHNH YTQKSLSLSPGK (SEQ ID NO: 80) |
| ABT-122 LC | DIQMTQSPSSLSASVGDRVTITCRA SQGIRNYLAWYQQKPGKAPKLLIYA ASTLQSGVPSRFSGSGSGTDFTLTI SSLQPEDVATYYCQRYNRAPYTFGQ GTKVEIKRGGSGGGGSGGEIVLTQSP DFQSVTPKEKVTITCRASQDIGSEL HWYQQKPDQPPKLLIKYASHSTSGV PSRFSGSGSGTDFTLTINGLEAEDA GTYYCHQTDSLPYTFGPGTKVDIKR TVAAPSVFIFPPSDEQLKSGTASVV CLLNNFYPREAKVQWKVDNALQSGN SQESVTEQDSKDSTYSLSSTLTLSK ADYEKHKVYACEVTHQGLSSPVTKS FNRGEC (SEQ ID NO: 81) |
| certolizumab pegol HC | SEQ ID NO: 68 |
| certolizumab pegol LC | SEQ ID NO: 75 |
| Certolizumab HC | EVQLVESGGGLVQPGGSLRLSCAAS GYVFTDYGMNWVRQAPGKGLEWMGW INTYIGEPIYADSVKGRFTFSLDTS KSTAYLQMNSLRAEDTAVYYCARGY RSYAMDYWGQGTLVTVSSASTKGPS VFPLAPSSKSTSGGTAALGCLVKDY FPEPVTVSWNSGALTSGVHTFPAVL QSSGLYSLSSVVTVPSSSLGTQTYI CNVNHKPSNTKVDKKVEPKSCDKTH TCAAHHHHHH (SEQ ID NO: 82) |
| Certolizumab LC | DIQMTQSPSSLSASVGDRVTITCKA SQNVGTNVAWYQQKPGKAPKALIYS ASFLYSGVPYRFSGSGSGTDFTLTI SSLQPEDFATYYCQQYNIYPLTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC (SEQ ID NO: 83) |
| Adalimumab Fab HC | EVQLVESGGGLVQPGRSLRLSCAAS GFTFDDYAMHWVRQAPGKGLEWVSA ITWNSGHIDYADSVEGRFTISRDNA KNSLYLQMNSLRAEDTAVYYCAKVS YLSTASSLDYWGQGTLVTVSSASTK GPSVFPLAPSSKSTSGGTAALGCLV KDYFPEPVTVSWNSGALTSGVHTFP AVLQSSGLYSLSSVVTVPSSSLGTQ TYICNVNHKPSNTKVDKKVEPKSCD KTHTCAAHHHHHH (SEQ ID NO: 84) |
| Adalimumab Fab LC | DIQMTQSPSSLSASVGDRVTITCRA SQGIRNYLAWYQQKPGKAPKLLIYA ASTLQSGVPSRFSGSGSGTDFTLTI SSLQPEDVATYYCQRYNRAPYTFGQ GTKVEIKRTVAAPSVFIFPPSDEQL KSGTASVVCLLNNFYPREAKVQWKV DNALQSGNSQESVTEQDSKDSTYSL SSTLTLSKADYEKHKVYACEVTHQG LSSPVTKSFNRGEC (SEQ ID NO: 85) |
| Affibody[1] | GVDNKFNKENIAAMTEITRLPNLNP YQRAAFIWSLSDDPSQSANLLAEAK KLNDAQAPKC (SEQ ID NO: 86) |
| Ozoralizumab Nanobody | EVQLVESGGGLVQPGGSLRLSCAAS GFTFSDYWMYWVRQAPGKGLEWVSE INTNGLITKYPDSVKGRFTISRDNA KNTLYLQMNSLRPEDTAVYYCARSP SGFNRGQGTLVTVSSGGGGSGGGSE VQLVESGGGLVQPGNSLRLSCAASG FTFSSFGMSWVRQAPGKGLEWVSSI SGSGSDTLYADSVKGRFTISRDNAK TTLYLQMNSLRPEDTAVYYCTIGGS LSRSSQGTLVTVSSGGGGSGGGSEV QLVESGGGLVQPGGSLRLSCAASGF TFSDYWMYWVRQAPGKGLEWVSEIN TNGLITKYPDSVKGRFTISRDNAKN TLYLQMNSLRPEDTAVYYCARSPSG FNRGQGTLVTVSSGSEQKLISEEDL CHHHHHH (SEQ ID NO: 87) |

[1]Kronqvist J et al. Protein Engineering, Design & Selection 21 (4):247-255 (2008)

Activity of Anti-Human TNF Alpha Immunoconjugates in GRE Reporter Assay

Anti-human TNF alpha immunoconjugates (also referred to as anti-human TNF alpha ADCs, or anti-hTNF alpha steroid ADCs) were tested for activity in the K562 parental GRE (pGL4.36[luc2P/MMTV/hydgro]) and K562 hTNF delta 1-12 GRE (pGL4.36[luc2P/MMTV/hydgro]) cell lines under conditions as described in Example 79. The results shown in Table 15 indicate that all anti-hTNF alpha steroid ADCs tested demonstrate potent antigen-dependent activity dissociated from their activity on the parental cell line.

TABLE 15

In vitro activity of anti-human TNF alpha ADCs in human transmembrane TNFa GRE reporter assay
(ADC concentrations were normalized for MW and DAR)

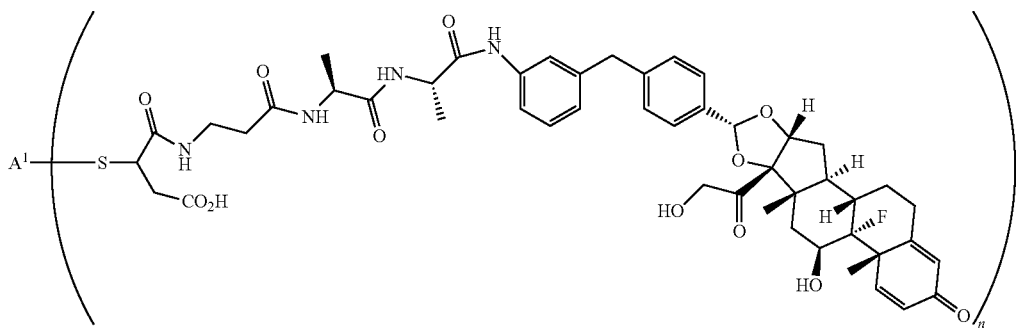

| Cpd. No. | A$^1$ | SEQ ID | n | % monomer | hTNFa GRE EC50 (nM) | hTNFa GRE (% max) | K562 GRE EC50 (nM) | K562 GRE (% max) |
|---|---|---|---|---|---|---|---|---|
| 233 | infliximab | 67/74 | 3.3 | 99.99 | 1.3 | 122 | 374 | 55.3 |
| 234 | golimumab | 72/78 | 4.9 | 99 | 3.3 | 144 | 1633 | 67.5 |
| 235 | etanercept | 79 | 2.3 | 87.6 | 0.6 | 105.5 | 164 | 104 |
| 236 | ABT-122 | 80/81 | 4.1 | 99.98 | 1.02 | 116.9 | 608 | 61.3 |
| 237 | certolizumab pegol | 68/75 | 2 | 95.9 | 0.44 | 97 | 1111 | 39 |
| 238 | certolizumab | 82/83 | 1 | ND | 0.4 | 95 | 266 | 60 |
| 239 | adalimumab Fab | 84/85 | 1 | ND | 1 | 118 | 190 | 137 |
| 240 | affibody | 86 | 1 | 100 | 9.1 | 98 | 26 | 84 |
| 241 | ozoralizumab (nanobody) | 87 | 1 | 98 | 0.5 | 131 | 875 | 99 |

Binding of Anti-Human TNF Alpha Immunoconjugates to Human TNF Alpha

Binding kinetics of anti-h TNF alpha steroid ADCs to recombinant soluble TNFα trimer were determined by surface plasmon resonance-based measurements made on Biacore T200 instrument (GE Healthcare) at 25° C. using either anti-human Fc/anti-human F(ab')$_2$ capture (used for all ADCs except affibody and ozoralizumab ADCs) or direct NHS/EDC mediated amine coupling approach (used only for ozoralizumab ADC). Approximately 10000 RU of goat anti-human IgG Fc polyclonal antibody (Thermo Fisher Scientific Inc., cat. No. 31125) or goat anti-human F(ab')$_2$ polyclonal antibody (Jackson Immunoresearch Laboratories, Inc. cat. No. 109-006-006) was diluted to 5 µg/mL in 10 mM sodium acetate (pH 4.5) and was immobilized across a CM5 biosensor chip using a standard amine coupling kit according to manufacturer's instructions and procedures. Unreacted moieties on the biosensor surface were blocked with 1M ethanolamine. For direct amine coupling approach, approximately 750 RU of ozoralizumab steroid conjugate was directly immobilized onto CM5 chip. Chip preparation and binding kinetic measurements were made in the assay buffer HBS-EP+(10 mM Hepes, pH 7.4, 150 mM NaCl, 3 mM EDTA, 0.05% Tween 20). For binding kinetic measurements in capture format, each assay cycle consisted of the following steps: 1) capture of test ADC on test surface at a concentration of 0.5 µg/mL and at a flow rate of 5 µL/min for 60 s; 2) analyte injection (human TNFα or buffer only) over both reference and test surface for 300 s at 50 µl/min, after which the dissociation was monitored for 600 seconds at 50 µl/min; 3) regeneration of capture surface by 10 mM Glycine-HCl, pH 1.5 or 100 mM HCl (for directly coupled ADC) injections over both reference and test surface. For binding kinetics measurements in direct amine coupling format, only step 2) and step 3) were performed. During the assay, all measurements were referenced against the blank surface alone (i.e. with no captured test antibody or immobilized nanobody) and buffer-only injections were used for double referencing. TNFα injections ranged in concentration from 50 nM to 0.39 nM in a 2-fold dilution series, respectively. Data were processed and fitted globally to a 1:1 binding model using Biacore T200 Evaluation software to determine the binding kinetic rate constants, $k_a$ (M$^{-1}$ s$^{-1}$) and $k_d$ (s$^{-1}$), and the equilibrium dissociation constant $K_D$ (M). Two independent experiments were conducted. Reported values in Table 16 are averages from these experiments.

TABLE 16

Binding affinities of anti-hTNF alpha steroid ADCs to human TNF alpha

| Cpd No. | anti-TNF ADC | $k_a$ (1/Ms) | $k_d$ (1/s) | $K_D$ (M) |
|---|---|---|---|---|
| 233 | infliximab | 9.90E+05 | 3.10E−04 | 3.10E−10 |
| 234 | golimumab | 9.70E+05 | 2.40E−04 | 2.50E−10 |
| 235 | etanercept | 6.30E+06 | 9.80E−05 | 1.60E−11 |
| 236 | ABT-122 | 4.00E+05 | 6.90E−05 | 1.80E−10 |
| 237 | certolizumab pegol | 2.30E+06 | 1.70E−04 | 7.30E−11 |
| 238 | certolizumab | 2.70E+06 | 1.60E−04 | 6.00E−11 |
| 239 | adalimumab Fab | 1.50E+06 | 1.80E−04 | 1.30E−10 |
| 240 | affibody | ND | ND | ND |
| 241 | ozoralizumab (nanobody) | 1.30E+06 | 7.00E−05 | 5.20E−11 |

(ND = not determined)

Example 81: Activity of Anti-hTNF Alpha Steroid ADCs in Lipopolysacharride Stimulated Human PBMC Cytokine Release Assay Primary human peripheral blood mononuclear cells (PBMCs) were purchased from Biological Specialty Corporation (cat #214-00-10), washed in 50 mL PBS, re-suspended in FBS with 5% DMSO, aliquoted and cryopreserved in liquid nitrogen until use. The PBMCs were thawed, resuspended in RPMI supplemented with 2% FBS, and 1% Penicillin-Streptomycin, and plated into a cell assay plate (Costar #3799). The cells were incubated with varying concentration of anti-hTNF alpha steroid ADCs at 37° C. and 5% $CO_2$ for 4 hours. Cells were then stimulated with 100 ng/ml LPS for overnight. On the following day, plate was spun for five minutes at 1000 rpm, and 100 µL of supernatant media was directly transferred to an additional 96-well plate and analyzed for IL-6 (MSD, # K151AKB) and IL-1 beta(MSD, # K151AGB) concentrations. The dose response data were fitted to a sigmoidal curve using non-linear regression. and the IC50 values calculated with the aid of GraphPad 5.0 (GraphPad Software, Inc.). The results shown in Table 17 demonstrate that the anti-hTNF alpha steroid ADCs have potent activity in inhibiting the release of pro-inflammatory cytokines IL-6 and IL-1beta from activated primary immune cells.

TABLE 17

In vitro activity of anti-human TNF alpha ADCs in LPS-stimulated human PBMC cytokine release assay (n = 2)

| | Cytokine Release IC50 (ng/ml) | |
|---|---|---|
| Cpd No. | IL-6 | IL-1beta |
| 203 | 14.3 ± 3.5 | 3.6 ± 1.2 |
| 201 | 86.8 ± 69.6 | 25.5 ± 21.3 |
| 205 | 42.4 ± 27.9 | 22 ± 18 |

Example 82: Activity of Anti-TNF-Alpha Immunoconjugate in TNFa-Induced Cytotoxicity Assay in L929 Cells L929 is a murine aneuploid fibrosarcoma cell line that is sensitized by pretreatment with actinomycin D. Treatment with TNFa initiates apoptosis and subsequent cell death. L929 cells in log phase were harvested using trypsin 0.05%, washed twice with D-PBS and counted by CEDEX. The cells were resuspended at 1E6 cell/mL in assay media containing 4 µg/mL actinomycin D and 50 µL was added to all wells. Anti-murine TNF alpha steroid ADC (anti-murine TNF alpha 8C11 conjugated to Cpd 71; also referred to as anti-mTNF alpha steroid ADC) and anti-murine TNF mAb (8C11) were diluted to a 4× concentration in assay media and serial 1:3 dilutions were performed. Mouse TNFα was diluted to a 4× concentration of 600 pg/mL. The anti-mTNF steroid ADC and anti-mTNF mAb (125 µL) were added to the mTNFu (125 µL) in a 1:2 dilution scheme and allowed to incubate for 1 hour at room temperature, gently shaking. The antibody/mTNFu (or ADC/mTNFu) mixture was added to wells at 50 µL/well in triplicate. The plates were incubated for 20 hours at 37° C., 5% $CO_2$. To quantify viability, 10 µL of WST-1 reagent (Roche cat #11644807001) was added to wells. Plates were incubated under assay conditions for 3.5 hours, centrifuged at 500×g and 75 µL supernatant transferred to an ELISA plate (Costar cat #3369). The plates were read at OD 420-600 nm using a Spectromax 190 ELISA plate reader. Data was analyzed and $IC_{50}$ values calculated using a sigmoidal dose response (variable slope) fit in GraphPad Prism 5.

Anti-mTNF alpha steroid ADC had comparable neutralizing potency ($IC_{50}$ 1.9 nM) to unconjugated anti-mTNF alpha mAb ($IC_{50}$ 1.5 nM).

Anti-human TNF alpha immunoconjugates were tested for neutralizing activity under conditions described above. The results are shown in Table 18 and indicate the anti-human TNF alpha immunoconjugates tested demonstrate potent neutralization of human TNF alpha.

TABLE 18

Neutralization potencies of anti-hTNF alpha steroid ADCs to human TNF alpha-induced cytoxicity in L929 cells

| Compound | anti-TNF | SEQ ID | ADC DAR | % monomer | IC50 (nM) |
|---|---|---|---|---|---|
| 233 | infliximab | 67/74 | 3.3 | 99.99 | ND |
| 234 | golimumab | 72/78 | 4.9 | 99 | 0.050 |
| 235 | etanercept | 79 | 2.3 | 87.6 | 0.002 |
| 236 | ABT-122 | 80/81 | 4.1 | 99.98 | 0.074 |
| 237 | certolizumab pegol | 68/75 | 2 | 95.9 | 0.046 |
| 238 | certolizumab | 82/83 | 1 | ND | 0.085 |
| 239 | adalimumab Fab | 84/85 | 1 | ND | 0.6 |
| 240 | affibody | 86 | 1 | 100 | ND |
| 241 | ozoralizumab (nanobody) | 87 | 1 | 98 | 0.018 |

(ND = not determined)

Example 83: Binding of anti-mTNF-alpha steroid ADC to mouse Fcgamma receptors SPR (surface plasmon resonance) based Biacore T200 instrument (GE Healthcare) was used to evaluate binding of anti-mTNF-alpha steroid ADC (anti-mTNF 8C11 conjugated to Cpd 71) and anti-mTNF-alpha mAb to recombinant mouse FcgRs (all R&D Systems). The FcgRs were directly immobilized on the surface of the flow cells two, three and/or four of the CM5 type S Biacore chip(s) to achieve densities of ~1000-2000 RU (resonance units). Blank modified surface of the flow cell one of each Biacore chip was used as a reference surface. Each experiment consisted of association and dissociation phases. Association phase consisted of titrating parental mAb and ADC over all flow cells at a flow rate of 50 ul/min and concentrations of 4000, 2000, 1000, 500, 250, 125, 62.5, 31.25 and 0 nM for FcgRIIB and FcgRIII and 100, 50, 25, 12.5, 6.25, 3.13, 1.56 and 0 nM for receptors I and IV. Dissociation phase consisted of the continuous flow of the running buffer (HBS-EP+, pH 7.4, GE Healthcare) at the flow rate of 50 ul/min. Association and dissociation phases were monitored for 5 min each (receptors I and IV) or 1 min (receptors II and III). Chip surfaces were regenerated with a 5 s pulse of 100 mM HCl at a flow rate of 100 ul/min after each binding cycle. Biacore Evaluation software was used to fit the raw data to 1:1 (FcgRI and IV) or Steady State (receptors IIB and III) binding models. Results are shown in Table 19. $k_a$ is the association rate constant (1/Ms); $k_d$ is the dissociation rate constant (1/s); $K_D$ is the equilibrium dissociation constant (M).

TABLE 19

Binding affinities of anti-TNF-alpha immunoconjugate to mouse Fcgamma receptors

|  | muFcgRI | | | muFcgRIIb | muFcgRIII | muFcgRIV | | |
|---|---|---|---|---|---|---|---|---|
|  | $k_a$ (1/Ms) | $k_d$ (1/s) | $K_D$ (M) | $K_D$ (M) | $K_D$ (M) | $k_a$ (1/Ms) | $k_d$ (1/s) | $K_D$ (M) |
| Anti-mTNF mAb | 7.4E+05 | 1.6E−02 | 2.1E−08 | 3.7E−06 | 3.1E−06 | 1.2E+05 | 5.3E−03 | 4.6E−08 |
| Anti-mTNF ADC | 3.2E+05 | 8.7E−03 | 2.8E−08 | 5.9E−06 | 3.3E−06 | 8.4E+04 | 4.6E−03 | 5.5E−08 |

Example 84: Activity of Anti mTNF-Alpha Steroid ADCs in Contact Hypersensitivity Model Anti-mTNF alpha steroid ADCs were evaluated in an acute contact hypersensitivity model, an elicitation of acute skin inflammation using delayed-type hypersensitivity (DTH) response (T-cell driven) via application of a sensitizing agent (fluorescein isothiocyanate (FITC)). The efficacy of anti-mTNF alpha steroid ADCs was measured by the ability to reduce ear swelling. The steroid biomarkers corticosterone and procollagen type 1 N-terminal propeptide (P1NP) were included as readouts to assess the putative impact of anti-mTNF alpha steroid ADC treatment on the Hypothalamus-Pituitary-Adrenal (HPA) axis and bone turnover respectively.

Ear Swelling

On day 0 mice were placed under general anesthesia and the abdomens were shaved. Using a micropipettor, mice were sensitized by epicutaneous applicaton of 400 uL of FITC solution (1.5% solution in 1:1 acetone:DBP) on the abdomen. 6 days later mice were dosed with vehicle or therapeutic agent 1 hour prior to ear challenge with FITC. For ear challenge, mice were placed under general anesthesia and were challenged with 20 µl FITC applied onto right ear. 24 hours after challenge mice were placed under general anesthesia and their ear thickness is measured by caliper. Difference between challenged and unchallenged ears was calculated. 72 hours after ear challenge, mice were injected with ACTH at 1mpk IP, and terminally bled at 30 min post-ACTH. Plasma is collected and analyzed P1NP, corticosterone, free steroid, and large molecule levels.

Quantification of Released Free Steroid and Endogenous Corticosterone

Calibration curve of steroid was prepared in mouse plasma with final concentrations from 0.03 nM to 0.1 µM at 8 different concentration levels. Corticosterone calibration curve ranging from 0.3 nM to 1 µM final corticosterone concentrations was prepared in 70 mg/mL bovine serum albumin solution in PBS buffer. A solution of 160 µL MeCN with 0.1% formic acid was added to 40 µL study plasma samples or calibration standards. Supernatants were diluted with distilled water and 30 µL final sample solution was injected for LC/MS analysis.

Quantification of released free steroid and corticosterone was conducted on an AB Sciex 5500 triple quadruple mass spectrometer connected to a Shimadzu AC20 HPLC system interfaced with an electrospray ionization source operating in positive mode. A Waters XBridge BEH C18, 2.1×30 mm, 3.5 µm column was used for chromatography separation. The mobile phase A was 0.1% formic acid in Milli Q HPLC water, and mobile phase B was 0.1% formic acid in MeCN. A linear gradient from 2% of mobile phase B to 98% mobile phase B was applied from 0.6 to 1.2 minutes. The total run time was 2.6 min at a flow rate of 0.8 mL/min. The mass spectrometer was operated in positive MRM mode at source temperature of 700° C.

Quantification of Plasma P1NP

Quantification of plasma P1NP was conducted on a LC/MS platform based on protein trypsin digestion. Plasma samples were partially precipitated and fully reduced by adding MeCN/0.1M ammonium bicarbonate/DTT mixture. Supernatant was collected and alkylated by adding iodoacetic acid. The alkylated proteins were digested by trypsin and resulting tryptic peptides were analyzed by LC/MS. Calibration curve were generated by using synthetic tryptic peptide spiked into horse serum (non-interfering surrogate matrix). Stable isotope labeled flanking peptide (3-6 amino acids extension on both termini of the tryptic peptide) was used as internal standard added in the MeCN/DTT protein precipitation mixture to normalize both digestion efficiency and LC/MS injection.

A Columnex Chromenta BB-C18, 2.1×150 mm, 5 µm column was used for chromatography separation. The mobile phase A was 0.1% formic acid in Milli Q HPLC water and mobile phase B was 0.1% formic acid in MeCN. A linear gradient from 2% of mobile phase B to 65% mobile phase B was applied from 0.6 to 3 min. The total run time was 8 min at a flow rate of 0.45 mL/min. An AB Sciex 4000Qtrap mass spectrometer was used in positive MRM mode to quantify P1NP peptides, at source temperature of 700° C.

Quantification of Total ADC in Plasma

Concentrations of total antibody (ADC and backbone mAb) were measured byligand binding assay using Mesoscale Discovery (MSD) platform. Biotin labeled mouse TNF was used as the capture reagent for anti-mTNF alpha steroid ADCs and Sulfo-TAG conjugated goat anti-mouse detection antibody was used for detection. A calibration curve was generated by serial dilution of the ADC molecule in matching matrix and QC samples were used to qualify the assay Results The results are shown in Table 20 below:

TABLE 20

Comparison of anti-mTNF alpha steroid ADC activity on ear swelling and steroid biomarkers in CHS model of inflammation

| ADC | Ear swelling (% inhib @ 10 mpk) | SEM | P1NP (% inhib. @ 10 mpk) | SEM | Corticosterone (% inhib @ 10 mpk) | SEM |
| --- | --- | --- | --- | --- | --- | --- |
| Cpd. No. 151 | 87.8 | 3.5 | 32.3 | 3.9 | 71.5 | 5.6 |
| Cpd. No. 145 | 87.8 | 3.4 | 19.2 | 6.3 | 15.1 | 9.9 |
| Cpd. No. 169 | 90.2 | 2.2 | 38.3 | 2.8 | 60.1 | 4.7 |
| Cpd. No. 167 | 86.1 | 2.4 | 26.1 | 6.9 | 48.3 | 5.1 |
| Cpd. No. 162 | 76.3 | 2.7 | 25.9 | 6.5 | 50.4 | 5.5 |
| Cpd. No. 161 | 64.4 | 4.6 | 1.4 | 7.2 | 37.1 | 4.1 |
| Cpd. No. 172 | 79.8 | 3.9 | 14.6 | 4.9 | 6.3 | 6.8 |
| Cpd. No. 176 | 81.4 | 3.9 | 20.0 | 7.9 | 15.0 | 9.4 |
| Cpd. No. 177 | 94.3 | 1.2 | 27.0 | 6.0 | 17.1 | 9.0 |
| Cpd. No. 180 | 80.8 | 2.1 | 45.7 | 6.0 | 39.9 | 3.8 |
| Cpd. No. 149 | 92.4 | 2.3 | 52.8 | 2.8 | 74.4 | 3.7 |
| Cpd. No. 175 | 66.5 | 4.7 | 12.1 | 4.5 | 49.3 | 3.5 |
| Cpd. No. 207 | 87.3 | 3.6 | 44.0 | 5.4 | 54.6 | 5.2 |
| Cpd. No. 178 | 94.4 | 1.8 | 58.0 | 2.4 | 73.8 | 4.7 |
| Cpd. No. 181 | 78.8 | 4.6 | −13.2 | 7.2 | 29.4 | 8.0 |
| Cpd. No. 182 | 60.1 | 5.6 | −15.1 | 11.5 | 3.4 | 4.8 |
| Cpd. No. 185 | 85.0 | 4.0 | 51.6 | 7.0 | 43.9 | 9.6 |
| Cpd. No. 186 | 70.5 | 3.9 | 1.5 | 9.4 | 19.1 | 3.9 |

These results demonstrate that anti-mTNF alpha steroid ADCs can obtain an efficacious response equivalent to small molecule steroid treatment while sparing the undesired effects on corticosterone and P1NP.

An additional contact hypersensitivity (CHS) study was conducted to address whether conjugation of the steroid payload to anti-TNF mAb was required for enhanced efficacy. Mice were dosed i.p. once according to the protocol described above with either vehicle, anti-mTNF alpha mAb (10mpk), anti-mTNF alpha steroid ADC (10mpk) (cpd no 139) or a mixture of anti-mTNF alpha mAb co-dosed (concurrently delivered in a single i.p. injection) with an equivalent amount of small molecule steroid to match the ADC stoichiometry. For a 10mpk dose of anti-mTNF alpha steroid ADC with a DAR of 4, this was calculated to be 4 μg of small molecule steroid (Cpd. No. 42). The results shown in FIG. 9 demonstrate that anti-mTNF alpha steroid ADC treatment had significantly increased efficacy in reducing ear inflammation when compared to the combination of anti-mTNF alpha mAb and small molecule steroid or anti-mTNF alpha mAb alone.

Example 85: Activity of Anti-mTNF-Alpha Steroid ADCs in Collagen-Induced Arthritis The ability of anti-mTNF alpha steroid ADC (Cpd. No. 137) to impact disease was assessed in the collagen-induced arthritis (CIA) model of arthritis.

In these experiments, male DBA/1J mice were obtained from Jackson Labs (Bar Harbor, Me.). Mice were used at 6 to 12 weeks of age. All animals were maintained at constant temperature and humidity under a 12-hour light/dark cycle and fed with rodent chow (Lab Diet 5010 PharmaServ, Framingham, Mass.) and water ad libitum. AbbVie is AAALAC (Association for Assessment and Accreditation of Laboratory Animal Care) accredited, and all procedures were approved by the Institutional Animal Care and Use Committee (IACUC) and monitored by an attending veterinarian. Body weight and condition were monitored, and animals were euthanized if exhibiting >20% weight loss.

The male DBA/J mice were immunized intradermally (i.d.) at the base of the tail with 100 μL of emulsion containing 100 gig of type II bovine collagen (MD Biosciences) dissolved in 0.1 N acetic acid and 200 μg of heat-inactivated *Mycobacterium tuberculosis* H37Ra (Complete Freund's Adjuvant, Difco, Laurence, Kans.). Twenty-one days after immunization with collagen, mice were boosted IP with 1 mg of Zymosan A (Sigma, St. Louis, Mo.) in PBS. Following the boost, mice were monitored 3 to 5 times per week for arthritis. Rear paws were evaluated for paw swelling using Dyer spring calipers (Dyer 310-115)

Mice were enrolled between days 24 and 28 at the first clinical signs of disease and distributed into groups of equivalent arthritic severity. Early therapeutic treatment began at the time of enrollment.

Animals were dosed once orally (p.o.) with steroid (Cpd. No. 3) (10mpk) in a 0.5% HPMC/0.02% Tween80 vehicle [v/] or intraperitoneal (i.p.) with anti-mTNF alpha mAb (10mpk) (8C11) or anti-mTNF alpha steroid ADC (10mpk) (Cpd. No. 137) in 0.9% saline. Blood was collected for antibody exposure by tail nick at 24 and 72 hours after dose. Paws were collected at the terminal timepoint for histopathology. Blood was collected at the terminal timepoint by cardiac puncture for complete blood counts (Sysmex XT-2000iV). Statistical significance was determined by ANOVA.

Figure 3:
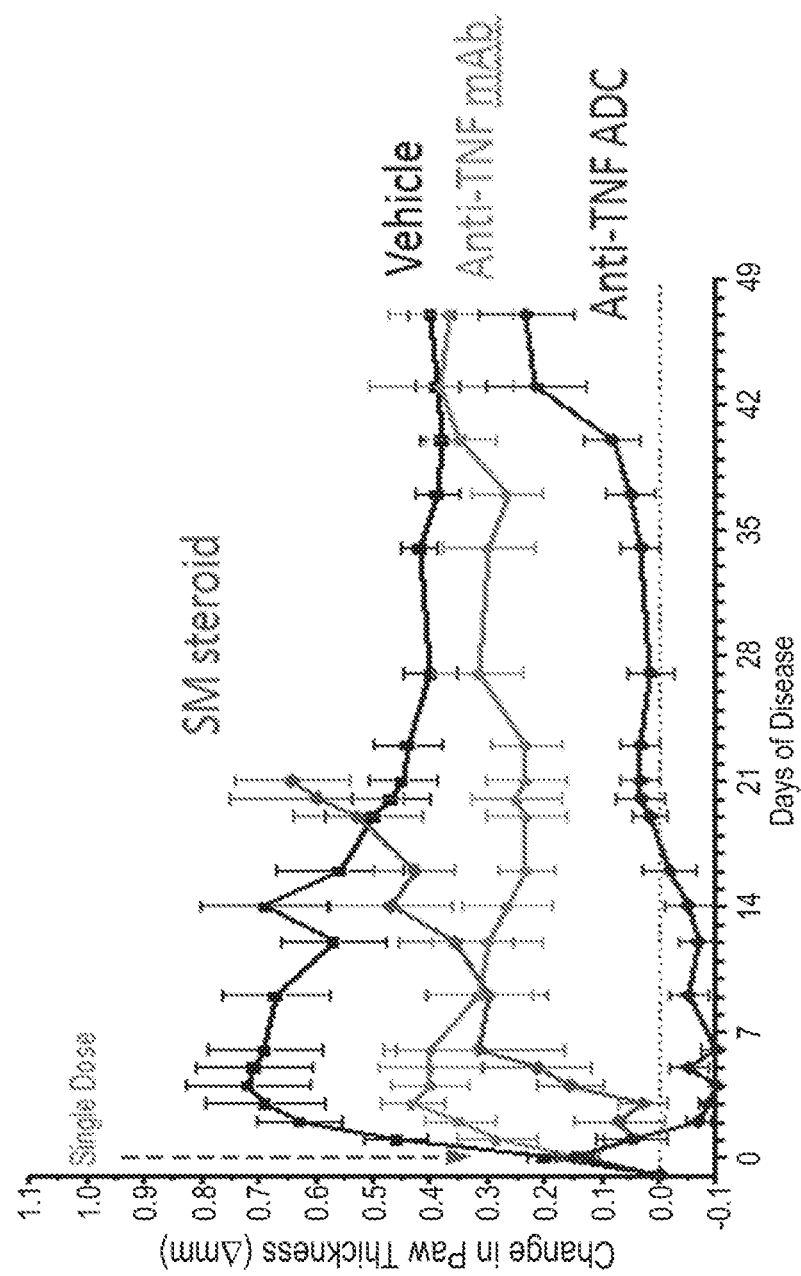
FIG. 3 shows the activity of a single therapeutic dose response of anti-mTNFa steroid ADC in a mouse model of arthritis. (See Example 85.)

The results are shown in FIG. 3 and demonstrate that a single dose of anti-mTNF alpha steroid ADC can exhibit an extended duration of action through amelioration of paw swelling for ~6 weeks compared to anti-mTNF alpha mAb or small molecule steroid alone.

In a separate study designed to address the TNF-targeting functionality of the anti-mTNF alpha steroid ADC, animals were dosed once i.p. with anti-mTNF alpha mAb (10mpk) or anti-mTNF alpha steroid ADC (10mpk) (Cpd. No. 145) or with isotype steroid ADC (10mpk) (Cpd. No. 224):

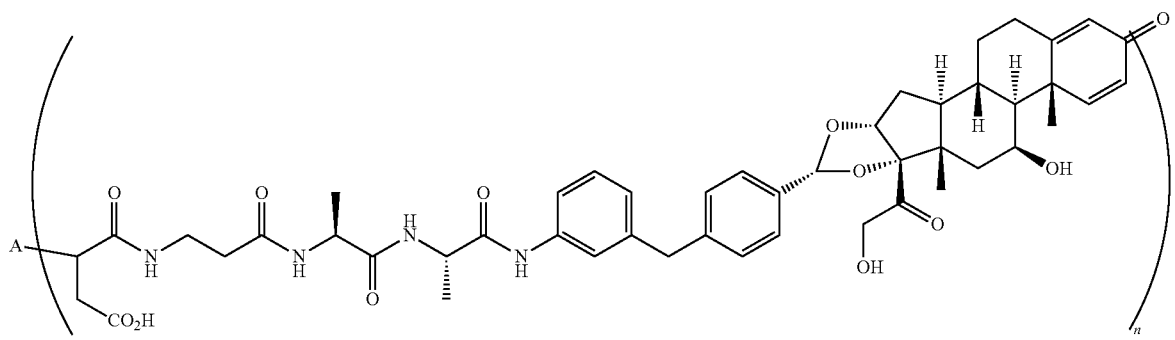

A = Anti-OVAL (Gallus gallus)

which recognizes the hen egg protein ovalbumin, an antigen not expressed in mice. Both ADCs had equivalent drug load. Small molecule steroid (3mpk) was dosed orally once daily (q.d). The results are shown in FIG. 10 and demonstrate that a single dose of anti-mTNF alpha steroid ADC has equivalent efficacy to small molecule steroid dosed daily over a 21 day period. A single dose of the non-targeted isotype steroid ADC had only partial efficacy, similar to anti-mTNF mAb alone over the same time-frame. Percentages denote % inhibition compared to vehicle. An evaluation of the animals' body weights throughout the course of this study (FIG. 11) revealed all the treatment groups with the exception of the anti-mTNF alpha steroid ADC group lost weight. In contrast, the anti-mTNF alpha steroid ADC treated mice exhibited normal weight gain throughout the 21 day study.

Example 86: Activity of Various Anti-mTNF Alpha Steroid ADCs in Collagen-Induced Arthritis Several anti-mTNF alpha steroid ADCs with different steroid payloads or drug:antibody ratios (DARs) were tested for efficacy in a mouse model of arthritis. The studies were conducted according to the procedure outlined in Example 85. The results are shown in Table 21 below.

TABLE 21

Efficay of anti-mTNF alpha steroid ADCs in model of arthritis

| Cpd No. | DAR (n) | % inhibition of paw swelling vs vehicle ($AUC_{0-21\ d}$) (at 10 mpk) | SEM |
|---|---|---|---|
| 136 | 2 | 75 | 3.7 |
| 137 | 4 | 91 | 6.5 |
| 139 | 4 | 93 | 2.9 |
| 143 | 2 | 96 | 3.3 |
| 145 | 4 | 95 | 4 |
| 151 | 4 | 101 | 2.5 |
| 172 | 4 | 74 | 9.3 |
| 176 | 4 | 85 | 8.3 |
| 177 | 4 | 99 | 4.2 |

Example 87: Activity of Anti-hTNF-Alpha Immunoconjugates in Human TNF Transgenic Tg1278TNF Knock-Out Mouse Model of Collagen Antibody Induced Arthritis The efficacy of anti-human TNF alpha ADCs was assessed in a human TNFα transgenic mouse model of arthritis.

The Collagen Antibody-Induced Arthritis (CAIA) model (Moore, A R *J Transl Med* 12:285 (2014)) was performed using the human TNF transgenic Tg1278TNF knock-out mice as previously described (Moore A et al. *J Transl Med* 12 (1): 285 (2014)). Eight mgs of a cocktail of monoclonal antibodies that target different epitopes of collagen type II (ArthritoMab™) were administered intraperitoneally (i.p.) to the mice on day 0. On day 3, the mice were injected i.p. with 10 µg LPS to boost the disease pathology. Animals were evaluated for arthritic score daily starting from day 3 until day 14 of the study. Eight male mice were used per group and test articles or PBS vehicle were administered i.p. twice a week for two weeks.

Figure 4:
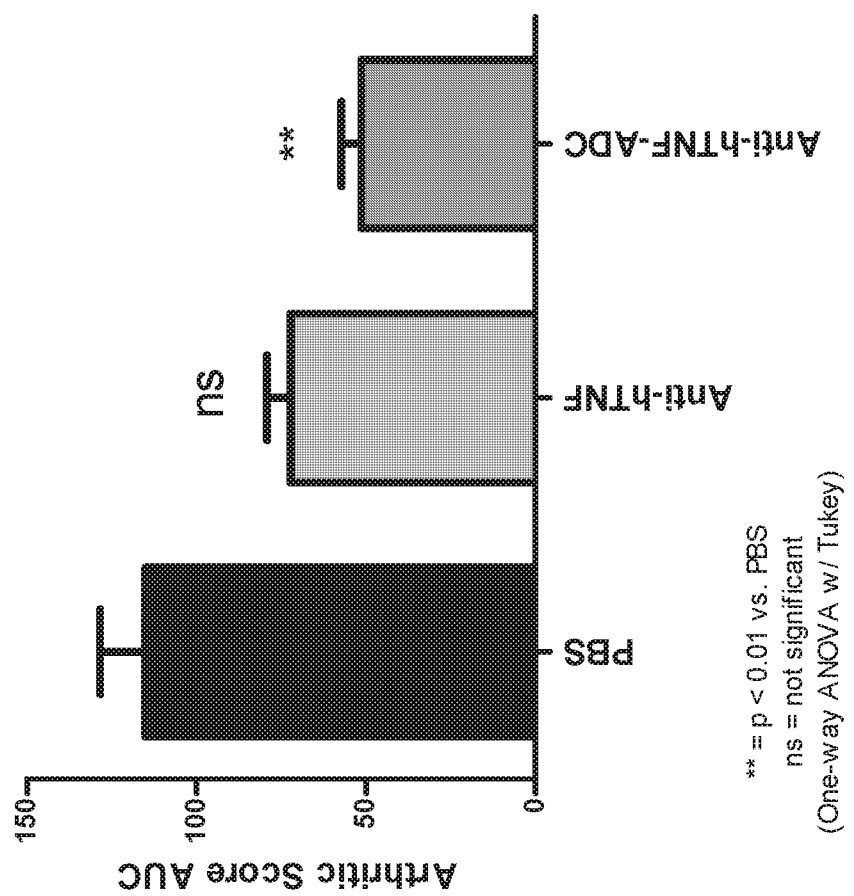
FIG. 4 shows the activity of anti-human TNFa steroid in huTNFa Tg CAIA mouse model of arthritis. (See Example 87.)

The results are shown in FIG. 4 and demonstrate that anti-human TNF alpha ADCs can significantly reduce disease score compared to an anti-human TNF alpha mAb (adalimumab).

Example 88: Activity of Anti-mTNF Alpha Steroid ADCs on Peak Inflammation

A mouse CIA experiment was conducted to establish the efficacy of anti-mTNF alpha steroid ADC on animals with peak inflammation. For late therapeutic dosing, mice were enrolled in the study at first clinical signs of disease and dosed 6 days after enrollment. A group of animals was sacrificed at day 7 of disease to provide a baseline for arthritic changes by micro-computed tomography (µCT) and histologic analysis at the time all other groups were dosed. All animals were dosed once on day 6 with either vehicle (0.9% saline), anti-mTNF alpha mAb (10mpk) (8C11) or anti-mTNF alpha steroid ADC (10mpk) (Cpd. No. 145) and sacrificed on day 21. Arthritic hind paws were collected and µCT analysis was performed. The same paws were then used for histologic evaluation. At the termination of the experiment, whole blood was collected by cardiac puncture to evaluate complete blood counts (CBCs).

Micro-Computed Tomography (µCT)

Rear paws were removed intact at the tibia/fibula and fixed in 10% Formalin. Paws were scanned by µCT (Scanco Medical AG, Micro-CT40) at 55 kVp at 145 µA at High Resolution setting (1000 Projections/180° at 2048×2048 Pixel Reconstruction) using Isotropic Voxels and 300 millisecond integration time. A cylindrical contour was manually drawn around region of interest from the tibiotalar junction and extending into the ankle for 100 slices (1.8 mm). Evaluation was performed by Scanco software utilizing 0.8 sigma gauss, with an upper threshold of 1000 and a lower threshold of 320.

Histologic Evaluation

Rear paws from treated mice were immersion fixed in 10% neutral buffered formalin and partially decalcified in Calrite solution for 48 hours to allow trimming of the lateral and medial edges of the tarsus. Paws were then placed back into Calrite for −48 hours to complete decalcification. Samples were routinely processed, embedded in paraffin in the sagittal plane, sectioned at 5 microns and stained with hematoxylin and eosin. Slides were evaluated microscopically for the presence of inflammation/pannus formation, neutrophil infiltration, bone erosion and cartilage damage using a 0-4 scale: 0=none present, 1=mild, 2=moderate, 3=marked, 4=severe.

The results shown in FIG. 12 demonstrate that a single dose of anti-mTNF alpha steroid ADC can reverse established disease and reduce paw swelling to near baseline. In contrast, a single dose of anti-mTNF alpha mAb had a minimal effect on inflammation.

The effect of treatment on tarsal bone loss as measured by μCT is shown in FIG. 13. The results demonstrate that a single dose of anti-mTNF alpha steroid ADC administered at peak of inflammation is able to significantly inhibit disease-mediated joint bone erosion compared to anti-mTNF alpha mAb alone.

The results of histological evaluation of the joints of treated CIA mice are shown in FIGS. 14-17. They demonstrate that a single dose of anti-mTNF alpha steroid ADC administered at peak disease resulted in a significant decrease in inflammation, pannus formation, bone erosion and cartilage damage by day 21 relative to age-matched vehicle controls (p<0.001), and levels of disease were equivalent to the levels observed in controls at baseline (vehicle d6). In two of six paws evaluated, no disease was detectable in the tarsus/phalangeal joints of anti-mTNF alpha steroid ADC treated animals at day 21, as compared to 100% incidence in mice at day 6 baseline (prior to treatment) and day 21 vehicle treated mice.

In contrast, a single dose of anti-mTNF alpha mAb at peak disease did not inhibit inflammation, bone erosion, pannus formation, or cartilage destruction, relative to age-matched vehicle controls at d21. Levels of disease were more severe than baseline controls, and a mild trend for improved inflammation was observed.

Whole blood was analyzed to evaluate changes in peripheral blood cell subsets with treatment. The results shown in FIG. 18-23 demonstrate that the increase in some peripheral blood cell populations observed in diseased animals can be resolved with a single dose of anti-mTNF alpha steroid ADC. Statistically significant reductions in overall white blood cells, neutrophils and monocytes were observed with anti-mTNF alpha steroid ADC treatment.

Example 89: Comparison of Anti-mTNF-Alpha Steroid ADCs and Anti-CD163 ADCs

To demonstrate the enhanced therapeutic efficacy of an anti-TNF immunoconjugate in the treatment of inflammatory disease, we compared its activity to an ADC targeting the hemoglobin scavenger receptor CD163, a glucocorticoid immunoconjugate approach described in the literature to have targeted anti-inflammatory functionality (PCT Int. Appl. WO2011039510A2 by Graversen NJH, et al.; Graversen J H et al., *Mol. Ther.* 20 (8): 1550-8 (2012)).

Generation of a Mouse CD163 GRE Report Cell Line

A parental cell line was created similar to that described in Example 78 but with CHO-K1 cells instead of K562 cells. The resulting parental cell line CHO pGL4.36[Luc2P/MMTV/Hygro]_PGL4.75[hRLuc/CMV] was then transfected with a plasmid which encodes mouse CD163 (Origene cat. no. MR216798) under conditions described in Example 78. The resulting cell line CHO mCD163 GRE (pGL4.36[luc2P/MMTV/Hygro]) was used to test the in vitro activity of both anti-mTNF-alpha and anti-mouse CD163 immunoconjugates (also referred to as anti-mCD 163 immunoconjugates or anti-mCD 163 steroid ADC).

Preparation of an Anti-Mouse CD163 Immunoconjugate

A chimeric rat anti-mouse CD163 mIgG2a/k antibody was generated from the VH and VL sequence for clone 3E10B10 as described (SEQ ID NO: 87/88 from PCT Int. Appl. WO 2011/039510A$^2$). This antibody was conjugated to Cpd. No. 99 using conditions highlighted under the general cysteine conjugation protocol in Example 36 to give a drug:antibody ratio (DAR) of 4.

Activity of an Anti-Mouse CD163 Immunoconjugate in Mouse CD163 GRE Reporter Assay The anti-mouse CD163 immunoconjugate was tested for activity on the CHO mCD163 GRE (pGL4.36[luc2P/MMTV/Hygro]) cell line under conditions described in Example 79. An anti-mTNF alpha steroid ADC (Cpd. No. 145) was included as a negative control. The results in Table 22 demonstrate the anti-mouse CD163 immunoconjugate (Cpd. No. 223):

Cpd. No. 223

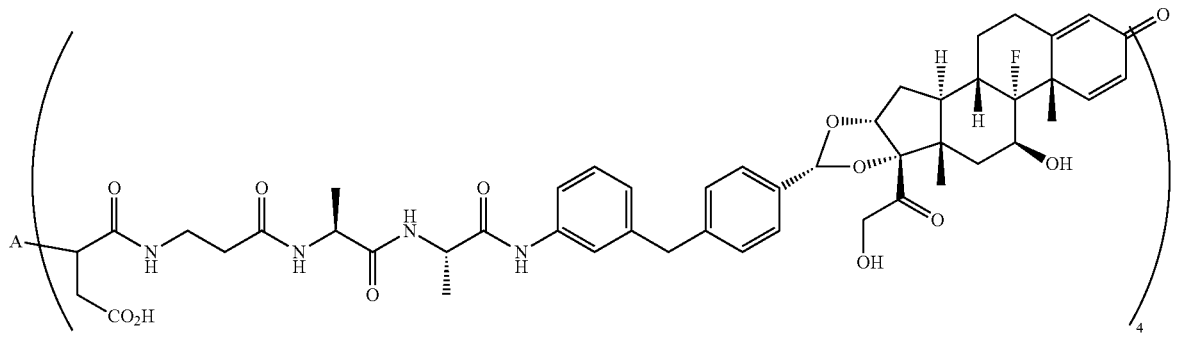

A = anti-CD163 shows antigen-dependent activity dissociated from the anti-mTNF alpha steroid ADC on the mouse CD163 GRE cell line.

TABLE 22

| Cpd No. | DAR | % monomer | mCD163 GRE EC50 (ug/ml) | mCD163 GRE (% max) | CHO GRE EC50 (ug/ml) | CHO GRE (% max) |
|---|---|---|---|---|---|---|
| 223 | 4 | 93 | 0.2 | 92 | >50 | 55 |
| 145 | 4 | 97 | >20 | 70 | >50 | 39 |

Activity of Anti-Mouse CD163 Immunoconjugate in Mouse Collagen-Induced Arthritis The ability of anti-mouse CD163 steroid immunoconjugate to impact paw swelling was assessed in the collagen-induced arthritis (CIA) model of RA. A control anti-mTNF alpha steroid ADC (cpd 139) with the same drug-linker and DAR as the anti-mCD163 steroid ADC was also evaluated in the same study and the parental mAbs for both ADCs were also included as treatment groups. The experiment was conducted according to the procedure outlined in Example 85. The results are shown in FIG. 24 and demonstrate that while the anti-mCD 163 steroid ADC initially reduces paw swelling in the first few days after single dose treatment, this effect is transient. In comparison, a single dose of anti-mTNF alpha steroid ADC is sufficient to completely suppress inflammation through the duration of the study It is to be appreciated that the Detailed Description section, and not the Summary and Abstract sections, is intended to be used to interpret the claims. The Summary and Abstract sections sets forth one or more, but not all, exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A compound of the formula

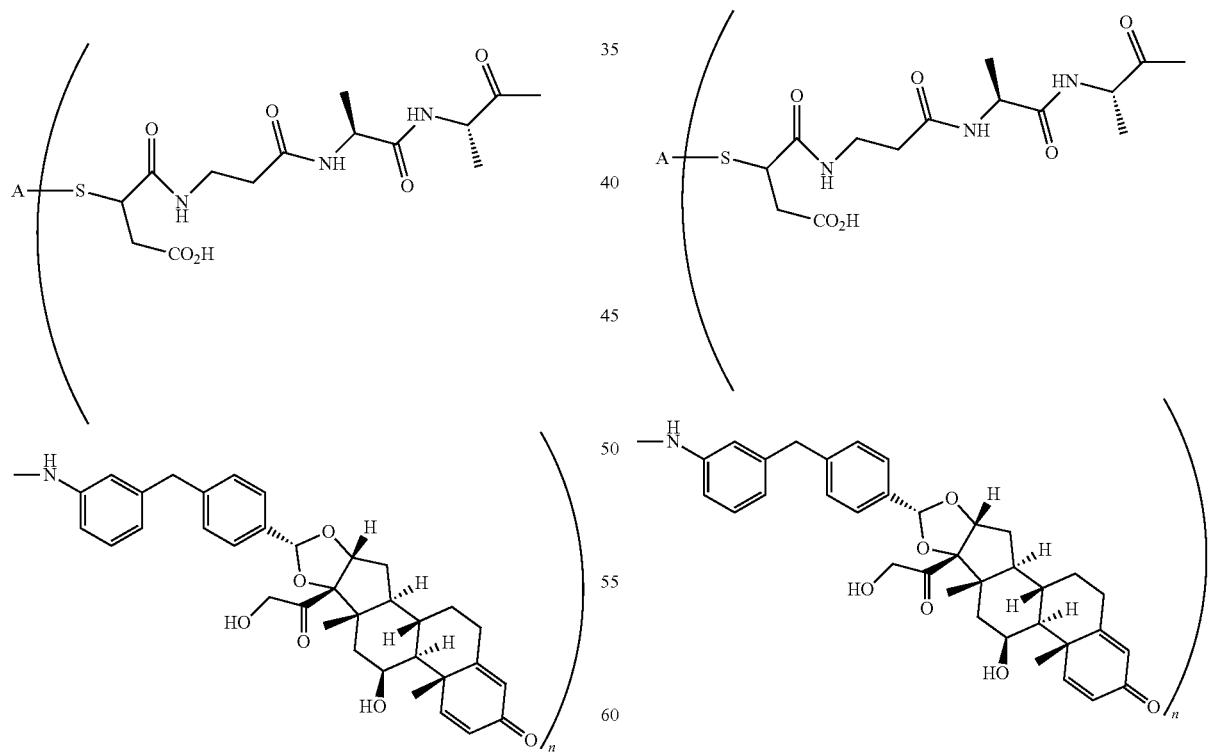

wherein n is 4, and A is an IgG1 antibody comprising a heavy chain comprising the amino acid sequence of SEQ ID NO: 66 and a light chain comprising the amino acid sequence of SEQ ID NO:73.

2. A compound of the formula wherein n is 2, and A is an IgG1 antibody comprising a heavy chain comprising the amino acid sequence of SEQ ID NO: 66 and a light chain comprising the amino acid sequence of SEQ ID NO:73.

807
3. A compound of the formula
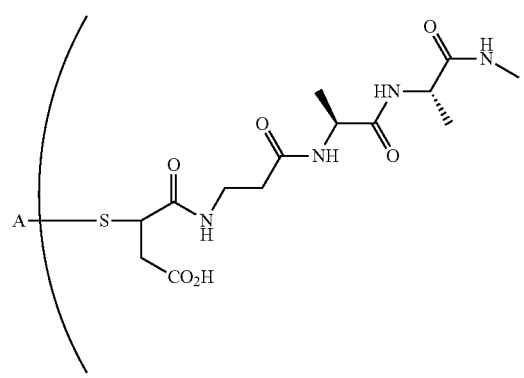
wherein n is 4, and A is adalimumab.
808
4. A compound of the formula
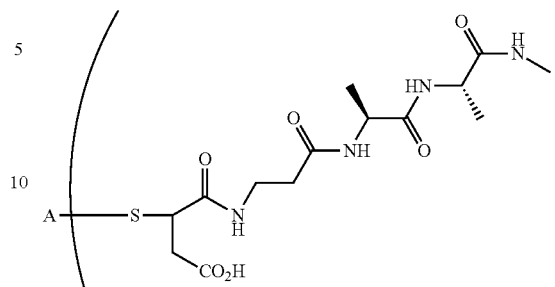
wherein n is 2, and A is adalimumab.
* * * * *

SEQUENCE LISTING

```
<160> NUMBER OF SEQ ID NOS: 94

<210> SEQ ID NO 1
<211> LENGTH: 233
<212> TYPE: PRT
<213> ORGANISM: homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
```

```
                145                 150                 155                 160
Val Ser Tyr Gln Thr Lys Val Asn Leu Leu Ser Ala Ile Lys Ser Pro
                    165                 170                 175

Cys Gln Arg Glu Thr Pro Glu Gly Ala Glu Ala Lys Pro Trp Tyr Glu
                    180                 185                 190

Pro Ile Tyr Leu Gly Gly Val Phe Gln Leu Glu Lys Gly Asp Arg Leu
                    195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230

<210> SEQ ID NO 2
<211> LENGTH: 235
<212> TYPE: PRT
<213> ORGANISM: murine

<400> SEQUENCE: 2

Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
                20                  25                  30

Leu Ser Leu Phe Ser Phe Leu Leu Val Ala Gly Ala Thr Thr Leu Phe
            35                  40                  45

Cys Leu Leu Asn Phe Gly Val Ile Gly Pro Gln Arg Asp Glu Lys Phe
        50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
                100                 105                 110

Asn Ala Leu Leu Ala Asn Gly Met Asp Leu Lys Asp Asn Gln Leu Val
            115                 120                 125

Val Pro Ala Asp Gly Leu Tyr Leu Val Tyr Ser Gln Val Leu Phe Lys
        130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
                180                 185                 190

Tyr Glu Pro Ile Tyr Leu Gly Gly Val Phe Gln Leu Glu Lys Gly Asp
                195                 200                 205

Gln Leu Ser Ala Glu Val Asn Leu Pro Lys Tyr Leu Asp Phe Ala Glu
            210                 215                 220

Ser Gly Gln Val Tyr Phe Gly Val Ile Ala Leu
225                 230                 235

<210> SEQ ID NO 3
<211> LENGTH: 5
<212> TYPE: PRT
<213> ORGANISM: artificial sequence
<220> FEATURE:
<223> OTHER INFORMATION: adalimumab VH-CDR1

<400> SEQUENCE: 3
```

```
Asp Tyr Ala Met His
1               5

<210> SEQ ID NO 4
<211> LENGTH: 17
<212> TYPE: PRT
<213> ORGANISM: artificial sequence
<220> FEATURE:
<223> OTHER INFORMATION: adalimumab VH-CDR2

<400> SEQUENCE: 4

Ala Ile Thr Trp Asn Ser Gly His Ile Asp Tyr Ala Asp Ser Val Glu
1               5                   10                  15

Gly

<210> SEQ ID NO 5
<211> LENGTH: 9
<212> TYPE: PRT
<213> ORGANISM: artificial sequence
<220> FEATURE:
<223> OTHER INFORMATION: adalimumab VH-CDR3

<400> SEQUENCE: 5

Val Ser Tyr Leu Ser Thr Ala Ser Ser
1               5

<210> SEQ ID NO 6
<211> LENGTH: 10
<212> TYPE: PRT
<213> ORGANISM: artificial sequence
<220> FEATURE:
<223> OTHER INFORMATION: adalimumab VH-CDR1

<400> SEQUENCE: 6

Gly Phe Thr Phe Asp Asp Tyr Ala Met His
1               5                   10

<210> SEQ ID NO 7
<211> LENGTH: 10
<212> TYPE: PRT
<213> ORGANISM: artificial sequence
<220> FEATURE:
<223> OTHER INFORMATION: infliximab VH-CDR1

<400> SEQUENCE: 7

Gly Phe Ile Phe Ser Asn His Trp Met Asn
1               5                   10

<210> SEQ ID NO 8
<211> LENGTH: 19
<212> TYPE: PRT
<213> ORGANISM: artificial sequence
<220> FEATURE:
<223> OTHER INFORMATION: infliximab VH-CDR2

<400> SEQUENCE: 8

Glu Ile Arg Ser Lys Ser Ile Asn Ser Ala Thr His Tyr Ala Glu Ser
1               5                   10                  15

Val Lys Gly

<210> SEQ ID NO 9
<211> LENGTH: 9
<212> TYPE: PRT
<213> ORGANISM: artificial sequence
<220> FEATURE:
```

```
<223> OTHER INFORMATION: infliximab VH-CDR3

<400> SEQUENCE: 9

Asn Tyr Tyr Gly Ser Thr Tyr Asp Tyr
1               5

<210> SEQ ID NO 10
<211> LENGTH: 5
<212> TYPE: PRT
<213> ORGANISM: artificial sequence
<220> FEATURE:
<223> OTHER INFORMATION: certolizumab VH-CDR1

<400> SEQUENCE: 10

Asp Tyr Gly Met Asn
1               5

<210> SEQ ID NO 11
<211> LENGTH: 17
<212> TYPE: PRT
<213> ORGANISM: artificial sequence
<220> FEATURE:
<223> OTHER INFORMATION: certolizumab VH-CDR2

<400> SEQUENCE: 11

Trp Ile Asn Thr Tyr Ile Gly Glu Pro Ile Tyr Ala Asp Ser Val Lys
1               5                   10                  15

Gly

<210> SEQ ID NO 12
<211> LENGTH: 9
<212> TYPE: PRT
<213> ORGANISM: artificial sequence
<220> FEATURE:
<223> OTHER INFORMATION: certolizumab VH-CDR3

<400> SEQUENCE: 12

Gly Tyr Arg Ser Tyr Ala Met Asp Tyr
1               5

<210> SEQ ID NO 13
<211> LENGTH: 10
<212> TYPE: PRT
<213> ORGANISM: artificial sequence
<220> FEATURE:
<223> OTHER INFORMATION: certolizumab VH-CDR1

<400> SEQUENCE: 13

Gly Tyr Val Phe Thr Asp Tyr Gly Met Asn
1               5                   10

<210> SEQ ID NO 14
<211> LENGTH: 5
<212> TYPE: PRT
<213> ORGANISM: artificial sequence
<220> FEATURE:
<223> OTHER INFORMATION: afelimomab VH-CDR1

<400> SEQUENCE: 14

Asp Tyr Gly Val Asn
1               5

<210> SEQ ID NO 15
<211> LENGTH: 16
<212> TYPE: PRT
<213> ORGANISM: artificial sequence
```

```
<220> FEATURE:
<223> OTHER INFORMATION: afelimomab VH-CDR2

<400> SEQUENCE: 15

Met Ile Trp Gly Asp Gly Ser Thr Asp Tyr Asp Ser Thr Leu Lys Ser
1               5                   10                  15

<210> SEQ ID NO 16
<211> LENGTH: 9
<212> TYPE: PRT
<213> ORGANISM: artificial sequence
<220> FEATURE:
<223> OTHER INFORMATION: afelimomab VH-CDR3

<400> SEQUENCE: 16

Glu Trp His His Gly Pro Val Ala Tyr
1               5

<210> SEQ ID NO 17
<211> LENGTH: 5
<212> TYPE: PRT
<213> ORGANISM: artificial sequence
<220> FEATURE:
<223> OTHER INFORMATION: nerelimomab VH-CDR1

<400> SEQUENCE: 17

Asp Tyr Asn Val Asp
1               5

<210> SEQ ID NO 18
<211> LENGTH: 17
<212> TYPE: PRT
<213> ORGANISM: artificial sequence
<220> FEATURE:
<223> OTHER INFORMATION: nerelimomab VH-CDR2

<400> SEQUENCE: 18

Asn Ile Asn Pro Asn Asn Gly Gly Thr Ile Tyr Asn Gln Lys Phe Lys
1               5                   10                  15

Gly

<210> SEQ ID NO 19
<211> LENGTH: 12
<212> TYPE: PRT
<213> ORGANISM: artificial sequence
<220> FEATURE:
<223> OTHER INFORMATION: nerelimomab VH-CDR3

<400> SEQUENCE: 19

Ser Ala Phe Tyr Asn Asn Tyr Glu Tyr Phe Asp Val
1               5                   10

<210> SEQ ID NO 20
<211> LENGTH: 5
<212> TYPE: PRT
<213> ORGANISM: artificial sequence
<220> FEATURE:
<223> OTHER INFORMATION: ozoralizumab VH-CDR1

<400> SEQUENCE: 20

Asp Tyr Trp Met Tyr
1               5

<210> SEQ ID NO 21
<211> LENGTH: 17
<212> TYPE: PRT
```

```
<213> ORGANISM: artificial sequence
<220> FEATURE:
<223> OTHER INFORMATION: ozoralizumab VH-CDR2

<400> SEQUENCE: 21

Glu Ile Asn Thr Asn Gly Leu Ile Thr Lys Tyr Pro Asp Ser Val Lys
1               5                   10                  15
Gly

<210> SEQ ID NO 22
<211> LENGTH: 7
<212> TYPE: PRT
<213> ORGANISM: artificial sequence
<220> FEATURE:
<223> OTHER INFORMATION: ozoralizumab VH-CDR3

<400> SEQUENCE: 22

Ser Pro Ser Gly Phe Asn Arg
1               5

<210> SEQ ID NO 23
<211> LENGTH: 5
<212> TYPE: PRT
<213> ORGANISM: artificial sequence
<220> FEATURE:
<223> OTHER INFORMATION: ozoralizumab VH-CDR1

<400> SEQUENCE: 23

Ser Phe Gly Met Ser
1               5

<210> SEQ ID NO 24
<211> LENGTH: 17
<212> TYPE: PRT
<213> ORGANISM: artificial sequence
<220> FEATURE:
<223> OTHER INFORMATION: ozoralizumab VH-CDR2

<400> SEQUENCE: 24

Ser Ile Ser Gly Ser Gly Ser Asp Thr Leu Tyr Ala Asp Ser Val Lys
1               5                   10                  15
Gly

<210> SEQ ID NO 25
<211> LENGTH: 8
<212> TYPE: PRT
<213> ORGANISM: artificial sequence
<220> FEATURE:
<223> OTHER INFORMATION: ozoralizumab VH-CDR3

<400> SEQUENCE: 25

Gly Gly Ser Leu Ser Arg Ser Ser
1               5

<210> SEQ ID NO 26
<211> LENGTH: 5
<212> TYPE: PRT
<213> ORGANISM: artificial sequence
<220> FEATURE:
<223> OTHER INFORMATION: ozoralizumab VH-CDR1

<400> SEQUENCE: 26

Asp Tyr Trp Met Tyr
1               5
```

```
<210> SEQ ID NO 27
<211> LENGTH: 17
<212> TYPE: PRT
<213> ORGANISM: artificial sequence
<220> FEATURE:
<223> OTHER INFORMATION: ozoralizumab VH-CDR2

<400> SEQUENCE: 27

Glu Ile Asn Thr Asn Gly Leu Ile Thr Lys Tyr Pro Asp Ser Val Lys
1               5                   10                  15
Gly

<210> SEQ ID NO 28
<211> LENGTH: 7
<212> TYPE: PRT
<213> ORGANISM: artificial sequence
<220> FEATURE:
<223> OTHER INFORMATION: ozoralizumab VH-CDR3

<400> SEQUENCE: 28

Ser Pro Ser Gly Phe Asn Arg
1               5

<210> SEQ ID NO 29
<211> LENGTH: 10
<212> TYPE: PRT
<213> ORGANISM: artificial sequence
<220> FEATURE:
<223> OTHER INFORMATION: golimumab VH-CDR1

<400> SEQUENCE: 29

Gly Phe Ile Phe Ser Ser Tyr Ala Met His
1               5                   10

<210> SEQ ID NO 30
<211> LENGTH: 17
<212> TYPE: PRT
<213> ORGANISM: artificial sequence
<220> FEATURE:
<223> OTHER INFORMATION: golimumab VH-CDR2

<400> SEQUENCE: 30

Phe Met Ser Tyr Asp Gly Ser Asn Lys Lys Tyr Ala Asp Ser Val Lys
1               5                   10                  15
Gly

<210> SEQ ID NO 31
<211> LENGTH: 17
<212> TYPE: PRT
<213> ORGANISM: artificial sequence
<220> FEATURE:
<223> OTHER INFORMATION: golimumab VH-CDR3

<400> SEQUENCE: 31

Asp Arg Gly Ile Ala Ala Gly Gly Asn Tyr Tyr Tyr Tyr Gly Met Asp
1               5                   10                  15
Val

<210> SEQ ID NO 32
<211> LENGTH: 11
<212> TYPE: PRT
<213> ORGANISM: artificial sequence
<220> FEATURE:
<223> OTHER INFORMATION: adalimumab VL-CDR1

<400> SEQUENCE: 32
```

```
Arg Ala Ser Gln Gly Ile Arg Asn Tyr Leu Ala
1               5                   10

<210> SEQ ID NO 33
<211> LENGTH: 7
<212> TYPE: PRT
<213> ORGANISM: artificial sequence
<220> FEATURE:
<223> OTHER INFORMATION: adalimumab VL-CDR2

<400> SEQUENCE: 33

Ala Ala Ser Thr Leu Gln Ser
1               5

<210> SEQ ID NO 34
<211> LENGTH: 9
<212> TYPE: PRT
<213> ORGANISM: artificial sequence
<220> FEATURE:
<223> OTHER INFORMATION: adalimumab VL-CDR3

<400> SEQUENCE: 34

Gln Arg Tyr Asn Arg Ala Pro Tyr Thr
1               5

<210> SEQ ID NO 35
<211> LENGTH: 11
<212> TYPE: PRT
<213> ORGANISM: artificial sequence
<220> FEATURE:
<223> OTHER INFORMATION: infliximab VL-CDR1

<400> SEQUENCE: 35

Arg Ala Ser Gln Phe Val Gly Ser Ser Ile His
1               5                   10

<210> SEQ ID NO 36
<211> LENGTH: 7
<212> TYPE: PRT
<213> ORGANISM: artificial sequence
<220> FEATURE:
<223> OTHER INFORMATION: infliximab VL-CDR2

<400> SEQUENCE: 36

Tyr Ala Ser Glu Ser Met Ser
1               5

<210> SEQ ID NO 37
<211> LENGTH: 9
<212> TYPE: PRT
<213> ORGANISM: artificial sequence
<220> FEATURE:
<223> OTHER INFORMATION: infliximab VL-CDR3

<400> SEQUENCE: 37

Gln Gln Ser His Ser Trp Pro Phe Thr
1               5

<210> SEQ ID NO 38
<211> LENGTH: 11
<212> TYPE: PRT
<213> ORGANISM: artificial sequence
<220> FEATURE:
<223> OTHER INFORMATION: certolizumab VL-CDR1

<400> SEQUENCE: 38
```

Lys Ala Ser Gln Asn Val Gly Thr Asn Val Ala
1               5                   10

<210> SEQ ID NO 39
<211> LENGTH: 7
<212> TYPE: PRT
<213> ORGANISM: artificial sequence
<220> FEATURE:
<223> OTHER INFORMATION: certolizumab VL-CDR2

<400> SEQUENCE: 39

Ser Ala Ser Phe Leu Tyr Ser
1               5

<210> SEQ ID NO 40
<211> LENGTH: 9
<212> TYPE: PRT
<213> ORGANISM: artificial sequence
<220> FEATURE:
<223> OTHER INFORMATION: certolizumab VL-CDR3

<400> SEQUENCE: 40

Gln Gln Tyr Asn Ile Tyr Pro Leu Thr
1               5

<210> SEQ ID NO 41
<211> LENGTH: 11
<212> TYPE: PRT
<213> ORGANISM: artificial sequence
<220> FEATURE:
<223> OTHER INFORMATION: afelimomab VL-CDR1

<400> SEQUENCE: 41

Lys Ala Ser Gln Ala Val Ser Ser Ala Val Ala
1               5                   10

<210> SEQ ID NO 42
<211> LENGTH: 7
<212> TYPE: PRT
<213> ORGANISM: artificial sequence
<220> FEATURE:
<223> OTHER INFORMATION: afelimomab VL-CDR2

<400> SEQUENCE: 42

Trp Ala Ser Thr Arg His Thr
1               5

<210> SEQ ID NO 43
<211> LENGTH: 9
<212> TYPE: PRT
<213> ORGANISM: artificial sequence
<220> FEATURE:
<223> OTHER INFORMATION: afelimomab VL-CDR3

<400> SEQUENCE: 43

Gln Gln His Tyr Ser Thr Pro Phe Thr
1               5

<210> SEQ ID NO 44
<211> LENGTH: 17
<212> TYPE: PRT
<213> ORGANISM: artificial sequence
<220> FEATURE:
<223> OTHER INFORMATION: nerelimomab VL-CDR1

<400> SEQUENCE: 44

Lys Ser Ser Gln Ser Leu Leu Tyr Ser Asn Asn Gln Lys Asn Tyr Leu

```
1               5                   10                  15
Ala

<210> SEQ ID NO 45
<211> LENGTH: 7
<212> TYPE: PRT
<213> ORGANISM: artificial sequence
<220> FEATURE:
<223> OTHER INFORMATION: nerelimomab VL-CDR2

<400> SEQUENCE: 45

Trp Ala Ser Thr Arg Glu Ser
1               5

<210> SEQ ID NO 46
<211> LENGTH: 9
<212> TYPE: PRT
<213> ORGANISM: artificial sequence
<220> FEATURE:
<223> OTHER INFORMATION: nerelimomab VL-CDR3

<400> SEQUENCE: 46

Gln Gln Tyr Tyr Asp Tyr Pro Trp Thr
1               5

<210> SEQ ID NO 47
<211> LENGTH: 11
<212> TYPE: PRT
<213> ORGANISM: artificial sequence
<220> FEATURE:
<223> OTHER INFORMATION: golimumab VL-CDR1

<400> SEQUENCE: 47

Arg Ala Ser Gln Ser Val Tyr Ser Tyr Leu Ala
1               5                   10

<210> SEQ ID NO 48
<211> LENGTH: 7
<212> TYPE: PRT
<213> ORGANISM: artificial sequence
<220> FEATURE:
<223> OTHER INFORMATION: golimumab VL-CDR2

<400> SEQUENCE: 48

Asp Ala Ser Asn Arg Ala Thr
1               5

<210> SEQ ID NO 49
<211> LENGTH: 10
<212> TYPE: PRT
<213> ORGANISM: artificial sequence
<220> FEATURE:
<223> OTHER INFORMATION: golimumab VL-CDR3

<400> SEQUENCE: 49

Gln Gln Arg Ser Asn Trp Pro Pro Phe Thr
1               5                   10

<210> SEQ ID NO 50
<211> LENGTH: 121
<212> TYPE: PRT
<213> ORGANISM: artificial sequence
<220> FEATURE:
<223> OTHER INFORMATION: adalimumab VH

<400> SEQUENCE: 50
```

-continued

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
            115                 120
```

<210> SEQ ID NO 51
<211> LENGTH: 119
<212> TYPE: PRT
<213> ORGANISM: artificial sequence
<220> FEATURE:
<223> OTHER INFORMATION: infliximab VH

<400> SEQUENCE: 51

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
50                  55                  60

Ser Val Lys Gly Arg Phe Thr Ile Ser Arg Asp Asp Ser Lys Ser Ala
65                  70                  75                  80

Val Tyr Leu Gln Met Asn Ser Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser
        115
```

<210> SEQ ID NO 52
<211> LENGTH: 118
<212> TYPE: PRT
<213> ORGANISM: artificial sequence
<220> FEATURE:
<223> OTHER INFORMATION: certolizumab VH

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
50                  55                  60
```

```
Lys Gly Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 53
<211> LENGTH: 117
<212> TYPE: PRT
<213> ORGANISM: artificial sequence
<220> FEATURE:
<223> OTHER INFORMATION: afelimomab VH

<400> SEQUENCE: 53

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Asp Tyr
                20                  25                  30

Gly Val Asn Trp Val Arg Gln Pro Pro Gly Lys Gly Leu Glu Trp Leu
            35                  40                  45

Gly Met Ile Trp Gly Asp Gly Ser Thr Asp Tyr Asp Ser Thr Leu Lys
 50                  55                  60

Ser Arg Leu Ser Ile Ser Lys Asp Asn Ser Lys Ser Gln Ile Phe Leu
 65                  70                  75                  80

Lys Asn Asn Ser Leu Gln Thr Asp Asp Thr Ala Arg Tyr Tyr Cys Ala
                 85                  90                  95

Arg Glu Trp His His Gly Pro Val Ala Tyr Trp Gly Gln Gly Thr Leu
            100                 105                 110

Val Thr Val Ser Ala
        115

<210> SEQ ID NO 54
<211> LENGTH: 121
<212> TYPE: PRT
<213> ORGANISM: artificial sequence
<220> FEATURE:
<223> OTHER INFORMATION: nerelimomab VH

<400> SEQUENCE: 54

Gln Val Gln Leu Val Gln Ser Gly Ala Glu Val Val Lys Pro Gly Ser
 1               5                  10                  15

Ser Val Lys Val Ser Cys Lys Ala Ser Gly Tyr Thr Phe Thr Asp Tyr
                20                  25                  30

Asn Val Asp Trp Val Lys Gln Ala Pro Gly Gln Gly Leu Gln Trp Ile
            35                  40                  45

Gly Asn Ile Asn Pro Asn Asn Gly Gly Thr Ile Tyr Asn Gln Lys Phe
 50                  55                  60

Lys Gly Lys Gly Thr Leu Thr Val Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Ala Arg Ser Ala Phe Tyr Asn Asn Tyr Glu Tyr Phe Asp Val Trp Gly
            100                 105                 110

Gln Gly Thr Thr Val Thr Val Ser Ser
```

```
              115                 120

<210> SEQ ID NO 55
<211> LENGTH: 115
<212> TYPE: PRT
<213> ORGANISM: artificial sequence
<220> FEATURE:
<223> OTHER INFORMATION: ozoralizumab VH V1

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Ser Pro Ser Gly Phe Asn Arg Gly Gln Gly Thr Leu Val Thr
            100                 105                 110

Val Ser Ser
        115

<210> SEQ ID NO 56
<211> LENGTH: 115
<212> TYPE: PRT
<213> ORGANISM: artificial sequence
<220> FEATURE:
<223> OTHER INFORMATION: ozoralizumab VH V2

<400> SEQUENCE: 56

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 57
<211> LENGTH: 115
<212> TYPE: PRT
<213> ORGANISM: artificial sequence
<220> FEATURE:
<223> OTHER INFORMATION: ozoralizumab VH V3

<400> SEQUENCE: 57
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Tyr Trp Val Arg Gln Ala Pro Gly Lys Gly Leu Glu Trp Val
        35                  40                  45

Ser Glu Ile Asn Thr Asn Gly Leu Ile Thr Lys Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Ser Pro Ser Gly Phe Asn Arg Gly Gln Gly Thr Leu Val Thr
            100                 105                 110

Val Ser Ser
        115
```

<210> SEQ ID NO 58
<211> LENGTH: 126
<212> TYPE: PRT
<213> ORGANISM: artificial sequence
<220> FEATURE:
<223> OTHER INFORMATION: golimumab VH

<400> SEQUENCE: 58

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser
        115                 120                 125
```

<210> SEQ ID NO 59
<211> LENGTH: 107
<212> TYPE: PRT
<213> ORGANISM: artificial sequence
<220> FEATURE:
<223> OTHER INFORMATION: adalimumab VL

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
```

```
                    50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                     85                  90                  95

Thr Phe Gly Gln Gly Thr Lys Val Glu Ile Lys
                100                 105

<210> SEQ ID NO 60
<211> LENGTH: 107
<212> TYPE: PRT
<213> ORGANISM: artificial sequence
<220> FEATURE:
<223> OTHER INFORMATION: infliximab VL

<400> SEQUENCE: 60

Asp Ile Leu Leu Thr Gln Ser Pro Ala Ile Leu Ser Val Ser Pro Gly
  1               5                  10                  15

Glu Arg Val Ser Phe Ser Cys Arg Ala Ser Gln Phe Val Gly Ser Ser
                 20                  25                  30

Ile His Trp Tyr Gln Gln Arg Thr Asn Gly Ser Pro Arg Leu Leu Ile
             35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                     85                  90                  95

Thr Phe Gly Ser Gly Thr Asn Leu Glu Val Lys
                100                 105

<210> SEQ ID NO 61
<211> LENGTH: 107
<212> TYPE: PRT
<213> ORGANISM: artificial sequence
<220> FEATURE:
<223> OTHER INFORMATION: certolizumab VL

<400> SEQUENCE: 61

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Val Gly Thr Asn
                 20                  25                  30

Val Ala Trp Tyr Gln Gln Lys Pro Gly Lys Ala Pro Lys Ala Leu Ile
             35                  40                  45

Tyr Ser Ala Ser Phe Leu Tyr Ser Gly Val Pro Tyr Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Leu
                     85                  90                  95

Thr Phe Gly Gln Gly Thr Lys Val Glu Ile Lys
                100                 105

<210> SEQ ID NO 62
<211> LENGTH: 107
<212> TYPE: PRT
<213> ORGANISM: artificial sequence
<220> FEATURE:
```

<223> OTHER INFORMATION: afelimomab VL

<400> SEQUENCE: 62

Asp Ile Val Met Thr Gln Ser His Lys Phe Met Ser Thr Thr Val Gly
1               5                   10                  15

Asp Arg Val Ser Ile Thr Cys Lys Ala Ser Gln Ala Val Ser Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Val Thr Asp Phe Thr Leu Thr Ile His Asn Leu Gln Ala
65                  70                  75                  80

Glu Asp Leu Ala Leu Tyr Tyr Cys Gln Gln His Tyr Ser Thr Pro Phe
                85                  90                  95

Thr Phe Gly Ser Gly Thr Lys Leu Glu Ile Lys
            100                 105

<210> SEQ ID NO 63
<211> LENGTH: 114
<212> TYPE: PRT
<213> ORGANISM: artificial sequence
<220> FEATURE:
<223> OTHER INFORMATION: nerelimomab VL

<400> SEQUENCE: 63

Asp Ile Met Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ala Pro Lys Leu Leu Ile Ser Trp Ala Ser Thr Arg Glu Ser Gly Val
    50                  55                  60

Pro Ser Arg Phe Ile Gly Ser Gly Ser Gly Thr Glu Phe Thr Leu Thr
65                  70                  75                  80

Ile Ser Ser Leu Gln Pro Asp Asp Val Ala Thr Tyr Tyr Cys Gln Gln
                85                  90                  95

Tyr Tyr Asp Tyr Pro Trp Thr Phe Gly Gln Gly Thr Lys Val Glu Ile
            100                 105                 110

Lys Arg

<210> SEQ ID NO 64
<211> LENGTH: 107
<212> TYPE: PRT
<213> ORGANISM: artificial sequence
<220> FEATURE:
<223> OTHER INFORMATION: placulumab VL

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asp Ser Tyr
            20                  25                  30

Leu His Trp Tyr Gln Gln Lys Pro Gly Lys Ala Pro Lys Leu Leu Ile
        35                  40                  45

Tyr Ser Ala Ser Asn Leu Glu Thr Gly Val Pro Ser Arg Phe Ser Gly
    50                  55                  60

```
Ser Gly Ser Gly Thr Asp Phe Thr Leu Thr Ile Ser Ser Leu Leu Pro
 65                  70                  75                  80

Glu Asp Phe Ala Thr Tyr Tyr Cys Gln Gln Val Val Trp Arg Pro Phe
                 85                  90                  95

Thr Phe Gly Gln Gly Thr Lys Val Glu Ile Lys
            100                 105
```

<210> SEQ ID NO 65
<211> LENGTH: 108
<212> TYPE: PRT
<213> ORGANISM: artificial sequence
<220> FEATURE:
<223> OTHER INFORMATION: golimumab VL

<400> SEQUENCE: 65

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Tyr Ser Tyr
                 20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys
            100                 105
```

<210> SEQ ID NO 66
<211> LENGTH: 451
<212> TYPE: PRT
<213> ORGANISM: artificial sequence
<220> FEATURE:
<223> OTHER INFORMATION: Adalimumab (D2E7) Full-Length Heavy Chain

<400> SEQUENCE: 66

```
Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
```

```
                145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 67
<211> LENGTH: 450
<212> TYPE: PRT
<213> ORGANISM: artificial sequence
<220> FEATURE:
<223> OTHER INFORMATION: infliximab Full-Length Heavy Chain

<400> SEQUENCE: 67

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
                20                  25                  30

Trp Met Asn Trp Val Arg Gln Ser Pro Glu Lys Gly Leu Glu Trp Val
                35                  40                  45

Ala Glu Ile Arg Ser Lys Ser Ile Asn Ser Ala Thr His Tyr Ala Glu
```

```
            50                  55                  60
Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 68
```

<211> LENGTH: 229
<212> TYPE: PRT
<213> ORGANISM: artificial sequence
<220> FEATURE:
<223> OTHER INFORMATION: certolizumab Full-Length Heavy Chain

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225

<210> SEQ ID NO 69
<211> LENGTH: 447
<212> TYPE: PRT
<213> ORGANISM: artificial sequence
<220> FEATURE:
<223> OTHER INFORMATION: afelimomab Full-Length Heavy Chain

<400> SEQUENCE: 69

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asp Ser Thr Leu Lys
    50                  55                  60

Ser Arg Leu Ser Ile Ser Lys Asp Asn Ser Lys Ser Gln Ile Phe Leu
65                  70                  75                  80

Lys Asn Asn Ser Leu Gln Thr Asp Asp Thr Ala Arg Tyr Tyr Cys Ala

-continued

```
                    85                  90                  95
Arg Glu Trp His His Gly Pro Val Ala Tyr Trp Gly Gln Gly Thr Leu
                100                 105                 110

Val Thr Val Ser Ala Ala Thr Thr Thr Ala Pro Ser Val Tyr Pro Leu
            115                 120                 125

Val Pro Gly Cys Ser Asp Thr Ser Gly Ser Ser Val Thr Leu Gly Cys
130                 135                 140

Leu Val Lys Gly Tyr Phe Pro Glu Pro Val Thr Val Lys Trp Asn Tyr
145                 150                 155                 160

Gly Ala Leu Ser Ser Gly Val Arg Thr Val Ser Ser Val Leu Gln Ser
                165                 170                 175

Gly Phe Tyr Ser Leu Ser Ser Leu Val Thr Val Pro Ser Ser Thr Trp
            180                 185                 190

Pro Ser Gln Thr Val Ile Cys Asn Val Ala His Pro Ala Ser Lys Thr
        195                 200                 205

Glu Leu Ile Lys Arg Ile Glu Pro Arg Ile Pro Lys Pro Ser Thr Pro
210                 215                 220

Pro Gly Ser Ser Cys Pro Pro Gly Asn Ile Leu Gly Gly Pro Ser Val
225                 230                 235                 240

Phe Ile Phe Pro Pro Lys Pro Lys Asp Ala Leu Met Ile Ser Leu Thr
                245                 250                 255

Pro Lys Val Thr Cys Val Val Asp Val Ser Glu Asp Asp Pro Asp
            260                 265                 270

Val His Val Ser Trp Phe Val Asp Asn Lys Glu Val His Thr Ala Trp
        275                 280                 285

Thr Gln Pro Arg Glu Ala Gln Tyr Asn Ser Thr Phe Arg Val Val Ser
    290                 295                 300

Ala Leu Pro Ile Gln His Gln Asp Trp Met Arg Gly Lys Glu Phe Lys
305                 310                 315                 320

Cys Lys Val Asn Asn Lys Ala Leu Pro Ala Pro Ile Glu Arg Thr Ile
                325                 330                 335

Ser Lys Pro Lys Gly Arg Ala Gln Thr Pro Gln Val Tyr Thr Ile Pro
            340                 345                 350

Pro Pro Arg Glu Gln Met Ser Lys Lys Val Ser Leu Thr Cys Leu
        355                 360                 365

Val Thr Asn Phe Phe Ser Glu Ala Ile Ser Val Glu Trp Glu Arg Asn
    370                 375                 380

Gly Glu Leu Glu Gln Asp Tyr Lys Asn Thr Pro Pro Ile Leu Asp Ser
385                 390                 395                 400

Asp Gly Thr Tyr Phe Leu Tyr Ser Lys Leu Thr Val Asp Thr Asp Ser
                405                 410                 415

Trp Leu Gln Gly Glu Ile Phe Thr Cys Ser Val Val His Glu Ala Leu
            420                 425                 430

His Asn His His Thr Gln Lys Asn Leu Ser Arg Ser Pro Gly Lys
        435                 440                 445

<210> SEQ ID NO 70
<211> LENGTH: 363
<212> TYPE: PRT
<213> ORGANISM: artificial sequence
<220> FEATURE:
<223> OTHER INFORMATION: ozoralizumab Full-Length Heavy Chain

<400> SEQUENCE: 70

Glu Val Gln Leu Val Glu Ser Gly Gly Gly Leu Val Gln Pro Gly Gly
```

```
            1               5              10              15
          Ser Leu Arg Leu Ser Cys Ala Ala Ser Gly Phe Thr Phe Ser Asp Tyr
                        20              25              30

Trp Met Tyr Trp Val Arg Gln Ala Pro Gly Lys Gly Leu Glu Trp Val
                        35              40              45

Ser Glu Ile Asn Thr Asn Gly Leu Ile Thr Lys Tyr Pro Asp Ser Val
                  50              55              60

Lys Gly Arg Phe Thr Ile Ser Arg Asp Asn Ala Lys Asn Thr Leu Tyr
          65              70              75              80

Leu Gln Met Asn Ser Leu Arg Pro Glu Asp Thr Ala Val Tyr Tyr Cys
                        85              90              95

Ala Arg Ser Pro Ser Gly Phe Asn Arg Gly Gln Gly Thr Leu Val Thr
                        100             105             110

Val Ser Ser Gly Gly Gly Gly Ser Gly Gly Gly Ser Glu Val Gln Leu
                        115             120             125

Val Glu Ser Gly Gly Gly Leu Val Gln Pro Gly Asn Ser Leu Arg Leu
                        130             135             140

Ser Cys Ala Ala Ser Gly Phe Thr Phe Ser Ser Phe Gly Met Ser Trp
          145             150             155             160

Val Arg Gln Ala Pro Gly Lys Gly Leu Glu Trp Val Ser Ser Ile Ser
                        165             170             175

Gly Ser Gly Ser Asp Thr Leu Tyr Ala Asp Ser Val Lys Gly Arg Phe
                        180             185             190

Thr Ile Ser Arg Asp Asn Ala Lys Thr Thr Leu Tyr Leu Gln Met Asn
                        195             200             205

Ser Leu Arg Pro Glu Asp Thr Ala Val Tyr Tyr Cys Thr Ile Gly Gly
                        210             215             220

Ser Leu Ser Arg Ser Ser Gln Gly Thr Leu Val Thr Val Ser Ser Gly
          225             230             235             240

Gly Gly Gly Ser Gly Gly Ser Glu Val Gln Leu Val Glu Ser Gly
                        245             250             255

Gly Gly Leu Val Gln Pro Gly Gly Ser Leu Arg Leu Ser Cys Ala Ala
                        260             265             270

Ser Gly Phe Thr Phe Ser Asp Tyr Trp Met Tyr Trp Val Arg Gln Ala
                        275             280             285

Pro Gly Lys Gly Leu Glu Trp Val Ser Glu Ile Asn Thr Asn Gly Leu
                        290             295             300

Ile Thr Lys Tyr Pro Asp Ser Val Lys Gly Arg Phe Thr Ile Ser Arg
          305             310             315             320

Asp Asn Ala Lys Asn Thr Leu Tyr Leu Gln Met Asn Ser Leu Arg Pro
                        325             330             335

Glu Asp Thr Ala Val Tyr Tyr Cys Ala Arg Ser Pro Ser Gly Phe Asn
                        340             345             350

Arg Gly Gln Gly Thr Leu Val Thr Val Ser Ser
                        355             360

<210> SEQ ID NO 71
<211> LENGTH: 234
<212> TYPE: PRT
<213> ORGANISM: artificial sequence
<220> FEATURE:
<223> OTHER INFORMATION: placulumab Full-Length Heavy Chain

<400> SEQUENCE: 71

Arg Val Glu Pro Lys Ser Ser Asp Lys Thr His Thr Cys Pro Pro Cys
```

```
             1               5                  10                 15
             Pro Ala Pro Glu Leu Leu Gly Gly Pro Ser Val Phe Leu Phe Pro Pro
                           20                 25                 30

Lys Pro Lys Asp Thr Leu Met Ile Ser Arg Thr Pro Glu Val Thr Cys
                           35                 40                 45

Val Val Val Asp Val Ser His Glu Asp Pro Glu Val Lys Phe Asn Trp
              50                 55                 60

Tyr Val Asp Gly Val Glu Val His Asn Ala Lys Thr Lys Pro Arg Glu
              65                 70                 75                 80

Glu Gln Tyr Asn Ser Thr Tyr Arg Val Val Ser Val Leu Thr Val Leu
                               85                 90                 95

His Gln Asp Trp Leu Asn Gly Lys Glu Tyr Lys Cys Lys Val Ser Asn
                              100                105                110

Lys Ala Leu Pro Ala Pro Ile Glu Lys Thr Ile Ser Lys Ala Lys Gly
                              115                120                125

Gln Pro Arg Glu Pro Gln Val Tyr Thr Leu Pro Pro Ser Arg Asp Glu
                              130                135                140

Leu Thr Lys Asn Gln Val Ser Leu Thr Cys Leu Val Lys Gly Phe Tyr
             145                150                155                160

Pro Ser Asp Ile Ala Val Glu Trp Glu Ser Asn Gly Gln Pro Glu Asn
                              165                170                175

Asn Tyr Lys Thr Thr Pro Pro Val Leu Asp Ser Asp Gly Ser Phe Phe
                              180                185                190

Leu Tyr Ser Lys Leu Thr Val Asp Lys Ser Arg Trp Gln Gln Gly Asn
                              195                200                205

Val Phe Ser Cys Ser Val Met His Glu Ala Leu His Asn His Tyr Thr
                              210                215                220

Gln Lys Ser Leu Ser Leu Ser Pro Gly Lys
             225                230

<210> SEQ ID NO 72
<211> LENGTH: 456
<212> TYPE: PRT
<213> ORGANISM: artificial sequence
<220> FEATURE:
<223> OTHER INFORMATION: golimumab Full-Length Heavy Chain

<400> SEQUENCE: 72

Gln Val Gln Leu Val Glu Ser Gly Gly Gly Val Val Gln Pro Gly Arg
             1                 5                 10                 15

Ser Leu Arg Leu Ser Cys Ala Ala Ser Gly Phe Ile Phe Ser Ser Tyr
                           20                 25                 30

Ala Met His Trp Val Arg Gln Ala Pro Gly Asn Gly Leu Glu Trp Val
                           35                 40                 45

Ala Phe Met Ser Tyr Asp Gly Ser Asn Lys Lys Tyr Ala Asp Ser Val
              50                 55                 60

Lys Gly Arg Phe Thr Ile Ser Arg Asp Asn Ser Lys Asn Thr Leu Tyr
              65                 70                 75                 80

Leu Gln Met Asn Ser Leu Arg Ala Glu Asp Thr Ala Val Tyr Tyr Cys
                               85                 90                 95

Ala Arg Asp Arg Gly Ile Ala Ala Gly Gly Asn Tyr Tyr Tyr Tyr Gly
                              100                105                110

Met Asp Val Trp Gly Gln Gly Thr Thr Val Thr Val Ser Ser Ala Ser
                              115                120                125

Thr Lys Gly Pro Ser Val Phe Pro Leu Ala Pro Ser Ser Lys Ser Thr
```

```
                    130                 135                 140
Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Lys Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 73
<211> LENGTH: 214
<212> TYPE: PRT
<213> ORGANISM: artificial sequence
<220> FEATURE:
<223> OTHER INFORMATION: Adalimumab (D2E7) Full-Length Light Chain

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
```

```
            35                  40                  45
Tyr Ala Ala Ser Thr Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Val Ala Thr Tyr Tyr Cys Gln Arg Tyr Asn Arg Ala Pro Tyr
                 85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 74
<211> LENGTH: 214
<212> TYPE: PRT
<213> ORGANISM: artificial sequence
<220> FEATURE:
<223> OTHER INFORMATION: infliximab Full-Length Light Chain

<400> SEQUENCE: 74

Asp Ile Leu Leu Thr Gln Ser Pro Ala Ile Leu Ser Val Ser Pro Gly
 1                5                  10                  15
Glu Arg Val Ser Phe Ser Cys Arg Ala Ser Gln Phe Val Gly Ser Ser
                 20                  25                  30
Ile His Trp Tyr Gln Gln Arg Thr Asn Gly Ser Pro Arg Leu Leu Ile
            35                  40                  45
Lys Tyr Ala Ser Glu Ser Met Ser Gly Ile Pro Ser Arg Phe Ser Gly
 50                  55                  60
Ser Gly Ser Gly Thr Asp Phe Thr Leu Ser Ile Asn Thr Val Glu Ser
 65                  70                  75                  80
Glu Asp Ile Ala Asp Tyr Tyr Cys Gln Gln Ser His Ser Trp Pro Phe
                 85                  90                  95
Thr Phe Gly Ser Gly Thr Asn Leu Glu Val Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
```

```
                      180                 185                 190
Ala Cys Glu Val Thr His Gln Gly Leu Ser Ser Pro Val Thr Lys Ser
            195                 200                 205

Phe Asn Arg Gly Glu Cys
            210

<210> SEQ ID NO 75
<211> LENGTH: 214
<212> TYPE: PRT
<213> ORGANISM: artificial sequence
<220> FEATURE:
<223> OTHER INFORMATION: certolizumab Full-Length Light Chain

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 76
<211> LENGTH: 214
<212> TYPE: PRT
<213> ORGANISM: artificial sequence
<220> FEATURE:
<223> OTHER INFORMATION: afelimomab Full-Length Light Chain

<400> SEQUENCE: 76

Asp Ile Val Met Thr Gln Ser His Lys Phe Met Ser Thr Thr Val Gly
1               5                   10                  15

Asp Arg Val Ser Ile Thr Cys Lys Ala Ser Gln Ala Val Ser Ser Ala
            20                  25                  30

Val Ala Trp Tyr Gln Gln Lys Pro Gly Gln Ser Pro Lys Leu Leu Ile
        35                  40                  45
```

```
Tyr Trp Ala Ser Thr Arg His Thr Gly Val Pro Asp Arg Phe Thr Gly
         50                  55                  60

Ser Gly Ser Val Thr Asp Phe Thr Leu Thr Ile His Asn Leu Gln Ala
 65                  70                  75                  80

Glu Asp Leu Ala Leu Tyr Tyr Cys Gln Gln His Tyr Ser Thr Pro Phe
                 85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 77
<211> LENGTH: 108
<212> TYPE: PRT
<213> ORGANISM: artificial sequence
<220> FEATURE:
<223> OTHER INFORMATION: placulumab Full-Length Light Chain

<400> SEQUENCE: 77

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ala Ile Asp Ser Tyr
             20                  25                  30

Leu His Trp Tyr Gln Gln Lys Pro Gly Lys Ala Pro Lys Leu Leu Ile
         35                  40                  45

Tyr Ser Ala Ser Asn Leu Glu Thr Gly Val Pro Ser Arg Phe Ser Gly
     50                  55                  60

Ser Gly Ser Gly Thr Asp Phe Thr Leu Thr Ile Ser Ser Leu Leu Pro
 65                  70                  75                  80

Glu Asp Phe Ala Thr Tyr Tyr Cys Gln Gln Val Val Trp Arg Pro Phe
                 85                  90                  95

Thr Phe Gly Gln Gly Thr Lys Val Glu Ile Lys Arg
            100                 105

<210> SEQ ID NO 78
<211> LENGTH: 215
<212> TYPE: PRT
<213> ORGANISM: artificial sequence
<220> FEATURE:
<223> OTHER INFORMATION: golimumab Full-Length Light Chain

<400> SEQUENCE: 78

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Tyr Ser Tyr
             20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 79
<211> LENGTH: 467
<212> TYPE: PRT
<213> ORGANISM: Artificial Sequence
<220> FEATURE:
<223> OTHER INFORMATION: etanercept

<400> SEQUENCE: 79

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
                100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

```
Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 80
<211> LENGTH: 587
<212> TYPE: PRT
<213> ORGANISM: Artificial Sequence
<220> FEATURE:
<223> OTHER INFORMATION: ABT-122 Heavy Chain

<400> SEQUENCE: 80

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60
```

```
Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Gly Gly Gly Ser Gly Gly
        115                 120                 125

Gly Gly Ser Glu Val Gln Leu Val Gln Ser Gly Ala Glu Val Lys Lys
        130                 135                 140

Pro Gly Ser Ser Val Lys Val Ser Cys Lys Ala Ser Gly Gly Ser Phe
145                 150                 155                 160

Gly Gly Tyr Gly Ile Gly Trp Val Arg Gln Ala Pro Gly Gln Gly Leu
                165                 170                 175

Glu Trp Met Gly Gly Ile Thr Pro Phe Phe Gly Phe Ala Asp Tyr Ala
            180                 185                 190

Gln Lys Phe Gln Gly Arg Val Thr Ile Thr Ala Asp Glu Ser Thr Thr
        195                 200                 205

Thr Ala Tyr Met Glu Leu Ser Gly Leu Thr Ser Asp Asp Thr Ala Val
    210                 215                 220

Tyr Tyr Cys Ala Arg Asp Pro Asn Glu Phe Trp Asn Gly Tyr Tyr Ser
225                 230                 235                 240

Thr His Asp Phe Asp Ser Trp Gly Gln Gly Thr Thr Val Thr Val Ser
                245                 250                 255

Ser Ala Ser Thr Lys Gly Pro Ser Val Phe Pro Leu Ala Pro Ser Ser
            260                 265                 270

Lys Ser Thr Ser Gly Gly Thr Ala Ala Leu Gly Cys Leu Val Lys Asp
        275                 280                 285

Tyr Phe Pro Glu Pro Val Thr Val Ser Trp Asn Ser Gly Ala Leu Thr
    290                 295                 300

Ser Gly Val His Thr Phe Pro Ala Val Leu Gln Ser Ser Gly Leu Tyr
305                 310                 315                 320

Ser Leu Ser Ser Val Val Thr Val Pro Ser Ser Ser Leu Gly Thr Gln
                325                 330                 335

Thr Tyr Ile Cys Asn Val Asn His Lys Pro Ser Asn Thr Lys Val Asp
            340                 345                 350

Lys Lys Val Glu Pro Lys Ser Cys Asp Lys Thr His Thr Cys Pro Pro
        355                 360                 365

Cys Pro Ala Pro Glu Leu Leu Gly Gly Pro Ser Val Phe Leu Phe Pro
    370                 375                 380

Pro Lys Pro Lys Asp Thr Leu Met Ile Ser Arg Thr Pro Glu Val Thr
385                 390                 395                 400

Cys Val Val Val Asp Val Ser His Glu Asp Pro Glu Val Lys Phe Asn
                405                 410                 415

Trp Tyr Val Asp Gly Val Glu Val His Asn Ala Lys Thr Lys Pro Arg
            420                 425                 430

Glu Glu Gln Tyr Asn Ser Thr Tyr Arg Val Val Ser Val Leu Thr Val
        435                 440                 445

Leu His Gln Asp Trp Leu Asn Gly Lys Glu Tyr Lys Cys Lys Val Ser
    450                 455                 460

Asn Lys Ala Leu Pro Ala Pro Ile Glu Lys Thr Ile Ser Lys Ala Lys
465                 470                 475                 480
```

```
Gly Gln Pro Arg Glu Pro Gln Val Tyr Thr Leu Pro Pro Ser Arg Asp
                485                 490                 495

Glu Leu Thr Lys Asn Gln Val Ser Leu Thr Cys Leu Val Lys Gly Phe
            500                 505                 510

Tyr Pro Ser Asp Ile Ala Val Glu Trp Glu Ser Asn Gly Gln Pro Glu
            515                 520                 525

Asn Asn Tyr Lys Thr Thr Pro Pro Val Leu Asp Ser Asp Gly Ser Phe
        530                 535                 540

Phe Leu Tyr Ser Lys Leu Thr Val Asp Lys Ser Arg Trp Gln Gln Gly
545                 550                 555                 560

Asn Val Phe Ser Cys Ser Val Met His Glu Ala Leu His Asn His Tyr
                565                 570                 575

Thr Gln Lys Ser Leu Ser Leu Ser Pro Gly Lys
            580                 585

<210> SEQ ID NO 81
<211> LENGTH: 331
<212> TYPE: PRT
<213> ORGANISM: Artificial Sequence
<220> FEATURE:
<223> OTHER INFORMATION: ABT-122 Light Chain

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Gly Gly Ser Gly
            100                 105                 110

Gly Gly Gly Ser Gly Glu Ile Val Leu Thr Gln Ser Pro Asp Phe Gln
        115                 120                 125

Ser Val Thr Pro Lys Glu Lys Val Thr Ile Thr Cys Arg Ala Ser Gln
130                 135                 140

Asp Ile Gly Ser Glu Leu His Trp Tyr Gln Gln Lys Pro Asp Gln Pro
145                 150                 155                 160

Pro Lys Leu Leu Ile Lys Tyr Ala Ser His Ser Thr Ser Gly Val Pro
                165                 170                 175

Ser Arg Phe Ser Gly Ser Gly Ser Gly Thr Asp Phe Thr Leu Thr Ile
            180                 185                 190

Asn Gly Leu Glu Ala Glu Asp Ala Gly Thr Tyr Tyr Cys His Gln Thr
        195                 200                 205

Asp Ser Leu Pro Tyr Thr Phe Gly Pro Gly Thr Lys Val Asp Ile Lys
    210                 215                 220

Arg Thr Val Ala Ala Pro Ser Val Phe Ile Phe Pro Pro Ser Asp Glu
225                 230                 235                 240

Gln Leu Lys Ser Gly Thr Ala Ser Val Val Cys Leu Leu Asn Asn Phe
                245                 250                 255
```

```
Tyr Pro Arg Glu Ala Lys Val Gln Trp Lys Val Asp Asn Ala Leu Gln
            260                 265                 270

Ser Gly Asn Ser Gln Glu Ser Val Thr Glu Gln Asp Ser Lys Asp Ser
        275                 280                 285

Thr Tyr Ser Leu Ser Ser Thr Leu Thr Leu Ser Lys Ala Asp Tyr Glu
    290                 295                 300

Lys His Lys Val Tyr Ala Cys Glu Val Thr His Gln Gly Leu Ser Ser
305                 310                 315                 320

Pro Val Thr Lys Ser Phe Asn Arg Gly Glu Cys
                325                 330

<210> SEQ ID NO 82
<211> LENGTH: 235
<212> TYPE: PRT
<213> ORGANISM: Artificial Sequence
<220> FEATURE:
<223> OTHER INFORMATION: Certolizumab Heavy Chain

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala His His His His His His
225                 230                 235

<210> SEQ ID NO 83
<211> LENGTH: 214
<212> TYPE: PRT
<213> ORGANISM: Artificial Sequence
<220> FEATURE:
<223> OTHER INFORMATION: Certolizumab Light Chain

<400> SEQUENCE: 83
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 238
<212> TYPE: PRT
<213> ORGANISM: Artificial Sequence
<220> FEATURE:
<223> OTHER INFORMATION: Adalimumab Fab Heavy Chain

<400> SEQUENCE: 84

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Ala Ala His His His His His His
225                 230                 235
```

<210> SEQ ID NO 85
<211> LENGTH: 214
<212> TYPE: PRT
<213> ORGANISM: Artificial Sequence
<220> FEATURE:
<223> OTHER INFORMATION: Adalimumab Fab Light Chain

<400> SEQUENCE: 85

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 86
<211> LENGTH: 60
<212> TYPE: PRT
<213> ORGANISM: Artificial Sequence
<220> FEATURE:
<223> OTHER INFORMATION: Affibody

<400> SEQUENCE: 86

Gly Val Asp Asn Lys Phe Asn Lys Glu Asn Ile Ala Ala Met Thr Glu
1               5                   10                  15
Ile Thr Arg Leu Pro Asn Leu Asn Pro Tyr Gln Arg Ala Ala Phe Ile
            20                  25                  30
Trp Ser Leu Ser Asp Asp Pro Ser Gln Ser Ala Asn Leu Leu Ala Glu
        35                  40                  45
Ala Lys Lys Leu Asn Asp Ala Gln Ala Pro Lys Cys
    50                  55                  60

<210> SEQ ID NO 87
<211> LENGTH: 382
<212> TYPE: PRT
<213> ORGANISM: Artificial Sequence
<220> FEATURE:
<223> OTHER INFORMATION: Ozoralizumab Nanobody

<400> SEQUENCE: 87

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Trp Met Tyr Trp Val Arg Gln Ala Pro Gly Lys Gly Leu Glu Trp Val
        35                  40                  45
Ser Glu Ile Asn Thr Asn Gly Leu Ile Thr Lys Tyr Pro Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Pro Glu Asp Thr Ala Val Tyr Tyr Cys
                85                  90                  95
Ala Arg Ser Pro Ser Gly Phe Asn Arg Gly Gln Gly Thr Leu Val Thr
            100                 105                 110
Val Ser Ser Gly Gly Gly Ser Gly Gly Gly Ser Glu Val Gln Leu
            115                 120                 125
Val Glu Ser Gly Gly Gly Leu Val Gln Pro Gly Asn Ser Leu Arg Leu
130                 135                 140
Ser Cys Ala Ala Ser Gly Phe Thr Phe Ser Ser Phe Gly Met Ser Trp
145                 150                 155                 160
Val Arg Gln Ala Pro Gly Lys Gly Leu Glu Trp Val Ser Ser Ile Ser
                165                 170                 175
Gly Ser Gly Ser Asp Thr Leu Tyr Ala Asp Ser Val Lys Gly Arg Phe
            180                 185                 190
Thr Ile Ser Arg Asp Asn Ala Lys Thr Thr Leu Tyr Leu Gln Met Asn
            195                 200                 205
Ser Leu Arg Pro Glu Asp Thr Ala Val Tyr Tyr Cys Thr Ile Gly Gly
        210                 215                 220
Ser Leu Ser Arg Ser Ser Gln Gly Thr Leu Val Thr Val Ser Ser Gly
225                 230                 235                 240
Gly Gly Gly Ser Gly Gly Gly Ser Glu Val Gln Leu Val Glu Ser Gly
                245                 250                 255
Gly Gly Leu Val Gln Pro Gly Gly Ser Leu Arg Leu Ser Cys Ala Ala
            260                 265                 270
Ser Gly Phe Thr Phe Ser Asp Tyr Trp Met Tyr Trp Val Arg Gln Ala
        275                 280                 285
Pro Gly Lys Gly Leu Glu Trp Val Ser Glu Ile Asn Thr Asn Gly Leu

```
                290                 295                 300

Ile Thr Lys Tyr Pro Asp Ser Val Lys Gly Arg Phe Thr Ile Ser Arg
305                 310                 315                 320

Asp Asn Ala Lys Asn Thr Leu Tyr Leu Gln Met Asn Ser Leu Arg Pro
                325                 330                 335

Glu Asp Thr Ala Val Tyr Tyr Cys Ala Arg Ser Pro Ser Gly Phe Asn
            340                 345                 350

Arg Gly Gln Gly Thr Leu Val Thr Val Ser Ser Gly Ser Glu Gln Lys
        355                 360                 365

Leu Ile Ser Glu Glu Asp Leu Cys His His His His His His
    370                 375                 380

<210> SEQ ID NO 88
<211> LENGTH: 11
<212> TYPE: PRT
<213> ORGANISM: Artificial Sequence
<220> FEATURE:
<223> OTHER INFORMATION: placulumab VH-CDR1

<400> SEQUENCE: 88

Arg Ala Ser Gln Ala Ile Asp Ser Tyr Leu His
1               5                   10

<210> SEQ ID NO 89
<211> LENGTH: 7
<212> TYPE: PRT
<213> ORGANISM: Artificial Sequence
<220> FEATURE:
<223> OTHER INFORMATION: placulumab VH-CDR2

<400> SEQUENCE: 89

Ser Ala Ser Asn Leu Glu Thr
1               5

<210> SEQ ID NO 90
<211> LENGTH: 9
<212> TYPE: PRT
<213> ORGANISM: Artificial Sequence
<220> FEATURE:
<223> OTHER INFORMATION: placulumab VH-CDR3

<400> SEQUENCE: 90

Gln Gln Val Val Trp Arg Pro Phe Thr
1               5

<210> SEQ ID NO 91
<211> LENGTH: 120
<212> TYPE: PRT
<213> ORGANISM: Artificial Sequence
<220> FEATURE:
<223> OTHER INFORMATION: infliximab VH

<400> SEQUENCE: 91

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
                20                  25                  30

Trp Met Asn Trp Val Arg Gln Ser Pro Glu Lys Gly Leu Glu Trp Val
            35                  40                  45

Ala Glu Ile Arg Ser Lys Ser Ile Asn Ser Ala Thr His Tyr Ala Glu
        50                  55                  60

Ser Val Lys Gly Arg Phe Thr Ile Ser Arg Asp Asp Ser Lys Ser Ala
```

```
                65                  70                  75                  80
Val Tyr Leu Gln Met Thr Asp Leu Arg Thr Glu Asp Thr Gly Val Tyr
                    85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser Ser
            115                 120

<210> SEQ ID NO 92
<211> LENGTH: 113
<212> TYPE: PRT
<213> ORGANISM: Artificial Sequence
<220> FEATURE:
<223> OTHER INFORMATION: nerelimomab VL

<400> SEQUENCE: 92

Asp Ile Met Met Thr Gln Ser Pro Ser Thr Leu Ser Ala Ser Val Gly
1               5                   10                  15

Asp Arg Val Thr Ile Thr Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ala Pro Lys Leu Leu Ile Ser Trp Ala Ser Thr Arg Glu Ser Gly Val
    50                  55                  60

Pro Ser Arg Phe Ile Gly Ser Gly Ser Gly Thr Glu Phe Thr Leu Thr
65                  70                  75                  80

Ile Ser Ser Leu Gln Pro Asp Asp Val Ala Thr Tyr Tyr Cys Gln Gln
                85                  90                  95

Tyr Tyr Asp Tyr Pro Trp Thr Phe Gly Gln Gly Thr Lys Val Glu Ile
                100                 105                 110

Lys

<210> SEQ ID NO 93
<211> LENGTH: 233
<212> TYPE: PRT
<213> ORGANISM: Artificial Sequence
<220> FEATURE:
<223> OTHER INFORMATION: placulumab Full-Length Heavy Chain

<400> SEQUENCE: 93

Val Glu Pro Lys Ser Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
```

```
                130              135             140
Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
                180                 185                 190

Tyr Ser Lys Leu Thr Val Asp Lys Ser Arg Trp Gln Gln Gly Asn Val
                195                 200                 205

Phe Ser Cys Ser Val Met His Glu Ala Leu His Asn His Tyr Thr Gln
                210                 215                 220

Lys Ser Leu Ser Leu Ser Pro Gly Lys
225                 230

<210> SEQ ID NO 94
<211> LENGTH: 12
<212> TYPE: PRT
<213> ORGANISM: Artificial Sequence
<220> FEATURE:
<223> OTHER INFORMATION: adalimumab VH-CDR3

<400> SEQUENCE: 94

Val Ser Tyr Leu Ser Thr Ala Ser Ser Leu Asp Tyr
1               5                   10
```